(12) United States Patent
Berthel et al.

(10) Patent No.: US 7,741,327 B2
(45) Date of Patent: Jun. 22, 2010

(54) PYRROLIDINONE GLUCOKINASE ACTIVATORS

(75) Inventors: Steven Joseph Berthel, Mendham Township, NJ (US); John A Brinkman, West Caldwell, NJ (US); Stuart Hayden, Manalapan, NJ (US); Nancy-Ellen Haynes, Cranford, NJ (US); Robert Francis Kester, West Orange, NJ (US); Lee Apostle McDermott, East Windsor, NJ (US); Yimin Qian, Wayne, NJ (US); Ramakanth Sarabu, Towaco, NJ (US); Nathan Robert Scott, Livingston, NJ (US); Jefferson Wright Tilley, North Caldwell, NJ (US)

(73) Assignee: Hoffmann-La Roche Inc., Nutley, NJ (US)

( * ) Notice: Subject to any disclaimer, the term of this patent is extended or adjusted under 35 U.S.C. 154(b) by 0 days.

(21) Appl. No.: 12/400,065

(22) Filed: Mar. 9, 2009

(65) Prior Publication Data

US 2009/0264445 A1    Oct. 22, 2009

Related U.S. Application Data

(60) Provisional application No. 61/145,761, filed on Jan. 20, 2009, provisional application No. 61/045,370, filed on Apr. 16, 2008.

(51) Int. Cl.
| | |
|---|---|
| A61K 31/497 | (2006.01) |
| A61K 31/4439 | (2006.01) |
| A61K 31/433 | (2006.01) |
| A61K 31/428 | (2006.01) |
| A61K 31/426 | (2006.01) |
| A61K 31/423 | (2006.01) |
| A61K 31/421 | (2006.01) |
| A61K 31/4155 | (2006.01) |
| C07D 403/12 | (2006.01) |
| C07D 401/12 | (2006.01) |
| C07D 285/08 | (2006.01) |
| C07D 277/82 | (2006.01) |
| C07D 277/38 | (2006.01) |
| C07D 263/54 | (2006.01) |
| C07D 263/48 | (2006.01) |
| C07D 231/56 | (2006.01) |
| C07D 231/38 | (2006.01) |

(52) U.S. Cl. .............. 514/255.05; 514/343; 514/361; 514/367; 514/371; 514/375; 514/376; 514/407; 544/405; 546/278.7; 548/128; 548/163; 548/195; 548/217; 548/229; 548/361.1; 548/364.1; 548/364.4; 548/365.7

(58) Field of Classification Search ............ 514/255.05, 514/343, 371, 367, 361, 376, 375, 407; 544/405; 546/278.7; 548/195, 163, 128, 229, 217, 548/361.1, 364.1, 365.7, 364.4

See application file for complete search history.

(56) References Cited

U.S. PATENT DOCUMENTS

| 6,528,543 B1 | 3/2003 | Bizzarro et al. |
| 2006/0167053 A1 | 7/2006 | Iino et al. |
| 2006/0258701 A1 | 11/2006 | Mitsuya et al. |

FOREIGN PATENT DOCUMENTS

| EP | 1 600 442 A1 | 11/2005 |
| WO | WO 00/58293 | 10/2000 |
| WO | WO 01/62726 | 8/2001 |
| WO | WO 01/83465 A2 | 11/2001 |
| WO | WO 01/85706 A1 | 11/2001 |
| WO | WO 01/85707 A1 | 11/2001 |
| WO | WO 02/46173 | 6/2002 |
| WO | WO 03/015774 A1 | 2/2003 |
| WO | WO 03/095438 A1 | 11/2003 |
| WO | WO 2004/050645 A1 | 6/2004 |
| WO | WO 2004/052869 A1 | 6/2004 |
| WO | WO 2004/072031 A2 | 8/2004 |
| WO | WO 2004/072066 A1 | 8/2004 |
| WO | WO 2004/076420 A1 | 9/2004 |
| WO | WO 2004/081001 A1 | 9/2004 |
| WO | WO 2005/080359 A1 | 9/2005 |
| WO | WO 2005/080360 A1 | 9/2005 |
| WO | WO 2005/090332 A1 | 9/2005 |
| WO | WO 2005/095417 A1 | 10/2005 |
| WO | WO 2005/095418 A1 | 10/2005 |
| WO | WO 2005/103021 A1 | 11/2005 |
| WO | WO 2005/121110 A1 | 12/2005 |
| WO | WO 2006/016178 A | 2/2006 |

(Continued)

OTHER PUBLICATIONS

M.C.T. Fyfe, Diabetologia, DOI 10.1007/s00125-007-0646-8.

*Primary Examiner*—Kamal A Saeed
*Assistant Examiner*—Kristin Bianchi
(74) *Attorney, Agent, or Firm*—George W. Johnston; Dennis P. Tramaloni; Samuel H. Megerditchian

(57) ABSTRACT

Provided herein are compounds of the formula (I):

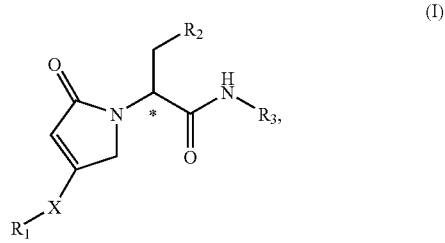

as well as pharmaceutically acceptable salts thereof, wherein the substituents are as those disclosed in the specification. These compounds, and the pharmaceutical compositions containing them, are useful for the treatment of metabolic diseases and disorders such as, for example, type II diabetes mellitus.

31 Claims, No Drawings

FOREIGN PATENT DOCUMENTS

| | | |
|---|---|---|
| WO | WO 2006/016194 A1 | 2/2006 |
| WO | WO 2006/040529 A1 | 4/2006 |
| WO | WO 2006/058923 A1 | 6/2006 |
| WO | WO 2006/125972 A1 | 11/2006 |
| WO | WO 2007/007040 A1 | 1/2007 |
| WO | WO 2007/007041 A1 | 1/2007 |
| WO | WO 2007/007042 A1 | 1/2007 |
| WO | WO 2007/007886 A1 | 1/2007 |
| WO | WO 2007/017649 A1 | 2/2007 |
| WO | WO 2007/026761 A1 | 3/2007 |
| WO | WO 2007/041365 A2 | 4/2007 |
| WO | WO 2007/041366 A1 | 4/2007 |
| WO | WO 2007/051845 A1 | 5/2007 |
| WO | WO 2007/051846 A1 | 5/2007 |
| WO | WO 2007/051847 A1 | 5/2007 |
| WO | WO 2007/104034 A2 | 9/2007 |
| WO | WO 2007/122482 A1 | 11/2007 |
| WO | WO 2008/012227 | 1/2008 |
| WO | WO 2008/014311 A2 * | 1/2008 |
| WO | WO 2008/132139 | 11/2008 |

* cited by examiner

US 7,741,327 B2

PYRROLIDINONE GLUCOKINASE ACTIVATORS

PRIORITY TO RELATED APPLICATION(S)

This application claims the benefit of U.S. Provisional Application No. 61/145,761, filed Jan. 20, 2009 and U.S. Provisional Application No. 61/045,370, filed Apr. 16, 2008. The entire contents of the above-identified applications are hereby incorporated by reference.

FIELD OF THE INVENTION

The invention is directed to compounds of the formula (I):

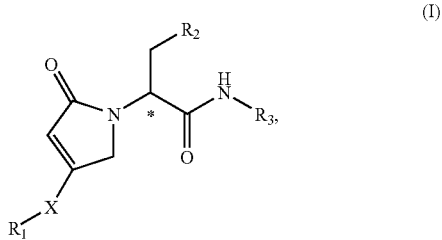

and to pharmaceutical compositions comprising said compounds. The compounds and compositions disclosed herein are glucokinase activators useful for the treatment of metabolic diseases and disorders, preferably diabetes mellitus, more preferably type II diabetes mellitus.

All documents cited or relied upon below are expressly incorporated herein by reference.

BACKGROUND OF THE INVENTION

Glucokinase (GK) is one of four hexokinases that are found in mammals (Colowick, S. P., in *The Enzymes*, Vol. 9 (P. Boyer, ed). Academic Press, New York, N.Y., pages 1-48, 1973). The hexokinases catalyze the first step in the metabolism of glucose, i.e., the conversion of glucose to glucose-6-phosphate. Glucokinase has a limited cellular distribution, being found principally in pancreatic β-cells and liver parenchymal cells. In addition, GK is a rate-controlling enzyme for glucose metabolism in these two cell types that are known to play critical roles in whole-body glucose homeostasis (Chipkin, S. R., Kelly, K. L., and Ruderman, N. B. in *Joslin's Diabetes* (C. R. Khan and G. C. Wier, eds)., Lea and Febiger, Philadelphia, Pa., pages 97-115, 1994). The concentration of glucose at which GK demonstrates half-maximal activity is approximately 8 mM. The other three hexokinases are saturated with glucose at much lower concentrations (<1 mM). Therefore, the flux of glucose through the GK pathway rises as the concentration of glucose in the blood increases from fasting (5 mM) to postprandial (≈10-15 mM) levels following a carbohydrate-containing meal (Printz, R. G., Magnuson, M. A., and Granner, D. K. in *Ann. Rev. Nutrition* Vol. 13 (R. E. Olson, D. M. Bier, and D. B. McCormick, eds)., Annual Review, Inc., Palo Alto, Calif., pages 463-496, 1993). These findings contributed over a decade ago to the hypothesis that GK functions as a glucose sensor in β-cells and hepatocytes (Meglasson, M. D. and Matschinsky, F. M. *Amer. J. Physiol.* 246, E1-E13, 1984). In recent years, studies in transgenic animals have confirmed that GK does indeed play a critical role in whole-body glucose homeostasis. Animals that do not express GK die within days of birth with severe diabetes while animals overexpressing GK have improved glucose tolerance (Grupe, A., Hultgren, B., Ryan, A. et al., *Cell* 83, 69-78, 1995; Ferrie, T., Riu, E., Bosch, F. et al., *FASEB J.,* 10, 1213-1218, 1996). An increase in glucose exposure is coupled through GK in β-cells to increased insulin secretion and in hepatocytes to increased glycogen deposition and perhaps decreased glucose production.

The finding that type II maturity-onset diabetes of the young (MODY-2) is caused by loss of function mutations in the GK gene suggests that GK also functions as a glucose sensor in humans (Liang, Y., Kesavan, P., Wang, L. et al., *Biochem. J.* 309, 167-173, 1995). Additional evidence supporting an important role for GK in the regulation of glucose metabolism in humans was provided by the identification of patients that express a mutant form of GK with increased enzymatic activity. These patients exhibit a fasting hypoglycemia associated with an inappropriately elevated level of plasma insulin (Glaser, B., Kesavan, P., Heyman, M. et al., *New England J. Med.* 338, 226-230, 1998). While mutations of the GK gene are not found in the majority of patients with type II diabetes, compounds that activate GK and, thereby, increase the sensitivity of the GK sensor system will still be useful in the treatment of the hyperglycemia characteristic of all type II diabetes. Glucokinase activators will increase the flux of glucose metabolism in β-cells and hepatocytes, which will be coupled to increased insulin secretion. Such agents would be useful for treating type II diabetes.

SUMMARY OF THE INVENTION

The present invention is directed to compounds of the formula I: as well as pharmaceutically acceptable salts thereof, pharmaceutical compositions containing them and to methods of treating diseases and disorders. The compounds and compositions disclosed herein are glucokinase activators useful for the treatment of metabolic diseases and disorders, preferably diabetes mellitus, more preferably type II diabetes mellitus.

DETAILED DESCRIPTION OF THE INVENTION

In an embodiment of the present invention, provided are compounds of formula I:

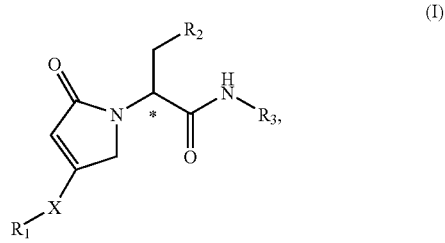

wherein:
X is O, NH or N(lower alkyl);
$R_1$ is -lower alkyl,
 -cycloalkyl,
 —$CH_2$-cycloalkyl,
 -heterocycloalkyl,
 -aryl, unsubstituted or mono-, bi- or tri-substituted independently with alkenyl, hydroxy, —$NH_2$, halogen, alkoxy, —$CF_3$, —$OCF_3$, —$S(CH_3)$, —$OCH_3$, —$S(O_2)$ $CH_3$, —$CH_2$-aryl, heteroaryl, cyano, alkoyl, —O-aryl, —O—$CH_2$-aryl, —$N(CH_3)_2$, cycloalkyl, heterocycloalkyl, —C(O)-heterocycloalkyl, unsubstituted lower alkyl, or lower alkyl mono- or bi-substituted with hydroxy,
—CH₂-aryl,
-heteroaryl, unsubstituted or substituted with lower alkyl or halogen,
-1-methyl-1H-indazol-4yl,
-benzooxazol-4-yl
-2-methyl-benzooxazol-4yl,
-2,3-dihydro-benzo[1,4]dioxin-5-yl,
-2,3-dihydro-benzo[1,4]dioxin-2-ylmethyl
-5,6,7,8-tetrahydro-naphthalen-1-yl,
-naphthalen-1-yl or
-isoquinolin;
$R_2$ is -lower alkyl,
-ether,
-alkoxy,
-cycloalkyl,
-heterocycloalkyl,
-aryl, unsubstituted or mono- or bi-substituted independently with halogen, or
-heteroaryl having at least one ring heteroatom being either O or S; and
$R_3$ is -lower alkyl-carbamoyl or
-an unsubstituted or substituted heteroaryl connected by a ring carbon atom to the amine group shown, with one heteroatom being nitrogen which is adjacent to the connecting ring carbon atom, said substituted heteroaryl being substituted at a position other than adjacent to said connecting carbon atom independently with halogen, ester, cyano, acid, cycloalkyl, aryl, 2-oxo-oxazolidin-5-ylmethyl, —N(lower alkyl)₂, —CH₂-dimethyl-[1,3]dioxolane, t-butyl-dimethyl-silanyloxy ethyl, unsubstituted —CH₂-aryl, —CH₂-aryl substituted with cyano or alkoxy, heterocycloalkyl, —CH₂-heterocycloalkyl, -6-(CH₂)-2,2-dimethyl-[1,3]dioxan-4-yl-acetic acid tert-butyl ester, unsubstituted lower alkyl, or lower alkyl mono-, bi- or tri-substituted independently with hydroxy, alkoxy, —N(lower alkyl)₂, —NH₂, ester, acid or carboxamide, or a pharmaceutically acceptable salt thereof.

In another embodiment of the present invention, provided is a compound according to formula I above wherein:
$R_1$ is -aryl, unsubstituted or mono-, bi- or tri-substituted independently with alkenyl, hydroxy, —NH₂, halogen, alkoxy, —CF₃, —OCF₃, —S(CH₃), —OCH₃, —S(O₂)CH₃, —CH₂-aryl, heteroaryl, cyano, alkoyl, —O-aryl, —O—CH₂-aryl, —N(CH₃)₂, cycloalkyl, heterocycloalkyl, —C(O)-heterocycloalkyl, unsubstituted lower alkyl, or lower alkyl mono- or bi-substituted with hydroxy; and
$R_3$ is -an unsubstituted or substituted heteroaryl connected by a ring carbon atom to the amine group shown, with one heteroatom being nitrogen which is adjacent to the connecting ring carbon atom, said substituted heteroaryl being substituted at a position other than adjacent to said connecting carbon atom independently with halogen, ester, cyano, acid, cycloalkyl, aryl, 2-oxo-oxazolidin-5-ylmethyl, —N(lower alkyl)₂, —CH₂-dimethyl-[1,3]dioxolane, t-butyl-dimethyl-silanyloxy ethyl, unsubstituted —CH₂-aryl, —CH₂-aryl substituted with cyano or alkoxy, heterocycloalkyl, —CH₂-heterocycloalkyl, -6-(CH₂)-2,2-dimethyl-[1,3]dioxan-4-yl-acetic acid tert-butyl ester, unsubstituted lower alkyl, or lower alkyl mono-, bi- or tri-substituted independently with hydroxy, alkoxy, —N(lower alkyl)₂, —NH₂, ester, acid or carboxamide.

In a further embodiment of the present invention, provided is a compound according to formula (Ia):

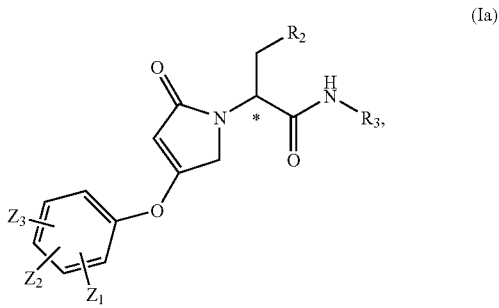

wherein:
$Z_1$, $Z_2$, $Z_3$ independently of each other, are hydrogen, alkenyl, hydroxy, —NH₂, halogen, alkoxy, —CF₃, —OCF₃, —S(CH₃), —OCH₃, —S(O₂)CH₃, —CH₂-aryl, heteroaryl, cyano, alkoyl, —O-aryl, —O—CH₂-aryl, —N(CH₃)₂, cycloalkyl, heterocycloalkyl, —C(O)-heterocycloalkyl, unsubstituted lower alkyl, or lower alkyl mono- or bi-substituted with hydroxy;
$R_2$ is lower alkyl, alkoxy, ether, cycloalkyl, heterocycloalkyl, heteroaryl or aryl, said aryl being unsubstituted or mono- or bi-substituted independently with halogen; and
$R_3$ is -lower alkyl-carbamoyl, or
-an unsubstituted or substituted heteroaryl connected by a ring carbon atom to the amine group shown, with one heteroatom being nitrogen which is adjacent to the connecting ring carbon atom, said substituted heteroaryl being substituted at a position other than adjacent to said connecting carbon atom independently with halogen, ester, cyano, acid, cycloalkyl, aryl, 2-oxo-oxazolidin-5-ylmethyl, —N(lower alkyl)₂, —CH₂-dimethyl-[1,3]dioxolane, t-butyl-dimethyl-silanyloxy ethyl, unsubstituted —CH₂-aryl, —CH₂-aryl substituted with cyano or alkoxy, heterocycloalkyl, —CH₂-heterocycloalkyl, -6-(CH₂)-2,2-dimethyl-[1,3]dioxan-4-yl-acetic acid tert-butyl ester, unsubstituted lower alkyl, or lower alkyl mono-, bi- or tri-substituted independently with hydroxy, alkoxy, —N(lower alkyl)₂, —NH₂, ester, acid or carboxamide.

In another embodiment, provided is a compound according to formula (1a) wherein: $Z_1$, $Z_2$, $Z_3$ independently of each other, are halogen, alkyl, alkoxy, —CF₃, —OCF₃, —S(O₂) CH₃, —CH₂-aryl or heteroaryl;
$R_2$ is 2,6-difluoro-phenyl, cyclohexyl, cyclopentyl, isopropyl, 1-ethoxy-ethyl phenyl, tert-butoxy, tetrahydro-furan-2-yl, tetrahydro-pyran-2-yl, tetrahydro-pyran-4-yl or cyclobutyl; and
$R_3$ is 3-Methyl-[1,2,4]thiadiazol-5-yl, 1-(2-Hydroxy-ethyl)-1H-pyrazol-3-yl, 1-(2-Methoxy-ethyl)-1H-pyrazol-3-yl, 1-(2-Hydroxy-2-methyl-propyl)-1H-pyrazol-3-yl, 1-(2-Methoxy-2-methyl-propyl)-1H-pyrazol-3-yl, 1-(2-Isopropoxy-ethyl)-1H-pyrazol-3-yl, 1-((S)-2,3-dihydroxy-propyl)-1H-pyrazol-3-yl, 1-((R)-2,3-dihydroxy-propyl)-1H-pyrazol-3-yl, 1-((R)-2,2-dimethyl-[1,3]dioxolan-4-ylmethyl)-1H-pyrazol-3-yl, 1-(3-Cyano-benzyl)-1H-pyrazol-3-yl, 1-(2-tert-Butoxycarbonylamino-ethyl)-1H-pyrazol-3 yl, 5-Fluoro-thiazol-2-yl, 1-Methyl-1H-pyrazol-3-yl, 5-Carboxy-pyridin-2-yl, 5-Chloro-thiazol-2-yl, 5-Methoxycarbonyl-pyridin-2-yl, Benzothiazol-2-yl, Methylcarbamoyl, Pyrazin-2-yl or Thiazol-2-yl.

In a further embodiment of the present invention, provided is a compound according to formula (Ib):

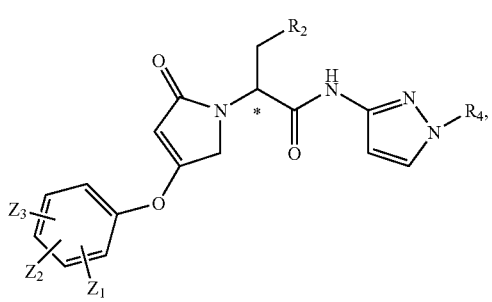

wherein:
Z₁, Z₂, Z₃ independently of each other, are hydrogen, alkenyl, hydroxy, —NH₂, halogen, alkoxy, —CF₃, —OCF₃, —S(CH₃), —OCH₃, —S(O₂)CH₃, —CH₂-aryl, heteroaryl, cyano, alkoyl, —O-aryl, —O—CH₂-aryl, —N(CH₃)₂, cycloalkyl, heterocycloalkyl, —C(O)-heterocycloalkyl, unsubstituted lower alkyl, or lower alkyl mono- or bi-substituted with hydroxy;

R₂ is lower alkyl, alkoxy, ether, cycloalkyl, heterocycloalkyl, heteroaryl or aryl, said aryl being unsubstituted or mono- or bi-substituted independently with halogen; and R₄ is hydrogen, ester, cycloalkyl, aryl, 2-oxo-oxazolidin-5-ylmethyl, —CH₂-dimethyl-[1,3]dioxolane, t-butyl-dimethyl-silanyloxy ethyl, unsubstituted —CH₂-aryl, —CH₂-aryl substituted with cyano or alkoxy, heterocycloalkyl, —CH₂-heterocycloalkyl, unsubstituted lower alkyl, or lower alkyl mono-, bi- or tri-substituted independently with hydroxy, alkoxy, —N(lower alkyl)₂ or —NH₂.

In a still further embodiment of the present invention, provided is a pharmaceutical composition, comprising a therapeutically effective amount of a compound according to formula (I) or a pharmaceutically acceptable salt thereof and a pharmaceutically acceptable carrier.

It is to be understood that the terminology employed herein is for the purpose of describing particular embodiments, and is not intended to be limiting. Further, although any methods, devices and materials similar or equivalent to those described herein can be used in the practice or testing of the invention, the preferred methods, devices and materials are now described.

As used herein, the term "alkyl", alone or in combination with other groups, refers to a branched or straight-chain monovalent saturated aliphatic hydrocarbon radical of one to twenty carbon atoms, preferably one to sixteen carbon atoms, more preferably one to ten carbon atoms.

As used herein, the term "alkenyl", alone or in combination with other groups, refers to a straight-chain or branched hydrocarbon residue having an olefinic bond.

The term "cycloalkyl" refers to a monovalent mono- or polycarbocyclic radical of three to ten, preferably three to six carbon atoms. This term is further exemplified by radicals such as cyclopropyl, cyclobutyl, cyclopentyl, cyclohexyl, cycloheptyl, norbornyl, adamantyl, indanyl and the like. In a preferred embodiment, the "cycloalkyl" moieties can optionally be substituted with one, two, three or four substituents, with the with the understanding that said substituents are not, in turn, substituted further unless indicated otherwise in the Examples or claims below. Each substituent can independently be, alkyl, alkoxy, halogen, amino, hydroxyl or oxygen (O=) unless otherwise specifically indicated. Examples of cycloalkyl moieties include, but are not limited to, optionally substituted cyclopropyl, optionally substituted cyclobutyl, optionally substituted cyclopentyl, optionally substituted cyclopentenyl, optionally substituted cyclohexyl, optionally substituted cyclohexylene, optionally substituted cycloheptyl, and the like or those which are specifically exemplified herein.

The term "heterocycloalkyl" denotes a mono- or polycyclic alkyl ring, wherein one, two or three of the carbon ring atoms is replaced by a heteroatom such as N, O or S. Examples of heterocycloalkyl groups include, but are not limited to, morpholinyl, thiomorpholinyl, piperazinyl, piperidinyl, pyrrolidinyl, tetrahydropyranyl, tetrahydrofuranyl, 1,3-dioxanyl and the like. The heterocycloalkyl groups may be unsubstituted or substituted and attachment may be through their carbon frame or through their heteroatom(s) where appropriate, with the understanding that said substituents are not, in turn, substituted further unless indicated otherwise in the Examples or claims below.

The term "lower alkyl", alone or in combination with other groups, refers to a branched or straight-chain alkyl radical of one to nine carbon atoms, preferably one to six carbon atoms, more preferably one to four carbon atoms. This term is further exemplified by radicals such as methyl, ethyl, n-propyl, isopropyl, n-butyl, s-butyl, isobutyl, t-butyl, n-pentyl, 3-methylbutyl, n-hexyl, 2-ethylbutyl and the like.

The term "aryl" refers to an aromatic mono- or polycarbocyclic radical of 6 to 12 carbon atoms having at least one aromatic ring. Examples of such groups include, but are not limited to, phenyl, naphthyl, 1,2,3,4-tetrahydronaphthalene, 1,2-dihydronaphthalene, indanyl, 1H-indenyl and the like.

The alkyl, lower alkyl and aryl groups may be substituted or unsubstituted. When substituted, there will generally be, for example, 1 to 4 substituents present, with the understanding that said substituents are not, in turn, substituted further unless indicated otherwise in the Examples or claims below. These substituents may optionally form a ring with the alkyl, lower alkyl or aryl group with which they are connected. Substituents may include, for example: carbon-containing groups such as alkyl, aryl, arylalkyl (e.g. substituted and unsubstituted phenyl, substituted and unsubstituted benzyl); halogen atoms and halogen-containing groups such as haloalkyl (e.g. trifluoromethyl); oxygen-containing groups such as alcohols (e.g. hydroxyl, hydroxyalkyl, aryl(hydroxyl) alkyl), ethers (e.g. alkoxy, aryloxy, alkoxyalkyl, aryloxyalkyl, more preferably, for example, methoxy and ethoxy), aldehydes (e.g. carboxaldehyde), ketones (e.g. alkylcarbonyl, alkylcarbonylalkyl, arylcarbonyl, arylalkylcarbonyl, arycarbonylalkyl), acids (e.g. carboxy, carboxyalkyl), acid derivatives such as esters (e.g. alkoxycarbonyl, alkoxycarbonylalkyl, alkylcarbonyloxy, alkylcarbonyloxyalkyl), amides (e.g. aminocarbonyl, mono- or di-alkylaminocarbonyl, aminocarbonylalkyl, mono- or di-alkylaminocarbonylalkyl, arylaminocarbonyl), carbamates (e.g. alkoxycarbonylamino, aryloxycarbonylamino, aminocarbonyloxy, mono- or di-alkylaminocarbonyloxy, arylminocarbonloxy) and ureas (e.g. mono- or di-alkylaminocarbonylamino or arylaminocarbonylamino); nitrogen-containing groups such as amines (e.g. amino, mono- or di-alkylamino, aminoalkyl, mono- or di-alkylaminoalkyl), azides, nitriles (e.g. cyano, cyanoalkyl), nitro; sulfur-containing groups such as thiols, thioethers, sulfoxides and sulfones (e.g. alkylthio, alkylsulfinyl, alkylsulfonyl, alkylthioalkyl, alkylsulfinylalkyl, alkylsulfonylalkyl, arylthio, arysulfinyl, arysulfonyl, arythioalkyl, arylsulfinylalkyl, arylsulfonylalkyl); and heterocyclic groups containing one or more heteroatoms, (e.g. thienyl, furanyl, pyrrolyl, imidazolyl, pyrazolyl, thiazolyl, isothiazolyl, oxazolyl, oxadiazolyl, thiadiazolyl, aziridinyl, azetidinyl, pyrrolidinyl, pyrrolinyl, imidazolidinyl, imidazolinyl, pyrazolidinyl, tetrahydrofuranyl, pyranyl, pyronyl, pyridyl, pyrazinyl, pyridazinyl, piperidyl, hexahydroazepinyl, piperazinyl, morpholinyl, thianaphthyl, benzofuranyl, isobenzofuranyl, indolyl, oxyindolyl, isoindolyl, indazolyl, indolinyl, 7-azaindolyl, benzopyranyl, coumarinyl, isocoumarinyl, quinolinyl, isoquinolinyl, naphthridinyl, cinnolinyl, quinazolinyl, pyridopyridyl, benzoxazinyl, quinoxalinyl, chromenyl, chromanyl, isochromanyl, phthalazinyl and carbolinyl).

The term "heteroaryl," refers to an aromatic mono- or polycyclic radical of 5 to 12 atoms having at least one aromatic ring containing one, two, or three ring heteroatoms selected from N, O, and S, with the remaining ring atoms being C. One or two ring carbon atoms of the heteroaryl group may be replaced with a carbonyl group.

The heteroaryl group described above may be substituted independently with one, two, or three substituents, with the understanding that said substituents are not, in turn, substituted further unless indicated otherwise in the Examples or claims below. These substituents may optionally form a ring with the heteroaryl group to which they are connected. Substituents may include, for example: carbon-containing groups such as alkyl, aryl, arylalkyl (e.g. substituted and unsubstituted phenyl, substituted and unsubstituted benzyl); halogen atoms and halogen-containing groups such as haloalkyl (e.g. trifluoromethyl); oxygen-containing groups such as alcohols (e.g. hydroxyl, hydroxyalkyl, aryl(hydroxyl)alkyl), ethers (e.g. alkoxy, aryloxy, alkoxyalkyl, aryloxyalkyl), aldehydes (e.g. carboxaldehyde), ketones (e.g. alkylcarbonyl, alkylcarbonylalkyl, arylcarbonyl, arylalkylcarbonyl, arycarbonylalkyl), acids (e.g. carboxy, carboxyalkyl), acid derivatives such as esters (e.g. alkoxycarbonyl, alkoxycarbonylalkyl, alkylcarbonyloxy, alkylcarbonyloxyalkyl), amides (e.g. aminocarbonyl, mono- or di-alkylaminocarbonyl, aminocarbonylalkyl, mono- or di-alkylaminocarbonylalkyl, arylaminocarbonyl), carbamates (e.g. alkoxycarbonylamino, aryloxycarbonylamino, aminocarbonyloxy, mono- or di-alkylaminocarbonyloxy, arylminocarbonloxy) and ureas (e.g. mono- or di- alkylaminocarbonylamino or arylaminocarbonylamino); nitrogen-containing groups such as amines (e.g. amino, mono- or di-alkylamino, aminoalkyl, mono- or di-alkylaminoalkyl), azides, nitriles (e.g. cyano, cyanoalkyl), nitro; sulfur-containing groups such as thiols, thioethers, sulfoxides and sulfones (e.g. alkylthio, alkylsulfinyl, alkylsulfonyl, alkylthioalkyl, alkylsulfinylalkyl, alkylsulfonylalkyl, arylthio, arysulfinyl, arysulfonyl, arythioalkyl, arylsulfinylalkyl, arylsulfonylalkyl); and heterocyclic groups containing one or more heteroatoms, (e.g. thienyl, furanyl, pyrrolyl, imidazolyl, pyrazolyl, thiazolyl, isothiazolyl, oxazolyl, oxadiazolyl, thiadiazolyl, aziridinyl, azetidinyl, pyrrolidinyl, pyrrolinyl, imidazolidinyl, imidazolinyl, pyrazolidinyl, tetrahydrofuranyl, pyranyl, pyronyl, pyridyl, pyrazinyl, pyridazinyl, piperidyl, hexahydroazepinyl, piperazinyl, morpholinyl, thianaphthyl, benzofuranyl, isobenzofuranyl, indolyl, oxyindolyl, isoindolyl, indazolyl, indolinyl, 7-azaindolyl, benzopyranyl, coumarinyl, isocoumarinyl, quinolinyl, isoquinolinyl, naphthridinyl, cinnolinyl, quinazolinyl, pyridopyridyl, benzoxazinyl, quinoxalinyl, chromenyl, chromanyl, isochromanyl, phthalazinyl, benzothiazoyl and carbolinyl).

As used herein, the term "alkoxy" means alkyl-O—; and "alkoyl" means alkyl-CO—. Alkoxy substituent groups or alkoxy-containing substituent groups may be substituted by, for example, one or more alkyl groups, with the understanding that said substituents are not, in turn, substituted further unless indicated otherwise in the Examples or claims below.

As used herein, the term "halogen" means a fluorine, chlorine, bromine or iodine radical, preferably a fluorine, chlorine or bromine radical, and more preferably a fluorine or chlorine radical.

Compounds of formula I can have one or more asymmetric carbon atoms and can exist in the form of optically pure enantiomers, mixtures of enantiomers such as, for example, racemates, optically pure diastereoisomers, mixtures of diastereoisomers, diastereoisomeric racemates or mixtures of diastereoisomeric racemates. The optically active forms can be obtained for example by resolution of the racemates, by asymmetric synthesis or asymmetric chromatography (chromatography with a chiral adsorbents or eluant). The invention embraces all of these forms.

As used herein, the term "pharmaceutically acceptable salt" means any pharmaceutically acceptable salt of the compound of formula (I). Salts may be prepared from pharmaceutically acceptable non-toxic acids and bases including inorganic and organic acids and bases. Such acids include, for example, acetic, benzenesulfonic, benzoic, camphorsulfonic, citric, ethenesulfonic, dichloroacetic, formic, fumaric, gluconic, glutamic, hippuric, hydrobromic, hydrochloric, isethionic, lactic, maleic, malic, mandelic, methanesulfonic, mucic, nitric, oxalic, pamoic, pantothenic, phosphoric, succinic, sulfuric, tartaric, oxalic, p-toluenesulfonic and the like. Particularly preferred are fumaric, hydrochloric, hydrobromic, phosphoric, succinic, sulfuric and methanesulfonic acids. Acceptable base salts include alkali metal (e.g. sodium, potassium), alkaline earth metal (e.g. calcium, magnesium) and aluminum salts.

In the practice of the method of the present invention, an effective amount of any one of the compounds of this invention or a combination of any of the compounds of this invention or a pharmaceutically acceptable salt thereof, is administered via any of the usual and acceptable methods known in the art, either singly or in combination. The compounds or compositions can thus be administered orally (e.g., buccal cavity), sublingually, parenterally (e.g., intramuscularly, intravenously, or subcutaneously), rectally (e.g., by suppositories or washings), transdermally (e.g., skin electroporation) or by inhalation (e.g., by aerosol), and in the form or solid, liquid or gaseous dosages, including tablets and suspensions. The administration can be conducted in a single unit dosage form with continuous therapy or in a single dose therapy ad libitum. The therapeutic composition can also be in the form of an oil emulsion or dispersion in conjunction with a lipophilic salt such as pamoic acid, or in the form of a biodegradable sustained-release composition for subcutaneous or intramuscular administration.

Useful pharmaceutical carriers for the preparation of the compositions hereof, can be solids, liquids or gases. Thus, the compositions can take the form of tablets, pills, capsules, suppositories, powders, enterically coated or other protected formulations (e.g. binding on ion-exchange resins or packaging in lipid-protein vesicles), sustained release formulations, solutions, suspensions, elixirs, aerosols, and the like. The carrier can be selected from the various oils including those of petroleum, animal, vegetable or synthetic origin, e.g., peanut oil, soybean oil, mineral oil, sesame oil, and the like. Water, saline, aqueous dextrose, and glycols are preferred liquid carriers, particularly (when isotonic with the blood) for injectable solutions. For example, formulations for intravenous administration comprise sterile aqueous solutions of the active ingredient(s) which are prepared by dissolving solid active ingredient(s) in water to produce an aqueous solution, and rendering the solution sterile. Suitable pharmaceutical excipients include starch, cellulose, talc, glucose, lactose, talc, gelatin, malt, rice, flour, chalk, silica, magnesium stearate, sodium stearate, glycerol monostearate, sodium chloride, dried skim milk, glycerol, propylene glycol, water, ethanol, and the like. The compositions may be subjected to conventional pharmaceutical additives such as preservatives, stabilizing agents, wetting or emulsifying agents, salts for adjusting osmotic pressure, buffers and the like. Suitable pharmaceutical carriers and their formulation are described in Remington's Pharmaceutical Sciences by E. W. Martin. Such compositions will, in any event, contain an effective amount of the active compound together with a suitable carrier so as to prepare the proper dosage form for proper administration to the recipient.

The dose of a compound of the present invention depends on a number of factors, such as, for example, the manner of administration, the age and the body weight of the subject, and the condition of the subject to be treated, and ultimately will be decided by the attending physician or veterinarian. Such an amount of the active compound as determined by the attending physician or veterinarian is referred to herein, and in the claims, as a "therapeutically effective amount". For example, the dose of a compound of the present invention is typically in the range of about 1 to about 1000 mg per day. Preferably, the therapeutically effective amount is in an amount of from about 1 mg to about 500 mg per day.

It will be appreciated, that the compounds of general formula I in this invention may be derivatized at functional groups to provide derivatives which are capable of conversion back to the parent compound in vivo. Physiologically acceptable and metabolically labile derivatives, which are capable of producing the parent compounds of general formula I in vivo are also within the scope of this invention.

Compounds of the present invention can be prepared beginning with commercially available starting materials and utilizing general synthetic techniques and procedures known to those skilled in the art. Chemicals may be purchased from companies such as for example Aldrich, Argonaut Technologies, VWR and Lancaster. Chromatography supplies and equipment may be purchased from such companies as for example AnaLogix, Inc, Burlington, Wis.; Biotage AB, Charlottesville, Va.; Analytical Sales and Services, Inc., Pompton Plains, N.J.; Teledyne Isco, Lincoln, Nebr.; VWR International, Bridgeport, N.J.; Varian Inc., Palo Alto, Calif., and Multigram II Mettler Toledo Instrument Newark, Del. Biotage, ISCO and Analogix columns are pre-packed silica gel columns used in standard chromatography.

The compounds of formula I can be prepared by the following General Reaction Scheme:

GENERAL REACTION SCHEME

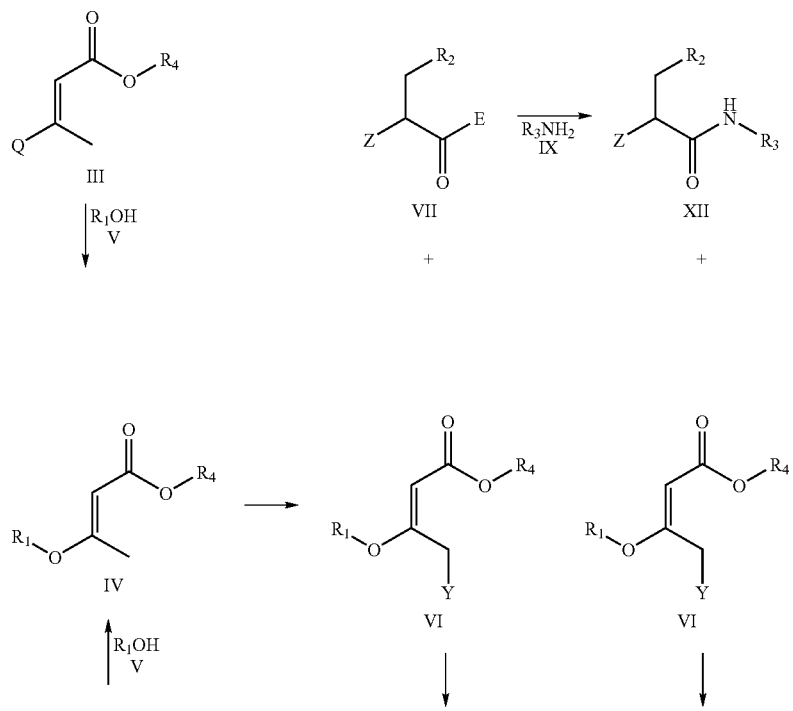

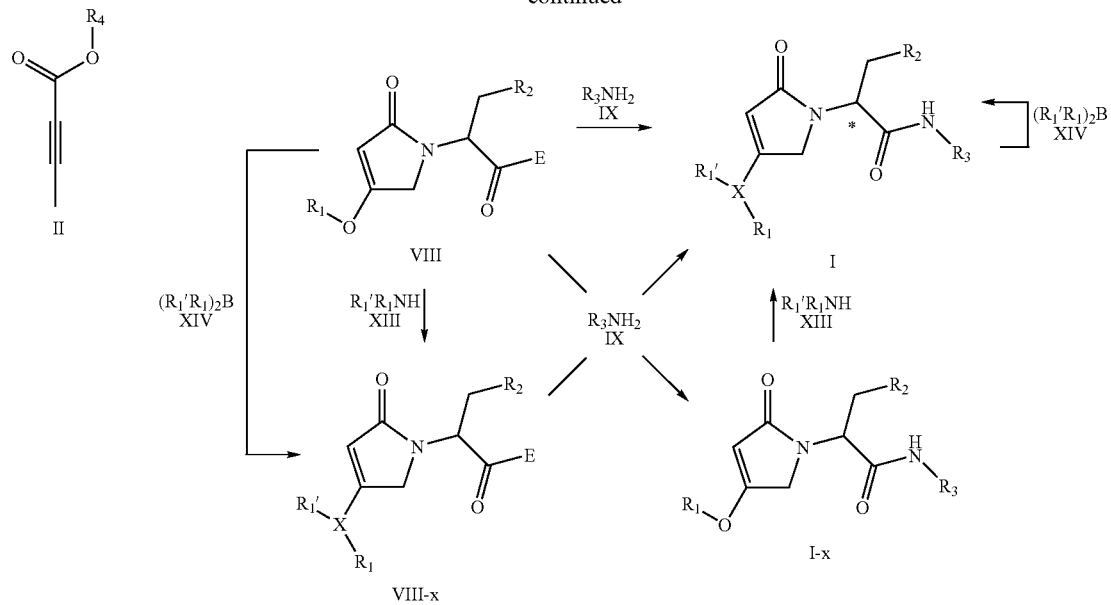
-continued

Compounds of formula IV, where $R_4$ is lower alkyl, for example, methyl or ethyl, and $R_1$ is an aryl group, for example substituted with one, two or three hydrogen, halo, alkyl, fluoroalkyl and perfluoro alkyl, alkoxy, or perfluoroalkoxy groups or combinations thereof, for example, 2,3-dichlorophenyl, 2,3-dihydro-benzo[1,4]dioxin-5-yl, 2,6-difluoro-phenyl, 3-chloro-2,6-difluoro-phenyl, 2-chloro-3-methoxy-phenyl, 2-chloro-6-fluoro-phenyl, 2-ethoxy-phenyl, 2-methoxy-phenyl, or 2-trifluoromethyl-phenyl, can be prepared by treating compounds of formula II, where $R_4$ is lower alkyl, for example, methyl or ethyl with compounds of formula V, where $R_1$ is an aryl group, for example substituted with one, two or three hydrogen, halo, alkyl, fluoro and perfluoro alkyl, alkoxy, or perfluoroalkoxy groups or combinations thereof, for example 2,3-dichloro-phenyl, 2,3-dihydro-benzo[1,4]dioxin-5-yl, 2,6-difluoro-phenyl, 3-chloro-2,6-difluoro-phenyl, 2-chloro-3-methoxy-phenyl, 2-chloro-6-fluoro-phenyl, 2-ethoxy-phenyl, 2-methoxy-phenyl, or 2-trifluoromethyl-phenyl, under basic conditions such as 1,8-diazabicyclo[5.4.0]undec-7-ene in tetrahydrofuran under reflux (J. Am. Chem. Soc. 1997, 119, 479) or potassium t-butoxide in tetrahydrofuran.

Compounds of formula IV, where $R_4$ is lower alkyl, for example methyl or ethyl and $R_1$ is a heteroaryl group, for example unsubstituted or substituted with one, two or three hydrogen, halo, alkyl, fluoro and perfluoro alkyl, alkoxy, or perfluoroalkoxy groups or combinations thereof, for example a 3-pyridyl, 8-quinolyl, 5-isoquinolyl, or 5-quinolyl group can be prepared by treating compounds of formula II, where $R_4$ is lower alkyl, for example methyl or ethyl with compounds of formula V, where $R_1$ is a heteroaryl group, for example unsubstituted or substituted with one, two or three halo, alkyl, fluoro and perfluoro alkyl, alkoxy, or perfluoroalkoxy groups or combinations thereof, for example a 3-pyridyl, 8-quinolyl, 5-isoquinolyl, or 5-quinolyl group under basic conditions such as 1,8-diazabicyclo[5.4.0]undec-7-ene in tetrahydrofuran under reflux (under similar conditions to those described in J. Am. Chem. Soc. 1997, 119, 479).

Compounds of formula IV, where $R_4$ is lower alkyl, for example methyl or ethyl and $R_1$ is an alkyl, cycloalkyl, or heterocycloalkyl group, for example a (2,3-dihydro-benzo[1,4]dioxin-2-yl)-methyl group can be prepared by treating compounds of formula II, where $R_4$ is lower alkyl, for example methyl or ethyl with compounds of formula V, where $R_1$ is an alkyl, cycloalkyl, or heterocycloalkyl group, for example a (2,3-dihydro-benzo[1,4]dioxin-2-yl)-methyl group under basic conditions such as 1,8-diazabicyclo[5.4.0] undec-7-ene in tetrahydrofuran under reflux (under similar conditions to those described in J. Am. Chem. Soc. 1997, 119, 479) or tributylphosphine in tetrahydrofuran (under similar conditions to those described in Tetrahedron 1998, 54, 637).

Compounds of formula II, where $R_4$ is methyl or ethyl are commercially available.

Alternatively compounds of formula IV, where $R_4$ is lower alkyl, for example methyl or ethyl and $R_1$ is an aryl group, for example substituted with one, two or three hydrogen, halo, alkyl, fluoro and perfluoro alkyl, alkoxy, or perfluoroalkoxy groups or combinations thereof, for example 2,3-dichloro-phenyl, 2,3-dihydro-benzo[1,4]dioxin-5-yl, 2,6-difluoro-phenyl, 3-chloro-2,6-difluoro-phenyl, 2-chloro-3-methoxy-phenyl, 2-chloro-6-fluoro-phenyl, 2-ethoxy-phenyl, 2-methoxy-phenyl, or 2-trifluoromethyl-phenyl, can be prepared by treating compounds of formula III, where $R_4$ is lower alkyl, for example methyl or ethyl and Q is halo, for example chloro, with the alkali metal salts, for example sodium or potassium, of compounds of formula V. Alkoxide salts of compounds of formula V can be prepared in a separate step from compounds of formula V using any conventional method of deprotonating a phenolic hydroxyl group with an appropriate base. Alternatively compounds of formula IV can be prepared by treating compounds of formula III and compounds of formula V with an alkali metal, such as sodium, dissolved in an alcohol, such as ethanol (J. Pharm. Sci. 1964, 53, 902).

Alternatively compounds of formula IV, where $R_4$ is lower alkyl, for example methyl or ethyl, and $R_1$ is a heteroaryl group, for example unsubstituted or substituted with one, two or three halo, alkyl, fluoro and perfluoro alkyl, alkoxy, or perfluoroalkoxy groups or combinations thereof, for example a 3-pyridyl, 8-quinolyl, 5-isoquinolyl, or 5-quinolyl group can be prepared by treating compounds of formula III, where $R_4$ is lower alkyl, for example methyl or ethyl and Q is halo, for example chloro, with the alkali metal salts, for example sodium or potassium, of compounds of formula V. Salts of compounds of formula V can be prepared from compounds of formula V using any conventional method of deprotonating a phenolic hydroxyl group. Alternatively compounds of formula IV can be prepared by treating compounds of formula III and compounds of formula V with an alkali metal, such as sodium, dissolved in an alcohol, such as ethanol (under similar conditions to those described in *J. Pharm. Sci.* 1964, 53, 902).

Alternatively compounds of formula IV, where $R_4$ is lower alkyl, for example methyl or ethyl, and $R_1$ is an alkyl, cycloalkyl or heterocycloalkyl group, can be prepared by treating compounds of formula III, where $R_4$ is lower alkyl, for example methyl or ethyl and Q is halo, for example chloro, with the alkali metal salts, for example sodium or potassium, of compounds of formula V. Salts of compounds of formula V can be prepared from compounds of formula V using any conventional method of deprotonating an alcohol. Alternatively compounds of formula IV can be prepared by treating compounds of formula III and compounds of formula V with an alkali metal, such as sodium, dissolved in an alcohol, such as ethanol (under similar conditions to those described in *J. Pharm. Sci.* 1964, 53, 902-905).

Compounds of formula III, where $R_4$ is lower alkyl, for example methyl or ethyl and Q is halo, for example chloro can be prepared from compounds of formula III, where $R_4$ is lower alkyl, for example methyl or ethyl, and Q is hydroxyl, as drawn or in keto tautomeric form, by any conventional method of forming a vinyl halide from a keto compound such as treatment with phosphorus pentachloride in diethyl ether (under similar conditions to those described in *Synth. Commun.* 1981, 11, 419; *J. Am. Chem. Soc.* 1955, 77, 1136; *Arch. Pharm. (Weinheim, Ger).* 1977, 310, 522).

Compounds of formula III, where $R_4$ is lower alkyl, for example methyl or ethyl, and Q is hydroxyl, as drawn or in keto tautomeric form, are commercially available.

Compounds of formula V, where $R_1$ is an aryl group for example substituted with one, two or three halo, alkyl, fluoro and perfluoro alkyl, alkoxy, or perfluoroalkoxy groups or combinations thereof are commercially available or can be prepared by conventional methods (under similar conditions to those described in Chemistry of Phenols 2003, 1 395; *J. Chem. Soc., Perkin Trans.* 1 2000, 16, 2529 and references cited therein). For example the following compounds of formula V are commercially available: phenol, 2-chloro-3-methoxy-phenol, 2-methoxy-phenol, 3-methoxy-phenol, 4-methoxy-phenol, 2-trifluoromethyl-phenol, 3-trifluoromethyl-phenol, 4-trifluoromethyl-phenol, (2-hydroxy-phenyl)-pyrrolidin-1-yl-methanone, 2-cyclohexylphenol, 2-cyclopentylphenol, 2-phenylphenol, 1-naphthol, 5,6,7,8-tetrahydro-1-naphthol, 2'-hydroxyacetophenone, 2-hydroxybenzonitrile, o-cresol, 3-fluorophenol, 2-fluorophenol, 2,3-difluorophenol, 2,4-difluorophenol, 2,5-difluorophenol, 2,6-difluorophenol, 2-(methylsulfonyl)phenol, 3-phenoxyphenol, 3-hydroxy-2-methylpyridine, 2-(1-pyrrolidino)phenol, 2-(1-piperidino)phenol, 2-(4-morpholino) phenol, 3-hydroxypyridine, 8-hydroxyquinoline, 5-hydroxyisoquinoline, and 5-hydroxyquinoline. Phenols can also be prepared from aryl boronic acids by treatment with hydrogen peroxide (under similar conditions to those described in *Liquid Crystals*, 2007, 34, 489). Functional groups on phenols may be manipulated prior to reactions with compounds of formula II or III. Phenols with side chains containing ester functionality may be converted to phenols with side chains containing alcohol functionality by reduction of the ester, or addition of Grignard reagents using standard conditions. Phenols with side chains containing α-hydroxy acid functionality may be converted to diols or protected diols using standard conditions. The phenolic hydroxyl group may require protection/deprotection during these modifications. Benzooxazol-4-ols may be prepared from the corresponding hydroxy substituted 2-hydroxy anilines by treatment with alkyl orthoformates or orthoacetates.

Compounds of formula VI, where $R_4$ is lower alkyl, for example methyl or ethyl, Y is halo, for example bromo and $R_1$ is an aryl or heteroaryl group, for example substituted with one, two or three hydrogen, halo, alkyl, fluoro and perfluoro alkyl, alkoxy, or perfluoroalkoxy groups or combinations thereof, for example 2,3-dichloro-phenyl, 2,3-dihydro-benzo[1,4]dioxin-5-yl, 2,6-difluoro-phenyl, 3-chloro-2,6-difluoro-phenyl, 2-chloro-3-methoxy-phenyl, 2-chloro-6-fluoro-phenyl, 2-ethoxy-phenyl, 2-methoxy-phenyl, or 2-trifluoromethyl-phenyl, can be prepared by treating the corresponding compounds of formula IV with any suitable allylic halogenating conditions such as N-bromosuccinimide/benzoyl peroxide in refluxing carbon tetrachloride (under similar conditions to those described in *Tetrahedron Lett.* 1986, 27, 5285; *J. Chem. Soc., Perkin Trans.* 1 1987, 717) or N-bromosuccinimide/2,2'-azobis(2,4-dimethylvaleronitrile) in dichloromethane (under similar conditions to those described in *J. Het. Chem.* 1986, 23, 813).

Compounds of formula VI, where $R_4$ is lower alkyl, for example methyl or ethyl, Y is halo, for example bromo and $R_1$ is an alkyl, cycloalkyl or heterocycloalkyl group can be prepared by treating the corresponding compounds of formula IV with any suitable allylic halogenating conditions such as N-bromosuccinimide/benzoyl peroxide in refluxing carbon tetrachloride (under similar conditions to those described in *Tetrahedron Lett.* 1986, 27, 5285; *J. Chem. Soc., Perkin Trans.* 1 1987, 717).

If it is desired to produce a compound of formula VIII, where E is lower alkoxy, $R_2$ is alkyl, branched alkyl, cycloalkyl, heterocycloalkyl or aryl, wherein said alkyl, branched alkyl, cycloalkyl, heterocycloalkyl and aryl can be mono or disubstituted with halo, alkyl, hydroxy, alkoxy, or keto groups, and $R_1$ is alkyl, cycloalkyl or heterocycloalkyl, such a compound can be made from the corresponding compound of formula VII where Z is amino and the corresponding compound of formula VI where $R_4$ is lower alkyl, Y is t-butyl-dimethyl-silanyloxy and $R_1$ is alkyl, cycloalkyl or heterocycloalkyl (under similar conditions to those described in *Synthesis*, 2002, 869). Compounds of formula VI where $R_4$ is lower alkyl, Y is t-butyl-dimethyl-silanyloxy and $R_1$ is alkyl, cycloalkyl or heterocycloalkyl such compounds may be prepared under similar conditions to those described in *Synthesis*, 2002, 869.

Compounds of formula VIII, where E is lower alkyloxy or benzyloxy, for example methoxy, ethoxy, benzyloxy or t-butoxy, $R_1$ is an aryl or heteroaryl group, for example substituted with one, two or three hydrogen, halo, alkyl, fluoro and perfluoro alkyl, alkoxy, or perfluroalkoxy groups or combinations thereof, for example 2,3-dichloro-phenyl, 2,3-dihydro-benzo[1,4]dioxin-5-yl, 2,6-difluoro-phenyl, 3-chloro-2,6-difluoro-phenyl, 2,3-dihydro-benzo[1,4]dioxin-2-ylmethyl, 2-chloro-3-methoxy-phenyl, 2-chloro-6-fluoro-phenyl, 2-ethoxy-phenyl, 2-methoxy-phenyl, or 2-trifluoromethyl-phenyl, and $R_2$ is alkyl, branched alkyl, cycloalkyl, heterocycloalkyl, aryl or heteroaryl, unsubstituted or substituted with halo, alkyl, hydroxy, alkoxy, or keto groups, for example 2,6-dichloro-phenyl, 2,6-difluoro-phenyl, cyclohexyl, cyclopentyl, isopropyl, phenyl, t-butoxy, tetrahydro-furan-2-yl, tetrahydro-pyran-2-yl, or tetrahydro-pyran-4-yl, can be prepared by treating the corresponding compounds of formula VI, where $R_4$ is lower alkyl, for example methyl or ethyl, Y is halo, for example bromo, with the corresponding compounds of formula VII where Z is amino, E is lower alkyloxy or benzyloxy, for example methoxyl, ethoxy, benzyloxy or t-butoxy under basic condensation conditions such as an organic amine base followed by heating (under similar conditions to those described in *Org. Lett.* 2003, 5, 4341; *Tetrahedron Lett.* 1986, 27, 5285; *J. Org. Chem.* 1984, 49, 3222; *Synlett* 2004, 247; *Tetrahedron Lett.* 2007, 48, 2819; *Tetrahedron Lett.* 2005, 46, 525) or microwave irradiation. Alternatively compounds of formula VI can be treated with compounds of formula VII where Z is an amino hydrochloride under basic conditions such as sodium bicarbonate in ethanol with azeotropic removal of water, followed by heating with acetic acid (acetic acid conditions are similar to those described in *Bioorg. Med. Chem. Lett.*, 2008, 18, 1628).

Compounds of formula VIII, where E is lower alkyloxy or benzyloxy, for example methoxyl, ethoxy, benzyloxy or t-butoxy, $R_1$ is alkyl, cycloalkyl or heterocycloalkyl and $R_2$ is alkyl, branched alkyl, cycloalkyl, heterocycloalkyl or aryl, wherein said alkyl, branched alkyl, cycloalkyl, heterocycloalkyl and aryl can be mono or disubstituted with halo, alkyl, hydroxy, alkoxy, or keto groups, for example 2,6-dichloro-phenyl, 2,6-difluoro-phenyl, cyclohexyl, cyclopentyl, isopropyl, phenyl, t-butoxy, tetrahydro-furan-2-yl, tetrahydro-pyran-2-yl, or tetrahydro-pyran-4-yl, can be prepared by treating the corresponding compounds of formula VI, where $R_4$ is lower alkyl, for example methyl or ethyl, Y is halo, for example chloro and $R_1$ is alkyl, cycloalkyl or heterocycloalkyl with the corresponding compounds of formula VII where Z is amino, E is lower alkyloxy or benzyloxy, for example methoxyl, ethoxy, benzyloxy or t-butoxy under basic condensation conditions such as an organic amine base followed by heating (under similar conditions to those described in *Org. Lett.* 2003, 5, 4341; *Tetrahedron Lett.* 1986, 27, 5285; *J. Org. Chem.* 1984, 49, 3222; *Synlett* 2004, 247; *Tetrahedron Lett.* 2007, 48, 2819; *Tetrahedron Lett.* 2005, 46, 525) or microwave irradiation.

Compounds of formula VIII, where E is hydroxyl, $R_1$ is an alkyl, cycloalkyl, or heterocycloalkyl group, for example methyl or ethyl, and $R_2$ is alkyl, branched alkyl, cycloalkyl, heterocycloalkyl or aryl, wherein said alkyl, branched alkyl, cycloalkyl, heterocycloalkyl and aryl can be mono or disubstituted with halo, alkyl, hydroxy, alkoxy, or keto groups, for example 2,6-dichloro-phenyl, 2,6-difluoro-phenyl, cyclohexyl, cyclopentyl, isopropyl, phenyl, t-butoxy, tetrahydro-furan-2-yl, tetrahydro-pyran-2-yl, or tetrahydro-pyran-4-yl, can be prepared by hydrolysis of compounds of formula VIII where E is lower alkyloxy or benzyloxy, for example methoxy, ethoxy, benzyloxy or t-butoxy, under standard conditions known to a skilled artisan (see for example, Greene, T. W. Protective Groups in Organic Synthesis; John Wiley & Sons, Inc.: New York, 1991).

Compounds of formula V where $R_1$ is an alkyl, substituted alkyl, cycloalkyl, or heterocycloalkyl group, for example benzyl, cyclobutyl, cyclohexyl, cyclopentyl, isopropyl, methyl, propyl, or tetrahydro-pyran-4-yl are commercially available or can be prepared by any conventional method of producing an alcohol. For example, alcohols can be readily synthesized from alkyl halides, olefins or carbonyl compounds by standard procedures. The compounds of formula V having functional groups typically needing transformation, conversion or protection may be transformed, converted or deprotected to the desired functionality using conventional methods at an appropriate time during the synthesis (see for example, Greene, T. W. Protective Groups in Organic Synthesis; John Wiley & Sons, Inc.: New York, 1991).

Compounds of formula VI, where $R_1$ and $R_4$ are methyl, or $R_1$ and $R_4$ or ethyl, and Y is chloro are commercially available.

Compounds of formula VIII, where E is lower alkoxy, for example methoxy or ethoxy, $R_1$ is an alkyl, substituted alkyl, cycloalkyl, or heterocycloalkyl group, for example benzyl, cyclobutyl, cyclohexyl, cyclopentyl, isopropyl, methyl, propyl, or tetrahydro-pyran-4-yl, and $R_2$ is alkyl, branched alkyl, cycloalkyl, heterocycloalkyl or aryl, wherein said alkyl, branched alkyl, cycloalkyl, heterocycloalkyl and aryl can be mono or disubstituted with hydrogen, halo, alkyl, hydroxy, alkoxy, or keto groups, for example 2,6-dichloro-phenyl, 2,6-difluoro-phenyl, cyclohexyl, cyclopentyl, isopropyl, phenyl, t-butoxy, tetrahydro-furan-2-yl, tetrahydro-pyran-2-yl, or tetrahydro-pyran-4-yl, can be prepared by treating the corresponding precursor of formula VIII where E is lower alkoxy, for example methoxy or ethoxy, and $R_1$ is methyl, with compounds of formula V, where $R_1$ is an alkyl, substituted alkyl, cycloalkyl, or heterocycloalkyl group, for example benzyl, cyclobutyl, cyclohexyl, cyclopentyl, isopropyl, methyl, propyl, or tetrahydro-pyran-4-yl, under two-step thermal acidic conditions. Compounds of formula VIII, where $R_1$ is hydrogen can be prepared from compounds of formula VIII, where $R_1$ is methyl by acidic hydrolysis (under similar conditions to those described in EP 252363). Compounds of formula VIII, where $R_1$ is alkyl can be prepared from compounds of formula VIII, where $R_1$ is hydrogen by treatment with compounds of formula V under acidic conditions. Alternatively, these two steps can be run without isolation of compounds of formula VIII, where $R_1$ is hydrogen (under similar conditions to those described in *J. Org. Chem.* 2008, 73, 2345; EP 252363).

The compounds of formula I where X is O, $R_1$ is H, $R_1'$ is absent, $R_2$ is alkyl, branched alkyl, cycloalkyl, heterocycloalkyl or aryl, wherein said alkyl, branched alkyl, cycloalkyl, heterocycloalkyl and aryl can be mono or disubstituted with hydrogen, halo, alkyl, hydroxy, alkoxy, or keto groups, and $R_3$ is any unsubstituted or substituted heteroaryl groups which are commercially available or known in the literature, may be produced from the corresponding compounds of formula VIII, where E is hydroxyl and $R_1$ is H, and compounds of formula IX through any conventional means to form an amide bond between a carboxylic acid and an amine (under similar conditions to those described in *Tetrahedron*, 2005, 61, 10827). Said heteroaryl groups may include, for example, unsubstituted and substituted 1H-pyrazol-3-yl, pyrazin-2-yl, pyridin-2-yl, thiazol-2-yl, [1,3,4]thiadiazol-2-yl and [1,2,4]thiadiazol-5-yl. The compound of formula VIII, where E is hydroxyl and $R_1$ is H, can be made from a precursor compound wherein $R_1$ is methyl and E is lower alkoxy under the thermal acidic conditions, followed by hydrolysis of the resulting ester.

The compounds of formula I where X is N, $R_1'$ is alkyl, cycloalkyl, aryl or heteroaryl, $R_1$ is H, alkyl, cycloalkyl, aryl or heteroaryl, $R_2$ is alkyl, branched alkyl, cycloalkyl, heterocycloalkyl or aryl, wherein said alkyl, branched alkyl, cycloalkyl, heterocycloalkyl and aryl can be mono or disubstituted with hydrogen, halo, alkyl, hydroxy, alkoxy, or keto groups, and $R_3$ is any unsubstituted or substituted heteroaryl groups which are commercially available or known in the literature, may be produced from the corresponding compounds of formula I-x and $R_1$ is methyl by treatment with the corresponding compounds of formula XIII, where $R_1$ is alkyl, cycloalkyl, aryl or heteroaryl, for example methyl or ethyl, and $R_1$ is H, alkyl, cycloalkyl, aryl or heteroaryl, under two-step thermal acidic conditions. Compounds of formula I-x, where $R_1$ is hydrogen can be prepared from compounds of formula I-x, where $R_1$ is methyl by acidic hydrolysis (under similar conditions to those described in EP 252363). Compounds of formula I, where X is N, $R_1'$ is alkyl, cycloalkyl, aryl or heteroaryl, $R_1$ is H, alkyl, cycloalkyl, aryl or heteroaryl can be prepared from compounds of formula I-x, where $R_1$ is hydrogen by treatment with compounds of formula XIII under acidic conditions (under similar conditions to those described in *Org. Lett.* 2003, 5, 4341-4344). Compounds of formula XIII, where $R_1'$ is alkyl, cycloalkyl, aryl or heteroaryl, for example methyl or ethyl, and $R_1$ is H, alkyl, cycloalkyl, aryl or heteroaryl, are commercially available or readily prepared using conventional methods. If the compounds of formula I are a mixture of enantiomers or diastereomers, the appropriate chromatographic techniques, such as supercritical fluid chromatography, may be utilized to produce chirally pure or chirally enriched compounds of formula I. Said heteroaryl groups may include, for example, unsubstituted and substituted 1H-pyrazol-3-yl, pyrazin-2-yl, pyridin-2-yl, thiazol-2-yl, [1,3,4]thiadiazol-2-yl and [1,2,4]thiadiazol-5-yl.

The compounds of formula I, where X is O, $R_1'$ is absent, $R_1$ is an alkyl, cycloalkyl, or heterocycloalkyl group, may be produced from compounds of formula VIII, where E is OH and the compounds of formula IX, where $R_3$ is any unsubstituted or substituted heteroaryl groups which are commercially available or known in the literature, may be made by any conventional means to form an amide bond between a carboxylic acid and an amine (under similar conditions to those described in *Tetrahedron*, 2005, 61, 10827). If the compounds of formula I are a mixture of enantiomers or diastereomers, the appropriate chromatographic techniques, such as supercritical fluid chromatography, may be utilized to produce chirally pure or chirally enriched compounds of formula I. Said heteroaryl groups may include, for example, unsubstituted and substituted 1H-pyrazol-3-yl, pyrazin-2-yl, pyridin-2-yl, thiazol-2-yl, [1,3,4]thiadiazol-2-yl, and [1,2,4]thiadiazol-5-yl.

The compounds of formula I, where X is O, $R_1'$ is absent, $R_1$ is an aryl or heteroaryl group, may be produced from compounds of formula VIII or VIII-x, where E is OH and the compounds of formula IX, where $R_3$ is any unsubstituted or substituted heteroaryl groups which are commercially available or known in the literature, may be made by any conventional means to form an amide bond between a carboxylic acid and an amine (under similar conditions to those described in *Tetrahedron*, 2005, 61, 10827). Alternatively this transformation can be accomplished utilizing 1-propanephosphonic acid cyclic anhydride as a reagent (*Bioorg. Med. Chem. Lett.*, 2006, 16, 2648). If the compounds of formula I are a mixture of enantiomers or diastereomers, the appropriate chromatographic techniques, such as supercritical fluid chromatography, may be utilized to produce chirally pure or chirally enriched compounds of formula I. Said heteroaryl groups may include, for example, unsubstituted and substituted 1H-pyrazol-3-yl, pyrazin-2-yl, pyridin-2-yl, thiazol-2-yl, [1,3,4]thiadiazol-2-yl, and [1,2,4]thiadiazol-5-yl.

The compounds of formula I where X is O, $R_1'$ is absent, $R_1$ is lower alkyl or cycloalkyl, for example isopropyl, n-propyl and (S)-1-methoxy-propyl can alternatively be prepared from the compounds of formula I where $R_1$ is methyl by treatment with compounds of formula V, where $R_1$ is lower alkyl, for example isopropyl, n-propyl and (S)-1-methoxy-propyl, with the $R_2$ and $R_3$ groups as above, under a two-step thermal acidic conditions. Compounds of formula I-x, where $R_1$ is hydrogen can be prepared from compounds of formula I-x, where $R_1$ is methyl by acidic hydrolysis (under similar conditions to those described in EP 252363). Compounds of formula I, where X is O, $R_1'$ is absent, $R_1$ is lower alkyl or cycloalkyl, for example isopropyl, n-propyl and (S)-1-methoxy-propyl can be prepared from compounds of formula I-x, where $R_1$ is hydrogen by treatment with compounds of formula V under acidic conditions. Alternatively, these two steps can be run without isolation of compounds of formula I-x, where $R_1$ is hydrogen (under similar conditions to those described in *J. Org. Chem.* 2008, 73, 2345; EP 252363).

The compounds of formula I where X is O, $R_1$ is alkyl, cycloalkyl, aryl or heteroaryl, $R_1'$ is absent, $R_2$ is alkyl, branched alkyl, cycloalkyl, heterocycloalkyl or aryl, wherein said alkyl, branched alkyl, cycloalkyl, heterocycloalkyl and aryl can be mono or disubstituted with hydrogen, halo, alkyl, hydroxy, alkoxy, or keto groups, and $R_3$ is any unsubstituted or substituted heteroaryl groups which are commercially available or known in the literature may alternatively be produced from the corresponding compounds of formula XII, where Z is an amino group by treatment with the corresponding compounds of formula VI where Y is halo, for example bromo, such as an organic amine base followed by heating (under similar conditions to those described in *Org. Lett.* 2003, 5, 4341; *Tetrahedron Lett.* 1986, 27, 5285; *J. Org. Chem.* 1984, 49, 3222; *Synlett* 2004, 247; *Tetrahedron Lett.* 2007, 48, 2819; *Tetrahedron Lett.* 2005, 46, 525) or microwave irradiation. Said heteroaryl groups may include, for example, unsubstituted and substituted 1H-pyrazol-3-yl, pyrazin-2-yl, pyridin-2-yl, thiazol-2-yl, [1,3,4]thiadiazol-2-yl, and [1,2,4]thiadiazol-5-yl.

The compounds of formula XII where Z is amino, $R_2$ is alkyl, branched alkyl, cycloalkyl, heterocycloalkyl or aryl, wherein said alkyl, branched alkyl, cycloalkyl, heterocycloalkyl and aryl can be mono or disubstituted with hydrogen, halo, alkyl, hydroxy, alkoxy, or keto groups, and $R_3$ is any unsubstituted or substituted heteroaryl groups which are commercially available or known in the literature, may be produced from the corresponding compounds of formula VII where Z is protected amino, such as t-butoxycarbonyl, E is hydroxyl, and formula IX using any conventional means to form an amide bond between a carboxylic acid and an amine (under similar conditions to those described in *Tetrahedron*, 2005, 61, 10827) followed by deprotection of the amino nitrogen using standard conditions, such as treatment with acid. Said heteroaryl groups may include, for example, unsubstituted and substituted 1H-pyrazol-3-yl, pyrazin-2-yl, pyridin-2-yl, thiazol-2-yl, [1,3,4]thiadiazol-2-yl, and [1,2,4]thiadiazol-5-yl.

The compounds of formula I-x where $R_1$ is methyl, $R_2$ is alkyl, branched alkyl, cycloalkyl, heterocycloalkyl or aryl, wherein said alkyl, branched alkyl, cycloalkyl, heterocycloalkyl and aryl can be mono or disubstituted with hydrogen, halo, alkyl, hydroxy, alkoxy, or keto groups, and $R_3$ is any unsubstituted or substituted heteroaryl groups which are commercially available or known in the literature may be produced from the corresponding compounds of formula VIII, where $R_1$ is methyl and E is OH and formula IX using any conventional means to form an amide bond between a carboxylic acid and an amine (under similar conditions to those described in *Tetrahedron*, 2005, 61, 10827). Said heteroaryl groups may include, for example, unsubstituted and substituted 1H-pyrazol-3-yl, pyrazin-2-yl, pyridin-2-yl, thiazol-2-yl, [1,3,4]thiadiazol-2-yl, and [1,2,4]thiadiazol-5-yl.

The compounds of formula I where X is N, $R_1'$ is alkyl, cycloalkyl, aryl or heteroaryl, $R_1$ is H, alkyl, cycloalkyl, aryl or heteroaryl, $R_2$ is alkyl, branched alkyl, cycloalkyl, heterocycloalkyl or aryl, wherein said alkyl, branched alkyl, cycloalkyl, heterocycloalkyl and aryl can be mono or disubstituted with hydrogen, halo, alkyl, hydroxy, alkoxy, or keto groups, and $R_3$ is any unsubstituted or substituted heteroaryl groups which are commercially available or known in the literature may alternatively be produced from the corresponding compounds of formula VIII-x, where E is hydroxyl, X is N, $R_1'$ is alkyl, cycloalkyl, aryl or heteroaryl, $R_1$ is H, alkyl, cycloalkyl, aryl or heteroaryl and the corresponding compounds of formula IX using any conventional means to form an amide bond between a carboxylic acid and an amine (under similar conditions to those described in *Tetrahedron,* 2005, 61, 10827-10852). Said heteroaryl groups may include, for example, unsubstituted and substituted 1H-pyrazol-3-yl, pyrazin-2-yl, pyridin-2-yl, thiazol-2-yl, [1,3,4]thiadiazol-2-yl, and [1,2,4]thiadiazol-5-yl.

Compounds of formula VIII-x, where E is lower alkoxy, for example methoxy or ethoxy, where X is N, $R_1'$ is alkyl, cycloalkyl, aryl or heteroaryl, $R_1$ is H, alkyl, cycloalkyl, aryl or heteroaryl, $R_2$ is alkyl, branched alkyl, cycloalkyl, heterocycloalkyl or aryl, wherein said alkyl, branched alkyl, cycloalkyl, heterocycloalkyl and aryl can be mono or disubstituted with hydrogen, halo, alkyl, hydroxy, alkoxy, or keto groups, for example 2,6-dichloro-phenyl, 2,6-difluoro-phenyl, cyclohexyl, cyclopentyl, isopropyl, phenyl, t-butoxy, tetrahydro-furan-2-yl, tetrahydro-pyran-2-yl, or tetrahydro-pyran-4-yl, can be prepared by treating the corresponding compound of formula VIII where E is lower alkoxy, for example methoxy or ethoxy, and $R_1$ is methyl, with compounds of formula XIII, where $R_1'$ is alkyl, for example methyl or ethyl, cycloalkyl, aryl or heteroaryl, and $R_1$ is H, alkyl, cycloalkyl, aryl or heteroaryl, under two-step thermal acidic conditions. Compounds of formula VIII, where $R_1$ is hydrogen can be prepared from compounds of formula VIII, where $R_1$ is methyl by acidic hydrolysis (under similar conditions to those described in EP 252363). Compounds of formula VIII-x, where X is N, $R_1'$ is alkyl, cycloalkyl, aryl or heteroaryl, $R_1$ is H, alkyl, cycloalkyl, aryl or heteroaryl can be prepared from compounds of formula VIII, where $R_1$ is hydrogen by treatment with compounds of formula XIII under acidic conditions (under similar conditions to those described *Org. Lett.* 2003, 5, 4341). Compounds of formula XIII, where $R_1'$ is alkyl, cycloalkyl, aryl or heteroaryl, for example methyl or ethyl, and $R_1$ is H, alkyl, cycloalkyl, aryl or heteroaryl, are commercially available or readily prepared using conventional methods. Compounds of formula VIII-x where E is OH can be made from the corresponding compounds of formula VIII-x where E is lower alkoxy via hydrolysis.

Alternatively, compounds of formula VIII-x, where X is O, $R_1'$ is absent, $R_1$ is an aryl or heteroaryl group, for example substituted with one, two or three halo, alkyl, fluoro and perfluoro alkyl, alkoxy, or perfluoroalkoxy groups or combinations thereof, for example 2,3-dichloro-phenyl, 2,3-dihydro-benzo[1,4]dioxin-5-yl, 2,6-difluoro-phenyl, (R)-2-methoxy-1-methyl-ethyl, 3-chloro-2,6-difluoro-phenyl, 2,3-dihydro-benzo[1,4]dioxin-2-ylmethyl, 2-chloro-3-methoxy-phenyl, 2-chloro-6-fluoro-phenyl, 2-ethoxy-phenyl, 2-methoxy-phenyl, or 2-trifluoromethyl-phenyl, and $R_2$ is alkyl, branched alkyl, cycloalkyl, heterocycloalkyl, aryl or heteroaryl, unsubstituted or substituted with halo, alkyl, hydroxy, alkoxy, or keto groups, for example 2,6-dichloro-phenyl, 2,6-difluoro-phenyl, cyclohexyl, cyclopentyl, isopropyl, phenyl, t-butoxy, tetrahydro-furan-2-yl, tetrahydro-pyran-2-yl, or tetrahydro-pyran-4-yl, can be prepared by the direct coupling of the corresponding compounds of formula V with compounds of formula VIII-x, where X is boron and $R_1'$ and $R_1$ are alkoxy individually or together to form a ring and E is an alkoxy group under basic conditions catalyzed by cupric acetate (under similar conditions to those described in *Tetrahedron Lett.* 1998, 39, 2933; *J. Org. Chem.* 2004, 69, 5087). The corresponding compounds of formula VIII-x, where X is boron and $R_1'$ and $R_1$ are alkoxy individually or together to form a ring and E is an alkoxy group can be prepared from corresponding compounds of formula VIII, where $R_1$ is trifluoromethanesulfonyl, by treating with compounds of formula XIV, where $R_1'$ and $R_1$ are alkoxy individually or together to form a ring (under similar conditions to those described in *J. Organometallic Chem.* 2003, 687, 284). The corresponding compounds of formula VIII where $R_1$ is trifluoromethanesulfonyl can be prepared from the compounds of formula VIII where $R_1$ is hydrogen by treatment with base and triflic anhydride (under similar conditions to those described in *Synthesis* 2007, 15, 2317). The corresponding compounds of formula VIII where $R_1$ is hydrogen can be prepared from the compounds of formula VIII where $R_1$ is lower alkyl, for example methyl using thermal acidic conditions (under similar conditions to those described in CN 101121688; *J. Org. Chem.* 1993, 58, 4010).

Alternatively, compounds of formula I, where X is O, $R_1'$ is absent, $R_1$ is an aryl or heteroaryl group, for example substituted with one, two or three halo, alkyl, fluoro and perfluoro alkyl, alkoxy, or perfluoroalkoxy groups or combinations thereof, for example 2,3-dichloro-phenyl, 2,3-dihydro-benzo[1,4]dioxin-5-yl, 2,6-difluoro-phenyl, (R)-2-methoxy-1-methyl-ethyl, 3-chloro-2,6-difluoro-phenyl, 2,3-dihydro-benzo[1,4]dioxin-2-ylmethyl, 2-chloro-3-methoxy-phenyl, 2-chloro-6-fluoro-phenyl, 2-ethoxy-phenyl, 2-methoxy-phenyl, or 2-trifluoromethyl-phenyl and $R_2$ is alkyl, branched alkyl, cycloalkyl, heterocycloalkyl, aryl or heteroaryl, unsubstituted or substituted with halo, alkyl, hydroxy, alkoxy, or keto groups, for example 2,6-dichloro-phenyl, 2,6-difluoro-phenyl, cyclohexyl, cyclopentyl, isopropyl, phenyl, t-butoxy, tetrahydro-furan-2-yl, tetrahydro-pyran-2-yl, or tetrahydro-pyran-4-yl, and $R_2$ and $R_3$ are as above, can be prepared by the direct coupling of the corresponding compounds of formula V with the corresponding compounds of formula I where X is boron and $R_1'$ and $R_1$ are alkoxy individually or together to form a ring under basic conditions catalyzed by cupric acetate (under similar conditions to those described in *Tetrahedron Lett.* 1998, 39, 2933; *J. Org. Chem.* 2004, 69, 5087). The corresponding compounds of formula I, where X is boron and $R_1'$ and $R_1$ are alkoxy individually or together to form a ring and $R_3$ is any unsubstituted or substituted heteroaryl groups which are commercially available or known in the literature can be prepared from the corresponding compounds of formula I, where X is O, $R_1$ is H, $R_1'$ is absent by treating with compounds of formula XIV, where $R_1'$ and $R_1$ are alkoxy individually or together to form a ring (under similar conditions to those described in *J. Organometallic Chem.* 2003, 687, 284). The corresponding compounds of formula I where $R_1$ is trifluoromethanesulfonyl and $R_1'$ is absent can be prepared from the compounds of formula I where $R_1$ is hydrogen and $R_1'$ is absent by treatment with base and triflic anhydride (under similar conditions to those described in *Synthesis* 2007, 15, 2317). The corresponding compounds of formula I where $R_1$ is hydrogen and $R_1'$ is absent can be prepared from the compounds of formula I where $R_1$ is lower alkyl for example methyl and $R_1'$ is absent, using thermal acidic conditions (under similar conditions to those described in CN 101121688; *J. Org. Chem.* 1993, 58, 4010). Examples of heteroaryl groups include 1H-pyrazol-3-yl, pyrazin-2-yl, pyridin-2-yl, thiazol-2-yl, [1,3,4]thiadiazol-2-yl and [1,2,4]thiadiazol-5-yl.

The compounds of formula I, where $R_3$ is alkylcarbamoyl can be prepared from the corresponding compounds of formula VIII where E is lower alkoxy, for example methoxy or ethoxy, by treatment with N-alkylureas, for example N-methyl urea, in the presence of magnesium methoxide (under similar conditions to those described in U.S. Pat. No. 6,528, 543).

The compounds of formula I or formula I-x having functional groups that may need transformation, conversion or protection may be transformed, converted or deprotected to the desired functionality using conventional methods at an appropriate intermediate step or after the amide coupling step of the synthesis (under similar conditions to those described in Greene, T. W. Protective Groups in Organic Synthesis; John Wiley & Sons, Inc.: New York, 1991). Such conversions may include saponification of an ester to an acid or alcohol under basic conditions, removal of acetals or ketals used to afford aldehydes, ketones or diols, removal of a silyl protecting group from an alcohol, conversion of an acid to an amide, conversion of an olefin to an alcohol, diol, aldehyde, acid or ester or removal of a protecting group from an amine nitrogen. Alcohols may be converted to leaving groups such as halides, mesylates or tosylates and then displaced with nucleophiles such as amines, alcohols or thiols. Such conversions also include dehalogenation of benzylic mono-, di-, and trihalides (under similar conditions to those described in *J. Amer. Chem. Soc.* 2007, 129, 12656; *Synlett* 2001, 4, 485; *Russian J. Org. Chem.* (Translation) 2000, 36, 1488; *Chem. Ber.* 1959, 92 1700) hydrogenation of alkenes and alkynes or coupling of aryl halides or triflates with alkyl or aryl coupling partners such as but not limited to boronic acids, amines, alkynes, vinyl or alkyl halides (under similar conditions to those described in *Curr. Opin. Drug Discovery Dev.* 2007, 10, 672; *Chem. Rev.* 2007, 107, 5318; *Eur. J. Org. Chem.* 2007, 4166; *Chem. Rev* 2007, 107, 874; *Chem. Rev.* 2007, 107, 133). Also, if the compounds of formula I or formula I-x are a mixture of enantiomers or diastereomers, the appropriate chromatographic techniques, such as supercritical fluid chromatography, may be utilized to produce chirally pure or chirally enriched compounds of formula I or formula I-x.

Compounds of formula VII, where Z is an amino group and E is hydroxyl are amino acids, a number of which are available from commercial sources. Several natural and unnatural amino acids are commercially available or readily available via several methods reported in the literature (under similar conditions to those described in D. J. Ager, in Handbook of chiral chemicals, 2$^{nd}$ Edition, p 11-30, CRC Press). Among these methods are asymmetric hydrogenation of the enamides (under similar conditions to those described in Ager, D. J., Laneman, S. A., The Synthesis of Unnatural Amino Acids, in Asymmetic Catalysis on Industrial Scale, Blaser, H.-U., Schmidt, E., Wiley-VCH: Weinheim, 2004, p 23), chiral auxiliary derived asymmetric induction methods (under similar conditions to those described in *Pure and App. Chem.* 1983, 55, 1799; *Tetrahedron*, 1988, 44, 5541; *J. Amer. Chem. Soc.*, 1990, 112, 4011); asymmetric methods using chiral phase transfer catalyzed alkylations (under similar conditions to those described in *Acc. Chem. Research* 2004, 37, 506); condensing the corresponding aldehydes with glycine, protected glycine or protected glycine phosphonate derivatives followed by hydrogenation (under similar conditions to those described in *J. Org. Chem.* 1989, 54, 4511; *Org. Lett.* 2005, 7, 5433; *J. Org. Chem.* 2005, 70, 5840); and alkylating 2-(acetylamino)-propanedioic acid diesters with an appropriate alkylating reagents followed by either enzymatic resolution or decarboxylation (under similar conditions to those described in *Chemistry & Biology,* 2006, 13, 607; *Acc. Chem. Research* 2004, 37, 506 and references cited therein); by alkylating (benzhydrylidene-amino)-acetic acid alkyl esters with halides, triflate, tosylate or mesylate derivatives and the resulting benzhydrylidene derivatives can be converted to the amino acids using standard procedures (under similar conditions to those described in *J. Med. Chem.;* 2006 49, 6074). The halides, triflates, tosylates or mesylates can be prepared from the corresponding alcohols using any conditions known for converting an alcohol to a halide, triflate, tosylate or mesylate. Aldehydes may be prepared by oxidizing the corresponding alcohols using standard conditions, or by reducing the corresponding acids, esters, or Weinreb amides using standard conditions. Alcohols may be purchased or prepared from the corresponding acids, esters, or aldehydes using any conditions known for preparing an alcohol. Using these methods, compounds of formula VII, where $R_2$ is alkyl, cycloalkyl, heterocycloalkyl, aryl or heteroaryl groups can be prepared.

The alkyl and cycloalkyl amino acids such as, cyclopentyl alanine, cyclohexyl alanine, and cyclobutyl alanine are either commercially available or are readily available from corresponding halides or tosylates or mesylates via the general methods described above. Similarly, aryl and heteroaryl containing amino acids are either commercially available or can be prepared from readily accessible aryl or heteroaryl methyl halides, using the standard methods described before. Amino acids such as, 2,6-difluorophenyl alanine, 2-thienyl alanine, 2-amino-3-isoxazol-5-yl-propionic acid can be prepared. Several fluoro- and chloro-substituted leucines, for example, 2-amino-4-fluoro-4-methyl-pentanoic acid, 2-amino-4-chloro-4-methyl-pentanoic acid, 2-amino-5,5,5-trifluoro-4-methyl-pentanoic acid, 2-amino-4,4-difluoro-butyric acid and 2-amino-4,4-dichloro-butyric acid are readily accessible from known methods described in the literature (under similar conditions to those described in *Bioorg. & Med. Chem. Lett.,* 2008, 923; *Synthesis* 1996, 12, 1419). Alternatively fluorinated compounds can be prepared from the corresponding alcohols, aldehydes or ketones by treatment with fluorinated agents such as diethylaminosulfurtrifluoride (under similar conditions to those described in *Organic Syn.* 1977, 57, 50; *Chimia,* 1985, 35, 134). For example 2-amino-4,4-difluoro-pentanoic acid can be prepared from the corresponding ketone, (S)-2-benzyloxycarbonylamino-4-oxo-pentanoic acid methyl ester (under similar conditions to those described in WO 2005040142) using diethylaminosulfurtrifluoride. Alternatively 2-amino-4,4-difluoro-butyric acid may be prepared by alkylating a 2-(acetylamino)-propanedioic acid diester with trifluoro-methanesulfonic acid 2,2-difluoro-ethyl ester. Trifluoro-methanesulfonic acid 2,2-difluoro-ethyl ester can be prepared as described in the literature (under similar conditions to those described in WO 9964442). Hydroxy substituted leucine, 2-amino-4-hydroxy-4-methyl-pentanoic acid, can be prepared from appropriately substituted leucine, via its reaction with N-bromosuccinimide, as reported (under similar conditions to those described in *Tetrahedron Lett.,* 1990, 31, 7059). Similarly, fluoro-substituted amino acids can be obtained via known methods (under similar conditions to those described in *Tetrahedron,* 2004, 60, 6711). If a gem-difluoro cycloalkyl is required, it can be obtained via the corresponding keto-derivative, using diethylaminosulfurtrifluoride (under similar conditions to those described in *Organic Syn.,* 1977, 57, 50; *Chimia,* 1985, 35, 134). The vicinal difluorocyclopentane derivative 2-amino-3-((1R,3S,4R)-3,4-difluoro-cyclopentyl)-propionic acid methyl ester can be prepared by reacting the corresponding aldehyde with a protected glycine phosphonate derivative followed by hydrogenation (under similar conditions to those described in *J. Org. Chem.* 1989, 54, 4511; *Org. Lett.* 2005, 7, 5433; *J. Org. Chem.* 2005, 70, 5840). The aldehyde may be prepared from the corresponding alcohol using any known procedure for oxidizing an alcohol to an aldehyde such as a Swern oxidation. The corresponding alcohol, ((1R,3S,4R)-3, 4-difluoro-cyclopentyl)-methanol, can be prepared under similar conditions to those described in WO2008111473.

Cycloalkanone containing amino acids, for example, cyclopentan-3-one, can be prepared using the appropriately protected cyclopentane-3-one methyl tosylate or mesylate (under similar conditions to those described in PCT Int. Appl. WO2003095438; PCT Int. Appl. WO2007115968) resulting in the preparation of protected amino acid, 2-amino-3-(8,8-dimethyl-6,10-dioxa-spiro[4.5]dec-2-yl)-propionic acid via the general methods of amino acid synthesis described above. Amino acid derivatives with a pyrrolidinone ring in the side chain such as 2-amino-3-(2-oxo-pyrrolidin-3-yl)-propionic acid can be prepared using literature reports (WO9957135). Heterocycloalkyl containing amino acid 2-amino-3-(tetrahydro-pyran-4-yl)-propionic acid is commercially available, while the corresponding analog 2-amino-3-(tetrahydro-pyran-2-yl)-propionic acid can be prepared using reported procedures (under similar conditions to those described in PCT Int. Appl. WO2001005783; PCT Int. Appl. WO2007070201). The amino acids with 2-tetrahydrofuran ring, 2-amino-3-(tetrahydro-furan-2-yl)-propionic acid can be prepared from the 2-furyl derivative via the hydrogenation of 2-furyl ring and subsequent diastereomer separation using standard methods (under similar conditions to those described in PCT Int. Appl. WO 2004033462; PCT Int. Appl. WO9214706).

Amino acids with bicyclic systems such as norbornyl rings can be prepared by reacting the corresponding aldehydes with a protected glycine phosphonate derivative followed by hydrogenation (under similar conditions to those described in *J. Org. Chem.* 1989, 54, 4511; *Org. Lett.* 2005, 7, 5433; *J. Org. Chem.* 2005, 70, 5840). The aldehydes may be prepared from the corresponding alcohols using any known procedure for oxidizing an alcohol to an aldehyde such as a Swern oxidation. The corresponding alcohols are either commercially available (such as 2-norborananemethanol) or can be prepared using literature methods (such as bicyclo[2.2.1]hept-7-yl-methanol, under similar conditions to those described in *J. Med. Chem.* 2005, 48, 8103).

For amino acid derivatives of formula VII where $R_2$ is cycloalkyl substituted with a fluorine on the methine ring attachment carbon atom, such as 2-amino-3-(1-fluoro-cyclobutyl)-propionic acid, 2-amino-3-(1-fluoro-cyclopentyl)-propionic acid, or 2-amino-3-(1-fluoro-cyclohexyl)-propionic acid, these compounds can be prepared by alkylating (benzhydrylidene-amino)-acetic acid alkyl esters with triflate, tosylate or mesylate derivatives of the corresponding (1-fluoro-cycloalkyl)-methanol analogs or the corresponding bromides. The resulting benzhydrylidene derivatives can be converted to the amino acids using standard procedures (under similar conditions to those described in *J. Med. Chem.;* 2006 49, 6074). The triflate, tosylate or mesylate derivatives of the corresponding (1-fluoro-cycloalkyl)-methanol analogs can be prepared from the alcohols using any conditions known for converting an alcohol to a triflate, tosylate or mesylate. The bromide derivatives can be prepared from the alcohols using any conditions known for converting an alcohol to a bromide. The (1-fluoro-cycloalkyl)-methanol analogs are known in the literature (under similar conditions to those described in *Synthesis* 1988, 4, 310; PCT Int. Appl. WO 2006064286) or can be prepared from the corresponding epoxide (under similar conditions to those described in *Chem. Ber.* 1922, 55, 2725) by treatment with an appropriate fluorinating reagent, for example pyridine hydrofluoride (under similar conditions to those described in *J. Fluorine Chem.;* 1995; 74; 283). The corresponding epoxides can be prepared from the corresponding exocyclic alkenes directly or via the halohydrins using standard conditions (under similar conditions to those described in *J. Amer. Chem. Soc.* 1954, 76, 4373). The corresponding halohydrins can be prepared under similar conditions to those described in *J. Org. Chem.* 1971, 36, 2915. The related acyclic analog, 4-fluoro-leucine ethyl ester, can be prepared via literature procedures (under similar conditions to those described in *J. Org. Chem.* 2005, 70, 2372).

For amino acid derivatives of formula VII where $R_2$ is alkyl or cycloalkyl substituted with a hydroxyl group on the methine ring attachment carbon atom, such as 2-amino-4-hydroxy-4-methyl-pentanoic acid, 2-amino-3-(1-hydroxy-cyclobutyl)-propionic acid, 2-amino-3-(1-hydroxy-cyclopentyl)-propionic acid, or 2-amino-3-(1-hydroxy-cyclohexyl)-propionic acid, these compounds can be prepared by alkylating (benzhydrylidene-amino)-acetic acid alkyl esters with triflate, tosylate or mesylate derivatives of the corresponding (1-hydroxy-cycloalkyl)-methanol analogs (1-hydroxymethyl-cyclohexanol is commercially available, for 2-methyl-propane-1,2-diol see *J. Org. Chem.* 1989, 54, 4677; *J. Org. Chem* 1989, 54, 3523; for 1-hydroxymethyl-cyclopentanol see *Tetrahedron Lett.* 1984, 25, 4245, for 1-hydroxymethyl-cyclobutanol see *J. Am. Chem. Soc.* 1949, 71, 3925; *J. Org. Chem.* 1993, 58, 3140), corresponding bromides (for 1-halo-2-methyl-propan-2-ol see *Organometal. Chem. Syn.* 1971, 1, 127; for 1-halomethyl-cyclopentanol see *Tetrahedron* 1959, 7, 165; *Bull. Chem. Soc. Jpn* 1982, 55, 1498; *J. Org. Chem.* 1984, 49, 4497; *Tetrahedron Lett.* 1986, 27, 3891; *Can. J. Chem.* 1988, 66, 168; *Green Chem.* 2005, 7, 100; for 1-halomethyl-cyclobutanol see *Tetrahedron* 1959, 7, 165; *J. Org. Chem* 1971, 36, 2915; *J. Org. Chem.* 1973, 38, 1463, for 1-halomethyl-cyclohexanol see *J. Org. Chem* 1980, 45, 924; *J. Org. Chem.* 1981, 46, 1283; *J. Org. Chem.* 1984, 49, 4497), or corresponding tertiary alcohol protected analogs (for 1-hydroxy-2-methyl-propan-2-ol see *J. Am. Chem. Soc.* 2000, 122, 8837; for 1-hydroxymethyl-cyclopentanol see PCT Inter. Appl. WO19960117; for 1-hydroxymethyl-cyclohexanol see *J. Org. Chem.* 1998, 63, 2422). The resulting benzhydrylidene derivatives can be converted to the amino acids using standard procedures (under similar conditions to those described in *J. Med. Chem.;* 2006 49, 6074). The triflate, tosylate or mesylate derivatives can be prepared from the alcohols using any conditions known for converting an alcohol to a triflate, tosylate or mesylate. The bromide derivatives can be prepared from the alcohols using any conditions known for converting an alcohol to a bromide. Alternatively these compounds can be prepared by condensing the corresponding aldehydes with glycine, protected glycine or protected glycine phosphonate derivatives followed by hydrogenation (under similar conditions to those described in *J. Org. Chem.* 1989, 54, 4511; *Org. Lett.* 2005, 7, 5433; *J. Org. Chem.* 2005, 70, 5840). The corresponding alcohol protected aldehydes are known in the literature (for protected 2-hydroxy-2-methyl-propionaldehyde see *J. Am. Chem. Soc.* 2000, 122, 8837; *Tetrahedron Lett.* 2005, 46, 6495; for protected 1-hydroxy-cyclopentanecarbaldehyde see *J. Chem. Soc., Perkin Trans.* 1 1988, 1119, for protected 1-hydroxy-cyclohexanecarbaldehyde see *Synlett* 1991, 479; *Tetrahedron* 1994, 50, 2821; *J. Org. Chem.* 1998, 63, 2422) or can be prepared from the alcohols using any method suitable for oxidizing a primary alcohol to an aldehyde. Unmasking of the alcohol functionality can be accomplished using any conditions known for converting a protected alcohol such as a silyl protected alcohol or an ester protected alcohol to an alcohol.

For amino acid derivatives of formula VII, where $R_2$ is a geminal dihaloalkyl group such as 2-amino-4,4-difluoro-butyric acid, 2-amino-4,4-dichloro-butyric acid or 2-amino-4,4-difluoro-pentanoic acid, these compounds, or their suitably protected derivatives, can be prepared as described in the literature (under similar conditions to those described in PCT Int. Appl. WO 2005040142; *Synthesis* 1996, 12, 1419).

The compounds of formula VII, where $R_2$ is aryl, substituted aryl, heteroaryl, substituted heteroaryl, alkyl, cycloalkyl, substituted cycloalkyl, heteroalkyl, substituted heteroalkyl, heterocycloalkyl, or substituted heterocycloalkyl and E is hydroxyl or a functionalized hydroxyl and Z is halogen, for example bromide, or any functional group that may be displaced or coupled through a carbon may be produced from commercially available materials. For example, the appropriate $R_2$ derivative may be reacted with a malonate derivative under standard conditions to produce a substituted malonate (under similar conditions to those described in *J. Med. Chem.*, 1990, 33, 263). The resulting substituted malonate may then be treated under hydrolysis conditions to form the resulting diacid (under similar conditions to those described in *J. Med. Chem.*, 1990, 33, 263). The diacid may then be heated under such conditions that will promote a decarboxylation to form the appropriately substituted acid. (under similar conditions to those described in *J. Med. Chem.*, 1990, 33, 263). In some instances, the desired mono-acid is available from commercial sources. The resulting substituted acid can then be treated under conditions that may form an acid chloride. In some instances, the desired acid chloride is available from commercial sources. The resulting acid chloride can then be treated under standard conditions to form the corresponding compound of formula VII where Z is a halogen for example bromine and E is a chlorine, (under similar conditions to those described in Eur. Pat. Appl., 864564; *J. Org. Chem.* 1985, 50, 5507; *J. Med. Chem.*, 1981, 24, 481). The acid chlorides can then be treated with a hydroxyl containing reagent, such as methanol, to form the corresponding compound of formula VII where E is alkoxy, cycloalkoxy, aryloxy, heteroaryloxy or the acid chloride may be treated with an amine or functionalized amine to form the corresponding compound of formula VII where E is a substituted or unsubstituted aminoheteroaryl, the heteroaryl group for example 2H-[1,2,3]triazol-4-yl, 2H-[1,2,4]Triazol-3-yl, pyrimidin-4-yl, furazan-3-yl, pyridazin-3-yl, thiazol-4-yl, dihydro-1H-[1,2,4]triazol-3-yl, 1H-imidazol-2-yl, 1H-benzoimidazol-2-yl, [1,2,5]thiadiazol-3-yl, oxazol-2-yl, benzooxazol-2-yl, 4,5-dihydro-oxazol-2-yl, pyrimidin-2-yl, [1,2,4]oxadiazol-5-yl, isoxazol-3-yl, [1,2,4]triazin-3-yl, [1,2,4]triazolo[1,5-a]pyridin-2-yl, isoquinolin-3-yl, quinolin-2-yl, 1H-pyrazol-3-yl, pyrazin-2-yl, pyridin-2-yl, thiazol-2-yl, [1,3,4]thiadiazol-2-yl and [1,2,4]thiadiazol-5-yl. This sequence can also be carried out in one pot, under similar conditions to those described in *J. Med. Chem.*, 1981, 24, 481.

Compounds of formula IX may be unsubstituted or substituted heteroaryl or heterocycloalkyl groups which are commercially available or known in the literature. More preferred heteroaryl groups include 2H-[1,2,3]triazol-4-yl, 2H-[1,2,4]triazol-3-yl, pyrimidin-4-yl, furazan-3-yl, pyridazin-3-yl, thiazol-4-yl, dihydro-1H-[1,2,4]triazol-3-yl, 1H-imidazol-2-yl, 1H-benzoimidazol-2-yl, [1,2,5]thiadiazol-3-yl, oxazol-2-yl, benzooxazol-2-yl, 4,5-dihydro-oxazol-2-yl, pyrimidin-2-yl, [1,2,4]oxadiazol-5-yl, isoxazol-3-yl, [1,2,4]triazin-3-yl, [1,2,4]triazolo[1,5-a]pyridin-2-yl, isoquinolin-3-yl, and quinolin-2-yl. Most preferred heteroaryl groups include 1H-pyrazol-3-yl, pyrazin-2-yl, pyridin-2-yl, thiazol-2-yl, [1,3,4]thiadiazol-2-yl, and [1,2,4]thiadiazol-5-yl.

If it is desired to produce the compound of formula IX, where $R_3$ is a substituted 1H-pyrazol-3-yl group, for example: 1,5-dimethyl-1H-pyrazol-3-yl, or 5-methyl-1H-pyrazol-3-yl, these compounds are commercially available.

If it is desired to produce the compound of formula IX, where $R_3$ is a substituted 1H-pyrazol-3-yl group, for example: 1-t-butoxycarbonyl-5-methyl-1H-pyrazol-3-yl, this compounds can be prepared as described in PCT Int. Appl., 2005121110.

If it is desired to produce the compound of formula IX, where $R_3$ is a substituted 1H-pyrazol-3-yl group, for example: 1-(2-t-butoxycarbonylamino-ethyl)-1H-pyrazol-3-yl, 1-(2-isopropoxy-ethyl)-1H-pyrazol-3-yl, 1-(2-methoxy-2-methyl-propyl)-1H-pyrazol-3-yl, 1-(2-hydroxy-2-methyl-propyl)-1H-pyrazol-3-yl, 1-(2-hydroxy-propyl)-1H-pyrazol-3-yl, 1-(2-methyl-2-triethylsilanyloxy-propyl)-1H-pyrazol-3-yl, 1-(1-hydroxy-cyclopropylmethyl)-1H-pyrazol-3-yl, 1-(4-methoxycarbonyl-cyclohexylmethyl)-1H-pyrazol-3-yl, 1-2-(t-butyl-dimethyl-silanyloxy)-ethyl-1H-pyrazol-3-yl, 1-(3-carboxy-benzyl)-1H-pyrazol-3-yl, 1-1-(4-methoxycarbonyl-phenyl)-butyl-1H-pyrazol-3-yl, 1-(3-t-butoxycarbonylamino-benzyl)-1H-pyrazol-3-yl, 1-(3-methoxycarbonyl-benzyl)-1H-pyrazol-3-yl, 1-(4-t-butoxycarbonylamino-but-2-ynyl)-1H-pyrazol-3-yl, 1-(4-hydroxy-but-2-ynyl)-1H-pyrazol-3-yl, 1-(3-methyl-but-2-enyl)-1H-pyrazol-3-yl, 1-(3-hydroxy-3-methyl-butyl)-1H-pyrazol-3-yl, 1-(4-methoxycarbonyl-benzyl)-1H-pyrazol-3-yl, 1-(3-methyl-butyl)-1H-pyrazol-3-yl, 1-isobutyl-1H-pyrazol-3-yl, 1-octyl-1H-pyrazol-3-yl, 1-hexyl-1H-pyrazol-3-yl, 1-(3-hydroxy-3-methyl-butyryl)-1H-pyrazol-3-yl, 1-((R)-2,3-dihydroxy-propyl)-1H-pyrazol-3-yl, 1-((S)-2,3-dihydroxy-propyl)-1H-pyrazol-3-yl, 1-ethanesulfonyl-1H-pyrazol-3-yl, 1-(4-methoxy-benzyl)-1H-pyrazol-3-yl, 1-(4-cyano-benzyl)-1H-pyrazol-3-yl, 1-(3-hydroxy-propyl)-1H-pyrazol-3-yl, 1-methanesulfonylmethyl-1H-pyrazol-3-yl, 1-(4-methanesulfonyl-benzyl)-1H-pyrazol-3-yl, 1-carbamoylmethyl-1H-pyrazol-3-yl, 1-(2-t-butoxycarbonyl-ethyl)-1H-pyrazol-3-yl, 1-t-butoxycarbonylmethyl-1H-pyrazol-3-yl, 1-propyl-1H-pyrazol-3-yl, 1-(4-chloro-benzyl)-1H-pyrazol-3-yl, 1-(2-methoxy-ethyl)-1H-pyrazol-3-yl, 1-cyclopropylmethyl-1H-pyrazol-3-yl, 1-(3,4-dichloro-benzyl)-1H-pyrazol-3-yl, 1-phenethyl-1H-pyrazol-3-yl, 1-t-butoxycarbonyl-1H-pyrazol-3-yl, 1-isopropyl-1H-pyrazol-3-yl, 1-(4-methyl-benzyl)-1H-pyrazol-3-yl, 1-(4-hydroxy-butyl)-1H-pyrazol-3-yl, 1-butyl-1H-pyrazol-3-yl, 1-ethyl-1H-pyrazol-3-yl, 1-benzyl-1H-pyrazol-3-yl, 1-methyl-1H-pyrazol-3-yl, or 1H-pyrazol-3-yl, these compounds are commercially available or can be prepared as described in U.S. Pat. Appl. US 2008021032.

If it is desired to produce the compound of formula IX, where $R_3$ is a substituted 1H-pyrazol-3-yl group, for example: 1-(dimethyl-phosphinoylmethyl)-1H-pyrazol-3-yl, 1-(diethoxy-phosphorylmethyl)-5-methyl-1H-pyrazol-3-yl, or 1-(diethoxy-phosphorylmethyl)-1H-pyrazol-3-yl, 1-(ethoxy-methyl-phosphinoylmethyl)-1H-pyrazol-3-yl these compounds can be prepared as described in PCT Int. Appl. WO2008005964.

If it is desired to produce the compound of formula IX, where R3 is 1-difluoromethyl-1H-pyrazol-3-yl, this compound can be prepared as described in PCT Int. Appl. WO2005090332.

If it is desired to produce the compound of formula IX, where $R_3$ is a substituted pyrazin-2-yl group, for example: 5-cyano-pyrazin-2-yl, 5-methylsulfanyl-pyrazin-2-yl, 5-chloro-pyrazin-2-yl, pyrazin-2-yl, 5-methoxy-pyrazin-2-yl, 5-methyl-pyrazin-2-yl or 5-bromo-pyrazin-2-yl these compounds are commercially available.

If it is desired to produce the compound of formula IX, where $R_3$ is a substituted pyrazin-2-yl group, for example:

5-(diethoxy-phosphorylmethyl)-pyrazin-2-yl, 5-(diisopropoxy-phosphorylmethyl)-pyrazin-2-yl, or 5-(ethoxy-methyl-phosphinoylmethyl)-pyrazin-2-yl these compounds can be prepared as described in PCT Int. Appl. WO2008005964.

If it is desired to produce the compound of formula IX, where $R_3$ is a substituted pyrazin-2-yl group, for example: 5-methoxycarbonyl-pyrazin-2-yl, 5-dimethylamino-pyrazin-2-yl, 5-thiophen-2-yl-pyrazin-2-yl, 5-(3-methoxy-phenyl)-pyrazin-2-yl, 5-(2-hydroxy-phenyl)-pyrazin-2-yl, 5-(2-methoxy-phenyl)-pyrazin-2-yl, 5-vinyl-pyrazin-2-yl, 5-methanesulfonylamino-pyrazin-2-yl, 5-dimethoxymethyl-pyrazin-2-yl, 5-{1-[(E)-t-butoxyimino]-ethyl}-pyrazin-2-yl, 5-t-butoxycarbonyl-pyrazin-2-yl, 5-methylsulfanylmethyl-pyrazin-2-yl, 5-cyanomethyl-pyrazin-2-yl, 5-(1,1-dimethoxy-ethyl)-pyrazin-2-yl, 5-(bis-ethoxycarbonyl-methyl)-pyrazin-2-yl, 5-[1,3]dioxolan-2-yl-pyrazin-2-yl, 5-[1,3]dioxolan-2-ylmethyl-pyrazin-2-yl, 5-(2-ethoxy)-pyrazin-2-yl, 5-allyloxy-pyrazin-2-yl, 5-(2,2-dimethoxy-ethyl)-pyrazin-2-yl, 5-(2,2-dimethyl-[1,3]dioxolan-4-yl)-pyrazin-2-yl, 5-(2-benzyloxy-1-benzyloxymethyl-ethoxycarbonyl)-pyrazin-2-yl, 5-[2-(tetrahydro-pyran-2-yloxy)-ethoxy]-pyrazin-2-yl, 5-(2-methyl-propenyl)-pyrazin-2-yl, 5-(4-methyl-2,5-dioxo-imidazolidin-4-yl)-pyrazin-2-yl, 5-(tetrahydro-furan-2-yl)-pyrazin-2-yl, 5-(2-methoxy-ethylamino)-pyrazin-2-yl, 5-(2-triethylsilanyloxy-ethylamino)-pyrazin-2-yl, 5-(1H-indol-5-yl)-pyrazin-2-yl, 5-(5,6-dihydro-4H-pyran-2-yl)-pyrazin-2-yl, 5-thiophen-3-yl-pyrazin-2-yl, 5-furan-3-yl-pyrazin-2-yl, 5-(5-cyano-thiophen-2-yl)-pyrazin-2-yl, 5-(4,5-dihydro-1H-imidazol-2-yl)-pyrazin-2-yl, 5-allyl-pyrazin-2-yl these compounds can be prepared as described in PCT Int. Appl. WO2004052869.

If it is desired to produce the compound of formula IX, where $R_3$ is a substituted pyrazin-2-yl group, for example: 5-cyclopropyl-pyrazin-2-yl, 5-t-butoxycarbonylamino-pyrazin-2-yl, 5-(t-butoxycarbonyl-methyl-amino)-pyrazin-2-yl, 5-(2-oxo-pyrrolidin-1-yl)-pyrazin-2-yl, 5-[2-(t-butyl-dimethyl-silanyloxy)-ethoxy]-pyrazin-2-yl, 5-isopropoxy-pyrazin-2-yl, or 5-(4-acetyl-3-methyl-piperazin-1-ylmethyl)-pyrazin-2-yl these compounds can be prepared as described in PCT Int. Appl. WO2007007886.

If it is desired to produce the compound of formula IX, where $R_3$ is a substituted thiazol-2-yl group, for example: 4-(4-isopropyl-phenyl)-thiazol-2-yl, 4,5,6,7-tetrahydro-benzothiazol-2-yl, 4,5-dimethyl-thiazol-2-yl, 4,5-dimethyl-thiazol-2-yl, 4-acetyl-thiazol-2-yl, 4-carbamoyl-thiazol-2-yl, 4-carboxymethyl-thiazol-2-yl, 4-chloromethyl-thiazol-2-yl, 4-cyano-thiazol-2-yl, 4-ethoxycarbonyl-4,5,6,7-tetrahydro-benzothiazol-2-yl, 4-ethoxycarbonylmethyl-5-ethyl-thiazol-2-yl, 4-ethoxycarbonylmethyl-5-methyl-thiazol-2-yl, 4-ethoxycarbonylmethyl-thiazol-2-yl, 4-ethoxycarbonyl-thiazol-2-yl, 4-ethoxyoxalyl-thiazol-2-yl, 4-formyl-thiazol-2-yl, 4-hydroxymethyl-thiazol-2-yl, 4-isopropyl-thiazol-2-yl, 4-methoxycarbonylmethyl-thiazol-2-yl, 4-methoxycarbonyl-thiazol-2-yl, 4-methyl-thiazol-2-yl, 4-t-butyl-thiazol-2-yl, 4-trifluoromethyl-thiazol-2-yl, 5-(2-hydroxy-ethylcarbamoyl)-4-methyl-thiazol-2-yl, 5-acetyl-4-methyl-thiazol-2-yl, 5-bromo-thiazol-2-yl, 5-bromo-thiazol-2-yl, 5-bromo-thiazol-2-yl, 5-chloro-thiazol-2-yl, 5-chloro-thiazol-2-yl, 5-chloro-thiazolo[5,4-b]pyridin-2-yl, 5-ethoxycarbonyl-4-methyl-thiazol-2-yl, 5-ethoxycarbonyl-methylsulfanyl-thiazol-2-yl, 5-ethoxycarbonyl-thiazol-2-yl, 5-fluoro-thiazol-2-yl, 5-fluoro-thiazol-2-yl, 5-formyl-thiazol-2-yl, 5-hydroxymethyl-thiazol-2-yl, 5-isopropyl-4-methoxycarbonyl-thiazol-2-yl, 5-methanesulfonyl-thiazol-2-yl, 5-methoxycarbonylmethyl-thiazol-2-yl, 5-methoxycarbonyl-thiazol-2-yl, 5-methoxy-thiazol-2-yl, 5-methoxy-thiazolo[5,4-b]pyridin-2-yl, 5-methyl-4,5,6,7-tetrahydro-thiazolo[5,4-c]pyridin-2-yl, 5-methyl-thiazol-2-yl, 5-nitro-thiazol-2-yl, 5-thiocyanato-thiazol-2-yl, 6,7-dihydro-4H-pyrano[4,3-d]thiazol-2-yl, 6-bromo-thiazolo[4,5-b]pyrazin-2-yl, 6-carboxymethyl-benzothiazol-2-yl, 6-fluoro-benzothiazol-2-yl, 6-methanesulfonyl-benzothiazol-2-yl, 6-nitro-benzothiazol-2-yl, benzothiazol-2-yl, thiazol-2-yl, thiazolo[5,4-b]pyridin-2-yl, 4-chloromethyl-thiazol-2-yl, or 4,5,6,7-tetrahydro-benzothiazol-2-yl these compounds are commercially available.

If it is desired to produce the compound of formula IX, where $R_3$ is a substituted thiazol-2-yl group, for example: 5-(3-cyano-phenoxy)-thiazol-2-yl, 5-(3-methoxycarbonyl-phenoxy)-thiazol-2-yl, 5-(4-methoxycarbonyl-phenoxy)-thiazol-2-yl, 5-(5-methoxycarbonyl-pyridin-3-yloxy)-thiazol-2-yl, 5-(6-fluoro-pyridin-3-yloxy)-thiazol-2-yl, or 5-(3,4-bis-methoxycarbonyl-phenoxy)-thiazol-2-yl these compounds can be prepared as described in PCT Int. Appl. WO 2008005914.

If it is desired to produce the compound of formula IX, where $R_3$ is a substituted thiazol-2-yl group, for example: 4-(diethoxy-phosphorylmethyl)-5-isopropyl-thiazol-2-yl, 4-(diisopropoxy-phosphorylmethyl)-thiazol-2-yl, 4-(dimethyl-phosphinoyloxymethyl)-thiazol-2-yl, 4-(ethoxy-methyl-phosphinoyloxymethyl)-thiazol-2-yl, 4-(ethoxy-methyl-phosphinoyloxymethyl)-thiazol-2-yl, 4-[2-(diethoxy-phosphoryl))-1-hydroxy-ethyl]-thiazol-2-yl, 4-[2-(diethoxy-phosphoryl)-ethyl]-thiazol-2-yl, 5-(diethoxy-phosphoryl)-thiazol-2-yl, 5-(diethoxy-phosphorylmethyl)-thiazol-2-yl, 4-(2-oxido-[1,3,2]dioxaphosphinan-2-ylmethyl)-thiazol-2-yl, 4-((S)-ethoxy-methyl-phosphinoylmethyl)-thiazol-2-yl, 4-(diethoxy-phosphorylmethyl)-thiazol-2-yl, 4-(diethoxy-phosphoryl)-thiazol-2-yl or 4-bromo-thiazol-2-yl these compounds can be prepared as described in PCT Int. Appl. WO 2008005964.

If it is desired to produce the compound of formula IX, where $R_3$ is a substituted thiazol-2-yl group, for example: 4-(2-ethoxycarbonyl-ethylsulfanylmethyl)-thiazol-2-yl, 4-carboxymethylsulfanylmethyl-thiazol-2-yl, or 5-(2-ethoxycarbonyl-ethylsulfanyl)-thiazol-2-yl these compounds can be prepared as described in PCT Int. Appl. WO 2007125103.

If it is desired to produce the compound of formula IX, where $R_3$ is a substituted thiazol-2-yl group, for example: 4-methoxy-6-methoxycarbonyl-benzothiazol-2-yl this compound can be prepared as described in PCT Int. Appl. WO 2007122482.

If it is desired to produce the compound of formula IX, where $R_3$ is a substituted thiazol-2-yl group, for example: 4-(1-acetyl-piperidin-4-yl)-thiazol-2-yl this compound can be prepared as described in PCT Int. Appl. WO 2007089512.

If it is desired to produce the compound of formula IX, where $R_3$ is a substituted thiazol-2-yl group, for example: 5-bromo-thiazolo[5,4-b]pyridin-2-yl this compound can be prepared as described in PCT Int. Appl. WO 2007041365.

If it is desired to produce the compound of formula IX, where $R_3$ is a substituted thiazol-2-yl group, for example: 4-(1,2-bis-benzoyloxy-ethyl)-thiazol-2-yl, 4-(1,3-diacetoxy-propyl)-thiazol-2-yl, 4-(2,2,4-trimethyl-[1,3]dioxolan-4-yl)-thiazol-2-yl, 4-(2,2,5,5-tetramethyl-[1,3]dioxolan-4-yl)-thiazol-2-yl, 4-(2,2-dimethyl-[1,3]dioxolan-4-yl)-thiazol-2-yl, 4-(2-acetoxy-1-acetoxymethyl-1-methyl-ethyl)-thiazol-2-yl, 4-(2-acetoxy-1-acetoxymethyl-ethyl)-thiazol-2-yl, 4-(3-acetoxy-2-acetoxymethyl-propyl)-thiazol-2-yl, 4-(4-ethyl-2,2-dimethyl-[1,3]dioxolan-4-yl)-thiazol-2-yl, 4-(ethoxycarbonyl-hydroxy-methyl)-5-ethyl-thiazol-2-yl, 5-bromo-4-ethoxyoxalyl-thiazol-2-yl, 5-chloro-4-ethoxyoxalyl-thiazol-2-yl, 4-(1,1-bis-ethoxycarbonyl-ethyl)-thiazol- 2-yl, 5-(ethoxycarbonyl-hydroxy-methyl)-thiazol-2-yl or 4-((S)-1,2-bis-benzoyloxy-ethyl)-thiazol-2-yl these compounds can be prepared as described in PCT Int. Appl. WO 2007026761.

If it is desired to produce the compound of formula IX, where $R_3$ is a substituted thiazol-2-yl group, for example: 5-(1-ethoxycarbonyl-1-methyl-ethylsulfanyl)-thiazol-2-yl, 5-(1-ethoxycarbonyl-cyclopropylsulfamoyl)-thiazol-2-yl, 5-(1-methoxycarbonyl-cyclobutylsulfamoyl)-thiazol-2-yl, 5-(2,6-dimethyl-piperidine-1-sulfonyl)-thiazol-2-yl, 5-(2-ethoxycarbonyl-ethylsulfamoyl)-thiazol-2-yl, 5-(2-methoxycarbonyl-ethylsulfanyl)-thiazol-2-yl, 5-(2-methoxycarbonyl-pyrrolidine-1-sulfonyl)-thiazol-2-yl, 5-(ethoxycarbonylmethyl-sulfamoyl)-4-methyl-thiazol-2-yl, 5-(ethoxycarbonylmethyl-sulfamoyl)-thiazol-2-yl, 5-(methoxycarbonylmethyl-methyl-sulfamoyl)-4-methyl-thiazol-2-yl, 5-(methoxycarbonylmethyl-sulfamoyl)-thiazol-2-yl, 5-(piperidine-1-sulfonyl)-thiazol-2-yl, 5-imidazol-1-yl-thiazol-2-yl, 5-isopropylsulfamoyl-thiazol-2-yl, 5-t-butylsulfamoyl-thiazol-2-yl, or 5-((S)-2-methoxycarbonyl-pyrrolidine-1-sulfonyl)-thiazol-2-yl these compounds can be prepared as described in PCT Int. Appl. WO 2007006760.

If it is desired to produce the compound of formula IX, where $R_3$ is a substituted thiazol-2-yl group, for example: 5-(2-carboxy-ethylsulfanyl)-thiazol-2-yl this compound can be prepared as described in PCT Int. Appl. WO 2007006814.

If it is desired to produce the compound of formula IX, where $R_3$ is a substituted thiazol-2-yl group, for example: 4-methyl-5-(4-methyl-piperazine-1-sulfonyl)-thiazol-2-yl, 5-(4-methyl-piperazin-1-yl)-thiazol-2-yl, 5-chloro-4-ethoxycarbonylmethyl-thiazol-2-yl, or 5-chloro-4-ethoxycarbonylmethyl-thiazol-2-yl these compounds can be prepared as described in PCT Int. Appl. WO 2006058923.

If it is desired to produce the compound of formula IX, where $R_3$ is a substituted thiazol-2-yl group, for example: 5-fluoro-thiazolo[5,4-b]pyridin-2-yl or thiazolo[4,5-b]pyrazin-2-yl these compounds can be prepared as described in PCT Int. Appl. WO 2005090332.

If it is desired to produce the compound of formula IX, where $R_3$ is a substituted thiazol-2-yl group, for example: 4-ethoxycarbonylmethyl-5-imidazol-1-yl-thiazol-2-yl, 4-methyl-5-(1-methyl-piperidin-4-ylsulfamoyl)-thiazol-2-yl, 5-(2-ethoxycarbonyl-ethylsulfanyl)-4-methyl-thiazol-2-yl, 5-(4-methyl-piperazine-1-sulfonyl)-thiazol-2-yl, 5-(ethoxycarbonylmethyl-methyl-amino)-thiazol-2-yl, or 4-carboxymethylsulfanyl-thiazol-2-yl these compounds can be prepared as described in PCT Int. Appl. WO 2005066145.

If it is desired to produce the compound of formula IX, where $R_3$ is a substituted thiazol-2-yl group, for example: 4-methoxymethyl-thiazol-2-yl, 5-(1-amino-1-methyl-ethyl)-thiazol-2-yl, 5-trifluoromethyl-thiazol-2-yl, 4-acetoxymethyl-thiazol-2-yl or thiazolo[4,5-b]pyridin-2-yl these compounds can be prepared as described in PCT Int. Appl. WO 2004081001.

If it is desired to produce the compound of formula IX, where $R_3$ is a substituted thiazol-2-yl group, for example: 4-(1-hydroxy-1-methyl-ethyl)-thiazol-2-yl, 4-(t-butyl-dimethyl-silanyloxymethyl)-thiazol-2-yl, 4-[1-(t-butyl-dimethyl-silanyloxy)-ethyl]-thiazol-2-yl, 4-[(R)-1-(t-butyl-dimethyl-silanyloxy)-ethyl]-thiazol-2-yl, thieno[3,2-d]thiazol-2-yl or 4-[1-(t-butyl-dimethyl-silanyloxy)-ethyl]-thiazol-2-yl these compounds can be prepared as described in PCT Int. Appl. WO 2004076420.

If it is desired to produce the compound of formula IX, where $R_3$ is a substituted thiazol-2-yl group, for example: 5-fluoro-thiazol-2-yl this compound can be prepared as described in PCT Int. Appl. WO 2004072031.

If it is desired to produce the compound of formula IX, where $R_3$ is a substituted thiazol-2-yl group, for example: 4-(2-methoxycarbonyl-ethylsulfanylmethyl)-thiazol-2-yl, 4-[2-(t-butyl-dimethyl-silanyloxy)-ethyl]-thiazol-2-yl, 4-azidomethyl-thiazol-2-yl, or 4-methylcarbamoylmethyl-thiazol-2-yl these compounds can be prepared as described in PCT Int. Appl. WO 2004002481.

If it is desired to produce the compound of formula IX, where $R_3$ is a substituted thiazol-2-yl group, for example: 5-ethoxyoxalyl-thiazol-2-yl this compound can be prepared as described in U.S. Pat. No. 6,610,846.

If it is desired to produce the compound of formula IX, where $R_3$ is a substituted thiazol-2-yl group, for example: 4-hydroxymethyl-thiazol-2-yl this compound can be prepared as described in PCT Int. Appl. WO 2001085706.

If it is desired to produce the compound of formula IX, where $R_3$ is a substituted thiazol-2-yl group, for example: 5-formyl-thiazol-2-yl, 5-methoxymethyl-thiazol-2-yl, 5-(2-dimethylamino-ethoxy)-thiazolo[5,4-b]pyridin-2-yl, 5-ethoxycarbonylmethoxy-thiazolo[5,4-b]pyridin-2-yl, 5-t-butoxycarbonylmethoxy-thiazolo[5,4-b]pyridin-2-yl, 5-(2-hydroxy-ethoxy)-thiazolo[5,4-b]pyridin-2-yl, 5-carbamoylmethoxy-thiazolo[5,4-b]pyridin-2-yl, 5-methylcarbamoylmethoxy-thiazolo[5,4-b]pyridin-2-yl, 5-(2-t-butoxycarbonylamino-ethoxy)-thiazolo[5,4-b]pyridin-2-yl, 5-(2-amino-ethoxy)-thiazolo[5,4-b]pyridin-2-yl, 5-[2-(t-butoxycarbonyl-methyl-amino)-ethoxy]-thiazolo[5,4-b]pyridin-2-yl, 5-dimethylsulfamoyl-thiazol-2-yl, 4-(2-dimethylcarbamoyl-ethyl)-thiazol-2-yl, 5-(3-dimethylamino-propyl)-thiazol-2-yl, 5-(3-dimethylamino-propyl)-thiazol-2-yl, 5-[2-(t-butyl-dimethyl-silanyloxy)-ethoxy]-thiazolo[5,4-b]pyridin-2-yl, 5-(2-dimethylamino-ethylsulfanyl)-thiazol-2-yl, 5-(4-methyl-4H-[1,2,4]triazol-3-ylsulfanyl)-thiazol-2-yl, 5-(2-hydroxy-ethylsulfanyl)-thiazol-2-yl, 5-(3-hydroxy-propylsulfanyl)-thiazol-2-yl, 5-(2-t-butoxycarbonylamino-ethylsulfanyl)-thiazol-2-yl, 6-methoxy-thiazolo[4,5-b]pyrazin-2-yl, thiazolo[5,4-d]pyrimidin-2-yl, 5-methoxy-thiazolo[5,4-d]pyrimidin-2-yl, 5-dimethylamino-thiazolo[5,4-b]pyridin-2-yl, 5-hydroxymethyl-thiazolo[5,4-b]pyridin-2-yl, 5-(t-butyl-dimethyl-silanyloxymethyl)-thiazolo[5,4-b]pyridin-2-yl, 5-[(2-dimethylamino-ethyl)-methyl-amino]-thiazolo[5,4-b]pyridin-2-yl, 6-{[2-(t-butoxycarbonyl-methyl-amino)-ethyl]-methyl-amino}-thiazolo[5,4-b]pyridin-2-yl, 5-(2-dimethylamino-ethylamino)-thiazolo[5,4-b]pyridin-2-yl, 5-{[2-(t-butyl-dimethyl-silanyloxy)-ethyl]-methyl-amino}-thiazolo[5,4-b]pyridin-2-yl, 5-[2-(t-butyl-dimethyl-silanyloxy)-ethylamino]-thiazolo[5,4-b]pyridin-2-yl, 5-methylamino-thiazolo[5,4-b]pyridin-2-yl, 5-(1-t-butoxycarbonyl-piperidin-4-yloxy)-thiazolo[5,4-b]pyridin-2-yl, 5-((S)-1-t-butoxycarbonyl-pyrrolidin-3-yloxy)-thiazolo[5,4-b]pyridin-2-yl, 5-(1-t-butoxycarbonyl-pyrrolidin-3-yloxy)-thiazolo[5,4-b]pyridin-2-yl, 5-(1-t-butoxycarbonyl-azetidin-3-yloxy)-thiazolo[5,4-b]pyridin-2-yl, 5-(2-t-butoxycarbonylamino-2-methyl-propoxy)-thiazolo[5,4-b]pyridin-2-yl, 5-[3-(t-butoxycarbonyl-methyl-amino)-propoxy]-thiazolo[5,4-b]pyridin-2-yl, 4-(4-methyl-piperazin-1-ylmethyl)-thiazol-2-yl, 4-(4-methyl-[1,4]diazepan-1-ylmethyl)-thiazol-2-yl, 5-(4-acetyl-3-methyl-piperazin-1-ylmethyl)-thiazol-2-yl, 5-(4-methyl-piperazin-1-ylmethyl)-thiazol-2-yl, 5-(1-t-butoxycarbonyl-piperidin-4-ylsulfanyl)-thiazol-2-yl, 6-[2-(t-butyl-dimethyl-silanyloxy)-ethoxy]-benzothiazol-2-yl, 6-[2-(t-butoxycarbonyl-methyl-amino)-ethoxy]-benzothiazol-2-yl, 6-(2-dimethylamino-ethoxy)-benzothiazol-2-yl, 5-amino-thiazolo[5,4-b]pyridin-2-yl, or 5-oxo-4,5-dihydro-thiazolo[5,4-b]pyridin-2-yl, these compounds can be prepared as described in PCT Int. Appl WO 2007007886.

If it is desired to produce the compound of formula IX, where $R_3$ is a substituted pyridin-2-yl group, for example: 5-hydroxymethyl-pyridin-2-yl, 5-trifluoromethyl-pyridin-2-yl, 5-sulfamoyl-pyridin-2-yl, 5-bromo-6-methyl-pyridin-2-yl, 5-carboxymethyl-pyridin-2-yl, 5-methoxycarbonyl-pyridin-2-yl, 5-phenyl-pyridin-2-yl, 4-ethyl-pyridin-2-yl, isoquinolin-3-yl, 5-fluoro-pyridin-2-yl, 5-acetyl-pyridin-2-yl, 6-bromo-pyridin-2-yl, 4-ethoxycarbonyl-pyridin-2-yl, 4-methoxy-pyridin-2-yl, 5-nitro-pyridin-2-yl, 5-cyano-pyridin-2-yl, 5-carboxy-pyridin-2-yl, 6-methyl-pyridin-2-yl, 5-methyl-pyridin-2-yl, 5-chloro-pyridin-2-yl, 5-bromo-pyridin-2-yl, 4-methyl-pyridin-2-yl, quinolin-2-yl, pyridin-2-yl, or 5-carbamoyl-pyridin-2-yl these compounds are commercially available.

If it is desired to produce the compound of formula IX, where $R_3$ is a substituted pyridin-2-yl, for example: 4-bromo-pyridin-2-yl or 5-(diethoxy-phosphorylmethyl)-pyridin-2-yl these compounds can be prepared as described in PCT Int. Appl. WO 2008005964.

If it is desired to produce the compound of formula IX, where $R_3$ is a substituted pyridin-2-yl group, for example: 5-(t-butyl-dimethyl-silanyloxymethyl)-pyridin-2-yl this compound can be prepared as described in PCT Int. Appl. WO 2007122482.

If it is desired to produce the compound of formula IX, where $R_3$ is a substituted pyridin-2-yl group, for example: 5-benzyloxy-pyridin-2-yl this compound can be prepared as described in PCT Int. Appl. WO 2007117381.

If it is desired to produce the compound of formula IX, where $R_3$ is a substituted pyridin-2-yl group, for example: 4-(2,6-difluoro-phenoxy)-pyridin-2-yl, 4-(quinolin-5-yloxy)-pyridin-2-yl, 5-bromo-4-(2,6-difluoro-phenoxy)-pyridin-2-yl, 5-bromo-4-(5-ethoxycarbonyl-2,4-dimethyl-pyridin-3-yloxy)-pyridin-2-yl, 5-bromo-4-ethoxycarbonylmethyl-pyridin-2-yl, 4-ethoxycarbonylmethyl-pyridin-2-yl, 4-benzyloxy-5-bromo-pyridin-2-yl, 5-bromo-4-(4-methoxy-benzylsulfanyl)-pyridin-2-yl, 4-(4-methoxy-benzylsulfanyl)-pyridin-2-yl, 4-(2-chloro-5-ethoxycarbonyl-phenoxy)-pyridin-2-yl, or 4-benzyloxy-pyridin-2-yl these compounds can be prepared as described in PCT Int. Appl. WO 2007089512.

If it is desired to produce the compound of formula IX, where $R_3$ is a substituted pyridin-2-yl group, for example: 5-[5-(2-methoxy-phenyl)-1H-pyrazol-3-yl]-pyridin-2-yl this compound can be prepared as described in PCT Int. Appl. WO 2007061923.

If it is desired to produce the compound of formula IX, where $R_3$ is a substituted pyridin-2-yl group, for example: 5-benzyloxycarbonyl-pyridin-2-yl, 5-methoxymethoxymethyl-pyridin-2-yl, 3-trimethylsilyloxycarbonyl-pyridin-2-yl, 5-((E)-2-ethoxycarbonyl-vinyl)-pyridin-2-yl, or 5-methanesulfonyl-pyridin-2-yl these compounds can be prepared as described in U.S. Pat. Appl. US 2007099930.

If it is desired to produce the compound of formula IX, where $R_3$ is a substituted pyridin-2-yl group, for example: 5-(4-acetyl-3-methyl-piperazin-1-ylmethyl)-pyridin-2-yl, 5-methoxycarbonylmethylsulfanyl-pyridin-2-yl, or 2-aminothiazolo[5,4-b]pyridin-5-yl these compounds can be prepared as described in PCT Int. Appl WO 2007007886.

If it is desired to produce the compound of formula IX, where $R_3$ is a substituted pyridin-2-yl group, for example 5-((E)-2-ethoxycarbonyl-vinyl)-pyridin-2-yl this compound can be prepared as described in PCT Int. Appl. WO 2005066145.

If it is desired to produce the compound of formula IX, where $R_3$ is a substituted pyridin-2-yl group, for example: 5-(tetrahydro-furan-2-yl)-pyridin-2-yl, 5-methanesulfonylamino-pyridin-2-yl or 5-dimethylamino-pyridin-2-yl these compounds can be prepared as described in PCT Int. Appl. WO 2004052869.

If it is desired to produce the compound of formula IX, where $R_3$ is a substituted pyridin-2-yl group, for example: 5-[t-butoxycarbonyl-(2-methoxy-ethyl)-amino]-pyridin-2-yl this compound can be prepared as described in PCT Int. Appl. WO 2003015774.

If it is desired to produce the compound of formula IX, where $R_3$ is a substituted [1,3,4]thiadiazol-2-yl, group, for example: 5-hydroxymethyl-[1,3,4]thiadiazol-2-yl this compound can be prepared as described in *Pharmazie* 2003, 58, 367.

If it is desired to produce the compound of formula IX, where $R_3$ is a substituted [1,2,4]thiadiazol-5-yl, group, for example: 3-(2-hydroxy-ethyl)-[1,2,4]thiadiazol-5-yl, this compound can be prepared as described in Jpn. Kokai Tokkyo Koho JP 08151386.

If it is desired to produce the compound of formula IX, where $R_3$ is a substituted [1,3,4]thiadiazol-2-yl group, for example: 5-(thiazol-2-ylcarbamoylmethylsulfanyl)-[1,3,4]thiadiazol-2-yl, 5-(1-t-butoxycarbonyl-1-methyl-ethylsulfanyl)-[1,3,4]thiadiazol-2-yl, 5-ethoxycarbonylmethyl-[1,3,4]thiadiazol-2-yl, 5-ethoxycarbonyl-[1,3,4]thiadiazol-2-yl, 5-cyclopropyl-[1,3,4]thiadiazol-2-yl, 5-ethoxycarbonylmethylsulfanyl-[1,3,4]thiadiazol-2-yl, 5-ethylsulfanyl-[1,3,4]thiadiazol-2-yl, 5-trifluoromethyl-[1,3,4]thiadiazol-2-yl, 5-methylsulfanyl-[1,3,4]thiadiazol-2-yl, 5-furan-2-yl-[1,3,4]thiadiazol-2-yl, [1,3,4]thiadiazol-2-yl, 5-thioxo-4,5-dihydro-[1,3,4]thiadiazol-2-yl, 5-phenyl-[1,3,4]thiadiazol-2-yl, or 5-methyl-[1,3,4]thiadiazol-2-yl these compounds are commercially available.

If it is desired to produce the compound of formula IX, where $R_3$ is a substituted [1,3,4]thiadiazol-2-yl group, for example: 5-phenylsulfamoyl-[1,3,4]thiadiazol-2-yl, 5-isopropylsulfamoyl-[1,3,4]thiadiazol-2-yl, 5-(2-methoxy-ethylsulfamoyl)-[1,3,4]thiadiazol-2-yl, 5-(piperidine-1-sulfonyl)-[1,3,4]thiadiazol-2-yl, 5-(ethoxycarbonylmethyl-methyl-sulfamoyl)-[1,3,4]thiadiazol-2-yl, or 5-(ethoxycarbonylmethyl-sulfamoyl)-[1,3,4]thiadiazol-2-yl, these compounds can be prepared as described in PCT Int. Appl. WO2007006760.

If it is desired to produce the compound of formula IX, where $R_3$ is a substituted [1,3,4]thiadiazol-2-yl group, for example: 5-(3-ethoxycarbonyl-propylsulfanyl)-[1,3,4]thiadiazol-2-yl this compound can be prepared as described in PCT Int. Appl. WO 2005080360.

If it is desired to produce the compound of formula IX, where $R_3$ is a substituted [1,3,4]thiadiazol-2-yl group, for example: 5-(2-ethoxycarbonyl-ethylsulfanyl)-[1,3,4]thiadiazol-2-yl or 5-(2-methoxycarbonyl-ethyl)-[1,3,4]thiadiazol-2-yl these compounds can be prepared as described in PCT Int. Appl. WO 2007006814.

If it is desired to produce the compound of formula IX, where $R_3$ is a substituted [1,2,4]thiadiazol-5-yl group, for example: 3-methoxy-[1,2,4]thiadiazol-5-yl, 3-methyl-[1,2,4]thiadiazol-5-yl, [1,2,4]thiadiazol-5-yl, or 3-methylsulfanyl-[1,2,4]thiadiazol-5-yl these compounds are commercially available.

If it is desired to produce the compound of formula IX, where $R_3$ is a substituted [1,2,4]thiadiazol-5-yl group, for example: 3-hydroxymethyl-[1,2,4]thiadiazol-5-yl or 3-cyclopropyl-[1,2,4]thiadiazol-5-yl these compounds can be prepared as described in PCT Int. Appl. WO 2004081001.

If it is desired to produce the compound of formula IX, where $R_3$ is a substituted [1,2,4]thiadiazol-5-yl group, for example: 3-(t-butyl-dimethyl-silanyloxymethyl)-[1,2,4]thiadiazol-5-yl this compound can be prepared as described in PCT Int. Appl. WO 2004076420.

If it is desired to produce the compound of formula IX, where R₃ is a substituted [1,2,4]thiadiazol-5-yl group, for example: 3-(t-butyl-dimethyl-silanyloxymethyl)-[1,2,4]thiadiazol-5-yl this compound can be prepared as described in PCT Int. Appl. WO 2004076420.

If it is desired to produce the compound of formula IX, where R3 is a substituted 2H-[1,2,3]triazol-4-yl group, for example: 2-methyl-2H-[1,2,3]triazol-4-yl this compound can be prepared as described in PCT Int. Appl. WO 2007122482.

If it is desired to produce the compound of formula IX, where R₃ is a substituted 2H-[1,2,4]triazol-3-yl group, for example: 2-fluoro-phenyl-2H-[1,2,4]triazol-3-yl, 3,5-dimethoxy-phenyl-2H-[1,2,4]triazol-3-yl, 2,4-dinitro-phenyl-2H-[1,2,4]triazol-3-yl, 2-methoxy-phenyl-2H-[1,2,4] triazol-3-yl, 4-chloro-phenyl-2H-[1,2,4]triazol-3-yl, 3,4,5-trimethoxy-phenyl-2H-[1,2,4]triazol-3-yl, 5-isopropyl-2H-[1,2,4]triazol-3-yl, or 2H-[1,2,4]triazol-3-yl these compounds are commercially available.

If it is desired to produce the compound of formula IX, where R₃ is a substituted or unsubstituted pyrimidin-4-yl group, for example: pyrimidin-4-yl or 2-methyl-pyrimidin-4-yl these compounds are commercially available.

If it is desired to produce the compound of formula IX, where R₃ is a substituted pyridazin-3-yl group, for example: 6-methyl-pyridazin-3-yl, pyridazin-3-yl or 6-chloro-pyridazin-3-yl these compounds are commercially available.

If it is desired to produce the compound of formula IX, where R₃ is a thiazol-4-yl group, for example: thiazol-4-yl this compound can be prepared as described in PCT Int. Appl. WO 2004081001.

If it is desired to produce the compound of formula IX, where R₃ is a substituted dihydro-1H-[1,2,4]triazol-3-yl group, for example: 5-thioxo-2,5-dihydro-1H-[1,2,4]triazol-3-yl this compound is commercially available.

If it is desired to produce the compound of formula IX, where R₃ is a 1H-imidazol-2-yl group, for example: 1H-imidazol-2-yl this compound is commercially available.

If it is desired to produce the compound of formula IX, where R₃ is a 1H-benzoimidazol-2-yl group, for example: 1H-benzoimidazol-2-yl this compound is commercially available.

If it is desired to produce the compound of formula IX, where R₃ is a [1,2,5]thiadiazol-3-yl group, for example: [1,2,5]thiadiazol-3-yl this compound is commercially available.

If it is desired to produce the compound of formula IX, where R₃ is a oxazol-2-yl group, for example: oxazol-2-yl this compound is commercially available.

If it is desired to produce the compound of formula IX, where R₃ is a benzooxazol-2-yl group, for example: benzooxazol-2-yl this compound is commercially available.

If it is desired to produce the compound of formula IX, where R₃ is a substituted 4,5-dihydro-oxazol-2-yl group, for example: 4-trifluoromethyl-phenyl-4,5-dihydro-oxazol-2-yl this compound is commercially available.

If it is desired to produce the compound of formula IX, where R₃ is a substituted or unsubstituted pyrimidin-2-yl group, for example: pyrimidin-2-yl or 4-methyl-pyrimidin-2-yl these compounds are commercially available.

If it is desired to produce the compound of formula IX, where R₃ is a substituted [1,2,4]oxadiazol-5-yl group, for example: 3-methyl-[1,2,4]oxadiazol-5-yl this compound is commercially available.

If it is desired to produce the compound of formula IX, where R₃ is a isoxazol-3-yl group, for example: isoxazol-3-yl or 5-methyl-isoxazol-3-yl these compounds are commercially available.

If it is desired to produce the compound of formula IX, where R₃ is a [1,2,4]triazin-3-yl group, for example: [1,2,4]triazin-3-yl this compound is commercially available.

If it is desired to produce the compound of formula IX, where R₃ is a [1,2,4]triazolo[1,5-a]pyridin-2-yl group, for example: [1,2,4]triazolo[1,5-a]pyridin-2-yl this compound can be prepared as described in PCT Int. Appl. WO 2004081001.

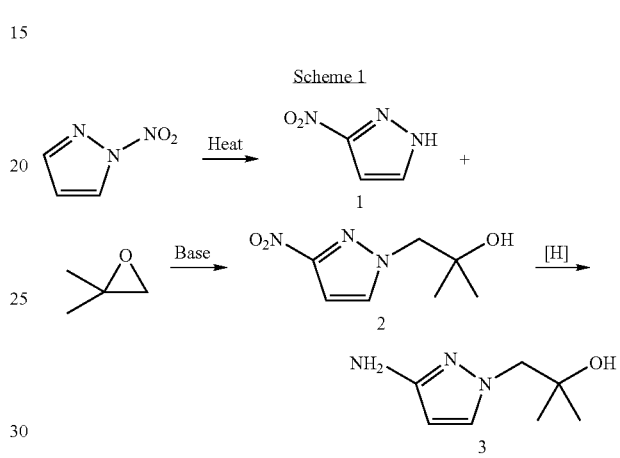

Scheme 1

Compound 3 may be synthesized following the reactions outlined in Scheme 1. The nitropyrazole of compound 1 can be prepared by methods described in the literature (under similar conditions to those described in *J. Org. Chem.*, 1971, 36, 3081; *J. Org. Chem.*, 1973, 38, 1777). Compound 1 may then be treated with an epoxide, such as 2,2-dimethyl-oxirane, under basic conditions to produce compound 2 (under similar conditions to those described in *Tet. Lett.* 1992, 33, 4069; *J. Med. Chem.* 1990, 33, 868; *J. Med. Chem.*, 2005, 48, 5162). The nitro group of compound 2 may then be converted to an amino group under standard reduction conditions to produce compound 3 as shown in Scheme 1 (under similar conditions to those described in *J. Chem. Soc., Perkin Trans. I* 1977, 672; U.S. Pat. Appl. US 2008021032).

Scheme 2

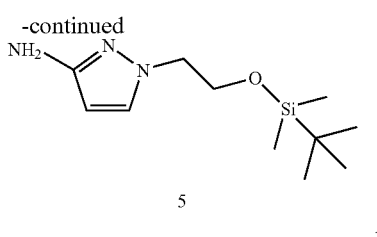

5

Compound 5 may be synthesized following the reactions outlined in Scheme 2. The nitropyrazole of compound 1 can be prepared by methods described in the literature (under similar conditions to those described in *J. Org. Chem.*, 1971, 36, 3081-4; *J. Org. Chem.*, 1973, 38, 1777-82). Compound 1 may then be treated with a commercially available reagent, for example, (2-bromo-ethoxy)-t-butyl-dimethyl-silane, under basic conditions to produce compound 4 (under similar conditions to those described in *J. Med. Chem.*, 2005, 48, 5162). A commercially available alkyl halide containing an unprotected hydroxyl group may also be converted to an appropriate reagent for this alkylation (for representative examples see Greene, T. W. Protective Groups in Organic Synthesis; John Wiley & Sons, Inc.: New York, 1991, p. 77-81). The nitro group of compound 4 may then be converted to an amino group under standard reduction conditions to produce compound 5 as shown in Scheme 2 (under similar conditions to those described in *J. Chem. Soc., Perkin Trans. I*, 1977, 672; U.S. Pat. Appl. US 2008021032).

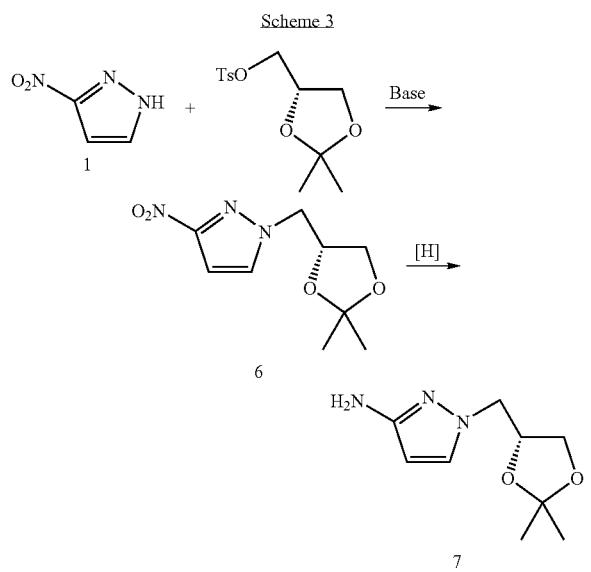

Compound 7 may be synthesized following the reactions outlined in Scheme 3. The nitropyrazole of compound 1 can be prepared by methods described in the literature (under similar conditions to those described in *J. Org. Chem.*, 1971, 36, 3081; *J. Org. Chem.*, 1973, 38, 1777). Compound 1 may then be treated with a commercially available reagent, for example, p-toluenesulfonic acid ((4R)-2,2-dimethyl-1,3-dioxolan-4-yl)methyl ester, under basic conditions to produce compound 6 (under similar conditions to those described in *J. Med. Chem.*, 1987, 30, 552; *J. Med. Chem.*, 2005, 48, 5162). The nitro group of compound 6 may then be converted to an amino group under standard reduction conditions to produce compound 7 as shown in Scheme 3 (under similar conditions to those described in *J. Chem. Soc., Perkin Trans. I*, 1977, 672). The opposite enantiomer may be made in the same manner utilizing starting materials of the opposite chirality.

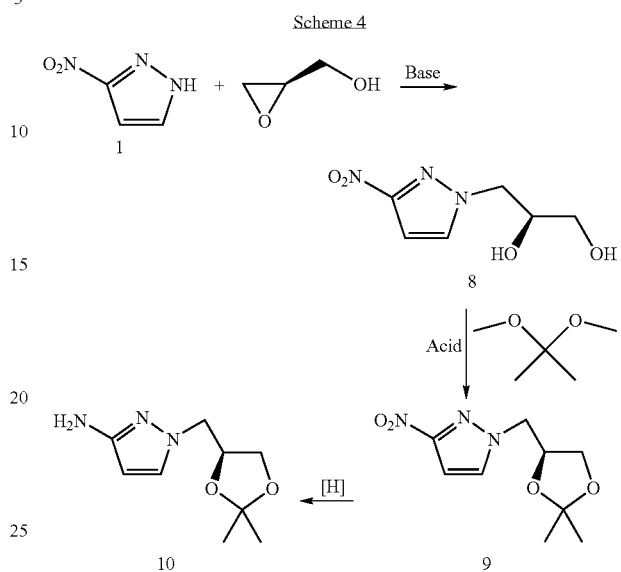

Compound 10 may be synthesized following the reactions outlined in Scheme 4. The nitropyrazole of compound 1 can be prepared by methods described in the literature (under similar conditions to those described in *J. Org. Chem.*, 1971, 36, 3081; *J. Org. Chem.*, 1973, 38, 1777). Compound 1 may then be treated with a commercially available reagent, for example, (R)-1-oxiranyl-methanol, under basic conditions to produce compound 8 (under similar conditions to those described in *Tet. Lett.* 1992, 33, 4069; *J. Med. Chem.* 1990, 33, 868; *J. Med. Chem.*, 2005, 48, 5162). Compound 8 may then be treated with 2,2-dimethoxypropane under acidic conditions to produce the compound 9 (for representative examples see Greene, T. W. Protective Groups in Organic Synthesis; John Wiley & Sons, Inc.: New York, 1991, p. 123-127; *J. Org. Chem.* 1986, 51, 2637). The nitro group of compound 9 may then be converted to an amino group under standard reduction conditions to produce compound 10 as shown in Scheme 4 (under similar conditions to those described in *J. Chem. Soc., Perkin Trans. I*, 1977, 672; U.S. Pat. Appl. US 2008021032). The opposite enantiomer may be made in the same manner utilizing starting materials of the opposite chirality.

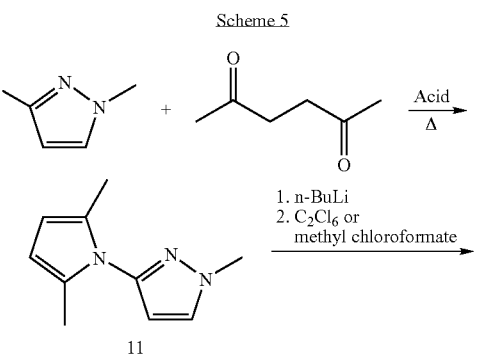

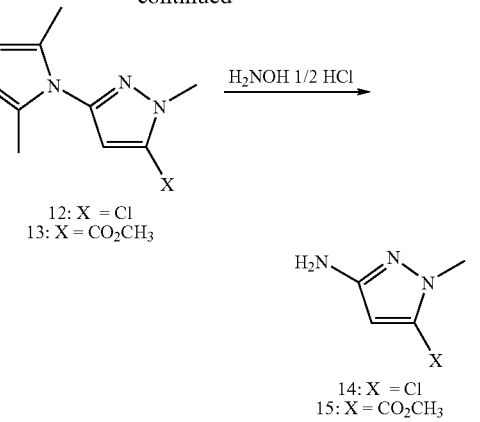

Compounds 14 and 15 may be synthesized following the reactions outlined in Scheme 5. Commercially available 1-methyl-1H-pyrazole-3-amine may be treated with acetonylacetone to afford compound 11 (under similar conditions to those described in *Synthesis,* 1998, 1599; PCT Int. Appl. WO 2005044264). The pyrazole of compound 11 can then be converted to either compound 12 or compound 13 by methods described in the literature (under similar conditions to those described in PCT Int. Appl WO 2003087098; Eur. Pat. Appl EP 0138622) The dimethylpyrrole protecting group then can be removed to unmask the corresponding free amine to produce compound 14 and 15 as shown in Scheme 5 (under similar conditions to those described in *Synthesis,* 1998, 1599; PCT Int. Appl. WO 2005044264 Eur. Pat. Appl. EP 0138622).

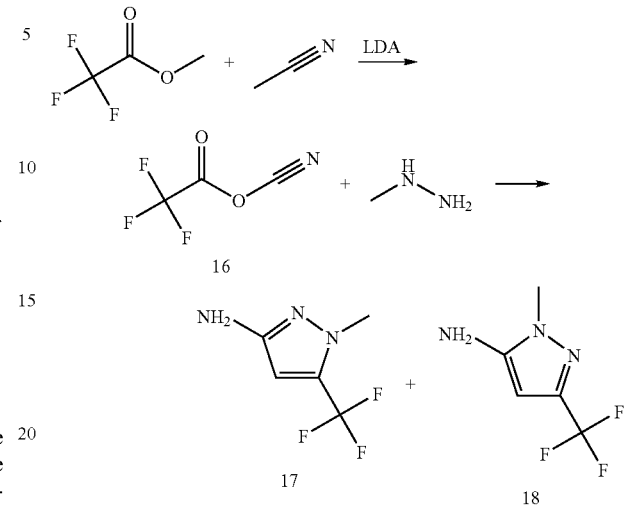

Compounds 17 and 18 may be synthesized following the reactions outlined in Scheme 6. Commercially available methyl trifluoracetate may be treated with acetonitrile in the presence of base to afford compound 16 (under similar conditions to those described in Eur. Pat. App. EP 0220025). Compound 16 can then be treated with methylhydrazine at elevated temperatures to afford a mixture of compounds 17 and 18 as shown in Scheme 6 (under similar conditions to those described in Eur. Pat. Appl. EP 0542388).

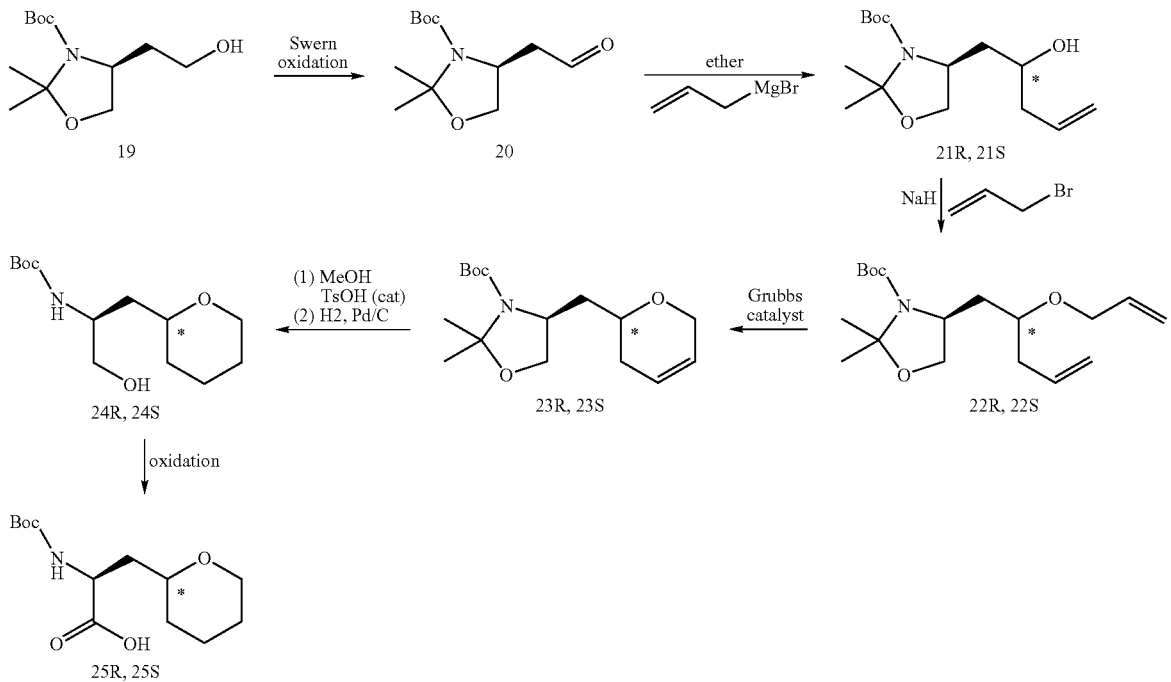

Compounds 25R and 25S may be synthesized following the reactions outlined in Scheme 7. Compound 19 can be prepared and oxidized under Swern conditions to give the corresponding aldehyde 20 as described in PCT Int. Appl. 2006094770; *J. Org. Chem.* 2001, 66, 206. Aldehyde 20 can be treated with allyl magnesium bromide to afford a mixture of diasteromeric alcohols 21R and 21S (under similar conditions to those described in *Synlett*, 2005, 13, 2083) which can be chromatographically separated. Either diastereomer 21R or 21S can be treated with base, such as sodium hydride and then allylated with allyl bromide to afford the corresponding ethers 22R or 22S. Either ether can be cyclized under Grubbs ring closing methasis conditions to give dihydropyrans 23R or 23S (under similar conditions to those described in *Tetrahedron Lett.*, 2007, 48, 1417). These compounds can be treated with methanol under acidic conditions and further hydrogenated to give the corresponding protected amino alcohols 24R or 24S. Oxidation of the alcohol to an acid yields the corresponding protected amino acids 25R or 25S.

Scheme 8

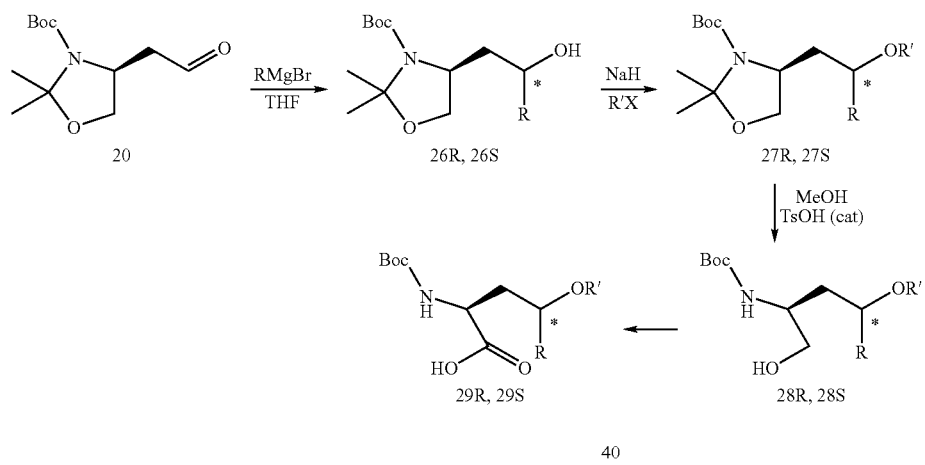

Compounds 29R and 29S may be synthesized following the reactions outlined in Scheme 8. Aldehyde 20 can be treated with alkyl magnesium bromides (under similar conditions to those described in *Synlett*, 2005, 13, 2083) to afford a mixture of diasteromeric alcohols 26R and 26S which can be chromatographically separated. Either diastereomer 26R or 26S can be treated with base, such as sodium hydride and then allylated with alkyl halides to afford the corresponding ethers 27R or 27S. These compounds can be treated with methanol under acidic conditions to give the corresponding protected amino alcohols 28R or 28S. Oxidation of the alcohol to an acid yields the corresponding protected amino acids 29R or 29S.

Scheme 9

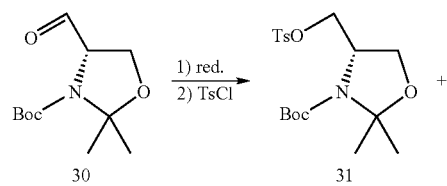

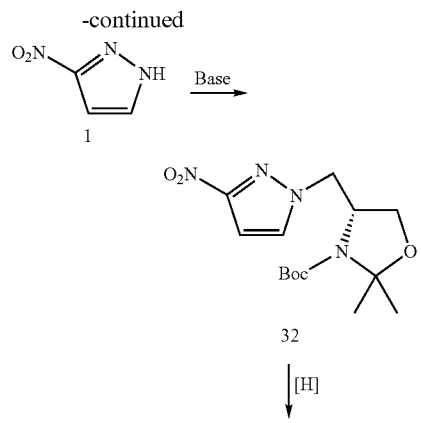

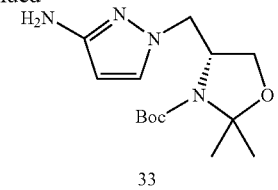

Compound 33 may be synthesized following the reactions outlined in Scheme 9. The nitropyrazole of compound 1 can be prepared by methods described in the literature (under similar conditions to those described in *J. Org. Chem.*, 1971, 36, 3081; *J. Org. Chem.*, 1973, 38, 1777). Compound 31 may be prepared by treating commercially available Compound 30 by a two step procedure involving first the reduction of the aldehyde to an alcohol followed by treatment with tosyl chloride. Compound 1 may then be treated with Compound 30 under basic conditions to produce compound 32 (under similar conditions to those described in *J. Med. Chem.*, 1987, 30, 552; *J. Med. Chem.*, 2005, 48, 5162). The nitro group of compound 32 may then be converted to an amino group under standard reduction conditions to produce compound 33 as shown in Scheme 9 (under similar conditions to those described in *J. Chem. Soc., Perkin Trans. I*, 1977, 672). The opposite enantiomer may be made in the same manner utilizing starting materials of the opposite chirality.

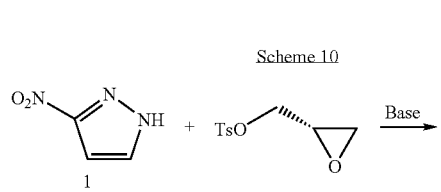

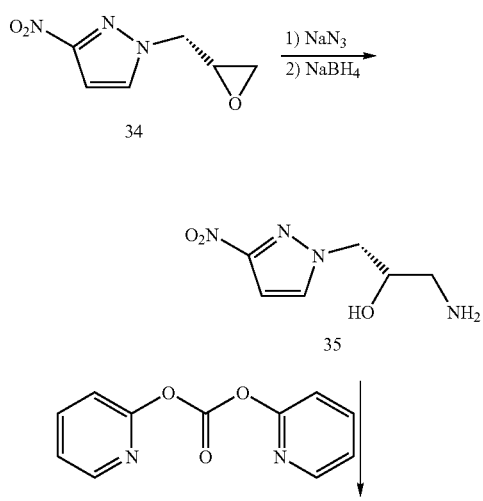

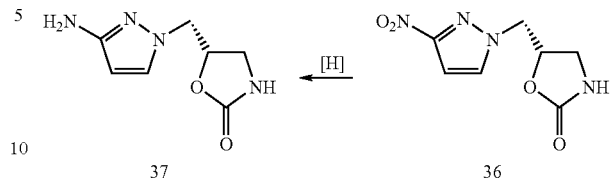

Compound 37 may be synthesized following the reactions outlined in Scheme 10. The nitropyrazole of compound 1 can be prepared by methods described in the literature (under similar conditions to those described in *J. Org. Chem.*, 1971, 36, 3081; *J. Org. Chem.*, 1973, 38, 1777). Compound 1 may then be treated with a commercially available reagent, for example, (S)-glycidol tosylate, under basic conditions to produce compound 34 (under similar conditions to those described in *Tet. Lett.* 1992, 33, 4069; *J. Med. Chem.* 1990, 33, 868; *J. Med. Chem.*, 2005, 48, 5162). Compound 34 may then be treated sodium azide, followed by sodium borohydride reduction to produce the compound 35. Compound 35 may then be treated with di-2-pyridyl carbonate to give compound 36. The nitro group of compound 36 may then be converted to an amino group under standard reduction conditions to produce compound 37 as shown in Scheme 10 (under similar conditions to those described in *J. Chem. Soc., Perkin Trans. I*, 1977, 672; U.S. Pat. Appl. US 2008021032). The opposite enantiomer may be made in the same manner utilizing starting materials of the opposite chirality.

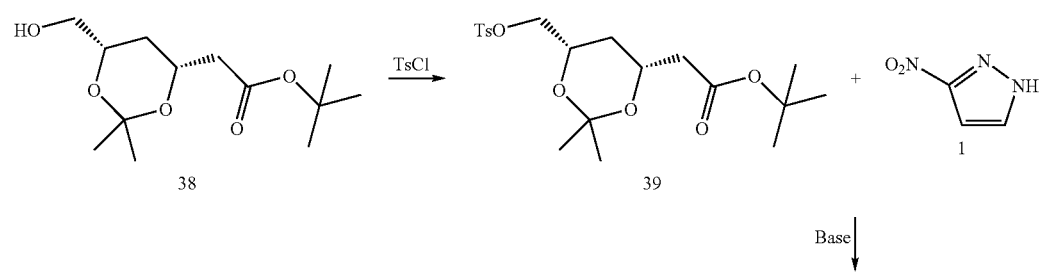

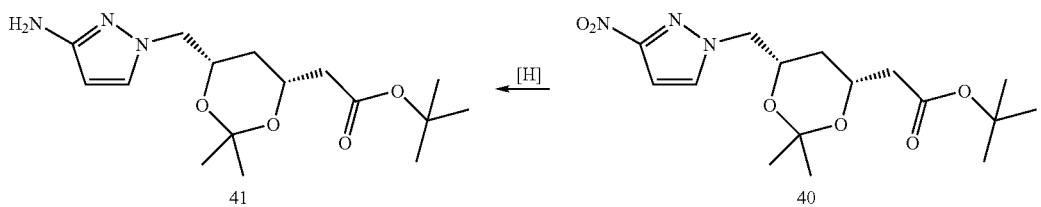

Compound 41 may be synthesized following the reactions outlined in Scheme 11. The nitropyrazole of compound 1 can be prepared by methods described in the literature (under similar conditions to those described in *J. Org. Chem.*, 1971, 36, 3081; *J. Org. Chem.*, 1973, 38, 1777). Compound 39 may be prepared by treating commercially available compound 38 by treatment with tosyl chloride. Compound 1 may then be treated with compound 39 under basic conditions to produce compound 40 (under similar conditions to those described in *J. Med. Chem.*, 1987, 30, 552; *J. Med. Chem.*, 2005, 48, 5162). The nitro group of compound 40 may then be converted to an amino group under standard reduction conditions to produce compound 41 as shown in Scheme 11 (under similar conditions to those described in *J. Chem. Soc., Perkin Trans. I*, 1977, 672).

opposite enantiomer may be made in the same manner utilizing starting materials of the opposite chirality.

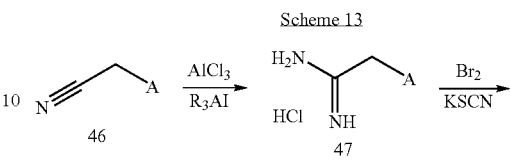

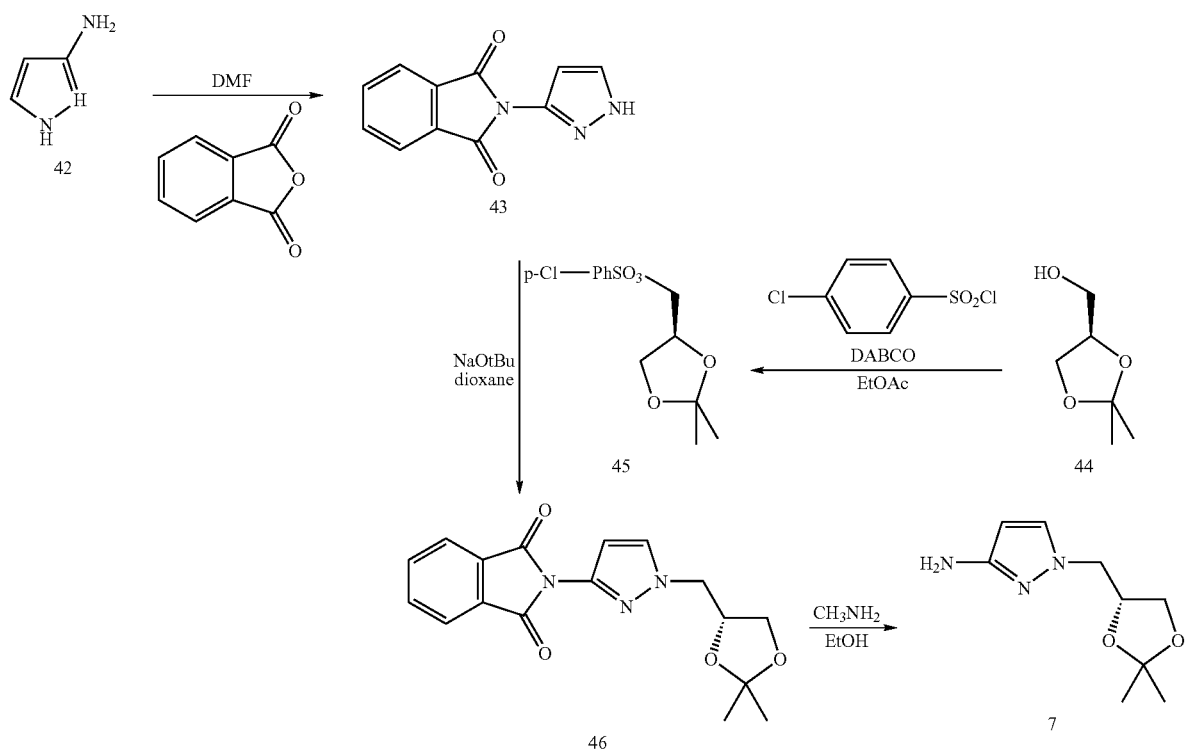

Compound 7 may also be synthesized following the reactions outlined in Scheme 12. aminopyrazole, compound 42 is commercially available and can be treated with phthalic anhydride to give compound 43 (under similar conditions to those described in *J. Med. Chem.* 2007, 50, 1584). Compound 44 may be treated with 4-chlorobenzenesulfonyl chloride under basic conditions to produce compound 45 (under similar conditions to those described in *Eur. J. Org. Chem.* 2006, 24, 5543). Compound 43 may then be treated with compound 45 under basic conditions to give compound 46 (under similar conditions to those described in *J. Med. Chem.*, 1987, 30, 552; *J. Med. Chem.*, 2005, 48, 5162). The phthalimide group of compound 46 may then be converted to an amino group under standard deprotection conditions to produce compound 7 as shown in Scheme 12 (under similar conditions to those described in *Angew. Chem., Int. Ed.*, 2007, 46, 8266). The -continued

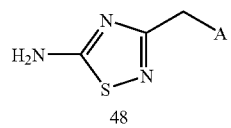

A = e.g. OMe, CH$_2$OMe, CH$_2$CF$_3$

Compounds of formula 48 may be synthesized following the reactions outlined in Scheme 13. Nitriles of formula 46, such as methoxy acetonitrile, 3-methoxy-propionitrile, and 4,4,4-trifluoro-butyronitrile are commercially available, or can be prepared using standard methods from alkyl halides, alkyl mesylates, alkyl tosylates or aldehydes and can be converted to Compounds of formula 47 by treatment with Lewis acids (under similar conditions to those described in PCT Int. Appl., 2005090291). Compounds of formula 47 can then be treated with bromine and potassium thiocyanate to give the corresponding thiadiazole compounds of formula 48 (under similar conditions to those described in Jpn. Kokai Tokkyo Koho, 04077477).

Scheme 14

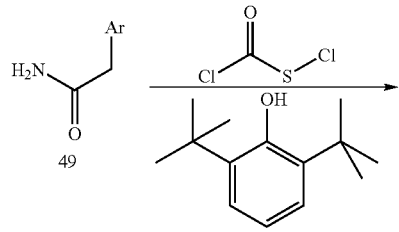

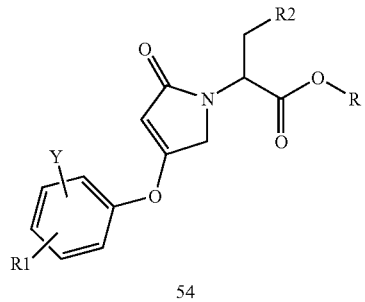

Compounds of formula 52 may be synthesized following the reactions outlined in Scheme 14. Aryl acetamides of formula 49, such asp-methoxyphenylacetamide are commercially available and can be converted to compounds of formula 50 by treatment with chlorocarbonylsulfenyl chloride (under similar conditions to those described in *J. Chem. Soc., Perk. Trans. 1*; 1981, 11, 2991). Compounds of formula 50 can then be treated with 4-toluenesulfonylcyanide to give the corresponding tosyl thiadiazole compounds of formula 51 which can then be treated with ammonia to give compounds of formula 52 (under similar conditions to those described in *Bioorg. & Med. Chem.*, 2003, 11, 5529).

Scheme 15

Compounds of formula 54, where R1 is alkyl amino, dialkyl amino, vinyl, or cyclopropyl may be synthesized following the reaction outlined in Scheme 15. Compounds of formula 53, where X is bromo or iodo, can be coupled with alkyl amines, dialkyl amines, vinyl tin compounds or cyclopropyl boronic acids with palladium catalysts to afford compounds of formula 54 (under similar conditions to those described in U.S. Pat. Appl. 2006270725; *Ange. Chem., Int. Ed.* 2008, 47, 6338-6361; Hartwig, J. F. in Handbook of Organopalladium Chemistry for Organic Synthesis 2002, 1 1051-1096; Farina, V.; Krishnamurthy, V.; Scott, W. J. The Stille reaction. Organic Reactions 1997, 50).

The invention will now be further described in the Examples below, which are intended as an illustration only and do not limit the scope of the invention.

EXAMPLES

Example 1

(S)-3-Cyclopentyl-N-[1-(2-hydroxy-2-methyl-propyl)-1H-pyrazol-3-yl]-2-(4-methoxy-2-oxo-2,5-dihydro-pyrrol-1-yl)-propionamide

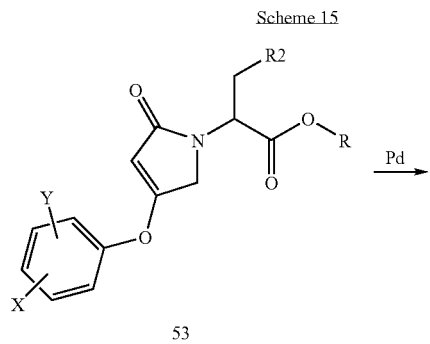

A solution of (S)-2-amino-3-cyclopentyl-propionic acid (commercial source—Chem-Impex) (2.00 g, 12.62 mmol) in saturated methanolic hydrogen chloride (30 mL) was heated at 50° C. for 18 h in a sealed tube. The mixture was cooled to 25° C. and the solution was concentrated to dryness to yield (S)-2-amino-3-cyclopentyl-propionic acid methyl ester hydrochloride in quantitative yield as a white powder (2.71 g).

A suspension of (S)-2-amino-3-cyclopentyl-propionic acid methyl ester hydrochloride (1.92 g, 9.13 mmol) in acetonitrile (18 mL) was treated with triethylamine (1.3 mL, 9.34 mmol). The mixture was then heated to 60° C., and kept at that temperature for 1 h. Then, additional triethylamine (1.3 mL, 9.34 mmol) was added followed by methyl-4-chloro-3-methoxy-(E)-2-butenoate (1367 mg, 8.30 mmol) in acetonitrile, via a syringe drop wise. The mixture was then heated to reflux by lowering into a pre-heated oil bath kept at 100° C. for 18 h, under nitrogen. The mixture was cooled to 25° C., and the precipitated triethylammonium hydrochloride was filtered off. The supernatant was concentrated and purified by ISCO flash chromatography (Teledyne Isco RediSep Flash Column 120 g; 0% to 100% ethyl acetate/hexanes) to afford, (S)-3-cyclopentyl-2-(4-methoxy-2-oxo-2,5-dihydro-pyrrol-1-yl)-propionic acid methyl ester (1.42 g, 58.2%) as light yellow oil: $^1$H NMR (DMSO-$d_6$, 300 MHz) δ ppm 1.06 (m, 2H), 1.36-1.90 (m, 9H), 3.61 (s, 3H), 3.77 (s, 3H), 3.94 (AB, Jgem=17.8 Hz, 2H), 4.62 (dd, J=4.8 Hz, 11.0 Hz, 1 H), 5.16 (s 1H).

To a solution containing (S)-3-cyclopentyl-2-(4-methoxy-2-oxo-2,5-dihydro-pyrrol-1-yl)-propionic acid methyl ester (1.42 g, 5.20 mmol) in tetrahydrofuran (10 mL) was treated with an aqueous solution of lithium hydroxide monohydrate (273 mg, 6.4 mmol) in water (10 mL). The mixture was stirred at 25° C. for 2.5 h, it was then acidified with 2N aqueous hydrochloric acid. The mixture was extracted with dichloromethane (2×30 mL). The combined organic layers was dried over magnesium sulfate and concentrated to afford (S)-3-cyclopentyl-2-(4-methoxy-2-oxo-2,5-dihydro-pyrrol-1-yl)-propionic acid, (855 mg, 65%), as an off-white solid: $^1$H NMR (400 MHz, DMSO-$d_6$) δ ppm 1.08 (m, 2H), 1.36-1.88 (m, 9H), 3.78 (s, 3H), 3.95 (J=17.7 Hz, 2H), 4.54 (dd, J=4.5 Hz, 11.0 Hz, 1H), 5.16 (s 1H), 12.80 (s, 1H).

A solution of (S)-3-cyclopentyl-2-(4-methoxy-2-oxo-2,5-dihydro-pyrrol-1-yl)-propionic acid (643 mg, 2.53 mmol) in benzene (8 mL) was treated with oxalyl chloride (342 mg, 2.7 mmol), and N,N-dimethylformamide (1 drop). Effervescence was observed. The reaction mixture was stirred for 3 h at 25° C., under nitrogen. The reaction mixture was concentrated, and dissolved in dichloromethane (8 mL) and treated with 1-(3-amino-pyrazol-1-yl)-2-methyl-propan-2-ol (prepared in U.S. Pat. Appl. US2008021032 Example 80, 442 mg, 2.8 mmol), and N,N-diisopropylethylamine (497 mg, 3.8 mmol). The reaction mixture was stirred at 25° C., under nitrogen for 18 h. The reaction mixture was diluted with dichloromethane, washed with 2N aqueous hydrochloric acid, saturated sodium chloride solution and dried. The organic layer was concentrated, and the crude product was purified by ISCO flash chromatography (Teledyne Isco RediSep Flash Column 80 g; 0% to 10% methanol/dichloromethane) to afford (S)-3-cyclopentyl-N-[1-(2-hydroxy-2-methyl-propyl)-1H-pyrazol-3-yl]-2-(4-methoxy-2-oxo-2,5-dihydro-pyrrol-1-yl)-propionamide (542 mg, 55%) as an off-white powder: LR-ES-MS m/z calculated for $C_{20}H_{30}N_4O_4$ [M]$^+$ 390, observed [M+H]$^+$ 391; $^1$H NMR (DMSO-$d_6$, 300 MHz) δ ppm 1.04 (s, 3 H), 1.06 (s, 3H), 1.08 (m, 1H), 1.26 (m, 1H), 1.44 (m, 2H), 1.50-1.86 (m, 7H), 3.78 (s, 3H), 3.88 (s, 2H), 3.95 (d, J$_{gem}$=18.0 Hz, 1H), 4.33 (d, J$_{gem}$=18.0 Hz, 1H), 4.66 (s, 1H), 4.78 (dd, J=4.6 Hz, 10.6 Hz, 1H), 5.15 (s 1H), 6.42 (d, J=2.3 Hz, 1H), 7.52 (d, J=2.3 Hz, 1H), 10.70 (s, 1H).

Example 2

(S)-N-(5-Chloro-thiazol-2-yl)-3-cyclopentyl-2-(4-methoxy-2-oxo-2,5-dihydro-pyrrol-1-yl)-propionamide

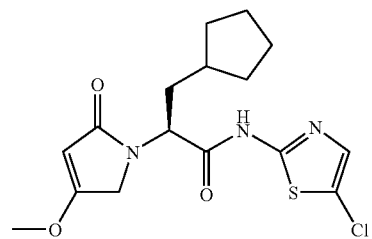

A solution of (S)-3-cyclopentyl-2-(4-methoxy-2-oxo-2,5-dihydro-pyrrol-1-yl)-propionic acid (prepared as in Example 1, 122.3 mg, 0.48 mmol) in benzene (10 mL) was treated with oxalyl chloride (92 mg, 0.72 mmol), and N,N-dimethylformamide (1 drop). Effervescence was observed. The reaction mixture was stirred for 3 h at 25° C., under nitrogen. The reaction mixture was concentrated, and dissolved in dichloromethane (15 mL) and treated with 2-amino-5-chlorothiazole (103 mg, 0.6 mmol), and N,N-diisopropylethylamine (255 mg, 2.0 mmol). The reaction mixture was stirred at 25° C., under nitrogen for 18 h. The reaction mixture was diluted with methylene chloride, washed with 2N aqueous hydrochloric acid, saturated sodium chloride solution and dried. The organic layer was concentrated, and the crude product was purified by ISCO flash chromatography (Teledyne Isco RediSep Flash Column 25 g; 10% to 80% ethyl acetate/hexanes) to afford, (S)-N-(5-chloro-thiazol-2-yl)-3-cyclopentyl-2-(4-methoxy-2-oxo-2,5-dihydro-pyrrol-1-yl)-propionamide (38 mg, 22%) as a white powder: LR-ES-MS m/z calculated for $C_{16}H_{20}ClN_3O_3S$ [M]$^+$ 370, observed 370 [M]$^+$; $^1$H NMR (300 MHz, DMSO-$d_6$) δ ppm 0.97-1.97 (m, 11H) 3.79 (s, 3H) 4.02 (d, J=17.8 Hz, 1H) 4.25 (d, J=17.8 Hz, 1H), 4.87 (dd, J=10.3, 4.8 Hz, 1H) 5.18 (s, 1H) 7.54 (s, 1H) 12.75 (s, 1H).

Example 3

(S)-N-Benzothiazol-2-yl-3-cyclopentyl-2-(4-methoxy-2-oxo-2,5-dihydro-pyrrol-1-yl)-propionamide

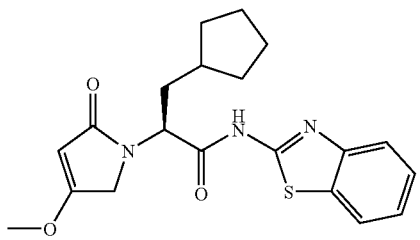

A solution of (S)-3-cyclopentyl-2-(4-methoxy-2-oxo-2,5-dihydro-pyrrol-1-yl)-propionic acid (prepared as in Example 1, 122.3 mg, 0.48 mmol) in benzene (10 mL) was treated with oxalyl chloride (92 mg, 0.72 mmol), and N,N-dimethylformamide (1 drop). Effervescence was observed. The reaction mixture was stirred for 3 h at 25° C., under nitrogen. The reaction mixture was concentrated, and dissolved in dichloromethane (15 mL) and treated with 2-aminobenzothiazole (97 mg, 0.64 mmol), and N,N-diisopropylethylamine (94 mg, 0.73 mmol). The reaction mixture was stirred at 25° C., under nitrogen for 18 h. The reaction mixture was diluted with methylene chloride, washed with 2N aqueous hydrochloric acid, saturated sodium chloride solution and dried. The organic layer was concentrated, and the crude product was purified by ISCO flash chromatography (Teledyne Isco RediSep Flash Column 25 g; 10% to 80% ethyl acetate/hexanes) to afford, (S)-N-benzothiazol-2-yl-3-cyclopentyl-2-(4-methoxy-2-oxo-2,5-dihydro-pyrrol-1-yl)-propionamide (60 mg, 32%) as a white powder: LR-ES-MS m/z calculated for $C_{20}H_{23}N_3O_3S$ [M]$^+$ 385, observed [M+H]$^+$ 386; $^1$H NMR (300 MHz, DMSO-d$_6$) δ ppm 0.99-1.97 (m, 11H) 3.80 (s, 3H) 4.04 (d, J=17.9 Hz, 1H) 4.30 (d, J=17.9 Hz, 1H) 4.93 (dd, J=10.4, 5.0 Hz, 1H) 5.20 (s, 1H) 7.31 (t, J=7.8 Hz, 1H) 7.44 (t, J=7.8 Hz, 1H) 7.76 (d, J=7.8 Hz, 1H) 7.98 (d, J=7.8 Hz, 1H) 12.73 (s, 1H).

Example 4

((S)-3-Cyclopentyl-2-(4-methoxy-2-oxo-2,5-dihydro-pyrrol-1-yl)-N-(3-methyl-[1,2,4]thiadiazol-5-yl)-propionamide

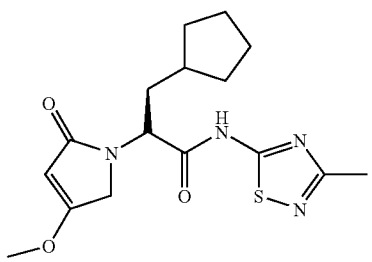

A solution of (S)-3-cyclopentyl-2-(4-methoxy-2-oxo-2,5-dihydro-pyrrol-1-yl)-propionic acid (prepared as in Example 1, 102 mg, 0.40 mmol) in dichloromethane (2 mL) was treated with oxalyl chloride (218 μL of 2M solution in dichloromethane), and N,N-dimethylformamide (1 drop). Effervescence was observed. The reaction mixture was stirred for 0.5 h at 25° C., under nitrogen. The reaction mixture was concentrated, and dissolved in N,N-dimethylformamide (2 mL) and treated with 5-amino-3-methyl-1,2,4-thiadiazole (48 mg, 0.41 mmol), and 2,6-lutidine (64 mg, 0.60 mmol). The reaction mixture was stirred at 25° C., under nitrogen for 18 h. The reaction mixture was diluted with methylene chloride, washed with 2N aqueous hydrochloric acid, saturated sodium chloride solution and dried. The organic layer was concentrated, and the crude product was purified by ISCO flash chromatography (Teledyne Isco RediSep Flash Column 4 g; 0% to 35% methanol/dichloromethane) to afford ((S)-3-cyclopentyl-2-(4-methoxy-2-oxo-2,5-dihydro-pyrrol-1-yl)-N-(3-methyl-[1,2,4]thiadiazol-5-yl)-propionamide (30 mg, 22% as a white powder: LR-ES-MS m/z calculated for $C_{16}H_{22}N_4O_3S$ [M]$^+$ 350, observed [M+H]$^+$ 351; $^1$H NMR (300 MHz, CDCl$_3$) δ ppm 0.74-0.96 (m, 1H) 1.03-1.42 (m, 3H) 1.38-2.15 (m, 7H) 2.53 (s, 3H) 3.83 (s, 3H) 3.98 (d, J=17.8 Hz, 1H) 4.13 (d, J=17.8 Hz, 1H) 5.24 (t, J=7.7 Hz, 1H) 5.38 (s, 1H).

Example 5

(S)-3-Cyclopentyl-N-[1-(2-methoxy-2-methyl-propyl)-1H-pyrazol-3-yl]-2-(4-methoxy-2-oxo-2,5-dihydro-pyrrol-1-yl)-propionamide

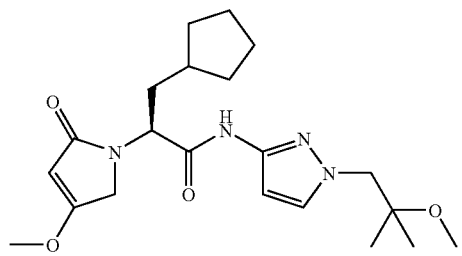

A solution of 1-nitro-1H-pyrazole (4.00 g, 35.4 mmol) in 40 mL of benzonitrile was refluxed for 2 h. After being cooled to 25° C., the mixture was poured into hexanes (160 mL). A white solid precipitated which was filtered and dried in vacuo, to afford 3-nitro-1H-pyrazole (3.16 g, 79%): H$^1$-NMR (400 MHz, DMSO-d$_6$) δ 7.01 (1H, d, J=2.4 Hz), 8.01 (d, 1H, J=3.4 Hz).

A solution of 3-nitro-1H-pyrazole (200 mg, 1.77 mmol) in N,N-dimethylformamide (5 mL) was treated with solid potassium carbonate (352 mg, 2.55 mmol) and 2,2-dimethyl-oxirane (3.14 mL, 3.54 mmol) and placed in a sealed tube and heated at 100° C. for 1 h in an oil bath. After this time the reaction was cooled to 25° C. and diluted with water (10 mL) and extracted with ethyl acetate (3×10 mL). The organic layers were then combined and dried over sodium sulfate, filtered and concentrated in vacuo. Purification by AnaLogix Intelliflash system (12 g column, 50% ethyl acetate/hexanes to 60% ethyl acetate/hexanes) afforded 2-methyl-1-(3-nitro-pyrazol-1-yl)-propan-2-ol (175 mg, 54%) as a clear colorless oil: ES-HRMS m/z calculated for $C_7H_{11}N_3O_3$ [M+H]$^+$ 186.0873, observed 186.0873; $^1$H NMR (300 MHz, CDCl$_3$) δ ppm 1.25 (s, 6H), 2.11 (br. s., 1H), 4.18 (s, 2H), 6.92 (d, J=2.4 Hz, 1H), 7.60 (d, J=2.4 Hz, 1H).

In a round bottom flask was placed 2-methyl-1-(3-nitro-pyrazol-1-yl)-propan-2-ol (1.39 g, 7.51 mmol) dissolved in N,N-dimethylformamide (25 mL). To this solution was added sodium hydride (667 mg, 9.01 mmol, 60% dispersion in oil) and it was stirred for 15 min until gas evolution ceased. To this was then added methyl iodide (700 μL, 11.26 mmol) and it was stirred for 2 h at 25° C. The reaction was then quenched with water (250 mL). The reaction was transferred to a separatory funnel and extracted with ethyl acetate (250 mL). The organics were dried over sodium sulfate and then concentrated with silica gel (3 g) in vacuo and purified on Biotage Flash chromatography system (40M column, silica gel, 20% ethyl acetate/hexanes) to afford 1-(2-methoxy-2-methyl-propyl)-3-nitro-1H-pyrazole (1.33 g, 88%) as a colorless oil.

In a Parr shaker bottle was placed 1-(2-methoxy-2-methyl-propyl)-3-nitro-1H-pyrazole (1.33 g, 6.68 mmol), 10% palladium on activated carbon (135 mg) and ethanol (50 mL). The bottle was then placed on the Parr shaker at 50 psi of hydrogen pressure for 2 h. The reaction was then filtered through a pad of celite and washed with ethanol and concentrated in vacuo with silica gel (3 g) and purified on Biotage Flash chromatography system (40S column, silica gel, 5% methanol/ethyl acetate) to afford 1-(2-methoxy-2-methyl-propyl)-1H-pyrazol-3-ylamine (802 mg, 71%) as a colorless oil: ES-HRMS m/z calculated for $C_{23}H_{33}N_3O_5S$ [M+H]$^+$ 464.2214, observed 464.2208; ¹H NMR (300 MHz, DMSO-d₆) δ ppm 1.04 (s, 6H), 3.13 (s, 3H), 3.80 (s, 2H), 4.48 (brs, 2H), 5.38 (d, J=2.3 Hz, 1H), 7.21 (d, J=2.3 Hz, 1H).

A solution of (S)-3-cyclopentyl-2-(4-methoxy-2-oxo-2,5-dihydro-pyrrol-1-yl)-propionic acid (prepared as in Example 1, 99 mg, 0.38 mmol), 1-(2-methoxy-2-methyl-propyl)-1H-pyrazol-3-yl-amine (85 mg, 0.49 mmol), benzotrizol-1-yl-oxy-tris(dimethylamino)phosphonium hexafluorophosphate (208 mg, 0.46 mmol), N,N-diisopropylethylamine (148 mg, 1.15 mmol) in dichloromethane (5 mL) was stirred for 18 h under nitrogen at 23° C. The reaction mixture was diluted with dichloromethane, washed with 2N aqueous hydrochloric acid, saturated sodium chloride solution and dried. The organic layer was concentrated, and the crude product was purified by ISCO flash chromatography (Teledyne Isco RediSep Flash Column 12 g silica gel; 0% to 10% methanol/dichloromethane) to afford, (S)-3-cyclopentyl-N-[1-(2-methoxy-2-methyl-propyl)-1H-pyrazol-3-yl]-2-(4-methoxy-2-oxo-2,5-dihydro-pyrrol-1-yl)-propionamide (117 mg, 74%) as a white foam: LR-ES-MS m/z calculated for C₂₁H₃₂N₄O₄ [M]⁺ 404, observed [M+H]⁺ 405; ¹H NMR (300 MHz, CDCl₃) δ ppm 1.02-1.36 (m, 2H) 1.10 (br. s., 6H) 1.38-2.10 (m, 9H) 3.20 (br. s., 3H) 3.78 (br. s., 3H) 3.88 (d, J=17.8 Hz, 1H) 3.96 (br. s., 2H) 4.09 (d, J=17.8 Hz, 1H) 4.74-4.89 (m, 1H) 5.10 (br. s., 1H) 6.57 (br. s., 1H) 7.32 (br. s., 1H) 8.85 (br. s., 1H).

Example 6

(S)-3-Cyclopentyl-2-(4-methoxy-2-oxo-2,5-dihydro-pyrrol-1-yl)-N-(1-methyl-1H-pyrazol-3-yl)-propionamide

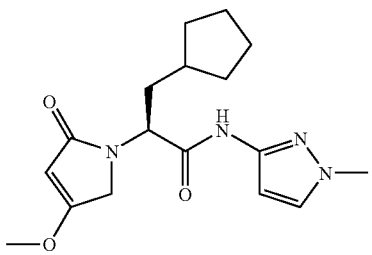

A solution of (S)-3-cyclopentyl-2-(4-methoxy-2-oxo-2,5-dihydro-pyrrol-1-yl)-propionic acid (prepared as in Example 1, 83 mg, 0.32 mmol) in benzene (10 mL) was treated with oxalyl chloride (49 mg, 0.38 mmol), and N,N-dimethylformamide (2 drops). Effervescence was observed. The reaction mixture was stirred for 1.5 h at 25° C., under nitrogen. The reaction mixture was concentrated, and dissolved in dichloromethane (10 mL) and treated with 1-methyl-1H-pyrazol-3-ylamine (52 mg, 0.53 mmol), and N,N-diisopropylethylamine (127 mg, 0.97 mmol). The reaction mixture was stirred at 25° C., under nitrogen for 18 h. The reaction mixture was diluted with methylene chloride, washed with 2N aqueous hydrochloric acid, saturated sodium chloride solution and dried. The organic layer was concentrated, and the crude product was purified by ISCO flash chromatography (Teledyne Isco RediSep Flash Column 4 g; 50% to 100% ethyl acetate/hexanes) to afford, (S)-3-cyclopentyl-2-(4-methoxy-2-oxo-2,5-dihydro-pyrrol-1-yl)-N-(1-methyl-1H-pyrazol-3-yl)-propionamide (44 mg, 41%) as an amorphous white solid: LR-ES-MS m/z calculated for C₁₇H₂₄N₄O₃ [M]⁺ 332, observed [M+H]⁺ 333; ¹H NMR (300 MHz, DMSO-d₆) δ ppm 0.98-1.89 (m, 11H) 3.72 (s, 3H) 3.77 (s, 3H) 3.95 (d, J=17.9 Hz, 1H) 4.31 (d, J=17.9 Hz, 1H) 4.77 (dd, J=10.0, 5.1 Hz, 1H) 5.15 (s, 1H) 6.37 (d, J=2.1 Hz, 1H) 7.53 (d, J=2.1 Hz, 1H) 10.65 (s, 1H).

Example 7

(2-{3-[(S)-3-Cyclopentyl-2-(4-methoxy-2-oxo-2,5-dihydro-pyrrol-1-yl)-propionylamino]-pyrazol-1-yl}-ethyl)-carbamic acid t-butylester

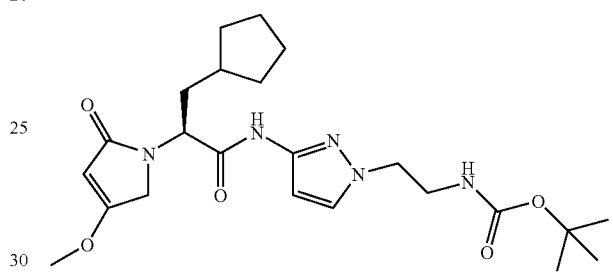

To a solution of 3-nitro-1H-pyrazole (prepared as in Example 5, 1.56 g, 13.79 mmol) in anhydrous N,N-dimethylformamide (20 mL), a 60% dispersion of sodium hydride in mineral oil (592 mg, 25.72 mmol) was added while stirring under nitrogen. After the effervescence ceased and the mixture was stirred for an additional 15 min, (2-bromoethyl)-carbamic acid t-butyl ester (3.94 g, 17.58 mmol) was added. The mixture was continued to stir under nitrogen for an additional 12 h. The solvent was removed in vacuo, diluted with dichloromethane and then washed with a 1N aqueous hydrochloric acid solution, and a saturated sodium chloride solution. The crude product thus obtained was purified by ISCO flash column chromatography (Teledyne Isco RediSep Flash Column 40 g; 0% ethyl acetate/hexanes to 50% ethyl acetate/hexanes) to afford 1-(2-ethyl-carbamic acid t-butylester)-3-nitro-1H-pyrazole (1.07 g, 30%) as a white solid.

To a solution containing 1-(2-ethyl-carbamic acid t-butylester)-3-nitro-1H-pyrazole (205 mg, 0.80 mmol) in ethanol (10 mL), palladium, 10 wt. % on activated carbon, wet (~50 mg) was added to the solution. The vial was charged with hydrogen gas (via balloon) and the mixture was stirred for 3 h at 25° C. The mixture was passed through a plug of celite and concentrated in vacuo to afford 1-(2-ethyl-carbamic acid t-butylester)-3-amino-1H-pyrazole (177 mg, 86%) as a solid.

A solution of (S)-3-cyclopentyl-2-(4-methoxy-2-oxo-2,5-dihydro-pyrrol-1-yl)-propionic acid (prepared as in Example 1, 78 mg, 0.30 mmol) in benzene (8 mL) was treated with oxalyl chloride (46 mg, 0.36 mmol), and N,N-dimethylformamide (1 drop). Effervescence was observed. The reaction mixture was stirred for 2 h at 25° C., under nitrogen. The reaction mixture was concentrated, and dissolved in dichloromethane (8 mL) and treated with 1-(2-ethyl-carbamic acid t-butylester)-3-amino-1H-pyrazole (82 mg, 0.36 mmol), and N,N-diisopropylethylamine (118 mg, 0.90 mmol). The reaction mixture was stirred at 25° C., under nitrogen for 18 h. The reaction mixture was diluted with dichloromethane, washed with 2N aqueous hydrochloric acid, saturated sodium chloride solution and dried. The organic layer was concentrated, and the crude product was purified by ISCO flash chromatography (Teledyne Isco RediSep Flash Column 12 g; 0% to 5% methanol/dichloromethane) to afford, (2-{3-[(S)-3-cyclopentyl-2-(4-methoxy-2-oxo-2,5-dihydro-pyrrol-1-yl)-propionylamino]-pyrazol-1-yl}-ethyl)-carbamic acid t-butyl ester (65 mg, 47%) as an off-white solid: LR-ES-MS m/z calculated for $C_{23}H_{35}N_5O_5$ $[M]^+$ 461, observed $[M+H]^+$ 462; $^1$H NMR (300 MHz, DMSO-$d_6$) δ ppm 1.03-1.88 (m, 11H) 1.36 (s, 9H) 3.21-3.32 (m, 2H) 3.78 (s, 3H) 3.96 (m, J=17.8 Hz, 1H) 3.99-4.05 (m, 2H) 4.32 (d, J=17.8 Hz, 1H) 4.78 (dd, J=9.8, 5.3 Hz, 1H) 5.15 (s, 1H) 6.40 (d, J=2.1 Hz, 1H) 6.74-7.04 (m, 1H) 7.52 (d, J=2.1 Hz, 1H) 10.72 (s, 1H).

Example 8

(S)-3-Cyclopentyl-N-(5-fluoro-thiazol-2-yl)-2-(4-methoxy-2-oxo-2,5-dihydro-pyrrol-1-yl)-propionamide

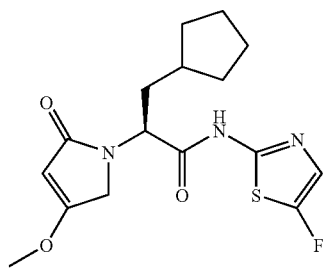

A solution of (S)-3-cyclopentyl-2-(4-methoxy-2-oxo-2,5-dihydro-pyrrol-1-yl)-propionic acid (prepared as in Example 1, 81 mg, 0.32 mmol), 5-fluoro-thiazol-2-ylamine hydrochloride (prepared as in Example 2, PCT Int. Appl. WO 2006016174, 55 mg, 0.35 mmol), benzotriazol-1-yl-oxy-tris (dimethylamino)phosphonium hexafluorophosphate (172 mg, 0.38 mmol), N,N-diisopropylethylamine (146 mg, 1.12 mmol) in dichloromethane (5 mL) was stirred for 18 h under nitrogen at 23° C. The reaction mixture was diluted with dichloromethane, washed with 2N aqueous hydrochloric acid, saturated sodium chloride solution and dried. The organic layer was concentrated, and the crude product was purified by ISCO flash chromatography (Teledyne Isco RediSep Flash Column 4 g silica gel; 20% to 80% ethyl acetate/hexanes) to afford, (S)-3-cyclopentyl-N-(5-fluoro-thiazol-2-yl)-2-(4-methoxy-2-oxo-2,5-dihydro-pyrrol-1-yl)-propionamide (4 mg, 4%) as an off-white solid: LR-ES-MS m/z calculated for $C_{16}H_{20}FN_3O_3S$ $[M]^+$ 353, observed $[M+H]^+$ 354; $^1$H NMR (300 MHz, CDCl$_3$) δ ppm 1.16 (br. s., 2H) 1.41-2.12 (m, 9H) 3.82 (s, 3H) 3.95 (d, J=17.8 Hz, 1H) 4.12 (d, J=17.8 Hz, 1H) 4.96 (dd, J=9.1, 6.6 Hz, 1H) 5.18 (s, 1H) 7.15 (d, J=1.8 Hz, 1H).

Example 9

(S)-3-Cyclopentyl-2-(4-methoxy-2-oxo-2,5-dihydro-pyrrol-1-yl)-N-pyrazin-2-yl-propionamide

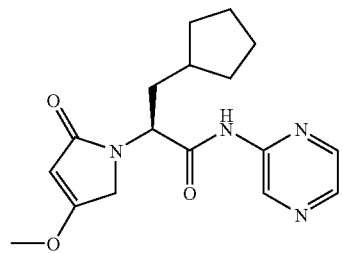

A solution of (S)-3-cyclopentyl-2-(4-methoxy-2-oxo-2,5-dihydro-pyrrol-1-yl)-propionic acid (prepared as in Example 1, 106 mg, 0.41 mmol) in benzene (10 mL) was treated with oxalyl chloride (55 mg, 0.43 mmol), and N,N-dimethylformamide (1 drop). Effervescence was observed. The reaction mixture was stirred for 2 h at 25° C., under nitrogen. The reaction mixture was concentrated, and dissolved in dichloromethane (10 mL) and treated with pyrazin-2-ylamine (42 mg, 0.43 mmol), and N,N-diisopropylethylamine (161 mg, 1.23 mmol). The reaction mixture was stirred at 25° C., under nitrogen for 18 h. The reaction mixture was diluted with dichloromethane, washed with 2N aqueous hydrochloric acid, saturated sodium chloride solution and dried. The organic layer was concentrated, and the crude product was purified by ISCO flash chromatography (Teledyne Isco RediSep Flash Column 4 g; 0% to 10% methanol/dichloromethane) to afford (S)-3-cyclopentyl-2-(4-methoxy-2-oxo-2,5-dihydro-pyrrol-1-yl)-N-pyrazin-2-yl-propionamide (5 mg, 3%) as a white solid: LR-ES-MS m/z calculated for $C_{17}H_{22}N_4O_3$ $[M]^+$ 330, observed $[M+H]^+$ 331; $^1$H NMR (400 MHz, CDCl$_3$) δ ppm 1.13-1.23 (m, 2H) 1.48-1.98 (m, 8H) 1.98-2.09 (m, 1H) 3.82 (s, 3H) 3.94 (d, J=17.5 Hz, 1H) 4.03 (d, J=17.5 Hz, 1H) 4.83 (dd, J=9.1, 6.5 Hz, 1H) 5.15 (s, 1H) 8.28 (dd, J=2.6, 1.5 Hz, 1H) 8.33 (d, J=2.6 Hz, 1H) 9.09 (s, 1H) 9.47 (d, J=1.5 Hz, 1H).

Example 10

6-[(S)-3-Cyclopentyl-2-(4-methoxy-2-oxo-2,5-dihydro-pyrrol-1-yl)-propionylamino]-nicotinic acid methyl ester

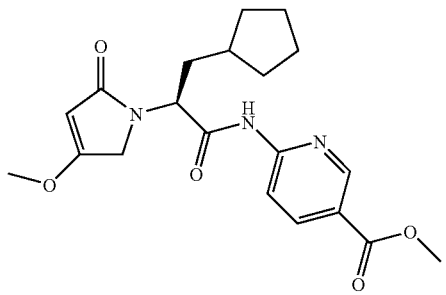

A solution of (S)-3-cyclopentyl-2-(4-methoxy-2-oxo-2,5-dihydro-pyrrol-1-yl)-propionic acid (prepared as in Example 1, 49.4 mg, 0.20 mmol) in benzene (5 mL) was treated with oxalyl chloride (26 mg, 0.20 mmol), and N,N-dimethylformamide (1 drop). Effervescence was observed. The reaction mixture was stirred for 2 h at 25° C., under nitrogen. The reaction mixture was concentrated, and dissolved in dichloromethane (5 mL) and treated with 6-amino-nicotinic acid methyl ester (37 mg, 0.23 mmol), and N,N-diisopropylethylamine (45 mg, 0.34 mmol). The reaction mixture was stirred at 25° C., under nitrogen for 12 h. The reaction mixture was diluted with dichloromethane, washed with 2N aqueous hydrochloric acid, saturated sodium chloride solution and dried. The organic layer was concentrated, and the crude product was purified by ISCO flash chromatography (Teledyne Isco RediSep Flash Column 4 g; 0% to 10% methanol/dichloromethane) to afford, 6-[(S)-3-cyclopentyl-2-(4-methoxy-2-oxo-2,5-dihydro-pyrrol-1-yl)-propionylamino]-nicotinic acid methyl ester (27 mg, 36%) as a light orange solid: LR-ES-MS m/z calculated for $C_{20}H_{25}N_3O_5$ [M]$^+$ 387, observed [M+H]$^+$ 388; $^1$H NMR (300 MHz, CDCl$_3$) δ ppm 0.98-1.37 (m, 2H) 1.37-2.13 (m, 9H) 3.80 (br. s., 3H) 3.84-4.15 (m, 2H) 3.91 (br. s., 3H) 4.89 (br. s., 1H) 5.16 (br. s., 1H) 7.99-8.38 (m, 2H) 8.90 (br. s., 1H) 9.34 (br. s., 1H).

Example 11

6-[(S)-3-Cyclopentyl-2-(4-methoxy-2-oxo-2,5-dihydro-pyrrol-1-yl)-propionylamino]-nicotinic acid

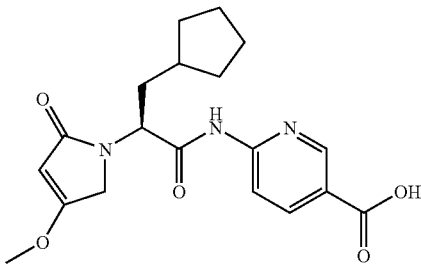

A solution of 6-[(S)-3-cyclopentyl-2-(4-methoxy-2-oxo-2,5-dihydro-pyrrol-1-yl)-propionylamino]-nicotinic acid methyl ester (prepared as in Example 10, 62 mg, 0.16 mmol) in tetrahydrofuran (2 mL) was treated with a solution of lithium hydroxide monohydrate (8 mg, 0.18 mmol) in water (1 mL). The mixture was stirred for 1 h. It was then acidified with 2N aqueous hydrochloric acid and diluted with dichloromethane, washed with saturated sodium chloride solution and dried to afford 6-[(S)-3-cyclopentyl-2-(4-methoxy-2-oxo-2,5-dihydro-pyrrol-1-yl)-propionylamino]-nicotinic acid, (23 mg, 39%) as a white powder: LR-ES-MS m/z calculated for $C_{19}H_{23}N_3O_5$ [M]$^+$ 373, observed [M+H]$^+$ 374; $^1$H NMR (400 MHz, DMSO-d$_6$) δ ppm 0.95-1.97 (m, 11H) 3.79 (s, 3H) 4.01 (d, J=17.9 Hz, 1H) 4.33 (d, J=17.7 Hz, 1H) 4.93 (dd, J=10.9, 4.5 Hz, 1H) 5.18 (s, 1H) 8.12 (d, J=8.5 Hz, 1H) 8.24 (dd, J=8.7, 2.3 Hz, 1H) 8.83 (d, J=2.3 Hz, 1H) 11.18 (s, 1H) 12.81 (br. s., 1H).

Example 12

(S)-N-[1-(3-Cyano-benzyl)-1H-pyrazol-3-yl]-3-cyclopentyl-2-(4-methoxy-2-oxo-2,5-dihydro-pyrrol-1-yl)-propionamide

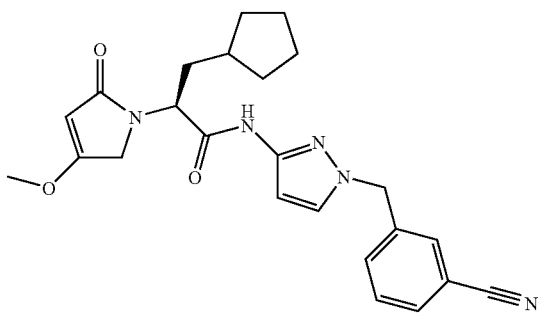

A solution of 3-nitropyrazole (prepared as in Example 5, 938 mg, 8.3 mmol) in N,N-dimethylformamide (15 mL) was treated with sodium hydride (519 mg, 60% suspension, 12.97 mmol). Effervescence was observed. The mixture was stirred for 30 min. Then, a solution of 1-bromo-3-cyano-toluene (2.14 g, 10.37 mmol) in N,N-dimethylformamide (5 mL) was added. The mixture was stirred for 24 h at room temperature. The reaction mixture was diluted with water, and extracted with dichloromethane. The organic layer was washed with saturated sodium chloride solution, and dried over magnesium sulfate. The crude product was purified by ISCO flash chromatography (Teledyne Isco RediSep Flash Column 40 g; 0% to 90% ethyl acetate/hexanes) to afford, 3-(3-nitro-pyrazol-1-ylmethyl)-benzonitrile (1.17 g, 59%), as a white solid.

A solution of 3-(3-nitro-pyrazol-1-ylmethyl)-benzonitrile (507 mg, 2.22 mmol) in ethanol (25 mL) was hydrogenated in a Parr hydrogenator using 10% palladium on carbon (53 mg, 0.05 mmol) for 4 h at 50 psi at room temperature. The product was isolated, after filtration through a Celite plug, and purification by ISCO flash chromatography (Teledyne Isco RediSep Flash Column 4 g; 0% to 10% methanol/dichloromethane) to afford 3-(3-amino-pyrazol-1-ylmethyl)-benzonitrile, (283 mg, 64%) as light orange solid.

A solution of (S)-3-cyclopentyl-2-(4-methoxy-2-oxo-2,5-dihydro-pyrrol-1-yl)-propionic acid (prepared as in Example 1, 86 mg, 0.34 mmol) in benzene (8 mL) was treated with oxalyl chloride (59 mg, 0.46 mmol), and N,N-dimethylformamide (1 drop). Effervescence was observed. The reaction mixture was stirred for 1 h at 25° C., under nitrogen. The reaction mixture was concentrated, and dissolved in dichloromethane (10 mL) and treated with 3-(3-amino-pyrazol-1-ylmethyl)-benzonitrile (96 mg, 0.46 mmol), and N,N-diisopropylethylamine (133 mg, 1.02 mmol). The reaction mixture was stirred at 25° C., under nitrogen for 18 h. The reaction mixture was diluted with dichloromethane, washed with 2N aqueous hydrochloric acid, saturated sodium chloride solution and dried. The organic layer was concentrated to afford, (S)-N-[1-(3-cyano-benzyl)-1H-pyrazol-3-yl]-3-cyclopentyl-2-(4-methoxy-2-oxo-2,5-dihydro-pyrrol-1-yl)-propionamide (137 mg, 93%) as an off-white foam: LR-ES-MS m/z calculated for $C_{24}H_{27}N_5O_3$ [M]$^+$ 433, observed [M+H]$^+$ 434; $^1$H NMR (300 MHz, DMSO-d$_6$) δ ppm 0.86-1.90 (m, 11H) 3.76 (s, 3H) 3.94 (d, J=17.8 Hz, 1H) 4.30 (d, J=17.8 Hz, 1H) 4.66-4.80 (m, 1H) 5.14 (s, 1H) 5.28 (s, 2H) 6.46 (d, J=2.1 Hz, 1H) 7.48-7.53 (m, 1H) 7.56 (t, J=7.8 Hz, 1H) 7.69 (s, 1H) 7.73-7.83 (m, 2H) 10.74 (s, 1H).

Example 13

(S)-3-Cyclopentyl-N-[1-(2-hydroxy-2-methyl-propyl)-1H-pyrazol-3-yl]-2-[4-((S)-2-methoxy-1-methyl-ethoxy)-2-oxo-2,5-dihydro-pyrrol-1-yl]-propionamide

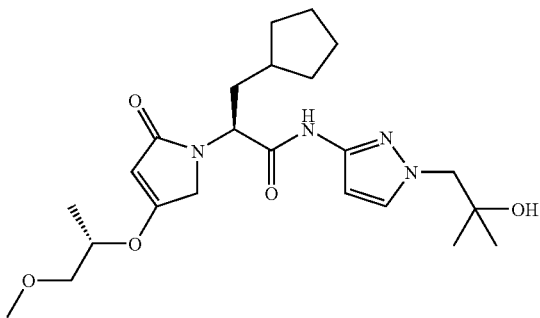

A solution of (S)-3-cyclopentyl-N-[1-(2-hydroxy-2-methyl-propyl)-1H-pyrazol-3-yl]-2-(4-methoxy-2-oxo-2,5-dihydro-pyrrol-1-yl)-propionamide (prepared as in Example 1, 35 mg, 0.09 mmol) in a hydrochloric acid (gas) saturated acetic acid (5 mL) solution was heated in a sealed tube at 75° C. for 2 h. After that, the reaction mixture was cooled to room temperature, and concentrated. The residue was added to (S)-1-methoxy-propan-2-ol (162 mg, 1.76 mmol), and toluene-4-sulfonic acid hydrate (10 mg). The mixture was heated to 90° C., for 18 h. The reaction mixture was concentrated and the residue was dissolved in dichloromethane. The organic layer was washed with saturated sodium bicarbonate solution, saturated sodium chloride solution, and dried over magnesium sulfate. The crude product was purified using reverse phase HPLC (Biosystems MDS-SCIEX LC/MS, Pursuit C-18 2×10 mm, water/acetonitrile 0.05% trifluoroacetic acid) to afford (S)-3-cyclopentyl-N-[1-(2-hydroxy-2-methyl-propyl)-1H-pyrazol-3-yl]-2-[4-((S)-2-methoxy-1-methyl-ethoxy)-2-oxo-2,5-dihydro-pyrrol-1-yl]-propionamide (3 mg, 9%) as a white foam: LR-ES-MS m/z calculated for $C_{23}H_{36}N_4O_5$ [M]$^+$ 448, observed [M+H]$^+$ 449; $^1$H NMR (300 MHz, CDCl$_3$) δ ppm 1.08-1.25 (m, 2H) 1.16 (s, 6H) 1.32 (d, J=6.3 Hz, 3H) 1.43-2.07 (m, 9H) 3.40 (s, 3H) 3.44-3.59 (m, 2H) 3.66 (br. s., 1H) 3.90-4.00 (d, J=17.8 Hz, 1H) 3.95 (s, 2H) 4.08 (d, J=17.8 Hz, 1H) 4.34-4.47 (m, 1H) 4.80 (dd, J=8.9, 6.5 Hz, 1H) 5.12 (s, 1H) 6.67 (d, J=2.0 Hz, 1H) 7.30 (d, J=2.0 Hz, 1H) 8.85 (br. s., 1H).

Example 14

(S)-2-(4-Benzyloxy-2-oxo-2,5-dihydro-pyrrol-1-yl)-3-cyclopentyl-N-[1-(2-hydroxy-2-methyl-propyl)-1H-pyrazol-3-yl]-propionamide

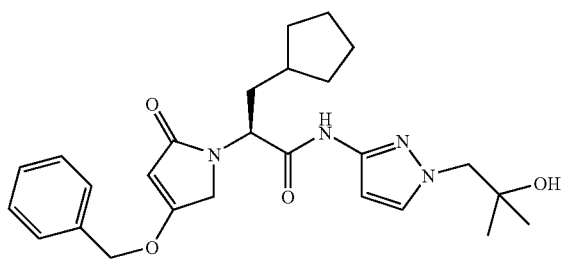

A solution of (S)-3-cyclopentyl-N-[1-(2-hydroxy-2-methyl-propyl)-1H-pyrazol-3-yl]-2-(4-methoxy-2-oxo-2,5-dihydro-pyrrol-1-yl)-propionamide (prepared as in Example 1, 94 mg, 0.24 mmol) in a hydrochloric acid (gas) saturated acetic acid (5 mL) was heated in a sealed tube at 75° C. for 2 h. After that time the reaction mixture was cooled to room temperature, and concentrated. The residue was added to benzyl alcohol (1000 mg, 9.15 mmol), and toluene-4-sulfonic acid hydrate (10 mg), cesium chloride hexahydrate (0.3 g) on silica gel (Sabitha, G.; Reddy, M. N.; Sudhakar, K.; Yadav, J. S.; *Letters Org. Chem*, 2005, 2, 763-766). The mixture was stirred at room temperature for 72 h. The reaction mixture was concentrated and the residue was dissolved in dichloromethane. The organic layer was washed with saturated sodium bicarbonate solution, saturated sodium chloride solution, and dried over magnesium sulfate and purified by ISCO flash chromatography (Teledyne Isco RediSep Flash Column 12 g; 0% to 100% ethyl acetate/hexanes) to afford (S)-2-(4-benzyloxy-2-oxo-2,5-dihydro-pyrrol-1-yl)-3-cyclopentyl-N-[1-(2-hydroxy-2-methyl-propyl)-1H-pyrazol-3-yl]-propionamide (6 mg, 5%): LR-ES-MS m/z calculated for $C_{26}H_{34}N_4O_4$ [M]$^+$ 466, observed [M+H]$^+$ 467; $^1$H NMR (300 MHz, CDCl$_3$) δ ppm 0.77 (br. s., 1H) 1.08 (br. s., 2H) 1.08 (br. s., 6H) 1.32-2.07 (m, 8H) 2.89 (br. s., 1H) 3.79-3.96 (m, 1H) 3.88 (br. s., 2H) 3.98-4.15 (m, 1H) 4.78 (br. s., 1H) 4.92 (br. s., 2H) 5.16 (br. s., 1H) 6.61 (br. s., 1H) 7.08-7.43 (m, 5H) 8.81 (br. s., 1H).

Example 15

(S)-3-Cyclopentyl-N-[1-(2-hydroxy-2-methyl-propyl)-1H-pyrazol-3-yl]-2-(4-isopropoxy-2-oxo-2,5-dihydro-pyrrol-1-yl)-propionamide

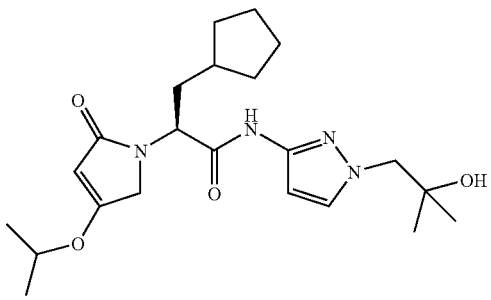

A solution of (S)-3-cyclopentyl-N-[1-(2-hydroxy-2-methyl-propyl)-1H-pyrazol-3-yl]-2-(4-methoxy-2-oxo-2,5-dihydro-pyrrol-1-yl)-propionamide (as prepared in Example 1, 1.20 g, 3.08 mmol) in a hydrochloric acid (gas) saturated acetic acid (15 mL) solution was heated in a sealed tube at 50° C. for 3 h. After that time the reaction mixture was cooled to room temperature, and concentrated to afford, (S)-3-cyclopentyl-2-(2,4-dioxo-pyrrolidin-1-yl)-N-[1-(2-hydroxy-2-methyl-propyl)-1H-pyrazol-3-yl]-propionamide as a heavy yellow oil, (990 mg, 85%).

(S)-3-cyclopentyl-2-(2,4-dioxo-pyrrolidin-1-yl)-N-[1-(2-hydroxy-2-methyl-propyl)-1H-pyrazol-3-yl]-propionamide (100 mg, 0.27 mmol) was added to isopropyl alcohol (10 mL), and toluene-4-sulfonic acid hydrate (10 mg). The mixture was stirred at 100° C. for 2 h. The reaction mixture was concentrated and the crude product obtained was purified by ISCO flash chromatography (Teledyne Isco RediSep Flash Column 12 g; 0% to 10% methanol/dichloromethane) to afford, (S)-3-cyclopentyl-N-[1-(2-hydroxy-2-methyl-propyl)-1H-pyrazol-3-yl]-2-(4-isopropoxy-2-oxo-2,5-dihydro-pyrrol-1-yl)-propionamide (52 mg, 47%) as an off-white solid: LR-ES-MS m/z calculated for $C_{22}H_{34}N_4O_4$ [M]$^+$ 418, observed [M+H]$^+$ 419; $^1$H NMR (300 MHz, DMSO-d$_6$) δ ppm 1.04 (s, 3H) 1.05 (s, 3H) 1.06 (m, 1H) 1.25 (m, 1H) 1.27 (d, J=6.0 Hz, 6H) 1.35-1.87 (m, 9H) 3.90 (d, J=17.6 Hz, 1H) 3.88 (s, 2H) 4.28 (d, J=17.6 Hz, 1H) 4.38-4.50 (m, 1H) 4.67 (s, 1H) 4.76 (dd, J=10.6, 4.2 Hz, 1H) 5.12 (s, 1H) 6.42 (d, J=2.1 Hz, 1H) 7.52 (d, J=2.1 Hz, 1H) 10.72 (s, 1H).

Example 16

(S)-3-Cyclopentyl-N-[1-(2-hydroxy-2-methyl-propyl)-1H-pyrazol-3-yl]-2-(4-cyclopentyloxy-2-oxo-2,5-dihydro-pyrrol-1-yl)-propionamide

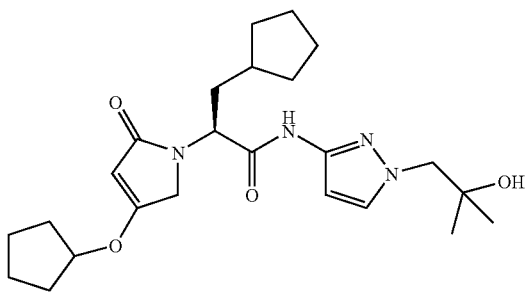

(S)-3-cyclopentyl-2-(2,4-dioxo-pyrrolidin-1-yl)-N-[1-(2-hydroxy-2-methyl-propyl)-1H-pyrazol-3-yl]-propionamide (prepared as in Example 15, 275 mg, 0.73 mmol) was added to cyclopentyl alcohol (12 mL), and toluene-4-sulfonic acid hydrate (10 mg). The mixture was stirred at 100° C. for 2 h. The reaction mixture was concentrated and the crude product obtained was purified by ISCO flash chromatography (Teledyne Isco RediSep Flash Column 40 g; 0% to 5% methanol/dichloromethane) to afford, (S)-3-cyclopentyl-N-[1-(2-hydroxy-2-methyl-propyl)-1H-pyrazol-3-yl]-2-(4-cyclopentyloxy-2-oxo-2,5-dihydro-pyrrol-1-yl)-propionamide (155 mg, 48%) as a yellow solid: LR-ES-MS m/z calculated for $C_{24}H_{36}N_4O_4$ [M]$^+$ 444, observed [M+H]$^-$ 445; $^1$H NMR (300 MHz, DMSO-d$_6$) δ ppm 1.05 (br. s., 6H) 1.17-2.04 (m, 19H) 3.80-3.99 (m, 3H) 4.28 (d, J=17.8 Hz, 1H) 4.67 (br. s., 2H) 4.72-4.84 (m, 1H) 5.09 (br. s., 1H) 6.42 (br. s., 1H) 7.52 (br. s., 1H) 10.71 (br. s., 1H).

Example 17

(S)-3-Cyclopentyl-N-[1-(2-hydroxy-2-methyl-propyl)-1H-pyrazol-3-yl]-2-(4-cyclohexyloxy-2-oxo-2,5-dihydro-pyrrol-1-yl)-propionamide

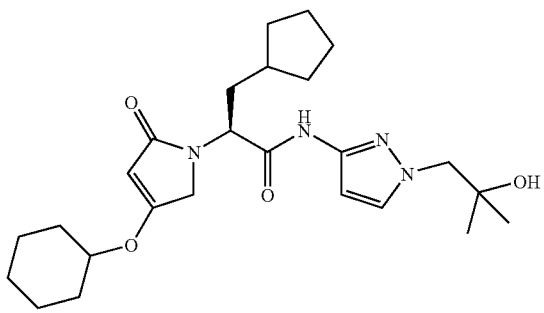

(S)-3-cyclopentyl-2-(2,4-dioxo-pyrrolidin-1-yl)-N-[1-(2-hydroxy-2-methyl-propyl)-1H-pyrazol-3-yl]-propionamide (prepared as in Example 15, 90 mg, 0.24 mmol) was added to cyclohexyl alcohol (5 mL), and toluene-4-sulfonic acid hydrate (10 mg). The mixture was stirred at 100° C. for 2 h. The reaction mixture was concentrated and the crude product obtained was purified by ISCO flash chromatography (Teledyne Isco RediSep Flash Column 12 g; 0% to 5% methanol/dichloromethane) to afford, (S)-3-cyclopentyl-N-[1-(2-hydroxy-2-methyl-propyl)-1H-pyrazol-3-yl]-2-(4-cyclohexyloxy-2-oxo-2,5-dihydro-pyrrol-1-yl)-propionamide (40 mg, 36%) as a yellow solid: LR-ES-MS m/z calculated for $C_{25}H_{38}N_4O_4$ [M]$^+$ 458, observed [M+H]$^+$ 459; $^1$H NMR (300 MHz, DMSO-d$_6$) δ ppm 1.04 (br. s., 3H) 1.06 (br. s., 3H) 1.06-2.03 (m, 21H) 3.84-3.98 (m, 1H) 3.88 (s, 2H) 4.14-4.26 (m, 1H) 4.30 (d, J=18.1 Hz, 1H) 4.67 (s, 1H) 4.70-4.82 (m, 1H) 5.15 (s, 1H) 6.42 (d, J=2.2 Hz, 1H) 7.52 (d, J=2.2 Hz, 1H) 10.71 (s, 1H).

Example 18

(S)-3-Cyclopentyl-N-[1-(2-hydroxy-2-methyl-propyl)-1H-pyrazol-3-yl]-2-[2-oxo-4-(tetrahydro-pyran-4-yloxy)-2,5-dihydro-pyrrol-1-yl]-propionamide

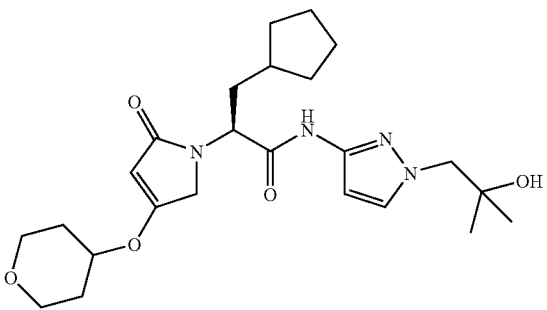

(S)-3-cyclopentyl-2-(2,4-dioxo-pyrrolidin-1-yl)-N-[1-(2-hydroxy-2-methyl-propyl)-1H-pyrazol-3-yl]-propionamide (prepared as in Example 15, 100 mg, 0.27 mmol) was added to tetrahydro-4H-pyran-4-ol (2 mL), and toluene-4-sulfonic acid hydrate (10 mg). The mixture was stirred at 100° C. for 3 h. The reaction mixture was concentrated and the crude product obtained was purified by ISCO flash chromatography (Teledyne Isco RediSep Flash Column 12 g; 0% to 5% methanol/dichloromethane) to afford, (S)-3-cyclopentyl-N-[1-(2-hydroxy-2-methyl-propyl)-1H-pyrazol-3-yl]-2-[2-oxo-4-(tetrahydro-pyran-4-yloxy)-2,5-dihyrdo-pyrrol-1-yl]-propionamide (38 mg, 31%) as a yellow oil: LR-ES-MS m/z calculated for $C_{24}H_{36}N_4O_5$ [M]$^+$ 460, observed [M+H]$^+$ 461; $^1$H NMR (300 MHz, DMSO-d$_6$) δ ppm 1.04 (br. s., 3H) 1.05 (br. s., 3H) 1.11-1.91 (m, 13H) 1.90-2.05 (m, 2H) 3.38-3.55 (m, 2H) 3.72-3.86 (m, 2H) 3.88 (s, 2H) 3.94 (d, J=18.0 Hz, 1H) 4.32 (d, J=18.0 Hz, 1H) 4.38-4.52 (m, 1H) 4.67 (s, 1H) 4.71-4.83 (m, 1H) 5.24 (s, 1H) 6.42 (d, J=2.0 Hz, 1H) 7.52 (d, J=2.0 Hz, 1H) 10.72 (s, 1H).

Example 19

(S)-3-Cyclopentyl-N-[1-(2-hydroxy-2-methyl-propyl)-1H-pyrazol-3-yl]-2-(4-cyclobutoxy-2-oxo-2,5-dihydro-pyrrol-1-yl)-propionamide

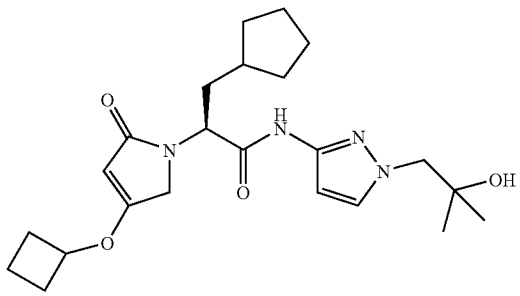

(S)-3-Cyclopentyl-2-(2,4-dioxo-pyrrolidin-1-yl)-N-[1-(2-hydroxy-2-methyl-propyl)-1H-pyrazol-3-yl]-propionamide (prepared as in Example 15, 100 mg, 0.27 mmol) was added to cyclobutyl alcohol (5 mL), and toluene-4-sulfonic acid hydrate (10 mg). The mixture was stirred at 100° C. for 2 h. The reaction mixture was concentrated and the crude product obtained was purified by ISCO flash chromatography (Teledyne Isco RediSep Flash Column 12 g; 0% to 5% methanol/dichloromethane) to afford, (S)-3-cyclopentyl-N-[1-(2-hydroxy-2-methyl-propyl)-1H-pyrazol-3-yl]-2-(4-cyclobutoxy-2-oxo-2,5-dihydro-pyrrol-1-yl)-propionamide (60 mg, 53%) as a yellow oil: LR-ES-MS m/z calculated for $C_{23}H_{34}N_4O_4$ [M]+430, observed [M+H]$^+$ 431; $^1$H NMR (300 MHz, DMSO-d$_6$) δ ppm 1.04 (s, 3H) 1.05 (s, 3H) 1.14-1.90 (m, 13H) 1.94-2.15 (m, 2H) 2.32-2.46 (m, 2H) 3.88 (s, 2H) 3.92 (d, J=18.1 Hz, 1H) 4.30 (d, J=17.8 Hz, 1H) 4.53-4.65 (m, 1H) 4.67 (s, 1H) 4.76 (dd, J=10.6, 4.5 Hz, 1H) 5.03 (s, 1H) 6.42 (d, J=2.4 Hz, 1H) 7.52 (d, J=2.4 Hz, 1H) 10.72 (s, 1H).

Example 20

(S)-3-Cyclopentyl-N-[1-(2-isopropoxy-ethyl)-1H-pyrazol-3-yl]-2-(4-cyclopentyloxy-2-oxo-2,5-dihydro-pyrrol-1-yl)-propionamide

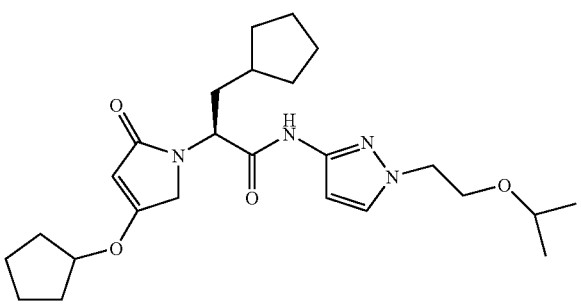

A solution of (S)-3-cyclopentyl-2-(4-methoxy-2-oxo-2,5-dihydro-pyrrol-1-yl)-propionic acid (prepared as in Example 1, 300 mg, 1.19 mmol) in dichloromethane (15 mL) was treated with 1-(2-isopropoxy-ethyl)-1H-pyrazol-3-ylamine (prepared in U.S. Pat. Appl. US 2008021032 Example 101, 220 mg, 1.30 mmol), benzotriazol-1-yl-oxy-tris(dimethylamino)phosphonium hexafluorophosphate reagent (630 mg, 1.42 mmol) and triethylamine (360 mg, 3.56 mmol). The reaction mixture was stirred for 18 h at 25° C., under nitrogen. The reaction mixture was diluted with dichloromethane, washed with 2N aqueous hydrochloric acid, saturated sodium bicarbonate solution, saturated sodium chloride solution and dried. The organic layer was concentrated, and the crude product was purified by ISCO flash chromatography (Teledyne Isco RediSep Flash Column 12 g; 0% to 10% methanol/dichloromethane) to afford, (S)-3-cyclopentyl-N-[1-(2-isopropoxy-ethyl)-1H-pyrazol-3-yl]-2-(4-methoxy-2-oxo-2,5-dihydro-pyrrol-1-yl)-propionamide as a heavy yellow oil, (293 mg, 61%): LR-ES-MS m/z calculated for $C_{21}H_{32}N_4O_4$ [M]$^+$ 404, observed [M+H]$^+$ 405.

A solution of (S)-3-cyclopentyl-N-[1-(2-isopropoxy-ethyl)-1H-pyrazol-3-yl]-2-(4-methoxy-2-oxo-2,5-dihydro-pyrrol-1-yl)-propionamide (290 mg, 0.72 mmol) in a hydrochloric acid (gas) saturated acetic acid (15 mL) was heated in a sealed tube at 50° C. for 3 h. After that, the reaction mixture was cooled to room temperature, and concentrated to afford, (S)-3-cyclopentyl-2-(2,4-dioxo-pyrrolidin-1-yl)-N-[1-(2-isopropoxy-ethyl)-1H-pyrazol-3-yl]-propionamide (220 mg, 79%) as a heavy yellow oil.

(S)-3-Cyclopentyl-2-(2,4-dioxo-pyrrolidin-1-yl)-N-[1-(2-isopropoxy-ethyl)-1H-pyrazol-3-yl]-propionamide (110 mg, 0.28 mmol) was added to cyclopentyl alcohol (10 mL), and toluene-4-sulfonic acid hydrate (10 mg). The mixture was stirred at 100° C. for 3 h. The reaction mixture was concentrated and the crude product obtained was purified by ISCO flash chromatography (Teledyne Isco RediSep Flash Column 12 g; 0% to 5% methanol/dichloromethane) to afford, (S)-3-cyclopentyl-N-[1-(2-isopropoxy-ethyl)-1H-pyrazol-3-yl]-2-(4-cyclopentyl-2-oxo-2,5-dihydro-pyrrol-1-yl)-propionamide (68 mg, 53%) as a yellow solid: LR-ES-MS m/z calculated for $C_{25}H_{38}N_4O_4$ [M]$^+$ 458, observed [M+H]$^+$ 459; $^1$H NMR (300 MHz, DMSO-d$_6$) δ ppm 1.02 (d, J=6.0 Hz, 6H) 1.05-2.02 (m, 19H) 3.42-3.54 (m, 1H) 3.66 (t, J=5.5 Hz, 2H) 3.90 (d, J=17.7 Hz, 1H) 4.09 (t, J=5.5 Hz, 2H) 4.27 (d, J=17.7 Hz, 1H) 4.63-4.71 (m, 1H) 4.71-4.84 (m, 1H) 5.09 (s, 1H) 6.38 (d, J=2.2 Hz, 1H) 7.55 (d, J=2.2 Hz, 1H) 10.69 (s, 1H).

Example 21

(S)-3-Cyclopentyl-N-[1-(2-methoxy-2-methyl-propyl)-1H-pyrazol-3-yl]-2-(4-cyclopentyloxy-2-oxo-2,5-dihydro-pyrrol-1-yl)-propionamide

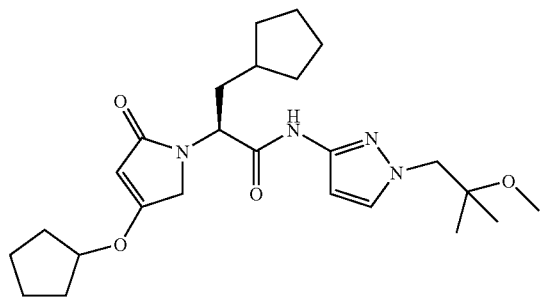

A solution of (S)-3-cyclopentyl-2-(4-methoxy-2-oxo-2,5-dihydro-pyrrol-1-yl)-propionic acid (prepared as in Example 1, 100 mg, 0.40 mmol) in dichloromethane (10 mL) was treated with 1-(2-methoxy-2-methyl-propyl)-1H-pyrazol-3-ylamine (prepared as in Example 5, 74 mg, 0.43 mmol), benzotriazol-1-yl-oxy-tris(dimethylamino)phosphonium hexafluorophosphate (210 mg, 0.47 mmol) and triethylamine (120 mg, 1.19 mmol). The reaction mixture was stirred for 18 h at 25° C., under nitrogen. The reaction mixture was diluted with dichloromethane, washed with 2N aqueous hydrochloric acid, saturated sodium bicarbonate solution, saturated sodium chloride solution and dried. The organic layer was concentrated, and the crude product was purified by ISCO flash chromatography (Teledyne Isco RediSep Flash Column 12 g; 0% to 10% methanol/dichloromethane) to afford, (S)-3-cyclopentyl-N-[1-(2-methoxy-2-methyl-propyl)-1H-pyrazol-3-yl]-2-(4-methoxy-2-oxo-2,5-dihydro-pyrrol-1-yl)-propionamide (112 mg, 70%) as a heavy yellow oil: LR-ES-MS m/z calculated for $C_{21}H_{32}N_4O_4$ [M]+ 404, observed [M+H]+ 405.

A solution of (S)-3-cyclopentyl-N-[1-(2-methoxy-2-methyl-propyl)-1H-pyrazol-3-yl]-2-(4-methoxy-2-oxo-2,5-dihydro-pyrrol-1-yl)-propionamide (225 mg, 0.56 mmol) in a hydrochloric acid (gas) saturated acetic acid (10 mL) was heated in a sealed tube at 50° C. for 4 h. After that, the reaction mixture was cooled to room temperature, and concentrated to afford, (S)-3-cyclopentyl-2-(2,4-dioxo-pyrrolidin-1-yl)-N-[1-(2-methoxy-2-methyl-propyl)-1H-pyrazol-3-yl]-propionamide (150 mg, 69%) as a heavy yellow oil.

(S)-3-cyclopentyl-2-(2,4-dioxo-pyrrolidin-1-yl)-N-[1-(2-methoxy-2-methyl-propyl)-1H-pyrazol-3-yl]-propionamide (170 mg, 0.44 mmol) was added to cyclopentyl alcohol (10 mL), and toluene-4-sulfonic acid hydrate (10 mg). The mixture was stirred at 100° C. for 3 h. The reaction mixture was concentrated and the crude product obtained was purified by ISCO flash chromatography (Teledyne Isco RediSep Flash Column 12 g; 0% to 5% methanol/dichloromethane) to afford, (S)-3-cyclopentyl-N-[1-(2-methoxy-2-methyl-propyl)-1H-pyrazol-3-yl]-2-(4-cyclopentyloxy-2-oxo-2,5-dihydro-pyrrol-1-yl)-propionamide (63 mg, 32%) as a yellow solid: LR-ES-MS m/z calculated for $C_{25}H_{38}N_4O_4$ [M]+ 458, observed [M+H]+ 459; $^1$H NMR (300 MHz, DMSO-$d_6$) δ ppm 1.06 (br. s., 3H) 1.07 (br. s., 3H) 1.16-2.02 (m, 19H) 3.15 (s, 3H) 3.90 (d, J=18.1 Hz, 1H) 3.99 (s, 2H) 4.28 (d, J=18.1 Hz, 1H) 4.62-4.72 (m, 1H) 4.72-4.82 (m, 1H) 5.09 (s, 1H) 6.42 (d, J=2.2 Hz, 1H) 7.48 (d, J=2.2 Hz, 1H) 10.70 (s, 1H).

Example 22

(S)-3-Cyclopentyl-N-[1-(2-methoxy-2-methyl-propyl)-1H-pyrazol-3-yl]-2-(4-isopropoxy-2-oxo-2,5-dihydro-pyrrol-1-yl)-propionamide

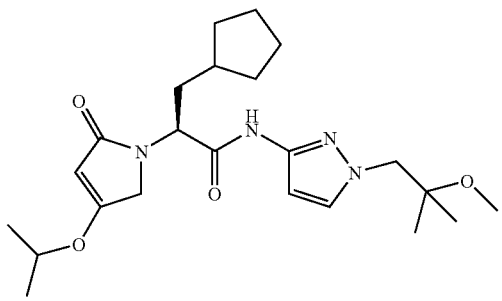

(S)-3-cyclopentyl-2-(2,4-dioxo-pyrrolidin-1-yl)-N-[1-(2-methoxy-2-methyl-propyl)-1H-pyrazol-3-yl]-propionamide (prepared as in Example 21, 150 mg, 0.44 mmol) was added to isopropyl alcohol (10 mL), and toluene-4-sulfonic acid hydrate (10 mg). The mixture was stirred at 100° C. for 2 h. The reaction mixture was concentrated and the crude product obtained was purified by ISCO flash chromatography (Teledyne Isco RediSep Flash Column 12 g; 0% to 5% methanol/dichloromethane) to afford, (S)-3-cyclopentyl-N-[1-(2-methoxy-2-methyl-propyl)-1H-pyrazol-3-yl]-2-(4-isopropoxy-2-oxo-2,5-dihydro-pyrrol-1-yl)-propionamide (24 mg, 14%) as a yellow solid: LR-ES-MS m/z calculated for $C_{23}H_{36}N_4O_4$ [M]+ 432, observed [M+H]+ 433; $^1$H NMR (300 MHz, DMSO-$d_6$) δ ppm 1.06 (s, 3H) 1.06 (m, 1H) 1.07 (br. s., 3H) 1.26 (m, 1H) 1.27 (d, J=6.0 Hz, 6H) 1.36-1.90 (m, 9H) 3.15 (s, 3H) 3.90 (d, J=18.0 Hz, 1H) 3.99 (s, 2H) 4.28 (d, J=18.0 Hz, 1H) 4.37-4.51 (m, 1H) 4.77 (dd, J=10.0, 3.9 Hz, 1H) 5.12 (s, 1H) 6.42 (d, J=2.4 Hz, 1H) 7.48 (d, J=2.4 Hz, 1H) 10.71 (s, 1H).

Example 23

(S)-3-Cyclopentyl-N-(pyrazin-2-yl)-2-(4-isopropoxy-2-oxo-2,5-dihydro-pyrrol-1-yl)-propionamide

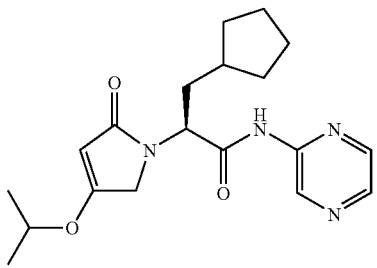

A solution of (S)-3-cyclopentyl-2-(4-methoxy-2-oxo-2,5-dihydro-pyrrol-1-yl)-propionic acid (prepared as in Example 1, 300 mg, 1.19 mmol) in benzene (5 mL) was treated with oxalyl chloride (180 mg, 1.42 mmol), and N,N-dimethylformamide (1 drop). Effervescence was observed. The reaction mixture was stirred for 2 h at 25° C., under nitrogen. The reaction mixture was concentrated, and dissolved in dichloromethane (5 mL) and treated with aminopyrazine (125 mg, 1.30 mmol), and N,N-diisopropylethylamine (460 mg, 3.56 mmol). The reaction mixture was stirred at 25° C., under nitrogen for 18 h. The reaction mixture was diluted with dichloromethane, washed with 2N aqueous hydrochloric acid, saturated sodium chloride solution and dried. The organic layer was concentrated, and the crude product was purified by ISCO flash chromatography (Teledyne Isco RediSep Flash Column 12 g; 0% to 10% methanol/ethyl acetate) to afford, (S)-3-cyclopentyl-2-(4-methoxy-2-oxo-2,5-dihydro-pyrrol-1-yl)-N-pyrazin-2-yl-propionamide (312 mg, 80%) as a dark yellow oil: LR-ES-MS m/z calculated for $C_{17}H_{22}N_4O_3$ [M]$^+$ 330, observed [M+H]$^+$ 331.

A solution of (S)-3-cyclopentyl-2-(4-methoxy-2-oxo-2,5-dihydro-pyrrol-1-yl)-N-pyrazin-2-yl-propionamide (310 mg, 0.94 mmol) in a hydrochloric acid (gas) saturated acetic acid (15 mL) was heated in a sealed tube at 50° C. for 3 h. After that, the reaction mixture was cooled to room temperature, and concentrated to afford, (S)-3-cyclopentyl-2-(2,4-dioxo-pyrrolidin-1-yl)-N-pyrazin-2-yl-propionamide as a heavy yellow oil, (108 mg, 36%).

(S)-3-cyclopentyl-2-(2,4-dioxo-pyrrolidin-1-yl)-N-pyrazin-2-yl-propionamide (108 mg, 0.34 mmol) was added to isopropyl alcohol (10 mL), and toluene-4-sulfonic acid hydrate (10 mg). The mixture was stirred at 100° C. for 2 h. The reaction mixture was concentrated and the crude product obtained was purified by ISCO flash chromatography (Teledyne Isco RediSep Flash Column 12 g; 0% to 5% methanol/dichloromethane) to afford, (S)-3-cyclopentyl-2-(4-isopropoxy-2-oxo-2,5-dihydro-pyrrol-1-yl)-N-pyrazin-2-yl-propionamide (8 mg, 6%) as a white solid: LR-ES-MS m/z calculated for $C_{19}H_{26}N_4O_3$ [M]$^+$ 358, observed [M+H]$^+$ 359; $^1$H NMR (300 MHz, DMSO-d$_6$) δ ppm 1.04 (br. s, 3H), 1.05 (br. s, 3H), 1.06-1.13 (m, 1H), 1.19-1.32 (m, 1H), 1.36-1.98 (m, 9H), 3.90 (d, J=17.8 Hz, 1H), 4.28 (d, J=17.8 Hz, 1H), 4.67 (s, 1H), 4.64-4.72 (m, 1H), 4.76 (dd, J=10.3, 3.9 Hz, 1H), 8.42 (s, 1H), 8.52 (s, 1H), 8.72 (s, 1H), 10.71 (s, 1H).

Example 24

(S)-3-Cyclohexyl-N-[1-(2-hydroxy-2-methyl-propyl)-1H-pyrazol-3-yl]-2-(2-oxo-4-propoxy-2,5-dihydro-pyrrol-1-yl)-propionamide

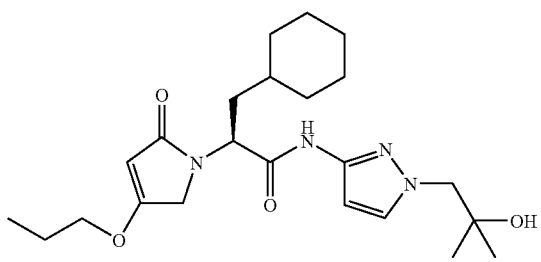

A suspension of (S)-2-amino-3-cyclohexyl-propionic acid methyl ester hydrochloride (8.42 g, 37.97 mmol) in acetonitrile (50 mL) was treated with triethylamine (6.0 mL, 43.05 mmol). The mixture was then heated to 60° C., and kept at that temperature for 1 h. Then, additional triethylamine (3.5 mL, 25.11 mmol) was added followed by methyl-4-chloro-3-methoxy-(E)-2-butenoate (5.0 g, 30.38 mmol) in acetonitrile (25 mL), via addition funnel. The mixture was then heated to reflux by lowering into a pre-heated oil bath kept at 100° C. for 18 h, under nitrogen. The mixture was cooled to 25° C., and the precipitated triethylammonium hydrochloride was filtered off. The supernatant was concentrated and purified by ISCO flash chromatography (Teledyne Isco RediSep Flash Column 80 g; 10% to 90% ethyl acetate/hexanes) to afford, (S)-3-cyclohexyl-2-(4-methoxy-2-oxo-2,5-dihydro-pyrrol-1-yl)-propionic acid methyl ester (3.63 g, 43%) as a dark yellow oil: LR-ES-MS m/z calculated for $C_{15}H_{23}NO_4$ [M]$^+$ 281, observed [M+H]$^+$ 282.

To a solution containing (S)-3-cyclohexyl-2-(4-methoxy-2-oxo-2,5-dihydro-pyrrol-1-yl)-propionic acid methyl ester (1.82 g, 6.48 mmol) in tetrahydrofuran (15 mL) was treated with an aqueous solution of lithium hydroxide monohydrate (8.4 mL, 1.0 M, 8.42 mmol). The mixture was stirred at 25° C. for 2 h then, acidified with 2N aqueous hydrochloric acid. The mixture was extracted with ethyl acetate (2×30 mL). The combined organic layers were dried over magnesium sulfate and concentrated to afford (S)-3-cyclohexyl-2-(4-methoxy-2-oxo-2,5-dihydro-pyrrol-1-yl)-propionic acid, (1.35 g, 75%) as a yellow solid.

A solution of (S)-3-cyclohexyl-2-(4-methoxy-2-oxo-2,5-dihydro-pyrrol-1-yl)-propionic acid (1.3 g, 4.87 mmol) in dichloromethane (25 mL) was treated with 1-(3-amino-pyrazol-1-yl)-2-methyl-propan-2-ol (prepared in U.S. Pat. Appl. US2008021032 Example 80, 830 mg, 5.36 mmol), benzotriazol-1-yl-oxy-tris(dimethylamino)phosphonium hexafluorophosphate (2.60 g, 5.84 mmol) and triethylamine (1.48 g, 14.61 mmol). The reaction mixture was stirred for 18 h at 25° C., under nitrogen. The reaction mixture was diluted with dichloromethane, washed with 2N aqueous hydrochloric acid, saturated sodium bicarbonate solution, saturated sodium chloride solution and dried. The organic layer was concentrated, and the crude product was purified by ISCO flash chromatography (Teledyne Isco RediSep Flash Column 80 g; 0% to 10% methanol/dichloromethane) to afford (S)-3-cyclohexyl-N-[1-(2-hydroxy-2-methyl-propyl)-1H-pyrazol-3-yl]-2-(4-methoxy-2-oxo-2,5-dihydro-pyrrol-1-yl)-propionamide (1.0 g, 51%) as a heavy yellow oil: LR-ES-MS m/z calculated for $C_{21}H_{32}N_4O_4$ [M]$^+$ 404, observed [M+H]$^+$ 405.

A solution of (S)-3-cyclohexyl-N-[1-(2-hydroxy-2-methyl-propyl)-1H-pyrazol-3-yl]-2-(4-methoxy-2-oxo-2,5-dihydro-pyrrol-1-yl)-propionamide (1.90 g, 4.70 mmol) in a hydrochloric acid (gas) saturated acetic acid (10 mL) was heated in a sealed tube at 50° C. for 3 h. After that, the reaction mixture was cooled to room temperature, and concentrated to afford, (S)-3-cyclohexyl-2-(2,4-dioxo-pyrrolidin-1-yl)-N-[1-(2-hydroxy-2-methyl-propyl)-1H-pyrazol-3-yl]-propionamide (1.85 g, 99%) as a heavy yellow oil.

(S)-3-cyclohexyl-2-(2,4-dioxo-pyrrolidin-1-yl)-N-[1-(2-hydroxy-2-methyl-propyl)-1H-pyrazol-3-yl]-propionamide (100 mg, 0.26 mmol) was added to n-propyl alcohol (3 mL), and toluene-4-sulfonic acid hydrate (10 mg). The mixture was stirred at 100° C. for 3 h. The reaction mixture was concentrated and the crude product obtained was purified by ISCO flash chromatography (Teledyne Isco RediSep Flash Column 12 g; 0% to 10% methanol/dichloromethane) to afford (S)-3-cyclohexyl-N-[1-(2-hydroxy-2-methyl-propyl)-1H-pyrazol-3-yl]-2-(2-oxo-4-propoxy-2,5-dihydro-pyrrol-1-yl)-propionamide (24 mg, 22%) as an off-white solid: LR-ES-MS m/z calculated for $C_{22}H_{34}N_4O_4$ [M]$^+$ 432, observed [M+H]$^+$ 433; $^1$H NMR (300 MHz, DMSO-d$_6$) δ ppm 0.82-0.95 (m, 5H), 0.96-1.14 (m, 2H), 1.27 (d, J=6.0 Hz, 6H), 1.37-1.89 (m, 11H), 3.90 (d, J=17.6 Hz, 1H), 3.88 (s, 2H), 4.28 (d, J=17.6 Hz, 1H), 4.44 (d, J=6.0 Hz, 2H), 4.67 (s, 1H), 4.76 (dd, J=10.3, 3.9 Hz, 1H), 5.12 (s, 1H), 6.42 (d, J=1.5 Hz, 1H), 7.52 (d, J=1.5 Hz, 1H), 10.72 (s, 1H).

Example 25

(S)-3-Cyclohexyl-N-[1-(2-hydroxy-2-methyl-propyl)-1H-pyrazol-3-yl]-2-(4-isopropoxy-2-oxo-2,5-dihydro-pyrrol-1-yl)-propionamide

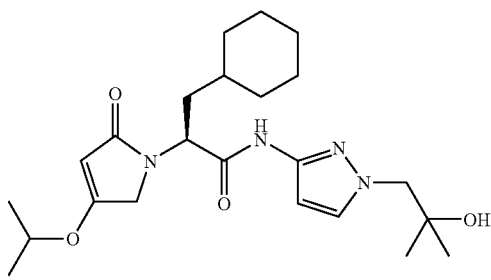

(S)-3-Cyclohexyl-2-(2,4-dioxo-pyrrolidin-1-yl)-N-[1-(2-hydroxy-2-methyl-propyl)-1H-pyrazol-3-yl]-propionamide (prepared as in Example 24, 100 mg, 0.26 mmol) was added to isopropyl alcohol (10 mL), and toluene-4-sulfonic acid hydrate (10 mg). The mixture was stirred at 100° C. for 4 h. The reaction mixture was concentrated and the crude product obtained was purified by ISCO flash chromatography (Teledyne Isco RediSep Flash Column 12 g; 0% to 10% methanol/dichloromethane) to afford, (S)-3-cyclohexyl-N-[1-(2-hydroxy-2-methyl-propyl)-1H-pyrazol-3-yl]-2-(4-isopropoxy-2-oxo-2,5-dihydro-pyrrol-1-yl)-propionamide (20 mg, 18%) as an off-white solid: LR-ES-MS m/z calculated for $C_{22}H_{34}N_4O_4$ [M]$^+$ 432, observed [M+H]$^+$ 433; $^1$H NMR (300 MHz, DMSO-$d_6$) δ ppm 0.77-1.21 (m, 6H) 1.02 (s, 3H) 1.04 (s, 3H) 1.25 (d, J=2.7 Hz, 3H) 1.27 (d, J=2.7 Hz, 3H) 1.43-1.83 (m, 7H) 3.78-3.90 (m, 1H) 3.87 (s, 2H) 4.27 (d, J=17.8 Hz, 1H) 4.36-4.51 (m, 1H) 4.65 (s, 1H) 4.82 (dd, J=11.0, 4.7 Hz, 1H) 5.11 (s, 1H) 6.39 (d, J=2.1 Hz, 1H) 7.50 (d, J=2.1 Hz, 1H) 10.68 (s, 1H).

Example 26

(S)-3-Cyclopentyl-2-[4-(2-methoxy-phenoxy)-2-oxo-2,5-dihydro-pyrrol-1-yl]-N-thiazol-2-yl-propionamide

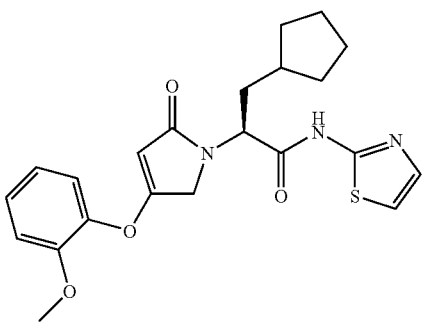

To a stirred mixture of ethyl acetoacetate (15.0 g, 0.12 mol) in petroleum ether (30 mL) under a nitrogen atmosphere was added phosphorus pentachloride (12.7 g, 0.06 mol) gradually. After addition was complete the mixture was stirred at 25° C. for 1 h. Upon completion of the reaction water (50 mL) was added in small portions, transferred to a separatory funnel and the layers separated, followed by washing the aqueous layer with petroleum ether (2×50 mL). The combined petroleum ether extracts were washed with a 20% potassium carbonate solution, followed by a saturated sodium chloride solution and dried over magnesium sulfate. The combined organic layers were concentrated to give a yellow oil. Distillation of the residue yielded 3-chloro-but-2-enoic acid ethyl ester (7.4 g, 43%) as a clear oil: LR-ES-MS m/z calculated for $C_6H_9ClO_2$ [M]$^+$ 148, observed [M+H]$^+$ 149.

To a stirred mixture of sodium metal (340 mg, 14.81 mmol) dissolved in ethanol (20 mL) under a nitrogen atmosphere was added 2-methoxy phenol (1.67 g, 13.47 mmol) and 3-chloro-but-2-enoic acid ethyl ester (2.0 g, 13.47 mmol). After addition was complete the mixture was stirred at reflux for 1 h. Upon completion of the reaction the ethanol was removed in vacuo and water (50 mL) was added. The aqueous layer was extracted with ethyl acetate (3×30 mL). Excess phenol was removed by washing the combined ethyl acetate layers with a 5% solution of sodium hydroxide (2×50 mL). The ethyl acetate solution was dried over magnesium sulfate, filtered and concentrated and the crude product obtained was purified by ISCO flash chromatography (Teledyne Isco RediSep Flash Column 40 g; 0% to 50% ethyl acetate/hexanes) to afford, 3-(2-methoxy-phenoxy)-but-2-enoic acid ethyl ester (1.58 g, 50%) as a clear oil: LR-ES-MS m/z calculated for $C_{13}H_{16}O_4$ [M]$^+$ 236, observed [M+H]$^+$ 237.

To a stirred mixture of 3-(2-methoxy-phenoxy)-but-2-enoic acid ethyl ester (1.80 g, 7.63 mmol) dissolved in carbon tetrachloride (20 mL) under a nitrogen atmosphere was added N-bromosuccinimide (1.49 g, 8.39 mmol) and benzoyl peroxide (0.21 g, 0.61 mmol). After addition was complete, the mixture was stirred at reflux for 4 h. The reaction mixture was then placed in the refrigerator overnight. The solids formed were removed by filtration and the filtrate concentrated in vacuo. The crude product obtained was purified by ISCO flash chromatography (Teledyne Isco RediSep Flash Column 40 g; 0% to 50% ethyl acetate/hexanes) to afford, 4-bromo-3-(2-methoxy-phenoxy)-but-2-enoic acid ethyl ester (2.0 g, 84%) as a yellow oil: LR-ES-MS m/z calculated for $C_{13}H_{15}BrO_4$ [M]$^+$ 314, observed [M+H]$^+$ 315.

To a stirred mixture of (S)-2-amino-3-cyclopentyl-propionic acid methyl ester hydrochloride (prepared as in Example 1, 1.05 g, 5.08 mmol) dissolved in acetonitrile (10 mL) under a nitrogen atmosphere was added triethylamine (500 mg, 4.94 mmol). After addition was complete the mixture was stirred at 60° C. for 1 h. The reaction was cooled to 25° C. and treated with triethylamine (500 mg, 4.94 mmol) and acetonitrile (10 mL) and heated to 80° C. at which time 4-bromo-3-(2-methoxy-phenoxy)-but-2-enoic acid ethyl ester (1.45 g, 4.62 mmol) in acetonitrile (10 mL) was added slowly. After the addition was complete, the reaction mixture was heated to 100° C. and stirred overnight. The reaction mixture was cooled to 25° C., filtered and concentrated. The residue was diluted with dichloromethane and washed with 2N aqueous hydrochloric acid, a saturated sodium bicarbonate solution, a saturated sodium chloride solution and dried over magnesium sulfate. The crude product obtained was purified by ISCO flash chromatography (Teledyne Isco RediSep Flash Column 40 g; 0% to 80% ethyl acetate/hexanes) to afford, (S)-3-cyclopentyl-2-[4-(2-methoxy-phenoxy)-2-oxo-2,5-dihydro-pyrrol-1-yl]-propionic acid methyl ester (500 mg, 30%) as a red oil: LR-ES-MS m/z calculated for $C_{20}H_{25}NO_5$ [M]$^+$ 359, observed [M+H]$^+$ 360.

To a stirred mixture of (S)-3-cyclopentyl-2-[4-(2-methoxy-phenoxy)-2-oxo-2,5-dihydro-pyrrol-1-yl]-propionic acid methyl ester (500 mg, 1.39 mmol) dissolved in tetrahydrofuran (9 mL) and water (3 mL) was added lithium hydroxide (76 mg, 1.81 mmol) After addition was complete, the mixture was stirred at 25° C. for 2 h. The reaction mixture was poured into water and diethyl ether and the layers separated. The aqueous layer was made acidic with 2N aqueous hydrochloric acid and extracted with ethyl acetate (3×30 mL). The combined ethyl acetate fractions were washed with a saturated sodium chloride solution, dried over magnesium sulfate, filtered and concentrated to afford, (S)-3-cyclopentyl-2-[4-(2-methoxy-phenoxy)-2-oxo-2,5-dihydro-pyrrol-1-yl]-propionic acid (390 mg, 81%) as a light brown solid: LR-ES-MS m/z calculated for $C_{19}H_{23}NO_5$ $[M]^+$ 345, observed $[M+H]^+$ 346.

A solution of (S)-3-cyclopentyl-2-[4-(2-methoxy-phenoxy)-2-oxo-2,5-dihydro-pyrrol-1-yl)-propionic acid (135 mg, 0.39 mmol) in dichloromethane (10 mL) was treated with 2-aminothiazole (43 mg, 0.43 mmol), benzotriazol-1-yl-oxy-tris(dimethylamino)phosphonium hexafluorophosphate (208 mg, 0.47 mmol) and N,N-diisopropylethylamine (150 mg, 1.17 mmol). The reaction mixture was stirred for 18 h at 25° C., under nitrogen. The reaction mixture was diluted with dichloromethane, washed with 2N aqueous hydrochloric acid, saturated sodium bicarbonate solution, saturated sodium chloride solution and dried. The organic layer was concentrated, and the crude product was purified by ISCO flash chromatography (Teledyne Isco RediSep Flash Column 12 g; 0% to 100% ethyl acetate/hexanes) to afford, (S)-3-cyclopentyl-2-[4-(2-methoxy-phenoxy)-2-oxo-2,5-dihydro-pyrrol-1-yl]-N-thiazol-2-yl-propionamide (8 mg, 6%) as brown solid: LR-ES-MS m/z calculated for $C_{22}H_{25}N_3O_4S$ $[M]^+$ 427, observed $[M+H]^+$ 428; $^1$H NMR (300 MHz, DMSO-$d_6$) δ ppm 1.02-2.00 (m, 11H) 3.81 (s, 3H) 4.20 (d, J=18.2 Hz, 1H) 4.48 (d, J=18.2 Hz, 1H) 4.72 (s, 1H) 4.91 (dd, J=10.3, 4.5 Hz, 1H) 7.00 (td, J=7.7, 1.5 Hz, 1H) 7.17-7.23 (m, 1H) 7.25 (d, J=3.6 Hz, 1H) 7.26-7.35 (m, 2H) 7.49 (d, J=3.6 Hz, 1H) 12.51 (s, 1H).

Example 27

(S)-3-Cyclopentyl-N-[1-(2-hydroxy-2-methyl-propyl)-1H-pyrazol-3-yl]-2-[4-(2-methoxy-phenoxy)-2-oxo-2,5-dihydro-pyrrol-1-yl]-propionamide

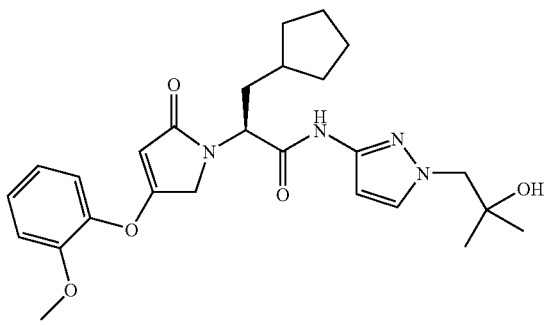

A solution of (S)-3-cyclopentyl-2-[4-(2-methoxy-phenoxy)-2-oxo-2,5-dihydro-pyrrol-1-yl)-propionic acid (prepared as in Example 26, 150 mg, 0.43 mmol) in dichloromethane (10 mL) was treated with 1-(3-amino-pyrazol-1-yl)-2-methyl-propan-2-ol (prepared in U.S. Pat. Appl. US2008021032 Example 80, 75 mg, 0.48 mmol), benzotriazol-1-yl-oxy-tris(dimethylamino)phosphonium hexafluorophosphate (230 mg, 0.52 mmol) and N,N-diisopropylethylamine (170 mg, 1.30 mmol). The reaction mixture was stirred for 18 h at 25° C., under nitrogen. The reaction mixture was diluted with dichloromethane, washed with 2N aqueous hydrochloric acid, saturated sodium bicarbonate solution, saturated sodium chloride solution and dried. The organic layer was concentrated, and the crude product was purified by ISCO flash chromatography (Teledyne Isco RediSep Flash Column 12 g; 0% to 100% ethyl acetate/hexanes) to afford (S)-3-cyclopentyl-N-[1-(2-hydroxy-2-methyl-propyl)-1H-pyrazol-3-yl]-2-[4-(2-methoxy-phenoxy)-2-oxo-2,5-dihydro-pyrrol-1-yl)-propionamide (47 mg, 22%) as a white solid: LR-ES-MS m/z calculated for $C_{26}H_{34}N_4O_5$ $[M]^+$ 482, observed $[M+H]^+$ 483; $^1$H NMR (300 MHz, DMSO-$d_6$) δ ppm 1.00-1.94 (m, 11H) 1.04 (br. s., 3H) 1.06 (br. s., 3H) 3.81 (s, 3H) 3.89 (s, 2H) 4.13 (d, J=18.4 Hz, 1H) 4.52 (d, J=18.4 Hz, 1H) 4.68 (s, 1H) 4.70 (s, 1H) 4.81 (dd, J=10.4, 4.7 Hz, 1H) 6.44 (d, J=2.2 Hz, 1H) 6.95-7.05 (m, 1H) 7.18-7.24 (m, 1H) 7.25-7.36 (m, 2H) 7.53 (d, J=2.2 Hz, 1H) 10.79 (s, 1H).

Example 28

(S)-3-Cyclohexyl-N-[1-(2-hydroxy-2-methyl-propyl)-1H-pyrazol-3-yl]-2-[4-(2-methoxy-phenoxy)-2-oxo-2,5-dihydro-pyrrol-1-yl]-propionamide

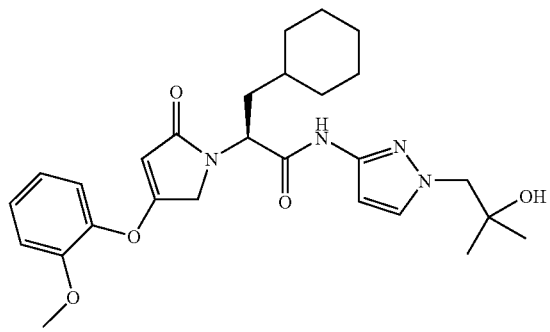

To a stirred mixture of (S)-2-amino-3-cyclohexyl-propionic acid methyl ester hydrochloride (776 mg, 3.50 mmol) dissolved in acetonitrile (10 mL) under a nitrogen atmosphere was added triethylamine (365 mg, 3.61 mmol). After addition was complete the mixture was stirred at 60° C. for 1 h. The reaction was cooled to 25° C. and treated with triethylamine (360 mg, 3.60 mmol) and acetonitrile (10 mL) and heated to 80° C. at which time 4-bromo-3-(2-methoxy-phenoxy)-but-2-enoic acid ethyl ester (prepared as in Example 26, 1.0 g, 3.18 mmol) in acetonitrile (10 mL) was added slowly. After the addition was complete, the reaction mixture was heated to 100° C. and stirred overnight. The reaction mixture was cooled to 25° C., filtered and concentrated. The residue was diluted with dichloromethane and washed with 2N aqueous hydrochloric acid, a saturated sodium bicarbonate solution, a saturated sodium chloride solution and dried over magnesium sulfate. The crude product obtained was purified by ISCO flash chromatography (Teledyne Isco RediSep Flash Column 40 g; 0% to 80% ethyl acetate/hexanes) to afford, (S)-3-cyclohexyl-2-[4-(2-methoxy-phenoxy)-2-oxo-2,5-dihydro-pyrrol-1-yl]-propionic acid methyl ester (400 mg, 34%) as a yellow oil: LR-ES-MS m/z calculated for $C_{21}H_{27}NO_5$ $[M]^+$ 373, observed $[M+H]^+$ 374.

To a stirred mixture of (S)-3-cyclohexyl-2-[4-(2-methoxy-phenoxy)-2-oxo-2,5-dihydro-pyrrol-1-yl]-propionic acid methyl ester (400 mg, 1.07 mmol) dissolved in tetrahydrofuran (9 mL) and water (3 mL) was added lithium hydroxide (60 mg, 1.39 mmol). After addition was complete the mixture was stirred at 25° C. for 2 h. The reaction mixture was poured into water and diethyl ether and the layers separated. The aqueous layer was made acidic with 2N aqueous hydrochloric acid and extracted with ethyl acetate (3×30 mL). The combined ethyl acetate fractions were washed with a saturated sodium chloride solution, dried over magnesium sulfate, filtered and concentrated to afford, (S)-3-cyclohexyl-2-[4-(2-methoxy-phenoxy)-2-oxo-2,5-dihydro-pyrrol-1-yl]-propionic acid (375 mg, 98%) as a yellow oil: LR-ES-MS m/z calculated for $C_{20}H_{25}NO_5$ [M]$^+$ 359, observed [M+H]$^+$ 360.

A solution of (S)-3-cyclohexyl-2-[4-(2-methoxy-phenoxy)-2-oxo-2,5-dihydro-pyrrol-1-yl)-propionic acid (375 mg, 1.04 mmol) in dichloromethane (15 mL) was treated with 1-(3-dimethylaminopropyl)-3-ethylcarbodiimide (164 mg, 1.06 mmol) and 1-hydroxybenzotriazole (150 mg, 2.00 mmol). The reaction mixture was stirred at 25° C. for 2 h followed by the addition of 1-(3-amino-pyrazol-1-yl)-2-methyl-propan-2-ol (prepared in U.S. Pat. Appl. US2008021032 Example 80, 178 mg, 1.15 mmol). The reaction mixture was then stirred for 18 h at 25° C., under nitrogen. The reaction mixture was diluted with dichloromethane, washed with 2N aqueous hydrochloric acid, saturated sodium bicarbonate solution, a saturated sodium chloride solution and dried over magnesium sulfate. The organic layer was concentrated, and the crude product was purified by ISCO flash chromatography (Teledyne Isco RediSep Flash Column 12 g; 0% to 100% ethyl acetate/hexanes) to afford (S)-3-cyclohexyl-N-[1-(2-hydroxy-2-methyl-propyl)-1H-pyrazol-3-yl]-2-[4-(2-methoxy-phenoxy)-2-oxo-2,5-dihydro-pyrrol-1-yl)-propionamide (200 mg, 40%) as an off-white solid: LR-ES-MS m/z calculated for $C_{27}H_{36}N_4O_5$ [M]$^+$ 496, observed [M+H]$^+$ 497; $^1$H NMR (300 MHz, DMSO-d$_6$) δ ppm 0.69-1.35 (m, 6H) 1.05 (br. s., 3H) 1.06 (br. s, 3H) 1.49-1.89 (m, 7H) 3.81 (s, 3H) 3.89 (s, 2H) 4.10 (d, J=18.4 Hz, 1H) 4.52 (d, J=18.4 Hz, 1H) 4.68 (s, 1H) 4.71 (s, 1H) 4.82-4.96 (m, 1H) 6.44 (d, J=2.2 Hz, 1H) 6.94-7.07 (m, 1H) 7.18-7.24 (m, 1H) 7.30 (m, 2H) 7.54 (d, J=2.2 Hz, 1H) 10.77 (s, 1H).

Example 29

(S)-3-Cyclohexyl-N-(1-methyl-1H-pyrazol-3-yl)-2-[4-(2-methoxy-phenoxy)-2-oxo-2,5-dihydro-pyrrol-1-yl]-propionamide

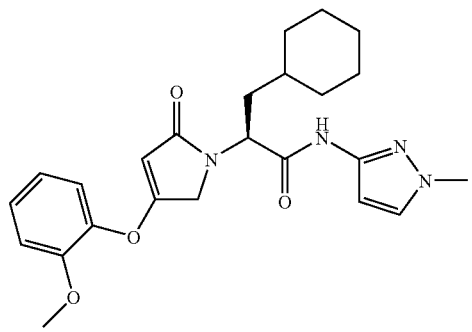

A solution of (S)-3-cyclohexyl-2-[4-(2-methoxy-phenoxy)-2-oxo-2,5-dihydro-pyrrol-1-yl)-propionic acid (prepared as in Example 28, 200 mg, 0.56 mmol) in dichloromethane (10 mL) was treated with 1-(3-dimethylaminopropyl)-3-ethylcarbodiimide (87 mg, 0.56 mmol) and 1-hydroxybenzotriazole (80 mg, 0.58 mmol). The reaction mixture was stirred at 25° C. for 2 h followed by the addition of 1-methyl-1H-pyrazol-3-amine (60 mg, 0.61 mmol). The reaction mixture was then stirred for 18 h at 25° C., under nitrogen. The reaction mixture was diluted with dichloromethane, washed with 2N aqueous hydrochloric acid, saturated sodium bicarbonate solution, a saturated sodium chloride solution and dried over magnesium sulfate. The organic layer was concentrated, and the crude product was purified by ISCO flash chromatography (Teledyne Isco RediSep Flash Column 12 g; 0% to 100% ethyl acetate/hexanes) to afford (S)-3-cyclohexyl-N-(1-methyl-1H-pyrazol-3-yl)-2-[4-(2-methoxy-phenoxy)-2-oxo-2,5-dihydro-pyrrol-1-yl)-propionamide (80 mg, 33%) as a light yellow solid: LR-ES-MS m/z calculated for $C_{24}H_{30}N_4O_4$ [M]$^+$ 438, observed [M+H]$^+$ 439; $^1$H NMR (300 MHz, DMSO-d$_6$) δ ppm 0.78-1.28 (m, 6H) 1.44-1.86 (m, 7H) 3.73 (s, 3H) 3.81 (s, 3H) 4.10 (d, J=18.2 Hz, 1H) 4.49 (d, J=18.2 Hz, 1H) 4.71 (s, 1H) 4.89 (dd, J=10.6, 5.1 Hz, 1H) 6.39 (d, J=2.1 Hz, 1H) 6.95-7.06 (m, 1H) 7.21 (d, J=7.5 Hz, 1H) 7.25-7.36 (m, 2H) 7.54 (d, J=2.1 Hz, 1H) 10.70 (s, 1H).

Example 30

(S)-3-Cyclohexyl-N-[1-((S)-2,3-dihydroxy-propyl)-1H-pyrazol-3-yl]-2-[4-(2-methoxy-phenoxy)-2-oxo-2,5-dihydro-pyrrol-1-yl]-propionamide

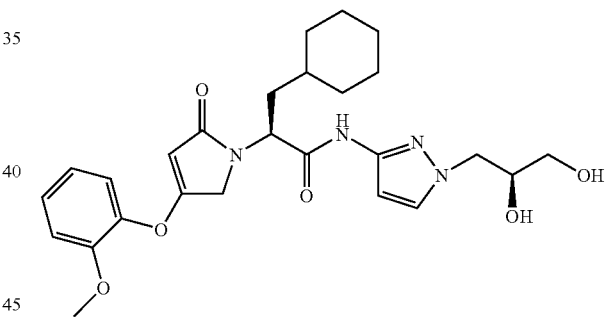

A solution of 3-nitro-1H-pyrazole (prepared as in Example 5, 3.00 g, 26.55 mmol) in N,N-dimethylformamide (15 mL) was treated with solid potassium carbonate (11.0 g, 79.65 mmol) and (R)-(+)-glycidol (3.93 g, 53.10 mmol) and placed in a sealed tube and heated at 100° C. for 1 h in an oil bath. After this time the N,N-dimethylformamide was removed in vacuo. Purification by AnaLogix Intelliflash system (80 g column, 0% to 10% methanol/dichloromethane) afforded (S)-3-(3-nitro-pyrazol-1-yl)-propane-1,2-diol (2.28 g, 46%) as a yellow oil: LR-ES-MS m/z calculated for $C_6H_9N_3O_4$ [M]$^+$ 187, observed [M+H]$^+$ 188.

In a Parr shaker bottle was placed (S)-3-(3-nitro-pyrazol-1-yl)-propane-1,2-diol (2.28 g, 12.19 mmol), 10% palladium on activated carbon (200 mg) and ethanol (30 mL). The bottle was then placed on the Parr shaker at 50 psi of hydrogen pressure for 5 h. The reaction was then filtered through a pad of celite and washed with ethanol and concentrated in vacuo to afford (S)-3-(3-amino-pyrazol-1-yl)-propane-1,2-diol (1.69 g, 88%) as a yellow oil: LR-ES-MS m/z calculated for $C_6H_{11}N_3O_2$ [M]$^+$ 157, observed [M+H]$^+$ 158.

A solution of (S)-3-cyclohexyl-2-[4-(2-methoxy-phenoxy)-2-oxo-2,5-dihydro-pyrrol-1-yl]-propionic acid (prepared as in Example 28, 210 mg, 0.58 mmol) in dichloromethane (10 mL) was treated with oxalyl chloride (0.35 mL, 2M in dichloromethane), and N,N-dimethylformamide (1 drop). Effervescence was observed. The reaction mixture was stirred for 2 h at 25° C., under nitrogen. The reaction mixture was concentrated, and dissolved in dichloromethane (5 mL) and treated with (S)-3-(3-amino-pyrazol-1-yl)-propane-1,2-diol (140 mg, 0.88 mmol), and N,N-diisopropyl-ethylamine (225 mg, 1.75 mmol). The reaction mixture was stirred at 25° C., under nitrogen for 18 h. The reaction mixture was diluted with dichloromethane, washed with water, 2N aqueous hydrochloric acid, saturated sodium bicarbonate solution, a saturated sodium chloride solution and dried over magnesium sulfate. The organic layer was concentrated, and the crude product was purified by ISCO flash chromatography (Teledyne Isco RediSep Flash Column 12 g; 0% to 10% methanol/dichloromethane) to afford, (S)-3-cyclohexyl-N-[1-((S)-2,3-dihydroxy-propyl)-1H-pyrazol-3-yl]-2-[4-(2-methoxy-phenoxy)-2-oxo-2,5-dihydro-pyrrol-1-yl]-propionamide (37 mg, 13%) as an off-white solid: LR-ES-MS m/z calculated for $C_{26}H_{34}N_4O_6$ $[M]^+$ 498, observed $[M+H]^+$ 499; $^1$H NMR (300 MHz, DMSO-$d_6$) δ ppm 0.68-1.38 (m, 6H) 1.47-1.86 (m, 7H) 3.17-3.41 (m, 2H) 3.63-3.97 (m, 2H) 3.81 (s, 3H) 4.03-4.15 (m, 2H) 4.50 (d, J=18.1 Hz, 1H) 4.65-4.77 (m, 2H) 4.88 (dd, J=10.6, 4.8 Hz, 1H) 4.94 (d, J=5.1 Hz, 1H) 6.40 (d, j=2.1 Hz, 1H) 6.92-7.06 (m, 1H) 7.16-7.24 (m, 1H) 7.23-7.36 (m, 2H) 7.53 (d, J=2.1 Hz, 1H) 10.74 (s, 1H).

Example 31

(S)-N-[1-(2-hydroxy-2-methyl-propyl)-1H-pyrazol-3-yl]-2-[4-(2-methoxy-phenoxy)-2-oxo-2,5-dihydro-pyrrol-1-yl]-3-(tetrahydro-furan-2-yl)-propionamide

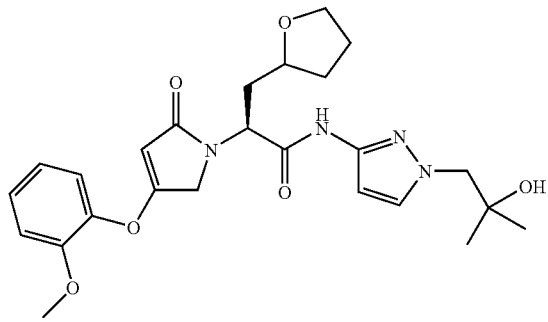

A solution of (L)-2-furylalanine (2.00 g, 12.89 mmol) in methanol (30 mL) was treated with triethylamine (1.96 g, 19.34 mmol) and di-t-butyl-dicarbonate (3.09 g, 14.18 mmol). The reaction mixture was stirred for 30 min at 60° C., under nitrogen. The reaction mixture was concentrated and diluted with ethyl acetate, washed 2N aqueous hydrochloric acid, a saturated sodium chloride solution and dried over magnesium sulfate. The organic layer was concentrated to afford, (S)-2-t-butoxycarbonylamino-3-furan-2-yl-propionic acid (3.88 g, 100%) as a yellow oil: LR-ES-MS m/z calculated for $C_{12}H_{17}NO_5$ $[M]^+$ 255, observed $[M+H]^+$ 256.

In a Parr shaker bottle was placed (S)-2-t-butoxycarbonyl-lamino-3-furan-2-yl-propionic acid (3.88 g, 15.22 mmol), platinum oxide (200 mg) and ethyl acetate (40 mL). The bottle was then placed on the Parr shaker at 50 psi of hydrogen pressure for 5 h. The reaction was then filtered through a pad of celite and washed with ethyl acetate and concentrated in vacuo to afford (S)-2-t-butoxycarbonylamino-3-(tetrahydro-furan-2-yl)-propionic acid (3.60 g, 91%) as a yellow oil: LR-ES-MS m/z calculated for $C_{12}H_{21}NO_5$ $[M]^+$ 259, observed $[M+H]^+$ 260.

A solution of (S)-2-t-butoxycarbonylamino-3-(tetrahydro-furan-2-yl)-propionic acid (3.60 g, 13.90 mmol) in saturated methanolic hydrogen chloride (30 mL) was heated at 50° C. for 18 h in a sealed tube. The mixture was cooled to 25° C. and the solution was concentrated to dryness to yield (S)-2-amino-3-(tetrahydro-furan-2-yl)-propionic acid methyl ester hydrochloride (2.20 g, 76%) as a heavy yellow oil.

To a stirred mixture of (S)-2-amino-3-(tetrahydro-furan-2-yl)-propionic acid methyl ester hydrochloride (0.74 g, 3.50 mmol) dissolved in acetonitrile (10 mL) under a nitrogen atmosphere was added triethylamine (360 mg, 3.59 mmol). After the addition was complete the mixture was stirred at 60° C. for 1 h. The reaction was cooled to 25° C. and treated with triethylamine (360 mg, 3.59 mmol) and acetonitrile (10 mL) and heated to 80° C. at which time 4-bromo-3-(2-methoxy-phenoxy)-but-2-enoic acid ethyl ester (prepared as in Example 26, 1.00 g, 3.18 mmol) in acetonitrile (10 mL) was added slowly. After the addition was complete the reaction mixture was heated to 100° C. and stirred overnight. The reaction mixture was cooled to 25° C., filtered and concentrated. The residue was diluted with dichloromethane and washed with 2N aqueous hydrochloric acid, a saturated sodium bicarbonate solution, a saturated sodium chloride solution and dried over magnesium sulfate. The crude product obtained was purified by ISCO flash chromatography (Teledyne Isco RediSep Flash Column 40 g; 0% to 10% methanol/dichloromethane) to afford, (S)-2-[4-(2-methoxy-phenoxy)-2-oxo-2,5-dihydro-pyrrol-1-yl]-3-(tetrahydro-furan-2-yl)-propionic acid methyl ester (316 mg, 27%) as a yellow oil: LR-ES-MS m/z calculated for $C_{19}H_{23}NO_6$ $[M]^+$ 361, observed $[M+H]^+$ 362.

To a stirred mixture of (S)-2-[4-(2-methoxy-phenoxy)-2-oxo-2,5-dihydro-pyrrol-1-yl]-3-(tetrahydro-furan-2-yl)-propionic acid methyl ester (315 mg, 0.87 mmol) dissolved in tetrahydrofuran (10 mL) and water (3 mL) was added lithium hydroxide (48 mg, 1.13 mmol) After addition was complete the mixture was stirred at 25° C. for 2 h. The reaction mixture was poured into water and diethyl ether and the layers separated. The aqueous layer was made acidic with 2N aqueous hydrochloric acid and extracted with ethyl acetate (3×30 mL). The combined ethyl acetate fractions were washed with a saturated sodium chloride solution, dried over magnesium sulfate, filtered and concentrated to afford, (S)-2-[4-(2-methoxy-phenoxy)-2-oxo-2,5-dihydro-pyrrol-1-yl]-3-(tetrahydro-furan-2-yl)-propionic acid (176 mg, 58%) as a light brown solid: LR-ES-MS m/z calculated for $C_{18}H_{21}NO_6$ $[M]^+$ 347, observed $[M+H]^+$ 348.

A solution of (S)-2-[4-(2-methoxy-phenoxy)-2-oxo-2,5-dihydro-pyrrol-1-yl]-3-(tetrahydro-furan-2-yl)-propionic acid (90 mg, 0.26 mmol) in dichloromethane (10 mL) was treated with 1-(3-amino-pyrazol-1-yl)-2-methyl-propan-2-ol (prepared in U.S. Pat. Appl. US2008021032 Example 80, 45 mg, 0.29 mmol), Benzotriazol-1-yl-oxy-tris(dimethylamino) phosphonium hexafluorophosphate (140 mg, 0.31 mmol) and N,N-diisopropylethylamine (100 mg, 0.78 mmol). The reaction mixture was stirred for 18 h at 25° C., under nitrogen. The reaction mixture was diluted with dichloromethane, washed with 2N aqueous hydrochloric acid, saturated sodium bicarbonate solution, saturated sodium chloride solution and dried over magnesium sulfate. The organic layer was concentrated, and the crude product was purified by ISCO flash chromatography (Teledyne Isco RediSep Flash Column 12 g; 0% to 10% methanol/dichloromethane) to afford (S)-N-[1-(2-hydroxy-2-methyl-propyl)-1H-pyrazol-3-yl]-2-[4-(2-methoxy-phenoxy)-2-oxo-2,5-dihydro-pyrrol-1-yl]-3-(tetrahydro-furan-2-yl)-propionamide (45 mg, 36%) as a yellow solid: LR-ES-MS m/z calculated for $C_{25}H_{32}N_4O_6$ [M]$^+$ 484, observed [M+H]$^+$ 485; $^1$H NMR (300 MHz, DMSO-d$_6$) δ ppm 1.05 (br. s., 3H) 1.06 (br. s., 3H) 1.35-2.11 (m, 6H) 3.54-3.79 (m, 3H) 3.81 (s, 3H) 3.89 (s, 2H) 4.18, 4.22 (2×d, J=18.0, 1H) 4.45 (d, J=18.0 Hz, 1H) 4.68 (s, 1H) 4.70 (s, 1H) 4.77-4.91 (m, 1H) 6.40-6.48 (m, 1H) 6.95-7.06 (m, 1H) 7.18-7.25 (m, 1H) 7.25-7.36 (m, 2H) 7.51-7.56 (m, 1H) 10.70, 10.73 (2×s, 1H).

Example 32

(S)-3-Cyclohexyl-N-[1-(2-hydroxy-2-methyl-propyl)-1H-pyrazol-3-yl]-2-[2-oxo-4-(2-trifluoromethyl-phenoxy)-2,5-dihydro-pyrrol-1-yl]-propionamide

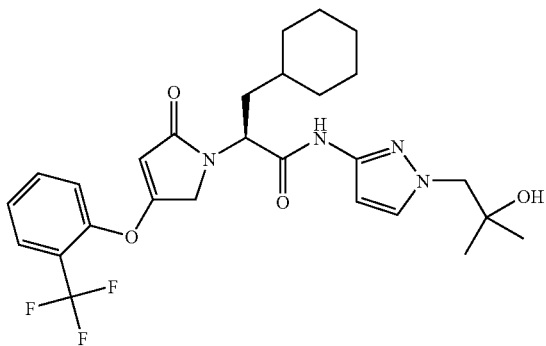

To a stirred mixture of sodium metal (340 mg, 14.81 mmol) dissolved in ethanol (20 mL) under a nitrogen atmosphere was added 2-hydroxy-benzotrifluoride (2.20 g, 13.47 mmol) and 3-chloro-but-2-enoic acid ethyl ester (prepared as in Example 26, 2.0 g, 13.47 mmol). After addition was complete the mixture was stirred at reflux for 1 h. Upon completion of the reaction the ethanol was removed in vacuo and water (50 mL) was added. The aqueous layer was extracted with ethyl acetate (3×30 mL). Excess phenol was removed by washing the combined ethyl acetate layers with a 5% aqueous solution of sodium hydroxide (2×50 mL). The ethyl acetate solution was dried over magnesium sulfate, filtered and concentrated and the crude product obtained was purified by ISCO flash chromatography (Teledyne Isco RediSep Flash Column 40 g; 0% to 50% ethyl acetate/hexanes) to afford, 3-(2-trifluoro-phenoxy)-but-2-enoic acid ethyl ester (540 mg, 16%) as a yellow oil: LR-ES-MS m/z calculated for $C_{13}H_{13}F_3O_3$ [M]$^+$ 274, observed [M+H]$^+$ 275.

To a stirred mixture of 3-(2-trifluoro-phenoxy)-but-2-enoic acid ethyl ester (1.15 g, 4.20 mmol) dissolved in carbon tetrachloride (20 mL) under a nitrogen atmosphere was added N-bromosuccinimide (0.75 g, 4.20 mmol) and benzoyl peroxide (0.11 g, 0.34 mmol). After addition was complete, the mixture was stirred at reflux for 4 h. The reaction mixture was then placed in the refrigerator overnight. The solids formed were removed by filtration and the filtrate concentrated in vacuo. The crude product obtained was purified by ISCO flash chromatography (Teledyne Isco RediSep Flash Column 40 g; 0% to 50% ethyl acetate/hexanes) to afford, 4-bromo-3-(2-trifluoro-phenoxy)-but-2-enoic acid ethyl ester (690 mg, 46%) as a yellow oil: LR-ES-MS m/z calculated for $C_{13}H_{12}BrF_3O_3$ [M]$^+$ 314, observed [M+H]$^+$ 315.

To a stirred mixture of (S)-2-amino-3-cyclohexyl-propionic acid methyl ester hydrochloride (480 mg, 2.14 mmol) dissolved in acetonitrile (8 mL) under a nitrogen atmosphere was added triethylamine (230 mg, 2.20 mmol). After addition was complete, the mixture was stirred at 60° C. for 1 h. The reaction was cooled to 25° C. and treated with triethylamine (220 mg, 2.20 mmol) and acetonitrile (8 mL) and heated to 80° C. at which time 4-bromo-3-(2-trifluoro-phenoxy)-but-2-enoic acid ethyl ester (690 mg, 1.95 mmol) in acetonitrile (8 mL) was added slowly. After the addition was complete the reaction mixture was heated to 100° C. and stirred overnight. The reaction mixture was cooled to 25° C., filtered and concentrated. The residue was diluted with dichloromethane and washed with 2N aqueous hydrochloric acid, a saturated sodium bicarbonate solution, a saturated sodium chloride solution and dried over magnesium sulfate. The crude product obtained was purified by ISCO flash chromatography (Teledyne Isco RediSep Flash Column 40 g; 0% to 80% ethyl acetate/hexanes) to afford, (S)-3-cyclohexyl-2-[2-oxo-4-(2-trifluoromethyl-phenoxy)-2,5-dihydro-pyrrol-1-yl]-propionic acid methyl ester (220 mg, 27%) as a dark yellow oil: LR-ES-MS m/z calculated for $C_{21}H_{24}F_3NO_4$ [M]$^+$ 411, observed [M+H]$^+$ 412.

To a magnetically stirred mixture of ((S)-3-cyclohexyl-2-[2-oxo-4-(2-trifluoromethyl-phenoxy)-2,5-dihydro-pyrrol-1-yl]-propionic acid methyl ester in tetrahydrofuran (9 mL) and water (3 mL) was added lithium hydroxide (30 mg, 0.68 mol) After addition was complete the mixture was stirred at 25° C. for 2 h. The reaction mixture was poured into water and diethyl ether and the layers separated. The aqueous layer was made acidic with 2N aqueous hydrochloric acid and extracted with ethyl acetate (3×30 mL). The combined ethyl acetate fractions were washed with a saturated sodium chloride solution, dried over magnesium sulfate, filtered and concentrated to afford, (S)-3-cyclohexyl-2-[2-oxo-4-(2-trifluoromethyl-phenoxy)-2,5-dihydro-pyrrol-1-yl]-propionic acid (145 mg, 70%) as a yellow oil: LR-ES-MS m/z calculated for $C_{20}H_{22}F_3NO_4$ [M]$^+$ 397, observed [M+H]$^+$ 398.

A solution of (S)-3-cyclohexyl-2-[2-oxo-4-(2-trifluoromethyl-phenoxy)-2,5-dihydro-pyrrol-1-yl]-propionic acid (145 mg, 0.37 mmol) in dichloromethane (10 mL) was treated with 1-(3-amino-pyrazol-1-yl)-2-methyl-propan-2-ol (prepared in U.S. Pat. Appl. US2008021032 Example 80, 62 mg, 0.40 mmol), benzotriazol-1-yl-oxy-tris(dimethylamino) phosphonium hexafluorophosphate (195 mg, 0.44 mmol) and N,N-diisopropylethylamine (141 mg, 1.10 mmol). The reaction mixture was stirred for 18 h at 25° C., under nitrogen. The reaction mixture was diluted with dichloromethane, washed with 2N aqueous hydrochloric acid, saturated sodium bicarbonate solution, a saturated sodium chloride solution and dried over magnesium sulfate. The organic layer was concentrated, and the crude product was purified by ISCO flash chromatography (Teledyne Isco RediSep Flash Column 12 g; 0% to 100% ethyl acetate/hexanes) to afford (S)-3-cyclohexyl-N-[1-(2-trifluoro-2-methyl-propyl)-1H-pyrazol-3-yl]-2-[4-(2-methoxy-phenoxy)-2-oxo-2,5-dihydro-pyrrol-1-yl)-propionamide (54 mg, 28%) as a white solid: LR-ES-MS m/z calculated for $C_{27}H_{33}F_3N_4O_4$ [M]$^+$ 534, observed [M+H]$^+$ 535; $^1$H NMR (300 MHz, DMSO-d$_6$) δ ppm 0.77-1.30 (m, 6H) 1.04 (s, 3H) 1.06 (s, 3H) 1.63 (m, 7H) 3.89 (s, 2H) 4.18 (d, J=18.4 Hz, 1H) 4.60 (d, J=18.4 Hz, 1H) 4.68 (s, 1H) 4.91 (dd, J=10.7, 5.3 Hz, 1H) 4.96 (s, 1H) 6.44 (d, J=2.1 Hz, 1H)

7.47-7.57 (m, 2H) 7.65 (d, J=8.2 Hz, 1H) 7.81 (t, J=7.8 Hz, 1H) 7.85 (d, J=7.8 Hz, 1H) 10.79 (s, 1H).

Example 33

(S)-3-Cyclohexyl-2-[4-(2,3-dihydro-benzo[1,4]dioxin-5-yloxy)-2-oxo-2,5-dihydro-pyrrol-1-yl]-N-[1-(2-hydroxy-2-methyl-propyl)-1H-pyrazol-3-yl]-propionmide

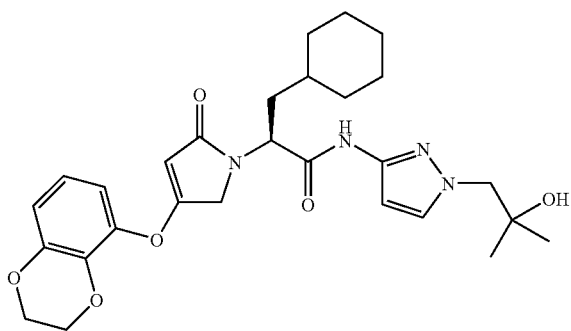

To a stirred mixture of 2,3-dihydro-1,4-benzodioxin-5-ol (1.00 g, 6.58 mmol) and ethyl-2-butynoate (1.48 g, 13.16 mmol) in tetrahydrofuran (10 mL) was added 1,8-diazabicyclo[5.4.0]undec-7-ene (1.00 g, 6.58 mmol). After addition was complete the mixture was stirred at 130° C. for 2 h. Upon completion of the reaction the tetrahydrofuran was removed in vacuo and the residue redissolved in dichloromethane and washed with 2N aqueous hydrochloric acid, 5% aqueous sodium hydroxide solution, a saturated sodium chloride solution and dried over magnesium sulfate. The crude product obtained was purified by ISCO flash chromatography (Teledyne Isco RediSep Flash Column 40 g; 0% to 50% ethyl acetate/hexanes) to afford, 3-(2,3-dihydro-benzo[1,4]dioxin-5-yloxy)-but-2-enoic acid ethyl ester (750 mg, 43%) as a colorless oil: LR-ES-MS m/z calculated for $C_{14}H_{16}O_5$ $[M]^+$ 264, observed $[M+H]^+$ 265.

To a stirred mixture of 3-(2,3-dihydro-benzo[1,4]dioxin-5-yloxy)-but-2-enoic acid ethyl ester (0.75 g, 2.84 mmol) dissolved in carbon tetrachloride (25 mL) under a nitrogen atmosphere was added N-bromosuccinimide (0.56 g, 3.12 mmol) and benzoyl peroxide (0.08 g, 0.23 mmol). After addition was complete the mixture was stirred at reflux for 5 h. The reaction mixture was then placed in the refrigerator overnight. The solids formed were removed by filtration and the filtrate concentrated in vacuo. The crude product obtained was purified by ISCO flash chromatography (Teledyne Isco RediSep Flash Column 40 g; 0% to 50% ethyl acetate/hexanes) to afford, 4-bromo-3-(2,3-dihydro-benzo[1,4]dioxin-5-yloxy)-but-2-enoic acid ethyl ester (770 mg, 79%) as a clear oil: LR-ES-MS m/z calculated for $C_{14}H_{15}BrO_5$ $[M]^+$ 342, observed $[M+H]^+$ 343.

To a stirred mixture of (S)-2-amino-3-cyclohexyl-propionic acid methyl ester hydrochloride (0.55 g, 2.46 mmol) dissolved in acetonitrile (7 mL) under a nitrogen atmosphere was added N,N-diisopropylethylamine (330 mg, 2.50 mmol). After addition was complete the mixture was stirred at 60° C. for 1 h. The reaction was cooled to 25° C. and treated with N,N-diisopropylethylamine (320 mg, 2.50 mmol) and acetonitrile (8 mL) and heated to 80° C. at which time 4-bromo-3-(2,3-dihydro-benzo[1,4]dioxin-5-yloxy)-but-2-enoic acid ethyl ester (0.77 g, 2.24 mmol) in acetonitrile (8 mL) was added slowly. After the addition was complete, the reaction mixture was heated to 100° C. and stirred overnight. The reaction mixture was cooled to 25° C., filtered and concentrated. The residue was diluted with dichloromethane and washed with 2N aqueous hydrochloric acid, saturated sodium bicarbonate solution, saturated sodium chloride solution and dried over magnesium sulfate. The crude product obtained was purified by ISCO flash chromatography (Teledyne Isco RediSep Flash Column 40 g; 0% to 50% ethyl acetate/hexanes) to afford, (S)-3-cyclohexyl-2-[4-(2,3-dihydro-benzo[1,4]dioxin-5-yloxy)-2-oxo-2,5-dihydro-pyrrol-1-yl]-propionic acid methyl ester (540 mg, 61%) as a yellow oil: LR-ES-MS m/z calculated for $C_{22}H_{27}NO_6$ $[M]^+$ 401, observed $[M+H]^+$ 402.

To a stirred mixture of (S)-3-cyclohexyl-2-[4-(2,3-dihydro-benzo[1,4]dioxin-5-yloxy)-2-oxo-2,5-dihydro-pyrrol-1-yl]-propionic acid methyl ester (540 mg, 1.35 mmol) in tetrahydrofuran (10 mL) and water (3 mL) was added lithium hydroxide (74 mg, 1.75 mmol) After addition was complete the mixture was stirred at 25° C. for 2 h. The reaction mixture was poured into water and diethyl ether and the layers separated. The aqueous layer was made acidic with 2N aqueous hydrochloric acid and extracted with ethyl acetate (3×30 mL). The combined ethyl acetate fractions were washed with a saturated sodium chloride solution, dried over magnesium sulfate, filtered and concentrated to afford, (S)-3-cyclohexyl-2-[4-(2,3-dihydro-benzo[1,4]dioxin-5-yloxy)-2-oxo-2,5-dihydro-pyrrol-1-yl]-propionic acid (430 mg, 83%) as a yellow oil: LR-ES-MS m/z calculated for $C_{21}H_{25}NO_6$ $[M]^+$ 387, observed $[M+H]^+$ 388.

A solution of (S)-3-cyclohexyl-2-[4-(2,3-dihydro-benzo[1,4]dioxin-5-yloxy)-2-oxo-2,5-dihydro-pyrrol-1-yl]-propionic acid (200 mg, 0.52 mmol) in dichloromethane (10 mL) was treated with 1-(3-dimethylaminopropyl)-3-ethylcarbodiimide (81 mg, 0.52 mmol) and 1-hydroxybenzotriazole (75 mg, 0.54 mmol). The reaction mixture was stirred at 25° C. for 2 h followed by the addition of 1-(3-amino-pyrazol-1-yl)-2-methyl-propan-2-ol (prepared in U.S. Pat. Appl. US2008021032 Example 80, 88 mg, 0.57 mmol). The reaction mixture was stirred for 18 h at 25° C., under nitrogen. The reaction mixture was diluted with dichloromethane, washed with 2N aqueous hydrochloric acid, saturated sodium bicarbonate solution, a saturated sodium chloride solution and dried over magnesium sulfate. The organic layer was concentrated, and the crude product was purified by ISCO flash chromatography (Teledyne Isco RediSep Flash Column 12 g; 0% to 100% ethyl acetate/hexanes) to afford (S)-3-cyclohexyl-2-[4-(2,3-dihydro-benzo[1,4]dioxin-5-yloxy)-2-oxo-2,5-dihydro-pyrrol-1-yl]-N-[1-(2-hydroxy-2-methyl-propyl)-1H-pyrazol-3-yl]-propionamide (117 mg, 43%) as a white solid: LR-ES-MS m/z calculated for $C_{28}H_{36}N_4O_6$ $[M]^+$ 524, observed $[M+H]^+$ 525; $^1$H NMR (300 MHz, DMSO-$d_6$) δ ppm 0.74-1.33 (m, 6H) 1.04 (s, 3H) 1.06 (s, 3H) 1.49-1.89 (m, 7H) 3.89 (s, 2H) 4.11 (d, J=18.4 Hz, 1H) 4.28 (s, 4H) 4.52 (d, J=18.4 Hz, 1H) 4.68 (s, 1H) 4.84 (s, 1H) 4.89 (dd, J=10.6, 4.8 Hz, 1H) 6.44 (d, J=2.1 Hz, 1H) 6.72-6.95 (m, 3H) 7.53 (d, J=2.1 Hz, 1H) 10.77 (s, 1H).

Example 34

N-[1-(2-hydroxy-2-methyl-propyl)-1H-pyrazol-3-yl]-2-[4-(2-methoxy-phenoxy)-2-oxo-2,5-dihydro-pyrrol-1-yl]-3-(tetrahydropyran-4-yl)-propionamide

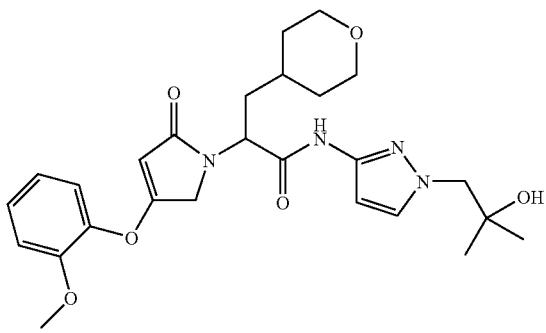

A solution of 2-t-butoxycarbonylamino-3-(tetrahydro-pyran-4-yl)-propionic acid (500 mg, 1.83 mmol) in dichloromethane (15 mL) was treated with 1-(3-dimethylaminopropyl)-3-ethylcarbodiimide (285 mg, 1.85 mmol) and 1-hydroxybenzotriazole (260 mg, 1.92 mmol). The reaction mixture was stirred at 25° C. for 2 h followed by the addition of 1-(3-amino-pyrazol-1-yl)-2-methyl-propan-2-ol (prepared in U.S. Pat. Appl. US2008021032 Example 80, 312 mg, 2.01 mmol). The reaction mixture was then stirred for 18 h at 25° C. under nitrogen. The reaction mixture was diluted with dichloromethane, washed with 2N aqueous hydrochloric acid, saturated sodium bicarbonate solution, a saturated sodium chloride solution and dried over magnesium sulfate. The organic layer was concentrated, to afford [1-[1-(2-hydroxy-2-methyl-propyl)-1H-pyrazol-3-ylcarbamoyl]-2-(tetrahydro-pyran-4-yl)-ethyl]-carbamic acid t-butyl ester (700 mg, 93%) as a white solid: LR-ES-MS m/z calculated for $C_{20}H_{34}N_4O_5$ $[M]^+$ 410, observed $[M+H]^+$ 411.

A solution of [1-[1-(2-hydroxy-2-methyl-propyl)-1H-pyrazol-3-ylcarbamoyl]-2-(tetrahydro-pyran-4-yl)-ethyl]-carbamic acid t-butyl ester) (700 mg, 1.71 mmol) in dichloromethane (10 mL) was treated with trifluoroacetic acid (5 mL). The reaction mixture was stirred at 25° C. for 30 min and then concentrated to afford the trifluoroacetic acid salt of 2-amino-N-[1-(2-hydroxy-2-methyl-propyl)-1H-pyrazol-3-yl]-3-(tetrahydro-pyran-4-yl)-propionamide (720 mg, 99%) as a white solid: LR-ES-MS m/z calculated for $C_{15}H_{26}N_4O_3$—$CF_3COOH$ $[M]^-$ 310, observed $[M+H]^+$ 311.

To a stirred mixture of 2-amino-N-[1-(2-hydroxy-2-methyl-propyl)-1H-pyrazol-3-yl]-3-(tetrahydro-pyran-4-yl)-propionamide trifluoracetic acid (300 mg, 0.70 mmol) dissolved in acetonitrile (10 mL) under a nitrogen atmosphere was added N,N-diisopropylethylamine (95 mg, 0.74 mmol). After addition was complete the mixture was stirred at 60° C. for 1 h. The reaction was cooled to 25° C. and treated with N,N-diisopropylethylamine (90 mg, 0.74 mmol) and acetonitrile (10 mL) and heated to 80° C. at which time 4-bromo-3-(2-methoxy-phenoxy)-but-2-enoic acid ethyl ester (prepared as in Example 26, 1.00 g, 3.18 mmol) in acetonitrile (10 mL) was added slowly. After the addition was complete the reaction mixture was heated to 100° C. and stirred overnight. The reaction mixture was cooled to 25° C., filtered and concentrated. The residue was diluted with dichloromethane and washed with 2N aqueous hydrochloric acid, a saturated sodium bicarbonate solution, a saturated sodium chloride solution and dried over magnesium sulfate. The crude product obtained was purified by ISCO flash chromatography (Teledyne Isco RediSep Flash Column 12 g; 0% to 80% ethyl acetate/hexanes) to afford, N-[1-(2-hydroxy-2-methyl-propyl)-1H-pyrazol-3-yl]-2-[4-(2-methoxy-phenoxy)-2-oxo-2,5-dihydro-pyrrol-1-yl]-3-(tetrahydropyran-4-yl)-propionamide (34 mg, 11%) as a light brown solid: LR-ES-MS m/z calculated for $C_{26}H_{34}N_4O_6$ $[M]^+$ 498, observed $[M+H]^+$ 499; $^1H$ NMR (300 MHz, DMSO-$d_6$) δ ppm 1.05 (s, 3H) 1.06 (s, 3H) 1.11-1.50 (m, 3H) 1.50-1.91 (m, 4H) 3.08-3.33 (m, 2H) 3.81 (br. s., 2H) 3.89 (s, 3H) 4.16 (m, J=18.2 Hz, 1H) 4.53 (d, J=18.2 Hz, 2H) 4.68 (s, 2H) 4.71 (s, 1H) 4.91 (dd, J=10.7, 4.4 Hz, 1H) 6.44 (d, J=2.2 Hz, 1H) 7.01 (td, J=7.6, 1.7 Hz, 1H) 7.17-7.24 (m, 1H) 7.26-7.34 (m, 2H) 7.54 (d, J=2.2 Hz, 1H) 10.79 (s, 1H).

Example 35

3-t-Butoxy-N-[1-(2-hydroxy-2-methyl-propyl)-1H-pyrazol-3-yl]-2-[4-(2-methoxy-phenoxy)-2-oxo-2,5-dihydro-pyrrol-1-yl]-propionamide

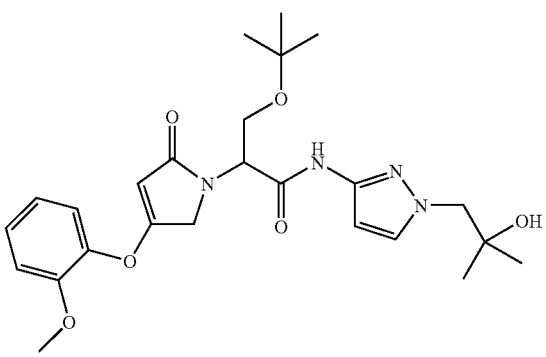

To a stirred mixture of (S)-2-amino-3-t-butoxy-propionic acid methyl ester hydrochloride (740 mg, 3.50 mmol) dissolved in acetonitrile (10 mL) under a nitrogen atmosphere was added triethylamine (365 mg, 3.61 mmol). After addition was complete the mixture was stirred at 60° C. for 1 h. The reaction was cooled to 25° C. and treated with triethylamine (360 mg, 3.60 mmol) and acetonitrile (10 mL) and heated to 80° C. at which time 4-bromo-3-(2-methoxy-phenoxy)-but-2-enoic acid ethyl ester (prepared as in Example 26, 1.0 g, 3.18 mmol) in acetonitrile (10 mL) was added slowly. After the addition was complete the reaction mixture was heated to 100° C. and stirred overnight. The reaction mixture was cooled to 25° C., filtered and concentrated. The residue was diluted with dichloromethane and washed with 2N aqueous hydrochloric acid, a saturated sodium bicarbonate solution, a saturated sodium chloride solution and dried over magnesium sulfate. The crude product obtained was purified by ISCO flash chromatography (Teledyne Isco RediSep Flash Column 40 g; 0% to 80% ethyl acetate/hexanes) to afford, 3-t-butoxy-2-[4-(2-methoxy-phenoxy)-2-oxo-2,5-dihydro-pyrrol-1-yl]-propionic acid methyl ester (292 mg, 25%) as a yellow oil: LR-ES-MS m/z calculated for $C_{19}H_{25}NO_6$ $[M]^+$ 363, observed $[M+H]^+$ 364.

To a stirred mixture of 3-t-butoxy-2-[4-(2-methoxy-phenoxy)-2-oxo-2,5-dihydro-pyrrol-1-yl]-propionic acid methyl ester (290 mg, 0.80 mmol) dissolved in tetrahydrofuran (9 mL) and water (3 mL) was added lithium hydroxide (44 mg, 1.04 mmol). After addition was complete, the mixture was stirred at 25° C. for 2 h. The reaction mixture was poured into water and diethyl ether and the layers separated. The aqueous layer was made acidic with 2N aqueous hydrochloric acid and extracted with ethyl acetate (3×30 mL). The combined ethyl acetate fractions were washed with a saturated sodium chloride solution, dried over magnesium sulfate, filtered and concentrated to afford, 3-t-butoxy-2-[4-(2-methoxy-phenoxy)-2-oxo-2,5-dihydro-pyrrol-1-yl]-propionic acid (212 mg, 76%) as a light brown solid: LR-ES-MS m/z calculated for $C_{18}H_{23}NO_6$ [M]+ 349, observed [M+H]+ 350.

A solution of 3-t-butoxy-2-[4-(2-methoxy-phenoxy)-2-oxo-2,5-dihydro-pyrrol-1-yl)-propionic acid (100 mg, 0.29 mmol) in dichloromethane (10 mL) was treated with 1-(3-dimethylaminopropyl)-3-ethylcarbodiimide (45 mg, 0.29 mmol) and 1-hydroxybenzotriazole (40 mg, 0.30 mmol). The reaction mixture was stirred at 25° C. for 2 h followed by the addition of 1-(3-amino-pyrazol-1-yl)-2-methyl-propan-2-ol (prepared in U.S. Pat. Appl. US2008021032 Example 80, 50 mg, 0.32 mmol). The reaction mixture was then stirred for 18 h at 25° C., under nitrogen. The reaction mixture was diluted with dichloromethane, washed with 2N aqueous hydrochloric acid, saturated sodium bicarbonate solution, a saturated sodium chloride solution and dried over magnesium sulfate. The organic layer was concentrated, and the crude product was purified by ISCO flash chromatography (Teledyne Isco RediSep Flash Column 12 g; 0% to 100% ethyl acetate/hexanes) to afford 3-t-butoxy-N-[1-(2-hydroxy-2-methyl-propyl)-1H-pyrazol-3-yl]-2-[4-(2-methoxy-phenoxy)-2-oxo-2,5-dihydro-pyrrol-1-yl)-propionamide (45 mg, 32%) as an off-white solid: LR-ES-MS m/z calculated for $C_{25}H_{34}N_4O_6$ [M]+ 486, observed [M+H]+ 487; $^1$H NMR (300 MHz, DMSO-$d_6$) δ ppm 1.05 (s, 6H) 1.12 (s, 9H) 3.64-3.78 (m, 2H) 3.81 (s, 3H) 3.89 (s, 2H) 4.15 (d, J=18.4 Hz, 1H) 4.45 (d, J=18.4 Hz, 1H) 4.67 (s, 1H) 4.73 (s, 1H) 4.80 (dd, J=7.1, 4.7 Hz, 1H) 6.43 (d, J=2.2 Hz, 1H) 6.94-7.09 (m, 1H) 7.13-7.39 (m, 3H) 7.53 (d, J=2.2 Hz, 1H) 10.64 (s, 1H).

Example 36

(S)-3-Cyclohexyl-2-[4-(2,6-difluoro-phenoxy)-2-oxo-2,5-dihydro-pyrrol-1-yl]-N-[1-(2-hydroxy-2-methyl-propyl)-1H-pyrazol-3-yl]-propionamide

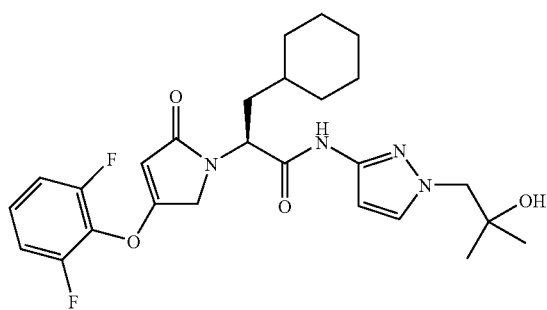

To a stirred mixture of 2,6-difluorophenol (1.00 g, 7.69 mmol) and ethyl-2-butynoate (1.72 g, 15.31 mmol) in tetrahydrofuran (10 mL) was added 1,8-diazabicyclo[5.4.0]undec-7-ene (1.17 g, 7.69 mmol). After addition was complete the mixture was stirred at 130° C. for 2 h. Upon completion of the reaction the tetrahydrofuran was removed in vacuo and the residue redissolved in dichloromethane and washed with 2N aqueous hydrochloric acid, 5% aqueous sodium hydroxide solution, a saturated sodium chloride solution and dried over magnesium sulfate. The crude product obtained was purified by ISCO flash chromatography (Teledyne Isco RediSep Flash Column 40 g; 0% to 50% ethyl acetate/hexanes) to afford, 3-(2,6-difluoro-phenoxy)-but-2-enoic acid ethyl ester (1.56 g, 84%) as a colorless oil: LR-ES-MS m/z calculated for $C_{12}H_{12}F_2O_3$ [M]+ 242, observed [M+H]+ 243.

To a stirred mixture of 3-(2,6-difluoro-phenoxy)-but-2-enoic acid ethyl ester (1.56 g, 6.45 mmol) dissolved in carbon tetrachloride (25 mL) under a nitrogen atmosphere was added N-bromosuccinimide (1.26 g, 7.09 mmol) and benzoyl peroxide (0.17 g, 0.52 mmol). After addition was complete, the mixture was stirred at reflux for 5 h. The reaction mixture was then placed in the refrigerator overnight. The solids formed were removed by filtration and the filtrate concentrated in vacuo. The crude product obtained was purified by ISCO flash chromatography (Teledyne Isco RediSep Flash Column 40 g; 0% to 50% ethyl acetate/hexanes) to afford, 4-bromo-3-(2,6-difluoro-phenoxy)-but-2-enoic acid ethyl ester (1.66 g, 81%) as a yellow oil: LR-ES-MS m/z calculated for $C_{12}H_{11}BrF_2O_3$ [M]+ 320, observed [M+H]+ 321.

To a stirred mixture of (S)-2-amino-3-cyclohexyl-propionic acid methyl ester hydrochloride (1.26 g, 5.71 mmol) dissolved in acetonitrile (10 mL) under a nitrogen atmosphere was added N,N-diisopropylethylamine (0.75 g, 5.80 mmol). After addition was complete the mixture was stirred at 60° C. for 1 h. The reaction was cooled to 25° C. and treated with N,N-diisopropylethylamine (750 mg, 5.80 mmol) and acetonitrile (10 mL) and heated to 80° C. at which time 4-bromo-3-(2,6-difluoro-phenoxy)-but-2-enoic acid ethyl ester (1.66 g, 5.19 mmol) in acetonitrile (10 mL) was added slowly. After the addition was complete the reaction mixture was heated to 100° C. and stirred overnight. The reaction mixture was cooled to 25° C., filtered and concentrated. The residue was diluted with dichloromethane and washed with 2N aqueous hydrochloric acid, a saturated sodium bicarbonate solution, a saturated sodium chloride solution and dried over magnesium sulfate. The crude product obtained was purified by ISCO flash chromatography (Teledyne Isco RediSep Flash Column 40 g; 0% to 50% ethyl acetate/hexanes) to afford, (S)-3-cyclohexyl-2-[4-(2,6-difluoro-phenoxy)-2-oxo-2,5-dihydro-pyrrol-1-yl]-propionic acid methyl ester (980 mg, 50%) as a yellow oil: LR-ES-MS m/z calculated for $C_{20}H_{23}F_2NO_4$ [M]+ 379, observed [M+H]+ 380.

To a stirred mixture of (S)-3-cyclohexyl-2-[4-(2,6-difluoro-phenoxy)-2-oxo-2,5-dihydro-pyrrol-1-yl]-propionic acid methyl ester (981 mg, 2.59 mmol) in tetrahydrofuran (10 mL) and water (3 mL) was added lithium hydroxide (140 mg, 3.36 mmol). After addition was complete the mixture was stirred at 25° C. for 2 h. The reaction mixture was poured into water and diethyl ether and the layers separated. The aqueous layer was made acidic with 2N aqueous hydrochloric acid and extracted with ethyl acetate (3×30 mL). The combined ethyl acetate fractions were washed with a saturated sodium chloride solution, dried over magnesium sulfate, filtered and concentrated to afford, (S)-3-cyclohexyl-2-[4-(2,6-difluoro-phenoxy)-2-oxo-2,5-dihydro-pyrrol-1-yl]-propionic acid (700 mg, 74%) as a light brown solid: LR-ES-MS m/z calculated for $C_{19}H_{21}F_2NO_4$ [M]+ 365, observed [M+H]+ 366.

A solution of (S)-3-cyclohexyl-2-[4-(2,6-difluoro-phenoxy)-2-oxo-2,5-dihydro-pyrrol-1-yl]-propionic acid (200 mg, 0.55 mmol) in dichloromethane (10 mL) was treated with 1-(3-dimethylaminopropyl)-3-ethylcarbodiimide (86 mg, 0.55 mmol) and 1-hydroxybenzotriazole (80 mg, 0.58 mmol). The reaction mixture was stirred at 25° C. for 2 h followed by the addition of 1-(3-amino-pyrazol-1-yl)-2-methyl-propan-2-ol (prepared in U.S. Pat. Appl. US2008021032 Example 80, 95 mg, 0.60 mmol). The reaction mixture was stirred for 18 h at 25° C., under nitrogen. The reaction mixture was diluted with dichloromethane, washed with 2N aqueous hydrochloric acid, saturated sodium bicarbonate solution, a saturated sodium chloride solution and dried over magnesium sulfate. The organic layer was concentrated, and the crude product was purified by ISCO flash chromatography (Teledyne Isco RediSep Flash Column 12 g; 0% to 100% ethyl acetate/hexanes) to afford (S)-3-cyclohexyl-2-[4-(2,6-difluoro-phenoxy)-2-oxo-2,5-dihydro-pyrrol-1-yl]-N-[1-(2-hydroxy-2-methyl-propyl)-1H-pyrazol-3-yl]-propionamide (197 mg, 72%) as a white solid: LR-ES-MS m/z calculated for $C_{26}H_{32}F_2N_4O_4$ [M]$^+$ 502, observed [M+H]$^+$ 503; $^1$H NMR (300 MHz, DMSO-$d_6$) δ ppm 0.77-1.35 (m, 6H) 1.04 (s, 3H) 1.06 (s, 3H) 1.48-1.85 (m, 7H) 3.89 (s, 2H) 4.26 (d, J=18.8 Hz, 1H) 4.64 (d, J=18.8 Hz, 1H) 4.68 (s, 1H) 4.90 (dd, J=10.7, 4.7 Hz, 1H) 5.03 (s, 1H) 6.44 (d, J=2.1 Hz, 1H) 7.20-7.50 (m, 3H) 7.53 (d, J=2.1 Hz, 1H) 10.80 (s, 1H).

Example 37

(S)-3-Cyclohexyl-2-[4-(2,6-difluoro-phenoxy)-2-oxo-2,5-dihydro-pyrrol-1-yl]-N-[1-((S)-2,3-dihydroxy-propyl)-1H-pyrazol-3-yl]-propionamide

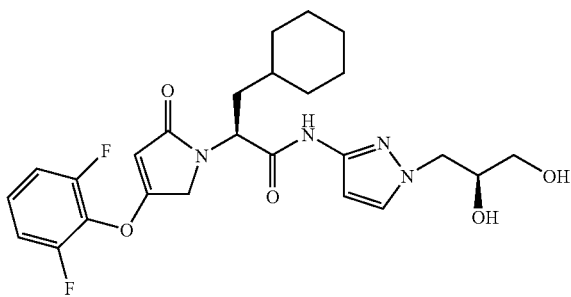

A solution of (S)-3-cyclohexyl-2-[4-(2,6-difluoro-phenoxy)-2-oxo-2,5-dihydro-pyrrol-1-yl)-propionic acid (prepared as in Example 36, 200 mg, 0.55 mmol) in dichloromethane (10 mL) was treated with oxalyl chloride (0.33 mL, 2M in dichloromethane), and N,N-dimethylformamide (1 drop). Effervescence was observed. The reaction mixture was stirred for 2 h at 25° C., under nitrogen. The reaction mixture was concentrated, and dissolved in dichloromethane (5 mL) and treated with (S)-3-(3-amino-pyrazol-1-yl)-propane-1,2-diol (prepared as in Example 30, 103 mg, 0.66 mmol), and N,N-diisopropylethylamine (215 mg, 1.64 mmol). The reaction mixture was stirred at 25° C., under nitrogen for 18 h. The reaction mixture was diluted with dichloromethane, washed with water, 2N aqueous hydrochloric acid, saturated sodium bicarbonate solution, a saturated sodium chloride solution and dried over magnesium sulfate. The organic layer was concentrated, and the crude product was purified by ISCO flash chromatography (Teledyne Isco RediSep Flash Column 12 g; 0% to 10% methanol/dichloromethane) to afford, (S)-3-cyclohexyl-2-[4-(2,6-difluoro-phenoxy)-2-oxo-2,5-dihydro-pyrrol-1-yl]-N-[1-((S)-2,3-dihydroxy-propyl)-1H-pyrazol-3-yl]-propionamide (113 mg 43%) as a light yellow solid: LR-ES-MS m/z calculated for $C_{25}H_{30}F_2N_4O_5$ [M]$^+$ 504, observed [M+H]$^+$ 505; $^1$H NMR (300 MHz, DMSO-$d_6$) δ ppm 0.71-1.35 (m, 6H) 1.50-1.86 (m, 7H) 3.18-3.43 (m, 2H) 3.66-3.97 (m, 2H) 4.09 (dd, J=13.1, 3.5 Hz, 1H) 4.27 (d, J=18.7 Hz, 1H) 4.62 (d, J=18.7 Hz, 1H) 4.71 (t, J=5.6 Hz, 1H) 4.89 (dd, J=10.1, 5.3 Hz, 1H) 4.94 (d, J=5.1 Hz, 1H) 5.04 (s, 1H) 6.41 (d, J=2.1 Hz, 1H) 7.24-7.51 (m, 3H) 7.54 (d, J=2.1 Hz, 1H) 10.78 (s, 1H).

Example 38

(S)-3-Cyclohexyl-2-[4-(2,6-difluoro-phenoxy)-2-oxo-2,5-dihydro-pyrrol-1-yl]-N-[1-((R)-2,3-dihydroxy-propyl)-1H-pyrazol-3-yl]-propionamide

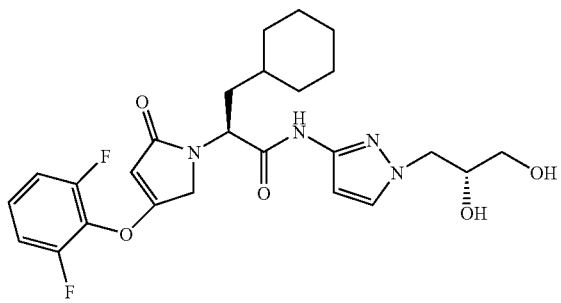

A solution of 3-nitro-1H-pyrazole (prepared as in Example 5, 3.00 g, 26.55 mmol) in N,N-dimethylformamide (15 mL) was treated with solid potassium carbonate (5.50 g, 39.82 mmol) and (S)-(−)-glycidol (3.93 g, 53.10 mmol) and placed in a sealed tube and heated at 100° C. for 1 h in an oil bath. After this time the N,N-dimethylformamide was removed in vacuo. Purification by ISCO flash chromatography (Teledyne Isco RediSep Flash Column 12 g; 0% to 10% methanol/dichloromethane) afforded (R)-3-(3-nitro-pyrazol-1-yl)-propane-1,2-diol (3.17 g, 64%) as a yellow oil: LR-ES-MS m/z calculated for $C_6H_9N_3O_4$ [M]$^+$ 187, observed [M+H]$^+$ 188.

In a Parr shaker bottle was placed (R)-3-(3-nitro-pyrazol-1-yl)-propane-1,2-diol (3.17 g, 16.95 mmol), 10% palladium on activated carbon (200 mg) and ethanol (30 mL). The bottle was then placed on the Parr shaker at 50 psi of hydrogen pressure for 5 h. The reaction was then filtered through a pad of celite and washed with ethanol and concentrated in vacuo to afford (R)-3-(3-amino-pyrazol-1-yl)-propane-1,2-diol (2.60 g, 98%) as a yellow oil: LR-ES-MS m/z calculated for $C_6H_{11}N_3O_2$ [M]$^+$ 157, observed [M+H]$^+$ 158.

A solution of (S)-3-cyclohexyl-2-[4-(2,6-difluoro-phenoxy)-2-oxo-2,5-dihydro-pyrrol-1-yl)-propionic acid (as prepared in Example 36, 200 mg, 0.55 mmol) in dichloromethane (10 mL) was treated with oxalyl chloride (0.33 mL, 2M in dichloromethane), and N,N-dimethylformamide (1 drop). Effervescence was observed. The reaction mixture was stirred for 2 h at 25° C., under nitrogen. The reaction mixture was concentrated, and dissolved in dichloromethane (5 mL) and treated with (R)-3-(3-amino-pyrazol-1-yl)-propane-1,2-diol (103 mg, 0.66 mmol), and N,N-diisopropylethylamine (215 mg, 1.64 mmol). The reaction mixture was stirred at 25° C., under nitrogen for 18 h. The reaction mixture was diluted with dichloromethane, washed with water, 2N aqueous hydrochloric acid, saturated sodium bicarbonate solution, a saturated sodium chloride solution and dried over magnesium sulfate. The organic layer was concentrated, and the crude product was purified by ISCO flash chromatography (Teledyne Isco RediSep Flash Column 12 g; 0% to 10% methanol/dichloromethane) to afford, (S)-3-cyclohexyl-2-[4-(2,6-difluoro-phenoxy)-2-oxo-2,5-dihydro-pyrrol-1-yl)-N-[1-((R)-2,3-dihydroxy-propyl)-1H-pyrazol-3-yl]-propionamide (140 mg, 51%) as an off-white solid: LR-ES-MS m/z calculated for $C_{25}H_{30}F_2N_4O_5$ [M]$^+$ 504, observed [M+H]$^+$ 505; $^1$H NMR (300 MHz, DMSO-$d_6$) δ ppm 0.83-1.30 (m, 6H) 1.49-1.82 (m, 7H) 3.19-3.33 (m, 2H) 3.68-3.94 (m, 2H) 4.09 (dd, J=13.6, 3.9 Hz, 1H) 4.27 (d, J=18.9 Hz, 1H)

4.63 (d, J=18.9 Hz, 1H) 4.71 (t, J=5.6 Hz, 1H) 4.89 (dd, J=10.4, 5.0 Hz, 1H) 4.94 (d, J=5.1 Hz, 1H) 5.04 (s, 1H) 6.41 (d, J=2.1 Hz, 1H) 7.25-7.49 (m, 3H) 7.53 (d, J=2.1 Hz, 1H) 10.77 (s, 1H).

Example 39

6-{(S)-3-Cyclohexyl-2-[4-(2,6-difluoro-phenoxy)-2-oxo-2,5-dihydro-pyrrol-1-yl]-propionylamino}-nicotinic acid methyl ester

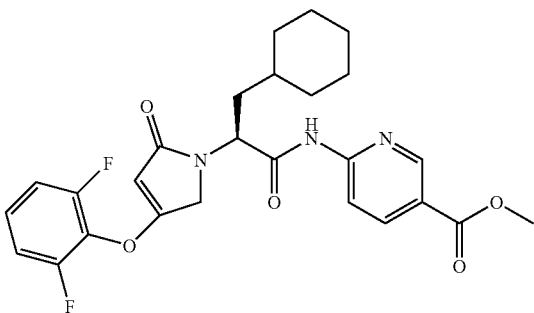

A solution of (S)-3-cyclohexyl-2-[4-(2,6-difluoro-phenoxy)-2-oxo-2,5-dihydro-pyrrol-1-yl]-propionic acid (prepared in Example 36, 90 mg, 0.25 mmol) in dichloromethane (10 mL) was treated with bromotripyrrolidinophosphonium hexafluorophosphate (138 mg, 0.30 mmol), N,N-diisopropylethylamine (95 mg, 0.74 mmol) and 6-aminonicotinic acid methyl ester (45 mg, 0.30 mmol). The reaction mixture was stirred at 25° C. for 18 h under nitrogen. The reaction mixture was diluted with dichloromethane, washed with 2N aqueous hydrochloric acid, saturated sodium bicarbonate solution, a saturated sodium chloride solution and dried over magnesium sulfate. The organic layer was concentrated, and the crude product was purified by ISCO flash chromatography (Teledyne Isco RediSep Flash Column 12 g; 0% to 100% ethyl acetate/hexanes) to afford 6-{(S)-3-cyclohexyl-2-[4-(2,6-difluoro-phenoxy)-2-oxo-2,5-dihydro-pyrrol-1-yl]-propionylamino}-nicotinic acid methyl ester (49 mg, 40%) as a white solid: LR-ES-MS m/z calculated for $C_{26}H_{27}F_2N_3O_5$ [M]+ 499, observed [M+H]+ 500; $^1$H NMR (300 MHz, DMSO-$d_6$) δ ppm 0.85-1.35 (m, 6H) 1.49-1.88 (m, 7H) 3.86 (s, 3H) 4.31 (d, J=18.3 Hz, 1H) 4.63 (d, J=18.3 Hz, 1H) 5.03 (m, 1H) 5.07 (s, 1H) 7.30-7.52 (m, 3H) 8.16 (d, J=9.1 Hz, 1H) 8.28 (dd, J=9.1, 2.4 Hz, 1H) 8.87 (d, J=2.4 Hz, 1H) 11.32 (s, 1H).

Example 40

6-[2-[4-(2,6-difluoro-phenoxy)-2-oxo-2,5-dihydro-pyrrol-1-yl]-3-(tetrahydro-pyran-4-yl)-propionylamino]-nicotinic acid methyl ester

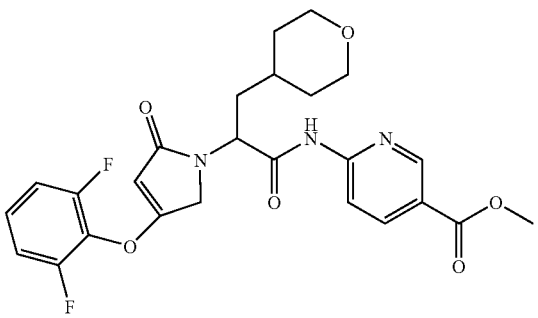

A solution of 2-t-butoxycarbonylamino-3-(tetrahydro-pyran-4-yl)-propionic acid (1.00 g, 3.66 mmol) in saturated methanolic hydrogen chloride (30 mL) was heated at 50° C. for 18 h in a sealed tube. The mixture was cooled to 25° C. and the solution was concentrated to dryness to yield 2-amino-3-(tetrahydro-pyran-4-yl)-propionic acid methyl ester hydrochloride (620 mg, 76%) as a white solid.

To a stirred mixture of 2-amino-3-(tetrahydro-pyran-4-yl)-propionic acid methyl ester hydrochloride (620 mg, 2.77 mmol) dissolved in acetonitrile (10 mL) under a nitrogen atmosphere was added N,N-diisopropylethylamine (0.41 g, 3.15 mmol) After addition was complete the mixture was stirred at 60° C. for 1 h. The reaction was cooled to 25° C. and treated with N,N-diisopropylethylamine (410 mg, 3.15 mmol) and acetonitrile (10 mL) and heated to 80° C. at which time 4-bromo-3-(2,6-difluoro-phenoxy)-but-2-enoic acid ethyl ester (as prepared in Example 36, 810 mg, 2.52 mmol) in acetonitrile (10 mL) was added slowly. After the addition was complete the reaction mixture was heated to 100° C. and stirred overnight. The reaction mixture was cooled to 25° C., filtered and concentrated. The residue was diluted with dichloromethane and washed with 2N aqueous hydrochloric acid, a saturated sodium bicarbonate solution, a saturated sodium chloride solution and dried over magnesium sulfate. The crude product obtained was purified by ISCO flash chromatography (Teledyne Isco RediSep Flash Column 40 g; 0% to 50% ethyl acetate/hexanes) to afford, 2-[4-(2,6-difluoro-phenoxy)-2-oxo-2,5-dihydro-pyrrol-1-yl]-3-(tetrahydro-pyran-4-yl)-propionic acid methyl ester (210 mg, 22%) as a yellow oil: LR-ES-MS m/z calculated for $C_{19}H_{21}F_2NO_5$ [M]+ 381, observed [M+H]+ 382.

To a stirred mixture of 2-[4-(2,6-difluoro-phenoxy)-2-oxo-2,5-dihydro-pyrrol-1-yl]-3-(tetrahydro-pyran-4-yl)-propionic acid methyl ester (200 mg, 0.53 mmol) in tetrahydrofuran (10 mL) and water (3 mL) was added lithium hydroxide (26 mg, 0.63 mmol). After addition was complete the mixture was stirred at 25° C. for 2 h. The reaction mixture was poured into water and diethyl ether and the layers separated. The aqueous layer was made acidic with 2N aqueous hydrochloric acid and extracted with ethyl acetate (3×30 mL). The combined ethyl acetate fractions were washed with a saturated sodium chloride solution, dried over magnesium sulfate, filtered and concentrated to afford, 2-[4-(2,6-difluoro-phenoxy)-2-oxo-2,5-dihydro-pyrrol-1-yl]-3-(tetrahydro-pyran-4-yl)-propionic acid (155 mg, 80%) as a white solid: LR-ES-MS m/z calculated for $C_{18}H_{19}F_2NO_5$ [M]+ 367, observed [M+H]+ 368.

A solution of 2-[4-(2,6-difluoro-phenoxy)-2-oxo-2,5-dihydro-pyrrol-1-yl]-3-(tetrahydro-pyran-4-yl)-propionic acid (155 mg, 0.42 mmol) in dichloromethane (10 mL) was treated with bromotripyrrolidinophosphonium hexafluorophosphate (240 mg, 0.051 mmol), N,N-diisopropylethylamine (165 mg, 0.127 mmol) and 6-aminonicotinic acid methyl ester (80 mg, 0.51 mmol). The reaction mixture was stirred at 25° C. for 18 h under nitrogen. The reaction mixture was diluted with dichloromethane, washed with 2N aqueous hydrochloric acid, saturated sodium bicarbonate solution, a saturated sodium chloride solution and dried over magnesium sulfate. The organic layer was concentrated, and the crude product was purified by ISCO flash chromatography (Teledyne Isco RediSep Flash Column 12 g; 0% to 100% ethyl acetate/ hexanes) to afford 6-[2-[4-(2,6-difluoro-phenoxy)-2-oxo-2, 5-dihydro-pyrrol-1-yl]-3-(tetrahydro-pyran-4-yl)-propionylamino]-nicotinic acid methyl ester (110 mg, 55%), as an off-white solid: LR-ES-MS m/z calculated for $C_{25}H_{25}F_2N_3O_6$ [M]$^+$ 501, observed [M+H]$^+$ 502; $^1$H NMR (300 MHz, DMSO-d$_6$) δ ppm 1.20-1.95 (m, 7H) 3.11-3.32 (m, 2H) 3.70-3.92 (m, 2H) 3.86 (s, 3H) 4.37 (d, J=18.1 Hz, 1H) 4.64 (d, J=18.1 Hz, 1H) 4.98-5.12 (m, 2H) 7.30-7.51 (m, 3H) 8.13-8.20 (m, 1H) 8.28 (dd, J=8.8, 2.4 Hz, 1H) 8.87 (d, J=2.4 Hz, 1H) 11.33 (s, 1H).

Example 41

(S)-6-[2-[4-(2,6-difluoro-phenoxy)-2-oxo-2,5-dihydro-pyrrol-1-yl]-3-(tetrahydro-pyran-4-yl)-propionylamino]-nicotinic acid methyl ester

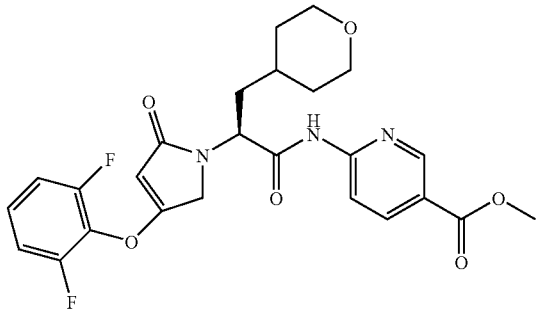

Separation of the enantiomers of 6-[2-[4-(2,6-difluoro-phenoxy)-2-oxo-2,5-dihydro-pyrrol-1-yl]-3-(tetrahydro-pyran-4-yl)-propionylamino]-nicotinic acid methyl ester (as prepared in Example 40) via supercritical fluid chromatography on a SFC DAICEL OJ column, 20% methanol as mobile phase modifier, 70 mL/min afforded (S)-6-[2-[4-(2,6-difluoro-phenoxy)-2-oxo-2,5-dihydro-pyrrol-1-yl]-3-(tetrahydro-pyran-4-yl)-propionylamino]-nicotinic acid methyl ester (29 mg) as a white solid. LR-ES-MS m/z calculated for $C_{25}H_{25}F_2N_3O_6$ [M]$^+$ 501, observed [M+H]$^+$ 502

Example 42

2-[4-(2,6-Difluoro-phenoxy)-2-oxo-2,5-dihydro-pyrrol-1-yl]-N-[1-(2-hydroxy-2-methyl-propyl)-1H-pyrazol-3-yl]-3-(tetrahydro-pyran-4-yl)-propionamide

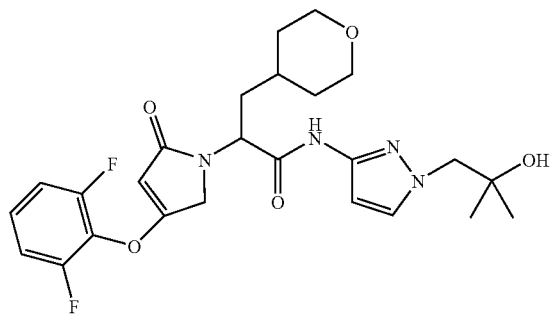

A solution of 2-[4-(2,6-difluoro-phenoxy)-2-oxo-2,5-dihydro-pyrrol-1-yl]-3-(tetrahydro-pyran-4-yl)-propionic acid (as prepared in Example 40, 200 mg, 0.54 mmol) in dichloromethane (10 mL) was treated with 1-(3-dimethylaminopropyl)-3-ethylcarbodiimide (85 mg, 0.55 mmol) and 1-hydroxybenzotriazole (80 mg, 0.57 mmol). The reaction mixture was stirred at 25° C. for 2 h followed by the addition of 1-(3-amino-pyrazol-1-yl)-2-methyl-propan-2-ol (prepared in U.S. Pat. Appl. US2008021032 Example 80, 101 mg, 0.65 mmol). The reaction mixture was stirred for 18 h at 25° C., under nitrogen. The reaction mixture was diluted with dichloromethane, washed with 2N aqueous hydrochloric acid, saturated sodium bicarbonate solution, a saturated sodium chloride solution and dried over magnesium sulfate. The organic layer was concentrated, and the crude product was purified by ISCO flash chromatography (Teledyne Isco RediSep Flash Column 12 g; 0% to 10% methanol/dichloromethane) to afford 2-[4-(2,6-difluoro-phenoxy)-2-oxo-2,5-dihydro-pyrrol-1-yl]-N-[1-(2-hydroxy-2-methyl-propyl)-1H-pyrazol-3-yl]-3-(tetrahydro-pyran-4-yl)-propionamide (186 mg, 68%) as a white solid: LR-ES-MS m/z calculated for $C_{25}H_{30}F_2N_4O_5$ [M]$^+$ 504, observed [M+H]$^+$ 505; $^1$H NMR (300 MHz, DMSO-d$_6$) δ ppm 1.05 (s, 3H) 1.06 (s, 3H) 1.11-1.52 (m, 3H) 1.52-1.74 (m, 3H) 1.74-1.88 (m, 1H) 3.07-3.32 (m, 2H) 3.75-3.87 (m, 2H) 3.89 (s, 2H) 4.33 (d, J=19.0 Hz, 1H) 4.65 (d, J=19.0 Hz, 1H) 4.68 (s, 1H) 4.91 (dd, J=10.6, 4.5 Hz, 1H) 5.04 (s, 1H) 6.45 (d, J=2.2 Hz, 1H) 7.26-7.51 (m, 3H) 7.54 (d, J=2.2 Hz, 1H) 10.83 (s, 1H).

Example 43

(S)-2-[4-(2,6-Difluoro-phenoxy)-2-oxo-2,5-dihydro-pyrrol-1-yl]-N-[1-(2-hydroxy-2-methylpropyl)-1H-pyrazol-3-yl]-3-(tetrahydro-pyran-4-yl)-propionamide

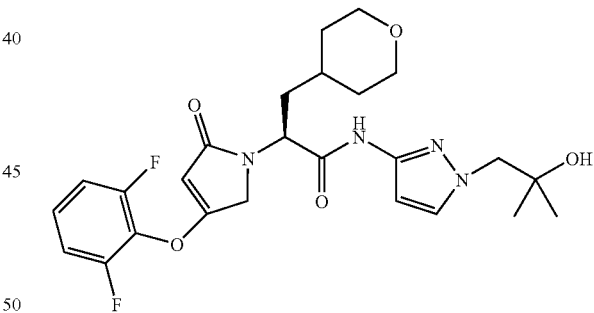

Separation of the enantiomers of 2-[4-(2,6-difluoro-phenoxy)-2-oxo-2,5-dihydro-pyrrol-1-yl]-N-[1-(2-hydroxy-2-methyl-propyl)-1H-pyrazol-3-yl]-3-(tetrahydro-pyran-4-propionamide (as prepared in Example 42) via supercritical fluid chromatography on a SFC DAICEL OD column, 20% isopropanol as mobile phase modifier, 200 mL/min afforded (S)-2-[4-(2,6-difluoro-phenoxy)-2-oxo-2,5-dihydro-pyrrol-1-yl]-N-[1-(2-hydroxy-2-methyl-propyl)-1H-pyrazol-3-yl]-3-(tetrahydro-pyran-4-yl)-propionamide (64 mg) as a white solid. LR-ES-MS m/z calculated for $C_{25}H_{30}F_2N_4O_5$ [M]$^+$ 504, observed [M+H]$^+$ 505; $^1$H NMR (300 MHz, DMSO-d$_6$) δ ppm 1.03 (s, 3H) 1.04 (br. s., 3H) 1.12-1.30 (m, 2H) 1.34 (br. s., 1H) 1.51-1.72 (m, 3H) 1.71-1.89 (m, 1H) 3.10-3.30 (m, 2H) 3.66-3.85 (m, 2H) 3.88 (s, 2H) 4.31 (d, J=18.7 Hz, 1H)

4.50-4.73 (m, 2H) 4.89 (dd, J=10.9, 4.5 Hz, 1H) 5.02 (s, 1H) 6.43 (d, J=2.1 Hz, 1H) 7.23-7.49 (m, 3H) 7.52 (d, J=2.1 Hz, 1H) 10.81 (s, 1H).

Example 44

2-[4-(2,6-Difluoro-phenoxy)-2-oxo-2,5-dihydro-pyrrol-1-yl]-N-[1-((R)-2,3-dihydroxy-propyl)-1H-pyrazol-3-yl]-3-(tetrahydro-pyran-4-yl)-propionamide

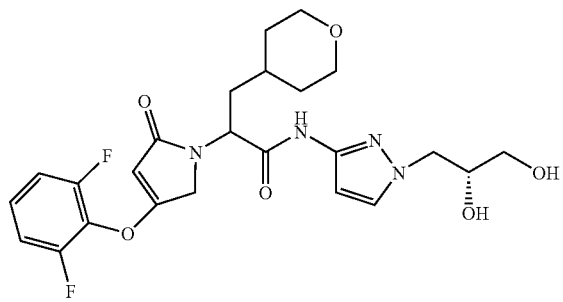

A solution of 2-[4-(2,6-difluoro-phenoxy)-2-oxo-2,5-dihydro-pyrrol-1-yl]-3-(tetrahydro-pyran-4-yl)-propionic acid (as prepared in Example 40, 200 mg, 0.55 mmol) in dichloromethane (10 mL) was treated with oxalyl chloride (0.33 mL, 2M in dichloromethane), and N,N-dimethylformamide (1 drop). Effervescence was observed. The reaction mixture was stirred for 2 h at 25° C., under nitrogen. The reaction mixture was concentrated, and dissolved in dichloromethane (5 mL) and treated with (R)-3-(3-amino-pyrazol-1-yl)-propane-1,2-diol (as prepared in Example 38, 103 mg, 0.66 mmol), and N,N-diisopropylethylamine (210 mg, 1.63 mmol). The reaction mixture was stirred at 25° C., under nitrogen for 18 h. The reaction mixture was diluted with dichloromethane, washed with water, 2N aqueous hydrochloric acid, saturated sodium bicarbonate solution, a saturated sodium chloride solution and dried over magnesium sulfate. The organic layer was concentrated, and the crude product was purified by ISCO flash chromatography (Teledyne Isco RediSep Flash Column 12 g; 0% to 10% methanol/dichloromethane) to afford, 2-[4-(2,6-difluoro-phenoxy)-2-oxo-2,5-dihydro-pyrrol-1-yl]-N-[1-((R)-2,3-dihydroxy-propyl)-1H-pyrazol-3-yl]-3-(tetrahydro-pyran-4-yl)-propionamide (25 mg, 9%) as a light yellow solid: LR-ES-MS m/z calculated for $C_{24}H_{28}F_2N_4O_6$ [M]$^+$ 506, observed [M+H]$^+$ 507; $^1$H NMR (300 MHz, DMSO-d$_6$) δ ppm 1.07-1.47 (m, 3H) 1.49-1.71 (m, 3H) 1.71-1.86 (m, 1H) 3.06-3.30 (m, 4H) 3.67-3.90 (m, 4H) 4.07 (dd, J=13.6, 3.8 Hz, 1H) 4.31 (d, J=18.7 Hz, 1H) 4.62 (d, J=18.7 Hz, 1H) 4.70 (t, J=5.6 Hz, 1H) 4.88 (dd, J=10.6, 4.7 Hz, 1H) 4.93 (d, J=5.3 Hz, 1H) 5.03 (s, 1H) 6.39 (d, J=1.5 Hz, 1H) 7.26-7.49 (m, 3H) 7.52 (br. s., 1H) 10.79 (s, 1H).

Example 45

(S)-2-[4-(2,6-difluoro-phenoxy)-2-oxo-2,5-dihydro-pyrrol-1-yl]-4-methyl-pentanoic acid [1-(2-hydroxy-2-methyl-propyl)-1H-pyrazol-3-yl]-amide

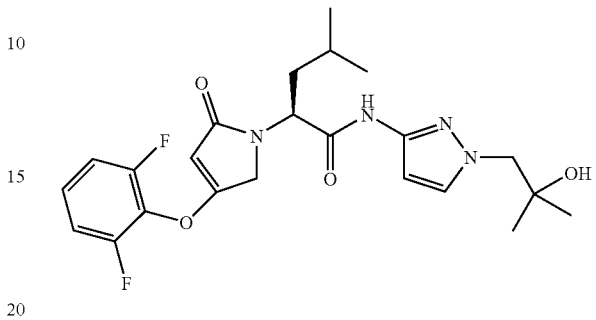

To a stirred mixture of (L)-leucine methyl ester hydrochloride (1.25 g, 6.88 mmol) dissolved in acetonitrile (10 mL) under a nitrogen atmosphere was added N,N-diisopropylethylamine (900 mg, 7.00 mmol). After addition was complete the mixture was stirred at 60° C. for 1 h. The reaction was cooled to 25° C. and treated with N,N-diisopropylethylamine (900 mg, 7.00 mmol) and acetonitrile (10 mL) and heated to 80° C. at which time 4-bromo-3-(2,6-difluoro-phenoxy)-but-2-enoic acid ethyl ester (as prepared in Example 36, 2.00 g, 6.25 mmol) in acetonitrile (10 mL) was added slowly. After the addition was complete the reaction mixture was heated to 100° C. and stirred overnight. The reaction mixture was cooled to 25° C., filtered and concentrated. The residue was diluted with dichloromethane and washed with 2N aqueous hydrochloric acid, a saturated sodium bicarbonate solution, a saturated sodium chloride solution and dried over magnesium sulfate. The crude product obtained was purified by ISCO flash chromatography (Teledyne Isco RediSep Flash Column 40 g; 0% to 50% ethyl acetate/hexanes) to afford, (S)-2-[4-(2,6-difluoro-phenoxy)-2-oxo-2,5-dihydro-pyrrol-1-yl]-4-methyl-pentanoic acid methyl ester (900 mg, 42%) as a yellow oil: LR-ES-MS m/z calculated for $C_{17}H_{19}F_2NO_4$ [M]$^+$ 339, observed [M+H]$^+$ 340.

To a stirred mixture of (S)-2-[4-(2,6-difluoro-phenoxy)-2-oxo-2,5-dihydro-pyrrol-1-yl]-4-methyl-pentanoic acid methyl ester (900 mg, 2.65 mmol) in tetrahydrofuran (10 mL) and water (3 mL) was added lithium hydroxide (135 mg, 3.19 mmol). After addition was complete the mixture was stirred at 25° C. for 2 h. The reaction mixture was poured into water and diethyl ether and the layers separated. The aqueous layer was made acidic with 2N aqueous hydrochloric acid and extracted with ethyl acetate (3×30 mL). The combined ethyl acetate fractions were washed with a saturated sodium chloride solution, dried over magnesium sulfate, filtered and concentrated to afford (S)-2-[4-(2,6-difluoro-phenoxy)-2-oxo-2,5-dihydro-pyrrol-1-yl]-4-methyl-pentanoic acid (710 mg, 82%) as a yellow solid: LR-ES-MS m/z calculated for $C_{16}H_{17}F_2NO_4$ [M]$^+$ 325, observed [M+H]$^+$ 326.

A solution of (S)-2-[4-(2,6-difluoro-phenoxy)-2-oxo-2,5-dihydro-pyrrol-1-yl]-4-methyl-pentanoic acid (100 mg, 0.31 mmol) in dichloromethane (10 mL) was treated with 1-(3-dimethylaminopropyl)-3-ethylcarbodiimide (48 mg, 0.31 mmol) and 1-hydroxybenzotriazole (45 mg, 0.32 mmol). The reaction mixture was stirred at 25° C. for 2 h followed by the addition of 1-(3-amino-pyrazol-1-yl)-2-methyl-propan-2-ol (prepared in U.S. Pat. Appl. US2008021032 Example 80, 60 mg, 0.37 mmol). The reaction mixture was stirred for 18 h at 25° C., under nitrogen. The reaction mixture was diluted with dichloromethane, washed with 2N aqueous hydrochloric acid, saturated sodium bicarbonate solution, a saturated sodium chloride solution and dried over magnesium sulfate. The organic layer was concentrated, and the crude product was purified by ISCO flash chromatography (Teledyne Isco RediSep Flash Column 12 g; 0% to 100% ethyl acetate/hexanes) to afford (S-2-[4-(2,6-difluoro-phenoxy)-2-oxo-2,5-dihydro-pyrrol-1-yl]-4-methyl-pentanoic acid [1-(2-hydroxy-2-methyl-propyl)-1H-pyrazol-3-yl]-amide (56 mg, 39%) as a light yellow solid: LR-ES-MS m/z calculated for $C_{23}H_{28}F_2N_4O_4$ $[M]^+$ 462, observed $[M+H]^+$ 463; $^1H$ NMR (300 MHz, DMSO-$d_6$) δ ppm 1.05 (s, 3H) 1.06 (s, 3H) 1.11-1.52 (m, 3H) 1.52-1.74 (m, 3H) 1.74-1.88 (m, 1H) 3.07-3.32 (m, 2H) 3.75-3.87 (m, 2H) 3.89 (s, 2H) 4.33 (d, J=19.0 Hz, 1H) 4.65 (d, J=19.0 Hz, 1H) 4.68 (s, 1H) 4.91 (dd, J=10.6, 4.5 Hz, 1H) 5.04 (s, 1H) 6.45 (d, J=2.2 Hz, 1H) 7.26-7.51 (m, 3H) 7.54 (d, J=2.2 Hz, 1H) 10.83 (s, 1H).

Example 46

6-{(S)-2-[4-(2,6-difluoro-phenoxy)-2-oxo-2,5-dihydro-pyrrol-1-yl]-4-methyl-pentanoylamino}-nicotinic acid methyl ester

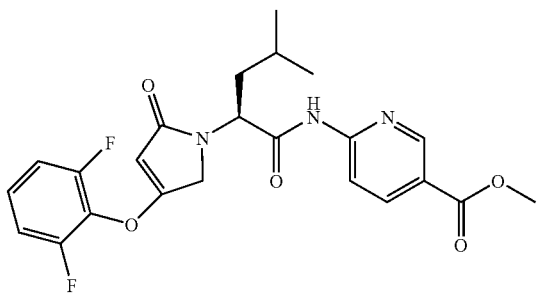

A solution of (S)-2-[4-(2,6-difluoro-phenoxy)-2-oxo-2,5-dihydro-pyrrol-1-yl]-4-methyl-pentanoic acid (as prepared in Example 45, 200 mg, 0.62 mmol) in dichloromethane (10 mL) was treated with bromotripyrrolidinophosphonium hexafluorophosphate (345 mg, 0.74 mmol), N,N-diisopropylethylamine (240 mg, 1.85 mmol) and 6-aminonicotinic acid methyl ester (115 mg, 0.74 mmol). The reaction mixture was stirred at 25° C. for 18 h under nitrogen. The reaction mixture was diluted with dichloromethane, washed with 2N aqueous hydrochloric acid, saturated sodium bicarbonate solution, a saturated sodium chloride solution and dried over magnesium sulfate. The organic layer was concentrated, and the crude product was purified by ISCO flash chromatography (Teledyne Isco RediSep Flash Column 12 g; 0% to 100% ethyl acetate/hexanes) to afford 6-{(S)-2-[4-(2,6-difluoro-phenoxy)-2-oxo-2,5-dihydro-pyrrol-1-yl]-4-methyl-pentanoylamino}-nicotinic acid methyl ester (57 mg, 20%) as a light yellow solid: LR-ES-MS m/z calculated for $C_{23}H_{23}F_2N_3O_5$ $[M]^+$ 459, observed $[M+H]^+$ 460; $^1H$ NMR (300 MHz, DMSO-$d_6$) δ ppm 0.92 (d, J=6.9 Hz, 3H) 0.94 (d, J=6.9 Hz, 3H) 1.39-1.74 (m, 2H) 1.73-1.92 (m, 1H) 3.86 (s, 3H) 4.32 (d, J=18.7 Hz, 1H) 4.64 (d, J=18.7 Hz, 1H) 4.95-5.05 (m, 1H) 5.06 (s, 1H) 7.25-7.53 (m, 3H) 8.17 (d, J=8.8 Hz, 1H) 8.29 (dd, J=8.8, 2.1 Hz, 1H) 8.87 (d, J=2.1 Hz, 1H) 11.34 (s, 1H).

Example 47

(S)-2-[4-(2,6-difluoro-phenoxy)-2-oxo-2,5-dihydro-pyrrol-1-yl]-4-methyl-pentanoic acid [1-((R)-2,3-dihydroxy-propyl)-1H-pyrazol-3-yl]-amide

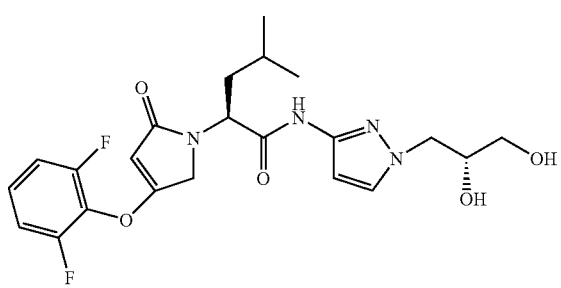

A solution of (S)-2-[4-(2,6-difluoro-phenoxy)-2-oxo-2,5-dihydro-pyrrol-1-yl]-4-methyl-pentanoic acid (as prepared in Example 45, 200 mg, 0.62 mmol) in dichloromethane (10 mL) was treated with oxalyl chloride (0.37 mL, 2M in dichloromethane), and N,N-dimethylformamide (1 drop). Effervescence was observed. The reaction mixture was stirred for 2 h at 25° C., under nitrogen. The reaction mixture was concentrated, and dissolved in dichloromethane (5 mL) and treated with (R)-3-(3-amino-pyrazol-1-yl)-propane-1,2-diol (as prepared in Example 38, 116 mg, 0.74 mmol), and N,N-diisopropylethylamine (240 mg, 1.85 mmol). The reaction mixture was stirred at 25° C., under nitrogen for 18 h. The reaction mixture was diluted with dichloromethane, washed with water, 2N aqueous hydrochloric acid, saturated sodium bicarbonate solution, a saturated sodium chloride solution and dried over magnesium sulfate. The organic layer was concentrated, and the crude product was purified by ISCO flash chromatography (Teledyne Isco RediSep Flash Column 12 g; 0% to 10% methanol/dichloromethane) to afford, (S)-2-[4-(2,6-difluoro-phenoxy)-2-oxo-2,5-dihydro-pyrrol-1-yl]-4-methyl-pentanoic acid [1-((R)-2,3-dihydroxy-propyl)-1H-pyrazol-3-yl]-amide (120 mg, 42%) as a light brown solid: LR-ES-MS m/z calculated for $C_{22}H_{26}F_2N_4O_5$ $[M]^+$ 464, observed $[M+H]^+$ 465; $^1H$ NMR (300 MHz, DMSO-$d_6$) δ ppm 0.90 (d, J=6.3 Hz, 3H) 0.94 (d, J=6.3 Hz, 3H) 1.34-1.85 (m, 3H) 3.18-3.32 (m, 2H) 3.64-3.94 (m, 2H) 4.09 (dd, J=13.6, 3.6 Hz, 1H) 4.28 (d, J=18.7 Hz, 1H) 4.64 (d, J=18.7 Hz, 1H) 4.71 (t, J=5.6 Hz, 1H) 4.87 (dd, J=10.7, 4.7 Hz, 1H) 4.94 (d, J=5.4 Hz, 1H) 5.03 (s, 1H) 6.41 (d, J=1.2 Hz, 7.24-7.50 (m, 3H) 7.53 (s, 1H) 10.79 (s, 1H).

Example 48

(S)-2-[4-(2-Chloro-3-methoxy-phenoxy)-2-oxo-2,5-dihydro-pyrrol-1-yl]-4-methyl-pentanoic acid [1-(2-hydroxy-2-methyl-propyl)-1H-pyrazol-3-yl]-amide

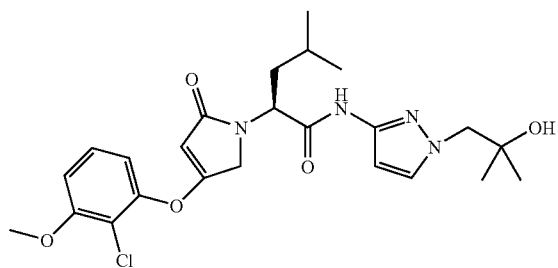

To a stirred mixture of 2-chloro-3-methoxyphenol (1.00 g, 6.31 mmol) and ethyl-2-butynoate (1.42 g, 12.62 mmol) in tetrahydrofuran (10 mL) was added 1,8-diazabicyclo[5.4.0]undec-7-ene (960 mg, 6.31 mmol). After addition was complete the mixture was stirred at 130° C. for 2 h. Upon completion of the reaction the tetrahydrofuran was removed in vacuo and the residue redissolved in dichloromethane and washed with 2N aqueous hydrochloric acid, 5% aqueous sodium hydroxide solution, a saturated sodium chloride solution and dried over magnesium sulfate. The crude product obtained was purified by ISCO flash chromatography (Teledyne Isco RediSep Flash Column 40 g; 0% to 50% ethyl acetate/hexanes) to afford, 3-(2-chloro-3-methoxy-phenoxy)-but-2-enoic acid ethyl ester (1.00 g, 58%) as a colorless oil: LR-ES-MS m/z calculated for $C_{13}H_{15}ClO_4$ $[M]^+$ 270, observed $[M+H]^+$ 271.

To a stirred mixture of 3-(2-chloro-3-methoxy-phenoxy)-but-2-enoic acid ethyl ester (1.00 g, 3.70 mmol) dissolved in carbon tetrachloride (20 mL) under a nitrogen atmosphere was added N-bromosuccinimide (0.76 g, 4.07 mmol) and benzoyl peroxide (0.10 g, 0.30 mmol). After addition was complete the mixture was stirred at reflux for 5 h. The reaction mixture was then placed in the refrigerator overnight. The solids formed were removed by filtration and the filtrate concentrated in vacuo. The crude product obtained was purified by ISCO flash chromatography (Teledyne Isco RediSep Flash Column 40 g; 0% to 50% ethyl acetate/hexanes) to afford, 4-bromo-3-(2-chloro-3-methoxy-phenoxy)-but-2-enoic acid ethyl ester (1.52 g, 84%) as a yellow oil: LR-ES-MS m/z calculated for $C_{13}H_{14}BrClO_4$ $[M]^+$ 348, observed $[M+H]^+$ 349.

To a stirred mixture of (L)-leucine methyl ester hydrochloride (0.86 g, 4.73 mmol) dissolved in acetonitrile (10 mL) under a nitrogen atmosphere was added N,N-diisopropylethylamine (650 mg, 4.65 mmol). After addition was complete the mixture was stirred at 60° C. for 1 h. The reaction was cooled to 25° C. and treated with N,N-diisopropylethylamine (650 mg, 4.65 mmol) and acetonitrile (10 mL) and heated to 80° C. at which time 4-bromo-3-(2-chloro-3-methoxy-phenoxy)-but-2-enoic acid ethyl ester (1.50 g, 4.30 mmol) in acetonitrile (10 mL) was added slowly. After the addition was complete the reaction mixture was heated to 100° C. and stirred overnight. The reaction mixture was cooled to 25° C., filtered and concentrated. The residue was diluted with dichloromethane and washed with 2N aqueous hydrochloric acid, a saturated sodium bicarbonate solution, a saturated sodium chloride solution and dried over magnesium sulfate. The crude product obtained was purified by ISCO flash chromatography (Teledyne Isco RediSep Flash Column 40 g; 0% to 50% ethyl acetate/hexanes) to afford, (S)-2-[4-(2-chloro-3-methoxy-phenoxy)-2-oxo-2,5-dihydro-pyrrol-1-yl]-4-methyl-pentanoic acid methyl ester (540 mg, 34%) as a yellow oil: LR-ES-MS m/z calculated for $C_{18}H_{22}ClNO_5$ $[M]^+$ 367, observed $[M+H]^+$ 368.

To a stirred mixture of (S)-2-[4-(2-chloro-3-methoxy-phenoxy)-2-oxo-2,5-dihydro-pyrrol-1-yl]-4-methyl-pentanoic acid methyl ester (540 mg, 1.47 mmol) in tetrahydrofuran (9 mL) and water (3 mL) was added lithium hydroxide (75 mg, 1.76 mmol). After addition was complete the mixture was stirred at 25° C. for 2 h. The reaction mixture was poured into water and diethyl ether and the layers separated. The aqueous layer was made acidic with 2N aqueous hydrochloric acid and extracted with ethyl acetate (3×30 mL). The combined ethyl acetate fractions were washed with a saturated sodium chloride solution, dried over magnesium sulfate, filtered and concentrated to afford, (S)-2-[4-(2-chloro-3-methoxy-phenoxy)-2-oxo-2,5-dihydro-pyrrol-1-yl]-4-methyl-pentanoic acid (435 mg, 84%) as a yellow solid: LR-ES-MS m/z calculated for $C_{17}H_{20}ClNO_5$ $[M]^+$ 353, observed $[M+H]^+$ 354.

A solution of (S)-2-[4-(2-chloro-3-methoxy-phenoxy)-2-oxo-2,5-dihydro-pyrrol-1-yl]-4-methyl-pentanoic acid (200 mg, 0.57 mmol) in dichloromethane (10 mL) was treated with 1-(3-dimethylaminopropyl)-3-ethylcarbodiimide (96 mg, 0.62 mmol) and 1-hydroxybenzotriazole (80 mg, 0.60 mmol). The reaction mixture was stirred at 25° C. for 2 h followed by the addition of 1-(3-amino-pyrazol-1-yl)-2-methyl-propan-2-ol (prepared in U.S. Pat. Appl. US2008021032 Example 80, 105 mg, 0.68 mmol). The reaction mixture was stirred for 18 h at 25° C., under nitrogen. The reaction mixture was diluted with dichloromethane, washed with 2N aqueous hydrochloric acid, saturated sodium bicarbonate solution, a saturated sodium chloride solution and dried over magnesium sulfate. The organic layer was concentrated, and the crude product was purified by ISCO flash chromatography (Teledyne Isco RediSep Flash Column 12 g; 0% to 100% ethyl acetate/hexanes) to afford (S)-2-[4-(2-Chloro-3-methoxy-phenoxy)-2-oxo-2,5-dihydro-pyrrol-1-yl]-4-methyl-pentanoic acid [1-(2-hydroxy-2-methyl-propyl)-1H-pyrazol-3-yl]-amide (198 mg, 71%) as an off-white solid: LR-ES-MS m/z calculated for $C_{24}H_{31}ClN_4O_5$ $[M]^-$ 490, observed $[M+H]^+$ 491; $^1H$ NMR (300 MHz, DMSO-$d_6$) δ ppm 0.90 (d, J=6.6 Hz, 3H), 0.93 (d, J=6.6 Hz, 3H), 1.05 (s, 3H), 1.06 (s, 3H), 1.43 (br. s., 1H), 1.48-1.65 (m, 1H), 1.68-1.84 (m, 1H), 3.89 (br. s., 2H), 3.90 (s, 3H), 4.19 (d, J=18.6 Hz, 1H), 4.60 (d, J=18.6 Hz, 1H), 4.68 (s, 1H), 4.80 (s, 1H), 4.89 (dd, J=10.9, 4.8 Hz, 1H), 6.44 (d, J=2.1 Hz, 1H), 7.09 (dd, J=8.5, 1.3 Hz, 1H), 7.13 (dd, J=8.5, 1.3 Hz, 1H), 7.41 (t, J=8.5 Hz, 1H), 7.54 (d, J=2.1 Hz, 1H), 10.81 (s, 1H).

Example 49

(S)-2-[4-(2-Chloro-3-methoxy-phenoxy)-2-oxo-2,5-dihydro-pyrrol-1-yl]-4-methyl-pentanoic acid [1-((R-2,3-dihydroxy-propyl)-1H-pyrazol-3-yl]-amide

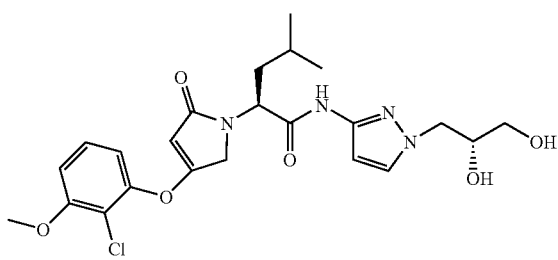

A solution of 3-nitro-1H-pyrazole (prepared as in Example 5, 12.0 g, 106 mmol) in N,N-dimethylformamide (150 mL) was treated with para-toluenesulfonic acid (S)-2,2-dimethyl-[1,3]dioxolan-4-yl-methyl ester (25.5 g, 89.0 mmol), and potassium carbonate (24.5 g, 178 mmol). The reaction mixture was heated to 90° C. for 6 h under nitrogen. After this time, the reaction mixture was diluted with ethyl acetate, washed with water and a saturated aqueous sodium chloride solution, dried over sodium sulfate, filtered, rinsed and concentrated in vacuo. Purification by ISCO flash chromatography (128 g, 5-30% ethyl acetate/hexanes) afforded 1-((R)-2,2-dimethyl-[1,3]dioxolan-4-yl-methyl)-3-nitro-1H-pyrazole (14.5 g, 73%) as a light yellow oil.

1-((R)-2,2-Dimethyl-[1,3]dioxolan-4-yl-methyl)-3-nitro-1H-pyrazole (14.5 g, 63.8 mmol) was diluted in 60 mL of ethanol and 10% palladium on carbon (1.4 g) was added. The mixture was hydrogenated on a Parr apparatus at 50 psi for 16 h. The mixture was filtered and the solvent was removed to afford the product 1-((R)-2,2-dimethyl-[1,3]dioxolan-4-yl-methyl)-1H-pyrazol-3-ylamine (12.4 g, 98%) as a pale yellow oil. LR-ES-MS m/z calculated for $C_9H_{15}N_3O_2$ [M]$^+$ 197, observed [M+H]$^+$ 198. $^1$H NMR (300 MHz, DMSO-d$_6$) δ ppm 1.24 (s, 3H), 1.30 (s, 3H), 3.70 (dd, J=8.5, 6.0 Hz, 1H), 3.85-4.02 (m, 3H), 4.28 (quin, J=6.0 Hz, 1H), 4.56 (s, 2H), 5.36 (d, J=2.1 Hz, 1H), 7.30 (d, J=2.1 Hz, 1H).

A solution of (S)-2-[4-(2-chloro-3-methoxy-phenoxy)-2-oxo-2,5-dihydro-pyrrol-1-yl]-4-methyl-pentanoic acid (as prepared in Example 48, 250 mg, 0.71 mmol) in dichloromethane (10 mL) was treated with 1-(3-dimethylaminopropyl)-3-ethylcarbodiimide (120 mg, 0.78 mmol) and 1-hydroxybenzotriazole (100 mg, 0.74 mmol). The reaction mixture was stirred at 25° C. for 2 h followed by the addition of 1-((R)-2,2-dimethyl-[1,3]dioxolan-4-yl-methyl)-1H-pyrazol-3-ylamine (167 mg, 0.85 mmol). The reaction mixture was stirred for 18 h at 25° C., under nitrogen. The reaction mixture was diluted with dichloromethane, washed with 2N aqueous hydrochloric acid, saturated sodium bicarbonate solution, a saturated sodium chloride solution and dried over magnesium sulfate. The organic layer was concentrated, and the crude product was purified by ISCO flash chromatography (Teledyne Isco RediSep Flash Column 12 g; 0% to 100% ethyl acetate/hexanes) to afford, (S)-2-[4-(2-chloro-3-methoxy-phenoxy)-2-oxo-2,5-dihydro-pyrrol-1-yl]-4-methyl-pentanoic acid [1-((R)-2,2-dimethyl-[1,3]dioxolan-4-yl-methyl)-1H-pyrazol-3-yl]-amide (154 mg, 41%) as a yellow oil: LR-ES-MS m/z calculated for $C_{26}H_{33}ClN_4O_6$ [M]$^+$ 532, observed [M+H]$^+$ 533.

A solution of (S)-2-[4-(2-chloro-3-methoxy-phenoxy)-2-oxo-2,5-dihydro-pyrrol-1-yl]-4-methyl-pentanoic acid [1-((R)-2,2-dimethyl-[1,3]dioxolan-4-yl-methyl)-1H-pyrazol-3-yl]-amide (150 mg, 0.28 mmol) in tetrahydrofuran (6 mL) was treated with 2N aqueous hydrochloric acid solution (3 mL). The reaction mixture was stirred at 25° C. for 4 h. The reaction mixture was diluted with ethyl acetate, washed with water, saturated sodium bicarbonate solution, a saturated sodium chloride solution and dried over magnesium sulfate. The organic layer was concentrated to afford, (S)-2-[4-(2-chloro-3-methoxy-phenoxy)-2-oxo-2,5-dihydro-pyrrol-1-yl]-4-methyl-pentanoic acid [1-((R)-2,3-dihydroxy-propyl)-1H-pyrazol-3-yl]-amide (123 mg, 88%) as a white solid: LR-ES-MS m/z calculated for $C_{23}H_{29}ClN_4O_6$ [M]$^+$ 492, observed [M+H]$^+$ 493; $^1$H NMR (300 MHz, DMSO-d$_6$) δ ppm 0.90 (d, J=6.4 Hz, 3H) 0.93 (d, J=6.4 Hz, 3H) 1.37-1.50 (m, 1H) 1.50-1.66 (m, 1H) 1.66-1.84 (m, 1H) 3.18-3.42 (m, 2H) 3.69-3.89 (m, 2H) 3.90 (s, 3H) 4.09 (dd, J=13.3, 3.6 Hz, 1H) 4.19 (d, J=18.4 Hz, 1H) 4.59 (d, J=18.4 Hz, 1H) 4.71 (t, J=5.4 Hz, 1H) 4.80 (s, 1H) 4.88 (dd, J=10.6, 4.8 Hz, 1H) 4.94 (d, J=5.4 Hz, 1H) 6.40 (d, J=1.8 Hz, 1H) 7.09 (d, J=8.5 Hz, 1H) 7.13 (d, J=8.5 Hz, 1H) 7.41 (t, J=8.5 Hz, 1H) 7.53 (d, J=1.8 Hz, 1H) 10.78 (s, 1H).

Example 50

2-[4-(2-Chloro-3-methoxy-phenoxy)-2-oxo-2,5-dihydro-pyrrol-1-yl]-N-[1-(2-hydroxy-2-methyl-propyl)-1H-pyrazol-3-yl]-3-(tetrahydro-pyran-4-yl)-propionamide

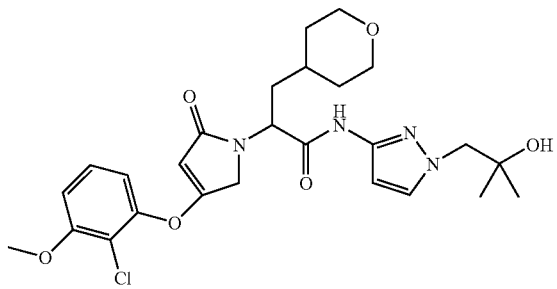

To a stirred mixture of 2-amino-3-(tetrahydro-pyran-4-yl)-propionic acid methyl ester hydrochloride (0.90 g, 4.73 mmol) dissolved in acetonitrile (15 mL) under a nitrogen atmosphere was added N,N-diisopropylethylamine (600 mg, 4.65 mmol). After addition was complete the mixture was stirred at 60° C. for 1 h. The reaction was cooled to 25° C. and treated with N,N-diisopropylethylamine (600 mg, 4.65 mmol) and acetonitrile (10 mL) and heated to 80° C. at which time 4-bromo-3-(2-chloro-3-methoxy-phenoxy)-but-2-enoic acid ethyl ester (prepared as Example 48, 1.30 g, 3.73 mmol) in acetonitrile (10 mL) was added slowly. After the addition was complete the reaction mixture was heated to 100° C. and stirred overnight. The reaction mixture was cooled to 25° C., filtered and concentrated. The residue was diluted with dichloromethane and washed with 2N aqueous hydrochloric acid, a saturated sodium bicarbonate solution, a saturated sodium chloride solution and dried over magnesium sulfate. The crude product obtained was purified by ISCO flash chromatography (Teledyne Isco RediSep Flash Column 40 g; 0% to 80% ethyl acetate/hexanes) to afford, 2-[4-(2-chloro-3-methoxy-phenoxy)-2-oxo-2,5-dihydro-pyrrol-1-yl]-3-(tetrahydro-pyran-4-yl)-propionic acid methyl ester (620 mg, 40%) as a yellow oil: LR-ES-MS m/z calculated for $C_{20}H_{24}ClNO_6$ $[M]^+$ 409, observed $[M+H]^+$ 410.

To a stirred mixture of 2-[4-(2-chloro-3-methoxy-phenoxy)-2-oxo-2,5-dihydro-pyrrol-1-yl]-3-(tetrahydro-pyran-4-yl)-propionic acid methyl ester (615 mg, 1.50 mmol) in tetrahydrofuran (9 mL) and water (3 mL) was added lithium hydroxide (76 mg, 1.80 mmol). After addition was complete the mixture was stirred at 25° C. for 2 h. The reaction mixture was poured into water and diethyl ether and the layers separated. The aqueous layer was made acidic with 2N aqueous hydrochloric acid and extracted with ethyl acetate (3×30 mL). The combined ethyl acetate fractions were washed with a saturated sodium chloride solution, dried over magnesium sulfate, filtered and concentrated to afford, 2-[4-(2-chloro-3-methoxy-phenoxy)-2-oxo-2,5-dihydro-pyrrol-1-yl]-3-(tetrahydro-pyran-4-yl)-propionic acid (465 mg, 78%) as a yellow solid: LR-ES-MS m/z calculated for $C_{19}H_{22}ClNO_6$ $[M]^+$ 395, observed $[M+H]^+$ 396.

A solution of 2-[4-(2-chloro-3-methoxy-phenoxy)-2-oxo-2,5-dihydro-pyrrol-1-yl]-3-(tetrahydro-pyran-4-yl)-propionic acid (200 mg, 0.51 mmol) in dichloromethane (10 mL) was treated with 1-(3-dimethylaminopropyl)-3-ethylcarbodiimide (86 mg, 0.56 mmol) and 1-hydroxybenzotriazole (72 mg, 0.53 mmol). The reaction mixture was stirred at 25° C. for 2 h followed by the addition of 1-(3-amino-pyrazol-1-yl)-2-methyl-propan-2-ol (prepared in U.S. Pat. Appl. US2008021032 Example 80, 94 mg, 0.61 mmol). The reaction mixture was stirred for 18 h at 25° C., under nitrogen. The reaction mixture was diluted with dichloromethane, washed with 2N aqueous hydrochloric acid, saturated sodium bicarbonate solution, a saturated sodium chloride solution and dried over magnesium sulfate. The organic layer was concentrated, and the crude product was purified by ISCO flash chromatography (Teledyne Isco RediSep Flash Column 12 g; 0% to 10% methanol/dichloromethane) to afford 2-[4-(2-chloro-3-methoxy-phenoxy)-2-oxo-2,5-dihydro-pyrrol-1-yl]-N-[1-(2-hydroxy-2-methyl-propyl)-1H-pyrazol-3-yl]-3-(tetrahydro-pyran-4-yl)-propionamide (166 mg, 62%), as an off-white solid: LR-ES-MS m/z calculated for $C_{26}H_{33}ClN_4O_6$ $[M]^+$ 532, observed $[M+H]^+$ 533; $^1H$ NMR (300 MHz, DMSO-$d_6$) δ ppm 1.04 (s, 3H), 1.06 (s, 3H), 1.13-1.30 (m, 2H), 1.37 (br. s., 1H), 1.55-1.73 (m, 3H), 1.72-1.87 (m, 1H), 3.13-3.31 (m, 2H), 3.74-3.87 (m, 2H), 3.89 (br. s., 2H), 3.90 (s, 3H), 4.24 (d, J=18.6 Hz, 1H), 4.60 (d, J=18.6 Hz, 1H), 4.68 (s, 1H), 4.82 (s, 1H), 4.92 (dd, J=10.7, 4.7 Hz, 1H), 6.44 (d, J=2.1 Hz, 1H), 7.09 (d, J=8.5 Hz, 1H), 7.13 (d, J=8.5 Hz, 1H), 7.42 (t, J=8.5 Hz, 1H), 7.54 (d, J=2.1 Hz, 1H), 10.81 (s, 1H).

Example 51

(S)-2-[4-(2-Chloro-3-methoxy-phenoxy)-2-oxo-2,5-dihydro-pyrrol-1-yl]-N-[1-(2-hydroxy-2-methyl-propyl)-1H-pyrazol-3-yl]-3-(tetrahydro-pyran-4-yl)-propionamide

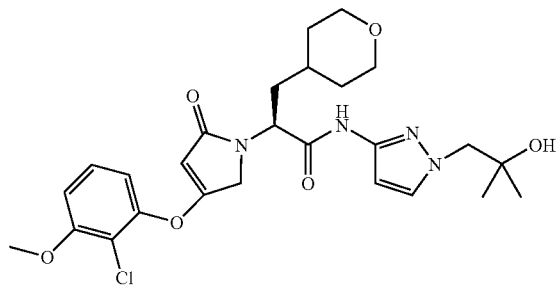

Separation of the enantiomers of 2-[4-(2-chloro-3-methoxy-phenoxy)-2-oxo-2,5-dihydro-pyrrol-1-yl]-N-[1-(2-hydroxy-2-methyl-propyl)-1H-pyrazol-3-yl]-3-(tetrahydro-pyran-4-yl)-propionamide (as prepared in Example 50) via supercritical fluid chromatography on a SFC KROMASIL OD column, 20% methanol as mobile phase modifier, 70 mL/min afforded (S)-2-[4-(2-chloro-3-methoxy-phenoxy)-2-oxo-2,5-dihydro-pyrrol-1-yl]-N-[1-(2-hydroxy-2-methyl-propyl)-1H-pyrazol-3-yl]-3-(tetrahydro-pyran-4-yl)-propionamide (60 mg) as a white solid. LR-ES-MS m/z calculated for $C_{26}H_{33}ClN_4O_6$ $[M]^+$ 532, observed [M+H]+533.

Example 52

(R)-2-[4-(2-Chloro-3-methoxy-phenoxy)-2-oxo-2,5-dihydro-pyrrol-1-yl]-N-[1-(2-hydroxy-2-methyl-propyl)-1H-pyrazol-3-yl]-3-(tetrahydro-pyran-4-yl)-propionamide

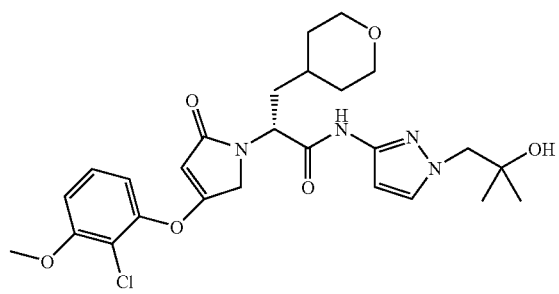

Separation of the enantiomers of 2-[4-(2-chloro-3-methoxy-phenoxy)-2-oxo-2,5-dihydro-pyrrol-1-yl]-N-[1-(2-hydroxy-2-methyl-propyl)-1H-pyrazol-3-yl]-3-(tetrahydro-pyran-4-yl)-propionamide via supercritical fluid chromatography on a SFC KROMASIL OD column, 20% methanol as mobile phase modifier, 70 mL/min afforded (R)-2-[4-(2-chloro-3-methoxy-phenoxy)-2-oxo-2,5-dihydro-pyrrol-1-yl]-N-[1-(2-hydroxy-2-methyl-propyl)-1H-pyrazol-3-yl]-3-(tetrahydro-pyran-4-yl)-propionamide (45 mg) as a white solid. LR-ES-MS m/z calculated for $C_{26}H_{33}ClN_4O_6$ $[M]^+$ 532, observed $[M+H]^+$ 533.

Example 53

2-[4-(2-Chloro-3-methoxy-phenoxy)-2-oxo-2,5-dihydro-pyrrol-1-yl]-N-[1-((R)-2,3-dihydroxy-propyl)-1H-pyrazol-3-yl]-3-(tetrahydro-pyran-4-yl)-propionamide

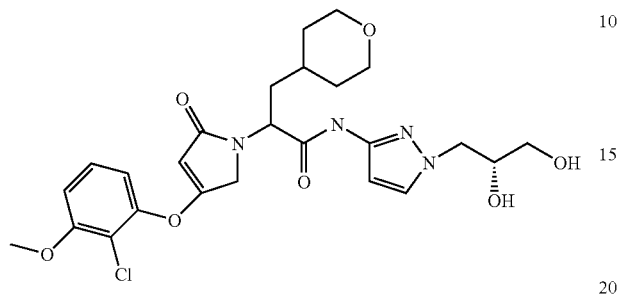

A solution of 2-[4-(2-chloro-3-methoxy-phenoxy)-2-oxo-2,5-dihydro-pyrrol-1-yl]-3-(tetrahydro-pyran-4-yl)-propionic acid (as prepared in Example 50, 200 mg, 0.51 mmol) in dichloromethane (10 mL) was treated with 1-(3-dimethylaminopropyl)-3-ethylcarbodiimide (86 mg, 0.56 mmol) and 1-hydroxybenzotriazole (72 mg, 0.53 mmol). The reaction mixture was stirred at 25° C. for 2 h followed by the addition of 1-((R)-2,2-dimethyl-[1,3]dioxolan-4-yl-methyl)-1H-pyrazol-3-ylamine (prepared in Example 49, 120 mg, 0.61 mmol). The reaction mixture was stirred for 18 h at 25° C., under nitrogen. The reaction mixture was diluted with dichloromethane, washed with 2N aqueous hydrochloric acid, saturated sodium bicarbonate solution, a saturated sodium chloride solution and dried over magnesium sulfate. The organic layer was concentrated, and the crude product was purified by ISCO flash chromatography (Teledyne Isco RediSep Flash Column 12 g; 0% to 10% methanol/dichloromethane) to afford, 2-[4-(2-chloro-3-methoxy-phenoxy)-2-oxo-2,5-dihydro-pyrrol-1-yl]-N-[1-((R)-2,2-dimethyl-[1,3]dioxolan-4-yl-methyl)-1H-pyrazol-3-yl]-3-(tetrahydro-pyran-4-yl)-propionamide (285 mg, 98%) as a yellow oil: LR-ES-MS m/z calculated for $C_{28}H_{35}ClN_4O_7$ [M]$^+$ 574 observed [M+H]$^+$ 575.

A solution of 2-[4-(2-chloro-3-methoxy-phenoxy)-2-oxo-2,5-dihydro-pyrrol-1-yl]-N-[1-((R)-2,2-dimethyl-[1,3]dioxolan-4-yl-methyl)-1H-pyrazol-3-yl]-3-(tetrahydro-pyran-4-yl)-propionamide (285 mg, 0.50 mmol) in tetrahydrofuran (10 mL) was treated with 2N aqueous aqueous hydrochloric acid solution (3 mL). The reaction mixture was stirred at 25° C. for 4 h. The reaction mixture was diluted with ethyl acetate, washed with water, saturated sodium bicarbonate solution, a saturated sodium chloride solution and dried over magnesium sulfate. The organic layer was concentrated to afford, 2-[4-(2-chloro-3-methoxy-phenoxy)-2-oxo-2,5-dihydro-pyrrol-1-yl]-N-[1-((R)-2,3-dihydroxy-propyl)-1H-pyrazol-3-yl]-3-(tetrahydro-pyran-4-yl)-propionamide (87 mg, 33%) as a white solid: LR-ES-MS m/z calculated for $C_{25}H_{31}ClN_4O_7$ [M]$^+$ 534, observed [M+H]$^+$ 535; $^1$H NMR (400 MHz, DMSO-$d_6$) δ ppm 10.77 (s, 1H), 7.54 (t, J=1.7 Hz, 1H), 7.42 (t, J=8.3 Hz, 1H), 7.14 (dd, J=8.3, 1.0 Hz, 1H), 7.09 (dd, J=8.3, 1.0 Hz, 1H), 6.41 (d, J=2.1 Hz, 1H), 4.88-4.93 (m, 1H), 4.93 (d, J=5.3 Hz, 1H), 4.82 (s, 1H), 4.70 (t, J=5.4 Hz, 1H), 4.59 (dd, J=18.2, 2.5 Hz, 1H), 4.24 (d, J=18.8 Hz, 1H), 4.09 (dd, J=13.5, 3.9 Hz, 1H), 3.91 (s, 3H), 3.72-3.90 (m, 4H), 3.14-3.32 (m, 4H), 1.73-1.85 (m, 1H), 1.55-1.73 (m, 3H), 1.31-1.43 (m, 1H), 1.14-1.32 (m, 2H).

Example 54

(S)-2-[4-(2-Chloro-3-methoxy-phenoxy)-2-oxo-2,5-dihydro-pyrrol-1-yl]-3-cyclopentyl-N-[1-(2-hydroxy-2-methyl-propyl)-1H-pyrazol-3-yl]-propionamide

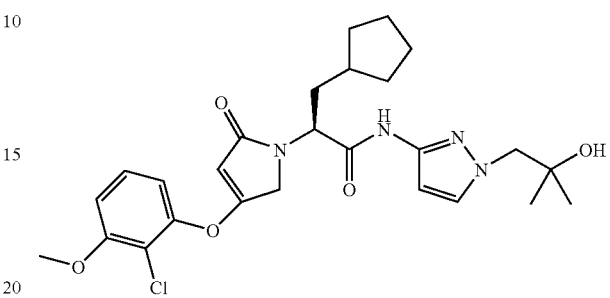

To a stirred mixture of (S)-2-amino-3-cyclopentyl-propionic acid methyl ester hydrochloride (prepared in Example 1, 980 mg, 4.73 mmol) dissolved in acetonitrile (10 mL) under a nitrogen atmosphere was added N,N-diisopropylethylamine (0.60 g, 4.65 mmol). After addition was complete the mixture was stirred at 60° C. for 1 h. The reaction was cooled to 25° C. and treated with N,N-diisopropylethylamine (600 mg, 4.65 mmol) and acetonitrile (10 mL) and heated to 80° C. at which time 4-bromo-3-(2-chloro-3-methoxy-phenoxy)-but-2-enoic acid ethyl ester (as prepared in Example 48, 1.50 g, 4.30 mmol) in acetonitrile (10 mL) was added slowly. After the addition was complete the reaction mixture was heated to 100° C. and stirred overnight. The reaction mixture was cooled to 25° C., filtered and concentrated. The residue was diluted with dichloromethane and washed with 2N aqueous hydrochloric acid, a saturated sodium bicarbonate solution, a saturated sodium chloride solution and dried over magnesium sulfate. The crude product obtained was purified by ISCO flash chromatography (Teledyne Isco RediSep Flash Column 40 g; 0% to 80% ethyl acetate/hexanes) to afford, (S)-2-[4-(2-chloro-3-methoxy-phenoxy)-2-oxo-2,5-dihydro-pyrrol-1-yl]-3-cyclopentyl-propionic acid methyl ester (1.02 g, 60%) as a yellow oil: LR-ES-MS m/z calculated for $C_{20}H_{24}ClNO_5$ [M]$^+$ 393, observed [M+H]$^+$ 394.

To a stirred mixture of (S)-2-[4-(2-chloro-3-methoxy-phenoxy)-2-oxo-2,5-dihydro-pyrrol-1-yl]-3-cyclopentyl-propionic acid methyl ester (1.0 g, 2.54 mmol) in tetrahydrofuran (9 mL) and water (3 mL) was added lithium hydroxide (0.13 g, 3.05 mmol). After addition was complete the mixture was stirred at 25° C. for 2 h. The reaction mixture was poured into water and diethyl ether and the layers separated. The aqueous layer was made acidic with 2N aqueous hydrochloric acid and extracted with ethyl acetate (3×30 mL). The combined ethyl acetate fractions were washed with a saturated sodium chloride solution, dried over magnesium sulfate, filtered and concentrated to afford, (S)-2-[4-(2-chloro-3-methoxy-phenoxy)-2-oxo-2,5-dihydro-pyrrol-1-yl]-3-cyclopentyl-propionic acid (850 mg, 88%) as a yellow solid: LR-ES-MS m/z calculated for $C_{19}H_{22}ClNO_5$ [M]$^+$ 379, observed [M+H]$^+$ 380.

A solution of (S)-2-[4-(2-chloro-3-methoxy-phenoxy)-2-oxo-2,5-dihydro-pyrrol-1-yl]-3-cyclopentyl-propionic acid (200 mg, 0.53 mmol) in dichloromethane (10 mL) was treated with 1-(3-dimethylaminopropyl)-3-ethylcarbodiimide (90 mg, 0.58 mmol) and 1-hydroxybenzotriazole (75 mg, 0.55 mmol). The reaction mixture was stirred at 25° C. for 2 h followed by the addition of 1-(3-amino-pyrazol-1-yl)-2-methyl-propan-2-ol (prepared in U.S. Pat. Appl. US2008021032 Example 80, 94 mg, 0.61 mmol). The reaction mixture was stirred for 18 h at 25° C., under nitrogen. The reaction mixture was diluted with dichloromethane, washed with 2N aqueous hydrochloric acid, saturated sodium bicarbonate solution, a saturated sodium chloride solution and dried over magnesium sulfate. The organic layer was concentrated, and the crude product was purified by ISCO flash chromatography (Teledyne Isco RediSep Flash Column 12 g; 0% to 10% methanol/dichloromethane) to afford (S)-2-[4-(2-chloro-3-methoxy-phenoxy)-2-oxo-2,5-dihydro-pyrrol-1-yl]-3-cyclopentyl-N-[1-(2-hydroxy-2-methyl-propyl)-1H-pyrazol-3-yl]-propionamide (147 mg, 54%) as a light yellow solid: $^1$H NMR (300 MHz, DMSO-$d_6$) δ ppm 1.04 (br. s., 3H) 1.06 (br. s., 3H) 1.08-1.95 (m, 11H) 3.89 (br. s., 2H) 3.90 (s, 3H) 4.21 (d, J=18.4 Hz, 1H) 4.59 (d, J=18.4 Hz, 1H) 4.67 (s, 1H) 4.80 (s, 1H) 4.81-4.87 (m, 1H) 6.45 (d, J=2.1 Hz, 1H) 7.09 (d, J=8.2 Hz, 1H) 7.13 (d, J=8.5 Hz, 1H) 7.41 (t, J=8.5 Hz, 1H) 7.53 (d, J=2.1 Hz, 1H) 10.80 (s, 1H).

Example 55

(S)-2-[4-(2-Chloro-3-methoxy-phenoxy)-2-oxo-2,5-dihydro-pyrrol-1-yl]-3-cyclopentyl-N-[1-((R)-2,3-dihydroxy-propyl)-1H-pyrazol-3-yl]-propionamide

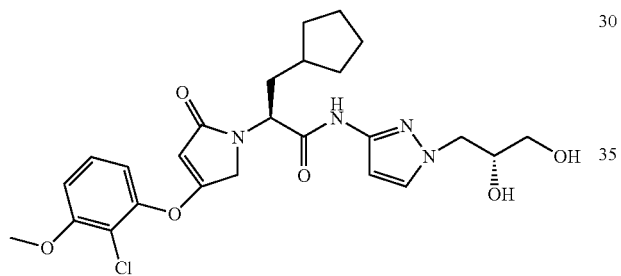

A solution of (S)-2-[4-(2-chloro-3-methoxy-phenoxy)-2-oxo-2,5-dihydro-pyrrol-1-yl]-3-cyclopentyl-propionic acid (as prepared in Example 54, 200 mg, 0.53 mmol) in dichloromethane (10 mL) was treated with 1-(3-dimethylaminopropyl)-3-ethylcarbodiimide (90 mg, 0.58 mmol) and 1-hydroxybenzotriazole (75 mg, 0.55 mmol). The reaction mixture was stirred at 25° C. for 2 h followed by the addition of 1-((R)-2,2-dimethyl-[1,3]dioxolan-4-yl-methyl)-1H-pyrazol-3-ylamine (prepared as in Example 49, 125 mg, 0.63 mmol). The reaction mixture was stirred for 18 h at 25° C., under nitrogen. The reaction mixture was diluted with dichloromethane, washed with 2N aqueous hydrochloric acid, saturated sodium bicarbonate solution, a saturated sodium chloride solution and dried over magnesium sulfate. The organic layer was concentrated, and the crude product was purified by ISCO flash chromatography (Teledyne Isco RediSep Flash Column 12 g; 0% to 10% methanol/dichloromethane) to afford, (S)-2-[4-(2-chloro-3-methoxy-phenoxy)-2-oxo-2,5-dihydro-pyrrol-1-yl]-N-[1-((R)-2,2-dimethyl-[1,3]dioxolan-4-yl-methyl)-1H-pyrazol-3-yl]-3-cyclopentyl-propionamide (207 mg, 70%) as a yellow oil: LR-ES-MS m/z calculated for $C_{28}H_{35}ClN_4O_6$ [M]$^+$ 558 observed [M+H]$^+$ 559.

A solution of (S)-2-[4-(2-chloro-3-methoxy-phenoxy)-2-oxo-2,5-dihydro-pyrrol-1-yl]-N-[1-((R)-2,2-dimethyl-[1,3]dioxolan-4-yl-methyl)-1H-pyrazol-3-yl]-3-cyclopentyl-propionamide (205 mg, 0.37 mmol) in tetrahydrofuran (6 mL) was treated with 2N aqueous hydrochloric acid solution (3 mL). The reaction mixture was stirred at 25° C. for 4 h. The reaction mixture was diluted with ethyl acetate, washed with water, saturated sodium bicarbonate solution, a saturated sodium chloride solution and dried over magnesium sulfate. The organic layer was concentrated to afford, (S)-2-[4-(2-chloro-3-methoxy-phenoxy)-2-oxo-2,5-dihydro-pyrrol-1-yl]-3-cyclopentyl-N-[1-((R)-2,3-dihydroxy-propyl)-1H-pyrazol-3-yl]-propionamide (162 mg, 85%) as a light yellow solid: LR-ES-MS m/z calculated for $C_{25}H_{31}ClN_4O_6$ [M]$^+$ 518, observed [M+H]$^+$ 519; $^1$H NMR (300 MHz, DMSO-$d_6$) δ ppm 1.02-1.20 (m, 1H) 1.20-1.37 (m, 1H) 1.38-1.93 (m, 9H) 3.20-3.33 (m, 2H) 3.69-3.89 (m, 2H) 3.90 (s, 3H) 4.05-4.15 (m, 1H) 4.21 (d, J=18.4 Hz, 1H) 4.58 (d, J=18.4 Hz, 1H) 4.72 (t, J=5.4 Hz, 1H) 4.81 (s, 1H) 4.77-4.86 (m, 1H) 4.94 (d, J=5.1 Hz, 1H) 6.41 (d, J=1.8 Hz, 1H) 7.09 (d, J=8.2 Hz, 1H) 7.13 (d, J=8.2 Hz, 1H) 7.41 (t, J=8.2 Hz, 1H) 7.53 (d, J=1.8 Hz, 1H) 10.78 (s, 1H).

Example 56

(S)-3-Cyclohexyl-N-[1-(2-hydroxy-2-methyl-propyl)-1H-pyrazol-3-yl]-2-(4-methoxy-2-oxo-2,5-dihydro-pyrrol-1-yl)-propionamide

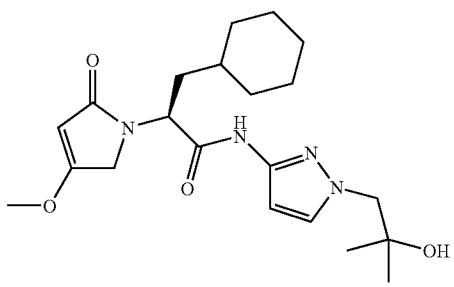

A suspension of (S)-2-amino-3-cyclohexyl-propionic acid methyl ester hydrochloride (3.91 g, 17.63 mmol) in acetonitrile (10 mL) was treated with triethylamine (2.5 mL, 17.93 mmol). The mixture was then heated to 60° C., and kept at that temperature for 0.25 h. Then, additional triethylamine (2.0 mL, 14.35 mmol) was added followed by methyl-4-chloro-3-methoxy-(E)-2-butenoate (2.32 g, 14.1 mmol) in acetonitrile (10 mL) dropwise. The mixture was then heated to reflux by lowering into a pre-heated oil bath kept at 100° C. for 3 h, under nitrogen. The mixture was cooled to 0° C., and the precipitated triethylammonium hydrochloride was filtered off. After aqueous acid work-up, the crude product was purified by ISCO flash chromatography (Teledyne Isco RediSep Flash Column 120 g; 0% to 100% ethylacetate/hexanes) to afford, (S)-3-cyclohexyl-2-(4-methoxy-2-oxo-2,5-dihydro-pyrrol-1-yl)-propionic acid methyl ester (950 mg, 19%) as light yellow oil.

To a solution containing (S)-3-cyclohexyl-2-(4-methoxy-2-oxo-2,5-dihydro-pyrrol-1-yl)-propionic acid methyl ester (160 mg, 0.57 mmol) in tetrahydrofuran (3 mL) was treated with an aqueous solution of lithium hydroxide monohydrate (26 mg, 1.08 mmol) in water (3 mL). The mixture was stirred at 25° C. for 2.5 h. The mixture was then acidified with 2N aqueous hydrochloric acid. The mixture was extracted with dichloromethane (2×30 mL). The combined organic layers were dried over magnesium sulfate and concentrated. To afford (S)-3-cyclohexyl-2-(4-methoxy-2-oxo-2,5-dihydro-pyrrol-1-yl)-propionic acid (145 mg, 95%) as an off-white solid.

A solution of (S)-3-cyclohexyl-2-(4-methoxy-2-oxo-2,5-dihydro-pyrrol-1-yl)-propionic acid (138 mg, 0.52 mmol), 1-(3-amino-pyrazol-1-yl)-2-methyl-propan-2-ol (prepared in U.S. Pat. Appl. US2008021032 Example 80, 98 mg, 0.63 mmol), benzotriazol-1-yl-oxy-tris(dimethylamino)phosphonium hexafluorophosphate (326 mg, 0.75 mmol), N,N-diisopropylethylamine (200 mg, 1.54 mmol) in dichloromethane (10 mL) was stirred for 18 h under nitrogen at 23° C. The reaction mixture was diluted with dichloromethane, washed with 2N aqueous hydrochloric acid, saturated sodium chloride solution and dried. The organic layer was concentrated, and the crude product was purified by ISCO flash chromatography (Teledyne Isco RediSep Flash Column 12 g silica gel; 0% to 10% methanol/dichloromethane) to afford, (S)-3-cyclopentyl-N-[1-(2-methoxy-2-methyl-propyl)-1H-pyrazol-3-yl]-2-(4-methoxy-2-oxo-2,5-dihydro-pyrrol-1-yl)-propionamide (123 mg, 59%) as a white foam, LR-ES-MS m/z calculated for $C_{21}H_{32}N_4O_4$ [M]$^+$ 404, observed [M+H]$^+$ 405; $^1$H NMR (300 MHz, CDCl$_3$) δ ppm 0.78-1.31 (m, 7H) 1.15 (s, 6H) 1.55-1.77 (m, 5H) 1.77-1.95 (m, 2H) 3.82 (s, 3H) 3.87 (d, J=17.8 Hz, 1H) 3.94 (s, 2H) 4.05 (d, J=17.8 Hz, 1H) 4.92 (dd, J=9.5, 5.9 Hz, 1H) 5.14 (s, 1H) 6.67 (d, J=2.1 Hz, 1H) 7.28 (d, J=2.1 Hz, 1H) 8.72 (br. s., 1H).

Example 57

(S)-2-[4-(2-Chloro-3-methoxy-phenoxy)-2-oxo-2,5-dihydro-pyrrol-1-yl]-3-cyclohexyl-N-[1-(2-hydroxy-2-methyl-propyl)-1H-pyrazol-3-yl]-propionamide

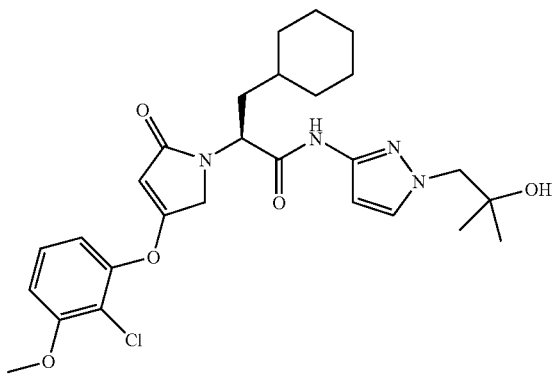

To a stirred mixture of sodium metal (340 mg, 14.81 mmol) dissolved in ethanol (20 mL) under a nitrogen atmosphere was added 2-chloro-3-methoxy phenol (2.16 g, 13.37 mmol) and 3-chloro-but-2-enoic acid ethyl ester (2.2 g, 13.37 mmol). After addition was complete the mixture was stirred at reflux for 1 h. Upon completion of the reaction the ethanol was removed in vacuo and water (50 mL) was added. The aqueous layer was extracted with ethyl acetate (2×50 mL). Excess phenol was removed by washing the combined ethyl acetate layers with 5% solution of sodium hydroxide (2×50 mL). The ethyl acetate solution was dried over magnesium sulfate, filtered and concentrated and the crude product obtained was purified by ISCO flash chromatography (Teledyne Isco RediSep Flash Column 120 g; 0% to 100% ethyl acetate/hexanes) to afford, 3-(2-chloro-3-methoxy-phenoxy)-but-2-enoic acid ethyl ester (1.61 g, 44.5%) as a clear oil: LR-ES-MS m/z calculated for $C_{13}H_{16}ClO_4$ [M]$^+$ 270, observed [M+H]$^+$271.

To a stirred mixture of 3-(2-chloro-3-methoxy-phenoxy)-but-2-enoic acid ethyl ester (1.52 g, 5.6 mmol) dissolved in carbon tetrachloride (25 mL) under a nitrogen atmosphere was added N-bromosuccinimide (1.7 g, 9.44 mmol) and benzoyl peroxide (0.26 g, 0.77 mmol). After addition was complete the mixture was stirred at reflux for 18 h. The reaction mixture was then cooled to room temperature, the succinimide removed by filtration and the solvent removed in vacuo. The crude product obtained was purified by ISCO flash chromatography (Teledyne Isco RediSep Flash Column 40 g; 0% to 100% ethyl acetate/hexanes) to afford, 4-bromo-3-(2-chloro-3-methoxy-phenoxy)-but-2-enoic acid ethyl ester (1.6 g, 81%) as a yellow oil: LR-ES-MS m/z calculated for $C_{13}H_{15}BrClO_4$ [M]$^+$ 349, observed [M+H]$^+$ 350.

A solution of (S)-2-t-butoxycarbonylamino-3-cyclohexyl-propionic acid (2.0 g, 7.4 mmol) in dichloromethane (25 mL) was treated with 1-(3-dimethylaminopropyl)-3-ethylcarbodiimide (1.16 g, 7.44 mmol) and 1-hydroxybenzotriazole (1.05 g, 7.74 mmol). The mixture was stirred at room temperature for 2 h. Then, 1-(3-amino-pyrazol-1-yl)-2-methyl-propan-2-ol (prepared in U.S. Pat. Appl US2008021032 Example 80, 1.26 g, 8.11 mmol) was added and stirred for 18 h at room temperature. The crude product obtained after aqueous work-up, was purified by ISCO flash chromatography (Teledyne Isco RediSep Flash Column 40 g; 0% to 100% ethyl acetate/hexanes) to afford, {(S)-2-cyclohexyl-1-[1-(2-hydroxy-2-methyl-propyl)-1H-pyrazol-3-ylcarbamoyl]-ethyl}-carbamic acid t-butyl ester (610 mg, 20%) as a white solid.

A solution of {(S)-2-cyclohexyl-1-[1-(2-hydroxy-2-methyl-propyl)-1H-pyrazol-3-ylcarbamoyl]-ethyl}-carbamic acid t-butyl ester (0.61 g 1.5 mmol) in dichloromethane (10 mL) was treated with trifluoroacetic acid (5 mL). The mixture was stirred at room temperature for 0.5 h, and concentrated to afford (S)-2-amino-3-cyclohexyl-N-[1-(2-hydroxy-2-methyl-propyl)-1H-pyrazol-3-yl]-propionamide trifluoroacetate (630 mg, 100%) as a white solid.

A solution of (S)-2-amino-3-cyclohexyl-N-[1-(2-hydroxy-2-methyl-propyl)-1H-pyrazol-3-yl]-propionamide trifluoroacetate (96 mg 0.30 mmol) in acetonitrile (8 mL) was refluxed with triethylamine (34 mg, 0.34 mmol) for 0.5 h. The reaction mixture was cooled to room temperature and precipitated triethyl ammonium trifluoroacetate was filtered off and the solution was transferred to a microwave reaction vessel. The reaction mixture was treated with 4-bromo-3-(2-chloro-3-methoxy-phenoxy)-but-2-enoic acid ethyl ester (99 mg, 0.28 mmol) and heated in the Emery Reaction Optimizer microwave reactor at 140° C. for 1 h. The reaction mixture was then concentrated and diluted with dichloromethane. The crude product obtained after aqueous work-up, was purified by ISCO flash chromatography (Teledyne Isco RediSep Flash Column 40 g; 0% to 100% ethyl acetate/hexanes) to afford, (S)-2-[4-(2-chloro-3-methoxy-phenoxy)-2-oxo-2,5-dihydro-pyrrol-1-yl]-3-cyclohexyl-N-[1-(2-hydroxy-2-methyl-propyl)-1H-pyrazol-3-yl]-propionamide (37 mg, 25%) as a light orange solid: HR-ES-MS m/z calculated for $C_{27}H_{35}ClN_4O_5$ [M+H]$^+$ 531.2369, observed 531.2369; $^1$H NMR (400 MHz, DMSO-d$_6$) δ ppm 1.01-1.22 (m, 4H) 1.04 (s, 3H) 1.06 (s, 3H) 1.49-1.88 (m, 9H) 3.89 (s, 2H) 3.90 (s, 3H) 4.18 (d, J=18.4 Hz, 1H) 4.58 (d, J=18.4 Hz, 1H) 4.67 (s, 1H) 4.81 (s, 1H) 4.86-4.95 (m, 1H) 6.44 (d, J=2.2 Hz, 1H)

7.09 (dd, J=8.4, 1.2 Hz, 1H) 7.13 (dd, J=8.4, 1.2 Hz, 1H) 7.42 (t, J=8.4 Hz, 1H) 7.53 (d, J=2.2 Hz, 1H) 10.78 (s, 1H).

Example 58

1-{2-[4-(2-Chloro-3-methoxy-phenoxy)-2-oxo-2,5-dihydro-pyrrol-1-yl]-3-cyclohexyl-propionyl}-3-methyl-urea

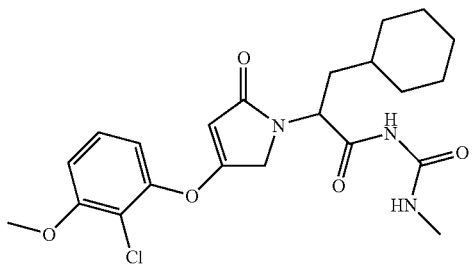

A solution of (S)-2-amino-3-cyclohexyl-propionic acid methyl ester hydrochloride (144 mg, 0.64 mmol) in acetonitrile (6 mL) was refluxed with triethylamine (136 mg, 1.34 mmol) for 0.5 h. The reaction mixture was cooled to room temperature, and the precipitated triethylammonium hydrochloride was filtered off. The acetonitrile solution was then transferred to the Emry Optimizer microwave reaction vessel, and 4-bromo-3-(2-chloro-3-methoxy-phenoxy)-but-2-enoic acid ethyl ester (prepared in Example 57, 206 mg, 0.58 mmol) was added, and heated at 140° C., for 1.75 h. The crude product obtained after aqueous work-up, was purified by ISCO flash chromatography (Teledyne Isco RediSep Flash Column 4 g; 0% to 60% ethyl acetate/hexanes) to afford, (S)-2-[4-(2-chloro-3-methoxy-phenoxy)-2-oxo-2,5-dihydro-pyrrol-1-yl]-3-cyclohexyl-propionic acid methyl ester (63 mg, 27%) as a light orange oil.

A solution of (S)-2-[4-(2-chloro-3-methoxy-phenoxy)-2-oxo-2,5-dihydro-pyrrol-1-yl]-3-cyclohexyl-propionic acid methyl ester (63 mg, 0.15 mmol) in methanol (2 mL) was heated in an Emry Optimized microwave reactor at 140° C. for 2 h, in the presence of N-methylurea (33 mg, 0.46 mmol) and an 8% magnesium methoxide solution in methanol (6 mL, 490 mg, 0.45 mmol). The crude product obtained after concentration, was purified by ISCO flash chromatography (Teledyne Isco RediSep Flash Column 4 g; 0% to 100% ethyl acetate/hexanes) to afford, 1-{2-[4-(2-chloro-3-methoxy-phenoxy)-2-oxo-2,5-dihydro-pyrrol-1-yl]-3-cyclohexyl-propionyl}-3-methyl-urea (6 mg, 9%) as a light yellow solid: HR-ES-MS m/z calculated for $C_{22}H_{28}ClN_3O_5$ $[M+H]^+$ 450.1790, observed 450.2153; $^1$H NMR (300 MHz, CDCl$_3$) δ ppm 0.76-1.96 (m, 13H) 2.79 (d, J=4.8 Hz, 3H) 3.95 (s, 3H) 4.09 (d, J=18.4 Hz, 1H) 4.31 (d, J=18.4 Hz, 1H) 4.67 (t, J=7.7 Hz, 1H) 4.87 (s, 1H) 6.25 (br. s., 1H) 6.88 (d, J=8.2 Hz, 2H) 7.22-7.33 (m, 1H).

Example 59

2-[4-(2,6-Difluoro-phenoxy)-2-oxo-2,5-dihydro-pyrrol-1-yl]-3-(2,6-difluoro-phenyl)-N-[1-(2-hydroxy-2-methyl-propyl)-1-H-pyrazol-3-yl]-propionamide

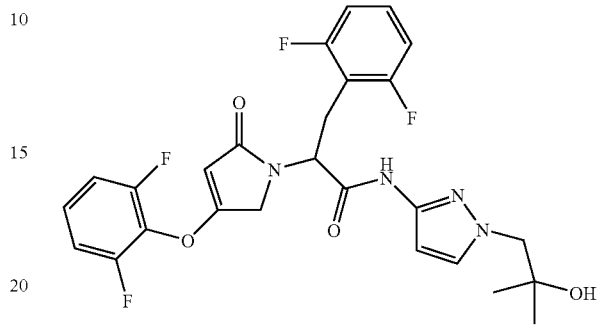

To a stirred mixture of 2-amino-3-(2,6-difluoro-phenyl)-propionic acid ethyl ester (0.26 g, 1.02 mmol) dissolved in acetonitrile (5 mL) under a nitrogen atmosphere was added N,N-diisopropylethylamine (280 mg, 2.14 mmol). After addition was complete the mixture was stirred at 60° C. for 1 h. The reaction was cooled to 25° C. and treated with N,N-diisopropylethylamine (600 mg, 4.65 mmol) and acetonitrile (10 mL) and heated to 100° C. at which time 4-bromo-3-(2,6-difluoro-phenoxy)-but-2-enoic acid ethyl ester (as prepared in Example 36, 300 mg, 0.93 mmol) in acetonitrile (5 mL) was added slowly. After the addition was complete the reaction mixture was heated to 100° C. and stirred overnight. The reaction mixture was cooled to 25° C., filtered and concentrated. The residue was diluted with dichloromethane and washed with 2N aqueous hydrochloric acid, a saturated sodium chloride solution and dried over magnesium sulfate. The crude product obtained was purified by ISCO flash chromatography (Teledyne Isco RediSep Flash Column 4 g; 0% to 100% ethyl acetate/hexanes) to afford, 2-[4-(2,6-difluoro-phenoxy)-2-oxo-2,5-dihydro-pyrrol-1-yl]-3-(2,6-difluoro-phenyl)-propionic acid ethyl ester (110 mg, 28%) as an orange red oil: LR-ES-MS m/z calculated for $C_{20}H_{15}F_4NO_4$ $[M]^+$ 409, observed $[M+H]^+$ 410.

To a solution containing 2-[4-(2,6-difluoro-phenoxy)-2-oxo-2,5-dihydro-pyrrol-1-yl]-3-(2,6-difluoro-phenyl)-propionic acid ethyl ester (96 mg, 0.23 mmol) in tetrahydrofuran (1 mL) was treated with an aqueous solution of lithium hydroxide monohydrate (12 mg, 0.27 mmol) in water (2 mL). The mixture was stirred at 25° C. for 3 h, then acidified with 2N aqueous hydrochloric acid. The mixture was extracted with dichloromethane (2×30 mL). The combined organic layers were dried over magnesium sulfate and concentrated to afford 2-[4-(2,6-difluoro-phenoxy)-2-oxo-2,5-dihydro-pyrrol-1-yl]-3-(2,6-difluoro-phenyl)-propionic acid (90 mg, 100%) as an off-white solid. LR-ES-MS m/z calculated for $C_{19}H_{13}F_4NO_4$ $[M]^+$ 395, observed $[M+H]^+$ 396.

A solution of 2-[4-(2,6-difluoro-phenoxy)-2-oxo-2,5-dihydro-pyrrol-1-yl]-3-(2,6-difluoro-phenyl)-propionic acid (86 mg, 0.21 mmol), 1-(3-amino-pyrazol-1-yl)-2-methyl-propan-2-ol (prepared in U.S. Pat. Appl. US2008021032 Example 80, 39.7 mg, 0.26 mmol), benzotriazol-1-yl-oxy-tris (dimethylamino)phosphonium hexafluorophosphate (105 mg, 0.23 mmol), N,N-diisopropylethylamine (83 mg, 0.64 mmol) in dichloromethane (6 mL) was stirred for 18 h under nitrogen at 23° C. The reaction mixture was diluted with dichloromethane, washed with 2N aqueous hydrochloric acid, saturated sodium chloride solution and dried. The organic layer was concentrated, and the crude product was purified by ISCO flash chromatography (Teledyne Isco RediSep Flash Column 12 g silica gel; 0% to 10% methanol/dichloromethane) to afford, 2-[4-(2,6-difluoro-phenoxy)-2-oxo-2,5-dihydro-pyrrol-1-yl]-3-(2,6-difluoro-phenyl)-N-[1-(2-hydroxy-2-methyl-propyl)-1-H-pyrazol-3-yl]-propionamide (48 mg, 42%) as a white foam: HR-ES-MS m/z calculated for $C_{26}H_{24}F_4N_4O_4$ [M+H]$^+$ 533.1807, observed 533.1807; $^1$H NMR (300 MHz, DMSO-d$_6$) δ ppm 1.04 (s, 6H) 3.05-3.28 (m, 2H) 3.88 (s, 2H) 4.38 (br. s., 2H) 4.67 (s, 1H) 4.97 (s, 1H) 5.00-5.10 (m, 1H) 6.47 (d, J=2.2 Hz, 1H) 6.95-7.09 (m, 2H) 7.22-7.50 (m, 4H) 7.54 (d, J=2.2 Hz, 1H) 10.77 (s, 1H).

Example 60

(S)-3-Cyclohexyl-2-[4-(2,3-dihydro-benzo[1,4]dioxin-2-ylmethoxy)-2-oxo-2,5-dihydro-pyrrol-1-yl]-N-[1-(2-hydroxy-2-methyl-propyl)-1-H-pyrazol-3-yl]-propionamide

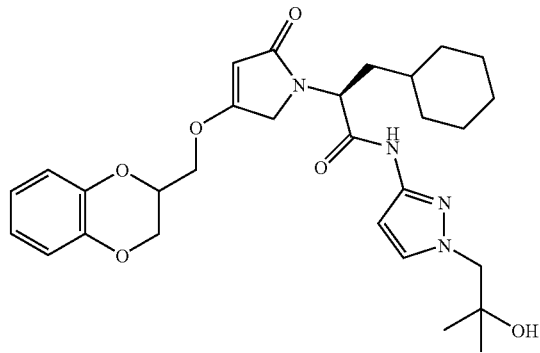

To a stirred mixture of (2,3-dihydro-benzo[1,4]dioxin-2-yl)-methanol (1.01 g, 5.90 mmol) and ethyl-2-butynoate (820 mg, 7.08 mmol) in tetrahydrofuran (15 mL) was added tri-n-butylphosphine (0.25 g, 1.18 mmol). The mixture was stirred at room temperature for 1.5 h. Upon completion of the reaction the tetrahydrofuran was removed in vacuo. The crude product obtained was purified by ISCO flash chromatography (Teledyne Isco RediSep Flash Column 40 g; 0% to 50% ethyl acetate/hexanes) to afford (E)-3-(2,3-dihydro-benzo[1,4]dioxin-2-ylmethoxy)-but-2-enoic acid ethyl ester (660 mg, 40%) as a colorless oil: LR-ES-MS m/z calculated for $C_{15}H_{18}O_5$ [M]$^+$ 278, observed [M+H]$^+$ 279.

To a stirred mixture of (E)-3-(2,3-dihydro-benzo[1,4]dioxin-2-ylmethoxy)-but-2-enoic acid ethyl ester (0.66 g, 2.33 mmol) dissolved in carbon tetrachloride (10 mL) under a nitrogen atmosphere was added N-bromosuccinimide (0.63 g, 3.50 mmol) and benzoyl peroxide (0.11 g, 0.35 mmol). After addition was complete the mixture was stirred at reflux for 2 h. The reaction mixture was then placed in the refrigerator overnight. The solids formed were removed by filtration and the filtrate concentrated in vacuo. The crude product obtained was purified by ISCO flash chromatography (Teledyne Isco RediSep Flash Column 40 g; 0% to 50% ethyl acetate/hexanes) to afford, (E)-4-bromo-3-(2,3-dihydro-benzo[1,4]dioxin-2-ylmethoxy)-but-2-enoic acid ethyl ester (650 mg, 78%) as a colorless oil: LR-ES-MS m/z calculated for $C_{15}H_{17}BrO_5$ [M]$^+$ 357, observed 358 [M+H]$^+$.

To a stirred mixture of (S)-2-amino-3-cyclohexyl-propionic acid methyl ester hydrochloride (430 mg, 1.9 mmol) dissolved in acetonitrile (10 mL) under a nitrogen atmosphere was added N,N-diisopropylethylamine (260 mg, 2.0 mmol). After addition was complete the mixture was stirred at 100° C. for 1 h. The reaction was cooled to 25° C. and treated with N,N-diisopropylethylamine (260 mg, 2.0 mmol) and acetonitrile (10 mL) and heated to 100° C. at which time (E)-4-bromo-3-(2,3-dihydro-benzo[1,4]dioxin-2-ylmethoxy)-but-2-enoic acid ethyl ester (650 mg, 1.72 mmol) in acetonitrile (10 mL) was added slowly. After the addition was complete the reaction mixture was heated to 100° C. and stirred overnight. The reaction mixture was cooled to 25° C., filtered and concentrated. The residue was diluted with dichloromethane and washed with 2N aqueous hydrochloric acid, a saturated sodium chloride solution and dried over magnesium sulfate. The crude product obtained was purified by ISCO flash chromatography (Teledyne Isco RediSep Flash Column 12 g; 0% to 100% ethyl acetate/hexanes) to afford, (S)-3-cyclohexyl-2-[4-(2,3-dihydro-benzo[1,4]dioxin-2-ylmethoxy)-2-oxo-2,5-dihydro-pyrrol-1-yl]-propionic acid methyl ester (250 mg, 35%) as a light orange oil: LR-ES-MS m/z calculated for $C_{23}H_{29}NO_6$ [M]$^+$ 415, observed [M+H]$^+$ 416.

To a mixture of (S)-3-cyclohexyl-2-[4-(2,3-dihydro-benzo[1,4]dioxin-2-ylmethoxy)-2-oxo-2,5-dihydro-pyrrol-1-yl]-propionic acid methyl ester (0.25 g, 0.58 mmol) in tetrahydrofuran (1 mL) and was added lithium hydroxide (0.029 g, 0.7 mmol) in water (1 mL). After addition was complete the mixture was stirred at 25° C. for 2 h. The reaction mixture was poured into water and diethyl ether and the layers separated. The aqueous layer was made acidic with 2N aqueous hydrochloric acid and extracted with ethyl acetate (3×30 mL). The combined ethyl acetate fractions were washed with a saturated sodium chloride solution, dried over magnesium sulfate, filtered and concentrated to afford, (S)-3-cyclohexyl-2-[4-(2,3-dihydro-benzo[1,4]dioxin-2-ylmethoxy)-2-oxo-2,5-dihydro-pyrrol-1-yl]-propionic acid (151 mg, 64%) as a white solid: LR-ES-MS m/z calculated for $C_{22}H_{27}NO_6$ [M]$^+$ 401, observed [M+H]$^+$ 402.

A solution of (S)-3-cyclohexyl-2-[4-(2,3-dihydro-benzo[1,4]dioxin-2-ylmethoxy)-2-oxo-2,5-dihydro-pyrrol-1-yl]-propionic acid (151 mg, 0.55 mmol) in dichloromethane (10 mL) was treated with 1-(3-dimethylaminopropyl)-3-ethyl-carbodiimide (63 mg, 0.39 mmol) and 1-hydroxybenzotriazole (52 mg, 0.38 mmol). The reaction mixture was stirred at 25° C. for 2 h followed by the addition of 1-(3-amino-pyrazol-1-yl)-2-methyl-propan-2-ol (prepared in U.S. Pat. Appl. US2008021032 Example 80, 67 mg, 0.43 mmol). The reaction mixture was stirred for 18 h at 25° C., under nitrogen. The reaction mixture was diluted with dichloromethane, washed with 2N aqueous hydrochloric acid, saturated sodium bicarbonate solution, a saturated sodium chloride solution and dried over magnesium sulfate. The organic layer was concentrated, and the crude product was purified on Gilson HPLC system (C18 column, 10-99% acetonitrile/water gradient) to afford (S)-3-cyclohexyl-2-[4-(2,3-dihydro-benzo[1,4]dioxin-2-ylmethoxy)-2-oxo-2,5-dihydro-pyrrol-1-yl]-N-[1-(2-hydroxy-2-methyl-propyl)-1-H-pyrazol-3-yl]-propionamide (47 mg, 24%) as a white solid: HR-ES-MS m/z calculated for $C_{29}H_{38}N_4O_6$ [M+H]$^+$ 539.2864, observed 539.2865; $^1$H NMR (300 MHz, DMSO-d$_6$) δ ppm 0.81-0.99 (m, 2H) 1.05 (s, 3H) 1.07-1.30 (m, 4H) 1.50-1.83 (m, 7H) 3.89 (s, 2H) 3.98 (dd, J=18.1, 4.0 Hz, 1H) 4.09 (dd, J=11.3, 7.5 Hz, 1H) 4.18-4.34 (m, 2H) 4.34-4.45 (m, 1H) 4.53-4.63 (m, 1H) 4.67 (s, 1H) 4.86 (dd, J=11.3, 4.0 Hz, 1H) 5.25 (s, 1H) 6.42 (d, J=2.1 Hz, 1H) 6.79-6.99 (m, 4H) 7.52 (d, J=2.1 Hz, 1H) 10.70 (s, 1H).

Example 61

(S)-2-[4-(2-Chloro-phenoxy)-2-oxo-2,5-dihydro-pyrrol-1-yl]-3-cyclohexyl-N-[1-(2-hydroxy-2-methyl-propyl)-1-H-pyrazol-3-yl]-propionamide

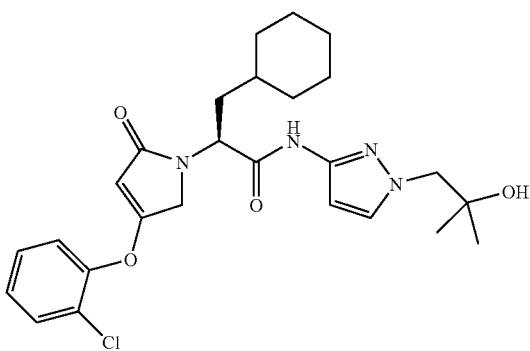

To a stirred mixture of 2-chlorophenol (3.03 g, 23.36 mmol) and ethyl-2-butynoate (5.3 g, 46.72 mmol) in tetrahydrofuran (30 mL) was added 1,8-diazabicyclo[5.4.0]-undec-7-ene (3.6 g, 1.18 mmol). The mixture was heated in a sealed tube at 130° C. for 2 h. Upon completion of the reaction the tetrahydrofuran was removed in vacuo and the residue redissolved in dichloromethane and washed with 2N aqueous hydrochloric acid, 5% aqueous sodium hydroxide solution, a saturated sodium chloride solution and dried over magnesium sulfate. The crude product obtained was purified by ISCO flash chromatography (Teledyne Isco RediSep Flash Column 120 g; 0% to 30% ethyl acetate/hexanes) to afford, (E)-3-(2-chloro-phenoxy)-but-2-enoic acid ethyl ester (2.69 g, 23.9%) as a colorless oil: LR-ES-MS m/z calculated for $C_{12}H_{13}ClO_3$ $[M]^+$ 240, observed $[M+H]^+$ 241.

To a stirred mixture of (E)-3-(2-chloro-phenoxy)-but-2-enoic acid ethyl ester (2.62 g, 10.78 mmol) dissolved in carbon tetrachloride (25 mL) under a nitrogen atmosphere was added N-bromosuccinimide (3.3 g, 18.33 mmol) and benzoyl peroxide (0.56 g, 1.61 mmol). After addition was complete the mixture was stirred at reflux for 18 h. The reaction mixture was cooled to room temperature, the succinimide removed by filtration and the solvent removed in vacuo. The crude product obtained was purified by ISCO flash chromatography (Teledyne Isco RediSep Flash Column 80 g; 0% to 30% ethyl acetate/hexanes) to afford, (E)-4-bromo-3-(2-chloro-phenoxy)-but-2-enoic acid ethyl ester (3.39 g, 98%) as a colorless oil.

To a stirred mixture of (S)-2-amino-3-cyclohexyl-propionic acid methyl ester hydrochloride (670 mg, 3 mmol) dissolved in acetonitrile (15 mL) under a nitrogen atmosphere was added N,N-diisopropylethylamine (400 mg, 3.1 mmol). After addition was complete the mixture was stirred at 105° C. for 1 h. The reaction was cooled to 25° C. and treated with N,N-diisopropylethylamine (400 mg, 3.1 mmol) and heated to 105° C. at which time (E)-4-bromo-3-(2-chloro-phenoxy)-but-2-enoic acid ethyl ester (900 mg, 2.70 mmol) in acetonitrile (10 mL) was added slowly. After the addition was complete the reaction mixture was heated to 105° C. and stirred for 18 h. The reaction mixture was cooled to 25° C., filtered and concentrated. The residue was diluted with dichloromethane and washed with 2N aqueous hydrochloric acid, a saturated sodium chloride solution and dried over magnesium sulfate. The crude product obtained was purified by ISCO flash chromatography (Teledyne Isco RediSep Flash Column 40 g; 0% to 50% ethyl acetate/hexanes) to afford, (S)-2-[4-(2-chloro-phenoxy)-2-oxo-2,5-dihydro-pyrrol-1-yl]-3-cyclohexyl-propionic acid methyl ester (640 mg, 62%) as a red oil: LR-ES-MS m/z calculated for $C_{20}H_{24}ClNO_4$ $[M]^+$ 377, observed $[M+H]^+$ 378.

To a stirred mixture of (S)-2-[4-(2-chloro-phenoxy)-2-oxo-2,5-dihydro-pyrrol-1-yl]-3-cyclohexyl-propionic acid methyl ester (0.63 g, 1.63 mmol) in tetrahydrofuran (6 mL) was added lithium hydroxide (0.083 g, 1.96 mmol) in water (8 mL). After addition was complete the mixture was stirred at 25° C. for 3 h. The reaction mixture was poured into water and diethyl ether and the layers separated. The aqueous layer was made acidic with 2N aqueous hydrochloric acid and extracted with dichloromethane. The combined dichloromethane fractions were washed with a saturated sodium chloride solution, dried over magnesium sulfate, filtered and concentrated to afford, (S)-2-[4-(2-chloro-phenoxy)-2-oxo-2,5-dihydro-pyrrol-1-yl]-3-cyclohexyl-propionic acid (525 mg, 88%) as a light brown solid: LR-ES-MS m/z calculated for $C_{19}H_{22}ClNO_4$ $[M]^+$ 363, observed $[M+H]^+$ 364.

A solution of (S)-2-[4-(2-chloro-phenoxy)-2-oxo-2,5-dihydro-pyrrol-1-yl]-3-cyclohexyl-propionic acid (152 mg, 0.41 mmol) in dichloromethane (10 mL) was treated with 1-(3-dimethylaminopropyl)-3-ethylcarbodiimide (71 mg, 0.45 mmol) and 1-hydroxybenzotriazole (59 mg, 0.43 mmol). The reaction mixture was stirred at 25° C. for 1 h followed by the addition of 1-(3-amino-pyrazol-1-yl)-2-methyl-propan-2-ol (prepared in U.S. Pat. Appl. US2008021032 Example 80, 78 mg, 0.49 mmol). The reaction mixture was stirred for 18 h at 25° C., under nitrogen. The reaction mixture was diluted with dichloromethane, washed with 2N aqueous hydrochloric acid, saturated sodium bicarbonate solution, a saturated sodium chloride solution and dried over magnesium sulfate. The crude product obtained after concentration, was purified by ISCO flash chromatography (Teledyne Isco RediSep Flash Column 4 g; 0% to 100% ethyl acetate/hexanes) to afford, S)-2-[4-(2-chloro-phenoxy)-2-oxo-2,5-dihydro-pyrrol-1-yl]-3-cyclohexyl-N-[1-(2-hydroxy-2-methyl-propyl)-1-H-pyrazol-3-yl]-propionamide (139 mg, 68%) as a white powder: HR-ES-MS m/z calculated for $C_{26}H_{33}ClN_4O_4$ $[M+H]^+$ 501.2263, observed 501.2263; $^1H$ NMR (300 MHz, DMSO-$d_6$) δ ppm 0.87 (s, 2H), 1.04 (s, 3H), 1.06 (s, 3H), 1.07-1.33 (m, 4H), 1.53-1.84 (m, 7H), 3.89 (s, 2H), 4.19 (d, J=18.5 Hz, 1H), 4.60 (d, J=18.5 Hz, 1H), 4.67 (s, 1H), 4.80 (s, 1H), 4.91 (dd, J=10.7, 5.0 Hz, 1H), 6.44 (d, J=2.1 Hz, 1H), 7.33-7.41 (m, 1H), 7.47 (td, J=7.6, 1.4 Hz, 1H), 7.50-7.56 (m, 2H), 7.65 (dd, J=7.8, 1.4 Hz, 1H), 10.79 (s, 1H).

Example 62

((S)-2-[4-(2-Chloro-phenoxy)-2-oxo-2,5-dihydro-pyrrol-1-yl]-3-cyclohexyl-N-[1-((R)-2,2-dimethyl-[1,3]dioxolan-4-yl-methyl)-1-H-pyrazol-3-yl]-propionamide

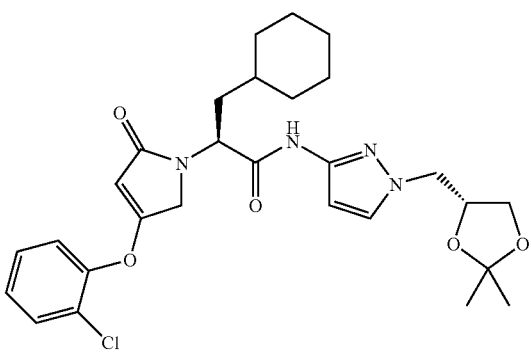

A solution of (S)-2-[4-(2-chloro-phenoxy)-2-oxo-2,5-dihydro-pyrrol-1-yl]-3-cyclohexyl-propionic acid (prepared as in Example 61, 237 mg, 0.64 mmol) in dichloromethane (10 mL) was treated with 1-(3-dimethylaminopropyl)-3-ethyl-carbodiimide (111 mg, 0.70 mmol) and 1-hydroxybenzotriazole (97 mg, 0.70 mmol). The reaction mixture was stirred at 25° C. for 1 h followed by the addition of 1-((R)-2,2-dimethyl-[1,3]dioxolan-4-yl-methyl)-1H-pyrazol-3-ylamine (prepared as in Example 49, 156 mg, 0.77 mmol). The reaction mixture was stirred for 18 h at 25° C., under nitrogen. The reaction mixture was diluted with dichloromethane, washed with 2N aqueous hydrochloric acid, a saturated sodium chloride solution and dried over magnesium sulfate. The crude product obtained after concentration, was purified by ISCO flash chromatography (Teledyne Isco RediSep Flash Column 4 g; 0% to 100% ethyl acetate/hexanes) to afford, ((S)-2-[4-(2-chloro-phenoxy)-2-oxo-2,5-dihydro-pyrrol-1-yl]-3-cyclohexyl-N-[1-((R)-2,2-dimethyl-[1,3]dioxolan-4-yl-methyl)-1-H-pyrazol-3-yl]-propionamide (215 mg, 62%) as a fluffy white solid: HR-ES-MS m/z calculated for $C_{28}H_{35}ClN_4O_5$ $[M+H]^+$ 543.2269, observed 543.2266; $^1H$ NMR (300 MHz, DMSO-$d_6$) δ ppm 0.95 (br. s., 2H), 1.01-1.21 (m, 4H), 1.24 (s, 3H), 1.30 (s, 3H), 1.53-1.86 (m, 7H), 3.73 (dd, J=8.3, 5.7 Hz, 1H), 3.93-4.14 (m, 3H), 4.20 (d, J=18.4 Hz, 1H), 4.35 (quin, J=5.7 Hz, 1H), 4.59 (d, J=18.4 Hz, 1H), 4.80 (s, 1H), 4.91 (dd, J=10.3, 5.1 Hz, 1H), 6.43 (d, J=2.1 Hz, 1H), 7.31-7.41 (m, 1H), 7.47 (t, J=7.8 Hz, 1H), 7.52 (d, J=7.8 Hz, 1H), 7.60 (d, J=2.1 Hz, 1H), 7.65 (d, J=7.8 Hz, 1H), 10.79 (s, 1H).

Example 63

(S)-2-[4-(2-Chloro-phenoxy)-2-oxo-2,5-dihydro-pyrrol-1-yl]-3-cyclohexyl-N-[1-((R)-2,3-dihydroxy-propyl)-1-H-pyrazol-3-yl]-propionamide A solution of ((S)-2-[4-(2-chloro-phenoxy)-2-oxo-2,5-dihydro-pyrrol-1-yl]-3-cyclohexyl-N-[1-((R)-2,2-dimethyl-[1,3]dioxolan-4-yl-methyl)-1-H-pyrazol-3-yl]-propionamide (prepared in Example 62, 201 mg, 0.37 mmol) in tetrahydrofuran (6 mL) was treated with 1N aqueous hydrochloric acid (3 mL). The reaction mixture was stirred for 4 h at room temperature. The reaction mixture was diluted with ethyl acetate (60 mL), washed with saturated sodium bicarbonate, a saturated sodium chloride solution and dried over magnesium sulfate. Upon concentration afforded (S)-2-[4-(2-chloro-phenoxy)-2-oxo-2,5-dihydro-pyrrol-1-yl]-3-cyclohexyl-N-[1-((R)-2,3-dihydroxy-propyl)-1-H-pyrazol-3-yl]-propionamide (153 mg, 83%) as a white powder: HR-ES-MS m/z calculated for $C_{25}H_{31}ClN_4O_5$, $[M+H]^+$ 503.2056 observed 503.2056; $^1H$ NMR (300 MHz, DMSO-$d_6$) δ ppm 0.81-1.02 (m, 2H), 1.02-1.29 (m, 4H), 1.52-1.83 (m, 7H), 3.18-3.32 (m, 2H), 3.70-3.93 (m, 2H), 4.09 (dd, J=13.6, 3.6 Hz, 1H), 4.19 (d, J=18.4 Hz, 1H), 4.59 (d, J=18.4 Hz, 1H), 4.71 (t, J=5.4 Hz, 1H), 4.80 (s, 1H), 4.85-4.92 (m, 1H), 4.94 (d, J=5.4 Hz, 1H), 6.40 (d, J=1.8 Hz, 1H), 7.37 (td, J=7.8, 1.5 Hz, 1H), 7.46 (t, J=7.2 Hz, 1H), 7.50-7.56 (m, 2H), 7.65 (d, J=7.8 Hz, 1H), 10.76 (s, 1H).

Example 64

(S)-2-[4-(2-Chloro-phenoxy)-2-oxo-2,5-dihydro-pyrrol-1-yl]-4-methyl-pentanoic acid [1-(2-hydroxy-2-methyl-propyl)-1H-pyrazol-3-yl]-amide

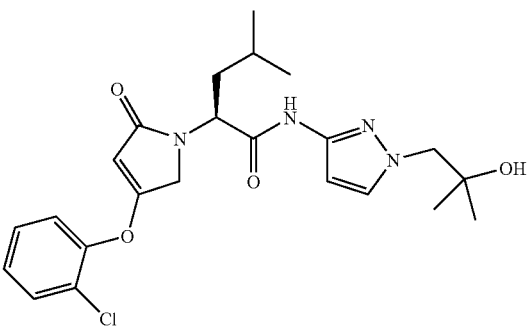

To a stirred mixture of L-leucine methyl ester hydrochloride (1.26 g, 6.8 mmol) dissolved in acetonitrile (40 mL) under a nitrogen atmosphere was added N,N-diisopropylethylamine (950 mg, 7.05 mmol). After addition was complete the mixture was stirred at 105° C. for 1 h. The reaction was cooled to 25° C. and treated with N,N-diisopropylethylamine (950 mg, 7.05 mmol) and heated to 105° C. at which time (E)-4-bromo-3-(2-chloro-phenoxy)-but-2-enoic acid ethyl ester (prepared as in Example 61, 2.05 g, 6.17 mmol) in acetonitrile (10 mL) was added slowly. After the addition was complete the reaction mixture was heated to 105° C. and stirred for 18 h. The reaction mixture was cooled to 25° C., filtered and concentrated. The residue was diluted with dichloromethane and washed with 2N aqueous hydrochloric acid, a saturated sodium chloride solution and dried over magnesium sulfate. The crude product obtained was purified by ISCO flash chromatography (Teledyne Isco RediSep Flash Column 40 g; 0% to 50% ethyl acetate/hexanes) to afford, (S)-2-[4-(2-chloro-phenoxy)-2-oxo-2,5-dihydro-pyrrol-1-yl]-4-methyl-pentanoic acid methyl ester (1.19 g, 57%) as a red oil: LR-ES-MS m/z calculated for $C_{17}H_{20}ClNO_4$ [M]$^+$ 337, observed [M+H]$^+$ 338.

To a stirred mixture of ((S)-2-[4-(2-chloro-phenoxy)-2-oxo-2,5-dihydro-pyrrol-1-yl]-4-methyl-pentanoic acid methyl ester (1.18 g, 3.40 mmol) in tetrahydrofuran (10 mL) and was added lithium hydroxide (173 mg, 4.09 mmol) in water (5 mL). After addition was complete the mixture was stirred at 25° C. for 1 h. The reaction mixture was poured into water and diethyl ether and the layers separated. The aqueous layer was made acidic with 2N aqueous hydrochloric acid and extracted with dichloromethane. The combined dichloromethane fractions were washed with a saturated sodium chloride solution, dried over magnesium sulfate, filtered and concentrated to afford, (S)-2-[4-(2-chloro-phenoxy)-2-oxo-2,5-dihydro-pyrrol-1-yl]-4-methyl-pentanoic acid (993 mg, 90%) as a light brown solid: LR-ES-MS m/z calculated for $C_{16}H_{18}ClNO_4$ [M]$^+$ 323, observed [M+H]$^+$ 324.

A solution of (S)-2-[4-(2-chloro-phenoxy)-2-oxo-2,5-dihydro-pyrrol-1-yl]-4-methyl-pentanoic acid (115 mg, 0.35 mmol) in dichloromethane (5 mL) was treated with 1-(3-dimethylaminopropyl)-3-ethylcarbodiimide (61 mg, 0.38 mmol) and 1-hydroxybenzotriazole (53 mg, 0.38 mmol). The reaction mixture was stirred at 25° C. for 0.5 h followed by the addition of 1-(3-amino-pyrazol-1-yl)-2-methyl-propan-2-ol (prepared in U.S. Pat. Appl. US2008021032 Example 80, 78 mg, 0.49 mmol). The reaction mixture was stirred for 18 h at 25° C., under nitrogen. The reaction mixture was diluted with dichloromethane, washed with 2N aqueous hydrochloric acid, saturated sodium bicarbonate solution, a saturated sodium chloride solution and dried over magnesium sulfate. The crude product obtained after concentration, was purified by ISCO flash chromatography (Teledyne Isco RediSep Flash Column 4 g; 0% to 100% ethyl acetate/hexanes) to afford, (S)-2-[4-(2-chloro-phenoxy)-2-oxo-2,5-dihydro-pyrrol-1-yl]-4-methyl-pentanoic acid [1-(2-hydroxy-2-methyl-propyl)-1H-pyrazol-3-yl]-amide (81 mg, 50%) as a white powder: HR-ES-MS m/z calculated for $C_{23}H_{29}ClN_4O_4$ [M+H]$^+$ 461.1950, observed 461.1951; $^1$H NMR (300 MHz, DMSO-d$_6$) δ ppm 0.90 (d, J=6.4 Hz, 3H), 0.94 (d, J=6.4 Hz, 3H), 1.05 (br. s., 3H), 1.06 (br. s., 3H), 1.36-1.64 (m, 2H), 1.68-1.84 (m, 1H), 3.89 (s, 2H), 4.20 (d, J=18.4 Hz, 1H), 4.62 (d, J=18.4 Hz, 1H), 4.68 (s, 1H), 4.78 (s, 1H), 4.90 (dd, J=10.7, 4.7 Hz, 1H), 6.44 (d, J=2.1 Hz, 1H), 7.37 (td, J=7.8, 1.8 Hz, 1H), 7.46 (td, J=7.8, 1.2 Hz, 1H), 7.50-7.56 (m, 2H), 7.66 (dd, J=7.8, 1.2 Hz, 1H), 10.81 (s, 1H).

Example 65

((S)-2-[4-(2-Chloro-phenoxy)-2-oxo-2,5-dihydro-pyrrol-1-yl]-4-methyl-pentanoic acid [1-((R)-2,2-dimethyl-[1,3]dioxolan-4-yl-methyl)-1H-pyrazol-3-yl]-amide

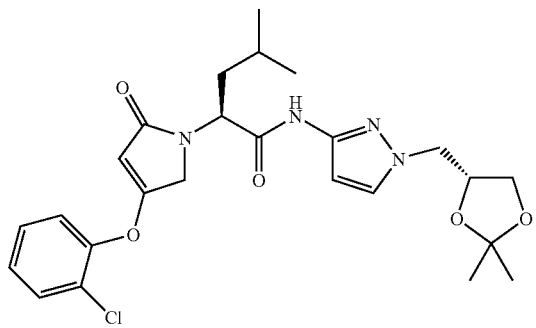

A solution of (S)-2-[4-(2-chloro-phenoxy)-2-oxo-2,5-dihydro-pyrrol-1-yl]-4-methyl-pentanoic acid (prepared as in Example 64, 507 mg, 1.53 mmol) in dichloromethane (20 mL) was treated with 1-(3-dimethylaminopropyl)-3-ethylcarbodiimide (267 mg, 1.68 mmol) and 1-hydroxybenzotriazole (232 mg, 1.68 mmol). The reaction mixture was stirred at 25° C. for 0.5 h followed by the addition of 1-((R)-2,2-dimethyl-[1,3]dioxolan-4-yl-methyl)-1H-pyrazol-3-ylamine (prepared as in Example 49, 374 mg, 1.84 mmol). The reaction mixture was stirred for 18 h at 25° C., under nitrogen. The reaction mixture was diluted with dichloromethane, washed with 2N aqueous hydrochloric acid, saturated sodium bicarbonate solution, a saturated sodium chloride solution and dried over magnesium sulfate. The crude product obtained after concentration, was purified by ISCO flash chromatography (Teledyne Isco RediSep Flash Column 40 g; 0% to 100% ethyl acetate/hexanes) to afford, ((S)-2-[4-(2-chloro-phenoxy)-2-oxo-2,5-dihydro-pyrrol-1-yl]-4-methyl-pentanoic acid [1-((R)-2,2-dimethyl-[1,3]dioxolan-4-yl-methyl)-1H-pyrazol-3-yl]-amide (376 mg, 49%) as a white powder: HR-ES-MS m/z calculated for $C_{25}H_{31}ClN_4O_5$ [M+H]$^+$ 503.2056, observed 503.2056; $^1$H NMR (300 MHz, DMSO-d$_6$) δ ppm 0.90 (d, J=6.4 Hz, 3H), 0.94 (d, J=6.4 Hz, 3H), 1.05 (br. s., 3H), 1.06 (br. s., 3H), 1.36-1.64 (m, 2H), 1.68-1.84 (m, 1H), 3.89 (s, 2H), 4.20 (d, J=18.4 Hz, 1H), 4.62 (d, J=18.4 Hz, 1H), 4.68 (s, 1H), 4.78 (s, 1H), 4.90 (dd, J=10.7, 4.7 Hz, 1H), 6.44 (d, J=2.1 Hz, 1H), 7.37 (td, J=7.8, 1.8 Hz, 1H), 7.46 (td, J=7.8, 1.2 Hz, 1H), 7.50-7.56 (m, 2H), 7.66 (dd, J=7.8, 1.2 Hz, 1H), 10.81 (s, 1H).

Example 66

(S)-2-[4-(2-Chloro-phenoxy)-2-oxo-2,5-dihydro-pyrrol-1-yl]-4-methyl-pentanoic acid [1-((R)-2,3-dihydroxy-propyl)-1H-pyrazol-3-yl]-amide

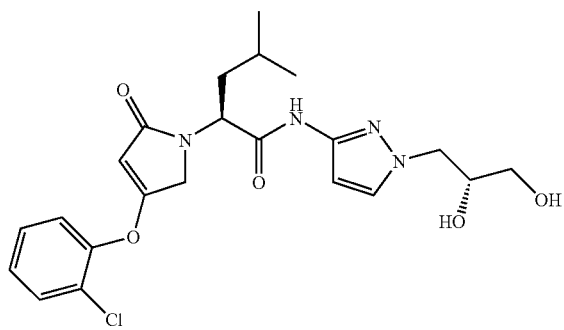

Method A

A solution of ((S)-2-[4-(2-chloro-phenoxy)-2-oxo-2,5-dihydro-pyrrol-1-yl]-4-methyl-pentanoic acid [1-((R)-2,2-dimethyl-[1,3]dioxolan-4-yl-methyl)-1H-pyrazol-3-yl]-amide (as prepared in Example 65, 354 mg, 0.68 mmol) in tetrahydrofuran (6 mL) was treated with 1N aqueous hydrochloric acid (3 mL). The reaction mixture was stirred for 4 h at room temperature. The reaction mixture was diluted with ethyl acetate (60 mL), washed with saturated sodium bicarbonate, a saturated sodium chloride solution and dried over magnesium sulfate. Upon concentration afforded, (S)-2-[4-(2-chloro-phenoxy)-2-oxo-2,5-dihydro-pyrrol-1-yl]-4-methyl-pentanoic acid [1-((R)-2,3-dihydroxy-propyl)-1H-pyrazol-3-yl]-amide (153 mg, 83%) as a white powder: HR-ES-MS m/z calculated for $C_{22}H_{27}ClN_4O_5$ 463.1743 [M+H]$^+$ observed 463.1744; $^1$H NMR (300 MHz, DMSO-d$_6$) δ ppm 0.90 (d, J=6.3 Hz, 3H), 0.94 (d, J=6.3 Hz, 3H), 1.33-1.50 (m, 1H), 1.49-1.67 (m, 1H), 1.68-1.85 (m, 1H), 3.16-3.32 (m, 2H), 3.70-3.93 (m, 2H), 4.09 (m, J=13.6, 3.6 Hz, 1H), 4.21 (d, J=18.4 Hz, 1H), 4.61 (d, J=18.4 Hz, 1H), 4.71 (t, J=5.6 Hz, 1H), 4.79 (s, 1H), 4.88 (dd, J=10.6, 4.8 Hz, 1H), 4.94 (d, J=5.1 Hz, 1H), 6.41 (d, J=1.5 Hz, 1H), 7.37 (t, J=7.5 Hz, 1H), 7.46 (t, J=7.5 Hz, 1H), 7.50-7.56 (m, 2H), 7.65 (d, J=7.5 Hz, 1H), 10.78 (s, 1H).

Method B

To a solution of 2-chlorophenol (3186 g, 24.78 mol) in tetrahydrofuran (14000 mL) at 12° C. was added a 20% potassium t-butoxide solution in tetrahydrofuran (8150 mL, 13.48 mol) over 45 min maintaining an internal temperature between 12-17° C. The solution was warmed to 22° C. and stirred for 1 h before ethyl 2-butynoate (1400 g, 12.48 mol) was added in one portion. The resulting mixture was warmed to 40° C., and stirred for 19.75 h. The reaction mixture was transferred to an extractor and was diluted with methyl t-butyl ether (21 L) and an aqueous 1N aqueous sodium hydroxide solution (14 L). The mixture was stirred and separated and the organic phase washed with an 1N aqueous sodium hydroxide solution (14 L). The aqueous phases were combined and extracted with methyl t-butyl ether (10 L). The organic layer was washed with an 1N aqueous sodium hydroxide solution (7 L). The combined organic phases were washed with a 20% sodium chloride solution (14 L). The solution was evaporated to give (E)-3-(2-chloro-phenoxy)-but-2-enoic acid ethyl ester (96.9% pure by HPLC, 3134 g, 101%) as a light yellow oil.

To a solution of (E)-3-(2-chloro-phenoxy)-but-2-enoic acid ethyl ester (1880 g, 7.82 mol) in dichloromethane (18.6 L) was added N-bromosuccinimide (1490 g, 8.29 mol) and 2,2'-azobis(2,4-dimethylvaleronitrile) (47 g, 0.188 mol) and the resulting solution heated to reflux for 23 h. The light yellow solution was cooled to room temperature and transferred to an extractor before water (19 L) was added. The biphasic mixture was stirred at room temperature for 1 h. The mixture was separated and the organic phase washed with a 20% sodium chloride solution (19 L). The solution was evaporated to give (E)-4-bromo-3-(2-chloro-phenoxy)-but-2-enoic acid ethyl ester (87.8% pure by HPLC, 2824 g, 99%) as a red oil.

To a solution of (L)-leucine methyl ester hydrochloride salt (152.6 g, 0.840 mol) in ethanol (200 proof denatured, 2500 mL) was added sodium bicarbonate (115.3 g, 1.37 mol) at room temperature and the resulting mixture stirred for 15 min. To this mixture was added (E)-4-bromo-3-(2-chloro-phenoxy)-but-2-enoic acid ethyl ester (87.7% pure by HPLC, 200 g, 0.549 mol). The resulting cloudy solution was heated to reflux and approx. 500 mL of solvent was removed via a Dean Stark trap before reflux was continued overnight. To this solution was added glacial acetic acid (200 mL) and the solution was heated to reflux for an additional 2 h. The reaction mixture was cooled to room temperature and methyl t-butyl ether (2.7 L) and water (2 L) were added. The mixture was separated and the organic phase washed with a 20% sodium chloride solution (2 L). The solution was evaporated, the residue treated with toluene (2 L) and evaporated again to give (S)-2-[4-(2-chloro-phenoxy)-2-oxo-2,5-dihydro-pyrrol-1-yl]-4-methyl-pentanoic acid methyl ester (83.3% pure by HPLC, 273 g) as a dark orange oil.

To a stirred mixture of crude (S)-2-[4-(2-chloro-phenoxy)-2-oxo-2,5-dihydro-pyrrol-1-yl]-4-methyl-pentanoic acid methyl ester (273 g, 0.512 mol, 83% pure) in 2-methyltetrahydrofuran (1030 mL) was added 2N sodium hydroxide (308 mL, 616 mmol) and the resulting mixture stirred at 21-26° C. for 20 min. To this mixture was added 2N sodium hydroxide (265 mL, 530 mmol) and the resulting mixture stirred vigorously for 2.5 h. The mixture was diluted with water (500 mL) and methyl t-butyl ether (300 mL) and stirred for 10 min. The aqueous layer was acidified with 2N hydrochloric acid (60.0 mL, 120 mmol) (pH=3) and extracted with ethyl acetate (300 mL). The organic layer was separated and washed with a sodium hydroxide solution (1N, 200 mL). The combined aqueous layers were washed with methyl t-butyl ether (500 mL). The aqueous layer was cooled to 15° C. before a hydrochloric acid solution (6N, 210 mL) was added over 20 min maintaining a temperature of 15-19° C. until a pH of 2.6 was obtained. To this solution was added dichloromethane (1000 mL) and the mixture was separated. The aqueous phase was extracted with dichloromethane (300 mL). The dichloromethane layers were combined and washed with an aqueous 20% sodium chloride solution (200 mL). The solution was evaporated and residue suspended in formic acid (1272 mL). The mixture was slowly stirred until a solution was achieved before water (1330 mL) and seed crystals (1 g) were added. The resulting mixture was stirred for 2.5 h at room temperature. The mixture was cooled to 5° C., filtered and the cake washed with water and dried under vacuum to give (S)-2-[4-(2-chloro-phenoxy)-2-oxo-2,5-dihydro-pyrrol-1-yl]-4-methyl-pentanoic acid (111 g, 56.9%) as a beige solid.

To a stirred mixture of 3-aminopyrazole (5.00 g, 60.2 mmol) dissolved in N,N-dimethylformamide (75 mL) was added phthalic anhydride (8.91 g, 60.2 mmol). After addition was complete, the mixture was stirred at 125° C. for 24 h.

Upon cooling to 25° C., water (100 mL) was added, which resulted in precipitation. The white suspension was cooled (−5° C.) and stirred for 30 min. Subsequent filtration, washing with water, and suction drying afforded 2-(1H-pyrazol-3-yl)-isoindole-1,3-dione (9.36 g, 73.0%) as a white solid: LR-ES-MS m/z calculated for $C_{11}H_7N_3O_2$ [M]$^+$ 213, observed [M+H]$^+$ 214.

To a solution of ((R)-2,2-dimethyl-[1,3]dioxolan-4-yl)-methanol (60.00 g, 454.0 mmol) and 1,4-diazabicyclo[2.2.2]octane (63.67 g, 567.6 mmol) in ethyl acetate 600 mL) at 15° C. was added 4-chlorobenzenesulfonyl chloride (100.6 g, 476.7 mmol) and the resulting cloudy solution stirred for 2 h before being warmed to room temperature. The resulting solution was stirred at room temperature for 4 h before cold water (300 mL) was added and the resulting mixture stirred at room temperature overnight. The mixture was diluted with heptane (600 mL) and the organic layer was separated and washed with water (3×600 mL). The mixture was concentrated under vacuum to provide a yellow oil which was treated with heptane (200 mL). The mixture was concentrated to remove any remaining ethyl acetate and heptane (500 mL) was added once more to induce crystallization. The thick white suspension was filtered, washed with heptane, and suction dried to provide 4-chloro-benzenesulfonic acid (S)-2,2-dimethyl-[1,3]dioxolan-4-ylmethyl ester (129.93 g, 93.3%, 98.9% pure HPLC, 99.89% e.e) as a white solid.

A mixture of 2-(1H-pyrazol-3-yl)-isoindole-1,3-dione (5.00 g, 23.5 mmol), 4-chloro-benzenesulfonic acid (S)-2,2-dimethyl-[1,3]dioxolan-4-yl-methyl ester (8.00 g, 26.1 mmol), and sodium t-butoxide (2.78 g, 28.9 mmol) in 1,4-dioxane (50 mL) was refluxed (103° C.) for 24 h. Upon cooling to 25° C., water (55 mL) was added. The mixture became cloudy and crystallization was observed. Then, water (50 mL) was slowly added over 30 min. Subsequent filtration, washing with water, and suction drying provided 2-[1-((R)-2,2-dimethyl-[1,3]dioxolan-4-yl-methyl)-1H-pyrazol-3-yl]-isoindole-1,3-dione (5.69 g, 74.1%) as an off-white solid: LR-ES-MS m/z calculated for $C_{17}H_{17}N_3O_4$ [M]$^+$ 327, observed [M+H]$^+$ 328.

A suspension of 2-[1-((R)-2,2-dimethyl-[1,3]dioxolan-4-yl-methyl)-1H-pyrazol-3-yl]-isoindole-1,3-dione (5.00 g, 15.3 mmol) in methyl t-butyl ether (50 mL) and ethanol (30 mL) was cooled with an ice water bath, and 33 wt. % methylamine in ethanol (20.0 mL, 161 mmol) was added. After 30 min, the mixture was warmed to room temperature and stirred for 2 h. Heptane (50 mL) was added and the mixture was cooled (−20° C.) for 30 min. The resulting solids were removed by filtration and rinsed with heptane. The filtrate was partially concentrated to a volume of ~50 mL. The resulting solids were removed by filtration and rinsed with methyl t-butyl ether and heptane. After concentration of the filtrate to dryness, a yellow oil remained, which was then dissolved in methyl t-butyl ether (15 mL) and cooled (−20° C.) for 30 min. Addition of seed crystals and scratching with a spatula initiated crystallization of the product. Heptane (30 mL) was added and the suspension was cooled (−20° C.) for 30 min. Subsequent filtration, washing with heptane, and suction drying afforded 1-((R)-2,2-dimethyl-[1,3]dioxolan-4-yl-methyl)-1H-pyrazol-3-ylamine (2.85 g, 94.6%) as a white solid: LR-ES-MS m/z calculated for $C_9H_{15}N_3O_2$ [M]$^+$ 197, observed [M+H]$^+$ 198.

A stirred mixture of (S)-2-[4-(2-chloro-phenoxy)-2-oxo-2,5-dihydro-pyrrol-1-yl]-4-methyl-pentanoic acid (1.00 g, 3.09 mmol), 1-((R)-2,2-dimethyl-[1,3]dioxolan-4-yl-methyl)-1H-pyrazol-3-ylamine (768 mg, 3.89 mmol), and N,N-diisopropylethylamine (2.10 mL, 11.9 mmol) in ethyl acetate (8 mL) was cooled with an ice water bath, and 50 wt. % 1-propanephosphonic acid cyclic anhydride in ethyl acetate (6.95 mL, 11.7 mmol) was added. After 1 h, water (20 mL) was added and the mixture was warmed to 25° C. The organic layer was separated and washed with 1N sodium hydroxide (15 mL×2), brine (15 mL), and then water (15 mL). Concentration of the organic layer provided 1.60 g of a pale yellow foam, which was dissolved in methyl t-butyl ether (5 mL) upon heating to 50° C. Heptane (5 mL) was slowly added to the warm solution resulting in a white precipitate. The mixture was cooled to 25° C. and heptane (5 mL) was added. After cooling with an ice water bath for 30 min, the resulting solid was collected by filtration, washed with heptane:methyl t-butyl ether (2:1), and suction dried to afford (S)-2-[4-(2-chloro-phenoxy)-2-oxo-2,5-dihydro-pyrrol-1-yl]-4-methyl-pentanoic acid [1-((R)-2,2-dimethyl-[1,3]dioxolan-4-yl-methyl)-1H-pyrazol-3-yl]-amide (1.42 g, 91.4%) as an off-white solid: LR-ES-MS m/z calculated for $C_{25}H_{31}ClN_4O_5$ [M]$^+$ 502, observed [M+H]$^+$ 503.

To a solution of (S)-2-[4-(2-chloro-phenoxy)-2-oxo-2,5-dihydro-pyrrol-1-yl]-4-methyl-pentanoic acid [1-((R)-2,2-dimethyl-[1,3]dioxolan-4-yl-methyl)-1H-pyrazol-3-yl]-amide (1.00 g, 1.99 mmol) in 2-propanol (4 mL) was added 2N hydrochloric acid (4.00 mL, 8.00 mmol). The mixture was stirred for 2 h at 25° C. Water (4 mL) was added and the mixture was thoroughly extracted with methyl t-butyl ether (30 mL). The organic layer was separated and washed with 1N sodium hydroxide (20 mL) and then brine (20 mL). Concentration of the organic layer provided a white foam. The foam was chopped up with a spatula to afford (S)-2-[4-(2-chloro-phenoxy)-2-oxo-2,5-dihydro-pyrrol-1-yl]-4-methyl-pentanoic acid [1-((R)-2,3-dihydroxy-propyl)-1H-pyrazol-3-yl]-amide (890 mg, 96.7%) as an off-white solid: LR-ES-MS m/z calculated for $C_{22}H_{27}ClN_4O_5$ [M]$^+$ 462, [M+H]$^+$ observed 463.

Example 67

(S)-2-[4-(2-Chloro-6-fluoro-phenoxy)-2-oxo-2,5-dihydro-pyrrol-1-yl]-3-cyclohexyl-N-[1-(2-hydroxy-2-methyl-propyl)-1H-pyrazol-3-yl]-propionamide

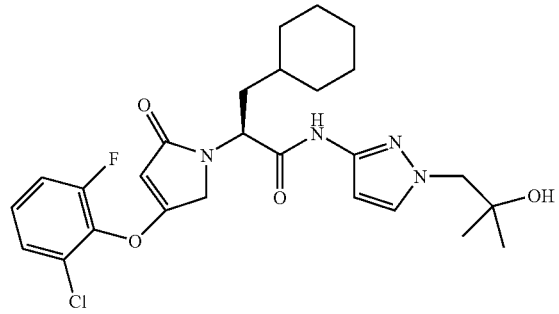

To a stirred mixture of 2-chloro-6-fluoro-phenol (2.92 g, 20.0 mmol) and ethyl-2-butynoate (4.37 g, 38.90 mmol) in tetrahydrofuran (30 mL) was added 1,8-diazabicyclo[5.4.0]undec-7-ene (3.04 g, 20.0 mmol) slowly. After addition was complete the mixture was stirred at reflux for 4 h. Upon completion of the reaction the tetrahydrofuran was removed in vacuo and the residue was diluted in diethyl ether and washed first with 1N aqueous hydrochloric acid, then 10% aqueous sodium hydroxide solution, a saturated sodium chloride solution and dried over magnesium sulfate. The crude product obtained was purified by ISCO flash chromatography (Teledyne Isco RediSep Flash Column 120 g, 0% to 20% ethyl acetate/hexanes) to afford, (E)-3-(2-chloro-6-fluoro-phenoxy)-but-2-enoic acid ethyl ester (3.70 g, 71%) as a colorless oil: $^1$H-NMR (300 MHz, CDCl$_3$) δ ppm 1.14-1.30 (m, 3H), 2.55 (s, 3H), 3.94-4.25 (m, 2H), 4.81 (br. s., 1H), 7.02-7.21 (m, 3H).

To a stirred mixture of (E)-3-(2-chloro-6-fluoro-phenoxy)-but-2-enoic acid ethyl ester (3.70 g, 14.34 mmol) dissolved in carbon tetrachloride (70 mL) under a nitrogen atmosphere was added N-bromosuccinimide (3.66 g, 17.20 mmol) and benzoyl peroxide (500 mg, 2.0 mmol). After addition was complete the mixture was stirred at reflux for 8 h. The reaction mixture was then placed in the refrigerator overnight, the succinimide was removed by filtration and the solvent was removed in vacuo. The crude product obtained was purified by ISCO flash chromatography (Teledyne Isco RediSep Flash Column 120 g, 0% to 20% ethyl acetate/hexanes) to afford, (E)-4-bromo-3-(2-chloro-6-fluoro-phenoxy)-but-2-enoic acid ethyl ester (2.95 g, 61%) as a yellow oil: $^1$H-NMR (300 MHz, CDCl$_3$) δ ppm 1.26 (t, J=7.0 Hz, 3H), 4.16 (q, J=7.0 Hz, 2H), 4.76 (s, 2H), 4.89 (s, 1H), 7.09-7.31 (m, 3H).

To a stirred mixture of (S)-2-amino-3-cyclohexyl-propionic acid methyl ester hydrochloride (2.14 g, 9.60 mmol) dissolved in acetonitrile (40 mL) under a nitrogen atmosphere was added triethylamine (1.0 g, 9.80 mmol). After addition was complete the mixture was stirred at 60° C. for 1 h. The reaction was cooled to 25° C. and treated with triethylamine (1.0 g, 9.80 mmol) and acetonitrile (20 mL) and heated to 80° C. at which time (E)-4-bromo-3-(2-chloro-6-fluoro-phenoxy)-but-2-enoic acid ethyl ester (2.95 g, 8.80 mmol) in acetonitrile (20 mL) was added slowly. After the addition was complete the reaction mixture was heated to 100° C. and stirred overnight. The reaction mixture was cooled to 25° C., filtered and concentrated. The residue was diluted with ethyl acetate and washed with saturated ammonium chloride, water, a saturated sodium chloride solution and dried over sodium sulfate. The crude product obtained was purified by ISCO flash chromatography (Teledyne Isco RediSep Flash Column 80 g, 0% to 50% ethyl acetate/hexanes) to afford, (S)-2-[4-(2-chloro-6-fluoro-phenoxy)-2-oxo-2,5-dihydro-pyrrol-1-yl]-3-cyclohexyl-propionic acid methyl ester (800 mg, 24%) as a yellow oil: LR-ES-MS m/z calculated for C$_{20}$H$_{23}$ClFNO$_4$ [M]$^+$ 395, observed [M+H]$^+$ 396.

To a stirred mixture of (S)-2-[4-(2-chloro-6-fluoro-phenoxy)-2-oxo-2,5-dihydro-pyrrol-1-yl]-3-cyclohexyl-propionic acid methyl ester (800 mg, 2.00 mmol) in tetrahydrofuran (10 mL) was added 0.5N lithium hydroxide solution (8.0 mL, 4.0 mmol). After addition was complete the mixture was stirred at 25° C. for 2 h. The reaction mixture was poured into water and diethyl ether and the layers were separated. The aqueous layer was made acidic with 1N aqueous hydrochloric acid and extracted with ethyl acetate (3×30 mL). The combined ethyl acetate fractions were washed with a saturated sodium chloride solution, dried over magnesium sulfate, filtered and concentrated to afford (S)-2-[4-(2-chloro-6-fluoro-phenoxy)-2-oxo-2,5-dihydro-pyrrol-1-yl]-3-cyclohexyl-propionic acid (740 mg, 97%) as a light brown solid: LR-ES-MS m/z calculated for C$_{19}$H$_{21}$ClFNO$_4$ [M]$^+$ 381, observed [M+H]$^+$ 382.

A solution of (S)-2-[4-(2-chloro-6-fluoro-phenoxy)-2-oxo-2,5-dihydro-pyrrol-1-yl]-3-cyclohexyl-propionic acid (154 mg, 0.40 mmol) in N,N-dimethylformamide (4 mL) was treated with 1-(3-amino-pyrazol-1-yl)-2-methyl-propan-2-ol (prepared in U.S. Pat. Appl. US2008021032 Example 80, 75 mg, 0.48 mmol), benzotriazol-1-yl-oxy-tris(dimethylamino) phosphonium hexafluorophosphate (424 mg, 0.96 mmol) and N,N-diisopropylethylamine (129 mg, 1.0 mmol). The reaction mixture was stirred for 4 h at 25° C., under nitrogen. The reaction mixture was diluted with ethyl acetate, washed with saturated ammonium chloride, water, a saturated sodium chloride solution and dried over sodium sulfate. The organic layer was concentrated, and the crude product was purified by ISCO flash chromatography (Teledyne Isco RediSep Flash Column 12 g, 0% to 100% ethyl acetate/hexanes) to afford (S)-2-[4-(2-chloro-6-fluoro-phenoxy)-2-oxo-2,5-dihydro-pyrrol-1-yl]-3-cyclohexyl-N-[1-(2-hydroxy-2-methyl-propyl)-1H-pyrazol-3-yl]-propionamide (85 mg, 41%) as a white solid: $^1$H NMR (300 MHz, DMSO-d$_6$) δ ppm 0.75-1.32 (m, 6H) 1.04 (s, 3H) 1.06 (s, 3H) 1.51-1.84 (m, 7H) 3.89 (s, 2H) 4.24 (d, J=18.7 Hz, 1H) 4.64 (d, J=18.7 Hz, 1H) 4.68 (s, 1H) 4.91 (dd, J=10.7, 5.0 Hz, 1H) 4.96 (s, 1H) 6.44 (d, J=2.1 Hz, 1H) 7.36-7.53 (m, 3H) 7.54 (d, J=2.1 Hz, 1H) 10.81 (s, 1H). HR-ES-MS m/z calculated for C$_{26}$H$_{32}$ClFN$_4$O$_4$ [M+H]$^+$ 519.2169, observed 519.2169.

Example 68

(S)-2-[4-(2-Chloro-6-fluoro-phenoxy)-2-oxo-2,5-dihydro-pyrrol-1-yl]-3-cyclohexyl-N-(1-methyl-1H-pyrazol-3-yl)-propionamide

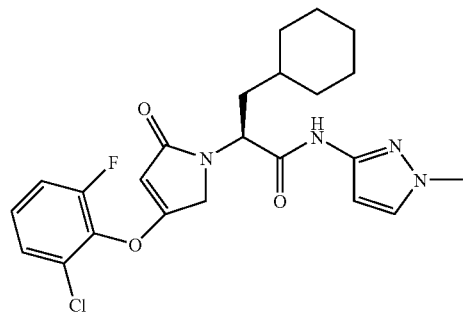

A solution of (S)-2-[4-(2-chloro-6-fluoro-phenoxy)-2-oxo-2,5-dihydro-pyrrol-1-yl]-3-cyclohexyl-propionic acid (prepared as in Example 67, 125 mg, 0.33 mmol) in N,N-dimethylformamide (3 mL) was treated with 1-methyl-1H-pyrazol-3-ylamine (40 mg, 0.40 mmol), benzotriazol-1-yl-oxy-tris(dimethylamino)phosphonium hexafluorophosphate (300 mg, 0.67 mmol) and N,N-diisopropylethylamine (85 mg, 0.65 mmol). The reaction mixture was stirred for 4 h at 25° C., under nitrogen. The reaction mixture was diluted with ethyl acetate, washed with saturated ammonium chloride, water, a saturated sodium chloride solution and dried over sodium sulfate. The organic layer was concentrated, and the crude product was purified by ISCO flash chromatography (Teledyne Isco RediSep Flash Column 12 g, 0% to 100% ethyl acetate/hexanes) to afford (S)-2-[4-(2-chloro-6-fluoro-phenoxy)-2-oxo-2,5-dihydro-pyrrol-1-yl]-3-cyclohexyl-N-(1-methyl-1H-pyrazol-3-yl)-propionamide (68 mg, 45%): $^1$H NMR (300 MHz, DMSO-d$_6$) δ ppm 0.60-1.36 (m, 6H) 1.42-1.91 (m, 7H) 3.73 (s, 3H) 4.25 (d, J=18.7 Hz, 1H) 4.62 (d, J=18.7 Hz, 1H) 4.90 (dd, J=10.3, 5.4 Hz, 1H) 4.96 (s, 1H) 6.40 (d, J=2.1 Hz, 1H) 7.38-7.54 (m, 3H) 7.55 (d, J=2.1 Hz, 1H) 10.74 (s, 1H). HR-ES-MS m/z calculated for C$_{23}$H$_{26}$ClFN$_4$O$_3$ [M+Na]$^+$ 483.1569, observed 483.1568.

Example 69

6-{(S)-2-[4-(2-Chloro-6-fluoro-phenoxy)-2-oxo-2,5-dihydro-pyrrol-1-yl]-3-cyclohexyl-propionylamino}-nicotinic acid methyl ester

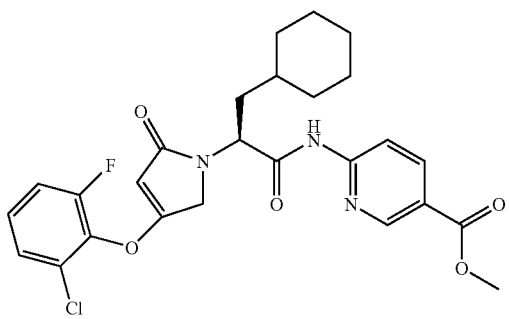

A solution of (S)-2-[4-(2-chloro-6-fluoro-phenoxy)-2-oxo-2,5-dihydro-pyrrol-1-yl]-3-cyclohexyl-propionic acid (prepared as in Example 67, 206 mg, 0.54 mmol) in dichloromethane (5 mL) was treated with 6-amino-nicotinic acid methyl ester (110 mg, 0.72 mmol), bromotripyrrolidinophosphonium hexafluorophosphate (503 mg, 1.1 mmol) and N,N-diisopropylethylamine (150 mg, 1.1 mmol). The reaction mixture was stirred for 4 h at 25° C., under nitrogen. The reaction mixture was diluted with ethyl acetate, washed with saturated ammonium chloride, water, a saturated sodium chloride solution and dried over sodium sulfate. The organic layer was concentrated, and the crude product was purified by ISCO flash chromatography (Teledyne Isco RediSep Flash Column 12 g, 0% to 100% ethyl acetate/hexanes) to afford 6-{(S)-2-[4-(2-chloro-6-fluoro-phenoxy)-2-oxo-2,5-dihydro-pyrrol-1-yl]-3-cyclohexyl-propionylamino}-nicotinic acid methyl ester (90 mg, 33%): $^1$H NMR (300 MHz, DMSO-d$_6$) δ ppm 0.77-1.36 (m, 6H) 1.40-1.92 (m, 7H) 3.86 (s, 3H) 4.29 (d, J=18.7 Hz, 1H) 4.64 (d, J=18.7 Hz, 1H) 5.00 (s, 1H) 5.01-5.10 (m, 1H) 7.30-7.61 (m, 3H) 8.16 (d, J=8.8 Hz, 1H) 8.29 (dd, J=8.8, 2.1 Hz, 1H) 8.87 (d, J=2.1 Hz, 1H) 11.32 (s, 1H). HR-ES-MS m/z calculated for C$_{26}$H$_{27}$ClFN$_3$O$_5$ [M+H]$^+$ 516.1696, observed 516.1696.

Example 70

6-{(S)-2-[4-(2-Chloro-6-fluoro-phenoxy)-2-oxo-2,5-dihydro-pyrrol-1-yl]-3-cyclohexyl-propionylamino}-nicotinic acid

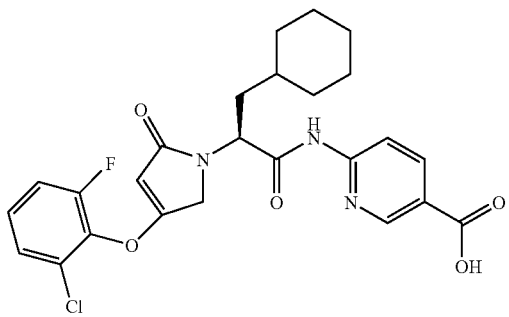

To a magnetically stirred mixture of 6-{(S)-2-[4-(2-chloro-6-fluoro-phenoxy)-2-oxo-2,5-dihydro-pyrrol-1-yl]-3-cyclohexyl-propionylamino}-nicotinic acid methyl ester (prepared as in Example 69, 80 mg, 0.16 mmol) in tetrahydrofuran (3.0 mL) was added 0.5N lithium hydroxide solution (1.0 mL, 0.5 mmol). After addition was complete the mixture was stirred at 25° C. for 4 h. The reaction mixture was diluted with ethyl acetate, washed with 1N aqueous hydrochloric acid, water, a saturated sodium chloride solution and dried over sodium sulfate. The crude product was recrystallized from ethyl acetate to afford 6-{(S)-2-[4-(2-chloro-6-fluoro-phenoxy)-2-oxo-2,5-dihydro-pyrrol-1-yl]-3-cyclohexyl-propionylamino}-nicotinic acid (10 mg, 13%) as a white solid: $^1$H NMR (300 MHz, DMSO-d$_6$) δ ppm 0.73-1.42 (m, 6H) 1.41-1.90 (m, 7H) 4.28 (d, J=18.7 Hz, 1H) 4.64 (d, J=18.7 Hz, 1H) 4.99 (s, 1H) 5.01-5.10 (m, 1H) 7.31-7.57 (m, 3H) 8.14 (d, J=8.5 Hz, 1H) 8.25 (dd, J=8.5, 2.1 Hz, 1H) 8.84 (d, J=2.1 Hz, 1H) 11.26 (s, 1H) 13.18 (br. s., 1H). HR-ES-MS m/z calculated for C$_{25}$H$_{25}$ClFN$_3$O$_5$ [M+H]$^+$ 502.1540, observed 502.1537.

Example 71

(S)-2-[4-(2-Chloro-6-fluoro-phenoxy)-2-oxo-2,5-dihydro-pyrrol-1-yl]-3-cyclohexyl-N-pyrazin-2-yl-propionamide Hydrochloride

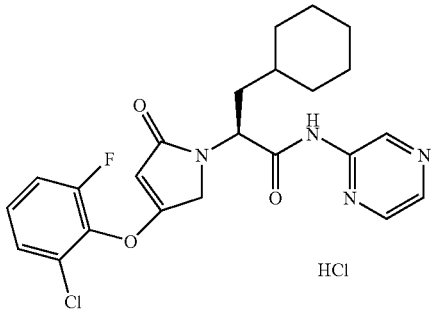

A solution of (S)-2-[4-(2-chloro-6-fluoro-phenoxy)-2-oxo-2,5-dihydro-pyrrol-1-yl]-3-cyclohexyl-propionic acid (prepared as in Example 67, 200 mg, 0.52 mmol) in dichloromethane (5 mL) was treated with pyrazin-2-ylamine (65 mg, 0.68 mmol), bromotripyrrolidinophosphonium hexafluorophosphate (503 mg, 1.1 mmol) and N,N-diisopropylethylamine (110 mg, 0.85 mmol). The reaction mixture was stirred for 4 h at 25° C., under nitrogen. The reaction mixture was diluted with ethyl acetate, washed with saturated ammonium chloride, water, a saturated sodium chloride solution and dried over sodium sulfate. The organic layer was concentrated, and the crude product was purified by ISCO flash chromatography (Teledyne Isco RediSep Flash Column 12 g, 0% to 100% ethyl acetate/hexanes) to give a waxy material. This material was dissolved in dichloromethane (2 mL). The clear solution was treated with hydrogen chloride in diethyl ether (1M, 4 mL) and solvents were evaporated. The residue was triturated with diethyl ether and filtered to afford (S)-2-[4-(2-chloro-6-fluoro-phenoxy)-2-oxo-2,5-dihydro-pyrrol-1-yl]-3-cyclohexyl-N-pyrazin-2-yl-propionamide hydrochloride (28 mg, 33%) as an orange solid: $^1$H NMR (300 MHz, DMSO-d$_6$) δ ppm 0.77-1.37 (m, 6H) 1.43-1.95 (m, 7H) 4.29 (d, J=18.7 Hz, 1H) 4.64 (d, J=18.7 Hz, 1H) 5.00 (s, 1H) 5.02-5.12 (m, 1H) 7.36-7.57 (m, 3H) 8.38 (d, J=2.4 Hz, 1H)

8.40-8.47 (m, 1H) 9.27 (d, J=1.2 Hz, 1H) 11.20 (s, 1H). HR-ES-MS m/z calculated for $C_{23}H_{24}ClFN_4O_3$ 459.1594, observed 459.1593 [M+H]$^+$.

Example 72

(S)-2-[4-(3-Chloro-2,6-difluoro-phenoxy)-2-oxo-2,5-dihydro-pyrrol-1-yl]-3-cyclohexyl-N-[1-(2-hydroxy-2-methyl-propyl)-1H-pyrazol-3-yl]-propionamide

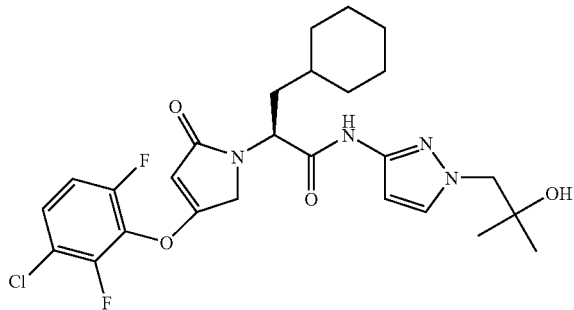

To a stirred mixture of 3-chloro-2,6-difluoro-phenol (4.60 g, 28.0 mmol) and ethyl-2-butynoate (6.30 g, 56.0 mmol) in tetrahydrofuran (30 mL) was added 1,8-diazabicyclo[5.4.0]undec-7-ene slowly (4.30 g, 28.0 mmol). After addition was complete the mixture was stirred at reflux for 4 h. Upon completion of the reaction the tetrahydrofuran was removed in vacuo and the residue was diluted in diethyl ether and washed with 1N aqueous hydrochloric acid, 10% aqueous sodium hydroxide solution, a saturated sodium chloride solution and dried over magnesium sulfate. The crude product obtained was purified by ISCO flash chromatography (Teledyne Isco RediSep Flash Column 120 g, 0% to 20% ethyl acetate/hexanes) to afford, (E)-3-(3-chloro-2,6-difluoro-phenoxy)-but-2-enoic acid ethyl ester (6.44 g, 84%) as a colorless oil: $^1$H NMR (300 MHz, CDCl$_3$) δ ppm 1.25 (t, J=7.0 Hz, 3H), 2.54 (s, 3H), 4.13 (q, J=7.0 Hz, 2H), 4.90 (s, 1H), 6.98 (td, J=9.2, 2.1 Hz, 1H), 7.15-7.33 (m, 1H).

To a stirred mixture of (E)-3-(3-chloro-2,6-difluoro-phenoxy)-but-2-enoic acid ethyl ester (6.00 g, 21.7 mmol) dissolved in carbon tetrachloride (70 mL) under a nitrogen atmosphere was added N-bromosuccinimide (7.70 g, 43.5 mmol) and benzoyl peroxide (1.05 g, 3.0 mmol). After addition was complete the mixture was stirred at reflux for 8 h. The reaction mixture was then placed in the refrigerator overnight, the succinimide was removed by filtration and the solvent was removed in vacuo. The crude product obtained was purified by ISCO flash chromatography (Teledyne Isco RediSep Flash Column 120 g, 0% to 20% ethyl acetate/hexanes) to afford, (E)-4-bromo-3-(3-chloro-2,6-difluoro-phenoxy)-but-2-enoic acid ethyl ester (4.40 g, 58%) as a yellow oil: $^1$H-NMR (300 MHz, CDCl$_3$) δ ppm 1.26 (t, J=7.2 Hz, 3H), 4.18 (q, J=7.2 Hz, 2H), 4.74 (s, 2H), 5.00 (s, 1H), 7.01 (td, J=9.2, 2.1 Hz, 1H), 7.27-7.37 (m, 1H).

To a stirred mixture of (S)-2-amino-3-cyclohexyl-propionic acid methyl ester hydrochloride (2.60 g, 11.60 mmol) dissolved in acetonitrile (40 mL) under a nitrogen atmosphere was added triethylamine (1.3 g, 12.70 mmol). After addition was complete the mixture was stirred at 60° C. for 1 h. The reaction was cooled to 25° C. and treated with triethylamine (1.3 g, 12.7 mmol) and acetonitrile (20 mL) and heated to 80° C. at which time, (E)-4-bromo-3-(3-chloro-2,6-difluoro-phenoxy)-but-2-enoic acid ethyl ester (4.10 g, 11.60 mmol) in acetonitrile (20 mL) was added slowly. After the addition was complete the reaction mixture was heated to 100° C. and stirred overnight. The reaction mixture was cooled to 25° C., filtered and concentrated. The residue was diluted with ethyl acetate and washed with saturated ammonium chloride, water, a saturated sodium chloride solution and dried over sodium sulfate. The crude product obtained was purified by ISCO flash chromatography (Teledyne Isco RediSep Flash Column 80 g, 0% to 50% ethyl acetate/hexanes) to afford, (S)-2-[4-(3-chloro-2,6-difluoro-phenoxy)-2-oxo-2,5-dihydro-pyrrol-1-yl]-3-cyclohexyl-propionic acid methyl ester as a yellow oil (1.33 g, 28%): $^1$H NMR (300 MHz, DMSO-d$_6$) δ ppm 0.71-1.33 (m, 7H), 1.47-1.91 (m, 6H), 3.65 (s, 3H), 4.28 (br. s., 2H), 4.74 (dd, J=10.7, 4.4 Hz, 1H), 5.28 (br. s., 1H), 7.39-7.54 (m, 1H), 7.57-7.82 (m, 1H).

To a magnetically stirred mixture of (S)-2-[4-(3-chloro-2,6-difluoro-phenoxy)-2-oxo-2,5-dihydro-pyrrol-1-yl]-3-cyclohexyl-propionic acid methyl ester (1.33 g, 3.22 mmol) in tetrahydrofuran (30 mL) was added 0.5N lithium hydroxide solution (15.0 mL, 7.5 mmol). After addition was complete the mixture was stirred at 25° C. for 2 h. The reaction mixture was poured into water and diethyl ether and the layers were separated. The aqueous layer was made acidic with 1N aqueous hydrochloric acid and extracted with ethyl acetate (3×30 mL). The combined ethyl acetate fractions were washed with a saturated sodium chloride solution, dried over magnesium sulfate, filtered and concentrated to afford, (S)-2-[4-(3-chloro-2,6-difluoro-phenoxy)-2-oxo-2,5-dihydro-pyrrol-1-yl]-3-cyclohexyl-propionic acid (1.30 g, 99%) as a yellow oil: $^1$H NMR (300 MHz, DMSO-d$_6$) δ ppm 0.75-1.28 (m, 7H), 1.53-1.82 (m, 6H), 4.11-4.46 (m, 2H), 4.64 (dd, J=10.6, 4.5 Hz, 1H), 5.25 (s, 1H), 7.38-7.52 (m, 1H), 7.61-7.73 (m, 1H), 12.55 (br. s., 1H).

A solution of (S)-2-[4-(3-chloro-2,6-difluoro-phenoxy)-2-oxo-2,5-dihydro-pyrrol-1-yl]-3-cyclohexyl-propionic acid (143 mg, 0.36 mmol) in N,N-dimethylformamide (3 mL) was treated with 1-(3-amino-pyrazol-1-yl)-2-methyl-propan-2-ol (prepared in U.S. Pat. Appl. US2008021032 Example 80, 70 mg, 0.45 mmol), benzotriazol-1-yl-oxy-tris(dimethylamino) phosphonium hexafluorophosphate (350 mg, 0.79 mmol) and N,N-diisopropylethylamine (103 mg, 0.80 mmol). The reaction mixture was stirred for 4 h at 25° C., under nitrogen. The reaction mixture was diluted with ethyl acetate, washed with saturated ammonium chloride, water, a saturated sodium chloride solution and dried over sodium sulfate. The organic layer was concentrated, and the crude product was purified by ISCO flash chromatography (Teledyne Isco RediSep Flash Column 12 g, 0% to 100% ethyl acetate/hexanes) to afford (S)-2-[4-(3-chloro-2,6-difluoro-phenoxy)-2-oxo-2,5-dihydro-pyrrol-1-yl]-3-cyclohexyl-N-[1-(2-hydroxy-2-methyl-propyl)-1H-pyrazol-3-yl]-propionamide (65 mg, 34%) as a light yellow solid: HR-ES-MS m/z calculated for $C_{26}H_{31}ClF_2N_4O_4$ [M+H]$^+$ 537.2075, observed 537.2071; $^1$H NMR (300 MHz, DMSO-d$_6$) δ ppm 0.79-1.31 (m, 6H) 1.05 (s, 3H) 1.06 (s, 3H) 1.52-1.85 (m, 7H) 3.89 (s, 2H) 4.29 (d, J=18.7 Hz, 1H) 4.64 (d, J=18.7 Hz, 1H) 4.68 (s, 1H) 4.90 (dd, J=10.7, 5.0 Hz, 1H) 5.24 (s, 1H) 6.44 (d, J=2.2 Hz, 1H) 7.45 (td, J=9.6, 2.0 Hz, 1H) 7.54 (d, J=2.2 Hz, 1H) 7.67 (td, J=8.7, 5.3 Hz, 1H) 10.81 (s, 1H).

Example 73

6-{(S)-2-[4-(3-Chloro-2,6-difluoro-phenoxy)-2-oxo-2,5-dihydro-pyrrol-1-yl]-3-cyclohexyl-propionylamino}-nicotinic acid methyl ester

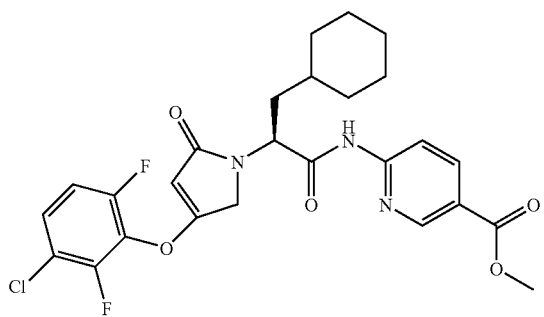

A solution of (S)-2-[4-(3-chloro-2,6-difluoro-phenoxy)-2-oxo-2,5-dihydro-pyrrol-1-yl]-3-cyclohexyl-propionic acid (prepared as in Example 72, 510 mg, 1.28 mmol) in dichloromethane (20 mL) was treated with 6-amino-nicotinic acid methyl ester (252 mg, 1.67 mmol), bromotripyrrolidinophosphonium hexafluorophosphate (1.20 g, 2.57 mmol) and N,N-diisopropylethylamine (438 mg, 2.52 mmol). The reaction mixture was stirred for 5 h at 25° C., under nitrogen. The reaction mixture was diluted with ethyl acetate, washed with saturated ammonium chloride, water, a saturated sodium chloride solution and dried over sodium sulfate. The organic layer was concentrated, and the crude product was purified by ISCO flash chromatography (Teledyne Isco RediSep Flash Column 12 g, 0% to 50% ethyl acetate/hexanes) to afford 6-{(S)-2-[4-(3-chloro-2,6-difluoro-phenoxy)-2-oxo-2,5-dihydro-pyrrol-1-yl]-3-cyclohexyl-propionylamino}-nicotinic acid methyl ester (160 mg, 24%) as a tan solid: HR-ES-MS m/z calculated for $C_{26}H_{26}ClF_2N_3O_5$ [M+H]$^+$ 534.1602, observed 534.1606; $^1$H NMR (300 MHz, DMSO-d$_6$) δ ppm 0.73-1.36 (m, 6H) 1.37-1.93 (m, 7H) 3.86 (s, 3H) 4.33 (d, J=18.5 Hz, 1H) 4.64 (d, J=18.5 Hz, 1H) 5.04 (dd, J=11.3, 5.0 Hz, 1H) 5.27 (s, 1H) 7.45 (td, J=9.5, 2.1 Hz, 1H) 7.68 (ddd, J=9.5, 8.1, 5.6 Hz, 1H) 8.13-8.19 (m, 1H) 8.29 (dd, J=8.8, 2.4 Hz, 1H) 8.87 (dd, J=2.4, 0.8 Hz, 1H) 11.32 (s, 1H).

Example 74

6-{(S)-2-[4-(3-Chloro-2,6-difluoro-phenoxy)-2-oxo-2,5-dihydro-pyrrol-1-yl]-3-cyclohexyl-propionylamino}-nicotinic acid

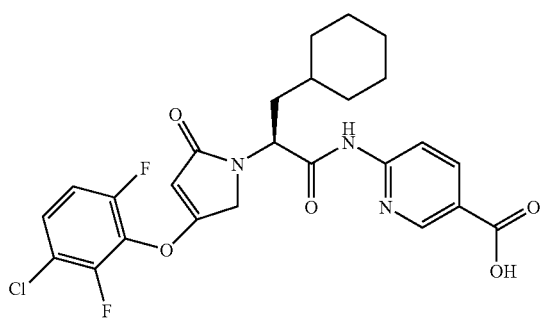

To a magnetically stirred mixture of 6-{(S)-2-[4-(3-chloro-2,6-difluoro-phenoxy)-2-oxo-2,5-dihydro-pyrrol-1-yl]-3-cyclohexyl-propionylamino}-nicotinic acid methyl ester (prepared as in Example 72, 150 mg, 0.28 mmol) in tetrahydrofuran (3.0 mL) was added 0.5N lithium hydroxide solution (2.0 mL, 1.0 mmol). After addition was complete the mixture was stirred at 25° C. for 4 h. The reaction mixture was diluted with ethyl acetate, washed with 1N aqueous hydrochloric acid, water, a saturated sodium chloride solution and dried over sodium sulfate. The crude product was recrystallized and triturated from ethyl acetate to afford 6-{(S)-2-[4-(3-chloro-2,6-difluoro-phenoxy)-2-oxo-2,5-dihydro-pyrrol-1-yl]-3-cyclohexyl-propionylamino}-nicotinic acid (30 mg, 21%) as a yellow solid: HR-ES-MS m/z calculated for $C_{25}H_{24}ClF_2N_3O_5$ [M+H]$^+$ 520.1446, observed 520.1447; $^1$H NMR (300 MHz, DMSO-d$_6$) δ ppm 0.61-1.38 (m, 5H) 1.44-1.87 (m, 8H) 4.33 (d, J=18.7 Hz, 1H) 4.64 (d, J=18.7 Hz, 1H) 4.91-5.14 (m, 1H) 5.27 (s, 1H) 7.16-7.56 (m, 1H) 7.57-7.82 (m, 1H) 7.87-8.49 (m, 2H) 8.84 (s, 1H) 11.27 (s, 1H) 13.16 (br. s., 1H).

Example 75

(S)-2-[4-(3-Chloro-2,6-difluoro-phenoxy)-2-oxo-2,5-dihydro-pyrrol-1-yl]-3-cyclohexyl-N-(1-methyl-1H-pyrazol-3-yl)-propionamide Hydrochloride

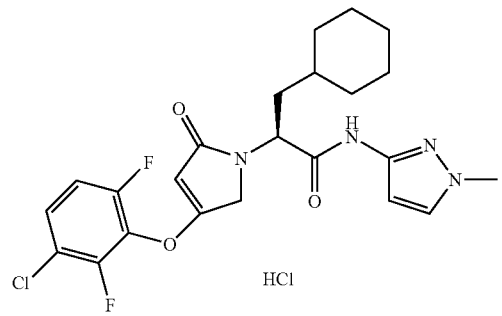

A solution of (S)-2-[4-(3-chloro-2,6-difluoro-phenoxy)-2-oxo-2,5-dihydro-pyrrol-1-yl]-3-cyclohexyl-propionic acid (prepared as in Example 72, 160 mg, 0.40 mmol) in N,N-dimethylformamide (3 mL) was treated with 1-methyl-1H-pyrazol-3-ylamine (50 mg, 0.51 mmol), benzotriazol-1-yl-oxy-tris(dimethylamino)phosphonium hexafluorophosphate (450 mg, 1.01 mmol) and N,N-diisopropylethylamine (130 mg, 1.01 mmol). The reaction mixture was stirred for 4 h at 25° C., under nitrogen. The reaction mixture was diluted with ethyl acetate, washed with saturated ammonium chloride, water, a saturated sodium chloride solution and dried over sodium sulfate. The organic layer was concentrated, and the crude product was purified by ISCO flash chromatography (Teledyne Isco RediSep Flash Column 12 g, 20% to 90% ethyl acetate/hexanes) to afford (S)-2-[4-(3-chloro-2,6-difluoro-phenoxy)-2-oxo-2,5-dihydro-pyrrol-1-yl]-3-cyclohexyl-N-(1-methyl-1H-pyrazol-3-yl)-propionamide as a waxy material. This material was dissolved in dichloromethane (4 mL) and treated with hydrogen chloride in diethyl ether (1 M, 4 mL). Solvents were evaporated and the residue was triturated with diethyl ether. The resulting mixture was filtered to give (S)-2-[4-(3-chloro-2,6-difluoro-phenoxy)-2-oxo-2,5-dihydro-pyrrol-1-yl]-3-cyclohexyl-N-(1-methyl-1H-pyrazol-3-yl)-propionamide hydrochloride (75 mg, 36%) as a tan solid: LR-ES-MS m/z calculated for $C_{23}H_{25}ClF_2N_4O_3$ [M]$^+$ 478, observed 479 [M+H]$^+$; $^1$H NMR (300 MHz, DMSO-d$_6$) δ ppm 0.65-1.30 (m, 6H) 1.42-1.83 (m, 7H) 3.71 (s, 3H) 4.27 (d, J=18.7 Hz, 1H) 4.61 (d, J=18.7 Hz, 1H) 4.87 (dd, J=10.3, 5.1 Hz, 1H) 5.22 (s, 1H) 6.38 (d, J=2.1 Hz, 1H) 7.43 (td, J=9.0, 1.7 Hz, 1H) 7.53 (d, J=2.1 Hz, 1H) 7.66 (td, J=9.0, 5.4 Hz, 1H) 10.72 (s, 1H).

Example 76

(S)-2-[4-(3-Chloro-2,6-difluoro-phenoxy)-2-oxo-2,5-dihydro-pyrrol-1-yl]-3-cyclohexyl-N-[1-((R)-2,3-dihydroxy-propyl)-1H-pyrazol-3-yl]-propionamide Hydrochloride

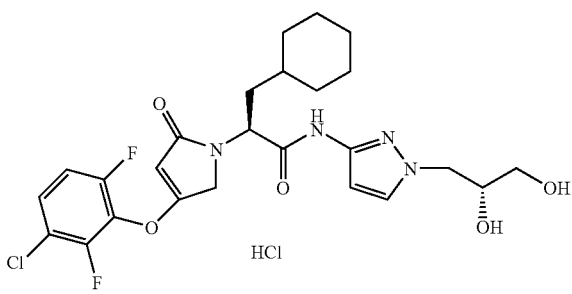

A solution of (S)-2-[4-(3-chloro-2,6-difluoro-phenoxy)-2-oxo-2,5-dihydro-pyrrol-1-yl]-3-cyclohexyl-propionic acid (prepared as in Example 72, 185 mg, 0.46 mmol) in dichloromethane (10 mL) was treated with oxalyl chloride (0.35 mL, 2M in dichloromethane), and N,N-dimethylformamide (1 drop). Effervescence was observed. The reaction mixture was stirred for 2 h at 25° C., under nitrogen. The reaction mixture was concentrated, and dissolved in dichloromethane (5 mL) and treated with (R)-3-(3-amino-pyrazol-1-yl)-propane-1,2-diol (as prepared in Example 38, 87 mg, 0.55 mmol), and triethylamine (102 mg, 1.00 mmol). The reaction mixture was stirred at 25° C., under nitrogen for 18 h. The reaction mixture was diluted with dichloromethane, washed with water, 2N aqueous hydrochloric acid, saturated sodium bicarbonate solution, a saturated sodium chloride solution and dried over magnesium sulfate. The organic layer was concentrated, and the crude product was purified by ISCO flash chromatography (Teledyne Isco RediSep Flash Column 12 g, 50% to 100% ethyl acetate/hexanes) to afford, (S)-2-[4-(3-chloro-2,6-difluoro-phenoxy)-2-oxo-2,5-dihydro-pyrrol-1-yl]-3-cyclohexyl-N-[1-((R)-2,3-dihydroxy-propyl)-1H-pyrazol-3-yl]-propionamide as a fluffy solid. This solid was dissolved in dichloromethane (4 mL) and treated with 1M hydrogen chloride in diethyl ether (4 mL). Solvents were evaporated and the residue was triturated with diethyl ether and filtered to give (S)-2-[4-(3-chloro-2,6-difluoro-phenoxy)-2-oxo-2,5-dihydro-pyrrol-1-yl]-3-cyclohexyl-N-[1-((R)-2,3-dihydroxy-propyl)-1H-pyrazol-3-yl]-propionamide hydrochloride (20 mg, 8%) as a solid: LR-ES-MS m/z calculated for $C_{25}H_{29}ClF_2N_4O_5$ [M]$^+$ 538.18, observed [M+H]$^+$ 539.1; $^1$H NMR (300 MHz, DMSO-d$_6$) δ ppm 0.58-1.41 (m, 6H) 1.38-1.89 (m, 7H) 3.18-3.41 (m, 2H) 3.80-3.92 (m, 2H) 4.09 (dd, J=13.9, 3.9 Hz, 1H) 4.29 (d, J=18.7 Hz, 1H) 4.64 (d, J=18.7 Hz, 1H) 4.82-4.96 (m, 1H) 5.24 (s, 1H) 6.41 (d, J=2.1 Hz, 1H) 7.40-7.50 (m, 1H) 7.53 (d, J=2.1 Hz, 1H) 7.60-7.74 (m, 1H) 10.78 (s, 1H).

Example 77

(S)-2-[4-(2,3-Dichloro-phenoxy)-2-oxo-2,5-dihydro-pyrrol-1-yl]-4-methyl-pentanoic acid [1-(2-hydroxy-2-methyl-propyl)-1H-pyrazol-3-yl]-amide Hydrochloride

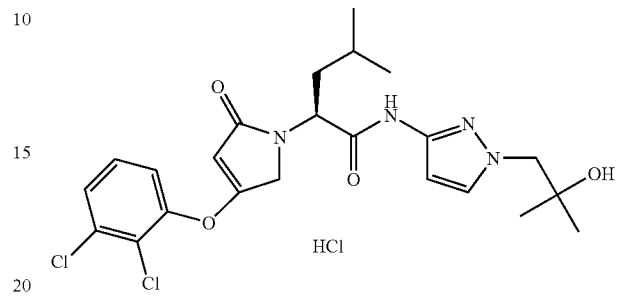

To a stirred mixture of 2,3-dichloro-phenol (10.0 g, 61.3 mmol) and ethyl-2-butynoate (13.70 g, 123.0 mmol) in tetrahydrofuran (60 mL) was added 1,8-diazabicyclo[5.4.0]undec-7-ene slowly (9.30 g, 61.3 mmol). After addition was complete the mixture was stirred at reflux for 4 h. Upon completion of the reaction the tetrahydrofuran was removed in vacuo and the residue was taken up in diethyl ether and washed with 1N aqueous hydrochloric acid, 10% aqueous sodium hydroxide solution, saturated sodium chloride solution and dried over magnesium sulfate. The crude product obtained was purified by ISCO flash chromatography (Teledyne Isco RediSep Flash Column 120 g, 0% to 20% ethyl acetate/hexanes) to afford, (E)-3-(2,3-dichloro-phenoxy)-but-2-enoic acid ethyl ester (10.5 g, 63%) as a colorless oil: $^1$H NMR (300 MHz, DMSO-d$_6$) δ ppm 1.12 (t, J=7.0 Hz, 3H), 2.46 (s, 3H), 4.01 (q, J=7.0 Hz, 2H), 4.61 (s, 1H), 7.35 (dd, J=8.2, 1.4 Hz, 1H), 7.48 (t, J=8.2 Hz, 1H), 7.63 (dd, J=8.2, 1.4 Hz, 1H).

To a stirred mixture of (E)-3-(2,3-dichloro-phenoxy)-but-2-enoic acid ethyl ester (10.5 g, 38.10 mmol) dissolved in carbon tetrachloride (70 mL) under a nitrogen atmosphere was added N-bromosuccinimide (9.50 g, 53.40 mmol) and benzoyl peroxide (75% purity by weight, 1.50 g, 4.64 mmol). After addition was complete the mixture was stirred at reflux for 8 h. The reaction mixture was then placed in the refrigerator overnight, the succinimide was removed by filtration and the solvent was removed in vacuo. The crude product obtained was purified by ISCO flash chromatography (Teledyne Isco RediSep Flash Column 120 g, 0% to 20% ethyl acetate/hexanes) to afford, 4-bromo-3-(2,3-dichloro-phenoxy)-but-2-enoic acid ethyl ester (12.80 g, 94%) as a yellow oil: $^1$H NMR (300 MHz, DMSO-d$_6$) δ ppm 1.15 (t, J=6.9 Hz, 3H), 4.07 (q, J=6.9 Hz, 2H), 4.78 (s, 1H), 4.81 (s, 2H), 7.32 (dd, J=8.2, 1.4 Hz, 1H), 7.50 (t, J=8.2 Hz, 1H), 7.65 (dd, J=8.2, 1.4 Hz, 1H).

To a stirred mixture of (L)-leucine methyl ester hydrochloride (3.70 g, 20.20 mmol) dissolved in acetonitrile (40 mL) under nitrogen atmosphere was added triethylamine (2.5 g, 24.50 mmol). After addition was complete the mixture was stirred at 60° C. for 1 h. The reaction was cooled to 25° C. and treated with triethylamine (2.5 g, 24.50 mmol) and acetonitrile (20 mL) and heated to 80° C. at which time, 4-bromo-3-(2,3-dichloro-phenoxy)-but-2-enoic acid ethyl ester (6.00 g, 17.0 mmol) in acetonitrile (20 mL) was added slowly. After the addition was complete the reaction mixture was heated to 100° C. and stirred overnight. The reaction mixture was cooled to 25° C., filtered and concentrated. The residue was diluted with ethyl acetate and washed with saturated ammonium chloride, water, a saturated sodium chloride solution and dried over sodium sulfate. The crude product obtained was purified by ISCO flash chromatography (Teledyne Isco RediSep Flash Column 120 g, 0% to 50% ethyl acetate/hexanes) to afford, (S)-2-[4-(2,3-dichloro-phenoxy)-2-oxo-2,5-dihydro-pyrrol-1-yl]-4-methyl-pentanoic acid methyl ester (1.23 g, 20%) as a yellow oil: LR-ES-MS m/z calculated for $C_{17}H_{19}Cl_2NO_4$ $[M]^+$ 371, observed $[M+H]^+$ 372.

To a magnetically stirred mixture of (S)-2-[4-(2,3-dichloro-phenoxy)-2-oxo-2,5-dihydro-pyrrol-1-yl]-4-methyl-pentanoic acid methyl ester (1.23 g, 3.30 mmol) in tetrahydrofuran (30 mL) was added 0.5N lithium hydroxide solution (20.0 mL, 10.0 mmol). After addition was complete the mixture was stirred at 25° C. for 2 h. The reaction mixture was poured into water and diethyl ether and the layers separated. The aqueous layer was made acidic with 1N aqueous hydrochloric acid and extracted with ethyl acetate (3×30 mL). The combined ethyl acetate fractions were washed with a saturated sodium chloride solution, dried over magnesium sulfate, filtered and concentrated to afford, (S)-2-[4-(2,3-dichloro-phenoxy)-2-oxo-2,5-dihydro-pyrrol-1-yl]-4-methyl-1-pentanoic acid (1.24 g, 99%) as a yellow solid: LRMS ES m/z calculated for $C_{16}H_{17}Cl_2NO_4$ $[M]^+$ 357, observed $[M+H]^+$ 358.

A solution of (S)-2-[4-(2,3-dichloro-phenoxy)-2-oxo-2,5-dihydro-pyrrol-1-yl]-4-methy-1-pentanoic acid (130 mg, 0.36 mmol) in N,N-dimethylformamide (4 mL) was treated with 1-(3-amino-pyrazol-1-yl)-2-methyl-propan-2-ol (prepared in U.S. Pat. Appl. US2008021032 Example 80, 80 mg, 0.51 mmol), benzotriazol-1-yl-oxy-tris(dimethylamino) phosphonium hexafluorophosphate (340 mg, 0.76 mmol) and N,N-diisopropylethylamine (120 mg, 0.93 mmol). The reaction mixture was stirred for 4 h at 25° C., under nitrogen. The reaction mixture was diluted with ethyl acetate, washed with saturated ammonium chloride, water, a saturated sodium chloride solution and dried over sodium sulfate. The organic layer was concentrated, and the crude product was purified by ISCO flash chromatography (Teledyne Isco RediSep Flash Column 12 g, 40% to 100% ethyl acetate/hexanes) to afford (S)-2-[4-(2,3-dichloro-phenoxy)-2-oxo-2,5-dihydro-pyrrol-1-yl]-4-methyl-pentanoic acid [1-(2-hydroxy-2-methyl-propyl)-1H-pyrazol-3-yl]-amide as a fluffy material. This material was dissolved in dichloromethane (4 mL) and treated with 1M hydrogen chloride in diethyl ether (4 mL). Solvents were evaporated and the residue was triturated with diethyl ether. Solid was filtered to give (S)-2-[4-(2,3-dichloro-phenoxy)-2-oxo-2,5-dihydro-pyrrol-1-yl]-4-methyl-pentanoic acid [1-(2-hydroxy-2-methyl-propyl)-1H-pyrazol-3-yl]-amide hydrochloride (60 mg, 31%): HR-ES-MS m/z calculated for $C_{23}H_{28}Cl_2N_4O_4$ $[M+H]^+$ 495.1561, observed 495.1564; $^1H$ NMR (300 MHz, DMSO-$d_6$) δ ppm 0.90 (d, J=6.3 Hz, 3H) 0.94 (d, J=6.3 Hz, 3H) 1.04 (s, 3H) 1.06 (s, 3H) 1.35-1.65 (m, 2H) 1.67-1.86 (m, 1H) 3.89 (s, 2H) 4.22 (d, J=18.5 Hz, 1H) 4.63 (d, J=18.5 Hz, 1H) 4.86-4.91 (m, 1H) 4.92 (s, 1H) 6.44 (d, J=2.1 Hz, 1H) 7.44-7.59 (m, 3H) 7.64 (dd, J=7.5, 1.8 Hz, 1H) 10.82 (s, 1H).

Example 78

(S)-2-[4-(2,3-Dichloro-phenoxy)-2-oxo-2,5-dihydro-pyrrol-1-yl]-4-methyl-pentanoic acid (1-methyl-1H-pyrazol-3-yl)-amide Hydrochloride

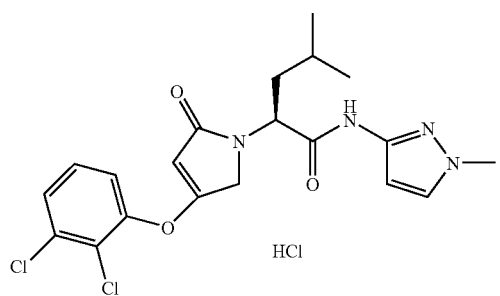

A solution of (S)-2-[4-(2,3-dichloro-phenoxy)-2-oxo-2,5-dihydro-pyrrol-1-yl]-4-methy-1-pentanoic acid (prepared as in Example 77, 120 mg, 0.34 mmol) in N,N-dimethylformamide (4 mL) was treated with 1-methyl-1H-pyrazol-3-ylamine (50 mg, 0.51 mmol), benzotriazol-1-yl-oxy-tris (dimethylamino)phosphonium hexafluorophosphate (303 mg, 0.68 mmol) and N,N-diisopropylethylamine (110 mg, 0.85 mmol). The reaction mixture was stirred for 4 h at 25° C., under nitrogen. The reaction mixture was diluted with ethyl acetate, washed with saturated ammonium chloride, water, a saturated sodium chloride solution and dried over sodium sulfate. The organic layer was concentrated, and the crude product was purified by ISCO flash chromatography (Teledyne Isco RediSep Flash Column 12 g, 0% to 70% ethyl acetate/hexanes) to afford (S)-2-[4-(2,3-dichloro-phenoxy)-2-oxo-2,5-dihydro-pyrrol-1-yl]-4-methyl-pentanoic acid (1-methyl-1H-pyrazol-3-yl)-amide as a waxy material. This material was dissolved in diethyl ether (4 mL) and treated with hydrogen chloride in diethyl ether (1 M, 2 mL). Solvents were evaporated and the residue was triturated with diethyl ether. The resulting mixture was filtered to give (S)-2-[4-(2,3-dichloro-phenoxy)-2-oxo-2,5-dihydro-pyrrol-1-yl]-4-methyl-pentanoic acid (1-methyl-1H-pyrazol-3-yl)-amide hydrochloride (58 mg, 36%) as an orange solid: HR-ES-MS m/z calculated for $C_{20}H_{22}Cl_2N_4O_3$ $[M+Na]^+$ 459.0961, observed 459.0961; $^1H$ NMR (300 MHz, DMSO-$d_6$) δ ppm 0.88 (d, J=6.6 Hz, 3H) 0.92 (d, J=6.6 Hz, 3H) 1.31-1.64 (m, 2H) 1.64-1.82 (m, 1H) 3.71 (s, 3H) 4.21 (d, J=18.4 Hz, 1H) 4.59 (d, J=18.4 Hz, 1H) 4.82-4.89 (m, 1H) 4.90 (s, 1H) 6.38 (d, J=2.1 Hz, 1H) 7.40-7.57 (m, 3H) 7.62 (dd, J=7.8, 1.5 Hz, 1H) 10.73 (s, 1H).

Example 79

(S)-2-[4-(2,3-Dichloro-phenoxy)-2-oxo-2,5-dihydro-pyrrol-1-yl]-4-methyl-pentanoic acid [1-((R)-2,2-dimethyl-[1,3]dioxolan-4-yl-methyl)-1H-pyrazol-3-yl]-amide

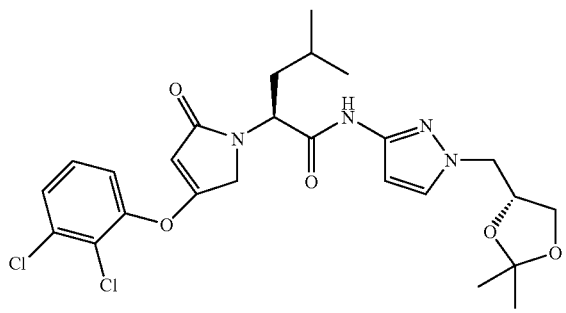

A solution of 3-nitro-1H-pyrazole (prepared as in Example 5, 12.0 g, 106 mmol) in N,N-dimethylformamide (150 mL) was treated with toluene-4-sulfonic acid (S)-2,2-dimethyl-[1,3]dioxolan-4-yl-methyl ester (25.5 g, 89.0 mmol), and potassium carbonate (24.5 g, 178 mmol). The reaction mixture was stirred for 6 h at 90° C., under nitrogen. The reaction mixture was diluted with ethyl acetate, washed with water twice, a saturated sodium chloride solution and dried over sodium sulfate. The organic layer was concentrated, and the crude product was purified by ISCO flash chromatography (Teledyne Isco RediSep Flash Column 330 g, 5% to 30% ethyl acetate/hexanes) to afford 1-((R)-2,2-dimethyl-[1,3]dioxolan-4-yl-methyl)-3-nitro-1H-pyrazole (14.5 g, 72%) as light yellow oil: LR-ES-MS m/z calculated for $C_9H_{13}N_3O_4$ $[M]^+$ 227, observed $[M+H]^+$ 228. $^1$H NMR (300 MHz, CDCl$_3$) δ ppm 1.35 (s, 3H), 1.40 (s, 3H), 3.77 (dd, J=8.8, 5.7 Hz, 1H), 4.13 (dd, J=8.8, 6.6 Hz, 1H), 4.27 (dd, J=14.0, 6.6 Hz, 1H), 4.39 (dd, J=14.0, 3.6 Hz, 1H), 4.45-4.59 (m, 1H), 6.92 (d, J=2.4 Hz, 1H), 7.59 (d, J=2.4 Hz, 1H)

1-((R)-2,2-dimethyl-[1,3]dioxolan-4-yl-methyl)-3-nitro-1H-pyrazole (14.5 g) was diluted in 60 mL of ethanol and 10% palladium on carbon (1.4 g) was added. The mixture was hydrogenated on a Parr apparatus at 50 psi for 16 hr. The mixture was filtered and the solvent was removed to afford the product 1-((R)-2,2-dimethyl-[1,3]dioxolan-4-yl-methyl)-1H-pyrazol-3-ylamine (12.4 g, 98%) as a pale yellow oil. LR-ES-MS m/z calculated for $C_9H_{15}N_3O_2$ $[M]^+$197, observed [M+H] 198; $^1$H NMR (300 MHz, DMSO-d$_6$) δ ppm 1.24 (s, 3H), 1.30 (s, 3H), 3.70 (dd, J=8.5, 6.0 Hz, 1H), 3.85-4.02 (m, 3H), 4.28 (quin, J=6.0 Hz, 1H), 4.56 (s, 2H), 5.36 (d, J=2.1 Hz, 1H), 7.30 (d, J=2.1 Hz, 1H).

A solution of (S)-2-[4-(2,3-dichloro-phenoxy)-2-oxo-2,5-dihydro-pyrrol-1-yl]-4-methyl-pentanoic acid (prepared as in Example 77, 192 mg, 0.54 mmol) in N,N-dimethylformamide (5 mL) was treated with 1-((R)-2,2-dimethyl-[1,3]dioxolan-4-yl-methyl)-1H-pyrazol-3-ylamine (127 mg, 0.65 mmol), benzotriazol-1-yl-oxy-tris(dimethylamino)phosphonium hexafluorophosphate (486 mg, 1.1 mmol) and N,N-diisopropylethylamine (142 mg, 1.1 mmol). The reaction mixture was stirred overnight at 25° C., under nitrogen. The reaction mixture was diluted with ethyl acetate, washed with saturated ammonium chloride, water, a saturated sodium chloride solution and dried over sodium sulfate. The organic layer was concentrated, and the crude product was purified by ISCO flash chromatography (Teledyne Isco RediSep Flash Column 12 g, 20% to 100% ethyl acetate/hexanes) to afford (S)-2-[4-(2,3-dichloro-phenoxy)-2-oxo-2,5-dihydro-pyrrol-1-yl]-4-methyl-pentanoic acid [1-((R)-2,2-dimethyl-[1,3]dioxolan-4-yl-methyl)-1H-pyrazol-3-yl]-amide (165 mg, 57%): HR-ES-MS m/z calculated for $C_{25}H_{30}Cl_2N_4O_5$ $[M+H]^+$ 537.1666, observed 537.1668; $^1$H NMR (300 MHz, DMSO-d$_6$) δ ppm 0.90 (d, J=6.3 Hz, 3H), 0.94 (d, J=6.3 Hz, 3H), 1.25 (s, 3H), 1.30 (s, 3H), 1.36-1.66 (m, 2H), 1.68-1.84 (m, 1H), 3.73 (dd, J=8.5, 6.0 Hz, 1H), 4.00 (dd, J=8.5, 6.3 Hz, 1H), 4.05-4.15 (m, 2H), 4.23 (d, J=18.4 Hz, 1H), 4.29-4.42 (m, 1H), 4.62 (d, J=18.4 Hz, 1H), 4.84-4.91 (m, 1H), 4.92 (s, 1H), 6.44 (d, J=2.1 Hz, 1H), 7.48 (t, J=7.8 Hz, 1H), 7.55 (dd, J=7.8, 1.8 Hz, 1H), 7.60 (d, J=2.1 Hz, 1H), 7.64 (m, J=7.8, 1.8 Hz, 1H), 10.82 (s, 1H).

Example 80

(S)-2-[4-(2,3-Dichloro-phenoxy)-2-oxo-2,5-dihydro-pyrrol-1-yl]-4-methyl-pentanoic acid [1-((R)-2,3-dihydroxy-propyl)-1H-pyrazol-3-yl]-amide Hydrochloride

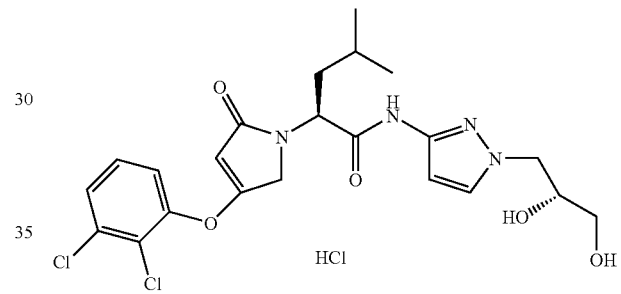

A solution of (S)-2-[4-(2,3-dichloro-phenoxy)-2-oxo-2,5-dihydro-pyrrol-1-yl]-4-methyl-pentanoic acid [1-((R)-2,2-dimethyl-[1,3]dioxolan-4-yl-methyl)-1H-pyrazol-3-yl]-amide (prepared as in Example 79, 145 mg, 0.27 mmol) in tetrahydrofuran (20 mL) was treated with 2N aqueous hydrochloric acid (10 mL). The reaction mixture was stirred for 4 h at 25° C. The reaction mixture was diluted with ethyl acetate, washed with water, a saturated sodium chloride solution and dried over sodium sulfate. The organic layer was concentrated to afford (S)-2-[4-(2,3-dichloro-phenoxy)-2-oxo-2,5-dihydro-pyrrol-1-yl]-4-methyl-pentanoic acid [1-((R)-2,3-dihydroxy-propyl)-1H-pyrazol-3-yl]-amide as a fluffy material. This material was dissolved in dichloromethane (20 mL) and treated with 1M hydrogen chloride in diethyl ether (2 mL). Solvents were evaporated and the residue was triturated with diethyl ether. The mixture was filtered to give (S)-2-[4-(2,3-dichloro-phenoxy)-2-oxo-2,5-dihydro-pyrrol-1-yl]-4-methyl-pentanoic acid [1-((R)-2,3-dihydroxy-propyl)-1H-pyrazol-3-yl]-amide hydrochloride (85 mg, 59%) as a yellow solid: HR-ES-MS m/z calculated for $C_{22}H_{26}Cl_2N_4O_5$ $[M+H]^+$ 497.1353, observed 497.1355; $^1$H NMR (300 MHz, DMSO-d$_6$) δ ppm 0.90 (d, J=6.3 Hz, 3H), 0.94 (d, J=6.3 Hz, 3H), 1.35-1.66 (m, 2H), 1.67-1.86 (m, 1H), 3.19-3.38 (m, 2H), 3.70-3.93 (m, 2H), 4.09 (dd, J=13.4, 3.5 Hz, 1H), 4.16-4.32 (br. s., 2H), 4.23 (m, J=18.4 Hz, 1H), 4.62 (d, J=18.4 Hz, 1H), 4.82-4.91 (m, 1H), 4.92 (s, 1H), 6.41 (d, J=1.5 Hz, 1H), 7.42-7.59 (m, 3H), 7.64 (d, J=7.5 Hz, 1H), 10.79 (s, 1H).

Example 81

(S)-2-[4-(2-Ethoxy-phenoxy)-2-oxo-2,5-dihydro-pyrrol-1-yl]-4-methyl pentanoic acid [1-(2-hydroxy-2-methyl-propyl)-1H-pyrazol-3-yl]-amide Hydrochlorde

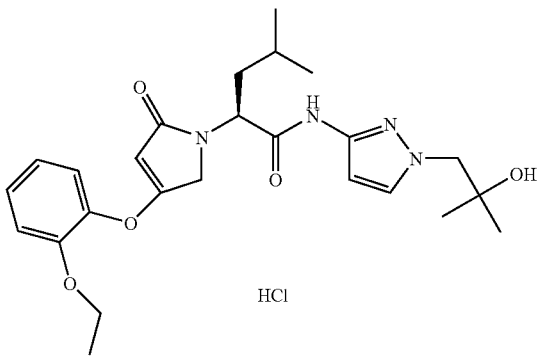

To a stirred mixture of 2-ethoxy-phenol (10.3 g, 74.5 mmol) and ethyl-2-butynoate (16.80 g, 149.0 mmol) in tetrahydrofuran (60 mL) was added 1,8-diazabicyclo[5.4.0]undec-7-ene slowly (16.80 g, 149.0 mmol). After addition was complete the mixture was stirred at reflux for 4 h. Upon completion of the reaction the tetrahydrofuran was removed in vacuo and the residue was taken up in diethyl ether and washed with 1N aqueous hydrochloric acid, 10% aqueous sodium hydroxide solution, saturated sodium chloride solution and dried over magnesium sulfate. The crude product obtained was purified by ISCO flash chromatography (Teledyne Isco RediSep Flash Column 120 g, 0% to 20% ethyl acetate/hexanes) to afford, (E)-3-(2-ethoxy-phenoxy)-but-2-enoic acid ethyl ester (8.57 g, 46%) as a colorless oil: $^1$H NMR (300 MHz, CDCl$_3$) δ ppm 1.22 (t, J=7.1 Hz, 3H), 1.37 (t, J=6.9 Hz, 3H), 2.51 (s, 3H), 3.95-4.19 (m, 4H), 4.83 (s, 1H), 6.88-7.08 (m, 3H), 7.09-7.24 (m, 1H).

To a stirred mixture of (E)-3-(2-ethoxy-phenoxy)-but-2-enoic acid ethyl ester (8.57 g, 34.3 mmol) dissolved in carbon tetrachloride (70 mL) under a nitrogen atmosphere was added N-bromosuccinimide (9.10 g, 51.10 mmol) and benzoyl peroxide (75%, 1.65 g, 5.10 mmol). After addition was complete the mixture was stirred at reflux for 8 h. The reaction mixture was then placed in the refrigerator overnight, the succinimide was removed by filtration and the solvent was removed in vacuo. The crude product obtained was purified by ISCO flash chromatography (Teledyne Isco RediSep Flash Column 120 g, 0% to 20% ethyl acetate/hexanes) to afford, (E)-4-bromo-3-(2-ethoxy-phenoxy)-but-2-enoic acid ethyl ester (8.0 g, 71%) as a yellow oil: $^1$H NMR (300 MHz, CDCl$_3$) δ ppm 1.24 (t, J=6.8 Hz, 3H), 1.39 (t, J=6.9 Hz, 3H), 3.94-4.23 (m, 4H), 4.73 (s, 2H), 4.90 (s, 1H), 6.85-7.12 (m, 3H), 7.14-7.25 (m, 1H).

To a stirred mixture of (L)-leucine methyl ester hydrochloride (2.70 g, 14.60 mmol) dissolved in acetonitrile (40 mL) under nitrogen atmosphere was added triethylamine (1.6 g, 16.0 mmol). After addition was complete the mixture was stirred at 60° C. for 1 h. The reaction was cooled to 25° C. and treated with triethylamine (1.6 g, 16.0 mmol) and acetonitrile (20 mL) and heated to 85° C. at which time, (E)-4-bromo-3-(2-ethoxy-phenoxy)-but-2-enoic acid ethyl ester (4.00 g, 12.2 mmol) in acetonitrile (20 mL) was added slowly. After the addition was complete the reaction mixture was heated to 100° C. and stirred overnight. The reaction mixture was cooled to 25° C., filtered and concentrated. The residue was diluted with ethyl acetate and washed with saturated ammonium chloride, water, a saturated sodium chloride solution and dried over sodium sulfate. The crude product obtained was purified by ISCO flash chromatography (Teledyne Isco RediSep Flash Column 120 g, 10% to 70% ethyl acetate/hexanes) to afford, (S)-2-[4-(2-ethoxy-phenoxy)-2-oxo-2,5-dihydro-pyrrol-1-yl]-4-methyl-pentanoic acid methyl ester (1.40 g, 33%) as a yellow oil: LR-ES-MS m/z calculated for C$_{19}$H$_{25}$NO$_5$ [M]$^+$ 347, observed [M+H]$^+$ 348.

To a stirred mixture of (S)-2-[4-(2-ethoxy-phenoxy)-2-oxo-2,5-dihydro-pyrrol-1-yl]-4-methyl-pentanoic acid methyl ester (1.40 g, 4.0 mmol) in tetrahydrofuran (30 mL) was added 0.5N lithium hydroxide solution (23.0 mL, 11.5 mmol). After addition was complete the mixture was stirred at 25° C. for 2 h. The reaction mixture was poured into water and diethyl ether and the layers were separated. The aqueous layer was made acidic with 1N aqueous hydrochloric acid and extracted with ethyl acetate (3×30 mL). The combined ethyl acetate fractions were washed with a saturated sodium chloride solution, dried over magnesium sulfate, filtered and concentrated to afford, (S)-2-[4-(2-ethoxy-phenoxy)-2-oxo-2,5-dihydro-pyrrol-1-yl]-4-methyl-pentanoic acid (1.20 g, 97%) as a yellow solid: LR-ES-MS m/z calculated for C$_{18}$H$_{23}$NO$_5$ [M]$^+$ 333, observed [M+H]$^+$ 334.

A solution of (S)-2-[4-(2-ethoxy-phenoxy)-2-oxo-2,5-dihydro-pyrrol-1-yl]-4-methyl-pentanoic acid (130 mg, 0.4 mmol) in N,N-dimethylformamide (4 mL) was treated with 1-(3-amino-pyrazol-1-yl)-2-methyl-propan-2-ol (prepared in U.S. Pat. Appl. US2008021032 Example 80, 75 mg, 0.46 mmol), benzotriazol-1-yl-oxy-tris(dimethylamino)phosphonium hexafluorophosphate (353 mg, 0.8 mmol) and N,N-diisopropylethylamine (103 mg, 0.8 mmol). The reaction mixture was stirred for 4 h at 25° C., under nitrogen. The reaction mixture was diluted with ethyl acetate, washed with saturated ammonium chloride, water, a saturated sodium chloride solution and dried over sodium sulfate. The organic layer was concentrated, and the crude product was purified by ISCO flash chromatography (Teledyne Isco RediSep Flash Column 12 g, 30% to 100% ethyl acetate/hexanes) to afford (S)-2-[4-(2-ethoxy-phenoxy)-2-oxo-2,5-dihydro-pyrrol-1-yl]-4-methyl-pentanoic acid [1-(2-hydroxy-2-methyl-propyl)-1H-pyrazol-3-yl]-amide as a fluffy material. This material was dissolved in diethyl ether (4 mL) and treated with hydrogen chloride in diethyl ether (1 M, 4 mL). Solvents were evaporated and the residue was triturated with diethyl ether. The solid was filtered to give (S)-2-[4-(2-ethoxy-phenoxy)-2-oxo-2,5-dihydro-pyrrol-1-yl]-4-methyl pentanoic acid [1-(2-hydroxy-2-methyl-propyl)-1H-pyrazol-3-yl]-amide hydrochloride (45 mg, 23%): HR-ES-MS m/z calculated for C$_{25}$H$_{34}$N$_4$O$_5$ [M+H]$^+$ 471.2602, observed 471.2603; $^1$H NMR (300 MHz, DMSO-d$_6$) δ ppm 0.89 (d, J=6.6 Hz, 3H), 0.92 (d, J=6.6 Hz, 3H), 1.04 (br. s., 3H), 1.06 (br. s., 3H), 1.26 (t, J=6.8 Hz, 3H), 1.32-1.64 (m, 2H), 1.64-1.82 (m, 1H), 3.89 (s, 2H), 4.00-4.13 (m, 3H), 4.35-4.62 (m, 2H), 4.74 (s, 1H), 4.89 (dd, J=10.9, 4.5 Hz, 1H), 6.43 (d, J=2.1 Hz, 1H), 6.99 (t, J=6.9 Hz, 1H), 7.15-7.22 (m, 1H), 7.22-7.32 (m, 2H), 7.53 (d, J=2.1 Hz, 1H), 10.77 (s, 1H).

Example 82

(S)-2-[4-(2-Ethoxy-phenoxy)-2-oxo-2,5-dihydro-pyrrol-1-yl]-4-methyl-pentanoic acid (1-methyl-1H-pyrazol-3-yl)-amide Hydrochloride

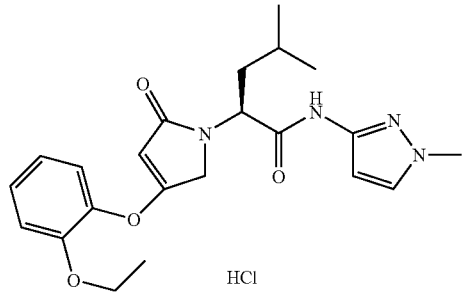

Example 83

(S)-2-[4-(2-Ethoxy-phenoxy)-2-oxo-2,5-dihydro-pyrrol-1-yl]-4-methyl-petanoic acid [1-((R)-2,2-dimethyl-[1,3]dioxolan-4-yl-methyl)-1H-pyrazol-3-yl]-amide

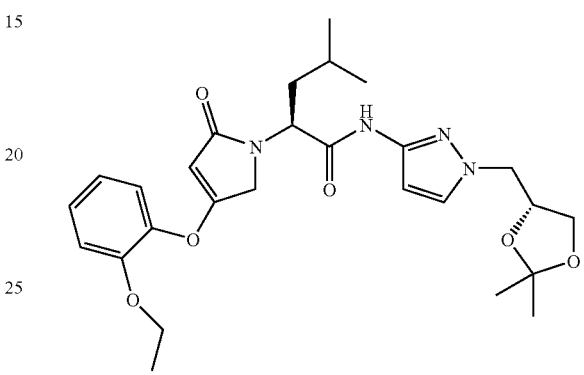

A solution of (S)-2-[4-(2-ethoxy-phenoxy)-2-oxo-2,5-dihydro-pyrrol-1-yl]-4-methyl-pentanoic acid (prepared as in Example 81, 120 mg, 0.36 mmol) in N,N-dimethylformamide (4 mL) was treated with 1-methyl-1H-pyrazol-3-ylamine (42 mg, 0.43 mmol), benzotriazol-1-yl-oxy-tris(dimethylamino)phosphonium hexafluorophosphate (320 mg, 0.72 mmol) and N,N-diisopropylethylamine (100 mg, 0.80 mmol). The reaction mixture was stirred for 4 h at 25° C., under nitrogen. The reaction mixture was diluted with ethyl acetate, washed with saturated ammonium chloride, water, a saturated sodium chloride solution and dried over sodium sulfate. The organic layer was concentrated, and the crude product was purified by ISCO flash chromatography (Teledyne Isco RediSep Flash Column 12 g, 20% to 70% ethyl acetate/hexanes) to afford (S)-2-[4-(2-ethoxy-phenoxy)-2-oxo-2,5-dihydro-pyrrol-1-yl]-4-methyl-pentanoic acid (1-methyl-1H-pyrazol-3-yl)-amide as a waxy material. This material was dissolved in diethyl ether (4 mL) and treated with hydrogen chloride in diethyl ether (1 M, 2 mL). Solvents were evaporated and the residue was triturated with diethyl ether. The resulting mixture was filtered to give (S)-2-[4-(2-ethoxy-phenoxy)-2-oxo-2,5-dihydro-pyrrol-1-yl]-4-methyl-pentanoic acid (1-methyl-1H-pyrazol-3-yl)-amide hydrochloride (30 mg, 19%) as a brown solid: HR-ES-MS m/z calculated for $C_{22}H_{28}N_4O_4$ [M+Na]$^+$ 435.2003, observed 435.2002; $^1$H NMR (300 MHz, DMSO-$d_6$) δ ppm 0.87 (d, J=6.6 Hz, 3H) 0.90 (d, J=6.6 Hz, 3H) 1.24 (t, J=6.9 Hz, 3H) 1.30-1.61 (m, 2H) 1.62-1.82 (m, 1H) 3.71 (s, 3H) 3.94-4.13 (m, 3H) 4.48 (d, J=18.1 Hz, 1H) 4.72 (s, 1H) 4.86 (dd, J=10.6, 4.5 Hz, 1H) 6.37 (d, J=1.2 Hz, 1H) 6.97 (t, J=7.4 Hz, 1H) 7.17 (d, J=8.2 Hz, 1H) 7.20-7.32 (m, 2H) 7.52 (s, 1H) 10.68 (s, 1H).

A solution of (S)-2-[4-(2-ethoxy-phenoxy)-2-oxo-2,5-dihydro-pyrrol-1-yl]-4-methyl-pentanoic acid (prepared as in Example 81, 160 mg, 0.48 mmol) in N,N-dimethylformamide (4 mL) was treated with 1-((R)-2,2-dimethyl-[1,3]dioxolan-4-yl-methyl)-1H-pyrazol-3-ylamine (prepared as in Example 49, 115 mg, 0.57 mmol), benzotriazol-1-yl-oxy-tris(dimethylamino)phosphonium hexafluorophosphate (442 mg, 1.0 mmol) and N,N-diisopropylethylamine (150 mg, 1.2 mmol). The reaction mixture was stirred overnight at 25° C., under nitrogen. The reaction mixture was diluted with ethyl acetate, washed with saturated ammonium chloride, water, a saturated sodium chloride solution and dried over sodium sulfate. The organic layer was concentrated, and the crude product was purified by ISCO flash chromatography (Teledyne Isco RediSep Flash Column 12 g, 20% to 100% ethyl acetate/hexanes) to afford (S)-2-[4-(2-ethoxy-phenoxy)-2-oxo-2,5-dihydro-pyrrol-1-yl]-4-methyl-pentanoic acid [1-((R)-2,2-dimethyl-[1,3]dioxolan-4-yl-methyl)-1H-pyrazol-3-yl]-amide (110 mg, 45%) as a tan solid: HR-ES-MS m/z calculated for $C_{27}H_{36}N_4O_6$ [M+H]$^+$ 513.2708, observed 513.2707; $^1$H NMR (300 MHz, DMSO-$d_6$) δ ppm 0.89 (d, J=6.6 Hz, 3H) 0.92 (d, J=6.6 Hz, 3H) 1.21-1.33 (m, 3H) 1.24 (s, 3H) 1.30 (s, 3H) 1.33-1.47 (m, 1H) 1.47-1.63 (m, 1H) 1.66-1.83 (m, 1H) 3.73 (dd, J=8.6, 5.9 Hz, 1H) 3.93-4.15 (m, 6H) 4.29-4.39 (m, 1H) 4.51 (d, J=18.4 Hz, 1H) 4.74 (s, 1H) 4.89 (dd, J=10.7, 4.7 Hz, 1H) 6.42 (d, J=2.1 Hz, 1H) 6.99 (td, J=7.5, 1.2 Hz, 1H) 7.16-7.22 (m, 1H) 7.22-7.36 (m, 2H) 7.59 (d, J=2.1 Hz, 1H) 10.77 (s, 1H).

Example 84

(S)-2-[4-(2-Ethoxy-phenoxy)-2-oxo-2,5-dihydro-pyrrol-1-yl]-4-methyl-pentanoic acid [1-((R)-2,3-dihydroxy-propyl)-1H-pyrazol-3-yl]-amide Hydrochloride

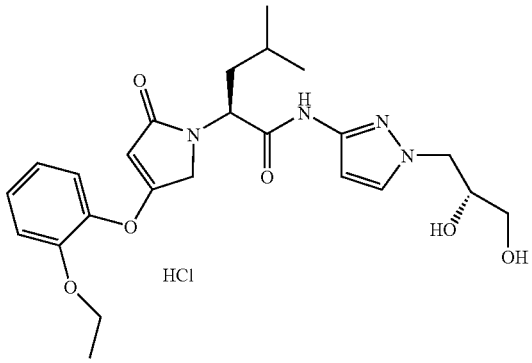

A solution of (S)-2-[4-(2-ethoxy-phenoxy)-2-oxo-2,5-dihydro-pyrrol-1-yl]-4-methyl-pentanoic acid [1-((R)-2,2-dimethyl-[1,3]dioxolan-4-yl-methyl)-1H-pyrazol-3-yl]-amide (prepared as in Example 83, 95 mg, 0.19 mmol) in tetrahydrofuran (20 mL) was treated with 2N aqueous hydrochloric acid (10 mL). The reaction mixture was stirred for 4 h at 25° C. The reaction mixture was diluted with ethyl acetate, washed with water, a saturated sodium chloride solution and dried over sodium sulfate. The organic layer was concentrated to afford (S)-2-[4-(2-ethoxy-phenoxy)-2-oxo-2,5-dihydro-pyrrol-1-yl]-4-methyl-pentanoic acid [1-((R)-2,3-dihydroxy-propyl)-1H-pyrazol-3-yl]-amide as a fluffy material. This material was dissolved in dichloromethane (20 mL) and treated with hydrogen chloride in diethyl ether (1 M, 2 mL). Solvents were evaporated and the residue was triturated with diethyl ether. The mixture was filtered to give (S)-2-[4-(2-ethoxy-phenoxy)-2-oxo-2,5-dihydro-pyrrol-1-yl]-4-methyl-pentanoic acid [1-((R)-2,3-dihydroxy-propyl)-1H-pyrazol-3-yl]-amide hydrochloride (51 mg, 61%) as a light yellow solid: HR-ES-MS m/z calculated for $C_{24}H_{32}N_4O_6$ [M+H]$^+$ 473.2395, observed 473.2395; $^1$H NMR (300 MHz, DMSO-$d_6$) δ ppm 0.88 (d, J=6.4 Hz, 3H) 0.91 (d, J=6.4 Hz, 3H) 1.24 (t, J=6.9 Hz, 3H) 1.40 (br. s., 1H) 1.46-1.62 (m, 1H) 1.64-1.80 (m, 1H) 3.17-3.40 (m, 2H) 3.69-3.79 (m, 1H) 3.79-3.90 (m, 1H) 3.98-4.11 (m, 4H) 4.49 (d, J=18.4 Hz, 1H) 4.72 (s, 1H) 4.86 (dd, J=11.0, 4.7 Hz, 1H) 6.38 (d, J=2.1 Hz, 1H) 6.97 (t, J=7.1 Hz, 1H) 7.13-7.20 (m, 1H) 7.21-7.33 (m, 2H) 7.51 (d, J=2.1 Hz, 1H) 10.72 (s, 1H).

Example 85

(S)-2-[4-(2-Ethoxy-phenoxy)-2-oxo-2,5-dihydro-pyrrol-1-yl]-4-methyl-pentanoic acid [1-(2-hydroxy-ethyl)-1H-pyrazol-3-yl]-amide Hydrochloride

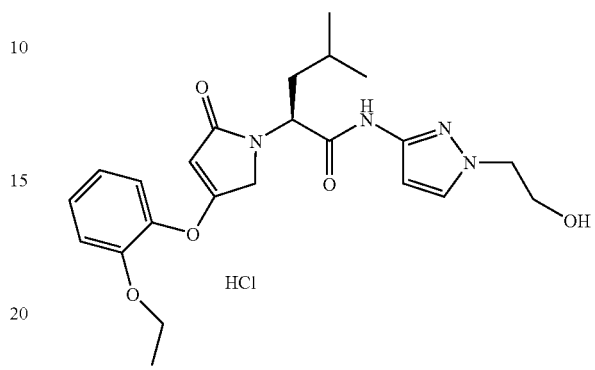

A solution of (S)-2-[4-(2-ethoxy-phenoxy)-2-oxo-2,5-dihydro-pyrrol-1-yl]-4-methyl-pentanoic acid (prepared as in Example 81, 170 mg, 0.5 mmol) in N,N-dimethylformamide (4 mL) was treated with 1-[2-(t-butyl-dimethyl-silanyloxy)-ethyl]-1H-pyrazol-3-ylamine (prepared in U.S. Pat. Appl. US2008021032, Example 67, 150 mg, 0.62 mmol), benzotriazol-1-yl-oxy-tris(dimethylamino)phosphonium hexafluorophosphate (470 mg, 1.06 mmol) and N,N-diisopropylethylamine (150 mg, 1.2 mmol). The reaction mixture was stirred overnight at 25° C., under nitrogen. The reaction mixture was diluted with ethyl acetate, washed with saturated ammonium chloride, water, a saturated sodium chloride solution and dried over sodium sulfate. The organic layer was concentrated, and the crude product was purified by ISCO flash chromatography (Teledyne Isco RediSep Flash Column 12 g, 0% to 60% ethyl acetate/hexanes) to afford (S)-2-[4-(2-ethoxy-phenoxy)-2-oxo-2,5-dihydro-pyrrol-1-yl]-4-methyl-pentanoic acid {1-[2-(t-butyl-dimethyl-silanyloxy)-ethyl]-1H-pyrazol-3-yl}-amide as a orange amorphous material (120 mg, 42%). This material (120 mg, 0.21 mmol) was dissolved in ethanol (20 mL) and treated with concentrated hydrochloric acid (10 drops). The mixture was stirred overnight and evaporated. The residue was diluted with ethyl acetate, washed with water, a saturated sodium chloride solution and dried over sodium sulfate. The organic layer was concentrated to afford (S)-2-[4-(2-ethoxy-phenoxy)-2-oxo-2,5-dihydro-pyrrol-1-yl]-4-methyl-pentanoic acid [1-(2-hydroxy-ethyl)-1H-pyrazol-3-yl]-amide as a fluffy material. This material was dissolved in dichloromethane (20 mL) and treated with hydrogen chloride in diethyl ether (1 M, 2 mL). Solvents were evaporated and the residue was triturated with diethyl ether. The mixture was filtered to give (S)-2-[4-(2-ethoxy-phenoxy)-2-oxo-2,5-dihydro-pyrrol-1-yl]-4-methyl-pentanoic acid [1-(2-hydroxy-ethyl)-1H-pyrazol-3-yl]-amide hydrochloride (60 mg, 25% two steps) as a yellow solid: HR-ES-MS m/z calculated for $C_{23}H_{30}N_4O_5$ [M+H]$^+$ 443.2289, observed 443.2289; $^1$H NMR (300 MHz, DMSO-$d_6$) δ ppm 0.91 (t, J=7.5 Hz, 6H) 1.26 (t, J=6.6 Hz, 3H) 1.33-1.48 (m, 1H) 1.48-1.63 (m, 1H) 1.65-1.81 (m, 1H) 3.68 (t, J=5.0 Hz, 2H) 3.92-4.16 (m, 5H) 4.51 (d, J=18.4 Hz, 1H) 4.74 (s, 1H) 4.88 (dd, J=10.3, 4.2 Hz, 1H) 6.39 (s, 1H) 6.99 (t, J=7.2 Hz, 1H) 7.12-7.32 (m, 3H) 7.56 (s, 1H) 10.74 (s, 1H).

Example 86

(S)-3-Cyclopentyl-2-[4-(2,6-difluoro-phenoxy)-2-oxo-2,5-dihydro-pyrrol-1-yl]-N-[1-(2-hydroxy-2-methyl-propyl)-1H-pyrazol-3-yl]-propionamide

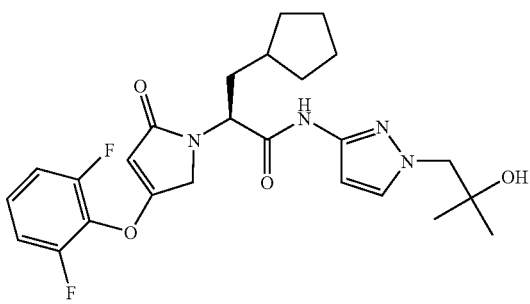

To a stirred mixture of (S)-2-amino-3-cyclopentyl-propionic acid methyl ester (prepared as in Example 1, 3.90 g, 18.80 mmol) dissolved in acetonitrile (40 mL) under nitrogen atmosphere was added triethylamine (3.0 g, 29.0 mmol). After addition was complete the mixture was stirred at 60° C. for 1 h. The reaction was cooled to 25° C. and treated with triethylamine (3.0 g, 29.0 mmol) and acetonitrile (20 mL) and heated to 85° C. at which time (E4-bromo-3-(2,6-difluoro-phenoxy)-but-2-enoic acid ethyl ester (prepared as in Example 36, 5.0 g, 15.7 mmol) in acetonitrile (20 mL) was added slowly. After the addition was complete the reaction mixture was heated to 100° C. and stirred overnight. The reaction mixture was cooled to 25° C., filtered and concentrated. The residue was diluted with ethyl acetate and washed with saturated ammonium chloride, water, a saturated sodium chloride solution and dried over sodium sulfate. The crude product obtained was purified by ISCO flash chromatography (Teledyne Isco RediSep Flash Column 80 g, 10% to 60% ethyl acetate/hexanes) to afford, (S)-3-cyclopentyl-2-[4-(2,6-difluoro-phenoxy)-2-oxo-2,5-dihydro-pyrrol-1-yl]-propionic acid methyl ester (0.60 g, 11%) as a yellow oil: $^1$H NMR (300 MHz, DMSO-d$_6$) δ ppm 1.00-1.21 (m, 2H), 1.35-1.98 (m, 9H), 3.66 (s, 3H), 4.29 (s, 2H), 4.66 (dd, J=10.7, 4.7 Hz, 1H), 5.07 (s, 1H), 7.28-7.55 (m, 3H).

To a stirred mixture of (S)-3-cyclopentyl-2-[4-(2,6-difluoro-phenoxy)-2-oxo-2,5-dihydro-pyrrol-1-yl]-propionic acid methyl ester (600 mg, 1.64 mmol) in tetrahydrofuran (10 mL) was added 0.5N lithium hydroxide solution (8.0 mL, 4.0 mmol). After addition was complete the mixture was stirred at 25° C. for 2 h. The reaction mixture was poured into water and diethyl ether and the layers were separated. The aqueous layer was made acidic with 1N aqueous hydrochloric acid and extracted with ethyl acetate (3×30 mL). The combined ethyl acetate fractions were washed with a saturated sodium chloride solution, dried over magnesium sulfate, filtered and concentrated to afford, (S)-3-cyclopentyl-2-[4-(2,6-difluoro-phenoxy)-2-oxo-2,5-dihydro-pyrrol-1-yl]-propionic acid (580 mg, 99%) as a yellow solid: $^1$H NMR (300 MHz, DMSO-d$_6$) δ ppm 1.00-1.20 (m, 2H), 1.35-2.03 (m, 9H), 4.27 (d, J=18.4 Hz, 1H), 4.28 (d, J=18.4 Hz, 1H), 4.56 (dd, J=10.9, 4.2 Hz, 1H), 5.05 (s, 1H), 7.28-7.52 (m, 3H), 12.91 (br. s., 1H).

A solution of (S)-3-cyclopentyl-2-[4-(2,6-difluoro-phenoxy)-2-oxo-2,5-dihydro-pyrrol-1-yl]-propionic acid (109 mg, 0.31 mmol) in N,N-dimethylformamide (4 mL) was treated with 1-(3-amino-pyrazol-1-yl)-2-methyl-propan-2-ol (prepared in U.S. Pat. Appl. US2008021032 Example 80, 62 mg, 0.40 mmol), benzotriazol-1-yl-oxy-tris(dimethylamino)phosphonium hexafluorophosphate (354 mg, 0.8 mmol) and N,N-diisopropylethylamine (103 mg, 0.8 mmol). The reaction mixture was stirred for 4 h at 25° C., under nitrogen. The reaction mixture was diluted with ethyl acetate, washed with saturated ammonium chloride, water, a saturated sodium chloride solution and dried over sodium sulfate. The organic layer was concentrated, and the crude product was purified by ISCO flash chromatography (Teledyne Isco RediSep Flash Column 12 g, 10% to 80% ethyl acetate/hexanes) to afford (S)-3-cyclopentyl-2-[4-(2,6-difluoro-phenoxy)-2-oxo-2,5-dihydro-pyrrol-1-yl]-N-[1-(2-hydroxy-2-methyl-propyl)-1H-pyrazol-3-yl]-propionamide (52 mg, 34%): HR-ES-MS m/z calculated for $C_{25}H_{30}F_2N_4O_4$ [M+H]$^+$ 489.2308 observed 489.2308; $^1$H NMR (300 MHz, DMSO-d$_6$) δ ppm 1.05 (br. s., 3H) 1.06 (br. s., 3H) 1.09-1.98 (m, 11H) 3.89 (s, 2H) 4.30 (d, J=18.7 Hz, 1H) 4.61 (d, J=18.7 Hz, 1H) 4.68 (s, 1H) 4.82 (dd, J=10.1, 4.4 Hz, 1H) 5.03 (s, 1H) 6.45 (d, J=2.1 Hz, 1H) 7.26-7.50 (m, 3H) 7.54 (d, J=2.1 Hz, 1H) 10.82 (s, 1H).

Example 87

(S)-3-Cyclopentyl-2-[4-(2,6-difluoro-phenoxy)-2-oxo-2,5-dihydro-pyrrol-1-yl]-N-[1-((R)-2,2-dimethyl-[1,3]dioxolan-4-yl-methyl)-1H-pyrazol-3-yl]-propionamide

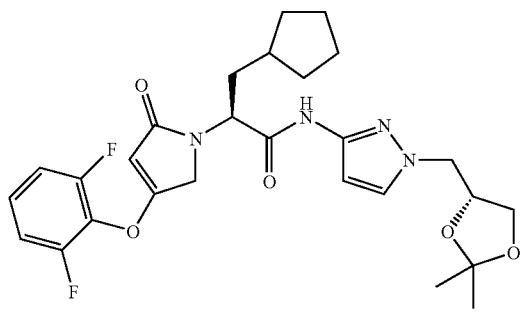

A solution of (S)-3-cyclopentyl-2-[4-(2,6-difluoro-phenoxy)-2-oxo-2,5-dihydro-pyrrol-1-yl]-propionic acid (prepared as in Example 86, 154 mg, 0.44 mmol) in N,N-dimethylformamide (6 mL) was treated with 1-((R)-2,2-dimethyl-[1,3]dioxolan-4-yl-methyl)-1H-pyrazol-3-ylamine (prepared as in Example 49, 110 mg, 0.56 mmol), benzotriazol-1-yl-oxy-tris(dimethylamino)phosphonium hexafluorophosphate (380 mg, 0.86 mmol) and N,N-diisopropylethylamine (150 mg, 1.2 mmol). The reaction mixture was stirred overnight at 25° C., under nitrogen. The reaction mixture was diluted with ethyl acetate, washed with saturated ammonium chloride, water, a saturated sodium chloride solution and dried over sodium sulfate. The organic layer was concentrated, and the crude product was purified by ISCO flash chromatography (Teledyne Isco RediSep Flash Column 12 g, 15% to 90% ethyl acetate/hexanes) to afford (S)-3-cyclopentyl-2-[4-(2,6-difluoro-phenoxy)-2-oxo-2,5-dihydro-pyrrol-1-yl]-N-[1-((R)-2,2-dimethyl-[1,3]dioxolan-4-yl-methyl)-1H-pyrazol-3-yl]-propionamide (140 mg, 60%) as a pale yellow solid: HR-ES-MS m/z calculated for $C_{27}H_{32}F_2N_4O_5$ [M+H]$^+$ 531.2414, observed 531.2414; $^1$H NMR (300 MHz, DMSO-d$_6$) δ ppm 1.00-1.19 (m, 2H) 1.25 (s, 3H) 1.30 (s, 3H) 1.38-1.96 (m, 9H) 3.73 (dd, J=8.3, 5.9 Hz, 1H) 3.94-4.20 (m, 3H) 4.30 (d, J=18.4 Hz, 1H) 4.33-4.42 (m, 1H) 4.63 (d, J=18.4 Hz, 1H) 4.82 (dd, J=10.1, 4.7 Hz, 1H) 5.03 (s, 1H) 6.44 (d, J=1.5 Hz, 1H) 7.26-7.54 (m, 3H) 7.60 (s, 1H) 10.82 (s, 1H).

Example 88

(S)-3-Cyclopentyl-2-[4-(2,6-difluoro-phenoxy)-2-oxo-2,5-dihydro-pyrrol-1-yl]-N-[1-((R)-2,3-dihydroxy-propyl)-1H-pyrazol-3-yl]-propionamide

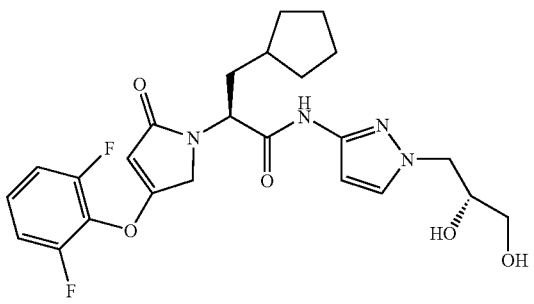

A solution of (S)-3-cyclopentyl-2-[4-(2,6-difluoro-phenoxy)-2-oxo-2,5-dihydro-pyrrol-1-yl]-N-[1-((R)-2,2-dimethyl-[1,3]dioxolan-4-yl-methyl)-1H-pyrazol-3-yl]-propionamide (prepared as in Example 87, 120 mg, 0.22 mmol) in tetrahydrofuran (20 mL) was treated with 2N aqueous hydrochloric acid (10 mL). The reaction mixture was stirred for 4 h at 25° C. The reaction mixture was adjusted to neutral and diluted with ethyl acetate, washed with water, a saturated sodium chloride solution and dried over sodium sulfate. The organic layer was concentrated to afford (S)-3-cyclopentyl-2-[4-(2,6-difluoro-phenoxy)-2-oxo-2,5-dihydro-pyrrol-1-yl]-N-[1-((R)-2,3-dihydroxy-propyl)-1H-pyrazol-3-yl]-propionamide (70 mg, 63%) as an off-white solid: HR-ES-MS m/z calculated for $C_{24}H_{28}F_2N_4O_5$ $[M+H]^+$ 491.2101, observed 491.2102; $^1$H NMR (300 MHz, DMSO-$d_6$) δ ppm 1.08 (br. s., 1H) 1.28 (br. s., 1H) 1.36-1.95 (m, 9H) 3.19-3.30 (m, 2H) 3.64-3.80 (m, 1H) 3.80-3.91 (m, 1H) 4.07 (dd, J=13.6, 3.9 Hz, 1H) 4.28 (d, J=18.7 Hz, 1H) 4.61 (d, J=18.7 Hz, 1H) 4.69 (t, J=5.6 Hz, 1H) 4.79 (dd, J=10.3, 4.8 Hz, 1H) 4.92 (d, J=5.4 Hz, 1H) 5.01 (s, 1H) 6.39 (d, J=2.1 Hz, 1H) 7.22-7.48 (m, 3H) 7.51 (d, J=2.1 Hz, 1H) 10.78 (s, 1H).

Example 89

(S)-3-Cyclopentyl-2-[4-(2,6-difluoro-phenoxy)-2-oxo-2,5-dihydro-pyrrol-1-yl]-N-[1-(2-hydroxy-ethyl)-1H-pyrazol-3-yl]-propionamide

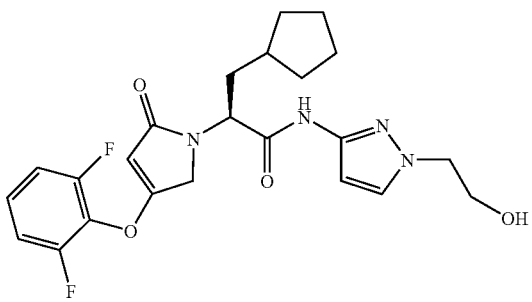

A solution of (S)-3-cyclopentyl-2-[4-(2,6-difluoro-phenoxy)-2-oxo-2,5-dihydro-pyrrol-1-yl]-propionic acid (prepared as in Example 86, 288 mg, 0.82 mmol) in N,N-dimethylformamide (4 mL) was treated with 1-[2-(t-butyl-dimethyl-silanyloxy)-ethyl]-1H-pyrazol-3-ylamine (prepared in U.S. Pat. Appl. US2008021032 Example 67, 237 mg, 0.98 mmol), benzotriazol-1-yl-oxy-tris(dimethylamino)phosphonium hexafluorophosphate (884 mg, 2.0 mmol) and N,N-diisopropylethylamine (260 mg, 2.0 mmol). The reaction mixture was stirred overnight at 25° C., under nitrogen. The reaction mixture was diluted with ethyl acetate, washed with saturated ammonium chloride, water, a saturated sodium chloride solution and dried over sodium sulfate. The organic layer was concentrated, and the crude product was purified by ISCO flash chromatography (Teledyne Isco RediSep Flash Column 12 g, 10% to 45% ethyl acetate/hexanes) to afford (S)-3-cyclopentyl-2-[4-(2,6-difluoro-phenoxy)-2-oxo-2,5-dihydro-pyrrol-1-yl]-propionic acid {1-[2-(t-butyl-dimethyl-silanyloxy)-ethyl]-1H-pyrazol-3-yl}-amide as a yellow oil (160 mg, 34%). This material (160 mg, 0.28 mmol) was dissolved in ethanol (20 mL) and treated with concentrated hydrochloric acid (12 drops). The mixture was stirred for 2 h and evaporated. The residue was diluted with ethyl acetate, washed with water, a saturated sodium chloride solution and dried over sodium sulfate. The organic layer was concentrated to afford (S)-3-cyclopentyl-2-[4-(2,6-difluoro-phenoxy)-2-oxo-2,5-dihydro-pyrrol-1-yl]-N-[1-(2-hydroxy-ethyl)-1H-pyrazol-3-yl]-propionamide (90 mg, 70%) as an off-white solid: HR-ES-MS m/z calculated for $C_{23}H_{26}F_2N_4O_4$ $[M+H]^+$ 461.1995, observed 461.1995; $^1$H NMR (300 MHz, DMSO-$d_6$) δ ppm 1.03-1.96 (m, 11H) 3.69 (q, J=5.6 Hz, 2H) 4.02 (t, J=5.6 Hz, 2H) 4.30 (d, J=18.7 Hz, 1H) 4.63 (d, J=18.7 Hz, 1H) 4.81 (dd, J=10.3, 5.1 Hz, 1H) 4.86 (t, J=5.3 Hz, 1H) 5.03 (s, 1H) 6.41 (d, J=2.1 Hz, 1H) 7.28-7.52 (m, 3H) 7.56 (d, J=2.1 Hz, 1H) 10.79 (s, 1H).

Example 90

(S)-3-Cyclohexyl-N-(1-methyl-1H-pyrazol-3-yl)-2-[2-oxo-4-(2-trifluoromethyl-phenoxy)-2,5-dihydro-pyrrol-1-yl]-propionamide Hydrochloride

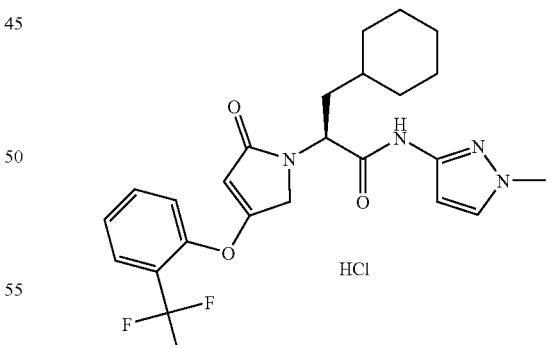

A solution of (S)-3-cyclohexyl-2-[2-oxo-4-(2-trifluoromethyl-phenoxy)-2,5-dihydro-pyrrol-1-yl]-propionic acid (prepared as in Example 32, 100 mg, 0.25 mmol) in dichloromethane (4 mL) was treated with a dichloromethane solution of oxalyl chloride (2 M, 0.25 mL) and one drop of N,N-dimethylformamide. The mixture was stirred for 45 min and solvents were evaporated. The residue was dissolved in dichloromethane (4 mL) and treated with 1-methyl-1H-pyrazol-3-ylamine (30 mg, 0.30 mmol), and triethylamine (50 mg, 0.5 mmol). The reaction mixture was stirred for 4 h at 25° C., under nitrogen. The reaction mixture was diluted with ethyl acetate, washed with saturated ammonium chloride solution, water, saturated sodium chloride solution and dried over sodium sulfate. The organic layer was concentrated, and the crude product was purified by ISCO flash chromatography (Teledyne Isco RediSep Flash Column 12 g, 30% to 100% ethyl acetate/hexanes) to afford (S)-3-cyclohexyl-N-(1-methyl-1H-pyrazol-3-yl)-2-[2-oxo-4-(2-trifluoromethyl-phenoxy)-2,5-dihydro-pyrrol-1-yl]-propionamide. This material was dissolved in dichloromethane (4 mL) and treated with 1M hydrogen chloride in diethyl ether (2 mL). Solvents were evaporated and the residue was triturated with diethyl ether and filtered to give (S)-3-cyclohexyl-N-(1-methyl-1H-pyrazol-3-yl)-2-[2-oxo-4-(2-trifluoromethyl-phenoxy)-2,5-dihydro-pyrrol-1-yl]-propionamide hydrochloride (20 mg, 16%) as a tan solid: LR-ES-MS m/z calculated for $C_{24}H_{27}F_3N_4O_3$ [M]$^+$ 476, observed [M+H]$^+$ 477; $^1$H NMR (300 MHz, DMSO-$d_6$) δ ppm 0.78-1.32 (m, 6H) 1.51-1.87 (m, 7H) 3.73 (s, 3H) 4.19 (d, J=18.7 Hz, 1H) 4.58 (d, J=18.7 Hz, 1H) 4.86-4.94 (m, 1H) 4.96 (s, 1H) 6.40 (d, J=2.1 Hz, 1H) 7.47-7.58 (m, 2H) 7.65 (d, J=7.8 Hz, 1H) 7.74-7.90 (m, 2H) 10.72 (s, 1H).

Example 91

(S)-3-Cyclohexyl-N-[1-(2-methoxy-ethyl)-1H-pyrazol-3-yl]-2-[2-oxo-4-(2-trifluoromethyl-phenoxy)-2,5-dihydro-pyrrol-1-yl]-propionamide Hydrochloride

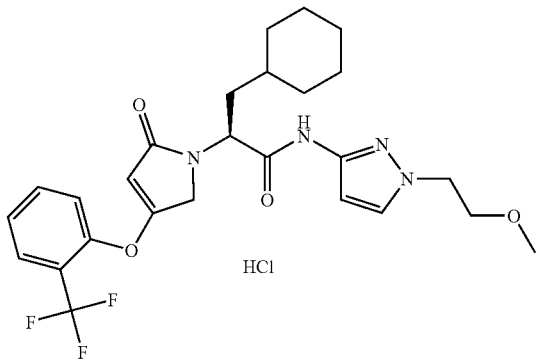

A solution of (S)-3-cyclohexyl-2-[2-oxo-4-(2-trifluoromethyl-phenoxy)-2,5-dihydro-pyrrol-1-yl]-propionic acid (prepared as in Example 32, 307 mg, 0.77 mmol) in N,N-dimethylformamide (4 mL) was treated with 1-(2-methoxy-ethyl)-1H-pyrazol-3-ylamine (prepared in U.S. Pat. Appl. US2008021032 Example 72, 130 mg, 0.92 mmol), benzotriazol-1-yl-oxy-tris(dimethylamino)phosphonium hexafluorophosphate (663 mg, 1.5 mmol) and N,N-diisopropylethylamine (193 mg, 1.5 mmol). The reaction mixture was stirred for 4 h at 25° C., under nitrogen. The reaction mixture was diluted with ethyl acetate, washed with saturated ammonium chloride, water, a saturated sodium chloride solution and dried over sodium sulfate. The organic layer was concentrated, and the crude product was purified by ISCO flash chromatography (Teledyne Isco RediSep Flash Column 12 g, 20% to 70% ethyl acetate/hexanes) to afford (S)-3-cyclohexyl-N-[1-(2-methoxy-ethyl)-1H-pyrazol-3-yl]-2-[2-oxo-4-(2-trifluoromethyl-phenoxy)-2,5-dihydro-pyrrol-1-yl]-propionamide. This material was dissolved in dichloromethane (4 mL) and treated with hydrogen chloride in diethyl ether (1 M, 2 mL). Solvents were evaporated and the residue was triturated with diethyl ether. The solid was filtered to give (S)-3-cyclohexyl-N-[1-(2-methoxy-ethyl)-1H-pyrazol-3-yl]-2-[2-oxo-4-(2-trifluoromethyl-phenoxy)-2,5-dihydro-pyrrol-1-yl]-propionamide hydrochloride (133 mg, 31%) as a light yellow solid: LR-ES-MS m/z calculated for $C_{26}H_{23}F_3N_4O_4$ [M]$^+$ 520, observed [M+H]$^+$ 521; $^1$H NMR (300 MHz, DMSO-$d_6$) δ ppm 0.68-1.40 (m, 6H) 1.40-1.83 (m, 7H) 3.19 (s, 3H) 3.62 (t, J=5.2 Hz, 2H) 4.12 (t, J=5.2 Hz, 2H) 4.16 (d, J=18.7 Hz, 1H) 4.57 (d, J=18.7 Hz, 1H) 4.88 (dd, J=10.6, 5.4 Hz, 1H) 4.94 (s, 1H) 6.39 (d, J=2.1 Hz, 1H) 7.51 (t, J=7.2 Hz, 1H) 7.55 (d, J=2.1 Hz, 1H) 7.64 (d, J=7.8 Hz, 1H) 7.73-7.90 (m, 2H) 10.75 (s, 1H).

Example 92

(S)-2-[4-(2,3-Dichloro-phenoxy)-2-oxo-2,5-dihydro-pyrrol-1-yl]-N-[1-(2-hydroxy-2-methyl-propyl)-1H-pyrazol-3-yl]-3-(tetrahydro-pyran-2-yl)-propionamide

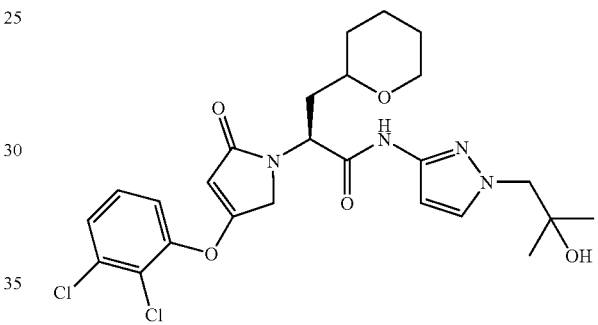

(S)-4-(2-Hydroxy-ethyl)-2,2-dimethyl-oxazolidine-3-carboxylic acid t-butyl ester was prepared according to the literature procedure (J. Org. Chem. 2001, 66, 206-215). A solution of dimethylsulfoxide (3.5 mL) in dichloromethane (15 mL) was added dropwise to a cooled solution (−78° C.) of oxalyl chloride (2M in dichloromethane, 13 mL) in dichloromethane (40 mL). The solution was stirred at −60° C. for 15 min before the slow addition of (S)-4-(2-hydroxy-ethyl)-2,2-dimethyl-oxazolidine-3-carboxylic acid t-butyl ester (4.5 g, 18.37 mmol) in dichloromethane (20 mL). The mixture was stirred at −60° C. for 30 min and triethylamine (13 mL) was added. After stirring for 30 min, the cooling bath was removed and the mixture was stirred for 1 h at room temperature. The mixture was extracted with dichloromethane and water. The organic layer was dried over sodium sulfate. Solvents were evaporated to give (S)-2,2-dimethyl-4-(2-oxo-ethyl)-oxazolidine-3-carboxylic acid t-butyl ester (4.50 g, 100%) as a colorless oil: $^1$H NMR (300 MHz, CDCl$_3$) δ ppm 1.42-1.52 (m, 12H), 1.51, 1.63 (2×s, 3H), 2.50-3.16 (m, 2H), 3.73 (d, J=9.1 Hz, 1H), 3.99-4.16 (m, 1H), 4.22-4.44 (m, 1H), 9.79 (s, 1H).

(S)-2,2-Dimethyl-4-(2-oxo-ethyl)-oxazolidine-3-carboxylic acid t-butyl ester (2.29 g, 9.44 mmol) was dissolved in dry tetrahydrofuran (25 mL). Then at −78° C., allyl magnesium bromide (1.0M in diethyl ether, 9.9 mL) was added. The mixture was warmed to −15° C. and stirred for 2 h. The mixture was extracted with diethyl ether and aqueous citric acid solution. The organic layer was washed with saturated sodium chloride solution, dried over sodium sulfate and solvents were evaporated to afford (S)-4-(2-hydroxy-pent-4-enyl)-2,2-dimethyl-oxazolidine-3-carboxylic acid tert-butyl ester (2.54 g) as an oil.

(S)-4-(2-Hydroxy-pent-4-enyl)-2,2-dimethyl-oxazolidine-3-carboxylic acid tert-butyl ester (2.54 g, 8.91 mmol) was dissolved in dry tetrahydrofuran (60 mL). Sodium hydride (60% suspension in mineral oil, 360 mg) was added. The mixture was stirred at 0° C. for 5 min. Then allylbromide (1.60 mL) was added. The mixture was stirred at room temperature for 18 h. Solvents were evaporated and the residue was extracted with diethyl ether and citric acid solution. The organic layer was washed with saturated sodium chloride solution and concentrated. The crude material was purified through flash column chromatography (silica gel, 5-30% ethyl acetate/hexanes) to afford (S)-4-(2-allyloxy-pent-4-enyl)-2,2-dimethyl-oxazolidine-3-carboxylic acid t-butyl ester (1.38 g, 48% yield for two steps) as an oil: $^1$H NMR (300 MHz, CDCl$_3$) δ ppm 1.48 (s, 12H), 1.56, 1.60 (2×s, 3H), 1.64-1.77 (m, 1H), 1.80-2.07 (m, 1H), 2.32 (br. s., 2H), 3.48 (br. s., 1H), 3.79-4.23 (m, 5H), 4.98-5.19 (m, 3H), 5.26 (d, J=17.2 Hz, 1H), 5.72-5.98 (m, 2H).

To a solution of (S)-4-(2-allyloxy-pent-4-enyl)-2,2-dimethyl-oxazolidine-3-carboxylic acid t-butyl ester (1.38 g, 4.24 mmol) in dichloromethane (10 mL) was added benzylidene[1,3-bis(2,4,6-trimethylphenyl)-2-imidazolidinylidene]dichloro-(tricyclohexylphosphine)ruthenium (144 mg, 4% equivalent). The mixture was stirred at room temperature for 4 h. Solvents were evaporated and the residue was purified through flash column chromatography (silica gel, 0-20% ethyl acetate/hexanes) to afford (S)-4-(3,6-dihydro-2H-pyran-2-ylmethyl)-2,2-dimethyl-oxazolidine-3-carboxylic acid t-butyl ester (1.16 g, 92%) as a brown oil: $^1$H NMR (300 MHz, CDCl$_3$) δ ppm 1.48 (s, 12H), 1.56, 16.0 (2×s, 3H), 1.69 (br. s., 1H), 1.81-2.20 (m, 3H), 3.55 (br. s., 1H), 3.83-4.02 (m, 2H), 4.00-4.28 (m, 3H), 5.61-5.93 (m, 2H).

To the a solution of (S)-4-(3,6-dihydro-2H-pyran-2-ylmethyl)-2,2-dimethyl-oxazolidine-3-carboxylic acid t-butyl ester (1.15 g, 3.8 mmol) in tetrahydrofuran (2 mL) was added methanol (15 mL) and p-toluene sulfonic acid monohydrate (40 mg). The mixture was stirred at room temperature overnight. Solvents were evaporated and the residue was extracted with ethyl acetate and sodium bicarbonate solution. The organic layer was washed with saturated sodium chloride solution and dried over sodium sulfate. After the evaporation of solvent, an oil was obtained (1.03 g). This oil (1.0 g) was dissolved in ethanol (25 mL) and 5% palladium on carbon (200 mg) was added. The mixture was hydrogenated at 50 psi for 45 min. The resulting mixture was filtered and solvents were evaporated to afford [(S)-2-hydroxy-1-(tetrahydro-pyran-2-ylmethyl)-ethyl]-carbamic acid t-butyl ester (948 mg) as an oil. $^1$H NMR (300 MHz, CDCl$_3$) δ ppm 1.45 (s, 9H), 1.47-1.74 (m, 6H), 1.74-1.94 (m, 2H), 3.30-3.51 (m, 2H), 3.62 (br. s., 2H), 3.69-3.85 (m, 2H), 3.98 (d, J=10.9 Hz, 1H), 5.25 (br. s., 1H).

[(S)-2-Hydroxy-1-(tetrahydro-pyran-2-ylmethyl)-ethyl]-carbamic acid t-butyl ester (843 mg, 3.64 mmol) was dissolved in acetonitrile (18 mL) and phosphate buffer (pH=7, 14 mL). Then 1-oxyl-2,2,6,6-tetramethylpiperidine (40 mg) was added. The mixture was warmed to 35° C. To this clear solution was added a solution of sodium chlorite (832 mg) in water (4 mL) and catalytic amount of bleach (1 mL of 5.25% sodium hypochlorite solution was diluted with water to 20 mL, 1.80 mL of the diluted solution was used). The mixture was stirred at 35° C. for 1.5 hr. Then a second portion of sodium chlorite (832 mg) in water (4 mL) and catalytic amount of diluted bleach was added over 2 h. The mixture was stirred for 1 h and then diluted with water (25 mL) and treated with sodium sulfite solution. The mixture was extracted with methyl t-butyl ether. The aqueous layer was acidified with 1N aqueous hydrochloric acid and extracted with methyl t-butyl ether. The organic layer was washed with saturated sodium chloride solution and solvents were evaporated to afford (S)-2-t-butoxycarbonylamino-3-(tetrahydro-pyran-2-yl)-propionic acid (707 mg, 71%) as an oil: [α]$_D$=+23.8 (chloroform); LR-ES-MS m/z calculated for C$_{13}$H$_{23}$NO$_5$ [M]$^+$ 273, observed [M+H]$^+$ 274; $^1$H NMR (300 MHz, CDCl$_3$) δ ppm 1.30-1.70 (m, 5H), 1.46 (s, 9H), 1.76-2.13 (m, 3H), 3.31-3.69 (m, 2H), 3.99, 4.07 (2×d, J=11.2 Hz, 1H), 4.35 (br. s., 1H), 5.52, 5.88 (2×br. s., 1H).

To a solution of (S)-2-t-butoxycarbonylamino-3-(tetrahydro-pyran-2-yl)-propionic acid (700 mg, 2.56 mmol) in N,N-dimethylformamide (6 mL) was added 1-(3-amino-pyrazol-1-yl)-2-methyl-propan-2-ol (prepared in U.S. Pat. Appl. US2008021032 Example 80, 398 mg, 2.57 mmol) and benzotriazol-1-yl-oxy-tris(dimethylamino)phosphonium hexafluorophosphate (1.36 g, 3.0 mmol). The mixture was stirred at 0° C. and N,N-diisopropylethylamine (0.4 mL) was added. The mixture was stirred at room temperature overnight and solvents were evaporated. The residue was treated with ethyl acetate and ammonium chloride solution, and the organic layer separated. The organic layer was washed with saturated sodium chloride solution and dried over sodium sulfate. Solvents were evaporated and the residue was purified through flash column chromatography (silica gel, 5 to 100% ethyl acetate/hexanes) to afford [(S)-1-[1-(2-hydroxy-2-methyl-propyl)-1H-pyrazol-3-ylcarbamoyl]-2-(tetrahydro-pyran-2-yl)-ethyl]-carbamic acid t-butyl ester (600 mg, 57%) as a white solid: LR-ES-MS m/z calculated for C$_{20}$H$_{34}$N$_4$O$_5$ [M]$^+$ 410, observed [M+H]$^+$ 411.

To a solution of [(S)-1-[1-(2-hydroxy-2-methyl-propyl)-1H-pyrazol-3-ylcarbamoyl]-2-(tetrahydro-pyran-2-yl)-ethyl]-carbamic acid t-butyl ester (570 mg) in dichloromethane (3 mL) was added trifluoroacetic acid (3 mL). The mixture was stirred at room temperature for 30 min. Solvents were evaporated and the residue was dried in vacuo. The waxy solid was dissolved in a methanolic hydrogen chloride solution. Solvents were evaporated and the residue was dried in vacuo. The white solid was triturated with diethyl ether and filtered to afford (S)-2-amino-N-[1-(2-hydroxy-2-methyl-propyl)-1H-pyrazol-3-yl]-3-(tetrahydropyran-2-yl)-propionamide hydrochloride (529 mg). LR-ES-MS m/z calculated for C$_{15}$H$_{26}$N$_4$O$_3$ 310 [M]$^+$, observed [M+H]$^+$ 311.

(S)-2-amino-N-[1-(2-hydroxy-2-methyl-propyl)-1H-pyrazol-3-yl]-3-(tetrahydropyran-2-yl)-propionamide hydrochloride (118 mg, 0.30 mmol) was dissolved in methanol (2 mL) and triethylamine (0.2 mL) was added. The mixture was evaporated to dryness. The residue was dissolved in acetonitrile (5 mL). To this solution was added (E)-4-bromo-3-(2,3-dichloro-phenoxy)-but-2-enoic acid ethyl ester (prepared as in Example 77, 109 mg, 0.30 mmol). The mixture was refluxed for 40 h. The mixture was evaporated and the residue was treated with ethyl acetate and water. The layers were separated and the organic layer was dried over sodium sulfate and concentrated to give a crude product (180 mg). One part of the crude product (30 mg) was purified through reverse phase preparative HPLC (acetonitrile in water, 25% to 100% linear gradient) to afford (S)-2-[4-(2,3-dichloro-phenoxy)-2-oxo-2,5-dihydro-pyrrol-1-yl]-N-[1-(2-hydroxy-2-methyl-propyl)-1H-pyrazol-3-yl]-3-(tetrahydro-pyran-2-yl)-propionamide as a white powder (6 mg): LR-ES-MS m/z calculated for C$_{25}$H$_{30}$Cl$_2$N$_4$O$_5$ [M]$^+$ 536, observed [M+H]$^+$ 537; $^1$H-NMR (CDCl$_3$) δ ppm 1.16 (s, 6H), 1.25-1.73 (m, 5H), 1.73-2.00 (m, 2H), 2.17-2.34 (m, 1H), 3.29-3.49 (m, 2H), 3.88-4.06 (m, 3H), 4.24 (d, J=17.8 Hz, 1H), 4.42 (d, J=17.8 Hz, 1H), 4.89 (s, 1H), 5.02-5.16 (m, 1H), 6.70 (br s, 1H), 7.14-7.23 (m, 1H), 7.28-7.37 (m, 3H), 7.42 (d, J=8.2 Hz, 1H), 8.76 (br s, 1H).

Example 93

(S)-2-[4-(2,6-Difluoro-phenoxy)-2-oxo-2,5-dihydro-pyrrol-1-yl]-N-[1-(2-hydroxy-2-methyl-propyl)-1H-pyrazol-3-yl]-3-(tetrahydro-pyran-2-yl)-propionamide

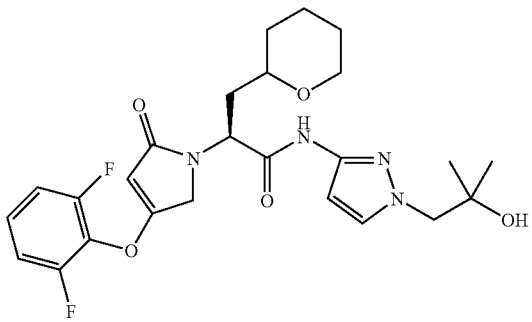

(S)-2-amino-N-[1-(2-hydroxy-2-methyl-propyl)-1H-pyrazol-3-yl]-3-(tetrahydropyran-2-yl)-propionamide hydrochloride (prepared as in Example 92, 300 mg, 0.78 mmol) was dissolved in methanol (5 mL) and N,N-diisopropylethylamine (0.5 mL) was added. The mixture was evaporated to dryness. The residue was dissolved acetonitrile (8 mL). To this solution was added (E)-4-bromo-3-(2,6-difluoro-phenoxy)-but-2-enoic acid ethyl ester (prepared as in Example 36, 296 mg, 0.92 mmol). The mixture was refluxed for 40 h. The mixture was evaporated and the residue was treated with ethyl acetate and water. The layers were separated and the organic layer was dried and concentrated. The crude material was purified through reverse phase preparative HPLC (acetonitrile in water, 25% to 100% linear gradient) to afford (S)-2-[4-(2,6-difluoro-phenoxy)-2-oxo-2,5-dihydro-pyrrol-1-yl]-N-[1-(2-hydroxy-2-methyl-propyl)-1H-pyrazol-3-yl]-3-(tetrahydro-pyran-2-yl)-propionamide (114 mg, 29%): HR-ES-MS m/z calculated for $C_{25}H_{30}N_4O_5F_2$ [M+H]$^+$ 505.2257, observed 505.2260; $^1$H NMR (300 MHz, CDCl$_3$) δ ppm 1.16 (s, 6H), 1.24-1.70 (m, 5H), 1.74-1.97 (m, 2H), 2.17-2.30 (m, 1H), 3.29-3.52 (m, 2H), 3.92-4.05 (m, 1H), 3.95 (s, 3H), 4.25 (d, J=17.8 Hz, 1H), 4.43 (d, J=17.8 Hz, 1H), 4.95 (s, 1H), 5.10 (dd, J=8.6, 6.5 Hz, 1H), 6.69 (s, 1H), 6.97-7.10 (m, 2H), 7.14-7.25 (m, 1H), 7.30 (s, 1H), 8.77 (br. s., 1H).

Example 94

(2S,4R)-2-[4-(2,3-Dichloro-phenoxy)-2-oxo-2,5-dihydro-pyrrol-1-yl]-4-ethoxy-pentanoic acid [1-(2-hydroxy-2-methyl-propyl)-1H-pyrazol-3-yl]-amide

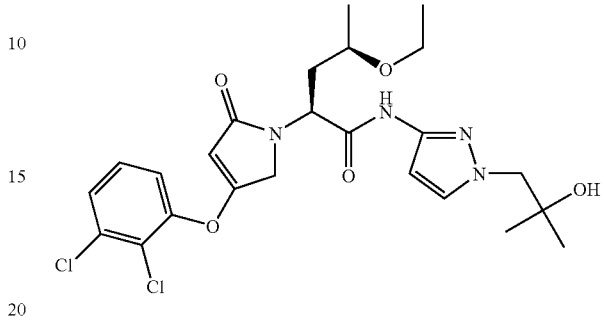

To a cooled solution of (S)-2,2-dimethyl-4-(2-oxo-ethyl)-oxazolidine-3-carboxylic acid t-butyl ester (2.05 g, 8.43 mmol) in dry tetrahydrofuran (25 mL) was added 1.4M methyl magnesium bromide in diethyl ether (6.02 mL) at −78° C. The mixture was stirred at −78° C. for 30 min and then warmed to −5° C. The mixture was extracted with diethyl ether and ammonium chloride solution. The organic layer was dried and concentrated. The crude mixture was purified by ISCO flash chromatography (0 to 60% ethyl acetate/hexanes) to give two fractions. The first fraction afforded (S)-4-((S)-2-hydroxy-propyl)-2,2-dimethyl-oxazolidine-3-carboxylic acid t-butyl ester as a colorless oil (870 mg): $^1$H NMR (300 MHz, CDCl$_3$) δ ppm 1.20 (d, J=6.0 Hz, 3H), 1.42-1.60 (m, 1H), 1.50 (s, 12H), 1.55 (s, 3H), 1.68-1.88 (m, 1H), 3.66 (d, J=8.8 Hz, 1H), 3.69-3.80 (m, 1H), 3.94-4.08 (m, 1H), 4.17-4.30 (m, 1H), 4.62 (br. s., 1H); The second fraction afforded (S)-4-((R)-2-hydroxy-propyl)-2,2-dimethyl-oxazolidine-3-carboxylic acid t-butyl ester as a white solid (740 mg): $^1$H NMR (300 MHz, CDCl$_3$) δ ppm 1.22 (d, J=6.0 Hz, 3H), 1.49 (s, 12H), 1.58 (br. s., 3H), 1.75-1.90 (m, 2H), 2.56 (br. s., 1H), 3.75-3.93 (m, 2H), 3.95-4.05 (m, 1H), 4.03-4.20 (m, 1H).

To a cooled solution of (S)-4-((R)-2-hydroxy-propyl)-2,2-dimethyl-oxazolidine-3-carboxylic acid t-butyl ester (730 mg, 2.81 mmol) in dry tetrahydrofuran (15 mL) was added sodium hydride at 0° C. (60% in mineral oil, 248 mg). The suspension was warmed to room temperature and ethyl iodide (1.2 mL) was added. The mixture was stirred overnight and extracted with diethyl ether and saturated sodium chloride solution. The organic layer was washed with saturated sodium chloride solution and dried over sodium sulfate. After the evaporation of solvents, an oily material was obtained (660 mg). This oily material was dissolved in a mixture of tetrahydrofuran (1 mL) and methanol (10 mL). To this solution was added p-toluene sulfonic acid (22 mg). The mixture was stirred at room temperature overnight. Solvents were evaporated and the residue was extracted with ethyl acetate and sodium bicarbonate solution. After the evaporation of solvents, the resulting oily compound (532 mg) was dissolved in a mixture of acetonitrile (11 mL) and phosphate buffer (8 mL, pH=7). Then 1-oxyl-2,2,6,6-tetramethylpiperidine (24 mg) and sodium chlorite (495 mg) in water (2.5 mL) were added. The solution was warmed to 35° C. and catalytic amount of diluted bleach (1 mL of 5.25% sodium hypochlorite solution diluted to 20 mL in water, 1 mL of the diluted solution was used) was added in 5 portions. The mixture was stirred for 2 h. Then second portion of sodium chlorite (495 mg) in water (2.5 mL) was added. The mixture was stirred at room temperature overnight. The mixture was cooled to 0° C. and adjusted to pH=9 with dilute sodium hydroxide solution. Sodium sulfite solution (2.7 g) in water (30 mL) was added and the mixture was stirred for 20 min. The resulting solution was extracted with methyl t-butyl ether. The organic layer was discarded and the aqueous layer was acidified with 1N aqueous hydrochloric acid to pH value about 2.0. The mixture was extracted with methyl t-butyl ether three times and dried over sodium sulfate. Solvents were evaporated to afford (2S,4R)-2-t-butoxycarbonylamino-4-ethoxy-pentanoic acid (279 mg) as a thick oil: LR-ES-MS m/z calculated for $C_{12}H_{23}NO_5$ [M] 261, observed 260 [M−H]; $^1$H NMR (300 MHz, CDCl$_3$) δ ppm 1.18 (t, 7.2 Hz, 3H), 1.22 (d, J=6.3 Hz, 3H), 1.46 (s, 9H), 1.88-2.16 (m, 2H), 3.26-3.43 (m, 1H), 3.55-3.72 (m, 2H), 4.27-4.39 (m, 1H), 5.59 (br. s., 1H), 10.51 (br. s., 1H).

(2S,4R)-2-t-butoxycarbonylamino-4-ethoxy-pentanoic acid (273 mg, 1.04 mmol) was mixed with 1-(3-amino-pyrazol-1-yl)-2-methyl-propan-2-ol (prepared in U.S. Pat. Appl. US2008021032 Example 80, 194.6 mg, 1.25 mmol) in N,N-dimethylformamide (10 mL). benzotriazol-1-yl-oxy-tris(dimethylamino)phosphonium hexafluorophosphate (695 mg, 1.57 mmol) and N,N-diisopropylethylamine (0.4 mL) was added at 0° C. The mixture was stirred at room temperature overnight. Solvents were evaporated and the residue was extracted with ethyl acetate and saturated sodium chloride solution. Solvents were evaporated and the crude material was purified by flash column chromatography (silica gel, 10-80% ethyl acetate/hexanes) to afford {(1S,3R)-3-ethoxy-1-[1-(2-hydroxy-2-methyl-propyl)-1H-pyrazol-3-ylcarbamoyl]-butyl}-carbamic acid t-butyl ester (306 mg, 73%) as a white solid: LR-ES-MS m/z calculated for $C_{19}H_{34}N_4O_5$ [M]$^+$ 398, observed [M+H]$^+$ 399; $^1$H NMR (300 MHz, CDCl$_3$, plus drops of CD$_3$OD) δ ppm 1.08-1.15 (m, 12H), 1.37 (s, 9H), 1.72-1.94 (m, 2H), 3.35-3.60 (m, 3H), 3.89 (s, 2H), 4.20 (m, 1H), 6.48 (br. s., 1H).

To a solution of {(1S,3R)-3-ethoxy-1-[1-(2-hydroxy-2-methyl-propyl)-1H-pyrazol-3-ylcarbamoyl]-butyl}-carbamic acid t-butyl ester (306 mg) in dichloromethane (3 mL) was added trifluoroacetic acid (2 mL). The solution was stirred at room temperature for 30 min. Solvents were evaporated and the residue was dried in vacuo. The resulting waxy material was dissolved in methanolic hydrogen chloride solution (5 mL). Solvents were evaporated and the residue was dried in vacuo. The white solid was triturated with dry diethyl ether and filtered to afford (2S,4R)-2-amino-4-ethoxy-pentanoic acid [1-(2-hydroxy-2-methyl-propyl)-1H-pyrazol-3-yl]-amide hydrochloride (274 mg). For the neutral free amine, LR-ES-MS m/z calculated for $C_{14}H_{26}N_4O_3$ [M]$^+$298, observed [M+H]$^+$ 299.

(2S,4R)-2-Amino-4-ethoxy-pentanoic acid [1-(2-hydroxy-2-methyl-propyl)-1H-pyrazol-3-yl]-amide hydrochloride (125 mg, 0.33 mmol) was dissolved in methanol (5 mL) and N,N-diisopropylethylamine (0.25 mL) was added. The solution was evaporated and the residue was dried. The resulting material was dissolved in acetonitrile (6 mL) containing N,N-diisopropylethylamine (0.25 mL). To this solution was added (E)-4-bromo-3-(2,3-dichloro-phenoxy)-but-2-enoic acid ethyl ester (prepared as in Example 77, 143 mg, 0.40 mmol). The mixture was refluxed for 7 h. Solvents were evaporated and the residue was extracted with ethyl acetate and water. The organic layer was dried and concentrated. The crude product was purified by flash column chromatography (silica gel, 20-100% ethyl acetate/hexanes) to afford 3-(2,3-dichloro-phenoxy)-4-{(1S,3R)-3-ethoxy-1-[1-(2-hydroxy-2-methyl-propyl)-1H-pyrazol-3-ylcarbamoyl]-butylamino}-but-2-enoic acid ethyl ester (60 mg). LR-ES-MS m/z calculated for $C_{26}H_{36}Cl_2N_4O_6$ [M]$^+$ 570, observed [M+H]$^+$ 571.

3-(2,3-Dichloro-phenoxy)-4-{(1S,3R)-3-ethoxy-1-[1-(2-hydroxy-2-methyl-propyl)-1H-pyrazol-3-ylcarbamoyl]-butylamino}-but-2-enoic acid ethyl ester (60 mg) was dissolved in tetrahydrofuran (2 mL). The sealed tube was heated in a microwave at 160° C. for 4 h. The resulting solution was concentrated and the residue was purified by reverse phase column chromatography (acetonitrile in water 25% to 100%) to afford (2S,4R)-2-[4-(2,3-dichloro-phenoxy)-2-oxo-2,5-dihydro-pyrrol-1-yl]-4-ethoxy-pentanoic acid [1-(2-hydroxy-2-methyl-propyl)-1H-pyrazol-3-yl]-amide (18 mg, 32%): HR-ES-MS m/z calculated for $C_{24}H_{30}Cl_2N_4O_5$ [M+H]$^+$ 525.1666, observed 525.1669; $^1$H NMR (300 MHz, CDCl$_3$) δ ppm 1.16 (s, 6H), 1.17-1.27 (m, 6H), 1.84-2.01 (m, 1H), 2.20-2.33 (m, 1H), 3.24-3.40 (m, 1H), 3.49-3.70 (m, 2H), 3.80 (br. s., 1H), 3.95 (s, 2H), 4.27 (d, J=17.8 Hz, 1H), 4.41 (d, J=17.8 Hz, 1H), 4.92 (s, 1H), 5.05 (t, J=7.2 Hz, 1H), 6.69 (d, J=1.9 Hz, 1H), 7.19 (dd, J=8.2, 1.2 Hz, 1H), 7.23-7.27 (m, 1H), 7.31 (d, J=1.9 Hz, 1H), 7.42 (dd, J=8.2, 1.2 Hz, 1H), 8.91 (br. s., 1H).

Example 95

(2S,4S)-2-[4-(2,3-Dichloro-phenoxy)-2-oxo-2,5-dihydro-pyrrol-1-yl]-4-ethoxy-pentanoic acid [1-(2-hydroxy-2-methyl-propyl)-1H-pyrazol-3-yl]-amide

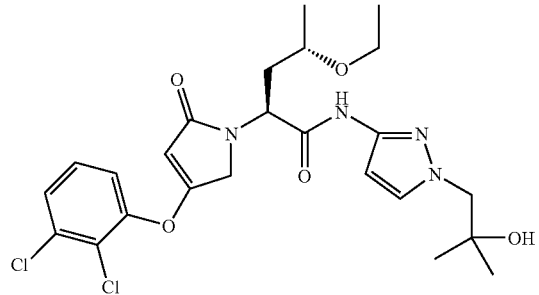

To a cooled solution of (S)-4-((S)-2-hydroxy-propyl)-2,2-dimethyl-oxazolidine-3-carboxylic acid t-butyl ester (prepared as in Example 94, 860 mg, 3.32 mmol) in dry tetrahydrofuran (15 mL) was added sodium hydride at 0° C. (60% in mineral oil, 292 mg). The suspension was warmed to room temperature and ethyl iodide (1.2 mL) was added. The mixture was stirred at room temperature for 20 h and extracted with diethyl ether and saturated sodium chloride solution. The organic layer was washed with saturated sodium chloride solution and dried over sodium sulfate. After the evaporation of solvents, an oily material was obtained (966 mg). This oily material was dissolved in a mixture of tetrahydrofuran (1 mL) and methanol (10 mL). To this solution was added p-toluene sulfonic acid monohydrate (32 mg). The mixture was stirred at room temperature overnight. Solvents were evaporated and the residue was extracted with ethyl acetate and sodium bicarbonate solution. After the evaporation of solvents, the resulting oily compound (800 mg) was dissolved in a mixture of acetonitrile (17 mL) and phosphate buffer (12 mL, pH=7). Then 1-oxyl-2,2,6,6-tetramethylpiperidine (41 mg) and sodium chlorite solution (731 mg in 4.0 mL of water) were added. The solution was warmed to 35° C. and catalytic amount of diluted bleach (1 mL of 5.25% sodium hypochlorite solution diluted to 20 mL in water, 1.6 mL of the diluted solution was used) was added in 5 portions. The mixture was stirred for 2 h. Then second portion of sodium chlorite (750 mg in 4.0 mL of water) was added. The mixture was stirred at room temperature overnight. The mixture was cooled to 0° C. and adjusted to pH=9 with dilute sodium hydroxide solution. Sodium sulfite solution (2.7 vg in 30 mL of water) was added and the mixture was stirred for 20 min. The resulting solution was extracted with methyl t-butyl ether. Organic layer was discarded and the aqueous layer was acidified with 1N aqueous hydrochloric acid to a pH value of about 2.0. The mixture was extracted with methyl t-butyl ether three times and dried over sodium sulfate. The solvents were evaporated to afford (2S,4S)-2-t-butoxycarbonylamino-4-ethoxy-pentanoic acid (401 mg) as a thick oil: LR-ES-MS m/z calculated for $C_{12}H_{23}NO_5$ [M] 261, observed 260 [M−H]; $^1$H NMR (300 MHz, CDCl$_3$) δ ppm 1.18-1.29 (m, 6H), 1.446 (s, 9H), 1.88-2.00 (m, 2H), 3.36-3.51 (m, 1H), 3.66-3.89 (m, 2H), 4.24-4.37 (m, 1H), 5.89 (d, J=4.5 Hz, 1H), 10.23 (br. s., 1H).

(2S,4S)-2-t-butoxycarbonylamino-4-ethoxy-pentanoic acid (401 mg, 1.536 mmol) was mixed with 1-(3-aminopyrazol-1-yl)-2-methyl-propan-2-ol (prepared in U.S. Pat. Appl. US2008021032 Example 80, 334 mg, 2.16 mmol) in N,N-dimethylformamide (10 mL). benzotriazol-1-yl-oxy-tris(dimethylamino)phosphonium hexafluorophosphate (1.23 g, 2.77 mmol) and N,N-diisopropylethylamine (0.7 mL) was added at 0° C. The mixture was stirred at room temperature overnight. Solvents were evaporated and the residue was extracted with ethyl acetate and saturated sodium chloride solution. The solvents were evaporated and the crude material was purified by flash column chromatography (silica gel, 10-80% ethyl acetate/hexanes) to afford {(1S,3S)-3-ethoxy-1-[1-(2-hydroxy-2-methyl-propyl)-1H-pyrazol-3-ylcarbamoyl]-butyl}-carbamic acid t-butyl ester (486 mg, 80%) as a white solid: LR-ES-MS m/z calculated for $C_{19}H_{34}N_4O_5$ [M]$^+$ 398, observed [M+H]$^+$ 399.

To a solution of {(1S,3S)-3-ethoxy-1-[1-(2-hydroxy-2-methyl-propyl)-1H-pyrazol-3-ylcarbamoyl]-butyl}-carbamic acid t-butyl ester (486 mg) in dichloromethane (3 mL) was added trifluoroacetic acid (2 mL). The solution was stirred at room temperature for 30 min. Solvents were evaporated and the residue was dried in vacuo. The resulting waxy material was dissolved in a methanolic hydrogen chloride solution (5 mL). The solvents were evaporated and the residue was dried in vacuo. The white solid was triturated with dry diethyl ether and filtered to afford (2S,4S)-2-amino-4-ethoxy-pentanoic acid [1-(2-hydroxy-2-methyl-propyl)-1H-pyrazol-3-yl]-amide hydrochloride (477 mg). For the neutral free amine, LR-ES-MS m/z calculated for $C_{14}H_{26}N_4O_3$ [M]$^+$ 298, observed [M+H]$^+$ 299.

(2S,4S)-2-Amino-4-ethoxy-pentanoic acid [1-(2-hydroxy-2-methyl-propyl)-1H-pyrazol-3-yl]-amide hydrochloride (150 mg, 0.40 mmol) was dissolved in methanol (5 mL) and N,N-diisopropylethylamine (0.3 mL) was added. The solution was evaporated and the residue was dried. The resulting material was dissolved in acetonitrile (6 mL) containing N,N-diisopropylethylamine (0.3 mL). To this solution was added (E)-4-bromo-3-(2,3-dichloro-phenoxy)-but-2-enoic acid ethyl ester (prepared as in Example 77, 286 mg, 0.80 mmol). The mixture was refluxed for 7 h. The solvents were evaporated and the residue was treated with ethyl acetate and water. The layers were separated and the organic layer was dried and concentrated. The crude product was purified by flash column chromatography (silica gel, 20-100% ethyl acetate/hexanes) to give 3-(2,3-dichloro-phenoxy)-4-{(1S,3S)-3-ethoxy-1-[1-(2-hydroxy-2-methyl-propyl)-1H-pyrazol-3-ylcarbamoyl]-butylamino}-but-2-enoic acid ethyl ester (120 mg): LR-ES-MS m/z calculated for $C_{26}H_{36}Cl_2N_4O_6$ [M]$^+$ 570, observed [M+H]$^+$ 571.

3-(2,3-Dichloro-phenoxy)-4-{(1S,3S)-3-ethoxy-1-[1-(2-hydroxy-2-methyl-propyl)-1H-pyrazol-3-ylcarbamoyl]-butylamino}-but-2-enoic acid ethyl ester (120 mg) was dissolved in tetrahydrofuran (2 mL). The sealed tube was heated in a microwave at 160° C. for 4 h. The resulting solution was concentrated and the residue was purified by reverse phase column chromatography (acetonitrile in water 25% to 100%) to give (2S,4S)-2-[4-(2,3-dichloro-phenoxy)-2-oxo-2,5-dihydro-pyrrol-1-yl]-4-ethoxy-pentanoic acid [1-(2-hydroxy-2-methyl-propyl)-1H-pyrazol-3-yl]-amide (40 mg) as a white powder: HR-ES-MS m/z calculated for $C_{24}H_{30}Cl_2N_4O_5$ [M+H]$^+$ 525.1666, observed 525.1669; $^1$H NMR (300 MHz, CDCl$_3$) δ ppm 1.14 (br. s., 6H), 1.19-1.30 (m, 6H), 1.88-2.09 (m, 1H), 2.18 (ddd, J=14.7, 9.3, 5.9 Hz, 1H), 3.30-3.46 (m, 1H), 3.54 (br. s., 1H), 3.61-3.77 (m, 1H), 3.94 (s, 2H), 4.14 (d, J=17.8 Hz, 1H), 4.47 (d, J=17.8 Hz, 1H), 4.92 (s, 1H), 5.01 (t, J=6.2 Hz, 1H), 6.68 (d, J=1.5 Hz, 1H), 7.16-7.33 (m, 4H), 7.42 (d, J=7.8 Hz, 1H), 9.35 (br. s., 1H).

Example 96

(S)-4-Methyl-2-[2-oxo-4-(3-trifluoromethyl-phenoxy)-2,5-dihydro-pyrrol-1-yl]-pentanoic acid [1-((R)-2,3-dihydroxy-propyl)-1H-pyrazol-3-yl]-amide

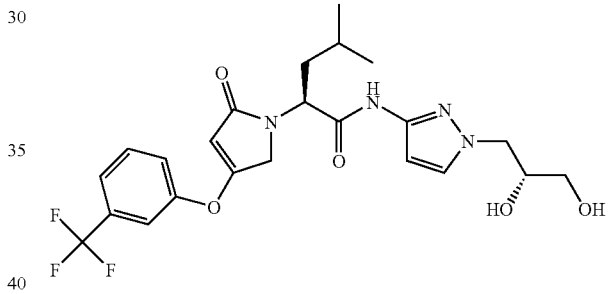

A mixture of 3-trifluoromethyl-phenol (1.09 mL, 8.96 mmol) and ethyl-2-butynoate (2.0 g, 17.83 mmol) in tetrahydrofuran (14 mL) was treated with 1,8-diazabicyclo[5.4.0]undec-7-ene (1.4 mL, 9.37 mmol). The reaction was then heated at 130° C. for 2 h. At this time, the reaction was concentrated in vacuo. The residue dissolved in dichloromethane (100 mL) and was washed with a 2N aqueous hydrochloric acid solution (1×100 mL), a 1N aqueous sodium hydroxide solution (1×100 mL) and a saturated aqueous sodium chloride solution (1×100 mL). The organics were then dried over magnesium sulfate, filtered, rinsed with dichloromethane and concentrated in vacuo. Purification by Analogix flash chromatography (40 g, 1-10% ethyl acetate/hexanes) afforded 3-(3-trifluoromethyl-phenoxy)-but-2-enoic acid ethyl ester (1.31 g, 53%) as a clear, colorless oil: HR-ES-MS m/z calculated for $C_{13}H_{13}O_3F_3$ [M+H]$^+$ 275.0890, observed 275.0889; $^1$H NMR (400 MHz, DMSO-d$_6$) δ ppm 1.13 (t, J=7.1 Hz, 3H), 2.45 (s, 3H), 4.01 (q, J=7.1 Hz, 2H), 4.68 (s, 1H), 7.49 (d, J=7.9 Hz, 1H), 7.57 (br. s., 1H), 7.66-7.75 (m, 2H).

A solution of 3-(3-trifluoromethyl-phenoxy)-but-2-enoic acid ethyl ester (1.31 g, 4.77 mmol) in carbon tetrachloride (25 mL) was treated with N-bromosuccinimide (0.94 g, 5.28 mmol) and benzoyl peroxide (0.12 g). The reaction was then warmed to reflux for 5 h. At this time, the reaction was cooled to 25° C. and then placed in the freezer over the weekend. At this time, the reaction was removed from the freezer and allowed to thaw. The resulting precipitate was removed by filtration. The filtrate was concentrated in vacuo. Purification by Analogix flash chromatography (40 g, 1-10% ethyl acetate/hexanes) afforded impure 4-bromo-3-(3-trifluoromethyl-phenoxy)-but-2-enoic acid ethyl ester (1.40 g, 83%) as a pale, yellow oil. The material was used without further purification.

A mixture of (L)-leucine methyl ester hydrochloride (0.79 g, 4.34 mmol) in acetonitrile (9.5 mL) was treated with N,N-diisopropylethylamine (0.70 mL, 4.26 mmol). After addition was complete, the mixture was stirred at 60° C. for 1 h. At this time, the reaction was cooled to 25° C., treated with N,N-diisopropylethylamine (0.70 mL, 4.26 mmol) and acetonitrile (9.5 mL) and then heated to 80° C. Upon reaching 80° C., the reaction was treated with a solution of 4-bromo-3-(3-trifluoromethyl-phenoxy)-but-2-enoic acid ethyl ester (1.40 g, 3.96 mmol) in acetonitrile (9.5 mL). After the addition was complete the reaction mixture was heated to 100° C. and stirred overnight. At this time, the reaction mixture was cooled to 25° C. and concentrated in vacuo. The residue was diluted with dichloromethane (100 mL) and was washed with a 2N aqueous hydrochloric acid solution (1×100 mL), a saturated aqueous sodium bicarbonate solution (1×100 mL), a saturated aqueous sodium chloride solution (1×100 mL), dried over magnesium sulfate, filtered, rinsed with dichloromethane and concentrated in vacuo. Purification by Analogix flash chromatography (40 g, 15-50% ethyl acetate/hexanes) afforded (S)-4-methyl-2-[2-oxo-4-(3-trifluoromethyl-phenoxy)-2,5-dihydro-pyrrol-1-yl]-pentanoic acid methyl ester (0.86 g, 59%) as a light, brown solid: HR-ES-MS m/z calculated for $C_{18}H_{20}NO_4F_3$ [M+H]$^+$ 372.1417, observed 372.1418; $^1$H NMR (400 MHz, DMSO-d$_6$) δ ppm 0.88 (d, J=6.6 Hz, 3H), 0.93 (d, J=6.6 Hz, 3H), 1.29-1.55 (m, 1H), 1.56-1.68 (m, 1H), 1.73-1.90 (m, 1H), 3.66 (s, 3H), 4.19 (d, J=18.1 Hz, 1H), 4.26 (d, J=18.1 Hz, 1H), 4.75 (dd, J=11.4, 4.6 Hz, 1H), 4.95 (s, 1H), 7.64-7.78 (m, 4H).

A mixture of (S)-4-methyl-2-[2-oxo-4-(3-trifluoromethyl-phenoxy)-2,5-dihydro-pyrrol-1-yl]-pentanoic acid methyl ester (0.86 g, 2.32 mmol) in tetrahydrofuran (15 mL) and water (5 mL) was treated with lithium hydroxide monohydrate (0.12 g, 2.85 mmol). The reaction was stirred at 25° C. for 3 h. At this time, the reaction was diluted with water (75 mL) and extracted with diethyl ether (1×75 mL). The aqueous layer was acidified with a 2N aqueous hydrochloric acid solution and then extracted with ethyl acetate (3×50 mL). The combined organics were dried over magnesium sulfate, filtered, rinsed with ethyl acetate and concentrated in vacuo to afford (S)-4-methyl-2-[2-oxo-4-(3-trifluoromethyl-phenoxy)-2,5-dihydro-pyrrol-1-yl]-pentanoic acid (0.71 g, 86%) as a light orange solid: HR-ES-MS m/z calculated for $C_{17}H_{18}NO_4F_3$ [M+H]$^+$ 358.1261, observed 358.1262. $^1$H NMR (400 MHz, DMSO-d$_6$) δ ppm 0.88 (d, J=6.5 Hz, 3H), 0.93 (d, J=6.5 Hz, 3H), 1.50 (m, 1H), 1.57-1.70 (m, 1H), 1.70-1.86 (m, 1H), 4.16 (d, J=17.9 Hz, 1H), 4.28 (d, J=17.9 Hz, 1H), 4.64 (dd, J=11.6, 4.2 Hz, 1H), 4.93 (s, 1H), 7.65-7.77 (m, 4H), 12.88 (br. s., 1H).

A solution of (S)-4-methyl-2-[2-oxo-4-(3-trifluoromethyl-phenoxy)-2,5-dihydro-pyrrol-1-yl]-pentanoic acid (0.71 g, 1.99 mmol) in dichloromethane (35 mL) was treated with 1-(3-dimethylaminopropyl)-3-ethylcarbodiimide (0.38 mL, 2.17 mmol) and 1-hydroxybenzotriazole (0.28 g, 2.07 mmol). The reaction was stirred at 25° C. for 20 min. At this time, the reaction was treated with 1-((R)-2,2-dimethyl-[1,3]dioxolan-4-yl-methyl)-1H-pyrazol-3-ylamine (prepared as in Example 49, 0.49 g, 2.48 mmol). The reaction mixture was stirred at 25° C. for 1.5 d. At this time, the reaction was diluted with dichloromethane (50 mL) and was washed with a saturated aqueous ammonium chloride solution (2×50 mL), a saturated aqueous sodium bicarbonate solution (1×100 mL), water (1×100 mL) and a saturated aqueous sodium chloride solution (1×100 mL), dried over magnesium sulfate, filtered, rinsed with dichloromethane and concentrated in vacuo. Purification by Analogix flash chromatography (40 g, 50-100% ethyl acetate/hexanes) afforded (S)-4-methyl-2-[2-oxo-4-(3-trifluoromethyl-phenoxy)-2,5-dihydro-pyrrol-1-yl]-pentanoic acid [1-((R)-2,2-dimethyl-[1,3]dioxolan-4-yl-methyl)-1H-pyrazol-3-yl]-amide (0.54 g, 51%) as a light, orange solid: HR-ES-MS m/z calculated for $C_{26}H_{31}N_4O_5F_3$ [M+H]$^+$ 537.2320, observed 537.2319; $^1$H NMR (400 MHz, DMSO-d$_6$) δ ppm 0.91 (d, J=6.4 Hz, 3H), 0.95 (d, J=6.4 Hz, 3H), 1.25 (s, 3H), 1.30 (s, 3H), 1.47 (br. s., 1H), 1.54-1.64 (m, 1H), 1.70-1.82 (m, 1H), 3.74 (dd, J=8.4, 5.9 Hz, 1H), 3.94-4.05 (m, 1H), 4.05-4.17 (m, 2H), 4.21 (d, J=18.4 Hz, 1H), 4.35 (quin, J=5.8 Hz, 1H), 4.60 (d, J=18.4 Hz, 1H), 4.84-4.92 (m, 1H), 4.91 (s, 1H), 6.44 (d, J=2.1 Hz, 1H), 7.60 (d, J=2.1 Hz, 1H), 7.65-7.78 (m, 4H), 10.79 (s, 1H).

A solution of (S)-4-methyl-2-[2-oxo-4-(3-trifluoromethyl-phenoxy)-2,5-dihydro-pyrrol-1-yl]-pentanoic acid [1-((R)-2,2-dimethyl[1,3]dioxolan-4-yl-methyl)-1H-pyrazol-3-yl]-amide (0.54 g, 1.00 mmol) in dichloromethane (10 mL) and methanol (10 mL) at 25° C. was treated with p-toluenesulfonic acid monohydrate (0.04 g, 0.21 mmol). The reaction was stirred at 25° C. overnight. At this time, the reaction was concentrated in vacuo. The residue was diluted with dichloromethane (50 mL) and was washed with a saturated aqueous sodium bicarbonate solution (1×50 mL), water (1×50 mL) and a saturated aqueous sodium chloride solution (1×50 mL), dried over magnesium sulfate, filtered, rinsed with dichloromethane and concentrated in vacuo. Purification by Analogix flash chromatography (40 g, 1-10% methanol/dichloromethane gradient) afforded (S)-4-methyl-2-[2-oxo-4-(3-trifluoromethyl-phenoxy)-2,5-dihydro-pyrrol-1-yl]-pentanoic acid [1-((R)-2,3-dihydroxy-propyl)-1H-pyrazol-3-yl]-amide (0.38 g, 78%) as a light, yellow solid: HR-ES-MS m/z calculated for $C_{23}H_{27}N_4O_5F_3$ [M+H]$^+$ 497.2007, observed 497.2007; $^1$H NMR (400 MHz, DMSO-d$_6$) δ ppm 0.91 (d, J=6.5 Hz, 3H), 0.95 (d, J=6.5 Hz, 3H), 1.36-1.54 (m, 1H), 1.54-1.64 (m, 1H), 1.70-1.84 (m, 1H), 3.22-3.32 (m, 2H), 3.72-3.81 (m, 1H), 3.87 (dd, J=13.6, 7.7 Hz, 1H), 4.09 (dd, J=13.6, 4.0 Hz, 1H), 4.21 (d, J=18.3 Hz, 1H), 4.60 (d, J=18.3 Hz, 1H), 4.70 (t, J=5.6 Hz, 1H), 4.86-4.96 (m, 3H), 6.42 (d, J=2.1 Hz, 1H), 7.54 (d, J=2.1 Hz, 1H), 7.65-7.74 (m, 3H), 7.75 (s, 1H), 10.76 (s, 1H).

Example 97

(S)-2-[4-(3-Chloro-2-fluoro-phenoxy)-2-oxo-2,5-dihydro-pyrrol-1-yl]-4-methyl-pentanoic acid [1-((R)-2,3-dihydroxy-propyl)-1H-pyrazol-3-yl]-amide

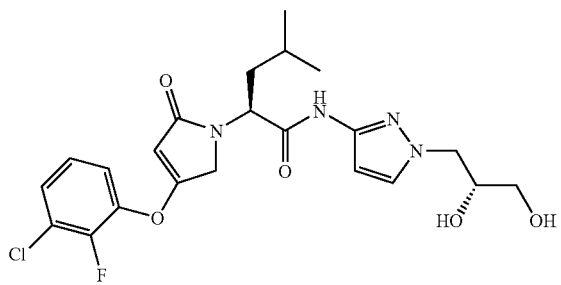

A mixture of 3-chloro-2-fluoro-phenol (1.31 g, 8.93 mmol) and ethyl-2-butynoate (2.0 g, 17.83 mmol) in tetrahydrofuran (14 mL) was treated with 1,8-diazabicyclo[5.4.0]undec-7-ene (1.4 mL, 9.37 mmol). The reaction was then heated at 130° C. for 2 h. At this time, the reaction was cooled to 25° C. and was stirred at 25° C. overnight. At this time, the reaction was concentrated in vacuo. The residue was dissolved in dichloromethane (100 mL) and was washed with a 2N aqueous hydrochloric acid solution (1×100 mL), a 1N aqueous sodium hydroxide solution (1×100 mL) and a saturated aqueous sodium chloride solution (1×100 mL). The organics were then dried over magnesium sulfate, filtered, rinsed with dichloromethane, and concentrated in vacuo. Purification by Analogix flash chromatography (40 g, 1-10% ethyl acetate/hexanes) afforded 3-(3-chloro-2-fluoro-phenoxy)-but-2-enoic acid ethyl ester (1.41 g, 61%) as a white solid: HR-ES-MS m/z calculated for $C_{12}H_{12}O_3FCl$ [M+H]$^+$ 259.0532, observed 259.0531; $^1$H NMR (400 MHz, DMSO-d$_6$) δ ppm 1.14 (t, J=7.1 Hz, 3H), 2.45 (s, 3H), 4.03 (q, J=7.1 Hz, 2H), 4.76 (s, 1H), 7.27-7.39 (m, 2H), 7.50-7.61 (m, 1H).

A solution of 3-(3-chloro-2-fluoro-phenoxy)-but-2-enoic acid ethyl ester (1.41 g, 5.45 mmol) in carbon tetrachloride (30 mL) was treated with N-bromosuccinimide (1.07 g, 6.01 mmol) and benzoyl peroxide (0.15 g). The reaction was then warmed to reflux for 5 h. At this time, the reaction was cooled to 25° C. and then placed in the freezer over the weekend. At this time, the reaction was removed from the freezer and allowed to thaw. The resulting precipitate was removed by filtration. The filtrate was concentrated in vacuo. Purification by Analogix flash chromatography (40 g, 1-10% ethyl acetate/hexanes) afforded impure 4-bromo-3-(3-chloro-2-fluoro-phenoxy)-but-2-enoic acid ethyl ester (1.59 g, 86%) as a white solid. The material was used without further purification.

A mixture of (L)-leucine methyl ester hydrochloride (0.94 g, 5.17 mmol) in acetonitrile (11 mL) was treated with N,N-diisopropylethylamine (0.84 mL, 5.08 mmol). After addition was complete, the mixture was stirred at 60° C. for 1 h. At this time, the reaction was cooled to 25° C., treated with N,N-diisopropylethylamine (0.84 mL, 5.08 mmol) and acetonitrile (11 mL) and then heated to 80° C. Upon reaching 80° C., the reaction was treated with a solution of 4-bromo-3-(3-chloro-2-fluoro-phenoxy)-but-2-enoic acid ethyl ester (1.59 g, 4.71 mmol) in acetonitrile (11 mL). After the addition was complete the reaction mixture was heated to 100° C. and stirred overnight. At this time, the reaction mixture was cooled to 25° C. and concentrated in vacuo. The residue was diluted with dichloromethane (100 mL) and was washed with a 2N aqueous hydrochloric acid solution (1×100 mL), a saturated aqueous sodium bicarbonate solution (1×100 mL), a saturated aqueous sodium chloride solution (1×100 mL), dried over magnesium sulfate, filtered, rinsed with dichloromethane and concentrated in vacuo. Purification by Analogix flash chromatography (40 g, 15-50% ethyl acetate/hexanes) afforded (S)-2-[4-(3-chloro-2-fluoro-phenoxy)-2-oxo-2,5-dihydro-pyrrol-1-yl]-4-methyl-pentanoic acid methyl ester (0.87 g, 52%) as a red/orange oil: HR-ES-MS m/z calculated for $C_{17}H_{19}NO_4FCl$ [M+H]$^+$ 356.1060, observed 356.1060; $^1$H NMR (400 MHz, DMSO-d$_6$) δ ppm 0.88 (d, J=6.6 Hz, 3H), 0.93 (d, J=6.6 Hz, 3H), 1.36-1.54 (m, 1H), 1.62 (ddd, J=14.0, 9.6, 4.6 Hz, 1H), 1.81 (ddd, J=14.0, 11.4, 4.6 Hz, 1H), 3.66 (s, 3H), 4.22 (d, J=18.3 Hz, 1H), 4.28 (d, J=18.3 Hz, 1H), 4.74 (dd, J=11.4, 4.6 Hz, 1H), 5.07 (s, 1H), 7.33 (td, J=8.1, 1.4 Hz, 1H), 7.48-7.55 (m, 1H), 7.58 (ddd, J=8.1, 6.7, 1.4 Hz, 1H).

A mixture of (S)-2-[4-(3-chloro-2-fluoro-phenoxy)-2-oxo-2,5-dihydro-pyrrol-1-yl]-4-methyl-pentanoic acid methyl ester (0.87 g, 2.46 mmol) in tetrahydrofuran (15 mL) and water (5 mL) was treated with lithium hydroxide monohydrate (0.12 g, 2.85 mmol). The reaction was stirred at 25° C. for 2.5 h. At this time, the reaction was diluted with water (75 mL) and extracted with diethyl ether (1×75 mL). The aqueous layer was acidified with a 2N aqueous hydrochloric acid solution and then extracted with ethyl acetate (3×50 mL). The combined organics were dried over magnesium sulfate, filtered, rinsed with ethyl acetate and concentrated in vacuo to afford (S)-2-[4-(3-chloro-2-fluoro-phenoxy)-2-oxo-2,5-dihydro-pyrrol-1-yl]-4-methyl-pentanoic acid (0.75 g, 90%) as a light orange solid: HR-ES-MS m/z calculated for $C_{16}H_{17}NO_4FCl$ [M+H]$^+$ 342.0903, observed 342.0904; $^1$H NMR (400 MHz, DMSO-d$_6$) δ ppm 0.87 (d, J=6.5 Hz, 3H), 0.93 (d, J=6.5 Hz, 3H), 1.35-1.56 (m, 1H), 1.56-1.70 (m, 1H), 1.72-1.86 (m, 1H), 4.19 (d, J=18.2 Hz, 1H), 4.29 (d, J=18.2 Hz, 1H), 4.63 (dd, J=11.5, 4.3 Hz, 1H), 5.05 (s, 1H), 7.33 (td, J=8.3, 1.4 Hz, 1H), 7.49-7.55 (m, 1H), 7.57 (ddd, J=8.3, 6.8, 1.4 Hz, 1H), 12.92 (br. s., 1H).

A solution of (S)-2-[4-(3-chloro-2-fluoro-phenoxy)-2-oxo-2,5-dihydro-pyrrol-1-yl]-4-methyl-pentanoic acid (0.75 g, 2.20 mmol) in dichloromethane (39 mL) was treated with 1-(3-dimethylaminopropyl)-3-ethylcarbodiimide (0.42 mL, 2.40 mmol) and 1-hydroxybenzotriazole (0.31 g, 2.29 mmol). The reaction was stirred at 25° C. for 20 min. At this time, the reaction was treated with 1-((R)-2,2-dimethyl-[1,3]dioxolan-4-yl-methyl)-1H-pyrazol-3-ylamine (prepared as in Example 49, 0.53 g, 2.68 mmol). The reaction mixture was stirred at 25° C. for 18 h. At this time, the reaction was diluted with dichloromethane (50 mL) and was washed with a saturated aqueous ammonium chloride solution (2×50 mL), a saturated aqueous sodium bicarbonate solution (1×100 mL), water (1×100 mL) and a saturated aqueous sodium chloride solution (1×100 mL), dried over magnesium sulfate, filtered, rinsed with dichloromethane and concentrated in vacuo. Purification by Analogix flash chromatography (40 g, 50-100% ethyl acetate/hexanes) afforded (S)-2-[4-(3-chloro-2-fluoro-phenoxy)-2-oxo-2,5-dihydro-pyrrol-1-yl]-4-methyl-pentanoic acid [1-((R)-2,2-dimethyl-[1,3]dioxolan-4-yl-methyl)-1H-pyrazol-3-yl]-amide (0.56 g, 49%) as a light yellow solid: HR-ES-MS m/z calculated for $C_{25}H_{30}N_4O_5FCl$ [M+H]$^+$ 521.1962, observed 521.1963; $^1$H NMR (400 MHz, DMSO-d$_6$) δ ppm 0.91 (d, J=6.4 Hz, 3H), 0.94 (d, J=6.4 Hz, 3H), 1.25 (s, 3H), 1.30 (s, 3H), 1.46 (br. s., 1H), 1.51-1.65 (m, 1H), 1.71-1.82 (m, 1H), 3.74 (dd, J=8.5, 5.8 Hz, 1H), 4.01 (dd, J=8.2, 6.3 Hz, 1H), 4.04-4.18 (m, 2H), 4.25 (d, J=18.5 Hz, 1H), 4.35 (dq, J=6.0, 5.8 Hz, 1H), 4.61 (d, J=18.5 Hz, 1H), 4.89 (dd, J=10.9, 4.7 Hz, 1H), 5.03 (s, 1H), 6.44 (d, J=2.1 Hz, 1H), 7.33 (td, J=8.3, 1.3 Hz, 1H), 7.50-7.60 (m, 2H), 7.60 (d, J=2.1 Hz, 1H), 10.80 (s, 1H).

A solution of (S)-2-[4-(3-chloro-2-fluoro-phenoxy)-2-oxo-2,5-dihydro-pyrrol-1-yl]-4-methyl-pentanoic acid [1-((R)-2,2-dimethyl-[1,3]dioxolan-4-yl-methyl)-1H-pyrazol-3-yl]-amide (0.56 g, 1.08 mmol) in dichloromethane (10 mL) and methanol (10 mL) at 25° C. was treated with p-toluenesulfonic acid monohydrate (0.04 g, 0.21 mmol). The reaction was stirred at 25° C. overnight. At this time, the reaction was concentrated in vacuo. The residue was diluted with dichloromethane (50 mL) and was washed with a saturated aqueous sodium bicarbonate solution (1×50 mL), water (1×50 mL) and a saturated aqueous sodium chloride solution (1×50 mL), dried over magnesium sulfate, filtered, rinsed with dichloromethane and concentrated in vacuo. Purification by Analogix flash chromatography (40 g, 1-10% methanol/dichloromethane gradient) afforded (S)-2-[4-(3-chloro-2-fluoro-phenoxy)-2-oxo-2,5-dihydro-pyrrol-1-yl]-4-methyl-pentanoic acid [1-((R)-2,3-dihydroxy-propyl)-1H-pyrazol-3-yl]-amide (0.41 g, 79%) as a light, yellow solid: HR-ES- MS m/z calculated for $C_{22}H_{27}N_4O_5FCl$ [M+H]$^+$ 481.1649, observed 481.1650; $^1$H NMR (400 MHz, DMSO-$d_6$) δ ppm 0.91 (d, J=6.4 Hz, 3H), 0.94 (d, J=6.4 Hz, 3H), 1.39-1.51 (m, 1H), 1.51-1.64 (m, 1H), 1.70-1.81 (m, 1H), 3.22-3.33 (m, 2H), 3.71-3.82 (m, 1H), 3.87 (dd, J=13.6, 7.5 Hz, 1H), 4.09 (dd, J=13.6, 3.8 Hz, 1H), 4.25 (d, J=18.5 Hz, 1H), 4.62 (d, J=18.5 Hz, 1H), 4.70 (t, J=5.6 Hz, 1H), 4.88 (dd, J=10.8, 5.0 Hz, 1H), 4.93 (d, J=5.3 Hz, 1H), 5.03 (s, 1H), 6.41 (d, J=2.1 Hz, 1H), 7.33 (td, J=8.3, 1.5 Hz, 1H), 7.49-7.61 (m, 3H), 10.77 (s, 1H).

Example 98

(S)-4-Methyl-2-[2-oxo-4-(5,6,7,8-tetrahydro-naphthalen-1-yloxy)-2,5-dihydro-pyrrol-1-yl]-pentanoic acid [1-((R)-2,3-dihydroxy-propyl)-1H-pyrazol-3-yl]-amide

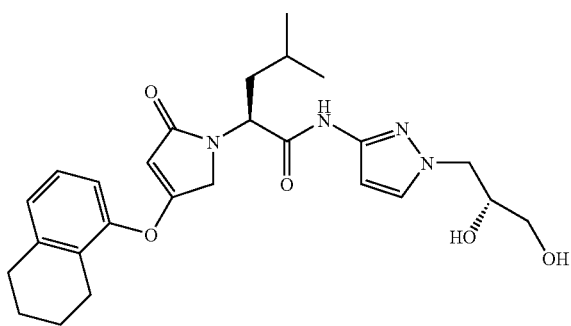

A mixture of 5,6,7,8-tetrahydro-naphthalen-1-ol (3.00 g, 20.24 mmol) and ethyl-2-butynoate (13.62 g, 121.46 mmol) in tetrahydrofuran (100 mL) was treated with potassium carbonate (3.10 g, 22.43 mmol) and 4-dimethylaminopyridine (0.26 g, 2.12 mmol). The reaction was then heated at 85° C. overnight. At this time, the reaction was cooled to 25° C. and was stirred at 25° C. overnight. At this time, the reaction was concentrated in vacuo. The residue was dissolved in ethyl acetate (200 mL) and was washed with water (1×100 mL) and a saturated aqueous sodium chloride solution (1×100 mL). The organics were then dried over magnesium sulfate, filtered, rinsed with ethyl acetate and concentrated in vacuo. The material was taken up in ethyl acetate and absorbed onto silica gel. Purification by Analogix flash chromatography (115 g, 1-10% ethyl acetate/hexanes) afforded 3-(5,6,7,8-tetrahydro-naphthalen-1-yloxy)-but-2-enoic acid ethyl ester (3.82 g, 72%) as a light yellow oil: HR-ES-MS m/z calculated for $C_{26}H_{34}N_4O_5$ [M+H]$^+$ 483.2602, observed 483.2603; $^1$H NMR (400 MHz, DMSO-$d_6$) δ ppm 1.11 (t, J=7.1 Hz, 3H), 1.61-1.77 (m, 4H), 2.44 (s, 3H), 2.46 (br. s., 2H), 2.76 (br. s., 2H), 3.98 (q, J=7.1 Hz, 2H), 4.57 (s, 1H), 6.84 (d, J=7.7 Hz, 1H), 7.03 (d, J=7.7 Hz, 1H), 7.18 (t, J=7.7 Hz, 1H).

A solution of 3-(5,6,7,8-tetrahydro-naphthalen-1-yloxy)-but-2-enoic acid ethyl ester (0.69 g, 2.65 mmol) in dichloromethane (14 mL) was treated with N-bromosuccinimide (0.50 g, 2.80 mmol) and 2,2'-azobis(2,4-dimethylvaleronitrile) (31.6 mg, 0.12 mmol). The reaction was then warmed to 45° C. where it stirred overnight. At this time, the reaction was diluted with dichloromethane (50 mL) and was washed with water (1×50 mL) and a saturated aqueous sodium chloride solution (1×50 mL), dried over magnesium sulfate, filtered, rinsed with dichloromethane, and concentrated in vacuo. Purification by Analogix flash chromatography (40 g, 1-10% ethyl acetate/hexanes) afforded impure 4-bromo-3-(5,6,7,8-tetrahydro-naphthalen-1-yloxy)-but-2-enoic acid ethyl ester (638.8 mg, 71%) as a yellow oil. The material was used without further purification.

A mixture of (L)-leucine methyl ester hydrochloride (0.38 g, 2.09 mmol) in acetonitrile (4.4 mL) was treated with N,N-diisopropylethylamine (0.33 mL, 2.02 mmol). After addition was complete, the mixture was stirred at 60° C. for 1.3 h. At this time, the reaction was cooled to 25° C., treated with N,N-diisopropylethylamine (0.33 mL, 2.02 mmol) and acetonitrile (4.4 mL) and then heated to 80° C. Upon reaching 80° C., the reaction was treated with a solution of 4-bromo-3-(5,6,7,8-tetrahydro-naphthalen-1-yloxy)-but-2-enoic acid ethyl ester (639 mg, 1.88 mmol) in acetonitrile (4.4 mL). After the addition was complete, the reaction mixture was heated to 100° C. where it stirred overnight. At this time, the reaction mixture was cooled to 25° C. and concentrated in vacuo. The residue was diluted with dichloromethane (100 mL) and was washed with a 2N aqueous hydrochloric acid solution (1×100 mL), a saturated aqueous sodium bicarbonate solution (1×100 mL), a saturated aqueous sodium chloride solution (1×100 mL), dried over magnesium sulfate, filtered, rinsed with dichloromethane and concentrated in vacuo. Purification by Analogix flash chromatography (40 g, 15-50% ethyl acetate/hexanes) afforded impure (S)-4-methyl-2-[2-oxo-4-(5,6,7,8-tetrahydro-naphthalen-1-yloxy)-2,5-dihydro-pyrrol-1-yl]-pentanoic acid methyl ester (102 mg, 15%) as an orange/red oil. The material was used without further purification.

A mixture of (S)-4-methyl-2-[2-oxo-4-(5,6,7,8-tetrahydro-naphthalen-1-yloxy)-2,5-dihydro-pyrrol-1-yl]-pentanoic acid methyl ester (94 mg, 0.26 mmol) in tetrahydrofuran (1.5 mL) and water (0.5 mL) was treated with lithium hydroxide monohydrate (14 mg, 0.33 mmol). The reaction was stirred at 25° C. for 3 h. At this time, the reaction was concentrated in vacuo. The residue was diluted with water (25 mL) and was extracted with diethyl ether (1×25 mL). The aqueous layer was then acidified with a 1N aqueous hydrochloric acid solution and then extracted with 10% methanol/dichloromethane (2×25 mL). The organics were then dried over magnesium sulfate, filtered, rinsed with dichloromethane and concentrated in vacuo to afford (S)-4-methyl-2-[2-oxo-4-(5,6,7,8-tetrahydro-naphthalen-1-yloxy)-2,5-dihydro-pyrrol-1-yl]-pentanoic acid (61 mg, 67%) as an orange solid: $^1$H NMR (300 MHz, DMSO-$d_6$) δ ppm 0.87 (d, J=6.3 Hz, 3H), 0.93 (d, J=6.3 Hz, 3H), 1.36-1.84 (m, 7H), 2.53-2.61 (m, 2H), 2.68-2.83 (m, 2H), 4.12 (d, J=17.8 Hz, 1H), 4.24 (d, J=17.8 Hz, 1H), 4.62 (dd, J=11.2, 4.2 Hz, 1H), 4.66 (s, 1H), 6.99-7.07 (m, 2H), 7.18 (t, J=7.8 Hz, 1H), 12.84 (br. s., 1H).

A solution of (S)-4-methyl-2-[2-oxo-4-(5,6,7,8-tetrahydro-naphthalen-1-yloxy)-2,5-dihydro-pyrrol-1-yl]-pentanoic acid (59 mg, 0.17 mmol) in N,N-dimethylformamide (1 mL) at 25° C. was treated with N,N-diisopropylethylamine (0.08 mL, 0.51 mmol), a solution of 1-((R)-2,2-dimethyl-[1,3]dioxolan-4-yl-methyl)-1H-pyrazol-3-ylamine (prepared as in Example 49, 41 mg, 0.20 mmol) in N,N-dimethylformamide (0.9 mL) and (benzotriazol-1-yloxy)tris(dimethylamino)phosphonium hexafluorophosphate (115 mg, 0.26 mmol). The reaction was stirred at 25° C. overnight. At this time, the reaction was diluted with ethyl acetate (25 mL) and was washed with a saturated aqueous ammonium chloride solution (1×25 mL), a saturated aqueous sodium bicarbonate solution (1×25 mL) and a saturated aqueous sodium chloride solution (1×25 mL), dried over magnesium sulfate, filtered, rinsed with ethyl acetate and concentrated in vacuo. Purification by Analogix flash chromatography (24 g, 50-100% ethyl acetate/hexanes) afforded (S)-4-methyl-2-[2-oxo-4-(5,6,7,8-tetrahydro-naphthalen-1-yloxy)-2,5-dihydro-pyrrol-1-yl]- pentanoic acid [1-((R)-2,2-dimethyl-[1,3]dioxolan-4-yl-methyl)-1H-pyrazol-3-yl]-amide (43 mg, 47%) as a light yellow solid: $^1$H NMR (300 MHz, DMSO-d$_6$) δ ppm 0.90 (d, J=6.3 Hz, 3H), 0.94 (d, J=6.3 Hz, 3H), 1.25 (s, 3H), 1.30 (s, 3H), 1.33-1.66 (m, 2H), 1.64-1.83 (m, 5H), 2.57 (br. s., 2H), 2.67-2.80 (m, 2H), 3.73 (dd, J=8.5, 5.7 Hz, 1H), 4.00 (dd, J=8.5, 6.5 Hz, 1H), 4.07-4.14 (m, 1H), 4.18 (d, J=18.4 Hz, 1H), 4.26-4.41 (m, 1H), 4.56 (d, J=18.4 Hz, 1H), 4.65 (s, 1H), 4.88 (dd, J=10.3, 4.8 Hz, 1H), 6.43 (d, J=2.1 Hz, 1H), 6.97-7.07 (m, 2H), 7.18 (t, J=8.2 Hz, 1H), 7.59 (d, J=2.1 Hz, 1H), 10.76 (s, 1H).

A solution of (S)-4-methyl-2-[2-oxo-4-(5,6,7,8-tetrahydro-naphthalen-1-yloxy)-2,5-dihydro-pyrrol-1-yl]-pentanoic acid [1-((R)-2,2-dimethyl-[1,3]dioxolan-4-yl-methyl)-1H-pyrazol-3-yl]-amide (43 mg, 0.08 mmol) in methanol (1 mL) at 25° C. was treated with p-toluenesulfonic acid monohydrate (4 mg, 0.02 mmol). The reaction was stirred at 25° C. overnight. At this time, the reaction was concentrated in vacuo. The residue was diluted with dichloromethane (25 mL) and was washed with a saturated aqueous sodium bicarbonate solution (1×25 mL), water (1×25 mL) and a saturated aqueous sodium chloride solution (1×25 mL), dried over magnesium sulfate, filtered, rinsed with dichloromethane and concentrated in vacuo. Purification by Analogix flash chromatography (8 g, 1-10% methanol/dichloromethane) afforded (S)-4-methyl-2-[2-oxo-4-(5,6,7,8-tetrahydro-naphthalen-1-yloxy)-2,5-dihydro-pyrrol-1-yl]-pentanoic acid [1-((R)-2,3-dihydroxy-propyl)-1H-pyrazol-3-yl]-amide (28 mg, 71%) as a white solid: HR-ES-MS m/z calculated for C$_{26}$H$_{34}$N$_4$O$_5$ [M+H]$^+$ 483.2602, observed 483.2603; $^1$H NMR (400 MHz, DMSO-d$_6$) δ ppm 0.90 (d, J=6.5 Hz, 3H), 0.94 (d, J=6.5 Hz, 3H), 1.46 (br. s., 1H), 1.53-1.65 (m, 1H), 1.65-1.85 (m, 5H), 2.57 (br. s., 2H), 2.76 (br. s., 2H), 3.21-3.31 (m, 2H), 3.72-3.82 (m, 1H), 3.87 (dd, J=13.4, 7.5 Hz, 1H), 4.09 (dd, J=13.6, 4.0 Hz, 1H), 4.18 (d, J=18.3 Hz, 1H), 4.56 (d, J=18.3 Hz, 1H), 4.65 (s, 1H), 4.71 (t, J=5.4 Hz, 1H), 4.87 (dd, J=10.7, 4.9 Hz, 1H), 4.93 (d, J=5.1 Hz, 1H), 6.41 (d, J=2.1 Hz, 1H), 7.04 (d, J=7.7 Hz, 2H), 7.18 (t, J=7.7 Hz, 1H), 7.53 (d, J=2.1 Hz, 1H), 10.75 (s, 1H).

Example 99

(S)-2-[4-(4-Methoxy-phenoxy)-2-oxo-2,5-dihydro-pyrrol-1-yl]-4-methyl-pentanoic acid [1-((R)-2,3-dihydroxy-propyl)-1H-pyrazol-3-yl]-amide

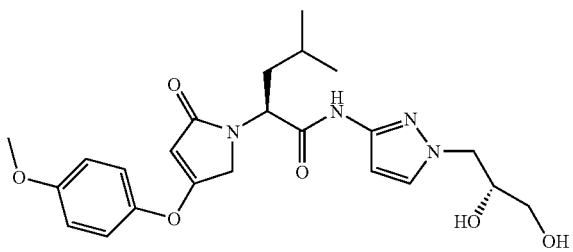

A mixture of 4-methoxy-phenol (1.10 g, 8.91 mmol) and ethyl-2-butynoate (2.0 g, 17.8 mmol) in tetrahydrofuran (13.7 mL) was treated with 1,8-diazabicyclo[5.4.0]undec-7-ene (1.33 mL, 8.91 mmol). The reaction was then heated at 130° C. for 1.5 h. At this time, the reaction was cooled to 25° C. and was stirred at 25° C. overnight. At this time, the reaction was concentrated in vacuo. The residue was dissolved in dichloromethane (40 mL) and was washed with a 2N aqueous hydrochloric acid solution (1×100 mL), a 1N aqueous sodium hydroxide solution (1×100 mL) and a saturated aqueous sodium chloride solution (1×100 mL). The organics were then dried over sodium sulfate, filtered, rinsed with dichloromethane and concentrated in vacuo. Purification by Analogix flash chromatography (40 g, 10-20% ethyl acetate/hexanes) afforded 3-(4-methoxy-phenoxy)-but-2-enoic acid ethyl ester (0.99 g, 47%) as a clear oil: HR-ES-MS m/z calculated for C$_{13}$H$_{16}$O$_4$ [M+H]$^+$ 237.1122, observed 237.1121; $^1$H NMR (300 MHz, DMSO-d$_6$) δ ppm 1.11 (t, J=7.0 Hz, 3H), 2.41 (s, 3H), 3.76 (s, 3H), 3.98 (q, J=7.0 Hz, 2H), 4.63 (s, 1H), 6.99 (d, J=9.1 Hz, 2H), 7.05 (d, J=9.1 Hz, 2H).

A solution of 3-(4-methoxy-phenoxy)-but-2-enoic acid ethyl ester (0.98 g, 4.17 mmol) in carbon tetrachloride (23.2 mL) was treated with N-bromosuccinimide (0.81 g, 4.59 mmol) and benzoyl peroxide (81 mg, 0.33 mmol). The reaction was then heated to reflux for 5 h. At this time, the reaction was cooled to 25° C. and then was placed in the freezer over the weekend. At this time, the reaction was removed from the freezer and allowed to thaw. The resulting precipitate was removed by filtration and was rinsed with carbon tetrachloride (5 mL). The filtrate was concentrated in vacuo. Purification by Analogix flash chromatography (40 g, 1-4% ethyl acetate/hexanes) afforded impure 4-bromo-3-(4-methoxy-phenoxy)-but-2-enoic acid ethyl ester (1.03 g, 78%) as a pale, yellow oil. The material was used without further purification.

A mixture of (L)-leucine methyl ester hydrochloride (0.64 g, 3.56 mmol) in acetonitrile (8.9 mL) was treated with N,N-diisopropylethylamine (0.57 mL, 3.49 mmol). After addition was complete, the mixture was stirred at 60° C. for 1 h. At this time, the reaction was cooled to 25° C., treated with N,N-diisopropylethylamine (0.57 mL, 3.49 mmol) and acetonitrile (8.9 mL) and then heated to 80° C. Upon reaching 80° C., the reaction was treated with a solution of 4-bromo-3-(4-methoxy-phenoxy)-but-2-enoic acid ethyl ester (1.02 g, 3.23 mmol) in acetonitrile (8.09 mL). After the addition was complete, the reaction mixture was heated to 100° C. where it stirred overnight. At this time, the reaction mixture was cooled to 25° C. and was concentrated in vacuo. The residue was diluted with dichloromethane (75 mL) and was washed with a 2N aqueous hydrochloric acid solution (1×100 mL), a saturated aqueous sodium bicarbonate solution (1×100 mL), a saturated aqueous sodium chloride solution (1×100 mL), dried over sodium sulfate, filtered and concentrated in vacuo. Purification by Analogix flash chromatography (40 g, 20-30% ethyl acetate/hexanes) afforded (S)-2-[3-ethoxycarbonyl-2-(4-methoxy-phenoxy)-allylamino]-4-methyl-pentanoic acid methyl ester (0.84 g, 68%) as a yellow oil: $^1$H NMR (300 MHz, DMSO-d$_6$) δ ppm 0.86 (d, J=6.3 Hz, 3H), 0.88 (d, J=6.3 Hz, 3H), 1.30-1.50 (m, 2H), 1.63-1.81 (m, 1H), 3.60 (s, 3H), 3.77 (s, 3H), 3.88 (dd, J=6.5, 3.2 Hz, 1H), 3.96 (d, J=6.9 Hz, 1H), 4.01 (d, J=6.9 Hz, 1H), 4.61 (s, 1H), 7.02 (s, 4H).

A solution of (S)-2-[3-ethoxycarbonyl-2-(4-methoxy-phenoxy)-allylamino]-4-methyl-pentanoic acid methyl ester (0.83 g, 2.51 mmol) in tetrahydrofuran (10 mL) was heated to 160° C. in a high pressure reaction vessel for 24 h. At this time, the reaction was cooled to 25° C. and was concentrated in vacuo. Purification by Analogix flash chromatography (40 g, 20-30% ethyl acetate/hexanes) afforded (S)-2-[4-(4-methoxy-phenoxy)-2-oxo-2,5-dihydro-pyrrol-1-yl]-4-methyl-pentanoic acid methyl ester (0.39 g, 46%) as a yellow oil: HR-ES-MS m/z calculated for C$_{18}$H$_{23}$NO$_5$ [M+H]$^+$ 334.1649, observed 334.1649; $^1$H NMR (300 MHz, DMSO-d$_6$) δ ppm 0.87 (d, J=6.6 Hz, 3H), 0.92 (d, J=6.6 Hz, 3H), 1.39-1.53 (m, 1H), 1.53-1.68 (m, 1H), 1.68-1.87 (m, 1H), 3.65 (s, 3H), 3.77 (s, 3H), 4.13 (d, J=18.1 Hz, 1H), 4.20 (d, J=18.1 Hz, 1H), 4.72 (dd, J=11.3, 4.4 Hz, 1H), 4.77 (s, 1H), 7.00 (d, J=9.1 Hz, 2H), 7.23 (d, J=9.1 Hz, 2H).

A mixture of (S)-2-[4-(4-methoxy-phenoxy)-2-oxo-2,5-dihydro-pyrrol-1-yl]-4-methyl-pentanoic acid methyl ester (0.38 g, 1.16 mmol) in tetrahydrofuran (8.75 mL) and water (2.9 mL) was treated with lithium hydroxide monohydrate (59 mg, 1.40 mmol). The reaction was stirred at 25° C. for 2.5 h. At this time, the reaction was diluted with water (50 mL), acidified with a 2N aqueous hydrochloric acid solution and then was extracted with 10% methanol/dichloromethane (3×75 mL). The combined organics were dried over sodium sulfate, filtered and concentrated in vacuo to afford (S)-2-[4-(4-methoxy-phenoxy)-2-oxo-2,5-dihydro-pyrrol-1-yl]-4-methyl-pentanoic acid (0.36 g, 99%) as a white solid: HR-ES-MS m/z calculated for $C_{17}H_{21}NO_5$ [M+H]$^+$ 320.1493, observed 320.1493. $^1$H NMR (300 MHz, DMSO-d$_6$) δ ppm 0.87 (d, J=6.5 Hz, 3H), 0.92 (d, J=6.5 Hz, 3H), 1.34-1.54 (m, 1H), 1.54-1.68 (m, 1H), 1.68-1.86 (m, 1H), 3.77 (s, 3H), 4.10 (d, J=18.1 Hz, 1H), 4.22 (d, J=18.1 Hz, 1H), 4.62 (dd, J=11.5, 4.2 Hz, 1H), 4.75 (s, 1H), 7.00 (d, J=9.1 Hz, 2H), 7.23 (d, J=9.1 Hz, 2H), 12.89 (br. s., 1H).

A solution of (S)-2-[4-(4-methoxy-phenoxy)-2-oxo-2,5-dihydro-pyrrol-1-yl]-4-methyl-pentanoic acid (0.36 g, 1.14 mmol) in N,N-dimethylformamide (4.41 mL) at 25° C. was treated with N,N-diisopropylethylamine (0.57 mL, 3.44 mmol), (benzotriazol-1-yloxy)tris(dimethylamino)phosphonium hexafluorophosphate (0.76 g, 1.72 mmol) and a solution of 1-((R)-2,2-dimethyl-[1,3]dioxolan-4-yl-methyl)-1H-pyrazol-3-ylamine (prepared as in Example 49, 0.24 g, 1.26 mmol) in N,N-dimethylformamide (0.5 mL). The reaction was stirred at 25° C. overnight. At this time, the reaction was diluted with ethyl acetate (50 mL) and was washed with a saturated aqueous ammonium chloride solution (1×100 mL), a saturated aqueous sodium bicarbonate solution (1×100 mL) and a saturated aqueous sodium chloride solution (1×100 mL), dried over sodium sulfate, filtered and concentrated in vacuo. Purification by Analogix flash chromatography (40 g, 50-100% ethyl acetate/hexanes) afforded (S)-2-[4-(4-methoxy-phenoxy)-2-oxo-2,5-dihydro-pyrrol-1-yl]-4-methyl-pentanoic acid [1-((R)-2,2-dimethyl-[1,3]dioxolan-4-yl-methyl)-1H-pyrazol-3-yl]-amide (0.38 g, 68%) as a white solid: HR-ES-MS m/z calculated for $C_{26}H_{34}N_4O_6$ [M+H]$^+$ 499.2551, observed 499.2551; $^1$H NMR (300 MHz, DMSO-d$_6$) δ ppm 0.90 (d, J=6.3 Hz, 3H), 0.93 (d, J=6.3 Hz, 3H), 1.25 (s, 3H), 1.30 (s, 3H), 1.45 (br. s., 1H), 1.50-1.63 (m, 1H), 1.63-1.82 (m, 1H), 3.67-3.76 (m, 1H), 3.77 (s, 3H), 4.00 (dd, J=8.5, 6.3 Hz, 1H), 4.05-4.22 (m, 3H), 4.28-4.41 (m, 1H), 4.53 (d, J=18.1 Hz, 1H), 4.75 (s, 1H), 4.88 (dd, J=10.7, 4.7 Hz, 1H), 6.43 (d, J=2.1 Hz, 1H), 7.00 (d, J=8.9 Hz, 2H), 7.23 (d, J=8.9 Hz, 2H), 7.60 (d, J=2.1 Hz, 1H), 10.78 (s, 1H).

A solution of (S)-2-[4-(4-methoxy-phenoxy)-2-oxo-2,5-dihydro-pyrrol-1-yl]-4-methyl-pentanoic acid [1-((R)-2,2-dimethyl-[1,3]dioxolan-4-yl-methyl)-1H-pyrazol-3-yl]-amide (0.38 g, 0.76 mmol) in methanol (7.66 mL) at 25° C. was treated with p-toluenesulfonic acid monohydrate (22 mg, 0.11 mmol). The reaction was stirred at 25° C. overnight. At this time, the reaction diluted with ethyl acetate (75 mL) and was washed with a saturated aqueous sodium bicarbonate solution (1×100 mL) and a saturated aqueous sodium chloride solution (1×100 mL), dried over sodium sulfate, filtered and concentrated in vacuo. Purification by Analogix flash chromatography (40 g, 1-10% methanol/dichloromethane gradient) afforded (S)-2-[4-(4-methoxy-phenoxy)-2-oxo-2,5-dihydro-pyrrol-1-yl]-4-methyl-pentanoic acid [1-((R)-2,3-dihydroxy-propyl)-1H-pyrazol-3-yl]-amide (0.30 g, 86%) as a white solid: HR-ES-MS m/z calculated for $C_{23}H_{30}N_4O_6$ [M+H]$^+$ 459.2238, observed 459.2237. $^1$H NMR (300 MHz, DMSO-d$_6$) δ ppm 0.90 (d, J=6.4 Hz, 3H), 0.93 (d, J=6.4 Hz, 2H), 1.36-1.64 (m, 2H), 1.66-1.81 (m, 1H), 3.20-3.32 (m, 2H), 3.77 (s, 4H), 3.86 (dd, J=13.3, 7.5 Hz, 1H), 4.04-4.11 (m, 1H), 4.14 (d, J=18.1 Hz, 1H), 4.53 (d, J=18.1 Hz, 1H), 4.71 (t, J=5.6 Hz, 1H), 4.75 (s, 1H), 4.87 (dd, J=10.6, 4.8 Hz, 1H), 4.93 (d, J=5.1 Hz, 1H), 6.40 (d, J=2.1 Hz, 1H), 7.00 (d, J=9.1 Hz, 2H), 7.23 (d, J=9.1 Hz, 2H), 7.53 (d, J=2.1 Hz, 1H), 10.74 (s, 1H).

Example 100

(S)-4-Methyl-2-[4-(naphthalen-1-yloxy)-2-oxo-2,5-dihydro-pyrrol-1-yl]-pentanoic acid [1-((R)-2,3-dihydroxy-propyl)-1H-pyrazol-3-yl]-amide

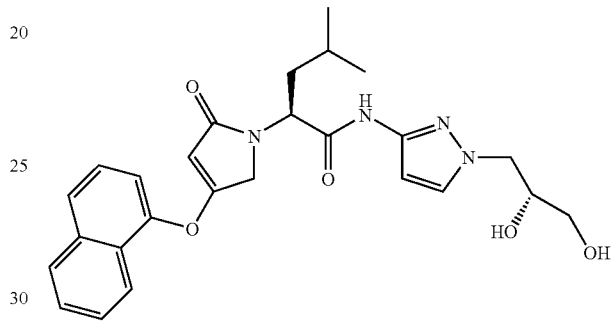

A mixture of naphthalen-1-ol (1.28 g, 8.91 mmol) and ethyl-2-butynoate (2.0 g, 17.8 mmol) in tetrahydrofuran (13.7 mL) was treated with 1,8-diazabicyclo[5.4.0]undec-7-ene (1.33 mL, 8.91 mmol). The reaction was then heated at 130° C. for 1.5 h. At this time, the reaction was cooled to 25° C. and was stirred at 25° C. overnight. At this time, the reaction was concentrated in vacuo. The residue was dissolved in dichloromethane (40 mL) and was washed with a 2N aqueous hydrochloric acid solution (1×100 mL), a 0.5N aqueous sodium hydroxide solution (1×100 mL) and a saturated aqueous sodium chloride solution (1×100 mL). The organics were then dried over sodium sulfate, filtered, rinsed with dichloromethane and concentrated in vacuo. Purification by Analogix flash chromatography (40 g, 5-10% ethyl acetate/hexanes) afforded 3-(naphthalen-1-yloxy)-but-2-enoic acid ethyl ester (1.16 g, 50%) as a clear oil: HR-ES-MS m/z calculated for $C_{16}H_{16}O_3$ [M+H]$^+$ 257.1172, observed 257.1172; $^1$H NMR (300 MHz, DMSO-d$_6$), δ ppm 1.04 (t, J=7.1 Hz, 3H), 2.60 (s, 3H), 3.93 (q, J=7.1 Hz, 2H), 4.52 (s, 1H), 7.31 (d, J=7.2 Hz, 1H), 7.53-7.65 (m, 3H), 7.78-7.84 (m, 1H), 7.90 (d, J=8.2 Hz, 1H), 7.99-8.07 (m, 1H).

A solution of 3-(naphthalen-1-yloxy)-but-2-enoic acid ethyl ester (1.15 g, 4.48 mmol) in carbon tetrachloride (24.9 mL) was treated with N-bromosuccinimide (0.87 g, 4.93 mmol) and benzoyl peroxide (87 mg, 0.35 mmol). The reaction was then heated to reflux for 5 h. At this time, the reaction was cooled to 25° C. and then was placed in the freezer over the weekend. At this time, the reaction was removed from the freezer and allowed to thaw. The resulting precipitate was removed by filtration and was rinsed with carbon tetrachloride (5 mL). The filtrate was concentrated in vacuo. Purification by Analogix flash chromatography (40 g, 2% ethyl acetate/hexanes) afforded impure 4-bromo-3-(naphthalen-1-yloxy)-but-2-enoic acid ethyl ester (1.28 g, 85%) as a light purple oil. The material was used without further purification.

A mixture of (L)-leucine methyl ester hydrochloride (0.68 g, 3.74 mmol) in acetonitrile (9.35 mL) was treated with N,N-diisopropylethylamine (0.60 mL, 3.67 mmol). After addition was complete, the mixture was stirred at 60° C. for 1 h. At this time, the reaction was cooled to 25° C., treated with N,N-diisopropylethylamine (0.60 mL, 3.67 mmol) and acetonitrile (9.35 mL) and then heated to 80° C. Upon reaching 80° C., the reaction was treated with a solution of 4-bromo-3-(naphthalen-1-yloxy)-but-2-enoic acid ethyl ester (1.14 g, 3.4 mmol) in acetonitrile (8.5 mL). After the addition was complete, the reaction mixture was heated to 100° C. where it stirred overnight. At this time, the reaction mixture was cooled to 25° C. and was concentrated in vacuo. The residue was diluted with dichloromethane (75 mL) and was washed with a 2N aqueous hydrochloric acid solution (1×100 mL), a saturated aqueous sodium bicarbonate solution (1×100 mL), a saturated aqueous sodium chloride solution (1×100 mL), dried over sodium sulfate, filtered and concentrated in vacuo. Purification by Analogix flash chromatography (40 g, 30% ethyl acetate/hexanes) afforded (S)-4-methyl-2-[4-(naphthalen-1-yloxy)-2-oxo-2,5-dihydro-pyrrol-1-yl]-pentanoic acid methyl ester (0.38 g, 32%) as a light orange oil: HR-ES-MS m/z calculated for $C_{21}H_{23}NO_4$ [M+H]$^+$ 354.1700, observed 354.1700; $^1$H NMR (300 MHz, DMSO-d$_6$) δ ppm 0.88 (d, J=6.3 Hz, 3H), 0.95 (d, J=6.3 Hz, 3H), 1.42-1.72 (m, 1H), 1.74-1.90 (m, 1H), 3.67 (s, 3H), 4.38 (s, 2H), 4.69-4.77 (m, 1H), 4.75 (s, 1H), 7.51 (d, J=6.9 Hz, 1H), 7.54-7.67 (m, 3H), 7.91 (d, J=8.2 Hz, 1H), 7.98-8.08 (m, 2H).

A mixture of (S)-4-methyl-2-[4-(naphthalen-1-yloxy)-2-oxo-2,5-dihydro-pyrrol-1-yl]-pentanoic acid methyl ester (0.38 g, 1.08 mmol) in tetrahydrofuran (8.1 mL) and water (2.7 mL) was treated with lithium hydroxide monohydrate (54 mg, 1.3 mmol). The reaction was stirred at 25° C. for 2 h. At this time, the reaction was diluted with water (50 mL), acidified with a 2N aqueous hydrochloric acid solution and then extracted with 10% methanol/dichloromethane (3×50 mL). The combined organics were dried over sodium sulfate, filtered and concentrated in vacuo to afford (S)-4-methyl-2-[4-(naphthalen-1-yloxy)-2-oxo-2,5-dihydro-pyrrol-1-yl]-pentanoic acid (0.37 g, 99%) as a pale yellow solid: HR-ES-MS m/z calculated for $C_{20}H_{21}NO_4$ [M+H]$^+$ 340.1544, observed 340.1545; The material was used without further purification. $^1$H NMR (300 MHz, DMSO-d$_6$) δ ppm 0.88 (d, J=6.3 Hz, 3H), 0.95 (d, J=6.3 Hz, 3H), 1.43-1.88 (m, 2H), 4.33 (d, J=18.1 Hz, 1H), 4.42 (d, J=18.1 Hz, 1H), 4.64 (dd, J=11.3, 4.4 Hz, 1H), 4.74 (s, 1H), 7.51 (d, J=7.5 Hz, 1H), 7.54-7.68 (m, 3H), 7.91 (d, J=8.2 Hz, 1H), 7.96-8.09 (m, 2H), 12.89 (br. s., 1H).

A solution of (S)-4-methyl-2-[4-(naphthalen-1-yloxy)-2-oxo-2,5-dihydro-pyrrol-1-yl]-pentanoic acid (0.37 g, 1.11 mmol) in N,N-dimethylformamide (4.27 mL) at 25° C. was treated with N,N-diisopropylethylamine (0.55 mL, 3.33 mmol), (benzotriazol-1-yloxy)tris(dimethylamino)phosphonium hexafluorophosphate (0.73 g, 1.66 mmol) and a solution of 1-((R)-2,2-dimethyl-[1,3]dioxolan-4-yl-methyl)-1H-pyrazol-3-ylamine (prepared as in Example 49, 0.24 g, 1.22 mmol) in N,N-dimethylformamide (0.5 mL). The reaction was stirred at 25° C. overnight. At this time, the reaction was diluted with ethyl acetate (75 mL) and was washed with a saturated aqueous ammonium chloride solution (1×150 mL), a saturated aqueous sodium bicarbonate solution (1×150 mL) and a saturated aqueous sodium chloride solution (1×150 mL), dried over sodium sulfate, filtered and concentrated in vacuo. Purification by Analogix flash chromatography (40 g, 10-30% ethyl acetate/hexanes) afforded (S)-4-methyl-2-[4-(naphthalen-1-yloxy)-2-oxo-2,5-dihydro-pyrrol-1-yl]-pentanoic acid [1-((R)-2,2-dimethyl-[1,3]dioxolan-4-yl-methyl)-1H-pyrazol-3-yl]-amide (0.43 g, 76%) as a light orange solid: HR-ES-MS m/z calculated for $C_{29}H_{34}N_4O_5$ [M+H]$^+$ 519.2602, observed 519.2604; $^1$H NMR (300 MHz, DMSO-d$_6$) δ ppm 0.91 (d, J=6.3 Hz, 3H), 0.96 (d, J=6.3 Hz, 3H), 1.25 (s, 3H), 1.30 (s, 3H), 1.41-1.69 (m, 2H), 1.70-1.85 (m, 1H), 3.74 (dd, J=8.3, 5.9 Hz, 1H), 4.00 (dd, J=8.3, 6.5 Hz, 1H), 4.11 (t, J=5.6 Hz, 2H), 4.28-4.44 (m, 2H), 4.65-4.77 (m, 2H), 4.90 (dd, J=10.4, 4.7 Hz, 1H), 6.46 (d, J=2.1 Hz, 1H), 7.51 (d, J=7.2 Hz, 1H), 7.54-7.67 (m, 4H), 7.91 (d, J=8.2 Hz, 1H), 7.99-8.09 (m, 2H), 10.80 (s, 1H).

A solution of (S)-4-methyl-2-[4-(naphthalen-1-yloxy)-2-oxo-2,5-dihydro-pyrrol-1-yl]-pentanoic acid [1-((R)-2,2-dimethyl-[1,3]dioxolan-4-yl-methyl)-1H-pyrazol-3-yl]-amide (0.43 g, 0.83 mmol) in methanol (8.38 mL) at 25° C. was treated with p-toluenesulfonic acid monohydrate (24 mg, 0.12 mmol). The reaction was stirred at 25° C. overnight. At this time, the reaction was diluted with ethyl acetate (50 mL) and was washed with a saturated aqueous sodium bicarbonate solution (1×100 mL) and a saturated aqueous sodium chloride solution (1×100 mL), dried over sodium sulfate, filtered and concentrated in vacuo. Purification by Analogix flash chromatography (40 g, 2.5-4% methanol/dichloromethane) afforded (S)-4-methyl-2-[4-(naphthalen-1-yloxy)-2-oxo-2,5-dihydro-pyrrol-1-yl]-pentanoic acid [1-((R)-2,3-dihydroxy-propyl)-1H-pyrazol-3-yl]-amide (0.32 g, 80%) as an off-white solid: HR-ES-MS m/z calculated for $C_{26}H_{30}N_4O_5$ [M+H]$^+$ 479.2289, observed 479.2287; $^1$H NMR (300 MHz, DMSO-d$_6$) δ ppm 0.91 (d, J=6.3 Hz, 3H), 0.96 (d, J=6.3 Hz, 3H), 1.43-1.67 (m, 2H), 1.71-1.84 (m, 1H), 3.20-3.32 (m, 2H), 3.70-3.82 (m, 1H), 3.87 (dd, J=13.5, 7.5 Hz, 1H), 4.09 (dd, J=13.5, 3.8 Hz, 1H), 4.39 (d, J=18.1 Hz, 1H), 4.66-4.77 (m, 3H), 4.89 (dd, J=10.4, 5.0 Hz, 1H), 4.95 (d, J=5.4 Hz, 1H), 6.43 (d, J=2.1 Hz, 1H), 7.48-7.66 (m, 5H), 7.91 (d, J=8.2 Hz, 1H), 7.99-8.09 (m, 2H), 10.77 (s, 1H).

Example 101

(S)-2-[4-(2,5-Difluoro-phenoxy)-2-oxo-2,5-dihydro-pyrrol-1-yl]-4-methyl-pentanoic acid [1-((R)-2,3-dihydroxy-propyl)-1H-pyrazol-3-yl]-amide

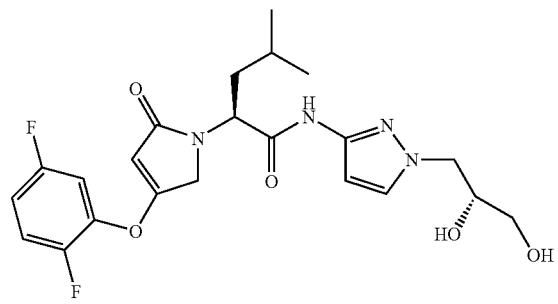

A mixture of 2,5-difluoro-phenol (1.15 g, 8.91 mmol) and ethyl-2-butynoate (2.0 g, 17.8 mmol) in tetrahydrofuran (13.7 mL) was treated with 1,8-diazabicyclo[5.4.0]undec-7-ene (1.33 mL, 8.91 mmol). The reaction was then heated at 130° C. for 2 h. At this time, the reaction was cooled to 25° C. and was concentrated in vacuo. The residue was dissolved in dichloromethane (50 mL) and was washed with a 2N aqueous hydrochloric acid solution (1×100 mL), a 0.5N aqueous sodium hydroxide solution (1×100 mL) and a saturated aqueous sodium chloride solution (1×100 mL). The organics were then dried over sodium sulfate, filtered and concentrated in vacuo. Purification by Analogix flash chromatography (40 g, 5% ethyl acetate/hexanes) afforded 3-(2,5-difluoro-phenoxy)-but-2-enoic acid ethyl ester (1.35 g, 63%) as a clear oil: HR-ES-MS m/z calculated for $C_{12}H_{12}O_3F_2$ [M+H]$^+$ 243.0828, observed 243.0827; $^1$H NMR (300 MHz, DMSO-d$_6$) δ ppm 1.13 (t, J=7.0 Hz, 3H), 2.43 (s, 3H), 4.02 (q, J=7.0 Hz, 2H), 4.78 (s, 1H), 7.16-7.30 (m, 1H), 7.37 (ddd, J=8.9, 6.2, 3.0 Hz, 1H), 7.51 (td, J=9.7, 5.1 Hz, 1H).

A solution of 3-(2,5-difluoro-phenoxy)-but-2-enoic acid ethyl ester (1.35 g, 5.57 mmol) in carbon tetrachloride (30.9 mL) was treated with N-bromosuccinimide (1.09 g, 6.13 mmol) and benzoyl peroxide (108 mg, 0.44 mmol). The reaction was then heated to reflux (105° C.) for 5 h. At this time, the reaction was cooled to 25° C. and then was placed in the refrigerator overnight. At this time, the reaction was removed from the refrigerator. The resulting precipitate was removed by filtration and was rinsed with carbon tetrachloride (25 mL). The filtrate was concentrated in vacuo. Purification by Analogix flash chromatography (40 g, 2% ethyl acetate/hexanes) afforded impure 4-bromo-3-(2,5-difluoro-phenoxy)-but-2-enoic acid ethyl ester (1.56 g, 87%) as a clear oil. The material was used without further purification.

A mixture of (L)-leucine methyl ester hydrochloride (1.28 g, 7.08 mmol) in acetonitrile (17.7 mL) was treated with N,N-diisopropylethylamine (1.15 mL, 6.95 mmol). After addition was complete, the mixture was stirred at 60° C. for 1 h. At this time, the reaction was cooled to 25° C., treated with N,N-diisopropylethylamine (1.15 mL, 6.95 mmol) and acetonitrile (17.7 mL) and then heated to 80° C. Upon reaching 80° C., the reaction was treated with a solution of 4-bromo-3-(2, 5-difluoro-phenoxy)-but-2-enoic acid ethyl ester (1.56 g, 6.44 mmol) in acetonitrile (16.1 mL). After the addition was complete, the reaction mixture was heated to 100° C. where it stirred overnight. At this time, the reaction mixture was cooled to 25° C. and was concentrated in vacuo. The residue was diluted with dichloromethane (75 mL) and was washed with a 2N aqueous hydrochloric acid solution (1×100 mL), a saturated aqueous sodium bicarbonate solution (1×100 mL), a saturated aqueous sodium chloride solution (1×100 mL), dried over sodium sulfate, filtered and concentrated in vacuo. Purification by Analogix flash chromatography (40 g, 15-50% ethyl acetate/hexanes) afforded (S)-2-[4-(2,5-difluoro-phenoxy)-2-oxo-2,5-dihydro-pyrrol-1-yl]-4-methyl-pentanoic acid methyl ester (0.38 g, 17%) as a yellow oil: HR-ES-MS m/z calculated for $C_{17}H_{19}NO_4F_2$ [M+H]$^+$ 340.1355, observed 340.1355; $^1$H NMR (300 MHz, DMSO-d$_6$) δ ppm 0.87 (d, J=6.6 Hz, 3H), 0.92 (d, J=6.6 Hz, 3H), 1.35-1.53 (m, 1H), 1.53-1.69 (m, 1H), 1.72-1.89 (m, 1H), 3.66 (s, 3H), 4.13-4.33 (m, 2H), 4.73 (dd, J=11.5, 4.5 Hz, 1H), 5.07 (s, 1H), 7.13-7.35 (m, 1H), 7.42-7.64 (m, 2H).

A mixture of (S)-2-[4-(2,5-difluoro-phenoxy)-2-oxo-2,5-dihydro-pyrrol-1-yl]-4-methyl-pentanoic acid methyl ester (0.38 g, 1.11 mmol) in tetrahydrofuran (8.4 mL) and water (2.8 mL) was treated with lithium hydroxide monohydrate (56 mg, 1.34 mmol). The reaction was stirred at 25° C. overnight. At this time, the reaction was diluted with water (100 mL), acidified with a 2N aqueous hydrochloric acid solution and then extracted with 10% methanol/dichloromethane (3×75 mL). The combined organics were dried over sodium sulfate, filtered and concentrated in vacuo to afford (S)-2-[4-(2,5-difluoro-phenoxy)-2-oxo-2,5-dihydro-pyrrol-1-yl]-4-methyl-pentanoic acid (0.36 g, 99%) as a light yellow foam: HR-ES-MS m/z calculated for $C_{16}H_{17}NO_4F_2$ [M+Na]$^+$ 348.1018, observed 348.1018; $^1$H NMR (400 MHz, DMSO-d$_6$) δ ppm 0.87 (d, J=6.5 Hz, 3H), 0.93 (d, J=6.5 Hz, 3H), 1.38-1.52 (m, 1H), 1.62 (ddd, J=14.0, 9.7, 4.4 Hz, 1H), 1.77-1.84 (m, 1H), 4.17 (d, J=18.2 Hz, 1H), 4.28 (d, J=18.2 Hz, 1H), 4.63 (dd, J=11.6, 4.4 Hz, 1H), 5.05 (s, 1H), 7.21-7.33 (m, 1H), 7.46-7.62 (m, 2H), 12.83 (br. s., 1H).

A solution of (S)-2-[4-(2,5-difluoro-phenoxy)-2-oxo-2,5-dihydro-pyrrol-1-yl]-4-methyl-pentanoic acid (0.36 g, 1.10 mmol) in N,N-dimethylformamide (4.25 mL) at 25° C. was treated with N,N-diisopropylethylamine (0.54 mL, 3.31 mmol), (benzotriazol-1-yloxy)tris(dimethylamino)phosphonium hexafluorophosphate (0.73 g, 1.65 mmol) and a solution of 1-((R)-2,2-dimethyl-[1,3]dioxolan-4-yl-methyl)-1H-pyrazol-3-ylamine (prepared as in Example 49, 0.22 g, 1.16 mmol) in N,N-dimethylformamide (0.5 mL). The reaction was stirred at 25° C. overnight. At this time, the reaction was diluted with ethyl acetate (100 mL) and was washed with a saturated aqueous sodium bicarbonate solution (1×150 mL) and a saturated aqueous sodium chloride solution (1×150 mL), dried over sodium sulfate, filtered and concentrated in vacuo. Purification by Analogix flash chromatography (40 g, 50-70% ethyl acetate/hexanes) afforded (S)-2-[4-(2,5-difluoro-phenoxy)-2-oxo-2,5-dihydro-pyrrol-1-yl]-4-methyl-pentanoic acid [1-((R)-2,2-dimethyl-[1,3]dioxolan-4-yl-methyl)-1H-pyrazol-3-yl]-amide (0.36 g, 64%) as a red/orange foam: HR-ES-MS m/z calculated for $C_{25}H_{30}N_4O_5F_2$ [M+H]$^-$ 505.2257, observed 505.2254; $^1$H NMR (300 MHz, DMSO-d$_6$) δ ppm 0.90 (d, J=6.4 Hz, 3H), 0.94 (d, J=6.4 Hz, 3H), 1.25 (s, 3H), 1.30 (s, 3H), 1.36-1.64 (m, 2H), 1.68-1.85 (m, 1H), 3.73 (dd, J=8.5, 5.7 Hz, 1H), 3.95-4.14 (m, 3H), 4.22 (d, J=18.6 Hz, 1H), 4.29-4.42 (m, 1H), 4.60 (d, J=18.6 Hz, 1H), 4.89 (dd, J=10.6, 4.5 Hz, 1H), 5.03 (s, 1H), 6.43 (d, J=2.1 Hz, 1H), 7.12-7.32 (m, 1H), 7.43-7.59 (m, 2H), 7.60 (d, J=2.1 Hz, 1H), 10.81 (s, 1H).

A solution of (S)-2-[4-(2,5-difluoro-phenoxy)-2-oxo-2,5-dihydro-pyrrol-1-yl]-4-methyl-pentanoic acid [1-((R)-2,2-dimethyl-[1,3]dioxolan-4-yl-methyl)-1H-pyrazol-3-yl]-amide (0.35 g, 0.70 mmol) in methanol (7.1 mL) at 25° C. was treated with p-toluenesulfonic acid monohydrate (20 mg, 0.10 mmol). The reaction was stirred at 25° C. overnight. At this time, the reaction was diluted with ethyl acetate (000 mL) and was washed with a saturated aqueous sodium bicarbonate solution (1×150 mL) and a saturated aqueous sodium chloride solution (1×150 mL), dried over sodium sulfate, filtered and concentrated in vacuo. Purification by Analogix flash chromatography (40 g, 2-5% methanol/dichloromethane) afforded (S)-2-[4-(2,5-difluoro-phenoxy)-2-oxo-2,5-dihydro-pyrrol-1-yl]-4-methyl-pentanoic acid [1-((R)-2,3-dihydroxy-propyl)-1H-pyrazol-3-yl]-amide (0.23 g, 71%) as a pale orange solid: HR-ES-MS m/z calculated for $C_{22}H_{26}N_4O_5F_2$ [M+H]$^+$ 465.1944, observed 465.1943; $^1$H NMR (300 MHz, DMSO-d$_6$) δ ppm 0.88 (d, J=6.3 Hz, 3H), 0.92 (d, J=6.3 Hz, 3H), 1.43 (br. s., 1H), 1.48-1.63 (m, 1H), 1.66-1.82 (m, 1H), 3.18-3.31 (m, 2H), 3.66-3.79 (m, 1H), 3.84 (dd, J=13.4, 7.5 Hz, 1H), 4.07 (dd, J=13.4, 3.6 Hz, 1H), 4.20 (d, J=18.4 Hz, 1H), 4.58 (d, J=18.4 Hz, 1H), 4.69 (t, J=5.6 Hz, 1H), 4.86 (dd, J=10.7, 4.7 Hz, 1H), 4.92 (d, J=5.4 Hz, 1H), 5.01 (s, 1H), 6.39 (d, J=2.1 Hz, 1H), 7.15-7.32 (m, 1H), 7.43-7.60 (m, 3H), 10.76 (s, 1H).

Example 102

(S)-2-[4-(2,4-Difluoro-phenoxy)-2-oxo-2,5-dihydro-pyrrol-1-yl]-4-methyl-pentanoic acid [1-((R)-2,3-dihydroxy-propyl)-1H-pyrazol-3-yl]-amide

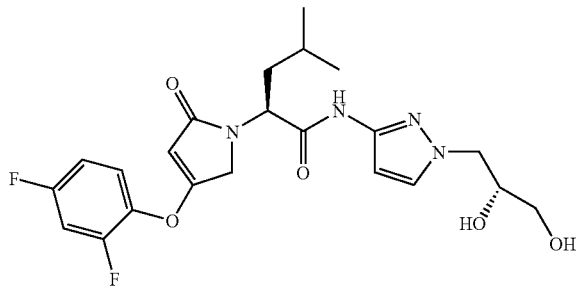

A mixture of 2,4-difluoro-phenol (0.85 mL, 8.91 mmol) and ethyl-2-butynoate (2.0 g, 17.8 mmol) in tetrahydrofuran (13.7 mL) was treated with 1,8-diazabicyclo[5.4.0]undec-7-ene (1.33 mL, 8.91 mmol). The reaction was then heated at 130° C. for 2.5 h. At this time, the reaction was cooled to 25° C. and was stirred at 25° C. overnight. At this time, the reaction was concentrated in vacuo. The residue was dissolved in dichloromethane (100 mL) and was washed with a 2N aqueous hydrochloric acid solution (1×100 mL), a 0.5N aqueous sodium hydroxide solution (1×100 mL) and a saturated aqueous sodium chloride solution (1×100 mL). The organics were then dried over magnesium sulfate, filtered, rinsed with dichloromethane and concentrated in vacuo. Purification by Analogix flash chromatography (40 g, 5% ethyl acetate/hexanes) afforded 3-(2,5-difluoro-phenoxy)-but-2-enoic acid ethyl ester (1.36 g, 63%) as a clear oil: HR-ES-MS m/z calculated for $C_{12}H_{12}O_3F_2$ [M+H]$^+$ 243.0828, observed 243.0827; $^1$H NMR (300 MHz, DMSO-d$_6$) δ ppm 1.13 (t, J=7.0 Hz, 3H), 2.44 (s, 3H), 4.01 (q, J=7.0 Hz, 2H), 4.70 (s, 1H), 7.13-7.25 (m, 1H), 7.40 (td, J=9.0, 5.7 Hz, 1H), 7.53 (ddd, J=11.2, 9.0, 3.0 Hz, 1H).

A solution of 3-(2,4-difluoro-phenoxy)-but-2-enoic acid ethyl ester (1.35 g, 5.57 mmol) in carbon tetrachloride (30.9 mL) was treated with N-bromosuccinimide (1.09 g, 6.13 mmol) and benzoyl peroxide (108 mg, 0.44 mmol). The reaction was then heated to reflux (105° C.) for 5 h. At this time, the reaction was cooled to 25° C. and then was placed in the refrigerator overnight. At this time, the reaction was removed from the refrigerator. The resulting precipitate was removed by filtration and was rinsed with carbon tetrachloride (10 mL). The filtrate was concentrated in vacuo. Purification by Analogix flash chromatography (40 g, 2% ethyl acetate/hexanes) afforded impure 4-bromo-3-(2,4-difluoro-phenoxy)-but-2-enoic acid ethyl ester (1.45 g, 81%) as a clear oil. The material was used without further purification.

A mixture of (L)-leucine methyl ester hydrochloride (0.90 g, 4.96 mmol) in acetonitrile (12.4 mL) was treated with N,N-diisopropylethylamine (0.80 mL, 4.87 mmol). After addition was complete, the mixture was stirred at 60° C. for 45 min. At this time, the reaction was cooled to 25° C., treated with N,N-diisopropylethylamine (0.80 mL, 4.87 mmol) and acetonitrile (12.4 mL) and then heated to 80° C. Upon reaching 80° C., the reaction was treated with a solution of 4-bromo-3-(2,4-difluoro-phenoxy)-but-2-enoic acid ethyl ester (1.45 g, 4.51 mmol) in acetonitrile (11.3 mL). After the addition was complete, the reaction mixture was heated to 80° C. where it stirred overnight. At this time, the reaction mixture was cooled to 25° C. and was concentrated in vacuo. The residue was diluted with dichloromethane (75 mL) and was washed with a 2N aqueous hydrochloric acid solution (1×100 mL), a saturated aqueous sodium bicarbonate solution (1×100 mL), a saturated aqueous sodium chloride solution (1×100 mL), dried over sodium sulfate, filtered and concentrated in vacuo. Purification by Analogix flash chromatography (40 g, 15-50% ethyl acetate/hexanes) afforded (S)-2-[4-(2,4-difluoro-phenoxy)-2-oxo-2,5-dihydro-pyrrol-1-yl]-4-methyl-pentanoic acid methyl ester (0.53 g, 35%) as a yellow oil: HR-ES-MS m/z calculated for $C_{17}H_{19}NO_4F_2$ [M+Na]$^+$ 362.1174, observed 362.1174; $^1$H NMR (300 MHz, DMSO-d$_6$) δ ppm 0.85 (d, J=6.5 Hz, 3H), 0.91 (d, J=6.5 Hz, 3H), 1.34-1.51 (m, 1H), 1.59 (ddd, J=13.8, 9.4, 4.4 Hz, 1H), 1.71-1.87 (m, 1H), 3.64 (s, 3H), 4.11-4.31 (m, 2H), 4.71 (dd, J=11.3, 4.4 Hz, 1H), 4.94 (s, 1H), 7.07-7.27 (m, 1H), 7.42-7.70 (m, 2H).

A mixture of (S)-2-[4-(2,4-difluoro-phenoxy)-2-oxo-2,5-dihydro-pyrrol-1-yl]-4-methyl-pentanoic acid methyl ester (0.53 g, 1.58 mmol) in tetrahydrofuran (12 mL) and water (4 mL) was treated with lithium hydroxide monohydrate (80 mg, 1.89 mmol). The reaction was stirred at 25° C. for 4 h. At this time, the reaction was diluted with water (75 mL), acidified with a 2N aqueous hydrochloric acid solution and then extracted with 10% methanol/dichloromethane (3×50 mL). The combined organics were dried over sodium sulfate, filtered and concentrated in vacuo to afford (S)-2-[4-(2,4-difluoro-phenoxy)-2-oxo-2,5-dihydro-pyrrol-1-yl]-4-methyl-pentanoic acid (0.50 g, 97%) as a light yellow solid: HR-ES-MS m/z calculated for $C_{16}H_{17}NO_4F_2$ [M+Na]$^+$ 348.1018, observed 348.1018; $^1$H NMR (300 MHz, DMSO-d$_6$) δ ppm 0.86 (d, J=6.4 Hz, 3H), 0.92 (d, J=6.4 Hz, 3H), 1.36-1.52 (m, 1H), 1.53-1.68 (m, 1H), 1.75-1.86 (m, 1H), 4.15 (d, J=18.4 Hz, 1H), 4.26 (d, J=18.4 Hz, 1H), 4.62 (dd, J=11.5, 4.2 Hz, 1H), 4.93 (s, 1H), 7.14-7.25 (m, 1H), 7.49-7.64 (m, 2H), 12.91 (br. s., 1H).

A solution of (S)-2-[4-(2,4-difluoro-phenoxy)-2-oxo-2,5-dihydro-pyrrol-1-yl]-4-methyl-pentanoic acid (0.49 g, 1.53 mmol) in N,N-dimethylformamide (5.9 mL) at 25° C. was treated with N,N-diisopropylethylamine (0.76 mL, 4.59 mmol), (benzotriazol-1-yloxy)tris(dimethylamino)phosphonium hexafluorophosphate (1.01 g, 2.29 mmol) and a solution of 1-((R)-2,2-dimethyl-[1,3]dioxolan-4-yl-methyl)-1H-pyrazol-3-ylamine (prepared as in Example 49, 0.31 g, 1.60 mmol) in N,N-dimethylformamide (0.5 mL). The reaction was stirred at 25° C. overnight. At this time, the reaction was diluted with ethyl acetate (100 mL) and was washed with a saturated aqueous sodium bicarbonate solution (1×150 mL) and a saturated aqueous sodium chloride solution (1×150 mL), dried over sodium sulfate, filtered and concentrated in vacuo. Purification by Analogix flash chromatography (40 g, 50-75% ethyl acetate/hexanes) afforded (S)-2-[4-(2,4-difluoro-phenoxy)-2-oxo-2,5-dihydro-pyrrol-1-yl]-4-methyl-pentanoic acid [1-((R)-2,2-dimethyl-[1,3]dioxolan-4-yl-methyl)-1H-pyrazol-3-yl]-amide (0.63 g, 81%) as a light orange foam: HR-ES-MS m/z calculated for $C_{25}H_{30}N_4O_5F_2$ [M+H]$^+$ 505.2257, observed 505.2257; $^1$H NMR (300 MHz, DMSO-d$_6$) δ ppm 0.88 (d, J=6.4 Hz, 3H), 0.91 (d, J=6.4 Hz, 3H), 1.23 (s, 3H), 1.28 (s, 3H), 1.43 (br. s., 1H), 1.48-1.63 (m, 1H), 1.66-1.81 (m, 1H), 3.71 (dd, J=8.5, 5.7 Hz, 1H), 3.94-4.13 (m, 3H), 4.19 (d, J=18.4 Hz, 1H), 4.27-4.38 (m, 1H), 4.57 (d, J=18.4 Hz, 1H), 4.86 (dd, J=10.9, 4.8 Hz, 1H), 4.90 (s, 1H), 6.41 (d, J=2.1 Hz, 1H), 7.12-7.23 (m, 1H), 7.48-7.62 (m, 3H), 10.79 (s, 1H).

A solution of (S)-2-[4-(2,4-difluoro-phenoxy)-2-oxo-2,5-dihydro-pyrrol-1-yl]-4-methyl-pentanoic acid [1-((R)-2,2- dimethyl-[1,3]dioxolan-4-yl-methyl)-1H-pyrazol-3-yl]-amide (0.62 g, 1.24 mmol) in methanol (12.4 mL) at 25° C. was treated with p-toluenesulfonic acid monohydrate (35 mg, 0.18 mmol). The reaction was stirred at 25° C. overnight. At this time, the reaction was diluted with ethyl acetate (100 mL) and was washed with a saturated aqueous sodium bicarbonate solution (1×150 mL) and a saturated aqueous sodium chloride solution (1×150 mL), dried over sodium sulfate, filtered and concentrated in vacuo. Purification by Analogix flash chromatography (40 g, 2-5% methanol/dichloromethane gradient) afforded (S)-2-[4-(2,4-difluoro-phenoxy)-2-oxo-2,5-dihydro-pyrrol-1-yl]-4-methyl-pentanoic acid [1-((R)-2,3-dihydroxy-propyl)-1H-pyrazol-3-yl]-amide (0.46 g, 80%) as an off-white solid: HR-ES-MS m/z calculated for $C_{22}H_{26}N_4O_5F_2$ [M+H]$^+$ 465.1944, observed 465.1944; $^1$H NMR (300 MHz, DMSO-d$_6$) δ ppm 0.90 (d, J=6.3 Hz, 3H), 0.94 (d, J=6.6 Hz, 3H), 1.34-1.50 (m, 1H), 1.50-1.67 (m, 1H), 1.67-1.89 (m, 1H), 3.21-3.32 (m, 2H), 3.78 (br. s., 1H), 3.87 (dd, J=13.6, 7.5 Hz, 1H), 4.09 (dd, J=13.6, 3.6 Hz, 1H), 4.22 (d, J=18.4 Hz, 1H), 4.60 (d, J=18.4 Hz, 1H), 4.71 (t, J=5.4 Hz, 1H), 4.81-4.99 (m, 3H), 6.41 (d, J=2.1 Hz, 1H), 7.12-7.26 (m, 1H), 7.48-7.66 (m, 3H), 10.78 (s, 1H).

Example 103

(S)-2-[4-(2-Fluoro-5-methyl-phenoxy)-2-oxo-2,5-dihydro-pyrrol-1-yl]-4-methyl-pentanoic acid [1-((R)-2,3-dihydroxy-propyl)-1H-pyrazol-3-yl]-amide

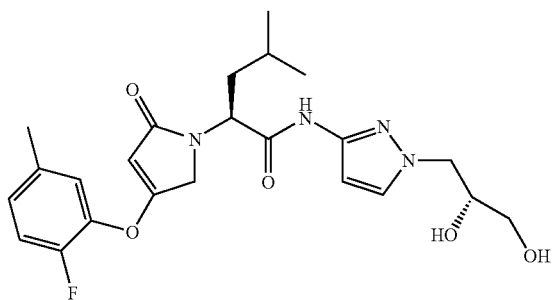

A mixture of 2-fluoro-5-methyl-phenol (0.97 mL, 8.91 mmol) and ethyl-2-butynoate (2.0 g, 17.8 mmol) in tetrahydrofuran (13.7 mL) was treated with 1,8-diazabicyclo[5.4.0]undec-7-ene (1.33 mL, 8.91 mmol). The reaction was then heated at 130° C. for 4 h. At this time, the reaction was cooled to 25° C. and was stirred at 25° C. overnight. At this time, the reaction was diluted with dichloromethane (100 mL) and was washed with a 2N aqueous hydrochloric acid solution (1×100 mL), a 0.5N aqueous sodium hydroxide solution (1×100 mL) and a saturated aqueous sodium chloride solution (1×100 mL). The organics were then dried over sodium sulfate, filtered and concentrated in vacuo. Purification by Analogix flash chromatography (40 g, 2% ethyl acetate/hexanes) afforded 3-(2-fluoro-5-methyl-phenoxy)-but-2-enoic acid ethyl ester (1.12 g, 52%) as a clear oil: HR-ES-MS m/z calculated for $C_{13}H_{15}O_3F$ [M+H]$^+$ 239.1078, observed 239.1078; $^1$H NMR (300 MHz, DMSO-d$_6$) δ ppm 1.12 (t, J=7.0 Hz, 3H), 2.30 (s, 3H), 2.43 (s, 3H), 4.00 (q, J=7.0 Hz, 2H), 4.69 (s, 1H), 7.01-7.19 (m, 2H), 7.30 (dd, J=10.7, 8.3 Hz, 1H).

A solution of 3-(2-fluoro-5-methyl-phenoxy)-but-2-enoic acid ethyl ester (1.11 g, 4.65 mmol) in dichloromethane (18.9 mL) was treated with N-bromosuccinimide (0.87 g, 4.89 mmol) and benzoyl peroxide (90 mg, 0.37 mmol). The reaction was then heated to 75° C. overnight. At this time, the reaction was cooled to 25° C. and then concentrated in vacuo. Purification by Analogix flash chromatography (40 g, 2% ethyl acetate/hexanes) afforded (E)-4-bromo-3-(2-fluoro-5-methyl-phenoxy)-but-2-enoic acid ethyl ester (1.31 g, 89%) as a light yellow oil: HR-ES-MS m/z calculated for $C_{13}H_{14}O_3FBr$ [M+H]$^+$ 317.0183, observed 317.0182; $^1$H NMR (300 MHz, DMSO-d$_6$) δ ppm 1.15 (t, J=7.2 Hz, 3H), 2.31 (s, 3H), 4.07 (q, J=7.2 Hz, 2H), 4.78 (s, 2H), 4.81 (s, 1H), 7.11 (dd, J=7.8, 1.8 Hz, 1H), 7.14-7.22 (m, 1H), 7.33 (dd, J=10.6, 8.5 Hz, 1H): and (Z)-4-bromo-3-(2-fluoro-5-methyl-phenoxy)-but-2-enoic acid ethyl ester (0.13 g, 9%) as a golden yellow oil: HR-ES-MS m/z calculated for $C_{13}H_{14}O_3FBr$ [M+H]$^+$ 317.0183, observed 317.0182; $^1$H NMR (300 MHz, DMSO-d$_6$) δ ppm 1.09 (t, J=7.1 Hz, 3H), 2.26 (s, 3H), 3.97 (q, J=7.1 Hz, 2H), 4.29 (s, 2H), 5.98 (s, 1H), 6.97 (m, 2H), 7.20 (dd, J=10.7, 8.9 Hz, 1H).

A mixture of (L)-leucine methyl ester hydrochloride (0.82 g, 4.56 mmol) in acetonitrile (11.4 mL) was treated with N,N-diisopropylethylamine (0.74 mL, 4.48 mmol). After addition was complete, the mixture was stirred at 60° C. for 45 min. At this time, the reaction was cooled to 25° C., treated with N,N-diisopropylethylamine (0.74 mL, 4.48 mmol) and acetonitrile (11.4 mL) and then heated to 80° C. Upon reaching 80° C., the reaction was treated with a solution of (E)-4-bromo-3-(2-fluoro-5-methyl-phenoxy)-but-2-enoic acid ethyl ester (1.31 g, 4.14 mmol) in acetonitrile (10.4 mL). After the addition was complete, the reaction mixture was heated to 100° C. where it stirred for 24 h. At this time, the reaction mixture was cooled to 25° C. and was stirred at 25° C. for 2 d. The reaction was then concentrated in vacuo. Purification by Analogix flash chromatography (40 g, 10-50% ethyl acetate/hexanes) afforded (S)-2-[4-(2-fluoro-5-methyl-phenoxy)-2-oxo-2,5-dihydro-pyrrol-1-yl]-4-methyl-pentanoic acid methyl ester (0.60 g, 43%) as an orange oil: HR-ES-MS m/z calculated for $C_{18}H_{22}NO_4F$ [M+H]$^+$ 336.1606, observed 336.1607; $^1$H NMR (300 MHz, DMSO-d$_6$) δ ppm 0.87 (d, J=6.6 Hz, 3H), 0.92 (d, J=6.6 Hz, 3H), 1.34-1.53 (m, 1H), 1.53-1.69 (m, 1H), 1.72-1.89 (m, 1H), 2.31 (s, 3H), 3.66 (s, 3H), 4.18 (d, J=18.4 Hz, 1H), 4.25 (d, J=18.4 Hz, 1H), 4.73 (dd, J=11.3, 4.4 Hz, 1H), 4.90 (s, 1H), 7.11-7.20 (m, 1H), 7.26-7.38 (m, 2H).

A mixture of (S)-2-[4-(2-fluoro-5-methyl-phenoxy)-2-oxo-2,5-dihydro-pyrrol-1-yl]-4-methyl-pentanoic acid methyl ester (0.59 g, 1.77 mmol) in tetrahydrofuran (13.3 mL) and water (4.4 mL) was treated with lithium hydroxide monohydrate (89 mg, 2.13 mmol). The reaction was stirred at 25° C. overnight. At this time, the reaction was diluted with water (75 mL), acidified with a 3N aqueous hydrochloric acid solution and then extracted with 10% methanol/dichloromethane (3×50 mL). The combined organics were dried over sodium sulfate, filtered and concentrated in vacuo to afford (S)-2-[4-(2-fluoro-5-methyl-phenoxy)-2-oxo-2,5-dihydro-pyrrol-1-yl]-4-methyl-pentanoic acid (0.51 g, 90%) as an off-white solid: HR-ES-MS m/z calculated for $C_{17}H_{20}NO_4F$ [M+H]$^+$ 322.1449, observed 322.1447; $^1$H NMR (300 MHz, DMSO-d$_6$) δ ppm 0.84 (d, J=6.4 Hz, 3H), 0.90 (d, J=6.4 Hz, 3H), 1.44 (br. s., 1H), 1.51-1.66 (m, 1H), 1.66-1.84 (m, 1H), 2.29 (s, 3H), 4.13 (d, J=18.1 Hz, 1H), 4.25 (d, J=18.1 Hz, 1H), 4.60 (dd, J=11.3, 4.1 Hz, 1H), 4.86 (s, 1H), 7.09-7.19 (m, 1H), 7.25-7.35 (m, 2H), 12.92 (br. s., 1H).

A solution of (S)-2-[4-(2-fluoro-5-methyl-phenoxy)-2-oxo-2,5-dihydro-pyrrol-1-yl]-4-methyl-pentanoic acid (0.51 g, 1.59 mmol) in N,N-dimethylformamide (6.14 mL) at 25° C. was treated with N,N-diisopropylethylamine (0.79 mL, 4.79 mmol), (benzotriazol-1-yloxy)tris(dimethylamino)phosphonium hexafluorophosphate (1.06 g, 2.39 mmol) and a solution of 1-((R)-2,2-dimethyl-[1,3]dioxolan-4-yl-methyl)-1H-pyrazol-3-ylamine (prepared as in Example 49, 0.33 g, 1.67 mmol) in N,N-dimethylformamide (0.5 mL). The reaction was stirred at 25° C. over the weekend. At this time, the reaction was diluted with ethyl acetate (75 mL) and was washed with a saturated aqueous ammonium chloride solution (1×150 mL), a saturated aqueous sodium bicarbonate solution (1×150 mL) and a saturated aqueous sodium chloride solution (1×150 mL), dried over sodium sulfate, filtered and concentrated in vacuo. Purification by Analogix flash chromatography (40 g, 50-100% ethyl acetate/hexanes) afforded (S)-2-[4-(2-fluoro-5-methyl-phenoxy)-2-oxo-2,5-dihydro-pyrrol-1-yl]-4-methyl-pentanoic acid [1-((R)-2,2-dimethyl-[1,3]dioxolan-4-yl-methyl)-1H-pyrazol-3-yl]-amide (0.70 g, 88%) as an orange solid: HR-ES-MS m/z calculated for $C_{26}H_{33}N_4O_5F$ [M+H]$^+$ 501.2508, observed 501.2507; $^1$H NMR (300 MHz, DMSO-d$_6$) δ ppm 0.90 (d, J=6.3 Hz, 3H), 0.93 (d, J=6.3 Hz, 3H), 1.24 (s, 3H), 1.30 (s, 3H), 1.35-1.64 (m, 2H), 1.66-1.86 (m, 1H), 2.31 (s, 3H), 3.73 (dd, J=8.5, 5.7 Hz, 1H), 3.96-4.14 (m, 3H), 4.20 (d, J=18.4 Hz, 1H), 4.30-4.40 (m, 1H), 4.59 (d, J=18.4 Hz, 1H), 4.83-4.93 (m, 2H), 6.43 (d, J=2.1 Hz, 1H), 7.08-7.20 (m, 1H), 7.27-7.38 (m, 2H), 7.60 (d, J=2.1 Hz, 1H), 10.80 (s, 1H).

A solution of (S)-2-[4-(2-fluoro-5-methyl-phenoxy)-2-oxo-2,5-dihydro-pyrrol-1-yl]-4-methyl-pentanoic acid [1-((R)-2,2-dimethyl-[1,3]dioxolan-4-yl-methyl)-1H-pyrazol-3-yl]-amide (0.70 g, 1.39 mmol) in methanol (13.9 mL) at 25° C. was treated with p-toluenesulfonic acid monohydrate (40 mg, 0.20 mmol). The reaction was stirred at 25° C. overnight. At this time, the reaction was diluted with dichloromethane (100 mL) and was washed with a saturated aqueous sodium bicarbonate solution (1×150 mL) and a saturated aqueous sodium chloride solution (1×150 mL), dried over sodium sulfate, filtered and concentrated in vacuo. Purification by Analogix flash chromatography (40 g, 1-10% methanol/dichloromethane) afforded (S)-2-[4-(2-fluoro-5-methyl-phenoxy)-2-oxo-2,5-dihydro-pyrrol-1-yl]-4-methyl-pentanoic acid [1-((R)-2,3-dihydroxy-propyl)-1H-pyrazol-3-yl]-amide (0.49 g, 77%) as an off-white solid: HR-ES-MS m/z calculated for $C_{23}H_{29}N_4O_5F$ [M+H]$^+$ 461.2195, observed 461.2194; $^1$H NMR (300 MHz, DMSO-d$_6$) δ ppm 0.88 (d, J=6.3 Hz, 3H), 0.92 (d, J=6.3 Hz, 3H), 1.32-1.48 (m, 1H), 1.48-1.63 (m, 1H), 1.63-1.82 (m, 1H), 2.29 (s, 3H), 3.17-3.30 (m, 2H), 3.68-3.79 (m, 1H), 3.79-3.91 (m, 1H), 4.07 (dd, J=13.4, 3.8 Hz, 1H), 4.18 (d, J=18.4 Hz, 1H), 4.57 (d, J=18.4 Hz, 1H), 4.69 (t, J=5.6 Hz, 1H), 4.81-4.89 (m, 2H), 4.92 (d, J=5.4 Hz, 1H), 6.39 (d, J=2.0 Hz, 1H), 7.08-7.18 (m, 1H), 7.24-7.35 (m, 2H), 7.51 (d, J=2.0 Hz, 1H), 10.75 (s, 1H).

Example 104

(S)-2-[4-(2-Chloro-phenoxy)-2-oxo-2,5-dihydro-pyrrol-1-yl]-4-methyl-pentanoic acid [3-(2-methoxy-ethyl)-[1,2,4]thiadiazol-5-yl]-amide

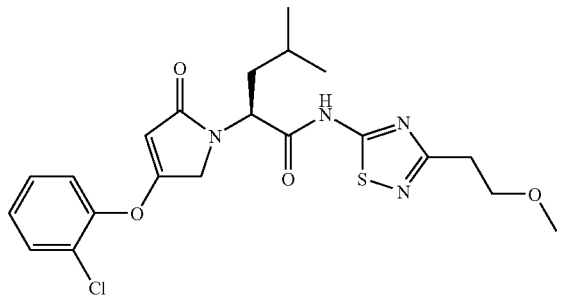

To a stirred suspension of aluminum chloride (4.81 g, 0.090 mol) in toluene (33.5 ml) at 0° C. under argon was slowly added a solution of 2M trimethylaluminum in toluene (42 mL, 0.084 mol) maintaining a temperature below 10° C. The resulting mixture was allowed to stir at room temperature for 2 h before a solution of 3-methoxypropionitrile (4.26 g, 0.050 mol) in toluene (16.5 ml) was added. The resulting mixture was warmed to 80° C. and allowed to stir for 18.5 h. the reaction mixture was cooled to room temperature and then slowly poured on to a cooled suspension of silica gel (50 g) in dichloromethane (100 mL). the resulting mixture was stirred for 15 min, filtered and the silica gel pad washed well with methanol. The filtrate was evaporated and the residue was redissolved in a solution of dichloromethane/methanol, filtered and evaporated which afforded a solid. The solid was suspended in a 3N hydrogen chloride solution in methanol (20 mL) and stirred vigorously while diethyl ether (500 mL) was added dropwise. The resulting mixture was stirred at room temperature for 1 h decanted and dried under vacuum which afforded 3-methoxy-propionamidine hydrochloride (4.8 g, 69%) as a white solid.

To a solution of 3-methoxy-propionamidine hydrochloride (4.8 g, 0.035 mol) in methanol (20 mL) at 0° C. under vigorous stirring was added dropwise bromine (1.78 mL, 0.035 mol) and a 5.4M sodium methylate solution in methanol (13 mL, 0.035 mol) simultaneously over 30 min maintaining a slight bromine excess by color. To the resulting nearly colorless suspension was added dropwise a solution of potassium thiocyanate (3.37 g, 0.035 mol) in methanol (20 mL) over 10 min at 0-10° C. The resulting mixture was stirred for 2 h at 0-10° C. and then filtered. The isolated material was washed with methanol and dried which afforded a brown solid which was purified by flash chromatography (300 g silica gel 60, 5% methanol/diethyl ether) and crystallized from diethyl ether/hexanes which afforded 3-(2-methoxy-ethyl)-[1,2,4]thiadiazol-5-ylamine (4.08 g, 74%) as a light yellow solid.

To a solution of (S)-2-[4-(2-chloro-phenoxy)-2-oxo-2,5-dihydro-pyrrol-1-yl]-4-methyl-pentanoic acid (prepared as in Example 64, 84 mg, 0.26 mmol) in dichloromethane (1.00 mL) was added 1-(3-dimethylaminopropyl)-3-ethylcarbodiimide hydrochloride (71 mg, 0.37 mmol) and 1-hydroxybenzotriazole (45 mg, 0.33 mmol). The resulting solution was stirred for 5 min before 3-(2-methoxy-ethyl)-[1,2,4]thiadiazol-5-ylamine (50 mg, 0.31 mmol) was added and the resulting mixture stirred at 25° C. overnight. The mixture was washed with saturated ammonium chloride (1 mL), evaporated and the crude product purified by HPLC (Gilson semi-prep; Supelcosil ABZ+Plus 12 μM 25 cm×21.2 mm column 20-95% acetonitrile/water) which afforded (S)-2-[4-(2-chloro-phenoxy)-2-oxo-2,5-dihydro-pyrrol-1-yl]-4-methyl-pentanoic acid [3-(2-methoxy-ethyl)-[1,2,4]thiadiazol-5-yl]-amide (34 mg, 28%) as a light orange solid: HR-ES-MS m/z calculated for $C_{21}H_{25}ClN_4O_4S$ [M+H]$^+$ 465.1359, observed 465.1358; $^1$H NMR (300 MHz, DMSO-d$_6$) ppm 0.91 (d, J=6.6 Hz, 3H), 0.94 (d, J=6.6 Hz, 3H), 1.47 (br. s., 1H), 1.58-1.74 (m, 1H), 1.80-1.95 (m, 1H), 3.01 (t, J=6.4 Hz, 2H), 3.22 (s, 3H), 3.74 (t, J=6.4 Hz, 2H), 4.19-4.36 (m, 1H), 4.41-4.61 (m, 1H), 4.83 (s, 1H), 4.94-5.07 (m, 1H), 7.37 (t, J=7.8 Hz, 1H), 7.47 (t, J=7.8 Hz, 1H), 7.54 (d, J=7.8 Hz, 1H), 7.66 (d, J=7.8 Hz, 1H), 13.32 (s, 1H).

Example 105

(S)-2-[4-(2-Chloro-phenoxy)-2-oxo-2,5-dihydro-pyrrol-1-yl]-4-methyl-pentanoic acid (3-cyclopropyl-[1,2,4]thiadiazol-5-yl)-amide

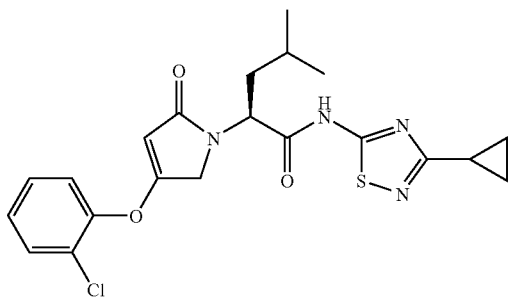

To a solution of (S)-2-[4-(2-chloro-phenoxy)-2-oxo-2,5-dihydro-pyrrol-1-yl]-4-methyl-pentanoic acid (prepared as in Example 64, 95 mg, 0.29 mmol) in dichloromethane (1.00 mL) was added 1-(3-dimethylaminopropyl)-3-ethylcarbodi-imide hydrochloride (62 mg, 0.32 mmol) and 1-hydroxyben-zotriazole (41 mg, 0.30 mmol). The resulting solution was stirred for 5 min before 3-cyclopropyl-[1,2,4]thiadiazol-5-ylamine (50 mg, 0.35 mmol) was added and the resulting mixture stirred at 25° C. overnight. The mixture was washed with saturated ammonium chloride (1 mL), evaporated and the crude product purified by HPLC (Gilson semi-prep; Supelcosil ABZ+Plus 12 μM 25 cm×21.2 mm column 20-95% acetonitrile/water gradient) which afforded (S)-2-[4-(2-chloro-phenoxy)-2-oxo-2,5-dihydro-pyrrol-1-yl]-4-methyl-pentanoic acid (3-cyclopropyl-[1,2,4]thiadiazol-5-yl)-amide (42 mg, 32%) as a light orange solid: HR-ES-MS m/z calculated for $C_{21}H_{23}ClN_4O_3S$ [M+H]$^+$ 447.1252, observed 447.1252; $^1$H NMR (300 MHz, DMSO-d$_6$) ppm 0.84-0.97 (m, 2H), 0.91 (d, J=6.6 Hz, 3H), 0.94 (d, J=6.6 Hz, 3H), 0.97-1.06 (m, 2H), 1.39-1.56 (m, 1H), 1.55-1.75 (m, 1H), 1.76-1.97 (m, 1H), 2.07-2.24 (m, 1H), 4.28 (d, J=18.4 Hz, 1H), 4.51 (d, J=18.4 Hz, 1H), 4.82 (s, 1H), 4.99 (dd, J=11.0, 4.4 Hz, 1H), 7.37 (td, J=8.0, 1.3 Hz, 1H), 7.47 (td, J=8.0, 1.1 Hz, 1H), 7.54 (dd, J=8.0, 1.3 Hz, 1H), 7.66 (dd, J=8.0, 1.1 Hz, 1H), 13.26 (s, 1H).

Example 106

(S)-2-[4-(2-Chloro-phenoxy)-2-oxo-2,5-dihydro-pyrrol-1-yl]-4-methyl-pentanoic acid [3-(3,3,3-trifluoro-propyl)-[1,2,4]thiadiazol-5-yl]-amide

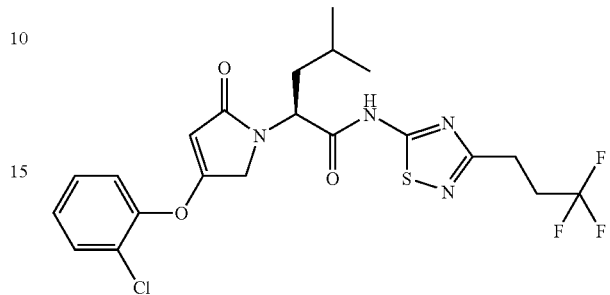

To a solution of 4,4,4-trifluoro-butyraldehyde (4.3 g, 0.031 mol) in water (20 mL) was added with stirring a solution of hydroxylamine-O-sulfonic acid (4.17 g, 0.037 mol) in water (20 mL). The resulting mixture was allowed to stand for 12 h at room temperature. The reaction mixture was extracted with dichloromethane (2×20 ml) and the combined extracts washed with water (10 mL) and dried over sodium sulfate. The mixture was filtered and evaporated which afforded an oil which was distilled (50° C., 350 mbar) which afforded 4,4,4-trifluoro-butyronitrile (4.1 g) as a colorless liquid.

To a stirred suspension of aluminum chloride (1.73 g, 0.032 mol) in toluene (15 mL) at 0° C. under argon was slowly added a solution of 2M trimethylaluminum in toluene (15 mL, 0.030 mol) maintaining a temperature below 10° C. The resulting mixture was allowed to stir at room temperature for 2 h before a solution of 4,4,4-trifluoro-butyronitrile (2.45 g, 0.018 mol) in toluene (10 mL) was added. The resulting mixture was warmed to 80° C. and allowed to stir for 20 h. The reaction mixture was cooled to room temperature and then slowly poured on to a cooled suspension of silica gel (20 g) in dichloromethane (40 mL). The resulting mixture was stirred for 15 min, filtered and the silica gel pad washed well with methanol. The filtrate was evaporated and the residue was redissolved in a solution of dichloromethane/methanol, filtered and evaporated which afforded a solid. The solid was suspended in a hydrogen chloride solution (8 mL, 3N in methanol) and stirred vigorously while diethyl ether (200 mL) was added dropwise. The resulting mixture was stirred at room temperature 1 h and decanted, washed with diethyl ether (100 mL) decanted and dried under vacuum which afforded 4,4,4-trifluoro-butyramidine hydrochloride (2.1 g, 66%) as a red oil.

To a solution of 4,4,4-trifluoro-butyramidine hydrochloride (2.1 g, 0.012 mol) in methanol (10 mL) at 0° C. under vigorous stirring was added dropwise bromine (0.61 mL, 0.012 mol) and a 5.4M sodium methylate solution in methanol (4.4 mL, 0.012 mol) simultaneously over 30 min maintaining a slight bromine excess by color. To the resulting nearly colorless suspension was added dropwise a solution of potassium thiocyanate (1.16 g, 0.012 mol) in methanol (10 mL) over 10 min at 0-10° C. The resulting mixture was stirred for 2 h at 0-10° C. and filtered. The isolated material was washed with methanol and dried which afforded a brown solid which was purified by flash chromatography (150 g silica gel 60 5% methanol/diethyl ether) and crystallized from diethyl ether/hexanes which afforded 3-(3,3,3-trifluoro-propyl)-[1,2,4]thiadiazol-5-ylamine (1.43 g, 61%) as a brown oil.

To a solution of (S)-2-[4-(2-chloro-phenoxy)-2-oxo-2,5-dihydro-pyrrol-1-yl]-4-methyl-pentanoic acid (prepared as in Example 64, 68 mg, 0.21 mmol) in dichloromethane (1.00 mL) was added 1-(3-dimethylaminopropyl)-3-ethylcarbodiimide hydrochloride (45 mg, 0.23 mmol) and 1-hydroxybenzotriazole (30 mg, 0.22 mmol). The resulting solution was stirred for 5 min before 3-(3,3,3-trifluoro-propyl)-[1,2,4]thiadiazol-5-ylamine (50 mg, 0.25 mmol) was added and the resulting mixture stirred at 25° C. overnight. The mixture was washed with saturated ammonium chloride (1 mL), evaporated and the crude product purified by HPLC (Gilson semi-prep; Supelcosil ABZ+Plus 12 μM 25 cm×21.2 mm column 20-95% acetonitrile/water gradient) which afforded (S)-2-[4-(2-chloro-phenoxy)-2-oxo-2,5-dihydro-pyrrol-1-yl]-4-methyl-pentanoic acid [3-(3,3,3-trifluoro-propyl)-[1,2,4]thiadiazol-5-yl]-amide (52 mg, 49%) as a light yellow solid: HR-ES-MS m/z calculated for $C_{21}H_{22}ClF_3N_4O_3S$ $[M+H]^+$ 503.1126, observed 503.1127; $^1$H NMR (300 MHz, DMSO-$d_6$) δ ppm 0.92 (d, J=6.6 Hz, 3H), 0.95 (d, J=6.6 Hz, 3H), 1.48 (br. s., 1H), 1.55-1.77 (m, 1H), 1.77-1.97 (m, 1H), 2.66-2.90 (m, 2H), 3.05 (t, J=6.9 Hz, 2H), 4.30 (d, J=18.4 Hz, 1H), 4.51 (d, J=18.4 Hz, 1H), 4.83 (s, 1H), 4.93-5.07 (m, 1H), 7.37 (td, J=8.0, 1.5 Hz, 1H), 7.47 (td, J=8.0, 1.5 Hz, 1H), 7.54 (dd, J=8.0, 1.2 Hz, 1H), 7.66 (dd, J=8.0, 1.2 Hz, 1H), 13.38 (s, 1H).

Example 107

(S)-2-[4-(2-Chloro-phenoxy)-2-oxo-2,5-dihydro-pyrrol-1-yl]-4-methyl-pentanoic acid (3-methyl-[1,2,4]thiadiazol-5-yl)-amide

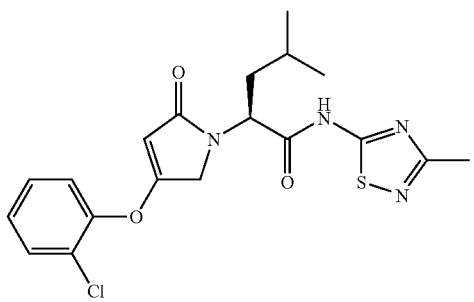

To a solution of (S)-2-[4-(2-chloro-phenoxy)-2-oxo-2,5-dihydro-pyrrol-1-yl]-4-methyl-pentanoic acid (prepared as in Example 64, 67 mg, 0.21 mmol) in dichloromethane (1.00 mL) was added 1-(3-dimethylaminopropyl)-3-ethylcarbodiimide hydrochloride (44 mg, 0.23 mmol) and 1-hydroxybenzotriazole (29 mg, 0.22 mmol). The resulting solution was stirred for 5 min before 5-amino-3-methyl-1,2,4-thiadiazole (50 mg, 0.43 mmol) was added and the resulting mixture stirred at 25° C. overnight. The mixture was washed with saturated ammonium chloride (1 mL), evaporated and the crude product purified by HPLC (Gilson semi-prep; Supelcosil ABZ+Plus 12 μM 25 cm×21.2 mm column 20-95% acetonitrile/water gradient) which afforded (S)-2-[4-(2-chloro-phenoxy)-2-oxo-2,5-dihydro-pyrrol-1-yl]-4-methyl-pentanoic acid (3-methyl-[1,2,4]thiadiazol-5-yl)-amide (37 mg, 43%) as a light yellow solid: HR-ES-MS m/z calculated for $C_{19}H_{21}ClN_4O_3S$ $[M+H]^+$ 421.1096, observed 421.1095; $^1$H NMR (300 MHz, DMSO-$d_6$) δ ppm 0.90 (d, J=6.4 Hz, 3H), 0.93 (d, J=6.4 Hz, 3H), 1.35-1.54 (m, 1H), 1.56-1.72 (m, 1H), 1.76-1.93 (m, 1H), 2.44 (s, 3H), 4.28 (d, J=18.4 Hz, 1H), 4.49 (d, J=18.4 Hz, 1H), 4.81 (s, 1H), 5.00 (dd, J=10.6, 4.2 Hz, 1H), 7.36 (t, J=7.8 Hz, 1H), 7.45 (t, J=7.8 Hz, 1H), 7.52 (d, J=7.8 Hz, 1H), 7.64 (d, J=7.8 Hz, 1H), 13.24 (s, 1H).

Example 108

(S)-2-[4-(2-Chloro-phenoxy)-2-oxo-2,5-dihydro-pyrrol-1-yl]-4-methyl-pentanoic acid (3-dimethylamino-[1,2,4]thiadiazol-5-yl)-amide

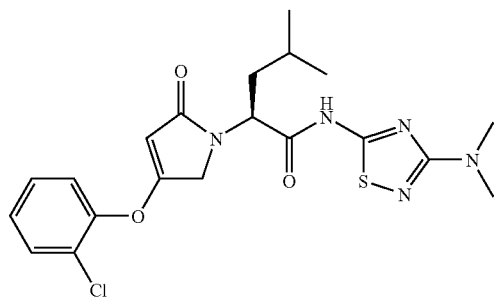

To a solution of (S)-2-[4-(2-chloro-phenoxy)-2-oxo-2,5-dihydro-pyrrol-1-yl]-4-methyl-pentanoic acid (prepared as in Example 64, 93 mg, 0.29 mmol) in dichloromethane (1.00 mL) was added 1-(3-dimethylaminopropyl)-3-ethylcarbodiimide hydrochloride (60 mg, 0.31 mmol) and 1-hydroxybenzotriazole (40 mg, 0.30 mmol). The resulting solution was stirred for 5 min before N3,N3-dimethyl-[1,2,4]thiadiazole-3,5-diamine (prepared in German Patent DE959191 Example 8, 50 mg, 0.35 mmol) was added and the resulting mixture stirred at 25° C. overnight. The mixture was washed with saturated aqueous ammonium chloride solution (1 mL), evaporated and the crude product purified by HPLC (Gilson semi-prep; Supelcosil ABZ+Plus 12 μM 25 cm×21.2 mm column 20-95% acetonitrile/water gradient) which afforded (S)-2-[4-(2-chloro-phenoxy)-2-oxo-2,5-dihydro-pyrrol-1-yl]-4-methyl-pentanoic acid (3-dimethylamino-[1,2,4]thiadiazol-5-yl)-amide (47 mg, 36%) as a yellow solid: HR-ES-MS m/z calculated for $C_{20}H_{24}ClN_5O_3S$ $[M+H]^+$ 450.1361, observed 450.1360; $^1$H NMR (300 MHz, DMSO-$d_6$) δ ppm 0.89 (d, J=6.4 Hz, 3H), 0.93 (d, J=6.4 Hz, 3H), 1.44 (br. s., 1H), 1.51-1.72 (m, 1H), 1.72-1.98 (m, 1H), 3.02 (s, 6H), 4.25 (d, J=18.4 Hz, 1H), 4.50 (d, J=18.4 Hz, 1H), 4.81 (s, 1H), 4.97 (dd, J=10.9, 4.5 Hz, 1H), 7.36 (td, J=7.8, 1.5 Hz, 1H), 7.45 (td, J=7.8, 1.4 Hz, 1H), 7.52 (dd, J=7.8, 1.5 Hz, 1H), 7.64 (dd, J=7.8, 1.4 Hz, 1H), 13.08 (s, 1H).

Example 109

(S)-2-[4-(2-Chloro-phenoxy)-2-oxo-2,5-dihydro-pyrrol-1-yl]-4-methyl-pentanoic acid [3-(4-methoxy-benzyl)-[1,2,4]thiadiazol-5-yl]-amide

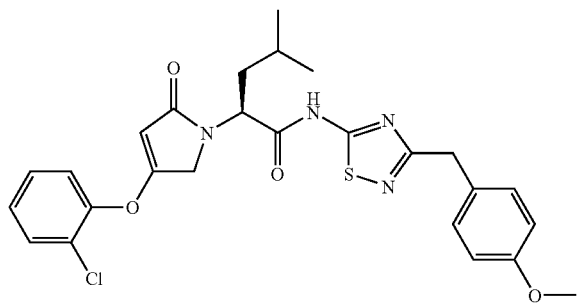

To a suspension of 4-methoxyphenylacetamide (5.06 g, 30.0 mmol) in toluene (10 mL) was added 2,6-di-t-butyl-4-hydroxytoluene (132 mg, 0.60 mmol) and chlorocarbonyl-sulfenyl chloride (5.52 mL, 60.0 mmol). The resulting mixture was warmed to 115° C. for 80 min during which time hydrochloric acid gas was evolved resulting in a yellow solution. To this solution additional chlorcarbonyl-sulfenylchloride (1.38 mL, 15.00 mmoles) was added and the mixture heated for 40 min and allowed to stand at room temperature overnight. The reaction mixture was cooled to 0° C. and stirred for 10 min before being filtered to remove a beige solid. The solid was washed with cold toluene (2×10 mL) and the filtrate was concentrated and purified by flash chromatography (silica gel, 20% ethyl acetate/hexanes) which afforded 5-(4-methoxy-benzyl)-[1,3,4]oxathiazol-2-one (1.12 g, 17%) as a yellow solid.

To a suspension of 5-(4-methoxy-benzyl)-[1,3,4]oxathiazol-2-one (335 mg, 1.50 mmol) in mesitylene (3 mL) was added 4-toluenesulfonylcyanide (572 mg, 3.00 mmol) and the resulting mixture heated to 150° C. for 135 min. The resulting brown solution was cooled and purified by flash chromatography (silica gel, 0% to 33% ethyl acetate/hexanes) which afforded 3-(4-methoxy-benzyl)-5-(toluene-4-sulfonyl)-[1,2,4]thiadiazole (462 mg, 86%) as a dark yellow solid.

3-(4-Methoxy-benzyl)-5-(toluene-4-sulfonyl)-[1,2,4]thiadiazole (361 mg, 1.00 mmol) was dissolved in 1,2-dimethoxyethane (3 mL) and placed in a pressure tube. Ammonia gas was bubbled into the solution for 5 h after which time the tube was sealed and stirred at room temperature overnight. Ammonia gas was bubbled for an additional 5 h, the tube resealed and warmed to 50° C. for 2 h. The vessel was cooled to 0° C. and let stand for 5 h during which time a beige precipitate formed. The mixture was filtered and the solid washed with cold 1,2-dimethoxyethane (2×2 mL) and dried which afforded 3-(4-methoxy-benzyl)-[1,2,4]thiadiazol-5-ylamine (207 mg, 94%) as a beige solid.

To a solution of (S)-2-[4-(2-chloro-phenoxy)-2-oxo-2,5-dihydro-pyrrol-1-yl]-4-methyl-pentanoic acid (prepared as in Example 64, 60 mg, 0.19 mmol) in dichloromethane (1.00 mL) was added 1-(3-dimethylaminopropyl)-3-ethylcarbodiimide hydrochloride (40 mg, 0.21 mmol) and 1-hydroxybenzotriazole (27 mg, 0.20 mmol). The resulting solution was stirred for 5 min before 3-(4-methoxy-benzyl)-[1,2,4]thiadiazol-5-ylamine (50 mg, 0.23 mmol) was added and the resulting mixture stirred at 25° C. overnight. The mixture was washed with saturated ammonium chloride (1 mL), evaporated and the crude product purified by HPLC (Gilson semi-prep; Supelcosil ABZ+Plus 12 μM 25 cm×21.2 mm column 20-95% acetonitrile/water) which afforded (S)-2-[4-(2-chloro-phenoxy)-2-oxo-2,5-dihydro-pyrrol-1-yl]-4-methyl-pentanoic acid [3-(4-methoxy-benzyl)-[1,2,4]thiadiazol-5-yl]-amide (48 mg, 49%) as a light yellow solid: HR-ES-MS m/z calculated for $C_{26}H_{27}ClN_4O_4S$ [M+H]$^+$ 527.1515, observed 527.1514; $^1$H NMR MHz, DMSO-d$_6$) δ ppm 0.88 (d, J=6.6 Hz, 3H), 0.91 (d, J=6.6 Hz, 3H), 1.22 (t, J=7.5 Hz, 3H), 1.44 (br. s., 1H), 1.54-1.71 (m, 1H), 1.71-1.90 (m, 1H), 2.76 (q, J=7.5 Hz, 2H), 4.25 (d, J=18.4 Hz, 1H), 4.48 (d, J=18.4 Hz, 1H), 4.79 (s, 1H), 4.97 (dd, J=10.9, 4.8 Hz, 1H), 7.33 (td, J=7.8, 1.5 Hz, 1H), 7.43 (td, J=7.8, 1.4 Hz, 1H), 7.50 (dd, J=7.8, 1.5 Hz, 1H), 7.62 (dd, J=7.8, 1.4 Hz, 1H), 13.24 (s, 1H).

Example 110

(S)-2-[4-(2-Chloro-phenoxy)-2-oxo-2,5-dihydro-pyrrol-1-yl]-4-methyl-pentanoic acid (3-ethyl-[1,2,4]thiadiazol-5-yl)-amide

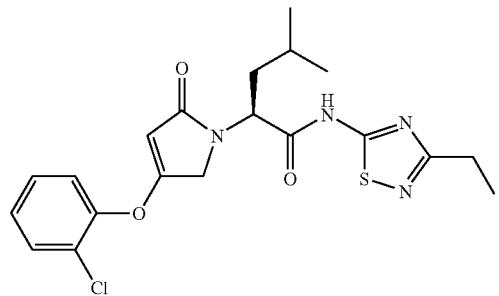

To a solution of (S)-2-[4-(2-chloro-phenoxy)-2-oxo-2,5-dihydro-pyrrol-1-yl]-4-methyl-pentanoic acid (prepared as in Example 64, 104 mg, 0.32 mmol) in dichloromethane (1.00 mL) was added 1-(3-dimethylaminopropyl)-3-ethylcarbodiimide hydrochloride (69 mg, 0.36 mmol) and 1-hydroxybenzotriazole (46 mg, 0.34 mmol). The resulting solution was stirred for 5 min before 3-ethyl-[1,2,4]thiadiazol-5-ylamine (50 mg, 0.39 mmol) was added and the resulting mixture stirred at 25° C. overnight. The mixture was washed with saturated ammonium chloride (1 mL), evaporated and the crude product purified by HPLC (Gilson semi-prep; Supelcosil ABZ+Plus 12 μM 25 cm×21.2 mm column 20-95% acetonitrile/water gradient) which afforded (S)-2-[4-(2-chloro-phenoxy)-2-oxo-2,5-dihydro-pyrrol-1-yl]-4-methyl-pentanoic acid (3-ethyl-[1,2,4]thiadiazol-5-yl)-amide (83 mg, 59%) as a light yellow solid: HR-ES-MS m/z calculated for $C_{20}H_{23}ClN_4O_3S$ [M+H]$^+$ 435.1252, observed 435.1252; $^1$H NMR (300 MHz, DMSO-d$_6$) δ ppm 0.88 (d, J=6.4 Hz, 3H), 0.91 (d, J=6.4 Hz, 3H), 1.45 (br. s., 1H), 1.53-1.72 (m, 1H), 1.83 (br. s., 1H), 3.69 (s, 3H), 4.04 (s, 2H), 4.26 (d, J=18.4 Hz, 1H), 4.48 (d, J=18.4 Hz, 1H), 4.80 (s, 1H), 4.96 (dd, J=11.2, 4.5 Hz, 1H), 6.84 (d, J=8.5 Hz, 2H), 7.17 (d, J=8.5 Hz, 2H), 7.35 (td, J=7.8, 1.5 Hz, 1H), 7.45 (t, J=7.8 Hz, 1H), 7.51 (d, J=7.8 Hz, 1H), 7.64 (d, J=7.8 Hz, 1H), 13.28 (s, 1H).

Example 111

(5-{(S)-2-[4-(2-Chloro-phenoxy)-2-oxo-2,5-dihydro-pyrrol-1-yl]-4-methyl-pentanoylamino}-[1,2,4]thiadiazol-3-yl)-acetic acid allyl ester

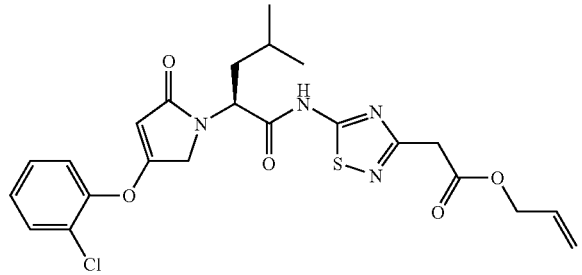

To allyl alcohol (1 L) at −20° C. was added thionyl chloride (55 mL, 0.76 mol) dropwise over 20 min. To this solution was added (5-t-butoxycarbonylamino-[1,2,4]thiadiazol-3-yl)-acetic acid (prepared as described in Chem. Ber. 1954, 87, 57, 178 g, 0.687 mol) in small portions. The reaction was warmed to 60° C. during which time gas was evolved and kept at this temperature for 3.5 h. The resulting mixture was stirred at room temperature overnight during which time a crystalline solid formed. The solid was isolated by filtration, washed with allyl alcohol and diethyl ether and dried which afforded (5-amino-[1,2,4]thiadiazol-3-yl)-carbamic acid allyl ester (160 g, 99%) as a white crystalline solid: mp=159-161° C.

To a solution of (S)-2-[4-(2-chloro-phenoxy)-2-oxo-2,5-dihydro-pyrrol-1-yl]-4-methyl-pentanoic acid (prepared as in Example 64, 132 mg, 0.41 mmol) in dichloromethane (2.00 mL) was added 1-(3-dimethylaminopropyl)-3-ethylcarbodiimide hydrochloride (91 mg, 0.47 mmol) and 1-hydroxybenzotriazole (62 mg, 0.46 mmol). The resulting solution was stirred for 5 min before (5-amino-[1,2,4]thiadiazol-3-yl)-acetic acid ally ester hydrochloride (1:1) (100 mg, 0.50 mmol) was added and the resulting mixture stirred at 25° C. overnight. The mixture was washed with saturated ammonium chloride (1 mL), evaporated and the crude product purified by HPLC (Gilson semi-prep; Supelcosil ABZ+Plus 12 µM 25 cm×21.2 mm column 20-95% acetonitrile/water) which afforded (5-{(S)-2-[4-(2-chloro-phenoxy)-2-oxo-2,5-dihydro-pyrrol-1-yl]-4-methyl-pentanoylamino}-[1,2,4]thiadiazol-3-yl)-acetic acid allyl ester (145 mg, 70%) as a light yellow solid: HR-ES-MS m/z calculated for $C_{23}H_{25}ClN_4O_5S$ $[M+H]^+$ 505.1307, observed 505.1306; $^1H$ NMR (300 MHz, DMSO-$d_6$) δ ppm 0.91 (d, J=6.4 Hz, 3H), 0.95 (d, J=6.4 Hz, 3H), 1.36-1.57 (m, 1H), 1.58-1.76 (m, 1H), 1.77-1.96 (m, 1H), 3.97 (s, 2H), 4.30 (d, J=18.0 Hz, 1H), 4.50 (d, J=18.0 Hz, 1H), 4.59 (d, J=5.6 Hz, 2H), 4.83 (s, 1H), 5.01 (dd, J=11.3, 5.6 Hz, 1H), 5.16-5.35 (m, 2H), 5.77-6.01 (m, 1H), 7.37 (ddd, J=8.0, 1.5 Hz, 1H), 7.47 (td, J=8.0, 1.5 Hz, 1H), 7.54 (dd, J=8.0, 1.5 Hz, 1H), 7.66 (dd, J=8.0, 1.5 Hz, 1H), 13.43 (s, 1H).

Example 112

(S)-2-[4-(2-Chloro-phenoxy)-2-oxo-2,5-dihydro-pyrrol-1-yl]-4-methyl-pentanoic acid (3-methoxymethyl-[1,2,4]thiadiazol-5-yl)-amide

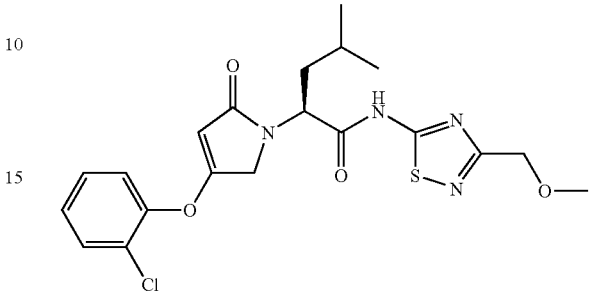

To a stirred suspension of aluminum chloride (4.81 g, 0.090 mol) in toluene (33.5 mL) at 0° C. under argon was slowly added a solution of 2M trimethylaluminum in toluene (42 mL, 0.030 mol) maintaining a temperature below 10° C. The resulting mixture was allowed to stir at room temperature for 2 h before a solution of 3-methoxyacetonitrile (5.56 g, 0.050 mol) in toluene (16.5 mL) was added. A fine light yellow precipitate formed and the resulting mixture was warmed to 80° C. and allowed to stand for 20 h. The reaction mixture was cooled to room temperature and then slowly poured on to a cooled suspension of silica gel (40 g) in dichloromethane (100 mL). The resulting mixture was stirred for 15 min, filtered and the silica gel pad washed well with methanol. The filtrate was evaporated and the residue was redissolved in a solution of dichloromethane/methanol, filtered and evaporated which afforded a solid. The solid was suspended in a 3N hydrogen chloride solution in methanol (20 mL) and stirred vigorously while diethyl ether (500 mL) was added dropwise. The resulting mixture was stirred at room temperature (30 min) decanted, washed with diethyl ether (250 mL) decanted and dried under vacuum which afforded 2-methoxy-acetamidine hydrochloride (4.66 g, 75%) as a light yellow semisolid.

To a solution of 2-methoxy-acetamidine hydrochloride (4.66 g, 0.037 mol) in methanol (20 mL) at 0° C. under vigorous stirring was added dropwise bromine (1.90 mL, 0.037 mol) and a 5.4M sodium methylate solution in methanol (13.7 mL, 0.037 mol) simultaneously over 30 min maintaining a slight bromine excess by color. To the resulting nearly colorless suspension was added dropwise a solution of potassium thiocyanate (3.64 g, 0.037 mol) in methanol (20 mL) over 10 min at 0-10° C. The resulting mixture was stirred for 2 h at 0-10° C. and filtered. The isolated material was washed with methanol and dried which afforded a brown solid which was purified by flash chromatography (silica gel 60, 5% methanol/diethyl ether) and crystallized from diethyl ether/hexanes which afforded 3-methoxymethyl-[1,2,4]thiadiazol-5-ylamine (3.25 g, 60%) as a light yellow solid.

To a solution of (S)-2-[4-(2-chloro-phenoxy)-2-oxo-2,5-dihydro-pyrrol-1-yl]-4-methyl-pentanoic acid (prepared as in Example 64, 94 mg, 0.29 mmol) in dichloromethane (1.00 mL) was added 1-(3-dimethylaminopropyl)-3-ethylcarbodiimide hydrochloride (61 mg, 0.32 mmol) and 1-hydroxybenzotriazole (42 mg, 0.31 mmol). The resulting solution was stirred for 5 min before 3-methoxymethyl-[1,2,4]thiadiazol-5-ylamine (50 mg, 0.34 mmol) was added and the resulting mixture stirred at 25° C. overnight. The mixture was washed with saturated ammonium chloride (1 mL), evaporated and the crude product purified by HPLC (Gilson semi-prep; Supelcosil ABZ+Plus 12 µM 25 cm×21.2 mm column 20-95% acetonitrile/water) which afforded (S)-2-[4-(2-chloro-phenoxy)-2-oxo-2,5-dihydro-pyrrol-1-yl]-4-methyl-pentanoic acid (3-methoxymethyl-[1,2,4]thiadiazol-5-yl)-amide (62 mg, 47%) as a light yellow solid: HR-ES-MS m/z calculated for $C_{20}H_{23}ClN_4O_4S$ $[M+H]^+$ 451.1202, observed 451.1202; $^1H$ NMR (300 MHz, DMSO-$d_6$) δ ppm 0.92 (d, J=6.6 Hz, 3H), 0.95 (d, J=6.6 Hz, 3H), 1.48 (br. s., 1H), 1.60-1.76 (m, 1H), 1.79-1.95 (m, 1H), 3.33 (s, 3H), 4.30 (d, J=18.1 Hz, 1H), 4.51 (d, J=18.1 Hz, 1H), 4.52 (s, 2H), 4.84 (s, 1H), 5.02 (dd, J=10.9, 4.5 Hz, 1H), 7.37 (td, J=7.5, 0.9 Hz, 1H), 7.47 (t, J=7.5 Hz, 1H), 7.54 (d, J=7.5 Hz, 1H), 7.66 (d, J=7.5 Hz, 1H), 13.40 (s, 1H).

Example 113

(S)-2-[4-(2-Chloro-phenoxy)-2-oxo-2,5-dihydro-pyrrol-1-yl]-4-methyl-pentanoic acid [3-(2-oxo-propyl)-[1,2,4]thiadiazol-5-yl]-amide

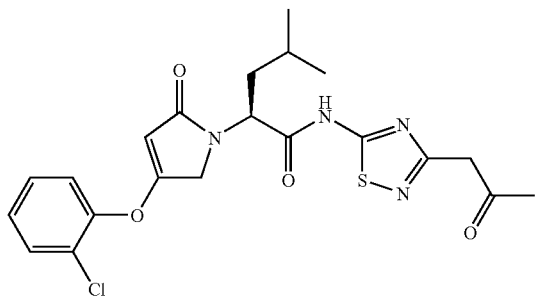

To a solution of (S)-2-[4-(2-chloro-phenoxy)-2-oxo-2,5-dihydro-pyrrol-1-yl]-4-methyl-pentanoic acid (prepared as in Example 64, 90 mg, 0.28 mmol) in dichloromethane (1.00 mL) was added 1-(3-dimethylaminopropyl)-3-ethylcarbodiimide hydrochloride (67 mg, 0.35 mmol) and 1-hydroxybenzotriazole (41 mg, 0.30 mmol). The resulting solution was stirred for 5 min before 1-(5-amino-1,2,4-thiadiazol-3-yl)-2-propanone (56 mg, 0.29 mmol) was added and the resulting mixture stirred at 25° C. overnight. The mixture was washed with saturated ammonium chloride (1 mL), evaporated and the crude product purified by HPLC (Gilson semi-prep; Supelcosil ABZ+Plus 12 µM 25 cm×21.2 mm column 20-95% acetonitrile/water gradient) which afforded (S)-2-[4-(2-chloro-phenoxy)-2-oxo-2,5-dihydro-pyrrol-1-yl]-4-methyl-pentanoic acid [3-(2-oxo-propyl)-[1,2,4]thiadiazol-5-yl]-amide (51 mg, 40%) as a light yellow solid: HR-ES-MS m/z calculated for $C_{21}H_{23}ClN_4O_4S$ $[M+H]^+$ 463.1202, observed 463.1202; $^1H$ NMR (300 MHz, DMSO-$d_6$) δ ppm 0.91 (d, J=6.6 Hz, 3H), 0.95 (d, J=6.6 Hz, 3H), 1.47 (br. s., 1H), 1.59-1.76 (m, 1H), 1.79-1.95 (m, 1H), 2.18 (s, 3H), 4.00 (s, 2H), 4.29 (d, J=18.4 Hz, 1H), 1.59 (d, J=18.4 Hz, 1H), 4.83 (s, 1H), 5.01 (dd, J=10.9, 4.8 Hz, 1H), 7.37 (td, J=7.5, 1 Hz, 1H), 7.47 (t, J=7.5 Hz, 1H), 7.54 (m, J=7.5 Hz, 1H), 7.66 (d, J=7.5 Hz, 1H), 13.37 (s, 1H).

Example 114

(S)-2-[4-(3-Ethoxy-2-fluoro-phenoxy)-2-oxo-2,5-dihydro-pyrrol-1-yl]-4-methyl-pentanoic acid [1-(2-hydroxy-2-methyl-propyl)-1H-pyrazol-3-yl]-amide

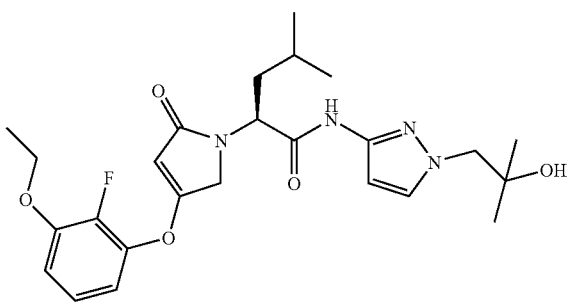

To a solution of 3-ethoxy-2-fluoro-phenylboronic acid (10.0 g, 0.054 mol) in tetrahydrofuran (150 mL) was added glacial acetic acid (60 mL). The resulting mixture was cooled to 0° C. before hydrogen peroxide (50% aqueous solution, 8 mL) was added. The resulting mixture was allowed to come to room temperature and stirred for 23 h. The mixture was evaporated and the residue was dissolved in ethyl acetate, washed with hydrochloric acid (0.5N), water and brine. The organic phase was dried, filtered and evaporated to give 3-ethoxy-2-fluoro-phenol (6.00 g, 71%) as a brown oil.

To a stirred mixture of 3-ethoxy-2-fluoro-phenol (6.00 g, 0.038 mol) and ethyl-2-butynoate (8.60 g, 0.077 mol) in tetrahydrofuran (50 mL) was added 1,8-diazabicyclo[5.4.0]undec-7-ene (5.80 g, 0.038 mol) slowly. After addition was complete the mixture was stirred at reflux for 7 h. Upon completion of the reaction the tetrahydrofuran was removed in vacuo and the residue was diluted in diethyl ether and washed first with 1N aqueous hydrochloric acid, then 10% aqueous sodium hydroxide solution, a saturated sodium chloride solution and dried over magnesium sulfate. The crude product, (E)-3-(3-ethoxy-2-fluoro-phenoxy)-but-2-enoic acid ethyl ester, was obtained as a brown oil (6.00 g, 58%) and used without further purification.

To a stirred mixture of (E)-3-(3-ethoxy-2-fluoro-phenoxy)-but-2-enoic acid ethyl ester (6.00 g, 0.022 mol) dissolved in carbon tetrachloride (70 mL) under a nitrogen atmosphere was added N-bromosuccinimide (5.97 g, 0.034 mol) and benzoyl peroxide (75%, 0.72 g, 2.2 mmol). After addition was complete, the mixture was stirred at reflux for 6 h. The reaction mixture was then placed in the refrigerator overnight. The solids formed were removed by filtration and the filtrate concentrated in vacuo. The crude product obtained was purified by ISCO flash chromatography (Teledyne Isco RediSep Flash Column 128 g; 0% to 10% ethyl acetate/hexanes) to afford, (E)-4-bromo-3-(3-ethoxy-2-fluoro-phenoxy)-but-2-enoic acid ethyl ester (6.40 g, 82%) as an impure yellow oil.

To a solution of (L)-leucine methyl ester hydrochloride (3.50 g, 19.4 mmol) dissolved in acetonitrile (50 mL) containing N,N-diisopropylethylamine (2.58 g, 20 mmol) was added (E)-4-bromo-3-(3-ethoxy-2-fluoro-phenoxy)-but-2-enoic acid ethyl ester (3.35 g) in acetonitrile (10 mL) and N,N-diisopropylethylamine (1.30 g, 10 mmol) and the resulting mixture was refluxed for 24 h. The reaction mixture was cooled to room temperature and then poured into ethyl acetate. The mixture was filtered to remove salts and the filtrate was washed successively with saturated ammonium chloride, water, and brine. The solution was dried over sodium sulfate, filtered and evaporated. The residue was dissolved in tetrahydrofuran (6 mL) and then transferred to an Emry Optimizer microwave reaction vessel and heated at 160° C., for 2 h. The crude product obtained after aqueous work-up, was purified by ISCO flash chromatography (Teledyne Isco RediSep Flash Column 80 g, 10% to 80% ethyl acetate/hexanes) to afford, (S)-2-[4-(3-ethoxy-2-fluoro-phenoxy)-2-oxo-2,5-dihydro-pyrrol-1-yl]-4-methyl-pentanoic acid methyl ester (2.40 g, 68%) as a yellow semisolid.

To a solution containing (S)-2-[4-(3-ethoxy-2-fluoro-phenoxy)-2-oxo-2,5-dihydro-pyrrol-1-yl]-4-methyl-pentanoic acid methyl ester (2.40 g, 0.007 mol) in tetrahydrofuran (40 mL) was treated with an aqueous solution of lithium hydroxide monohydrate (0.5N, 30 mL, 0.015 mol). The mixture was stirred at room temperature for 2H, and the solvents evaporated. The residue was dissolved in water and washed with diethyl ether, and the diethyl ether layer discarded. The aqueous phase was acidified with dilute hydrochloric acid (pH <2), and extracted with ethyl acetate. The combined organic layers were dried over sodium sulfate and concentrated to afford (S)-2-[4-(3-ethoxy-2-fluoro-phenoxy)-2-oxo-2,5-dihydro-pyrrol-1-yl]-4-methyl-pentanoic acid (2.00 g, 87%) as a white solid after triturating with diethyl ether.

To a solution of (S)-2-[4-(3-ethoxy-2-fluoro-phenoxy)-2-oxo-2,5-dihydro-pyrrol-1-yl]-4-methyl-pentanoic acid (0.460 g, 1.31 mmol) in N,N-dimethylformamide (10 mL) was added 1-(3-amino-pyrazol-1-yl)-2-methyl-propan-2-ol (prepared in U.S. Pat. Appl. US2008021032, Example 80, 0.264 g, 1.70 mmol), and benzotriazol-1-yl-oxy-tris(dimethylamino)phosphonium hexafluorophosphate (1.22 g, 2.76 mmol). The mixture was stirred at 0° C. and N,N-diisopropylethylamine (0.340 g, 2.63 mmol) was added. The mixture was stirred at room temperature for 7 h and the solvents were evaporated. The residue was treated with ethyl acetate and ammonium chloride solution, and the organic layer separated. The organic layer was washed with brine and dried over sodium sulfate. The solvents were evaporated and the residue was purified by ISCO flash chromatography (Teledyne Isco RediSep Flash Column 25 g, 30% to 100% ethyl acetate/hexanes) which afforded (S)-2-[4-(3-ethoxy-2-fluoro-phenoxy)-2-oxo-2,5-dihydro-pyrrol-1-yl]-4-methyl-pentanoic acid [1-(2-hydroxy-2-methyl-propyl)-1H-pyrazol-3-yl]-amide (0.350 g, 55%) as a yellow solid: HR-ES-MS m/z calculated for $C_{25}H_{33}FN_4O_5$ $[M+H]^+$ 489.2508, observed 489.2508, $^1$H NMR (300 MHz, DMSO-$d_6$) δ ppm 1.00 0.90 (d, J=6.3 Hz, 3H), 0.93 (d, J=6.3 Hz, 3H), 1.05 (br. s., 3H), 1.06 (br. s., 3H), 1.36 (t, J=6.8 Hz, 3H), 1.47 (br. s., 1H), 1.50-1.64 (m, 1H), 1.63-1.86 (m, 1H), 3.89 (s, 2H), 4.15 (q, J=6.8 Hz, 2H), 4.21 (d, J=18.7 Hz, 1H), 4.60 (d, J=18.7 Hz, 1H), 4.68 (s, 1H), 4.83-4.93 (m, 1H), 4.89 (s, 1H), 6.44 (d, J=2.1 Hz, 1H), 6.96-7.07 (m, 1H), 7.07-7.26 (m, 2H), 7.53 (d, J=2.1 Hz, 1H), 10.80 (s, 1H).

Example 115

(S)-2-[4-(3-Ethoxy-2-fluoro-phenoxy)-2-oxo-2,5-dihydro-pyrrol-1-yl]-4-methyl-pentanoic acid [1-((R)-2,3-dihydroxy-propyl)-1H-pyrazol-3-yl]-amide

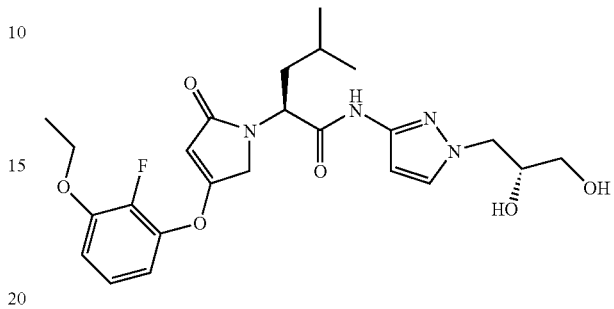

To a solution of (S)-2-[4-(3-ethoxy-2-fluoro-phenoxy)-2-oxo-2,5-dihydro-pyrrol-1-yl]-4-methyl-pentanoic acid (prepared as in Example 114, 570 mg, 1.62 mmol) in N,N-dimethylformamide (10 mL) was added 1-((R)-2,2-dimethyl-[1,3]dioxolan-4-yl-methyl)-1H-pyrazol-3-ylamine (prepared as in Example 49, 382 mg, 1.94 mmol) and benzotriazol-1-yl-oxy-tris(dimethylamino)phosphonium hexafluorophosphate (1.43 g, 3.23 mmol). The mixture was stirred at 0° C. and N,N-diisopropylethylamine (0.417 g, 3.23 mmol) was added. The mixture was stirred at room temperature for 4 h and the solvents were evaporated. The residue was treated with ethyl acetate and ammonium chloride solution, and the organic layer separated. The organic layer was washed with brine and dried over sodium sulfate. The solvents were evaporated and the residue was purified by ISCO flash chromatography (Teledyne Isco RediSep Flash Column 40 g, 10% to 80% ethyl acetate/hexanes) which afforded (S)-2-[4-(3-ethoxy-2-fluoro-phenoxy)-2-oxo-2,5-dihydro-pyrrol-1-yl]-4-methyl-pentanoic acid [1-((R)-2,2-dimethyl-[1,3]dioxolan-4-yl-methyl)-1H-pyrazol-3-yl]-amide (0.750 g, 87%) as a white solid.

A solution of (S)-2-[4-(3-ethoxy-2-fluoro-phenoxy)-2-oxo-2,5-dihydro-pyrrol-1-yl]-4-methyl-pentanoic acid [1-((R)-2,2-dimethyl-[1,3]dioxolan-4-yl-methyl)-1H-pyrazol-3-yl]-amide (0.750 g, 1.41 mmol) in tetrahydrofuran (30 mL) was treated with 2N aqueous hydrochloric acid (50 mL). The reaction mixture was stirred for 3 h at room temperature. The reaction mixture was diluted with ethyl acetate, washed with saturated sodium bicarbonate, a saturated sodium chloride solution and dried over magnesium sulfate. Upon concentration afforded, (S)-2-[4-(3-ethoxy-2-fluoro-phenoxy)-2-oxo-2,5-dihydro-pyrrol-1-yl]-4-methyl-pentanoic acid [1-((R)-2,3-dihydroxy-propyl)-1H-pyrazol-3-yl]-amide (0.650 g, 94%) as a white solid: HR-ES-MS m/z calculated for $C_{24}H_{31}FN_4O_6$, $[M+H]^+$ 491.2301 observed 491.2298; $^1$H NMR (300 MHz, DMSO-$d_6$) δ ppm 0.88 (d, J=6.4 Hz, 3H), 0.91 (d, J=6.4 Hz, 3H), 1.34 (t, J=6.7 Hz, 3H), 1.38-1.48 (m, 1H), 1.48-1.63 (m, 1H), 1.65-1.80 (m, 1H), 3.19-3.31 (m, 2H), 3.66-3.92 (m, 2H), 4.03-4.10 (m, 1H), 4.13 (q, J=6.7 Hz, 2H), 4.19 (d, J=18.4 Hz, 1H), 4.57 (d, J=18.4 Hz, 1H), 4.65-4.75 (m, 1H), 4.80-4.90 (m, 1H), 4.87 (s, 1H), 4.90-4.97 (m, 1H), 6.38 (d, J=1.8 Hz, 1H), 7.00 (t, J=7.4 Hz, 1H), 7.06-7.22 (m, 2H), 7.51 (d, J=1.8 Hz, 1H), 10.75 (br. s., 1H).

Example 116

(S)-2-[4-(3-Ethoxy-2,6-difluoro-phenoxy)-2-oxo-2,5-dihydro-pyrrol-1-yl]-4-methyl-pentanoic acid [1-((R)-2,2-dimethyl-[1,3]dioxolan-4-yl-methyl)-1H-pyrazol-3-yl]-mide

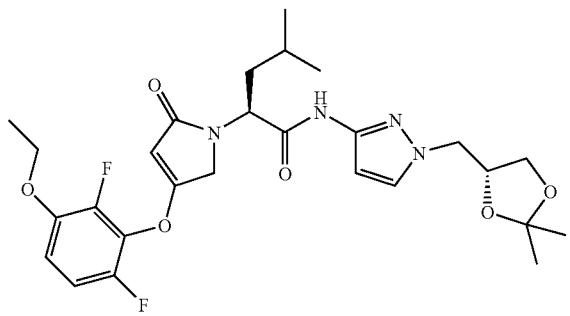

To a solution of 3-ethoxy-2,6-difluoro-phenylboronic acid (5.0 g, 0.025 mol) in tetrahydrofuran (80 mL) was added glacial acetic acid (30 mL). The resulting mixture was cooled to 0° C. before hydrogen peroxide (50% aqueous solution, 4 mL) was added. The resulting mixture was allowed to come to room temperature and stirred for 65 h. The mixture was evaporated and the residue was dissolved in ethyl acetate, washed with hydrochloric acid (0.5N), water and brine. The organic phase was dried, filtered and evaporated which afforded 3-ethoxy-2,6-difluoro-phenol (4.25 g, 99%) as a brown oil.

To a stirred mixture of 3-ethoxy-2,6-difluoro-phenol (4.26 g, 0.024 mol) and ethyl-2-butynoate (5.48 g, 0.049 mol) in tetrahydrofuran (30 mL) was added 1,8-diazabicyclo[5.4.0]undec-7-ene (3.73 g, 0.025 mol) slowly. After addition was complete the mixture was stirred at reflux for 6 h. Upon completion of the reaction the tetrahydrofuran was removed in vacuo and the residue was diluted in diethyl ether and washed first with 1N aqueous hydrochloric acid, then 10% aqueous sodium hydroxide solution, a saturated sodium chloride solution and dried over magnesium sulfate. The crude product was purified by ISCO column chromatography (Teledyne Isco RediSep Flash Column 120 g, 0% to 20% ethyl acetate/hexanes) which afforded (E)-3-(3-ethoxy-2,6-difluoro-phenoxy)-but-2-enoic acid ethyl ester (4.63 g, 66%) as a white crystalline solid.

To a stirred mixture of (E)-3-(3-ethoxy-2,6-difluoro-phenoxy)-but-2-enoic acid ethyl ester (4.60 g, 0.016 mol) dissolved in carbon tetrachloride (30 mL) under a nitrogen atmosphere was added N-bromosuccinimide (4.60 g, 0.026 mol) and benzoyl peroxide (0.39 g, 0.002 mol). After addition was complete the mixture was stirred at reflux for 24 h. To this mixture was added N-bromosuccinimide (3.00 g, 0.013 mol) and benzoyl peroxide (0.200 g, 0.0013 mol) and the resulting mixture heated for an additional 3 h. The reaction mixture was cooled, the succinimide removed by filtration and the solvent removed in vacuo. The crude product obtained was purified by ISCO flash chromatography (Teledyne Isco RediSep Flash Column 120 g; 0% to 20% ethyl acetate/hexanes) to afford, (E)-4-bromo-3-(3-ethoxy-2,6-difluoro-phenoxy)-but-2-enoic acid ethyl ester (1.38 g, 24%) as an oil.

To a solution of (L)-leucine methyl ester hydrochloride (6.00 g, 0.033 mol) dissolved in acetonitrile (50 mL) was added (E)-4-bromo-3-(3-ethoxy-2,6-difluoro-phenoxy)-but-2-enoic acid ethyl ester (6.05 g) in acetonitrile (10 mL) and N,N-diisopropylethylamine (7.27 g, 0.056 mol) and the resulting mixture refluxed for 14 h. The reaction mixture was cooled to room temperature and then poured into ethyl acetate. The mixture was filtered to remove salts and the filtrate washed successively with saturated ammonium chloride, water, and brine. The solution was dried over sodium sulfate, filtered and evaporated. The residue was dissolved in tetrahydrofuran (10 mL) and then transferred to an Emry Optimizer microwave reaction vessel and heated at 160° C., for 4 h. The crude product obtained after aqueous work-up, was purified by ISCO flash chromatography (Teledyne Isco RediSep Flash Column 100 g, 5% to 60% ethyl acetate/hexanes) to afford (S)-2-[4-(3ethoxy-2,6-difluoro-phenoxy)-2-oxo-2,5-dihydro-pyrrol-1-yl]-4-methyl-pentanoic acid methyl ester (1.80 g, 28%) as an oil.

To a solution containing (S)-2-[4-(3-ethoxy-2,6-difluoro-phenoxy)-2-oxo-2,5-dihydro-pyrrol-1-yl]-4-methyl-pentanoic acid methyl ester (1.68 g, 0.004 mol) in tetrahydrofuran (60 mL) was treated with an aqueous solution of lithium hydroxide monohydrate (0.5N, 18 mL, 0.009 mol). The mixture was stirred at 5° C. for 3 h, and the solvents evaporated. The residue was dissolved in water and washed with diethyl ether, and the diethyl ether layer discarded. The aqueous phase was acidified with dilute hydrochloric acid (pH <2), and extracted with ethyl acetate. The combined organic layers were dried over sodium sulfate and concentrated to afford (S)-2-[4-(3-ethoxy-2,6-difluoro-phenoxy)-2-oxo-2,5-dihydro-pyrrol-1-yl]-4-methyl-pentanoic acid, (1.56 g, 96%), as a pale brown solid.

To a solution of (S)-2-[4-(3-ethoxy-2,6-difluoro-phenoxy)-2-oxo-2,5-dihydro-pyrrol-1-yl]-4-methyl-pentanoic acid (0.837 g, 2.27 mmol) in N,N-dimethylformamide (50 mL) was added 1-((R)-2,2-dimethyl-[1,3]dioxolan-4-yl-methyl)-1H-pyrazol-3-ylamine (prepared as in Example 49, 0.559 g, 2.83 mmol) and benzotriazol-1-yl-oxy-tris(dimethylamino)phosphonium hexafluorophosphate (1.505 g, 3.40 mmol). The mixture was stirred at 0° C. and N,N-diisopropylethylamine (0.732 g, 5.66 mmol) was added. The mixture was stirred at room temperature overnight and the solvents were evaporated. The residue was treated with ethyl acetate and ammonium chloride solution, and the organic layer separated. The organic layer was washed with brine and dried over sodium sulfate. The solvents were evaporated and the residue was purified by ISCO flash chromatography (Teledyne Isco RediSep Flash Column 40 g, 50% to 90% ethyl acetate/hexanes) which afforded (S)-2-[4-(3-ethoxy-2,6-difluoro-phenoxy)-2-oxo-2,5-dihydro-pyrrol-1-yl]-4-methyl-pentanoic acid [1-((R)-2,2-dimethyl-[1,3]dioxolan-4-yl-methyl)-1H-pyrazol-3-yl]-amide (1.180 g, 95%) as a pale yellow solid: HR-ES-MS m/z calculated for $C_{27}H_{34}F_2N_4O_6$ [M+H]$^+$ 549.2519, observed 549.2514, $^1$H NMR (300 MHz, DMSO-$d_6$) δ ppm 1.00 0.90 (d, J=6.4 Hz, 3H), 0.93 (d, J=6.4 Hz, 3H), 1.25 (s, 3H), 1.30 (s, 3H), 1.35 (t, J=6.9 Hz, 3H), 1.38-1.49 (m, 1H), 1.50-1.67 (m, 1H), 1.68-1.84 (m, 1H), 3.73 (dd, J=8.5, 6.0 Hz, 1H), 3.96-4.19 (m, 5H), 4.27 (d, J=18.7 Hz, 1H), 4.31-4.40 (m, 1H), 4.63 (d, J=18.7 Hz, 1H), 4.88 (dd, J=10.7, 4.7 Hz, 1H), 5.06 (s, 1H), 6.43 (d, J=2.1 Hz, 1H), 7.11-7.22 (m, 1H), 7.27 (dt, J=9.7, 1.5 Hz, 1H), 7.60 (d, J=2.1 Hz, 1H), 10.82 (s, 1H).

Example 117

(S)-2-[4-(3-Ethoxy-2,6-difluoro-phenoxy)-2-oxo-2,5-dihydro-pyrrol-1-yl]-4-methyl-pentanoic acid [1-((R)-2,3-dihydroxy-propyl)-1H-pyrazol-3-yl]-amide

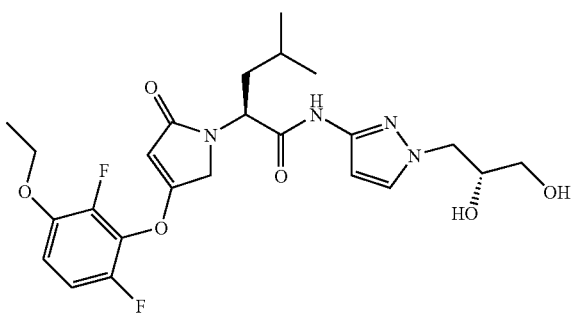

A solution of (S)-2-[4-(3-ethoxy-2,6-difluoro-phenoxy)-2-oxo-2,5-dihydro-pyrrol-1-yl]-4-methyl-pentanoic acid [1-((R)-2,2-dimethyl-[1,3]dioxolan-4-yl-methyl)-1H-pyrazol-3-yl]-amide (prepared in Example 116, 1.140 g, 2.08 mmol) in tetrahydrofuran (100 mL) was treated with 2N aqueous hydrochloric acid (150 mL). The reaction mixture was stirred for 2.5 h at room temperature. The reaction mixture was diluted with ethyl acetate, washed with saturated sodium bicarbonate, a saturated sodium chloride solution and dried over magnesium sulfate. The mixture was filtered and evaporated and the residue purified by ISCO flash chromatography (Teledyne Isco RediSep Flash Column 40 g, 30% to 100% (9:1 dichloromethane:methanol)/hexanes) which afforded (S)-2-[4-(3-ethoxy-2,6-difluoro-phenoxy)-2-oxo-2,5-dihydro-pyrrol-1-yl]-4-methyl-pentanoic acid [1-((R)-2,3-dihydroxy-propyl)-1H-pyrazol-3-yl]-amide (0.780 g, 74%) as a white solid: HR-ES-MS m/z calculated for $C_{24}H_{30}F_2N_4O_6$, $[M+H]^+$ 509.2206 observed 509.2206; $^1$H NMR (300 MHz, DMSO-$d_6$) δ ppm 0.90 (d, J=6.6 Hz, 3H), 0.93 (d, J=6.6 Hz, 3H), 1.35 (t, J=6.8 Hz, 3H), 1.38-1.50 (m, 1H), 1.50-1.67 (m, 1H), 1.68-1.85 (m, 1H), 3.20-3.33 (m, 2H), 3.71-3.94 (m, 2H), 4.04-4.20 (m, 3H), 4.26 (d, J=18.7 Hz, 1H), 4.63 (d, J=18.7 Hz, 1H), 4.71 (t, J=5.3 Hz, 1H), 4.87 (dd, J=10.3, 4.5 Hz, 1H), 4.94 (d, J=4.8 Hz, 1H), 5.05 (s, 1H), 6.41 (s, 1H), 7.09-7.35 (m, 2H), 7.53 (s, 1H), 10.79 (s, 1H).

Example 118

(S)-2-[4-(2,6-Difluoro-3-methoxy-phenoxy)-2-oxo-2,5-dihydro-pyrrol-1-yl]-4-methyl-pentanoic acid [1-((R)-2,2-dimethyl-[1,3]dioxolan-4-yl-methyl)-1H-pyrazol-3-yl]-amide

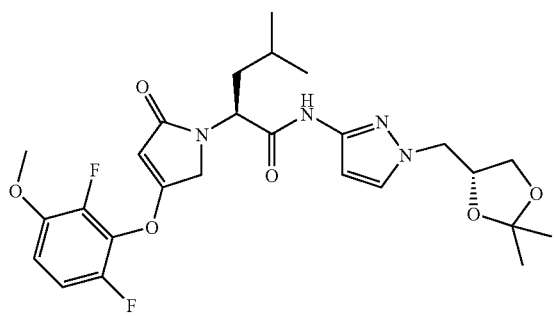

To a solution of 2,6-difluoro-3-methoxy-phenylboronic acid (10.0 g, 0.053 mol) in tetrahydrofuran (160 mL) was added glacial acetic acid (60 mL). The resulting mixture was cooled to 0° C. before hydrogen peroxide (50% aqueous solution, 8 mL) was added. The resulting mixture was allowed to come to room temperature and stirred for 120 h. The mixture was evaporated and the residue was dissolved in ethyl acetate, washed with hydrochloric acid (0.5N), water and brine. The organic phase was dried, filtered and evaporated which afforded 2,6-difluoro-3-methoxy-phenol (7.50 g, 88%) as a pale brown solid.

To a stirred mixture of 2,6-difluoro-3-methoxy-phenol (5.00 g, 0.031 mol) and ethyl-2-butynoate (7.00 g, 0.062 mol) in tetrahydrofuran (40 mL) was added 1,8-diazabicyclo[5.4.0]undec-7-ene (4.76 g, 0.031 mol) in tetrahydrofuran (10 mL) slowly. After addition was complete the mixture was stirred at reflux overnight. Upon completion of the reaction the tetrahydrofuran was removed in vacuo and the residue was diluted in diethyl ether and washed first with 1N aqueous hydrochloric acid, then 10% aqueous sodium hydroxide solution, a saturated sodium chloride solution and dried over magnesium sulfate. The mixture was filtered and evaporated and the residue purified by ISCO column chromatography (Teledyne Isco RediSep Flash Column 120 g, 0% to 15%) ethyl acetate/hexanes which afforded (E)-3-(2,6-difluoro-3-methoxy-phenoxy)-but-2-enoic acid ethyl ester (6.42 g, 76%) as a colorless oil.

To a stirred mixture of (E)-3-(2,6-difluoro-3-methoxy-phenoxy)-but-2-enoic acid ethyl ester (6.42 g, 0.024 mol) dissolved in carbon tetrachloride (60 mL) under a nitrogen atmosphere was added N-bromosuccinimide (6.30 g, 0.035 mol) and benzoyl peroxide (0.45 g, 0.002 mol). After addition was complete, the mixture was stirred at reflux for 14 h. The reaction mixture was then placed in the refrigerator overnight. The solids formed were removed by filtration and the filtrate concentrated in vacuo. The crude product obtained was purified by ISCO flash chromatography (Teledyne Isco RediSep Flash Column 120 g; 0% to 15% ethyl acetate/hexanes) to afford, (E)-4-bromo-3-(2,6-difluoro-3-methoxy-phenoxy)-but-2-enoic acid ethyl ester (2.41 g, 29%) as a white solid.

To a solution of (L)-leucine methyl ester hydrochloride (2.42 g, 13.3 mmol) dissolved in acetonitrile (100 mL) was added (E)-4-bromo-3-(2,6-difluoro-3-methoxy-phenoxy)-but-2-enoic acid ethyl ester (2.34 g) in acetonitrile (10 mL) and triethylamine (2.90 g, 0.029 mol) and the resulting mixture refluxed for 12 h. The reaction mixture was cooled to room temperature and then poured into ethyl acetate. The mixture was filtered to remove salts and the filtrate washed successively with saturated ammonium chloride, water, and brine. The solution was dried over sodium sulfate, filtered and evaporated. The residue was dissolved in tetrahydrofuran (10 mL) and then transferred to an Emry Optimizer microwave reaction vessel and heated at 160° C., for 1.5 h. The crude product obtained after aqueous work-up, was purified by ISCO flash chromatography (Teledyne Isco RediSep Flash Column 120 g, 10 to 70% ethyl acetate/hexanes) to afford, (S)-2-[4-(2,6-difluoro-3-methoxy-phenoxy)-2-oxo-2,5-dihydro-pyrrol-1-yl]-4-methyl-pentanoic acid methyl ester (0.254 g, 10%) as a oil.

To a solution containing (S)-2-[4-(2,6-difluoro-3-methoxy-phenoxy)-2-oxo-2,5-dihydro-pyrrol-1-yl]-4-methyl-pentanoic acid methyl ester (0.254 g, 0.001 mol) in tetrahydrofuran (10 mL) was treated with an aqueous solution of lithium hydroxide monohydrate (0.5N, 3 mL, 0.002 mol). The mixture was stirred at 5° C. for 3 h, and the solvents evaporated. The residue was dissolved in water and washed with diethyl ether, and the diethyl ether layer discarded. The aqueous phase was acidified with dilute hydrochloric acid (pH <2), and extracted with ethyl acetate. The combined organic layers were dried over sodium sulfate and concentrated to afford (S)-2-[4-(2,6-difluoro-3-methoxy-phenoxy)-2-oxo-2,5-dihydro-pyrrol-1-yl]-4-methyl-pentanoic acid, (0.212 g, 87%), as a light brown solid.

To a solution of (S)-2-[4-(2,6-difluoro-3-methoxy-phenoxy)-2-oxo-2,5-dihydro-pyrrol-1-yl]-4-methyl-pentanoic acid (0.200 g, 0.56 mmol) in N,N-dimethylformamide (7 mL) was added 1-((R)-2,2-dimethyl-[1,3]dioxolan-4-yl-methyl)-1H-pyrazol-3-ylamine (prepared as in Example 49, 0.139 g, 0.70 mmol) and benzotriazol-1-yl-oxy-tris(dimethylamino) phosphonium hexafluorophosphate (0.374 g, 0.85 mmol). The mixture was stirred at 0° C. and N,N-diisopropylethylamine (0.193 g, 1.49 mmol) was added. The mixture was stirred at room temperature overnight and the solvents were evaporated. The residue was treated with ethyl acetate and ammonium chloride solution, and the organic layer separated. The organic layer was washed with brine and dried over sodium sulfate. The solvents were evaporated and the residue was purified by ISCO flash chromatography (Teledyne Isco RediSep Flash Column 40 g, 50% to 90% ethyl acetate/hexanes) which afforded (S)-2-[4-(2,6-difluoro-3-methoxy-phenoxy)-2-oxo-2,5-dihydro-pyrrol-1-yl]-4-methyl-pentanoic acid [1-((R)-2,2-dimethyl-[1,3]dioxolan-4-yl-methyl)-1H-pyrazol-3-yl]-amide (0.193 g, 64%) as a pale brown solid: HR-ES-MS m/z calculated for $C_{26}H_{32}F_2N_4O_6$ [M+H]$^+$ 535.2363, observed 535.2363, $^1$H NMR (300 MHz, DMSO-d$_6$) δ ppm 1.00 0.90 (d, J=6.3 Hz, 3H), 0.93 (d, J=6.3 Hz, 3H), 1.25 (s, 3H), 1.30 (s, 3 H), 1.36-1.50 (m, 1H), 1.50-1.65 (m, 1H), 1.69-1.84 (m, 1H), 3.73 (dd, J=8.4, 5.7 Hz, 1H), 3.87 (s, 3H), 4.00 (dd, J=8.4, 6.5 Hz, 1H), 4.11 (t, J=5.4 Hz, 2H), 4.27 (d, J=18.7 Hz, 1H), 4.35 (t, J=5.7 Hz, 1H), 4.62 (d, J=18.7 Hz, 1H), 4.88 (dd, J=10.6, 4.8 Hz, 1H), 5.06 (s, 1H), 6.43 (d, J=2.1 Hz, 1H), 7.18 (td, J=9.3, 5.1 Hz, 1H), 7.30 (td, J=9.5, 1.8 Hz, 1H), 7.60 (d, J=2.1 Hz, 1H), 10.82 (s, 1H).

Example 119

(S)-2-[4-(2,6-Difluoro-3-methoxy-phenoxy)-2-oxo-2,5-dihydro-pyrrol-1-yl]-4-methyl-pentanoic acid [1-((R)-2,3-dihydroxy-propyl)-1H-pyrazol-3-yl]-amide

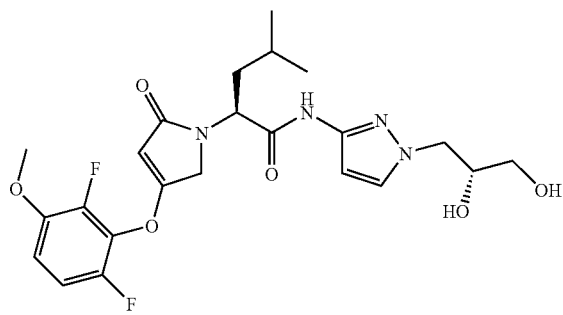

A solution of (S)-2-[4-(2,6-difluoro-3-methoxy-phenoxy)-2-oxo-2,5-dihydro-pyrrol-1-yl]-4-methyl-pentanoic acid [1-((R)-2,2-dimethyl-[1,3]dioxolan-4-yl-methyl)-1H-pyrazol-3-yl]-amide (prepared in Example 118, 0.163 g, 0.30 mmol) in tetrahydrofuran (15 mL) was treated with 2N aqueous hydrochloric acid (7.5 mL). The reaction mixture was stirred for 3.5 h at room temperature. The reaction mixture was diluted with ethyl acetate, washed with saturated sodium bicarbonate, a saturated sodium chloride solution and dried over magnesium sulfate. The mixture was filtered and evaporated and the residue purified by ISCO column chromatography (Teledyne Isco RediSep Flash Column 12 g, 30% to 100%, (9:1 dichloromethane:methanol)/hexanes) which afforded (S)-2-[4-(2,6-difluoro-3-methoxy-phenoxy)-2-oxo-2,5-dihydro-pyrrol-1-yl]-4-methyl-pentanoic acid [1-((R)-2,3-dihydroxy-propyl)-1H-pyrazol-3-yl]-amide (0.135 g, 90%) as an off-white solid: HR-ES-MS m/z calculated for $C_{23}H_{28}F_2N_4O_6$, [M+H]$^+$ 495.205 observed 495.205; $^1$H NMR (300 MHz, DMSO-d$_6$) δ ppm 0.90 (d, J=6.4 Hz, 3H), 0.93 (d, J=6.4 Hz, 3H), 1.43 (br. s., 1H), 1.49-1.67 (m, 1H), 1.67-1.87 (m, 1H), 3.18-3.32 (m, 2H), 3.69-3.86 (m, 2H), 3.87 (s, 3H), 4.09 (dd, J=13.6, 2.7 Hz, 1H), 4.27 (d, J=18.7 Hz, 1H), 4.63 (d, J=18.7 Hz, 1H), 4.71 (t, J=4.8 Hz, 1H), 4.81-4.91 (m, 1H), 4.94 (d, J=4.8 Hz, 1H), 5.06 (s, 1H), 6.40 (br. s., 1H), 7.09-7.24 (m, 1H), 7.24-7.38 (m, 1H), 7.53 (br. s., 1H), 10.79 (br. s., 1H).

Example 120

(S)-4-Methyl-2-(2-oxo-4-o-tolyloxy-2,5-dihydro-pyrrol-1-yl)-pentanoic acid (1-methyl-1H-pyrazol-3-yl)-amide

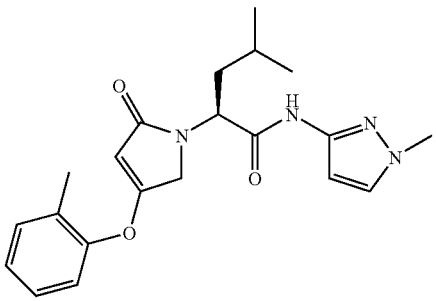

To a stirred mixture of 2-methyl-phenol (4.90 g, 0.045 mol) and ethyl-2-butynoate (10.1 g, 0.09 mol) in tetrahydrofuran (15 mL) was added 1,8-diazabicyclo[5.4.0]undec-7-ene (6.80 g, 0.045 mol) slowly. After addition was complete the mixture was stirred at reflux for 6 h. Upon completion of the reaction the tetrahydrofuran was removed in vacuo and the residue was diluted in diethyl ether and washed first with 1N aqueous hydrochloric acid, then 10% aqueous sodium hydroxide solution, a saturated sodium chloride solution and dried over magnesium sulfate. The crude product, (E)-3-o-tolyloxy-but-2-enoic acid ethyl ester, was obtained as a brown oil (6.45 g, 65%) and used without further purification.

To a stirred mixture of (E)-3-o-tolyloxy-but-2-enoic acid ethyl ester (6.45 g, 0.029 mol) dissolved in carbon tetrachloride (40 mL) under a nitrogen atmosphere was added N-bromosuccinimide (7.80 g, 0.044 mol) and benzoyl peroxide (1.00 g, 0.004 mol). After addition was complete, the mixture was stirred at reflux for 4 h. The reaction mixture was then placed in the refrigerator overnight. The solids formed were removed by filtration and the filtrate concentrated in vacuo. The crude product obtained was purified by ISCO flash chromatography (Teledyne Isco RediSep Flash Column 330 g; 0% to 18% ethyl acetate/hexanes) to afford, (E)-4-bromo-3-o-tolyloxy-but-2-enoic acid ethyl ester (5.00 g) as an impure brown oil.

To a solution of (L)-leucine methyl ester hydrochloride (3.05 g, 0.017 mol) dissolved in acetonitrile (50 mL) was added (E)-4-bromo-3-o-tolyloxy-but-2-enoic acid ethyl ester (5.00 g) in acetonitrile (10 mL) and triethylamine (2.50 g, 0.025 mol) and the resulting mixture refluxed for 12 h. The reaction mixture was cooled to room temperature, the solvents removed, and the residue then poured into ethyl acetate. The mixture was filtered to remove salts and the filtrate washed successively with saturated ammonium chloride, water, and brine. The solution was dried over sodium sulfate, filtered and evaporated. The residue was dissolved in tetrahydrofuran (15 mL) and then transferred to an Emry Optimizer microwave reaction vessel and heated at 160° C., for 4 h. The crude product obtained after aqueous work-up, was purified by ISCO flash chromatography (Teledyne Isco RediSep Flash Column 120 g, 10% to 70% ethyl acetate/hexanes) to afford, (S)-4-methyl-2-(2-oxo-4-o-tolyloxy-2,5-dihydro-pyrrol-1-yl)-pentanoic acid methyl ester (1.50 g, 28%).

To a solution containing (S)-4-methyl-2-(2-oxo-4-o-tolyloxy-2,5-dihydro-pyrrol-1-yl)-pentanoic acid methyl ester (1.50 g, 4.7 mmol) in tetrahydrofuran (30 mL) was treated with an aqueous solution of lithium hydroxide monohydrate (0.5N, 20 mL, 10.0 mmol). The mixture was stirred at 20° C. for 3 h, and the solvents evaporated. The residue was dissolved in water and washed with diethyl ether, and the diethyl ether layer discarded. The aqueous phase was acidified with dilute hydrochloric acid (pH <2), and extracted with ethyl acetate. The combined organic layers were dried over sodium sulfate and concentrated to afford (S)-4-methyl-2-(2-oxo-4-o-tolyloxy-2,5-dihydro-pyrrol-1-yl)-pentanoic acid (1.30 g, 91%) as a tan solid.

To a solution of (S)-4-methyl-2-(2-oxo-4-o-tolyloxy-2,5-dihydro-pyrrol-1-yl)-pentanoic acid (0.208 g, 0.69 mmol) in N,N-dimethylformamide (4 mL) was added 1-methyl-1H-pyrazol-3-ylamine (0.080 g, 0.82 mmol) and benzotriazol-1-yl-oxy-tris(dimethylamino)phosphonium hexafluorophosphate (0.620 g, 1.40 mmol). The mixture was stirred at 0° C. and triethylamine (0.150 g, 1.48 mmol) was added. The mixture was stirred at room temperature for 3 h and the solvents were evaporated. The residue was treated with ethyl acetate and ammonium chloride solution, and the organic layer separated. The organic layer was washed with brine and dried over sodium sulfate. The solvents were evaporated and the residue was purified by ISCO flash chromatography (Teledyne Isco RediSep Flash Column 25 g, 20% to 100% ethyl acetate/hexanes) which afforded (S)-4-methyl-2-(2-oxo-4-o-tolyloxy-2,5-dihydro-pyrrol-1-yl)-pentanoic acid (1-methyl-1H-pyrazol-3-yl)-amide (0.050 g, 19%) as a tan solid: HR-ES-MS m/z calculated for $C_{21}H_{26}N_4O_3$ [M+H]$^+$ 383.2078, observed 383.2077, $^1$H NMR (300 MHz, DMSO-$d_6$) δ ppm 1.00-0.90 (d, J=6.3 Hz, 3H), 0.94 (d, J=6.3 Hz, 3H), 1.20-1.92 (m, 3H), 2.19 (s, 3H), 3.73 (s, 3H), 4.20 (d, J=18.1 Hz, 1H), 4.57 (d, J=18.1 Hz, 1H), 4.63 (s, 1H), 4.87 (dd, J=10.3, 4.8 Hz, 1H), 6.40 (d, J=1.8 Hz, 1H), 7.17-7.33 (m, 3H), 7.36 (d, J=7.2 Hz, 1H), 7.55 (d, J=1.8 Hz, 1H), 10.72 (s, 1H).

Example 121

(S)-4-Methyl-2-(2-oxo-4-o-tolyloxy-2,5-dihydro-pyrrol-1-yl)-pentanoic acid {1-[2-(t-butyl-dimethyl-silanyloxy)-ethyl]-1H-pyrazol-3-yl}-amide

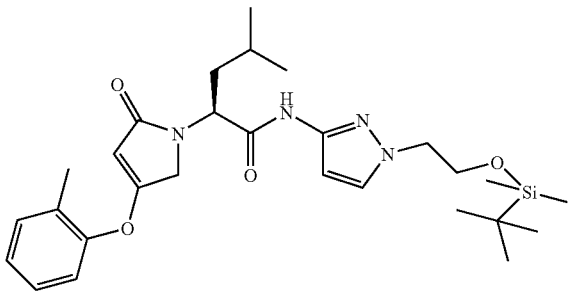

To a solution of (S)-4-methyl-2-(2-oxo-4-o-tolyloxy-2,5-dihydro-pyrrol-1-yl)-pentanoic acid (prepared as in Example 120, 0.250 g, 0.82 mmol) in N,N-dimethylformamide (5 mL) was added 1-[2-(t-butyl-dimethyl-silanyloxy)-ethyl]-1H-pyrazol-3-ylamine (prepared in U.S. Pat. Appl. US2008021032, Example 67, 0.240 g, 0.99 mmol) and benzotriazol-1-yl-oxy-tris(dimethylamino)phosphonium hexafluorophosphate (0.707 g, 1.60 mmol). The mixture was stirred at 0° C. and triethylamine (0.163 g, 1.61 mmol) was added. The mixture was stirred at room temperature for 3 h and the solvents were evaporated. The residue was treated with ethyl acetate and ammonium chloride solution, and the organic layer separated. The organic layer was washed with brine and dried over sodium sulfate. The solvents were evaporated and the residue was purified by ISCO flash chromatography (Teledyne Isco RediSep Flash Column 25 g, 0% to 40% ethyl acetate/hexanes) which afforded (S)-4-methyl-2-(2-oxo-4-o-tolyloxy-2,5-dihydro-pyrrol-1-yl)-pentanoic acid {1-[2-(t-butyl-dimethyl-silanyloxy)-ethyl]-1H-pyrazol-3-yl}-amide (0.229 g, 53%) as a tan solid: HR-ES-MS m/z calculated for $C_{28}H_{42}N_4O_4Si$ [M+H]$^+$ 527.3048, observed 527.3048, $^1$H NMR (300 MHz, DMSO-$d_6$) δ ppm 1.00-0.07 (s, 6H), 0.80 (s, 9H), 0.90 (d, J=6.3 Hz, 3H), 0.93 (d, J=6.3 Hz, 3H), 1.36-1.51 (m, 1H), 1.51-1.64 (m, 1H), 1.64-1.83 (m, 1H), 2.19 (s, 3H), 3.85 (t, J=5.1 Hz, 2H), 4.06 (t, J=5.1 Hz, 2H), 4.20 (d, J=18.4 Hz, 1H), 4.58 (d, J=18.4 Hz, 1H), 4.63 (s, 1H), 4.88 (dd, J=10.7, 5.0 Hz, 1H), 6.41 (d, J=2.1 Hz, 1H), 7.19-7.33 (m, 3H), 7.36 (d, J=7.2 Hz, 1H), 7.54 (d, J=2.1 Hz, 1H), 10.76 (s, 1H).

Example 122

(S)-4-Methyl-2-(2-oxo-4-o-tolyloxy-2,5-dihydro-pyrrol-1-yl)-pentanoic acid [1-(2-hydroxy-ethyl)-1H-pyrazol-3-yl]-amide

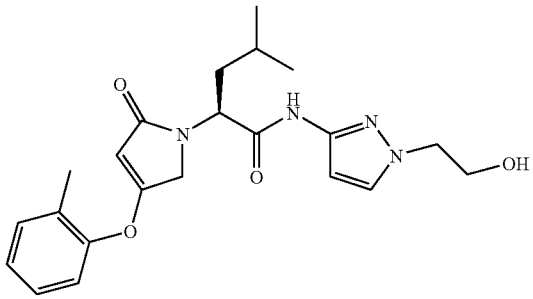

To a solution of (S)-4-methyl-2-(2-oxo-4-o-tolyloxy-2,5-dihydro-pyrrol-1-yl)-pentanoic acid {1-[2-(t-butyl-dimethyl-silanyloxy)-ethyl]-1H-pyrazol-3-yl}-amide (prepared as in Example 121, 200 mg, 0.38 mmol) in ethanol (15 mL) was added concentrated hydrochloric acid (10 drops). The reaction mixture was stirred for 1 h then poured into ethyl acetate (100 mL) and the organic phase washed with water (100 mL) and brine and dried over anhydrous sodium sulfate. The mixture was filtered and evaporated which afforded, after trituration with diethyl ether/hexane, (S)-4-methyl-2-(2-oxo-4-o-tolyloxy-2,5-dihydro-pyrrol-1-yl)-pentanoic acid [1-(2-hydroxy-ethyl)-1H-pyrazol-3-yl]-amide (0.110 g, 71%) as an off-white solid.

Example 123

(S)-4-Methyl-2-(2-oxo-4-o-tolyloxy-2,5-dihydro-pyrrol-1-yl)-pentanoic acid [1-((R)-2,2-dimethyl-[1,3]dioxolan-4-yl-methyl)-1H-pyrazol-3-yl]-amide

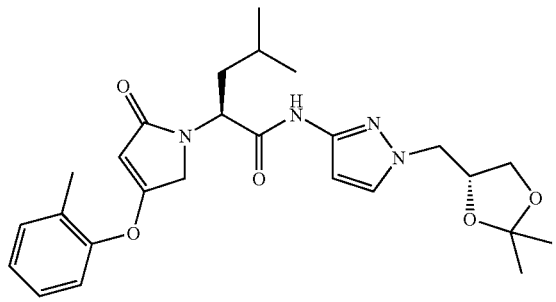

To a solution of (S)-4-methyl-2-(2-oxo-4-o-tolyloxy-2,5-dihydro-pyrrol-1-yl)-pentanoic acid (prepared as in Example 120, 0.228 g, 0.75 mmol) in N,N-dimethylformamide (4 mL) was added 1-((R)-2,2-dimethyl-[1,3]dioxolan-4-yl-methyl)-1H-pyrazol-3-ylamine (prepared as in Example 49, 0.192 g, 0.97 mmol) and benzotriazol-1-yl-oxy-tris(dimethylamino)phosphonium hexafluorophosphate (0.663 g, 1.50 mmol). The mixture was stirred at 0° C. and triethylamine (0.153 g, 1.51 mmol) was added. The mixture was stirred at room temperature for 4 h and the solvents were evaporated. The residue was treated with ethyl acetate and ammonium chloride solution, and the organic layer separated. The organic layer was washed with brine and dried over sodium sulfate. The solvents were evaporated and the residue was purified by ISCO flash chromatography (Teledyne Isco RediSep Flash Column 25 g, 30% to 70% ethyl acetate/hexanes) which afforded (S)-4-methyl-2-(2-oxo-4-o-tolyloxy-2,5-dihydro-pyrrol-1-yl)-pentanoic acid [1-((R)-2,2-dimethyl-[1,3]dioxolan-4-yl-methyl)-1H-pyrazol-3-yl]-amide (0.175 g, 48%) as a pink solid: HR-ES-MS m/z calculated for $C_{26}H_{34}N_4O_5$ [M+H]$^+$ 483.2602, observed 483.2603, $^1$H NMR (200 MHz, DMSO-$d_6$) δ ppm 1.00 0.90 (d, J=6.5 Hz, 3H), 0.94 (d, J=6.5 Hz, 3H), 1.25 (s, 3H), 1.30 (s, 3H), 1.36-1.66 (m, 2H), 1.68-1.81 (m, 1H), 2.19 (s, 3H), 3.73 (dd, J=8.5, 5.7 Hz, 1H), 4.00 (dd, J=8.5, 6.3 Hz, 1H), 4.11 (t, J=5.7 Hz, 2H), 4.20 (d, J=18.4 Hz, 1H), 4.28-4.42 (m, 1H), 4.58 (d, J=18.4 Hz, 1H), 4.63 (s, 1H), 4.88 (dd, J=10.6, 4.8 Hz, 1H), 6.44 (d, J=2.4 Hz, 1H), 7.16-7.33 (m, 3H), 7.36 (d, J=7.5 Hz, 1H), 7.60 (d, J=2.4 Hz, 1H), 10.80 (s, 1H).

Example 124

(S)-4-Methyl-2-(2-oxo-4-o-tolyloxy-2,5-dihydro-pyrrol-1-yl)-pentanoic acid [1-((R)-2,3-dihydroxy-propyl)-1H-pyrazol-3-yl]-amide

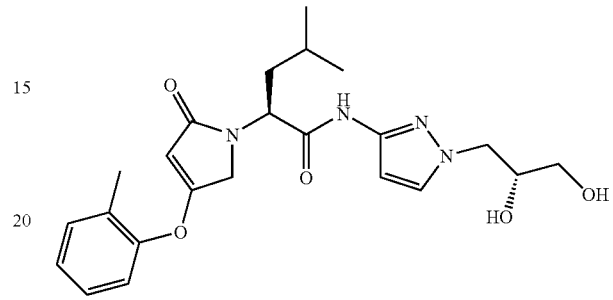

A solution of (S)-4-methyl-2-(2-oxo-4-o-tolyloxy-2,5-dihydro-pyrrol-1-yl)-pentanoic acid [1-((R)-2,2-dimethyl-[1,3]dioxolan-4-yl-methyl)-1H-pyrazol-3-yl]-amide (prepared in Example 123, 0.150 g, 0.31 mmol) in tetrahydrofuran (25 mL) was treated with 2N aqueous hydrochloric acid (20 mL). The reaction mixture was stirred for 2 h at room temperature. The reaction mixture was diluted with ethyl acetate, washed with saturated sodium bicarbonate, a saturated sodium chloride solution and dried over magnesium sulfate. Upon concentration afforded, (S)-4-methyl-2-(2-oxo-4-o-tolyloxy-2,5-dihydro-pyrrol-1-yl)-pentanoic acid [1-((R)-2,3-dihydroxy-propyl)-1H-pyrazol-3-yl]-amide (0.080 g, 58%) as a tan solid: HR-ES-MS m/z calculated for $C_{23}H_{30}N_4O_5$, [M+H]$^+$ 443.2289 observed 443.2289; $^1$H NMR (300 MHz, DMSO-$d_6$) δ ppm 0.88 (d, J=6.3 Hz, 3H), 0.92 (d, J=6.3 Hz, 3H), 1.36-1.64 (m, 2H), 1.66-1.80 (m, 1H), 2.18 (s, 3H), 3.20-3.31 (m, 2H), 3.72 (br. s., 1H), 3.85 (dd, J=13.0, 7.2 Hz, 1H), 4.07 (dd, J=13.4, 3.8 Hz, 1H), 4.19 (d, J=18.4 Hz, 1H), 4.56 (d, J=18.4 Hz, 1H), 4.62 (s, 1H), 4.64-4.75 (m, 1H), 4.86 (dd, J=10.7, 5.0 Hz, 1H), 4.92 (d, J=5.1 Hz, 1H), 6.39 (d, J=2.1 Hz, 1H), 7.15-7.31 (m, 3H), 7.34 (d, J=7.2 Hz, 1H), 7.51 (d, J=2.1 Hz, 1H), 10.74 (s, 1H).

Example 125

(S)-4-Methyl-2-(2-oxo-4-o-tolyloxy-2,5-dihydro-pyrrol-1-yl)-pentanoic acid [1-(2-hydroxy-2-methyl-propyl)-1H-pyrazol-3-yl]-amide

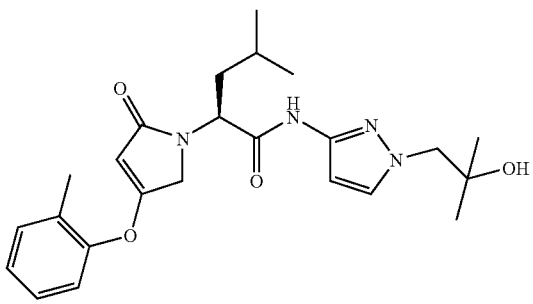

To a solution of (S)-4-methyl-2-(2-oxo-4-o-tolyloxy-2,5-dihydro-pyrrol-1-yl)-pentanoic acid (prepared as in Example 120, 0.214 g, 0.71 mmol) in N,N-dimethylformamide (4.5 mL) was added 1-(3-amino-pyrazol-1-yl)-2-methyl-propan-2-ol (prepared in U.S. Pat. Appl. US2008021032 Example 80, 0.142 g, 0.91 mmol) and benzotriazol-1-yl-oxy-tris(dimethylamino)phosphonium hexafluorophosphate (0.618 g, 1.40 mmol). The mixture was stirred at 0° C. and triethylamine (0.142 g, 1.40 mmol) was added. The mixture was stirred at room temperature for 4 h and the solvents were evaporated. The residue was treated with ethyl acetate and ammonium chloride solution, and the organic layer separated. The organic layer was washed with brine and dried over sodium sulfate. The solvents were evaporated and the residue was purified by ISCO flash chromatography (Teledyne Isco RediSep Flash Column 25 g, 30% to 100% ethyl acetate/hexanes) which afforded (S)-4-methyl-2-(2-oxo-4-o-tolyloxy-2,5-dihydro-pyrrol-1-yl)-pentanoic acid [1-(2-hydroxy-2-methyl-propyl)-1H-pyrazol-3-yl]-amide (0.112 g, 36%) as a tan solid: HR-ES-MS m/z calculated for $C_{24}H_{32}N_4O_4$ $[M+H]^+$ 441.2497, observed 441.2496, $^1$H NMR (300 MHz, DMSO-$d_6$) δ ppm 1.00 0.89 (d, J=6.3 Hz, 3H), 0.93 (d, J=6.3 Hz, 3H), 1.04 (br. s., 3H), 1.06 (br. s., 3H), 1.37-1.64 (m, 2H), 1.66-1.85 (m, 1H), 2.19 (s, 3H), 3.89 (br. s., 2H), 4.20 (d, J=18.1 Hz, 1H), 4.59 (d, J=18.1 Hz, 1H), 4.63 (s, 1H), 4.68 (s, 1H), 4.88 (dd, J=10.4, 4.4 Hz, 1H), 6.44 (d, J=2.1 Hz, 1H), 7.11-7.32 (m, 3H), 7.35 (d, J=6.6 Hz, 1H), 7.53 (d, J=2.1 Hz, 1H), 10.79 (br. s., 1H).

Example 126

(S)-2-[4-(2-Fluoro-3-hydroxy-phenoxy)-2-oxo-2,5-dihydro-pyrrol-1-yl]-4-methyl-pentanoic acid [1-(2-hydroxy-2-methyl-propyl)-1H-pyrazol-3-yl]-amide

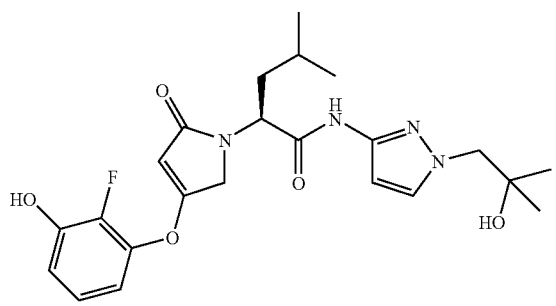

To a solution of 2-fluoro-3-methoxy-phenylboronic acid (10.0 g, 0.059 mol) in tetrahydrofuran (160 mL) was added glacial acetic acid (60 mL). The resulting mixture was cooled to 0° C. before hydrogen peroxide (50% aqueous solution, 8 mL) was added. The resulting mixture was allowed to come to room temperature and stirred for 65 h. The mixture was evaporated and the residue was dissolved in ethyl acetate, washed with hydrochloric acid (0.5N), water and brine. The organic phase was dried, filtered and evaporated which afforded 2-fluoro-3-methoxy-phenol (6.77 g, 81%) as a pale yellow oil.

To a stirred mixture of 2-fluoro-3-methoxy-phenol (3.88 g, 0.027 mol) and methyl-2-butynoate (5.97 g, 0.061 mol) in tetrahydrofuran (30 mL) was added 1,8-diazabicyclo[5.4.0]undec-7-ene (4.64 g, 0.030 mol) slowly. After addition was complete the mixture was stirred at reflux overnight. Upon completion of the reaction the tetrahydrofuran was removed in vacuo and the residue was diluted in diethyl ether and washed first with 1N aqueous hydrochloric acid, then 10% aqueous sodium hydroxide solution, a saturated sodium chloride solution and dried over magnesium sulfate. The mixture was filtered and evaporated and the residue dried under high vacuum which afforded (E)-3-(2-fluoro-3-methoxy-phenoxy)-but-2-enoic acid methyl ester (4.37 g, 63%) as a colorless oil and used without further purification.

To a stirred mixture of (E)-3-(2-fluoro-3-methoxy-phenoxy)-but-2-enoic acid ethyl ester (4.35 g, 18 mmol) dissolved in carbon tetrachloride (60 mL) under a nitrogen atmosphere was added N-bromosuccinimide (4.52 g, 0.025 mol) and benzoyl peroxide (0.29 g, 0.001 mol). After addition was complete, the mixture was stirred at reflux for 24 h. The reaction mixture was then placed in the refrigerator overnight. The solids formed were removed by filtration and the filtrate concentrated in vacuo. The crude product obtained was purified by ISCO flash chromatography (Teledyne Isco RediSep Flash Column 100 g; 0% to 15% ethyl acetate/hexanes) to afford, (E)-4-bromo-3-(2-fluoro-3-methoxy-phenoxy)-but-2-enoic acid methyl ester (5.75 g, 99%) as a pale yellow oil.

To a solution of (L)-leucine methyl ester hydrochloride (4.93 g, 0.027 mol) dissolved in acetonitrile (50 mL) was added (E)-4-bromo-3-(2-fluoro-3-methoxy-phenoxy)-but-2-enoic acid methyl ester (5.75 g) in acetonitrile (10 mL) and triethylamine (5.66 g, 0.056 mol) and the resulting mixture refluxed for 3 h. The reaction mixture was cooled to room temperature, the solvents evaporated and the residue poured into ethyl acetate. The mixture was filtered to remove salts and the filtrate washed successively with saturated ammonium chloride, water, and brine. The solution was dried over sodium sulfate, filtered and evaporated. The residue was dissolved in tetrahydrofuran (10 mL) and then transferred to an Emry Optimizer microwave reaction vessel and heated at 160° C. for 4 h. The crude product obtained after aqueous work-up, was purified by ISCO flash chromatography (Teledyne Isco RediSep Flash Column 120 g, 20% to 80% ethyl acetate/hexanes) to afford, (S)-2-[4-(2-fluoro-3-methoxy-phenoxy)-2-oxo-2,5-dihydro-pyrrol-1-yl]-4-methyl-pentanoic acid methyl ester (1.50 g, 24%) as a brown oil.

To a solution of (S)-2-[4-(2-fluoro-3-methoxy-phenoxy)-2-oxo-2,5-dihydro-pyrrol-1-yl]-4-methyl-pentanoic acid methyl ester (1.35 g, 3.83 mmol) in dichloromethane (20 mL) was added a boron tribromide in dichloromethane solution (1 M, 11.50 mL, 11.50 mmol) at 0° C. The resulting mixture was stirred at 0° C. for 2 h and then poured into ice water containing hydrochloric acid (2N, 30 mL). The organic phase was separated, washed with water and brine. The solvents were removed by evaporation and the residue purified by ISCO flash chromatography (Teledyne Isco RediSep Flash Column 50 g, 30% to 100% (9:1 dichloromethane:methanol)/hexanes) which afforded (S)-2-[4-(2-fluoro-3-hydroxy-phenoxy)-2-oxo-2,5-dihydro-pyrrol-1-yl]-4-methyl-pentanoic acid methyl ester (1.05 g, 81%) as a brown oil.

To a solution containing (S)-2-[4-(2-fluoro-3-hydroxy-phenoxy)-2-oxo-2,5-dihydro-pyrrol-1-yl]-4-methyl-pentanoic acid methyl ester (1.00 g, 0.003 mol) in tetrahydrofuran (18 mL) was treated with an aqueous solution of lithium hydroxide monohydrate (0.5N, 18 mL, 0.009 mol). The mixture was stirred at 0° C. for 2H, and the solvents evaporated. The residue was dissolved in water and washed with diethyl ether, and the diethyl ether layer discarded. The aqueous phase was acidified with dilute hydrochloric acid (pH <2), and extracted with ethyl acetate. The combined organic layers were dried over sodium sulfate and concentrated to afford (S)-2-[4-(2-fluoro-3-hydroxy-phenoxy)-2-oxo-2,5-dihydro-pyrrol-1-yl]-4-methyl-pentanoic acid (0.82 g, 86%) as a pale orange solid.

To a solution of (S)-2-[4-(2-fluoro-3-hydroxy-phenoxy)-2-oxo-2,5-dihydro-pyrrol-1-yl]-4-methyl-pentanoic acid (0.100 g, 0.31 mmol) in dichloromethane (3 mL) was added 1-(3-amino-pyrazol-1-yl)-2-methyl-propan-2-ol (prepared in U.S. Pat. Appl. US2008021032 Example 80, 0.100 g, 0.64 mmol) and benzotriazol-1-yl-oxy-tris(dimethylamino)phosphonium hexafluorophosphate (0.137 g, 0.31 mmol). The mixture was stirred at 0° C. and N,N-diisopropylethylamine (0.04 g, 0.31 mmol) was added. The mixture was stirred at room temperature for 4 h and the solvents were evaporated. The residue was extracted with ethyl acetate and washed with a citric acid solution. The organic layer was washed with brine and dried over sodium sulfate. The solvents were evaporated and the residue was purified by reverse phase HPLC ($C_{18}$, 20% to 100% acetonitrile/water) which afforded (S)-2-[4-(2-fluoro-3-hydroxy-phenoxy)-2-oxo-2,5-dihydro-pyrrol-1-yl]-4-methyl-pentanoic acid [1-(2-hydroxy-2-methyl-propyl)-1H-pyrazol-3-yl]-amide (0.097 g, 57%) as an off-white solid: HR-ES-MS m/z calculated for $C_{23}H_{29}FN_4O_5$ [M+H]$^+$ 461.2195, observed 461.2194, $^1$H NMR (400 MHz, DMSO-$d_6$) δ ppm 1.00 0.90 (d, J=6.4 Hz, 3H), 0.94 (d, J=6.4 Hz, 3H), 1.05 (s, 3H), 1.07 (s, 3H), 1.37-1.51 (m, 1H), 1.57 (ddd, J=13.6, 9.1, 4.8 Hz, 1H), 1.68-1.84 (m, 1H), 3.90 (s, 2H), 4.20 (d, J=18.5 Hz, 1H), 4.59 (d, J=18.5 Hz, 1H), 4.67 (s, 1H), 4.85-4.92 (m, 1H), 4.88 (s, 1H), 6.45 (d, J=1.9 Hz, 1H), 6.85 (t, J=7.4 Hz, 1H), 6.91 (t, J=7.9 Hz, 1H), 6.98-7.10 (m, 1H), 7.54 (d, J=1.9 Hz, 1H), 10.36 (br. s., 1H), 10.79 (s, 1H).

Example 127

(S)-2-[4-(2-Fluoro-3-hydroxy-phenoxy)-2-oxo-2,5-dihydro-pyrrol-1-yl]-4-methyl-pentanoic acid (1-methyl-1H-pyrazol-3-yl)-amide

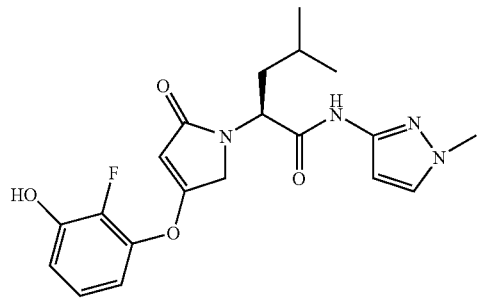

To a solution of (S)-2-[4-(2-fluoro-3-hydroxy-phenoxy)-2-oxo-2,5-dihydro-pyrrol-1-yl]-4-methyl-pentanoic acid (prepared as in Example 126, 0.226 g, 0.70 mmol) in N,N-dimethylformamide (4 mL) was added 1-methyl-1H-pyrazol-3-ylamine (0.340 g, 3.50 mmol) and benzotriazol-1-yl-oxy-tris(dimethylamino)phosphonium hexafluorophosphate (0.340 g, 0.77 mmol). The mixture was stirred at 0° C. and N,N-diisopropylethylamine (0.108 g, 0.84 mmol) was added. The mixture was stirred at room temperature overnight and the solvents were evaporated. The residue was extracted with ethyl acetate and washed with a citric acid solution. The organic layer was washed with brine and dried over sodium sulfate. The solvents were evaporated and the residue was purified by ISCO flash chromatography (Teledyne Isco RediSep Flash Column 12 g, 10% to 100% (9:1 dichloromethane:methanol)/hexanes) which afforded (S)-2-[4-(2-fluoro-3-hydroxy-phenoxy)-2-oxo-2,5-dihydro-pyrrol-1-yl]-4-methyl-pentanoic acid (1-methyl-1H-pyrazol-3-yl)-amide (0.115 g, 41%) as a white solid: HR-ES-MS m/z calculated for $C_{20}H_{23}FN_4O_4$ [M+Na]+ 425.1595, observed 425.1597, $^1$H NMR (400 MHz, DMSO-$d_6$) δ ppm 1.00 0.90 (d, J=6.4 Hz, 3H), 0.93 (d, J=6.4 Hz, 3H), 1.45 (m, 1H), 1.53-1.63 (m, 1H), 1.67-1.79 (m, 1H), 3.73 (s, 3H), 4.20 (d, J=18.5 Hz, 1H), 4.57 (d, J=18.5 Hz, 1H), 4.84-4.92 (m, 2H), 6.40 (d, J=1.7 Hz, 1H), 6.85 (t, J=7.8 Hz, 1H), 6.91 (t, J=7.8 Hz, 1H), 7.05 (t, J=7.8 Hz, 1H), H), 7.54 (d, J=1.7 Hz, 1H), 10.35 (br. s., 1H), 10.72 (s, 1H).

Example 128

(S)-2-[4-(3-Bromo-2-fluoro-phenoxy)-2-oxo-2,5-dihydro-pyrrol-1-yl]-4-methyl-pentanoic acid [1-((R)-2,2-dimethyl-[1,3]dioxolan-4-yl-methyl)-1H-pyrazol-3-yl]-amide

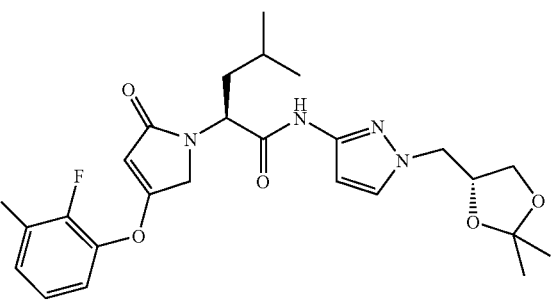

To a solution of 3-bromo-2-fluoro-phenylboronic acid (25.0 g, 0.114 mol) in tetrahydrofuran (250 mL) was added glacial acetic acid (150 mL). The resulting mixture was cooled to 0° C. before hydrogen peroxide (50% aqueous solution, 25 mL) was added. The resulting mixture was allowed to come to room temperature and stirred for 24 h. The mixture was evaporated and the residue was dissolved in ethyl acetate, washed with hydrochloric acid (0.5N), water and brine. The organic phase was dried, filtered and evaporated which afforded 3-bromo-2-fluoro-phenol (19.50 g, 89%) as a brown solid.

To a stirred mixture of 3-bromo-2-fluoro-phenol (19.5 g, 0.102 mol) and ethyl-2-butynoate (22.0 g, 0.196 mol) in tetrahydrofuran (100 mL) was added 1,8-diazabicyclo[5.4.0]undec-7-ene (15.6 g, 0.102 mol) slowly. After addition was complete the mixture was stirred at reflux for overnight. Upon completion of the reaction the tetrahydrofuran was removed in vacuo and the residue was diluted in diethyl ether and washed first with 1N aqueous hydrochloric acid, then 10% aqueous sodium hydroxide solution, a saturated sodium chloride solution and dried over magnesium sulfate. The mixture was filtered and evaporated, and the residue dried under high vacuum which afforded (E)-3-(3-bromo-2-fluoro-phenoxy)-but-2-enoic acid ethyl ester as a brown oil (21.5 g, 69%) and used without further purification.

To a stirred mixture of (E)-3-(3-bromo-2-fluoro-phenoxy)-but-2-enoic acid ethyl ester (21.50 g, 0.071 mol) dissolved in carbon tetrachloride (200 mL) under a nitrogen atmosphere was added N-bromosuccinimide (17.7 g, 0.100 mol) and benzoyl peroxide (2.50 g, 0.010 mol). After addition was complete, the mixture was stirred at reflux for 6 h. The reaction mixture was then placed in the refrigerator overnight. The solids formed were removed by filtration and the filtrate concentrated in vacuo. The crude product obtained was purified by ISCO flash chromatography (Teledyne Isco RediSep Flash Column 330 g; 0% to 20% ethyl acetate/hexanes) to afford, (E)-4-bromo-3-(3-bromo-2-fluoro-phenoxy)-but-2-enoic acid ethyl ester (18.00 g, 66%) as an impure pale yellow solid.

To a stirred mixture of (L)-leucine ethyl ester hydrochloride (12.4 g, 63.0 mmol) dissolved in acetonitrile (250 mL) under nitrogen atmosphere was added triethylamine (8.16 g, 0.081 mol). After addition was complete the mixture was stirred at 60° C. for 1 h. The reaction was cooled to 25° C. and treated with triethylamine (8.16 g, 0.081 mol) and heated to 85° C. at which time, (E)-4-bromo-3-(3-bromo-2-fluoro-phenoxy)-but-2-enoic acid ethyl ester (12.0 g) was added slowly over 15 min. After the addition was complete the reaction mixture was heated to 100° C. and stirred for 12 h. The reaction mixture was cooled to 25° C., filtered and concentrated. The residue was diluted with ethyl acetate and washed with saturated ammonium chloride, water, a saturated sodium chloride solution and dried over sodium sulfate. The crude product obtained was purified by ISCO flash chromatography (Teledyne Isco RediSep Flash Column 330 g, 10% to 50% ethyl acetate/hexanes) to afford, 2-[4-(3-bromo-2-fluoro-phenoxy)-2-oxo-2,5-dihydro-pyrrol-1-yl]-4-methyl-pentanoic acid ethyl ester (3.00 g, 23%) as a orange oil.

To a solution containing (S)-2-[4-(3-bromo-2-fluoro-phenoxy)-2-oxo-2,5-dihydro-pyrrol-1-yl]-4-methyl-pentanoic acid ethyl ester (0.260 g, 0.63 mmol) in tetrahydrofuran (8 mL) was treated with an aqueous solution of lithium hydroxide monohydrate (0.5N, 3 mL, 1.5 mmol). The mixture was stirred at 15° C. for 3 h, and the solvents evaporated. The residue was dissolved in water and washed with diethyl ether, and the diethyl ether layer discarded. The aqueous phase was acidified with dilute hydrochloric acid (pH <2), and extracted with ethyl acetate. The combined organic layers were dried over sodium sulfate and concentrated to afford (S)-2-[4-(3-bromo-2-fluoro-phenoxy)-2-oxo-2,5-dihydro-pyrrol-1-yl]-4-methyl-pentanoic acid, (0.250 g, 100%), as a yellow solid.

To a solution of (S)-2-[4-(3-bromo-2-fluoro-phenoxy)-2-oxo-2,5-dihydro-pyrrol-1-yl]-4-methyl-pentanoic acid (0.250 g, 0.65 mmol) in N,N-dimethylformamide (10 mL) was added 1-((R)-2,2-dimethyl-[1,3]dioxolan-4-yl-methyl)-1H-pyrazol-3-ylamine (prepared as in Example 49, 0.166 g, 0.84 mmol) and benzotriazol-1-yl-oxy-tris(dimethylamino) phosphonium hexafluorophosphate (0.576 g, 1.30 mmol). The mixture was stirred at 0° C. and triethylamine (0.140 g, 1.37 mmol) was added. The mixture was stirred at room temperature for 4 h and the solvents were evaporated. The residue was treated with ethyl acetate and ammonium chloride solution, and the organic layer separated. The organic layer was washed with brine and dried over sodium sulfate. The solvents were evaporated and the residue was purified by ISCO flash chromatography (Teledyne Isco RediSep Flash Column 12 g, 10% to 50% ethyl acetate/hexanes) which afforded (S)-2-[4-(3-bromo-2-fluoro-phenoxy)-2-oxo-2,5-dihydro-pyrrol-1-yl]-4-methyl-pentanoic acid [1-((R)-2,2-dimethyl-[1,3]dioxolan-4-yl-methyl)-1H-pyrazol-3-yl]-amide (0.200 g, 55%) as a fluffy powder: HR-ES-MS m/z calculated for $C_{25}H_{30}BrFN_4O_5$ [M+H]$^+$ 565.1457, observed 565.1457, $^1$H NMR (300 MHz, DMSO-d$_6$) δ ppm 1.00 0.90 (d, J=6.4 Hz, 3H), 0.94 (d, J=6.4 Hz, 3H), 1.25 (s, 3H), 1.30 (s, 3H), 1.45 (br. s., 1H), 1.50-1.65 (m, 1H), 1.68-1.83 (m, 1H), 3.73 (dd, J=8.5, 5.7 Hz, 1H), 4.00 (dd, J=8.5, 6.3 Hz, 1H), 4.03-4.20 (m, 2H), 4.24 (d, J=18.7 Hz, 1H), 4.29-4.41 (m, 1H), 4.61 (d, J=18.7 Hz, 1H), 4.89 (dd, J=10.9, 4.8 Hz, 1H), 5.00 (s, 1H), 6.44 (d, J=2.1 Hz, 1H), 7.27 (td, J=8.2, 1.4 Hz, 1H), 7.49-7.59 (m, 1H), 7.60 (d, J=2.1 Hz, 1H), 7.63-7.74 (m, 1H), 10.81 (s, 1H).

Example 129

(S)-2-[4-(3-Bromo-2-fluoro-phenoxy)-2-oxo-2,5-dihydro-pyrrol-1-yl]-4-methyl-pentanoic acid [1-((R)-2,3-dihydroxy-propyl)-1H-pyrazol-3-yl]-amide

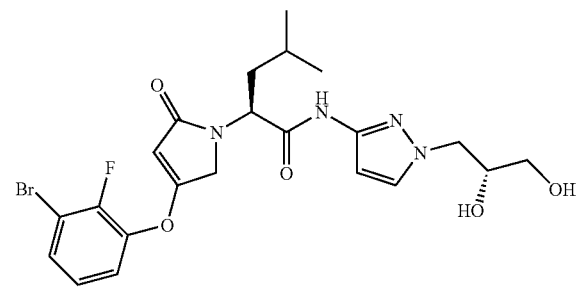

A solution of (S)-2-[4-(3-bromo-2-fluoro-phenoxy)-2-oxo-2,5-dihydro-pyrrol-1-yl]-4-methyl-pentanoic acid [1-((R)-2,2-dimethyl-[1,3]dioxolan-4-yl-methyl)-1H-pyrazol-3-yl]-amide (prepared in Example 128, 0.175 g, 0.31 mmol) in tetrahydrofuran (15 mL) was treated with 2N aqueous hydrochloric acid (8 mL). The reaction mixture was stirred for 3 h at room temperature. The reaction mixture was diluted with ethyl acetate, washed with saturated sodium bicarbonate, a saturated sodium chloride solution and dried over magnesium sulfate. Upon concentration afforded, (S)-2-[4-(3-bromo-2-fluoro-phenoxy)-2-oxo-2,5-dihydro-pyrrol-1-yl]-4-methyl-pentanoic acid [1-((R)-2,3-dihydroxy-propyl)-1H-pyrazol-3-yl]-amide (0.160 g, 98%) as a pink solid: HR-ES-MS m/z calculated for $C_{22}H_{26}BrFN_4O_5$, [M+H]$^+$ 525.1144. observed 525.1143; $^1$H NMR (300 MHz, DMSO-d$_6$) δ ppm 0.90 (d, J=6.3 Hz, 3H), 0.94 (d, J=6.3 Hz, 3H), 1.49 (br. s., 1H), 1.51-1.66 (m, 1H), 1.66-1.84 (m, 1H), 3.18-3.32 (m, 2H), 3.63-3.81 (m, 1H), 3.81-3.96 (m, 1H), 4.09 (dd, J=13.6, 3.9 Hz, 1H), 4.24 (d, J=18.4 Hz, 1H), 4.61 (d, J=18.4 Hz, 1H), 4.71 (t, J=5.6 Hz, 1H), 4.88 (dd, J=10.6, 4.8 Hz, 1H), 4.94 (d, J=5.1 Hz, 1H), 5.01 (s, 1H), 6.41 (d, J=2.4 Hz, 1H), 7.27 (td, J=8.2, 1.2 Hz, 1H), 7.50-7.60 (m, 2H), 7.61-7.73 (m, 1H), 10.78 (s, 1H).

Example 130

(S)-2-[4-(2-Fluoro-3-methyl-phenoxy)-2-oxo-2,5-dihydro-pyrrol-1-yl]-4-methyl-pentanoic acid [1-((R)-2,2-dimethyl-[1,3]dioxolan-4-yl-methyl)-1H-pyrazol-3-yl]-amide

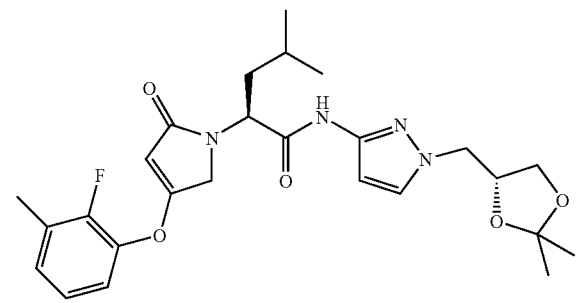

To a solution of 2-fluoro-3-methyl-phenylboronic acid (25.0 g, 0.162 mol) in tetrahydrofuran (220 mL) was added glacial acetic acid (150 mL). The resulting mixture was cooled to 0° C. before hydrogen peroxide (50% aqueous solution, 30 mL) was added. The resulting mixture was allowed to come to room temperature and stirred for 24 h. The mixture was evaporated and the residue was dissolved in ethyl acetate, washed with hydrochloric acid (0.5N), water and brine. The organic phase was dried, filtered and evaporated which afforded 2-fluoro-3-methyl-phenol (20.0 g, 98%) as an oil.

To a stirred mixture of 2-fluoro-3-methyl-phenol (20.0 g, 0.158 mol) and ethyl-2-butynoate (33.6 g, 0.300 mol) in tetrahydrofuran (100 mL) was added 1,8-diazabicyclo[5.4.0]undec-7-ene (25.4 g, 0.167 mol) slowly. After addition was complete the mixture was stirred at reflux overnight. Upon completion of the reaction the tetrahydrofuran was removed in vacuo and the residue was diluted in diethyl ether and washed first with 1N aqueous hydrochloric acid, then 10% aqueous sodium hydroxide solution, a saturated sodium chloride solution and dried over magnesium sulfate. The mixture was filtered and evaporated and residue purified by ISCO flash chromatography (Teledyne Isco RediSep Flash Column 330 g, 0% to 15% ethyl acetate/hexanes) which afforded (E)-3-(2-fluoro-3-methyl-phenoxy)-but-2-enoic acid ethyl ester (8.40 g, 23%) as a clear oil.

To a stirred mixture of (E)-3-(2-fluoro-3-methyl-phenoxy)-but-2-enoic acid ethyl ester (8.40 g, 0.035 mol) dissolved in carbon tetrachloride (100 mL) under a nitrogen atmosphere was added N-bromosuccinimide (8.80 g, 0.049 mol) and benzoyl peroxide (1.20 g, 0.005 mol). After addition was complete, the mixture was stirred at reflux for 5 h. The reaction mixture was then placed in the refrigerator overnight. The solids formed were removed by filtration and the filtrate concentrated in vacuo. The crude product obtained was purified by ISCO flash chromatography (Teledyne Isco RediSep Flash Column 120 g; 0% to 15% ethyl acetate/hexanes) to afford, (E)-4-bromo-3-(2-fluoro-3-methyl-phenoxy)-but-2-enoic acid ethyl ester (10.80 g, 97%) as an impure yellow oil.

To a solution of (L)-leucine ethyl ester hydrochloride (6.20 g, 0.032 mol) suspended in acetonitrile (100 mL) was added (E)-4-bromo-3-(2-fluoro-3-methyl-phenoxy)-but-2-enoic acid ethyl ester (5.00 g) in acetonitrile (10 mL) and triethylamine (6.50 g, 0.064 mol) and the resulting mixture refluxed for 12 h. The reaction mixture was cooled to room temperature, the solvents removed by evaporation and the residue poured into ethyl acetate. The mixture was filtered to remove salts and the filtrate washed successively with saturated ammonium chloride, water, and brine. The solution was dried over sodium sulfate, filtered and evaporated. The residue was dissolved in tetrahydrofuran (15 mL) and then transferred to an Emry Optimizer microwave reaction vessel and heated at 160° C., for 2 h. The crude product obtained after aqueous work-up, was purified by ISCO flash chromatography (Teledyne Isco RediSep Flash Column 120 g, 10% to 60% ethyl acetate/hexanes) to afford, (S)-2-[4-(2-fluoro-3-methyl-phenoxy)-2-oxo-2,5-dihydro-pyrrol-1-yl]-4-methyl-pentanoic acid ethyl ester (1.50 g, 27%) as an orange oil.

To a solution containing (S)-2-[4-(2-fluoro-3-methyl-phenoxy)-2-oxo-2,5-dihydro-pyrrol-1-yl]-4-methyl-pentanoic acid ethyl ester (1.50 g, 0.004 mol) in tetrahydrofuran (40 mL) was treated with an aqueous solution of lithium hydroxide monohydrate (0.5N, 20 mL, 0.010 mol). The mixture was stirred at 20° C. for 2 h, and the solvents evaporated. The residue was dissolved in water and washed with diethyl ether, and the diethyl ether layer discarded. The aqueous phase was acidified with dilute hydrochloric acid (pH <2), and extracted with ethyl acetate. The combined organic layers were dried over sodium sulfate and concentrated to afford (S)-2-[4-(2-fluoro-3-methyl-phenoxy)-2-oxo-2,5-dihydro-pyrrol-1-yl]-4-methyl-pentanoic acid (1.2 g, 87%) as a tan solid.

To a solution of (S)-2-[4-(2-fluoro-3-methyl-phenoxy)-2-oxo-2,5-dihydro-pyrrol-1-yl]-4-methyl-pentanoic acid (0.254 g, 0.79 mmol) in N,N-dimethylformamide (5 mL) was added 1-((R)-2,2-dimethyl-[1,3]dioxolan-4-yl-methyl)-1H-pyrazol-3-ylamine (prepared as in Example 49, 0.187 g, 0.95 mmol) and benzotriazol-1-yl-oxy-tris(dimethylamino)phosphonium hexafluorophosphate (0.795 g, 1.80 mmol). The mixture was stirred at 0° C. and triethylamine (0.194 g, 1.90 mmol) was added. The mixture was stirred at room temperature for 4 h and the solvents were evaporated. The residue was treated with ethyl acetate and ammonium chloride solution, and the organic layer separated. The organic layer was washed with brine and dried over sodium sulfate. The solvents were evaporated and the residue was purified by ISCO flash chromatography (Teledyne Isco RediSep Flash Column 25 g, 10% to 70% ethyl acetate/hexanes) which afforded (S)-2-[4-(2-fluoro-3-methyl-phenoxy)-2-oxo-2,5-dihydro-pyrrol-1-yl]-4-methyl-pentanoic acid [1-((R)-2,2-dimethyl-[1,3]dioxolan-4-yl-methyl)-1H-pyrazol-3-yl]-amide (0.200 g, 51%) as a tan solid: HR-ES-MS m/z calculated for $C_{26}H_{33}FN_4O_5$ [M+H]$^+$ 501.2508, observed 501.2511, $^1$H NMR (300 MHz, DMSO-d$_6$) δ ppm 1.00 0.90 (d, J=6.3 Hz, 3H), 0.93 (d, J=6.3 Hz, 3H), 1.25 (s, 3H), 1.30 (s, 3H), 1.36-1.49 (m, 1H), 1.49-1.64 (m, 1H), 1.68-1.83 (m, 1H), 2.29 (s, 3H), 3.73 (dd, J=8.5, 5.7 Hz, 1H), 4.00 (dd, J=8.5, 6.3 Hz, 1H), 4.04-4.16 (m, 2H), 4.21 (d, J=18.7 Hz, 1H), 4.35 (quin, J=5.8 Hz, 1H), 4.59 (d, J=18.7 Hz, 1H), 4.85 (s, 1H), 4.85-4.92 (m, 1H), 6.43 (d, J=2.1 Hz, 1H), 7.13-7.34 (m, 3H), 7.60 (d, J=2.1 Hz, 1H), 10.80 (s, 1H).

Example 131

(S)-2-[4-(2-Fluoro-3-methyl-phenoxy)-2-oxo-2,5-dihydro-pyrrol-1-yl]-4-methyl-pentanoic acid [1-((R)-2,3-dihydroxy-propyl)-1H-pyrazol-3-yl]-amide

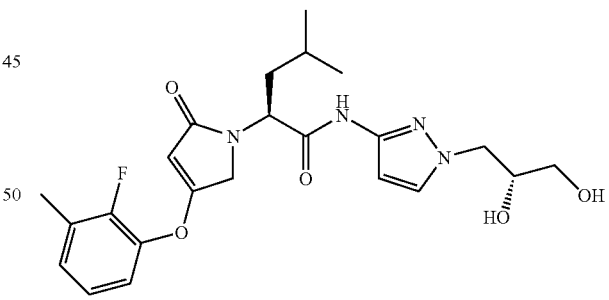

A solution of (S)-2-[4-(2-fluoro-3-methyl-phenoxy)-2-oxo-2,5-dihydro-pyrrol-1-yl]-4-methyl-pentanoic acid [1-((R)-2,2-dimethyl-[1,3]dioxolan-4-yl-methyl)-1H-pyrazol-3-yl]-amide (prepared in Example 130, 0.170 g, 0.34 mmol) in tetrahydrofuran (20 mL) was treated with 2N aqueous hydrochloric acid (15 mL). The reaction mixture was stirred for 2 h at room temperature. The reaction mixture was diluted with ethyl acetate, washed with water and saturated sodium bicarbonate, a saturated sodium chloride solution and dried over magnesium sulfate. Upon concentration afforded, (S)-2-[4-(2-fluoro-3-methyl-phenoxy)-2-oxo-2,5-dihydro-pyrrol-1-yl]-4-methyl-pentanoic acid [1-((R)-2,3-dihydroxypropyl)-1H-pyrazol-3-yl]-amide (0.080 g, 51%) as a off-white solid: HR-ES-MS m/z calculated for $C_{23}H_{29}FN_4O_5$, $[M+H]^+$ 461.2195 observed 461.2198; $^1$H NMR (300 MHz, DMSO-$d_6$) δ ppm 0.90 (d, J=6.3 Hz, 3H), 0.94 (d, J=6.3 Hz, 3H), 1.38-1.50 (m, 1H), 1.50-1.64 (m, 1H), 1.66-1.84 (m, 1H), 2.29 (s, 3H), 3.21-3.32 (m, 2H), 3.69-3.81 (m, 1H), 3.86 (dd, J=13.3, 7.2 Hz, 1H), 4.09 (dd, J=13.3, 3.8 Hz, 1H), 4.21 (d, J=18.4 Hz, 1H), 4.59 (d, J=18.4 Hz, 1H), 4.71 (t, J=5.6 Hz, 1H), 4.85 (s, 1H), 4.85-4.92 (m, 1H), 4.94 (d, J=5.4 Hz, 1H), 6.41 (d, J=2.1 Hz, 1H), 7.13-7.36 (m, 3H), 7.53 (d, J=2.1 Hz, 1H), 10.77 (s, 1H).

Example 132

(S)-2-[4-(2-Fluoro-3-methyl-phenoxy)-2-oxo-2,5-dihydro-pyrrol-1-yl]-4-methyl-pentanoic acid {1-[2-(t-butyl-dimethyl-silanyloxy)-ethyl]-1H-pyrazol-3-yl}-amide

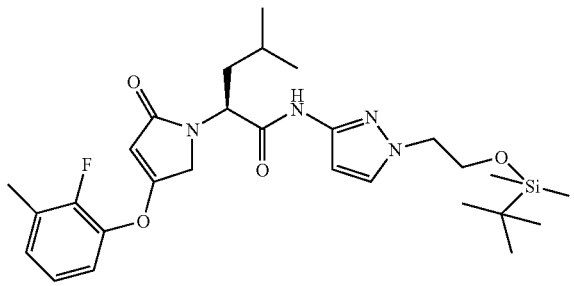

To a solution of (S)-2-[4-(2-fluoro-3-methyl-phenoxy)-2-oxo-2,5-dihydro-pyrrol-1-yl]-4-methyl-pentanoic acid (prepared as in Example 130, 0.248 g, 0.77 mmol) in N,N-dimethylformamide (5 mL) was added 1-[2-(t-butyl-dimethyl-silanyloxy)-ethyl]-1H-pyrazol-3-ylamine (prepared in U.S. Pat. Appl. US2008021032, Example 67, 0.223 g, 0.92 mmol) and benzotriazol-1-yl-oxy-tris(dimethylamino)phosphonium hexafluorophosphate (0.680 g, 1.54 mmol). The mixture was stirred at 0° C. and triethylamine (0.150 g, 1.47 mmol) was added. The mixture was stirred at room temperature for 4 h and the solvents were evaporated. The residue was treated with ethyl acetate and ammonium chloride solution, and the organic layer separated. The organic layer was washed with brine and dried over sodium sulfate. The solvents were evaporated and the residue was purified by ISCO flash chromatography (Teledyne Isco RediSep Flash Column 25 g, 10% to 60% ethyl acetate/hexanes) which afforded (S)-2-[4-(2-fluoro-3-methyl-phenoxy)-2-oxo-2,5-dihydro-pyrrol-1-yl]-4-methyl-pentanoic acid {1-[2-(t-butyl-dimethyl-silanyloxy)-ethyl]-1H-pyrazol-3-yl}-amide (0.250 g, 59%) as a tan solid: HR-ES-MS m/z calculated for $C_{28}H_{41}FN_4O_4Si$ $[M+H]^+$ 545.2954, observed 545.2955, $^1$H NMR (300 MHz, DMSO-$d_6$) δ ppm 1.00-0.08 (s, 6H), 0.79 (s, 9H), 0.89 (d, J=6.3 Hz, 3H), 0.93 (d, J=6.3 Hz, 3 H), 1.44 (br. s., 1H), 1.49-1.59 (m, 1H), 1.64-1.84 (m, 1H), 2.29 (s, 3H), 3.80-3.91 (m, 2H), 4.06 (t, J=5.1 Hz, 2H), 4.21 (d, J=18.4 Hz, 1H), 4.59 (d, J=18.4 Hz, 1H), 4.85 (s, 1H), 4.86-4.92 (m, 1H), 6.40 (d, J=2.1 Hz, 1H), 7.12-7.33 (m, 3H), 7.54 (d, J=2.1 Hz, 1H), 10.76 (s, 1H).

Example 133

(S)-2-[4-(2-Fluoro-3-methyl-phenoxy)-2-oxo-2,5-dihydro-pyrrol-1-yl]-4-methyl-pentanoic acid [1-(2-hydroxy-ethyl)-1H-pyrazol-3-yl]-amide

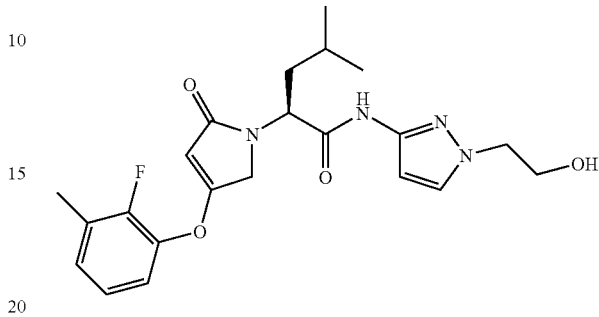

To a solution of (S)-2-[4-(2-fluoro-3-methyl-phenoxy)-2-oxo-2,5-dihydro-pyrrol-1-yl]-4-methyl-pentanoic acid {1-[2-(t-butyl-dimethyl-silanyloxy)-ethyl]-1H-pyrazol-3-yl}-amide (prepared as in Example 132, 0.220 g, 0.40 mmol) in ethanol (15 mL) was added concentrated hydrochloric acid (10 drops). The reaction mixture was stirred at room temperature for 1 h and then poured into ethyl acetate (100 mL) and the organic phase washed with water (100 mL) and brine and dried over anhydrous sodium sulfate. The mixture was filtered and evaporated which afforded, after trituration with diethyl ether/hexanes, (S)-2-[4-(2-fluoro-3-methyl-phenoxy)-2-oxo-2,5-dihydro-pyrrol-1-yl]-4-methyl-pentanoic acid [1-(2-hydroxy-ethyl)-1H-pyrazol-3-yl]-amide (0.130 g, 75%) as an off-white solid.

Example 134

(S)-2-[4-(2,6-Difluoro-3-isopropoxy-phenoxy)-2-oxo-2,5-dihydro-pyrrol-1-yl]-4-methyl-pentanoic acid [1-((R)-2,3-dihydroxy-propyl)-1H-pyrazol-3-yl]-amide

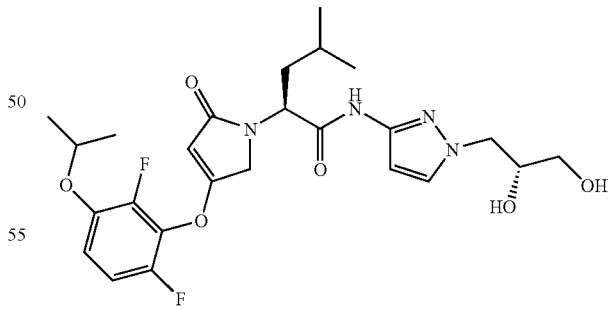

To a solution of 2,6-difluoro-3-isopropoxy-phenylboronic acid (10.0 g, 0.046 mol) in tetrahydrofuran (160 mL) was added glacial acetic acid (60 mL). The resulting mixture was cooled to 0° C. before hydrogen peroxide (50% aqueous solution, 8 mL) was added. The resulting mixture was allowed to come to room temperature and stirred for 40 h. The mixture was evaporated and the residue was dissolved in ethyl acetate, washed with hydrochloric acid (0.5N), water and brine. The organic phase was dried, filtered and evaporated which afforded 2,6-difluoro-3-isopropoxy-phenol (8.70 g, 100%) as a brown oil.

To a stirred mixture of 2,6-difluoro-3-isopropoxy-phenol (5.74 g, 0.031 mol) and ethyl-2-butynoate (6.85 g, 0.061 mol) in tetrahydrofuran (50 mL) was added 1,8-diazabicyclo [5.4.0]undec-7-ene (4.64 g, 0.030 mol) slowly. After addition was complete the mixture was stirred at reflux for 6 h. Upon completion of the reaction the tetrahydrofuran was removed in vacuo and the residue was diluted in diethyl ether and washed first with 1N aqueous hydrochloric acid, then 10% aqueous sodium hydroxide solution, a saturated sodium chloride solution and dried over magnesium sulfate. The mixture was filtered and evaporated which afforded (E)-3-(2,6-difluoro-3-isopropoxy-phenoxy)-but-2-enoic acid ethyl ester as a brown oil (6.85 g, 75%) and used without further purification.

To a stirred mixture of (E)-3-(2,6-difluoro-3-isopropoxy-phenoxy)-but-2-enoic acid ethyl ester (6.85 g, 0.023 mol) dissolved in carbon tetrachloride (50 mL) under a nitrogen atmosphere was added N-bromosuccinimide (4.47 g, 0.025 mol) and benzoyl peroxide (0.74 g, 0.003 mol). After addition was complete, the mixture was stirred at reflux for 16 h. The reaction mixture was then placed in the refrigerator overnight. The solids formed were removed by filtration and the filtrate concentrated in vacuo. The crude product obtained was purified by ISCO flash chromatography (Teledyne Isco RediSep Flash Column 120 g; 0% to 15% ethyl acetate/hexanes) to afford, (E)-4-bromo-3-(2,6-difluoro-3-isopropoxy-phenoxy)-but-2-enoic acid ethyl ester (6.30 g, 73%) as an impure light yellow oil.

(L)-leucine methyl ester hydrochloride (6.00 g, 0.033 mol) and N,N-diisopropylethylamine (4.50 g, 0.035 mol) were suspended in acetonitrile (50 mL) and the resulting mixture was warmed to 60° C. before (E)-4-bromo-3-(2,6-difluoro-3-isopropoxy-phenoxy)-but-2-enoic acid ethyl ester (6.30 g) in acetonitrile (10 mL) and N,N-diisopropylethylamine (4.50 g, 0.035 mol) was added. The resulting mixture was heated to reflux for 12 h. The reaction mixture was cooled to room temperature, the solvents evaporated and the residue poured into ethyl acetate. The mixture was filtered to remove salts and the filtrate washed successively with saturated ammonium chloride, water, and brine. The solution was dried over sodium sulfate, filtered and evaporated. The residue was dissolved in tetrahydrofuran (7 mL) and then transferred to an Emry Optimizer microwave reaction vessel and heated at 160° C., for 2 h. The crude product obtained after aqueous work-up, was purified by ISCO flash chromatography (Teledyne Isco RediSep Flash Column 80 g, 10% to 40% ethyl acetate/hexanes) to afford, (S)-2-[4-(2,6-difluoro-3-isopropoxy-phenoxy)-2-oxo-2,5-dihydro-pyrrol-1-yl]-4-methyl-pentanoic acid methyl ester (3.10 g, 47%) as a brown oil.

To a solution containing (S)-2-[4-(2,6-difluoro-3-isopropoxy-phenoxy)-2-oxo-2,5-dihydro-pyrrol-1-yl]-4-methyl-pentanoic acid methyl ester (3.10 g, 0.008 mol) in tetrahydrofuran (35 mL) was treated with an aqueous solution of lithium hydroxide monohydrate (0.5N, 35 mL, 0.018 mol). The mixture was stirred at 20° C. for 2H, and the solvents evaporated. The residue was dissolved in water and washed with diethyl ether, and the diethyl ether layer discarded. The aqueous phase was acidified with dilute hydrochloric acid (pH <2), and extracted with ethyl acetate. The combined organic layers were dried over sodium sulfate and concentrated to afford (S)-2-[4-(2,6-difluoro-3-isopropoxy-phenoxy)-2-oxo-2,5-dihydro-pyrrol-1-yl]-4-methyl-pentanoic acid (2.64 g, 88%) as a tan solid.

To a solution of (S)-2-[4-(2,6-difluoro-3-isopropoxy-phenoxy)-2-oxo-2,5-dihydro-pyrrol-1-yl]-4-methyl-pentanoic acid (0.530 g, 1.38 mmol) in N,N-dimethylformamide (10 mL) was added 1-((R)-2,2-dimethyl-[1,3]dioxolan-4-yl-methyl)-1H-pyrazol-3-ylamine (prepared as in Example 49, 0.354 g, 1.79 mmol) and benzotriazol-1-yl-oxy-tris(dimethylamino)phosphonium hexafluorophosphate (1.21 g, 2.73 mmol). The mixture was stirred at 0° C. and N,N-diisopropylethylamine (0.356 g, 2.75 mmol) was added. The mixture was stirred at room temperature for 5 h and the solvents were evaporated. The residue was treated with ethyl acetate and ammonium chloride solution, and the organic layer separated. The organic layer was washed with brine and dried over sodium sulfate. The solvents were evaporated and the residue was purified by ISCO flash chromatography (Teledyne Isco RediSep Flash Column 25 g, 10% to 70% ethyl acetate/hexanes) which afforded (S)-2-[4-(2,6-difluoro-3-isopropoxy-phenoxy)-2-oxo-2,5-dihydro-pyrrol-1-yl]-4-methyl-pentanoic acid [1-((R)-2,2-dimethyl-[1,3]dioxolan-4-yl-methyl)-1H-pyrazol-3-yl]-amide (0.500 g, 64%) as a off-white solid.

A solution of (S)-2-[4-(2,6-difluoro-3-isopropoxy-phenoxy)-2-oxo-2,5-dihydro-pyrrol-1-yl]-4-methyl-pentanoic acid [1-((R)-2,2-dimethyl-[1,3]dioxolan-4-yl-methyl)-1H-pyrazol-3-yl]-amide (0.500 g, 0.89 mmol) in tetrahydrofuran (30 mL) was treated with 2N aqueous hydrochloric acid (40 mL). The reaction mixture was stirred for 2 h at room temperature. The reaction mixture was diluted with ethyl acetate, washed with water, saturated sodium bicarbonate, a saturated sodium chloride solution and dried over magnesium sulfate. Upon concentration afforded, (S)-2-[4-(2,6-difluoro-3-isopropoxy-phenoxy)-2-oxo-2,5-dihydro-pyrrol-1-yl]-4-methyl-pentanoic acid [1-((R)-2,3-dihydroxy-propyl)-1H-pyrazol-3-yl]-amide (0.450 g, 97%) as a white solid: HR-ES-MS m/z calculated for $C_{25}H_{32}F_2N_4O_6$, $[M+H]^+$ 523.2363 observed 523.2363; $^1$H NMR (300 MHz, DMSO-d$_6$) δ ppm 0.90 (d, J=6.3 Hz, 3H), 0.93 (d, J=6.3 Hz, 3 H), 1.27 (s, 3H), 1.29 (s, 3H), 1.43 (br. s., 1H), 1.50-1.65 (m, 1H), 1.66-1.84 (m, 1H), 3.21-3.32 (m, 2H), 3.70-3.81 (m, 1H), 3.86 (dd, J=13.3, 7.2 Hz, 1H), 4.09 (dd, J=13.3, 3.6 Hz, 1H), 4.26 (d, J=18.7 Hz, 1H), 4.57-4.68 (m, 2H), 4.71 (t, J=5.6 Hz, 1H), 4.87 (d, J=10.7, 4.7 Hz, 1H), 4.94 (d, J=5.1 Hz, 1H), 5.05 (s, 1H), 6.40 (s, 1H), 7.14-7.32 (m, 2H), 7.53 (s, 1H), 10.79 (s, 1H).

Example 135

(S)-2-[4-(2,6-Difluoro-3-isopropoxy-phenoxy)-2-oxo-2,5-dihydro-pyrrol-1-yl]-4-methyl-pentanoic acid [1-(2-hydroxy-2-methyl-propyl)-1H-pyrazol-3-yl]-amide

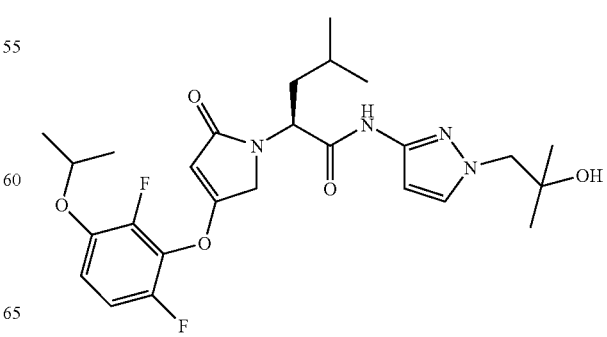

To a solution of (S)-2-[4-(2,6-difluoro-3-isopropoxy-phenoxy)-2-oxo-2,5-dihydro-pyrrol-1-yl]-4-methyl-pentanoic acid (prepared as in Example 134, 0.363 g, 0.95 mmol) in N,N-dimethylformamide (10 mL) was added 1-(3-aminopyrazol-1-yl)-2-methyl-propan-2-ol (prepared in U.S. Pat. Appl. US2008021032 Example 80, 0.190 g, 1.22 mmol) and benzotriazol-1-yl-oxy-tris(dimethylamino)phosphonium hexafluorophosphate (0.884 g, 2.00 mmol). The mixture was stirred at 0° C. and N,N-diisopropylethylamine (0.258 g, 2.00 mmol) was added. The mixture was stirred at room temperature for 2 h and the solvents were evaporated. The residue was treated with ethyl acetate and ammonium chloride solution, and the organic layer separated. The organic layer was washed with brine and dried over sodium sulfate. The solvents were evaporated and the residue was purified by ISCO flash chromatography (Teledyne Isco RediSep Flash Column 25 g, 5% to 80% ethyl acetate/hexanes) which afforded (S)-2-[4-(2,6-difluoro-3-isopropoxy-phenoxy)-2-oxo-2,5-dihydro-pyrrol-1-yl]-4-methyl-pentanoic acid [1-(2-hydroxy-2-methyl-propyl)-1H-pyrazol-3-yl]-amide (0.280 g, 57%) as a light yellow solid: HR-ES-MS m/z calculated for $C_{26}H_{34}F_2N_4O_5$ [M+H]$^+$ 521.2570, observed 521.2574, $^1$H NMR (300 MHz, DMSO-d$_6$) δ ppm 1.00 0.90 (d, J=6.4 Hz, 3H), 0.93 (d, J=6.4 Hz, 3H), 1.05 (br. s. 3H), 1.06 (br. s., 3H), 1.28 (d, J=6.0 Hz, 6H), 1.35-1.51 (m, 1H), 1.51-1.65 (m, 1H), 1.68-1.84 (m, 1H), 3.89 (s, 2H), 4.26 (d, J=18.7 Hz, 1H), 4.57-4.71 (m, 3H), 4.88 (dd, J=10.9, 4.5 Hz, 1H), 5.05 (s, 1H), 6.44 (d, J=2.1 Hz, 1H), 7.15-7.31 (m, 2H), 7.54 (d, J=2.1 Hz, 1H), 10.82 (s, 1H).

Example 136

(S)-2-[4-(2-Bromo-phenoxy)-2-oxo-2,5-dihydro-pyrrol-1-yl]-4-methyl-pentanoic acid [1-((R)-2,2-dimethyl-[1,3]dioxolan-4-yl-methyl)-1H-pyrazol-3-yl]-amide

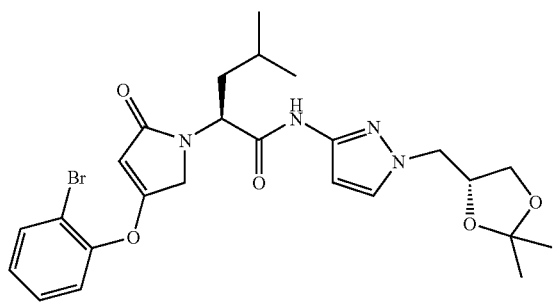

To a stirred mixture of 2-bromo-phenol (9.02 g, 0.052 mol) and ethyl-2-butynoate (11.7 g, 0.104 mol) in tetrahydrofuran (50 mL) was added 1,8-diazabicyclo[5.4.0]undec-7-ene (8.05 g, 0.053 mol) slowly. After addition was complete the mixture was stirred at reflux overnight. Upon completion of the reaction the tetrahydrofuran was removed in vacuo and the residue was diluted in diethyl ether and washed first with 1N aqueous hydrochloric acid, then 10% aqueous sodium hydroxide solution, a saturated sodium chloride solution and dried over magnesium sulfate. The mixture was filtered and evaporated and the residue dried under high vacuum which afforded (E)-3-(2-bromo-phenoxy)-but-2-enoic acid ethyl ester as a yellow oil (10.0 g, 67%) and used without further purification.

To a stirred mixture of (E)-3-(2-bromo-phenoxy)-but-2-enoic acid ethyl ester (10.0 g, 0.035 mol) dissolved in carbon tetrachloride (80 mL) under a nitrogen atmosphere was added N-bromosuccinimide (9.00 g, 0.051 mol) and benzoyl peroxide (1.20 g, 0.005 mol). After addition was complete, the mixture was stirred at reflux for 7 h. The reaction mixture was then placed in the refrigerator overnight. The solids formed were removed by filtration and the filtrate concentrated in vacuo. The crude product obtained was purified by ISCO flash chromatography (Teledyne Isco RediSep Flash Column 330 g; 0% to 15% ethyl acetate/hexanes) to afford, (E)-4-bromo-3-(2-bromo-phenoxy)-but-2-enoic acid ethyl ester (9.00 g, 70%) as an impure yellow oil.

To a stirred mixture of (L)-leucine methyl ester hydrochloride (3.00 g, 0.017 mol) suspended in acetonitrile (80 mL) under nitrogen atmosphere was added N,N-diisopropylethylamine (2.70 g, 0.021 mol). After addition was complete the mixture was stirred at 60° C. for 5 min. The reaction was cooled to 25° C. and treated with N,N-diisopropylethylamine (2.7 g, 2.10 mmol) and heated to 85° C. at which time, (E)-4-bromo-3-(2-bromo-phenoxy)-but-2-enoic acid ethyl ester (5.00 g) in acetonitrile (70 mL) was added slowly. After the addition was complete the reaction mixture was heated to 100° C. and stirred for 96 h. The reaction mixture was cooled to 25° C., filtered and concentrated. The residue was diluted with ethyl acetate and washed with saturated ammonium chloride, water, a saturated sodium chloride solution and dried over sodium sulfate. The crude product obtained was purified by ISCO flash chromatography (Teledyne Isco RediSep Flash Column 120 g, 10% to 70% ethyl acetate/hexanes) to afford, (S)-2-[4-(2-bromo-phenoxy)-2-oxo-2,5-dihydro-pyrrol-1-yl]-4-methyl-pentanoic acid methyl ester (2.00 g, 38%) as a orange oil.

To a solution containing (S)-2-[4-(2-bromo-phenoxy)-2-oxo-2,5-dihydro-pyrrol-1-yl]-4-methyl-pentanoic acid methyl ester (2.00 g, 0.005 mol) in tetrahydrofuran (40 mL) was treated with an aqueous solution of lithium hydroxide monohydrate (0.5N, 21 mL, 0.011 mol). The mixture was stirred at 20° C. for 2H, and the solvents evaporated. The residue was dissolved in water and washed with diethyl ether, and the diethyl ether layer discarded. The aqueous phase was acidified with dilute hydrochloric acid (pH <2), and extracted with ethyl acetate. The combined organic layers were dried over sodium sulfate and concentrated to afford (S)-2-[4-(2-bromo-phenoxy)-2-oxo-2,5-dihydro-pyrrol-1-yl]-4-methyl-pentanoic acid (1.90 g, 99%) as a tan solid.

To a solution of (S)-2-[4-(2-bromo-phenoxy)-2-oxo-2,5-dihydro-pyrrol-1-yl]-4-methyl-pentanoic acid (0.260 g, 0.71 mmol) in N,N-dimethylformamide (10 mL) was added 1-((R)-2,2-dimethyl-[1,3]dioxolan-4-yl-methyl)-1H-pyrazol-3-ylamine (prepared as in Example 49, 0.180 g, 0.91 mmol) and benzotriazol-1-yl-oxy-tris(dimethylamino)phosphonium hexafluorophosphate (0.663 g, 1.50 mmol). The mixture was stirred at 0° C. and N,N-diisopropylethylamine (0.200 g, 1.55 mmol) was added. The mixture was stirred at room temperature for 5 h and the solvents were evaporated. The residue was treated with ethyl acetate and ammonium chloride solution, and the organic layer separated. The organic layer was washed with brine and dried over sodium sulfate. The solvents were evaporated and the residue was purified by ISCO flash chromatography (Teledyne Isco RediSep Flash Column 12 g, 20% to 100% ethyl acetate/hexanes) which afforded (S)-2-[4-(2-bromo-phenoxy)-2-oxo-2,5-dihydro-pyrrol-1-yl]-4-methyl-pentanoic acid [1-((R)-2,2-dimethyl-[1,3]dioxolan-4-yl-methyl)-1H-pyrazol-3-yl]-amide (0.290 g, 75%) as a yellow solid: HR-ES-MS m/z calculated for C$_{25}$H$_{31}$BrN$_4$O$_5$ [M+H]$^+$ 547.1551, observed 547.1549, $^1$H NMR (300 MHz, DMSO-d$_6$) δ ppm 1.00 0.90 (d, J=6.4 Hz, 3 H), 0.94 (d, J=6.4 Hz, 3H), 1.25 (s, 3H), 1.30 (s, 3H), 1.37-1.50 (m, 1H), 1.50-1.65 (m, 1H), 1.69-1.83 (m, 1H), 3.73 (dd, J=8.4, 5.8 Hz, 1H), 4.00 (dd, J=8.4, 6.5 Hz, 1H), 4.11 (t, J=5.8 Hz, 2H), 4.20 (d, J=18.4 Hz, 1H), 4.35 (quin, J=5.8 Hz, 1H), 4.61 (d, J=18.4 Hz, 1H), 4.77 (s, 1H), 4.90 (dd, J=10.6, 4.8 Hz, 1H), 6.44 (d, J=2.1 Hz, 1H), 7.24-7.35 (m, 1H), 7.50 (m, 2H), 7.60 (d, J=2.1 Hz, 1H), 7.79 (d, J=7.8 Hz, 1H), 10.82 (s, 1H).

Example 137

(S)-2-[4-(2-Bromo-phenoxy)-2-oxo-2,5-dihydro-pyrrol-1-yl]-4-methyl-pentanoic acid [1-((R)-2,3-dihydroxy-propyl)-1H-pyrazol-3-yl]-amide

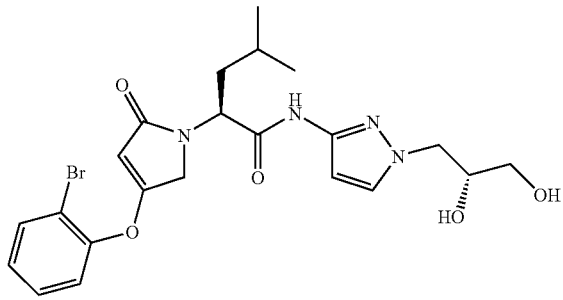

A solution of (S)-2-[4-(2-bromo-phenoxy)-2-oxo-2,5-dihydro-pyrrol-1-yl]-4-methyl-pentanoic acid [1-((R)-2,2-dimethyl-[1,3]dioxolan-4-yl-methyl)-1H-pyrazol-3-yl]-amide (prepared in Example 136, 0.270 g, 0.49 mmol) in tetrahydrofuran (25 mL) was treated with 2N aqueous hydrochloric acid (20 mL). The reaction mixture was stirred for 3 h at room temperature. The reaction mixture was diluted with ethyl acetate, washed with water, saturated sodium bicarbonate, a saturated sodium chloride solution and dried over magnesium sulfate. Upon concentration afforded, (S)-2-[4-(2-bromo-phenoxy)-2-oxo-2,5-dihydro-pyrrol-1-yl]-4-methyl-pentanoic acid [1-((R)-2,3-dihydroxy-propyl)-1H-pyrazol-3-yl]-amide (0.250 g, 100%) as an amorphous solid: HR-ES-MS m/z calculated for C$_{22}$H$_{27}$BrN$_4$O$_5$, [M+H]$^+$ 507.1238 observed 507.1237; $^1$H NMR (300 MHz, DMSO-d$_6$) δ ppm 0.90 (d, J=6.4 Hz, 3H), 0.94 (d, J=6.4 Hz, 3 H), 1.44 (br. s., 1H), 1.49-1.85 (m, 2H), 3.21-3.33 (m, 2H), 3.69-3.94 (m, 2H), 4.05-4.14 (m, 1H), 4.19 (d, J=18.4 Hz, 1H), 4.61 (d, J=18.4 Hz, 1H), 4.72 (t, J=5.6 Hz, 1H), 4.77 (s, 1H), 4.89 (dd, J=10.6, 4.8 Hz, 1H), 4.95 (d, J=5.1 Hz, 1H), 6.41 (d, J=2.1 Hz, 1H), 7.24-7.35 (m, 1H), 7.46-7.54 (m, 3H), 7.79 (d, J=8.2 Hz, 1H), 10.78 (s, 1H).

Example 138

(S)-2-[4-(3-Cyano-phenoxy)-2-oxo-2,5-dihydro-pyrrol-1-yl]-4-methyl-pentanoic acid [1-(2-hydroxy-2-methyl-propyl)-1H-pyrazol-3-yl]-amide

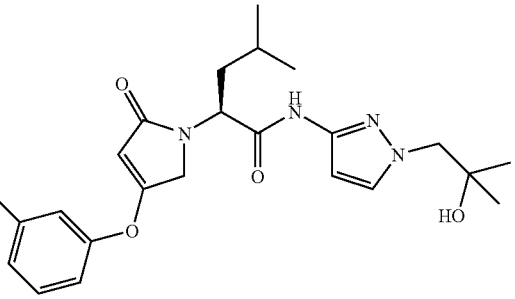

To a stirred mixture of 3-hydroxy-benzonitrile (3.30 g, 0.028 mol) and methyl-2-butynoate (5.40 g, 0.055 mol) in tetrahydrofuran (50 mL) was added 1,8-diazabicyclo[5.4.0]undec-7-ene (4.20 g, 0.028 mol) slowly. After addition was complete the mixture was stirred at reflux for 6 h. Upon completion of the reaction the tetrahydrofuran was removed in vacuo and the residue was diluted in diethyl ether and washed first with 1N aqueous hydrochloric acid, then 10% aqueous sodium hydroxide solution, a saturated sodium chloride solution and dried over magnesium sulfate. The mixture was filtered and evaporated and the residue dried under high vacuum which afforded (E)-3-(3-cyano-phenoxy)-but-2-enoic acid methyl ester as an oil (4.60 g, 76%) and used without further purification.

To a stirred mixture of (E)-3-(3-cyano-phenoxy)-but-2-enoic acid methyl ester (4.60 g, 0.021 mol) dissolved in carbon tetrachloride (80 mL) under a nitrogen atmosphere was added N-bromosuccinimide (5.60 g, 0.031 mol) and benzoyl peroxide (0.68 g, 0.003 mol). After addition was complete, the mixture was stirred at reflux for 8 h. The reaction mixture was then placed in the refrigerator overnight. The solids formed were removed by filtration and the filtrate concentrated in vacuo. The crude product obtained was purified by ISCO flash chromatography (Teledyne Isco RediSep Flash Column 120 g; 0% to 20% ethyl acetate/hexanes) to afford, (E)-4-bromo-3-(3-cyano-phenoxy)-but-2-enoic acid methyl ester (5.00 g, 80%) as an impure light yellow oil.

To a stirred mixture of (L)-leucine methyl ester hydrochloride (3.50 g, 0.019 mol) suspended in acetonitrile (60 mL) under a nitrogen atmosphere was added N,N-diisopropylethylamine (3.00 g, 0.023 mol). After addition was complete the mixture was stirred at 60° C. for 5 min. The reaction was cooled to 25° C. and treated with N,N-diisopropylethylamine (3 g, 0.023 mol) and heated to 85° C. at which time, (E)-4-bromo-3-(3-cyano-phenoxy)-but-2-enoic acid ethyl ester (5.00 g) in acetonitrile (10 mL) was added slowly. After the addition was complete the reaction mixture was heated to 100° C. and stirred for 20 h. The reaction mixture was cooled to 25° C., filtered and concentrated. The residue was diluted with ethyl acetate and washed with saturated ammonium chloride, water, a saturated sodium chloride solution and dried over sodium sulfate. The crude product obtained was purified by ISCO flash chromatography (Teledyne Isco RediSep Flash Column 80 g, 30% to 80% ethyl acetate/ hexanes) to afford, (S)-2-[4-(3-cyano-phenoxy)-2-oxo-2,5-dihydro-pyrrol-1-yl]-4-methyl-pentanoic acid methyl ester (2.20 g, 42%) as a yellow oil.

To a solution containing (S)-2-[4-(3-cyano-phenoxy)-2-oxo-2,5-dihydro-pyrrol-1-yl]-4-methyl-pentanoic acid methyl ester (2.20 g, 0.007 mol) in tetrahydrofuran (35 mL) was treated with an aqueous solution of lithium hydroxide monohydrate (0.5N, 28 mL, 0.014 mol). The mixture was stirred at 20° C. for 2 h, and the solvents evaporated. The residue was dissolved in water and washed with diethyl ether, and the diethyl ether layer discarded. The aqueous phase was acidified with dilute hydrochloric acid (pH <2), and extracted with ethyl acetate. The combined organic layers were dried over sodium sulfate and concentrated to afford (S)-2-[4-(3-cyano-phenoxy)-2-oxo-2,5-dihydro-pyrrol-1-yl]-4-methyl-pentanoic acid (1.80 g, 85%) as an off-white solid.

To a solution of (S)-2-[4-(3-cyano-phenoxy)-2-oxo-2,5-dihydro-pyrrol-1-yl]-4-methyl-pentanoic acid (0.205 g, 0.65 mmol) in N,N-dimethylformamide (15 mL) was added 1-(3-amino-pyrazol-1-yl)-2-methyl-propan-2-ol (prepared in U.S. Pat. Appl. US2008021032 Example 80, 0.131 g, 0.84 mmol) and benzotriazol-1-yl-oxy-tris(dimethylamino)phosphonium hexafluorophosphate (0.574 g, 1.30 mmol). The mixture was stirred at 0° C. and N,N-diisopropylethylamine (0.168 g, 1.30 mmol) was added. The mixture was stirred at room temperature for 5 h and the solvents were evaporated. The residue was treated with ethyl acetate and ammonium chloride solution, and the organic layer separated. The organic layer was washed with brine and dried over sodium sulfate. The solvents were evaporated and the residue was purified by ISCO flash chromatography (Teledyne Isco RediSep Flash Column 4 g, 30% to 100% ethyl acetate/hexanes) which afforded (S)-2-[4-(3-cyano-phenoxy)-2-oxo-2,5-dihydro-pyrrol-1-yl]-4-methyl-pentanoic acid [1-(2-hydroxy-2-methyl-propyl)-1H-pyrazol-3-yl]-(0.150 g, 51%) as a yellow solid: HR-ES-MS m/z calculated for $C_{24}H_{29}N_5O_4$ [M+H]$^+$ 452.2293, observed 42.2292, $^1$H NMR (300 MHz, DMSO-d$_6$) δ ppm 1.00 0.90 (d, J=6.2 Hz, 3H), 0.94 (d, J=6.2 Hz, 3H), 1.05 (br. s., 3H), 1.06 (br. s., 3H), 1.37-1.65 (m, 2H), 1.67-1.82 (m, 1H), 3.89 (s, 2H), 4.19 (d, J=18.4 Hz, 1H), 4.59 (d, J=18.4 Hz, 1H), 4.68 (s, 1H), 4.90 (dd, J=10.7, 4.4 Hz, 1H), 4.99 (s, 1H), 6.44 (d, J=2.1 Hz, 1H), 7.53 (d, J=2.1 Hz, 1H), 7.66-7.73 (m, 2H), 7.80 (d, J=5.7 Hz, 1H), 7.92 (s, 1H), 10.80 (s, 1H).

Example 139

(S)-2-[4-(3-Dimethylamino-2-fluoro-phenoxy)-2-oxo-2,5-dihydro-pyrrol-1-yl]-4-methyl-pentanoic acid [1-((R)-2,2-dimethyl-[1,3]dioxolan-4-yl-methyl)-1H-pyrazol-3-yl]-amide

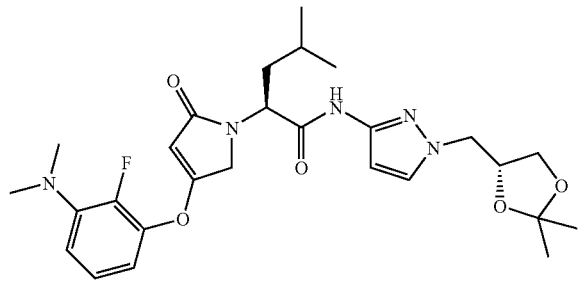

To a mixture of (S)-2-[4-(3-bromo-2-fluoro-phenoxy)-2-oxo-2,5-dihydro-pyrrol-1-yl]-4-methyl-pentanoic acid ethyl ester (prepared as in Example 128, 0.850 g, 2.05 mmol), palladium(II) acetate (0.050 g, 0.22 mmol), 2,2'-bis(diphenylphosphino)-1,1'-binaphthyl (0.250 g, 0.40 mmol), and cesium carbonate (1.90 g, 5.83 mmol) in 1,4-dioxane (5 mL) was added a dimethylamine solution in tetrahydrofuran (2M, 3 mL, 6.00 mmol) and the resulting mixture was sealed in a tube and heated at 100° C. for 6 h. The cooled solution was poured into ethyl acetate (100 mL), filtered and the filtrate washed with water, brine and dried over anhydrous sodium sulfate. The resulting mixture was filtered, evaporated and the residue purified by ISCO flash chromatography (Teledyne Isco RediSep Flash Column 40 g, 10% to 60% ethyl acetate/hexanes) which afforded (S)-2-[4-(3-dimethylamino-2-fluoro-phenoxy)-2-oxo-2,5-dihydro-pyrrol-1-yl]-4-methyl-pentanoic acid ethyl ester (0.261 g, 34%) as a yellow oil.

To a solution containing (S)-2-[4-(3-dimethylamino-2-fluoro-phenoxy)-2-oxo-2,5-dihydro-pyrrol-1-yl]-4-methyl-pentanoic acid ethyl ester (0.261 g, 0.001 mol) in tetrahydrofuran (4 mL) was treated with an aqueous solution of lithium hydroxide monohydrate (0.5N, 2 mL, 0.001 mol). The mixture was stirred at 20° C. for 2 h, and the solvents evaporated. The residue was dried under high vacuum and rinsed with diethyl ether to afford (S)-2-[4-(3-dimethylamino-2-fluoro-phenoxy)-2-oxo-2,5-dihydro-pyrrol-1-yl]-4-methyl-pentanoic acid lithium salt (0.257 g, 100%) as a yellow solid.

To a solution of (S)-2-[4-(3-dimethylamino-2-fluoro-phenoxy)-2-oxo-2,5-dihydro-pyrrol-1-yl]-4-methyl-pentanoic acid lithium salt (0.257 g, 0.73 mmol) in N,N-dimethylformamide (5 mL) was added 1-((R)-2,2-dimethyl-[1,3]dioxolan-4-yl-methyl)-1H-pyrazol-3-ylamine (prepared as in Example 49, 0.160 g, 0.81 mmol) and benzotriazol-1-yl-oxy-tris(dimethylamino)phosphonium hexafluorophosphate (1.91 g, 4.32 mmol). The mixture was stirred at room temperature overnight and the solvents were evaporated. The residue was treated with ethyl acetate and ammonium chloride solution, and the organic layer separated. The organic layer was washed with a saturated sodium chloride solution and dried over sodium sulfate. The solvents were evaporated and the residue was purified by ISCO flash chromatography (Teledyne Isco RediSep Flash Column 25 g, 10% to 75% ethyl acetate/hexanes) which afforded (S)-2-[4-(3-dimethylamino-2-fluoro-phenoxy)-2-oxo-2,5-dihydro-pyrrol-1-yl]-4-methyl-pentanoic acid [1-((R)-2,2-dimethyl-[1,3]dioxolan-4-yl-methyl)-1H-pyrazol-3-yl]-amide (0.200 g, 51%) as a yellow solid: HR-ES-MS m/z calculated for $C_{27}H_{36}FN_5O_5$ [M+H]$^+$ 530.2773, observed 530.2771, $^1$H NMR (300 MHz, DMSO-d$_6$) δ ppm 1.00 0.90 (d, J=6.3 Hz, 3H), 0.94 (d, J=6.3 Hz, 3H), 1.25 (s, 3H), 1.31 (d, J=3.0 Hz, 3H), 1.38-1.50 (m, 1H), 1.50-1.65 (m, 1H), 1.69-1.85 (m, 1H), 2.82 (s, 6H), 3.74 (dd, J=8.3, 5.9 Hz, 1H), 4.01 (dd, J=8.5, 6.3 Hz, 1H), 4.04-4.15 (m, 2H), 4.20 (d, J=18.4 Hz, 1H), 4.29-4.43 (m, 1H), 4.58 (d, J=18.4 Hz, 1H), 4.86 (s, 1H), 4.87-4.95 (m, 1H), 6.44 (d, J=2.1 Hz, 1H), 6.79-6.98 (m, 2H), 7.12 (t, J=8.5 Hz, 1H), 7.61 (br. s., 1H), 10.80 (s, 1H).

Example 140

(S)-2-[4-(3-Dimethylamino-2-fluoro-phenoxy)-2-oxo-2,5-dihydro-pyrrol-1-yl]-4-methyl-pentanoic acid [1-((R)-2,3-dihydroxy-propyl)-1H-pyrazol-3-yl]-amide hydrochloride

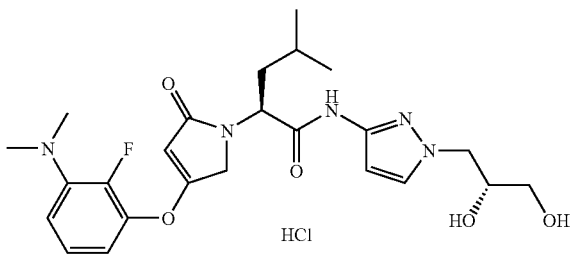

A solution of (S)-2-[4-(3-dimethylamino-2-fluoro-phenoxy)-2-oxo-2,5-dihydro-pyrrol-1-yl]-4-methyl-pentanoic acid [1-((R)-2,2-dimethyl-[1,3]dioxolan-4-yl-methyl)-1H-pyrazol-3-yl]-amide (prepared in Example 139, 0.180 g, 0.34 mmol) in tetrahydrofuran (5 mL) was treated with 2N aqueous hydrochloric acid (3 mL). The reaction mixture was stirred for 3 h at room temperature. The solvents were evaporated and the residue was treated with a saturated sodium bicarbonate solution and extracted with ethyl acetate. The organic phase was washed with a saturated sodium chloride solution and concentrated. The residue was taken up in ethyl acetate and treated with hydrochloric acid in diethyl ether. The solvents were evaporated and the residue was washed with diethyl ether, acetonitrile and dried which afforded (S)-2-[4-(3-dimethylamino-2-fluoro-phenoxy)-2-oxo-2,5-dihydro-pyrrol-1-yl]-4-methyl-pentanoic acid hydrochloride salt [1-((R)-2,3-dihydroxy-propyl)-1H-pyrazol-3-yl]-amide (0.090 g, 54%) as a yellow solid: HR-ES-MS m/z calculated for $C_{24}H_{32}FN_5O_5$, [M+H]$^+$ 490.246 observed 490.2459; $^1$H NMR (300 MHz, DMSO-$d_6$) δ ppm 0.88 (d, J=6.3 Hz, 3H), 0.92 (d, J=6.3 Hz, 3H), 1.35-1.48 (m, 1H), 1.48-1.65 (m, 1H), 1.65-1.82 (m, 1H), 2.81 (s, 6H), 3.18-3.39 (m, 2H), 3.67-3.79 (m, 1H), 3.79-3.92 (m, 1H), 4.07 (dd, J=13.6, 3.9 Hz, 1H), 4.18 (d, J=18.4 Hz, 1H), 4.56 (d, J=18.4 Hz, 1H), 4.79-4.89 (m, 2H), 6.39 (d, J=2.1 Hz, 1H), 6.84-6.96 (m, 2H), 7.05-7.20 (m, 1H), 7.52 (d, J=2.1 Hz, 1H), 10.76 (s, 1H).

Example 141

(S)-2-[4-(2-Fluoro-3-pyrrolidin-1-yl-phenoxy)-2-oxo-2,5-dihydro-pyrrol-1-yl]-4-methyl-pentanoic acid [1-((R)-2,2-dimethyl-[1,3]dioxolan-4-yl-methyl)-1H-pyrazol-3-yl]-amide

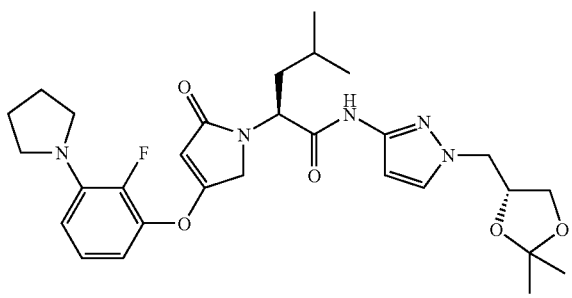

To a mixture of (S)-2-[4-(3-bromo-2-fluoro-phenoxy)-2-oxo-2,5-dihydro-pyrrol-1-yl]-4-methyl-pentanoic acid ethyl ester (prepared as in Example 128, 0.300 g, 0.72 mmol), palladium(II) acetate (0.023 g, 0.10 mmol), 2,2'-bis(diphenylphosphino)-1,1'-binaphthyl (0.124 g, 0.20 mmol), and cesium carbonate (0.650 g, 1.99 mmol) in 1,4-dioxane (10 mL) was added pyrrolidine (0.103 g, 1.45 mmol) and the resulting mixture heated to 100° C. in a sealed tube under argon for 6 h. The resulting mixture was taken up in ethyl acetate and water, separated and the organic phase washed with a saturated sodium chloride solution and concentrated. The residue was purified by ISCO flash chromatography (Teledyne Isco RediSep Flash Column 50 g, 5% to 40% ethyl acetate/hexanes) which afforded (S)-2-[4-(2-fluoro-3-pyrrolidin-1-yl-phenoxy)-2-oxo-2,5-dihydro-pyrrol-1-yl]-4-methyl-pentanoic acid ethyl ester (0.120, 41%) as an oil.

To a solution containing (S)-2-[4-(2-fluoro-3-pyrrolidin-1-yl-phenoxy)-2-oxo-2,5-dihydro-pyrrol-1-yl]-4-methyl-pentanoic acid ethyl ester (0.120 g, 0.29 mmol) in tetrahydrofuran (4 mL) was treated with an aqueous solution of lithium hydroxide monohydrate (0.5N, 1.2 mL, 0.6 mmol). The mixture was stirred at 25° C. for 2 h, and the solvents evaporated. The residue was rinsed with diethyl ether which afforded (S)-2-[4-(2-fluoro-3-pyrrolidin-1-yl-phenoxy)-2-oxo-2,5-dihydro-pyrrol-1-yl]-4-methyl-pentanoic acid lithium salt (0.140 g, 100%) as a yellow solid.

To a solution of (S)-2-[4-(2-fluoro-3-pyrrolidin-1-yl-phenoxy)-2-oxo-2,5-dihydro-pyrrol-1-yl]-4-methyl-pentanoic acid (0.140 g, 0.37 mmol) in N,N-dimethylformamide (5 mL) was added 1-((R)-2,2-dimethyl-[1,3]dioxolan-4-yl-methyl)-1H-pyrazol-3-ylamine (prepared as in Example 49, 0.090 g, 0.46 mmol) and benzotriazol-1-yl-oxy-tris(dimethylamino) phosphonium hexafluorophosphate (0.655 g, 1.48 mmol). The mixture was stirred at room temperature overnight and the solvents were evaporated. The residue was treated with ethyl acetate and ammonium chloride solution, and the organic layer separated. The organic layer was washed with brine and dried over sodium sulfate. The solvents were evaporated and the residue was purified by ISCO flash chromatography (Teledyne Isco RediSep Flash Column 25 g, 0% to 80% ethyl acetate/hexanes) which afforded (S)-2-[4-(2-fluoro-3-pyrrolidin-1-yl-phenoxy)-2-oxo-2,5-dihydro-pyrrol-1-yl]-4-methyl-pentanoic acid [1-((R)-2,2-dimethyl-[1,3]dioxolan-4-yl-methyl)-1H-pyrazol-3-yl]-amide (0.110 g, 53%) as a white solid: HR-ES-MS m/z calculated for $C_{29}H_{38}FN_5O_5$ [M+H]$^+$ 556.2930, observed 556.2928, $^1$H NMR (300 MHz, DMSO-$d_6$) δ ppm 1.00 0.90 (d, J=6.6 Hz, 3H), 0.93 (d, J=6.6 Hz, 3H), 1.25 (s, 3H), 1.29, 1.31 (2×s, 3H), 1.35-1.64 (m, 2H), 1.66-1.83 (m, 1H), 1.84-1.95 (m, 4H), 3.29-3.39 (m, 4H), 3.73 (dd, J=8.3, 5.9 Hz, 1H), 4.00 (dd, J=8.3, 6.5 Hz, 1H), 4.04-4.14 (m, 2H), 4.18 (d, J=18.4 Hz, 1H), 4.25-4.41 (m, 1H), 4.56 (d, J=18.4 Hz, 1H), 4.84-4.93 (m, 2H), 6.43 (d, J=2.1 Hz, 1H), 6.59-6.70 (m, 2H), 7.03 (t, J=8.2 Hz, 1H), 7.60 (br. s., 1H), 10.79 (s, 1H).

Example 142

(S)-2-[4-(2-Fluoro-3-pyrrolidin-1-yl-phenoxy)-2-oxo-2,5-dihydro-pyrrol-1-yl]-4-methyl-pentanoic acid [1-((R)-2,3-dihydroxy-propyl)-1H-pyrazol-3-yl]-amide

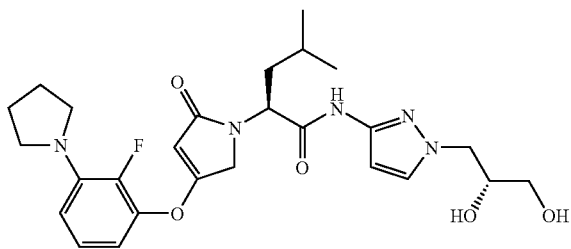

A solution of (S)-2-[4-(2-fluoro-3-pyrrolidin-1-yl-phenoxy)-2-oxo-2,5-dihydro-pyrrol-1-yl]-4-methyl-pentanoic acid [1-((R)-2,2-dimethyl-[1,3]dioxolan-4-yl-methyl)-1H-pyrazol-3-yl]-amide (prepared in Example 141, 0.095 g, 0.17 mmol) in tetrahydrofuran (3 mL) was treated with 2N aqueous hydrochloric acid (3 mL). The reaction mixture was stirred for 2 h at room temperature. The reaction mixture was diluted with ethyl acetate, washed with saturated sodium bicarbonate, a saturated sodium chloride solution and dried over magnesium sulfate. Upon concentration afforded, (S)-2-[4-(2-fluoro-3-pyrrolidin-1-yl-phenoxy)-2-oxo-2,5-dihydro-pyrrol-1-yl]-4-methyl-pentanoic acid [1-((R)-2,3-dihydroxy-propyl)-1H-pyrazol-3-yl]-amide (0.050 g, 57%) as a off-white solid: HR-ES-MS m/z calculated for $C_{26}H_{34}FN_5O_5$, [M+H]$^+$ 516.2617 observed 516.2613; $^1$H NMR (300 MHz, DMSO-d$_6$) δ ppm 0.90 (d, J=6.6 Hz, 3H), 0.93 (d, J=6.3 Hz, 3H), 1.36-1.49 (m, 1H), 1.49-1.65 (m, 1H), 1.65-1.80 (m, 1H), 1.80-2.0 (m, 4H), 3.22-3.35 (m, 6H), 3.75 (br. s., 1H), 3.86 (dd, J=13.6, 7.5 Hz, 1H), 4.09 (dd, J=13.4, 3.8 Hz, 1H), 4.18 (d, J=18.4 Hz, 1H), 4.57 (d, J=18.4 Hz, 1H), 4.72 (br. s., 1H), 4.83-4.91 (m, 1H), 4.86 (s, 1H), 4.95 (br. s., 1H), 6.40 (d, J=2.1 Hz, 1H), 6.60-6.71 (m, 2H), 7.03 (t, J=8.5 Hz, 1H), 7.53 (s, 1H), 10.77 (s, 1H).

Example 143

(S)-2-{4-[2-Fluoro-3-(1-hydroxy-1-methyl-ethyl)-phenoxy]-2-oxo-2,5-dihydro-pyrrol-1-yl}-4-methyl-pentanoic acid (1-methyl-1H-pyrazol-3-yl)-amide

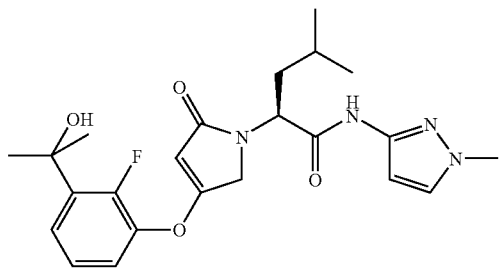

To a solution of (3-acetyl-2-fluorophenyl)boronic acid (10.0 g, 0.055 mol) in tetrahydrofuran (160 mL) was added glacial acetic acid (60 mL). The resulting mixture was cooled to 0° C. before hydrogen peroxide (50% aqueous solution, 8 mL) was added. The resulting mixture was allowed to come to room temperature and stirred for 5 h. The mixture was evaporated and the residue was dissolved in ethyl acetate, washed with hydrochloric acid (0.5N), water and brine. The organic phase was dried, filtered and evaporated which afforded 1-(2-fluoro-3-hydroxy-phenyl)-ethanone (8.50 g, 100%) as a white solid.

To a solution of 1-(2-fluoro-3-hydroxy-phenyl)-ethanone (8.50 g, 55.0 mmol) in tetrahydrofuran (80 mL) was slowly added a methyl magnesium bromide solution in diethyl ether (3.0 M, 46.5 mL, 0.15 mol) at −78° C. The resulting mixture was stirred at −78° C. for 10 min and then allowed to come to room temperature and stirred for an additional 40 min. The reaction mixture was diluted with diethyl ether (100 mL) and cooled in an ice bath before an aqueous hydrochloric acid solution (1N, 200 mL) was added dropwise. The biphasic mixture was separated and the aqueous phase extracted with diethyl ether (2×60 mL). The combined organic phases were washed with water, brine and dried over sodium sulfate. The resulting mixture was filtered and evaporated and the resulting oil was dried under vacuum which afforded 2-fluoro-3-(1-hydroxy-1-methyl-ethyl)-phenol (9.40 g, 100%) as an off-white solid.

To a stirred mixture of 2-fluoro-3-(1-hydroxy-1-methyl-ethyl)-phenol (5.00 g, 0.029 mol) and ethyl-2-butynoate (6.50 g, 0.058 mol) in tetrahydrofuran (40 mL) was added 1,8-diazabicyclo[5.4.0]undec-7-ene (4.48 g, 0.029 mol) in tetrahydrofuran (5 mL) slowly. After addition was complete the mixture was stirred at reflux overnight. Upon completion of the reaction the tetrahydrofuran was removed in vacuo and the residue was diluted in ethyl acetate and washed first with 1N aqueous hydrochloric acid, then 10% aqueous sodium hydroxide solution, a saturated sodium chloride solution and dried over magnesium sulfate. The mixture was filtered and evaporated and the residue dried under high vacuum. The residue was purified by ISCO flash chromatography (Teledyne Isco RediSep Flash Column 120 g; (5% to 30% ethyl acetate/hexanes) to afford, (E)-3-[2-fluoro-3-(1-hydroxy-1-methyl-ethyl)-phenoxy]-but-2-enoic acid ethyl ester (3.96 g, 48%) as a white solid.

To a stirred mixture of (E)-3-[2-fluoro-3-(1-hydroxy-1-methyl-ethyl)-phenoxy]-but-2-enoic acid ethyl ester (3.96 g, 0.014 mol) dissolved in dichloromethane (50 mL) under a nitrogen atmosphere was added N-bromosuccinimide (2.67 g, 0.015 mol) and 2,2'-azobis(2,4-dimethylvaleronitrile) (0.348 g, 1.4 mmol). After addition was complete, the mixture was stirred at reflux for 8 h. The reaction mixture was diluted with dichloromethane, washed with a saturated sodium chloride solution, and evaporated. The crude product obtained was purified by ISCO flash chromatography (Teledyne Isco RediSep Flash Column 120 g; 5% to 50% ethyl acetate/hexanes) to afford, (E)-4-bromo-3-[2-fluoro-3-(1-hydroxy-1-methyl-ethyl)-phenoxy]-but-2-enoic acid ethyl ester (3.30 g, 65%) as an impure pale yellow oil.

To a warmed solution of (L)-leucine methyl ester hydrochloride (2.00 g, 11.0 mmol) and N,N-diisopropylethylamine (1.50 g, 11.6 mmol) suspended in acetonitrile (30 mL) was added (E)-4-bromo-3-[2-fluoro-3-(1-hydroxy-1-methyl-ethyl)-phenoxy]-but-2-enoic acid ethyl ester (3.30 g) in acetonitrile (10 mL) and N,N-diisopropylethylamine (1.50 g, 11.6 mmol) and the resulting mixture refluxed for 18 h. The reaction mixture was cooled to room temperature, concentrated and then poured into ethyl acetate. The mixture was filtered to remove salts and the filtrate washed successively with saturated ammonium chloride, water, and brine. The solution was dried over sodium sulfate, filtered and evaporated. The residue was dissolved in tetrahydrofuran (12 mL) and then transferred to an Emry Optimizer microwave reaction vessel and heated at 160° C., for 2 h. The crude product obtained after aqueous work-up, was purified by ISCO flash chromatography (Teledyne Isco RediSep Flash Column 80 g, 20% to 70% ethyl acetate/hexanes) to afford, (S)-2-{4-[2-fluoro-3-(1-hydroxy-1-methyl-ethyl)-phenoxy]-2-oxo-2,5-dihydro-pyrrol-1-yl}-4-methyl-pentanoic acid methyl ester (2.05 g, 59%) as a yellow oil.

To a solution containing (S)-2-{4-[2-fluoro-3-(1-hydroxy-1-methyl-ethyl)-phenoxy]-2-oxo-2,5-dihydro-pyrrol-1-yl}-4-methyl-pentanoic acid methyl ester (2.00 g, 0.005 mol) in tetrahydrofuran (20 mL) was treated with an aqueous solution of lithium hydroxide monohydrate (0.5N, 20 mL, 0.010 mol). The mixture was stirred at 25° C. for 2H, and the solvents evaporated. The residue was dissolved in water and washed with diethyl ether, and the diethyl ether layer discarded. The aqueous phase was acidified with dilute hydrochloric acid (pH <2), and extracted with ethyl acetate. The combined organic layers were dried over sodium sulfate and concentrated to afford (S)-2-{4-[2-fluoro-3-(1-hydroxy-1-methyl-ethyl)-phenoxy]-2-oxo-2,5-dihydro-pyrrol-1-yl}-4-methyl-pentanoic acid (1.93 g, 100%) as a fluffy solid.

To a solution of (S)-2-{4-[2-fluoro-3-(1-hydroxy-1-methyl-ethyl)-phenoxy]-2-oxo-2,5-dihydro-pyrrol-1-yl}-4-methyl-pentanoic acid (0.392 g, 1.07 mmol) in dichloromethane (10 mL) was added 1-methyl-1H-pyrazol-3-ylamine (0.208 g, 2.14 mmol) and benzotriazol-1-yl-oxy-tris(dimethylamino)phosphonium hexafluorophosphate (0.522 g, 1.18 mmol). The mixture was stirred at 0° C. and N,N-diisopropylethylamine (0.304 g, 2.35 mmol) was added. The mixture was stirred at room temperature overnight and the solvents were evaporated. The residue was treated with ethyl acetate and ammonium chloride solution, and the organic layer separated. The organic layer was washed with brine and dried over sodium sulfate. The solvents were evaporated and the residue was purified by ISCO flash chromatography (Teledyne Isco RediSep Flash Column 112 g, 60% to 100% ethyl acetate/hexanes) which afforded (S)-2-{4-[2-fluoro-3-(1-hydroxy-1-methyl-ethyl)-phenoxy]-2-oxo-2,5-dihydro-pyrrol-1-yl}-4-methyl-pentanoic acid (1-methyl-1H-pyrazol-3-yl)-amide (0.441 g, 92%) as an off-white solid: HR-ES-MS m/z calculated for $C_{23}H_{29}FN_4O_4$ $[M+H]^+$ 445.2246, observed 445.2246, $^1$H NMR (300 MHz, DMSO-$d_6$) δ 1.00 0.90 (d, J=6.4 Hz, 3H), 0.93 (d, J=6.4 Hz, 3H), 1.36-1.47 (m, 1H), 1.49 (s, 6H), 1.52-1.65 (m, 1H), 1.67-1.82 (m, 1H), 3.73 (s, 3H), 4.20 (d, J=18.4 Hz, 1H), 4.58 (d, J=18.4 Hz, 1H), 4.81 (s, 1H), 4.88 (dd, J=10.7, 5.0 Hz, 1H), 5.42 (s, 1H), 6.40 (d, J=2.1 Hz, 1H), 7.23 (t, J=7.8 Hz, 1H), 7.29-7.40 (m, 1H), 7.54 (d, J=2.1 Hz, 1H), 7.51-7.60 (m, 1H), 10.73 (s, 1H).

Example 144

(S)-2-[4-(2-Fluoro-3-vinyl-phenoxy)-2-oxo-2,5-dihydro-pyrrol-1-yl]-4-methyl-pentanoic acid [1-((R)-2,2-dimethyl-[1,3]dioxolan-4-yl-methyl)-1H-pyrazol-3-yl]-amide

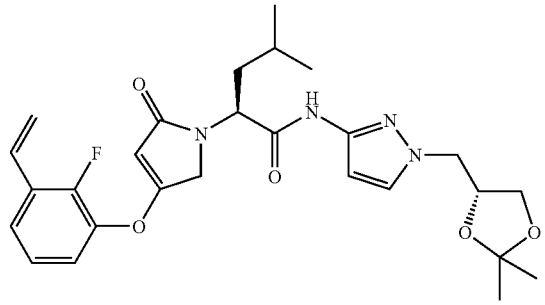

To a mixture of (S)-2-[4-(3-bromo-2-fluoro-phenoxy)-2-oxo-2,5-dihydro-pyrrol-1-yl]-4-methyl-pentanoic acid ethyl ester (prepared as in Example 128, 0.624 g, 1.51 mmol), tetrakis(triphenylphosphine)palladium(0) (0.200 g, 0.17 mmol) in N,N-dimethylformamide (7 mL) was added tributyl(vinyl)tin (0.652 g, 2.05 mmol) and the resulting mixture stirred at 80° C. for 14 h. The mixture was taken up in ethyl acetate and dilute hydrochloric acid and separated. The organic phase was washed with, saturated sodium bicarbonate solution, a saturated sodium chloride solution and dried over sodium sulfate. The mixture was filtered, evaporated and the residue purified by ISCO flash chromatography (Teledyne Isco RediSep Flash Column 50 g, 10% to 50% ethyl acetate/hexanes) which afforded (S)-2-[4-(2-fluoro-3-vinyl-phenoxy)-2-oxo-2,5-dihydro-pyrrol-1-yl]-4-methyl-pentanoic acid ethyl ester (0.400 g, 73%) as a clear oil.

To a solution containing (S)-2-[4-(2-fluoro-3-vinyl-phenoxy)-2-oxo-2,5-dihydro-pyrrol-1-yl]-4-methyl-pentanoic acid ethyl ester (0.400 g, 0.001 mol) in tetrahydrofuran (6 mL) was treated with an aqueous solution of lithium hydroxide monohydrate (0.5N, 3 mL, 0.002 mol). The mixture was stirred at 20° C. for 2 h, and the solvents evaporated. The residue was dissolved in water and washed with diethyl ether, and the diethyl ether layer discarded. The aqueous phase was acidified with dilute hydrochloric acid (pH <2), and extracted with ethyl acetate. The combined organic layers were dried over sodium sulfate and concentrated to afford (S)-2-[4-(2-fluoro-3-vinyl-phenoxy)-2-oxo-2,5-dihydro-pyrrol-1-yl]-4-methyl-pentanoic acid (0.35 g, 95%) as a white solid.

To a solution of (S)-2-[4-(2-fluoro-3-vinyl-phenoxy)-2-oxo-2,5-dihydro-pyrrol-1-yl]-4-methyl-pentanoic acid (0.215 g, 0.64 mmol) in N,N-dimethylformamide (5 mL) was added 1-((R)-2,2-dimethyl-[1,3]dioxolan-4-yl-methyl)-1H-pyrazol-3-ylamine (prepared as in Example 49, 0.153 g, 0.78 mmol) and benzotriazol-1-yl-oxy-tris(dimethylamino)phosphonium hexafluorophosphate (0.530 g, 1.20 mmol). The mixture was stirred at 0° C. and triethylamine (0.122 g, 1.21 mmol) was added. The mixture was stirred at room temperature for 4 h and the solvents were evaporated. The residue was treated with ethyl acetate and ammonium chloride solution, and the organic layer separated. The organic layer was washed with brine and dried over sodium sulfate. The solvents were evaporated and the residue was purified by ISCO flash chromatography (Teledyne Isco RediSep Flash Column 25 g, 10% to 80% ethyl acetate/hexanes) which afforded (S)-2-[4-(2-fluoro-3-vinyl-phenoxy)-2-oxo-2,5-dihydro-pyrrol-1-yl]-4-methyl-pentanoic acid [1-((R)-2,2-dimethyl-[1,3]dioxolan-4-yl-methyl)-1H-pyrazol-3-yl]-amide (0.214 g, 65%) as a white solid: HR-ES-MS m/z calculated for $C_{27}H_{33}FN_4O_5$ [M+H]$^+$ 513.2508, observed 513.2505, $^1$H NMR (300 MHz, DMSO-d$_6$) δ ppm 1.00 0.90 (d, J=6.3 Hz, 3H), 0.94 (d, J=6.3 Hz, 3H), 1.25 (s, 3H), 1.30 (s, 3H), 1.45 (br. s., 1H), 1.49-1.67 (m, 1H), 1.67-1.84 (m, 1H), 3.73 (dd, J=8.4, 5.7 Hz, 1H), 4.00 (dd, J=8.4, 6.5 Hz, 1H), 4.04-4.18 (m, 2H), 4.23 (d, J=18.4 Hz, 1H), 4.35 (dq, J=6.0, 5.7 Hz, 1H), 4.60 (d, J=18.4 Hz, 1H), 4.81-4.93 (m, 1H), 4.91 (s, 1H), 5.52 (d, J=11.4 Hz, 1H), 6.00 (d, J=17.8 Hz, 1H), 6.44 (d, J=2.1 Hz, 1H), 6.86 (dd, J=17.8, 11.4 Hz, 1H), 7.27 (t, J=7.8 Hz, 1H), 7.42 (td, J=7.8, 1.2 Hz, 1H), 7.57-7.64 (m, 2H), 10.81 (s, 1H).

Example 145

(S)-2-[4-(2-Fluoro-3-vinyl-phenoxy)-2-oxo-2,5-dihydro-pyrrol-1-yl]-4-methyl-pentanoic acid [1-((R)-2,3-dihydroxy-propyl)-1H-pyrazol-3-yl]-amide

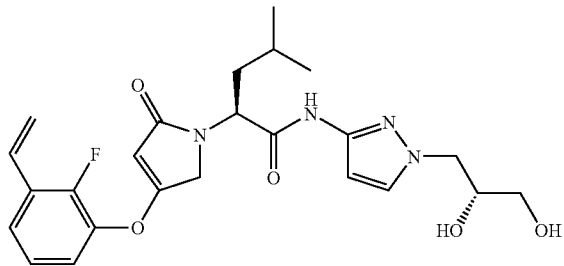

A solution of (S)-2-[4-(2-fluoro-3-vinyl-phenoxy)-2-oxo-2,5-dihydro-pyrrol-1-yl]-4-methyl-pentanoic acid [1-((R)-2,2-dimethyl-[1,3]dioxolan-4-yl-methyl)-1H-pyrazol-3-yl]-amide (prepared as in Example 144, 0.200 g, 0.39 mmol) in tetrahydrofuran (10 mL) was treated with 2N aqueous hydrochloric acid (5 mL). The reaction mixture was stirred for 2 h at room temperature. The reaction mixture was diluted with ethyl acetate, washed with water, saturated sodium bicarbonate, a saturated sodium chloride solution and dried over magnesium sulfate. Upon concentration afforded, (S)-2-[4-(2-fluoro-3-vinyl-phenoxy)-2-oxo-2,5-dihydro-pyrrol-1-yl]-4-methyl-pentanoic acid [1-((R)-2,3-dihydroxy-propyl)-1H-pyrazol-3-yl]-amide (0.100 g, 54%) as a white solid: HR-ES-MS m/z calculated for $C_{24}H_{29}FN_4O_5$, [M+H]$^+$ 473.2195 observed 473.2196; $^1$H NMR (300 MHz, DMSO-d$_6$) δ ppm 0.88 (d, J=6.3 Hz, 3H), 0.92 (d, J=6.3 Hz, 3H), 1.36-1.49 (m, 1H), 1.49-1.66 (m, 1H), 1.66-1.82 (m, 1H), 3.17-3.31 (m, 2H), 3.63-3.79 (m, 1H), 3.85 (dd, J=13.4, 7.5 Hz, 1H), 4.07 (dd, J=13.4, 3.9 Hz, 1H), 4.21 (d, J=18.4 Hz, 1H), 4.59 (d, J=18.4 Hz, 1H), 4.70 (t, J=5.1 Hz, 1H), 4.78-4.96 (m, 2H), 4.89 (s, 1H), 5.50 (d, J=11.4 Hz, 1H), 5.98 (d, J=17.6 Hz, 1H), 6.39 (d, J=2.1 Hz, 1H), 6.84 (dd, J=17.6, 11.4 Hz, 1H), 7.25 (t, J=7.8 Hz, 1H), 7.34-7.47 (m, 1H), 7.52 (d, J=2.1 Hz, 1H), 7.59 (t, J=6.8 Hz, 1H), 10.76 (s, 1H).

Example 146

(S)-2-[4-(3-Cyclopropyl-2-fluoro-phenoxy)-2-oxo-2,5-dihydro-pyrrol-1-yl]-4-methyl-pentanoic acid [1-((R)-2,2-dimethyl-[1,3]dioxolan-4-yl-methyl)-1H-pyrazol-3-yl]-amide

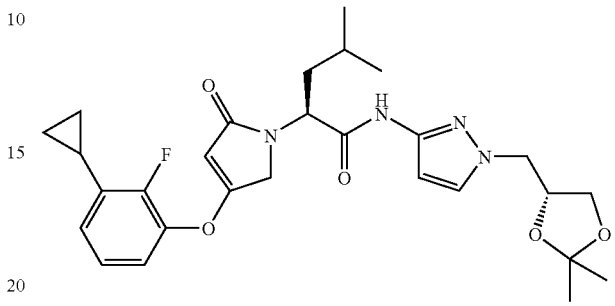

To a mixture of (S)-2-[4-(3-bromo-2-fluoro-phenoxy)-2-oxo-2,5-dihydro-pyrrol-1-yl]-4-methyl-pentanoic acid ethyl ester (prepared as in Example 128, 1.2 g, 2.9 mmol), palladium(II) acetate (0.035 g, 0.15 mmol), tricyclohexylphosphine (0.084 g, 0.30 mmol), and tripotassium phosphate (2.0 g, 9.0 mmol) in toluene (8 mL) was added cyclopropylboronic acid (0.325 g, 3.8 mmol) and water (0.2 mL) and the resulting mixture was sparged with nitrogen and transferred to an Emry Optimizer microwave reaction vessel and heated at 130° C., for 2.5 h. The mixture was taken up in ethyl acetate and dilute hydrochloric acid and separated. The organic phase was washed with a saturated sodium bicarbonate solution, a saturated sodium chloride solution and dried over sodium sulfate. The mixture was filtered and evaporated and the residue purified by ISCO flash chromatography (Teledyne Isco RediSep Flash Column 80 g, 0% to 50% ethyl acetate/hexanes) which afforded (S)-2-[4-(3-cyclopropyl-2-fluoro-phenoxy)-2-oxo-2,5-dihydro-pyrrol-1-yl]-4-methyl-pentanoic acid ethyl ester (0.80 g, 74%) as a pale yellow solid.

To a solution containing (S)-2-[4-(3-cyclopropyl-2-fluoro-phenoxy)-2-oxo-2,5-dihydro-pyrrol-1-yl]-4-methyl-pentanoic acid ethyl ester (0.800 g, 0.002 mol) in tetrahydrofuran (30 mL) was treated with an aqueous solution of lithium hydroxide monohydrate (0.5N, 15 mL, 0.008 mol). The mixture was stirred at room temperature for 1 h, and the solvents evaporated. The residue was dissolved in water and washed with diethyl ether, and the diethyl ether layer discarded. The aqueous phase was acidified with dilute hydrochloric acid (pH <2), and extracted with ethyl acetate. The combined organic layers were dried over sodium sulfate and concentrated to afford (S)-2-[4-(3-cyclopropyl-2-fluoro-phenoxy)-2-oxo-2,5-dihydro-pyrrol-1-yl]-4-methyl-pentanoic acid (0.71 g, 96%) as a yellow solid.

To a solution of (S)-2-[4-(3-cyclopropyl-2-fluoro-phenoxy)-2-oxo-2,5-dihydro-pyrrol-1-yl]-4-methyl-pentanoic acid (0.200 g, 0.58 mmol) in N,N-dimethylformamide (10 mL) was added 1-((R)-2,2-dimethyl-[1,3]dioxolan-4-yl-methyl)-1H-pyrazol-3-ylamine (prepared as in Example 49, 0.136 g, 0.69 mmol) and benzotriazol-1-yl-oxy-tris(dimethylamino)phosphonium hexafluorophosphate (0.530 g, 1.20 mmol). The mixture was stirred at 0° C. and triethylamine (0.122 g, 1.21 mmol) was added. The mixture was stirred at room temperature for 5 h and the solvents were evaporated. The residue was treated with ethyl acetate and ammonium chloride solution, and the organic layer separated. The organic layer was washed with brine and dried over sodium sulfate. The solvents were evaporated and the residue was purified by ISCO flash chromatography (Teledyne Isco RediSep Flash Column 25 g, 10% to 70% ethyl acetate/ hexanes) which afforded (S)-2-[4-(3-cyclopropyl-2-fluoro-phenoxy)-2-oxo-2,5-dihydro-pyrrol-1-yl]-4-methyl-pentanoic acid [1-((R)-2,2-dimethyl-[1,3]dioxolan-4-yl-methyl)-1H-pyrazol-3-yl](0.250 g, 82%) as a white solid: HR-ES-MS m/z calculated for $C_{28}H_{35}FN_4O_5$ [M+H]$^+$ 527.2664, observed 527.2665, $^1$H NMR (300 MHz, DMSO-d$_6$) δ ppm 1.00 0.67-0.83 (m, 2H), 0.90 (d, J=6.3 Hz, 3H), 0.93 (d, J=6.3 Hz, 3H), 0.97-1.08 (m, 2H), 1.24 (s, 3H), 1.30 (s, 3H), 1.43 (d, J=8.5 Hz, 1H), 1.51-1.64 (m, 1H), 1.68-1.85 (m, 1H), 1.99-2.15 (m, 1H), 3.73 (dd, J=8.0, 6.2 Hz, 1H), 4.00 (t, J=7.4 Hz, 1H), 4.03-4.16 (m, 2H), 4.21 (d, J=18.4 Hz, 1H), 4.28-4.41 (m, 1H), 4.59 (d, J=18.4 Hz, 1H), 4.86 (s, 1H), 4.86-4.94 (m, 1H), 6.44 (s, 1H), 6.94 (t, J=7.8 Hz, 1H), 7.15 (t, J=7.8 Hz, 1H), 7.25 (t, J=7.8 Hz, 1H), 7.60 (s, 1H), 10.80 (s, 1H).

Example 147

(S)-2-[4-(3-Cyclopropyl-2-fluoro-phenoxy)-2-oxo-2,5-dihydro-pyrrol-1-yl]-4-methyl-pentanoic acid [1-((R)-2,3-dihydroxy-propyl)-1H-pyrazol-3-yl]-amide

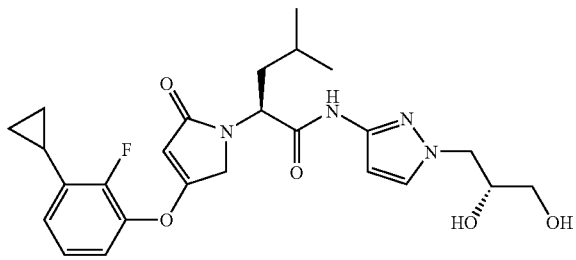

A solution of (S)-2-[4-(3-cyclopropyl-2-fluoro-phenoxy)-2-oxo-2,5-dihydro-pyrrol-1-yl]-4-methyl-pentanoic acid [1-((R)-2,2-dimethyl-[1,3]dioxolan-4-yl-methyl)-1H-pyrazol-3-yl]-amide (prepared in Example 146, 0.225 g, 0.43 mmol) in tetrahydrofuran (25 mL) was treated with 2N aqueous hydrochloric acid (12 mL). The reaction mixture was stirred for 2.5 h at room temperature. The reaction mixture was diluted with ethyl acetate, washed with water, saturated sodium bicarbonate, a saturated sodium chloride solution and dried over magnesium sulfate. Upon concentration afforded, (S)-2-[4-(3-cyclopropyl-2-fluoro-phenoxy)-2-oxo-2,5-dihydro-pyrrol-1-yl]-4-methyl-pentanoic acid [1-((R)-2,3-dihydroxy-propyl)-1H-pyrazol-3-yl]-amide (0.130 g, 63%) as an off-white powder: HR-ES-MS m/z calculated for $C_{25}H_{31}FN_4O_5$, [M+H]$^+$ 487.2351 observed 487.2352; $^1$H NMR (300 MHz, DMSO-d$_6$) δ ppm 0.72-0.81 (m, 2H), 0.90 (d, J=6.3 Hz, 3H), 0.94 (d, J=6.3 Hz, 3H), 0.97-1.06 (m, 2H), 1.37-1.51 (m, 1H), 1.52-1.65 (m, 1H), 1.66-1.84 (m, 1H), 2.01-2.15 (m, 1H), 3.24-3.33 (m, 2H), 3.69-3.81 (m, 1H), 3.86 (dd, J=13.4, 7.5 Hz, 1H), 4.09 (dd, J=13.4, 3.6 Hz, 1H), 4.21 (d, J=18.4 Hz, 1H), 4.60 (d, J=18.4 Hz, 1H), 4.72 (br. s., 1H), 4.86 (s, 1H), 4.87-4.93 (m, 1H), 4.95 (br. s., 1H), 6.41 (d, J=2.0 Hz, 1H), 6.89-6.98 (m, 1H), 7.15 (t, J=8.0 Hz, 1H), 7.20-7.31 (m, 1H), 7.53 (d, J=2.0 Hz, 1H), 10.77 (s, 1H).

Example 148

(3-{(S)-2-[4-(3-Cyclopropyl-2-fluoro-phenoxy)-2-oxo-2,5-dihydro-pyrrol-1-yl]-4-methyl-pentanoylamino}-pyrazol-1-yl)-acetic acid ethyl ester

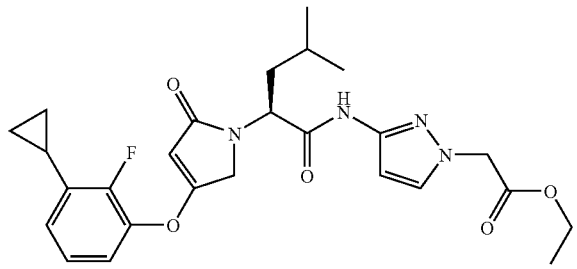

To a solution of (S)-2-[4-(3-cyclopropyl-2-fluoro-phenoxy)-2-oxo-2,5-dihydro-pyrrol-1-yl]-4-methyl-pentanoic acid (prepared as in Example 146, 0.305 g, 0.88 mmol) in N,N-dimethylformamide (10 mL) was added (3-amino-pyrazol-1-yl)-acetic acid ethyl ester (0.180 g, 1.06 mmol) and benzotriazol-1-yl-oxy-tris(dimethylamino)phosphonium hexafluorophosphate (0.778 g, 1.76 mmol). The mixture was stirred at 0° C. and triethylamine (0.183 g, 1.81 mmol) was added. The mixture was stirred at room temperature for 3 h and the solvents were evaporated. The residue was treated with ethyl acetate and ammonium chloride solution, and the organic layer separated. The organic layer was washed with brine and dried over sodium sulfate. The solvents were evaporated and the residue was purified by ISCO flash chromatography (Teledyne Isco RediSep Flash Column 40 g, 0% to 70% ethyl acetate/hexanes) which afforded (3-{(S)-2-[4-(3-cyclopropyl-2-fluoro-phenoxy)-2-oxo-2,5-dihydro-pyrrol-1-yl]-4-pentanoylamino}-pyrazol-1-yl)-acetic acid ethyl ester (0.090 g, 21%) as an off-white solid: HR-ES-MS m/z calculated for $C_{26}H_{31}FN_4O_5$ [M+H]$^+$ 499.2351, observed 499.2352, $^1$H NMR (300 MHz, DMSO-d$_6$) δ ppm 1.00 0.72-0.82 (m, 2H), 0.90 (d, J=6.3 Hz, 3H), 0.94 (d, J=6.3 Hz, 3H), 0.97-1.06 (m, 2H), 1.20 (t, J=7.0 Hz, 3H), 1.34-1.67 (m, 2H), 1.67-1.85 (m, 1H), 2.00-2.18 (m, 1H), 4.14 (q, J=7.0 Hz, 2H), 4.22 (d, J=18.4 Hz, 1H), 4.59 (d, J=18.4 Hz, 1H), 4.86 (s, 1H), 4.86-4.91 (m, 1H), 4.95 (s, 2H), 6.48 (d, J=2.2 Hz, 1H), 6.94 (t, J=7.1 Hz, 1H), 7.16 (t, J=8.2 Hz, 1H), 7.21-7.33 (m, 1H), 7.63 (d, J=2.2 Hz, 1H), 10.82 (s, 1H).

Example 149

(3-{(S)-2-[4-(3-Cyclopropyl-2-fluoro-phenoxy)-2-oxo-2,5-dihydro-pyrrol-1-yl]-4-methyl-pentanoylamino}-pyrazol-1-yl)-acetic acid

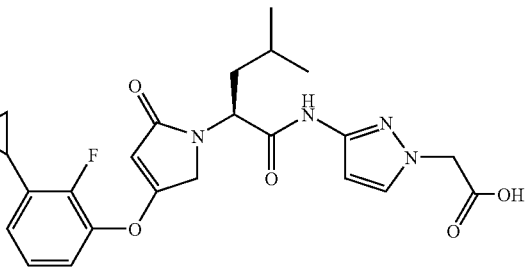

To a solution of (3-{(S)-2-[4-(3-cyclopropyl-2-fluoro-phenoxy)-2-oxo-2,5-dihydro-pyrrol-1-yl]-4-methyl-pentanoylamino}-pyrazol-1-yl)-acetic acid ethyl ester (prepared as in Example 148, 0.130 g, 0.26 mmol) in tetrahydrofuran (5 mL) was added an aqueous lithium hydroxide solution (0.5N, 2 mL). The resulting mixture was stirred at room temperature for 3 h. The solvents were evaporated and the residue neutralized with 1N aqueous hydrochloric acid, extracted with ethyl acetate. The combined organic layers were washed with water, saturated sodium chloride solution and dried over sodium sulfate. The mixture was filtered and evaporated which afforded (3-{(S)-2-[4-(3-cyclopropyl-2-fluoro-phenoxy)-2-oxo-2,5-dihydro-pyrrol-1-yl]-4-methyl-pentanoylamino}-pyrazol-1-yl)-acetic acid (0.118 g, 96%) as a white solid: HR-ES-MS m/z calculated for $C_{24}H_{27}FN_4O_5$ [M+H]$^+$ 471.2038 observed 471.2036; $^1$H NMR (300 MHz, DMSO-d$_6$) δ ppm 0.72-0.81 (m, 2H), 0.90 (d, J=6.3 Hz, 3H), 0.93 (d, J=6.3 Hz, 3H), 0.97-1.06 (m, 2H), 1.37-1.51 (m, 1H), 1.52-1.65 (m, 1H), 1.65-1.82 (m, 1H), 2.00-2.15 (m, 1H), 4.21 (d, J=18.4 Hz, 1H), 4.59 (d, J=18.4 Hz, 1H), 4.62 (s, 2H), 4.86 (s, 1H), 4.85-4.93 (m, 1H), 6.42 (d, J=2.0 Hz, 1H), 6.94 (t, J=6.9 Hz, 1H), 7.15 (t, J=7.8 Hz, 1H), 7.21-7.31 (m, 1H), 7.54 (d, J=2.0 Hz, 1H), 10.75 (s, 1H).

Example 150

(S)-2-[4-(3-Ethoxy-2-fluoro-phenoxy)-2-oxo-2,5-dihydro-pyrrol-1-yl]-4-methyl-pentanoic acid [5-((S)-2,2-dimethyl-[1,3]dioxolan-4-yl)-pyrazin-2-yl]-amde

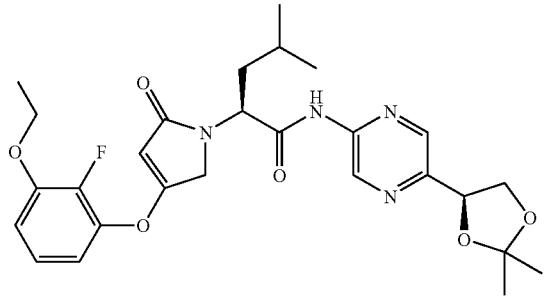

A solution of (S)-2-[4-(3-ethoxy-2-fluoro-phenoxy)-2-oxo-2,5-dihydro-pyrrol-1-yl]-4-methyl-pentanoic acid (prepared as in Example 114, 0.351 g, 1.00 mmol) in dichloromethane (5 mL) was treated with a 2M oxalyl chloride solution in dichloromethane (0.6 mL, 1.20 mmol), and N,N-dimethylformamide (1 drop). Effervescence was observed. The reaction mixture was stirred for 30 min at 25° C., under nitrogen. The reaction mixture was concentrated, and dissolved in dichloromethane (4 mL) and treated with 5-((S)-2,2-dimethyl-[1,3]dioxolan-4-yl)-pyrazin-2-ylamine (prepared in PCT Int. Appl. WO2004052869, Example 54 method B 0.195 g, 1.00 mmol) in dichloromethane (5 mL) and pyridine (162 μL). The reaction mixture was stirred at 25° C., under nitrogen for 4 h. The reaction mixture was diluted with dichloromethane, washed with 2N aqueous hydrochloric acid, brine and dried. The organic layer was concentrated, and the crude product was purified by ISCO flash chromatography (Teledyne Isco RediSep Flash Column 40 g; 10% to 70% ethyl acetate/hexanes) to afford, (S)-2-[4-(3-ethoxy-2-fluoro-phenoxy)-2-oxo-2,5-dihydro-pyrrol-1-yl]-4-methyl-pentanoic acid [5-((S)-2,2-dimethyl-[1,3]dioxolan-4-yl)-pyrazin-2-yl]-amide (0.335 g, 63%) as a fluffy white solid: HRMS m/z calculated for $C_{27}H_{33}FN_4O_6$ [M+H]$^+$ 529.2457, observed 529.2457; $^1$H NMR (DMSO-d$_6$, 300 MHz) δ 0.92 (d, J=6.9 Hz, 3H), 0.95 (d, J=6.9 Hz, 3H), 1.36 (t, J=6.9 Hz, 3H), 1.41 (s, 3H), 1.42-1.54 (m, 1H), 1.44 (s, 3H), 1.56-1.72 (m, 1H), 1.73-1.91 (m, 1H), 3.94 (dd, J=8.2, 6.6 Hz, 1H), 4.15 (q, J=6.9 Hz, 2H), 4.26 (d, J=18.4 Hz, 1H), 4.36 (dd, J=8.2, 6.8 Hz, 1H), 4.59 (d, J=18.4 Hz, 1H), 4.92 (s, 1H), 5.04 (dd, J=11.0, 4.4 Hz, 1H), 5.17 (t, J=6.8 Hz, 1H), 6.96-7.07 (m, 1H), 7.09-7.24 (m, 2H), 8.48 (s, 1H), 9.22 (s, 1H), 11.25 (s, 1H) ppm.

Example 151

(S)-2-[4-(3-Ethoxy-2-fluoro-phenoxy)-2-oxo-2,5-dihydro-pyrrol-1-yl]-4-methyl-pentanoic acid [5-((S)-1,2-dihydroxy-ethyl)-pyrazin-2-yl]-amide

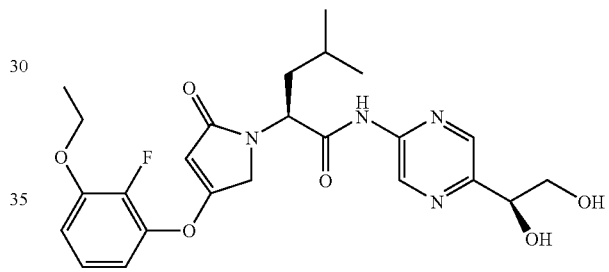

A solution of (S)-2-[4-(3-ethoxy-2-fluoro-phenoxy)-2-oxo-2,5-dihydro-pyrrol-1-yl]-4-methyl-pentanoic acid [5-((S)-2,2-dimethyl-[1,3]dioxolan-4-yl)-pyrazin-2-yl]-amide (prepared in Example 150, 0.300 g, 0.57 mmol) in tetrahydrofuran (20 mL) was treated with 1N aqueous hydrochloric acid (10 mL). The reaction mixture was stirred for 20 h at room temperature. The reaction mixture was diluted with ethyl acetate, washed with saturated sodium bicarbonate, a saturated sodium chloride solution and dried over magnesium sulfate. The solvents were evaporated and the residue was purified by ISCO flash chromatography (Teledyne Isco RediSep Flash Column 40 g; 10% to 100% (9:1 dichloromethane:methanol)/hexanes) to afford (S)-2-[4-(3-ethoxy-2-fluoro-phenoxy)-2-oxo-2,5-dihydro-pyrrol-1-yl]-4-methyl-pentanoic acid [5-((S)-1,2-dihydroxy-ethyl)-pyrazin-2-yl]-amide (0.188 g, 68%) as a fluffy white solid: HR-ES-MS m/z calculated for $C_{24}H_{29}FN_4O_6$, [M+H]$^+$ 489.2144 observed 489.2143; $^1$H NMR (300 MHz, DMSO-d$_6$) δ ppm 0.92 (d, J=6.9 Hz, 3H), 0.95 (d, J=6.9 Hz, 3H), 1.36 (t, J=6.9 Hz, 3H), 1.42-1.57 (m, 1H), 1.57-1.73 (m, 1H), 1.74-1.90 (m, 1H), 3.47-3.61 (m, 1H), 3.68 (dt, J=10.8, 5.3 Hz, 1H), 4.15 (q, J=6.9 Hz, 2H), 4.26 (d, J=18.4 Hz, 1H), 4.53-4.68 (m, 2H), 4.73 (t, J=5.7 Hz, 1H), 4.92 (s, 1H), 5.03 (dd, J=10.6, 4.2 Hz, 1H), 5.55 (d, J=4.8 Hz, 1H), 6.98-7.08 (m, 1H), 7.08-7.25 (m, 2H), 8.45 (s, 1H), 9.17 (s, 1H), 11.15 (s, 1H).

Example 152

(S)-2-[4-(3-Ethoxy-2,6-difluoro-phenoxy)-2-oxo-2,5-dihydro-pyrrol-1-yl]-4-methyl-pentanoic acid [5-((S)-2,2-dimethyl-[1,3]dioxolan-4-yl)-pyrazin-2-yl]-amide

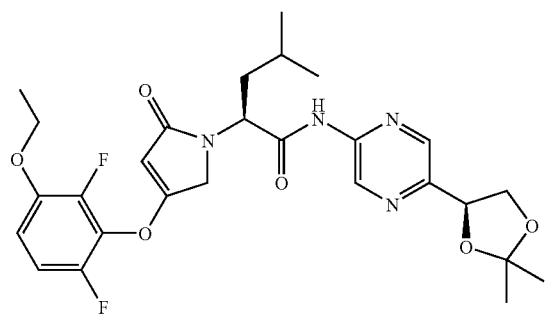

A solution of (S)-2-[4-(3-ethoxy-2,6-difluoro-phenoxy)-2-oxo-2,5-dihydro-pyrrol-1-yl]-4-methyl-pentanoic acid (prepared as in Example 116, 0.369 g, 1.00 mmol) in dichloromethane (5 mL) was treated with a 2M oxalyl chloride solution in dichloromethane (0.5 mL, 1.00 mmol), and N,N-dimethylformamide (1 drop). Effervescence was observed. The reaction mixture was stirred for 30 min at 25° C., under nitrogen. The reaction mixture was concentrated, dried under vacuum and the residue dissolved in dichloromethane (4 mL) and treated with 5-((S)-2,2-dimethyl-[1,3]dioxolan-4-yl)-pyrazin-2-ylamine (prepared in PCT Int. Appl. WO2004052869, Example 54 method B 0.195 g, 1.00 mmol) in dichloromethane and pyridine (162 µL). The reaction mixture was stirred at 25° C., under nitrogen for 3 h. The reaction mixture was diluted with dichloromethane, washed with 2N aqueous hydrochloric acid, brine and dried. The organic layer was concentrated, and the crude product was purified by ISCO flash chromatography (Teledyne Isco RediSep Flash Column 40 g; 10% to 70% ethyl acetate/hexanes) to afford, (S)-2-[4-(3-ethoxy-2,6-difluoro-phenoxy)-2-oxo-2,5-dihydro-pyrrol-1-yl]-4-methyl-pentanoic acid [5-((S)-2,2-dimethyl-[1,3]dioxolan-4-yl)-pyrazin-2-yl]-amide (0.277 g, 51%) as a fluffy white solid: HRMS m/z calculated for $C_{27}H_{32}F_2N_4O_6$ [M+H]+ 547.2363, observed 547.2366; 1H NMR (DMSO-$d_6$, 300 MHz) δ 0.92 (d, J=6.9 Hz, 3H), 0.94 (d, J=6.9 Hz, 3H), 1.35 (t, J=6.8 Hz, 3H), 1.40 (s, 3H), 1.39-1.53 (m, 1H), 1.44 (s, 3H), 1.56-1.73 (m, 1H), 1.75-1.92 (m, 1H), 3.94 (t, J=7.4 Hz, 1H), 4.13 (q, J=6.8 Hz, 2H), 4.26-4.41 (m, 2H), 4.63 (d, J=18.7 Hz, 1H), 5.03 (dd, J=10.7, 4.4 Hz, 1H), 5.08 (s, 1H), 5.17 (t, J=6.6 Hz, 1H), 7.04-7.23 (m, 1H), 7.23-7.36 (m, 1H), 8.48 (s, 1H), 9.21 (s, 1H), 11.27 (s, 1H) ppm.

Example 153

(S)-2-[4-(3-Ethoxy-2,6-difluoro-phenoxy)-2-oxo-2,5-dihydro-pyrrol-1-yl]-4-methyl-pentanoic acid [5-((S)-1,2-dihydroxy-ethyl)-pyrazin-2-yl]-amide

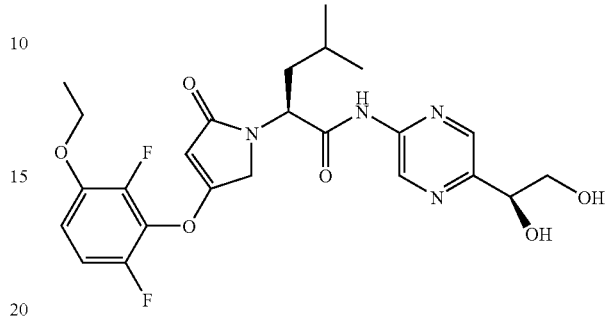

A solution of (S)-2-[4-(3-ethoxy-2,6-difluoro-phenoxy)-2-oxo-2,5-dihydro-pyrrol-1-yl]-4-methyl-pentanoic acid [5-((S)-2,2-dimethyl-[1,3]dioxolan-4-yl)-pyrazin-2-yl]-amide (prepared in Example 152, 0.251 g, 0.46 mmol) in tetrahydrofuran (25 mL) was treated with 1N aqueous hydrochloric acid (10 mL). The reaction mixture was stirred for 20 h at room temperature. The reaction mixture was diluted with ethyl acetate, washed with saturated sodium bicarbonate, a saturated sodium chloride solution and dried over magnesium sulfate. The mixture was filtered and evaporated and the residue purified by ISCO flash chromatography (Teledyne Isco RediSep Flash Column 12 g; 10% to 100% (9:1 dichloromethane:methanol)/hexanes) to afford (S)-2-[4-(3-ethoxy-2,6-difluoro-phenoxy)-2-oxo-2,5-dihydro-pyrrol-1-yl]-4-methyl-pentanoic acid [5-((S)-1,2-dihydroxy-ethyl)-pyrazin-2-yl]-amide (0.210 g, 90%) as a fluffy white solid: HR-ES-MS m/z calculated for $C_{24}H_{28}F_2N_4O_6$, [M+H]+ 507.2050 observed 507.2051; 1H NMR (300 MHz, DMSO-$d_6$) δ ppm 0.92 (d, J=6.9 Hz, 3H), 0.95 (d, J=6.9 Hz, 3H), 1.35 (t, J=6.9 Hz, 3H), 1.40-1.56 (m, 1H), 1.56-1.73 (m, 1H), 1.75-1.93 (m, 1H), 3.42-3.62 (m, 1H), 3.61-3.74 (m, 1H), 4.13 (q, J=6.9 Hz, 2H), 4.31 (d, J=18.7 Hz, 1H), 4.51-4.69 (m, 2H), 4.73 (t, J=5.7 Hz, 1H). 5.02 (dd, J=10.6, 4.2 Hz, 1H), 5.08 (s, 1H), 5.55 (d, J=5.1 Hz, 1H), 7.12-7.23 (m, 1H), 7.23-7.33 (m, 1H), 8.45 (s, 1H), 9.17 (s, 1H), 11.16 (s, 1H).

Example 154

(S)-2-[4-(2-Fluoro-3-vinyl-phenoxy)-2-oxo-2,5-dihydro-pyrrol-1-yl]-4-methyl-pentanoic acid pyrazin-2-ylamide

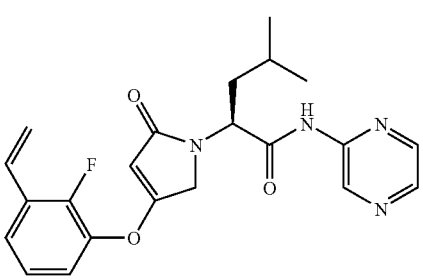

A solution of (S)-2-[4-(2-fluoro-3-vinyl-phenoxy)-2-oxo-2,5-dihydro-pyrrol-1-yl]-4-methyl-pentanoic acid (prepared as in Example 144, 0.350 g, 1.05 mmol) in dichloromethane (8 mL) was treated with a 2M oxalyl chloride solution in dichloromethane (0.5 mL, 1.00 mmol), and N,N-dimethyl-formamide (I drop). Effervescence was observed. The reaction mixture was stirred for 30 min at 25° C., under nitrogen. The reaction mixture was concentrated and dried under vacuum. The residue was dissolved in dichloromethane (8 mL) and treated with a solution of pyrazin-2-ylamine (0.110 g, 1.16 mmol) dissolved in a mixture of tetrahydrofuran (1 mL) dichloromehtane (2 mL) and pyridine (169 μL). The reaction mixture was stirred at 25° C., under nitrogen for 18 h. The reaction mixture was diluted with dichloromethane, washed with 2N aqueous hydrochloric acid, brine and dried. The organic layer was concentrated, and the crude product was purified by ISCO flash chromatography (Teledyne Isco RediSep Flash Column 12 g; 10% to 50% ethyl acetate/hexanes) to afford, (S)-2-[4-(2-fluoro-3-vinyl-phenoxy)-2-oxo-2,5-dihydro-pyrrol-1-yl]-4-methyl-pentanoic acid pyrazin-2-ylamide (0.085 g, 20%) as an off-white solid: HRMS m/z calculated for $C_{22}H_{23}FN_4O_3$ $[M+H]^+$ 411.1827, observed 411.1828; $^1H$ NMR (DMSO-$d_6$, 300 MHz) δ 0.93 (d, J=7.5 Hz, 3H), 0.95 (d, J=7.5 Hz, 3H), 1.38-1.56 (m, 1H), 1.56-1.73 (m, 1H), 1.73-1.94 (m, 1H), 4.27 (d, J=18.4 Hz, 1H), 4.62 (d, J=18.4 Hz, 1H), 4.94 (s, 1H), 5.05 (dd, J=10.9, 4.5 Hz,1H), 5.52 (d, J=11.4 Hz, 1H), 6.00 (d, J=17.7 Hz, 1H), 6.86 (dd, J=17.7, 11.4 Hz, 1H), 7.21-7.32 (m, 1H), 7.31-7.49 (m, 1H), 7.61 (t, J=6.8 Hz, 1H), 8.38 (d, J=2.4 Hz, 1H), 8.40-8.45 (m, 1H), 9.28 (s, 1H), 11.20 (s, 1H) ppm.

Example 155

(S)-2-{4-[3-(1,2-Dihydroxy-ethyl)-2-fluoro-phenoxy]-2-oxo-2,5-dihydro-pyrrol-1-yl}-4-methyl-pentanoic acid pyrazin-2-ylamide

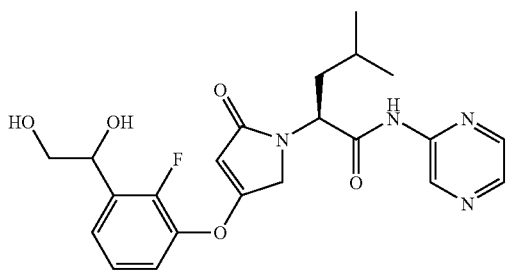

To a solution of (S)-2-[4-(2-fluoro-3-vinyl-phenoxy)-2-oxo-2,5-dihydro-pyrrol-1-yl]-4-methyl-pentanoic acid pyrazin-2-ylamide (prepared as in Example 154, 0.076 g, 0.19 mmol) in tetrahydrofuran (5 mL) was added 4-methyl-morpholine N-oxide (0.044 g, 0.38 mmol) and an osmium tetroxide solution (0.25 mL, 2.5 wt.% in t-butanol). The resulting solution was stirred at room temperature for 4 h. The reaction mixture was diluted with ethyl acetate (100 mL) and the organic phase was washed with 1N aqueous hydrochloric acid (100 mL), a saturated sodium chloride solution and dried over anhydrous sodium sulfate. The mixture was filtered and evaporated and the residue was triturated with diethyl ether which afforded (S)-2-{4-[3-(1,2-dihydroxy-ethyl)-2-fluoro-phenoxy]-2-oxo-2,5-dihydro-pyrrol-1-yl}-4-methyl-pentanoic acid pyrazin-2-ylamide (0.040 g, 49%) as a tan solid: HRMS m/z calculated for $C_{22}H_{25}FN_4O_5$ $[M+H]^+$ 445.1882, observed 445.1880; $^1H$ NMR (300 MHz, DMSO-$d_6$) d ppm 0.92 (t, J=7.1 Hz, 6H), 1.48 (br. s., 1H), 1.54-1.71 (m, 1H), 1.73-1.94 (m, 1H), 3.38-3.57 (m, 3H), 4.24 (dd, J=18.4, 4.2 Hz, 1H), 4.59 (d, J=18.7 Hz, 1H), 4.79-4.90 (m, 2H), 4.95-5.09 (m, 1H), 5.51 (br. s., 1H), 7.17-7.30 (m, 1H), 7.30-7.46 (m, 2H), 8.37 (s, 1H), 8.41 (br. s., 1H), 9.26 (s, 1H), 11.18 (br. s., 1H).

Example 156

(S)-2-[4-(3-Cyclopropyl-2-fluoro-phenoxy)-2-oxo-2,5-dihydro-pyrrol-1-yl]-4-methyl-pentanoic acid (1-carbamoylmethyl-1H-pyrazol-3-yl)-aide

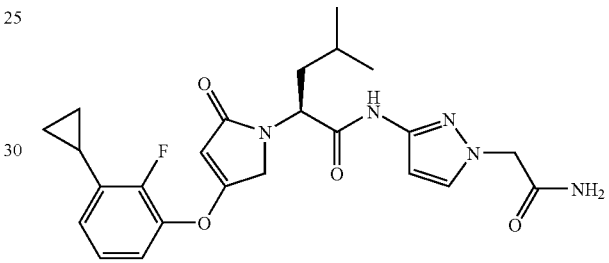

To a solution of (3-{(S)-2-[4-(3-cyclopropyl-2-fluoro-phenoxy)-2-oxo-2,5-dihydro-pyrrol-1-yl]-4-methyl-pentanoylamino}-pyrazol-1-yl)-acetic acid (prepared as in Example 149, 0.100 g, 0.21 mmol) in dichloromethane (5 mL) was treated with a 2M oxalyl chloride solution in dichloromethane (0.13 mL, 0.26 mmol), and N,N-dimethylformamide (1 drop). The reaction mixture was stirred for 30 min at 25° C., under nitrogen. The reaction mixture was concentrated, dried under vacuum and the residue dissolved in dichloromethane (4 mL) and treated with ammonium hydroxide (4 mL) and the resulting reaction mixture was stirred at 25° C., under nitrogen for 30 min. The solvents were removed and the residue was purified by Gilson reverse phase HPLC ($C_{18}$, 5% to 95% acetonitrile/water). The isolated pure fraction was taken up in ethyl acetate (25 mL), washed with saturated sodium bicarbonate solution dried and evaporated which afforded (S)-2-[4-(3-cyclopropyl-2-fluoro-phenoxy)-2-oxo-2,5-dihydro-pyrrol-1-yl]-4-methyl-pentanoic acid (1-carbamoylmethyl-1H-pyrazol-3-yl)-amide (0.025 g, 25%) as a yellow solid: $^1H$ NMR (300 MHz, DMSO-$d_6$) δ ppm 0.72-0.81 (m, 2H), 0.90 (d, J=6.6 Hz, 3H), 0.94 (d, J=6.6 Hz, 3H), 0.97-1.05 (m, 2H), 1.38-1.67 (m, 2H), 1.67-1.84 (m, 1H), 1.99-2.16 (m, 1H), 4.22 (d, J=18.4 Hz, 1H), 4.59 (d, J=18.4 Hz, 1H), 4.63 (s, 2H), 4.83-4.91 (m, 1H), 4.86 (s, 1H), 6.44 (d, J=2.1 Hz, 1H), 6.94 (t, J=6.8 Hz, 1H), 7.10-7.20 (m, 1H), 7.21-7.29 (m, 2H), 7.42 (br. s., 1H), 7.58 (d, J=2.1 Hz, 1H), 10.78 (s, 1H).

Example 157

(S)-2-[4-(2,6-Difluoro-phenoxy)-2-oxo-2,5-dihydro-pyrrol-1-yl]-pentanoic acid [1-((R)-2,3-dihydroxy-propyl)-1H-pyrazol-3-yl]-amide

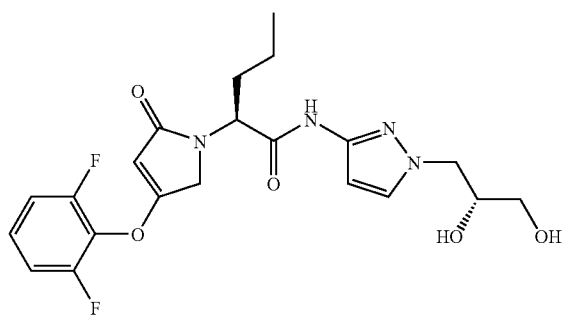

Dry hydrochloric acid gas was bubbled through a mixture of (S)-2-amino-pentanoic acid (1.00 g, 8.53 mmol) in methanol cooled to 0° C. for 5 min. The vessel was sealed and the mixture heated to 50° C. overnight. The mixture was cooled, the solvent removed and the residue treated with methanol (repeated 3×). The residue was triturated with diethyl ether, dried under high vacuum to yield (S)-2-amino-pentanoic acid methyl ester hydrochloride (1.21 g, 85%) as a light yellow solid: $^1$H NMR (300 MHz, DMSO-$d_6$) δ ppm 0.87 (t, J=6.9 Hz, 3H), 1.12-1.51 (m, 2H), 1.76 (m, J=6.0 Hz, 2H), 3.74 (s, 3H), 3.98 (t, J=6.0 Hz, 1H), 8.59 (br. s., 3H).

To a stirred mixture of (S)-2-amino-pentanoic acid methyl ester hydrochloride (0.170 g, 1.30 mmol) dissolved in acetonitrile (4 mL) under nitrogen atmosphere was added N,N-diisopropylethylamine (0.134 g, 1.03 mmol). After addition was complete the mixture was stirred at 60° C. for 1 h. The reaction was cooled to 25° C. and treated with a second equivalent of N,N-diisopropylethylamine (0.134 g, 1.03 mmol) and heated to 85° C. at which time, 4-bromo-3-(2,6-difluoro-phenoxy)-but-2-enoic acid methyl ester (prepared as in Example 36, 0.300 g, 0.98 mmol) in acetonitrile (6 mL) was added slowly. After the addition was complete the reaction mixture was heated to reflux overnight. The reaction mixture was cooled to 25° C. and concentrated. The residue was dissolved in dichloromethane washed with 1N aqueous hydrochloric acid, saturated sodium bicarbonate solution, saturated sodium chloride solution and dried over sodium sulfate. The mixture was filtered and evaporated and the crude product obtained was purified by AnaLogix flash chromatography (Supelco Flash Column 23 g, 30% to 50% ethyl acetate/hexanes) to afford, (S)-2-[4-(2,6-difluoro-phenoxy)-2-oxo-2,5-dihydro-pyrrol-1-yl]-pentanoic acid methyl ester (0.088 g, 28%) as a light brown oil: $^1$H NMR (300 MHz, DMSO-$d_6$) δ ppm 0.89 (t, J=7.2 Hz, 3H), 1.08-1.44 (m, 2H), 1.71-1.89 (m, 2H), 3.66 (s, 3H), 4.28 (s, 2H), 4.65 (dd, J=8.6, 7.1 Hz, 1H), 5.06 (s, 1H), 7.03-7.66 (m, 3H).

To a solution of (S)-2-[4-(2,6-difluoro-phenoxy)-2-oxo-2,5-dihydro-pyrrol-1-yl]-pentanoic acid methyl ester (0.108 g, 0.33 mol) in tetrahydrofuran:water (1:1, 8 mL) was added lithium hydroxide monohydrate (0.042 g 1.00 mmol). The mixture was stirred at room temperature for 2 h. The reaction mixture was poured into water and washed with diethyl ether and the diethyl ether layer discarded. The aqueous phase was acidified with 1N aqueous hydrochloric acid (pH <2), and extracted with ethyl acetate (2×30 mL). The combined ethyl acetate layers were dried over magnesium sulfate, filtered and concentrated to afford (S)-2-[4-(2,6-difluoro-phenoxy)-2-oxo-2,5-dihydro-pyrrol-1-yl]-pentanoic acid, (0.086 g, 87%), as an off-white solid: LR-ES-MS m/z calculated for $C_{15}H_{15}F_2NO_4$ [M+H]$^+$ 312, observed 312.

To a solution of (S)-2-[4-(2,6-difluoro-phenoxy)-2-oxo-2,5-dihydro-pyrrol-1-yl]-pentanoic acid (0.086 g, 0.28 mmol) in dry N,N-dimethylformamide (5 mL) was added 1-((R)-2,2-dimethyl-[1,3]dioxolan-4-yl-methyl)-1H-pyrazol-3-ylamine (prepared as in Example 49, 0.068 g, 0.34 mmol), and benzotriazol-1-yl-oxy-tris(dimethylamino)phosphonium hexafluorophosphate (0.183 g, 0.41 mmol). To this mixture was added N,N-diisopropylethylamine (0.109 g, 0.85 mmol) and the resulting mixture stirred at room temperature overnight. The reaction mixture was diluted with ethyl acetate and washed with an ammonium chloride solution, a saturated sodium bicarbonate solution, saturated sodium chloride solution and then dried over magnesium sulfate. The solvents were evaporated and the residue was purified by AnaLogix flash chromatography (Teledyne Isco RediSep Flash Column 12 g, 100% ethyl acetate) which afforded (S)-2-[4-(2,6-difluoro-phenoxy)-2-oxo-2,5-dihydro-pyrrol-1-yl]-pentanoic acid [1-((R)-2,2-dimethyl-[1,3]dioxolan-4-yl-methyl)-1H-pyrazol-3-yl]-amide (0.102 g, 75%) as a light yellow solid: $^1$H NMR (300 MHz, DMSO-$d_6$) δ ppm 0.91 (t, J=7.2 Hz, 3H), 1.10-1.43 (m, 2H), 1.25 (s, 3H), 1.30 (s, 3H), 1.77 (q, J=7.7 Hz, 2H), 3.73 (dd, J=8.5, 6.0 Hz, 1H), 4.00 (dd, J=8.5, 6.3 Hz, 1H), 4.04-4.20 (m, 2H), 4.24-4.41 (m, 2H), 4.61 (d, J=18.7 Hz, 1H), 4.79 (t, J=7.7 Hz, 1H), 5.03 (s, 1H), 6.44 (d, J=2.1 Hz, 1H), 7.27-7.51 (m, 3H), 7.60 (d, J=2.1 Hz, 1H), 10.75 (s, 1H).

A solution of (S)-2-[4-(2,6-difluoro-phenoxy)-2-oxo-2,5-dihydro-pyrrol-1-yl]-pentanoic acid [1-((R)-2,2-dimethyl-[1,3]dioxolan-4-yl-methyl)-1H-pyrazol-3-yl]-amide (0.102 g, 0.21 mmol) in methanol (5 mL) was treated with p-toluenesulfonic acid (0.008 g, 0.04 mmol). The reaction mixture was stirred at room temperature overnight. The solvents were removed under vacuum and dichloromethane was added to the residue. The resulting mixture was washed with saturated sodium bicarbonate, a saturated sodium chloride solution and dried over magnesium sulfate. The mixture was filtered and evaporated which afforded (S)-2-[4-(2,6-difluoro-phenoxy)-2-oxo-2,5-dihydro-pyrrol-1-yl]-pentanoic acid [1-((R)-2,3-dihydroxy-propyl)-1H-pyrazol-1H-pyrazol-3-yl]-amide (0.068 g, 73%) as a light gray solid: HR-ES-MS m/z calculated for $C_{21}H_{24}F_2N_4O_5$, [M+H]$^+$ 451.1788, observed 451.1781; $^1$H NMR (300 MHz, DMSO-$d_6$) δ ppm 0.91 (t, J=7.2 Hz, 3H), 1.12-1.43 (m, 2H), 1.77 (q, J=7.2 Hz, 2H), 3.23-3.32 (m, 2H), 3.71-3.81 (m, 1H), 3.86 (dd, J=13.5, 7.5 Hz, 1H), 4.09 (dd, J=13.5, 3.9 Hz, 1H), 4.30 (d, J=18.7 Hz, 1H), 4.61 (d, J=18.7 Hz, 1H), 4.71 (t, J=5.5 Hz, 1H), 4.78 (t, J=7.7 Hz, 1H), 4.94 (d, J=5.5 Hz, 1H), 5.03 (s, 1H), 6.41 (d, J=2.1 Hz, 1H), 7.29-7.50 (m, 3H), 7.53 (d, J=2.1 Hz, 1H), 10.72 (s, 1H).

Example 158

(S)-2-[4-(2,6-Difluoro-phenoxy)-2-oxo-2,5-dihydro-pyrrol-1-yl]-N-[1-((R)-2,2-dimethyl-[1,3]dioxolan-4-yl-methyl)-1H-pyrazol-3-yl]-butyramide

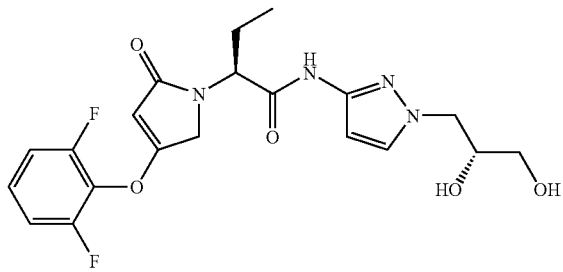

Dry hydrochloric acid gas was bubbled through a solution of (S)-2-amino-butyric acid (1.00 g, 9.70 mmol) in methanol cooled to 0° C. for 5 min. The vessel was sealed and the mixture heated to 50° C. overnight. The mixture was cooled, the solvent removed and the residue treated with methanol (repeated 3×). The residue was triturated with diethyl ether, dried under high vacuum to yield (S)-2-amino-butyric acid methyl ester (1.34 g, 90%) as a light yellow solid. $^1$H NMR (300 MHz, DMSO-$d_6$) δ ppm 0.92 (t, J=7.5 Hz, 3H), 1.58-1.99 (m, 2H), 3.75 (s, 3H), 3.99 (t, J=5.7 Hz, 1H), 8.55 (br. s., 3H).

To a stirred mixture of (S)-2-amino-butyric acid methyl ester hydrochloride (0.210 g, 1.79 mmol) dissolved in acetonitrile (5 mL) under nitrogen atmosphere was added N,N-diisopropylethylamine (0.193 g, 1.49 mmol). After addition was complete the mixture was stirred at 60° C. for 1 h. The reaction was cooled to 25° C. and treated with a second equivalent of N,N-diisopropylethylamine (0.193 g, 1.49 mmol) and heated to 85° C. at which time, 4-bromo-3-(2,6-difluoro-phenoxy)-but-2-enoic acid methyl ester (prepared as in Example 36, 0.400 g, 1.30 mmol) in acetonitrile (6 mL) was added slowly. After the addition was complete the reaction mixture was heated to reflux overnight. The reaction mixture was cooled to 25° C. and concentrated. The residue was dissolved in dichloromethane washed with 1N aqueous hydrochloric acid, saturated sodium bicarbonate solution, saturated sodium chloride solution and dried over magnesium sulfate. The mixture was filtered and evaporated and the crude product obtained was purified by AnaLogix flash chromatography (Supelco Flash Column 23 g, 30% to 50% ethyl acetate/hexanes) to afford, (S)-2-[4-(2,6-difluoro-phenoxy)-2-oxo-2,5-dihydro-pyrrol-1-yl]-butyric acid methyl ester (0.119 g, 29%) as a light brown oil: LR-ES-MS m/z calculated for $C_{15}H_{15}F_2NO_4$ [M+H]$^+$ 312, observed 312.

To a solution of (S)-2-[4-(2,6-difluoro-phenoxy)-2-oxo-2,5-dihydro-pyrrol-1-yl]-butyric acid methyl ester (0.119 g, 0.38 mol) in tetrahydrofuran:water (1:1, 8 mL) was added lithium hydroxide monohydrate (0.050 g 1.19 mmol). The mixture was stirred at room temperature for 2 h. The reaction mixture was poured into water and washed with diethyl ether and the ether layer discarded. The aqueous phase was acidified with 1N aqueous hydrochloric acid (pH <2), and extracted with ethyl acetate (2×30 mL). The combined ethyl acetate layers were dried over magnesium sulfate, filtered and concentrated to afford (S)-2-[4-(2,6-difluoro-phenoxy)-2-oxo-2,5-dihydro-pyrrol-1-yl]-butyric acid (0.090 g, 83%) as an off-white solid. $^1$H NMR (300 MHz, DMSO-$d_6$) δ ppm 0.87 (t, J=7.4 Hz, 3H), 1.60-2.06 (m, 2H), 4.23 (d, J=18.7 Hz, 1H), 4.31 (d, J=18.7 Hz, 1H), 4.43 (dd, J=10.7, 5.0 Hz, 1H), 5.05 (s, 1H), 7.21-7.54 (m, 3H), 12.94 (br. s., 1H).

To a solution of (S)-2-[4-(2,6-difluoro-phenoxy)-2-oxo-2,5-dihydro-pyrrol-1-yl]-butyric acid (0.090 g, 0.30 mmol) in dry N,N-dimethylformamide (5 mL) was added 1-((R)-2,2-dimethyl-[1,3]dioxolan-4-yl-methyl)-1H-pyrazol-3-ylamine (prepared as in Example 49 0.075 g, 0.38 mmol), and benzotriazol-1-yl-oxy-tris(dimethylamino)phosphonium hexafluorophosphate (0.200 g, 0.45 mmol). To this mixture was added N,N-diisopropylethylamine (0.117 g, 0.91 mmol) and the resulting mixture stirred at room temperature overnight. The reaction mixture was diluted with ethyl acetate and washed with an ammonium chloride solution, a saturated sodium bicarbonate solution, saturated sodium chloride solution and then dried over sodium sulfate. The solvents were evaporated and the residue was purified by AnaLogix flash chromatography (AnaLogix SuperFlash Flash Column 23 g, 100% ethyl acetate) which afforded (S)-2-[4-(2,6-difluoro-phenoxy)-2-oxo-2,5-dihydro-pyrrol-1-yl]-N-[1-((R)-2,2-dimethyl-[1,3]dioxolan-4-yl-methyl)-1H-pyrazol-3-yl]-butyramide (0.061 g, 42%) as a off-white solid: LR-ES-MS m/z calculated for $C_{23}H_{26}F_2N_4O_5$ [M+H]$^+$ 477 observed 477.

A solution of (S)-2-[4-(2,6-difluoro-phenoxy)-2-oxo-2,5-dihydro-pyrrol-1-yl]-N-[1-((R)-2,2-dimethyl-[1,3]dioxolan-4-yl-methyl)-1H-pyrazol-3-yl]-butyramide (0.061 g, 0.13 mmol) in methanol (5 mL) was treated with p-toluenesulfonic acid (0.020 g, 0.11 mmol). The reaction mixture was stirred at room temperature overnight. The solvents were removed under vacuum and dichloromethane was added to the residue. The resulting mixture was washed with saturated sodium bicarbonate, a saturated sodium chloride solution and dried over magnesium sulfate. The mixture was filtered and evaporated and the crude product purified by HPLC (Dynamax Impaq $C_{18}$, 5% to 95% acetonitrile/water) which afforded (S)-2-[4-(2,6-difluoro-phenoxy)-2-oxo-2,5-dihydro-pyrrol-1-yl]-N-[1-((R)-2,2-dimethyl-[1,3]dioxolan-4-yl-methyl)-1H-pyrazol-3-yl]-butyramide (9 mg, 16%) as a off-white solid: HR-ES-MS m/z calculated for $C_{20}H_{22}F_2N_4O_5$ [M+H]$^+$, 437.1361 observed 437.1362; $^1$H NMR (300 MHz, DMSO-$d_6$) δ ppm 0.85 (t, J=7.1 Hz, 3H), 1.65-1.93 (m, 2H), 3.20-3.29 (m, 2H), 3.69-3.90 (m, 2H), 4.07 (dd, J=13.4, 3.8 Hz, 1 H), 4.29 (d, J=18.7 Hz, 1H), 4.59 (d, J=18.7 Hz, 1H), 4.62-4.75 (m, 2H), 4.92 (d, J=5.1 Hz, 1H), 5.02 (s, 1H), 6.40 (d, J=2.1 Hz, 1H), 7.29-7.48 (m, 3H), 7.52 (d, J=1.8 Hz, 1H), 10.67 (s, 1H).

Example 159

2-[4-(2,6-Difluoro-phenoxy)-2-oxo-2,5-dihydro-pyrrol-1-yl]-N-[1-((R)-2,3-dihydroxy-propyl)-1H-pyrazol-3-yl]-3-(1-fluoro-cyclopentyl)-propionamide

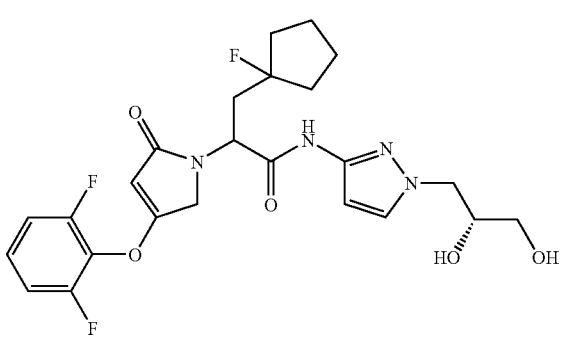

To a mixture of N-bromosuccinimide (11.7 g, 0.065 mol) in water (40 mL) cooled in an ice bath was added methylenecyclopentane (5.08 g, 0.061 mol) and the resulting mixture was stirred for 1.5 h. The mixture was diluted with water (200 mL) and then extracted with diethyl ether (2×200 mL). The combined organic layers were washed with a sodium bisulfate solution (1N, 150 mL) and dried over magnesium sulfate. The mixture was filtered and evaporated and the residue purified by AnaLogix flash chromatography (AnaLogix SuperFlash Flash Column 400 g, 5% to 20% ethyl acetate/hexanes) which afforded 1-bromomethyl-cyclopentanol (6.81 g, 61%) as a clear oil: $^1$H NMR (300 MHz, CDCl$_3$) δ ppm 1.56-2.19 (m, 9H), 3.60 (br. s., 2H).

To a solution of 1-bromomethyl-cyclopentanol (6.81 g, 0.038 mol) in diethyl ether (100 mL) was added powdered potassium hydroxide (2.77 g, 0.049 mol) and the resulting mixture stirred at room temperature overnight. The mixture was filtered and the filter cake washed with diethyl ether. The filtrate was concentrated carefully under vacuum (150 mbar) which afforded 1-oxa-spiro[2.4]heptane (3.73 g, 100%): $^1$H NMR (300 MHz, CDCl$_3$) δ ppm 1.59-2.03 (m, 8H), 2.85 (s, 2H).

To as solution of 1-oxa-spiro[2.4]heptane (3.73 g, 0.038 mol) in methyl t-butyl ether (60 mL) at −30° C. was added pyridine hydrofluoride (70% solution, 3.12 g, 0.109 mol) slowly over 30 min. The resulting mixture was allowed to warm to room temperature overnight. The mixture was poured into water and carefully neutralized with a saturated sodium carbonate solution. The organic phase was separated and washed with saturated sodium chloride solution, dried over magnesium sulfate. The mixture was filtered and evaporated and the residue purified by AnaLogix flash chromatography (AnaLogix SuperFlash Flash Column 100 g, 15% ethyl acetate/hexanes) which afforded (1-fluoro-cyclopentyl)-methanol (1.06 g, 24%) as a clear oil: $^1$H NMR (300 MHz, CDCl$_3$) δ ppm 1.51-2.16 (m, 10H), 3.71 (m, J=20.8 Hz, 2H).

To a solution of (1-fluoro-cyclopentyl)-methanol (1.06 g, 8.97 mmol) and triethylamine (0.995 g, 9.83 mmol) in anhydrous dichloromethane (40 mL) at −30° C. was added trifluoromethanesulfonic anhydride (2.78 g, 9.87 mmol) over 30 min. The mixture was allowed to warm to 0° C. and stirred for 1.5 h. The resulting mixture was diluted with dichloromethane, poured into ice and neutralized with 1N aqueous hydrochloric acid. The mixture was separated and the organic phase washed with a 20% sodium carbonate solution, saturated sodium chloride solution and dried over anhydrous magnesium sulfate. The resulting mixture was filtered and evaporated which afforded trifluoro-methanesulfonic acid 1-fluoro-cyclopentylmethyl ester (2 g, 89%) as a brown oil: $^1$H NMR (300 MHz, CDCl$_3$) δ ppm 1.51-2.25 (m, 8H), 4.57 (d, J=19.6 Hz, 2H).

To a solution of N-(diphenylmethylene)glycine ethyl ester (1.94 g, 7.26 mmol) in N,N-dimethylformamide (10 mL) at 0° C. was added solid potassium t-butoxide (0.89 g, 7.93 mmol) over 10 min and the resulting solution stirred for an additional 15 min. A trifluoro-methanesulfonic acid 1-fluoro-cyclopentylmethyl ester (2 g, 7.99 mmol) solution in N,N-dimethylformamide (2 mL) was added and the resulting mixture allowed to warm to room temperature over 2 h. The resulting mixture was poured into saturated ammonium chloride and extracted with dichloromethane (200 mL). The organic phase was separated, washed with saturated sodium chloride solution and dried over magnesium sulfate. The mixture was filtered and evaporated and the residue purified by AnaLogix flash chromatography (AnaLogix SuperFlash Flash Column 120 g, 10% to 20% ethyl acetate/hexanes) which afforded 2-(benzhydrylidene-amino)-3-(1-fluoro-cyclopentyl)-propionic acid ethyl ester (1.36 g, 58%) as a yellow oil: $^1$H NMR (300 MHz, CDCl$_3$) δ ppm 1.26 (t, J=7.1 Hz, 3H), 1.39-1.97 (m, 8H), 2.11-2.41 (m, 1H), 2.45-2.76 (m, 1H), 4.01-4.27 (m, 2H), 4.37 (dd, J=7.5, 4.5 Hz, 1H), 7.16-7.25 (m, 2H), 7.29-7.41 (m, 3H), 7.41-7.56 (m, 3H), 7.64 (d, J=7.8 Hz, 2H).

To a solution of 2-(benzhydrylidene-amino)-3-(1-fluorocyclopentyl)-propionic acid ethyl ester (1.36 g, 3.70 mmol) in dichloromethane (10 mL) at 0° C. was added a hydrochloric acid solution (1N, 7.4 mL) and the resulting mixture stirred at room temperature for 17 h. The mixture was separated, the aqueous layer diluted with water (10 mL) and cooled to 0° C. before sodium bicarbonate (1.24 g, 14.8 mmol) was added portionwise. The resulting mixture was extracted with dichloromethane (2×50 mL), the organic phases combined and dried over magnesium sulfate. The mixture was filtered and evaporated which afforded 2-amino-3-(1-fluoro-cyclopentyl)-propionic acid ethyl ester (0.56 g, 75%) as a clear oil: $^1$H NMR (300 MHz, CDCl$_3$) δ ppm 1.29 (t, J=7.1 Hz, 3H), 1.68 (br. s., 6H), 1.77-1.89 (m, 2H), 1.89-2.15 (m, 3H), 2.15-2.36 (m, 1H), 3.72 (t, J=5.9 Hz, 1H), 4.19 (q, J=7.1 Hz, 2H).

To a stirred mixture of 2-amino-3-(1-fluoro-cyclopentyl)-propionic acid ethyl ester (0.560 g, 2.76 mmol) dissolved in acetonitrile (8 mL) under nitrogen atmosphere was added N,N-diisopropylethylamine (0.393 g, 3.04 mmol). After addition was complete the mixture was stirred at 80° C. at which time, 4-bromo-3-(2,6-difluoro-phenoxy)-but-2-enoic acid methyl ester (prepared as in Example 36, 0.880 g, 2.85 mmol) in acetonitrile (10 mL) was added slowly. After the addition was complete the reaction mixture was heated to reflux overnight. The reaction mixture was cooled to 25° C. and concentrated. The residue was dissolved in dichloromethane washed with 1N aqueous hydrochloric acid, saturated sodium bicarbonate solution, saturated sodium chloride solution and dried over magnesium sulfate. The mixture was filtered and evaporated and the crude product obtained was purified by AnaLogix flash chromatography (AnaLogix SuperFlash Flash Column 40 g, 30% to 50% ethyl acetate/hexanes) to afford, 2-[4-(2,6-difluoro-phenoxy)-2-oxo-2,5-dihydro-pyrrol-1-yl]-3-(1-fluoro-cyclopentyl)-propionic acid ethyl ester (0.440 g, 39%) as a light brown oil: $^1$H NMR (300 MHz, DMSO-d$_6$) δ ppm 1.19 (t, J=7.1 Hz, 3H), 1.45-1.98 (m, 8H), 2.25-2.42 (m, 2H), 4.02-4.18 (m, 2H), 4.23 (d, J=18.4 Hz, 1H), 4.34 (d, J=18.4 Hz, 1H), 4.91 (t, J=6.8 Hz, 1H), 5.08 (s, 1H), 7.27-7.50 (m, 3H).

To a solution of 2-[4-(2,6-difluoro-phenoxy)-2-oxo-2,5-dihydro-pyrrol-1-yl]-3-(1-fluoro-cyclopentyl)-propionic acid ethyl ester (0.440 g, 1.11 mol) in tetrahydrofuran:water (1:1, 10 mL) was added lithium hydroxide monohydrate (0.140 g 3.34 mmol). The mixture was stirred at room temperature for 2 h. The reaction mixture was poured into water and washed with diethyl ether and the diethyl ether layer discarded. The aqueous phase was acidified with 1N aqueous hydrochloric acid (pH <2), and extracted with ethyl acetate (2×30 mL). The combined ethyl acetate layers were dried over magnesium sulfate, filtered and concentrated to afford 2-[4-(2,6-difluoro-phenoxy)-2-oxo-2,5-dihydro-pyrrol-1-yl]-3-(1-fluoro-cyclopentyl)-propionic acid, (0.358 g, 88%) as a yellow solid: $^1$H NMR (300 MHz, DMSO-d$_6$) δ ppm 1.64 (br. s., 8H), 2.34 (dd, J=22.6, 6.9 Hz, 2H), 4.23 (d, J=18.4 Hz, 1H), 4.31 (d, J=18.4 Hz, 1H), 4.84 (t, J=6.9 Hz, 1H), 5.05 (s, 1H), 7.26-7.55 (m, 3H), 13.05 (br. s., 1H).

To a solution of 2-[4-(2,6-difluoro-phenoxy)-2-oxo-2,5-dihydro-pyrrol-1-yl]-3-(1-fluoro-cyclopentyl)-propionic acid (0.264 g, 0.71 mmol) in dry N,N-dimethylformamide (6 mL) was added 1-((R)-2,2-dimethyl-[1,3]dioxolan-4-yl-methyl)-1H-pyrazol-3-ylamine (prepared as in Example 49

0.170 g, 0.86 mmol), and benzotriazol-1-yl-oxy-tris(dimethylamino)phosphonium hexafluorophosphate (0.470 g, 1.06 mmol). To this mixture was added N,N-diisopropylethylamine (0.282 g, 2.18 mmol) and the resulting mixture stirred at room temperature overnight. The reaction mixture was diluted with ethyl acetate and washed with an ammonium chloride solution, a saturated sodium bicarbonate solution, saturated sodium chloride solution and then dried over magnesium sulfate. The solvents were evaporated and the residue was purified by AnaLogix flash chromatography (Supelco Flash Column 23 g, 50% to 60% ethyl acetate/hexanes) which afforded 2-[4-(2,6-difluoro-phenoxy)-2-oxo-2,5-dihydro-pyrrol-1-yl]-N-[1-((R)-2,2-dimethyl-[1,3]dioxolan-4-yl-methyl)-1H-pyrazol-3-yl]-3-(1-fluoro-cyclopentyl)-propionamide (0.330 g, 84%) as a light brown oil: $^1$H NMR (300 MHz, DMSO-$d_6$) δ ppm 1.24 (s, 3H), 1.30 (s, 3H), 1.46-2.02 (m, 8H), 2.04-2.47 (m, 2H), 3.73 (dd, J=8.4, 6.0 Hz, 1H), 4.00 (dd, J=8.4, 6.5 Hz, 1H), 4.06-4.20 (m, 2H), 4.28-4.39 (m, 2H), 4.53 (d, J=18.7 Hz, 1H), 5.03 (s, 1H), 5.09 (dd, J=9.5, 4.4 Hz, 1H), 6.44 (d, J=2.1 Hz, 1H), 7.28-7.49 (m, 3H), 7.61 (s, 1H), 10.84 (s, 1H).

A solution of 2-[4-(2,6-difluoro-phenoxy)-2-oxo-2,5-dihydro-pyrrol-1-yl]-N-[1-((R)-2,2-dimethyl-[1,3]dioxolan-4-yl-methyl)-1H-pyrazol-3-yl]-3-(1-fluoro-cyclopentyl)-propionamide (0.330 g, 0.60 mmol) in methanol (6 mL) was treated with p-toluenesulfonic acid (0.017 g, 0.09 mmol). The reaction mixture was stirred at room temperature overnight. The solvents were removed under vacuum and ethyl acetate was added to the residue. The resulting mixture was washed with saturated sodium bicarbonate, a saturated sodium chloride solution and dried over magnesium sulfate. The mixture was filtered and evaporated which afforded 2-[4-(2,6-difluoro-phenoxy)-2-oxo-2,5-dihydro-pyrrol-1-yl]-N-[1-((R)-2,3-dihydroxy-propyl)-1H-pyrazol-3-yl]-3-(1-fluoro-cyclopentyl)-propionamide (0.260 g, 87%) as a light yellow solid: $^1$H NMR (300 MHz, DMSO-$d_6$) δ ppm 1.51-1.96 (m, 8H), 2.10-2.43 (m, 2H), 3.22-3.32 (m, 2H), 3.69-3.94 (m, 2H), 4.09 (dd, J=13.3, 3.3 Hz, 1H), 4.33 (d, J=18.3 Hz, 1H), 4.53 (d, J=18.3 Hz, 1H), 4.71 (t, J=5.3 Hz, 1H), 4.94 (d, J=5.1 Hz, 1H), 5.02 (s, 1H), 5.05-5.13 (m, 1H), 6.41 (s, 1H), 7.29-7.50 (m, 3H), 7.54 (s, 1H), 10.81 (s, 1H) HR-ES-MS m/z calculated for $C_{24}H_{27}F_3N_4O_5$ [M+H]$^+$, 509.2007 observed 509.2009.

Example 160

(S)-2-[4-(3-Methoxy-phenoxy)-2-oxo-2,5-dihydro-pyrrol-1-yl]-4-methyl-pentanoic acid [1-((R)-2,3-dihydroxy-propyl)-1H-pyrazol-3-yl]-amide

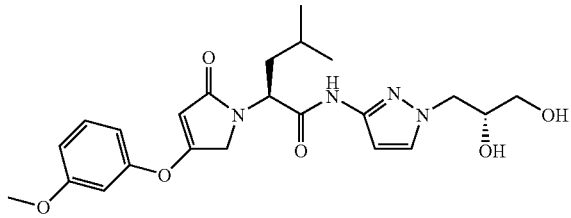

To a stirred mixture of 3-methoxyphenol (5.00 g, 40.28 mmol) and ethyl-2-butynoate (9.04 g, 80.55 mmol) in tetrahydrofuran (50 mL) was added 1,8-diazabicyclo[5.4.0]undec-7-ene (6.13 g, 40.28 mmol). After addition was complete the mixture was stirred at 130° C. for 2 h. Upon completion of the reaction the tetrahydrofuran was removed in vacuo and the residue redissolved in dichloromethane and washed with 2N hydrochloric acid, 5% aqueous sodium hydroxide solution, a saturated sodium chloride solution and dried over magnesium sulfate. The crude product obtained was purified by ISCO flash chromatography (Teledyne Isco RediSep Flash Column 120 g; 0% to 50% ethyl acetate/hexanes) to afford, 3-(3-methoxy-phenoxy)-but-2-enoic acid ethyl ester (3.74 g, 39%) as a colorless oil: LR-ES-MS m/z calculated for $C_{13}H_{16}O_4$ [M]$^+$ 236, observed 237 [M+H]$^+$.

To a stirred mixture of 3-(3-methoxy-phenoxy)-but-2-enoic acid ethyl ester (3.74 g, 15.85 mmol) dissolved in carbon tetrachloride (40 mL) under a nitrogen atmosphere was added N-bromosuccinimide (3.10 g, 17.43 mmol) and benzoyl peroxide (0.41 g, 1.27 mmol). After addition was complete the mixture was stirred at reflux for 5 h. The reaction mixture was then placed in the refrigerator overnight. The solids formed were removed by filtration and the filtrate concentrated in vacuo. The crude product obtained was purified by ISCO flash chromatography (Teledyne Isco RediSep Flash Column 40 g; 0% to 50% ethyl acetate/hexanes) to afford, 4-bromo-3-(3-methoxy-phenoxy)-but-2-enoic acid ethyl ester (4.95 g, 99%) as a red oil: LR-ES-MS m/z calculated for $C_{13}H_{15}BrO_4$ [M]$^+$ 314, observed 315 [M+H]$^+$.

To a stirred mixture of (L)-leucine methyl ester hydrochloride (3.15 g, 17.34 mmol) dissolved in acetonitrile (25 mL) under a nitrogen atmosphere was added N,N-diisopropylethylamine (2.29 g, 17.73 mmol). After addition was complete the mixture was stirred at 60° C. for 1 h. The reaction was cooled to 25° C. and treated with N,N-diisopropylethylamine (2.29 g, 17.73 mmol) and acetonitrile (25 mL) and heated to 80° C. at which time 4-bromo-3-(3-methoxy-phenoxy)-but-2-enoic acid ethyl ester (4.95 g, 15.76 mmol) in acetonitrile (25 mL) was added slowly. After the addition was complete the reaction mixture was heated to 100° C. and stirred overnight. The reaction mixture was cooled to 25° C., filtered and concentrated. The residue was diluted with dichloromethane and washed with 2N hydrochloric acid, a saturated sodium bicarbonate solution, a saturated sodium chloride solution and dried over magnesium sulfate. The crude product obtained was purified by ISCO flash chromatography (Teledyne Isco RediSep Flash Column 40 g; 0% to 80% ethyl acetate/hexanes) to afford, (S)-2-[4-(3-methoxy-phenoxy)-2-oxo-2,5-dihydro-pyrrol-1-yl]-4-methyl-pentanoic acid methyl ester (3.50 g, 67%) as a red oil: LR-ES-MS m/z calculated for $C_{18}H_{23}NO_5$ [M]$^+$ 333, observed 334 [M+H]$^+$.

To a stirred mixture of (S)-2-[4-(3-methoxy-phenoxy)-2-oxo-2,5-dihydro-pyrrol-1-yl]-4-methyl-pentanoic acid methyl ester (3.50 g, 10.51 mmol) in tetrahydrofuran (25 mL) and water (8 mL) was added lithium hydroxide (0.53 g, 12.60 mmol). After addition was complete the mixture was stirred at 25° C. for 2 h. The reaction mixture was poured into water and diethyl ether and the layers separated. The aqueous layer was made acidic with 2N hydrochloric acid and extracted with ethyl acetate (3×30 mL). The combined ethyl acetate fractions were washed with a saturated sodium chloride solution, dried over magnesium sulfate, filtered and concentrated to afford, (S)-2-[4-(3-methoxy-phenoxy)-2-oxo-2,5-dihydro-pyrrol-1-yl]-4-methyl-pentanoic acid (2.78 g, 83%) as an off-white solid: LR-ES-MS m/z calculated for $C_{17}H_{21}NO_5$ [M]$^+$ 319, observed [M+H]$^+$ 320.

A solution of (S)-2-[4-(3-methoxy-phenoxy)-2-oxo-2,5-dihydro-pyrrol-1-yl]-4-methyl-pentanoic acid (300 mg, 0.94 mmol) in dichloromethane (20 mL) was treated with 1-(3-dimethylaminopropyl)-3-ethylcarbodiimide (161 mg, 1.03 mmol) and 1-hydroxybenzotriazole (135 mg, 0.99 mmol).

The reaction mixture was stirred at 25° C. for 2 h followed by the addition of 1-((R)-2,2-dimethyl-[1,3]dioxolan-4-yl-methyl)-1H-pyrazol-3-ylamine (prepared as in Example 49, 225 mg, 1.13 mmol). The reaction mixture was stirred for 18 h at 25° C., under nitrogen. The reaction mixture was diluted with dichloromethane, washed with 2N hydrochloric acid, saturated sodium bicarbonate solution, a saturated sodium chloride solution and dried over magnesium sulfate. The organic layer was concentrated, and the crude product was purified by ISCO flash chromatography (Teledyne Isco RediSep Flash Column 40 g; 20% to 100% ethyl acetate/hexanes) to afford, (S)-2-[4-(3-methoxy-phenoxy)-2-oxo-2,5-dihydro-pyrrol-1-yl]-4-methyl-pentanoic acid [1-((R)-2,2-dimethyl-[1,3]dioxolan-4-yl-methyl)-1H-pyrazol-3-yl]-amide (274 mg, 59%) as a yellow oil: LR-ES-MS m/z calculated for $C_{26}H_{34}N_4O_6$ $[M]^+$ 498, observed $[M+H]^+$ 499.

A solution of (S)-2-[4-(3-methoxy-phenoxy)-2-oxo-2,5-dihydro-pyrrol-1-yl]-4-methyl-pentanoic acid [1-((R)-2,2-dimethyl-[1,3]dioxolan-4-yl-methyl)-1H-pyrazol-3-yl]-amide (270 mg, 0.54 mmol) in tetrahydrofuran (10 mL) was treated with 2N aqueous hydrochloric acid solution (10 mL). The reaction mixture was stirred at 25° C. for 4 h. The reaction mixture was diluted with ethyl acetate, washed with water, saturated sodium bicarbonate solution, a saturated sodium chloride solution and dried over magnesium sulfate. The organic layer was concentrated to afford, (S)-2-[4-(3-methoxy-phenoxy)-2-oxo-2,5-dihydro-pyrrol-1-yl]-4-methyl-pentanoic acid [1-((R)-2,3-dihydroxy-propyl)-1H-pyrazol-3-yl]-amide (207 mg, 83%) as a white solid: LR-ES-MS m/z calculated for $C_{23}H_{30}N_4O_6$ $[M]^+$ 458, observed 459 $[M+H]^+$; $^1$H NMR (300 MHz, DMSO-$d_6$) δ ppm 0.90 (d, J=6.3 Hz, 3H), 0.94 (d, J=6.3 Hz, 3H), 1.37-1.67 (m, 2H), 1.67-1.83 (m, 1H), 3.21-3.32 (m, 2H), 3.71-3.81 (m, 1H), 3.77 (s, 3H), 3.81-3.93 (m, 1H), 4.09 (dd, J=13.4, 3.8 Hz, 1H), 4.17 (d, J=18.4 Hz, 1H), 4.56 (d, J=18.4 Hz, 1H), 4.71 (t, J=5.6 Hz, 1H), 4.81-4.91 (m, 1H), 4.87 (s, 1H), 4.94 (d, J=5.1 Hz, 1H), 6.41 (d, J=2.1 Hz, 1H), 6.83-6.92 (m, 3H), 7.32-7.43 (m, 1H), 7.53 (d, J=2.1 Hz, 1H), 10.76 (s, 1H).

Example 161

(S)-2-[4-(2-chloro-3-ethoxy-phenoxy)-2-oxo-2,5-dihydro-pyrrol-1-yl]-4-methyl-pentanoic acid [1-((R)-2,3-dihydroxy-propyl)-1H-pyrazol-3-yl]-amide

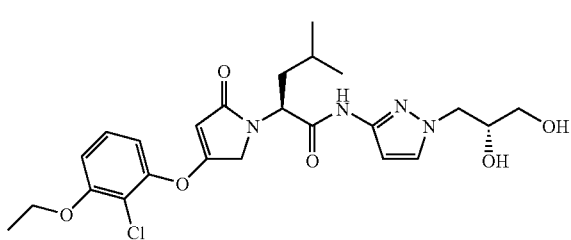

To a stirred mixture of 2-chloro-3-ethoxyphenol (5.55 g, 32.27 mmol) and ethyl-2-butynoate (7.24 g, 64.53 mmol) in tetrahydrofuran (50 mL) was added 1,8-diazabicyclo[5.4.0]undec-7-ene (4.91 g, 32.27 mmol). After addition was complete the mixture was stirred at 130° C. for 2 h. Upon completion of the reaction the tetrahydrofuran was removed in vacuo and the residue redissolved in dichloromethane and washed with 2N hydrochloric acid, 5% aqueous sodium hydroxide solution, a saturated sodium chloride solution and dried over magnesium sulfate. The crude product obtained was purified by ISCO flash chromatography (Teledyne Isco RediSep Flash Column 120 g; 0% to 50% ethyl acetate/hexanes) to afford, 3-(2-chloro-3-ethoxy-phenoxy)-but-2-enoic acid ethyl ester (4.91 g, 54%) as a colorless oil: LR-ES-MS m/z calculated for $C_{14}H_{17}ClO_4$ $[M]^+$ 284, observed $[M+H]^+$ 285.

To a stirred mixture of 3-(2-chloro-3-ethoxy-phenoxy)-but-2-enoic acid ethyl ester (4.91 g, 17.26 mmol) dissolved in carbon tetrachloride (50 mL) under a nitrogen atmosphere was added N-bromosuccinimide (3.38 g, 18.98 mmol) and benzoyl peroxide (0.45 g, 1.38 mmol). After addition was complete the mixture was stirred at reflux for 6 h. The reaction mixture was then placed in the refrigerator overnight. The solids formed were removed by filtration and the filtrate concentrated in vacuo. The crude product obtained was purified by ISCO flash chromatography (Teledyne Isco RediSep Flash Column 120 g; 0% to 50% ethyl acetate/hexanes) to afford, 4-bromo-3-(2-chloro-3-ethoxy-phenoxy)-but-2-enoic acid ethyl ester (6.30 g, 99%) as a red oil: LR-ES-MS m/z calculated for $C_{14}H_{16}BrClO_4$ $[M]^+$ 362, observed $[M+H]^+$ 363.

To a stirred mixture of (L)-leucine methyl ester hydrochloride (3.47 g, 17.38 mmol) dissolved in acetonitrile (25 mL) under a nitrogen atmosphere was added N,N-diisopropylethylamine (2.50 g, 19.55 mmol). After addition was complete the mixture was stirred at 60° C. for 1 h. The reaction was cooled to 25° C. and treated with N,N-diisopropylethylamine (2.50 g, 19.55 mmol) and acetonitrile (25 mL) and heated to 80° C. at which time 4-bromo-3-(2-chloro-3-ethoxy-phenoxy)-but-2-enoic acid ethyl ester (6.30 g, 17.38 mmol) in acetonitrile (25 mL) was added slowly. After the addition was complete the reaction mixture was heated to 100° C. and stirred overnight. The reaction mixture was cooled to 25° C., filtered and concentrated. The residue was diluted with dichloromethane and washed with 2N hydrochloric acid, a saturated sodium bicarbonate solution, a saturated sodium chloride solution and dried over magnesium sulfate. The crude product obtained was purified by ISCO flash chromatography (Teledyne Isco RediSep Flash Column 120 g; (30% to 100% ethyl acetate/hexanes) to afford, (S)-2-[4-(2-chloro-3-ethoxy-phenoxy)-2-oxo-2,5-dihydro-pyrrol-1-yl]-4-methyl-pentanoic acid methyl ester (4.10 g, 62%) as a yellow oil: LR-ES-MS m/z calculated for $C_{19}H_{24}ClNO_5$ $[M]^+$ 381, observed $[M+H]^+$ 382.

To a stirred mixture of (S)-2-[4-(2-chloro-3-ethoxy-phenoxy)-2-oxo-2,5-dihydro-pyrrol-1-yl]-4-methyl-pentanoic acid methyl ester (4.10 g, 10.75 mmol) in tetrahydrofuran (25 mL) and water (8 mL) was added lithium hydroxide (0.54 g, 12.90 mmol). After addition was complete the mixture was stirred at 25° C. for 2 h. The reaction mixture was poured into water and diethyl ether and the layers separated. The aqueous layer was made acidic with 2N hydrochloric acid and extracted with ethyl acetate (3×30 mL). The combined ethyl acetate fractions were washed with a saturated sodium chloride solution, dried over magnesium sulfate, filtered and concentrated to afford, (S)-2-[4-(2-chloro-3-ethoxy-phenoxy)-2-oxo-2,5-dihydro-pyrrol-1-yl]-4-methyl-pentanoic acid (3.45 g, 87%) as a yellow solid: LR-ES-MS m/z calculated for $C_{18}H_{22}ClNO_5$ $[M]^+$ 367, observed $[M+H]^+$ 368.

A solution of (S)-2-[4-(2-chloro-3-ethoxy-phenoxy)-2-oxo-2,5-dihydro-pyrrol-1-yl]-4-methyl-pentanoic acid (300 mg, 0.82 mmol) in dichloromethane (15 mL) was treated with 1-(3-dimethylaminopropyl)-3-ethylcarbodiimide (140 mg, 0.90 mmol) and 1-hydroxybenzotriazole (116 mg, 0.86 mmol). The reaction mixture was stirred at 25° C. for 2 h followed by the addition of 1-((R)-2,2-dimethyl-[1,3]dioxolan-4-yl-methyl)-1H-pyrazol-3-ylamine (prepared as in Example 49, 193 mg, 0.98 mmol). The reaction mixture was stirred for 18 h at 25° C., under nitrogen. The reaction mixture was diluted with dichloromethane, washed with 2N hydrochloric acid, saturated sodium bicarbonate solution, a saturated sodium chloride solution and dried over magnesium sulfate. The organic layer was concentrated, and the crude product was purified by ISCO flash chromatography (Teledyne Isco RediSep Flash Column 12 g; 0% to 100% ethyl acetate/hexanes) to afford, (S)-2-[4-(2-chloro-3-ethoxy-phenoxy)-2-oxo-2,5-dihydro-pyrrol-1-yl]-4-methyl-pentanoic acid [1-((R)-2,2-dimethyl-[1,3]dioxolan-4-yl-methyl)-1H-pyrazol-3-yl]-amide (260 mg, 58%) as a yellow oil: LR-ES-MS m/z calculated for $C_{27}H_{35}ClN_4O_6$ [M]$^+$ 546, observed [M+H]$^+$ 547.

A solution of (S)-2-[4-(2-chloro-3-ethoxy-phenoxy)-2-oxo-2,5-dihydro-pyrrol-1-yl]-4-methyl-pentanoic acid [1-((R)-2,2-dimethyl-[1,3]dioxolan-4-yl-methyl)-1H-pyrazol-3-yl]-amide (260 mg, 0.48 mmol) in tetrahydrofuran (10 mL) was treated with 2N aqueous hydrochloric acid solution (10 mL). The reaction mixture was stirred at 25° C. for 4 h. The reaction mixture was diluted with ethyl acetate, washed with water, saturated sodium bicarbonate solution, a saturated sodium chloride solution and dried over magnesium sulfate. The organic layer was concentrated to afford, (S)-2-[4-(2-chloro-3-ethoxy-phenoxy)-2-oxo-2,5-dihydro-pyrrol-1-yl]-4-methyl-pentanoic acid [1-((R)-2,3-dihydroxy-propyl)-1H-pyrazol-3-yl]-amide (178 mg, 74%) as a white solid: LR-ES-MS m/z calculated for $C_{24}H_{31}ClN_4O_6$ [M]$^+$ 506, observed [M+H]$^+$507; $^1$H NMR (300 MHz, DMSO-d$_6$) δ ppm 0.90 (d, J=6.3 Hz, 3H), 0.93 (d, J=6.3 Hz, 3H), 1.37 (t, J=6.9 Hz, 3H), 1.40-1.50 (m, 1H), 1.50-1.66 (m, 1H), 1.67-1.83 (m, 1H), 3.19-3.33 (m, 2H), 3.70-3.82 (m, 1H), 3.86 (dd, J=13.6, 7.5 Hz, 1H), 4.00-4.25 (m, 4H), 4.59 (d, J=18.4 Hz, 1H), 4.71 (t, J=5.4 Hz, 1H), 4.79 (s, 1H), 4.88 (dd, J=10.6, 4.8 Hz, 1H), 4.94 (d, J=5.1 Hz, 1H), 6.41 (d, J=2.1 Hz, 1H), 7.07 (d, J=8.2 Hz, 1H), 7.11 (d, J=8.2 Hz, 1H), 7.39 (t, J=8.2 Hz, 1H), 7.53 (d, J=2.1 Hz, 1H), 10.78 (s, 1H).

Example 162

(S)-2-[4-(3-Ethoxy-phenoxy)-2-oxo-2,5-dihydro-pyrrol-1-yl]-4-methyl-pentanoic acid [1-((R)-2,3-dihydroxy-propyl)-1H-pyrazol-3-yl]-amide

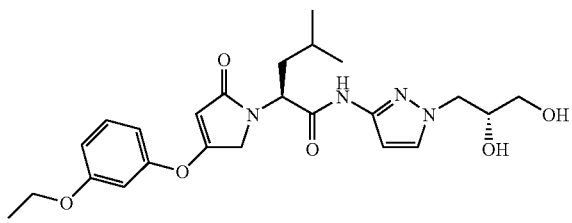

To a stirred mixture of 3-ethoxyphenol (5.00 g, 36.19 mmol) and ethyl-2-butynoate (8.12 g, 72.38 mmol) in tetrahydrofuran (50 mL) was added 1,8-diazabicyclo[5.4.0]undec-7-ene (5.50 g, 36.19 mmol). After addition was complete the mixture was stirred at 130° C. for 2 h. Upon completion of the reaction the tetrahydrofuran was removed in vacuo and the residue redissolved in dichloromethane and washed with 2N hydrochloric acid, 5% aqueous sodium hydroxide solution, a saturated sodium chloride solution and dried over magnesium sulfate. The crude product obtained was purified by ISCO flash chromatography (Teledyne Isco RediSep Flash Column 120 g; 0% to 50% ethyl acetate/hexanes) to afford, 3-(3-ethoxy-phenoxy)-but-2-enoic acid ethyl ester (2.86 g, 32%) as a colorless oil: LR-ES-MS m/z calculated for $C_{14}H_{18}O_4$ [M]$^+$ 250, observed 251 [M+H]$^+$.

To a stirred mixture of 3-(3-ethoxy-phenoxy)-but-2-enoic acid ethyl ester (2.86 g, 11.44 mmol) dissolved in carbon tetrachloride (40 mL) under a nitrogen atmosphere was added N-bromosuccinimide (2.24 g, 12.58 mmol) and benzoyl peroxide (0.30 g, 0.92 mmol). After addition was complete the mixture was stirred at reflux for 16 h. The reaction mixture was then placed in the refrigerator overnight. The solids formed were removed by filtration and the filtrate concentrated in vacuo. The crude product obtained was purified by ISCO flash chromatography (Teledyne Isco RediSep Flash Column 40 g; 0% to 50% ethyl acetate/hexanes) to afford, 4-bromo-3-(3-ethoxy-phenoxy)-but-2-enoic acid ethyl ester (4.36 g, 99%) as a red oil: LR-ES-MS m/z calculated for $C_{14}H_{17}BrO_4$ [M]$^+$ 328, observed 329 [M+H]$^+$.

To a stirred mixture of (L)-leucine methyl ester hydrochloride (2.66 g, 14.62 mmol) dissolved in acetonitrile (25 mL) under a nitrogen atmosphere was added N,N-diisopropylethylamine (1.93 g, 15.00 mmol). After addition was complete the mixture was stirred at 60° C. for 1 h. The reaction was cooled to 25° C. and treated with N,N-diisopropylethylamine (1.93 g, 15.00 mmol) and acetonitrile (25 mL) and heated to 80° C. at which time 4-bromo-3-(3-ethoxy-phenoxy)-but-2-enoic acid ethyl ester (4.36 g, 13.29 mmol) in acetonitrile (25 mL) was added slowly. After the addition was complete the reaction mixture was heated to 100° C. and stirred overnight. The reaction mixture was cooled to 25° C., filtered and concentrated. The residue was diluted with dichloromethane and washed with 2N hydrochloric acid, a saturated sodium bicarbonate solution, a saturated sodium chloride solution and dried over magnesium sulfate. The crude product obtained was purified by ISCO flash chromatography (Teledyne Isco RediSep Flash Column 80 g; 0% to 80% ethyl acetate/hexanes) to afford, (S)-2-[4-(3-ethoxy-phenoxy)-2-oxo-2,5-dihydro-pyrrol-1-yl]-4-methyl-pentanoic acid methyl ester (3.11 g, 67%) as a red oil: LR-ES-MS m/z calculated for $C_{19}H_{25}NO_5$ [M]$^+$ 347, observed 348 [M+H]$^+$.

To a stirred mixture of (S)-2-[4-(3-ethoxy-phenoxy)-2-oxo-2,5-dihydro-pyrrol-1-yl]-4-methyl-pentanoic acid methyl ester (3.11 g, 8.96 mmol) in tetrahydrofuran (25 mL) and water (8 mL) was added lithium hydroxide (0.45 g, 10.76 mmol). After addition was complete the mixture was stirred at 25° C. for 2 h. The reaction mixture was poured into water and diethyl ether and the layers separated. The aqueous layer was made acidic with 2N hydrochloric acid and extracted with ethyl acetate (3×30 mL). The combined ethyl acetate fractions were washed with a saturated sodium chloride solution, dried over magnesium sulfate, filtered and concentrated to afford, (S)-2-[4-(3-ethoxy-phenoxy)-2-oxo-2,5-dihydro-pyrrol-1-yl]-4-methyl-pentanoic acid (2.60 g, 87%) as a brown solid: LR-ES-MS m/z calculated for $C_{18}H_{23}NO_5$ [M]$^+$ 333, observed 334 [M+H]$^+$.

A solution of (S)-2-[4-(3-ethoxy-phenoxy)-2-oxo-2,5-dihydro-pyrrol-1-yl]-4-methyl-pentanoic acid (300 mg, 0.90 mmol) in dichloromethane (20 mL) was treated with 1-(3-dimethylaminopropyl)-3-ethylcarbodiimide (154 mg, 0.99 mmol) and 1-hydroxybenzotriazole (128 mg, 0.96 mmol). The reaction mixture was stirred at 25° C. for 2 h followed by the addition of 1-((R)-2,2-dimethyl-[1,3]dioxolan-4-yl-methyl)-1H-pyrazol-3-ylamine (prepared as in Example 49, 213 mg, 1.08 mmol). The reaction mixture was stirred for 18 h at 25° C., under nitrogen. The reaction mixture was diluted with dichloromethane, washed with 2N hydrochloric acid, saturated sodium bicarbonate solution, a saturated sodium chloride solution and dried over magnesium sulfate. The organic layer was concentrated, and the crude product was purified by ISCO flash chromatography (Teledyne Isco RediSep Flash Column 40 g; 20% to 100% ethyl acetate/hexanes) to afford, (S)-2-[4-(3-ethoxy-phenoxy)-2-oxo-2,5-dihydro-pyrrol-1-yl]-4-methyl-pentanoic acid [1-((R)-2,2-dimethyl-[1,3]dioxolan-4-yl-methyl)-1H-pyrazol-3-yl]-amide (268 mg, 58%) as a yellow oil: LR-ES-MS m/z calculated for $C_{27}H_{36}N_4O_6$ [M]+ 512, observed 513 [M+H]+.

A solution of (S)-2-[4-(3-ethoxy-phenoxy)-2-oxo-2,5-dihydro-pyrrol-1-yl]-4-methyl-pentanoic acid [1-((R)-2,2-dimethyl-[1,3]dioxolan-4-yl-methyl)-1H-pyrazol-3-yl]-amide (265 mg, 0.52 mmol) in tetrahydrofuran (10 mL) was treated with 2N aqueous hydrochloric acid solution (10 mL). The reaction mixture was stirred at 25° C. for 4 h. The reaction mixture was diluted with ethyl acetate, washed with water, saturated sodium bicarbonate solution, a saturated sodium chloride solution and dried over magnesium sulfate. The organic layer was concentrated to afford, (S)-2-[4-(3-ethoxy-phenoxy)-2-oxo-2,5-dihydro-pyrrol-1-yl]-4-methyl-pentanoic acid [1-((R)-2,3-dihydroxy-propyl)-1H-pyrazol-3-yl]-amide (200 mg, 82%) as a white solid: LR-ES-MS m/z calculated for $C_{24}H_{32}N_4O_6$ [M]+ 472, observed 473 [M+H]+; 1H NMR (300 MHz, DMSO-$d_6$) δ ppm 0.90 (d, J=6.4 Hz, 3H), 0.93 (d, J=6.4 Hz, 3H), 1.31 (t, J=3H), 1.39-1.65 (m, 2H), 1.64-1.82 (m, 1H), 3.20-3.41 (m, 2H), 3.71-3.92 (m, 2H), 3.96-4.12 (m, 3H), 4.16 (d, J=18.3 Hz, 1H), 4.55 (d, J=18.3 Hz, 1H), 4.80-4.93 (m, 2H), 6.40 (d, J=1.8 Hz, 1 H), 6.84 (m, 1H), 6.87 (s, 2H), 7.36 (t, J=8.3 Hz, 1H), 7.53 (d, J=1.8 Hz, 1H), 10.76 (s, 1H).

Example 163

(S)-2-[4-(3-Ethoxy-phenoxy)-2-oxo-2,5-dihydro-pyrrol-1-yl]-4-methyl-pentanoic acid [1-(2-hydroxy-2-methyl-propyl)-1H-pyrazol-3-yl]-amide

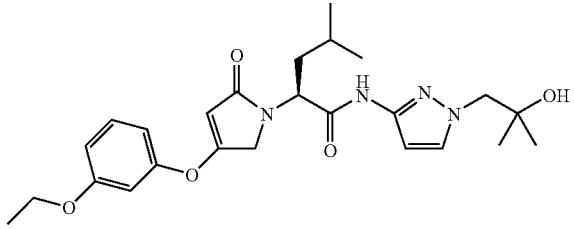

A solution of (S)-2-[4-(3-ethoxy-phenoxy)-2-oxo-2,5-dihydro-pyrrol-1-yl]-4-methyl-pentanoic acid (prepared as in Example 162, 300 mg, 0.90 mmol) in dichloromethane (20 mL) was treated with 1-(3-dimethylaminopropyl)-3-ethylcarbodiimide (154 mg, 0.99 mmol) and 1-hydroxybenzotriazole (128 mg, 0.95 mmol). The reaction mixture was stirred at 25° C. for 1 h followed by the addition of 1-(3-amino-pyrazol-1-yl)-2-methyl-propan-2-ol (prepared in U.S. Pat. Appl. US2008021032 Example 80, 168 mg, 1.08 mmol). The reaction mixture was stirred for 18 h at 25° C., under nitrogen. The reaction mixture was diluted with dichloromethane, washed with 2N hydrochloric acid, saturated sodium bicarbonate solution, a saturated sodium chloride solution and dried over magnesium sulfate. The crude product obtained after concentration, was purified by ISCO flash chromatography (Teledyne Isco RediSep Flash Column 40 g; (20% to 100% ethyl acetate/hexanes) to afford (S)-2-[4-(3-ethoxy-phenoxy)-2-oxo-2,5-dihydro-pyrrol-1-yl]-4-methyl-pentanoic acid [1-(2-hydroxy-2-methyl-propyl)-1H-pyrazol-3-yl]-amide (217 mg, 51%) as a yellow powder: HR-ES-MS m/z calculated for $C_{25}H_{34}N_4O_5$ [M+H]+ 470, observed 471; 1H NMR (300 MHz, DMSO-$d_6$) δ ppm 0.90 (d, J=6.3 Hz, 3H), 0.93 (d, J=6.3 Hz, 3H), 1.04 (br. s., 3H), 1.06 (br. s., 3H), 1.31 (t, J=6.8 Hz, 3H), 1.38-1.64 (m, 2H), 1.67-1.84 (m, 1H), 3.89 (s, 2H), 4.04 (q, J=6.8 Hz, 2H), 4.16 (d, J=18.1 Hz, 1H), 4.56 (d, J=18.1 Hz, 4.68 (s, 1H), 4.86 (s, 1H), 4.87-4.93 (m, 1H), 6.44 (d, J=1.8 Hz, 1H), 6.78-6.92 (m, 3H), 7.35 (t, J=8.3 Hz, 1H), 7.53 (d, J=1.8 Hz, 1H), 10.79 (s, 1H).

Example 164

(S)-3-Cyclohexyl-N-[1-((R)-2,3-dihydroxy-propyl)-1H-pyrazol-3-yl]-2-[4-(3-methoxy-phenoxy)-2-oxo-2,5-dihydro-pyrrol-1-yl]-propionamide

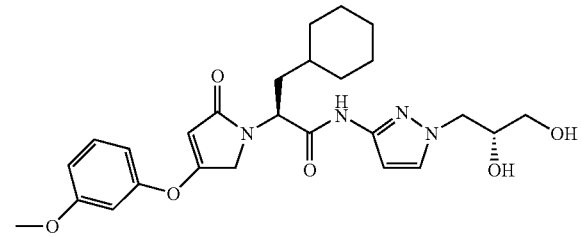

A solution of (S)-3-cyclohexyl-2-[4-(3-methoxy-phenoxy)-2-oxo-2,5-dihydro-pyrrol-1-yl]-propionic acid (prepared as in Example 210, 300 mg, 0.84 mmol) in dichloromethane (20 mL) was treated with 1-(3-dimethylaminopropyl)-3-ethylcarbodiimide (143 mg, 0.92 mmol) and 1-hydroxybenzotriazole (120 mg, 0.88 mmol). The reaction mixture was stirred at 25° C. for 2 h followed by the addition of 1-((R)-2,2-dimethyl-[1,3]dioxolan-4-yl-methyl)-1H-pyrazol-3-ylamine (prepared as in Example 49, 200 mg, 1.00 mmol). The reaction mixture was stirred for 18 h at 25° C., under nitrogen. The reaction mixture was diluted with dichloromethane, washed with saturated ammonium chloride solution, saturated sodium bicarbonate solution, a saturated sodium chloride solution and dried over magnesium sulfate. The organic layer was concentrated, and the crude product was purified by ISCO flash chromatography (Teledyne Isco RediSep Flash Column 12 g; 0% to 100% ethyl acetate/hexanes) to afford, (S)-3-cyclohexyl-N-[1-((R)-2,2-dimethyl-[1,3]dioxolan-4-yl-methyl)-1H-pyrazol-3-yl]-2-[4-(3-methoxy-phenoxy)-2-oxo-2,5-dihydro-pyrrol-1-yl]-propionamide (202 mg, 45%) as a clear oil: LR-ES-MS m/z calculated for $C_{29}H_{38}N_4O_6$ [M]+ 538, observed 539 [M+H]+.

A solution of (S)-3-cyclohexyl-N-[1-((R)-2,2-dimethyl-[1,3]dioxolan-4-yl-methyl)-1H-pyrazol-3-yl]-2-[4-(3-methoxy-phenoxy)-2-oxo-2,5-dihydro-pyrrol-1-yl]-propionamide (200 mg, 0.37 mmol) in tetrahydrofuran (10 mL) was treated with 2N aqueous hydrochloric acid solution (10 mL). The reaction mixture was stirred at 25° C. for 3 h. The reaction mixture was diluted with ethyl acetate, washed with water, saturated sodium bicarbonate solution, a saturated sodium chloride solution and dried over magnesium sulfate. The organic layer was concentrated to afford, (S)-3-cyclohexyl-N-[1-((R)-2,3-dihydroxy-propyl)-1H-pyrazol-3-yl]-2-[4-(3-methoxy-phenoxy)-2-oxo-2,5-dihydro-pyrrol-1-yl]-propionamide (145 mg, 78%) as a white solid: LR-ES-MS m/z calculated for $C_{26}H_{34}N_4O_6$ [M]+ 498, observed 499 [M+H]+; 1H NMR (300 MHz, DMSO-$d_6$ δ ppm 0.83-1.03 (m, 2H), 1.03-1.29 (m, 4H), 1.51-1.83 (m, 7H), 3.19-3.32 (m, 2H), 3.77 (s, 4H), 3.81-3.93 (m, 1H), 4.09 (dd, J=13.7, 3.8 Hz, 1H), 4.16 (d, J=18.4 Hz, 1H), 4.55 (d, J=18.4 Hz, 1H), 4.71 (t, J=5.4 Hz, 1H), 4.84-4.92 (m, 2H), 4.94 (d, J=5.4 Hz, 1H), 6.40 (d, J=2.1 Hz, 1H), 6.86 (d, J=2.1 Hz, 1H), 6.89 (s, 2H), 7.30-7.46 (m, 1H), 7.53 (d, J=2.1 Hz, 1H), 10.74 (s, 1H).

Example 165

(S)-2-[4-(3-Methoxy-phenoxy)-2-oxo-2,5-dihydro-pyrrol-1-yl]-4-methyl-pentanoic acid [1-(2-hydroxy-2-methyl-propyl)-1H-pyrazol-3-yl]-amide

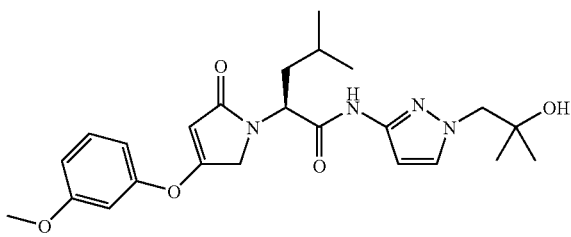

A solution of (S)-2-[4-(3-methoxy-phenoxy)-2-oxo-2,5-dihydro-pyrrol-1-yl]-4-methyl-pentanoic acid (prepared as in Example 160, 300 mg, 0.94 mmol) in dichloromethane (20 mL) was treated with 1-(3-dimethylaminopropyl)-3-ethyl-carbodiimide (161 mg, 1.03 mmol) and 1-hydroxybenzotriazole (135 mg, 0.99 mmol). The reaction mixture was stirred at 25° C. for 1 h followed by the addition of 1-(3-amino-pyrazol-1-yl)-2-methyl-propan-2-ol (prepared in U.S. Pat. Appl. US2008021032 Example 80, 175 mg, 1.13 mmol). The reaction mixture was stirred for 18 h at 25° C., under nitrogen. The reaction mixture was diluted with dichloromethane, washed with 2N hydrochloric acid, saturated sodium bicarbonate solution, a saturated sodium chloride solution and dried over magnesium sulfate. The crude product obtained after concentration, was purified by ISCO flash chromatography (Teledyne Isco RediSep Flash Column 40 g; 0% to 10% methanol/dichloromethane) to afford (S)-2-[4-(3-methoxy-phenoxy)-2-oxo-2,5-dihydro-pyrrol-1-yl]-4-methyl-pentanoic acid [1-(2-hydroxy-2-methyl-propyl)-1H-pyrazol-3-yl]-amide (340 mg, 79%) as a light brown powder: HR-ES-MS m/z calculated for $C_{24}H_{32}N_4O_5$ [M+H]$^+$ 456, observed 457; $^1$H NMR (300 MHz, DMSO-d$_6$) δ ppm 0.90 (d, J=6.3 Hz, 3H), 0.93 (d, J=6.3 Hz, 3H), 1.04 (br. s., 3H), 1.06 (br. s., 3H), 1.39-1.64 (m, 2H), 1.67-1.82 (m, 1H), 3.77 (s, 3H), 3.89 (s, 2H), 4.16 (d, J=18.4 Hz, 1H), 4.57 (d, J=18.4 Hz, 1H), 4.68 (s, 1H), 4.84-4.93 (m 1H), 4.87 (s, 1H), 6.44 (d, J=2.1 Hz, 1H), 6.83-6.91 (m, 3H), 7.37 (t, J=8.2 Hz, 1H), 7.53 (d, J=2.1 Hz, 1H), 10.79 (s, 1H).

Example 166

(S)-2-[4-(2-Fluoro-phenoxy)-2-oxo-2,5-dihydro-pyrrol-1-yl]-4-methyl-pentanoic acid [1-((R)-2,3-dihydroxy-propyl)-1H-pyrazol-3-yl]-amide

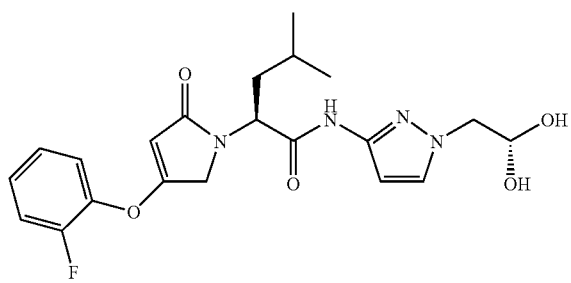

To a stirred mixture of 2-fluorophenol (5.00 g, 44.60 mmol) and ethyl-2-butynoate (10.0 g, 89.20 mmol) in tetrahydrofuran (50 mL) was added 1,8-diazabicyclo[5.4.0]undec-7-ene (6.79 g, 44.60 mmol). After addition was complete the mixture was stirred at 130° C. for 2 h. Upon completion of the reaction the tetrahydrofuran was removed in vacuo and the residue redissolved in dichloromethane and washed with 2N hydrochloric acid, 5% aqueous sodium hydroxide solution, a saturated sodium chloride solution and dried over magnesium sulfate. The crude product obtained was purified by ISCO flash chromatography (Teledyne Isco RediSep Flash Column 120 g; 0% to 50% ethyl acetate/hexanes) to afford, 3-(2-fluoro-phenoxy)-but-2-enoic acid ethyl ester (5.86 g, 59%) as a colorless oil: LR-ES-MS m/z calculated for $C_{12}H_{13}FO_3$ [M]$^+$ 224, observed 225 [M+H]$^+$.

To a stirred mixture of 3-(2-fluoro-phenoxy)-but-2-enoic acid ethyl ester (5.85 g, 26.12 mmol) dissolved in carbon tetrachloride (40 mL) under a nitrogen atmosphere was added N-bromosuccinimide (5.11 g, 28.73 mmol) and benzoyl peroxide (0.68 g, 2.09 mmol). After addition was complete the mixture was stirred at reflux for 16 h. The reaction mixture was then placed in the refrigerator overnight. The solids formed were removed by filtration and the filtrate concentrated in vacuo. The crude product obtained was purified by ISCO flash chromatography (Teledyne Isco RediSep Flash Column 120 g; 0% to 50% ethyl acetate/hexanes) to afford, 4-bromo-3-(2-fluoro-phenoxy)-but-2-enoic acid ethyl ester (6.45 g, 82%) as a yellow oil: LR-ES-MS m/z calculated for $C_{12}H_{12}BrFO_3$ [M]$^+$ 302, observed 303 [M+H]$^+$.

To a stirred mixture of (L)-leucine methyl ester hydrochloride (1.32 g, 7.28 mmol) dissolved in acetonitrile (20 mL) under a nitrogen atmosphere was added N,N-diisopropylethylamine (0.96 g, 7.45 mmol). After addition was complete the mixture was stirred at 60° C. for 1 h. The reaction was cooled to 25° C. and treated with N,N-diisopropylethylamine (0.96 g, 7.45 mmol) and acetonitrile (20 mL) and heated to 80° C. at which time 4-bromo-3-(2-fluoro-phenoxy)-but-2-enoic acid ethyl ester (2.00 g, 6.62 mmol) in acetonitrile (20 mL) was added slowly. After the addition was complete the reaction mixture was heated to 100° C. and stirred overnight. The reaction mixture was cooled to 25° C., filtered and concentrated. The residue was diluted with dichloromethane and washed with 2N hydrochloric acid, a saturated sodium bicarbonate solution, a saturated sodium chloride solution and dried over magnesium sulfate. The crude product obtained was purified by ISCO flash chromatography (Teledyne Isco RediSep Flash Column 40 g; 0% to 80% ethyl acetate/hexanes) to afford, (S)-2-[4-(2-fluoro-phenoxy)-2-oxo-2,5-dihydro-pyrrol-1-yl]-4-methyl-pentanoic acid methyl ester (1.25 g, 59%) as a red oil: LR-ES-MS m/z calculated for $C_{17}H_{20}FNO_4$ [M]$^+$ 321, observed 322 [M+H]$^+$.

To a stirred mixture of (S)-2-[4-(2-fluoro-phenoxy)-2-oxo-2,5-dihydro-pyrrol-1-yl]-4-methyl-pentanoic acid methyl ester (1.25 g, 3.89 mmol) in tetrahydrofuran (15 mL) and water (5 mL) was added lithium hydroxide (0.20 g, 4.67 mmol). After addition was complete the mixture was stirred at 25° C. for 2 h. The reaction mixture was poured into water and diethyl ether and the layers separated. The aqueous layer was made acidic with 2N hydrochloric acid and extracted with ethyl acetate (3×30 mL). The combined ethyl acetate fractions were washed with a saturated sodium chloride solution, dried over magnesium sulfate, filtered and concentrated to afford, (S)-2-[4-(2-fluoro-phenoxy)-2-oxo-2,5-dihydro-pyrrol-1-yl]-4-methyl-pentanoic acid (1.05 g, 88%) as a yellow solid: LR-ES-MS m/z calculated for $C_{16}H_{18}FNO_4[M]^+$ 307, observed 308 $[M+H]^+$.

A solution of (S)-2-[4-(2-fluoro-phenoxy)-2-oxo-2,5-dihydro-pyrrol-1-yl]-4-methyl-pentanoic acid (400 mg, 1.30 mmol) in dichloromethane (20 mL) was treated with 1-(3-dimethylaminopropyl)-3-ethylcarbodiimide (220 mg, 1.43 mmol) and 1-hydroxybenzotriazole (185 mg, 1.36 mmol). The reaction mixture was stirred at 25° C. for 2 h followed by the addition of 1-((R)-2,2-dimethyl-[1,3]dioxolan-4-yl-methyl)-1H-pyrazol-3-ylamine (prepared as in Example 49, 308 mg, 1.56 mmol). The reaction mixture was stirred for 18 h at 25° C., under nitrogen. The reaction mixture was diluted with dichloromethane, washed with 2N hydrochloric acid, saturated sodium bicarbonate solution, a saturated sodium chloride solution and dried over magnesium sulfate. The organic layer was concentrated, and the crude product was purified by ISCO flash chromatography (Teledyne Isco RediSep Flash Column 12 g; 0% to 100% ethyl acetate/hexanes) to afford, (S)-2-[4-(2-fluoro-phenoxy)-2-oxo-2,5-dihydro-pyrrol-1-yl]-4-methyl-pentanoic acid [1-((R)-2,2-dimethyl-[1,3]dioxolan-4-yl-methyl)-1H-pyrazol-3-yl]-amide (362 mg, 57%) as a yellow oil: LR-ES-MS m/z calculated for $C_{25}H_{31}FN_4O_5$ $[M]^+$ 486, observed 487 $[M+H]^+$.

A solution of (S)-2-[4-(2-fluoro-phenoxy)-2-oxo-2,5-dihydro-pyrrol-1-yl]-4-methyl-pentanoic acid [1-((R)-2,2-dimethyl-[1,3]dioxolan-4-yl-methyl)-1H-pyrazol-3-yl]-amide (362 mg, 0.74 mmol) in tetrahydrofuran (10 mL) was treated with 2N aqueous hydrochloric acid solution (10 mL). The reaction mixture was stirred at 25° C. for 4 h. The reaction mixture was diluted with ethyl acetate, washed with water, saturated sodium bicarbonate solution, a saturated sodium chloride solution and dried over magnesium sulfate. The organic layer was concentrated to afford, (S)-2-[4-(2-fluoro-phenoxy)-2-oxo-2,5-dihydro-pyrrol-1-yl]-4-methyl-pentanoic acid [1-((R)-2,3-dihydroxy-propyl)-1H-pyrazol-3-yl]-amide (250 mg, 75%) as a white solid: LR-ES-MS m/z calculated for $C_{22}H_{27}FN_4O_5$ $[M]^+$ 446, observed 447 $[M+H]^+$; $^1$H NMR (300 MHz, DMSO-$d_6$) δ ppm 0.90 (d, J=6.5 Hz, 3H), 0.94 (d, J=6.5 Hz, 3H), 1.37-1.51 (m, 1H), 1.51-1.66 (m, 1H), 1.66-1.86 (m, 1H), 3.19-3.32 (m, 2H), 3.70-3.82 (m, 1H), 3.86 (dd, J=13.6, 7.5 Hz, 1H), 4.09 (dd, J=13.6, 3.6 Hz, 1H), 4.22 (d, J=18.4 Hz, 1H), 4.60 (d, J=18.4 Hz, 1H), 4.71 (t, J=5.6 Hz, 1H), 4.87 (s, 1H), 4.86-4.92 (m, 1H), 4.94 (d, J=5.4 Hz, 1H), 6.41 (d, J=1.8 Hz, 1H), 7.25-7.51 (m, 4H), 7.53 (s, 1H), 10.77 (s, 1H).

Example 167

(S)-2-[4-(2-Fluoro-phenoxy)-2-oxo-2,5-dihydro-pyrrol-1-yl]-4-methyl-pentanoic acid [1-(2-hydroxy-2-methyl-propyl)-1H-pyrazol-3-yl]-amide

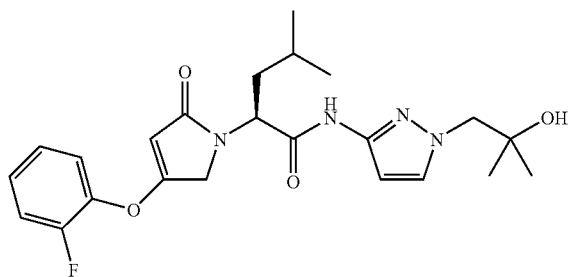

A solution of (S)-2-[4-(2-fluoro-phenoxy)-2-oxo-2,5-dihydro-pyrrol-1-yl]-4-methyl-pentanoic acid (prepared as in Example 166, 200 mg, 0.65 mmol) in dichloromethane (20 mL) was treated with 1-(3-dimethylaminopropyl)-3-ethylcarbodiimide (110 mg, 0.72 mmol) and 1-hydroxybenzotriazole (93 mg, 0.68 mmol). The reaction mixture was stirred at 25° C. for 1 h followed by the addition of 1-(3-amino-pyrazol-1-yl)-2-methyl-propan-2-ol (prepared in U.S. Pat. Appl. US2008021032 Example 80, 121 mg, 0.78 mmol). The reaction mixture was stirred for 18 h at 25° C., under nitrogen. The reaction mixture was diluted with dichloromethane, washed with 2N hydrochloric acid, saturated sodium bicarbonate solution, a saturated sodium chloride solution and dried over magnesium sulfate. The crude product obtained after concentration, was purified by ISCO flash chromatography (Teledyne Isco RediSep Flash Column 40 g; 0% to 10% methanol/dichloromethane) to afford (S)-2-[4-(2-fluoro-phenoxy)-2-oxo-2,5-dihydro-pyrrol-1-yl]-4-methyl-pentanoic acid [1-(2-hydroxy-2-methyl-propyl)-1H-pyrazol-3-yl]-amide (177 mg, 74%) as a light yellow powder: LR-ES-MS m/z calculated for $C_{23}H_{29}FN_4O_4$ $[M+H]^+$ 444, observed 445; $^1$H NMR (300 MHz, DMSO-$d_6$) δ ppm 0.90 (d, J=6.3 Hz, 3H), 0.93 (d, J=6.3 Hz, 3H), 1.05 (br. s., 3H), 1.06 (br. s., 3H), 1.37-1.65 (m, 2H), 1.69-1.84 (m, 1H), 3.89 (s, 2H), 4.22 (d, J=18.4 Hz, 1H), 4.61 (d, J=18.4 Hz, 1H), 4.68 (s, 1H), 4.86 (s, 1H), 4.87-4.93 (m, 1H), 6.44 (d, J=1.8 Hz, 1H), 7.25-7.52 (m, 4H), 7.53 (d, J=1.8 Hz, 1H), 10.80 (s, 1H).

Example 168

(S)-2-[4-(2-Fluoro-phenoxy)-2-oxo-2,5-dihydro-pyrrol-1-yl]-4-methyl-pentanoic acid [1-((R)-2,3-dihydroxy-propyl)-1H-pyrazol-3-yl]-amide

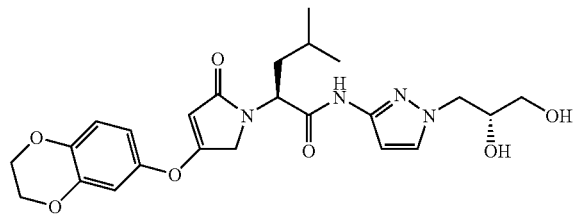

To a stirred mixture of 2,3-dihydro-1,4-benzodioxin-6-ol (1.00 g, 6.58 mmol) and ethyl-2-butynoate (1.48, 13.16 mmol) in tetrahydrofuran (15 mL) was added 1,8-diazabicyclo[5.4.0]undec-7-ene (1.0 g, 6.58 mmol). After addition was complete the mixture was stirred at 130° C. for 2 h. Upon completion of the reaction the tetrahydrofuran was removed in vacuo and the residue redissolved in dichloromethane and washed with 2N hydrochloric acid, 5% aqueous sodiuhydroxide solution, a saturated sodium chloride solution and dried over magnesium sulfate. The crude product obtained was purified by ISCO flash chromatography (Teledyne Isco RediSep Flash Column 40 g; 0% to 50% ethyl acetate/hexanes) to afford, 3-(2,3-dihydro-benzo[1,4]dioxin-6-yloxy)-but-2-enoic acid ethyl ester (0.58 g, 33%) as a colorless oil: LR-ES-MS m/z calculated for $C_{14}H_{16}O_5$ $[M]^+$ 264, observed 265 $[M+H]^+$. m To a stirred mixture of 3-(2,3-dihydro-benzo[1,4]dioxin-6-yloxy)-but-2-enoic acid ethyl ester (0.58 g, 2.20 mmol) dissolved in carbon tetrachloride (20 mL) under a nitrogen atmosphere was added N-bromosuccinimide (0.43 g, 2.42 mmol) and benzoyl peroxide (0.057 g, 0.0002 mol). After addition was complete the mixture was stirred at reflux for 16 h. The reaction mixture was then placed in the refrigerator overnight. The solids formed were removed by filtration and the filtrate concentrated in vacuo. The crude product obtained was purified by ISCO flash chromatography (Teledyne Isco RediSep Flash Column 120 g; 0% to 50% ethyl acetate/hexanes) to afford, 4-bromo-3-(2,3-dihydro-benzo[1,4]dioxin-6-yloxy)-but-2-enoic acid ethyl ester (0.69 g, 92%) as a yellow oil: LR-ES-MS m/z calculated for $C_{14}H_{15}BrO_5$ [M]$^+$ 342, observed 343 [M+H]$^+$.

To a stirred mixture of (L)-leucine methyl ester hydrochloride (0.40 g, 2.22 mmol) dissolved in acetonitrile (20 mL) under a nitrogen atmosphere was added N,N-diisopropylethylamine (0.30 g, 2.72 mmol). After addition was complete the mixture was stirred at 60° C. for 1 h. The reaction was cooled to 25° C. and treated with N,N-diisopropylethylamine (0.29 g, 2.72 mmol) and acetonitrile (20 mL) and heated to 80° C. at which time 4-bromo-3-(2,3-dihydro-benzo[1,4]dioxin-6-yloxy)-(but-2-enoic acid ethyl ester (69 g, 2.02 mmol) in acetonitrile (20 mL) was added slowly. After the addition was complete the reaction mixture was heated to 100° C. and stirred overnight. The reaction mixture was cooled to 25° C., filtered and concentrated. The residue was diluted with dichloromethane and washed with 2N hydrochloric acid, a saturated sodium bicarbonate solution, a saturated sodium chloride solution and dried over magnesium sulfate. The crude product obtained was purified by ISCO flash chromatography (Teledyne Isco RediSep Flash Column 40 g; 20% to 100% ethyl acetate/hexanes) to afford, (S)-2-[4-(2,3-dihydro-benzo[1,4]dioxin-6-yloxy)-2-oxo-2,5-dihydro-pyrrol-1-yl]-4-methyl-pentanoic acid methyl ester (0.38 g, 52%) as a yellow oil: LR-ES-MS m/z calculated for $C_{19}H_{23}NO_6$ [M]$^+$ 361, observed 362 [M+H]$^+$.

To a magnetically stirred mixture of (S)-2-[4-(2,3-dihydro-benzo[1,4]dioxin-6-yloxy)-2-oxo-2,5-dihydro-pyrrol-1-yl]-4-methyl-pentanoic acid methyl ester (0.38 g, 1.05 mmol) in tetrahydrofuran (152 mL) and water (4 mL) was added lithium hydroxide (0.05 g, 1.05 mmol). After addition was complete the mixture was stirred at 25° C. for 2 h. The reaction mixture was poured into water and diethyl ether and the layers separated. The aqueous layer was made acidic with 2N hydrochloric acid and extracted with ethyl acetate (3×30 mL). The combined ethyl acetate fractions were washed with a saturated sodium chloride solution, dried over magnesium sulfate, filtered and concentrated to afford, (S)-2-[4-(2,3-dihydro-benzo[1,4]dioxin-6-yloxy)-2-oxo-2,5-dihydro-pyrrol-1-yl]-4-methyl-pentanoic acid (0.22 g, 60%) as an off-white solid: LR-ES-MS m/z calculated for $C_{18}H_{21}NO_6$ [M]$^+$ 347, observed 348 [M+H]$^+$.

A solution of (S)-2-[4-(2,3-dihydro-benzo[1,4]dioxin-6-yloxy)-2-oxo-2,5-dihydro-pyrrol-1-yl]-4-methyl-pentanoic acid (215 mg, 0.62 mmol) in dichloromethane (10 mL) was treated with 1-(3-dimethylaminopropyl)-3-ethylcarbodiimide (106 mg, 0.68 mmol), 1-hydroxybenzotriazole (92 mg, 0.68 mmol) and 1-((R)-2,2-dimethyl-[1,3]dioxolan-4-yl-methyl)-1H-pyrazol-3-ylamine (prepared as in Example 49, 146 mg, 0.74 mmol). The reaction mixture was stirred for 18 h at 25° C., under nitrogen. The reaction mixture was diluted with dichloromethane, washed with saturated ammonium chloride solution, saturated sodium bicarbonate solution, a saturated sodium chloride solution and dried over magnesium sulfate. The organic layer was concentrated, and the crude product was purified by ISCO flash chromatography (Teledyne Isco RediSep Flash Column 40 g; 20% to 100% ethyl acetate/hexanes) to afford, (S)-2-[4-(2,3-dihydro-benzo[1,4]dioxin-6-yloxy)-2-oxo-2,5-dihydro-pyrrol-1-yl]-4-methyl-pentanoic acid [1-((R)-2,2-dimethyl-[1,3]dioxolan-4-yl-methyl)-1H-pyrazol-3-yl]-amide (225 mg, 69%) as a white solid: LR-ES-MS m/z calculated for $C_{27}H_{34}N_4O_7$ [M]$^+$ 526, observed 527 [M+H]$^+$.

A solution of (S)-2-[4-(2,3-dihydro-benzo[1,4]dioxin-6-yloxy)-2-oxo-2,5-dihydro-pyrrol-1-yl]-4-methyl-pentanoic acid [1-((R)-2,2-dimethyl-[1,3]dioxolan-4-yl-methyl)-1H-pyrazol-yl]-amide (225 mg, 0.43 mmol) in tetrahydrofuran (10 mL) was treated with 2N aqueous hydrochloric acid solution (10 mL). The reaction mixture was stirred at 25° C. for 3 h. The reaction mixture was diluted with ethyl acetate, washed with water, saturated sodium bicarbonate solution, a saturated sodium chloride solution and dried over magnesium sulfate. The organic layer was concentrated to afford, (S)-2-[4-(2,3-dihydro-benzo[1,4]dioxin-6-yloxy)-2-oxo-2,5-dihydro-pyrrol-1-yl]-4-methyl-pentanoic acid [1-((R)-2,3-dihydroxy-propyl)-1H-pyrazol-3-yl]-amide (170 mg, 82%) as a white solid: LR-ES-MS m/z calculated for $C_{24}C_{30}N_4O_7$ [M]$^+$ 486, observed 487 [M+H]$^+$; $^1$H NMR (300 MHz, DMSO-$d_6$) δ ppm 0.89 (d, J=6.6 Hz, 3H), 0.93 (d, J=6.6 Hz, 3H), 1.45 (br. s., 1H), 1.50-1.63 (m, 1H), 1.63-1.81 (m, 1H), 3.20-3.32 (m, 2H), 3.67-3.81 (m, 1H), 3.86 (dd, J=13.3, 7.2 Hz, 1H), 3.98-4.18 (m, 2H), 4.25 (s, 4H), 4.51 (d, J=18.1 Hz, 1H), 4.71 (t, J=5.6 Hz, 1H), 4.80 (s, 1H), 4.86 (dd, J=10.7, 4.7 Hz, 1H), 4.94 (d, J=5.1 Hz, 1H), 6.40 (d, J=2.1 Hz, 1H), 6.76 (dd, J=8.8, 2.7 Hz, 1H), 6.84 (d, J=2.7 Hz, 1H), 6.92 (d, J=8.8 Hz, 1H), 7.53 (d, J=2.1 Hz, 1H), 10.75 (s, 1H).

Example 169

2-[4-(2-chloro-phenoxy)-2-oxo-2,5-dihydro-pyrrol-1-yl]-3-cyclobutyl-N-[1-((R)-2,3-dihydroxy-propyl)-1H-pyrazol-3-yl]-propionamide

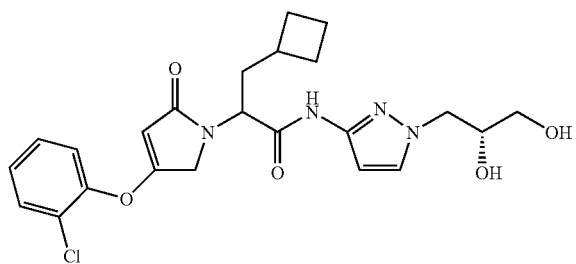

To a stirred mixture of N-(diphenylmethylene)-glycine ethyl ester (4.00 g, 14.96 mmol) in N,N-dimethylformamide (20 mL) at 0° C. was added potassium t-butoxide (1.85 g, 16.46 mmol) portionwise. After addition was complete the mixture was stirred at 0° C. for 15 min followed by the addition of bromomethyl-cyclobutane (2.45 g, 16.46 mmol). The reaction mixture was allowed to warm to room temperature and stirred for 3 h. Upon completion of the reaction the mixture was poured into ethyl acetate and washed with a saturated ammonium chloride solution, water and a saturated sodium chloride solution and then dried over magnesium sulfate. The crude product obtained was purified by ISCO flash chromatography (Teledyne Isco RediSep Flash Column 120 g; 0% to 50% ethyl acetate/hexanes) to afford, 2-(benzhydrylidene-amino)-3-cyclobutyl-propionic acid ethyl ester (3.06 g, 61%) a light yellow oil: LR-ES-MS m/z calculated for $C_{22}H_{25}NO_2$ $[M]^+$ 335, observed 336 $[M+H]^+$.

To a stirred mixture of 2-(benzhydrylidene-amino)-3-cyclobutyl-propionic acid ethyl ester (3.06 g, 9.13 mmol) in methyl t-butyl ether (15 mL) was added a 1N aqueous hydrochloric acid solution (18 mL). The reaction mixture was allowed to stir at 25° C. for 16 h. Upon completion of the reaction the mixture was poured into water and methyl t-butyl ether. The layers were separated and the organic layer discarded. To the aqueous layer was added solid sodium bicarbonate (3.07 g, 36.54 mmol) and the reaction mixture stirred at 25° C. for 1 h. The reaction mixture was then poured into water and diethyl ether and the layers separated. The aqueous layer was washed twice with diethyl ether. The combined organic layers are washed with a saturated sodium chloride solution and then dried over magnesium sulfate. The crude product obtained, 2-amino-3-cyclobutyl-propionic acid ethyl ester (1.15 g, 74%) was a clear colorless oil and used without further purification: LR-ES-MS m/z calculated for $C_9H_{17}NO_2$ $[M]^+$ 171, observed 172 $[M+H]^+$ To a stirred mixture of 2-amino-3-cyclobutyl-propionic acid ethyl ester (1.15 g, 6.73 mmol) dissolved in acetonitrile (20 mL) under a nitrogen atmosphere was added N,N-diisopropylethylamine (1.03 g, 7.96 mmol). After addition was complete the mixture was warmed to 80° C. at which time 4-bromo-3-(2-chloro-phenoxy)-but-2-enoic acid ethyl ester (prepared as in Example 61, 1.95 g, 6.12 mmol) in acetonitrile (20 mL) was added slowly. After the addition was complete the reaction mixture was heated to 100° C. and stirred overnight. The reaction mixture was cooled to 25° C., filtered and concentrated. The residue was diluted with dichloromethane and washed with 2N hydrochloric acid, a saturated sodium bicarbonate solution, a saturated sodium chloride solution and dried over magnesium sulfate. The crude product obtained was purified by ISCO flash chromatography (Teledyne Isco RediSep Flash Column 40 g; 0% to 80% ethyl acetate/hexanes) to afford, 2-[4-(2-chloro-phenoxy)-2-oxo-2,5-dihydro-pyrrol-1-yl]-3-cyclobutyl-propionic acid ethyl ester (1.51 g, 68%) as a yellow oil: LR-ES-MS m/z calculated for $C_{19}H_{22}ClNO_4$ $[M]^+$ 363, observed 364 $[M+H]^+$.

To a stirred mixture of 2-[4-(2-chloro-phenoxy)-2-oxo-2,5-dihydro-pyrrol-1-yl]-3-cyclobutyl-propionic acid ethyl ester (1.51 g, 4.15 mmol) in tetrahydrofuran (15 mL) and water (5 mL) was added lithium hydroxide (0.21 g, 4.98 mmol). After addition was complete the mixture was stirred at 25°C. for 2 h. The reaction mixture was poured into water and diethyl ether and the layers separated. The aqueous layer was made acidic with 2N hydrochloric acid and extracted with ethyl acetate (3×30 mL). The combined ethyl acetate fractions were washed with a saturated sodium chloride solution, dried over magnesium sulfate, filtered and concentrated to afford, 2-[4-(2-chloro-phenoxy)-2-oxo-2,5-dihydro-pyrrol-1-yl]-3-cyclobutyl-propionic acid (1.13 g, 98%) as a yellow solid: LR-ES-MS m/z calculated for $C_{18}H_{20}ClNO_4$ $[M]^+$ 349, observed 350 $[M+H]^+$.

A solution of 2-[4-(2-chloro-phenoxy)-2-oxo-2,5-dihydro-pyrrol-1-yl]-3-cyclobutyl-propionic acid (1130 mg, 3.23 mmol) in dichloromethane (20 mL) was treated with 1-(3-dimethylaminopropyl)-3-ethylcarbodiimide (555 mg, 3.56 mmol), 1-hydroxybenzotriazole (460 mg, 3.39 mmol) and 1-((R)-2,2-dimethyl-[1,3]dioxolan-4-yl-methyl)-1H-pyrazol-3-ylamine (prepared as in Example 49, 765 mg, 3.88 mmol). The reaction mixture was stirred for 18 h at 25° C., under nitrogen. The reaction mixture was diluted with dichloromethane, washed with 2N hydrochloric acid, saturated sodium bicarbonate solution, a saturated sodium chloride solution and dried over magnesium sulfate. The organic layer was concentrated, and the crude product was purified by ISCO flash chromatography (Teledyne Isco RediSep Flash Column 40 g; 0% to 100% ethyl acetate/hexanes) to afford, 2-[4-(2-chloro-phenoxy)-2-oxo-2,5-dihydro-pyrrol-1-yl]-3-cyclobutyl-propionic acid [1-((R)-2,2-dimethyl-[1,3]dioxolan-4-yl-methyl)-1H-pyrazol-3yl]-amide (720 mg, 42%) as a white solid: LR-ES-MS m/z calculated for $C_{26}H_{31}ClN_4O_5$ $[M]^+$ 514, observed 515 $[M+H]^+$.

A solution of 2-[4-(2-chloro-phenoxy)-2-oxo-2,5-dihydro-pyrrol-1-yl]-3-cyclobutyl-propionic acid [1-((R)-2,2-dimethyl-[1,3]dioxolan-4-yl-methyl)-1H-pyrazol-3-yl]-amide (720 mg, 1.39 mmol) in tetrahydrofuran (15 mL) was treated with 2N aqueous hydrochloric acid solution (15 mL). The reaction mixture was stirred at 25°C. for 3 h. The reaction mixture was diluted with ethyl acetate, washed with water, saturated sodium bicarbonate solution, a saturated sodium chloride solution and dried over magnesium sulfate. The organic layer was concentrated to afford, 2-[4-(2-chloro-phenoxy)-2-oxo-2,5-dihydro-pyrrol-1-yl]-3-cyclobutyl-N-[1-((R)-2,3-dihydroxy-propyl)-1H-pyrazol-3-yl]-propionamide (580 mg, 87%) as a white solid: LR-ES-MS m/z calculated for $C_{23}H_{27}ClN_4O_6$ $[M]^+$ 474, observed 475 $[M+H]^+$; $^1$H NMR (300 MHz, DMSO-$d_6$) δ ppm 1.56-1.95 (m, 7H), 1.95-2.11 (m, 1H), 2.18 (br. s., 1H), 3.22-3.33 (m, 2H), 3.70-3.95 (m, 2H), 3.97-4.14 (m, 1H), 4.21 (d, J=18.4 Hz, 1H), 4.57 (d, J=18.4 Hz, 1H), 4.72 (br. s., 2H), 4.78 (br. s., 1H), 4.95 (d, J=4.5 Hz, 1H), 6.41 (br. s., 1H), 7.31-7.57 (m, 4H), 7.65 (d, J=6.9 Hz, 1H), 10.75 (br. s., 1H).

Example 170

2-[4-(2-Chloro-3-methoxyphenoxy)-2-oxo-2,5-dihydro-pyrrol-1-yl]-4-fluoro-4-methyl-pentanoic acid-[1-((R)-2,3-dihydroxy-propyl)-1H-pyrazol-3-yl]-amide

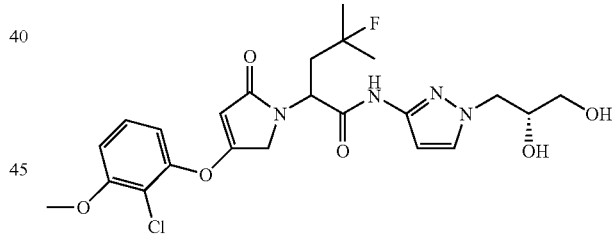

To a stirred mixture of isobutylene oxide (5.00 g, 69.4 mmol) in methyl t-butyl ether (50 mL) at −10° C. was added hydrogen fluoride pyridine complex (4 mL, 138.9 mmol, 70% solution) slowly. After addition was complete the reaction mixture was allowed to warm to room temperature and stirred for 16 h. Upon completion of the reaction the mixture was poured into water and the layers separated. The organic layer was neutralized with a saturated sodium bicarbonate solution and then washed with a saturated sodium chloride solution and then dried over magnesium sulfate. The crude product obtained, 2-fluoro-2-methyl-propan-1-ol (2.56 g, 40%) as a clear colorless oil was used without further purification.

To a stirred mixture of 2-fluoro-2-methyl-propan-1-ol (2.56 g, 27.83 mmol) in methyl t-butyl ether (15 mL) at −10° C. was added triethylamine (3.1 g, 30.61 mmol) and trifluoromethane sulfonic anhydride (8.64 g, 30.61 mmol). After addition was complete the reaction mixture was stirred at 0° C. for 2 h. Upon completion of the reaction the mixture was diluted with methyl t-butyl ether and poured onto ice and then treated with 1N aqueous hydrochloric acid solution. The layers were separated and the organic layer was washed with a saturated sodium bicarbonate solution, a saturated sodium chloride solution and then dried over magnesium sulfate. The mixture was filtered and evaporated to afford trifluoro-methanesulfonic acid 2-fluoro-2-methyl-propyl ester (4.23 g, 68%) as a red oil and was used without further purification.

To a stirred mixture of N-(diphenylmethylene)-glycine ethyl ester (4.55 g, 17.06 mmol) in N,N-dimethylformamide (20 mL) at 0° C. was added potassium t-butoxide (2.10 g, 18.75 mmol) portionwise. After addition was complete the mixture was stirred at 0° C. for 15 min followed by the addition of trifluoro-methanesulfonic acid 2-fluoro-2-methyl-propyl ester (4.20 g, 18.75 mmol). The reaction mixture was allowed to warm to room temperature and stirred for 3 h. Upon completion of the reaction the mixture was poured into methyl t-butyl ether and washed with a saturated ammonium chloride solution, water and a saturated sodium chloride solution and then dried over magnesium sulfate. The crude product obtained was purified by ISCO flash chromatography (Teledyne Isco RediSep Flash Column 120 g; 0% to 50% ethyl acetate/hexanes) to afford, 2-(benzhydrylidene-amino)-4-fluoro-4-methyl-pentanoic acid ethyl ester (2.00 g, 34%) a light yellow oil: LR-ES-MS m/z calculated for $C_{21}H_{25}FNO_2$ [M]+ 342, observed 343 [M+H]+.

To a stirred mixture of 2-(benzhydrylidene-amino)-4-fluoro-4-methyl-pentanoic acid ethyl ester (2.00 g, 5.90 mmol) in methyl t-butyl ether (10 mL) was added a 1N aqueous hydrochloric acid solution (12 mL). The reaction mixture was allowed to stir at 25° C. for 16 h. Upon completion of the reaction the mixture was poured into water and methyl t-butyl ether. The layers were separated and the organic layer discarded. To the aqueous layer was added solid sodium bicarbonate (3.07 g, 36.54 mmol) and the reaction mixture stirred at 25° C. for 1 h. The reaction mixture was then poured into water and diethyl ether and the layers separated. The aqueous layer was washed twice with diethyl ether. The combined organic layers are washed with a saturated sodium chloride solution and then dried over magnesium sulfate. The crude product obtained, 2-amino-4-fluoro-4-methyl-pentanoic acid ethyl ester (0.66 g, 63%) was a clear colorless oil and used without further purification. LR-ES-MS m/z calculated for $C_8H_{16}FNO_2$ [M]+ 177, observed 178 [M+H]+.

To a stirred mixture of 2-amino-4-fluoro-4-methyl-pentanoic acid ethyl ester (0.66 g, 3.73 mmol) dissolved in acetonitrile (15 mL) under a nitrogen atmosphere was added N,N-diisopropylethylamine (0.57 g, 4.40 mmol). After addition was complete the mixture was heated to 80° C. at which time 4-bromo-3-(2-chloro-3-methoxy-phenoxy)-but-2-enoic acid ethyl ester (prepared as in Example 48, 1.18 g, 3.40 mmol) in acetonitrile (15 mL) was added slowly. After the addition was complete the reaction mixture was heated to 100° C. and stirred for 48 h. The reaction mixture was cooled to 25° C., filtered and concentrated. The residue was diluted with dichloromethane and washed with 2N hydrochloric acid, a saturated sodium bicarbonate solution, a saturated sodium chloride solution and dried over magnesium sulfate. The crude product obtained was purified by ISCO flash chromatography (Teledyne Isco RediSep Flash Column 40 g; 0% to 80% ethyl acetate/hexanes) to afford, 2-[4-(2-chloro-3-methoxy-phenoxy)-2-oxo-2,5-dihydro-pyrrol-1-yl]-4-fluoro-4-methyl-pentanoic acid ethyl ester (0.78 g, 57%) as a yellow oil: LR-ES-MS m/z calculated for $C_{19}H_{23}ClFNO_5$ [M]+ 399, observed 400 [M+H]+.

To a magnetically stirred mixture of 2-[4-(2-chloro-3-methoxy-phenoxy)-2-oxo-2,5-dihydro-pyrrol-1-yl]-4-fluoro-4-methyl-pentanoic acid ethyl ester (775 mg, 1.94 mmol) in tetrahydrofuran (15 mL) and water (5 mL) was added lithium hydroxide (98 mg, 2.33 mmol). After addition was complete the mixture was stirred at 25° C. for 2 h. The reaction mixture was poured into water and diethyl ether and the layers separated. The aqueous layer was made acidic with 2N hydrochloric acid and extracted with ethyl acetate (3×30 mL). The combined ethyl acetate fractions were washed with a saturated sodium chloride solution, dried over magnesium sulfate, filtered and concentrated to afford, 2-[4-(2-chloro-3-methoxy-phenoxy)-2-oxo-2,5-dihydro-pyrrol-1-yl]-4-fluoro-4-methyl-pentanoic acid (537 mg, 75%) as a light brown solid: LR-ES-MS m/z calculated for $C_{17}H_{19}ClFNO_5$ [M]+ 371, observed 372 [M+H]+.

A solution of 2-[4-(2-chloro-3-methoxy-phenoxy)-2-oxo-2,5-dihydro-pyrrol-1-yl]-4-fluoro-4-methyl-pentanoic acid (300 mg, 0.81 mmol) in dichloromethane (20 mL) was treated with 1-(3-dimethylaminopropyl)-3-ethylcarbodiimide (138 mg, 0.90 mmol), 1-hydroxybenzotriazole (115 mg, 0.86 mmol) and 1-((R)-2,2-dimethyl-[1,3]dioxolan-4-yl-methyl)-1H-pyrazol-3-ylamine (prepared as in Example 49, 191 mg, 0.97 mmol). The reaction mixture was stirred for 18 h at 25° C., under nitrogen. The reaction mixture was diluted with dichloromethane, washed with saturated ammonium chloride solution, saturated sodium bicarbonate solution, a saturated sodium chloride solution and dried over magnesium sulfate. The organic layer was concentrated, and the crude product was purified by ISCO flash chromatography (Teledyne Isco RediSep Flash Column 12 g; 0% to 10% methanol/dichloromethane) to afford, 2-[4-(2-chloro-3-methoxy-phenoxy)-2-oxo-2,5-dihydro-pyrrol-1-yl]-4-fluoro-4-methyl-pentanoic acid [1-((R)-2,2-dimethyl-[1,3]dioxolan-4-yl-methyl)-1H-pyrazol-3-yl]-amide (390 mg, 88%) as an off-white solid: LR-ES-MS m/z calculated for $C_{26}H_{32}ClFN_4O_6$ [M]+ 550, observed 551 [M+H]+.

A solution of 2-[4-(2-chloro-3-methoxy-phenoxy)-2-oxo-2,5-dihydro-pyrrol-1-yl]-4-fluoro-4-methyl-pentanoic acid [1-((R)-2,2-dimethyl-[1,3]dioxolan-4-yl-methyl)-1H-pyrazol-3-yl]-amide (390 mg, 0.71 mmol) in tetrahydrofuran (10 mL) was treated with 2N aqueous hydrochloric acid solution (10 mL). The reaction mixture was stirred at 25° C. for 4 h. The reaction mixture was diluted with ethyl acetate, washed with water, saturated sodium bicarbonate solution, a saturated sodium chloride solution and dried over magnesium sulfate. The organic layer was concentrated to afford, 2-[4-(2-chloro-3-ethoxy-phenoxy)-2-oxo-2,5-dihydro-pyrrol-1-yl]-4-fluoro-4-methyl-pentanoic acid [1-((R)-2,3-dihydroxy-propyl)-1H-pyrazol-3-yl]-amide (300 mg, 83%) as a white solid: LR-ES-MS m/z calculated for $C_{23}H_{28}ClFN_4O_6$ [M]+ 510, observed 511 [M+H]+; $^1H$ NMR (300 MHz, DMSO-$d_6$) δ ppm 1.27, 1.32 (2×d, J=3.0 Hz, 3H), 1.36, 1.39 (2×d, J=3.0 Hz, 3H), 1.99-2.34 (m, 2H), 3.19-3.33 (m, 2H), 3.69-3.89 (m, 2H), 3.90 (s, 3H), 4.09 (dd, J=13.6, 3.6 Hz, 1H), 4.26 (d, J=18.4 Hz, 1H), 4.37-4.58 (m, 1H), 4.71 (t, J=5.6 Hz, 1H), 4.77, 4.80 (2×s, 1H), 4.94 (d, J=5.1 Hz, 1H), 5.08 (dd, J=9.5, 4.4 Hz, 1H), 6.41 (d, J=2.1 Hz, 1H), 7.00, 7.06 (2×d, J=8.2 Hz, 1H), 7.13 (d, J=8.2 Hz, 1H), 7.41 (t, J=8.2 Hz, 1H), 7.54 (d, J=2.1 Hz, 1H), 10.68, 10.79 (2×s, 1H)

Example 171

2-[4-(2-Chloro-3-methoxy-phenoxy)-2-oxo-2,5-dihydro-pyrrol-1-yl]-4-fluoro-4-methyl-pentanoic acid [1-(2-hydroxy-2-methyl-propyl)-1H-pyrazol-3-yl]-amide

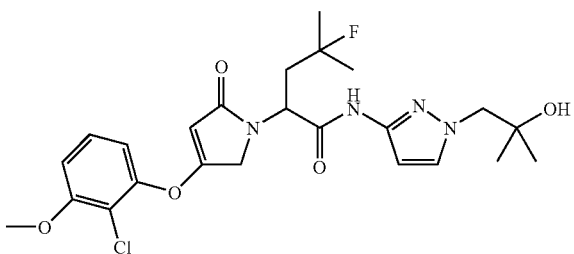

A solution of 2-[4-(2-chloro-3-methoxy-phenoxy)-2-oxo-2,5-dihydro-pyrrol-1-yl]-4-fluoro-4-methyl-pentanoic acid (prepared as in Example 170, 200 mg, 0.54 mmol) in dichloromethane (20 mL) was treated with 1-(3-dimethylaminopropyl)-3-ethylcarbodiimide (92 mg, 0.59 mmol), 1-hydroxybenzotriazole (76 mg, 0.57 mmol) and 1-(3-amino-pyrazol-1-yl)-2-methyl-propan-2-ol (prepared in U.S. Pat. Appl. US2008021032 Example 80, 100 mg, 0.65 mmol). The reaction mixture was stirred for 18 h at 25° C., under nitrogen and then diluted with dichloromethane, washed with 2N hydrochloric acid, saturated sodium bicarbonate solution, a saturated sodium chloride solution and dried over magnesium sulfate. The crude product obtained after concentration, was purified by ISCO flash chromatography (Teledyne Isco RediSep Flash Column 12 g; 0% to 10% methanol/dichloromethane) to afford 2-[4-(2-chloro-3-methoxy-phenoxy)-2-oxo-2,5-dihydro-pyrrol-1-yl]-4-fluoro-4-methyl-pentanoic acid [1-(2-hydroxy-2-methyl-propyl)-1H-pyrazol-3-yl]-amide (156 mg, 57%) as a white powder: LR-ES-MS m/z calculated for $C_{24}H_{30}ClFN_4O_5$ $[M]^+$ 508, observed 509 $[M+H]^+$; $^1H$ NMR (300 MHz, DMSO-$d_6$) δ ppm 1.05 (br. s., 3H), 1.06 (br. s., 3H), 1.19, 1.32 (2×d, J=3.0 Hz, 3H), 1.26, 1.39 (2×d, J=3.0 Hz, 3H), 1.96-2.33 (m, 2H), 3.90 (br. s., 5H), 4.25 (d, J=18.4 Hz, 1H), 4.52 (d, J=18.4 Hz, 1H), 4.67 (s, 1H), 4.77, 4.80 (2×s, 1H), 5.01, 5.10 (2×dd, J=9.8, 4.4 Hz, 1H), 6.44 (d, J=1.8 Hz, 1H), 7.00, 7.06 (2×d, J=8.2 Hz, 1H), 7.13 (d, J=8.2 Hz, 1H), 7.41 (t, J=8.2 Hz, 1H), 7.54 (d, J=1.8 Hz, 1H), 10.71, 10.82 (2×s, 1H).

Example 172

(S)-2-[4-(2-chloro-phenoxy)-2-oxo-2,5-dihydro-pyrrol-1-yl]-4-methyl-pentanoic acid [1-((S)-2-oxo-oxazolidin-5-ylmethyl)-1H-pyrazol-3-yl]-amide

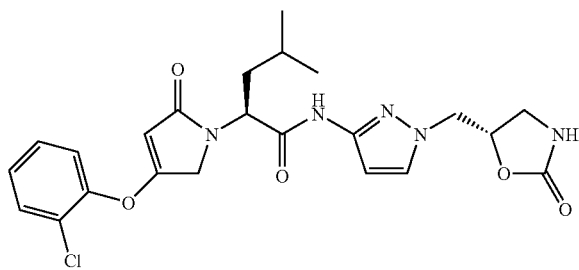

A solution of 3-nitro-1H-pyrazole (prepared as in Example 5, 5.00 g, 44.25 mmol) in N,N-dimethylformamide (20 mL) was treated with potassium carbonate (7.94 g, 57.52 mmol) and (S)-glycidol tosylate (12.12 g, 53.10 mmol). The reaction mixture was stirred for 2 h at 90° C. under nitrogen and then poured into ethyl acetate, washed with water and a saturated sodium chloride solution and dried over magnesium sulfate. The crude product obtained after concentration, was purified by ISCO flash chromatography (Teledyne Isco RediSep Flash Column 330 g; 0% to 80% ethyl acetate/hexanes) to afford 3-nitro-1-(R)-1-oxiranylmethyl-H-pyrazole (3.40 g, 45%) as a yellow oil: HR-ES-MS m/z calculated for $C_6H_7N_3O_3$ $[M]^+$ 169, observed 170 $[M+H]^+$.

A solution of 3-nitro-1-(R)-1-oxiranylmethyl-H-pyrazole (3.40 g, 20.12 mmol) in acetone (25 mL) and water (25 mL) was treated with sodium azide (3.92 g, 60.35 mmol). The reaction mixture was stirred for 2 h at reflux. The acetone was removed under reduced pressure and the mixture was poured into dichloromethane. The layers were separated and the organic layer washed with water and a saturated sodium chloride solution and dried over magnesium sulfate. The crude product obtained after concentration, was purified by ISCO flash chromatography (Teledyne Isco RediSep Flash Column 120 g; 0% to 70% ethyl acetate/hexanes) to afford (R)-1-azido-3-(3-nitro-pyrazole-1-yl)-propan-2-ol (2.75 g, 64%) as a yellow oil: LR-ES-MS m/z calculated for $C_6H_8N_6O_3$ $[M]^+$ 212, observed 213 $[M+H]^+$.

To a refluxing solution of (R)-1-azido-3-(3-nitro-pyrazole-1-yl)-propan-2-ol (2.75 g, 13.00 mmol) in tetrahydrofuran (25 mL) was added sodium borohydride (0.33 g, 8.70 mmol) and methanol (1 mL) dropwise. The reaction mixture was stirred for 24 h at reflux. The reaction mixture was cooled to room temperature and treated with 1N aqueous hydrochloric acid (10 mL). The reaction mixture was then made basic by the addition of 2N sodium hydroxide (10 mL) and poured into ethyl acetate. The layers were separated and the aqueous layer was extracted with dichloromethane four times. The combined organic fractions were washed with a saturated sodium chloride solution and dried over magnesium sulfate. The crude product obtained after concentration, (S)-1-amino-3-(3-nitro-pyrazole-1-yl)-propan-2-ol (0.65 g, 27%) as a yellow solid was used without further purification: LR-ES-MS m/z calculated for $C_6H_{10}N_4O_3$ $[M]^+$ 186, observed 187 $[M+H]^+$.

To a solution of (S)-1-amino-3-(3-nitro-pyrazole-1-yl)-propan-2-ol (0.65 g, 3.49 mmol) in dichloromethane (15 mL) was added di-2-pyridyl carbonate (0.76 g, 3.49 mmol). The reaction mixture was stirred at room temperature for 2 h and then diluted with dichloromethane. The organic layer was washed with a saturated sodium chloride solution and dried over magnesium sulfate. The crude product obtained after concentration, was purified by ISCO flash chromatography (Teledyne Isco RediSep Flash Column 40 g; 0% to 10% methanol/dichloromethane) to afford (S)-5-(3-nitro-pyrazol-1-ylmethyl)-oxazolidin-2-one (0.36 g, 49%) as a clear colorless oil: HR-ES-MS m/z calculated for $C_7H_8N_4O_4$ $[M]^+$ 212, observed 213 $[M+H]^+$.

In a Parr shaker bottle was placed (S)-5-(3-nitro-pyrazol-1-ylmethyl)-oxazolidin-2-one (364 mg, 1.72 mmol), 10% palladium on carbon (200 mg) and ethanol (25 mL). The bottle was then placed on the Parr shaker at 50 psi of hydrogen pressure for 4 h. The reaction was then filtered through a pad of celite and washed with ethanol and concentrated in vacuo to afford (S)-5-(3-amino-pyrazol-1-ylmethyl)-oxazolidin-2-one (3.60 mg, 91%) as a yellow oil: LR-ES-MS m/z calculated for $C_7H_{10}N_4O_2$ $[M]^+$ 182, observed 183 $[M+H]^+$.

A solution of (S)-2-[4-(2-chloro-phenoxy)-2-oxo-2,5-dihydro-pyrrol-1-yl]-4-methyl-pentanoic acid (prepared as in Example 64, 425 mg, 1.30 mmol) in dichloromethane (20 mL) was treated with 1-(3-dimethylaminopropyl)-3-ethylcarbodiimide hydrochloride salt (275 mg, 1.45 mmol), 1-hydroxybenzotriazole (195 mg, 1.45 mmol) and (S)-5-(3-amino-pyrazol-1-ylmethyl)-oxazolidin-2-one (285 mg, 1.57 mmol). The reaction mixture was stirred for 18 h at 25° C., under nitrogen and then diluted with dichloromethane, washed with 2N hydrochloric acid, saturated sodium bicarbonate solution, a saturated sodium chloride solution and dried over magnesium sulfate. The crude product obtained after concentration, was purified by ISCO flash chromatography (Teledyne Isco RediSep Flash Column 40 g; 0% to 10% methanol/dichloromethane) to afford (S)-2-[4-(2-chloro-phenoxy)-2-oxo-2,5-dihydro-pyrrol-1-yl]-4-methyl-pentanoic acid [1-((S)-2-oxo-oxazolidin-5-ylmethyl)-1H-pyrazol-3-yl]-amide (370 mg, 58%) as a white powder: LR-ES-MS m/z calculated for $C_{23}H_{26}ClN_5O_5$ $[M]^+$ 487, observed 488 $[M+H]^+$; $^1H$ NMR (300 MHz, DMSO-$d_6$) δ ppm 0.90 (d, J=6.4 Hz, 3H), 0.94 (d, J=6.4 Hz, 3H), 1.35-1.50 (m, 1H), 1.50-1.66 (m, 1H), 1.68-1.87 (m, 1H), 3.28 (dd, J=8.8, 6.0 Hz, 1 H), 3.55 (t, J=8.9 Hz, 1H), 4.21 (d, J=18.4 Hz, 1H), 4.27 (d, J=5.1 Hz, 2H), 4.61 (d, J=18.4 Hz, 1H), 4.79 (s, 1H), 4.80-4.95 (m, 2H), 6.47 (d, J=2.1 Hz, 1H), 7.37 (td, J=7.8, 1.2 Hz, 1H), 7.42-7.50 (m, 1H), 7.50-7.57 (m, 2H), 7.61 (d, J=2.1 Hz, 1H), 7.65 (d, J=7.8 Hz, 1H), 10.85 (s, 1H).

Example 173

(S)-2-[4-(2-chloro-phenoxy)-2-oxo-2,5-dihydro-pyrrol-1-yl]-4-methyl-pentanoic acid [1-((S)-3-diethylamino-2-hydroxy-propyl)-1H-pyrazol-3-yl]-amide

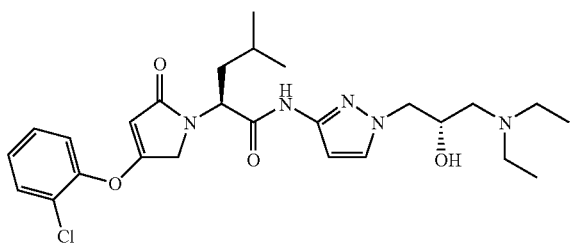

A solution of (S)-2-[4-(2-chloro-phenoxy)-2-oxo-2,5-dihydro-pyrrol-1-yl]-4-methyl-pentanoic acid [1-((R)-2,3-dihydroxy-propyl)-1H-pyrazol-3-yl]-amide (prepared as in Example 66, 500 mg, 1.08 mmol) in dichloromethane (15 mL) was treated with N,N-diisopropylethylamine (280 mg, 2.16 mmol) and 4-(dimethylamino)pyridine (132 mg, 1.08 mmol). p-Toluenesulfonyl chloride (230 mg, 1.19 mmol) dissolved in dichloromethane (10 mL) was added slowly to the reaction mixture. The reaction mixture was stirred for 16 h at room temperature. The reaction mixture was concentrated in vacuo and then diluted with ethyl acetate (60 mL), washed with 1N aqueous hydrochloric acid, a saturated sodium bicarbonate solution, a saturated sodium chloride solution and dried over magnesium sulfate. The crude product obtained after concentration, was purified by ISCO flash chromatography (Teledyne Isco RediSep Flash Column 40 g; 30% to 100% ethyl acetate/hexanes) to afford, toluene-4-sulfonic acid (R)-3-(3-{(S)-2-[4-(2-chloro-phenoxy)-2-oxo-2,5-dihydro-pyrrol-1-yl]-4-pentanoylamino}-pyrazol-1-yl)-2-hydroxy-propyl ester (150 mg, 23%) as a white powder: LR-ES-MS m/z calculated for $C_{29}H_{33}ClN_4O_7S$ $[M]^+$ 616, $[M+H]^+$ observed 617.

A solution of toluene-4-sulfonic acid (R)-3-(3-{(S)-2-[4-(2-chloro-phenoxy)-2-oxo-2,5-dihydro-pyrrol-1-yl]-4-methyl-pentanoylamino}-pyrazol-1-yl)-2-hydroxy-propyl ester (150 mg, 0.24 mmol) in tetrahydrofuran (10 mL) was treated with diethylamine (180 mg, 2.43 mmol). The reaction mixture was stirred for 3 days at 40° C. The reaction mixture was concentrated in vacuo and the crude product obtained was purified by ISCO flash chromatography (Teledyne Isco RediSep Flash Column 12 g; 0% to 10% methanol/dichloromethane) to afford, (S)-2-[4-(2-chloro-phenoxy)-2-oxo-2,5-dihydro-pyrrol-1-yl]-4-methyl-pentanoic acid [1-((S)-3-diethylamino-2-hydroxy-propyl)-1H-pyrazol-3-yl]-amide (22 mg, 17%) as a white powder: $^1H$ NMR (300 MHz, $CDCl_3$) δ ppm 0.82-1.13 (m, 12H), 1.47-1.69 (m, 1H), 1.68-1.95 (m, 2H), 2.23-2.74 (m, 6H), 3.77 (br. s., 1H), 3.88-4.09 (m, 3H), 4.14 (d, J=18.2 Hz, 1H), 4.40 (d, J=18.2 Hz, 1H), 4.91 (br. s., 2H), 6.66 (br. s., 1H), 7.16-7.37 (m, 3H), 7.41 (br. s., 1H), 7.49 (d, J=6.9 Hz, 1H), 8.91 (br. s., 1H).

Example 174

(S)-2-[4-(2-Chloro-phenoxy)-2-oxo-2,5-dihydro-pyrrol-1-yl]-4-methyl-pentanoic acid [1-((S)-2,2-dimethyl-[1,3]dioxolan-4-ylmethyl)-1H-pyrazol-3-yl]-amide

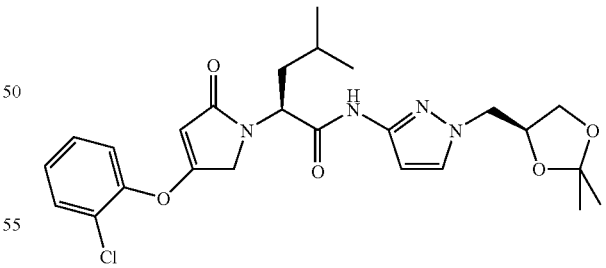

A solution of 3-nitro-1H-pyrazole (prepared as in Example 5, 2.00 g, 17.70 mmol) in N,N-dimethylformamide (20 mL) was treated with potassium carbonate (3.66 g, 26.55 mmol) and (R)-glycidol (2.62 g, 35.40 mmol). The reaction mixture was stirred for 2 h at 100° C. under nitrogen. Upon completion of the reaction the N,N-dimethylformamide was removed under reduced pressure and the crude product obtained was purified by ISCO flash chromatography (Teledyne Isco RediSep Flash Column 40 g; 0% to 10% methanol/dichloromethane) to afford (S)-3-(3-nitro-pyrazol-1-yl)propane-1,2-diol (1.00 g, 30%) as a yellow oil: LR-ES-MS m/z calculated for $C_6H_9N_3O_4$ $[M]^+$ 187, observed 188 $[M+H]^+$.

A solution of (S)-3-(3-nitro-pyrazol-1-yl)propane-1,2-diol (1.00 g, 5.35 mmol) in acetone (10 mL) was treated with concentrated sulfuric acid (5 drops) and 2,2-dimethoxypropane (3.34 g, 32.09 mmol). The reaction mixture was stirred for 5 h at room temperature. Upon completion of the reaction the mixture was concentrated at reduced pressure and then diluted with ethyl acetate, washed with a saturated sodium bicarbonate solution, a saturated sodium chloride solution and dried over magnesium sulfate The crude product obtained was purified by ISCO flash chromatography (Teledyne Isco RediSep Flash Column 40 g; 0% to 80% ethyl acetate/hexanes) to afford 1-((S)-2,2-dimethyl-[1,3]dioxolan-4-yl-methyl)-3-nitro-1H-pyrazole (0.70 g, 58%) as a yellow oil: LR-ES-MS m/z calculated for $C_9H_{13}N_3O_4$ $[M]^+$ 227, observed 228 $[M+H]^+$.

In a Parr shaker bottle was placed 1-((S)-2,2-dimethyl-[1,3]dioxolan-4-yl-methyl)-3-nitro-1H-pyrazole (700 mg, 3.08 mmol), 10% palladium on carbon (500 mg) and ethanol (25 mL). The bottle was then placed on the Parr shaker at 50 psi of hydrogen pressure for 4 h. The reaction was then filtered through a pad of celite and washed with ethanol and concentrated in vacuo to afford 1-((S)-2,2-dimethyl-[1,3]dioxolan-4-yl-methyl)-1H-pyrazol-3-ylamine (550 mg, 91%) as a yellow oil: LR-ES-MS m/z calculated for $C_9H_{15}N_3O_2$ $[M]^+$ 197, observed 198 $[M+H]^+$.

A solution of (S)-2-[4-(2-chloro-phenoxy)-2-oxo-2,5-dihydro-pyrrol-1-yl]-4-methyl-pentanoic acid (prepared in Example 64, 750 mg, 2.33 mmol) in dichloromethane (10 mL) was treated with 1-(3-dimethylaminopropyl)-3-ethyl-carbodiimide hydrochloride salt (490 mg, 2.55 mmol), 1-hydroxybenzotriazole (345 mg, 2.55 mmol) and 1-((S)-2,2-dimethyl-[1,3]dioxolan-4-yl-methyl)-1H-pyrazol-3-ylamine (550 mg, 2.79 mmol). The reaction mixture was stirred for 18 h at 25° C., under nitrogen and then diluted with dichloromethane, washed with saturated ammonium chloride solution, water, saturated sodium bicarbonate solution, a saturated sodium chloride solution and dried over magnesium sulfate. The crude product obtained after concentration, was purified by ISCO flash chromatography (Teledyne Isco RediSep Flash Column 40 g; 0% to 100% ethyl acetate/hexanes) to afford (S)-2-[4-(2-chloro-phenoxy)-2-oxo-2,5-dihydro-pyrrol-1-yl]-4-methyl-pentanoic acid [1-((S)-2,2-dimethyl-[1,3]dioxalan-4-ylmethyl)-1H-pyrazol-3-yl]-amide (774 mg, 67%) as a white powder: LR-ES-MS m/z calculated for $C_{25}H_{31}ClN_4O_5$ $[M]^+$ 502, observed 503 $[M+H]^+$; $^1H$ NMR (300 MHz, DMSO-$d_6$) δ ppm 0.90 (d, J=6.3 Hz, 3H), 0.94 (d, J=6.3 Hz, 3H), 1.25 (s, 3H), 1.31 (s, 3H), 1.36-1.50 (m, 1H), 1.50-1.67 (m, 1H), 1.67-1.86 (m, 1H), 3.73 (dd, J=8.4, 5.7 Hz, 1H), 4.00 (dd, J=8.4, 6.5 Hz, 1H), 4.06-4.15 (m, 2H), 4.21 (d, J=18.4 Hz, 1H), 4.34 (quin, J=5.8 Hz, 1H), 4.60 (d, J=18.4 Hz, 1H), 4.79 (s, 1H), 4.89 (dd, J=10.6, 4.8 Hz, 1H), 6.44 (d, J=2.1 Hz, 1H), 7.37 (td, J=7.5, 1.5 Hz, 1H), 7.46 (td, J=7.5, 1.2 Hz, 1H), 7.52 (dd, J=7.5, 1.5 Hz, 1H), 7.61 (d, J=2.1 Hz, 1H), 7.65 (dd, J=7.5, 1.2 Hz, 1H), 10.81 (s, 1H).

Example 175

(S)-2-[4-(2-Chloro-phenoxy)-2-oxo-2,5-dihydro-pyrrol-1-yl]-4-methyl-pentanoic acid [1-((S)-2,3-dihyrxy-propyl)-1H-pyrazol-3-yl]-amide

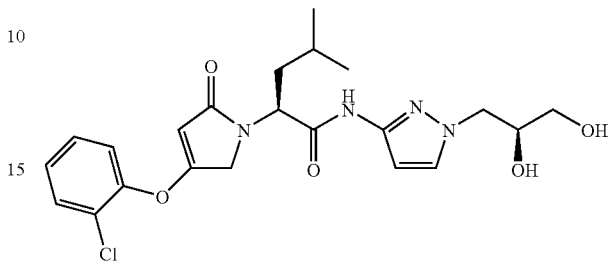

A solution of (S)-2-[4-(2-chloro-phenoxy)-2-oxo-2,5-dihydro-pyrrol-1-yl]-4-methyl-pentanoic acid [1-((S)-2,2-dimethyl-[1,3]dioxalan-4-ylmethyl)-1H-pyrazol-3-yl]-amide (prepared as in Example 174, 750 mg, 1.49 mmol) in tetrahydrofuran (10 mL) was treated with 2N aqueous hydrochloric acid solution (10 mL). The reaction mixture was stirred at 25° C. for 2 h. The reaction mixture was diluted with ethyl acetate, washed with water, saturated sodium bicarbonate solution, a saturated sodium chloride solution and dried over magnesium sulfate. The organic layer was concentrated to afford, (S)-2-[4-(2-chloro-phenoxy)-2-oxo-2,5-dihydro-pyrrol-1-yl]-4-methyl-pentanoic acid [1-((S)-2,3-dihydroxy-propyl)-1H-pyrazol-3-yl]-amide (625 mg, 91%) as a white solid: LR-ES-MS m/z calculated for $C_{22}H_{27}ClN_4O_5$ $[M]^+$ 462, observed 463 $[M+H]^+$; $^1H$ NMR (300 MHz, DMSO-$d_6$) δ ppm 0.90 (d, J=6.4 Hz, 3H), 0.94 (d, J=6.4 Hz, 3H), 1.35-1.50 (m, 1H), 1.50-1.65 (m, 1H), 1.68-1.85 (m, 1H), 3.19-3.41 (m, 2H), 3.71-3.81 (m, 1H), 3.86 (dd, J=13.3, 7.5 Hz, 1H), 4.09 (dd, J=13.7, 3.9 Hz, 1H), 4.21 (d, J=18.4 Hz, 1H), 4.72 (br. s., 2H), 4.60 (d, J=18.4 Hz, 1H), 4.78 (s, 1H), 4.88 (dd, J=10.9, 4.8 Hz, 1H), 6.41 (d, J=1.8 Hz, 1H), 7.37 (td, J=7.5, 1.2 Hz, 1H), 7.46 (td, J=7.5, 0.9 Hz, 1H), 7.49-7.54 (m, 1H), 7.54 (d, J=1.8 Hz, 1H), 7.65 (d, J=7.5 Hz, 1H), 10.78 (s, 1H).

Example 176

(S)-2-[4-(2-chloro-phenoxy)-2-oxo-2,5-dihydro-pyrrol-1-yl]-3-cyclobutyl-N-[1-((R)-2,3-dihydroxy-propyl)-1H-pyrazol-3-yl]-propionamide

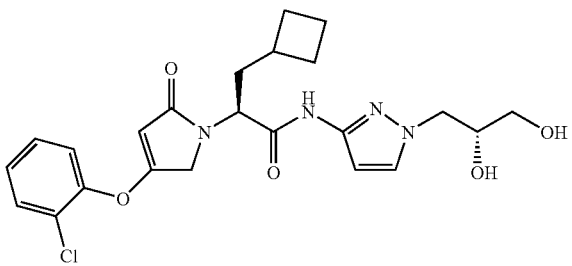

Separation of the enantiomers of 2-[4-(2-chloro-phenoxy)-2-oxo-2,5-dihydro-pyrrol-1-yl]-3-cyclobutyl-N-[1-((R)-2,3-dihydroxy-propyl)-1H-pyrazol-3-yl]-propionamide (prepared as in Example 169) via supercritical fluid chromatography on a SFC DIACEL AD column, 40% methanol as mobile phase modifier afforded (S)-2-[4-(2-chloro-phenoxy)-2-oxo-2,5-dihydro-pyrrol-1-yl]-3-cyclobutyl-N-[1-((R)-2,3-dihydroxy-propyl)-1H-pyrazol-3-yl]-propionamide as a white solid. LR-ES-MS m/z calculated for $C_{23}H_{27}ClN_4O_5$ [M]$^+$ 474, [M+H]$^+$ observed 475; $^1$H NMR (300 MHz, DMSO-$d_6$) δ ppm 1.55-1.96 (m, 7H), 1.96-2.10 (m, 1H), 2.09-2.30 (m, 1H), H), 3.20-3.32 (m, 2H), 3.70-3.81 (m, 1H), 3.87 (dd, J=13.4, 7.2 Hz, 1H), 4.09 (dd, J=13.4, 3.8 Hz, 1H), 4.21 (d, J=18.4 Hz, 1H), 4.57 (d, J=18.4 Hz, 1H), 4.68-4.76 (m, 1H), 4.72 (s, 1H), 4.78 (s, 1H), 4.95 (d, J=5.1 Hz, 1H), 6.40 (d, J=1.8 Hz, 1H), 7.30-7.41 (m, 1H), 7.46 (t, J=7.2 Hz, 1H), 7.50-7.55 (m, 1H), 7.53 (d, J=1.8 Hz, 1H), 7.65 (d, J=7.8 Hz, 1H), 10.74 (s, 1H).

Example 177

(R)-2-[4-(2-chloro-phenoxy)-2-oxo-2,5-dihydro-pyrrol-1-yl]-3-cyclobutyl-N-[1-((R)-2,3-dihydroxy-propyl)-1H-pyrazol-3-yl]-propionamide

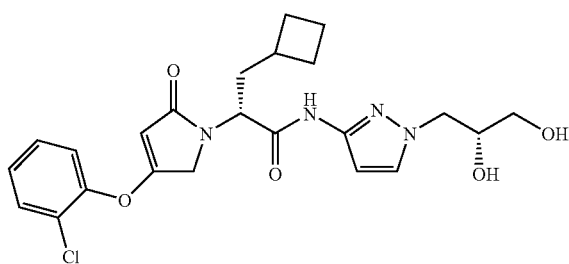

Separation of the enantiomers of 2-[4-(2-chloro-phenoxy)-2-oxo-2,5-dihydro-pyrrol-1-yl]-3-cyclobutyl-N-[1-((R)-2,3-dihydroxy-propyl)-1H-pyrazol-3-yl]-propionamide (prepared as in Example 169) via supercritical fluid chromatography on a SFC DIACEL AD column, 40% methanol as mobile phase modifier afforded (R)-2-[4-(2-chloro-phenoxy)-2-oxo-2,5-dihydro-pyrrol-1-yl]-3-cyclobutyl-N-[1-((R)-2,3-dihydroxy-propyl)-1H-pyrazol-3-yl]-propionamide as a white solid. LR-ES-MS m/z calculated for $C_{23}H_{27}ClN_4O_5$ [M]$^+$ 474, [M+H]$^+$ observed 475; $^1$H NMR (300 MHz, DMSO-$d_6$) δ ppm 1.55-1.70 (m, 1H), 1.70-1.95 (m, 6H), 1.95-2.11 (m, 1H), 2.11-2.28 (m, 1H), 3.22-3.33 (m, 2H), 3.72-3.81 (m, 1H), 3.86 (dd, J=13.3, 7.5 Hz, 1H), 4.09 (dd, J=13.3, 3.8 Hz, 1H), 4.21 (d, J=18.4 Hz, 1H), 4.57 (d, J=18.4 Hz, 1H), 4.66-4.75 (m, 2H), 4.78 (s, 1H), 4.94 (d, J=5.1 Hz, 1H), 6.40 (d, J=1.8 Hz, 1H), 7.37 (td, J=7.5, 1.5 Hz, 1H), 7.42-7.56 (m, 3H), 7.65 (d, J=8.2 Hz, 1H), 10.74 (s, 1H).

Example 178

(S)-N-[1-(2-hydroxy-2-methyl-propyl)-1H-pyrazol-3-yl]-2-[4-(2-methoxy-phenoxy)-2-oxo-2,5-dihydro-pyrrol-1-yl]-3-(tetrahydro-furan-2-yl)-propionamide

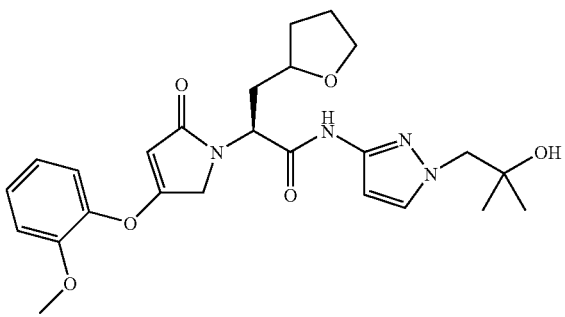

Separation of the enantiomers of (S)-N-[1-(2-hydroxy-2-methyl-propyl)-1H-pyrazol-3-yl]-2-[4-(2-methoxy-phenoxy)-2-oxo-2,5-dihydro-pyrrol-1-yl]-3-(tetrahydro-furan-2-yl)-propionamide (prepared as in Example 31) via supercritical fluid chromatography on a SFC KROMASIL OD column, 30% isopropanol as mobile phase modifier, afforded 1 epimer of (S)-N-[1-(2-hydroxy-2-methyl-propyl)-1H-pyrazol-3-yl]-2-[4-(2-methoxy-phenoxy)-2-oxo-2,5-dihydro-pyrrol-1-yl]-3-(tetrahydro-furan-2-yl)-propionamide as a white solid (stereocenter undefined). LR-ES-MS m/z calculated for $C_{25}H_{32}N_4O_6$ [M]$^+$ 484, observed 485 [M+H]$^+$; $^1$H NMR (300 MHz, DMSO-$d_6$) δ ppm 1.05 (s, 3H) 1.06 (br. s., 3H) 1.51-2.14 (m, 6H), 3.51-3.79 (m, 3H) 3.81 (s, 3H) 3.89 (s, 2H) 4.18 (d, J=18.1 Hz, 1H) 4.45 (d, J=18.1 Hz, 1H) 4.67 (s, 1H) 4.70 (s, 1H) 4.83 (dd, J=10.1, 5.3 Hz, 1H) 6.44 (d, J=2.0 Hz, 1H) 6.96-7.04 (m, 1H) 7.18-7.23 (m, 1H) 7.23-7.33 (m, 2H) 7.54 (d, J=2.0 Hz, 1H) 10.72 (s, 1H).

Example 179

(S)-N-[1-(2-hydroxy-2-methyl-propyl)-1H-pyrazol-3-yl]-2-[4-(2-methoxy-phenoxy)-2-oxo-2,5-dihydro-pyrrol-1-yl]-3-(tetrahydro-furan-2-yl)-propionamide

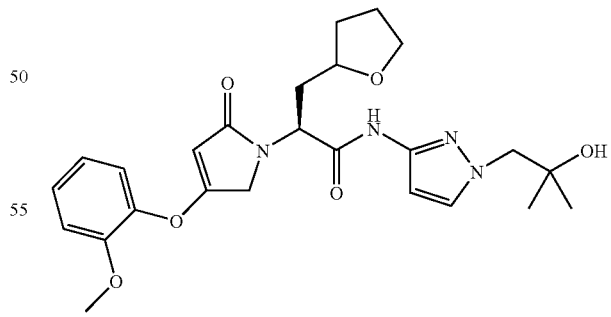

Separation of the enantiomers of (S)—N-[1-(2-hydroxy-2-methyl-propyl)-1H-pyrazol-3-yl]-2-[4-(2-methoxy-phenoxy)-2-oxo-2,5-dihydro-pyrrol-1-yl]-3-(tetrahydro-furan-2-yl)-propionamide (prepared as in Example 31) via supercritical fluid chromatography on a SFC KROMASIL OD column, 30% isopropanol as mobile phase modifier, afforded 1 epimer of (S)-N-[1-(2-hydroxy-2-methyl-propyl)-

1H-pyrazol-3-yl]-2-[4-(2-methoxy-phenoxy)-2-oxo-2,5-dihydro-pyrrol-1-yl]-3-(tetrahydro-furan-2-yl)-propionamide as a white solid (stereocenter undefined). LR-ES-MS m/z calculated for $C_{25}H_{32}N_4O_6$ [M]$^+$ 484, observed 485 [M+H]$^+$; $^1$H NMR (300 MHz, DMSO-d$_6$) δ ppm 1.04 (s, 3H) 1.05 (s, 3H) 1.37-1.60 (m, 1H) 1.66-2.09 (m, 5H) 3.53-3.65 (m, 1H) 3.67-3.79 (m, 2H) 3.81 (s, 3H) 3.89 (s, 2H) 4.21 (d, J=18.2 Hz, 1H) 4.45 (d, J=18.2 Hz, 1H) 4.67 (s, 1H) 4.69 (s, 1H) 4.79-4.91 (m, 1H) 6.43 (d, J=2.4 Hz, 1H) 6.94-7.05 (m, 1H) 7.17-7.23 (m, 1H) 7.24-7.37 (m, 2H) 7.53 (d, J=2.4 Hz, 1H) 10.69 (s, 1H).

Example 180

(S)-2-[4-(2-chloro-phenoxy)-2-oxo-2,5-dihydro-pyrrol-1-yl]-4-methyl-pentanoic acid [1-((R)-2-amino-3-hydroxy-propyl)-1H-pyrazol-3-yl]-amide

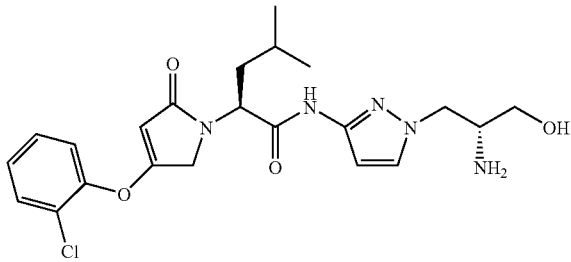

To an ice cold mixture of (S)-4-formyl-2,2-dimethyl-oxazolidine-3-carboxylic acid t-butyl ester (2.00 g, 8.72 mmol) in tetrahydrofuran (15 mL) and isopropanol (15 mL) was added sodium borohydride (0.99 g, 26.17 mmol). After addition was complete the mixture was stirred at 0° C. for 1 h. Upon completion of the reaction 1N aqueous hydrochloric acid (10 mL) was slowly added. The mixture was poured into water and extracted with ethyl acetate (3×30 mL). The combined organic fractions were washed with a saturated sodium chloride solution and dried over magnesium sulfate. The crude product obtained (R)-4-hydroxymethyl-2,2-dimethyl-oxazolidine-3-carboxylic acid t-butyl ester (1.88 g, 93%) as a colorless oil and was used without further purification: LR-ES-MS m/z calculated for $C_{11}H_{21}NO_4$ [M]$^+$ 231, observed 232 [M+H]$^+$.

To a stirred mixture of (R)-4-hydroxymethyl-2,2-dimethyl-oxazolidine-3-carboxylic acid t-butyl ester (1.88 g, 8.14 mmol) in dichloromethane (20 mL) was added N,N-diisopropylethylamine (2.10 g, 16.28 mmol), p-toluenesulfonyl chloride (1.71 g, 8.95 mmol) and 4-dimethylaminopyridine (1.00 g, 8.14 mmol). After addition was complete the mixture was stirred at room temperature for 4 h. Upon completion of the reaction the dichloromethane was removed under reduced pressure. The residue was diluted with ethyl acetate and washed with a 1N aqueous hydrochloric acid solution, water, a saturated sodium bicarbonate solution and a saturated sodium chloride solution and dried over magnesium sulfate. The crude product obtained (S)-2,2-dimethyl-4-(toluene-4-sulfonyloxymethyl-oxazolidine-3-carboxylic acid t-butyl ester (2.20 g, 92%) as a colorless oil and was used without further purification: LR-ES-MS m/z calculated for $C_{18}H_{27}NO_6S$ [M]$^+$ 385, observed 386 [M+H]$^+$.

To a stirred mixture of (S)-2,2-dimethyl-4-(toluene-4-sulfonyloxymethyl-oxazolidine-3-carboxylic acid t-butyl ester (2.20 g, 5.71 mmol) in N,N-dimethylformamide (10 mL) was added potassium carbonate (0.93 g, 6.73 mmol) and 3-nitro-1H-pyrazole (prepared as in Example 5, 0.59 mg, 5.20 mmol). After addition was complete the mixture was stirred at 60° C. for 18 h. The reaction mixture was diluted with ethyl acetate, washed with water followed by a saturated sodium chloride solution and dried over magnesium sulfate. The organic layer was concentrated, and the crude product was purified by ISCO flash chromatography (Teledyne Isco RediSep Flash Column 40 g; 0% to 100% ethyl acetate/hexanes) to afford (R)-2,2-dimethyl-4-(3-nitro-pyrazol-1-ylmethyl)-oxazolidine-3-carboxylic acid t-butyl ester (1.21 g, 65%) as a colorless oil: LR-ES-MS m/z calculated for $C_{14}H_{22}N_4O_5$ [M]$^+$ 326, observed 327 [M+H]$^+$.

In a Parr shaker bottle was placed (R)-2,2-dimethyl-4-(3-nitro-pyrazol-1-ylmethyl)-oxazolidine-3-carboxylic acid t-butyl ester (1.21 g, 3.71 mmol), 10% palladium on carbon (500 mg) and ethanol (25 mL). The bottle was then placed on the Parr shaker at 50 psi of hydrogen pressure for 5 h. The reaction was then filtered through a pad of celite and washed with ethanol and concentrated in vacuo to afford (R)-4-(3-amino-pyrazol-1-ylmethyl)-2,2-dimethyl-oxazolidine-3-carboxylic acid t-butyl ester (1.07 g, 97%) as a yellow oil: LR-ES-MS m/z calculated for $C_{14}H_{24}N_4O_3$ [M]$^+$ 296, observed 297 [M+H]$^+$.

A solution of (S)-2-[4-(2-chloro-phenoxy)-2-oxo-2,5-dihydro-pyrrol-1-yl]-4-methyl-pentanoic acid (prepared as in Example 64, 0.98 g, 3.01 mmol) in dichloromethane (15 mL) was treated with 1-(3-dimethylaminopropyl)-3-ethylcarbodiimide hydrochloride salt (0.64 g, 3.32 mmol), 1-hydroxybenzotriazole (0.45 g, 3.32 mmol) and (R)-4-(3-amino-pyrazol-1-ylmethyl)-2,2-dimethyl-oxazolidine-3-carboxylic acid t-butyl ester (1.07 g, 1.57 mmol). The reaction mixture was stirred for 18 h at 25° C., under nitrogen and then diluted with dichloromethane, washed with a saturated ammonium chloride solution, water, a saturated sodium bicarbonate solution, a saturated sodium chloride solution and dried over magnesium sulfate. The crude product obtained after concentration, was purified by ISCO flash chromatography (Teledyne Isco RediSep Flash Column 40 g; 0% to 100% ethyl acetate/hexanes) to afford (R)-4-(3-{(S)-2-[4-(2-chloro-phenoxy)-2-oxo-2,5-dihydro-pyrrol-1-yl]-4-methyl-pentanoylamino}-pyrazol-1-ylmethyl)-2,2-dimethyl-oxazolidin-3-carboxylic acid t-butyl ester (1.00 g, 55%) as a white powder: LR-ES-MS m/z calculated for $C_{30}H_{40}ClN_5O_6$ [M]$^+$ 601, observed 602 [M+H]$^+$.

Hydrochloric acid gas was bubbled into a stirred solution of (R)-4-(3-{(S)-2-[4-(2-chloro-phenoxy)-2-oxo-2,5-dihydro-pyrrol-1-yl]-4-methyl-pentanoylamino}-pyrazol-1-ylmethyl)-2,2-dimethyl-oxazolidin-3-carboxylic acid t-butyl ester (1.00 g, 16.63 mmol) in diethyl ether (20 mL) for 30 seconds. The reaction mixture was then stirred at room temperature for 30 min during which a white solid precipitates out of solution. The diethyl ether was decanted off and the solid washed with three portions of diethyl ether. The crude product was purified via supercritical fluid chromatography on a DAICEL AD column, 25% methanol, 70 mL/min to afford (S)-2-[4-(2-chloro-phenoxy)-2-oxo-2,5-dihydro-pyrrol-1-yl]-4-methyl-pentanoic acid [1-((R)-2-amino-3-hydroxy-propyl)-1H-pyrazol-3-yl]-amide (362 mg, 47%) as a white solid: LR-ES-MS m/z calculated for $C_{22}H_{28}ClN_5O_4$ [M]$^+$ 461, observed 462 [M+H]$^+$; $^1$H NMR (300 MHz, DMSO-d$_6$) δ ppm 0.90 (d, J=6.3 Hz, 3H), 0.94 (d, J=6.3 Hz, 3H), 1.34-1.85 (m, 5H), 3.00 (br. s., 1H), 3.22 (br. s., 2H), 3.80 (dd, J=13.4, 6.9 Hz, 1H), 4.02 (dd, J=13.4, 5.0 Hz, 1H), 4.21 (d, J=18.4 Hz, 1H), 4.61 (d, J=18.4 Hz, 1H), 4.65-4.75 (m, 1H), 4.79 (s, 1H), 4.89 (dd, J=9.8, 4.1 Hz, 1H) H), 6.42 (s, 1H), 7.31-7.42 (m, 1H), 7.42-7.55 (m, 2H), 7.57 (br. s., 1H), 7.65 (d, J=7.2 Hz, 1H), 10.79 (br. s., 1H).

Example 181

(S)-2-[4-(2-chloro-phenoxy)-2-oxo-2,5-dihydro-pyrrol-1-yl]-N-[1-((R)-2,3-dihydroxy-propyl)-1H-pyrazol-3-yl]-3-phenyl-propionamide

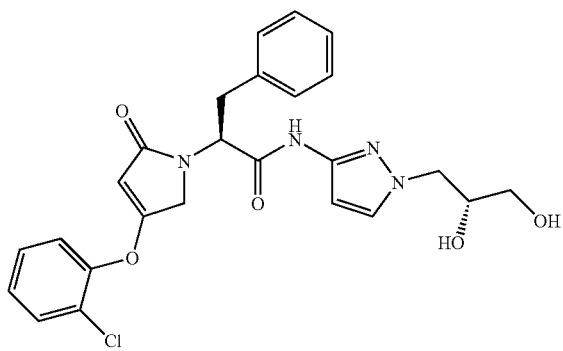

To a stirred mixture of L-phenylalanine methyl ester hydrochloride (0.45 g, 1.7 mmol) dissolved in acetonitrile (10 mL) under a nitrogen atmosphere was added N,N-diisopropylethylamine (0.23 g, 2.04 mmol). After addition was complete the mixture was stirred at 110° C. for 1 h. The reaction was cooled to 25° C. and treated with N,N-diisopropylethylamine (0.23 g, 2.04 mmol) and heated to 110° C. at which time (E)-4-bromo-3-(2-chloro-phenoxy)-but-2-enoic acid ethyl ester (prepared as in Example 61, 0.604 g, 1.70 mmol) in acetonitrile (10 mL) was added slowly. After the addition was complete the reaction mixture was heated to 110° C. and stirred for 16 h. The reaction mixture was cooled to 25° C., filtered and concentrated. The residue was diluted with ethyl acetate and washed with 2N hydrochloric acid, a saturated sodium chloride solution and dried over magnesium sulfate. The crude product obtained was purified by ISCO flash chromatography (Teledyne Isco RediSep Flash Column 40 g; 0% to 80% ethyl acetate/hexanes) to afford, (S)-2-[4-(2-chloro-phenoxy)-2-oxo-2,5-dihydro-pyrrol-1-yl]-3-phenyl-propanoic acid methyl ester (0.093 g, 15%) as a colorless oil: LR-ES-MS m/z calculated for $C_{20}H_{18}ClNO_4$ [M]$^+$ 371, [M+H]$^+$ observed 372.

To a magnetically stirred mixture of (S)-2-[4-(2-chloro-phenoxy)-2-oxo-2,5-dihydro-pyrrol-1-yl]-3-phenyl-propanoic acid methyl ester (0.09 g, 0.24 mmol) in tetrahydrofuran (1 mL) and was added lithium hydroxide (0.012 g, 0.28 mmol) in water (0.5 mL). After addition was complete the mixture was stirred at 25° C. for 4 h. The reaction mixture was poured into water and diethyl ether and the layers separated. The aqueous layer was made acidic with 2N hydrochloric acid and extracted in two portions with ethyl acetate. The combined ethyl acetate fractions were washed with a saturated sodium chloride solution, dried over magnesium sulfate, filtered and concentrated to afford, (S)-2-[4-(2-chloro-phenoxy)-2-oxo-2,5-dihydro-pyrrol-1-yl]-3-phenyl-propanoic acid (0.064 g, 75%) as a light brown gum: LR-ES-MS m/z calculated for $C_{19}H_{16}ClNO_4$ [M]$^+$ 357, observed 358 [M+H]$^+$.

A solution of (S)-2-[4-(2-chloro-phenoxy)-2-oxo-2,5-dihydro-pyrrol-1-yl]-3-phenyl-propanoic acid (0.064 g, 0.171 mmol) in dichloromethane (5 mL) was treated with 1-(3-dimethylaminopropyl)-3-ethylcarbodiimide (0.030 g, 0.188 mmol) and 1-hydroxybenzotriazole (0.025 g, 0.188 mmol). The reaction mixture was stirred at 25° C. for 0.3 h followed by the addition of 1-((R)-2,2-dimethyl-[1,3]dioxolan-4-yl-methyl)-1H-pyrazol-3-ylamine (prepared as in Example 49, 0.042 mg, 0.206 mmol). The reaction mixture was stirred for 16 h at 25° C., under nitrogen. The reaction mixture was diluted with dichloromethane, washed with 2N hydrochloric acid, saturated sodium bicarbonate solution, a saturated sodium chloride solution and dried over magnesium sulfate. The crude product obtained after concentration, was purified by ISCO flash chromatography (Teledyne Isco RediSep Flash Column 4 g; 0% to 100% ethyl acetate/hexanes) to afford, 2-[4-(2-chloro-phenoxy)-2-oxo-2,5-dihydro-pyrrol-1-yl]-3-phenyl-propionic acid [1-((R)-2,2-dimethyl-[1,3]dioxolan-4-yl-methyl)-1H-pyrazol-3-yl]-amide (0.010 g, 11%) as a colorless gum.

A solution of 2-[4-(2-chloro-phenoxy)-2-oxo-2,5-dihydro-pyrrol-1-yl]-3-phenyl-propionic acid [1-((R)-2,2-dimethyl-[1,3]dioxolan-4-yl-methyl)-1H-pyrazol-3-yl]-amide (0.010 g, 0.017 mmol) in tetrahydrofuran (1 mL) was treated with 2N aqueous hydrochloric acid solution (1 mL). The reaction mixture was stirred at 25° C. for 3 h. The reaction mixture was diluted with ethyl acetate, washed with water, saturated sodium bicarbonate solution, a saturated sodium chloride solution and dried over magnesium sulfate. The organic layer was concentrated to afford, 2-[4-(2-chloro-phenoxy)-2-oxo-2,5-dihydro-pyrrol-1-yl]-3-phenyl-N-[1-((R)-2,3-dihydroxy-propyl)-1H-pyrazol-3-yl]-propionamide (0.007 g, 82%) as an off-white powder: HR-ES-MS m/z calculated for $C_{23}H_{27}ClN_4O_6$ [M+H]$^+$ 497.1587, observed 497.1586; $^1$H NMR (300 MHz, CDCl$_3$) δ ppm 1.75 (br. s., 2H), 3.17 (dd, J=14.0, 8.8 Hz, 1H), 3.39 (dd, J=14.0, 6.9 Hz, 1H), 3.44-3.55 (m, 2H), 3.56-3.65 (m, 1H), 3.95-4.10 (m, 2H), 4.16 (d, J=18.1 Hz, 1H), 4.30 (d, J=18.1 Hz, 1H), 4.77 (s, 1H), 5.02 (t, J=7.8 Hz, 1H), 6.65 (d, J=1.8 Hz, 1H), 7.17 (dd, J=8.2, 1.8 Hz, 1H), 7.19-7.26 (m, 6H), 7.28-7.35 (m, 2H), 7.46 (dd, J=7.8, 1.5 Hz, 1H), 9.65 (s, 1H).

Example 182

(S)-2-[4-(2-chloro-phenoxy)-2-oxo-2,5-dihydro-pyrrol-1-yl]-N-[1-((R)-2,2-dimethyl-[1,3]dioxolan-4-yl-methyl)-1H-pyrazol-3-yl]-3-(2-fluoro-phenyl)-propionamide

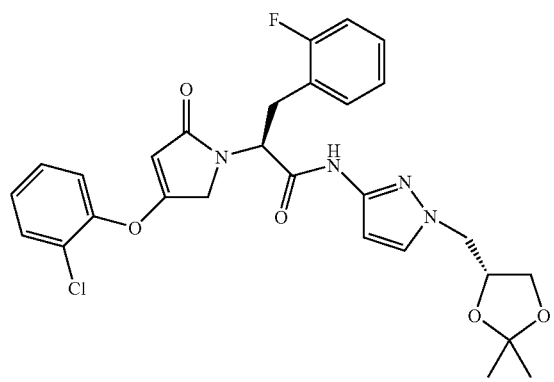

To a stirred mixture of L-2-fluorophenylalanine methyl ester hydrochloride (1.75 g, 6.16 mmol) dissolved in acetonitrile (25 mL) under a nitrogen atmosphere was added N,N-diisopropylethylamine (0.96 g, 7.40 mmol). After addition was complete the mixture was stirred at 105° C. for 0.5 h. The reaction was cooled to 25° C. and treated with N,N-diisopropylethylamine (0.96 g, 7.40 mmol) and heated to 105° C. at which time (E)-4-bromo-3-(2-chloro-phenoxy)-but-2-enoic acid ethyl ester (prepared as in Example 61, 2.01 g, 6.16 mmol) in acetonitrile (10 mL) was added slowly. After the addition was complete the reaction mixture was heated to 105° C. and stirred for 16 h. The reaction mixture was cooled to 25° C., filtered and concentrated and diluted with acetonitrile to 10 mL volume. The reaction mixture was then transferred to a microwave reaction vessel and heated to 150° C. in the Emrys Optimizer microwave reactor for 1 h. The reaction mixture was concentrated and the residue was diluted with ethyl acetate and washed with 2N hydrochloric acid, a saturated sodium chloride solution and dried over magnesium sulfate. The crude product obtained was purified by ISCO flash chromatography (Teledyne Isco RediSep Flash Column 40 g; 0% to 100% ethyl acetate/hexanes) to afford, (S)-2-[4-(2-chloro-phenoxy)-2-oxo-2,5-dihydro-pyrrol-1-yl]-3-(2-flouoro-phenyl)-propanoic acid methyl ester (1.21 g, 50%) as a orange red gum: LR-ES-MS m/z calculated for $C_{20}H_{17}ClFNO_4$ [M]$^+$ 389, [M+H]$^-$ observed 390.

To a stirred mixture of (S)-2-[4-(2-chloro-phenoxy)-2-oxo-2,5-dihydro-pyrrol-1-yl]-3-(2-fluorophenyl)-propanoic acid methyl ester (1.19 g, 2.90 mmol) in tetrahydrofuran (3 mL) and was added lithium hydroxide (0.147 g, 3.48 mmol) in water (3 mL). After addition was complete the mixture was stirred at 25° C. for 3 h. The reaction mixture was poured into water and diethyl ether and the layers separated. The aqueous layer was made acidic with 2N hydrochloric acid and extracted in two portions with ethyl acetate. The combined ethyl acetate fractions were washed with a saturated sodium chloride solution, dried over magnesium sulfate, filtered and concentrated to afford, (S)-2-[4-(2-chloro-phenoxy)-2-oxo-2,5-dihydro-pyrrol-1-yl]-3-(2-fluoro-phenyl)-propanoic acid (0.882 g, 81%) as a light orange foam: LR-ES-MS m/z calculated for $C_{19}H_{15}ClFNO_4$ [M]$^+$ 375, observed 376 [M+H]$^+$.

A solution of (S)-2-[4-(2-chloro-phenoxy)-2-oxo-2,5-dihydro-pyrrol-1-yl]-3-(2-fluorophenyl)-propanoic acid (0.405 g, 1.03 mmol) in dichloromethane (15 mL) was treated with 1-(3-dimethylaminopropyl)-3-ethylcarbodiimide hydrochloride (0.178 mg, 1.127 mmol) and 1-hydroxybenzotriazole (0.153 g, 1.127 mmol). The reaction mixture was stirred at 25° C. for 0.25 h followed by the addition of 1-((R)-2,2-dimethyl-[1,3]dioxolan-4-yl-methyl)-1H-pyrazol-3-ylamine (prepared as in Example 49, 0.252 mg, 1.23 mmol). The reaction mixture was stirred for 18 h at 25° C., under nitrogen. The reaction mixture was diluted with dichloromethane, washed with 2N hydrochloric acid, saturated sodium bicarbonate solution, a saturated sodium chloride solution and dried over magnesium sulfate. The crude product obtained after concentration, was purified by ISCO flash chromatography (Teledyne Isco RediSep Flash Column 12 g; 0% to 100% ethyl acetate/hexanes) to afford, (S)-2-[4-(2-chloro-phenoxy)-2-oxo-2,5-dihydro-pyrrol-1-yl]-N-[1-((R)-2,2-dimethyl-[1,3]dioxolan-4-yl-methyl)-1H-pyrazol-3-yl]-3-(2-fluoro-phenyl)-propionamide (0.414 g, 73%) as an off-white powder: HR-ES-MS m/z calculated for $C_{28}H_{28}ClFN_4O_5$ [M+H]$^+$ 555.1807, observed 555.1805. $^1$H NMR (300 MHz, DMSO-d$_6$) δ ppm 1.24 (s, 3H), 1.30 (s, 3H), 3.17 (d, J=7.8 Hz, 2H), 3.73 (dd, J=8.3, 5.9 Hz, 1H), 3.94-4.05 (m, 1H), 4.04-4.19 (m, 2H), 4.19-4.30 (m, 1H), 4.30-4.40 (m, 1H), 4.44-4.55 (m, 1H), 4.72 (s, 1H), 5.15 (t, J=7.8 Hz, 1H), 6.47 (d, J=1.8 Hz, 1H), 7.09-7.19 (m, 2H), 7.21-7.32 (m, 1H), 7.32-7.42 (m, 2H), 7.45 (m, 2H), 7.60-7.66 (m, 2H), 10.85 (s, 1H).

Example 183

(S)-2-[4-(2-chloro-phenoxy)-2-oxo-2,5-dihydro-pyrrol-1-yl]-N-[1-((R)-2,3-dihydroxy-propyl)-1H-pyrazol-3-yl]-3-(2-fluorophenyl)-propionamide

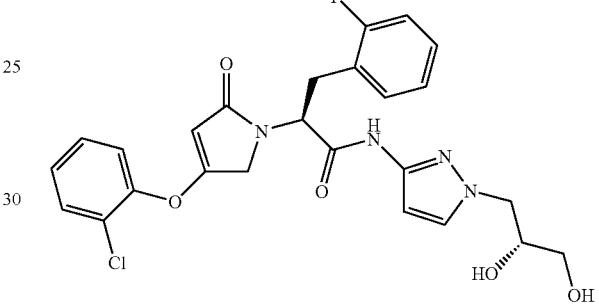

A solution of (S)-2-[4-(2-chloro-phenoxy)-2-oxo-2,5-dihydro-pyrrol-1-yl]-3-(2-fluorophenyl)-propionic acid [1-((R)-2,2-dimethyl-[1,3]dioxolan-4-yl-methyl)-1H-pyrazol-3-yl]-amide (prepared as in Example 182, 0.387 g, 0.669 mmol) in tetrahydrofuran (5 mL) was treated with 2N aqueous hydrochloric acid solution (4 mL). The reaction mixture was stirred at 25° C. for 3 h. The reaction mixture was diluted with ethyl acetate, washed with water, saturated sodium bicarbonate solution, a saturated sodium chloride solution and dried over magnesium sulfate. The organic layer was concentrated to afford, (S)-2-[4-(2-chloro-phenoxy)-2-oxo-2,5-dihydro-pyrrol-1-yl]-3-(2-fluorophenyl)-N-[1-((R)-2,3-dihydroxy-propyl)-1H-pyrazol-3-yl]-propionamide (0.260 g, 76%) as a white powder: HR-ES-MS m/z calculated for $C_{25}H_{24}ClFN_4O_5$ [M+H]$^-$ 515.1495, observed 515.1492; $^1$H NMR (300 MHz, DMSO-d$_6$) δ ppm 3.15 (d, J=7.8 Hz, 2H), 3.20-3.31 (m, 2H), 3.70-3.79 (m, 1H), 3.85 (dd, J=13.4, 7.5 Hz, 1H), 4.08 (dd, J=13.4, 3.9 Hz, 1H), 4.17-4.32 (m, 1H), 4.36-4.59 (m, 1H), 4.63-4.76 (m, 2H), 4.93 (d, J=5.1 Hz, 1H), 5.13 (t, J=7.8 Hz, 1H), 6.42 (d, J=2.1 Hz, 1H), 7.07-7.19 (m, 2H), 7.20-7.28 (m, 1H), 7.30-7.47 (m, 4H), 7.53 (d, J=2.1 Hz, 1H), 7.62 (d, J=7.8 Hz, 1H), 10.81 (s, 1H).

Example 184

(S)-2-[4-(2-chloro-phenoxy)-2-oxo-2,5-dihydro-pyrrol-1-yl]-N-[1-((R)-2,2-dimethyl-[1,3]dioxolan-4-yl-methyl)-1H-pyrazol-3-yl]-3-(2,6-difluoro-phenyl)-propionamide

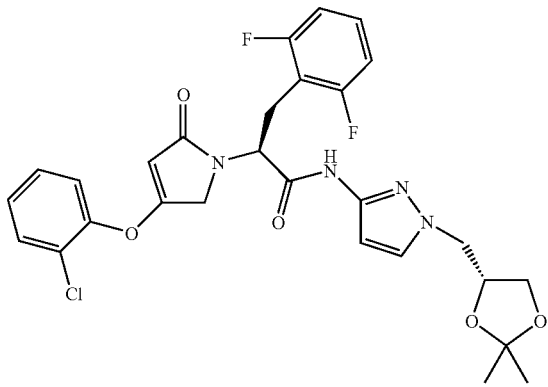

To a stirred mixture of L-2,6-difluorophenylalanine methyl ester hydrochloride (0.815 g, 3.17 mmol) dissolved in acetonitrile (25 mL) under a nitrogen atmosphere was added N,N-diisopropylethylamine (0.4 g, 3.15 mmol). After addition was complete the mixture was stirred at 105° C. for 0.5 h. The reaction was cooled to 25° C. and treated with N,N-diisopropylethylamine (0.4 g, 3.15 mmol) and heated to 105° C. at which time (E)-4-bromo-3-(2-chloro-phenoxy)-but-2-enoic acid ethyl ester (prepared as in Example 61, 2.01 g, 6.16 mmol) in acetonitrile (10 mL) was added slowly. After the addition was complete the reaction mixture was heated to 105° C. and stirred for 16 h. The reaction mixture was cooled to 25° C., filtered and concentrated and diluted with acetonitrile to 10 mL volume. The reaction mixture was then transferred to microwave reaction vessel and heated to 150° C. in the Emrys Optimizer microwave reactor for 2.5 h. The reaction mixture was concentrated and the residue was diluted with ethyl acetate and washed with 2N hydrochloric acid, a saturated sodium chloride solution and dried over magnesium sulfate. The crude product obtained was purified by ISCO flash chromatography (Teledyne Isco RediSep Flash Column 12 g; 0% to 100% ethyl acetate/hexanes) to afford, (S)-2-[4-(2-chloro-phenoxy)-2-oxo-2,5-dihydro-pyrrol-1-yl]-3-(2,6-diflouoro-phenyl)-propanoic acid methyl ester (0.597 g, 51%) as a light orange gum.

To a stirred mixture of (S)-2-[4-(2-chloro-phenoxy)-2-oxo-2,5-dihydro-pyrrol-1-yl]-3-(2,6-difluorophenyl)-propanoic acid methyl ester (0.58 g, 1.36 mmol) in tetrahydrofuran (3 mL) and was added lithium hydroxide (0.063 g, 1.50 mmol) in water (3 mL). After addition was complete the mixture was stirred at 25° C. for 3 h. The reaction mixture was poured into water and diethyl ether and the layers separated. The aqueous layer was made acidic with 2N hydrochloric acid and extracted in two portions with ethyl acetate. The combined ethyl acetate fractions were washed with a saturated sodium chloride solution, dried over magnesium sulfate, filtered and concentrated to afford, (S)-2-[4-(2-chloro-phenoxy)-2-oxo-2,5-dihydro-pyrrol-1-yl]-3-(2,6-difluorophenyl)-propanoic acid (0.594 g, 100%) as a light orange powder: LR-ES-MS m/z calculated for $C_{19}H_{15}ClF_2NO_4$ [M]$^+$ 393, observed 394 [M+H]$^+$.

A solution of (S)-2-[4-(2-chloro-phenoxy)-2-oxo-2,5-dihydro-pyrrol-1-yl]-3-(2,6-difluorophenyl)-propanoic acid (0.587 g, 1.45 mmol) in dichloromethane (15 mL) was treated with 1-(3-dimethylaminopropyl)-3-ethylcarbodiimide hydrochloride (0.252 mg, 1.59 mmol) and 1-hydroxybenzotriazole (0.219 g, 1.59 mmol). The reaction mixture was stirred at 25° C. for 0.25 h followed by the addition of 1-((R)-2,2-dimethyl-[1,3]dioxolan-4-yl-methyl)-1H-pyrazol-3-ylamine (prepared as in Example 49, 0.326 mg, 1.59 mmol). The reaction mixture was stirred for 18 h at 25° C., under nitrogen. The reaction mixture was diluted with dichloromethane, washed with 2N hydrochloric acid, saturated sodium bicarbonate solution, a saturated sodium chloride solution and dried over magnesium sulfate. The crude product obtained after concentration, was purified by ISCO flash chromatography (Teledyne Isco RediSep Flash Column 12 g; 0% to 100% ethyl acetate/hexanes) to afford, (S)-2-[4-(2-chloro-phenoxy)-2-oxo-2,5-dihydro-pyrrol-1-yl]-N-[1-((R)-2,2-dimethyl-[1,3]dioxolan-4-yl-methyl)-1H-pyrazol-3-yl]-3-(2,6-difluoro-phenyl)-propionamide (0.562 g, 68%) as an off-white powder: HR-ES-MS m/z calculated for $C_{28}H_{27}ClF_2N_4O_5$ [M+H]$^+$ 573.1714, observed 573.1711; $^1$H NMR (300 MHz, DMSO-d$_6$) δ ppm 1.23 (s, 3H), 1.28 (s, 3H), 3.04-3.26 (m, 2H), 3.70 (dd, J=8.3, 5.9 Hz, 1H), 3.97 (dd, J=8.8, 6.6 Hz, 1H), 4.00-4.19 (m, 2H), 4.33 (s, 3H), 4.70 (s, 1H), 5.07 (t, J=7.7 Hz, 1H), 6.45 (d, J=1.8 Hz, 1H), 7.01 (t, J=8.0 Hz, 2H), 7.21-7.39 (m, 2H), 7.39-7.49 (m, 2H), 7.59 (d, J=1.8 Hz, 1H), 7.63 (d, J=8.2 Hz, 1H), 10.77 (s, 1H).

Example 185

(S)-2-[4-(2-chloro-phenoxy)-2-oxo-2,5-dihydro-pyrrol-1-yl]-N-[1-((R)-2,3-dihydroxy-propyl)-1H-pyrazol-3-yl]-3-(2,6-difluorophenyl)-propionamide

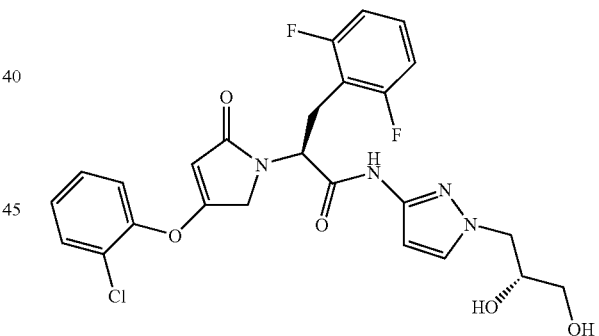

A solution of (S)-2-[4-(2-chloro-phenoxy)-2-oxo-2,5-dihydro-pyrrol-1-yl]-3-(2,6-difluorophenyl)-propionic acid [1-((R)-2,2-dimethyl-[1,3]dioxolan-4-yl-methyl)-1H-pyrazol-3-yl]-amide (prepared as in Example 184, 0.530 g, 0.898 mmol) in tetrahydrofuran (6 mL) was treated with 2N aqueous hydrochloric acid solution (4 mL). The reaction mixture was stirred at 25° C. for 3 h. The reaction mixture was diluted with ethyl acetate, washed with water, saturated sodium bicarbonate solution, a saturated sodium chloride solution and dried over magnesium sulfate. The organic layer was concentrated to afford, (S)-2-[4-(2-chloro-phenoxy)-2-oxo-2,5-dihydro-pyrrol-1-yl]-3-(2,6-difluorophenyl)-N-[1-((R)-2,3-dihydroxy-propyl)-1H-pyrazol-3-yl]-propionamide (0.417 g, 88%) as white powder: HR-ES-MS m/z calculated for $C_{25}H_{23}ClF_2N_4O_5$ [M+H]$^+$ 533.1395, observed 533.1395; $^1$H NMR (300 MHz, DMSO-d$_6$); $^1$H NMR (300 MHz, DMSO-d$_6$) δ ppm 2.98-3.30 (m, 4H), 3.67-3.79 (m, 1H), 3.84 (dd, J=13.5, 7.5 Hz, 1H), 4.07 (dd, J=13.5, 3.8 Hz, 1H), 4.32 (s, 2H), 4.65-4.74 (m, 2H), 4.93 (d, J=5.1 Hz, 1H), 5.06 (t, J=8.5 Hz, 1H), 6.42 (d, J=1.8 Hz, 1H), 7.02 (t, J=7.8 Hz, 2H), 7.22-7.38 (m, 2H), 7.38-7.49 (m, 2H), 7.53 (d, J=1.8 Hz, 1H), 7.63 (d, J=7.8 Hz, 1H), 10.75 (s, 1H).

Example 186

(S)-2-[4-(2-chloro-phenoxy)-2-oxo-2,5-dihydro-pyrrol-1-yl]-N-[1-((R)-2,2-dimethyl-[1,3]dioxolan-4-yl-methyl)-1H-pyrazol-3-yl]-3-(4-fluoro-phenyl)-propionamide

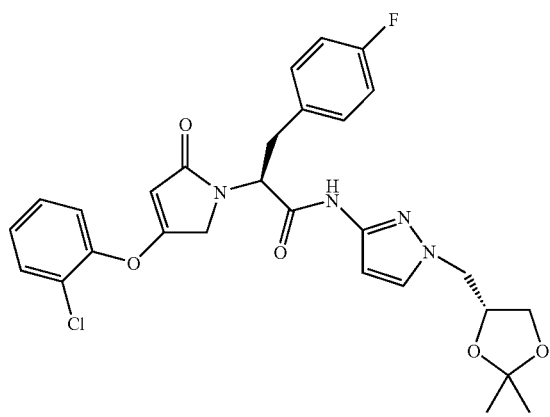

To a stirred mixture of L-4-fluorophenylalanine ethyl ester hydrochloride (0.533 g, 2.13 mmol) dissolved in acetonitrile (20 mL) under a nitrogen atmosphere was added N,N-diisopropylethylamine (0.3 g, 2.3 mmol). After addition was complete the mixture was stirred at 105° C. for 0.5 h. The reaction was cooled to 25° C. and treated with N,N-diisopropylethylamine (0.3 g, 2.3 mmol) and heated to 105° C. at which time (E)-4-bromo-3-(2-chloro-phenoxy)-but-2-enoic acid ethyl ester (prepared as in Example 61, 0.645 g, 1.94 mmol) in acetonitrile (10 mL) was added slowly. The reaction mixture was then transferred to microwave reaction vessel and heated to 150° C. in the Emrys Optimizer microwave reactor for 4 h. The reaction mixture was concentrated and the residue was diluted with ethyl acetate and washed with 2N hydrochloric acid, a saturated sodium chloride solution and dried over magnesium sulfate. The crude product obtained was purified by ISCO flash chromatography (Teledyne Isco RediSep Flash Column 12 g; 0% to 80% ethyl acetate/hexanes) to afford, (S)-2-[4-(2-chloro-phenoxy)-2-oxo-2,5-dihydro-pyrrol-1-yl]-3-(4-flouoro-phenyl)-propanoic acid methyl ester (0.376 g, 48%) as a light orange gum.

To a magnetically stirred mixture of (S)-2-[4-(2-chloro-phenoxy)-2-oxo-2,5-dihydro-pyrrol-1-yl]-3-(4-fluorophenyl)-propanoic acid methyl ester (0.358 g, 0.87 mmol) in tetrahydrofuran (3 mL) and was added lithium hydroxide (0.042 g, 1 mmol) in water (3 mL). After addition was complete the mixture was stirred at 25° C. for 3 h. The reaction mixture was poured into water and diethyl ether and the layers separated. The aqueous layer was made acidic with 2N hydrochloric acid and extracted in two portions with ethyl acetate. The combined ethyl acetate fractions were washed with a saturated sodium chloride solution, dried over magnesium sulfate, filtered and concentrated to afford, (S)-2-[4-(2-chloro-phenoxy)-2-oxo-2,5-dihydro-pyrrol-1-yl]-3-(4-fluoro-phenyl)-propanoic acid (0.267 g, 82%) as an off-white foam: LR-ES-MS m/z calculated for C$_{19}$H$_{15}$ClFNO$_4$ [M]$^+$ 375, observed 376 [M+H]$^-$.

A solution of (S)-2-[4-(2-chloro-phenoxy)-2-oxo-2,5-dihydro-pyrrol-1-yl]-3-(4-fluorophenyl)-propanoic acid (0.268 g, 0.69 mmol) in dichloromethane (10 mL) was treated with 1-(3-dimethylaminopropyl)-3-ethylcarbodiimide hydrochloride (0.121 mg, 0.77 mmol) and 1-hydroxybenzotriazole (0.105 g, 0.77 mmol). The reaction mixture was stirred at 25° C. for 0.25 h followed by the addition of 1-((R)-2,2-dimethyl-[1,3]dioxolan-4-yl-methyl)-1H-pyrazol-3-ylamine (prepared as in Example 49, 0.172 mg, 0.83 mmol). The reaction mixture was stirred for 16 h at 25° C., under nitrogen. The reaction mixture was diluted with dichloromethane, washed with 2N hydrochloric acid, saturated sodium bicarbonate solution, a saturated sodium chloride solution and dried over magnesium sulfate. The crude product obtained after concentration, was purified by ISCO flash chromatography (Teledyne Isco RediSep Flash Column 12 g; 0% to 100% ethyl acetate/hexanes) to afford, (S)-2-[4-(2-chloro-phenoxy)-2-oxo-2,5-dihydro-pyrrol-1-yl]-3-(4-fluorophenyl)-propionic acid [1-((R)-2,2-dimethyl-[1,3]dioxolan-4-yl-methyl)-1H-pyrazol-3-yl]-amide (0.195 g, 50%) as an off-white powder: HR-ES-MS m/z calculated for C$_{28}$H$_{28}$ClFN$_4$O$_5$ [M+H]$^+$ 555.1803, observed 555.1805. (39143-094-1). $^1$H NMR (300 MHz, DMSO-d$_6$) δ ppm 1.23 (s, 3H), 1.28 (s, 3H), 3.04-3.26 (m, 2H), 3.70 (dd, J=8.3, 5.9 Hz, 1H), 3.97 (dd, J=8.8, 6.6 Hz, 1H), 4.00-4.19 (m, 2H), 4.33 (s, 3H), 4.70 (s, 1H), 5.07 (t, J=7.7 Hz, 1H), 6.45 (d, J=1.8 Hz, 1H), 7.01 (t, J=8.0 Hz, 2H), 7.21-7.39 (m, 2H), 7.39-7.49 (m, 2H), 7.59 (d, J=1.8 Hz, 1H), 7.63 (d, J=8.2 Hz, 1H), 10.77 (s, 1H).

Example 187

(S)-2-[4-(2-chloro-phenoxy)-2-oxo-2,5-dihydro-pyrrol-1-yl]-N-[1-((R)-2,3-dihydroxy-propyl)-1H-pyrazol-3-yl]-3-(4-fluorophenyl)-propionamide

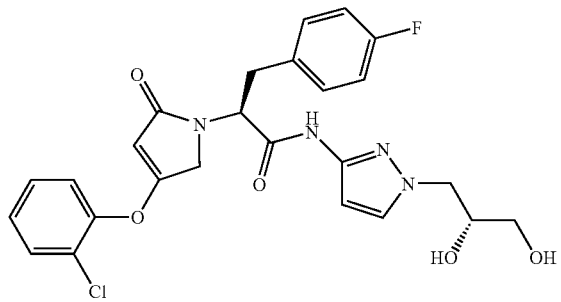

A solution of (S)-2-[4-(2-chloro-phenoxy)-2-oxo-2,5-dihydro-pyrrol-1-yl]-3-(4-fluorophenyl)-propionic acid [1-((R)-2,2-dimethyl-[1,3]dioxolan-4-yl-methyl)-1H-pyrazol-3-yl]-amide (prepared as in Example 186, 0.178 g, 0.314 mmol) in tetrahydrofuran (3 mL) was treated with 2N aqueous hydrochloric acid solution (3 mL). The reaction mixture was stirred at 25° C. for 3 h. The reaction mixture was diluted with ethyl acetate, washed with water, saturated sodium bicarbonate solution, a saturated sodium chloride solution and dried over magnesium sulfate. The organic layer was concentrated to afford, (S)-2-[4-(2-chloro-phenoxy)-2-oxo-2,5-dihydro-pyrrol-1-yl]-3-(4-fluorophenyl)-N-[1-((R)-2,3-dihydroxy-propyl)-1H-pyrazol-3-yl]-propionamide (0.119 g, 74%) as a white powder: HR-ES-MS m/z calculated for $C_{25}H_{24}ClFN_4O_5$ [M+H]$^-$ 515.1489, observed 515.1492; 1H NMR (300 MHz, DMSO-d$_6$); $^1$H NMR (300 MHz, DMSO-d$_6$) δ ppm 3.02-3.33 (m, 4H), 3.78 (br. s., 1H), 3.87 (dd, J=13.6, 7.5 Hz, 1H), 4.10 (dd, J=13.0, 3.0 Hz, 1H), 4.27 (d, J=18.4 Hz, 1H), 4.59 (d, J=18.4 Hz, 1H), 4.68 (s, 1H), 4.72 (t, J=5.1 Hz, 1H), 4.95 (d, J=4.5 Hz, 1H), 5.13 (dd, J=10.3, 4.2 Hz, 1H), 6.44 (br. s., 1H), 7.12 (t, J=8.2 Hz, 2H), 7.30-7.49 (m, 5H), 7.55 (s, 1H), 7.63 (d, J=7.8 Hz, 1H), 10.86 (s, 1H).

Example 188

(S)-2-[4-(2-chloro-phenoxy)-2-oxo-2,5-dihydro-pyrrol-1-yl]-N-[1-((R)-2,2-dimethyl-[1,3]dioxolan-4-yl-methyl)-1H-pyrazol-3-yl]-3-(2-chlorophenyl)-propionamide

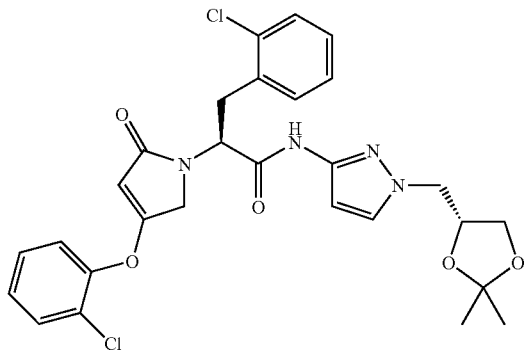

To a stirred mixture of L-2-chlorophenylalanine methyl ester hydrochloride (1.038 g, 4.11 mmol) dissolved in ethanol (25 mL) under a nitrogen atmosphere was added anhydrous potassium carbonate (1.052 g, 7.53 mmol). After addition was complete (E)-4-bromo-3-(2-chloro-phenoxy)-but-2-enoic acid ethyl ester (prepared as in Example 61, 1.117 g, 3.42 mmol) was added. The reaction mixture was then lowered into a pre-heated oil bath kept at 105° C. and heated for 2 h. Then, acetic acid (0.52 g, 8.56 mmol) was added and the reflux was continued for additional 20 h. The reaction mixture was cooled to 25° C., and poured into water and extracted with diethyl ether and washed with 2N hydrochloric acid, a saturated sodium chloride solution and dried over magnesium sulfate. The crude product obtained was purified by ISCO flash chromatography (Teledyne Isco RediSep Flash Column 40 g; 0% to 80% ethyl acetate/hexanes) to afford, (S)-2-[4-(2-chloro-phenoxy)-2-oxo-2,5-dihydro-pyrrol-1-yl]-3-(2-chorophenyl)-propanoic acid methyl ester (0.608 g, 44%) as a light orange gum.

To a stirred mixture of (S)-2-[4-(2-chloro-phenoxy)-2-oxo-2,5-dihydro-pyrrol-1-yl]-3-(2-chlorophenyl)-propanoic acid methyl ester (0.608 g, 1.43 mmol) in tetrahydrofuran (2 mL) and was added lithium hydroxide (0.073 g, 1.72 mmol) in water (1 mL). After addition was complete the mixture was stirred at 25° C. for 3 h. The reaction mixture was poured into water and diethyl ether and the layers separated. The aqueous layer was made acidic with 2N hydrochloric acid and extracted in two portions with ethyl acetate. The combined ethyl acetate fractions were washed with a saturated sodium chloride solution, dried over magnesium sulfate, filtered and concentrated to afford, (S)-2-[4-(2-chloro-phenoxy)-2-oxo-2,5-dihydro-pyrrol-1-yl]-3-(2-chlorophenyl)-propanoic acid (0.471 g, 84%) as an off-white powder.

A solution of (S)-2-[4-(2-chloro-phenoxy)-2-oxo-2,5-dihydro-pyrrol-1-yl]-3-(2-chlorophenyl)-propanoic acid (0.299 g, 0.574 mmol) in dichloromethane (10 mL) was treated with 1-(3-dimethylaminopropyl)-3-ethylcarbodiimide hydrochloride (0.100 g, 0.63 mmol) and 1-hydroxybenzotriazole (0.087 g, 0.63 mmol). The reaction mixture was stirred at 25° C. for 0.25 h followed by the addition of 1-((R)-2,2-dimethyl-[1,3]dioxolan-4-yl-methyl)-1H-pyrazol-3-ylamine (prepared as in Example 49, 0.141 g, 0.69 mmol). The reaction mixture was stirred for 16 h at 25° C., under nitrogen. The reaction mixture was diluted with dichloromethane, washed with 2N hydrochloric acid, saturated sodium bicarbonate solution, a saturated sodium chloride solution and dried over magnesium sulfate. The crude product obtained after concentration, was purified by ISCO flash chromatography (Teledyne Isco RediSep Flash Column 12 g; 0% to 100% ethyl acetate/hexanes) to afford, (S)-2-[4-(2-chloro-phenoxy)-2-oxo-2,5-dihydro-pyrrol-1-yl]-3-(4-chlorophenyl)-propionic acid [1-((R)-2,2-dimethyl-[1,3]dioxolan-4-yl-methyl)-1H-pyrazol-3-yl]-amide (0.171 g, 52%) as an off-white powder: HR-ES-MS m/z calculated for $C_{28}H_{28}Cl_2N_4O_5$ [M+H]$^+$ 571.1506, observed 571.1510. $^1$H NMR (300 MHz, DMSO-d$_6$) δ ppm 1.23 (s, 3H), 1.29 (s, 3H), 3.25 (d, J=7.8 Hz, 2H), 3.71 (dd, J=8.2, 6.0 Hz, 1H), 3.98 (t, J=7.2 Hz, 1H), 4.01-4.17 (m, 2H), 4.25 (d, J=18.4 Hz, 1H), 4.29-4.36 (m, 1H), 4.39 (d, J=18.4 Hz, 1H), 4.72 (s, 1H), 5.18 (t, J=7.5 Hz, 1H), 6.46 (d, J=1.5 Hz, 1H), 7.18-7.29 (m, 2H), 7.29-7.47 (m, 5H), 7.58-7.64 (m, 2H), 10.79 (s, 1H).

Example 189

(S)-2-[4-(2-chloro-phenoxy)-2-oxo-2,5-dihydro-pyrrol-1-yl]-N-[1-((R)-2,3-dihydroxy-propyl)-1H-pyrazol-3-yl]-3-(2-chlorophenyl)-propionamide

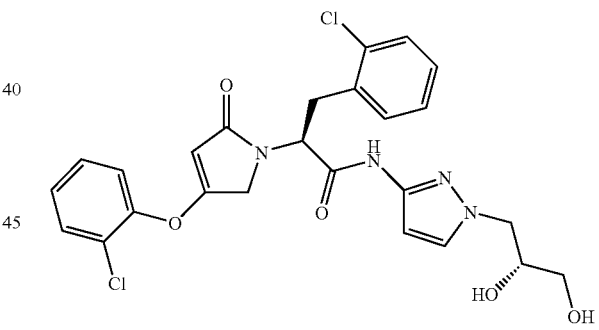

A solution of (S)-2-[4-(2-chloro-phenoxy)-2-oxo-2,5-dihydro-pyrrol-1-yl]-3-(4-chlorophenyl)-propionic acid [1-((R)-2,2-dimethyl-[1,3]dioxolan-4-yl-methyl)-1H-pyrazol-3-yl]-amide (prepared as in Example 188, 0.151 g, 0.259 mmol) in tetrahydrofuran (3 mL) was treated with 2N aqueous hydrochloric acid solution (3 mL). The reaction mixture was stirred at 25° C. for 3 h. The reaction mixture was diluted with ethyl acetate, washed with water, saturated sodium bicarbonate solution, a saturated sodium chloride solution and dried over magnesium sulfate. The organic layer was concentrated to afford, (S)-2-[4-(2-chloro-phenoxy)-2-oxo-2,5-dihydro-pyrrol-1-yl]-3-(4-chlorophenyl)-N-[1-((R)-2,3-dihydroxy-propyl)-1H-pyrazol-3-yl]-propionamide (0.110 g, 80%) as a white powder: HR-ES-MS m/z calculated for $C_{25}H_{24}Cl_2N_4O_5$ [M+H]$^+$ 531.1196, observed 531.1197; $^1$H NMR (300 MHz, DMSO-d$_6$); $^1$H NMR (300 MHz, DMSO-d$_6$) δ ppm 3.19-3.30 (m, 4H), 3.74 (br. s., 1H), 3.80-3.91 (m, 1H), 4.07 (dd, J=13.6, 3.6 Hz, 1H), 4.25 (d, J=18.2 Hz, 1H), 4.39 (d, J=18.2 Hz, 1H), 4.65-4.71 (m, 1H), 4.72 (s, 1H), 4.93 (d, J=5.1 Hz, 1H), 5.18 (t, J=7.5 Hz, 1H), 6.43 (d, J=1.5 Hz, 1H), 7.18-7.30 (m, 2H), 7.30-7.47 (m, 5H), 7.53 (d, J=1.5 Hz, 1H), 7.62 (d, J=7.8 Hz, 1H), 10.76 (s, 1H).

Example 190

(S)-2-[4-(2-chloro-phenoxy)-2-oxo-2,5-dihydro-pyrrol-1-yl]-4-methyl-pentanoic acid (5-chloro-thiazol-2-yl)-amide

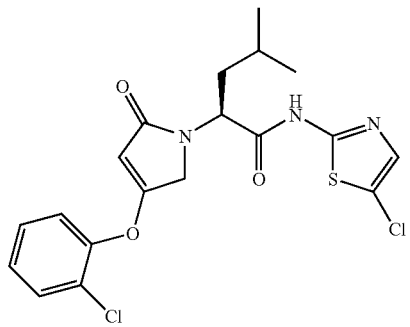

A solution of (S)-2-[4-(2-chloro-phenoxy)-2-oxo-2,5-dihydro-pyrrol-1-yl]-4-methyl-pentanoic acid (prepared as in Example 64, 0.345 g, 1.05 mmol) in dichloromethane (20 mL) was treated with 1-(3-dimethylaminopropyl)-3-ethyl-carbodiimide hydrochloride (0.184 g, 1.16 mmol) and 1-hydroxybenzotriazole (0.160 g, 1.16 mmol). The reaction mixture was stirred at 25° C. for 0.25 h followed by the addition of 5-chloro-2-amino-thizaole (prepared from the neutralization of the corresponding amine hydrochloride salt with N,N-diisopropylethylamine) (0.223 g, 1.26 mmol). The reaction mixture was stirred for 16 h at 25° C., under nitrogen. The reaction mixture was diluted with dichloromethane, washed with 2N hydrochloric acid, a saturated sodium chloride solution and dried over magnesium sulfate. The crude product obtained after concentration, was purified by ISCO flash chromatography (Teledyne Isco RediSep Flash Column 40 g; 0% to 100% ethyl acetate/hexanes) to afford, (S)-2-[4-(2-chloro-phenoxy)-2-oxo-2,5-dihydro-pyrrol-1-yl]-4-methyl-pentanoic acid (5-chloro-thiazol-2-yl)-amide (0.301 g, 65%) as an off-white powder: HR-ES-MS m/z calculated for $C_{19}H_{19}Cl_2N_3O_3S$ [M+H]$^+$ 440.0596, observed 440.0597; $^1$H NMR (300 MHz, DMSO-d$_6$) δ ppm 0.91 (d, J=6.4 Hz, 3H), 0.94 (d, J=6.4 Hz, 3H), 1.48 (m, 1H), 1.52-1.69 (m, 1H), 1.72-1.95 (m, 1H), 4.27 (d, J=18.4 Hz, 1H), 4.54 (d, J=18.4 Hz, 1H), 4.82 (s, 1H), 4.98 (dd, J=10.9, 4.8 Hz, 1H), 7.32-7.42 (m, 1H), 7.41-7.50 (m, 1H), 7.50-7.56 (m, 1H), 7.55 (s, 1H), 7.66 (d, J=7.8 Hz, 1H), 12.81 (s, 1H).

Example 191

(S)-2-[4-(2-chloro-phenoxy)-2-oxo-2,5-dihydro-pyrrol-1-yl]-4-methyl-pentanoic acid (5-chloro-thiazol-2-yl)-amide

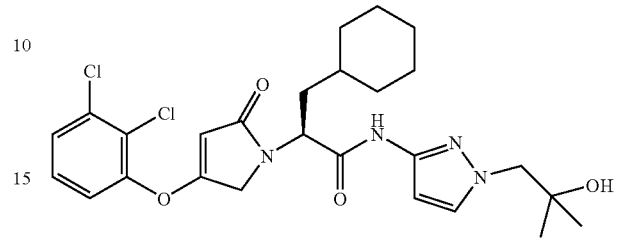

To a stirred solution of ethyl acetoacetate (150.0 g, 0.86 mol) in hexanes (200 mL) was added phosphorus pentachloride (95.0 g, 0.456 mol) at 23° C. under nitrogen and stirred for 3 h. Water (300 mL) was added to the reaction mixture while cooling in an ice-bath. The organic layer was separated, washed with an aqueous solution of 20% potassium carbonate (3×200 mL) followed by a saturated sodium chloride solution (2×100 mL), dried over sodium sulfate and concentrated in vacuo to afford 3-chloro-but-2-enoic acid ethyl ester which was purified by distillation (95.8 g, 75%): boiling range 160°-170° C.

Potassium t-butoxide (11.2 g, 0.100 mol) was added to a stirred solution of 2,3-dichlorophenol (8.2 g, 0.05 mol) in tetrahydrofuran (40 mL) at 23° C. under nitrogen and the reaction mixture was heated to reflux for 0.75 h. The reaction mixture was cooled to 23° C. and a solution of 3-chloro-but-2-enoic acid ethyl ester (6.5 g, 0.044 mol) in tetrahydrofuran (40 mL) was added to the reaction mixture. The reaction mixture was refluxed for an additional 3 h. After this time, the mixture was concentrated in vacuo and the residue was diluted with water and extracted with diethyl ether. The organic layer was then washed with 5% sodium hydroxide solution followed by a saturated sodium chloride solution. The combined organic layers were separated, dried over sodium sulfate and concentrated in vacuo to afford 3-(2,3-dichoro-phenoxy)-but-2-enoic acid ethyl ester (9.20 g, 76%) as a yellow oil.

To a stirred mixture of 3-(2,3-chloro-phenoxy)-but-2-enoic acid ethyl ester (10.1 g, 0.037 mol) in carbon tetrachloride (50 mL) under a nitrogen atmosphere was added N-bromosuccinimide (9.84 g, 0.055 mol) and benzoyl peroxide (0.89 g, 0.004 mol). Nitrogen gas was bubbled through the mixture for 5 min, and the resulting mixture was heated to reflux for 4 h. The reaction mixture was then placed in the refrigerator overnight. The solids formed were removed by filtration and the filtrate concentrated in vacuo. The crude product obtained was purified using flash column chromatography (silica gel (100-200 mesh), ethyl acetate/hexanes) to afford 4-bromo-3-(2,3-dichlooro-phenoxy)-but-2-enoic acid ethyl ester (6.20 g, 48%) as a yellow oil.

To a stirred solution of (S)-2-amino-3-cyclohexyl-propionic acid methyl ester (1.15 g, 0.062 mol) in N,N-dimethylformamide (5 mL) was added N,N-diisopropylethylamine (3.63 g, 0.282 mol) slowly at room temperature, under nitrogen. The resulting mixture was stirred for 5 min and then treated with 4-bromo-3-(2,3-dichloro-phenoxy)-but-2-enoic acid ethyl ester (2.0 g, 0.006 mol) and the reaction mixture was heated at 110° C.-120° C. for 16 h. After this time, ice water was added and the resulting mixture was extracted with ethyl acetate. The combined organic layers were washed with a saturated aqueous sodium chloride solution, dried over sodium sulfate and concentrated in vacuo. Purification using flash column chromatography (silica gel (100-200 mesh)) afforded (S)-3-cyclohexyl-2-[4-(2,3-dichloro-phenoxy)-2-oxo-2,5-dihydro-pyrrol-1-yl]-propionic acid methyl ester (0.40 g, 17%) as a yellow oil.

To a stirred solution of (S)-3-cyclohexyl-2-[4-(2,3-dichloro-phenoxy)-2-oxo-2,5-dihydro-pyrrol-1-yl]-propionic acid methyl ester (405 mg, 0.001 mol) in tetrahydrofuran-water (3:1) was added lithium hydroxide (128 mg, 0.003 mol). The reaction mixture was stirred at 23° C. for 2 h. After this time, the mixture was concentrated and the reaction mixture was diluted with water. The reaction mixture was acidified with 2N hydrochloric acid, during which time precipitation occurred. The precipitate was removed by filtration, washed with cold water and dried in vacuo to obtain (S)-3-cyclohexyl-2-[4-(2,3-dichloro-phenoxy)-2-oxo-2,5-dihydro-pyrrol-1-yl]-propionic acid (0.3 g, 77%) as a yellow solid.

To a stirred solution of (S)-3-cyclohexyl-2-[4-(2,3-dichloro-phenoxy)-2-oxo-2,5-dihydro-pyrrol-1-yl]-propionic acid (0.16 g, 0.4 mmol) in dichloromethane (10 mL) was gradually added 1-(3-dimethylaminopropyl)-3-ethylcarbodiimide hydrochloride (0.23 g, 0.0012 mol) and N,N-diisopropylethylamine (0.26 g, 0.002 mol) at room temperature, under nitrogen. After 15 min, 1-hydroxybenzotriazole (0.183 g, 0.0012 mol) and 1-(3-amino-pyrazol-1-yl)-2-methyl-propan-2-ol (prepared in U.S. Pat. Appl. US2008021032 Example 80, 0.062 g, 0.4 mmol) were added to the reaction mixture. The reaction mixture was then stirred at 23° C. for 48 h. The reaction mixture was diluted with ethyl acetate and washed with a saturated aqueous ammonium chloride solution followed by a saturated aqueous sodium bicarbonate solution. The organic layer was then washed with a saturated aqueous sodium chloride solution, separated, dried over sodium sulfate and concentrated in vacuo to afford the crude product, which was purified by flash column chromatography (silica gel (100-200 mesh)) which afforded (S)-2-[4-(2-chloro-phenoxy)-2-oxo-2,5-dihydro-pyrrol-1-yl]-4-methyl-pentanoic acid (5-chloro-thiazol-2-yl)-amide (0.07 g, 33%) as an off-white solid: $^1$H NMR (400 MHz, CDCl$_3$) δ ppm 0.78-1.11 (m, 2H), 1.17 (br. s., 6H), 1.19-1.35 (m, 3H), 1.62-2.00 (m, 8H), 3.61 (br. s., 1H), 3.95 (s, 2H), 4.14 (d, J=18.0 Hz, 1H), 4.33 (d, J=18.0 Hz, 1H), 4.88 (dd, J=8.3, 6.8 Hz, 1H), 4.91 (s, 1H), 6.70 (d, J=2.0 Hz, 1H), 7.13-7.25 (m, 2H), 7.31 (d, J=2.0 Hz, 1H), 7.43 (d, J=8.3 Hz, 1H), 8.50 (br. s., 1H).

Example 192

([6-(3-{(S)-2-[4-(2-chloro-phenoxy)-2-oxo-2,5-dihydro-pyrrol-1-yl]-[4R,6S]-4-methyl-pentanoylamino}-pyrazol-1-ylmethyl)-2,2-dimethyl-[1,3]dioxan-4-yl]-acetic acid t-butyl ester

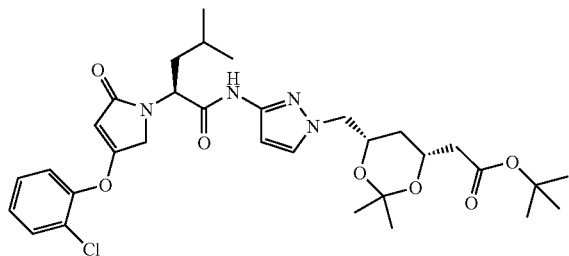

To a stirred solution of ((4R,6S)-6-hydroxymethyl-2,2-dimethyl-[1,3]dioxan-4-yl)-acetic acid t-butyl ester (2.24 g, 7.73 mmol), N,N-diisopropylethylamine (2.00 g, 15.46 mmol), 4-dimethylaminopyridine (0.95 g, 7.3 mmol) in dichloromethane (50 mL) was added p-toluenesulfonyl chloride (2.23 g, 11.59 mmol) at 23° C. under nitrogen and stirred for 3 h. The reaction mixture was diluted with dichloromethane and washed with 2N hydrochloric acid, saturated sodium chloride solution and the organic layer separated, dried over magnesium sulfate and concentrated in vacuo which afforded [(4R,6S)-2,2-dimethyl-6-(toluene-4-sulfonyloxymethyl)-[1,3]dioxan-4-yl]-acetic acid t-butyl ester (2.54 g, 80%) as a yellow waxy solid.

A solution of [(4R,6S)-2,2-dimethyl-6-(toluene-4-sulfonyloxymethyl)-[1,3]dioxan-4-yl]-acetic acid t-butyl ester (2.32 g, 5.38 mmol), 3-nitro-1H-pyrazole (prepared as in Example 5, 0.56 g, 4.89 mmol), and potassium carbonate (0.82 g, 5.87 mmol) in N,N-dimethyformamide (15 mL) was stirred at 23° C. under nitrogen for 16 h, followed by heating at 70° C. for 5 h. The reaction mixture was diluted with water and extracted with ethyl acetate. The organic layer was washed with a saturated sodium chloride solution and dried over magnesium sulfate. The crude product obtained after concentration, was purified by ISCO flash chromatography (Teledyne Isco RediSep Flash Column 40 g; 0% to 100% ethyl acetate/hexanes) to afford, [(4R,6S)-2,2-dimethyl-6-(3-nitro-pyrazol-1-ylmethyl)-[1,3]dioxan-4-yl]-acetic acid t-butyl ester (1.25 g, 72%) as yellow oil.

A solution of [(4R,6S)-2,2-dimethyl-6-(3-nitro-pyrazol-1-ylmethyl)-[1,3]dioxan-4-yl]-acetic acid t-butyl ester (1.56 g 3.52 mmol) in ethanol (25 mL) was hydrogenated in a Parr hydrogenator at 50 psi hydrogen pressure, using 10% palladium on carbon (0.2 g, 0.19 mmol), for 3 h. The reaction mixture was filtered through a celite plug, and the filtrate concentrated which afforded [(4R,6S)-6-(3-amino-pyrazol-1-ylmethyl)-2,2-dimethyl-[1,3]dioxan-4-yl]-acetic acid t-butyl ester (1.34 g, 94%) as a yellow solid.

A solution of (S)-2-[4-(2-chloro-phenoxy)-2-oxo-2,5-dihydro-pyrrol-1-yl]-4-methyl-pentanoic acid (prepared as in Example 64, 0.85 g, 2.6 mmol) in dichloromethane (20 mL) was treated with 1-(3-dimethylaminopropyl)-3-ethylcarbodiimide hydrochloride (0.45 g, 2.86 mmol) and 1-hydroxybenzotriazole (0.39 g, 2.86 mmol). The reaction mixture was stirred at 25° C. for 0.25 h followed by the addition of [(4R,6S)-6-(3-amino-pyrazol-1-ylmethyl)-2,2-dimethyl-[1,3]dioxan-4-yl]-acetic acid t-butyl ester (1.27 g, 3.11 mmol). The reaction mixture was stirred for 16 h at 25° C., under nitrogen. The reaction mixture was diluted with dichloromethane, washed with 2N hydrochloric acid, a saturated aqueous sodium chloride solution and the organic layer was separated and dried over magnesium sulfate. The crude product obtained after concentration, was purified by ISCO flash chromatography (Teledyne Isco RediSep Flash Column 80 g; 0% to 100% ethyl acetate/hexanes) which afforded, ([6-(3-{(S)-2-[4-(2-chloro-phenoxy)-2-oxo-2,5-dihydro-pyrrol-1-yl]-[4R,6S]-4-methyl-pentanoylamino}-pyrazol-1-ylmethyl)-2,2-dimethyl-[1,3]dioxan-4-yl]-acetic acid t-butyl ester (1.15 g, 71%) as an off-white powder: HR-ES-MS m/z calculated for $C_{32}H_{43}ClN_4O_7$ [M+H]$^+$ 631.2892, observed 631.2893; $^1$H NMR (300 MHz, DMSO-d$_6$) δ ppm 0.90 (d, J=6.3 Hz, 3H), 0.93 (d, J=6.3 Hz, 3H), 1.25 (s, 3H), 1.36 (s, 12H), 1.38-1.50 (m, 3H), 1.50-1.64 (m, 1H), 1.67-1.84 (m, 1H), 2.21 (dd, J=15.0, 7.8 Hz, 1H), 2.37 (dd, J=15.0, 4.7 Hz, 1H), 3.91-4.10 (m, 2H), 4.13-4.30 (m, 2H), 4.20 (d, J=18.4 Hz, 1H), 4.60 (d, J=18.4 Hz, 1H), 4.78 (s, 1H), 4.89 (dd, J=10.7, 4.7 Hz, 1H), 6.44 (d, J=1.8 Hz, 1H), 7.30-7.41 (m, 1H), 7.41-7.54 (m, 2H), 7.56 (d, J=1.8 Hz, 1H), 7.65 (d, J=7.8 Hz, 1H), 10.81 (s, 1H).

Example 193

(3R,5S)-6-(3-{(S)-2-[4-(2-chloro-phenoxy)-2-oxo-2,5-dihydro-pyrrol-1-yl]-4-methyl-pentanoylamino}-pyrazol-1-yl)-3,5-dihydroxy-hexanoic acid t-butyl eter

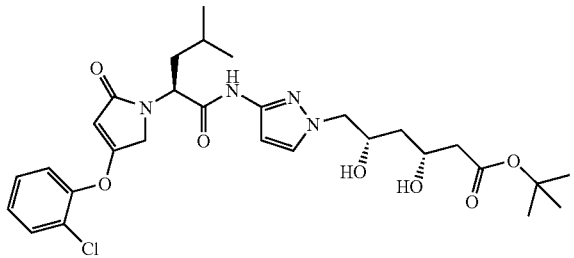

A solution of ([6-(3-{(S)-2-[4-(2-chloro-phenoxy)-2-oxo-2,5-dihydro-pyrrol-1-yl]-[4R,6S]-4-methyl-pentanoylamino}-pyrazol-1-ylmethyl)-2,2-dimethyl-[1,3]dioxan-4-yl]-acetic acid t-butyl ester (prepared as in Example 192, 1.1 g, 1.66 mmol) in tetrahydrofuran (5 mL) was treated with 2N aqueous hydrochloric acid solution (5 mL). The reaction mixture was stirred at 25° C. for 4 h. The reaction mixture was diluted with ethyl acetate, washed with water, saturated sodium bicarbonate solution, a saturated aqueous sodium chloride solution and the organic layer was separated and dried over magnesium sulfate. The organic layer was concentrated in vacuo which afforded (3R,5S)-6-(3-{(S)-2-[4-(2-chloro-phenoxy)-2-oxo-2,5-dihydro-pyrrol-1-yl]-4-methyl-pentanoylamino}-pyrazol-1-yl)-3,5-dihydroxy-hexanoic acid t-butyl ester (0.93 g, 95%) as an off-white powder: HR-ES-MS m/z calculated for $C_{29}H_{39}ClN_4O_7$ [M+H]$^+$ 591.2579, observed 591.2580; $^1$H NMR (300 MHz, DMSO-d$_6$) δ ppm 0.90 (d, J=6.3 Hz, 3H), 0.93 (d, J=6.3 Hz, 3H), 1.37 (s, 9H), 1.40-1.51 (m, 3H), 1.51-1.64 (m, 1H), 1.65-1.84 (m, 1H), 2.19 (dd, J=14.7, 8.2 Hz, 1H), 2.32 (dd, J=14.7, 4.5 Hz, 1H), 3.81-4.10 (m, 4H), 4.21 (d, J=18.7 Hz, 1H), 4.61 (d, J=18.7 Hz, 1H), 4.86 (br. s., 2H), 4.78 (s, 1H), 4.89 (dd, J=10.3, 4.2 Hz, 1H), 6.42 (s, 1H), 7.37 (t, J=7.6 Hz, 1H), 7.41-7.56 (m, 3H), 7.65 (d, J=7.6 Hz, 1H), 10.79 (s, 1H).

Example 194

(3R,5S)-6-(3-{(S)-2-[4-(2-chloro-phenoxy)-2-oxo-2,5-dihydro-pyrrol-1-yl]-4-methylpentanoylamino}-pyrazol-1-yl)-3,5-dihydroxy-hexanoic acid

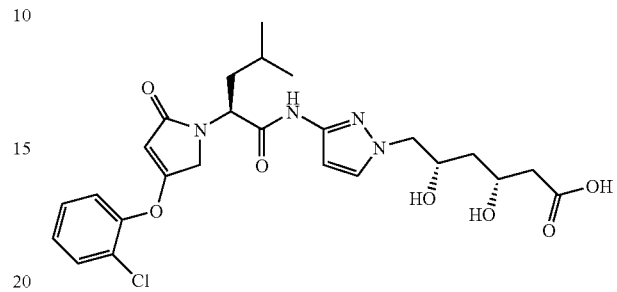

A solution of (3R,5S)-6-(3-{(S)-2-[4-(2-chloro-phenoxy)-2-oxo-2,5-dihydro-pyrrol-1-yl]-4-methyl-pentanoylamino}-pyrazol-1-yl)-3,5-dihydroxy-hexanoic acid t-butyl ester (prepared as in Example 193, 0.82 g 1.25 mmol) in methyl t-butyl ether (10 mL) was treated with 1N aqueous sodium hydroxide (3 mL). The biphasic mixture was lowered into a pre-heated oil bath, which was kept at 55° C. The mixture was heated for 1 h and cooled to 25° C. The layers were seperated and the aqueous layer was extracted with additional methyl t-butyl ether. The aqueous layer was treated with an aqueous solution of calcium acetate (3.2% solution, 12 mL) resulting in precipitation of a white solid. The mixture was heated to 55° C. for 1 h and cooled to 25° C. The solids were isolated by filtration and dried under vacuum, to afford (3R,5S)-6-(3-{(S)-2-[4-(2-chloro-phenoxy)-2-oxo-2,5-dihydro-pyrrol-1-yl]-4-methylpentanoylamino}-pyrazol-1-yl)-3,5-dihydroxy-hexanoic acid calcium salt (2:1) (0.62 g, 45%) as a white powder.

A solution of (3R,5S)-6-(3-{(S)-2-[4-(2-chloro-phenoxy)-2-oxo-2,5-dihydro-pyrrol-1-yl]-4-methylpentanoylamino}-pyrazol-1-yl)-3,5-dihydroxy-hexanoic acid calcium salt (2:1) (0.14 g, 0.23 mmol) was dissolved in 2N hydrochloric acid (10 mL) and stirred for 0.1 h at 25° C. The aqueous solution was extracted with ethyl acetate and the combined organic layers dried over magnesium sulfate and concentrated in vacuo. Purification by supercritical fluid chromatography on a SFC DAICEL OJ column, 35% methanol, afforded (3R,5S)-6-(3-{(S)-2-[4-(2-chloro-phenoxy)-2-oxo-2,5-dihydro-pyrrol-1-yl]-4-methylpentanoylamino}-pyrazol-1-yl)-3,5-dihydroxy-hexanoic acid (0.28 g, 44%) as a white powder: HR-ES-MS m/z calculated for $C_{25}H_{31}ClN_4O_7$ [M+H]$^+$ 535.1952, observed 535.1954; $^1$H NMR (400 MHz, DMSO-d$_6$) δ ppm 0.90 (d, J=6.5 Hz, 3H), 0.94 (d, J=6.5 Hz, 3H), 1.38-1.64 (m, 4H), 1.70-1.82 (m, 1H), 2.19 (dd, J=14.9, 8.3 Hz, 1H), 2.35 (dd, J=14.9, 4.7 Hz, 1H), 3.84-4.08 (m, 4H), 4.21 (d, J=18.5 Hz, 1H), 4.62 (d, J=18.5 Hz, 1H), 4.79 (s, 1H), 4.89 (dd, J=10.7, 4.7 Hz, 1H), 6.42 (d, J=2.0 Hz, 1H), 7.37 (td, J=7.8, 1.4 Hz, 1H), 7.47 (td, J=7.8, 1.4 Hz, 1H), 7.52 (dd, J=7.8, 1.4 Hz, 1H), 7.53 (d, J=2.0 Hz, 1H), 7.66 (dd, J=7.8, 1.4 Hz, 1H), 10.79 (s, 1H).

Example 195

(S)-3-cyclohexyl-N-[1-(2-hydroxy-2-methyl-propyl)-1H-pyrazol-3-yl]-2-[4-(2-isopropoxy-phenoxy)-2-oxo-2,5-dihydro-pyrrol-1yl]-propionamide

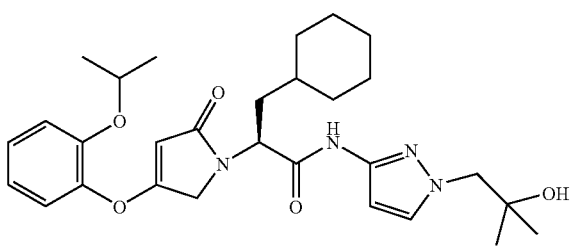

Potassium t-butoxide (7.36 g, 0.066 mol) was added to a stirred solution of 2-isopropoxy-phenol (5.00 g, 0.033 mol) in tetrahydrofuran (35 mL) at 23° C. under nitrogen and the reaction mixture was heated to reflux for 0.75 h. The reaction mixture was cooled to 23° C. and a solution of 3-chloro-but-2-enoic acid ethyl ester (prepared as in Example 191, 4.86 g, 0.033 mol) in tetrahydrofuran (40 mL) was added to the reaction mixture. The reaction mixture was refluxed for an additional 3 h. After this time, the mixture was concentrated in vacuo and the residue was diluted with water and extracted with diethyl ether. The organic layer was then washed with 5% aqueous sodium hydroxide solution followed by a saturated aqueous sodium chloride solution, dried over sodium sulfate and concentrated in vacuo to afford (E)-3-(2-isopropoxy-phenoxy)-but-2-enoic acid ethyl ester (5.60 g, 65%) as a yellow oil.

To a stirred mixture of (E)-3-(2-isopropoxy-phenoxy)-but-2-enoic acid ethyl ester (4.90 g, 0.019 mol) in carbon tetrachloride (35 mL) under a nitrogen atmosphere was added N-bromosuccinimide (4.95 g, 0.028 mol) and benzoyl peroxide (450 mg, 0.002 mol). Nitrogen gas was bubbled through the mixture for 5 min, and the resulting mixture was heated to reflux for 4 h. The reaction mixture was then placed in the refrigerator overnight. The solids formed were removed by filtration and the filtrate concentrated in vacuo. The crude product obtained was purified using flash column chromatography (silica gel (100-200 mesh), ethyl acetate/hexanes) to afford (E)-4-bromo-3-(2-isopropoxy-phenoxy)-but-2-enoic acid ethyl ester (4.10 g, 64%) as a yellow oil.

To a stirred solution of (S)-2-amino-3-cyclohexyl-propionic acid methyl ester (1.20 g, 0.006 mol) in N,N-dimethylformamide (8 mL) was added N,N-diisopropylethylamine (3.76 g, 0.029 mol) slowly at room temperature, under nitrogen. The resulting mixture was stirred for 5 min and then treated with (E)-4-bromo-3-(2-isopropoxy-phenoxy)-but-2-enoic acid ethyl ester (2.00 g, 0.006 mol) and the reaction mixture was heated at 110° C.-120° C. for 16 h. After this time, ice water was added and the resulting mixture was extracted with ethyl acetate. The combined organic layers were washed with a saturated aqueous sodium chloride solution, dried over sodium sulfate and concentrated in vacuo. Purification by flash column chromatography (silica gel (100-200 mesh)) afforded (S)-3-cyclohexyl-2-[4-(2-isopropoxy-phenoxy)-2-oxo-2,5-dihydro-pyrrol-1-yl]-propionic acid methyl ester (0.720 g, 28%) as a yellow oil.

To a stirred solution of (S)-3-cyclohexyl-2-[4-(2-isopropoxy-phenoxy)-2-oxo-2,5-dihydro-pyrrol-1-yl]-propionic acid methyl ester (710 mg, 0.002 mol) in tetrahydrofuran-water (3:1, 15 mL) was added lithium hydroxide (223 mg, 0.009 mol). The reaction mixture was stirred at 23° C. for 2 h. After this time, the mixture was concentrated and the reaction mixture was diluted with water. The reaction mixture was acidified with 2N hydrochloric acid, during which time precipitation occurred. The precipitate was removed by filtration, washed with cold water and dried in vacuo to obtain (S)-3-cyclohexyl-2-[4-(2-isopropoxy-phenoxy)-2-oxo-2,5-dihydro-pyrrol-1-yl]-propionic acid (620 mg, 90%) as a light brown solid.

To a stirred solution of (S)-3-cyclohexyl-2-[4-(2-isopropoxy-phenoxy)-2-oxo-2,5-dihydro-pyrrol-1-yl]-propionic acid (150 mg, 0.39 mmol) in dichloromethane (7 mL) was gradually added 1-(3-dimethylaminopropyl)-3-ethylcarbodiimide hydrochloride (221 mg, 1.15 mmol) and N,N-diisopropylethylamine (250 mg, 1.93 mmol) at room temperature, under nitrogen. After 15 min, 1-hydroxybenzotriazole (177 mg, 1.20 mmol) and 1-(3-amino-pyrazol-1-yl)-2-methyl-propan-2-ol (prepared in U.S. Pat. Appl. US2008021032 Example 80, 60 mg, 0.39 mmol) were added to the reaction mixture. The reaction mixture was then stirred at 23° C. for 48 h. The reaction mixture was diluted with ethyl acetate and washed with a saturated aqueous ammonium chloride solution followed by a saturated aqueous sodium bicarbonate solution. The organic layer was then washed with a saturated aqueous sodium chloride solution, separated, dried over sodium sulfate and concentrated in vacuo to afford the crude product, which was purified by flash column chromatography (silica gel (100-200 mesh)) which afforded (S)-3-cyclohexyl-N-[1-(2-hydroxy-2-methyl-propyl)-1H-pyrazol-3-yl]-2-[4-(2-isopropoxy-phenoxy)-2-oxo-2,5-dihydro-pyrrol-1-yl]-propionamide (70 mg, 34%) as a light yellow sticky solid: $^1$H NMR (400 MHz, CDCl$_3$) δ ppm 0.79-1.07 (m, 3H), 1.13 (br. s., 3H), 1.14 (br. s., 3H), 1.16-1.34 (m, 8H), 1.55-1.95 (m, 8H), 3.63 (br. s., 1H), 3.92 (s, 2H), 4.04 (d, J=18.1 Hz, 1H), 4.18 (d, J=18.1 Hz, 1H), 4.43-4.55 (m, 1H), 4.86 (s, 1H), 4.88 (dd, J=9.3, 1H), 6.67 (d, J=2.0 Hz, 1H), 6.93 (t, J=7.8 Hz, 1H), 6.98 (d, J=7.8 Hz, 1H), 7.13 (d, J=7.8 Hz, 1H), 7.18 (t, J=7.8 Hz, 1H), 7.28 (d, J=2.0 Hz, 1H), 8.54 (s, 1H).

Example 196

(S)-3-cyclohexyl-N-[1-(2-hydroxy-2-methyl-propyl)-1H-pyrazol-3-yl]-2-[4-(2-methylsulfanyl-phenoxy)-2-oxo-2,5-dihydro-pyrrol-1-yl]-propionamide

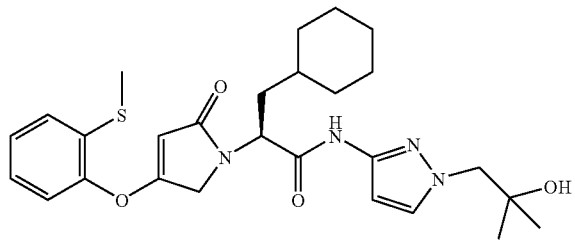

Potassium t-butoxide (1.23 g, 0.011 mol) was added to a stirred solution of 2-methylsulfanyl-phenol (1.00 g, 0.007 mol) in tetrahydrofuran (15 mL) at 23° C. under nitrogen and the reaction mixture was heated to reflux for 0.75 h. The reaction mixture was cooled to 23° C. and a solution of 3-chloro-but-2-enoic acid ethyl ester (prepared as in Example 191, 0.94 g, 0.006 mol) in tetrahydrofuran (40 mL) was added to the reaction mixture. The reaction mixture was refluxed for an additional 3 h. After this time, the mixture was concentrated in vacuo and the residue was diluted with water and extracted with diethyl ether. The organic layer was then washed with 5% aqueous sodium hydroxide solution followed by a saturated aqueous sodium chloride solution, dried over sodium sulfate and concentrated in vacuo to afford (E)-3-(2-methylsulfanyl-phenoxy)-but-2-enoic acid ethyl ester (1.15 g, 72%) as a yellow oil.

To a stirred mixture of (E)-3-(2-methylsulfanyl-phenoxy)-but-2-enoic acid ethyl ester (1.00 g, 0.004 mol) in carbon tetrachloride (15 mL) under a nitrogen atmosphere was added N-bromosuccinimide (1.00 g, 0.006 mol) and benzoyl peroxide (0.13 g, 0.001 mol). Nitrogen gas was bubbled through the mixture for 5 min, and the resulting mixture was heated to reflux for 4 h. The reaction mixture was then placed in the refrigerator overnight. The solids formed were removed by filtration and the filtrate concentrated in vacuo. The crude product obtained was purified using flash column chromatography (silica gel (100-200 mesh), ethyl acetate/hexanes) to afford (E)-4-bromo-3-(2-methylsulfanyl-phenoxy)-but-2-enoic acid ethyl ester (0.50 g, 38%) as a yellow oil: LR-ES-MS m/z calculated for $C_{13}H_{15}BrO_3S$ $[M]^+$ 330, observed 333.

To a stirred solution of (S)-2-amino-3-cyclohexyl-propionic acid methyl ester (1.10 g, 0.006 mol) in N,N-dimethylformamide (10 mL) was added N,N-diisopropylethylamine (3.51 g, 0.027 mol) slowly at room temperature, under nitrogen. The resulting mixture was stirred for 5 min and then treated with (E)-4-bromo-3-(2-methylsulfanyl-phenoxy)-but-2-enoic acid ethyl ester (1.80 g, 0.005 mol) and the reaction mixture was heated at 110° C.-120° C. for 16 h. After this time, ice water was added and the resulting mixture was extracted with ethyl acetate. The combined organic layers were washed with a saturated aqueous sodium chloride solution, dried over sodium sulfate and concentrated in vacuo. Purification by flash column chromatography (silica gel (100-200 mesh)) afforded (S)-3-cyclohexyl-2-[4-(2-methylsulfanyl-phenoxy)-2-oxo-2,5-dihydro-pyrrol-1-yl]-propionic acid methyl ester (250 mg, 11%) as a yellow oil.

To a stirred solution of (S)-3-cyclohexyl-2-[4-(2-methylsulfanyl-phenoxy)-2-oxo-2,5-dihydro-pyrrol-1-yl]-propionic acid methyl ester (250 mg, 0.001 mol) in tetrahydrofuran-water (3:1, 12 mL) was added lithium hydroxide (0.080 g, 0.003 mol). The reaction mixture was stirred at 23° C. for 2 h. After this time, the mixture was concentrated and the reaction mixture was diluted with water. The reaction mixture was acidified with 2N hydrochloric acid, during which time precipitation occurred. The precipitate was removed by filtration, washed with cold water and dried in vacuo to obtain (S)-3-cyclohexyl-2-[4-(2-methylsulfanyl-phenoxy)-2-oxo-2,5-dihydro-pyrrol-1-yl]-propionic acid (200 mg, 83%) as a semi-solid.

To a stirred solution of (S)-3-cyclohexyl-2-[4-(2-methylsulfanyl-phenoxy)-2-oxo-2,5-dihydro-pyrrol-1-yl]-propionic acid (200 mg, 0.53 mmol) in dichloromethane (12 mL) was gradually added 1-(3-dimethylaminopropyl)-3-ethylcarbodiimide hydrochloride (305 mg, 1.6 mmol) and N,N-diisopropylethylamine (387 mg, 3.0 mmol) at room temperature, under nitrogen. After 15 min, 1-hydroxybenzotriazole (245 mg, 1.7 mmol) and 1-(3-amino-pyrazol-1-yl)-2-methyl-propan-2-ol (prepared in U.S. Pat. Appl. US2008021032 Example 80, 82 mg, 0.53 mmol) were added to the reaction mixture. The reaction mixture was then stirred at 23° C. for 48 h. The reaction mixture was diluted with ethyl acetate and washed with a saturated aqueous ammonium chloride solution followed by a saturated aqueous sodium bicarbonate solution. The organic layer was then washed with a saturated aqueous sodium chloride solution, separated, dried over sodium sulfate and concentrated in vacuo to afford the crude product, which was purified by flash column chromatography (silica gel (100-200 mesh)) which afforded (S)-3-cyclohexyl-N-[1-(2-hydroxy-2-methyl-propyl)-1H-pyrazol-3-yl]-2-[4-(2-methylsulfanyl-phenoxy)-2-oxo-2,5-dihydro-pyrrol-1-yl]-propionamide (40 mg, 15%) as an light yellow solid.

Example 197

(S)-2-[4-(2-t-butyl-phenoxy)-2-oxo-2,5-dihydro-pyrrol-1-yl]-3-cyclohexyl-N-[1-(2-hydroxy-2-methyl-propyl)-1H-pyrazol-3-yl]-propionamide

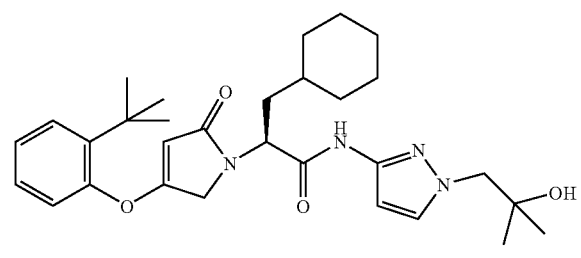

Potassium t-butoxide (11.3 g, 0.10 mol) was added to a stirred solution of 2-t-butyl-phenol (7.60 g, 0.05 mol) in tetrahydrofuran (40 mL) at 23° C. under nitrogen and the reaction mixture was heated to reflux for 0.75 h. The reaction mixture was cooled to 23° C. and a solution of 3-chloro-but-2-enoic acid ethyl ester (prepared as in Example 191, 7.50 g, 0.05 mol) in tetrahydrofuran (40 mL) was added to the reaction mixture. The reaction mixture was refluxed for an additional 3 h. After this time, the mixture was concentrated in vacuo and the residue was diluted with water and extracted with diethyl ether. The organic layer was then washed with 5% aqueous sodium hydroxide solution followed by a saturated aqueous sodium chloride solution, dried over sodium sulfate and concentrated in vacuo to afford (E)-3-(2-t-butyl-phenoxy)-but-2-enoic acid ethyl ester (10.2 g, 77%) as a yellow oil.

To a stirred mixture of (E)-3-(2-t-butyl-phenoxy)-but-2-enoic acid ethyl ester (3.20 g, 0.012 mol) in carbon tetrachloride (20 mL) under a nitrogen atmosphere was added N-bromosuccinimide (3.26 g, 0.018 mol) and benzoyl peroxide (295 mg, 0.001 mol). Nitrogen gas was bubbled through the mixture for 5 min, and the resulting mixture was heated to reflux for 4 h. The reaction mixture was then placed in the refrigerator overnight. The solids formed were removed by filtration and the filtrate concentrated in vacuo. The crude product obtained was purified using flash column chromatography (silica gel (100-200 mesh), ethyl acetate/hexanes) to afford (E)-4-bromo-3-(2-t-butyl-phenoxy)-but-2-enoic acid ethyl ester (2.10 g, 50%) as a yellow oil.

To a stirred solution of (S)-2-amino-3-cyclohexyl-propionic acid methyl ester (960 mg, 0.005 mol) in N,N-dimethylformamide (8 mL) was added N,N-diisopropylethylamine (3.00 g, 0.023 mol) slowly at room temperature, under nitrogen. The resulting mixture was stirred for 5 min and then treated with (E)-4-bromo-3-(2-t-butyl-phenoxy)-but-2-enoic acid ethyl ester (1.60 g, 0.005 mol) and the reaction mixture was heated at 110° C.-120° C. for 16 h. After this time, ice water was added and the resulting mixture was extracted with ethyl acetate. The combined organic layers were washed with a saturated aqueous sodium chloride solution, dried over sodium sulfate and concentrated in vacuo. Purification by flash column chromatography (silica gel (100-200 mesh)) afforded (S)-2-[4-(2-t-butyl-phenoxy)-2-oxo-2,5-dihydro-pyrrol-1-yl]-3-cyclohexyl-propionic acid methyl ester (585 mg, 28%) as yellow oil.

To a stirred solution of (S)-2-[4-(2-t-butyl-phenoxy)-2-oxo-2,5-dihydro-pyrrol-1-yl]-3-cyclohexyl-propionic acid methyl ester (585 mg, 0.001 mol) in tetrahydrofuran-water (3:1, 10 mL) was added lithium hydroxide (184 mg, 0.008 mol). The reaction mixture was stirred at 23° C. for 2 h. After this time, the mixture was concentrated and the reaction mixture was diluted with water. The reaction mixture was acidified with 2N hydrochloric acid, during which time precipitation occurred. The precipitate was removed by filtration, washed with cold water and dried in vacuo to obtain (S)-2-[4-(2-t-butyl-phenoxy)-2-oxo-2,5-dihydro-pyrrol-1-yl]-3-cyclohexyl-propionic acid (530 mg, 94%) as an off-white solid.

To a stirred solution of (S)-2-[4-(2-t-butyl-phenoxy)-2-oxo-2,5-dihydro-pyrrol-1-yl]-3-cyclohexyl-propionic acid (150 mg, 0.39 mmol) in dichloromethane (12 mL) was gradually added 1-(3-dimethylaminopropyl)-3-ethylcarbodiimide hydrochloride (228 mg, 1.2 mmol) and N,N-diisopropylethylamine (250 mg, 1.9 mmol) at room temperature, under nitrogen. After 15 min, 1-hydroxybenzotriazole (178 mg, 1.21 mmol) and 1-(3-amino-pyrazol-1-yl)-2-methyl-propan-2-ol (prepared in U.S. Pat. Appl. US2008021032 Example 80, 60 mg, 0.39 mmol) were added to the reaction mixture. The reaction mixture was then stirred at 23° C. for 48 h. The reaction mixture was diluted with ethyl acetate and washed with a saturated aqueous ammonium chloride solution followed by a saturated aqueous sodium bicarbonate solution. The organic layer was then washed with a saturated aqueous sodium chloride solution, separated, dried over sodium sulfate and concentrated in vacuo to afford the crude product, which was purified by flash column chromatography (silica gel (100-200 mesh)) which afforded (S)-2-[4-(2-t-butyl-phenoxy)-2-oxo-2,5-dihydro-pyrrol-1-yl]-3-cyclohexyl-N-[1-(2-hydroxy-2-methyl-propyl)-1H-pyrazol-3-yl]-propionamide (0.110 g, 54%) as a light brown sticky solid: $^1$H NMR (400 MHz, CDCl$_3$) δ ppm 0.81-1.08 (m, 3H), 1.15 (br. s., 6H), 1.17-1.30 (m, 3H), 1.33 (s, 9H), 1.61-1.87 (m, 6H), 1.86-1.99 (m, 1H), 3.61 (s, 1H), 3.93 (s, 2H), 4.08 (m, J=17.6 Hz, 1H), 4.29 (m, J=17.6 Hz, 1H), 4.87 (t, J=7.8 Hz, 1H), 4.99 (s, 1H), 6.68 (d, J=2.0 Hz, 1H), 7.10 (d, J=7.8 Hz, 1H), 7.13-7.24 (m, 2H), 7.29 (d, J=2.0 Hz, 1H), 7.40 (dd, J=7.8, 1.5 Hz, 1H), 8.63 (br. s., 1H).

Example 198

(S)-3-cyclohexyl-N-[1-(2-hydroxy-2-methyl-propyl)-1H-pyrazol-3-yl]-2-[2-oxo-4-(2-propyl-phenoxy)-2,5-dihydro-pyrrol-1-yl]-propionamide

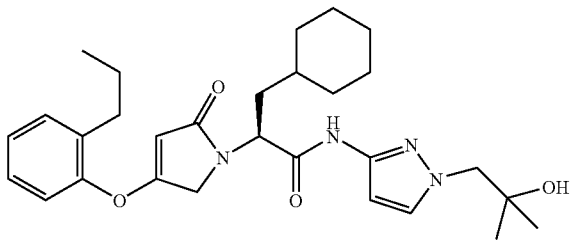

Potassium t-butoxide (11.2 g, 0.100 mol) was added to a stirred solution of 2-propyl-phenol (6.90 g, 0.051 mol) in tetrahydrofuran (40 mL) at 23° C. under nitrogen and the reaction mixture was heated to reflux for 0.75 h. The reaction mixture was cooled to 23° C. and a solution of 3-chloro-but-2-enoic acid ethyl ester (prepared as in Example 191, 7.50 g, 0.050 mol) in tetrahydrofuran (40 mL) was added to the reaction mixture. The reaction mixture was refluxed for an additional 3 h. After this time, the mixture was concentrated in vacuo and the residue was diluted with water and extracted with diethyl ether. The organic layer was then washed with 5% aqueous sodium hydroxide solution followed by a saturated aqueous sodium chloride solution, dried over sodium sulfate and concentrated in vacuo to afford (E)-3-(2-propyl-phenoxy)-but-2-enoic acid ethyl ester (5.20 g, 41%) as a yellow oil.

To a stirred mixture of (E)-3-(2-propyl-phenoxy)-but-2-enoic acid ethyl ester (3.10 g, 0.012 mol) in carbon tetrachloride (20 mL) under a nitrogen atmosphere was added N-bromosuccinimide (3.30 g, 0.019 mol) and benzoyl peroxide (300 mg, 0.001 mol). Nitrogen gas was bubbled through the mixture for 5 min, and the resulting mixture was heated to reflux for 4 h. The reaction mixture was then placed in the refrigerator overnight. The solids formed were removed by filtration and the filtrate concentrated in vacuo. The crude product obtained was purified using flash column chromatography (silica gel (100-200 mesh), ethyl acetate/hexanes) to afford (E)-4-bromo-3-(2-propyl-phenoxy)-but-2-enoic acid ethyl ester (1.95 g, 48%) as a yellow oil.

To a stirred solution of (S)-2-amino-3-cyclohexyl-propionic acid methyl ester (623 mg, 0.003 mol) in N,N-dimethylformamide (8 mL) was added N,N-diisopropylethylamine (1.98 g, 0.015 mol) slowly at room temperature, under nitrogen. The resulting mixture was stirred for 5 min and then treated with (E)-4-bromo-3-(2-propyl-phenoxy)-but-2-enoic acid ethyl ester (1.00 g, 0.003 mol) and the reaction mixture was heated at 110° C.-120° C. for 16 h. After this time, ice water was added and the resulting mixture was extracted with ethyl acetate. The combined organic layers were washed with a saturated aqueous sodium chloride solution, dried over sodium sulfate and concentrated in vacuo. Purification by flash column chromatography (silica gel (100-200 mesh)) afforded (S)-3-cyclohexyl-2-[2-oxo-4-(2-propyl-phenoxy)-2,5-dihydro-pyrrol-1-yl]-propionic acid methyl ester (0440 mg, 34%) as a yellow oil.

To a stirred solution of (S)-3-cyclohexyl-2-[2-oxo-4-(2-propyl-phenoxy)-2,5-dihydro-pyrrol-1-yl]-propionic acid methyl ester (440 mg, 0.001 mol) in tetrahydrofuran-water (3:1, 10 mL) was added lithium hydroxide (143 mg, 0.006 mol). The reaction mixture was stirred at 23° C. for 2 h. After this time, the mixture was concentrated and the reaction mixture was diluted with water. The reaction mixture was acidified with 2N hydrochloric acid, during which time precipitation occurred. The precipitate was removed by filtration, washed with cold water and dried in vacuo to obtain (S)-3-cyclohexyl-2-[2-oxo-4-(2-propyl-phenoxy)-2,5-dihydro-pyrrol-1-yl]-propionic acid (395 mg, 93%) as a yellow solid.

To a stirred solution of (S)-3-cyclohexyl-2-[2-oxo-4-(2-propyl-phenoxy)-2,5-dihydro-pyrrol-1-yl]-propionic acid (160 mg, 0.43 mmol) in dichloromethane (12 mL) was gradually added 1-(3-dimethylaminopropyl)-3-ethylcarbodiimide hydrochloride (230 mg, 1.2 mmol) and N,N-diisopropylethyl amine (260 mg, 2.0 mmol) at room temperature, under nitrogen. After 15 min, 1-hydroxybenzotriazole (184 mg, 1.2 mmol) and 1-(3-amino-pyrazol-1-yl)-2-methyl-propan-2-ol (prepared in U.S. Pat. Appl. US2008021032 Example 80, 63 mg, 0.39 mmol) were added to the reaction mixture. The reaction mixture was then stirred at 23° C. for 48 h. The reaction mixture was diluted with ethyl acetate and washed with a saturated aqueous ammonium chloride solution followed by a saturated aqueous sodium bicarbonate solution. The organic layer was then washed with a saturated aqueous sodium chloride solution, separated, dried over sodium sulfate and concentrated in vacuo to afford the crude product, which was purified by flash column chromatography (silica gel (100-200 mesh)) which afforded (S)-3-cyclohexyl-N-[1-(2-hydroxy-2-methyl-propyl)-1H-pyrazol-3-yl]-2-[2-oxo-4-(2-propyl-phenoxy)-2,5-dihydro-pyrrol-1-yl]-propionamide (58 mg, 26%) as an off-white solid: $^1$H NMR (400 MHz, CDCl$_3$) δ ppm 0.90 (t, J=7.3 Hz, 3H), 0.94-1.08 (m, 2H), 1.14 (br. s., 3H), 1.15 (br. s., 3H), 1.17-1.33 (m, 4H), 1.51-1.58 (m, 2H), 1.61-1.79 (m, 5H), 1.83 (d, J=12.7 Hz, 1H), 1.87-1.97 (m, 1H), 2.39-2.63 (m, 2H), 3.61 (br. s., 1H), 3.93 (s, 2H), 4.07 (d, J=17.9 Hz, 1H), 4.26 (d, J=17.9 Hz, 1H), 4.85 (s, 1H), 4.85-4.90 (m, 1H), 6.68 (d, J=2.0 Hz, 1H), 7.09 (d, J=7.8 Hz, 1 H), 7.15-7.23 (m, 3H), 7.29 (d, J=2.0 Hz, 1H), 8.57 (br. s., 1H).

Example 199

(S)-3-cyclohexyl-2-[4-(2,3-dimethoxy-phenoxy)-2-oxo-2,5-dihydro-pyrrol-1-yl]-N-[1-(2-hydroxy-2-methyl-propyl)-1H-pyrazol-3-yl]-propionamide

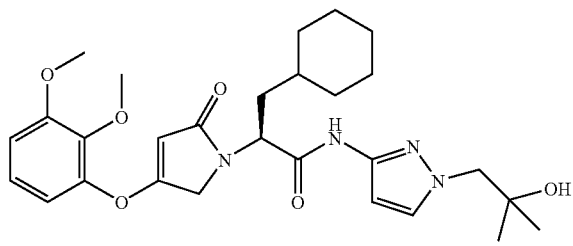

Potassium t-butoxide (7.54 g, 0.067 mol) was added to a stirred solution of 2,3-dimethoxy-phenol (5.20 g, 0.034 mol) in tetrahydrofuran (30 mL) at 23° C. under nitrogen and the reaction mixture was heated to reflux for 0.75 h. The reaction mixture was cooled to 23° C. and a solution of 3-chloro-but-2-enoic acid ethyl ester (prepared as in Example 191, 5.00 g, 0.034 mol) in tetrahydrofuran (40 mL) was added to the reaction mixture. The reaction mixture was refluxed for an additional 3 h. After this time, the mixture was concentrated in vacuo and the residue was diluted with water and extracted with diethyl ether. The organic layer was then washed with 5% aqueous sodium hydroxide solution followed by a saturated sodium chloride solution, dried over sodium sulfate and concentrated in vacuo to afford (E)-3-(2,3-dimethoxy-phenoxy)-but-2-enoic acid ethyl ester (4.20 g, 47%) as a yellow oil.

To a stirred mixture of (E)-3-(2,3-dimethoxy-phenoxy)-but-2-enoic acid ethyl ester (4.20 g, 0.016 mol) in carbon tetrachloride (25 mL) under a nitrogen atmosphere was added N-bromosuccinimide (4.22 g, 0.024 mol) and benzoyl peroxide (380 mg, 0.002 mol). Nitrogen gas was bubbled through the mixture for 5 min, and the resulting mixture was heated to reflux for 4 h. The reaction mixture was then placed in the refrigerator overnight. The solids formed were removed by filtration and the filtrate concentrated in vacuo. The crude product obtained was purified using flash column chromatography (silica gel (100-200 mesh), ethyl acetate/hexanes) to afford (E)-4-bromo-3-(2,3-dimethoxy-phenoxy)-but-2-enoic acid ethyl ester (3.10 g, 57%) as a yellow oil.

To a stirred solution of (S)-2-amino-3-cyclohexyl-propionic acid methyl ester (600 mg, 0.003 mol) in N,N-dimethylformamide (5 mL) was added N,N-diisopropylethylamine (1.80 g, 0.014 mol) slowly at room temperature, under nitrogen. The resulting mixture was stirred for 5 min and then treated with (E)-4-bromo-3-(2,3-dimethoxy-phenoxy)-but-2-enoic acid ethyl ester (1.00 g, 0.003 mol) and the reaction mixture was heated at 110° C.-120° C. for 16 h. After this time, ice water was added and the resulting mixture was extracted with ethyl acetate. The combined organic layers were washed with a saturated aqueous sodium chloride solution, dried over sodium sulfate and concentrated in vacuo. Purification by flash column chromatography (silica gel (100-200 mesh)) afforded (S)-3-cyclohexyl-2-[4-(2,3-dimethoxy-phenoxy)-2-oxo-2,5-dihydro-pyrrol-1-yl]-propionic acid methyl ester (430 mg, 33%) as a yellow oil.

To a stirred solution of (S)-3-cyclohexyl-2-[4-(2,3-dimethoxy-phenoxy)-2-oxo-2,5-dihydro-pyrrol-1-yl]-propionic acid methyl ester (600 mg, 0.001 mol) in tetrahydrofuran-water (3:1, 10 mL) was added lithium hydroxide (187 mg, 0.008 mol). The reaction mixture was stirred at 23° C. for 2 h. After this time, the mixture was concentrated and the reaction mixture was diluted with water. The reaction mixture was acidified with 2N hydrochloric acid, during which time precipitation occurred. The precipitate was removed by filtration, washed with cold water and dried in vacuo to obtain (S)-3-cyclohexyl-2-[4-(2,3-dimethoxy-phenoxy)-2-oxo-2,5-dihydro-pyrrol-1-yl]-propionic acid (500 mg, 86%) as a light yellow solid.

To a stirred solution of (S)-3-cyclohexyl-2-[4-(2,3-dimethoxy-phenoxy)-2-oxo-2,5-dihydro-pyrrol-1-yl]-propionic acid (150 mg, 0.39 mmol) in dichloromethane (8 mL) was gradually added 1-(3-dimethylaminopropyl)-3-ethylcarbodiimide hydrochloride (225 mg, 1.2 mol) and N,N-diisopropylethylamine (254 mg, 2.0 mol) at room temperature, under nitrogen. After 15 min, 1-hydroxybenzotriazole (180 mg, 1.2 mmol) and 1-(3-amino-pyrazol-1-yl)-2-methyl-propan-2-ol (prepared in U.S. Pat. Appl. US2008021032 Example 80, 60 mg, 0.39 mmol) were added to the reaction mixture. The reaction mixture was then stirred at 23° C. for 48 h. The reaction mixture was diluted with ethyl acetate and washed with a saturated aqueous ammonium chloride solution followed by a saturated aqueous sodium bicarbonate solution. The organic layer was then washed with a saturated aqueous sodium chloride solution, separated, dried over sodium sulfate and concentrated in vacuo to afford the crude product, which was purified by flash column chromatography (silica gel (100-200 mesh)) which afforded (S)-3-cyclohexyl-2-[4-(2,3-dimethoxy-phenoxy)-2-oxo-2,5-dihydro-pyrrol-1-yl]-N-[1-(2-hydroxy-2-methyl-propyl)-1H-pyrazol-3-yl]-propionamide (85 mg, 42%) as a light brown sticky solid: $^1$H NMR (400 MHz, CDCl$_3$) δ ppm 0.82-1.09 (m, 2H), 1.15 (br. s., 3H), 1.16 (br. s., 3H), 1.18-1.32 (m, 3H), 1.60-1.96 (m, 8H), 3.68 (s, 1H), 3.84 (s, 3H), 3.90 (s, 3H), 3.94 (s, 2H), 4.10 (d, J=17.9 Hz, 1H), 4.26 (d, J=17.9 Hz, 1H), 4.89 (dd, J=8.8, 6.8 Hz, 1H), 4.97 (s, 1H), 6.69 (d, J=2.1 Hz, 1H), 6.78 (d, J=8.3 Hz, 1H), 6.84 (d, J=8.3 Hz, 1H), 7.05 (t, J=8.3 Hz, 1H), 7.30 (d, J=2.1 Hz, 1H), 8.64 (s, 1H).

Example 200

(S)-3-cyclohexyl-2-[4-(2,3-difluoro-phenoxy)-2-oxo-2,5-dihydro-pyrrol-1-yl]-N-[1-(2-hydroxy-2-methyl-propyl)-1H-pyrazol-3-yl]-propionamide

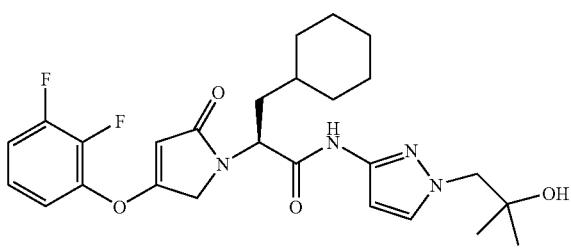

Potassium t-butoxide (11.2 g, 0.100 mol) was added to a stirred solution of 2,3-difluoro-phenol (6.58 g, 0.051 mol) in tetrahydrofuran (30 mL) at 23° C. under nitrogen and the reaction mixture was heated to reflux for 0.75 h. The reaction mixture was cooled to 23° C. and a solution of 3-chloro-but-2-enoic acid ethyl ester (prepared as in Example 191 7.50 g, 0.050 mol) in tetrahydrofuran (40 mL) was added to the reaction mixture. The reaction mixture was refluxed for an additional 3 h. After this time, the mixture was concentrated in vacuo and the residue was diluted with water and extracted with diethyl ether. The organic layer was then washed with 5% aqueous sodium hydroxide solution followed by a saturated aqueous sodium chloride solution, dried over sodium sulfate and concentrated in vacuo to afford (E)-3-(2,3-difluoro-phenoxy)-but-2-enoic acid ethyl ester (8.01 g, 66%) as a yellow oil.

To a stirred mixture of (E)-3-(2,3-difluoro-phenoxy)-but-2-enoic acid ethyl ester (8.01 g, 0.033 mol) in carbon tetrachloride (30 mL) under a nitrogen atmosphere was added N-bromosuccinimide (8.91 g, 0.050 mol) and benzoyl peroxide (810 mg, 0.003 mol). Nitrogen gas was bubbled through the mixture for 5 min, and the resulting mixture was heated to reflux for 4 h. The reaction mixture was then placed in the refrigerator overnight. The solids formed were removed by filtration and the filtrate concentrated in vacuo. The crude product obtained was purified using flash column chromatography (silica gel (100-200 mesh), ethyl acetate/hexanes) to afford (E)-4-bromo-3-(2,3-difluoro-phenoxy)-but-2-enoic acid ethyl ester (4.20 g, 40%) as a yellow oil.

To a stirred solution of (S)-2-amino-3-cyclohexyl-propionic acid methyl ester (640 mg, 0.003 mol) in N,N-dimethylformamide (7 mL) was added N,N-diisopropylethylamine (2.00 g, 0.015 mol) slowly at room temperature, under nitrogen. The resulting mixture was stirred for 5 min and then treated with (E)-4-bromo-3-(2,3-difluoro-phenoxy)-but-2-enoic acid ethyl ester (1.00 g, 0.003 mol) and the reaction mixture was heated at 110° C.-120° C. for 16 h. After this time, ice water was added and the resulting mixture was extracted with ethyl acetate. The combined organic layers were washed with a saturated aqueous sodium chloride solution, dried over sodium sulfate and concentrated in vacuo. Purification by flash column chromatography (silica gel (100-200 mesh)) afforded (S)-3-cyclohexyl-2-[4-(2,3-difluoro-phenoxy)-2-oxo-2,5-dihydro-pyrrol-1-yl]-propionic acid methyl ester (300 mg, 23%) as yellow oil.

To a stirred solution of (S)-3-cyclohexyl-2-[4-(2,3-difluoro-phenoxy)-2-oxo-2,5-dihydro-pyrrol-1-yl]-propionic acid methyl ester (370 mg, 0.001 mol) in tetrahydrofuran-water (3:1, 10 mL) was added lithium hydroxide (113 mg, 0.009 mol). The reaction mixture was stirred at 23° C. for 2 h. After this time, the mixture was concentrated and the reaction mixture was diluted with water. The reaction mixture was acidified with 2N hydrochloric acid, during which time precipitation occurred. The precipitate was removed by filtration, washed with cold water and dried in vacuo to obtain (S)-3-cyclohexyl-2-[4-(2,3-difluoro-phenoxy)-2-oxo-2,5-dihydro-pyrrol-1-yl]-propionic acid (235 mg, 52%) as a brown solid.

To a stirred solution of (S)-3-cyclohexyl-2-[4-(2,3-difluoro-phenoxy)-2-oxo-2,5-dihydro-pyrrol-1-yl]-propionic acid (125 mg, 0.34 mmol) in dichloromethane (10 mL) was gradually added 1-(3-dimethylaminopropyl)-3-ethylcarbodiimide hydrochloride (195 mg, 1.0 mmol) and N,N-diisopropylethylamine (220 mg, 1.7 mmol) at room temperature, under nitrogen. After 15 min, 1-hydroxybenzotriazole (157 mg, 1.1 mmol) and 1-(3-amino-pyrazol-1-yl)-2-methyl-propan-2-ol (prepared in U.S. Pat. Appl US2008021032 Example 80, 53 mg, 0.34 mmol) were added to the reaction mixture. The reaction mixture was then stirred at 23° C. for 48 h. The reaction mixture was diluted with ethyl acetate and washed with a saturated aqueous ammonium chloride solution followed by a saturated aqueous sodium bicarbonate solution. The organic layer was then washed with a saturated aqueous sodium chloride solution, separated, dried over sodium sulfate and concentrated in vacuo to afford the crude product, which was purified by flash column chromatography (silica gel (100-200 mesh)) which afforded (S)-3-cyclohexyl-2-[4-(2,3-difluoro-phenoxy)-2-oxo-2,5-dihydro-pyrrol-1-yl]-N-[1-(2-hydroxy-2-methyl-propyl)-1H-pyrazol-3-yl]-propionamide (68 mg, 40%) as an off-white solid: $^1$H NMR (400 MHz, CDCl$_3$) δ ppm 0.81-1.08 (m, 3H), 1.14 (s, 6H), 1.16-1.32 (m, 2H), 1.65-1.96 (m, 8H), 3.64 (br. s., 1H), 3.92 (s, 2H), 4.12 (d, J=18.0 Hz, 1H), 4.34 (d, J=18.0 Hz, 1H), 4.89 (dd, J=8.8, 6.8 Hz, 1H), 5.00 (s, 1H), 6.67 (d, J=1.5 Hz, 1H), 7.01-7.15 (m, 3H), 7.28 (d, J=1.5 Hz, 1H), 8.64 (br. s., 1H).

Example 201

(S)-3-cyclohexyl-2-[4-(2,5-dichloro-phenoxy)-2-oxo-2,5-dihydro-pyrrol-1-yl]-N-[1-(2-hydroxy-2-methyl-propyl)-1H-pyrazol-3-yl]-propionamide

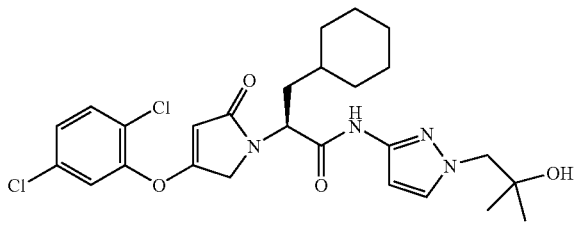

Potassium t-butoxide (7.50 g, 0.067 mol) was added to a stirred solution of 2,5-dichloro-phenol (5.46 g, 0.033 mol) in tetrahydrofuran (35 mL) at 23° C. under nitrogen and the reaction mixture was heated to reflux for 0.75 h. The reaction mixture was cooled to 23° C. and a solution of 3-chloro-but-2-enoic acid ethyl ester (prepared as in Example 191, 5.00 g, 0.034 mol) in tetrahydrofuran (40 mL) was added to the reaction mixture. The reaction mixture was refluxed for an additional 3 h. After this time, the mixture was concentrated in vacuo and the residue was diluted with water and extracted with diethyl ether. The organic layer was then washed with 5% aqueous sodium hydroxide solution followed by a saturated aqueous sodium chloride solution, dried over sodium sulfate and concentrated in vacuo to afford (E)-3-(2,5-dichloro-phenoxy)-but-2-enoic acid ethyl ester (3.45 g, 37%) as a yellow oil.

To a stirred mixture of (E)-3-(2,5-dichloro-phenoxy)-but-2-enoic acid ethyl ester (3.25 g, 0.012 mol) in carbon tetrachloride (20 mL) under a nitrogen atmosphere was added N-bromosuccinimide (3.20 g, 0.018 mol) and benzoyl peroxide (290 mg, 0.001 mol). Nitrogen gas was bubbled through the mixture for 5 min, and the resulting mixture was heated to reflux for 4 h. The reaction mixture was then placed in the refrigerator overnight. The solids formed were removed by filtration and the filtrate concentrated in vacuo. The crude product obtained was purified using flash column chromatography (silica gel (100-200 mesh), ethyl acetate/hexanes) to afford (E)-4-bromo-3-(2,5-dichloro-phenoxy)-but-2-enoic acid ethyl ester (1.80 g, 43%) as a yellow oil.

To a stirred solution of (S)-2-amino-3-cyclohexyl-propionic acid methyl ester (750 mg, 0.004 mol) in N,N-dimethylformamide (10 mL) was added N,N-diisopropylethylamine (2.6 g, 0.02 mol) slowly at room temperature, under nitrogen. The resulting mixture was stirred for 5 min and then treated with (E)-4-bromo-3-(2,5-dichloro-phenoxy)-but-2-enoic acid ethyl ester (1.5 g, 0.004 mol) and the reaction mixture was heated at 110° C.-120° C. for 16 h. After this time, ice water was added and the resulting mixture was extracted with ethyl acetate. The combined organic layers were washed with a saturated aqueous sodium chloride solution, dried over sodium sulfate and concentrated in vacuo. Purification by flash column chromatography (silica gel (100-200 mesh)) afforded (S)-3-cyclohexyl-2-[4-(2,5-dichloro-phenoxy)-2-oxo-2,5-dihydro-pyrrol-1-yl]-propionic acid methyl ester (250 mg, 15%) as yellow oil.

To a stirred solution of (S)-3-cyclohexyl-2-[4-(2,5-dichloro-phenoxy)-2-oxo-2,5-dihydro-pyrrol-1-yl]-propionic acid methyl ester (370 mg, 0.001 mol) in tetrahydrofuran-water (3:1, 10 mL) was added lithium hydroxide (106 mg, 0.004 mol). The reaction mixture was stirred at 23° C. for 2 h. After this time, the mixture was concentrated and the reaction mixture was diluted with water. The reaction mixture was acidified with 2N hydrochloric acid, during which time precipitation occurred. The precipitate was removed by filtration, washed with cold water and dried in vacuo to obtain (S)-3-cyclohexyl-2-[4-(2,5-dichloro-phenoxy)-2-oxo-2,5-dihydro-pyrrol-1-yl]-propionic acid (300 mg, 84%) as a light brown solid.

To a stirred solution of (S)-3-cyclohexyl-2-[4-(2,5-dichloro-phenoxy)-2-oxo-2,5-dihydro-pyrrol-1-yl]-propionic acid (160 mg, 0.4 mmol) in dichloromethane (5 mL) was gradually added 1-(3-dimethylaminopropyl)-3-ethylcarbodiimide hydrochloride (82 mg, 0.4 mmol) and N,N-diisopropylethylamine (210 mg, 1.6 mmol) at room temperature, under nitrogen. After 15 min., 1-hydroxybenzotriazole (61 mg, 0.4 mmol) and 1-(3-amino-pyrazol-1-yl)-2-methyl-propan-2-ol (prepared in U.S. Pat. Appl. US2008021032 Example 80, 160 mg, 0.4 mmol) were added to the reaction mixture. The reaction mixture was then stirred at 23° C. for 48 h. The reaction mixture was diluted with ethyl acetate and washed with a saturated aqueous ammonium chloride solution followed by a saturated aqueous sodium bicarbonate solution. The organic layer was then washed with a saturated aqueous sodium chloride solution, separated, dried over sodium sulfate and concentrated in vacuo to afford the crude product, which was purified by flash column chromatography (silica gel (100-200 mesh)) which afforded (S)-3-cyclohexyl-2-[4-(2,5-dichloro-phenoxy)-2-oxo-2,5-dihydro-pyrrol-1-yl]-N-[1-(2-hydroxy-2-methyl-propyl)-1H-pyrazol-3-yl]-propionamide (0.065 g, 30%) as a brown sticky liquid: $^1$H NMR (400 MHz, DMSO-$d_6$) δ ppm 0.80-1.01 (m, 2H), 1.05 (s, 3H), 1.06 (s, 3H), 1.07-1.20 (m, 3H), 1.50-1.84 (m, 8H), 3.89 (s, 2H), 4.19 (d, J=18.1 Hz, 1H), 4.60 (d, J=18.1 Hz, 1H), 4.66 (s, 1H), 4.92 (dd, J=10.5, 5.1 Hz, 1H), 4.95 (s, 1H), 6.44 (d, J=2.0 Hz, 1H), 7.46 (dd, J=8.8, 2.4 Hz, 1H), 7.53 (d, J=2.0 Hz, 1H), 7.69 (d, J=8.8 Hz, 1H), 7.75 (d, J=2.4 Hz, 1H), 10.76 (s, 1H).

Example 202

(S)-3-cyclohexyl-2-[4-(2,4-dichloro-phenoxy)-2-oxo-2,5-dihydro-pyrrol-1-yl]-N-[1-(2-hydroxy-2-methyl-propyl)-1H-pyrazol-3-yl]-propionamide

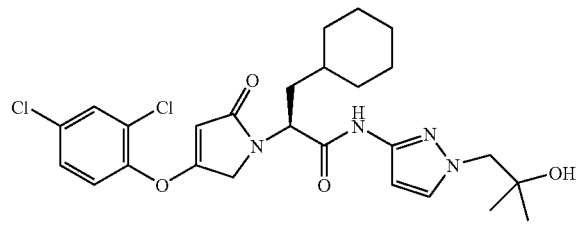

Potassium t-butoxide (7.50 g, 0.067 mol) was added to a stirred solution of 2,4-dichloro-phenol (5.46 g, 0.033 mol) in tetrahydrofuran (35 mL) at 23° C. under nitrogen and the reaction mixture was heated to reflux for 0.75 h. The reaction mixture was cooled to 23° C. and a solution of 3-chloro-but-2-enoic acid ethyl ester (prepared as in Example 191, 5.00 g, 0.034 mol) in tetrahydrofuran (40 mL) was added to the reaction mixture. The reaction mixture was refluxed for an additional 3 h. After this time, the mixture was concentrated in vacuo and the residue was diluted with water and extracted with diethyl ether. The organic layer was then washed with 5% aqueous sodium hydroxide solution followed by a saturated aqueous sodium chloride solution, dried over sodium sulfate and concentrated in vacuo to afford (E)-3-(2,4-dichloro-phenoxy)-but-2-enoic acid ethyl ester (3.50 g, 38%) as a yellow oil.

To a stirred mixture of (E)-3-(2,4-dichloro-phenoxy)-but-2-enoic acid ethyl ester (4.00 g, 0.015 mol) in carbon tetrachloride (25 mL) under a nitrogen atmosphere was added N-bromosuccinimide (2.32 g, 0.013 mol) and benzoyl peroxide (280 mg, 0.001 mol). Nitrogen gas was bubbled through the mixture for 5 min, and the resulting mixture was heated to reflux for 4 h. The reaction mixture was then placed in the refrigerator overnight. The solids formed were removed by filtration and the filtrate concentrated in vacuo. The crude product obtained was purified using flash column chromatography (silica gel (100-200 mesh), ethyl acetate/hexanes) to afford (E)-4-bromo-3-(2,4-dichloro-phenoxy)-but-2-enoic acid ethyl ester (3.00 g, 58%) as a yellow oil.

To a stirred solution of (S)-2-amino-3-cyclohexyl-propionic acid methyl ester (0.690 g, 0.004 mol) in N,N-dimethylformamide (10 mL) was added N,N-diisopropylethylamine (2.1 g, 0.016 mol) slowly at room temperature, under nitrogen. The resulting mixture was stirred for 5 min and then treated with (E)-4-bromo-3-(2,4-dichloro-phenoxy)-but-2-enoic acid ethyl ester (1.20 g, 0.003 mol) and the reaction mixture was heated at 110° C.-120° C. for 16 h. After this time, ice water was added and the resulting mixture was extracted with ethyl acetate. The combined organic layers were washed with a saturated aqueous sodium chloride solution, dried over sodium sulfate and concentrated in vacuo. Purification by flash column chromatography (silica gel (100-200 mesh)) afforded (S)-3-cyclohexyl-2-[4-(2,4-dichlorophenoxy)-2-oxo-2,5-dihydro-pyrrol-1-yl]-propionic acid methyl ester (410 mg, 27%) as a yellow oil.

To a stirred solution of (S)-3-cyclohexyl-2-[4-(2,4-dichloro-phenoxy)-2-oxo-2,5-dihydro-pyrrol-1-yl]-propionic acid methyl ester (340 mg, 0.001 mol) in tetrahydrofuran-water (3:1, 10 mL) was added lithium hydroxide (106 mg, 0.003 mol). The reaction mixture was stirred at 23° C. for 2 h. After this time, the mixture was concentrated and the reaction mixture was diluted with water. The reaction mixture was acidified with 2N hydrochloric acid, during which time precipitation occurred. The precipitate was removed by filtration, washed with cold water and dried in vacuo to obtain (S)-3-cyclohexyl-2-[4-(2,4-dichloro-phenoxy)-2-oxo-2,5-dihydro-pyrrol-1-yl]-propionic acid (300 mg, 78%) as a light yellow solid.

To a stirred solution of (S)-3-cyclohexyl-2-[4-(2,4-dichloro-phenoxy)-2-oxo-2,5-dihydro-pyrrol-1-yl]-propionic acid (210 mg, 0.5 mmol) in dichloromethane (10 mL) was gradually added 1-(3-dimethylaminopropyl)-3-ethylcarbodiimide hydrochloride (300 mg, 1.6 mmol) and N,N-diisopropylethylamine (340 mg, 2.6 mmol) at room temperature, under nitrogen. After 15 min, 1-hydroxybenzotriazole (240 mg, 1.6 mmol) and 1-(3-amino-pyrazol-1-yl)-2-methyl-propan-2-ol (prepared in U.S. Pat. Appl. US2008021032 Example 80, 82 mg, 0.5 mmol) were added to the reaction mixture. The reaction mixture was then stirred at 23° C. for 48 h. The reaction mixture was diluted with ethyl acetate and washed with a saturated aqueous ammonium chloride solution followed by a saturated aqueous sodium bicarbonate solution. The organic layer was then washed with a saturated aqueous sodium chloride solution, separated, dried over sodium sulfate and concentrated in vacuo to afford the crude product, which was purified by flash column chromatography (silica gel (100-200 mesh)) which afforded (S)-3-cyclohexyl-2-[4-(2,4-dichloro-phenoxy)-2-oxo-2,5-dihydro-pyrrol-1-yl]-N-[1-(2-hydroxy-2-methyl-propyl)-1H-pyrazol-3-yl]-propionamide (0.095 g, 34%) as a light brown solid: $^1$H NMR (400 MHz, CDCl$_3$) δ ppm 0.75-1.07 (m, 2H), 1.14 (br. s., 6H), 1.17-1.29 (m, 3H), 1.60-1.99 (m, 8H), 3.62 (br. s., 1H), 3.93 (s, 2H), 4.10 (d, J=18.1 Hz, 1H), 4.30 (d, J=18.1 Hz, 1H), 4.83-4.88 (m, 1H), 4.88 (s, 1H), 6.67 (d, J=2.0 Hz, 1H), 7.14-7.23 (m, 1H), 7.27-7.32 (m, 2H), 7.49 (d, J=2.0 Hz, 1H), 8.54 (br. s., 1H).

Example 203

(S)-2-[4-(2-benzyloxy-phenoxy)-2-oxo-2,5-dihydro-pyrrol-1-yl]-3-cyclohexyl-N-[1-(2-hydroxy-2-methyl-propyl)-1H-pyrazol-3-yl]-propionamide

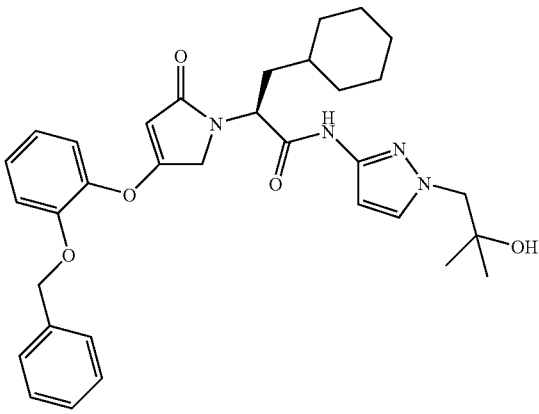

Potassium t-butoxide (5.60 g, 0.05 mol) was added to a stirred solution of 2-benzyloxy-phenol (5.00 g, 0.025 mol) in tetrahydrofuran (50 mL) at 23° C. under nitrogen and the reaction mixture was heated to reflux for 0.75 h. The reaction mixture was cooled to 23° C. and a solution of 3-chloro-but-2-enoic acid ethyl ester (prepared as in Example 191, 3.70 g, 0.025 mol) in tetrahydrofuran (40 mL) was added to the reaction mixture. The reaction mixture was refluxed for an additional 3 h. After this time, the mixture was concentrated in vacuo and the residue was diluted with water and extracted with diethyl ether. The organic layer was then washed with 5% aqueous sodium hydroxide solution followed by a saturated aqueous sodium chloride solution, dried over sodium sulfate and concentrated in vacuo to afford (E)-3-(2-benzyloxy-phenoxy)-but-2-enoic acid ethyl ester (5.70 g, 73%) as a yellow oil.

To a stirred mixture of (E)-3-(2-benzyloxy-phenoxy)-but-2-enoic acid ethyl ester (5.70 g, 0.018 mol) in carbon tetrachloride (35 mL) under a nitrogen atmosphere was added N-bromosuccinimide (4.90 g, 0.028 mol) and benzoyl peroxide (440 mg, 0.002 mol). Nitrogen gas was bubbled through the mixture for 5 min, and the resulting mixture was heated to reflux for 4 h. The reaction mixture was then placed in the refrigerator overnight. The solids formed were removed by filtration and the filtrate concentrated in vacuo. The crude product obtained was purified using flash column chromatography (silica gel (100-200 mesh), ethyl acetate/hexanes) to afford (E)-3-(2-benzyloxy-phenoxy)-4-bromo-but-2-enoic acid ethyl ester (4.60 g, 64%) as a yellow oil.

To a stirred solution of (S)-2-amino-3-cyclohexyl-propionic acid methyl ester (1.05 g, 0.006 mol) in N,N-dimethylformamide (8 mL) was added N,N-diisopropylethylamine (3.30 g, 0.026 mol) slowly at room temperature, under nitrogen. The resulting mixture was stirred for 5 min and then treated with (E)-3-(2-benzyloxy-phenoxy)-4-bromo-but-2-enoic acid ethyl ester (2.00 g, 0.005 mol) and the reaction mixture was heated at 110° C.-120° C. for 16 h. After this time, ice water was added and the resulting mixture was extracted with ethyl acetate. The combined organic layers were washed with a saturated aqueous sodium chloride solution, dried over sodium sulfate and concentrated in vacuo. Purification by flash column chromatography (silica gel (100-200 mesh)) afforded (S)-2-[4-(2-benzyloxy-phenoxy)-2-oxo-2,5-dihydro-pyrrol-1-yl]-3-cyclohexyl-propionic acid methyl ester (360 mg, 14%) as a yellow oil.

To a stirred solution of (S)-2-[4-(2-benzyloxy-phenoxy)-2-oxo-2,5-dihydro-pyrrol-1-yl]-3-cyclohexyl-propionic acid methyl ester (310 mg, 0.001 mol) in tetrahydrofuran-water (3:1, 10 mL) was added lithium hydroxide (87 mg, 0.004 mol). The reaction mixture was stirred at 23° C. for 2 h. After this time, the mixture was concentrated and the reaction mixture was diluted with water. The reaction mixture was acidified with 2N hydrochloric acid, during which time precipitation occurred. The precipitate was removed by filtration, washed with cold water and dried in vacuo to obtain (S)-2-[4-(2-benzyloxy-phenoxy)-2-oxo-2,5-dihydro-pyrrol-1-yl]-3-cyclohexyl-propionic acid (245 mg, 82%).

To a stirred solution of (S)-2-[4-(2-benzyloxy-phenoxy)-2-oxo-2,5-dihydro-pyrrol-1-yl]-3-cyclohexyl-propionic acid (150 mg, 0.3 mmol) in dichloromethane (10 mL) was gradually added 1-(3-dimethylaminopropyl)-3-ethylcarbodiimide hydrochloride (197 mg, 1.0 mmol) and N,N-diisopropylethylamine (220 mg, 1.7 mmol) at room temperature, under nitrogen. After 15 min, 1-hydroxybenzotriazole (158 mg, 1.0 mmol) and 1-(3-amino-pyrazol-1-yl)-2-methyl-propan-2-ol (prepared in U.S. Pat. Appl. US2008021032 Example 80, 54 mg, 0.3 mmol) were added to the reaction mixture. The reaction mixture was then stirred at 23° C. for 48 h. The reaction mixture was diluted with ethyl acetate and washed with a saturated aqueous ammonium chloride solution followed by a saturated aqueous sodium bicarbonate solution. The organic layer was then washed with a saturated aqueous sodium chloride solution, separated, dried over sodium sulfate and concentrated in vacuo to afford the crude product, which was purified by flash column chromatography (silica gel (100-200 mesh)) which afforded (S)-2-[4-(2-benzyloxy-phenoxy)-2-oxo-2,5-dihydro-pyrrol-1-yl]-3-cyclohexyl-N-[1-(2-hydroxy-2-methyl-propyl)-1H-pyrazol-3-yl]-propionamide (58 mg, 29%) as an off-white solid: $^1$H NMR (400 MHz, DMSO-$d_6$) δ ppm 0.79-0.97 (m, 2H), 1.05 (s, 3H), 1.06 (s, 3H), 1.08-1.31 (m, 4H), 1.53-1.82 (m, 7H), 3.90 (s, 2H), 4.10 (d, J=18.1 Hz, 1H), 4.56 (d, J=18.1 Hz, 1H), 4.66 (s, 1H), 4.73 (s, 1H), 4.91 (dd, J=10.5, 4.6 Hz, 1H), 5.17 (s, 2H), 6.45 (d, J=2.0 Hz, 1H), 6.99-7.07 (m, 1H), 7.21-7.41 (m, 8H), 7.54 (d, J=2.0 Hz, 1H), 10.75 (s, 1H).

Example 204

(S)-3-cyclohexyl-2-[4-(2,3-dimethyl-phenoxy)-2-oxo-2,5-dihydro-pyrrol-1-yl]-N-[1-(2-hydroxy-2-methyl-propyl)-1H-pyrazol-3-yl]-propionamide

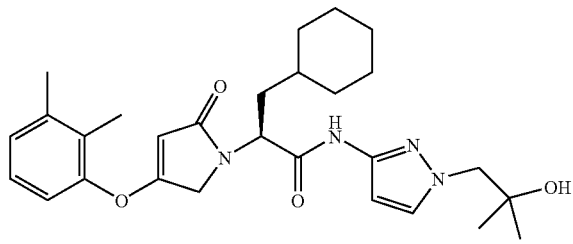

Potassium t-butoxide (11.2 g, 0.100 mol) was added to a stirred solution of 2,3-dimethyl-phenol (6.18 g, 0.051 mol) in tetrahydrofuran (40 mL) at 23° C. under nitrogen and the reaction mixture was heated to reflux for 0.75 h. The reaction mixture was cooled to 23° C. and a solution of 3-chloro-but-2-enoic acid ethyl ester (prepared as in Example 191, 7.50 g, 0.050 mol) in tetrahydrofuran (40 mL) was added to the reaction mixture. The reaction mixture was refluxed for an additional 3 h. After this time, the mixture was concentrated in vacuo and the residue was diluted with water and extracted with diethyl ether. The organic layer was then washed with 5% aqueous sodium hydroxide solution followed by a saturated sodium chloride solution, dried over sodium sulfate and concentrated in vacuo to afford (E)-3-(2,3-dimethyl-phenoxy)-but-2-enoic acid ethyl ester (4.10 g, 35%) as a yellow oil.

To a stirred mixture of (E)-3-(2,3-dimethyl-phenoxy)-but-2-enoic acid ethyl ester (7.19 g, 0.031 mol) in carbon tetrachloride (40 mL) under a nitrogen atmosphere was added N-bromosuccinimide (8.19 g, 0.046 mol) and benzoyl peroxide (730 mg, 0.003 mol). Nitrogen gas was bubbled through the mixture for 5 min, and the resulting mixture was heated to reflux for 4 h. The reaction mixture was then placed in the refrigerator overnight. The solids formed were removed by filtration and the filtrate concentrated in vacuo. The crude product obtained was purified using flash column chromatography (silica gel (100-200 mesh), ethyl acetate/hexanes) to afford (E)-4-bromo-3-(2,3-dimethyl-phenoxy)-but-2-enoic acid ethyl ester (3.00 g, 31%) as a yellow oil.

To a stirred solution of (S)-2-amino-3-cyclohexyl-propionic acid methyl ester (1.56 g, 0.008 mol) in N,N-dimethylformamide (10 mL) was added N,N-diisopropylethylamine (4.90 g, 0.038 mol) slowly at room temperature, under nitrogen. The resulting mixture was stirred for 5 min and then treated with (E)-4-bromo-3-(2,3-dimethyl-phenoxy)-but-2-enoic acid ethyl ester (2.40 g, 0.008 mol) and the reaction mixture was heated at 110° C.-120° C. for 16 h. After this time, ice water was added and the resulting mixture was extracted with ethyl acetate. The combined organic layers were washed with a saturated aqueous sodium chloride solution, dried over sodium sulfate and concentrated in vacuo. Purification by flash column chromatography (silica gel (100-200 mesh)) afforded (S)-3-cyclohexyl-2-[4-(2,3-dimethyl-phenoxy)-2-oxo-2,5-dihydro-pyrrol-1-yl]-propionic acid methyl ester (910 mg, 29%) as yellow oil.

To a stirred solution of (S)-3-cyclohexyl-2-[4-(2,3-dimethyl-phenoxy)-2-oxo-2,5-dihydro-pyrrol-1-yl]-propionic acid methyl ester (850 mg, 0.002 mol) in tetrahydrofuran-water (3:1, 10 mL) was added lithium hydroxide (287 mg, 0.012 mol). The reaction mixture was stirred at 23° C. for 2 h. After this time, the mixture was concentrated and the reaction mixture was diluted with water. The reaction mixture was acidified with 2N hydrochloric acid, during which time precipitation occurred. The precipitate was removed by filtration, washed with cold water and dried in vacuo to obtain (S)-3-cyclohexyl-2-[4-(2,3-dimethyl-phenoxy)-2-oxo-2,5-dihydro-pyrrol-1-yl]-propionic acid (720 mg, 88%) as an off-white solid.

To a stirred solution of (S)-3-cyclohexyl-2-[4-(2,3-dimethyl-phenoxy)-2-oxo-2,5-dihydro-pyrrol-1-yl]-propionic acid (240 mg, 0.7 mmol) in dichloromethane (10 mL) was gradually added 1-(3-dimethylaminopropyl)-3-ethylcarbodiimide hydrochloride (390 mg, 2.0 mmol) and N,N-diisopropylethylamine (440 mg, 3.4 mmol) at room temperature, under nitrogen. After 15 min,, 1-hydroxybenzotriazole (310 mg, 2.1 mmol) and 1-(3-amino-pyrazol-1-yl)-2-methyl-propan-2-ol (prepared in U.S. Pat. Appl. US2008021032 Example 80, 106 mg, 0.7 mmol) were added to the reaction mixture. The reaction mixture was then stirred at 23° C. for 48 h. The reaction mixture was diluted with ethyl acetate and washed with a saturated aqueous ammonium chloride solution followed by a saturated aqueous sodium bicarbonate solution. The organic layer was then washed with a saturated aqueous sodium chloride solution, separated, dried over sodium sulfate and concentrated in vacuo to afford the crude product, which was purified by flash column chromatography (silica gel (100-200 mesh)) which afforded (S)-3-cyclohexyl-2-[4-(2,3-dimethyl-phenoxy)-2-oxo-2,5-dihydro-pyrrol-1-yl]-N-[1-(2-hydroxy-2-methyl-propyl)-1H-pyrazol-3-yl]-propionamide (105 mg, 32%) as an off-white solid: $^1$H NMR (400 MHz, CDCl$_3$) δ ppm 0.82-1.08 (m, 2H), 1.14 (br. s., 6H), 1.17-1.30 (m, 3H), 1.57-1.98 (m, 8H), 2.09 (s, 3H), 2.29 (s, 3H), 3.92 (s, 2H), 4.08 (d, J=18.0 Hz, 1H), 4.28 (d, J=18.0 Hz, 1H), 4.75 (br. s., 2H), 4.78 (br. s., 1H), 4.87 (t, J=7.6 Hz, 1H), 6.67 (d, J=2.0 Hz, 1H), 6.93 (d, J=7.8 Hz, 1H), 7.02-7.14 (m, 2H), 7.28 (d, J=2.0 Hz, 1H).

Example 205

(S)-2-[4-(3-bromo-phenoxy)-2-oxo-2,5-dihydro-pyrrol-1-yl]-3-cyclohexyl-N-[1-(2-hydroxy-2-methyl-propyl)-1H-pyrazol-3-yl]-propionamide

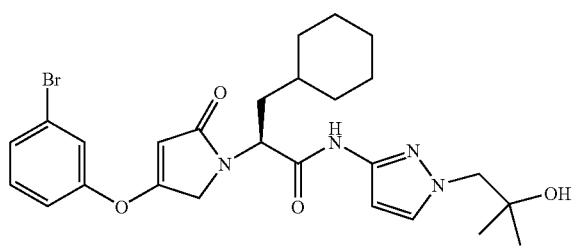

Potassium t-butoxide (10.5 g, 0.094 mol) was added to a stirred solution of 3-bromo-phenol (8.18 g, 0.047 mol) in tetrahydrofuran (30 mL) at 23° C. under nitrogen and the reaction mixture was heated to reflux for 0.75 h. The reaction mixture was cooled to 23° C. and a solution of 3-chloro-but-2-enoic acid ethyl ester (prepared as in Example 191, 7.00 g, 0.047 mol) in tetrahydrofuran (40 mL) was added to the reaction mixture. The reaction mixture was refluxed for an additional 3 h. After this time, the mixture was concentrated in vacuo and the residue was diluted with water and extracted with diethyl ether. The organic layer was then washed with 5% aqueous sodium hydroxide solution followed by a saturated aqueous sodium chloride solution, dried over sodium sulfate and concentrated in vacuo to afford (E)-3-(3-bromo-phenoxy)-but-2-enoic acid ethyl ester (5.20 g, 39%) as a yellow oil.

To a stirred mixture of (E)-3-(3-bromo-phenoxy)-but-2-enoic acid ethyl ester (5.80 g, 0.020 mol) in carbon tetrachloride (30 mL) under a nitrogen atmosphere was added N-bromosuccinimide (5.51 g, 0.031 mol) and benzoyl peroxide (500 mg, 0.002 mol). Nitrogen gas was bubbled through the mixture for 5 min, and the resulting mixture was heated to reflux for 4 h. The reaction mixture was then placed in the refrigerator overnight. The solids formed were removed by filtration and the filtrate concentrated in vacuo. The crude product obtained was purified using flash column chromatography (silica gel (100-200 mesh), ethyl acetate/hexanes) to afford (E)-4-bromo-3-(3-bromo-phenoxy)-but-2-enoic acid ethyl ester (2.30 g, 31%) as a yellow oil.

To a stirred solution of (S)-2-amino-3-cyclohexyl-propionic acid methyl ester (843 mg, 0.005 mol) in N,N-dimethylformamide (10 mL) was added N,N-diisopropylethylamine (2.64 g, 0.020 mol) slowly at room temperature, under nitrogen. The resulting mixture was stirred for 5 min and then treated with (E)-4-bromo-3-(3-bromo-phenoxy)-but-2-enoic acid ethyl ester (1.50 g, 0.004 mol) and the reaction mixture was heated at 110° C.-120° C. for 16 h. After this time, ice water was added and the resulting mixture was extracted with ethyl acetate. The combined organic layers were washed with a saturated aqueous sodium chloride solution, dried over sodium sulfate and concentrated in vacuo. Purification by flash column chromatography (silica gel (100-200 mesh)) afforded (S)-2-[4-(3-bromo-phenoxy)-2-oxo-2,5-dihydro-pyrrol-1-yl]-3-cyclohexyl-propionic acid methyl ester (490 mg, 25%) as yellow oil.

To a stirred solution of (S)-2-[4-(3-bromo-phenoxy)-2-oxo-2,5-dihydro-pyrrol-1-yl]-3-cyclohexyl-propionic acid methyl ester (450 mg, 0.001 mol) in tetrahydrofuran-water (3:1, 10 mL) was added lithium hydroxide (134 mg, 0.006 mol). The reaction mixture was stirred at 23° C. for 2 h. After this time, the mixture was concentrated and the reaction mixture was diluted with water. The reaction mixture was acidified with 2N hydrochloric acid, during which time precipitation occurred. The precipitate was removed by filtration, washed with cold water and dried in vacuo to obtain (S)-2-[4-(3-bromo-phenoxy)-2-oxo-2,5-dihydro-pyrrol-1-yl]-3-cyclohexyl-propionic acid (320 mg, 74%) as a off-white solid.

To a stirred solution of (S)-2-[4-(3-bromo-phenoxy)-2-oxo-2,5-dihydro-pyrrol-1-yl]-3-cyclohexyl-propionic acid (62 mg, 0.2 mmol) in dichloromethane (12 mL) was gradually added 1-(3-dimethylaminopropyl)-3-ethylcarbodiimide hydrochloride (85 mg, 0.4 mmol) and N,N-diisopropylethylamine (100 mg, 0.8 mmol) at room temperature, under nitrogen. After 15 min, 1-hydroxybenzotriazole (70 mg, 0.5 mmol) and 1-(3-amino-pyrazol-1-yl)-2-methyl-propan-2-ol (prepared in U.S. Pat. Appl. US2008021032 Example 80, 23 mg, 0.1 mmol) were added to the reaction mixture. The reaction mixture was then stirred at 23° C. for 48 h. The reaction mixture was diluted with ethyl acetate and washed with a saturated aqueous ammonium chloride solution followed by a saturated aqueous sodium bicarbonate solution. The organic layer was then washed with a saturated aqueous sodium chloride solution, separated, dried over sodium sulfate and concentrated in vacuo to afford the crude product, which was purified by flash column chromatography (silica gel (100-200 mesh)) which afforded (S)-2-[4-(3-bromo-phenoxy)-2-oxo-2,5-dihydro-pyrrol-1-yl]-3-cyclohexyl-N-[1-(2-hydroxy-2-methyl-propyl)-1H-pyrazol-3-yl]-propionamide (16 mg, 19%): $^1$H NMR (400 MHz, CDCl$_3$) δ ppm 0.84-1.09 (m, 2H), 1.16 (s, 6H), 1.26 (s, 3H), 1.60-1.94 (m, 8H), 3.64 (br. s., 1H), 3.94 (s, 3H), 4.09 (d, J=18.1 Hz, 2H), 4.32 (d, J=18.1 Hz, 1H), 4.92 (t, J=7.8 Hz, 1H), 5.03 (s, 1H), 6.69 (d, J=1.5 Hz, 1H), 7.14 (dd, J=8.3, 1.5 Hz, 1H), 7.27-7.33 (m, 2H), 7.35-7.39 (m, 1H), 7.42 (d, J=7.8 Hz, 1H), 8.82 (br. s., 1H).

Example 206

(S)-3-cyclohexyl-2-[4-(3-fluoro-phenoxy)-2-oxo-2,5-dihydro-pyrrol-1-yl]-N-[1-(2-hydroxy-2-methyl-propyl)-1H-pyrazol-3-yl]-propionamide

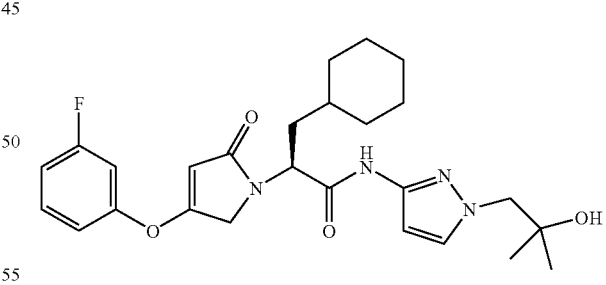

Potassium t-butoxide (7.40 g, 0.066 mol) was added to a stirred solution of 3-fluoro-phenol (3.78 g, 0.034 mol) in tetrahydrofuran (30 mL) at 23° C. under nitrogen and the reaction mixture was heated to reflux for 0.75 h. The reaction mixture was cooled to 23° C. and a solution of 3-chloro-but-2-enoic acid ethyl ester (prepared as in Example 191, 5.00 g, 0.034 mol) in tetrahydrofuran (40 mL) was added to the reaction mixture. The reaction mixture was refluxed for an additional 3 h. After this time, the mixture was concentrated in vacuo and the residue was diluted with water and extracted with diethyl ether. The organic layer was then washed with 5% aqueous sodium hydroxide solution followed by a saturated aqueous sodium chloride solution, dried over sodium sulfate and concentrated in vacuo to afford (E)-3-(3-fluoro-phenoxy)-but-2-enoic acid ethyl ester (6.50 g, 86%) as a yellow oil.

To a stirred mixture of (E)-3-(3-fluoro-phenoxy)-but-2-enoic acid ethyl ester (8.60 g, 0.038 mol) in carbon tetrachloride (35 mL) under a nitrogen atmosphere was added N-bromosuccinimide (10.3 g, 0.058 mol) and benzoyl peroxide (900 mg, 0.004 mol). Nitrogen gas was bubbled through the mixture for 5 min, and the resulting mixture was heated to reflux for 4 h. The reaction mixture was then placed in the refrigerator overnight. The solids formed were removed by filtration and the filtrate concentrated in vacuo. The crude product obtained was purified using flash column chromatography (silica gel (100-200 mesh), ethyl acetate/hexanes) to afford (E)-4-bromo-3-(3-fluoro-phenoxy)-but-2-enoic acid ethyl ester (2.30 g, 20%) as a yellow oil.

To a stirred solution of (S)-2-amino-3-cyclohexyl-propionic acid methyl ester (2.03 g, 0.011 mol) in N,N-dimethylformamide (10 mL) was added N,N-diisopropylethylamine (6.38 g, 0.049 mol) slowly at room temperature, under nitrogen. The resulting mixture was stirred for 5 min and then treated with (E)-4-bromo-3-(3-fluoro-phenoxy)-but-2-enoic acid ethyl ester (3.00 g, 0.010 mol) and the reaction mixture was heated at 110° C.-120° C. for 16 h. After this time, ice water was added and the resulting mixture was extracted with ethyl acetate. The combined organic layers were washed with a saturated aqueous sodium chloride solution, dried over sodium sulfate and concentrated in vacuo. Purification by flash column chromatography (silica gel (100-200 mesh)) afforded (S)-3-cyclohexyl-2-[4-(3-fluoro-phenoxy)-2-oxo-2,5-dihydro-pyrrol-1-yl]-propionic acid methyl ester (1.40 g, 35%) as a yellow oil.

To a stirred solution of (S)-3-cyclohexyl-2-[4-(3-fluoro-phenoxy)-2-oxo-2,5-dihydro-pyrrol-1-yl]-propionic acid methyl ester (1.10 g, 0.003 mol) in tetrahydrofuran-water (3:1, 10 mL) was added lithium hydroxide (382 mg, 0.016 mol). The reaction mixture was stirred at 23° C. for 2 h. After this time, the mixture was concentrated and the reaction mixture was diluted with water. The reaction mixture was acidified with 2N hydrochloric acid, during which time precipitation occurred. The precipitate was removed by filtration, washed with cold water and dried in vacuo to obtain (S)-3-cyclohexyl-2-[4-(3-fluoro-phenoxy)-2-oxo-2,5-dihydro-pyrrol-1-yl]-propionic acid (920 gm, 87%) as an off-white solid.

To a stirred solution of (S)-3-cyclohexyl-2-[4-(3-fluoro-phenoxy)-2-oxo-2,5-dihydro-pyrrol-1-yl]-propionic acid (200 mg, 0.6 mmol) in dichloromethane (10 mL) was gradually added 1-(3-dimethylaminopropyl)-3-ethylcarbodiimide hydrochloride (143 mg, 0.7 mmol) and N,N-diisopropylethylamine (223 mg, 1.7 mmol) at room temperature, under nitrogen. After 15 min, 1-hydroxybenzotriazole (117 mg, 0.8 mmol) and 1-(3-amino-pyrazol-1-yl)-2-methyl-propan-2-ol (prepared in U.S. Pat. Appl. US2008021032 Example 80, 110 mg, 0.7 mmol) were added to the reaction mixture. The reaction mixture was then stirred at 23° C. for 48 h. The reaction mixture was diluted with ethyl acetate and washed with a saturated aqueous ammonium chloride solution followed by a saturated aqueous sodium bicarbonate solution. The organic layer was then washed with a saturated aqueous sodium chloride solution, separated, dried over sodium sulfate and concentrated in vacuo to afford the crude product, which was purified by flash column chromatography (silica gel (100-200 mesh)) which afforded (S)-3-cyclohexyl-2-[4-(3-fluoro-phenoxy)-2-oxo-2,5-dihydro-pyrrol-1-yl]-N-[1-(2-hydroxy-2-methyl-propyl)-1H-pyrazol-3-yl]-propionamide (150 mg, 54%) as a brown sticky solid: $^1$H NMR (400 MHz, CDCl$_3$) δ ppm 0.83-1.08 (m, 2H), 1.16 (br. s., 6H), 1.18-1.33 (m, 4H), 1.67-1.81 (m, 5H), 1.81-2.00 (m, 2H), 3.67 (br. s., 1H), 3.94 (s, 2H), 4.09 (d, J=18.1 Hz, 1H), 4.30 (d, J=18.1 Hz, 1H), 4.91 (dd, J=8.8, 6.4 Hz, 1H), 5.05 (s, 1H), 6.69 (br. s., 1H), 6.93 (d, J=8.8 Hz, 1H), 6.99 (d, J=7.8 Hz, 2H), 7.30 (br. s., 1H), 7.34-7.45 (m, 1H), 8.64 (br. s., 1H).

Example 207

(S)-2-[4-(3-chloro-phenoxy)-2-oxo-2,5-dihydro-pyrrol-1-yl]-3-cyclohexyl-N-[1-(2-hydroxy-2-methyl-propyl)-1H-pyrazol-3-yl]-propionamide Potassium t-butoxide (7.40 g, 0.066 mol) was added to a stirred solution of 3-chloro-phenol (4.22 g, 0.033 mol) in tetrahydrofuran (35 mL) at 23° C. under nitrogen and the reaction mixture was heated to reflux for 0.75 h. The reaction mixture was cooled to 23° C. and a solution of 3-chloro-but-2-enoic acid ethyl ester (prepared as in Example 191, 5.00 g, 0.034 mol) in tetrahydrofuran (40 mL) was added to the reaction mixture. The reaction mixture was refluxed for an additional 3 h. After this time, the mixture was concentrated in vacuo and the residue was diluted with water and extracted with diethyl ether. The organic layer was then washed with 5% aqueous sodium hydroxide solution followed by a saturated aqueous sodium chloride solution, dried over sodium sulfate and concentrated in vacuo to afford (E)-3-(3-chloro-phenoxy)-but-2-enoic acid ethyl ester (3.20 g, 40%) as a yellow oil.

To a stirred mixture of (E)-3-(3-chloro-phenoxy)-but-2-enoic acid ethyl ester (3.45 g, 0.014 mol) in carbon tetrachloride (20 mL) under a nitrogen atmosphere was added N-bromosuccinimide (2.79 g, 0.016 mol) and benzoyl peroxide (347 mg, 0.001 mol). Nitrogen gas was bubbled through the mixture for 5 min, and the resulting mixture was heated to reflux for 4 h. The reaction mixture was then placed in the refrigerator overnight. The solids formed were removed by filtration and the filtrate concentrated in vacuo. The crude product obtained was purified using flash column chromatography (silica gel (100-200 mesh), ethyl acetate/hexanes) to afford (E)-4-bromo-3-(3-chloro-phenoxy)-but-2-enoic acid ethyl ester (2.90 g, 63%) as a yellow oil.

To a stirred solution of (S)-2-amino-3-cyclohexyl-propionic acid methyl ester (786 mg, 0.004 mol) in N,N-dimethylformamide (10 mL) was added N,N-diisopropylethylamine (2.58 g, 0.020 mol) slowly at room temperature, under nitrogen. The resulting mixture was stirred for 5 min and then treated with (E)-4-bromo-3-(3-chloro-phenoxy)-but-2-enoic acid ethyl ester (1.30 g, 0.004 mol) and the reaction mixture was heated at 110° C.-120° C. for 16 h. After this time, ice water was added and the resulting mixture was extracted with ethyl acetate. The combined organic layers were washed with a saturated aqueous sodium chloride solution, dried over sodium sulfate and concentrated in vacuo. Purification by flash column chromatography (silica gel (100-200 mesh)) afforded (S)-2-[4-(3-chloro-phenoxy)-2-oxo-2,5-dihydro-pyrrol-1-yl]-3-cyclohexyl-propionic acid methyl ester (530 mg, 33%) as a yellow oil.

To a stirred solution of (S)-2-[4-(3-chloro-phenoxy)-2-oxo-2,5-dihydro-pyrrol-1-yl]-3-cyclohexyl-propionic acid methyl ester (340 mg, 0.9 mmol) in tetrahydrofuran-water (3:1, 10 mL) was added lithium hydroxide (118 mg, 2.7 mmol). The reaction mixture was stirred at 23° C. for 2 h. After this time, the mixture was concentrated and the reaction mixture was diluted with water. The reaction mixture was acidified with 2N hydrochloric acid, during which time precipitation occurred. The precipitate was removed by filtration, washed with cold water and dried in vacuo to obtain (S)-2-[4-(3-chloro-phenoxy)-2-oxo-2,5-dihydro-pyrrol-1-yl]-3-cyclohexyl-propionic acid (280 mg, 86%) as an off-white solid.

To a stirred solution of (S)-2-[4-(3-chloro-phenoxy)-2-oxo-2,5-dihydro-pyrrol-1-yl]-3-cyclohexyl-propionic acid (200 mg, 0.6 mmol) in dichloromethane (10 mL) was gradually added 1-(3-dimethylaminopropyl)-3-ethylcarbodiimide hydrochloride (115 mg, 0.6 mmol) and N,N-diisopropylethylamine (213 mg, 1.7 mmol) at room temperature, under nitrogen. After 15 min,, 1-hydroxybenzotriazole (0.092 g, 0.625 mmol) and 1-(3-amino-pyrazol-1-yl)-2-methyl-propan-2-ol (prepared in U.S. Pat. Appl. US2008021032 Example 80, 85 mg, 0.5 mmol) were added to the reaction mixture. The reaction mixture was then stirred at 23° C. for 48 h. The reaction mixture was diluted with ethyl acetate and washed with a saturated aqueous ammonium chloride solution followed by a saturated aqueous sodium bicarbonate solution. The organic layer was then washed with a saturated aqueous sodium chloride solution, separated, dried over sodium sulfate and concentrated in vacuo to afford the crude product, which was purified by flash column chromatography (silica gel (100-200 mesh)) which afforded (S)-2-[4-(3-chloro-phenoxy)-2-oxo-2,5-dihydro-pyrrol-1-yl]-3-cyclohexyl-N-[1-(2-hydroxy-2-methyl-propyl)-1H-pyrazol-3-yl]-propionamide (0.075 g, 27%) as a white solid: $^1$H NMR (400 MHz, CDCl$_3$) δ ppm 0.84-1.11 (m, 2H), 1.16 (s, 3H), 1.19-1.35 (m, 3H), 1.27 (s, 3H), 1.60-1.98 (m, 8H), 3.39 (br. s., 1H), 3.95 (s, 2H), 4.09 (d, J=18.0 Hz, 1H), 4.28 (d, J=18.0 Hz, 1H), 4.89 (dd, J=9.2, 6.5 Hz, 1H), 5.03 (s, 1H), 6.69 (d, J=2.2 Hz, 1H), 7.09 (dd, J=8.2, 1.8 Hz, 1H), 7.21 (t, J=1.8 Hz, 1H), 7.27 (m, 1H), 7.30 (d, J=2.2 Hz, 1H), 7.36 (t, J=8.2 Hz, 1H), 8.49 (br. s., 1H).

Example 208

(S)-3-cyclohexyl-N-[1-(2-hydroxy-2-methyl-propyl)-1H-pyrazol-3-yl]-2-[4-(3-methoxy-phenoxy)-2-oxo-2,5-dihydro-pyrrol-1-yl]-propionamide

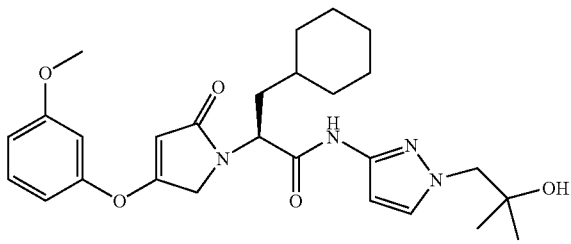

Potassium t-butoxide (11.2 g, 0.100 mol) was added to a stirred solution of 3-methoxy-phenol (6.24 g, 0.050 mol) in tetrahydrofuran (35 mL) at 23° C. under nitrogen and the reaction mixture was heated to reflux for 0.75 h. The reaction mixture was cooled to 23° C. and a solution of 3-chloro-but-2-enoic acid ethyl ester (prepared as in Example 191, 7.50 g, 0.050 mol) in tetrahydrofuran (40 mL) was added to the reaction mixture. The reaction mixture was refluxed for an additional 3 h. After this time, the mixture was concentrated in vacuo and the residue was diluted with water and extracted with diethyl ether. The organic layer was then washed with 5% aqueous sodium hydroxide solution followed by a saturated aqueous sodium chloride solution, dried over sodium sulfate and concentrated in vacuo to afford (E)-3-(3-methoxy-phenoxy)-but-2-enoic acid ethyl ester (5.50 g, 46%) as a yellow oil.

To a stirred mixture of (E)-3-(3-methoxy-phenoxy)-but-2-enoic acid ethyl ester (5.50 g, 0.023 mol) in carbon tetrachloride (20 mL) under a nitrogen atmosphere was added N-bromosuccinimide (6.22 g, 0.035 mol) and benzoyl peroxide (563 mg, 0.002 mol). Nitrogen gas was bubbled through the mixture for 5 min, and the resulting mixture was heated to reflux for 4 h. The reaction mixture was then placed in the refrigerator overnight. The solids formed were removed by filtration and the filtrate concentrated in vacuo. The crude product obtained was purified using flash column chromatography (silica gel (100-200 mesh), ethyl acetate/hexanes) to afford (E)-4-bromo-3-(3-methoxy-phenoxy)-but-2-enoic acid ethyl ester (4.00 g, 55%) as a yellow oil.

To a stirred solution of (S)-2-amino-3-cyclohexyl-propionic acid methyl ester (1.20 g, 0.006 mol) in N,N-dimethylformamide (10 mL) was added N,N-diisopropylethylamine (4.06 g, 0.031 mol) slowly at room temperature, under nitrogen. The resulting mixture was stirred for 5 min and then treated with (E)-4-bromo-3-(3-methoxy-phenoxy)-but-2-enoic acid ethyl ester (2.00 g, 0.006 mol) and the reaction mixture was heated at 110° C.-120° C. for 16 h. After this time, ice water was added and the resulting mixture was extracted with ethyl acetate. The combined organic layers were washed with a saturated aqueous sodium chloride solution, dried over sodium sulfate and concentrated in vacuo. Purification by flash column chromatography (silica gel (100-200 mesh)) afforded (S)-3-cyclohexyl-2-[4-(3-methoxy-phenoxy)-2-oxo-2,5-dihydro-pyrrol-1-yl]-propionic acid methyl ester (1.12 g, 46%) as a yellow oil.

To a stirred solution of (S)-3-cyclohexyl-2-[4-(3-methoxy-phenoxy)-2-oxo-2,5-dihydro-pyrrol-1-yl]-propionic acid methyl ester (1.12 g, 0.003 mol) in tetrahydrofuran-water (3:1, 10 mL) was added lithium hydroxide (387 mg, 0.009 mol). The reaction mixture was stirred at 23° C. for 2 h. After this time, the mixture was concentrated and the reaction mixture was diluted with water. The reaction mixture was acidified with 2N hydrochloric acid, during which time precipitation occurred. The precipitate was removed by filtration, washed with cold water and dried in vacuo to obtain (S)-3-cyclohexyl-2-[4-(3-methoxy-phenoxy)-2-oxo-2,5-dihydro-pyrrol-1-yl]-propionic acid (670 mg, 62%) as a light yellow solid.

To a stirred solution of (S)-3-cyclohexyl-2-[4-(3-methoxy-phenoxy)-2-oxo-2,5-dihydro-pyrrol-1-yl]-propionic acid (150 mg, 0.4 mmol) in dichloromethane (10 mL) was gradually added 1-(3-dimethylaminopropyl)-3-ethylcarbodiimide hydrochloride (85 mg, 0.4 mmol) and N,N-diisopropylethylamine (169 mg, 1.2 mmol) at room temperature, under nitrogen. After 15 min, 1-hydroxybenzotriazole (63 mg, 0.4 mmol) and 1-(3-amino-pyrazol-1-yl)-2-methyl-propan-2-ol (prepared in U.S. Pat. Appl. US2008021032 Example 80, 65 mg, 0.4 mmol) were added to the reaction mixture. The reaction mixture was then stirred at 23° C. for 48 h. The reaction mixture was diluted with ethyl acetate and washed with a saturated aqueous ammonium chloride solution followed by a saturated aqueous sodium bicarbonate solution. The organic layer was then washed with a saturated aqueous sodium chloride solution, separated, dried over sodium sulfate and concentrated in vacuo to afford the crude product, which was purified by flash column chromatography (silica gel (100-200 mesh)) which afforded (S)-3-cyclohexyl-N-[1-(2-hydroxy-2-methyl-propyl)-1H-pyrazol-3-yl]-2-[4-(3-methoxy-phenoxy)-2-oxo-2,5-dihydro-pyrrol-1-yl]-propionamide (0.030 g, 14%) as a light yellow sticky liquid: $^1$H NMR (400 MHz, CDCl$_3$) δ ppm 0.84-1.09 (m, 2H), 1.17 (s, 6H), 1.19-1.35 (m, 3H), 1.53-1.97 (m, 8H), 2.80 (br. s., 1H), 3.82 (s, 3H), 3.97 (s, 2H), 4.09 (d, J=18.0 Hz, 1H), 4.33 (d, J=18.0 Hz, 1H), 4.91 (dd, J=8.8, 6.1 Hz, 1H), 5.04 (s, 1H), 6.66-6.73 (m, 2H), 6.76 (d, J=7.8 Hz, 1H), 6.82 (dd, J=8.3, 1.7 Hz, 1H), 7.28-7.35 (m, 2H), 8.95 (br. s., 1H).

Example 209

(S)-3-cyclohexyl-N-[1-(2-hydroxy-2-methyl-propyl)-1H-pyrazol-3-yl]-2-[2-oxo-4-(3-trifluoromethyl-phenoxy)-2,5-dihydro-pyrrol-1-yl]-proonamide

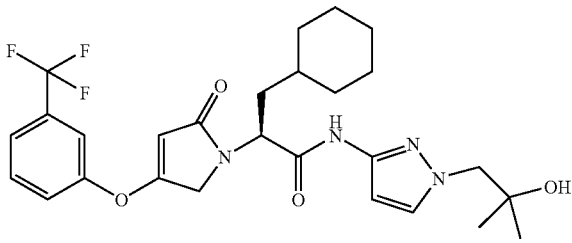

Potassium t-butoxide (6.90 g, 0.061 mol) was added to a stirred solution of 3-trifluoromethyl-phenol (5.00 g, 0.031 mol) in tetrahydrofuran (35 mL) at 23° C. under nitrogen and the reaction mixture was heated to reflux for 0.75 h. The reaction mixture was cooled to 23° C. and a solution of 3-chloro-but-2-enoic acid ethyl ester (prepared as in Example 191, 4.56 g, 0.031 mol) in tetrahydrofuran (40 mL) was added to the reaction mixture. The reaction mixture was refluxed for an additional 3 h. After this time, the mixture was concentrated in vacuo and the residue was diluted with water and extracted with diethyl ether. The organic layer was then washed with 5% aqueous sodium hydroxide solution followed by a saturated aqueous sodium chloride solution, dried over sodium sulfate and concentrated in vacuo to afford (E)-3-(3-trifluoromethyl-phenoxy)-but-2-enoic acid ethyl ester (5.33 g, 63%) as a yellow oil.

To a stirred mixture of (E)-3-(3-trifluoromethyl-phenoxy)-but-2-enoic acid ethyl ester (5.33 g, 0.019 mol) in carbon tetrachloride (30 mL) under a nitrogen atmosphere was added N-bromosuccinimide (5.20 g, 0.029 mol) and benzoyl peroxide (470 mg, 0.002 mol). Nitrogen gas was bubbled through the mixture for 5 min, and the resulting mixture was heated to reflux for 4 h. The reaction mixture was then placed in the refrigerator overnight. The solids formed were removed by filtration and the filtrate concentrated in vacuo. The crude product obtained was purified using flash column chromatography (silica gel (100-200 mesh), ethyl acetate/hexanes) to afford (E)-4-bromo-3-(3-trifluoromethyl-phenoxy)-but-2-enoic acid ethyl ester (3.80 g, 55%) as a yellow oil.

To a stirred solution of (S)-2-amino-3-cyclohexyl-propionic acid methyl ester (1.16 g, 0.006 mol) in N,N-dimethylformamide (10 mL) was added N,N-diisopropylethylamine (3.65 g, 0.028 mol) slowly at room temperature, under nitrogen. The resulting mixture was stirred for 5 min and then treated with (E)-4-bromo-3-(3-trifluoromethyl-phenoxy)-but-2-enoic acid ethyl ester (2.00 g, 0.006 mol) and the reaction mixture was heated at 110° C.-120° C. for 16 h. After this time, ice water was added and the resulting mixture was extracted with ethyl acetate. The combined organic layers were washed with a saturated aqueous sodium chloride solution, dried over sodium sulfate and concentrated in vacuo. Purification by flash column chromatography (silica gel (100-200 mesh)) afforded (S)-3-cyclohexyl-2-[2-oxo-4-(3-trifluoromethyl-phenoxy)-2,5-dihydro-pyrrol-1-yl]-propionic acid methyl ester (650 mg, 25%) as a yellow oil.

To a stirred solution of (S)-3-cyclohexyl-2-[2-oxo-4-(3-trifluoromethyl-phenoxy)-2,5-dihydro-pyrrol-1-yl]-propionic acid methyl ester (620 mg, 0.002 mol) in tetrahydrofuran-water (3:1, 10 mL) was added lithium hydroxide (190 mg, 0.008 mol). The reaction mixture was stirred at 23° C. for 2 h. After this time, the mixture was concentrated and the reaction mixture was diluted with water. The reaction mixture was acidified with 2N hydrochloric acid, during which time precipitation occurred. The precipitate was removed by filtration, washed with cold water and dried in vacuo to obtain (S)-3-cyclohexyl-2-[2-oxo-4-(3-trifluoromethyl-phenoxy)-2,5-dihydro-pyrrol-1-yl]-propionic acid (295 mg, 49%) as a light brown solid.

To a stirred solution of (S)-3-cyclohexyl-2-[2-oxo-4-(3-trifluoromethyl-phenoxy)-2,5-dihydro-pyrrol-1-yl]-propionic acid (180 mg, 0.5 mmol) in dichloromethane (10 mL) was gradually added 1-(3-dimethylaminopropyl)-3-ethylcarbodiimide hydrochloride (259 mg, 1.2 mmol) and N,N-diisopropylethylamine (292 mg, 2.3 mmol) at room temperature, under nitrogen. After 15 min, 1-hydroxybenzotriazole (208 mg, 1.41 mol) and 1-(3-amino-pyrazol-1-yl)-2-methyl-propan-2-ol (prepared in U.S. Pat. Appl. US2008021032 Example 80, 70 mg, 0.5 mmol) were added to the reaction mixture. The reaction mixture was then stirred at 23° C. for 48 h. The reaction mixture was diluted with ethyl acetate and washed with a saturated aqueous ammonium chloride solution followed by a saturated aqueous sodium bicarbonate solution. The organic layer was then washed with a saturated aqueous sodium chloride solution, separated, dried over sodium sulfate and concentrated in vacuo to afford the crude product, which was purified by flash column chromatography (silica gel (100-200 mesh)) which afforded (S)-3-cyclohexyl-N-[1-(2-hydroxy-2-methyl-propyl)-1H-pyrazol-3-yl]-2-[2-oxo-4-(3-trifluoromethyl-phenoxy)-2,5-dihydro-pyrrol-1-yl]-propionamide (45 mg, 19%) as an off-white sticky solid: $^1$H NMR (400 MHz, CDCl$_3$) δ ppm 0.78-1.04 (m, 2H), 1.13 (br. s., 6H), 1.15-1.31 (m, 3H), 1.56-1.93 (m, 8H), 2.66 (br. s., 1H), 3.92 (br. s., 2H), 4.10 (d, J=18.1 Hz, 1H), 4.40 (d, J=18.1 Hz, 1H), 4.94 (br. s., 1H), 5.00 (br. s., 1H), 6.64 (br. s., 1H), 7.27 (br. s., 1H), 7.39 (br. s., 1H), 7.45 (br. s., 1H), 7.54 (br. s., 2H), 9.02 (br. s., 1H).

Example 210

(S)-3-cyclohexyl-N-[1-(2-hydroxy-2-methyl-propyl)-1H-pyrazol-3-yl]-2-(2-oxo-4-m-tolyloxy-2,5-dihydro-pyrrol-1-yl)-propionamide

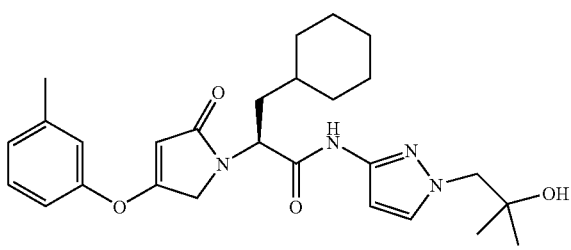

Potassium t-butoxide (10.4 g, 0.092 mol) was added to a stirred solution of 3-methyl-phenol (5.00 g, 0.046 mol) in tetrahydrofuran (35 mL) at 23° C. under nitrogen and the reaction mixture was heated to reflux for 0.75 h. The reaction mixture was cooled to 23° C. and a solution of 3-chloro-but-2-enoic acid ethyl ester (prepared as in Example 191, 6.85 g, 0.046 mol) in tetrahydrofuran (40 mL) was added to the reaction mixture. The reaction mixture was refluxed for an additional 3 h. After this time, the mixture was concentrated in vacuo and the residue was diluted with water and extracted with diethyl ether. The organic layer was then washed with 5% aqueous sodium hydroxide solution followed by a saturated aqueous sodium chloride solution, dried over sodium sulfate and concentrated in vacuo to afford (E)-3-m-tolyloxy-but-2-enoic acid ethyl ester (6.41 g, 63%) as a yellow oil.

To a stirred mixture of (E)-3-m-tolyloxy-but-2-enoic acid ethyl ester (6.41 g, 0.029 mol) in carbon tetrachloride (30 mL) under a nitrogen atmosphere was added N-bromosuccinimide (7.78 g, 0.044 mol) and benzoyl peroxide (704 mg, 0.003 mol). Nitrogen gas was bubbled through the mixture for 5 min, and the resulting mixture was heated to reflux for 4 h. The reaction mixture was then placed in the refrigerator overnight. The solids formed were removed by filtration and the filtrate concentrated in vacuo. The crude product obtained was purified using flash column chromatography (silica gel (100-200 mesh), ethyl acetate/hexanes) to afford (E)-4-bromo-3-m-tolyloxy-but-2-enoic acid ethyl ester (3.80 g, 44%) as a yellow oil.

To a stirred solution of (S)-2-amino-3-cyclohexyl-propionic acid methyl ester (1.03 g, 0.006 mol) in N,N-dimethylformamide (8 mL) was added N,N-diisopropylethylamine (3.22 g, 0.025 mol) slowly at room temperature, under nitrogen. The resulting mixture was stirred for 5 min and then treated with (E)-4-bromo-3-m-tolyloxy-but-2-enoic acid ethyl ester (1.50 g, 0.005 mol) and the reaction mixture was heated at 110° C.-120° C. for 16 h. After this time, ice water was added and the resulting mixture was extracted with ethyl acetate. The combined organic layers were washed with a saturated aqueous sodium chloride solution, dried over sodium sulfate and concentrated in vacuo. Purification by flash column chromatography (silica gel (100-200 mesh)) afforded (S)-3-cyclohexyl-2-(2-oxo-4-m-tolyloxy-2,5-dihydro-pyrrol-1-yl)-propionic acid methyl ester (495 mg, 25%) as a yellow oil.

To a stirred solution of (S)-3-cyclohexyl-2-(2-oxo-4-m-tolyloxy-2,5-dihydro-pyrrol-1-yl)-propionic acid methyl ester (0.570 g, 0.002 mol) in tetrahydrofuran-water (3:1, 10 mL) was added lithium hydroxide (0.201 g, 0.008 mol). The reaction mixture was stirred at 23° C. for 2 h. After this time, the mixture was concentrated and the reaction mixture was diluted with water. The reaction mixture was acidified with 2N hydrochloric acid, during which time precipitation occurred. The precipitate was removed by filtration, washed with cold water and dried in vacuo to obtain (S)-3-cyclohexyl-2-(2-oxo-4-m-tolyloxy-2,5-dihydro-pyrrol-1-yl)-propionic acid (430 mg, 79%) as a light brown solid.

To a stirred solution of (S)-3-cyclohexyl-2-(2-oxo-4-m-tolyloxy-2,5-dihydro-pyrrol-1-yl)-propionic acid (150 mg, 0.4 mmol) in dichloromethane (10 mL) was gradually added 1-(3-dimethylaminopropyl)-3-ethylcarbodiimide hydrochloride (250 mg, 1.3 mmol) and N,N-diisopropylethylamine (0.280 g, 2.17 mmol) at room temperature, under nitrogen. After 15 min, 1-hydroxybenzotriazole (200 mg, 1.3 mmol) and 1-(3-amino-pyrazol-1-yl)-2-methyl-propan-2-ol (prepared in U.S. Pat. Appl. US2008021032 Example 80, 67 mg, 0.4 mmol) were added to the reaction mixture. The reaction mixture was then stirred at 23° C. for 48 h. The reaction mixture was diluted with ethyl acetate and washed with a saturated aqueous ammonium chloride solution followed by a saturated aqueous sodium bicarbonate solution. The organic layer was then washed with a saturated aqueous sodium chloride solution, separated, dried over sodium sulfate and concentrated in vacuo to afford the crude product, which was purified by flash column chromatography (silica gel (100-200 mesh)) which afforded (S)-3-cyclohexyl-N-[1-(2-hydroxy-2-methyl-propyl)-1H-pyrazol-3-yl]-2-(2-oxo-4-m-tolyloxy-2,5-dihydro-pyrrol-1-yl)-propionamide (16 mg, 8%) as an off-white sticky solid: $^1$H NMR (400 MHz, CDCl$_3$) δ ppm 0.84-1.06 (m, 2H), 1.15 (s, 6H), 1.17-1.30 (m, 3H), 1.58-1.93 (m, 8H), 2.35 (s, 3H), 3.00 (br. s., 1H), 3.94 (s, 2H), 4.07 (d, J=18.0 Hz, 1H), 4.30 (d, J=18.0 Hz, 1H), 4.83-4.94 (m, 1H), 4.97 (s, 1H), 6.67 (br. s., 1H), 6.91-6.99 (m, 2H), 7.06 (d, J=7.8 Hz, 1H), 7.26-7.32 (m, 2H), 8.96 (br. s., 1H).

Example 211

(S)-3-cyclohexyl-N-[1-(2-hydroxy-2-methyl-propyl)-1H-pyrazol-3-yl]-2-[2-oxo-4-(3-trifluoromethoxy-phenoxy)-2,5-dihydro-pyrrol-1-yl]-propionamide

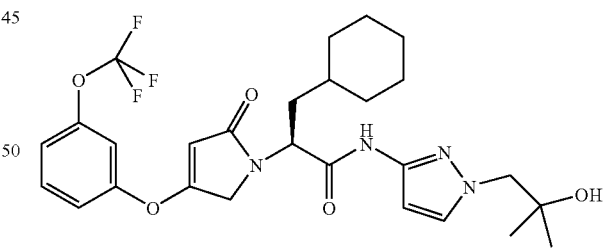

Potassium t-butoxide (1.23 g, 0.013 mol) was added to a stirred solution of 3-trifluoromethoxy-phenol (1.19 g, 0.007 mol) in tetrahydrofuran (15 mL) at 23° C. under nitrogen and the reaction mixture was heated to reflux for 0.75 h. The reaction mixture was cooled to 23° C. and a solution of 3-chloro-but-2-enoic acid ethyl ester (prepared as in Example 191, 1.00 g, 0.007 mol) in tetrahydrofuran (40 mL) was added to the reaction mixture. The reaction mixture was refluxed for an additional 3 h. After this time, the mixture was concentrated in vacuo and the residue was diluted with water and extracted with diethyl ether. The organic layer was then washed with 5% aqueous sodium hydroxide solution followed by a saturated aqueous sodium chloride solution, dried over sodium sulfate and concentrated in vacuo to afford (E)-3-(3-trifluoromethoxy-phenoxy)-but-2-enoic acid ethyl ester (1.40 g, 72%) as a yellow oil.

To a stirred mixture of (E)-3-(3-trifluoromethoxy-phenoxy)-but-2-enoic acid ethyl ester (9.87 g, 0.034 mol) in carbon tetrachloride (60 mL) under a nitrogen atmosphere was added N-bromosuccinimide (9.08 g, 0.051 mol) and benzoyl peroxide in water (75%, 1.09 g, 0.003 mol). Nitrogen gas was bubbled through the mixture for 5 min, and the resulting mixture was heated to reflux for 4 h. The reaction mixture was then placed in the refrigerator overnight. The solids formed were removed by filtration and the filtrate concentrated in vacuo. The crude product obtained was purified using flash column chromatography (silica gel (100-200 mesh), ethyl acetate/hexanes) to afford (E)-4-bromo-3-(3-trifluoromethoxy-phenoxy)-but-2-enoic acid ethyl ester (3.70 g, 29%) as a yellow oil.

To a stirred solution of (S)-2-amino-3-cyclohexyl-propionic acid methyl ester (556 mg, 0.003 mol) in N,N-dimethylformamide (8 mL) was added N,N-diisopropylethylamine (1.75 g, 0.014 mol) slowly at room temperature, under nitrogen. The resulting mixture was stirred for 5 min and then treated with (E)-4-bromo-3-(3-trifluoromethoxy-phenoxy)-but-2-enoic acid ethyl ester (1.00 g, 0.003 mol) and the reaction mixture was heated at 110° C.-120° C. for 16 h. After this time, ice water was added and the resulting mixture was extracted with ethyl acetate. The combined organic layers were washed with a saturated aqueous sodium chloride solution, dried over sodium sulfate and concentrated in vacuo. Purification by flash column chromatography (silica gel (100-200 mesh)) afforded (S)-3-cyclohexyl-2-[2-oxo-4-(3-trifluoromethoxy-phenoxy)-2,5-dihydro-pyrrol-1-yl]-propionic acid methyl ester (290 mg, 23%) as a yellow oil.

To a stirred solution of (S)-3-cyclohexyl-2-[2-oxo-4-(3-trifluoromethoxy-phenoxy)-2,5-dihydro-pyrrol-1-yl]-propionic acid methyl ester (0.520 g, 0.001 mol) in tetrahydrofuran-water (3:1, 20 mL) was added lithium hydroxide (153 mg, 0.006 mol). The reaction mixture was stirred at 23° C. for 2 h. After this time, the mixture was concentrated and the reaction mixture was diluted with water. The reaction mixture was acidified with 2N hydrochloric acid, during which time precipitation occurred. The precipitate was removed by filtration, washed with cold water and dried in vacuo to obtain (S)-3-cyclohexyl-2-[2-oxo-4-(3-trifluoromethoxy-phenoxy)-2,5-dihydro-pyrrol-1-yl]-propionic acid (380 mg, 76%) as a light yellow solid.

To a stirred solution of (S)-3-cyclohexyl-2-[2-oxo-4-(3-trifluoromethoxy-phenoxy)-2,5-dihydro-pyrrol-1-yl]-propionic acid (250 mg, 0.6 mmol) in dichloromethane (12 mL) was gradually added 1-(3-dimethylaminopropyl)-3-ethylcarbodiimide hydrochloride (344 mg, 1.8 mmol) and N,N-diisopropylethylamine (387 mg, 3.0 mmol) at room temperature, under nitrogen. After 15 min, 1-hydroxybenzotriazole (275 mg, 1.9 mmol) and 1-(3-amino-pyrazol-1-yl)-2-methyl-propan-2-ol (prepared in U.S. Pat. Appl. US2008021032 Example 80, 93 mg, 0.6 mmol) were added to the reaction mixture. The reaction mixture was then stirred at 23° C. for 48 h. The reaction mixture was diluted with ethyl acetate and washed with a saturated aqueous ammonium chloride solution followed by a saturated aqueous sodium bicarbonate solution. The organic layer was then washed with a saturated aqueous sodium chloride solution, separated, dried over sodium sulfate and concentrated in vacuo to afford the crude product, which was purified by flash column chromatography (silica gel (100-200 mesh)) which afforded (S)-3-cyclohexyl-N-[1-(2-hydroxy-2-methyl-propyl)-1H-pyrazol-3-yl]-2-[2- oxo-4-(3-trifluoromethoxy-phenoxy)-2,5-dihydro-pyrrol-1-yl]-propionamide (70 mg, 21%) as an off-white solid: $^1$H NMR (400 MHz, CDCl$_3$) δ PPM 0.81-1.09 (m, 2H), 1.15 (s, 6H), 1.16-1.32 (m, 3H), 1.60-1.97 (m, 8H), 3.60 (s, 1H), 3.93 (s, 2H), 4.08 (d, J=18.1 Hz, 1H), 4.28 (d, J=18.1 Hz, 1H), 4.88 (dd, J=9.0, 6.6 Hz, 1H), 5.02 (s, 1H), 6.67 (d, J=2.1 Hz, 1H), 7.07 (s, 1H), 7.10-7.16 (m, 2H), 7.29 (d, J=2.1 Hz, 1H), 7.44 (t, J=8.3 Hz, 1H), 8.49 (s, 1H).

Example 212

(S)-3-cyclohexyl-N-[1-(2-hydroxy-2-methyl-propyl)-1H-pyrazol-3-yl]-2-[4-(6-methyl-pyridin-3-yloxy)-2-oxo-2,5-dihydro-pyrrol-1-yl]-propionamide

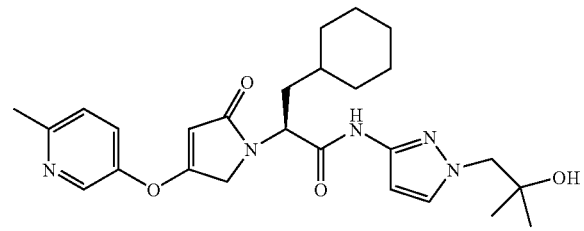

Potassium t-butoxide (10.4 g, 0.092 mol) was added to a stirred solution of 6-methyl-pyridin-3-ol (5.00 g, 0.046 mol) in tetrahydrofuran (35 mL) at 23° C. under nitrogen and the reaction mixture was heated to reflux for 0.75 h. The reaction mixture was cooled to 23° C. and a solution of 3-chloro-but-2-enoic acid ethyl ester (prepared as in Example 191, 6.80 g, 0.046 mol) in tetrahydrofuran (40 mL) was added to the reaction mixture. The reaction mixture was refluxed for an additional 3 h. After this time, the mixture was concentrated in vacuo and the residue was diluted with water and extracted with diethyl ether. The organic layer was then washed with 5% aqueous sodium hydroxide solution followed by a saturated aqueous sodium chloride solution, dried over sodium sulfate and concentrated in vacuo to afford (E)-3-(6-methyl-pyridin-3-yloxy)-but-2-enoic acid ethyl ester (5.72 g, 56%) as a yellow oil.

To a stirred mixture of (E)-3-(6-methyl-pyridin-3-yloxy)-but-2-enoic acid ethyl ester (3.50 g, 0.016 mol) in carbon tetrachloride (25 mL) under a nitrogen atmosphere was added N-bromosuccinimide (4.23 g, 0.024 mol) and benzoyl peroxide (383 mg, 0.002 mol). Nitrogen gas was bubbled through the mixture for 5 min, and the resulting mixture was heated to reflux for 4 h. The reaction mixture was then placed in the refrigerator overnight. The solids formed were removed by filtration and the filtrate concentrated in vacuo. The crude product obtained was purified using flash column chromatography (silica gel (100-200 mesh), ethyl acetate/hexanes) to afford (E)-4-bromo-3-(6-methyl-pyridin-3-yloxy)-but-2-enoic acid ethyl ester (2.10 g, 44%) as a yellow oil.

To a stirred solution of (S)-2-amino-3-cyclohexyl-propionic acid methyl ester (1.37 g, 0.007 mol) in N,N-dimethylformamide (8 mL) was added N,N-diisopropylethylamine (4.30 g, 0.033 mol) slowly at room temperature, under nitrogen. The resulting mixture was stirred for 5 min and then treated with (E)-4-bromo-3-(6-methyl-pyridin-3-yloxy)-but-2-enoic acid ethyl ester (2.00 g, 0.007 mol) and the reaction mixture was heated at 110° C.-120° C. for 16 h. After this time, ice water was added and the resulting mixture was extracted with ethyl acetate. The combined organic layers were washed with a saturated aqueous sodium chloride solution, dried over sodium sulfate and concentrated in vacuo. Purification by flash column chromatography (silica gel (100-200 mesh)) afforded (S)-3-cyclohexyl-2-[4-(6-methyl-pyridin-3-yloxy)-2-oxo-2,5-dihydro-pyrrol-1-yl]-propionic acid methyl ester (410 mg, 15%) as a yellow oil.

To a stirred solution of (S)-3-cyclohexyl-2-[4-(6-methyl-pyridin-3-yloxy)-2-oxo-2,5-dihydro-pyrrol-1-yl]-propionic acid methyl ester (490 mg, 1.36 mmol) in tetrahydrofuran-water (3:1, 10 mL) was added lithium hydroxide (172 mg, 4.1 mmol). The reaction mixture was stirred at 23° C. for 2 h. After this time, the mixture was concentrated and the reaction mixture was diluted with water. The reaction mixture was acidified with 2N hydrochloric acid, during which time precipitation occurred. The precipitate was removed by filtration, washed with cold water and dried in vacuo to obtain (S)-3-cyclohexyl-2-[4-(6-methyl-pyridin-3-yloxy)-2-oxo-2,5-dihydro-pyrrol-1-yl]-propionic acid (316 mg, 67%) as a brown solid.

To a stirred solution of (S)-3-cyclohexyl-2-[4-(6-methyl-pyridin-3-yloxy)-2-oxo-2,5-dihydro-pyrrol-1-yl]-propionic acid (150 mg, 0.4 mmol) in dichloromethane (12 mL) was gradually added 1-(3-dimethylaminopropyl)-3-ethylcarbodiimide hydrochloride (249 mg, 1.3 mmol) and N,N-diisopropylethylamine (280 mg, 2.2 mmol) at room temperature, under nitrogen. After 15 min, 1-hydroxybenzotriazole (200 mg, 1.31 mmol) and 1-(3-amino-pyrazol-1-yl)-2-methyl-propan-2-ol (prepared in U.S. Pat. Appl. US2008021032 Example 80, 67 mg, 0.4 mmol) were added to the reaction mixture. The reaction mixture was then stirred at 23° C. for 48 h. The reaction mixture was diluted with ethyl acetate and washed with a saturated aqueous ammonium chloride solution followed by a saturated aqueous sodium bicarbonate solution. The organic layer was then washed with a saturated aqueous sodium chloride solution, separated, dried over sodium sulfate and concentrated in vacuo to afford the crude product, which was purified by flash column chromatography (silica gel (100-200 mesh)) which afforded (S)-3-cyclohexyl-N-[1-(2-hydroxy-2-methyl-propyl)-1H-pyrazol-3-yl]-2-[4-(6-methyl-pyridin-3-yloxy)-2-oxo-2,5-dihydro-pyrrol-1-yl]-propionamide (105 mg, 50%) as a light brown sticky solid: NMR (400 MHz, CDCl$_3$) δ ppm 0.89-1.06 (m, 2H), 1.14 (br. s., 6H), 1.17-1.29 (m, 3H), 1.56-1.94 (m, 8H), 2.58 (br. s., 3H), 3.76 (br. s., 1H), 3.92 (br. s., 2H), 4.09 (d, J=18.1 Hz, 1H), 4.33 (d, J=18.1 Hz, 1H), 4.81-4.93 (m, 1H), 4.96 (br. s., 1H), 6.67 (br. s., 1H), 7.20 (d, J=8.8 Hz, 1H), 7.28 (br. s., 1H), 7.41 (d, J=8.3 Hz, 1H), 8.39 (br. s., 1H), 8.74 (br. s., 1H).

Example 213

(S)-3-cyclohexyl-N-[1-(2-hydroxy-2-methyl-propyl)-1H-pyrazol-3-yl]-2-(2-oxo-4-phenoxy-2,5-dihydro-pyrrol-1-yl)-propionamide

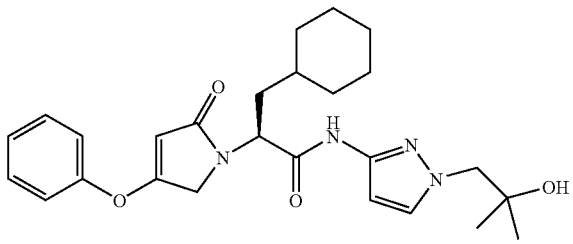

Potassium t-butoxide (11.9 g, 0.106 mol) was added to a stirred solution of phenol (7.86 g, 0.053 mol) in tetrahydrofuran (25 mL) at 23° C. under nitrogen and the reaction mixture was heated to reflux for 0.75 h. The reaction mixture was cooled to 23° C. and a solution of 3-chloro-but-2-enoic acid ethyl ester (prepared as in Example 191, 5.00 g, 0.034 mol) in tetrahydrofuran (40 mL) was added to the reaction mixture. The reaction mixture was refluxed for an additional 3 h. After this time, the mixture was concentrated in vacuo and the residue was diluted with water and extracted with diethyl ether. The organic layer was then washed with 5% aqueous sodium hydroxide solution followed by a saturated aqueous sodium chloride solution, dried over sodium sulfate and concentrated in vacuo to afford (E)-3-phenoxy-but-2-enoic acid ethyl ester (6.20 g, 89%) as a yellow oil.

To a stirred mixture of (E)-3-phenoxy-but-2-enoic acid ethyl ester (5.00 g, 0.024 mol) in carbon tetrachloride (20 mL) under a nitrogen atmosphere was added N-bromosuccinimide (6.50 g, 0.037 mol) and benzoyl peroxide (580 mg, 0.002 mol). Nitrogen gas was bubbled through the mixture for 5 min, and the resulting mixture was heated to reflux for 4 h. The reaction mixture was then placed in the refrigerator overnight. The solids formed were removed by filtration and the filtrate concentrated in vacuo. The crude product obtained was purified using flash column chromatography (silica gel (100-200 mesh), ethyl acetate/hexanes) to afford (E)-4-bromo-3-phenoxy-but-2-enoic acid ethyl ester (5.10 g, 74%) as a yellow oil.

To a stirred solution of (S)-2-amino-3-cyclohexyl-propionic acid methyl ester (962 mg, 0.005 mol) in N,N-dimethylformamide (10 mL) was added N,N-diisopropylethylamine (3.3 g, 0.026 mol) slowly at room temperature, under nitrogen. The resulting mixture was stirred for 5 min and then treated with (E)-4-bromo-3-phenoxy-but-2-enoic acid ethyl ester (1.5 g, 0.005 mol) and the reaction mixture was heated at 110° C.-120° C. for 16 h. After this time, ice water was added and the resulting mixture was extracted with ethyl acetate. The combined organic layers were washed with a saturated aqueous sodium chloride solution, dried over sodium sulfate and concentrated in vacuo. Purification by flash column chromatography (silica gel (100-200 mesh)) afforded (S)-3-cyclohexyl-2-(2-oxo-4-phenoxy-2,5-dihydro-pyrrol-1-yl)-propionic acid methyl ester (650 mg, 36%) as yellow oil.

To a stirred solution of (S)-3-cyclohexyl-2-(2-oxo-4-phenoxy-2,5-dihydro-pyrrol-1-yl)-propionic acid methyl ester (0.205 g, 0.006 mol) in tetrahydrofuran-water (3:1, 5 mL) was added lithium hydroxide (504 mg, 0.012 mol). The reaction mixture was stirred at 23° C. for 2 h. After this time, the mixture was concentrated and the reaction mixture was diluted with water. The reaction mixture was acidified with 2N hydrochloric acid, during which time precipitation occurred. The precipitate was removed by filtration, washed with cold water and dried in vacuo to obtain (S)-3-cyclohexyl-2-(2-oxo-4-phenoxy-2,5-dihydro-pyrrol-1-yl)-propionic acid (170 mg, 86%).

To a stirred solution of (S)-3-cyclohexyl-2-(2-oxo-4-phenoxy-2,5-dihydro-pyrrol-1-yl)-propionic acid (80 mg, 0.2 mmol) in dichloromethane (8 mL) was gradually added 1-(3-dimethylaminopropyl)-3-ethylcarbodiimide hydrochloride (137 mg, 0.7 mmol) and N,N-diisopropylethylamine (155 mg, 1.2 mmol) at room temperature, under nitrogen. After 15 min, 1-hydroxybenzotriazole (110 mg, 0.7 mmol) and 1-(3-amino-pyrazol-1-yl)-2-methyl-propan-2-ol (prepared in U.S. Pat. Appl. US2008021032 Example 80, 37 mg, 0.2 mmol) were added to the reaction mixture. The reaction mixture was then stirred at 23° C. for 48 h. The reaction mixture was diluted with ethyl acetate and washed with a saturated aqueous ammonium chloride solution followed by a saturated aqueous sodium bicarbonate solution. The organic layer was then washed with a saturated aqueous sodium chloride solution, separated, dried over sodium sulfate and concentrated in vacuo to afford the crude product, which was purified by flash column chromatography (silica gel (100-200 mesh)) which afforded (S)-3-cyclohexyl-N-[1-(2-hydroxy-2-methyl-propyl)-1H-pyrazol-3-yl]-2-(2-oxo-4-phenoxy-2,5-dihydro-pyrrol-1-yl)-propionamide (21 mg, 19%) as an off-white gummy solid: $^1$H NMR (400 MHz, CDCl$_3$) δ ppm 0.83-1.08 (m, 2H), 1.13 (s, 6H), 1.24 (s, 3H), 1.58-2.06 (m, 8H), 3.77 (br. s., 1H), 3.91 (s, 2H), 4.08 (d, J=18.1 Hz, 1H), 4.32 (d, J=18.1 Hz, 1H), 4.87-4.96 (m, 1H), 4.96 (s, 1H), 6.67 (s, 1H), 7.15 (d, J=7.8 Hz, 2H), 7.20-7.31 (m, 1H), 7.39 (t, J=7.8 Hz, 2H), 9.01 (s, 1H).

Example 214

2-[4-(2-Chloro-phenoxy)-2-oxo-2,5-dihydro-pyrrol-1-yl]-N-[1-(2-hydroxy-2-methyl-propyl)-1H-pyrazol-3-yl]-3-(trans-3-methyl-cyclobutyl)-propionamide

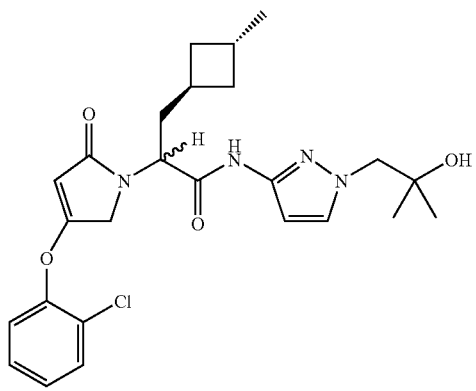

A solution of 3-methyl cyclobutane carboxylic acid (1.67 g, 14.63 mmol) in tetrahydrofuran (20 mL) was cooled to 0° C. in an ice bath and treated with a 2.0M solution of lithium aluminum hydride in tetrahydrofuran (14.63 mL, 29.26 mmol). After the addition was complete the mixture was heated at reflux for 4 h. The mixture was then cooled to 0° C. and slowly quenched with methanol. The mixture was then diluted with 6N aqueous hydrochloric acid (60 mL) and extracted with ethyl acetate (2×75 mL). The organics were combined, dried over sodium sodium sulfate and concentrated in vacuo with silica gel (4 g). Purification by Biotage flash chromatography (40S column, 33% ethyl acetate/hexanes) afforded (3-methyl-cyclobutyl)-methanol (950 mg, 65%) as a colorless oil.

A round bottom flask charged with methylene chloride (50 mL) and a 2M solution of oxalyl chloride in methylene chloride (9.5 mL, 18.97 mmol) was cooled to −70° C. and then treated dropwise with dimethyl sulfoxide (2.0 mL, 28.13 mmol). The reaction was then stirred for 30 min. After this time, a solution of (3-methyl-cyclobutyl)-methanol (0.95 g, 9.48 mmol) in methylene chloride (10 mL) was added dropwise and the mixture stirred at −70° C. for 15 min. After this time, triethylamine (5.25 mL, 37.6 mmol) was added and stirred at −70° C. for 15 min and then slowly warmed to 0° C. and quenched with a 1.0M aqueous solution of potassium bisulfate (100 mL) and extracted with methylene chloride (2×100 mL). The organic extracts were then combined, dried over sodium sulfate and concentrated to afford 3-methyl-cyclobutanecarbaldehyde (600 mg, 64%) as a yellow semi-solid.

In a round bottom flask under argon was placed N-(benzyloxycarbonyl)-α-phosphonoglycine methyl ester (3.04 g, 9.16 mmol) in dichloromethane (10 mL) and cooled to 0° C. This mixture was treated dropwise with 1,8-diazabicyclo [5.4.0]undec-7-ene (1.20 mL, 7.94 mmol) and stirred at 0° C. for 20 min. A solution of 3-methyl-cyclobutanecarbaldehyde (600 mg, 6.11 mmol) in dichloromethane (5 mL) was then added. After the addition was complete the reaction was warmed to 25° C. and stirred overnight. The mixture was then concentrated in vacuo and dissolved in ethyl acetate (100 mL). The ethyl acetate layer was washed with a saturated aqueous ammonium chloride solution (2×50 mL), a saturated aqueous solution of sodium chloride (50 mL), dried over sodium sulfate and concentrated in vacuo with silica gel (3 g). Purification by Biotage flash chromatography (40M column, 20% ethyl acetate/hexanes) afforded (Z)-2-benzyloxycarbonylamino-3-(3-methyl-cyclobutyl)-acrylic acid methyl ester (693 mg, 38%) as a yellow viscous oil.

The mixture of isomers (cis/trans methyl cyclobutane) was separated into the single compounds by supercritical fluid chromatography (SFC) on a Berger MultiGram II Supercritical Fluid Chromatography (SFC) system (Mettler-Toledo AutoChem Berger Instruments, Newark, Del.) (Chiral column: Daicel AD, 250 mm×30 mm i.d., 5 μm-particle size, temperature: 35° C., flow rate of 70 mL/min, and 100 bar back pressure, 10% methanol as mobile phase modifier and UV Detection: 220 nm) to afford the two pure compounds. The first peak to elute was the cis isomer, (Z)-2-benzyloxycarbonylamino-3-(cis-3-methyl-cyclobutyl)-acrylic acid methyl ester (276 mg) which was isolated as a colorless oil: HR-ES-MS m/z calculated for C$_{17}$H$_{21}$NO$_4$ [M+Na]$^+$ 326.1363, observed 326.1362; $^1$H NMR (400 MHz, CDCl$_3$) δ ppm 1.02 (d, J=6.2 Hz, 3H), 1.42-1.61 (m, 2H), 2.20-2.39 (m, 3H), 2.96-3.12 (m, 1H), 3.75 (s, 3H), 5.14 (s, 2H), 6.07 (br. s., 1H), 6.63 (d, J=8.3 Hz, 1H), 7.30-7.41 (m, 5H). The second peak to elute was the trans isomer, (Z)-2-benzyloxycarbonylamino-3-(trans-3-methyl-cyclobutyl)-acrylic acid methyl ester (304 mg) as a colorless oil: HR-ES-MS m/z calculated for C$_{17}$H$_{21}$NO$_4$ [M+Na]$^+$ 326.1363, observed 326.1362; $^1$H NMR (400 MHz, CDCl$_3$) δ ppm 1.11 (d, J=7.0 Hz, 3H), 1.80-1.95 (m, 2H), 2.00-2.13 (m, 2H), 2.36-2.51 (m, 1H), 3.19-3.33 (m, 1H), 3.76 (s, 3H), 5.14 (s, 2H), 6.05 (br. s., 1H), 6.84 (d, J=9.2 Hz, 1H), 7.30-7.41 (m, 5H).

In a Parr shaker bottle was placed (Z)-2-benzyloxycarbonylamino-3-(trans-3-methyl-cyclobutyl)-acrylic acid methyl ester (300 mg, 0.99 mmol), methanol (10 mL) and 10% palladium on activated carbon (60 mg). The mixture was placed on the Parr hydrogenator and charged with 40 psi hydrogen pressure and shaken for 1.5 h. After such time, the catalyst was filtered off through a plug of celite and the filterate concentrated in vacuo to afford 2-amino-3-(trans-3-methyl-cyclobutyl)-propionic acid methyl ester (148 mg, 87%) as a pale yellow oil.

In a small pressure bottle was placed a mixture of 2-amino-3-(trans-3-methyl-cyclobutyl)-propionic acid methyl ester (147 mg, 0.86 mmol), acetonitrile (6 mL) and N,N-diisopropylethylamine (220 μL, 1.03 mmol) which was heated to 80°

C. To this mixture was added (E)-4-bromo-3-(2-chloro-phenoxy)-but-2-enoic acid ethyl ester (prepared as in Example 61, 276 mg, 0.86 mmol) and the tube sealed and heated at 100° C. overnight. The mixture was cooled to room temperature and concentrated in vacuo with silica gel (2 g). Purification by Biotage flash chromatography (40S column, 16% ethyl acetate/hexanes to 40% ethyl acetate/hexanes) afforded 2-[4-(2-chloro-phenoxy)-2-oxo-2,5-dihydro-pyrrol-1-yl]-3-(trans-3-methyl-cyclobutyl)-propionic acid methyl ester (108 mg, 35%) as an amber oil: HR-ES-MS m/z calculated for $C_{19}H_{22}NO_4Cl$ [M+H]$^+$ 364.1310, observed 364.1310.

In a flask was placed 2-[4-(2-chloro-phenoxy)-2-oxo-2,5-dihydro-pyrrol-1-yl]-3-(trans-3-methyl-cyclobutyl)-propionic acid methyl ester (107 mg, 0.29 mmol) dissolved in a 1:1 solution of tetrahydrofuran:water (8 mL). To this mixture was added lithium hydroxide monohydrate (25 mg, 0.58 mmol) and the resulting mixture stirred for 1.5 h at 25° C. After such time, the mixture was concentrated in vacuo to remove the tetrahydrofuran and partioned between 1N aqueous hydrochloric acid (10 mL) and ethyl acetate (10 mL). The organic layer was separated and dried over sodium sulfate and concentrated in vacuo to afford 2-[4-(2-chloro-phenoxy)-2-oxo-2,5-dihydro-pyrrol-1-yl]-3-(trans-3-methyl-cyclobutyl)-propionic acid (102 mg, 100%) as a light amber semi-solid: HR-ES-MS m/z calculated for $C_{18}H_{20}NO_4Cl$ [M+H]$^+$ 350.1154, observed 350.1154.

In a round bottom flask under argon was placed 2-[4-(2-chloro-phenoxy)-2-oxo-2,5-dihydro-pyrrol-1-yl]-3-(trans-3-methyl-cyclobutyl)-propionic acid (100 mg, 0.29 mmol), dichloromethane (5 mL) and N,N-dimethylformamide (3 drops) at 25° C. To this mixture was added a 2.0M solution of oxalyl chloride in dichloromethane (180 µL, 0.36 mmol) dropwise, which resulted in gas evolution. The mixture was stirred for 15 min at 25° C. and then concentrated in vacuo. This residue was taken up in dichloromethane (5 mL) and added dropwise into another flask containing a solution of 1-(3-amino-pyrazol-1-yl)-2-methyl-propan-2-ol (prepared as in US20080021032, Example 80, 55 mg, 0.35 mmol), dichloromethane (5 mL) and 2,6-lutidine (180 µL, 0.58 mmol) at 25° C. and stirred for 1.5 h at 25° C. and then quenched with methanol. The mixture was diluted with dichloromethane and washed with a 1N aqueous hydrochloric acid solution. The organic layer was separated, dried over sodium sulfate and concentrated in vacuo with silica gel (2 g). Purification by Biotage flash chromatography (40S column, 25% ethyl acetate/hexanes) afforded 2-[4-(2-chloro-phenoxy)-2-oxo-2,5-dihydro-pyrrol-1-yl]-N-[1-(2-hydroxy-2-methyl-propyl)-1H-pyrazol-3-yl]-3-(trans-3-methyl-cyclobutyl)-propionamide (51 mg, 36%) as a light amber foam: HR-ES-MS m/z calculated for $C_{25}H_{31}N_4O_4Cl$ [M+H]$^+$ 487.2107, observed 487.2107; $^1$H NMR (500 MHz, DMSO-d$_6$) δ ppm 1.06 (d, J=6.8 Hz, 9H), 1.48-1.57 (m, 1H), 1.65-1.73 (m, 1H), 1.75-1.83 (m, 1H), 1.88-2.01 (m, 3H), 2.14-2.26 (m, 1H), 2.28-2.37 (m, 1H), 3.90 (s, 2H), 4.20 (d, J=18.6 Hz, 1H), 4.58 (d, J=18.6 Hz, 1H), 4.66 (s, 1H), 4.73 (dd, J=9.3, 6.3 Hz, 1H), 4.78 (s, 1H), 6.44 (d, J=2.4 Hz, 1H), 7.37 (td, J=7.8, 1.5 Hz, 1H), 7.47 (td, J=7.8, 1.5 Hz, 1H), 7.51 (dd, J=7.8, 1.5 Hz, 1H), 7.53 (d, J=2.4 Hz, 1H), 7.65 (dd, J=7.8, 1.5 Hz, 1H), 10.75 (s, 1H).

Example 215

(S)-2-[4-(2-Chloro-phenoxy)-2-oxo-2,5-dihydro-pyrrol-1-yl]-N-[1-(2-hydroxy-2-methyl-propyl)-1H-pyrazol-3-yl]-3-(trans-3-methyl-cyclobutyl)-propionamide

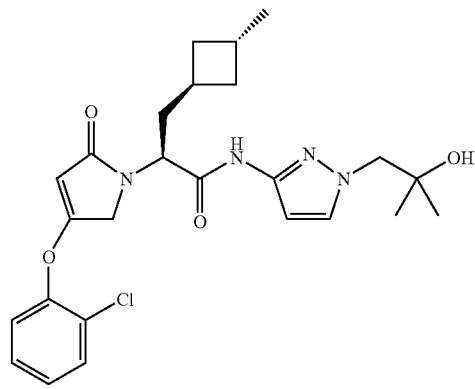

The mixture of stereoisomers of 2-[4-(2-chloro-phenoxy)-2-oxo-2,5-dihydro-pyrrol-1-yl]-N-[1-(2-hydroxy-2-methyl-propyl)-1H-pyrazol-3-yl]-3-(trans-3-methyl-cyclobutyl)-propionamide (prepared as in Example 214, 37 mg) was separated into the single enantiomers by supercritical fluid chromatography (SFC) on a Berger MultiGram II Supercritical Fluid Chromatography (SFC) system (Mettler-Toledo AutoChem Berger Instruments, Newark, Del.) (Chiral column: Kromasil OD Cellucoat, 250 mm×30 mm i.d., 5 µm-particle size, temperature: 35° C., flow rate of 70 mL/min, and 100 bar back pressure, 20% isopropanol as mobile phase modifier and UV Detection: 220 nm) to afford the two pure compounds. The first peak to elute was (S)-2-[4-(2-chloro-phenoxy)-2-oxo-2,5-dihydro-pyrrol-1-yl]-N-[1-(2-hydroxy-2-methyl-propyl)-1H-pyrazol-3-yl]-3-(trans-3-methyl-cyclobutyl)-propionamide (13 mg) as a white foam: $[α]^{30}_{589}$=−17.0° (c=0.1, dichloromethane); HR-ES-MS m/z calculated for $C_{25}H_{31}N_4O_4Cl$ [M+H]$^+$ 487.2107, observed 487.2108; $^1$H NMR (300 MHz, CDCl$_3$) δ ppm 1.10 (d, J=6.9 Hz, 3H), 1.16 (s, 6H), 1.65-2.04 (m, 5H), 2.14-2.51 (m, 3H), 2.92 (br. s., 1H), 3.96 (s, 2H), 4.15 (d, J=18.0 Hz, 1H), 4.34 (d, J=18.0 Hz, 1H), 4.69 (t, J=7.1 Hz, 1H), 4.88 (s, 1H), 6.70 (br. s., 1H), 7.21-7.27 (m, 2H), 7.29-7.38 (m, 2H), 7.49 (d, J=7.8 Hz, 1H), 8.85 (br. s., 1H).

Example 216

(R)-2-[4-(2-Chloro-phenoxy)-2-oxo-2,5-dihydro-pyrrol-1-yl]-N-[1-(2-hydroxy-2-methyl-propyl)-1H-pyrazol-3-yl]-3-(trans-3-methyl-cyclobutyl)-propionamide

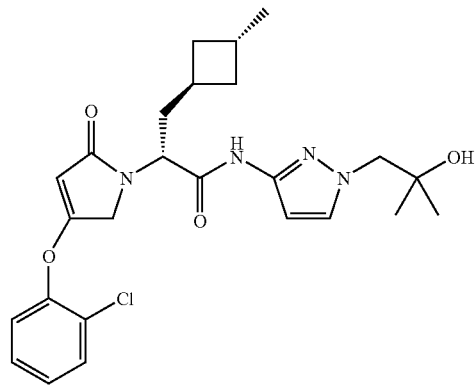

The mixture of stereoisomers of 2-[4-(2-chloro-phenoxy)-2-oxo-2,5-dihydro-pyrrol-1-yl]-N-[1-(2-hydroxy-2-methyl-propyl)-1H-pyrazol-3-yl]-3-(trans-3-methyl-cyclobutyl)-propionamide (prepared as in Example 214, 37 mg) was separated into the single enantiomers by supercritical fluid chromatography (SFC) on a Berger MultiGram II Supercritical Fluid Chromatography (SFC) system (Mettler-Toledo AutoChem Berger Instruments, Newark, Del.) (Chiral column: Kromasil OD Cellucoat, 250 mm×30 mm i.d., 5 µm-particle size, temperature: 35° C., flow rate of 70 mL/min, and 100 bar back pressure, 20% isopropanol as mobile phase modifier and UV Detection: 220 nm) to afford the two pure compounds. The second peak to elute was (R)-2-[4-(2-chloro-phenoxy)-2-oxo-2,5-dihydro-pyrrol-1-yl]-N-[1-(2-hydroxy-2-methyl-propyl)-1H-pyrazol-3-yl]-3-(trans-3-methyl-cyclobutyl)-propionamide (14 mg) as a white foam: $[\alpha]^{30}_{589}$=+12.9° (c=0.07, dichloromethane); HR-ES-MS m/z calculated for $C_{25}H_{31}N_4O_4Cl$ [M+H]$^+$ 487.2107, observed 487.2107; $^1$H NMR (300 MHz, CDCl$_3$) δ ppm 1.10 (d, J=6.6 Hz, 3H), 1.15 (s, 6H), 1.65-2.04 (m, 5H), 2.12-2.48 (m, 3H), 3.94 (s, 2H), 4.15 (d, J=18.0 Hz, 1H), 4.33 (d, J=18.0 Hz, 1H), 4.69 (t, J=7.2 Hz, 1H), 4.88 (s, 1H), 6.69 (br. s., 1H), 7.17-7.40 (m, 4H), 7.18-7.26 (m, 1H), 7.28-7.37 (m, 2H), 7.49 (d, J=7.8 Hz, 1H), 8.75 (br. s., 1H).

Example 217

2-[4-(2-Chloro-phenoxy)-2-oxo-2,5-dihydro-pyrrol-1-yl]-N-[1-(2-hydroxy-2-methyl-propyl)-1H-pyrazol-3-yl]-3-(cis-3-methyl-cyclobutyl)-propionamide

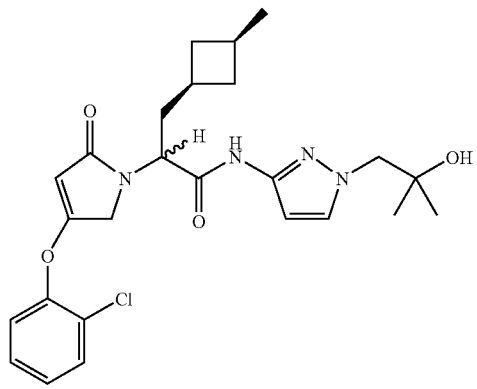

A mixture of (Z)-2-benzyloxycarbonylamino-3-(cis-3-methyl-cyclobutyl)-acrylic acid methyl ester (prepared in Example 214, 275 mg, 0.91 mmol), methanol (10 mL) and 10% palladium on activated carbon (50 mg) was placed in a Parr shaker bottle. It was then placed on the Parr hydrogenator apparatus and charged with hydrogen to 40 psi and shaken for 1 h. After such time, the catalyst was filtered through a plug of celite and the filterate was concentrated in vacuo to afford 2-amino-3-(trans-3-methyl-cyclobutyl)-propionic acid methyl ester (134 mg, 86%) as a pale yellow oil.

In a small pressure bottle was placed a mixture 2-amino-3-(cis-3-methyl-cyclobutyl)-propionic acid methyl ester (133 mg, 0.78 mmol), acetonitrile (10 mL) and N,N-diisopropyl-ethylamine (200 µL, 0.94 mmol) and the resulting mixture heated to 80° C. To this mixture was added (E)-4-bromo-3-(2-chloro-phenoxy)-but-2-enoic acid ethyl ester (prepared as in Example 61, 250 mg, 0.78 mmol) in dichloromethane (5 mL) and the tube sealed and heated at 100° C. overnight. The mixture was then cooled and concentrated in vacuo with silica gel (2 g). Purification by Biotage flash chromatography (40S column, 20% ethyl acetate/hexanes to 40% ethyl acetate/hexanes) afforded 2-[4-(2-chloro-phenoxy)-2-oxo-2,5-dihydro-pyrrol-1-yl]-3-(cis-3-methyl-cyclobutyl)-propionic acid methyl ester (103 mg, 36%) as an amber gum: HR-ES-MS m/z calculated for $C_{19}H_{22}NO_4Cl$ [M+Na]$^+$ 386.1129, observed 386.1130.

In a flask was placed 2-[4-(2-chloro-phenoxy)-2-oxo-2,5-dihydro-pyrrol-1-yl]-3-(cis-methyl-cyclobutyl)-propionic acid methyl ester (102 mg, 0.28 mmol) dissolved in a 1:1 solution of tetrahydrofuran:water (8 mL). To this mixture was added lithium hydroxide monohydrate (25 mg, 0.56 mmol) and the resulting mixture stirred for 1.5 h at 25° C. After such time, the mixture was concentrated in vacuo to remove the tetrahydrofuran and partioned between 1N aqueous hydrochloric acid (10 mL) and ethyl acetate (10 mL). The organic layer was separated, dried over sodium sulfate and concentrated in vacuo to afford 2-[4-(2-chloro-phenoxy)-2-oxo-2,5-dihydro-pyrrol-1-yl]-3-(cis-3-methyl-cyclobutyl)-propionic acid (92 mg, 94%) as a light amber foam: HR-ES-MS m/z calculated for $C_{18}H_{20}NO_4Cl$ [M+H]$^+$ 350.1154, observed 350.1154.

In a round bottom flask under argon was placed 2-[4-(2-chloro-phenoxy)-2-oxo-2,5-dihydro-pyrrol-1-yl]-3-(cis-3-methyl-cyclobutyl)-propionic acid (92 mg, 0.26 mmol), dichloromethane (6 mL) and N,N-dimethylformamide (3 drops) at 25° C. To this mixture was added a 2.0M solution of oxalyl chloride in dichloromethane (300 µL, 0.60 mmol) dropwise, which resulted in gas evolution. The mixture was stirred for 15 min at 25° C. and then concentrated in vacuo. The residue was taken up in dichloromethane (5 mL) and added dropwise into another flask containing a solution of 1-(3-amino-pyrazol-1-yl)-2-methyl-propan-2-ol (prepared as in US20080021032, Example 80, 50 mg, 0.31 mmol), dichloromethane (5 mL) and 2,6-lutidine (150 µL, 0.52 mmol) at 25° C. and stirred for 1 h at 25° C. The mixture was quenched with methanol and then diluted with dichloromethane. The organic layer was then washed with a 1N aqueous hydrochloric acid solution, dried over sodium sulfate and concentrated in vacuo with silica gel (2 g). Purification by Biotage flash chromatography (40S column, 33% ethyl acetate/hexanes) and then reverse phase HPLC afforded 2-[4-(2-chloro-phenoxy)-2-oxo-2,5-dihydro-pyrrol-1-yl]-N-[1-(2-hydroxy-2-methyl-propyl)-1H-pyrazol-3-yl]-3-(cis-3-methyl-cyclobutyl)-propionamide, as a mixture of enantiomers (17 mg, 13%): HR-ES-MS m/z calculated for $C_{25}H_{31}N_4O_4Cl$ [M+H]$^+$ 487.2107, observed 487.2105; $^1$H NMR (400 MHz, DMSO-d$_6$) δ ppm 0.98 (d, J=6.2 Hz, 3H), 1.05 (s, 3H), 1.06 (s, 3H), 1.16-1.29 (m, 2H), 1.29-1.40 (m, 1H), 1.74-2.25 (m, 6H), 3.90 (s, 2H), 4.21 (d, J=18.3 Hz, 1H), 4.57 (d, J=18.3 Hz, 1H), 4.71 (dd, J=9.6, 5.8 Hz, 1H), 4.78 (s, 1H), 6.44 (d, J=2.2 Hz, 1H), 7.37 (td, J=7.9, 1.7 Hz, 1H), 7.47 (td, J=7.9, 1.4 Hz, 1H), 7.50-7.53 (m, 1H), 7.53 (d, J=2.2 Hz, 1H), 7.66 (dd, J=7.9, 1.4 Hz, 1H), 10.75 (s, 1H).

Example 218

(S)-2-[4-(2-Chloro-phenoxy)-2-oxo-2,5-dihydro-pyrrol-1-yl]-4,4-difluoro-pentanoic acid [1-((R)-2,3-dihydroxy-propyl)-1H-pyrazol-3-yl]-amide

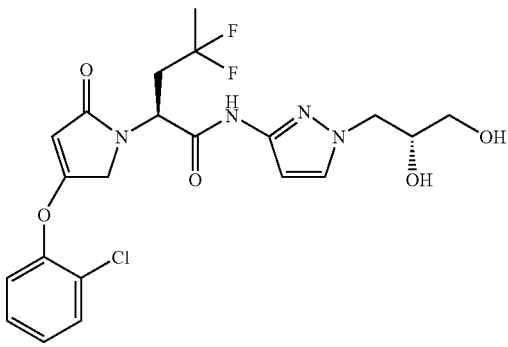

In a flask under argon was placed (S)-2-benzyloxycarbonylamino-succinic acid 1-methyl ester (3.0 g, 10.67 mmol) and tetrahydrofuran (50 mL). To this mixture was added carbonyldiimidazole (1.90 g, 11.74 mmol) and the resulting mixture was stirred at 25° C. for 6 h. In a separate round bottom flask was placed malonic acid mono t-butyl ester (1.98 g, 11.74 mmol), tetrahydrofuran (30 mL) and magnesium ethoxide (685 mg, 5.87 mmol) and the resulting mixture stirred at 25° C. for 1 h and then concentrated in vacuo. The residue was taken up in tetrahydrofuran (15 mL) and added to the flask containing the succinic acid and carbonyldiimidazole mixture and stirred at 25° C. for 16 h. The mixture was concentrated in vacuo and partitioned between diethyl ether (200 mL) and a 0.5N aqueous hydrochloric acid solution (200 mL). The organic layer was washed with a saturated aqueous sodium bicarbonate solution (150 mL), dried over sodium sulfate and concentrated. Purification by flash column chromatography (silica gel 60, 230-400 mesh; 40% ethyl acetate/hexanes) afforded (S)-2-benzyloxycarbonylamino-4-oxo-hexanedioic acid 6-t-butyl ester 1-methyl ester (3.04 g, 75%) as a pale yellow oil.

In a flask under argon was placed (S)-2-benzyloxycarbonylamino-4-oxo-hexanedioic acid 6-t-butyl ester 1-methyl ester (3.04 g, 8.01 mmol), toluene (80 mL) and para-toluene sulfonic acid hydrate (115 mg, 0.61 mmol) and refluxed for 6.5 h and then overnight for 16 h at room temperature. The mixture was concentrated in vacuo and purified by flash column chromatography (silica gel 60, 230-400 mesh; 50% ethyl acetate/hexanes) which afforded (S)-2-benzyloxycarbonylamino-4-oxo-pentanoic acid methyl ester (1.79 g, 80%) as a pale yellow viscous oil.

In a flask under argon was placed (S)-2-benzyloxycarbonylamino-4-oxo-pentanoic acid methyl ester (1.0 g, 3.58 mmol), dichloromethane (20 mL) and (diethylamino)sulfur trifluoride (3.80 mL, 28.64 mmol) which was heated at 55° C. overnight. The mixture was cooled and slowly poured into a saturated aqueous sodium bicarbonate solution (50 mL) and ice. The mixture was extracted with dichloromethane, the combined organic layers then washed with a saturated aqueous sodium bicarbonate solution, a saturated aqueous solution of sodium chloride, dried over sodium sulfate and concentrated in vacuo with silica gel (3 g). Purification by Biotage flash chromatography (Aspire 40 g column, 20% ethyl acetate/hexanes to 33% ethyl acetate/hexanes) afforded (S)-2-benzyloxycarbonylamino-4,4-difluoro-pentanoic acid methyl ester (578 mg, 53%) as a yellow oil.

In a flask under argon was placed (S)-2-benzyloxycarbonylamino-4,4-difluoro-pentanoic acid methyl ester (626 mg, 2.08 mmol), methanol (8 mL) and 10% palladium on activated carbon (100 mg). Triethylsilane (3 mL) was added slowly and the mixture stirred at 25° C. for 30 min. Another portion of 10% palladium on activated carbon (100 mg) and triethylsilane (3 mL) was added and the mixture was stirred for 30 min. A third portion of 10% palladium on activated carbon (100 mg) and triethylsilane (3 mL) was added and the mixture was stirred for 30 min. The mixture was filtered to remove the catalyst and the solids washed with methanol. The filtrate was concentrated in vacuo, azeotroped with toluene, dissolved in dichloromethane and concentrated in vacuo with silica gel (2 g). Purification by Biotage flash chromatography (Aspire 40 g column, 100% ethyl acetate) afforded (S)-2-amino-4,4-difluoro-pentanoic acid methyl ester (151 mg) as a clear colorless liquid.

A mixture of (S)-2-amino-4,4-difluoro-pentanoic acid methyl ester (145 mg, 0.87 mmol), acetonitrile (6 mL) and N,N-diisopropylethylamine (220 µL, 1.3 mmol) was heated to 80° C. A solution of (E)-4-bromo-3-(2-chloro-phenoxy)-but-2-enoic acid ethyl ester (prepared as in Example 61, 306 mg, 0.96 mmol) in acetonitrile (2 mL) was added and heated at 100° C. for 6 h. The mixture was concentrated with silica gel (2 g) and purified by Biotage flash chromatography (Aspire 40 g column, 16% ethyl acetate/hexanes) which afforded (S)-2-[2-(2-chloro-phenoxy)-3-propoxycarbonyl-allylamino]-4,4-difluoro-pentanoic acid methyl ester (261 mg) as a yellow oil.

A solution of (S)-2-[2-(2-chloro-phenoxy)-3-propoxycarbonyl-allylamino]-4,4-difluoro-pentanoic acid methyl ester (255 mg, 0.63 mmol) in acetonitrile (2 mL) was placed in a sealed microwave reaction tube and heated in a microwave reactor at 140° C. for 3.5 h. The mixture was diluted with dichloromethane and concentrated in vacuo with silica gel (2 g). Purification by Biotage flash chromatography (Aspire 40 g column, 16% ethyl acetate/hexanes to 50% ethyl acetate/hexanes) afforded (S)-2-[4-(2-chloro-phenoxy)-2-oxo-2,5-dihydro-pyrrol-1-yl]-4,4-difluoro-pentanoic acid methyl ester (100 mg, 32% over two steps) as a colorless gum: HR-ES-MS m/z calculated for $C_{16}H_{16}NO_4ClF_2$ [M+Na]$^+$ 382.0628, observed 382.0629.

In a flask was placed (S)-2-[4-(2-chloro-phenoxy)-2-oxo-2,5-dihydro-pyrrol-1-yl]-4,4-difluoro-pentanoic acid methyl ester (139 mg, 0.39 mmol) in a 1:1 solution of tetrahydrofuran:water (8 mL) which was treated with lithium hydroxide monohydrate (35 mg, 0.78 mmol) and stirred for 1.5 h at 25° C. After such time, the mixture was concentrated in vacuo to remove the tetrahydrofuran and partioned between 1N aqueous hydrochloric acid (10 mL) and ethyl acetate (10 mL). The organic layer was separated, dried over sodium sulfate and concentrated in vacuo to afford (S)-2-[4-(2-chloro-phenoxy)-2-oxo-2,5-dihydro-pyrrol-1-yl]-4,4-difluoro-pentanoic acid (130 mg, 96%) as a light amber foam: HR-ES-MS m/z calculated for $C_{15}H_{14}NO_4ClF_2$ [M+H]$^+$ 346.0652, observed 346.0652.

A solution of (S)-2-[4-(2-chloro-phenoxy)-2-oxo-2,5-dihydro-pyrrol-1-yl]-4,4-difluoro-pentanoic acid (117 mg, 0.34 mmol) and 1-((R)-2,2-dimethyl-[1,3]dioxolan-4-yl-methyl)-1H-pyrazol-3-ylamine (prepared as in Example 49, 82 mg, 0.42 mmol) in N,N-dimethylformamide (3 mL) was treated with N,N-diisopropylethylamine (170 µL, 1.02 mmol) and (benzotriazol-1-yloxy)tris(dimethylamino)phosphonium hexafluorophosphate (225 mg, 0.51 mmol) and stirred overnight at 25° C. After this time, the mixture was diluted with ethyl acetate (25 mL) and washed with a saturated aqueous solution of ammonium chloride (25 mL), saturated aqueous solution of sodium bicarbonate (25 mL) and a saturated aqueous solution of sodium chloride (25 mL) dried over sodium sulfate and concentrated with silica gel (2 g). Purification by Biotage flash chromatography (Aspire 40 g column, 20% ethyl acetate/hexanes) afforded (S)-2-[4-(2-chloro-phenoxy)-2-oxo-2,5-dihydro-pyrrol-1-yl]-4,4-difluoro-pentanoic acid [1-((R)-2,2-dimethyl-[1,3]dioxolan-4-yl-methyl)-1H-pyrazol-3-yl]-amide (72 mg, 40%) as a white foam: HR-ES-MS m/z calculated for $C_{24}H_{27}N_4O_5ClF_2$ [M+Na]$^+$ 547.1530, observed 547.1531.

In a round bottom flask was placed (S)-2-[4-(2-chloro-phenoxy)-2-oxo-2,5-dihydro-pyrrol-1-yl]-4,4-difluoro-pentanoic acid [1-((R)-2,2-dimethyl-[1,3]dioxolan-4-yl-methyl)-1H-pyrazol-3-yl]-amide (70 mg, 0.13 mmol), methanol (3 mL) and p-toluenesulfonic acid (5 mg, 0.15 mmol). The mixture was stirred at 25° C. for 24 h and then concentrated in vacuo and dissolved in ethyl acetate and concentrated in vacuo with silica gel (1 g). Purification by Biotage flash chromatography (AnaLogix SF15-12 g column, 100% ethyl acetate to 10% methanol/ethyl acetate) afforded (S)-2-[4-(2-chloro-phenoxy)-2-oxo-2,5-dihydro-pyrrol-1-yl]-4,4-difluoro-pentanoic acid [1-((R)-2,3-dihydroxy-propyl)-1H-pyrazol-3-yl]-amide (52 mg, 82%) as a white foam: HR-ES-MS m/z calculated for $C_{21}H_{23}N_4O_5ClF_2$ [M+H]$^+$ 485.1398, observed 485.1396; $^1$H NMR (300 MHz, DMSO-d$_6$) δ ppm 1.66 (t, J=19.3 Hz, 3H), 3.21-3.33 (m, 2H), 3.69-3.81 (m, 1H), 3.87 (dd, J=13.6, 7.5 Hz, 1H), 4.01-4.17 (m, 1H), 4.30 (d, J=18.4 Hz, 1H), 4.47 (d, J=18.4 Hz, 1H), 4.72 (t, J=5.6 Hz, 1H), 4.81 (s, 1H), 4.95 (d, J=5.1 Hz, 1H), 5.12 (dd, J=9.1, 5.1 Hz, 1H), 6.42 (d, J=2.1 Hz, 1H), 7.32-7.41 (m, 1H), 7.42-7.53 (m, 2H), 7.55 (dd, J=2.1 Hz, 1H), 7.66 (d, J=7.8 Hz, 1H), 10.85 (s, 1H).

Example 219

2-[4-(2-Chloro-phenoxy)-2-oxo-2,5-dihydro-pyrrol-1-yl]-5,5,5-trifluoro-4-trifluoromethyl-pentanoic acid [1-((R)-2,3-dihydroxy-propyl)-1H-pyrazol-3-yl]-amide

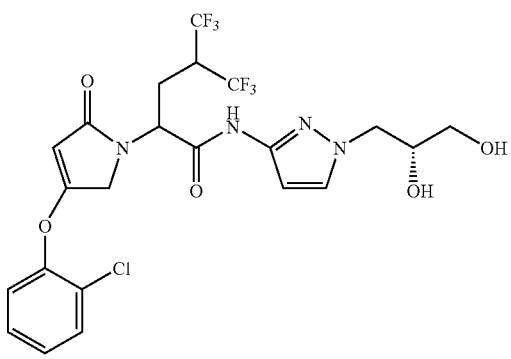

Hydrogen chloride gas was bubbled through methanol (5 mL) in a pressure bottle at 0° C. for 2-3 min. This solution was then treated with 2-amino-5,5,5-trifluoro-4-trifluoromethyl-pentanoic acid (505 mg, 1.83 mmol) sealed and heated at 50° C. overnight, and then at 25° C. over the weekend. The mixture was concentrated in vacuo, azeotroped with acetonitrile and dried under high vacuum to afford 2-amino-5,5,5-trifluoro-4-trifluoromethyl-pentanoic acid methyl ester hydrochloride salt (478 mg, 90%) as a grey white solid.

In a flask was placed 2-amino-5,5,5-trifluoro-4-trifluoromethyl-pentanoic acid methyl ester hydrochloride salt (475 mg, 1.59 mmol), acetonitrile (20 mL) and N,N-diisopropyl-ethylamine (190 μL, 1.75 mmol) which was stirred at 25° C. for 30 min. The mixture was then transferred to a pressure bottle and heated to 80° C. After this time, a solution of (E)-4-bromo-3-(2-chloro-phenoxy)-but-2-enoic acid ethyl ester (prepared as in Example 61, 560 mg, 1.75 mmol) and N,N-diisopropylethylamine (190 μL, 1.75 mmol) in acetonitrile (4 mL) was added. The mixture was heated at 100° C. for 16 h and then at 120° C. for another 24 h. The mixture was concentrated with silica gel (2 g) and purified by Biotage flash chromatography (Aspire 40 g column, 11% ethyl acetate/hexanes) which afforded 2-[2-(2-chloro-phenoxy)-3-ethoxy-carbonyl-allylamino]-5,5,5-trifluoro-4-trifluoromethyl-pentanoic acid methyl ester (144 mg) as a an amber oil.

A solution of 2-[2-(2-chloro-phenoxy)-3-ethoxycarbonyl-allylamino]-5,5,5-trifluoro-4-trifluoromethyl-pentanoic acid methyl ester (144 mg, 0.29 mmol) in acetonitrile (2 mL) was placed in a sealed microwave reaction tube and heated in a microwave reactor at 180° C. for 3 h. The mixture was cooled to room temperature and concentrated in vacuo with silica gel (1.2 g). Purification by Biotage flash chromatography (AnaLogix 25 g column, 16% ethyl acetate/hexanes to 33% ethyl acetate/hexanes) afforded 2-[4-(2-chloro-phenoxy)-2-oxo-2,5-dihydro-pyrrol-1-yl]-5,5,5-trifluoro-4-trifluoromethyl-pentanoic acid methyl ester (52 mg, 7% over two steps) as an amber oil: HR-ES-MS m/z calculated for $C_{17}H_{14}NO_4ClF_6$ [M+H]$^+$ 446.0589, observed 446.0588.

A mixture of 2-[4-(2-chloro-phenoxy)-2-oxo-2,5-dihydro-pyrrol-1-yl]-5,5,5-trifluoro-4-trifluoromethyl-pentanoic acid methyl ester (48 mg, 0.11 mmol) in a 1:1 solution of tetrahydrofuran:water (2 mL) was treated with lithium hydroxide monohydrate (11 mg, 0.22 mmol) and stirred for 2 h at 25° C. After such time, the mixture was concentrated in vacuo to remove the tetrahydrofuran and then diluted with water and the pH adjusted to pH=6 with 1N aqueous hydrochloric acid and extracted with ethyl acetate. The organic layers were dried over sodium sulfate and concentrated in vacuo to afford 2-[4-(2-chloro-phenoxy)-2-oxo-2,5-dihydro-pyrrol-1-yl]-5,5,5-trifluoro-4-trifluoromethyl-pentanoic acid (35 mg, 75%) as an off-white solid: HR-ES-MS m/z calculated for $C_{16}H_{12}NO_4ClF_6$ [M+H]$^+$ 432.0432, observed 432.0433.

In a round bottom flask under argon was placed 2-[4-(2-chloro-phenoxy)-2-oxo-2,5-dihydro-pyrrol-1-yl]-5,5,5-trifluoro-4-trifluoromethyl-pentanoic acid (31 mg, 0.072 mmol) and 1-((R)-2,2-dimethyl-[1,3]dioxolan-4-yl-methyl)-1H-pyrazol-3-ylamine (prepared as in Example 49, 20 mg, 0.086 mmol) in N,N-dimethylformamide (1 mL). To this mixture was added N,N-diisopropyethylamine (35 μL, 0.22 mmol) and (benzotriazol-1-yloxy)tris(dimethylamino)phosphonium hexafluorophosphate (48 mg, 0.11 mmol) and stirred overnight at 25° C. After this time, the mixture was diluted with ethyl acetate (15 mL) and washed with a saturated aqueous solution of ammonium chloride (10 mL), saturated aqueous solution of sodium bicarbonate (10 mL) and a saturated aqueous solution of sodium chloride (10 mL), dried over sodium sulfate, and concentrated with silica gel (1.5 g). Purification by Biotage flash chromatography (AnaLogix 12 g column, 40% ethyl acetate/hexanes) afforded 2-[4-(2-chloro-phenoxy)-2-oxo-2,5-dihydro-pyrrol-1-yl]-5,5,5-trifluoro-4-trifluoromethyl-pentanoic acid [1-((R)-2,2-dimethyl-[1,3]dioxolan-4-yl-methyl)-1H-pyrazol-3-yl]-amide (34 mg, 77%) as a cream colored foam: HR-ES-MS m/z calculated for $C_{25}H_{25}N_4O_5ClF_6$ [M+H]$^+$ 611.1491, observed 611.1487.

In a round bottom flask was placed 2-[4-(2-chloro-phenoxy)-2-oxo-2,5-dihydro-pyrrol-1-yl]-5,5,5-trifluoro-4-trifluoromethyl-pentanoic acid [1-((R)-2,2-dimethyl-[1,3]dioxolan-4-yl-methyl)-1H-pyrazol-3-yl]-amide (32 mg, 0.05 mmol), methanol (2 mL) and p-toluenesulfonic acid hydrate (5 mg, 0.15 mmol) and stirred at 25° C. for 48 h. The mixture was concentrated in vacuo and then taken up in ethyl acetate/methanol and concentrated in vacuo with silica gel (1.5 g). Purification by Biotage flash chromatography (AnaLogix SF15-12 g column, 100% ethyl acetate to 10% methanol/ethyl acetate) afforded 2-[4-(2-chloro-phenoxy)-2-oxo-2,5-dihydro-pyrrol-1-yl]-5,5,5-trifluoro-4-trifluoromethyl-pentanoic acid [1-((R)-2,3-dihydroxy-propyl)-1H-pyrazol-3-yl]-amide (25 mg, 84%) as a colorless gum: HR-ES-MS m/z calculated for $C_{22}H_{21}N_4O_5ClF_6$ [M+H]$^+$ 571.1178, observed 571.1177; $^1$H NMR (400 MHz, DMSO-d$_6$) δ ppm 2.20-2.37 (m, 1H), 2.38-2.48 (m, 1H), 3.21-3.32 (m, 2H), 3.71-3.82 (m, 1H), 3.82-3.98 (m, 2H), 4.10 (dd, J=13.6, 4.0 Hz, 1H), 4.29 (d, J=17.9 Hz, 1H), 4.45 (d, J=17.9 Hz, 1H), 4.71 (t, J=5.5 Hz, 1H), 4.89 (s, 1H), 4.89-4.98 (m, 2H), 6.43 (d, J=2.1 Hz, 1H), 7.31-7.42 (m, 1H), 7.43-7.53 (m, 3H), 7.56 (d, J=2.1 Hz, 1H), 7.66 (d, J=7.7 Hz, 1H), 10.91 (s, 1H).

Example 220

2-[4-(2-Chloro-phenoxy)-2-oxo-2,5-dihydro-pyrrol-1-yl]-5,5,5-trifluoro-pentanoic acid [1-((R)-2,3-dihydroxy-propyl)-1H-pyrazol-3-yl]-amide

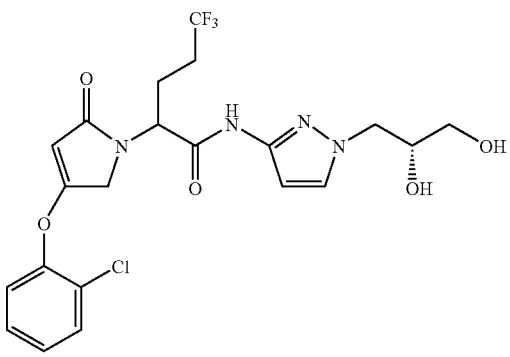

Hydrogen chloride gas was bubbled through methanol (20 mL) in a pressure bottle at 0° C. for 2-3 min. This solution was then treated with 2-amino-5,5,5-trifluoro-pentanoic acid (0.92 g, 5.37 mmol) and stirred at 50° C. for 24 h and then placed in a refrigerator over the weekend. The mixture was concentrated in vacuo, azeotroped with acetonitrile and dried under high vacuum to afford 2-amino-5,5,5-trifluoro-pentanoic acid methyl ester hydrochloride salt (1.19 g, 100%) as a white solid.

In a flask was placed 2-amino-5,5,5-trifluoro-pentanoic acid methyl ester hydrochloride salt (1.19 mg, 5.37 mmol), acetonitrile (40 mL) and N,N-diisopropylethylamine (1.0 mL, 5.91 mmol) which was stirred at 25° C. for 30 min. The mixture was then transferred to a pressure bottle and heated to 80° C. The mixture was then treated with N,N-diisopropylethylamine (1.0 mL, 5.91 mmol) and a solution of (E)-4-bromo-3-(2-chloro-phenoxy)-but-2-enoic acid ethyl ester (prepared as in Example 61, 1.88 g, 5.91 mmol) in acetonitrile (8 mL). The mixture was heated at 100° C. for 16 h and then concentrated with silica gel (3 g). Purification by Biotage flash chromatography (AnaLogix 40 g column, 16% ethyl acetate/hexanes) afforded 2-[2-(2-chloro-phenoxy)-3-ethoxycarbonyl-allylamino]-5,5,5-trifluoro-pentanoic acid methyl ester (1.43 g) as an amber oil.

A solution of 2-[2-(2-chloro-phenoxy)-3-ethoxycarbonyl-allylamino]-5,5,5-trifluoro-pentanoic acid methyl ester (1.43 g, 3.78 mmol) in acetonitrile (4 mL) was placed in a sealed microwave reaction tube and heated in a microwave reactor at 180° C. for 3 h. The mixture was then cooled and concentrated in vacuo with silica gel (3 g). Purification by Biotage flash chromatography (Aspire 40 g column, 16% ethyl acetate/hexanes to 50% ethyl acetate/hexanes) afforded 2-[4-(2-chloro-phenoxy)-2-oxo-2,5-dihydro-pyrrol-1-yl]-5,5,5-trifluoro-pentanoic acid methyl ester (1.02 g, 50% over two steps) as a an amber oil: HR-ES-MS m/z calculated for $C_{16}H_{15}NO_4ClF_3$ [M+H]$^+$ 378.0715, observed 378.0716.

A mixture of 2-[4-(2-chloro-phenoxy)-2-oxo-2,5-dihydro-pyrrol-1-yl]-5,5,5-trifluoro-pentanoic acid methyl ester (1.02 g, 2.70 mmol) in a 1:1 solution of tetrahydrofuran:water (30 mL) was treated with lithium hydroxide monohydrate (270 mg, 5.40 mmol). The mixture was stirred for 2 h at 25° C. After such time, the mixture was concentrated in vacuo to remove the tetrahydrofuran, diluted with water and the pH adjusted to pH=5 with 1N aqueous hydrochloric acid and extracted with ethyl acetate. The organic layer was dried over sodium sulfate and concentrated in vacuo to afford 2-[4-(2-chloro-phenoxy)-2-oxo-2,5-dihydro-pyrrol-1-yl]-5,5,5-trifluoro-pentanoic acid (766 mg, 78%) as a cream colored solid: HR-ES-MS m/z calculated for $C_{15}H_{13}NO_4ClF_3$ [M+H]$^+$ 364.0558, observed 364.0557.

In a round bottom flask under argon was placed 2-[4-(2-chloro-phenoxy)-2-oxo-2,5-dihydro-pyrrol-1-yl]-5,5,5-trifluoro-pentanoic acid (182 mg, 0.50 mmol) and 1-((R)-2,2-dimethyl-[1,3]dioxolan-4-yl-methyl)-1H-pyrazol-3-ylamine (prepared as in Example 49, 118 mg, 0.60 mmol) in N,N-dimethylformamide (4 mL). This mixture was treated with N,N-diisopropyethylamine (250 μL, 1.5 mmol) and (benzotriazol-1-yloxy)tris(dimethylamino)phosphonium hexafluorophosphate (330 mg, 0.75 mmol) and stirred overnight at 25° C. After this time, the reaction was diluted with ethyl acetate (25 mL) and washed with a saturated aqueous solution of ammonium chloride (25 mL), saturated aqueous solution of sodium bicarbonate (25 mL) and a saturated aqueous solution of sodium chloride (25 mL), dried over sodium sulfate and concentrated with silica gel (2 g). Purification by Biotage flash chromatography (Aspire 40 g column, 80% ethyl acetate/hexanes) afforded 2-[4-(2-chloro-phenoxy)-2-oxo-2,5-dihydro-pyrrol-1-yl]-5,5,5-trifluoro-pentanoic acid [1-((R)-2,2-dimethyl-[1,3]dioxolan-4-yl-methyl)-1H-pyrazol-3-yl]-amide (216 mg, 79%) as a white foam: HR-ES-MS m/z calculated for $C_{24}H_{26}N_4O_5ClF_3$ [M+H]$^+$ 543.1617, observed 543.1619.

In a round bottom flask was placed 2-[4-(2-chloro-phenoxy)-2-oxo-2,5-dihydro-pyrrol-1-yl]-5,5,5-trifluoro-pentanoic acid [1-((R)-2,2-dimethyl-[1,3]dioxolan-4-yl-methyl)-1H-pyrazol-3-yl]-amide (210 mg, 0.39 mmol), methanol (5 mL) and p-toluenesulfonic acid hydrate (17 mg). This mixture was stirred at 25° C. for 16 h and then diluted with dichloromethane and concentrated in vacuo with silica gel (2 g). Purification by Biotage flash chromatography (Aspire, 40 g column, 100% ethyl acetate to 5% methanol/ethyl acetate) afforded 2-[4-(2-chloro-phenoxy)-2-oxo-2,5-dihydro-pyrrol-1-yl]-5,5,5-trifluoro-pentanoic acid [1-((R)-2,3-dihydroxy-propyl)-1H-pyrazol-3-yl]-amide (140 mg, 71%) as a white foam: HR-ES-MS m/z calculated for $C_{21}H_{21}N_4O_5ClF_3$ [M+H]$^+$ 503.1304, observed 503.1300; $^1$H NMR (300 MHz, DMSO-d$_6$) δ ppm 1.88-2.46 (m, 4H), 3.20-3.33 (m, 2H), 3.68-3.82 (m, 1H), 3.86 (dd, J=13.4, 7.2 Hz, 1H), 4.09 (dd, J=13.4, 3.9 Hz, 1H), 4.32 (d, J=18.1 Hz, 1H), 4.53 (m, J=18.1 Hz, 1H), 4.72 (t, J=5.4 Hz, 1H), 4.78 (dd, J=9.1, 5.1 Hz, 1H), 4.83 (s, 1H), 4.94 (d, J=5.1 Hz, 1H), 6.42

(d, J=2.1 Hz, 1H), 7.33-7.40 (m, 1H), 7.42-7.57 (m, 3H), 7.66 (d, J=8.2 Hz, 1H), 10.75 (s, 1H).

Example 221

2-[4-(2-Chloro-phenoxy)-2-oxo-2,5-dihydro-pyrrol-1-yl]-N-[1-((R)-2,3-dihydroxy-propyl)-1H-pyrazol-3-yl]-4,4-difluoro-butyramide

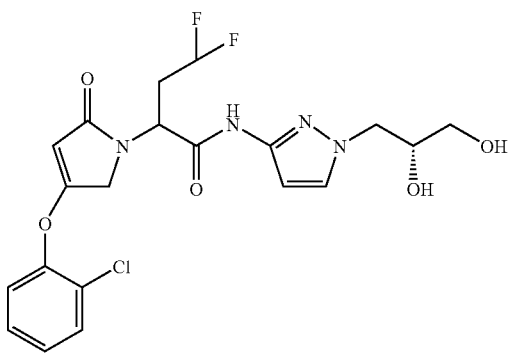

In a flask under argon was placed triflic anhydride (10.22 mL, 61 mmol) and dichloromethane (10 mL) and it was cooled to −70° C. To this cooled mixture was added slowly a solution of 2,2-difluoroethanol (5.00 g, 61 mmol) and triethylamine (8.5 mL, 61 mmol) in dichloromethane (10 mL). After the addition was complete, the mixture was warmed to 25° C. and then concentrated in vacuo. This material was distilled at 60° C. and 50 mm Hg which afforded trifluoro-methane-sulfonic acid 2,2-difluoro-ethyl ester (9.74 g, 75%) as a colorless oil.

In a flask under argon was placed diethylacetimidomalonate (8.95 g, 40.15 mmol), tetrahydrofuran (60 mL) and potassium t-butoxide (4.86 g, 40.15 mmol). This suspension was vigorously stirred at reflux temperature for 1.5 h. To this mixture was carefully added trifluoro-methanesulfonic acid 2,2-difluoro-ethyl ester (9.74 g, 45.99 mmol) and refluxed for an additional 3 h, cooled to room temperature and concentrated in vacuo. The residue was dissolved in ethyl acetate (100 mL) and washed with 0.5N aqueous hydrochloric acid solution (2×50 mL), water (2×50 mL), saturated aqueous sodium bicarbonate solution (50 mL), 1N aqueous sodium hydroxide solution (50 mL) and a saturated aqueous solution of sodium chloride (50 mL), dried over sodium sulfate, filtered and concentrated in vacuo. Diethyl ether (60 mL) and ethyl acetate were added to dissolve the solids and the solution was stored in the refrigerator, the solids were collected by filteration and washed with diethyl ether which afforded a white solid (0.6 g). The filterate was then purified by flash column chromatography (silica gel 60, 230-400 mesh; 40% ethyl acetate/hexanes) which afforded 2-acetylamino-2-(2,2-difluoro-ethyl)-malonic acid diethyl ester (8.34 g, combined with above 8.94 g, 79%) as a light pink solid.

In a flask was placed 2-acetylamino-2-(2,2-difluoro-ethyl)-malonic acid diethyl ester (8.94 g, 31.78 mmol) and 6N aqueous hydrochloric acid (140 mL). This mixture was refluxed overnight. After this time, the mixture was cooled to room temperature and extracted with diethyl ether (100 mL) the aqueous layer was concentrated in vacuo, azeotroped with acetonitrile and dried under high vacuum to afford 2-amino-4,4-difluoro-butyric acid hydrochloride salt (5.39 g, 97%) as a cream colored solid.

Hydrogen chloride gas was bubbled through methanol (20 mL) in a pressure bottle at 0° C. for 2-3 min. This solution was then treated with 2-amino-4,4-difluoro-butyric acid hydrochloride salt (1.00 g, 5.70 mmol) and heated at 50° C. for 16 h. The mixture was cooled to room temperature and nitrogen bubbled through for 5 min, concentrated in vacuo and azeotroped with acetonitrile and dried under high vacuum to afford 2-amino-4,4-difluoro-butyric acid methyl ester hydrochloride salt (1.09 g) as a white solid.

In a flask was placed 2-amino-4,4-difluoro-butyric acid methyl ester hydrochloride salt (1.08 g, 5.70 mmol), acetonitrile (40 mL) and N,N-diisopropylethylamine (1.03 mL, 6.38 mmol) which was stirred at 25° C. for 30 min. The mixture was then transferred to a pressure bottle and heated to 80° C. The mixture was then treated with N,N-diisopropylethylamine (1.03 mL, 6.38 mmol) and a solution of (E)-4-bromo-3-(2-chloro-phenoxy)-but-2-enoic acid ethyl ester (prepared as in Example 61, 2.00 g, 6.27 mmol) in acetonitrile (10 mL). The mixture was heated at 100° C. for 16 h and then concentrated with silica gel (4 g). Purification by Biotage flash chromatography (AnaLogix 40 g column, 16% ethyl acetate/hexanes) afforded 3-(2-chloro-phenoxy)-4-(3,3-difluoro-1-methoxycarbonyl-propylamino)-but-2-enoic acid ethyl ester (1.19 g) as a an amber oil.

A solution of 3-(2-chloro-phenoxy)-4-(3,3-difluoro-1-methoxycarbonyl-propylamino)-but-2-enoic acid ethyl ester (1.19 g, 3.04 mmol) in acetonitrile (4 mL) was placed in a sealed microwave reaction tube and heated in a microwave reactor at 180° C. for 3 h. The mixture was then cooled to room temperature and concentrated in vacuo with silica gel (3 g). Purification by Biotage flash chromatography (Aspire 40 g column, 16% ethyl acetate/hexanes to 50% ethyl acetate/hexanes) afforded 2-[4-(2-chloro-phenoxy)-2-oxo-2,5-dihydro-pyrrol-1-yl]-4,4-difluoro-butyric acid methyl ester (794 mg, 40% over two steps) as an amber oil: HR-ES-MS m/z calculated for $C_{15}H_{14}NO_4ClF_2$ [M+H]$^+$ 346.0652, observed 346.0651.

A mixture of 2-[4-(2-chloro-phenoxy)-2-oxo-2,5-dihydro-pyrrol-1-yl]-4,4-difluoro-butyric acid methyl ester (790 mg, 2.28 mmol) in a 1:1 solution of tetrahydrofuran:water (20 mL) was treated with lithium hydroxide monohydrate (230 mg, 4.56 mmol). The mixture was stirred for 2 h at 25° C. After such time, the mixture was concentrated in vacuo to remove the tetrahydrofuran and then diluted with water, and the pH adjusted to pH=5 with 1N aqueous hydrochloric acid and extracted with ethyl acetate. The organic layer was dried over sodium sulfate and concentrated in vacuo to afford 2-[4-(2-chloro-phenoxy)-2-oxo-2,5-dihydro-pyrrol-1-yl]-4,4-difluoro-butyric acid (571 mg, 75%) as a cream colored solid: HR-ES-MS m/z calculated for $C_{14}H_{12}NO_4ClF_2$ [M+H]$^+$ 332.0496, observed 332.0496.

In a round bottom flask under argon was placed 2-[4-(2-chloro-phenoxy)-2-oxo-2,5-dihydro-pyrrol-1-yl]-4,4-difluoro-butyric acid (166 mg, 0.50 mmol) and 1-((R)-2,2-dimethyl-[1,3]dioxolan-4-yl-methyl)-1H-pyrazol-3-ylamine (prepared as in Example 49, 118 mg, 0.60 mmol) in N,N-dimethylformamide (4 mL). To this mixture was added N,N-diisopropyethylamine (250 μL, 1.5 mmol) and (benzotriazol-1-yloxy)tris(dimethylamino)phosphonium hexafluorophosphate (330 mg, 0.75 mmol) and stirred overnight at 25° C. After this time, the mixture was diluted with ethyl acetate (25 mL) and washed with a saturated aqueous solution of ammonium chloride (25 mL), saturated aqueous solution of sodium bicarbonate (25 mL) and a saturated aqueous solution of sodium chloride (25 mL), dried over sodium sulfate, and then concentrated with silica gel (2 g). Purification by Biotage flash chromatography (Aspire 40 g column, 80% ethyl acetate/hexanes) afforded 2-[4-(2-chloro-phenoxy)-2-oxo-2,5-dihydro-pyrrol-1-yl]-N-[1-((R)-2,2-dimethyl-[1,3]dioxolan-4-yl-methyl)-1-H-pyrazol-3-yl]-4,4-difluoro-butyramide (185 mg, 72%) as a cream colored foam: HR-ES-MS m/z calculated for $C_{23}H_{25}N_4O_5ClF_2$ $[M+H]^+$ 511.1555, observed 511.1555.

In a round bottom flask was placed 2-[4-(2-chloro-phenoxy)-2-oxo-2,5-dihydro-pyrrol-1-yl]-N-[1-((R)-2,2-dimethyl-[1,3]dioxolan-4-yl-methyl)-1-H-pyrazol-3-yl]-4,4-difluoro-butyramide (180 mg, 0.35 mmol), methanol (5 mL) and p-toluenesulfonic acid hydrate (20 mg). The mixture was stirred at 25° C. for 16 h and then diluted with dichloromethane and concentrated in vacuo with silica gel (2 g). Purification by Biotage flash chromatography (Aspire, 40 g column, 100% ethyl acetate to 5% methanol/ethyl acetate) afforded 2-[4-(2-chloro-phenoxy)-2-oxo-2,5-dihydro-pyrrol-1-yl]-N-[1-((R)-2,3-dihydroxy-propyl)-1H-pyrazol-3-yl]-4,4-difluoro-butyramide (109 mg, 66%) as a white foam: HR-ES-MS m/z calculated for $C_{20}H_{21}N_4O_5ClF_2$ $[M+Na]^+$ 493.1061, observed 493.1057; $^1$H NMR (300 MHz, DMSO-$d_6$) δ ppm 2.43 (m, 2H), 3.19-3.31 (m, 2H), 3.76 (br. s., 1H), 3.85 (dd, J=13.3, 7.8 Hz, 1H), 4.08 (dd, J=13.3, 3.8 Hz, 1H), 4.35 (d, J=18.4 Hz, 1H), 4.45 (d, J=18.4 Hz, 1H), 4.70 (t, J=5.6 Hz, 1H), 4.81 (s, 1H), 4.93 (d, J=5.1 Hz, 1H), 4.94-5.02 (m, 1H), 6.10 (tt, J=56.1, 4.2 Hz, 1H), 6.40 (d, J=2.1 Hz, 1H), 7.31-7.39 (m, 1H), 7.41-7.52 (m, 2H), 7.53 (d, J=2.1 Hz, 1H), 7.64 (d, J=7.5 Hz, 1H), 10.76 (s, 1H).

Example 222

(S)-2-[4-(2-Chloro-phenoxy)-2-oxo-2,5-dihydro-pyrrol-1-yl]-N-[1-((R)-2,3-dihydroxy-propyl)-1H-pyrazol-3-yl]-4-hydroxy-butyramide

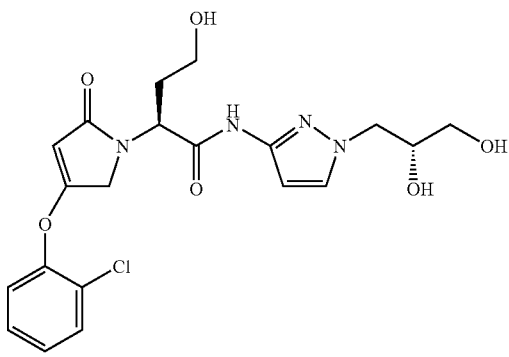

In a flask under argon was placed (S)-2-benzyloxycarbonylamino-succinic acid 1-methyl ester (7.00 g, 24.89 mmol) in tetrahydrofuran (15 mL) and cooled to −5° C. To this mixture was added a 1.0M solution of borane in tetrahydrofuran (50.6 mL, 50.6 mmol), slowly over a 15 min period. After the addition was complete, the mixture was stirred at 0° C. for 5 h and then quenched by slow addition of a 10% aqueous citric acid solution (100 mL) and then diethyl ether (100 mL). The mixture was then extracted with diethyl ether (3×50 mL) and the organic layers were combined and washed with a 1:1 solution of water:saturated aqueous sodium chloride solution (50 mL), dried over sodium sulfate and concentrated in vacuo. Purification by flash column chromatography (silica gel 60, 230-400 mesh; 40% ethyl acetate/hexanes to 80% ethyl acetate/hexanes) afforded (S)-2-benzyloxycarbonylamino-4-hydroxy-butyric acid methyl ester (4.50 g, 68%) as a colorless viscous oil.

In a flask under argon was placed (S)-2-benzyloxycarbonylamino-4-hydroxy-butyric acid methyl ester (535 mg, 2.0 mmol) in tetrahydrofuran (5 mL). To this mixture was then added imidazole (330 mg, 4.8 mmol) and t-butyl dimethyl silyl chloride (360 mg, 2.4 mmol) and within a minute solids started to appear and N,N-dimethylformamide (1 mL) was added to solubilize the material. The mixture was stirred for 16 h at 25° C. and then diluted with water (50 mL) and the aqueous layer extracted with diethyl ether (2×50 mL) dried over sodium sulfate, filtered and concentrated in vacuo with silica gel (2 g). Purification by Biotage flash chromatography (Aspire 40 g column, 16% ethyl acetate/hexanes) afforded (S)-2-benzyloxycarbonylamino-4-(t-butyl-dimethyl-silanyloxy)-butyric acid methyl ester (478 mg, 63%) as a colorless oil.

In a Parr shaker bottle was placed (S)-2-benzyloxycarbonylamino-4-(t-butyl-dimethyl-silanyloxy)-butyric acid methyl ester (478 mg, 1.25 mmol), methanol (10 mL) and 10% palladium on activated carbon (100 mg). The bottle was placed on the Parr Shaker and charged with hydrogen to 40 psi and shaken for 1.5 h. After this time, the mixture was filtered through celite and the filtrate concentrated in vacuo to afford (S)-2-amino-4-(t-butyl-dimethyl-silanyloxy)-butyric acid methyl ester (291 mg, 94%) as a colorless oil.

A solution of (S)-2-amino-4-(t-butyl-dimethyl-silanyloxy)-butyric acid methyl ester (291 mg, 1.18 mmol), acetonitrile (10 mL) and N,N-diisopropylethylamine (300 μL, 1.77 mmol) was heated at 80° C. and a then solution of (E)-4-bromo-3-(2-chloro-phenoxy)-but-2-enoic acid ethyl ester (prepared as in Example 61, 414 mg, 1.29 mmol) in acetonitrile (5 mL) was added slowly. The mixture was then heated at 100° C. for 16 h. After this time, the mixture was cooled to room temperature and concentrated in vacuo with silica gel (2 g). Purification by Biotage flash chromatography (AnaLogix 40 g column, 16% ethyl acetate/hexanes) afforded 4-[(S)-3-(t-butyl-dimethyl-silanyloxy)-1-methoxycarbonyl-propylamino]-3-(2-chloro-phenoxy)-but-2-enoic acid ethyl ester (501 mg) as a light yellow oil.

A solution of 4-[(S)-3-(t-butyl-dimethyl-silanyloxy)-1-methoxycarbonyl-propylamino]-3-(2-chloro-phenoxy)-but-2-enoic acid ethyl ester (495 mg, 1.02 mmol) in acetonitrile (4 mL) was placed in a sealed microwave reaction tube and heated in a microwave reactor at 140° C. for 3 h. After this time, the mixture was cooled to room temperature and concentrated in vacuo with silica gel (2 g). Purification by Biotage flash chromatography (Aspire 40 g column, 16% ethyl acetate/hexanes to 50% ethyl acetate/hexanes) afforded (S)-4-(t-butyl-dimethyl-silanyloxy)-2-[4-(2-chloro-phenoxy)-2-oxo-2,5-dihydro-pyrrol-1-yl]-butyric acid methyl ester (255 mg, 49% over two steps) as a golden oil: HR-ES-MS m/z calculated for $C_{21}H_{30}NO_5ClSi$ $[M+Na]^+$ 462.1474, observed 462.1473.

A mixture of (S)-4-(t-butyl-dimethyl-silanyloxy)-2-[4-(2-chloro-phenoxy)-2-oxo-2,5-dihydro-pyrrol-1-yl]-butyric acid methyl ester (250 mg, 0.57 mmol) in a 1:1 solution of tetrahydrofuran:water (8 mL) was treated with lithium hydroxide monohydrate (48 mg, 1.14 mmol) and stirred for 1.5 h at 25° C. After such time, the mixture was concentrated in vacuo to remove the tetrahydrofuran and diluted with water (10 mL) and the pH adjusted to pH=5 with 1N aqueous hydrochloric acid and extracted with ethyl acetate. The organic layers were then dried and concentrated in vacuo to afford (S)-4-(t-butyl-dimethyl-silanyloxy)-2-[4-(2-chloro-phenoxy)-2-oxo-2,5-dihydro-pyrrol-1-yl]-butyric acid (195 mg, 81%) as an off-white foam: HR-ES-MS m/z calculated for $C_{20}H_{28}NO_5ClSi$ $[M+H]^+$ 426.1498, observed 426.1498.

In a round bottom flask under argon was placed (S)-4-(t-butyl-dimethyl-silanyloxy)-2-[4-(2-chloro-phenoxy)-2-oxo-2,5-dihydro-pyrrol-1-yl]-butyric acid (190 mg, 0.45 mmol) and 1-((R)-2,2-dimethyl-[1,3]dioxolan-4-yl-methyl)-1H-pyrazol-3-ylamine (prepared as in Example 49, 105 mg, 0.54 mmol) in N,N-dimethylformamide (3 mL). To this mixture was added N,N-diisopropylethylamine (220 µL, 1.34 mmol) and (benzotriazol-1-yloxy)tris(dimethylamino)phosphonium hexafluorophosphate (295 mg, 0.57 mmol) and stirred for 5 h at 25° C. After this time, the mixture was diluted with ethyl acetate (25 mL) and washed with a saturated aqueous solution of ammonium chloride (25 mL), saturated aqueous solution of sodium bicarbonate (25 mL) and saturated aqueous sodium chloride solution (25 mL) dried over sodium sulfate, and concentrated in vacuo with silica gel (2 g). Purification by Biotage flash chromatography (Aspire 40 g column, 80% ethyl acetate/hexanes) afforded (S)-4-(t-butyl-dimethyl-silanyloxy)-2-[4-(2-chloro-phenoxy)-2-oxo-2,5-dihydro-pyrrol-1-yl]-N-[1-((R)-2,2-dimethyl-[1,3]dioxolan-4-yl-methyl)-1H-pyrazol-3-yl]-butyramide (131 mg, 49%) as a white foam: HR-ES-MS m/z calculated for $C_{29}H_{41}N_4O_6ClSi$ $[M+H]^+$ 605.2557, observed 605.2559.

In a round bottom flask was placed (S)-4-(t-butyl-dimethyl-silanyloxy)-2-[4-(2-chloro-phenoxy)-2-oxo-2,5-dihydro-pyrrol-1-yl]-N-[1-((R)-2,2-dimethyl-[1,3]dioxolan-4-yl-methyl)-1H-pyrazol-3-yl]-butyramide (128 mg, 0.21 mmol), methanol (5 mL) and p-toluenesulfonic acid monohydrate (10 mg) and stirred at 25° C. for 16 h. The mixture was then concentrated and treated with ethyl acetate and methanol to solubilize the material and concentrated in vacuo with silica gel (1 g). Purification by Biotage flash chromatography (AnaLogix, 25 g column, 100% ethyl acetate to 20% methanol/ethyl acetate) afforded material that was not pure. A second purification by Biotage flash chromatography (AnaLogix, 25 g column, 100% ethyl acetate to 20% methanol/ethyl acetate) afforded (S)-2-[4-(2-chloro-phenoxy)-2-oxo-2,5-dihydro-pyrrol-1-yl]-N-[1-((R)-2,3-dihydroxy-propyl)-1H-pyrazol-3-yl]-4-hydroxy-butyramide (43 mg, 45%) as a white foam: HR-ES-MS m/z calculated for $C_{20}H_{23}N_4O_6Cl$ $[M+H]^+$ 451.1379, observed 451.1379; $^1H$ NMR (400 MHz, DMSO-$d_6$) δ ppm 1.88-2.06 (m, 2H), 3.23-3.31 (m, 2H), 3.37-3.50 (m, 2H), 3.72-3.81 (m, 1H), 3.86 (dd, J=13.9, 7.9 Hz, 1H), 4.09 (dd, J=13.5, 3.9 Hz, 1H), 4.29 (d, J=18.3 Hz, 1H), 4.50-4.60 (m, 2H), 4.71 (t, J=5.6 Hz, 1H), 4.80 (s, 1H), 4.84 (dd, J=8.4, 5.4 Hz, 1H), 4.94 (d, J=5.3 Hz, 1H), 6.41 (d, J=2.1 Hz, 1H), 7.11 (d, J=7.9 Hz, 1H), 7.34-7.41 (m, 1H), 7.43-7.57 (m, 2H), 7.66 (dd, J=8.0, 1.2 Hz, 1H), 10.59 (s, 1H).

Example 223

(S)-2-[4-(2-Chloro-phenoxy)-2-oxo-2,5-dihydro-pyrrol-1-yl]-N-[1-((R)-2,3-dihydroxy-propyl)-1H-pyrazol-3-yl]-4-methylsulfanyl-butyramide

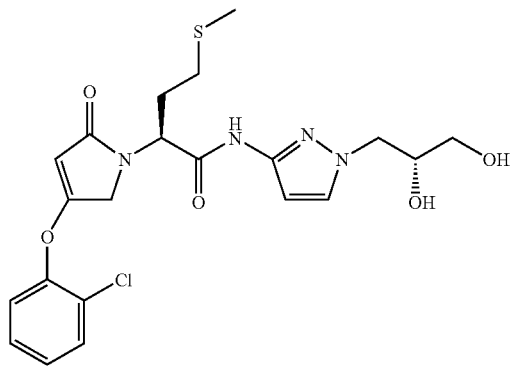

In a flask was placed (L)-methionine methyl ester hydrochloride salt (1.10 g, 5.5 mmol), acetonitrile (25 mL) and N,N-diisopropylethylamine (1.00 mL, 6.16 mmol) and the mixture was stirred at 60° C. for 1 h. After this time, another portion of N,N-diisopropylethylamine (1.00 mL, 6.16 mmol) was added and the temperature raised to 80° C., and a mixture of (E)-4-bromo-3-(2-chloro-phenoxy)-but-2-enoic acid ethyl ester (prepared as in Example 61, 1.60 g, 5.0 mmol) in acetonitrile (5 mL) was added slowly. After the addition was complete, the mixture was heated at 100° C. for 16 h and then concentrated in vacuo with silica gel (4 g). Purification by Biotage flash chromatography (AnaLogix 40 g column, 16% ethyl acetate/hexanes) afforded 3-(2-chloro-phenoxy)-4-((S)-1-methoxycarbonyl-3-methylsulfanyl-propylamino)-but-2-enoic acid ethyl ester (1.56 g) as a yellow oil.

A solution of 3-(2-chloro-phenoxy)-4-((S)-1-methoxycarbonyl-3-methylsulfanyl-propylamino)-but-2-enoic acid ethyl ester (1.56 g, 3.88 mmol) in acetonitrile (4 mL) was placed in a sealed microwave reaction tube and heated in a microwave reactor at 140° C. for 3 h. After this time, the mixture was cooled to room temperature and concentrated in vacuo with silica gel (4 g). Purification by Biotage flash chromatography (Aspire 40 g column, 16% ethyl acetate/hexanes to 50% ethyl acetate/hexanes) afforded (S)-2-[4-(2-chloro-phenoxy)-2-oxo-2,5-dihydro-pyrrol-1-yl]-4-methylsulfanyl-butyric acid methyl ester (477 mg, 24% over two steps) as a golden oil: HR-ES-MS m/z calculated for $C_{16}H_{18}NO_4ClS$ $[M+Na]^+$ 378.0537, observed 378.0538.

A mixture of (S)-2-[4-(2-chloro-phenoxy)-2-oxo-2,5-dihydro-pyrrol-1-yl]-4-methylsulfanyl-butyric acid methyl ester (513 mg, 1.44 mmol) in a 1:1 solution of tetrahydrofuran:water (20 mL) was treated with lithium hydroxide monohydrate (120 mg, 2.88 mmol) and stirred for 1.5 h at 25° C. After such time, the mixture was concentrated in vacuo to remove the tetrahydrofuran and partioned between 1N aqueous hydrochloric acid (10 mL) and ethyl acetate (20 mL). The organic layer was separated, dried over sodium sulfate and concentrated in vacuo to afford (S)-2-[4-(2-chloro-phenoxy)-2-oxo-2,5-dihydro-pyrrol-1-yl]-4-methylsulfanyl-butyric acid (438 mg, 89%) as a light amber gum.

In a round bottom flask under argon was placed (S)-2-[4-(2-chloro-phenoxy)-2-oxo-2,5-dihydro-pyrrol-1-yl]-4-methylsulfanyl-butyric acid (171 mg, 0.50 mmol) and 1-((R)-2,2-dimethyl-[1,3]dioxolan-4-yl-methyl)-1H-pyrazol-3- ylamine (prepared as in Example 49, 118 mg, 0.60 mmol) in N,N-dimethylformamide (4 mL). To this mixture was added N,N-diisopropyethylamine (250 µL, 1.5 mmol) and (benzotriazol-1-yloxy)tris(dimethylamino)phosphonium hexafluorophosphate (331 mg, 0.75 mmol) and the mixture was stirred for 3.5 h at 25° C. After this time, the mixture was diluted with ethyl acetate (30 mL) and washed with a saturated aqueous solution of ammonium chloride (25 mL), saturated aqueous solution of sodium bicarbonate (25 mL) and a saturated aqueous solution of sodium chloride (25 mL) dried over sodium sulfate and concentrated in vacuo with silica gel (2 g). Purification by Biotage flash chromatography (Aspire 40 g column, 100% ethyl acetate) afforded (S)-2-[4-(2-chloro-phenoxy)-2-oxo-2,5-dihydro-pyrrol-1-yl]-N-[1-((R)-2,2-dimethyl-[1,3]dioxolan-4-yl-methyl)-1H-pyrazol-3-yl]-4-methylsulfanyl-butyramide (121 mg, 46%) as a white foam: HR-ES-MS m/z calculated for $C_{24}H_{29}N_4O_5ClS$ $[M+H]^+$ 521.1620, observed 521.1622.

In a round bottom flask was placed (S)-2-[4-(2-chloro-phenoxy)-2-oxo-2,5-dihydro-pyrrol-1-yl]-N-[1-((R)-2,2-dimethyl-[1,3]dioxolan-4-yl-methyl)-1H-pyrazol-3-yl]-4-methylsulfanyl-butyramide (118 mg, 0.23 mmol), methanol (5 mL) and p-toluenesulfonic acid monohydrate (9 mg). The mixture was stirred at 25° C. for 16 h and then concentrated in vacuo, dissolved in ethyl acetate with a little methanol to solubilize the material and concentrated in vacuo with silica gel (1 g). Purification by Biotage flash chromatography (AnaLogix, 12 g column, 100% ethyl acetate to 10% methanol/ethyl acetate) afforded (S)-2-[4-(2-chloro-phenoxy)-2-oxo-2,5-dihydro-pyrrol-1-yl]-N-[1-((R)-2,3-dihydroxy-propyl)-1H-pyrazol-3-yl]-4-methylsulfanyl-butyramide (80 mg, 74%) as a white foam: HR-ES-MS m/z calculated for $C_{21}H_{25}N_4O_5ClS$ $[M+H]^+$ 481.1307, observed 491.1307; $^1H$ NMR (300 MHz, DMSO-$d_6$) δ ppm 1.96-2.19 (m, 2H), 2.09 (s, 3H), 2.29-2.48 (m, 2H), 3.21-3.33 (m, 2H), 3.69-3.81 (m, 1H), 3.86 (dd, J=13.5, 7.5 Hz, 1H), 4.09 (dd, J=13.5, 3.8 Hz, 1H), 4.27 (d, J=18.2 Hz, 1H), 4.56 (d, J=18.2 Hz, 1H), 4.71 (t, J=5.6 Hz, 1H), 4.78-4.86 (m, 1H), 4.81 (s, 1H), 4.94 (d, J=5.4 Hz, 1H), 6.41 (d, J=2.1 Hz, 1H), 7.37 (td, J=7.8, 1.8 Hz, 1H), 7.47 (td, J=7.8, 1.4 Hz, 1H), 7.50-7.55 (m, 2H), 7.66 (dd, J=7.8, 1.4 Hz, 1H), 10.72 (s, 1H).

Example 224

2-[4-(2-Chloro-phenoxy)-2-oxo-2,5-dihydro-pyrrol-1-yl]-N-[1-((R)-2,3-dihydroxy-propyl)-1H-pyrazol-3-yl]-4,4,4-trifluoro-butyramide

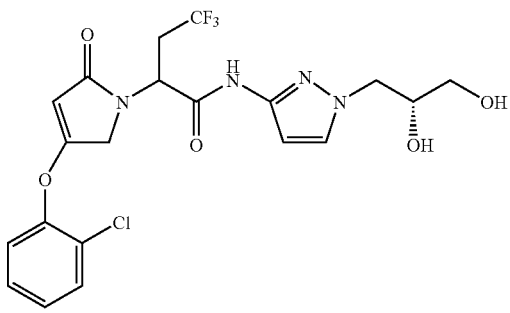

Hydrogen chloride gas was bubbled through methanol (5 mL) in a pressure bottle at 0° C. for 2-3 min. This solution was then treated with 2-amino-4,4,4-trifluoro-butyric acid hydrochloride salt (450 mg, 2.32 mmol) sealed and stirred at 50° C. for 16 h overnight. The mixture was then cooled and nitrogen gas bubbled through the mixture for 5 min, concentrated in vacuo, azeotroped with acetonitrile and dried under high vacuum to afford 2-amino-4,4,4-trifluoro-butyric acid methyl ester hydrochloride salt (474 mg, 98%) as a white solid.

In a flask was placed 2-amino-4,4,4-trifluoro-butyric acid methyl ester hydrochloride salt (472 mg, 2.27 mmol), acetonitrile (20 mL) and N,N-diisopropylethylamine (410 µL, 2.54 mmol). This mixture was stirred at 25° C. for 30 min and then warmed to 80° C. and a solution of N,N-diisopropylethylamine (410 µL, 2.54 mmol) and (E)-4-bromo-3-(2-chloro-phenoxy)-but-2-enoic acid ethyl ester (prepared as in Example 61, 800 mg, 2.50 mmol) in acetonitrile (5 mL) was added slowly. After addition was complete, the mixture was then heated at 100° C. for 16 h. The mixture was concentrated in vacuo with silica gel (3 g) and purified by Biotage flash chromatography (AnaLogix 40 g column, 16% ethyl acetate/hexanes) which afforded 3-(2-chloro-phenoxy)-4-(3,3,3-trifluoro-1-methoxycarbonyl-propylamino)-but-2-enoic acid ethyl ester (412 mg) as a yellow oil.

A solution of 3-(2-chloro-phenoxy)-4-(3,3,3-trifluoro-1-methoxycarbonyl-propylamino)-but-2-enoic acid ethyl ester (410 mg, 1.00 mmol) in acetonitrile (4 mL) was placed in a sealed microwave reaction tube and heated in a microwave reactor at 150° C. for 3 h. The mixture was then cooled to room temperature and concentrated in vacuo with silica gel (2 g). Purification by Biotage flash chromatography (Aspire 40 g column, 16% ethyl acetate/hexanes to 33% ethyl acetate/hexanes) afforded 2-[4-(2-chloro-phenoxy)-2-oxo-2,5-dihydro-pyrrol-1-yl]-4,4,4-trifluoro-butyric acid methyl ester (153 mg, 17% over two steps) as a yellow oil.

A mixture of 2-[4-(2-chloro-phenoxy)-2-oxo-2,5-dihydro-pyrrol-1-yl]-4,4,4-trifluoro-butyric acid methyl ester (212 mg, 0.58 mmol) in a 1:1 solution of tetrahydrofuran:water (8 mL) was treated with lithium hydroxide monohydrate (55 mg, 1.16 mmol) and stirred for 1.5 h at 25° C. After such time, the mixture was concentrated in vacuo to remove the tetrahydrofuran and then diluted with water (10 mL) and the pH adjusted to pH=4 with 1N aqueous hydrochloric acid and extracted with ethyl acetate. The organic layers were then dried over sodium sulfate and concentrated in vacuo to afford 2-[4-(2-chloro-phenoxy)-2-oxo-2,5-dihydro-pyrrol-1-yl]-4,4,4-trifluoro-butyric acid (149 mg, 73%) as a white solid: HR-ES-MS m/z calculated for $C_{14}H_{11}NO_4ClF_3$ $[M+Na]^+$ 372.0221, observed 372.0224.

In a round bottom flask under argon was placed 2-[4-(2-chloro-phenoxy)-2-oxo-2,5-dihydro-pyrrol-1-yl]-4,4,4-trifluoro-butyric acid (144 mg, 0.41 mmol) and 1-((R)-2,2-dimethyl-[1,3]dioxolan-4-yl-methyl)-1H-pyrazol-3-ylamine (prepared as in Example 49, 97 mg, 0.49 mmol) in N,N-dimethylformamide (4 mL). To this mixture was added N,N-diisopropyethylamine (200 µL, 1.23 mmol) and (benzotriazol-1-yloxy)tris(dimethylamino)phosphonium hexafluorophosphate (271 mg, 0.62 mmol) and stirred for 16 h at 25° C. After this time, the mixture was diluted with ethyl acetate (25 mL) and washed with a saturated aqueous solution of ammonium chloride (25 mL), saturated aqueous solution of sodium bicarbonate (25 mL) and a saturated aqueous solution of sodium chloride (25 mL), dried over sodium sulfate, and then concentrated with silica gel (2 g). Purification by Biotage flash chromatography (Aspire 40 g column, 80% ethyl acetate) afforded 2-[4-(2-chloro-phenoxy)-2-oxo-2,5-dihydro-pyrrol-1-yl]-N-[1-((R)-2,2-dimethyl-[1,3]dioxolan-4-yl-methyl)-1-H-pyrazol-3-yl]-4,4,4-trifluoro-butyramide (168 mg, 77%) as a white foam: HR-ES-MS m/z calculated for $C_{23}H_{24}N_4O_5ClF_3$ $[M+H]^+$ 529.1460, observed 529.1457.

In a round bottom flask was placed 2-[4-(2-chloro-phenoxy)-2-oxo-2,5-dihydro-pyrrol-1-yl]-N-[1-((R)-2,2-dimethyl-[1,3]dioxolan-4-yl-methyl)-1-H-pyrazol-3-yl]-4,4,4-trifluoro-butyramide (164 mg, 0.31 mmol), methanol (5 mL) and p-toluenesulfonic acid monohydrate (15 mg). The mixture was stirred at 25° C. for 16 h and then concentrated in vacuo with silica gel (1.3 g). Purification by Biotage flash chromatography (Aspire column, 100% ethyl acetate to 5% methanol/ethyl acetate) afforded 2-[4-(2-chloro-phenoxy)-2-oxo-2,5-dihydro-pyrrol-1-yl]-N-[1-((R)-2,3-dihydroxy-propyl)-1H-pyrazol-3-yl]-4,4,4-trifluoro-butyramide (116 mg, 77%) as a white foam: HR-ES-MS m/z calculated for $C_{20}H_{20}N_4O_5ClF_3$ [M+H]$^+$ 489.1147, observed 489.1148; $^1$H NMR (300 MHz, DMSO-d$_6$) δ ppm 2.80-3.13 (m, 2H), 3.20-3.32 (m, 2H), 3.70-3.81 (m, 1H), 3.87 (dd, J=13.4, 7.5 Hz, 1H), 4.10 (dd, J=13.4, 3.9 Hz, 1H), 4.38 (s, 2H), 4.72 (t, J=5.6 Hz, 1H), 4.84 (s, 1H), 4.95 (d, J=5.4 Hz, 1H), 5.18 (dd, J=9.4, 3.9 Hz, 1H), 6.43 (d, J=2.1 Hz, 1H), 7.31-7.41 (m, 1H), 7.42-7.53 (m, 2H), 7.56 (d, J=2.1 Hz, 1H), 7.65 (d, J=8.2 Hz, 1H), 10.92 (s, 1H).

Example 225

3-(2,6-Dichloro-phenyl)-2-[4-(2,6-difluoro-phenoxy)-2-oxo-2,5-dihydro-pyrrol-1-yl]-N-[1-(2-hydroxy-2-methyl-propyl)-1H-pyrazol-3-yl]-propionamide

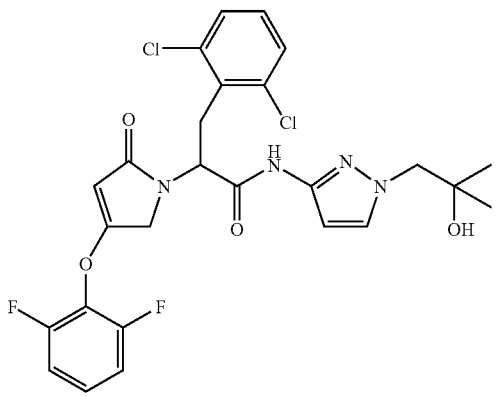

Hydrogen chloride gas was bubbled through methanol (20 mL) in a pressure bottle at 0° C. for 2-3 min. This solution was then treated with (L)-2,6-dichlorophenyl alanine (1.00 g, 4.28 mmol) and stirred at 50° C. for 16 h and then 25° C. over the weekend. The mixture was concentrated in vacuo, azeotroped with acetonitrile and dried under high vacuum to afford 2-amino-3-(2,6-dichloro-phenyl)-propionic acid methyl ester hydrochloride salt (1.00 g, 82%) as a white solid.

In a flask was placed 2-amino-3-(2,6-dichloro-phenyl)-propionic acid methyl ester hydrochloride salt (313 mg, 1.10 mmol), acetonitrile (5 mL) and N,N-diisopropylethylamine (200 μL, 1.23 mmol). This mixture was stirred at 60° C. for 1 h and then cooled to 25° C. The mixture was then treated with N,N-diisopropylethylamine (200 μL, 1.23 mmol) and heated at 80° C. and a solution of 4-bromo-3-(2,6-difluoro-phenoxy)-but-2-enoic acid ethyl ester (prepared as in Example 36, 321 mg, 1.00 mmol) in acetonitrile (1 mL) was added slowly. The mixture was heated at 100° C. for 16 h and then placed in a sealed microwave tube and heated at 140° C. for 1 h in the microwave. The mixture was then concentrated in vacuo with silica gel (2 g). Purification by Biotage flash chromatography (40S column, 10% ethyl acetate/hexanes to 100% ethyl acetate) afforded 3-(2,6-dichloro-phenyl)-2-[4-(2,6-difluoro-phenoxy)-2-oxo-2,5-dihydro-pyrrol-1-yl]-propionic acid methyl ester (58 mg, 12%) as a gold oil: HR-ES-MS m/z calculated for $C_{20}H_{15}NO_4Cl_2F_2$ [M+H]$^+$ 442.0419, observed 442.0420.

A mixture of 3-(2,6-dichloro-phenyl)-2-[4-(2,6-difluoro-phenoxy)-2-oxo-2,5-dihydro-pyrrol-1-yl]-propionic acid methyl ester (56 mg, 0.13 mmol) in a 1:1 solution of tetrahydrofuran:water (4 mL) was treated with lithium hydroxide monohydrate (11 mg, 0.26 mmol). The mixture was then stirred for 1 h at 25° C. After such time, the mixture was concentrated in vacuo to remove the tetrahydrofuran and then diluted with 1N aqueous hydrochloric acid until the pH was acidic and then extracted with ethyl acetate. The organic layers were dried over sodium sulfate and concentrated in vacuo to afford 3-(2,6-dichloro-phenyl)-2-[4-(2,6-difluoro-phenoxy)-2-oxo-2,5-dihydro-pyrrol-1-yl]-propionic acid (40 mg, 74%) as a tan solid: HR-ES-MS m/z calculated for $C_{19}H_{13}NO_4Cl_2F_2$ [M+H]$^+$ 428.0263, observed 428.0263.

In a round bottom flask under argon was placed 3-(2,6-dichloro-phenyl)-2-[4-(2,6-difluoro-phenoxy)-2-oxo-2,5-dihydro-pyrrol-1-yl]-propionic acid (38 mg, 0.089 mmol) in dichloromethane (3 mL) and N,N-dimethylformamide (3 drops) at 25° C. To this mixture was then added a 2.0M solution of oxalyl chloride in dichloromethane (50 μL, 0.10 mmol) dropwise which resulted in gas evolution. The mixture was then stirred for 15 min at 25° C. and concentrated in vacuo. The residue was taken up in dichloromethane (3 mL) and added dropwise into a flask containing a solution of 1-(3-amino-pyrazol-1-yl)-2-methyl-propan-2-ol (prepared as in US20080021032, Example 80, 17 mg, 0.107 mmol), dichloromethane (3 mL) and 2,6-lutidine (50 μL, 0.18 mmol) at 25° C. The mixture was then stirred for 1 h at 25° C. and then quenched with methanol and diluted with dichloromethane. This mixture was then washed with a 1N aqueous hydrochloric acid solution, dried over sodium sulfate and concentrated in vacuo with silica gel (2 g). Purification by Biotage flash chromatography (25% ethyl acetate/hexanes) afforded 3-(2,6-dichloro-phenyl)-2-[4-(2,6-difluoro-phenoxy)-2-oxo-2,5-dihydro-pyrrol-1-yl]-N-[1-(2-hydroxy-2-methyl-propyl)-1H-pyrazol-3-yl]-propionamide (18 mg, 36%) as a light amber foam: HR-ES-MS m/z calculated for $C_{26}H_{24}N_4O_4Cl_2F_2$ [M+H]$^+$ 565.1216, observed 565.1216; $^1$H NMR (400 MHz, DMSO-d$_6$) δ ppm 1.04 (s, 3H), 1.05 (s, 3H), 3.34-3.51 (m, 2H), 3.88 (s, 2H), 4.19 (d, J=18.3 Hz, 1H), 4.55 (d, J=18.3 Hz, 1H), 4.66 (s, 1H), 4.98 (s, 1H), 5.03 (dd, J=8.2, 6.0 Hz, 1H), 6.50 (d, J=2.1 Hz, 1H), 7.27 (dd, J=8.2, 7.7 Hz, 1H), 7.35 (t, J=8.7 Hz, 2H), 7.38-7.48 (m, 3H), 7.54 (d, J=2.1 Hz, 1H), 10.68 (s, 1H).

Example 226

2-[4-(2-Chloro-phenoxy)-2-oxo-2,5-dihydro-pyrrol-1-yl]-5,5,5-trifluoro-4-methyl-pentanoic acid [1-(2-hydroxy-2-methyl-propyl)-1H-pyrazol-3-yl]-amide

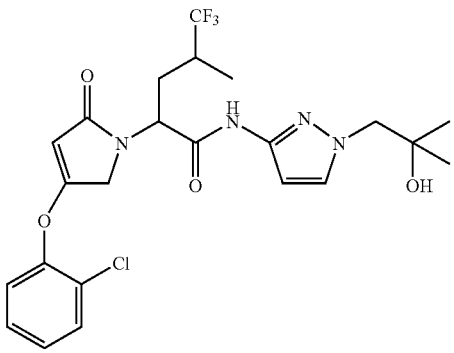

Hydrogen chloride gas was bubbled through methanol (25 mL) in a pressure bottle at 0° C. for ~2 min. This solution was then treated with 2-amino-5,5,5-trifluoro-4-methyl-pentanoic acid (1.0 g, 5.4 mmol) and heated at 50° C. for 16 h. After this time, the mixture was concentrated in vacuo and azeotroped with acetonitrile to afford impure 2-amino-5,5,5-trifluoro-4-methyl-pentanoic acid methyl ester hydrochloride salt (1.3 g, small solvent impurity).

A suspension of 2-amino-5,5,5-trifluoro-4-methyl-pentanoic acid methyl ester hydrochloride salt (814 mg, 3.5 mmol) in acetonitrile (5 mL) was treated with N,N-diisopropylethylamine (818 μL, 5.3 mmol) and heated for 1 h at 60° C. The mixture was then cooled to 25° C. and another portion of N,N-diisopropylethylamine (818 μL, 5.3 mmol) and acetonitrile (5 mL) was added. The mixture was then heated to 80° C. and slowly treated with a solution of (E)-4-bromo-3-(2-chloro-phenoxy)-but-2-enoic acid ethyl ester (prepared as in Example 61, 1.0 g, 3.14 mmol) in acetonitrile (3 mL). The temperature was then raised to 100° C. and the mixture stirred for 16 h. After this time, the mixture was concentrated to approximately 5 mL in total volume and placed in a sealed tube and heated overnight at 100° C. After this time, The mixture was concentrated in vacuo, diluted with dichloromethane and washed with a 1N aqueous hydrochloric acid solution (15 mL), water (15 mL) and a saturated aqueous sodium bicarbonate solution (10 mL). The organic layer was dried over magnesium sulfate concentrated in vacuo and purified by AnaLogix IntelliFlash flash chromatography (24 g column, 10% ethyl acetate/hexanes to 40% ethyl acetate/hexanes) which afforded 2-[2-(2-chloro-phenoxy)-3-ethoxycarbonyl-allylamino]-5,5,5-trifluoro-4-methyl-pentanoic acid methyl ester (726 mg, 53%) as a yellow oil.

A solution of 2-[2-(2-chloro-phenoxy)-3-ethoxycarbonyl-allylamino]-5,5,5-trifluoro-4-methyl-pentanoic acid methyl ester (726 mg, 1.66 mmol) in acetonitrile (5 mL) was placed in a sealed microwave reaction tube and heated in a microwave reactor at 140° C. for 2.5 h. The mixture was then concentrated in vacuo and purified by AnaLogix IntelliFlash flash chromatography (12 g column, 10% ethyl acetate/hexanes to 40% ethyl acetate/hexanes) which afforded 2-[4-(2-chloro-phenoxy)-2-oxo-2,5-dihydro-pyrrol-1-yl]-5,5,5-trifluoro-4-methyl-pentanoic acid methyl ester (379 mg, 58%) as a yellow oil.

In a flask was placed 2-[4-(2-chloro-phenoxy)-2-oxo-2,5-dihydro-pyrrol-1-yl]-5,5,5-trifluoro-4-methyl-pentanoic acid methyl ester (614 mg, 1.56 mmol) dissolved in tetrahydrofuran (10 mL). To this mixture at 25° C. was added a solution of lithium hydroxide monohydrate (131 mg, 3.13 mmol) in water (10 mL). The mixture was then stirred for 2 h at 25° C. After such time, the mixture was treated with a 1N aqueous hydrochloric acid solution until pH=2 and extracted with ethyl acetate (3×20 mL). The organics were combined and dried over magnesium sulfate, filtered and concentrated in vacuo to afford 2-[4-(2-chloro-phenoxy)-2-oxo-2,5-dihydro-pyrrol-1-yl]-5,5,5-trifluoro-4-methyl-pentanoic acid (575 mg, 98%) as a yellow-orange solid.

In a round bottom flask under argon was placed 2-[4-(2-chloro-phenoxy)-2-oxo-2,5-dihydro-pyrrol-1-yl]-5,5,5-trifluoro-4-methyl-pentanoic acid (575 mg, 1.52 mmol) in dichloromethane (25 mL). To this mixture was added 1-(3-dimethylaminopropyl)-3-ethylcarbodiimide (296 μL, 1.67 mmol) and 1-hydoxybenzotriazole (216 mg, 1.59 mmol) and stirred at 25° C. for 2 h. After this time, 1-(3-amino-pyrazol-1-yl)-2-methyl-propan-2-ol (prepared in US20080021032, Example 80, 283 mg, 1.83 mmol) was added and the mixture stirred for 16 h at 25° C. After this time, the mixture was diluted with dichloromethane (10 mL) and washed with a 1N aqueous hydrochloric acid solution (10 mL), water (10 mL) and a saturated aqueous sodium bicarbonate solution (10 mL) dried over magnesium sulfate, filtered and concentrated in vacuo. Purification by AnaLogix IntelliFlash flash chromatography (12 g column, 20% ethyl acetate/hexanes to 80% ethyl acetate/hexanes) afforded 2-[4-(2-chloro-phenoxy)-2-oxo-2,5-dihydro-pyrrol-1-yl]-5,5,5-trifluoro-4-methyl-pentanoic acid [1-(2-hydroxy-2-methyl-propyl)-1H-pyrazol-3-yl]-amide (460 mg, 59%) as a yellow foam: HR-ES-MS m/z calculated for $C_{23}H_{26}N_4O_4ClF_3$ [M+H]$^+$ 515.1668, observed 515.1664; $^1$H NMR (300 MHz, CDCl$_3$) δ ppm 1.15 (s, 3H), 1.16 (s, 3H), 1.20 (d, J=6.6 Hz, 3H), 1.89-2.19 (m, 2H), 2.30 (m, 1H), 3.94 (s, 2H), 4.28 (m, 1H), 4.31 (m, 1H), 4.90, 4.91 (2×s, 1H), 5.00 (dd, J=4.8, 10.9 Hz, 1H), 6.68 (br. s., 1H), 7.20-7.37 (m, 4H), 7.49 (d, J=7.9 Hz, 1H), 8.65, 8.89 (2×br. s., 1H).

Example 227

2-[4-(2-Chloro-phenoxy)-2-oxo-2,5-dihydro-pyrrol-1-yl]-5,5-dimethyl-hexanoic acid [1-((R)-2,3-dihydroxy-propyl)-1H-pyrazol-3-yl]amide

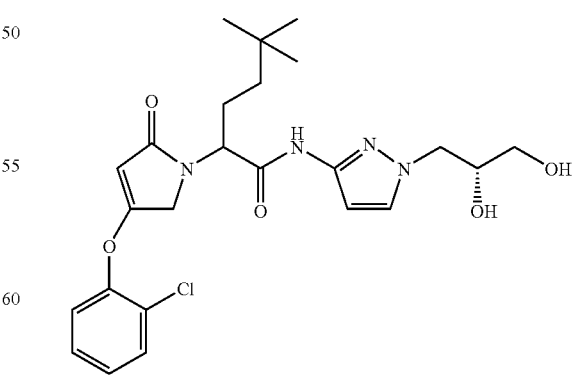

Hydrogen chloride gas was bubbled through methanol (10 mL) in a pressure bottle at 0° C. for ~2 min. This solution was then treated with 2-t-butoxycarbonylamino-5,5-dimethylhexanoic acid (300 g, 1.16 mmol) and heated at 50° C. for 16 h. After this time, the mixture was concentrated in vacuo and azeotroped with acetonitrile to afford 2-amino-5,5-dimethyl-hexanoic acid methyl ester hydrochloride salt (283 mg).

A suspension of 2-amino-5,5-dimethyl-hexanoic acid methyl ester hydrochloride salt (100 mg, 0.48 mmol) in acetonitrile (2 mL) was treated with N,N-diisopropylethylamine (113 µL, 0.72 mmol) and heated for 1 h at 60° C. The mixture was then cooled to 25° C. and another portion of N,N-diisopropylethylamine (113 µL, 0.72 mmol) and acetonitrile (1 mL) was added. The mixture was heated to 80° C. and slowly treated with a solution of (E)-4-bromo-3-(2-chloro-phenoxy)-but-2-enoic acid ethyl ester (prepared as in Example 61, 140 mg, 0.43 mmol) in acetonitrile (1 mL). The temperature was then raised to 100° C. and the mixture stirred for 1 h. After this time, the mixture was concentrated in vacuo, diluted with dichloromethane and washed with water (10 mL), a saturated sodium bicarbonate solution (10 mL), dried over magnesium sulfate and concentrated in vacuo. Purification by AnaLogix IntelliFlash flash chromatography (8 g column, 2% ethyl acetate/hexanes to 35% ethyl acetate/hexanes) afforded 2-[1-(2-chloro-phenoxy)-2-ethoxycarbonyl-vinylamino]-5,5-dimethyl-hexanoic acid methyl ester (66 mg) as a clear colorless oil.

A solution of 2-[1-(2-chloro-phenoxy)-2-ethoxycarbonyl-vinylamino]-5,5-dimethyl-hexanoic acid methyl ester (66 mg, 0.16 mmol) in acetonitrile (2 mL) was placed in a sealed microwave reaction tube and heated in a microwave reactor at 140° C. for 1 h, 160° C. for 1.5 h, and 120° C. for 2 h. The mixture was concentrated in vacuo and then purified by AnaLogix IntelliFlash flash chromatography (8 g column, 2% ethyl acetate/hexanes to 35% ethyl acetate/hexanes) which afforded 2-[4-(2-chloro-phenoxy)-2-oxo-2,5-dihydro-pyrrol-1-yl]-5,5-dimethyl-hexanoic acid methyl ester (34 mg, 20% over two steps) as a light yellow oil.

In a flask was placed 2-[4-(2-chloro-phenoxy)-2-oxo-2,5-dihydro-pyrrol-1-yl]-5,5-dimethyl-hexanoic acid methyl ester (34 mg, 0.093 mmol) in tetrahydrofuran (2 mL). To this mixture at 25° C. was added a solution of lithium hydroxide monohydrate (8 mg, 0.19 mmol) in water (2 mL). The mixture was then stirred for 1.5 h at 25° C. and then treated with a 1N aqueous hydrochloric acid solution to pH=2 and extracted with ethyl acetate (3×20 mL). The combined organic layers were dried over magnesium sulfate, filtered and concentrated in vacuo to afford 2-[4-(2-chloro-phenoxy)-2-oxo-2,5-dihydro-pyrrol-1-yl]-5,5-dimethyl-hexanoic acid (32 mg, 98% as a light yellow solid.

In a round bottom flask under argon was placed 2-[4-(2-chloro-phenoxy)-2-oxo-2,5-dihydro-pyrrol-1-yl]-5,5-dimethyl-hexanoic acid (32 mg, 0.091 mmol) in dichloromethane (3 mL). To this mixture was added 1-(3-dimethylaminopropyl)-3-ethylcarbodiimide (20 µL, 0.10 mmol) and 1-hydroxybenzotriazole (13 mg, 0.096 mmol) and stirred at 25° C. for 2 h. After this time period, 1-((R)-2,2-dimethyl-[1,3]dioxolan-4-yl-methyl)-1H-pyrazol-3-ylamine (prepared as in Example 49, 21 mg, 0.109 mmol) was added and stirred for 16 h at 25° C. After this time, the mixture was diluted with dichloromethane (10 mL) and washed with a 1N aqueous hydrochloric acid solution (10 mL), water (10 mL) and a saturated aqueous sodium bicarbonate solution (10 mL), dried over magnesium sulfate, filtered and concentrated in vacuo. Purification by AnaLogix IntelliFlash flash chromatography (4 g column, 30% ethyl acetate/hexanes to 100% ethyl acetate/hexanes) afforded 2-[4-(2-chloro-phenoxy)-2-oxo-2,5-dihydro-pyrrol-1-yl]-5,5-dimethyl-hexanoic acid [1-((R)-2,2-dimethyl-[1,3]dioxolan-4-yl-methyl)-1H-pyrazol-3-yl]-amide (14 mg, 29%) as a colorless oil.

In a round bottom flask under argon was placed 2-[4-(2-chloro-phenoxy)-2-oxo-2,5-dihydro-pyrrol-1-yl]-5,5-dimethyl-hexanoic acid [1-((R)-2,2-dimethyl-[1,3]dioxolan-4-yl-methyl)-1H-pyrazol-3-yl]-amide (14 mg, 0.026 mmol) in methanol (2 mL). To this mixture was then added p-toluenesulfonic acid monohydrate (1 mg, 0.004 mmol) and stirred at 25° C. for 16 h. After this time period, the mixture was concentrated in vacuo and purified by AnaLogix IntelliFlash flash chromatography (4 g column, 100% ethyl acetate to 40% methanol/ethyl acetate) To afford 2-[4-(2-chloro-phenoxy)-2-oxo-2,5-dihydro-pyrrol-1-yl]-5,5-dimethyl-hexanoic acid [1-((R)-2,3-dihydroxy-propyl)-1H-pyrazol-3-yl] amide (10 mg, 77%) as a white foam: HR-ES-MS m/z calculated for $C_{24}H_{31}N_4O_5Cl$ $[M+H]^+$ 491.2056, observed 491.2052; $^1H$ NMR (300 MHz, $CDCl_3$) δ ppm 0.91 (br. s., 9H), 1.04-1.35 (m, 2H), 1.79 (br. s., 1H), 1.99 (br. s., 1H), 3.38-3.84 (m, 2H), 3.97-4.29 (m, 4H), 4.41 (d, J=17.8 Hz, 1H), 4.66 (br. s., 1H), 4.86 (br. s., 1H), 6.65 (br. s., 1H), 7.26 (br. s., 4H), 7.47 (br. s., 1H), 9.56 (br. s., 1H).

Example 228

3-Bicyclo[2.2.1]hept-2-yl-2-[4-(2,6-difluoro-phenoxy)-2-oxo-2,5-dihydro-pyrrol-1-yl]-N-[1-(2-hydroxy-2-methyl-propyl)-1H-pyrazol-3-yl]-propionamide

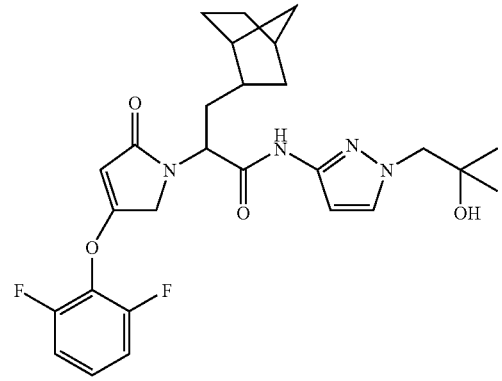

In a flask under argon was placed dichloromethane (25 mL) and to this was added a 2M solution of oxalyl chloride in dichloromethane (4.0 mL, 8.0 mmol). The mixture was then cooled to −78° C. and then slowly treated with dimethyl sulfoxide (846 µL, 11.92 mmol) and gas evolution occurred. The mixture was stirred at −78° C. for 20 min. After this time, a solution of bicyclo[2.2.1]hept-2-yl-methanol (505 mg, 4.0 mmol) in dichloromethane (15 mL) was added dropwise. The mixture was stirred at −78° C. for another 15 min and then triethylamine (2.2 mL, 15.6 mmol) was added and the reaction was slowly warmed to 0° C. The mixture was then quenched with a 1M aqueous sodium bisulfate solution (50 mL) and extracted with dichloromethane (3×20 mL). The organic layers were combined and dried over magnesium sulfate, filtered and concentrated in vacuo. Purification by AnaLogix IntelliFlash flash chromatography (12 g column, 3% ethyl acetate/hexanes to 40% ethyl acetate/hexanes) afforded slightly impure bicyclo[2.2.1]heptane-2-carbaldehyde (512 mg).

In a round bottom flask was placed N-(benzyloxycarbonyl)-α-phosphonoglycine methyl ester (2.05 g, 6.18 mmol) in dichloromethane (5 mL) and cooled to 0° C. in an ice bath. To this mixture was then added slowly 1,8-diazabicyclo[5.4.0]undec-7-ene (801 μL, 5.36 mmol) and it was stirred at 0° C. for 20 min. The mixture was then treated with a solution of bicyclo[2.2.1]heptane-2-carbaldehyde (512 mg, 4.12 mmol) in dichloromethane (5 mL). After the addition was complete, the mixture was allowed to warm to 25° C. and stirred overnight. The mixture was concentrated in vacuo and then dissolved in ethyl acetate (50 mL) and washed with a saturated aqueous ammonium chloride solution (2×25 mL). The organic layer was dried over sodium sulfate, filtered and concentrated in vacuo. Purification by AnaLogix IntelliFlash chromatography (25 g column, 15% ethyl acetate/hexanes to 34% ethyl acetate/hexanes) afforded 2-benzyloxycarbonylamino-3-bicyclo[2.2.1]hept-2-yl-acrylic acid methyl ester (491 mg, 36%) as a clear colorless oil.

In a flask was placed 2-benzyloxycarbonylamino-3-bicyclo[2.2.1]hept-2-yl-acrylic acid methyl ester (491 mg, 1.49 mmol) and methanol (15 mL). To this mixture added 10% palladium on activated carbon (60 mg) and the flask was fitted with a balloon filled with hydrogen. The mixture was allowed to stir at 25° C. for 1 h and then filtered through celite and concentrated in vacuo to afford 2-amino-3-bicyclo[2.2.1]hept-2-yl-propionic acid methyl ester (206 mg, 70%) as a white solid.

In a round bottom flask was placed 2-amino-3-bicyclo[2.2.1]hept-2-yl-propionic acid methyl ester (206 mg, 1.04 mmol), N,N-diisopropylethylamine (390 μL, 2.24 mmol) and 4-bromo-3-(2,6-difluoro-phenoxy)-but-2-enoic acid ethyl ester (prepared as in Example 36, 390 mg, 2.24 mmol) in acetonitrile (10 mL). This mixture was then split into two 5 mL portions and placed in two sealed microwave reaction tubes and heated in a microwave reactor at 140° C. for 1 h. The contents of the two reaction tubes were combined, concentrated in vacuo and diluted with dichloromethane (20 mL) and washed with a 1N aqueous hydrochloric acid solution (10 mL), a saturated sodium bicarbonate solution (10 mL), dried over magnesium sulfate, filtered and concentrated in vacuo. Purification by AnaLogix IntelliFlash flash chromatography (12 g column, 15% ethyl acetate/hexanes to 30% ethyl acetate/hexanes) afforded 3-bicyclo[2.2.1]hept-2-yl-2-[4-(2,6-difluoro-phenoxy)-2-oxo-2,5-dihydro-pyrrol-1-yl]-propionic acid methyl ester (87 mg, 15%) as a yellow oil.

In a flask was placed 3-bicyclo[2.2.1]hept-2-yl-2-[4-(2,6-difluoro-phenoxy)-2-oxo-2,5-dihydro-pyrrol-1-yl]-propionic acid methyl ester (87 mg, 0.22 mmol) dissolved in tetrahydrofuran (3 mL). To this mixture at 25° C. was added a solution of lithium hydroxide monohydrate (19 mg, 0.44 mmol) in water (3 mL) and stirred for 1 h at 25° C. The mixture was then treated with a 1N aqueous hydrochloric acid solution to pH=2 and extracted with ethyl acetate (3×20 mL). The combined organic layers were dried over magnesium sulfate, filtered and concentrated in vacuo to afford 3-bicyclo[2.2.1]hept-2-yl-2-[4-(2,6-difluoro-phenoxy)-2-oxo-2,5-dihydro-pyrrol-1-yl]-propionic acid (73 mg, 87%) as a yellow solid.

In a round bottom flask under argon was placed 3-bicyclo[2.2.1]hept-2-yl-2-[4-(2,6-difluoro-phenoxy)-2-oxo-2,5-dihydro-pyrrol-1-yl]-propionic acid (73 mg, 0.19 mmol) in dichloromethane (5 mL). To this mixture was added 1-(3-dimethylaminopropyl)-3-ethylcarbodiimide (38 μL, 0.21 mmol) and 1-hydoxybenzotriazole (27 mg, 0.20 mmol) and was stirred at 25° C. for 2 h. After this time period, 1-(3-amino-pyrazol-1-yl)-2-methyl-propan-2-ol (prepared as in US20080021032, Example 80, 36 mg, 0.23 mmol) was added and stirred for 16 h at 25° C. After this time, the mixture was diluted with dichloromethane (10 mL) and washed with a 1N aqueous hydrochloric acid solution (10 mL), water (10 mL), a saturated aqueous sodium bicarbonate solution (10 mL) and a saturated aqueous solution of sodium chloride (10 mL), dried over magnesium sulfate, filtered and concentrated in vacuo. Purification by AnaLogix IntelliFlash flash chromatography (12 g column, 40% ethyl acetate/hexanes to 80% ethyl acetate/hexanes) afforded 3-bicyclo[2.2.1]hept-2-yl-2-[4-(2,6-difluoro-phenoxy)-2-oxo-2,5-dihydro-pyrrol-1-yl]-N-[1-(2-hydroxy-2-methyl-propyl)-1H-pyrazol-3-yl]-propionamide (40 mg, 40%) as a light orange solid as a mixture of diastereomers: HR-ES-MS m/z calculated for $C_{27}H_{32}N_4O_4F_2$ [M+H]$^+$ 515.2465, observed 515.2464; $^1$H NMR (400 MHz, DMSO-d$_6$) δ ppm 1.05 (br. s., 3H), 1.06 (br. s., 3H), 1.10-2.10 (m, 11H), 2.15 (br. s., 2H), 3.89 (s, 2H), 4.28 (d, J=19.3 Hz, 1H), 4.57-4.65 (m, 1H), 4.67 (s, 1H), 472-486 (2×m, 1H), 5.04 (s, 1H), 6.41-6.49 (m, 1H), 7.29-7.51 (m, 3H), 7.54 (s, 1H), 10.81 (2×s, 1H).

Example 229

3-bicyclo[2.2.1]hept-7-yl-2-[4-(2-chloro-phenoxy)-2-oxo-2,5-dihydro-pyrrol-1-yl]-N-[1-(2-hydroxy-2-methyl-propyl)-1H-pyrazol-3-yl]-propionamide

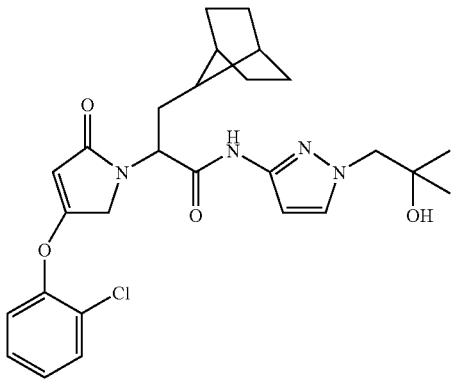

Lithium metal (78 mg, 11.2 mmol) was scraped under a tetrahydrofuran solution to remove the coating and then added to a solution of 4,4'-tertbutyl biphenyl (2.67 g, 10.02 mmol) in tetrahydrofuran (15 mL) under argon. The mixture was cooled to 0° C. and a blue-green color appeared over time. After 3 h, all the lithium metal was dissolved and the mixture was cannulated into a −78° C. mixture of 7-bromo-bicyclo[2.2.1]heptane (1.0 g, 5.71 mmol) in tetrahydrofuran (5 mL). The mixture turned colorless and then developed a red color and stirred at −78° C. for 30 min. The mixture was then quickly poured over freshly crushed dry ice. The resulting yellow mixture was allowed to warm to 25° C. and concentrated in vacuo. The residue was dissolved in diethyl ether (30 mL) and extracted with a 1N aqueous sodium hydroxide solution (2×15 mL). The combined aqueous extracts were acidified with concentrated hydrochloric acid and extracted with diethyl ether (3×10 mL). The combined organic layers were washed with a saturated aqueous solution of sodium chloride, dried over magnesium sulfate, filtered and concentrated in vacuo to afford bicyclo[2.2.1]hept-7-yl-acetic acid (554 mg, 63%)

In a flask was placed bicyclo[2.2.1]hept-7-yl-acetic acid (554 mg, 3.95 mmol), diethyl ether (20 mL) and methanol (5 mL) and cooled to 0° C. in an ice bath. The mixture was then treated with a 2M solution of (trimethylsilyl)diazomethane in diethyl ether (3.95 mL, 7.9 mmol) dropwise. After the addition was complete, the mixture was warmed to 25° C. and stirred for 1 h. The mixture was concentrated in vacuo to afford bicyclo[2.2.1]hept-7-yl-acetic acid methyl ester (theoretical yield 3.95 mmol) which was used on crude. Bicyclo[2.2.1]hept-7-yl-acetic acid methyl ester (3.95 mmol) in diethyl ether (10 mL) was added dropwise to a stirred suspension of lithium aluminum hydride (224 mg, 5.9 mmol) in diethyl ether (20 mL) cooled to 0° C. The mixture was stirred for an additional 3 h at 0° C. and quenched with a saturated sodium sulfate solution (15 mL), extracted with diethyl ether (3×20 mL). The combined organics were dried over sodium sulfate, concentrated in vacuo and purified by AnaLogix IntelliFlash flash chromatography (12 g column, 20% ethyl acetate/hexanes to 40% ethyl acetate/hexanes) to afford bicyclo[2.2.1]hept-7-yl-methanol (180 mg, 36%).

In a flask under argon was placed dichloromethane (10 mL) and a 2M solution of oxalyl chloride in dichloromethane (1.43 mL, 2.85 mmol) cooled to −78° C. To this mixture was slowly added dimethyl sulfoxide (303 µL, 4.26 mmol) and gas evolution occurred. The mixture was stirred at −78° C. for 30 min. After this time, a solution of bicyclo[2.2.1]hept-7-yl-methanol (180 mg, 1.43 mmol) in dichloromethane (5 mL) was added dropwise. The mixture was stirred at −78° C. for another 15 min and triethylamine (784 µL, 5.58 mmol) was added and the reaction was slowly warmed to 0° C. and stirred for 1 h. After this time, the mixture was quenched with a 1M aqueous sodium bisulfate solution (15 mL) and extracted with dichloromethane (3×10 mL). The combined organic layers were dried over magnesium sulfate, filtered and concentrated in vacuo. Purification by AnaLogix IntelliFlash flash chromatography system (4 g column, 10% ethyl acetate/hexanes) afforded bicyclo[2.2.1]heptane-7-carbaldehyde (170 mg, 96%).

In a round bottom flask was placed N-(benzyloxycarbonyl)-α-phosphonoglycine methyl ester (680 mg, 2.05 mmol) in dichloromethane (5 mL) and cooled to 0° C. in an ice bath. To this mixture was added slowly 1,8-diazabicyclo[5.4.0]undec-7-ene (266 µL, 1.78 mmol) and stirred at 0° C. for 20 min. The mixture was treated with a solution of bicyclo[2.2.1]heptane-7-carbaldehyde (170 mg, 1.36 mmol) in dichloromethane (5 mL). After the addition was complete, the mixture was allowed to warm to 25° C. and stirred overnight. The mixture was concentrated in vacuo and the residue taken up in ethyl acetate (50 mL) and washed with a saturated aqueous ammonium chloride solution (2×25 mL). The organic layer was dried over sodium sulfate and concentrated in vacuo. Purification by AnaLogix IntelliFlash flash chromatography (4 g column, 5% ethyl acetate/hexanes to 20% ethyl acetate/hexanes) afforded 2-benzyloxycarbonylamino-3-bicyclo[2.2.1]hept-7-yl-acrylic acid methyl ester (150 mg, 33%) as a clear colorless oil.

In a flask was placed 2-benzyloxycarbonylamino-3-bicyclo[2.2.1]hept-7-yl-acrylic acid methyl ester (130 mg, 0.40 mmol) and methanol (5 mL). To the mixture was added 10% palladium on activated carbon (15 mg) and the flask was fitted with a balloon filled with hydrogen. The mixture was allowed to stir at 25° C. for 1 h. After such time, the mixture was filtered through celite and concentrated in vacuo to afford crude 2-amino-3-bicyclo[2.2.1]hept-7-yl-propionic acid methyl ester (100 mg) which was used without purification.

A suspension of 2-amino-3-bicyclo[2.2.1]hept-7-yl-propionic acid methyl ester (78 mg, 0.40 mmol (theoretical)) in acetonitrile (3 mL) was treated with N,N-diisopropylethylamine (103 µL, 0.59 mmol) and (E)-4-bromo-3-(2-chloro-phenoxy)-but-2-enoic acid ethyl ester (prepared as in Example 61, 125 mg, 0.40 mmol). The mixture was heated at 100° C. for 2 h. After this time, the mixture was concentrated in vacuo and then taken up in dichloromethane and washed with water (10 mL), a saturated sodium bicarbonate solution (10 mL), dried over magnesium sulfate, filtered and concentrated in vacuo. Purification by AnaLogix IntelliFlash flash chromatography (4 g column, 5% ethyl acetate/hexanes to 30% ethyl acetate/hexanes) afforded 4-(2-bicyclo[2.2.1]hept-7-yl-1-methoxycarbonyl-ethylamino)-3-(2-chloro-phenoxy)-but-2-enoic acid ethyl ester (83 mg) as a light yellow oil.

A solution of 4-(2-bicyclo[2.2.1]hept-7-yl-1-methoxycarbonyl-ethylamino)-3-(2-chloro-phenoxy)-but-2-enoic acid ethyl ester (83 mg, 0.19 mmol) in acetonitrile (2 mL) was placed in a sealed microwave reaction tube and heated in a microwave reactor at 150° C. for 6 h. The mixture was concentrated in vacuo and purified by AnaLogix IntelliFlash flash chromatography (4 g column, 5% ethyl acetate/hexanes to 50% ethyl acetate/hexanes) which afforded 3-bicyclo[2.2.1]hept-7-yl-2-[4-(2-chloro-phenoxy)-2-oxo-2,5-dihydro-pyrrol-1-yl]-propionic acid methyl ester (35 mg, 23%, over two steps) as a yellow oil.

In a flask was placed 3-bicyclo[2.2.1]hept-7-yl-2-[4-(2-chloro-phenoxy)-2-oxo-2,5-dihydro-pyrrol-1-yl]-propionic acid methyl ester (35 mg, 0.089 mmol) in tetrahydrofuran (2 mL). To this mixture at 25° C. was added a solution of lithium hydroxide monohydrate (8 mg, 0.18 mmol) in water (2 mL) and stirred for 1.5 h at 25° C. The mixture was treated with a 1N aqueous hydrochloric acid solution to pH=2 and was extracted with ethyl acetate (3×20 mL). The combined organic layers were dried over magnesium sulfate, filtered and concentrated in vacuo to afford 3-bicyclo[2.2.1]hept-7-yl-2-[4-(2-chloro-phenoxy)-2-oxo-2,5-dihydro-pyrrol-1-yl]-propionic acid (32 mg, 97%) as a white solid.

In a round bottom flask under argon was placed 3-bicyclo[2.2.1]hept-7-yl-2-[4-(2-chloro-phenoxy)-2-oxo-2,5-dihydro-pyrrol-1-yl]-propionic acid (32 mg, 0.085 mmol) in dichloromethane (5 mL). To this mixture was added 1-(3-dimethylaminopropyl)-3-ethylcarbodiimide (16 µL, 0.094 mmol) and 1-hydoxybenzotriazole (12 mg, 0.089 mmol) and stirred at 25° C. for 2 h. After this time, 1-(3-amino-pyrazol-1-yl)-2-methyl-propan-2-ol (prepared as in US20080021032, Example 80, 16 mg, 0.102 mmol) was added and stirred for 16 h at 25° C. The reaction was diluted with dichloromethane (10 mL) and washed with a 1N aqueous hydrochloric acid solution (10 mL), water (10 mL), a saturated aqueous sodium bicarbonate solution (10 mL), dried over magnesium sulfate and concentrated in vacuo. Purification by AnaLogix IntelliFlash flash chromatography (4 g column, 20% ethyl acetate/hexanes to 80% ethyl acetate/hexanes) afforded 3-bicyclo[2.2.1]hept-7-yl-2-[4-(2-chloro-phenoxy)-2-oxo-2,5-dihydro-pyrrol-1-yl]-N-[1-(2-hydroxy-2-methyl-propyl)-1H-pyrazol-3-yl]-propionamide (27 mg, 61%) as yellow foam: HR-ES-MS m/z calculated for $C_{27}H_{33}N_4O_4Cl$ [M+H]$^+$ 513.2263, observed 513.2263; $^1$H NMR (300 MHz, CDCl$_3$) δ ppm 1.15 (s, 6H), 1.15-1.31 (m, 4H), 1.43-1.59 (m, 3H), 1.65 (d, J=8.5 Hz, 2H), 1.70-1.87 (m, 1H), 1.90-2.09 (m, 3H), 2.80 (br. s., 1H), 3.93 (s, 2H), 4.16 (d, J=18.1 Hz, 1H), 4.32 (d, J=18.1 Hz, 1H), 4.76 (t, J=7.7 Hz, 1H), 4.89 (s, 1H), 6.70 (s, 1H), 7.17-7.25 (m, 1H), 7.27-7.37 (m, 3H), 7.48 (d, J=8.2 Hz, 1H), 8.74 (br. s., 1H).

Example 230

(S)-2-[4-(2-Chloro-phenoxy)-2-oxo-2,5-dihydro-pyrrol-1-yl]-N-[1-((R)-2,3-dihydroxy-propyl)-1H-pyrazol-3-yl]-4-methoxy-butyramide

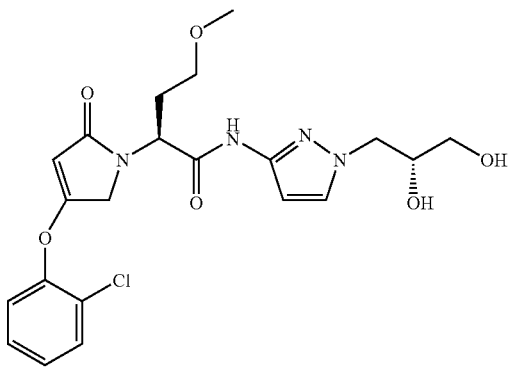

In a flask was placed (S)-2-(9H-fluoren-9-ylmethoxycarbonylamino)-4-methoxy-butyric acid (500 mg, 1.41 mmol), diethyl ether (20 mL) and methanol (5 mL) and cooled to 0° C. in an ice bath. To this mixture was added a 2M solution of (trimethylsilyl)diazomethane in diethyl ether (1.41 mL, 2.82 mmol) dropwise. The mixture was stirred and warmed to 25° C. The mixture was then concentrated to afford (S)-2-(9H-fluoren-9-ylmethoxycarbonylamino)-4-methoxy-butyric acid methyl ester (489 mg, 94%) as a white solid.

A mixture of (S)-2-(9H-fluoren-9-ylmethoxycarbonylamino)-4-methoxy-butyric acid methyl ester (200 mg, 0.54 mmol) in acetonitrile (5 mL) was treated with N,N-diisopropylethylamine (94 µL, 0.54 mmol) and heated for 2 h at 50° C. To this mixture was added another portion of N,N-diisopropylethylamine (100 µL) and heated to 70° C. for 8 h. After this time, the mixture was treated with (E)-4-bromo-3-(2-chloro-phenoxy)-but-2-enoic acid ethyl ester (prepared as in Example 61, 172 mg, 0.54 mmol) and the temperature raised to 100° C. and stirred for 2 h. Purification by AnaLogix IntelliFlash flash chromatography (8 g column, 5% ethyl acetate/hexanes to 40% ethyl acetate/hexanes) afforded 3-(2-chloro-phenoxy)-4-((S)-3-methoxy-1-methoxycarbonyl-propylamino)-but-2-enoic acid ethyl ester (112 mg).

A solution of 3-(2-chloro-phenoxy)-4-((S)-3-methoxy-1-methoxycarbonyl-propylamino)-but-2-enoic acid ethyl ester (112 mg, 0.29 mmol) in acetonitrile (2 mL) was placed in a sealed microwave reaction tube and heated in a microwave reactor at 130° C. for 2 h, 150° C. for 2 h, and 160° C. for 3 h. The mixture was then concentrated in vacuo and purified by AnaLogix IntelliFlash flash chromatography (8 g column, 20% ethyl acetate/hexanes to 70% ethyl acetate/hexanes) which afforded (S)-2-[4-(2-chloro-phenoxy)-2-oxo-2,5-dihydro-pyrrol-1-yl]-4-methoxy-butyric acid methyl ester (71 mg, 39% over two steps) as a clear colorless oil.

In a flask was placed (S)-2-[4-(2-chloro-phenoxy)-2-oxo-2,5-dihydro-pyrrol-1-yl]-4-methoxy-butyric acid methyl ester (71 mg, 0.21 mmol) in tetrahydrofuran (3 mL). To this mixture at 25° C. was added a solution of lithium hydroxide monohydrate (18 mg, 0.42 mmol) in water (3 mL) and stirred for 1.5 h at 25° C. The mixture was then treated with a 1N aqueous hydrochloric acid solution to pH=2 and extracted with ethyl acetate (3×20 mL). The combined organic layers were dried over magnesium sulfate, filtered and concentrated in vacuo to afford (S)-2-[4-(2-chloro-phenoxy)-2-oxo-2,5-dihydro-pyrrol-1-yl]-4-methoxy-butyric acid (32 mg, 98%) as a light yellow solid.

In a round bottom flask under argon was placed (S)-2-[4-(2-chloro-phenoxy)-2-oxo-2,5-dihydro-pyrrol-1-yl]-4-methoxy-butyric acid (62 mg, 0.19 mmol) in dichloromethane (5 mL). To this mixture was added 1-(3-dimethylaminopropyl)-3-ethylcarbodiimide (37 µL, 0.21 mmol) and 1-hydoxybenzotriazole (27 mg, 0.20 mmol) and stirred at 25° C. for 2 h. After this time period, 1-((R)-2,2-dimethyl-[1,3]dioxolan-4-yl-methyl)-1H-pyrazol-3-ylamine (prepared as in Example 49, 45 mg, 0.23 mmol) was added and stirred for 16 h at 25° C. After this time, the reaction was diluted with dichloromethane (10 mL) and washed with a 1N aqueous hydrochloric acid solution (10 mL), water (10 mL) and a saturated aqueous sodium bicarbonate solution (10 mL), dried over magnesium sulfate, filtered and concentrated in vacuo. Purification by AnaLogix IntelliFlash flash chromatography (4 g column, 50% ethyl acetate/hexanes to 100% ethyl acetate/hexanes) afforded (S)-2-[4-(2-chloro-phenoxy)-2-oxo-2,5-dihydro-pyrrol-1-yl]-N-[1-((R)-2,2-dimethyl-[1,3]dioxolan-4-yl-methyl)-1H-pyrazol-3-yl]-4-methoxy-butyramide (26 mg, 27%) as a colorless oil.

In a round bottom flask under argon was placed (S)-2-[4-(2-chloro-phenoxy)-2-oxo-2,5-dihydro-pyrrol-1-yl]-N-[1-((R)-2,2-dimethyl-[1,3]dioxolan-4-yl-methyl)-1H-pyrazol-3-yl]-4-methoxy-butyramide (26 mg, 0.051 mmol) dissolved in methanol (3 mL). This mixture was treated with p-toluenesulfonic acid monohydrate (1.5 mg, 0.008 mmol) and stirred at 25° C. for 16 h. After this time period, the mixture was concentrated in vacuo and purified by AnaLogix IntelliFlash flash chromatography (4 g column, 100% ethyl acetate to 5% methanol/ethyl acetate) to afford (S)-2-[4-(2-chloro-phenoxy)-2-oxo-2,5-dihydro-pyrrol-1-yl]-N-[1-((R)-2,3-dihydroxy-propyl)-1H-pyrazol-3-yl]-4-methoxy-butyramide (22 mg, 92%) as a light yellow foam: HR-ES-MS m/z calculated for $C_{21}H_{25}N_4O_6Cl$ [M+H]$^+$ 465.1536, observed 465.1536; $^1$H NMR (300 MHz, DMSO-d$_6$) δ ppm 2.06 (br. s., 2H), 3.20 (s, 3H), 3.22-3.31 (m, 4H), 3.67-3.78 (m, 1H), 3.78-3.90 (m, 1H), 4.07 (dd, J=13.6, 3.9 Hz, 1H), 4.27 (d, J=18.4 Hz, 1H), 4.50 (d, J=18.4 Hz, 1H), 4.69 (t, J=5.4 Hz, 1H), 4.78 (s, 1H), 4.79-4.88 (m, 1H), 4.92 (d, J=5.4 Hz, 1H), 6.39 (d, J=2.1 Hz, 1H), 7.30-7.40 (m, 1H), 7.41-7.55 (m, 3H), 7.64 (d, J=7.2 Hz, 1H), 10.64 (s, 1H).

Example 231

(S)-3-Cyclohexyl-2-[4-(3,4-dichloro-phenylamino)-2-oxo-2,5-dihydro-pyrrol-1-yl]-N-[1-(2-hydroxy-2-methyl-propyl)-1H-pyrazol-3-yl]-propionamide

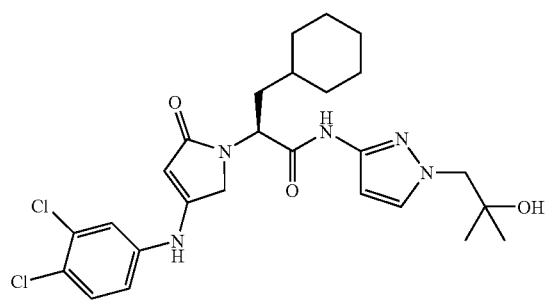

A solution of (S)-3-cyclohexyl-2-(2,4-dioxo-pyrrolidin-1-yl)-N-[1-(2-hydroxy-2-methyl-propyl)-1-pyrazol-3-yl]-propionamide (prepared as in Example 24, 289 mg, 0.70 mmol) and 3,4-dichloloaniline (119 mg, 0.73 mmol) in benzene (12.5 mL) was heated at reflux in the presence of a catalytic amount of p-toluenesulfonic acid (16 mg, 0.09 mmol) for 16 h. The reaction mixture was cooled to 25° C., and diluted with petroleum ether which resulted in precipitation of the product. The solid product was filtered and washed with dichloromethane to afford (S)-3-cyclohexyl-2-[4-(3,4-dichlorophenylamino)-2-oxo-2,5-dihydro-pyrrol-1-yl]-N-[1-(2-hydroxy-2-methyl-propyl)-1H-pyrazol-3-yl]-propionamide (105 mg, 28%) as a white powder: HR-ES-MS m/z calculated for $C_{26}H_{33}Cl_2N_5O_3$ [M+H]$^+$ 534.2036, observed 534.2033; $^1$H NMR (300 MHz, DMSO-d$_6$) δ ppm 0.81-1.01 (m, 2H), 1.04 (br. s., 3H), 1.06 (br. s., 3H), 1.08-1.29 (m, 4H), 1.52-1.86 (m, 7H), 3.89 (s, 2H), 4.04 (d, J=17.3 Hz, 1H), 4.52 (d, J=17.3 Hz, 1H), 4.87 (dd, J=9.7, 5.7 Hz, 1H), 5.37 (s, 1H), 6.43 (d, J=1.8 Hz, 1H), 7.15 (dd, J=8.8, 2.1 Hz, 1H), 7.28 (d, J=2.1 Hz, 1H), 7.49-7.57 (m, 2H), 9.46 (s, 1H), 10.73 (s, 1H).

Example 232

(S)-3-cyclohexyl-N-[1-(2-hydroxy-2-methyl-propyl)-1H-pyrazol-3-yl]-2-(4-isopropylamino-2-oxo-2,5-dihydro-pyrrol-1-yl)-propionamide

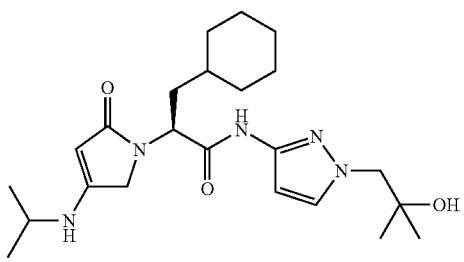

To a stirred solution of (S)-3-cyclohexyl-2-(2,4-dioxo-pyrrolidin-1-yl)-N-[1-(2-hydroxy-2-methyl-propyl)-1H-pyrazol-3-yl]-propionamide (prepared in Example 24, 100 mg, 0.26 mmol) in benzene (5 mL) was added isopropylamine (15 mg, 0.26 mmol) and glacial acetic acid (1 mL). The mixture was stirred at 100° C. for 30 min. The reaction mixture was concentrated in vacuo and the crude product obtained was purified by ISCO flash chromatography (Teledyne Isco RediSep Flash Column 40 g, 97:3 ethyl acetate/methanol) to afford, (S)-3-cyclohexyl-N-[1-(2-hydroxy-2-methyl-propyl)-1H-pyrazol-3-yl]-2-(4-isopropylamino-2-oxo-2,5-dihydro-pyrrol-1-yl)-propionamide (30.0 mg, 27%) as an orange solid: LR-ES-MS m/z calculated for $C_{23}H_{37}N_5O_3$ [M]$^+$ 431, observed 432 [M+H]$^+$; $^1$H NMR (300 MHz, DMSO-d$_6$) δ ppm 0.76-1.02 (m, 3H), 1.04 (br. s., 3H), 1.05 (br. s., 3H), 1.07-1.25 (m, 10H), 1.49-1.83 (m, 6H), 3.24-3.33 (m, 1H), 3.74 (d, J=16.8 Hz, 1H), 3.88 (s, 2H), 4.24 (d, J=16.8 Hz, 1H), 4.41 (s, 1H), 4.67 (s, 1H), 4.71-4.82 (m, 1H), 6.41 (s, 1H), 6.75 (d, J=7.2 Hz, 1H), 7.51 (s, 1H), 10.57 (s, 1H).

Example 233

(S)-3-cyclohexyl-2-[4-(ethyl-methyl-amino)-2-oxo-2,5-dihydro-pyrrol-1-yl]-N-[1-(2-hydroxy-2-methyl-propyl)-1H-pyrazol-3-yl]-propionamide

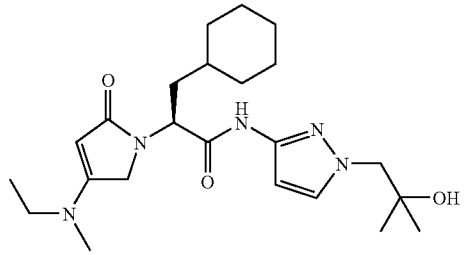

To a stirred solution of (S)-3-cyclohexyl-2-(2,4-dioxo-pyrrolidin-1-yl)-N-[1-(2-hydroxy-2-methyl-propyl)-1H-pyrazol-3-yl]-propionamide (prepared in Example 24, 100 mg, 0.26 mmol) in benzene (5 mL) was added N-ethylmethylamine (75 mg, 1.28 mmol) and glacial acetic acid (1 mL). The mixture was stirred at 100° C. for 30 min. The reaction mixture was concentrated in vacuo and the crude product obtained was purified by ISCO flash chromatography (Teledyne Isco RediSep Flash Column 40 g; 97:3 ethyl acetate/methanol) to afford, (S)-3-cyclohexyl-2-[4-(ethyl-methyl-amino)-2-oxo-2,5-dihydro-pyrrol-1-yl]-N-[1-(2-hydroxy-2-methyl-propyl)-1H-pyrazol-3-yl]-propionamide (44 mg, 40%) as a yellow solid: LR-ES-MS m/z calculated for $C_{23}H_{37}N_5O_3$ [M]$^+$ 431, observed 432 [M+H]$^+$; $^1$H NMR (300 MHz, DMSO-d$_6$) δ ppm 0.78-0.99 (m, 2H), 0.99-1.24 (m, 14H), 1.50-1.84 (m, 6H), 2.80 (s, 3H), 3.18 (q, J=7.0 Hz, 2H), 3.88 (s, 2H), 3.96 (d, J=16.9 Hz, 1H), 4.38 (d, J=16.9 Hz, 1H), 4.48 (s, 1H), 4.67 (s, 1H), 4.80 (dd, J=10.4, 5.0 Hz, 1H), 6.42 (d, J=1.8 Hz, 1H), 7.51 (d, J=1.8 Hz, 1H), 10.57 (s, 1H).

Example 234

(S)-3-cyclopentyl-N-[1-(2-hydroxy-2-methyl-propyl)-1H-pyrazol-3-yl]-2-(4-isopropylamino-2-oxo-2,5-dihydro-pyrrol-1-yl)-propionamide

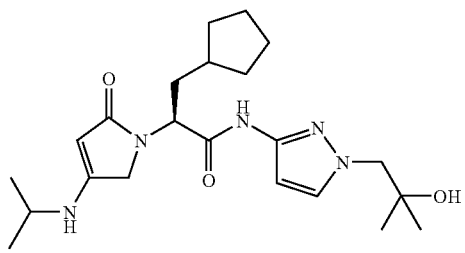

To a stirred solution of (S)-3-cyclopentyl-2-(2,4-dioxo-pyrrolidin-1-yl)-N-[1-(2-hydroxy-2-methyl-propyl)-1H-pyrazol-3-yl]-propionamide (prepared as in Example 15, 100 mg, 0.27 mmol) in benzene (5 mL) was added isopropylamine (16 mg, 0.27 mmol) and glacial acetic acid (1 mL). The mixture was stirred at 100° C. for 30 min. The reaction mixture was concentrated in vacuo and the crude product obtained was purified by ISCO flash chromatography (Teledyne Isco RediSep Flash Column 40 g; 95:5 ethyl acetate/methanol) to afford, (S)-3-cyclopentyl-N-[1-(2-hydroxy-2-methyl-propyl)-1H-pyrazol-3-yl]-2-(4-isopropylamino-2-oxo-2,5-dihydro-pyrrol-1-yl)-propionamide (40 mg, 37%) as a yellow solid: LR-ES-MS m/z calculated for $C_{22}H_{35}N_5O_3$ [M]$^+$ 417, observed 418 [M+H]$^+$; $^1$H NMR (300 MHz, DMSO-d$_6$) δ ppm 1.04 (br. s., 3H), 1.05 (br. s., 3H), 1.10 (d, J=6.3 Hz, 6H), 1.15-1.34 (m, 2H), 1.39-1.82 (m, 9H), 3.24-3.33 (m, 1H), 3.77 (d, J=16.9 Hz, 1H), 3.88 (s, 2H), 4.24 (d, J=16.9 Hz, 1H), 4.41 (s, 1H), 4.67 (s, 1H), 4.66-4.74 (m, 1H), 6.42 (d, J=2.1 Hz, 1H), 6.76 (d, J=7.2 Hz, 1H), 7.51 (d, J=2.1 Hz, 1H), 10.60 (s, 1H).

Example 235

(S)-2-{4-[3-(2-Hydroxy-2-methyl-propyl)-phenoxy]-2-oxo-2,5-dihydro-pyrrol-1-yl}-4-methyl-pentanoic acid (1-methyl-1H-pyrazol-3-yl)-amide

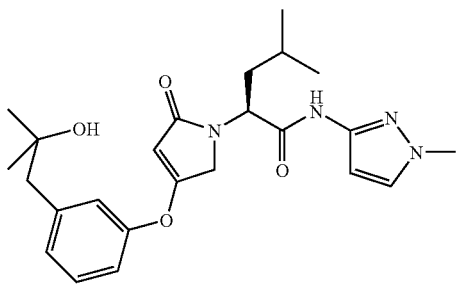

To a solution of methyl magnesium bromide (3 M, 12 mL, 36.06 mmol) cooled to 0° C. was added tetrahydrofuran (10 mL) and (3-hydroxy-phenyl)-acetic acid methyl ester (1 g, 6.01 mmol) as a solution in tetrahydrofuran (5 mL). The resulting mixture was warmed to room temperature stirred for 30 min and then poured carefully into a biphasic mixture of ethyl acetate and water. The water layer was made acidic (pH=1) with 1N aqueous hydrochloric acid and extracted twice with ethyl acetate. The combined organic phases were dried over sodium sulfate, filtered and concentrated in vacuo which afforded 3-(2-hydroxy-2-methyl-propyl)-phenol (1 g, 100%) as a white solid.

A mixture of 3-(2-hydroxy-2-methyl-propyl)-phenol (1.00 g, 6.01 mmol), ethyl-2-butynoate (4.00 g, 36.06 mol) and potassium carbonate (0.830 g, 6.01 mmol) in tetrahydrofuran (20 mL) in a sealed tube was heated to 80° C. for 3.75 h. The reaction mixture was then cooled and filtered. The solids were washed with a small amount of tetrahydrofuran and the combined filtrate was collected and concentrated in vacuo. The residue was purified by flash column chromatography (silica gel, 0% to 30% ethyl acetate/hexanes) to afford (E)-3-[3-(2-hydroxy-2-methyl-propyl)-phenoxy]-but-2-enoic acid ethyl ester (1.41 g, 84%) as a colorless oil.

To a stirred mixture of (E)-3-[3-(2-hydroxy-2-methyl-propyl)-phenoxy]-but-2-enoic acid ethyl ester (1.35 g, 4.87 mmol) in dichloromethane (85 mL), was added N-bromosuccinimide (0.94 g, 5.57 mmol) and 2,2'-azobis(2,4'-dimethylvaleronitrile) (0.126 g, 0.51 mmol) under a nitrogen atmosphere. The mixture was stirred at reflux for 2 h then cooled to room temperature and concentrated in vacuo. The residue was purified by flash column chromatography (silica gel, 0-30% ethyl acetate/hexanes). The intermediate obtained from the above purification was dissolved in acetonitrile (50 mL) and treated with (L)-leucine methyl ester hydrochloride (0.51 g, 5.32 mmol) and N,N-diisopropylethylamine (1.8 mL, 9.85 mmol). The resulting mixture was sealed in a tube and heated at 90° C. for 3.5 h, then cooled to room temperature and partitioned between ethyl acetate and water. The organic phase was collected, dried over sodium sulfate, filtered and concentrated in vacuo. The residue obtained was dissolved in tetrahydrofuran (5 mL) and transferred to an Emry Optimizer microwave reaction vessel and heated in a microwave reactor at 160° C., for 4 h. The mixture was then cooled and concentrated in vacuo. The resulting residue was purified by flash column chromatography (silica gel, 30-100% ethyl acetate/hexanes) to afford, (S)-2-{4-[3-(2-hydroxy-2-methyl-propyl)-phenoxy]-2-oxo-2,5-dihydro-pyrrol-1-yl}-4-methyl-pentanoic acid methyl ester (0.49 g, 27%) as a colorless oil.

To a solution of (S)-2-{4-[3-(2-hydroxy-2-methyl-propyl)-phenoxy]-2-oxo-2,5-dihydro-pyrrol-1-yl}-4-methyl-pentanoic acid methyl ester (0.480 g, 1.28 mmol) in tetrahydrofuran (10 mL) and water (2 mL) was added lithium hydroxide monohydrate (0.058 g 1.35 mmol). The mixture was stirred at room temperature for 2 h. The reaction mixture was poured into water and washed with diethyl ether. The aqueous phase was acidified with 1N aqueous hydrochloric acid solution (pH<2), and extracted with ethyl acetate. The combined organic layers were dried over sodium sulfate, filtered and concentrated in vacuo. The residue was precipitated from dichloromethane with an excess of hexanes to afford (S)-2-{4-[3-(2-hydroxy-2-methyl-propyl)-phenoxy]-2-oxo-2,5-dihydro-pyrrol-1-yl}-4-methyl-pentanoic acid (0.410 g, 89%), as an off-white solid.

To a solution of (S)-2-{4-[3-(2-hydroxy-2-methyl-propyl)-phenoxy]-2-oxo-2,5-dihydro-pyrrol-1-yl}-4-methyl-pentanoic acid (0.100 g, 0.28 mmol) in dichloromethane (10 mL) was added 1-methyl-1H-pyrazol-3-ylamine (0.040 g, 0.41 mmol), N,N-diisopropylethylamine (0.110 g, 0.85 mmol) and benzotriazol-1-yl-oxy-tris(dimethylamino)phosphonium hexafluorophosphate (0.180 g, 0.41 mmol) at 0° C. The mixture was allowed to slowly warm up to room temperature and then stirred for 2 h. The mixture was partioned between ethyl acetate and water. The organic layer was then collected and concentrated in vacuo. The residue was purified by flash column chromatography (silica gel 30% to 100% ethyl acetate/hexanes) which afforded (S)-2-{4-[3-(2-hydroxy-2-methyl-propyl)-phenoxy]-2-oxo-2,5-dihydro-pyrrol-1-yl}-4-methyl-pentanoic acid (1-methyl-1H-pyrazol-3-yl)-amide (0.075 g, 62%) as a white solid: HR-ES-MS m/z calculated for $C_{24}H_{32}N_4O_4$ [M+H]$^+$ 441.2497, observed 441.2497; $^1$H NMR (300 MHz, CDCl$_3$) δ ppm 0.92-1.01 (m, 6H), 1.24 (s, 6H), 1.40-1.69 (m, 2H), 1.68-1.97 (m, 2H), 2.78 (s, 2H), 3.82 (br. s., 3H), 4.07 (d, J=18.1 Hz, 1H), 4.27 (d, J=17.5 Hz, 1H), 4.79-4.94 (m, 1H), 4.97 (s, 1H), 6.60 (br. s., 1H), 7.07 (br. s., 2H), 7.14 (d, J=7.5 Hz, 1H), 7.30-7.40 (m, 2H), 8.55 (br. s., 1H).

Example 236

(S)-2-{4-[3-(2-Hydroxy-2-methyl-propyl)-phenoxy]-2-oxo-2,5-dihydro-pyrrol-1-yl}-4-methyl-pentanoic acid [1-(2-hydroxy-2-methyl-propyl)-1H-pyrazol-3-yl]-amid

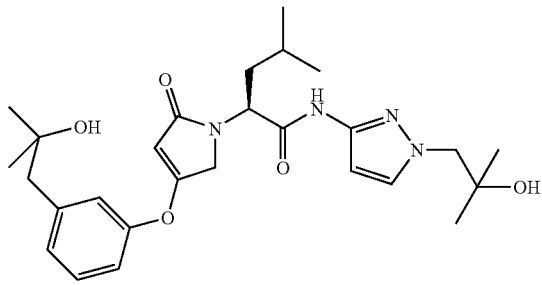

To a solution of (S)-2-{4-[3-(2-hydroxy-2-methyl-propyl)-phenoxy]-2-oxo-2,5-dihydro-pyrrol-1-yl}-4-methyl-pentanoic acid (prepared as in Example 235, 0.159 g, 0.44 mmol) in N,N-dimethylformamide (5 mL) was added 1-(3-amino-pyrazol-1-yl)-2-methyl-propan-2-ol (prepared in U.S. Pat. Appl. US2008021032 Example 80, 0.102 g, 0.66 mmol), N,N-diisopropylethylamine (0.312 g, 2.41 mmol) and benzotriazol-1-yl-oxy-tris(dimethylamino)phosphonium hexafluorophosphate (0.778 g, 1.76 mmol) at 0° C. The mixture was allowed to slowly warm up to room temperature and stirred for 48 h. The mixture was then concentrated in vacuo, the residue taken up in ethyl acetate and washed with aqueous saturated ammonium chloride and brine and then dried over sodium sulfate, filtered and concentrated in vacuo. The residue was purified by ISCO column chromatography (Silicycle 40 g, 10% to 100% ethyl acetate/hexanes) which afforded (S)-2-{4-[3-(2-hydroxy-2-methyl-propyl)-phenoxy]-2-oxo-2,5-dihydro-pyrrol-1-yl}-4-methyl-pentanoic acid [1-(2-hydroxy-2-methyl-propyl)-1H-pyrazol-3-yl]-amide (0.060 g, 30%) as a white solid: HR-ES-MS m/z calculated for $C_{27}H_{38}N_4O_5$ [M+H]$^+$ 499.2915, observed 499.2915; $^1$H NMR (300 MHz, DMSO-$d_6$) δ ppm 0.83-0.97 (m, 6H), 1.06 (br. s., 12H), 1.36-1.63 (m, 2H), 1.66-1.86 (m, 1H), 2.68 (s, 2H), 3.89 (s, 2H), 4.18 (d, J=18.1 Hz, 1H), 4.37 (d, J=1.8 Hz, 1H), 4.57 (d, J=18.1 Hz, 1H), 4.68 (d, J=1.5 Hz, 1H), 4.83 (s, 1H), 4.84-4.94 (m, 1H), 6.44 (s, 1H), 7.07-7.19 (m, 3H), 7.27-7.42 (m, 1H), 7.54 (s, 1H), 10.78 (s, 1H).

Example 237

(S)-2-{4-[3-(2-Hydroxy-2-methyl-propyl)-phenoxy]-2-oxo-2,5-dihydro-pyrrol-1-yl}-4-methyl-pentanoic acid [1-((R)-2,2-dimethyl-[1,3]dioxolan-4-ylmethyl)-1H-pyrazol-3-yl]-amide

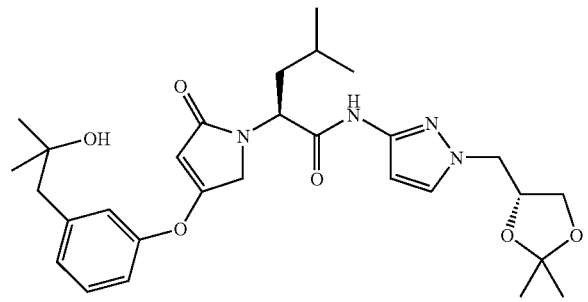

To a solution of (S)-2-{4-[3-(2-hydroxy-2-methyl-propyl)-phenoxy]-2-oxo-2,5-dihydro-pyrrol-1-yl}-4-methyl-pentanoic acid (prepared as in Example 235, 0.159 g, 0.44 mmol) in N,N-dimethylformamide (5 mL) was added 1-((R)-2,2-dimethyl-[1,3]dioxolan-4-yl-methyl)-1H-pyrazol-3-ylamine (prepared as in Example 49, 0.129 g, 0.65 mmol), N,N-diisopropylethylamine (0.312 g, 2.41 mmol) and benzotriazol-1-yl-oxy-tris(dimethylamino)phosphonium hexafluorophosphate (0.778 g, 1.76 mmol) at 0° C. The mixture was allowed to slowly warm up to room temperature and stirred for 48 h. The solvents were then concentrated in vacuo. The residue was dissolved in ethyl acetate and the mixture formed was washed with aqueous saturated ammonium chloride and brine, dried over sodium sulfate, filtered and concentrated in vacuo. The residue was initially purified by flash column chromatography (silica gel 10% to 100% ethyl acetate/hexanes). Then followed by reverse phase HPLC ($C_{18}$, 20×150 mm column and 45-100% water/acetonitrile gradient at a flow rate of 30 mL/min) to afford (S)-2-{4-[3-(2-hydroxy-2-methyl-propyl)-phenoxy]-2-oxo-2,5-dihydro-pyrrol-1-yl}-4-methyl-pentanoic acid [1-((R)-2,2-dimethyl-[1,3]dioxolan-4-ylmethyl)-1H-pyrazol-3-yl]-amide (0.181 g, 76%) as a white solid: HR-ES-MS m/z calculated for $C_{29}H_{40}N_4O_6$ [M+H]$^+$ 541.3021, observed 541.3017; $^1$H NMR (300 MHz, DMSO-$d_6$) δ ppm 0.89 (d, J=6.3 Hz, 3H), 0.93 (d, J=6.3 Hz, 3H), 1.05 (s, 6H), 1.24 (s, 3H), 1.29 (s, 3H), 1.36-1.64 (m, 2H), 1.63-1.80 (m, 1H), 2.67 (s, 2H), 3.73 (dd, J=8.4, 5.9 Hz, 1H), 4.00 (dd, J=8.4, 6.3 Hz, 1H), 4.03-4.14 (m, 2H), 4.17 (d, J=18.4 Hz, 1H), 4.28-4.37 (m, 1H), 4.36 (s, 1H), 4.55 (d, J=18.4 Hz, 1H), 4.82 (s, 1H), 4.87 (dd, J=10.7, 4.7 Hz, 1H), 6.43 (d, J=2.1 Hz, 1H), 7.03-7.17 (m, 3H), 7.24-7.41 (m, 1H), 7.59 (d, J=2.1 Hz, 1H), 10.77 (s, 1H).

Example 238

(S)-2-{4-[3-(2-Hydroxy-2-methyl-propyl)-phenoxy]-2-oxo-2,5-dihydro-pyrrol-1-yl}-4-methyl-pentanoic acid [1-((R)-2,3-dihydroxy-propyl)-1H-pyrazol-3-yl]-amide

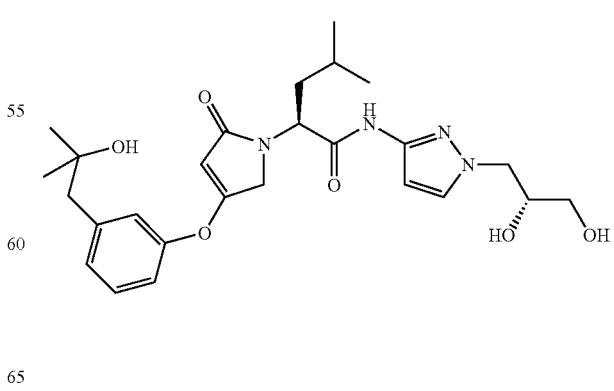

A solution of (S)-2-{4-[3-(2-hydroxy-2-methyl-propyl)-phenoxy]-2-oxo-2,5-dihydro-pyrrol-1-yl}-4-methyl-pentanoic acid [1-((R)-2,2-dimethyl-[1,3]dioxolan-4-ylmethyl)-1H-pyrazol-3-yl]-amide (prepared as in Example 237, 0.175 g, 0.32 mmol) in tetrahydrofuran (5 mL) was treated with hydrochloric acid (1 M, 1 mL). The reaction mixture was stirred at room temperature overnight and then neutralized with saturated sodium bicarbonate. The mixture was extracted with ethyl acetate (2×50 mL). The combined ethyl acetate extracts were dried over sodium sulfate, filtered and concentrated in vacuo which afforded (S)-2-{4-[3-(2-hydroxy-2-methyl-propyl)-phenoxy]-2-oxo-2,5-dihydro-pyrrol-1-yl}-4-methyl-pentanoic acid [1-((R)-2,3-dihydroxy-propyl)-1H-pyrazol-3-yl]-amide (0.097 g, 61%) as a white solid: HR-ES-MS m/z calculated for $C_{26}H_{36}N_4O_6$ $[M+H]^+$ 501.2708, observed 501.2705; $^1$H NMR (300 MHz, DMSO-$d_6$) δ ppm 0.90 (d, J=6.4 Hz, 3H), 0.94 (d, J=6.4 Hz, 3H), 1.06 (s, 6H), 1.36-1.65 (m, 2H), 1.65-1.83 (m, 1H), 2.68 (s, 2H), 3.19-3.33 (m, 2H), 3.78 (d, J=5.1 Hz, 1H), 3.86 (dd, J=13.5, 7.5 Hz, 1H), 4.09 (dd, J=13.5, 3.8 Hz, 1H), 4.18 (d, J=18.4 Hz, 1H), 4.37 (s, 1H), 4.56 (d, J=18.4 Hz, 1H), 4.71 (t, J=5.4 Hz, 1H), 4.83 (s, 1H), 4.87 (dd, J=11.0, 4.7 Hz, 1H), 4.94 (d, J=5.1 Hz, 1H), 6.40 (d, J=2.1 Hz, 1H), 7.06-7.19 (m, 3H), 7.28-7.43 (m, 1H), 7.53 (d, J=2.1 Hz, 1H), 10.75 (s, 1H).

Example 239

(S)-2-{4-[3-(2-Hydroxy-2-methyl-propyl)-phenoxy]-2-oxo-2,5-dihydro-pyrrol-1-yl}-4-methyl-pentanoic acid (1-methyl-1H-pyrazol-3-yl)-amide

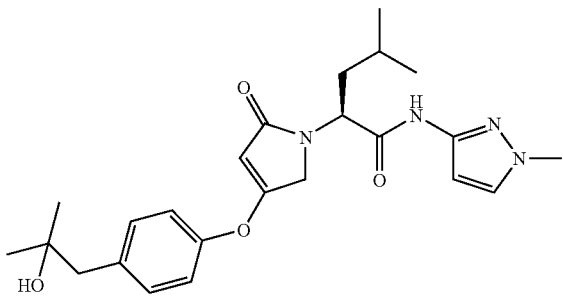

To a solution of methyl magnesium bromide (3 M, 14 mL, 39.94 mmol) cooled to 0° C. was added tetrahydrofuran (10 mL) and as solution of 1-(4-hydroxy-phenyl)-propan-2-one (1 g, 6.66 mmol) in tetrahydrofuran (30 mL). The resulting mixture was then warmed to room temperature and then stirred for 2 h. At this time, the reaction was partioned between ethyl acetate and water. The water layer was made acidic with 1N aqueous hydrochloric acid (pH=1). The organic phase was separated and concentrated in vacuo. The residue was dissolved in a small volume of tetrahydrofuran and the mixture was treated with an excess of hexanes. This resulted in the precipitation of the product 4-(2-hydroxy-2-methyl-propyl)-phenol (0.85 g, 77%) as a white solid.

To a stirred mixture of 4-(2-hydroxy-2-methyl-propyl)-phenol (0.850 g, 5.11 mmol) and ethyl-2-butynoate (3.45 g, 30.66 mmol) in tetrahydrofuran (20 mL) was added potassium carbonate (0.710 g, 5.11 mmol). The mixture was heated in a sealed tube at 80° C. for 5.5 h. The reaction mixture was then cooled to room temperature. The solids were isolated by filtration and washed with a small amount of tetrahydrofuran. The filtrate was concentrated in vacuo and the residue was purified by flash chromatography (silica gel, 0% to 30% ethyl acetate/hexanes) which afforded (E)-3-[4-(2-hydroxy-2-methyl-propyl)-phenoxy]-but-2-enoic acid ethyl ester (1.16 g, 81%) as a viscous colorless oil.

A solution of (E)-3-[4-(2-hydroxy-2-methyl-propyl)-phenoxy]-but-2-enoic acid ethyl ester (0.500 g, 1.80 mmol) in dichloromethane (40 mL) was treated with N-bromosuccinimide (0.350 g, 1.97 mmol) and 2,2'-azobis(2,4'-dimethylvaleronitrile) (0.045 g, 0.18 mmol) under nitrogen. The mixture was then refluxed for 5 h, cooled and concentrated in vacuo. The residue was purified by flash column chromatography (silica gel, 0% to 30% ethyl acetate/hexanes) to afford the intermediate (E)-4-bromo-3-[4-(2-hydroxy-2-methyl-propyl)-phenoxy]-but-2-enoic acid ethyl ester. A solution of (E)-4-bromo-3-[4-(2-hydroxy-2-methyl-propyl)-phenoxy]-but-2-enoic acid ethyl ester in acetonitrile (20 mL) was immediately treated with (L)-leucine methyl ester hydrochloride (0.21 g, 2.17 mmol) and N,N-diisopropylethylamine (0.510 g, 3.95 mmol). The resulting mixture was sealed in a tube and heated at 90° C. overnight and then cooled and partitioned between ethyl acetate and water. The organic layer was collected, dried over sodium sulfate, filtered and concentrated in vacuo. The residue was dissolved in tetrahydrofuran (approximately 5 mL) and heated at 160° C., for 6 h in a sealed tube. At this time, the reaction was cooled to room temperature and concentrated in vacuo. The residue was purified by flash column chromatography (silica gel, 30% to 100% ethyl acetate/hexanes) to afford, (S)-2-{4-[4-(2-hydroxy-2-methyl-propyl)-phenoxy]-2-oxo-2,5-dihydro-pyrrol-1-yl}-4-methyl-pentanoic acid methyl ester (0.180 g, 27%) as a waxy off-white solid.

A solution of (S)-2-{4-[4-(2-hydroxy-2-methyl-propyl)-phenoxy]-2-oxo-2,5-dihydro-pyrrol-1-yl}-4-methyl-pentanoic acid methyl ester (0.150 g, 0.40 mmol) in tetrahydrofuran (5 mL) and water (1 mL) was treated with lithium hydroxide monohydrate (0.017 g 0.40 mmol). The mixture was stirred at room temperature for 1.75 h and then partitioned between ethyl acetate and water. The water layer was made acidic with 1N aqueous hydrochloric acid (pH=1) and extracted with ethyl acetate. The combined organic layers were dried over sodium sulfate, filtered and concentrated in vacuo to afford (S)-2-{4-[4-(2-hydroxy-2-methyl-propyl)-phenoxy]-2-oxo-2,5-dihydro-pyrrol-1-yl}-4-methyl-pentanoic acid (0.120 g, 83%) as a white solid.

A solution of (S)-2-{4-[4-(2-hydroxy-2-methyl-propyl)-phenoxy]-2-oxo-2,5-dihydro-pyrrol-1-yl}-4-methyl-pentanoic acid (0.100 g, 0.28 mmol) in dichloromethane (10 mL) was treated with 1-methyl-1H-pyrazol-3-ylamine (0.040 g, 0.41 mmol), N,N-diisopropylethylamine (0.110 g, 0.85 mmol) and benzotriazol-1-yl-oxy-tris(dimethylamino)phosphonium hexafluorophosphate (0.180 g, 0.41 mmol) at 0° C. The reaction mixture was warmed to room temperature and stirred for 2.5 h. The mixture was partioned between ethyl acetate and water. The organic layer was collected, dried over sodium sulfate, filtered and concentrated in vacuo. The residue was purified by flash column chromatography (silica gel 30% to 100% ethyl acetate/hexanes) which afforded (S)-2-{4-[3-(2-hydroxy-2-methyl-propyl)-phenoxy]-2-oxo-2,5-dihydro-pyrrol-1-yl}-4-methyl-pentanoic acid (1-methyl-1H-pyrazol-3-yl)-amide (0.09 g, 74%) as a white solid: HR-ES-MS m/z calculated for $C_{24}H_{32}N_4O_4$ $[M+H]^+$ 441.2497, observed 441.2497; $^1$H NMR (400 MHz, DMSO-$d_6$) δ ppm 0.90 (d, J=6.4 Hz, 3H), 0.94 (d, J=6.4 Hz, 3H), 1.06 (s, 6H), 1.38-1.51 (m, 1H), 1.51-1.63 (m, 1H), 1.67-1.79 (m, 1H), 2.67 (s, 2H), 3.73 (s, 3H), 4.17 (d, J=18.2 Hz, 1H), 4.33 (s, 1H), 4.54 (d, J=18.2 Hz, 1H), 4.79 (s, 1H), 4.87 (dd, J=10.7, 4.9 Hz, 1H), 6.40 (d, J=2.0 Hz, 1H), 7.18 (d, J=8.5 Hz, 2H), 7.29 (d, J=8.5 Hz, 2H), 7.54 (d, J=2.0 Hz, 1H), 10.70 (s, 1H).

Example 240

(S)-4-Methyl-2-[4-(1-methyl-1H-indazol-4-yloxy)-2-oxo-2,5-dihydro-pyrrol-1-yl]-pentanoic acid [1-((R)-2,3-dihydroxy-propyl)-1H-pyrazol-3-yl]-ade

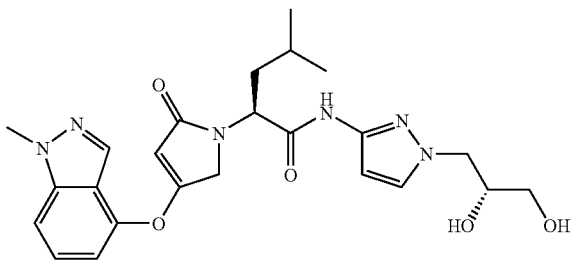

A mixture of 1-methyl-1H-indazol-4-ol (0.130 g, 0.88 mmol), ethyl-2-butynoate (0.59 g, 5.26 mmol), a catalytic amount of 4-dimethylaminopyridine, and potassium carbonate (0.120 g, 0.88 mmol) in tetrahydrofuran (10 mL) in a sealed tube was heated at 80° C. for 14 h. The reaction mixture was then filtered. The solids were washed with a small amount of tetrahydrofuran and the combined filtrate was concentrated in vacuo. The residue was purified by flash column chromatography (silica gel 0% to 40% ethyl acetate/hexanes) which afforded (E)-3-(1-methyl-1H-indazol-4-yloxy)-but-2-enoic acid ethyl ester (0.170 g, 74%) as a viscous tan oil.

A mixture of (E)-3-(1-methyl-1H-indazol-4-yloxy)-but-2-enoic acid ethyl ester (0.110 g, 0.42 mmol) in dichloromethane (30 mL) under a nitrogen atmosphere was treated with N-bromosuccinimide (0.082 g, 0.46 mmol) and a catalytic amount of 2,2'-azobis(2,4'-dimethylvaleronitrile). The resulting mixture was refluxed for 14 h, then cooled to room temperature and concentrated in vacuo. The residue was purified by flash column chromatography (silica gel) to afford, (E)-4-bromo-3-(1-methyl-1H-indazol-4-yloxy)-but-2-enoic acid ethyl ester (0.073 g, 51%) as an oil.

A mixture of (L)-leucine methyl ester hydrochloride (0.043 g, 0.24 mmol), (E)-4-bromo-3-(1-methyl-1H-indazol-4-yloxy)-but-2-enoic acid ethyl ester (0.073 g, 0.22 mmol) and N,N-diisopropylethylamine (0.070 g, 0.54 mmol) in acetonitrile (6 mL) in a sealed tube was heated at 90° C. for 18 h. The reaction mixture was then cooled to room temperature and concentrated in vacuo. The residue was purified by flash column chromatography (silica gel, 0% to 100% diethyl ether/hexanes) to afford (S)-2-[(E)-3-ethoxycarbonyl-2-(1-methyl-1H-indazol-4-yloxy)-allylamino]-4-methyl-pentanoic acid methyl ester (0.055 g, 66%).

A solution of (S)-2-[(E)-3-ethoxycarbonyl-2-(1-methyl-1H-indazol-4-yloxy)-allylamino]-4-methyl-pentanoic acid methyl ester (0.055 g, 0.14 mmol) in tetrahydrofuran (3 mL) in an Emry Optimizer microwave sealed reaction vessel was heated in a microwave reactor at 160° C., for 5.5 h. The reaction mixture was then cooled to room temperature and concentrated in vacuo. The residue was purified by flash column chromatography (silica gel 0% to 60% ethyl acetate/hexanes) to afford, (S)-4-methyl-2-[4-(1-methyl-1H-indazol-4-yloxy)-2-oxo-2,5-dihydro-pyrrol-1-yl]-pentanoic acid methyl ester (0.033 g, 67%).

A solution of (S)-4-methyl-2-[4-(1-methyl-1H-indazol-4-yloxy)-2-oxo-2,5-dihydro-pyrrol-1-yl]-pentanoic acid methyl ester (30 mg, 0.08 mmol) in tetrahydrofuran (5 mL) and water (1 mL) was treated with lithium hydroxide monohydrate (3.6 mg 0.08 mmol). The mixture was stirred at room temperature for 3.5 h and then partitioned between ethyl acetate and water. The aqueous phase was acidified with 1N aqueous hydrochloric acid (pH=1), and extracted with ethyl acetate. The organic layer was dried over sodium sulfate, filtered and concentrated in vacuo to afford (S)-4-methyl-2-[4-(1-methyl-1H-indazol-4-yloxy)-2-oxo-2,5-dihydro-pyrrol-1-yl]-pentanoic acid as an off-white solid. A mixture of (S)-4-methyl-2-[4-(1-methyl-1H-indazol-4-yloxy)-2-oxo-2,5-dihydro-pyrrol-1-yl]-pentanoic acid in dichloromethane (5 mL) was treated with 1-((R)-2,2-dimethyl-[1,3]dioxolan-4-yl-methyl)-1H-pyrazol-3-ylamine (prepared as in Example 49, 0.025 g, 0.13 mmol), N,N-diisopropylethylamine (0.033 g, 0.26 mmol) and benzotriazol-1-yl-oxy-tris(dimethylamino)phosphonium hexafluorophosphate (0.056 g, 0.13 mmol) at 0° C. The reaction mixture was allowed to warm to room temperature and stirred for 3.5 h. The mixture was partioned between dichloromethane and water. The organic layer was collected and concentrated in vacuo and the residue was purified by flash column chromatography (silica gel, 20% to 100% ethyl acetate/hexanes) which afforded (S)-4-Methyl-2-[4-(1-methyl-1H-indazol-4-yloxy)-2-oxo-2,5-dihydro-pyrrol-1-yl]-pentanoic acid [1-((R)-2,2-dimethyl-[1,3]dioxolan-4-ylmethyl)-1H-pyrazol-3-yl]-amide (0.025 g, 57%) as an off-white solid.

A solution of (S)-4-methyl-2-[4-(1-methyl-1H-indazol-4-yloxy)-2-oxo-2,5-dihydro-pyrrol-1-yl]-pentanoic acid [1-((R)-2,2-dimethyl-[1,3]dioxolan-4-ylmethyl)-1H-pyrazol-3-yl]-amide (0.025 g, 0.05 mmol) in tetrahydrofuran (5 mL) was treated with 1M aqueous hydrochloric acid (1 mL) and the resulting mixture was stirred at room temperature overnight. The mixture was partioned between ethyl acetate and water. The aqueous phase was made basic with 1N aqueous sodium hydroxide and extracted with ethyl acetate twice. The combined organic phase was concentrated in vacuo and the residue purified by flash column chromatography (silica gel, 0% to 40% tetrahydrofuran/ethyl acetate) which afforded (S)-4-methyl-2-[4-(1-methyl-1H-indazol-4-yloxy)-2-oxo-2,5-dihydro-pyrrol-1-yl]-pentanoic acid [1-((R)-2,3-dihydroxy-propyl)-1H-pyrazol-3-yl]-amide (0.013 g, 56%) as a white solid: HR-ES-MS m/z calculated for $C_{24}H_{30}N_6O_5$ [M+H]$^+$ 483.2351, observed 483.235; $^1$H NMR (300 MHz, CDCl$_3$) δ ppm 0.97 (d, J=6.6 Hz, 3H), 1.00 (d, J=6.6 Hz, 3H), 1.59 (br. s., 1H), 1.69-1.97 (m, 2H), 2.72 (br. s., 2H), 3.56 (dd, J=11.8, 4.8 Hz, 1H), 3.68 (dd, J=11.8, 3.3 Hz, 1H), 4.06-4.16 (m, 5H), 4.20 (d, J=18.4 Hz, 1H), 4.48 (d, J=18.4 Hz, 1H), 4.88 (t, J=7.8 Hz, 1H), 5.03 (s, 1H), 6.66 (d, J=2.1 Hz, 1H), 6.94 (d, J=7.2 Hz, 1H), 7.29-7.43 (m, 4H), 7.96 (s, 1H), 9.39 (br. s., 1H).

Example 241

(S)-2-[4-(2-Amino-3-hydroxy-phenoxy)-2-oxo-2,5-dihydro-pyrrol-1-yl]-4-methyl-pentanoic acid [1-(2-hydroxy-2-methyl-propyl)-1H-pyrazol-3-yl]-amide

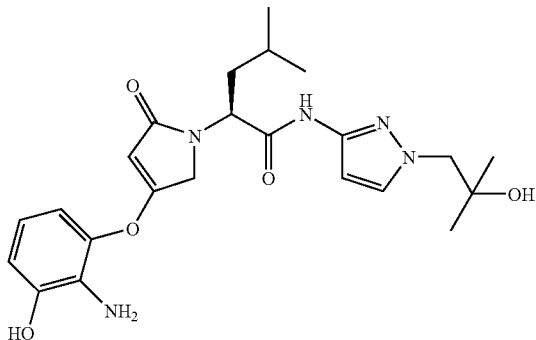

To a mixture of 2-amino-benzene-1,3-diol hydrochloride (4.20 g, 33.6 mmol) and triethyl orthoformate (25 mL) was added concentrated sulfuric acid (3 drops). The mixture was refluxed for 3 h, then cooled and allowed to stand at room temperature overnight. The mixture was then concentrated in vacuo and the residue was diluted with ethyl acetate (200 mL) and the ethyl acetate solution was washed with water (200 mL) and brine (100 mL). The combined aqueous phase was extracted with ethyl acetate (200 mL) and the organic phase was washed with brine, dried over sodium sulfate filtered and concentrated in vacuo. After recrystallization from ethyl acetate benzooxazol-4-ol (1.27 g, 28%) was obtained as a yellow crystalline solid.

A stirred mixture of benzooxazol-4-ol (0.388 g, 2.87 mmol), ethyl-2-butynoate (1.93 g, 17.2 mmol) a catalytic amount of 4-dimethylaminopyridine and potassium carbonate (0.595 g, 4.30 mmol) in tetrahydrofuran (20 mL) was placed in a sealed tube and heated at 80° C. for 2 h. The reaction mixture was filtered and the filtrate was collected and concentrated in vacuo. The resulting residue was purified by ISCO column chromatography (Silicycle 40 g, 2% to 15% ethyl acetate/hexanes) which afforded (E)-3-(benzooxazol-4-yloxy)-but-2-enoic acid ethyl ester (710 mg, 100%) as a light yellow solid.

To a solution of (E)-3-(benzooxazol-4-yloxy)-but-2-enoic acid ethyl ester (1.7 g, 1.27 mmol) in dichloromethane (20 mL) was added N-bromosuccinimide (0.249 g, 1.40 mmol) and 2,2'-azobis(2,4'-dimethylvaleronitrile) (0.032 g, 0.13 mmol) under a nitrogen atmosphere. The mixture was refluxed overnight then cooled to room temperature and concentrated in vacuo. The residue was purified by ISCO Combiflash flash chromatography (100 g Silicycle column, 0 to 60% (9:9:2 dichloromethane:hexane:ethyl acetate)/hexanes) to afford, (E)-3-(benzooxazol-4-yloxy)-4-bromo-but-2-enoic acid ethyl ester (0.300 g, 17%) as a white solid.

A solution of (L)-leucine methyl ester hydrochloride (0.209 g, 1.15 mmol), (E)-3-(benzooxazol-4-yloxy)-4-bromo-but-2-enoic acid ethyl ester (0.341 g, 1.05 mmol) and N,N-diisopropylethylamine (0.288 g, 2.21 mmol) in acetonitrile (10 mL) was placed in a sealed tube and heated at 100° C. for 5 h. The mixture was then cooled to room temperature and ethyl acetate was added. The resulting mixture was filtered and the filtrate was washed successively with aqueous saturated ammonium chloride, water, and brine, then dried over sodium sulfate, filtered and concentrated in vacuo. The residue was then dissolved in tetrahydrofuran (5 mL). The resulting solution was microwaved in an Emry Optimizer microwave sealed reaction vessel at 160° C., for 3 h, then cooled and concentrated in vacuo. The residue was purified by ISCO flash column chromatography (Silicycle 40 g, 5% to 80% ethyl acetate/hexanes) to afford, (S)-2-[4-(benzooxazol-4-yloxy)-2-oxo-2,5-dihydro-pyrrol-1-yl]-4-methyl-pentanoic acid methyl ester (0.140 g, 39%) as a dark yellow solid.

To a solution of (S)-2-[4-(benzooxazol-4-yloxy)-2-oxo-2,5-dihydro-pyrrol-1-yl]-4-methyl-pentanoic acid methyl ester (0.140 g, 0.41 mmol) in tetrahydrofuran (10 mL) and water (10 mL) was added lithium hydroxide monohydrate (0.033 g 0.77 mmol). The mixture was stirred at room temperature for 1.25 h and then partitioned between ethyl acetate and water. The aqueous phase was acidified with 1N aqueous hydrochloric acid (pH<2), and extracted with ethyl acetate. The combined organic layers were dried over magnesium sulfate, filtered and concentrated in vacuo. The resulting residue was treated with acetonitrile, dichloromethane/hexanes which formed a yellow precipitate. The precipitate was isolated by filtration and dissolved in N,N-dimethylformamide (2 mL). This mixture was treated with 1-(3-amino-pyrazol-1-yl)-2-methyl-propan-2-ol (prepared in U.S. Pat. Appl. US2008021032 Example 80, 0.021 g, 0.14 mmol), N,N-diisopropylethylamine (0.035 g, 0.27 mmol) and benzotriazol-1-yl-oxy-tris(dimethylamino)phosphonium hexafluorophosphate (0.060 g, 0.14 mmol) at 0° C. The reaction mixture was then warmed up to room temperature and stirred for 18 h. The mixture was concentrated in vacuo and the resulting residue was dissolved in ethyl acetate. The ethyl acetate layer was washed with aqueous saturated ammonium chloride and brine, and dried over sodium sulfate, filtered and concentrated in vacuo. The residue was purified by reverse phase HPLC ($C_{18}$, 20×150 mm column, 40% to 100% acetonitrile/water gradient) which afforded (S)-2-[4-(2-amino-3-hydroxy-phenoxy)-2-oxo-2,5-dihydro-pyrrol-1-yl]-4-methyl-pentanoic acid [1-(2-hydroxy-2-methyl-propyl)-1H-pyrazol-3-yl]-amide (0.007 g, 16%) as a yellow solid: HR-ES-MS m/z calculated for $C_{23}H_{31}N_5O_5$ [M+H]$^+$ 458.2398, observed 458.2397; $^1$H NMR (300 MHz, DMSO-$d_6$) δ ppm 0.88 (d, J=6.0 Hz, 3H), 0.92 (d, J=6.0 Hz, 3H), 1.03 (br. s., 3H), 1.04 (br. s., 3H), 1.38-1.60 (m, 2H), 1.62-1.80 (m, 1H), 3.87 (s, 2H), 4.18 (d, J=17.8 Hz, 1H), 4.47-4.60 (m, 3H), 4.62 (s, 1H), 4.66 (s, 1H), 4.87 (dd, J=10.6, 4.5 Hz, 1H), 6.38-6.45 (m, 2H), 6.54 (dd, J=8.2, 1.0 Hz, 1H), 6.59 (dd, J=7.5, 1.0 Hz, 1H), 7.52 (d, J=2.1 Hz, 1H), 9.47 (s, 1H), 10.75 (s, 1H).

Example 242

(S)-2-[4-(Benzooxazol-4-yloxy)-2-oxo-2,5-dihydro-pyrrol-1-yl]-4-methyl-pentanoic acid [1-(2-hydroxy-2-methyl-propyl)-1H-pyrazol-3-yl]-amide

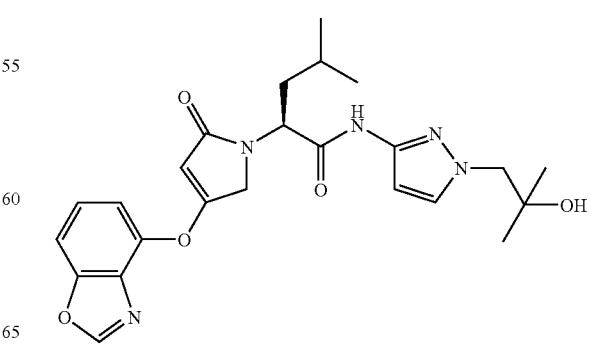

A solution of (S)-2-[4-(benzooxazol-4-yloxy)-2-oxo-2,5-dihydro-pyrrol-1-yl]-4-methyl-pentanoic acid methyl ester (prepared as in Example 241, 0.137 g, 0.40 mmol) in tetrahydrofuran (10 mL) and water (10 mL) was treated with lithium hydroxide monohydrate (0.033 g 0.77 mmol) and the resulting mixture stirred at room temperature for 1.25 h. The mixture was concentrated in vacuo and the residue treated with acetonitrile, and concentrated in vacuo (repeated 2 additional times). The residue was treated with N,N-dimethylformamide and to this mixture was added 1-(3-amino-pyrazol-1-yl)-2-methyl-propan-2-ol (prepared in U.S. Pat. Appl. US2008021032 Example 80, 0.156 g, 1.00 mmol), N,N-diisopropylethylamine (0.180 g, 1.39 mmol) and benzotriazol-1-yl-oxy-tris(dimethylamino)phosphonium hexafluorophosphate (0.616 g, 1.39 mmol) at 0° C. The mixture was warmed to room temperature and stirred for 18 h. The mixture was concentrated in vacuo and the residue dissolved in ethyl acetate, washed with aqueous saturated ammonium chloride, brine, and dried over anhydrous sodium sulfate. The mixture was filtered and concentrated in vacuo. The residue was purified by reverse phase HPLC ($C_{18}$, 20×150 mm column, 30% to 100% acetonitrile/water) to afford (S)-2-[4-(benzooxazol-4-yloxy)-2-oxo-2,5-dihydro-pyrrol-1-yl]-4-methyl-pentanoic acid [1-(2-hydroxy-2-methyl-propyl)-1H-pyrazol-3-yl]-amide (0.055 g, 31%) as a tan solid: HR-ES-MS m/z calculated for $C_{24}H_{29}N_5O_5$ $[M+H]^+$ 468.2242, observed 468.224; $^1H$ NMR (300 MHz, DMSO-$d_6$) δ ppm 0.91 (d, J=6.3 Hz, 3H), 0.94 (d, J=6.3 Hz, 3H), 1.05 (br. s., 3H), 1.06 (br. s., 3H), 1.36-1.64 (m, 2H), 1.68-1.86 (m, 1H), 3.89 (s, 2H), 4.25 (d, J=18.4 Hz, 1H), 4.65 (d, J=18.4 Hz, 1H), 4.68 (s, 1H), 4.86-4.95 (m, 1H), 4.88 (s, 1H), 6.45 (d, J=2.1 Hz, 1H), 7.38 (d, J=8.0 Hz, 1H), 7.53 (t, J=8.0 Hz, 1H), 7.54 (d, J=2.1 Hz, 1H), 7.76 (d, J=8.0 Hz, 1H), 8.81 (s, 1H), 10.80 (s, 1H).

Example 243

(S)-4-Methyl-2-[4-(2-methyl-benzooxazol-4-yloxy)-2-oxo-2,5-dihydro-pyrrol-1-yl]-pentanoic acid [1-(2-hydroxy-2-methyl-propyl)-1H-pyrazol-3-yl]-amide

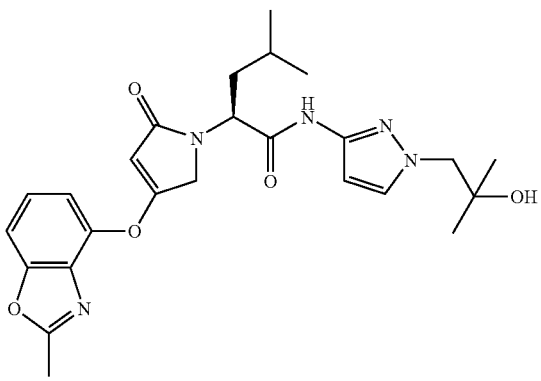

A mixture of 2-amino-benzene-1,3-diol hydrochloride (2.00 g, 12.4 mmol) and trimethyl orthoacetate (15 mL) was treated with concentrated sulfuric acid (5 drops) and the resulting mixture heated at reflux for 3 h, cooled and allowed to stand at room temperature overnight. The resulting mixture was concentrated in vacuo and the residue treated with ethyl acetate (200 mL), washed with water (200 mL) and brine (100 mL). The combined aqueous phases were extracted with ethyl acetate (200 mL) and the combined organic phases washed with brine and dried over sodium sulfate. The mixture was filtered and concentrated in vacuo which afforded benzooxazol-4-ol (0.94 g, 51%) as a yellow solid.

A mixture of 2-methyl-benzooxazol-4-ol (0.940 g, 6.30 mmol), ethyl-2-butynoate (4.24 g, 37.81 mmol) and potassium carbonate (0.956 g, 6.92 mmol) in tetrahydrofuran (20 mL) was placed in a sealed tube and heated at 100° C. for 5.5 h. The reaction mixture was cooled to room temperature, filtered and concentrated in vacuo. The residue was purified by ISCO Combiflash chromatography (Analogix SF-25, 2% to 15% ethyl acetate/hexanes) which afforded (E)-3-(2-methyl-benzooxazol-4-yloxy)-but-2-enoic acid ethyl ester (0.920 g, 56%) as a light yellow solid.

A mixture of (E)-3-(2-methyl-benzooxazol-4-yloxy)-but-2-enoic acid ethyl ester (900 mg, 3.44 mmol) in dichloromethane (40 mL) was treated with N-bromosuccinimide (0.674 g, 3.79 mmol) and 2,2'-azobis(2,4'-dimethylvaleronitrile) (0.085 g, 0.34 mmol) and heated to reflux for 3 h under a nitrogen atmosphere. To this mixture was added N-bromosuccinimide (0.142 g, 0.80 mmol) and 2,2'-azobis(2,4'-dimethylvaleronitrile) (0.061 g, 0.25 mmol) and the mixture was stirred at reflux overnight. The mixture was cooled to room temperature and concentrated in vacuo. The residue was purified by ISCO Combiflash flash chromatography (40 g Silicycle column, 0 to 50% dichloromethane in hexanes and then 0 to 10% ethyl acetate/hexanes) to afford, (E)-4-bromo-3-(2-methyl-benzooxazol-4-yloxy)-but-2-enoic acid ethyl ester (0.974 g, 83%) as a clear yellow viscous oil.

A mixture of (L)-leucine methyl ester hydrochloride (0.570 g, 3.14 mmol), (E)-4-bromo-3-(2-methyl-benzooxazol-4-yloxy)-but-2-enoic acid ethyl ester (0.970 g, 2.85 mmol) and N,N-diisopropylethylamine (0.809 g, 6.21 mmol) in acetonitrile (20 mL) in a sealed tube was heated at 100° C. for 5 h. The reaction mixture was then cooled to room temperature and ethyl acetate was added. The mixture was then filtered. The filtrate was washed successively with aqueous saturated ammonium chloride, water, and brine and then dried over sodium sulfate, filtered and concentrated in vacuo. The residue was dissolved in tetrahydrofuran (5 mL) and microwaved in an Emry Optimizer microwave reaction vessel at 160° C., for 3 h. The mixture was then cooled and concentrated in vacuo and the residue was purified by ISCO Combiflash chromatography (40 g Silicycle, 5% to 50% ethyl acetate/hexanes) to afford (S)-4-methyl-2-[4-(2-methyl-benzooxazol-4-yloxy)-2-oxo-2,5-dihydro-pyrrol-1-yl]-pentanoic acid methyl ester (0.570 g, 56%) as a brown oil.

A solution of (S)-4-methyl-2-[4-(2-methyl-benzooxazol-4-yloxy)-2-oxo-2,5-dihydro-pyrrol-1-yl]-pentanoic acid methyl ester (0.570 g, 1.59 mmol) in tetrahydrofuran (10 mL) and water (10 mL) was treated with lithium hydroxide monohydrate (0.134 g 3.12 mmol) and the resulting mixture stirred at room temperature for 1.5 h. The mixture was concentrated in vacuo and the residue treated with acetonitrile, and concentrated in vacuo (repeated 2 additional times). The resulting solid was treated with N,N-dimethylformamide (10 mL) and 1-(3-amino-pyrazol-1-yl)-2-methyl-propan-2-ol (prepared in U.S. Pat. Appl. US2008021032 Example 80, 0.371 g, 2.39 mmol), N,N-diisopropylethylamine (0.820 g, 6.34 mmol) and benzotriazol-1-yl-oxy-tris(dimethylamino)phosphonium hexafluorophosphate (2.811 g, 6.35 mmol) at 0° C. The reaction mixture was allowed to warm to room temperature and stirred for 18 h. The mixture was concentrated in vacuo, the residue dissolved in ethyl acetate, and the resulting solution was washed with aqueous saturated ammonium chloride solution, brine and dried over sodium sulfate. The mixture was filtered and concentrated in vacuo and the residue purified by ISCO flash column chromatography (Silicycle 40 g, 5% to 100% ethyl acetate/hexanes) which afforded (S)-4-methyl-2-[4-(2-methyl-benzooxazol-4-yloxy)-2-oxo-2,5-dihydro-pyrrol-1-yl]-pentanoic acid [1-(2-hydroxy-2-methyl-propyl)-1H-pyrazol-3-yl]-amide (400 mg, 52%) as a light yellow solid: HR-ES-MS m/z calculated for $C_{25}H_{31}N_5O_5$ [M+H]$^+$ 482.2398, observed 482.2398; $^1$H NMR (300 MHz, DMSO-$d_6$) δ ppm 0.90 (d, J=6.0 Hz, 3H), 0.94 (d, J=6.0 Hz, 3H), 1.05 (br. s., 3H), 1.06 (br. s., 3H), 1.37-1.64 (m, 2H), 1.65-1.85 (m, 1H), 2.62 (s, 3H), 3.89 (s, 2H), 4.24 (d, J=18.1 Hz, 1H), 4.62 (d, J=18.1 Hz, 1H), 4.67 (s, 1H), 4.83 (s, 1H), 4.89 (dd, J=11.0, 3.8 Hz, 1H), 6.45 (s, 1H), 7.29 (d, J=7.8 Hz, 1H), 7.42 (t, J=7.8 Hz, 1H), 7.54 (s, 1H), 7.64 (d, J=7.8 Hz, 1H), 10.80 (s, 1H).

Example 244

(S)-2-{4-[4-((S)-2,3-Dihydroxy-propyl)-phenoxy]-2-oxo-2,5-dihydro-pyrrol-1-yl}-4-methyl-pentanoic acid pyrazin-2-ylamide

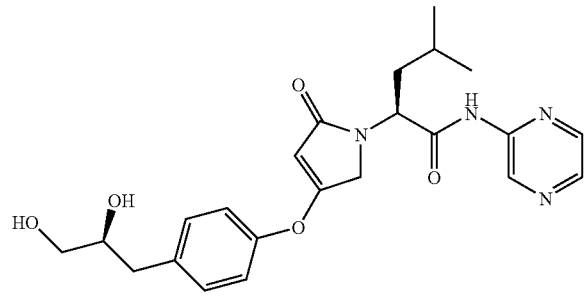

A solution of (S)-2-hydroxy-3-(4-hydroxy-phenyl)-propionic acid (3.00 g, 16.47 mmol) in ethanol (50 mL) was treated with benzyl chloride (4.20 g, 33.18 mmol) and potassium carbonate (4.60 g, 33.28 mmol) and the resulting mixture heated at reflux overnight. The mixture was cooled and treated with water (50 mL), and the resulting mixture stirred for 1 h. At this time ethyl acetate was added and the mixture acidified with 1N aqueous hydrochloric acid. The layers were separated and the aqueous phase extracted with ethyl acetate (3×). The organic phases were combined and concentrated in vacuo to an approximate volume of 10 mL. The resulting mixture was filtered and the isolated solid washed with diethyl ether and dried to afford (S)-3-(4-benzyloxy-phenyl)-2-hydroxy-propionic acid (3.00 g, 67%) as a white solid.

A solution of (S)-3-(4-benzyloxy-phenyl)-2-hydroxy-propionic acid (3.1 g, 11.38 mmol) in tetrahydrofuran (50 mL) was treated with a solution of borane tetrahydrofuran complex in tetrahydrofuran (1.0 M, 22.7 mL, 22.76 mmol) at 0° C. The mixture was allowed to slowly warm to room temperature and stirred at this temperature for 2 h. The resulting mixture was carefully quenched with 1N aqueous sodium hydroxide and treated with ethyl acetate. The layers were separated and the aqueous layer extracted twice more with ethyl acetate. The combined organic layers were dried over sodium sulfate, filtered and concentrated in vacuo. The residue was immediately treated with excess acetone dimethyl ketal and a catalytic amount of p-toluene sulfonic acid. The mixture was treated with ethyl acetate and water. The aqueous layer made basic with solid potassium carbonate (pH=9), and extracted with ethyl acetate. The organic layers were combined and dried over sodium sulfate, filtered and concentrated in vacuo which afforded (S)-4-(4-benzyloxy-benzyl)-2,2-dimethyl-[1,3]dioxolane (3.1 g, 91%) as a white solid.

A solution of (S)-4-(4-benzyloxy-benzyl)-2,2-dimethyl-[1,3]dioxolane (1.00 g, 3.35 mmol) in ethyl acetate (50 mL) was treated with 10% palladium on carbon (0.360 g, 0.34 mmol) and the resulting mixture hydrogenated under 1 atm of hydrogen pressure. The resulting mixture was filtered through a pad of Celite® and the pad of Celite washed with ethyl acetate. The filtrate was concentrated in vacuo to afford 4-((S)-2,2-dimethyl-[1,3]dioxolan-4-ylmethyl)-phenol (696 mg, 100%).

A mixture of 4-((S)-2,2-dimethyl-[1,3]dioxolan-4-ylmethyl)-phenol (0.696 g, 3.34 mol), potassium carbonate (0.463 g, 0.003 mol), ethyl-2-butynoate (2.25 g, 0.020 mol) and a catalytic amount of 4-dimethylaminopyridine in tetrahydrofuran (15 mL) was placed in a sealed tube and heated at 80° C. for 6 h. The reaction mixture was cooled, filtered and the isolated solids washed with tetrahydrofuran. The filtrate was concentrated in vacuo and the residue was purified by flash column chromatography (silica gel, 0% to 30% ethyl acetate/hexanes) which afforded (E)-3-[4-((S)-2,2-dimethyl-[1,3]dioxolan-4-ylmethyl)-phenoxy]-but-2-enoic acid ethyl ester (0.440 g, 41%) as a colorless oil.

A mixture of (E)-3-[4-((S)-2,2-dimethyl-[1,3]dioxolan-4-ylmethyl)-phenoxy]-but-2-enoic acid ethyl ester (0.430 g, 1.34 mmol) in dichloromethane (50 mL) was treated with N-bromosuccinimide (0.280 g, 1.57 mmol), 2,2'-azobis(2,4'-dimethylvaleronitrile) (0.034 g, 0.14 mmol) and the resulting mixture heated at reflux for 3 h under a nitrogen atmosphere. The mixture was cooled and concentrated in vacuo. The residue was purified by flash column chromatography (silica gel, 0% to 20% ethyl acetate/hexanes) to afford, (E)-4-bromo-3-[4-((S)-2,2-dimethyl-[1,3]dioxolan-4-ylmethyl)-phenoxy]-but-2-enoic acid ethyl ester (405 mg, 76%) as a colorless oil.

A solution of (L)-leucine methyl ester hydrochloride (0.200 g, 1.10 mmol), (E)-4-bromo-3-[4-((S)-2,2-dimethyl-[1,3]dioxolan-4-ylmethyl)-phenoxy]-but-2-enoic acid ethyl ester (0.400 g, 1.00 mmol) and N,N-diisopropylethylamine (0.285 g, 2.19 mmol) in acetonitrile (15 mL) was sealed in a tube and heated at 90° C. for 14 h. The reaction mixture was cooled to room temperature and partitioned between ethyl acetate and water. The layers were separated and the ethyl acetate layer was dried over sodium sulfate, filtered and concentrated in vacuo. The residue was dissolved in tetrahydrofuran (4 mL) placed in an Emry Optimizer microwave reaction vessel and microwaved at 160° C. for 2 h. At this time, the reaction was cooled to room temperature and concentrated in vacuo. The residue was purified by flash column chromatography (silica gel 0% to 70% ethyl acetate/hexanes) to afford, (S)-2-{4-[4-((S)-2,2-dimethyl-[1,3]dioxolan-4-ylmethyl)-phenoxy]-2-oxo-2,5-dihydro-pyrrol-1-yl}-4-methyl-pentanoic acid methyl ester (198 mg, 47%) as a viscous oil.

A solution of (S)-2-{4-[4-((S)-2,2-dimethyl-[1,3]dioxolan-4-ylmethyl)-phenoxy]-2-oxo-2,5-dihydro-pyrrol-1-yl}-4-methyl-pentanoic acid methyl ester (0.198 g, 0.47 mmol) in tetrahydrofuran (5 mL) and water (1 mL) was treated with lithium hydroxide monohydrate (0.022 g 0.51 mmol) and stirred at room temperature for 1.5 h. The mixture was partitioned between ethyl acetate and water and the layers separated. The aqueous phase was acidified with 1N aqueous hydrochloric acid (pH=1) and extracted with ethyl acetate. The combined organic layers from extraction of the acidic aqueous layer were dried over sodium sulfate, filtered and concentrated in vacuo. The residue was treated with dichloromethane/hexanes and the precipitate isolated by filtration to afford (S)-2-{4-[4-((S)-2,2-dimethyl-[1,3]dioxolan-4-ylmethyl)-phenoxy]-2-oxo-2,5-dihydro-pyrrol-1-yl}-4-methyl-pentanoic acid (148 mg, 77%), as a white solid.

A solution of (S)-2-{4-[4-((S)-2,2-dimethyl-[1,3]dioxolan-4-ylmethyl)-phenoxy]-2-oxo-2,5-dihydro-pyrrol-1-yl}-4-methyl-pentanoic acid (85 mg, 0.21 mmol) and pyridine (0.017 g, 0.21 mmol) in dichloromethane (5 mL) at −10° C. was treated with cyanuric fluoride (43 mg, 0.32 mmol) and the resulting mixture stirred at −10° C. for 3.5 h. The mixture was partioned between ice water and dichloromethane. The layers were separated and the organic phase was dried over sodium sulfate, filtered and concentrated in vacuo. The residue was dissolved in tetrahydrofuran (2 mL) treated with pyrazin-2-ylamine (200 mg, 2.1 mmol) and the resulting mixture was placed in an Emry Optimizer microwave reaction vessel and microwaved at 120° C., for 10 min. The mixture was cooled and partitioned between ethyl acetate and water. The layers were separated and the organic phase was collected, dried over sodium sulfate, filtered and concentrated in vacuo. The residue was purified by flash column chromatography (silica gel, 0% to 100% ethyl acetate/hexanes) to afford, (S)-2-{4-[4-((S)-2,2-dimethyl-[1,3]dioxolan-4-ylmethyl)-phenoxy]-2-oxo-2,5-dihydro-pyrrol-1-yl}-4-methyl-pentanoic acid pyrazin-2-ylamide (25 mg, 25%) as an off-white solid.

A solution of (S)-2-{4-[4-((S)-2,2-dimethyl-[1,3]dioxolan-4-ylmethyl)-phenoxy]-2-oxo-2,5-dihydro-pyrrol-1-yl}-4-methyl-pentanoic acid pyrazin-2-ylamide (0.025, 0.05 mmol) in tetrahydrofuran (5 mL) was treated with 1 M hydrochloric acid (1 mL) and stirred at room temperature overnight. The resulting mixture was partitioned between ethyl acetate and water. The layers were separated and the aqueous phase made basic (pH=8) by the addition of a 1N aqueous sodium hydroxide and extracted with ethyl acetate. The combined organic layers were concentrated in vacuo and the residue purified by flash column chromatography (silica gel 0% to 20% tetrahydrofuran/ethyl acetate) to afford (S)-2-{4-[4-((S)-2,3-dihydroxy-propyl)-phenoxy]-2-oxo-2,5-dihydro-pyrrol-1-yl}-4-methyl-pentanoic acid pyrazin-2-ylamide (15 mg, 65%) as a white solid: HR-ES-MS m/z calculated for $C_{23}H_{28}N_4O_5$ $[M+H]^+$ 441.2133, observed 441.2132; $^1$H NMR (300 MHz, CDCl$_3$) δ ppm 1.05 (d, J=6.4 Hz, 3H), 1.10 (d, J=6.4 Hz, 3H), 1.43-1.82 (m, 2H), 1.85-2.00 (m, 1H), 2.62 (dd, J=13.0, 11.2 Hz, 1H), 2.85 (d, J=13.9 Hz, 1H), 3.35 (br. s., 2H), 3.61-3.84 (m, 2H), 3.94-4.16 (m, 2H), 4.31 (d, J=18.1 Hz, 1H), 4.78-4.87 (m, 1H), 4.87 (br. s., 1H), 7.01 (d, J=8.2 Hz, 2H), 7.24-7.27 (m, 2H), 8.26 (s, 1H), 8.38 (s, 1H), 9.62 (s, 1H), 10.27 (br. s., 1H).

Example 245

(S)-2-{4-[4-(2-Hydroxy-2-methyl-propyl)-phenoxy]-2-oxo-2,5-dihydro-pyrrol-1-yl}-4-methyl-pentanoic acid pyrazin-2-ylamide

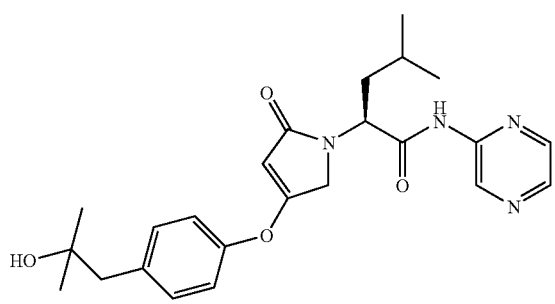

A solution of (S)-2-t-butoxycarbonylamino-4-methyl-pentanoic acid monohydrate (1.00 g, 4.01 mmol) in dichloromethane (50 mL) and pyridine (0.320 g, 4.01 mmol) at −10° C. was treated with cyanuric fluoride (0.812 g, 6.02 mmol) and stirred at −10° C. for 3 h. The resulting mixture was partitioned between ice water and dichloromethane and the layers separated. The organic phase was dried over sodium sulfate, filtered and concentrated in vacuo. The residue was dissolved in tetrahydrofuran (30 mL), treated with pyrazin-2-ylamine (1.90 g, 20.1 mmol), sealed in a tube and heated at 120° C. for 10 min. The mixture was cooled to room temperature and partitioned between ethyl acetate and water. The layers were separated and the ethyl acetate layer concentrated in vacuo. The residue was purified by flash column chromatography (silica gel 0% to 40% ethyl acetate/hexanes) to afford, [(S)-3-methyl-1-(pyrazin-2-ylcarbamoyl)-butyl]-carbamic acid t-butyl ester (0.71 g, 53%) as a white solid.

[(S)-3-Methyl-1-(pyrazin-2-ylcarbamoyl)-butyl]-carbamic acid t-butyl ester (0.645 g, 2.09 mmol) was treated with a 30% trifluoroacetic acid/dichloromethane (10 mL) solution at 0° C. and the resulting mixture allowed to warm to room temperature over 1.5 h. At this time the mixture was partioned between ethyl acetate and water and the layers separated. The aqueous phase was made basic (pH=10) by the addition of solid sodium hydroxide. The basic aqueous phase was extracted with ethyl acetate (3×) and the ethyl acetate layers were combined, dried over sodium sulfate, filtered and concentrated in vacuo to afford (S)-2-amino-4-methyl-pentanoic acid pyrazin-2-ylamide (0.341 g, 78%).

A solution of (E)-3-[4-(2-hydroxy-2-methyl-propyl)-phenoxy]-but-2-enoic acid ethyl ester (prepared as in Example 239, 0.500 g, 1.80 mmol) in dichloromethane (50 mL) was treated with N-bromosuccinimide (0.350 g, 1.97 mmol) and 2,2'-azobis(2,4'-dimethylvaleronitrile) (0.045 g, 0.18 mmol) and heated to reflux for 5.5 h under a nitrogen atmosphere. The mixture was cooled and concentrated in vacuo. The residue was purified by flash column chromatography (silica gel, 0% to 30% ethyl acetate/hexanes) to afford (E)-4-bromo-3-[4-(2-hydroxy-2-methyl-propyl)-phenoxy]-but-2-enoic acid ethyl ester which was immediately dissolved in acetonitrile (30 mL) and treated with (S)-2-amino-4-methyl-pentanoic acid pyrazin-2-ylamide (0.341 g, 1.64 mmol) and N,N-diisopropylethylamine (0.230 g, 17.9 mmol). The resulting mixture was sealed in a tube and heated at 90° C. for 14 h. The mixture was cooled to room temperature and partition between water and ethyl acetate. The layers were separated and the ethyl acetate layer was concentrated in vacuo. The residue was purified by consecutive flash column chromatography (silica gel, 0% to 50% ethyl acetate/hexanes; silica gel, 0% to 30% ethyl acetate/dichloromethane) and the material obtained dissolved in tetrahydrofuran. The mixture was sealed in a tube and heated at 160° C. for 19 h. At this time, the reaction was cooled to room temperature and concentrated in vacuo. The residue was purified by flash column chromatography (silica gel, 0% to 100% ethyl acetate/hexanes) to afford (S)-2-{4-[4-(2-hydroxy-2-methyl-propyl)-phenoxy]-2-oxo-2,5-dihydro-pyrrol-1-yl}-4-methyl-pentanoic acid pyrazin-2-ylamide (67 mg, 9%) as a white solid: HR-ES-MS m/z calculated for $C_{24}H_{30}N_4O_4$ $[M+H]^+$ 439.234, observed 439.2341; $^1$H NMR (300 MHz, CDCl$_3$) δ ppm 1.01 (d, J=6.3 Hz, 3H), 1.03 (m, J=6.3 Hz, 3H), 1.24 (s, 6H), 1.55-1.72 (m, 1H), 1.68-2.06 (m, 3H), 2.79 (s, 2H), 4.12 (d, J=18.1 Hz, 1H), 4.25 (d, J=18.1 Hz, 1H), 4.93 (dd, J=8.8, 6.6 Hz, 1H), 5.01 (s, 1H), 7.09 (d, J=8.5 Hz, 2H), 7.27 (d, J=8.5 Hz, 2H), 8.27 (s, 1H), 8.34 (d, J=2.4 Hz, 1H), 9.09 (s, 1H), 9.49 (s, 1H).

Example 246

(S)-2-{4-[3-(2-Hydroxy-2-methyl-propyl)-phenoxy]-2-oxo-2,5-dihydro-pyrrol-1-yl}-4-methyl-pentanoic acid pyrazin-2-ylamide

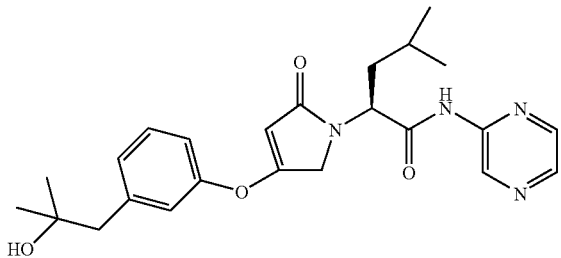

A mixture of (S)-2-amino-4-methyl-pentanoic acid pyrazin-2-ylamide (prepared as in Example 245, 0.400 g, 1.92 mmol), (E)-4-bromo-3-[3-(2-hydroxy-2-methyl-propyl)-phenoxy]-but-2-enoic acid ethyl ester (prepared as in Example 235, 0.462 g, 1.29 mmol) and N,N-diisopropylethylamine (0.734 g, 5.69 mmol) in acetonitrile (16.6 mL) were sealed in a tube and heated at 100° C. for 12 h. The mixture was cooled and concentrated in vacuo. The residue was partitioned between ethyl acetate (20 mL) and water (20 mL) and the phases separated. The organic phase was dried over sodium sulfate, filtered and concentrated in vacuo. The residue was dissolved in tetrahydrofuran (5 mL), sealed in an Emry Optimizer microwave tube and microwaved at 160° C. for 4 h. The mixture was cooled and concentrated in vacuo. The residue was purified by flash column chromatography (silica gel, 5% to 35% ethyl acetate/hexanes) to afford (S)-2-{4-[3-(2-hydroxy-2-methyl-propyl)-phenoxy]-2-oxo-2,5-dihydro-pyrrol-1-yl}-4-methyl-pentanoic acid pyrazin-2-ylamide (127 mg, 22%) as a tan solid: HR-ES-MS m/z calculated for $C_{24}H_{30}N_4O_4$ $[M+H]^+$ 439.234, observed 439.2341; $^1$H NMR (300 MHz, DMSO-$d_6$) δ ppm 0.91 (d, J=6.9 Hz, 3H), 0.93 (d, J=6.9 Hz, 3H), 1.04 (s, 6H), 1.39-1.70 (m, 2H), 1.72-1.87 (m, 1H), 2.66 (s, 2H), 4.21 (d, J=18.4 Hz, 1H), 4.36 (s, 1H), 4.55 (d, J=18.4 Hz, 1H), 4.83 (s, 1H), 5.02 (dd, J=10.9, 4.5 Hz, 1H), 6.94-7.19 (m, 3H), 7.34 (t, J=7.5 Hz, 1H), 8.36 (d, J=2.7 Hz, 1H), 8.41 (d, J=1.5 Hz, 1H), 9.26 (s, 1H), 11.16 (s, 1H).

Example 247

(S)-2-{4-[2-Fluoro-3-(1-hydroxy-1-methyl-ethyl)-phenoxy]-2-oxo-2,5-dihydro-pyrrol-1-yl}-4-methyl-pentanoic acid pyrazin-2-ylamide

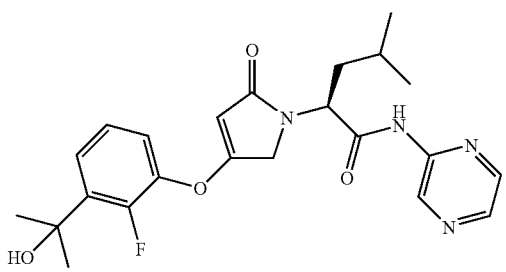

A solution of (S)-2-{4-[2-fluoro-3-(1-hydroxy-1-methyl-ethyl)-phenoxy]-2-oxo-2,5-dihydro-pyrrol-1-yl}-4-methyl-pentanoic acid (prepared as in Example 143, 400 mg, 1.10 mmol), 2-aminopyrazine (208 mg, 2.18 mmol) and carbonyldiimidazole (186 mg, 1.15 mmol) in N,N-dimethylformamide (2 mL) was stirred at room temperature for 12 h. At this time the mixture was transferred to an Emrys Optimizer microwave tube and microwaved at 120° C. for 5 h. The mixture was concentrated in vacuo and the residue partioned between ethyl acetate and 0.1N aqueous hydrochloric acid. The layers were separated and the organic layer was washed with water, aqueous sodium bicarbonate solution, and dried over sodium sulfate. The mixture was filtered and concentrated in vacuo. The residue was purified by ISCO flash chromatography (RediSep silica 40 g, 70% to 100% ethyl acetate/hexanes) to afford (S)-2-{4-[2-fluoro-3-(1-hydroxy-1-methyl-ethyl)-phenoxy]-2-oxo-2,5-dihydro-pyrrol-1-yl}-4-methyl-pentanoic acid pyrazin-2-ylamide (256 mg, 53%) as an off-white fluffy powder: HR-ES-MS (m/z) calculated for $C_{23}H_{27}FN_4O_4$ $[M+H]^+$ 443.2089, observed 443.2088. $^1$H NMR (300 MHz, DMSO-$d_6$) δ ppm 0.93 (t, J=6.8 Hz, 6H), 1.41-1.54 (m, 1H), 1.49 (s, 6H), 1.56-1.73 (m, 1H), 1.73-1.91 (m, 1H), 4.25 (d, J=18.4 Hz, 1H), 4.60 (d, J=18.4 Hz, 1H), 4.83 (s, 1H), 5.04 (dd, J=11.0, 4.4 Hz, 1H), 5.42 (br. s., 1H), 7.24 (t, J=7.7 Hz, 1H), 7.32-7.40 (td, J=7.7, 1.5 Hz, 1H), 7.56 (td, J=7.7, 1.5 Hz, 1H), 8.38 (d, J=2.4 Hz, 1H), 8.42 (s, 1H), 9.28 (s, 1H), 11.19 (s, 1H).

Example 248

(S)-2-[4-(2-Chloro-phenoxy)-2-oxo-2,5-dihydro-pyrrol-1-yl]-4-methyl-hexanoic acid [1-((R)-2,2-dimethyl-[1,3]dioxolan-4-ylmethyl)-1H-pyrazol-3-yl]-amide

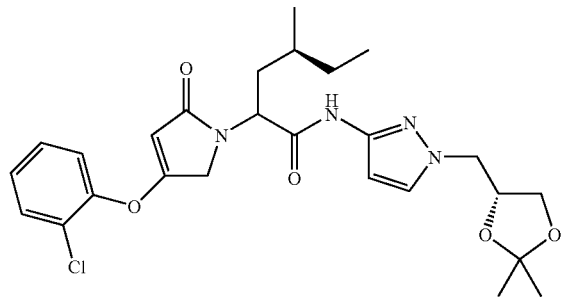

A solution of (benzhydrylidene-amino)-acetic acid ethyl ester (5.48 g, 20.5 mmol) in tetrahydrofuran (40 mL) was treated with potassium t-butoxide (2.83 g, 25.26 mmol) and stirred at 0° C. for 35 min. At this time a solution of (S)-1-iodo-2-methyl-butane (5.00 g, 25.25 mmol) in tetrahydrofuran (20 mL) was added via syringe and the resulting solution stirred at 0° C. for 10 min and then room temperature overnight. The reaction mixture was concentrated in vacuo and the residue partitioned between diethyl ether and dilute aqueous hydrochloric acid. The layers were separated, and the organic layer was washed with brine and concentrated in vacuo. The residue was purified by ISCO flash chromatography (RediSep silica 120 g, 0% to 10% ethyl acetate/hexanes) which afforded (S)-2-(benzhydrylidene-amino)-4-methyl-hexanoic acid ethyl ester (5.09 g, 74%) as an oil.

A solution of (S)-2-(benzhydrylidene-amino)-4-methyl-hexanoic acid (5.09 g, 15.1 mmol) in tetrahydrofuran (100 mL) was treated with a 2N aqueous hydrochloric acid solution (50 mL) and stirred at room temperature for 1.5 hr. The mixture was concentrated in vacuo and the residue partitioned between methyl t-butyl ether and water. The layers were separated and the aqueous phase was washed with methyl t-butyl ether. The organic phases were discarded and the aqueous phase neutralized with a 1N aqueous sodium hydroxide solution (150 mL) and extracted with methyl t-butyl ether. The combined organic layers were washed with brine and dried over anhydrous sodium sulfate. The mixture was concentrated in vacuo and the residue was dissolved in diethyl ether (20 mL). The diethyl ether solution was treated with 3M hydrogen chloride in diethyl ether (10 mL) and the mixture concentrated in vacuo. The residue was triturated with diethyl ether and hexanes which afforded (S)-2-amino-4-methyl-hexanoic acid ethyl ester hydrochloride (2.30 g, 73%) as a white solid.

A suspension of (S)-2-amino-4-methyl-hexanoic acid ethyl ester hydrochloride salt (1.05 g, 5.01 mmol) in acetonitrile (6 mL) was treated with N,N-diisopropylethylamine (1.0 mL) and stirred at 60° C. for 15 min. To this mixture was added N,N-diisopropylethylamine (1.2 mL) and a solution of (E)-4-bromo-3-(2-chloro-phenoxy)-but-2-enoic acid ethyl ester (prepared in Example 61, 1.6 g, 5.0 mmol) in acetonitrile (4 mL) via a dropping funnel and the resulting mixture refluxed for 20 h. The resulting mixture was concentrated in vacuo and the residue was partitioned between ethyl acetate and water. The layers were separated and the organic layer was dried over sodium sulfate. The mixture was filtered and concentrated in vacuo and the residue dissolved in tetrahydrofuran (8 mL). The resulting solution was transferred to an Emrys Optimizer microwave tube and microwaved at 160° C. for 4 h. The mixture was concentrated in vacuo and the residue purified by ISCO flash chromatography (RediSep silica column 80 g, 20% to 80% ethyl acetate/hexanes) which afforded (S)-2-[4-(2-chloro-phenoxy)-2-oxo-2,5-dihydro-pyrrol-1-yl]-4-methyl-hexanoic acid ethyl ester (950 mg, 52%).

A solution of (S)-2-[4-(2-chloro-phenoxy)-2-oxo-2,5-dihydro-pyrrol-1-yl]-4-methyl-hexanoic acid ethyl ester (0.95 g, 2.60 mmol) in tetrahydrofuran (15 mL) was treated with an aqueous 0.5N lithium hydroxide solution (10.4 mL) and stirred at 5° C. for 2 h. The mixture was concentrated in vacuo and the residue was dissolved in water (40 mL) and extracted with diethyl ether. The ether layer was discarded, and the aqueous layer was acidified with 1N aqueous hydrochloric acid (8 mL) and extracted with ethyl acetate. The combined ethyl acetate layers were concentrated in vacuo which afforded (S)-2-[4-(2-chloro-phenoxy)-2-oxo-2,5-dihydro-pyrrol-1-yl]-4-methyl-hexanoic acid (839 mg, 96%) as a pale orange solid.

A solution of (S)-2-[4-(2-chloro-phenoxy)-2-oxo-2,5-dihydro-pyrrol-1-yl]-4-methyl-hexanoic acid (337 mg, 1 mmol), 1-((R)-2,2-dimethyl-[1,3]dioxolan-4-yl-methyl)-1H-pyrazol-3-ylamine (prepared as in Example 49, 276 mg, 1.4 mmol) in N,N-dimethylformamide (7 mL) was treated with N,N-diisopropylethylamine (0.46 mL) and benzotriazol-1-yl-oxy-tris(dimethylamino)phosphonium hexafluorophosphate (664 mg, 1.5 mmol) and stirred at room temperature for 6 h. The mixture was concentrated in vacuo and the residue was partitioned between ethyl acetate and an aqueous ammonium chloride solution. The layers were separated and the organic layer washed with brine and dried with sodium sulfate. The mixture was filtered and the filterate concentrated in vacuo and the residue was purified by ISCO flash chromatography (RediSep silica column 40 g, 20% to 80% ethyl acetate/hexanes) which afforded (S)-2-[4-(2-chloro-phenoxy)-2-oxo-2,5-dihydro-pyrrol-1-yl]-4-methyl-hexanoic acid [1-((R)-2,2-dimethyl-[1,3]dioxolan-4-ylmethyl)-1H-pyrazol-3-yl]-amide (400 mg, 76%) as a pale yellow solid: HR-ES-MS (m/z) calculated for $C_{26}H_{33}ClN_4O_5$ $[M+H]^+$ 517.2212, observed 517.2209. $^1$H NMR showed mixture of diastereomers (300 MHz, DMSO-$d_6$) δ ppm 0.75-0.95 (m, 6H), 1.02-1.23 (m, 2H), 1.25 (s, 3H), 1.31 (s, 3H), 1.40-1.93 (m, 3H), 3.73 (dd, J=8.5, 5.7 Hz, 1H), 4.00 (dd, J=8.3, 6.5 Hz, 1H), 4.04-4.28 (m, 3H), 4.35 (quin, J=5.7 Hz, 1H), 4.60 (dd, J=18.4, 14.5 Hz, 1H), 4.80 (2xs, 1H), 4.86-4.96 (m, 1H), 6.42-6.46 (m, 1H), 7.37 (t, J=7.5 Hz, 1H), 7.42-7.57 (m, 2H), 7.60 (s, 1H), 7.65 (d, J=7.8 Hz, 1H), 10.76-10.84 (m, 1H).

Example 249

(S)-2-[4-(2-Chloro-phenoxy)-2-oxo-2,5-dihydro-pyrrol-1-yl]-4-methyl-hexanoic acid [1-((R)-2,3-dihydroxy-propyl)-1H-pyrazol-3-yl]-amie

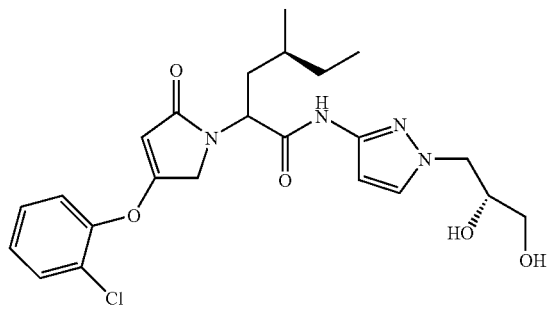

A solution of (S)-2-[4-(2-chloro-phenoxy)-2-oxo-2,5-dihydro-pyrrol-1-yl]-4-methyl-hexanoic acid [1-((R)-2,2-dimethyl-[1,3]dioxolan-4-ylmethyl)-1H-pyrazol-3-yl]-amide (360 mg, 0.7 mmol) in tetrahydrofuran (15 mL) was treated with 2N aqueous hydrochloric acid (7.5 mL) and stirred at room temperature for 2.5 h. At this time the mixture was partitioned between ethyl acetate and water. The layers were separated and the aqueous layer was extracted with ethyl acetate. The combined organic layers were washed with brine and dried over sodium sulfate. The mixture was filtered and concentrated in vacuo and the residue was purified by ISCO flash chromatography (RediSep silica column 12 g, 30% to 80% (10% methanol/dichloromethane)hexanes) which afforded (S)-2-[4-(2-chloro-phenoxy)-2-oxo-2,5-dihydro-pyrrol-1-yl]-4-methyl-hexanoic acid [1-((R)-2,3-dihydroxy-propyl)-1H-pyrazol-3-yl]-amide (285 mg, 86%) as a white fluffy solid: HR-ES-MS (m/z) calculated for $C_{23}H_{29}ClN_4O_5$ $[M+H]^+$ 477.1899, observed 477.1897. $^1$H NMR showed mixture of diastereomers (400 MHz, DMSO-$d_6$) δ ppm 0.77-0.96 (m, 6H), 1.04-1.93 (m, 5H), 3.23-3.33 (m, 2H), 3.77 (br. s., 1H), 3.82-3.91 (m, 1H), 4.04-4.14 (m, 1H), 4.11-4.29 (m, 1H), 4.58, 4.63 (2xd, J=18.7 Hz, 1H), 4.71 (br. s., 1H), 4.79, 4.81 (2xs, 1H), 4.86-4.97 (m, 2H), 6.42 (br. s., 1H), 7.37 (t, J=7.7 Hz, 1H), 7.46 (t, J=7.5 Hz, 1H), 7.49-7.56 (m, 2H), 7.65 (d, J=7.9 Hz, 1H), 10.77, 10.79 (2xs, 1H)

Example 250

(2R,4S)-2-[4-(2-Chloro-phenoxy)-2-oxo-2,5-dihydro-pyrrol-1-yl]-4-methyl-hexanoic acid [1-((R)-2,3-dihydroxy-propyl)-1H-pyrazol-3-yl]-amide

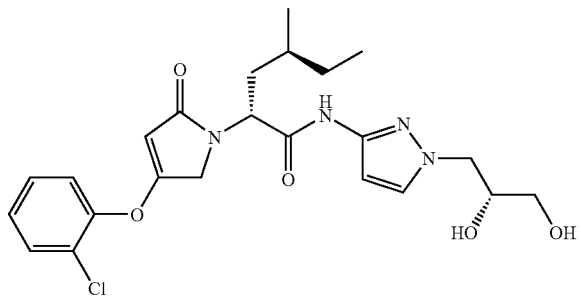

The mixture of stereoisomers of (S)-2-[4-(2-chloro-phenoxy)-2-oxo-2,5-dihydro-pyrrol-1-yl]-4-methyl-hexanoic acid [1-((R)-2,3-dihydroxy-propyl)-1H-pyrazol-3-yl]-amide (prepared as in Example 249) was separated into the single enantiomers by supercritical fluid chromatography on a Berger MultiGram II Supercritical Fluid Chromatography system (Model SD-1) from Mettler-Toledo AutoChem Berger Instruments, Newark, Del., USA (Chiral column: DAICEL AD, temperature of 30° C., a flow rate of 70 mL/min, 30% methanol and carbon dioxide pressure of 100 bar, Knauer variable wavelength UV detector with high pressure flow cell was used for SFC detection. Detection in SFC was performed by measurement of UV absorbance at 220 nm). The first peak from this separation gave (2R,4S)-2-[4-(2-chloro-phenoxy)-2-oxo-2,5-dihydro-pyrrol-1-yl]-4-methyl-hexanoic acid [1-((R)-2,3-dihydroxy-propyl)-1H-pyrazol-3-yl]-amide. HR-ES-MS (m/z) calculated for $C_{23}H_{29}ClN_4O_5$ [M+H]$^+$ 477.1899, observed 477.1903. $^1$H NMR (400 MHz, DMSO-d$_6$) δ ppm 0.80-0.98 (m, 6H), 1.12-1.29 (m, 2H), 1.29-1.42 (m, 1H), 1.42-1.61 (m, 1H), 1.86 (t, J=11.5 Hz, 1H), 3.20-3.33 (m, 2H), 3.72-3.82 (m, 1H), 3.87 (dd, J=13.4, 7.5 Hz, 1H), 4.04-4.11 (m, 1H), 4.14 (d, J=18.5 Hz, 1H), 4.63 (d, J=18.5 Hz, 1H), 4.71 (t, J=5.4 Hz, 1H), 4.81 (s, 1H), 4.88-4.96 (m, 2H), 6.41 (d, J=1.9 Hz, 1H), 7.31-7.40 (m, 1H), 7.47 (t, J=7.0 Hz, 1H), 7.50-7.56 (m, 2H), 7.65 (d, J=7.5 Hz, 1H), 10.77 (s, 1H).

Example 251

(2S,4S)-2-[4-(2-Chloro-phenoxy)-2-oxo-2,5-dihydro-pyrrol-1-yl]-4-methyl-hexanoic acid [1-((R)-2,3-dihydroxy-propyl)-1H-pyrazol-3-yl]-amide

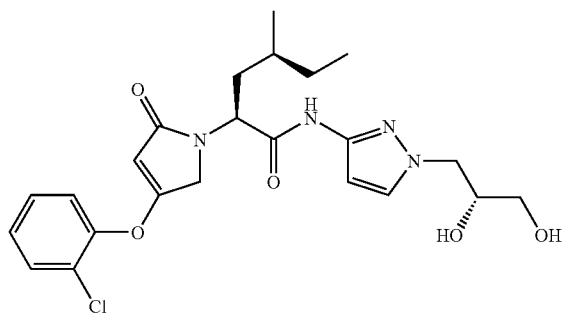

The mixture of stereoisomers of (S)-2-[4-(2-chloro-phenoxy)-2-oxo-2,5-dihydro-pyrrol-1-yl]-4-methyl-hexanoic acid [1-((R)-2,3-dihydroxy-propyl)-1H-pyrazol-3-yl]-amide (prepared as in Example 249) was separated into the single enantiomers by supercritical fluid chromatography on a Berger MultiGram II Supercritical Fluid Chromatography system (Model SD-1) from Mettler-Toledo AutoChem Berger Instruments, Newark, Del., USA (Chiral column: DAICEL AD, temperature of 30° C., a flow rate of 70 mL/min, 30% methanol and CO$_2$ pressure of 100 bar, Knauer variable wavelength UV detector with high pressure flow cell was used for SFC detection. Detection in SFC was performed by measurement of UV absorbance at 220 nm). The second peak from this separation gave (2S,4S)-2-[4-(2-chloro-phenoxy)-2-oxo-2,5-dihydro-pyrrol-1-yl]-4-methyl-hexanoic acid [1-((R)-2,3-dihydroxy-propyl)-1H-pyrazol-3-yl]-amide. HR-ES-MS (m/z) calculated for $C_{23}H_{29}ClN_4O_5$ [M+H]$^+$ 477.1899, observed 477.1900. $^1$H NMR (400 MHz, DMSO-d$_6$) δ ppm 0.83 (t, J=7.2 Hz, 3H), 0.92 (d, J=6.4 Hz, 3H), 1.04-1.18 (m, 1H), 1.24 (br. s., 1H), 1.40-1.53 (m, 1H), 1.56-1.67 (m, 1H), 1.69-1.80 (m, 1H), 3.23-3.33 (m, 2H), 3.78 (br. s., 1H), 3.87 (dd, J=13.6, 7.7 Hz, 1H), 4.09 (dd, J=13.6, 3.8 Hz, 1H), 4.23 (d, J=18.5 Hz, 1H), 4.58 (d, J=18.5 Hz, 1H), 4.70 (t, J=4.9 Hz, 1H), 4.79 (s, 1H), 4.87-4.96 (m, 2H), 6.42 (d, J=1.9 Hz, 1H), 7.37 (t, J=7.9 Hz, 1H), 7.46 (t, J=7.9 Hz, 1H), 7.49-7.53 (m, 1H), 7.53 (d, J=1.9 Hz, 1H), 7.65 (d, J=7.9 Hz, 1H), 10.79 (s, 1H).

Example 252

(R)-2-[4-(2-Chloro-phenoxy)-2-oxo-2,5-dihydro-pyrrol-1-yl]-4-methyl-hexanoic acid [1-((R)-2,2-dimethyl-[1,3]dioxolan-4-ylmethyl)-1H-pyrazol-3-yl]-amide

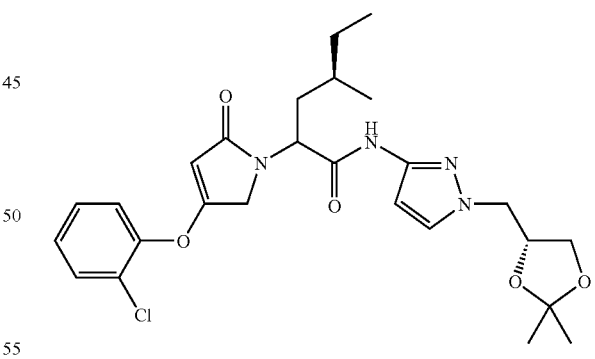

A solution of (D)-2-methyl-1-butanol (8.8 g, 100 mmol), triphenylphosphite (31 g, 100 mmol) in dichloromethane at 0° C. was treated with a solution of iodine (31.2 g, 123 mmol) in dichloromethane (1 L) over 1 h via a dropping funnel. The resulting mixture was stirred at room temperature overnight and treated with saturated sodium thiosulfate. The layers were separated and the organic layer was dried with sodium sulfate and concentrated in vacuo. The residue was distilled under reduced pressure (90° C., 200 mm Hg) and the distillate dissolved in a 10% diethyl ether/petroleum ether solution. The solution was washed with sodium thiosulfate, 0.1N aqueous sodium hydroxide solution, water and brine and dried over anhydrous sodium sulfate. The mixture was filtered and concentrated in vacuo which afforded (R)-1-iodo-2-methylbutane (9.67 g, 49%) as a colorless oil.

A solution of (benzhydrylidene-amino)-acetic acid ethyl ester (6.03 g, 22.58 mmol) in tetrahydrofuran (40 mL) was treated with potassium t-butoxide (2.53 g, 22.58 mmol) and stirred at 0° C. for 35 min. At this time a solution of (R)-1-iodo-2-methyl-butane (4.5 g, 22.72 mmol) in tetrahydrofuran (30 mL) was added via a syringe. The solution was stirred for 35 min and the resulting solution stirred at 0° C. for 10 min and then room temperature overnight. The resulting mixture was filtered through a layer of silica gel and rinsed with tetrahydrofuran and diethyl ether. The filtrate was concentrated in vacuo, the residue partitioned between tetrahydrofuran (130 mL) and a 2N hydrochloric acid solution (60 mL) and stirred at room temperature for 1.5 h. At this time the mixture was concentrated in vacuo and partitioned between with methyl t-butyl ether and water. The layers were separated and the aqueous phase was washed with methyl t-butyl ether. The organic phase was discarded and the aqueous phase was neutralized with a 1N aqueous sodium hydroxide solution (200 mL). The solution was extracted with methyl t-butyl ether. The organic layer was washed with brine and dried over sodium sulfate. The mixture was filtered and concentrated in vacuo and the residue was dissolved in diethyl ether (20 mL). The resulting solution was treated with 3M hydrogen chloride in diethyl ether (10 mL) and concentrated in vacuo. The residue was triturated with diethyl ether and hexanes which afforded (R)-2-amino-4-methyl-hexanoic acid ethyl ester hydrochloride (2.75 g, 58%) as a white solid.

A suspension of (R)-2-amino-4-methyl-hexanoic acid ethyl ester hydrochloride salt (1.57 g, 7.50 mmol) in acetonitrile (9 mL) was treated with N,N-diisopropylethylamine (1.62 mL) and stirred at 60° C. for 15 min. At this time the solution was treated with N,N-diisopropylethylamine (1.62 mL) and a solution of (E)-4-bromo-3-(2-chloro-phenoxy)-but-2-enoic acid ethyl ester (prepared as in Example 61, 2.39 g, 7.49 mmol) in acetonitrile (4 mL) via a dropping funnel and refluxed for 20 h. The mixture was concentrated in vacuo and the residue partitioned between ethyl acetate and water. The layers were separated and the organic layer was dried over anhydrous sodium sulfate. The mixture was filtered and concentrated in vacuo and the residue dissolved in tetrahydrofuran (8 mL) and transferred to an Emrys Optimizer microwave tube and microwaved at 160° C. for 4 h. The mixture was cooled and concentrated in vacuo and the residue was purified by ISCO flash chromatography (RediSep silica 80 g, 20% to 80% ethyl acetate/hexanes) which afforded (R)-2-[4-(2-chloro-phenoxy)-2-oxo-2,5-dihydro-pyrrol-1-yl]-4-methyl-hexanoic acid ethyl ester (1.26 g, 46%).

A solution of (R)-2-[4-(2-chloro-phenoxy)-2-oxo-2,5-dihydro-pyrrol-1-yl]-4-methyl-hexanoic acid ethyl ester (1.25 g, 3.42 mmol) in tetrahydrofuran (14 mL) was treated with a 0.5N lithium hydroxide solution (4 mL) and stirred at 5° C. for 2 h. The mixture was concentrated in vacuo and the residue was dissolved in water (40 mL) and washed with diethyl ether. The organic phase was discarded and the aqueous layer acidified with 1N aqueous hydrochloric acid (10 mL) and extracted with ethyl acetate. The combined ethyl acetate layers were concentrated in vacuo which afforded (R)-2-[4-(2-chloro-phenoxy)-2-oxo-2,5-dihydro-pyrrol-1-yl]-4-methyl-hexanoic acid (1.13 g, 98%) as a pale brown solid.

A solution of (S)-2-[4-(2-chloro-phenoxy)-2-oxo-2,5-dihydro-pyrrol-1-yl]-4-methyl-hexanoic acid (500 mg, 1.48 mmol) and 1-((R)-2,2-dimethyl-[1,3]dioxolan-4-yl-methyl)-1H-pyrazol-3-ylamine (364.8 mg, 1.85 mmol) in N,N-dimethylformamide (8 mL) was treated with N,N-diisopropylethylamine (0.68 mL) and benzotriazol-1-yl-oxy-tris(dimethylamino)phosphonium hexafluorophosphate (918 mg, 2.07 mmol) and the resulting mixture stirred at room temperature for 6 h. The mixture was concentrated in vacuo and the residue partitioned between ethyl acetate and an aqueous ammonium chloride solution. The layers were separated and the organic layer was washed with brine and dried with sodium sulfate. The mixture was filtered and concentrated in vacuo and the residue was purified by ISCO flash chromatography (RediSep silica 40 g, 20% to 80% ethyl acetate/hexanes,) which afforded (R)-2-[4-(2-chloro-phenoxy)-2-oxo-2,5-dihydro-pyrrol-1-yl]-4-methyl-hexanoic acid [1-((R)-2,2-dimethyl-[1,3]dioxolan-4-ylmethyl)-1H-pyrazol-3-yl]-amide (650 mg, 85%) as a gummy solid: HR-ES-MS (m/z) calculated for $C_{26}H_{33}ClN_4O_5$ $[M+H]^+$ 517.2212, observed 517.2211. $^1H$ NMR showed mixture of diastereomers (400 MHz, DMSO-$d_6$) δ ppm 0.81-0.91 (m, 3H), 1.25 (s, 3H), 1.26-1.35 (m, 9H), 1.68-1.86 (m, 2H), 3.74 (dd, J=8.3, 5.9 Hz, 1H), 4.01 (dd, J=8.3, 6.5 Hz, 1H), 4.04-4.17 (m, 2H), 4.22 (d, J=18.4 Hz, 1H), 4.29-4.41 (m, 1H), 4.58 (dd, J=18.4, 2.3 Hz, 1H), 4.78 (dd, J=9.8, 6.0 Hz, 1H), 4.80 (s, 1H), 6.44 (d, J=2.1 Hz, 1H), 7.37 (td, J=7.9, 1.2 Hz, 1H), 7.47 (td, J=7.9, 1.2 Hz, 1H), 7.52 (dd, J=7.9, 1.2 Hz, 1H), 7.61 (t, J=2.1 Hz, 1H), 7.66 (dd, J=7.9, 1.2 Hz, 1H), 10.73 (d, J=3.0 Hz, 1H).

Example 253

(R)-2-[4-(2-Chloro-phenoxy)-2-oxo-2,5-dihydro-pyrrol-1-yl]-4-methyl-hexanoic acid [1-((R)-2,3-dihydroxy-propyl)-1H-pyrazol-3-yl]-amide

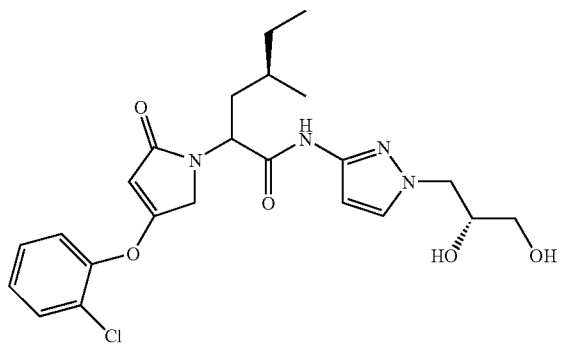

A solution of (R)-2-[4-(2-chloro-phenoxy)-2-oxo-2,5-dihydro-pyrrol-1-yl]-4-methyl-hexanoic acid [1-((R)-2,2-dimethyl-[1,3]dioxolan-4-ylmethyl)-1H-pyrazol-3-yl]-amide (prepared in Example 252, 600 mg, 1.16 mmol) in tetrahydrofuran (25 mL) was treated with 2N aqueous hydrochloric acid (12 mL) and stirred at room temperature for 2 h. At this time the mixture was concentrated in vacuo and the residue partitioned between 17% ethyl acetate/hexanes and water. The layers were separated and the organic layer was washed with brine and dried with sodium sulfate. The mixture was filtered and concentrated in vacuo which afforded (R)-2-[4-(2-chloro-phenoxy)-2-oxo-2,5-dihydro-pyrrol-1-yl]-4-methyl-hexanoic acid [1-((R)-2,3-dihydroxy-propyl)-1H-pyrazol-3-yl]-amide (500 mg, 90.4%) as a fluffy powder: HR-ES-MS (m/z) calculated for $C_{23}H_{29}ClN_4O_5$ $[M+H]^+$ 477.1899, observed 477.1896. ¹H NMR (300 MHz, DMSO-d₆) δ ppm 0.86 (br. s., 3H), 1.29 (br. s., 6H), 1.78 (br. s., 2H), 3.14-3.58 (m, 4H), 3.70-3.93 (m, 2H), 4.09 (dd, J=13.4, 2.6 Hz, 1H), 4.21 (d, J=18.4 Hz, 1H), 4.58 (d, J=18.4 Hz, 1H), 4.69-4.79 (m, 1H), 4.79 (s, 1H), 6.41 (br. s., 1H), 7.37 (t, J=7.2 Hz, 1H), 7.41-7.58 (m, 3H), 7.65 (d, J=7.8 Hz, 1H), 10.70 (br. s., 1H).

Example 254

(2R,4R)-2-[4-(2-Chloro-phenoxy)-2-oxo-2,5-dihydro-pyrrol-1-yl]-4-methyl-hexanoic acid [1-((R)-2,3-dihydroxy-propyl)-1H-pyrazol-3-yl]-amide

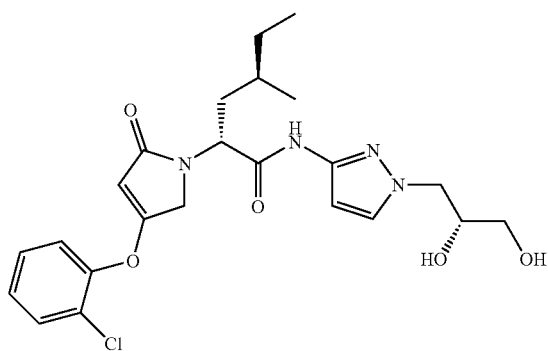

The mixture of stereoisomers of (S)-2-[4-(2-chloro-phenoxy)-2-oxo-2,5-dihydro-pyrrol-1-yl]-4-methyl-hexanoic acid [1-((R)-2,3-dihydroxy-propyl)-1H-pyrazol-3-yl]-amide (prepared as in Example 253) was separated into the single enantiomers by supercritical fluid chromatography on a Berger MultiGram II Supercritical Fluid Chromatography system (Model SD-1) from Mettler-Toledo AutoChem Berger Instruments, Newark, Del., USA (Chiral column: DAICEL AD, temperature of 30° C., a flow rate of 70 mL/min, 30% methanol and CO₂ pressure of 100 bar, Knauer variable wavelength UV detector with high pressure flow cell was used for SFC detection. Detection in SFC was performed by measurement of UV absorbance at 220 nm). The first peak from this separation gave (2R,4R)-2-[4-(2-chloro-phenoxy)-2-oxo-2,5-dihydro-pyrrol-1-yl]-4-methyl-hexanoic acid [1-((R)-2,3-dihydroxy-propyl)-1H-pyrazol-3-yl]-amide: HR-ES-MS (m/z) calculated for C₂₃H₂₉ClN₄O₅ [M+H]⁺ 477.1899, observed 477.1900. ¹H NMR (300 MHz, DMSO-d₆) δ ppm 0.85 (br. s., 3H), 1.28 (br. s., 6H), 1.78 (br. s., 2H), 3.32 (br. s., 2H), 3.66-3.97 (m, 2H), 4.09 (d, J=12.1 Hz, 1H), 4.21 (d, J=18.4 Hz, 1H), 4.58 (d, J=18.4 Hz, 1H), 4.67-4.85 (m, 3H), 4.95 (d, J=3.6 Hz, 1H), 6.41 (br. s., 1H), 7.27-7.58 (m, 4H), 7.64 (d, J=7.5 Hz, 1H), 10.70 (br. s., 1H).

Example 255

(2S,4R)-2-[4-(2-Chloro-phenoxy)-2-oxo-2,5-dihydro-pyrrol-1-yl]-4-methyl-hexanoic acid [1-((R)-2,3-dihydroxy-propyl)-1H-pyrazol-3-yl]-amide

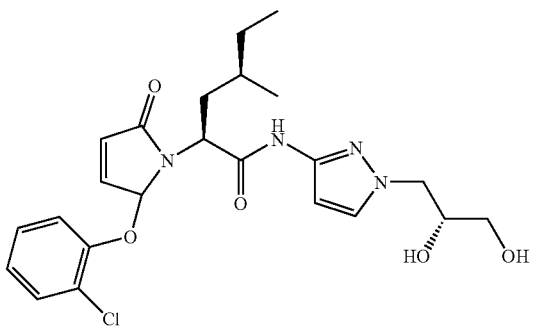

The mixture of stereoisomers of (S)-2-[4-(2-chloro-phenoxy)-2-oxo-2,5-dihydro-pyrrol-1-yl]-4-methyl-hexanoic acid [1-((R)-2,3-dihydroxy-propyl)-1H-pyrazol-3-yl]-amide (prepared as in Example 253) was separated into the single enantiomers by supercritical fluid chromatography on a Berger MultiGram II Supercritical Fluid Chromatography system (Model SD-1) from Mettler-Toledo AutoChem Berger Instruments, Newark, Del., USA (Chiral column: DAICEL AD, temperature of 30° C., a flow rate of 70 mL/min, 30% methanol and CO₂ pressure of 100 bar, Knauer variable wavelength UV detector with high pressure flow cell was used for SFC detection. Detection in SFC was performed by measurement of UV absorbance at 220 nm). The second peak from this separation gave (2S,4R)-2-[4-(2-chloro-phenoxy)-2-oxo-2,5-dihydro-pyrrol-1-yl]-4-methyl-hexanoic acid [1-((R)-2,3-dihydroxy-propyl)-1H-pyrazol-3-yl]-amide: HR-ES-MS (m/z) calculated for C₂₃H₂₉ClN₄O₅ [M+H]⁺ 477.1899, observed 477.1896; ¹H NMR (300 MHz, DMSO-d₆) δ ppm 0.77-0.93 (m, 3H), 1.29 (br. s., 6H), 1.63-1.92 (m, 2H), 3.31 (br. s., 2H), 3.69-3.81 (m, 1H), 3.86 (dd, J=13.5, 7.5 Hz, 1H), 4.09 (dd, J=13.5, 3.6 Hz, 1H), 4.21 (d, J=18.4 Hz, 1H), 4.58 (d, J=18.4 Hz, 1H), 4.66-4.78 (m, 2H), 4.79 (s, 1H), 4.94 (d, J=4.5 Hz, 1H), 6.41 (s, 1H), 7.36 (t, J=7.8 Hz, 1H), 7.42-7.55 (m, 3H), 7.65 (d, J=7.8 Hz, 1H), 10.70 (s, 1H).

Example 256

2-[4-(3-Ethoxy-2,6-difluoro-phenoxy)-2-oxo-2,5-dihydro-pyrrol-1-yl]-N-[1-(2-hydroxy-2-methyl-propyl)-1H-pyrazol-3-yl]-3-(tetrahydro-pyran-4-yl)-propionamide

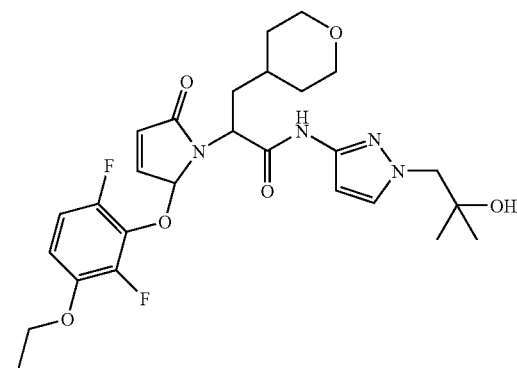

A solution of 2-t-butoxycarbonylamino-3-(tetrahydropyran-4-yl)-propionic acid (2.61 g, 9.55 mmol) and 1-(3-aminopyrazol-1-yl)-2-methyl-propan-2-ol (prepared in U.S. Pat. Appl. US2008021032 Example 80, 1.8 g, 11.6 mmol) in N,N-dimethylformamide (15 mL) was treated with N,N-diisopropylethylamine (2.58 g, 20 mmol) and benzotriazol-1-yl-oxy-tris(dimethylamino)phosphonium hexafluorophosphate (8.84 g, 20 mmol) and the resulting mixture stirred at room temperature for 12 h. At this time the mixture was concentrated in vacuo and the residue partitioned between ethyl acetate and a concentrated ammonium chloride solution. The layers were separated and the organic layer was washed with water and brine, and dried over anhydrous sodium sulfate. The mixture was filtered and concentrated in vacuo and the residue purified by ISCO flash chromatography (RediSep silica 120 g, 30% to 100% ethyl acetate/hexanes) which afforded [1-[1-(2-hydroxy-2-methyl-propyl)-1H-pyrazol-3-ylcarbamoyl]-2-(tetrahydro-pyran-4-yl)-ethyl]-carbamic acid t-butyl ester (3.2 g, 82%) as a white solid.

A solution of [1-[1-(2-hydroxy-2-methyl-propyl)-1H-pyrazol-3-ylcarbamoyl]-2-(tetrahydro-pyran-4-yl)-ethyl]-carbamic acid t-butyl ester (3.2 g, 7.8 mmol) in methanol (150 mL) was treated with hydrogen chloride gas for 2 min at 0° C. and then stirred at room temperature for 1 h. After this time the mixture was concentrated in vacuo and the residue treated with acetonitrile (50 mL). The mixture was concentrated in vacuo which afforded 2-amino-N-[1-(2-hydroxy-2-methyl-propyl)-1H-pyrazol-3-yl]-3-(tetrahydro-pyran-4-yl)-propionamide hydrochloride (3.0 g, 100%) as a white solid.

A suspension of 2-amino-N-[1-(2-hydroxy-2-methyl-propyl)-1H-pyrazol-3-yl]-3-(tetrahydro-pyran-4-yl)-propionamide hydrochloride salt (766 mg, 2.0 mmol) in acetonitrile (15 mL) was treated with N,N-diisopropylethylamine (1.0 mL) and the resulting mixture stirred at 60° C. for 15 min. After this time N,N-diisopropylethylamine (0.5 mL) and a solution of (E)-4-bromo-3-(3-ethoxy-2,6-difluoro-phenoxy)-but-2-enoic acid ethyl ester (prepared in Example 116, 705 mg, 1.93 mmol) in acetonitrile (10 mL) were added and the resulting solution refluxed for 20 h. The resulting mixture was concentrated in vacuo and the residue partitioned between ethyl acetate and water. The layers were separated and the organic layer was dried over anhydrous sodium sulfate. The mixture was filtered and concentrated in vacuo and the residue dissolved in tetrahydrofuran (4 mL) and transferred to an Emrys Optimizer microwave tube and microwaved at 160° C. for 6 h. The mixture was concentrated in vacuo and the residue was purified by ISCO flash chromatography (RediSep silica 40 g, 5% to 80% (10% methanol/dichloromethane)/hexanes) which afforded 2-[4-(3-ethoxy-2,6-difluoro-phenoxy)-2-oxo-2,5-dihydro-pyrrol-1-yl]-N-[1-(2-hydroxy-2-methyl-propyl)-1H-pyrazol-3-yl]-3-(tetrahydro-pyran-4-yl)-propionamide (148 mg, 14%): HR-ES-MS (m/z) calculated for $C_{27}H_{34}F_2N_4O_6$ [M+H]$^+$ 549.2519, observed 549.2520; $^1$H NMR (400 MHz, DMSO-$d_6$) δ ppm 1.05 (br. s., 3H), 1.07 (br. s., 3H), 1.13-1.31 (m, 3H), 1.35 (t, J=6.9 Hz, 3H), 1.55-1.74 (m, 3H), 1.75-1.88 (m, 1H), 3.09-3.31 (m, 2H), 3.82 (br. s., 2H), 3.90 (s, 2H), 4.14 (q, J=6.9 Hz, 2H), 4.32 (d, J=18.6 Hz, 1H), 4.66 (br. s., 1H), 4.64 (d, J=18.6 Hz, 1H), 4.91 (dd, J=10.8, 4.4 Hz, 1H), 5.06 (s, 1H), 6.45 (d, J=1.8 Hz, 1H), 7.17 (td, J=9.4, 4.9 Hz, 1H), 7.27 (td, J=9.4, 1.3 Hz, 1H), 7.54 (d, J=1.8 Hz, 1H), 10.81 (s, 1H).

Example 257

(S)-2-[4-(3-Ethoxy-2,6-difluoro-phenoxy)-2-oxo-2,5-dihydro-pyrrol-1-yl]-N-[1-(2-hydroxy-2-methyl-propyl)-1H-pyrazol-3-yl]-3-(tetrahydro-pyran-4-yl)-propionamide

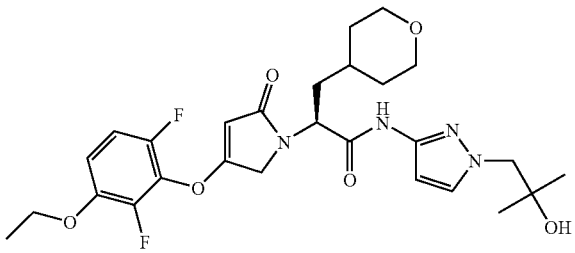

The mixture of stereoisomers of (S)-2-[4-(2-chloro-phenoxy)-2-oxo-2,5-dihydro-pyrrol-1-yl]-4-methyl-hexanoic acid [1-((R)-2,3-dihydroxy-propyl)-1H-pyrazol-3-yl]-amide (prepared as in Example 256) was separated into the single enantiomers by supercritical fluid chromatography on a Berger MultiGram II Supercritical Fluid Chromatography system (Model SD-1) from Mettler-Toledo AutoChem Berger Instruments, Newark, Del., USA (Chiral column: DAICEL AD, temperature of 30° C., a flow rate of 70 mL/min, 15% methanol and CO$_2$ pressure of 100 bar, Knauer variable wavelength UV detector with high pressure flow cell was used for SFC detection. Detection in SFC was performed by measurement of UV absorbance at 220 nm). The first peak from this separation gave (S)-2-[4-(3-ethoxy-2,6-difluoro-phenoxy)-2-oxo-2,5-dihydro-pyrrol-1-yl]-N-[1-(2-hydroxy-2-methyl-propyl)-1H-pyrazol-3-yl]-3-(tetrahydro-pyran-4-yl)-propionamide: HR-ES-MS (m/z) calculated for $C_{27}H_{34}F_2N_4O_6$ [M+H]$^+$ 549.2519, observed 549.2521; $^1$H NMR (400 MHz, DMSO-$d_6$) δ ppm 1.05 (br. s., 3H), 1.07 (br. s., 3H), 1.13-1.31 (m, 3H), 1.35 (t, J=6.8 Hz, 3H), 1.56-1.74 (m, 3H), 1.73-1.89 (m, 1H), 3.10-3.30 (m, 2H), 3.72-3.87 (m, 2H), 3.90 (s, 2H), 4.14 (q, J=6.8 Hz, 2H), 4.32 (d, J=18.8 Hz, 1H), 4.64 (d, J=18.8 Hz, 1H), 4.67 (br. s., 1H), 4.85-4.96 (m, 1H), 5.07 (s, 1H), 6.45 (s, 1H), 7.07-7.22 (m, 1H), 7.23-7.33 (m, 1H), 7.54 (s, 1H), 10.81 (s, 1H).

Example 258

(R)-2-[4-(3-Ethoxy-2,6-difluoro-phenoxy)-2-oxo-2,5-dihydro-pyrrol-1-yl]-N-[1-(2-hydroxy-2-methyl-propyl)-1H-pyrazol-3-yl]-3-(tetrahydro-pyran-4-yl)-propionamide

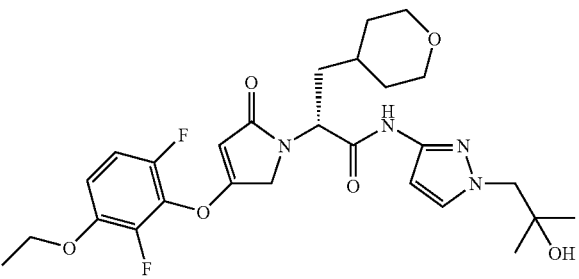

The mixture of stereoisomers of (S)-2-[4-(2-chloro-phenoxy)-2-oxo-2,5-dihydro-pyrrol-1-yl]-4-methyl-hexanoic acid [1-((R)-2,3-dihydroxy-propyl)-1H-pyrazol-3-yl]-amide (prepared as in Example 256) was separated into the single enantiomers by supercritical fluid chromatography on a Berger MultiGram II Supercritical Fluid Chromatography system (Model SD-1) from Mettler-Toledo AutoChem Berger Instruments, Newark, Del., USA (Chiral column: DAICEL AD, temperature of 30° C., a flow rate of 70 mL/min, 15% methanol and $CO_2$ pressure of 100 bar, Knauer variable wavelength UV detector with high pressure flow cell was used for SFC detection. Detection in SFC was performed by measurement of UV absorbance at 220 nm). The second peak from this separation gave (R)-2-[4-(3-ethoxy-2,6-difluoro-phenoxy)-2-oxo-2,5-dihydro-pyrrol-1-yl]-N-[1-(2-hydroxy-2-methyl-propyl)-1H-pyrazol-3-yl]-3-(tetrahydro-pyran-4-yl)-propionamide: HR-ES-MS (m/z) calculated for $C_{27}H_{34}F_2N_4O_6$ [M+H]$^+$ 549.2519, observed 549.2523; $^1$H NMR (400 MHz, DMSO-$d_6$) δ ppm 1.05 (br. s., 3H), 1.06 (br. s., 3H), 1.12-1.31 (m, 3H), 1.35 (t, J=6.8 Hz, 3H), 1.64 (d, J=13.4 Hz, 3H), 1.81 (br. s., 1H), 3.05-3.33 (m, 2H), 3.70-3.86 (m, 2H), 3.89 (s, 2H), 4.13 (q, J=6.8 Hz, 2H), 4.32 (d, J=18.8 Hz, 1H), 4.64 (d, J=18.8 Hz, 1H), 4.85-4.99 (m, 1H), 5.06 (s, 1H), 6.45 (s, 1H), 7.11-7.21 (m, 1H), 7.27 (br. s., 1H), 7.54 (s, 1H), 10.81 (s, 1H).

Example 259

(2S,4S)-4-Ethoxy-2-[4-(3-ethoxy-2-fluoro-phenoxy)-2-oxo-2,5-dihydro-pyrrol-1-yl]-pentanoic acid [1-(2-hydroxy-2-methyl-propyl)-1H-pyrazol-3-yl]-amide

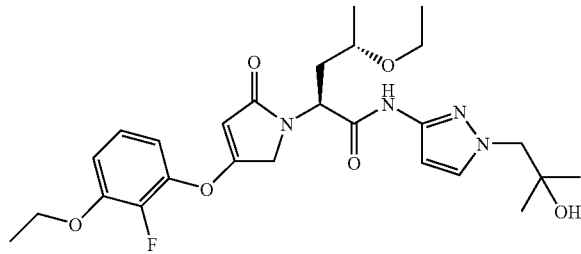

A suspension of (2S,4S)-2-amino-4-ethoxy-pentanoic acid [1-(2-hydroxy-2-methyl-propyl)-1H-pyrazol-3-yl]-amide hydrochloride salt (prepared as in Example 95, 124.5 mg, 0.335 mmol) in acetonitrile (7 mL) was treated with N,N-diisopropylethylamine (0.25 mL). At this time a solution of (E)-4-bromo-3-(3-ethoxy-2-fluoro-phenoxy)-but-2-enoic acid ethyl ester (prepared as in Example 114, 117 mg, 0.337 mmol) in acetonitrile (2 mL) was added and the resulting solution refluxed for 64 h. The mixture was concentrated in vacuo and the residue partitioned between ethyl acetate and water. The layers were separated and the organic layer was dried over anhydrous sodium sulfate. The mixture was filtered and concentrated in vacuo and the residue dissolved in tetrahydrofuran (2 mL) and transferred to an Emrys Optimizer microwave tube and microwaved at 160° C. for 1.5 h. The mixture was concentrated in vacuo and the residue was purified by ISCO flash chromatography (RediSep silica 12 g, 10% to 70% (10% methanol/dichloromethane)/hexanes,) which afforded (2S,4S)-4-ethoxy-2-[4-(3-ethoxy-2-fluoro-phenoxy)-2-oxo-2,5-dihydro-pyrrol-1-yl]-pentanoic acid [1-(2-hydroxy-2-methyl-propyl)-1H-pyrazol-3-yl]-amide (87 mg, 50%): HR-ES-MS (m/z) calculated for $C_{26}H_{35}FN_4O_6$ [M+H]$^+$ 519.2614, observed 519.2615. $^1$H NMR (300 MHz, DMSO-$d_6$) δ ppm 0.95-1.19 (m, 12H), 1.36 (t, J=6.0 Hz, 3H), 1.75-2.02 (m, 2H), 3.15-3.30 (m, 1H), 3.33 (br. s., 1H), 3.40-3.55 (m, 1H), 3.89 (br. s., 2H), 4.06-4.21 (m, 2H), 4.29 (d, J=18.4 Hz, 1H), 4.49 (d, J=18.4 Hz, 1H), 4.67 (br. s., 1H), 4.85-4.99 (m, 2H), 6.44 (br. s., 1H), 6.91-7.06 (m, 1H), 7.05-7.29 (m, 2H), 7.53 (br. s., 1H), 10.69 (br. s., 1H).

Example 260

(S)-2-[4-(3-Ethoxy-2,6-difluoro-phenoxy)-2-oxo-2,5-dihydro-pyrrol-1-yl]-4-methyl-pentanoic acid [1-(2-hydroxy-2-methyl-propyl)-1H-pyrazol-3-yl]-amide

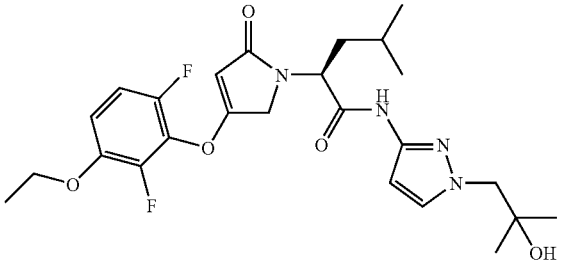

A solution of N-t-butoxycarbonyl-(L)-leucine mono-hydrate (2.81 g, 11.28 mmol) and 1-(3-amino-pyrazol-1-yl)-2-methyl-propan-2-ol (prepared in U.S. Pat. Appl. US2008021032 Example 80, 2.02 g, 13 mmol) in N,N-dimethylformamide (15 mL) was treated with N,N-diisopropylethylamine (3.5 mL, 20 mmol) and benzotriazol-1-yl-oxy-tris(dimethylamino)phosphonium hexafluorophosphate (8.84 g, 20 mmol) and stirred at room temperature for 12 h. At this time the mixture was concentrated in vacuo. The residue was partitioned between ethyl acetate and a concentrated ammonium chloride solution. The layers were separated and the organic layer was washed with water and brine, and dried over anhydrous sodium sulfate. The mixture was filtered and concentrated in vacuo and the residue purified by ISCO flash chromatography (RediSep silica 120 g, 20% to 80% ethyl acetate/hexanes) which afforded {(S)-1-[1-(2-hydroxy-2-methyl-propyl)-1H-pyrazol-3-ylcarbamoyl]-3-methyl-butyl}-carbamic acid t-butyl ester (4.15 g, 100%) as a white solid.

A solution of {(S)-1-[1-(2-hydroxy-2-methyl-propyl)-1H-pyrazol-3-ylcarbamoyl]-3-methyl-butyl}-carbamic acid t-butyl ester (4.15 g) in dichloromethane (8 mL) was treated with trifluoroacetic acid (8 mL) and stirred at room temperature for 1 h. At this time the mixture was concentrated in vacuo and the residue dissolved in methanol (10 mL) and treated with hydrogen chloride gas for 2 min. The mixture was concentrated in vacuo and the residue was dried under high vacuum. The solid obtained was triturated with diethyl ether which afforded (S)-2-amino-4-methyl-pentanoic acid [1-(2-hydroxy-2-methyl-propyl)-1H-pyrazol-3-yl]amide hydrochloride (3.86 g, 100%) as a white solid.

A suspension of (S)-2-amino-4-methyl-pentanoic acid [1-(2-hydroxy-2-methyl-propyl)-1H-pyrazol-3-yl]amide hydrochloride salt (2.0 g, 5.8 mmol) in acetonitrile (25 mL) was treated with N,N-diisopropylethylamine (4.0 mL) and stirred at 60° C. for 15 min. At this time N,N-diisopropylethylamine (2.5 mL) and a solution of (E)-4-bromo-3-(3- ethoxy-2,6-difluoro-phenoxy)-but-2-enoic acid ethyl ester (prepared in Example 116, 1.37 g, 3.75 mmol) in acetonitrile (10 mL) were added and the resulting solution refluxed for 48 h. The mixture was concentrated in vacuo and the residue partitioned between ethyl acetate and water. The layers were separated and the organic layer was dried over sodium sulfate. The mixture was filtered and concentrated in vacuo and the residue purified by ISCO flash chromatography (RediSep silica 40 g, 5% to 80% (10% methanol/dichloromethane)/hexanes) which afforded (S)-2-[4-(3-ethoxy-2,6-difluoro-phenoxy)-2-oxo-2,5-dihydro-pyrrol-1-yl]-4-methyl-pentanoic acid [1-(2-hydroxy-2-methyl-propyl)-1H-pyrazol-3-yl]-amide (295 mg, 16%): HR-ES-MS (m/z) calculated for $C_{25}H_{32}F_2N_4O_5$ [M+H]$^+$ 507.2414, observed 507.2414; $^1$H NMR (300 MHz, CDCl$_3$) δ ppm 0.96 (br. s., 6H), 1.13 (br. s., 6H), 1.42 (br. s., 3H), 1.48-1.64 (m, 1H), 1.66-1.95 (m, 2H), 3.73 (br. s., 1H), 3.91 (br. s., 2H), 4.01-4.24 (m, 3H), 4.38 (d, J=17.8 Hz, 1H), 4.88 (br. s., 1H), 4.99 (br. s., 1H), 6.66 (br. s., 1H), 6.73-7.00 (m, 2H), 7.27 (br. s., 1H), 8.79 (br. s., 1H).

Example 261

2-[4-(2-Bromo-phenoxy)-2-oxo-2,5-dihydro-pyrrol-1-yl]-N-[1-(2-hydroxy-2-methyl-propyl)-1H-pyrazol-3-yl]-3-(tetrahydro-pyran-4-yl)-propionamide

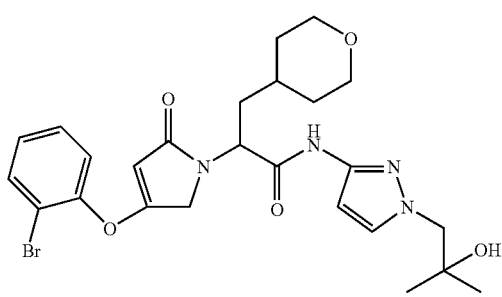

A suspension of 2-amino-N-[1-(2-hydroxy-2-methyl-propyl)-1H-pyrazol-3-yl]-3-(tetrahydro-pyran-4-yl)-propionamide hydrochloride salt (prepared as in Example 256, 591 mg, 1.54 mmol) in acetonitrile (20 mL) was treated with N,N-diisopropylethylamine (0.7 mL) and stirred at 60° C. for 15 min. At this time N,N-diisopropylethylamine (0.3 mL) and a solution of (E)-4-bromo-3-(2-bromo-phenoxy)-but-2-enoic acid ethyl ester (prepared in Example 136, 928 mg, 2.55 mmol) in acetonitrile (10 mL) were added and the resulting solution was stirred at 60° C. for 12 h and at 80° C. for 1 h. The mixture was concentrated in vacuo and the residue was partitioned between ethyl acetate and water. The layers were separated and the organic layer was dried over sodium sulfate. The mixture was filtered and concentrated in vacuo and the residue purified by ISCO flash chromatography (RediSep silica 40 g, 25% to 80% ethyl acetate/hexanes) which afforded (E)-3-(2-bromo-phenoxy)-4-{1-[1-(2-hydroxy-2-methyl-propyl)-1H-pyrazol-3-ylcarbamoyl]-2-(tetrahydro-pyran-4-yl)-ethylamino}-but-2-enoic acid ethyl ester (250 mg, 27%) as an off-white solid.

A solution of (E)-3-(2-bromo-phenoxy)-4-{1-[1-(2-hydroxy-2-methyl-propyl)-1H-pyrazol-3-ylcarbamoyl]-2-(tetrahydro-pyran-4-yl)-ethylamino}-but-2-enoic acid ethyl ester (250 mg) in tetrahydrofuran (8 mL) was placed in an Emrys Optimizer microwave tube and microwaved at 160° C. for 3 h. The mixture was concentrated in vacuo and the residue was purified by ISCO flash chromatography (Re-diSep silica 4 g, 30% to 100% ethyl acetate/hexanes) which afforded 2-[4-(2-bromo-phenoxy)-2-oxo-2,5-dihydro-pyrrol-1-yl]-N-[1-(2-hydroxy-2-methyl-propyl)-1H-pyrazol-3-yl]-3-(tetrahydro-pyran-4-yl)-propionamide (80 mg, 35%) as a light yellow solid: HR-ES-MS (m/z) calculated for $C_{25}H_{31}BrN_4O_5$ [M+H]$^+$ 547.1551, observed 547.1551. $^1$H NMR (300 MHz, DMSO-d$_6$) δ ppm 1.04 (br. s., 3H), 1.06 (br. s., 3H), 1.11-1.48 (m, 3H), 1.53-1.73 (m, 3H), 1.73-1.89 (m, 1H), 3.11-3.31 (m, 2H), 3.72-3.87 (m, 2H), 3.89 (s, 2H), 4.24 (d, J=18.4 Hz, 1H), 4.62 (d, J=18.4 Hz, 1H), 4.66-4.72 (m, 1H), 4.79 (s, 1H), 4.93 (dd, J=10.6, 4.8 Hz, 1H), 6.45 (d, J=2.1 Hz, 1H), 7.22-7.34 (m, 1H), 7.48-7.53 (m, 2H), 7.54 (d, J=2.1 Hz, 1H), 7.79 (d, J=8.2 Hz, 1H), 10.81 (br. s., 1H).

Example 262

(S)-2-[4-(2,6-Difluoro-phenoxy)-2-oxo-2,5-dihydro-pyrrol-1-yl]-N-[1-(2-hydroxy-2-methyl-propyl)-1H-pyrazol-3-yl]-3-tetrahydro-pyran-2-yl-propionamide

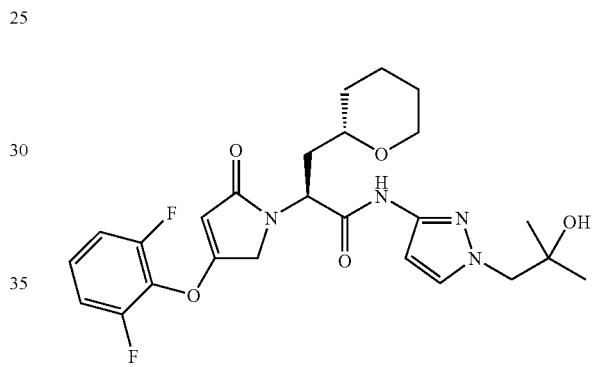

The mixture of stereoisomers of (S)-2-[4-(2-chloro-phenoxy)-2-oxo-2,5-dihydro-pyrrol-1-yl]-4-methyl-hexanoic acid [1-((R)-2,3-dihydroxy-propyl)-1H-pyrazol-3-yl]-amide (prepared as in Example 93) was separated into the single enantiomers by supercritical fluid chromatography on a Berger MultiGram II Supercritical Fluid Chromatography system (Model SD-1) from Mettler-Toledo AutoChem Berger Instruments, Newark, Del., USA (Chiral column: DAICEL AD, temperature of 30° C., a flow rate of 70 mL/min, 25% methanol and CO$_2$ pressure of 100 bar, Knauer variable wavelength UV detector with high pressure flow cell was used for SFC detection. Detection in SFC was performed by measurement of UV absorbance at 220 nm). The main peak from this separation gave (S)-2-[4-(2,6-difluoro-phenoxy)-2-oxo-2,5-dihydro-pyrrol-1-yl]-N-[1-(2-hydroxy-2-methyl-propyl)-1H-pyrazol-3-yl]-3-tetrahydro-pyran-2-yl-propionamide: HR-ES-MS (m/z) calculated for $C_{25}H_{30}F_2N_4O_6$ [M+H]$^+$ 505.2257, observed 505.2258; $^1$H NMR (300 MHz, DMSO-d$_6$) δ ppm 1.05 (br. s., 6H), 1.23 (br. s., 1H), 1.42 (br. s., 3H), 1.59 (d, J=11.8 Hz, 1H), 1.75 (br. s., 1H), 1.90 (br. s., 2H), 3.10-3.30 (d, J=11.5 Hz, 1H), 3.89 (s, 2H), 4.33 (d, J=18.4 Hz, 1H), 4.50 (m, J=18.4 Hz, 1H), 4.66 (br. s., 1H), 4.81-4.97 (m, 1H), 5.02 (s, 1H), 6.45 (br. s., 1H), 7.27-7.50 (m, 3H), 7.54 (br. s., 1H), 10.67 (br. s., 1H).

Example 263

2-[4-(2-Chloro-phenoxy)-2-oxo-2,5-dihydro-pyrrol-1-yl]-3-((1R,3S,4R)-3,4-difluoro-cyclopentyl)-N-[1-((R)-2,3-dihydroxy-propyl)-1H-pyrazol-3-yl]-propionamide

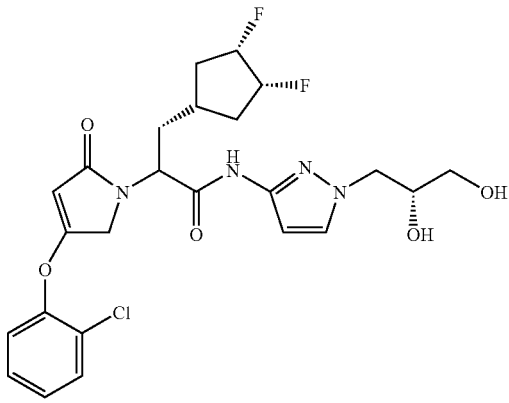

A suspension of lithium aluminum hydride (6.6 g, 174 mmol) in diethyl ether (60 mL) under argon was treated dropwise a solution of 3-cyclopentene-1-carboxyclic acid (10.00 g, 89.2 mmol) in diethyl ether (50 mL). After the addition was complete, the mixture was refluxed for 3 h, then cooled to room temperature and slowly quenched with water (28 mL) followed by 3N aqueous hydrochloric acid (60 mL). A thick precipitate formed and the slurry was diluted with more diethyl ether and water. This was then filtered through a cintered glass funnel to remove the salts and the filterate allowed to separate into layers. The organic layer was removed and dried over sodium sulfate, filtered and concentrated in vacuo to afford cyclopent-3-enyl-methanol (7.86 g, 90%) as a light yellow oil.

In a flask under argon was placed cyclopent-3-enyl-methanol (7.86 g, 80 mmol) and pyridine (100 mL). To this mixture was slowly added benzoyl chloride (9.30 mL, 80 mmol). After addition was complete, the mixture was stirred at 25° C. for 1.5 h. After this time, the mixture was slowly treated with water (15 mL) and concentrated in vacuo to remove most of the pyridine. The mixture was taken up into chloroform (400 mL) and washed with water (300 mL). The organic layer was separated, dried over sodium sulfate, filtered and concentrated in vacuo to afford benzoic acid cyclopent-3-enylmethyl ester (15.86 g, 98%) as a light yellow oil.

In a flask was placed a 50% solution of N-methylmorpholine-n-oxide in water (19.3 g, 0.082 mol), acetone (100 mL) and 2.5% osmium tetraoxide in t-butanol (1.5 mL). To this stirred mixture was then added dropwise over 1.5 h a solution of benzoic acid cyclopent-3-enylmethyl ester (15.86 g, 0.078 mol) in acetone (90 mL). The mixture was stirred overnight at 25° C. and then diluted with chloroform (250 mL) and water (75 mL). The layers were shaken and separated. The organic layer was washed with a 1N aqueous hydrochloric acid solution (2×75 mL), a saturated sodium bicarbonate solution (75 mL) dried over sodium sulfate, and concentrated in vacuo to afford an off-white solid. The solid was recrystallized from hot toluene to afford (1S,3R,4S)-3,4-dihydroxy-cyclopentylmethyl ester (12.33 g, 67%) as large white crystals.

A mixture of benzoic acid (1S,3R,4S)-3,4-dihydroxy-cyclopentylmethyl ester (3.00 g, 12.7 mmol), carbon tetrachloride (45 mL) and thionyl chloride (1.11 mL, 15.24 mmol) was refluxed for 2 h. The mixture was concentrated in vacuo to afford a colorless oil which was taken up in carbon tetrachloride (12 mL), acetonitrile (12 mL) and water (18 mL). The resulting mixture was vigorously stirred and sodium periodate (2.7 g, 12.70 mmol) and ruthenium(III) chloride hydrate (15 mg) were added and stirred at 25° C. for 1.5 h. After this time, an additional amount of sodium periodate (60 mg) was added and stirred for 1 h more. The mixture was extracted with methylene chloride (2×90 mL) and the combined organic layers washed with a saturated sodium bicarbonate solution (60 mL), a saturated aqueous solution of sodium chloride (60 mL), dried over sodium sulfate, filtered and concentrated in vacuo to afford benzoic acid (3aα,5α,6aα)-(tetrahydro-4H-cyclopenta-1,3,2-dioxathiol-5-yl)methyl ester S,S-dioxide (3.79 g, quant). as a white solid.

In a flask under argon was placed benzoic acid (3aα,5α,6aα)-(tetrahydro-4H-cyclopenta-1,3,2-dioxathiol-5-yl)methyl ester S,S-dioxide (3.79 g, 12.70 mmol), acetonitrile (125 mL) and tetramethylammonium fluoride (1.28 g, 13.34 mmol). The mixture was refluxed for 1 h. After this time, the mixture was concentrated in vacuo to afford a tan semisolid material (4.98 g). This material was treated with methanol (50 mL) and concentrated sulfuric acid (50 drops) and stirred at 25° C. for 6 h. After this time, the mixture was concentrated in vacuo and the residue taken up in ethyl acetate (200 mL) and washed with a saturated aqueous sodium bicarbonate solution (50 mL). The organic layer was separated, dried over sodium sulfate, filtered and concentrated with silica gel (6 g). Purification by Biotage flash chromatography (AnaLogix 40 g column, 10% ethyl acetate/hexanes to 30% ethyl acetate/hexanes) afforded (1S,3S,4S)-3-fluoro-4-hydroxy-cyclopentylmethyl ester (2.42 g, 80%): HR-ES-MS m/z calcd for $C_{13}H_{15}O_3F$ [M+H]$^+$ 239.1078, observed 239.1078.

In a flask under argon was placed benzoic acid (1S,3S,4S)-3-fluoro-4-hydroxy-cyclopentylmethyl ester (1.80 g, 7.55 mmol) in tetrahydrofuran (20 mL). To this mixture was added slowly a solution of bis(2-methoxyethyl)amino sulfurtrifluoride in tetrahydrofuran (7 mL). After addition was complete, the mixture was refluxed for 2 h. After this time, the mixture was cooled to room temperature and slowly poured into a saturated aqueous sodium bicarbonate solution (75 mL) which caused gas evolution. The mixture was then extracted with ethyl acetate (125 mL). The organic layer was washed with a saturated aqueous solution of sodium chloride (50 mL), dried over sodium sulfate, filtered and concentrated with silica gel (5 g). Purification by Biotage flash chromatography (AnaLogix 40 g column, 10% ethyl acetate/hexanes) afforded (1R,3S,4R)-3,4-difluoro-cyclopentylmethyl ester (1.06 g, 58%) as a colorless oil: HR-ES-MS m/z calcd for $C_{13}H_{14}O_2F_2$ [M+H]$^+$ 241.1035, observed 241.1035.

A solution of benzoic acid (1R,3S,4R)-3,4-difluoro-cyclopentylmethyl ester (1.05 g, 4.37 mmol) in ethanol (15 mL) was treated with a solution of potassium carbonate (908 mg, 6.55 mmol) in water (6 mL) and heated at 95° C. for 4 h. The mixture was cooled to room temperature and concentrated in vacuo. The residue was then azeotroped with acetonitrile and taken up in acetonitrile/methanol and concentrated in vacuo with silica gel (4 g). Purification by Biotage flash chromatography (AnaLogix 24 g column, 30% ethyl acetate/hexanes to 66% ethyl acetate/hexanes) afforded ((1R,3S,4R)-3,4-difluoro-cyclopentyl)-methanol (557 mg, 94%) as a colorless oil: HR-ES-MS m/z calcd for $C_6H_{10}OF_2$ (M−H) 135.0621, observed 135.0622.

In a round bottom flask was placed methylene chloride (4 mL) and a 2M solution of oxalyl chloride in methylene chloride (1.1 mL, 2.20 mmol) cooled to −78° C. This mixture was treated dropwise with dimethyl sulfoxide (240 µL, 3.3 mmol) and stirred for 1 h. After this time, a solution of ((1R,3S,4R)-3,4-difluoro-cyclopentyl)-methanol (150 mg, 1.10 mmol) in methylene chloride (1 mL) was added dropwise and stirred at −78° C. for 20 min. After this time, triethylamine was added (60 mL, 4.3 mmol) and warmed to 0° C. and stirred for 1 h. The mixture was quenched with a 1M aqueous solution of potassium bisulfate (6 mL) and extracted with methylene chloride (2×10 mL). The organic layers were combined, dried over sodium sulfate, filtered and concentrated in vacuo with silica gel (1.5 g). Purification by Biotage flash chromatography (AnaLogix 12 g column, 40% ethyl acetate/hexanes) afforded (1R,3S,4R)-3,4-difluoro-cyclopentanecarbaldehyde (122 mg, 83%) as a light yellow oil: HR-ES-MS m/z calcd for $C_6H_8OF_2$ (M−H) 133.0465, observed 133.0466.

In a round bottom flask under argon was placed N-(benzyloxycarbonyl)-α-phosphonoglycine methyl ester (408 mg, 1.23 mmol) in methylene chloride (2 mL) and cooled to 0° C. in an ice bath. To this mixture was added slowly 1,8-diazabicyclo[5.4.0]undec-7-ene (170 µL, 1.07 mmol) and then stirred at 0° C. for 20 min. After this time, the mixture was treated with a solution of (1R,3S,4R)-3,4-difluoro-cyclopentanecarbaldehyde (110 mg, 0.82 mmol) in methylene chloride (1 mL). After the addition was complete, the mixture was allowed to warm to 25° C. and stirred overnight. The mixture was concentrated in vacuo and the residue dissolved in ethyl acetate (15 mL), and washed with a saturated aqueous ammonium chloride solution (8 mL). The aqueous layer was then extracted with ethyl acetate (10 mL). The organic layers were combined, dried over sodium sulfate, filtered and concentrated in vacuo with silica gel (1.5 g). Purification by Biotage flash chromatography (AnaLogix 24 g column, 30% ethyl acetate/hexanes) afforded 2-benzyloxycarbonylamino-3-((1R,3S,4R)-3,4-difluoro-cyclopentyl)-acrylic acid methyl ester (212 mg, 76%) as a colorless viscous oil: HR-ES-MS m/z calcd for $C_{17}H_{19}NO_4F_2$ [M+H]$^+$ 340.1355, observed 340.1355.

In a small Parr shaker bottle was placed 2-benzyloxycarbonylamino-3-((1R,3S,4R)-3,4-difluoro-cyclopentyl)-acrylic acid methyl ester (202 mg, 0.59 mmol) in methanol (10 mL) and 10% palladium on activated carbon (40 mg). The flask was placed under an atmosphere of hydrogen at 40 psi on a Parr shaker for 2 h. After this time, the mixture was filtered through celite and the filterate concentrated in vacuo to afford crude 2-amino-3-((1R,3S,4R)-3,4-difluoro-cyclopentyl)-propionic acid methyl ester (131 mg) as an off-white semi solid. This material was used without purification.

In a small pressure bottle was placed 2-amino-3-((1R,3S,4R)-3,4-difluoro-cyclopentyl)-propionic acid methyl ester (125 mg, 0.60 mmol), acetonitrile (10 mL) and N,N-diisopropylethylamine (170 µL, 0.90 mmol) and stirred at 80° C. To this mixture was added a solution of (E)-4-bromo-3-(2-chloro-phenoxy)-but-2-enoic acid ethyl ester (prepared as in Example 61, 218 mg, 0.66 mmol) in acetonitrile (5 mL) slowly and the resulting mixture heated at 100° C. for 16 h. The mixture was then concentrated in vacuo with silica gel (2 g). Purification by Biotage flash chromatography (AnaLogix 24 g column, 5% ethyl acetate/hexanes to 25% ethyl acetate/hexanes) afforded (E)-3-(2-chloro-phenoxy)-4-[2-((1R,3S,4R)-3,4-difluoro-cyclopentyl)-1-methoxycarbonyl-ethylamino]-but-2-enoic acid ethyl ester (110 mg) as a light yellow oil: HR-ES-MS m/z calcd for $C_{21}H_{26}NO_5ClF_2$ [M+H]$^+$ 446.1541, observed 446.1541.

A solution of (E)-3-(2-chloro-phenoxy)-4-[2-((1R,3S,4R)-3,4-difluoro-cyclopentyl)-1-methoxycarbonyl-ethylamino]-but-2-enoic acid ethyl ester (105 mg, 0.24 mmol) in acetonitrile (2 mL) was placed in a sealed microwave reaction tube and heated in a microwave reactor at 180° C. for 3 h. The mixture was cooled to room temperature and concentrated in vacuo with silica gel (1.5 g). Purification by Biotage flash chromatography (AnaLogix 12 g column, 50% ethyl acetate/hexanes) afforded 2-[4-(2-chloro-phenoxy)-2-oxo-2,5-dihydro-pyrrol-1-yl]-3-((1R,3S,4R)-3,4-difluoro-cyclopentyl)-propionic acid methyl ester (60 mg) as a light pink oil: HR-ES-MS m/z calcd for $C_{19}H_{20}NO_4ClF_2$ [M+H]$^+$ 400.1122, observed 400.1124.

A mixture of 2-[4-(2-chloro-phenoxy)-2-oxo-2,5-dihydro-pyrrol-1-yl]-3-((1R,3S,4R)-3,4-difluoro-cyclopentyl)-propionic acid methyl ester (55 mg, 0.14 mmol) in a 1:1 solution of tetrahydrofuran:water (4 mL) was treated with lithium hydroxide monohydrate (13 mg, 0.28 mmol). The mixture was stirred for 1 h at 25° C. After such time, the mixture was concentrated in vacuo to remove the tetrahydrofuran and diluted with water (10 mL) and the pH adjusted to pH=3 with 1N aqueous hydrochloric acid and extracted with ethyl acetate (10 mL). The organic layer was dried over sodium sulfate, filtered and concentrated in vacuo to afford 2-[4-(2-chloro-phenoxy)-2-oxo-2,5-dihydro-pyrrol-1-yl]-3-((1R,3S,4R)-3,4-difluoro-cyclopentyl)-propionic acid (48 mg, 90%) as a light pink solid: HR-ES-MS m/z calcd for $C_{18}H_{18}NO_4ClF_2$ [M+H]$^+$ 386.0965, observed 386.0966.

In a round bottom flask under argon was placed 2-[4-(2-chloro-phenoxy)-2-oxo-2,5-dihydro-pyrrol-1-yl]-3-((1R,3S,4R)-3,4-difluoro-cyclopentyl)-propionic acid (45 mg, 0.12 mmol) and 1-((R)-2,2-dimethyl-[1,3]dioxolan-4-yl-methyl)-1H-pyrazol-3-ylamine (prepared as in Example 49, 28 mg, 0.14 mmol) in N,N-dimethylformamide (1.5 mL). To this mixture was added N,N-diisopropyethylamine (60 µL, 0.35 mmol) and (benzotriazol-1-yloxy)tris(dimethylamino)phosphonium hexafluorophosphate (78 mg, 0.18 mmol) and stirred 16 h at 25° C. After this time, the mixture was diluted with ethyl acetate (20 mL) and washed with a saturated aqueous solution of ammonium chloride (15 mL), a saturated aqueous solution of sodium bicarbonate (15 mL) and a saturated aqueous solution of sodium chloride (15 mL). The organic layer was separated and dried over sodium sulfate, filtered and concentrated in vacuo with silica gel (1.5 g). Purification by Biotage flash chromatography (AnaLogix 12 g column, 70% ethyl acetate/hexanes to 100% ethyl acetate) afforded 2-[4-(2-chloro-phenoxy)-2-oxo-2,5-dihydro-pyrrol-1-yl]-3-((1R,3S,4R)-3,4-difluoro-cyclopentyl)-N-[1-((R)-2,2-dimethyl-[1,3]dioxolan-4-ylmethyl)-1H-pyrazol-3-yl]-propionamide (45 mg, 68%) as an off-white foam: HR-ES-MS m/z calcd for $C_{27}H_{31}N_4O_5ClF_2$ [M+H]$^+$ 565.2024, observed 565.2025.

In a round bottom flask under argon was placed 2-[4-(2-chloro-phenoxy)-2-oxo-2,5-dihydro-pyrrol-1-yl]-3-((1R,3S,4R)-3,4-difluoro-cyclopentyl)-N-[1-((R)-2,2-dimethyl-[1,3]dioxolan-4-ylmethyl)-1H-pyrazol-3-yl]-propionamide (42 mg, 0.074 mmol) dissolved in methanol (2 mL). To this mixture was then added p-toluenesulfonic acid monohydrate (7 mg) and stirred at 25° C. overnight. After this time period, the mixture was diluted with methanol (4 mL) and chloroform (9 mL) and washed with a saturated aqueous solution of sodium bicarbonate (5 mL). The aqueous layer was extracted with methanol/chloroform (2:3/10 mL) and the organic layers were combined and then concentrated in vacuo with silica gel (1.5 g). Purification by Biotage flash chromatography (AnaLogix 12 g column, 5% methanol/ethyl acetate) afforded 2-[4-(2-chloro-phenoxy)-2-oxo-2,5-dihydro-pyrrol-1-yl]-3-((1R,3S,4R)-3,4-difluoro-cyclopentyl)-N-[1-((R)-2,3-dihydroxy-propyl)-1H-pyrazol-3-yl]-propionamide (26 mg, 67%) as a colorless gum: HR-ES-MS m/z calcd for $C_{24}H_{27}N_4O_5ClF_2$ [M+H]$^+$ 525.1711, observed 525.1712; $^1$H NMR (300 MHz, DMSO-d$_6$) δ ppm 1.41-2.32 (m, 7H), 3.18-3.30 (m, 2H), 3.69-3.82 (m, 1H), 3.87 (dd, J=13.4, 7.5 Hz, 1H), 4.09 (dd, J=13.4, 3.6 Hz, 1H), 4.25 (d, J=18.7 Hz, 1H), 4.62 (d, J=18.7 Hz, 1H), 4.66-4.75 (m, 1H), 4.75-5.08 (m, 4H), 4.81 (s, 1H), 6.41 (d, J=1.8 Hz, 1H), 7.32-7.41 (m, 1H), 7.42-7.56 (m, 3H), 7.65 (d, J=7.5 Hz, 1H), 10.78-10.93 (m, 1H).

Example 264

In Vitro Glucokinase Activity

The compounds of formula I which include the compounds set forth in the Examples activated glucokinase in vitro by the procedure of this Example. In this manner, they increase the flux of glucose metabolism which causes increased insulin secretion. Therefore, the compounds of formula I are glucokinase activators useful for increasing insulin secretion.

Glucokinase In Vitro Assay Protocol: Glucokinase (GK) was assayed by coupling the production of glucose-6-phosphate to the generation of NADH with glucose-6-phosphate dehydrogenase (G6PDH, 0.75-1 kunits/mg; Boehringer Mannheim, Indianapolis, Ind.) from Leuconostoc mesenteroides as the coupling enzyme (Scheme 2).

Scheme 2

Recombinant human liver GK1 was expressed in *E. coli* as a glutathione S-transferase fusion protein (GST-GK) [Liang et al, 1995] and was purified by chromatography over a glutathione-Sepharose 4B affinity column using the procedure provided by the manufacturer (Amersham Pharmacia Biotech, Piscataway, N.J.). Previous studies have demonstrated that the enzymatic properties of native GK and GST-GK are essentially identical (Liang et al, 1995; Neet et al., 1990).

The assay was conducted at 30° C. in a flat bottom 96-well tissue culture plate from Costar (Cambridge, Mass.) with a final incubation volume of 120 μL. The incubation reaction contained the following: 25 mM Hepes buffer (pH 7.1), 25 mM KCl, 5 mM D-glucose, 1 mM ATP, 1.8 mM NAD, 2 mM MgCl2, 1 μM sorbitol-6-phosphate, 1 mM dithiothreitol, test drug or 10% dimethylsulfoxide, ~7 units/ml G6PDH, and GK (see below). All organic reagents were >98% pure and were from Boehringer Mannheim with the exceptions of D-glucose and Hepes which were from Sigma Chemical Co, St Louis, Mo. Test compounds were dissolved in dimethylsulfoxide and were added to the incubation reaction minus GST-GK in a volume of 12 μL to yield a final dimethylsulfoxide concentration of 10%. This mix was pre-incubated in the temperature controlled chamber of a SPECTRAmax 250 microplate spectrophotometer (Molecular Devices Corporation, Sunnyvale, Calif.) for 10 min to allow temperature equilibrium and then the reaction was started by the addition of 20 μL GST-GK.

After addition of enzyme, the increase in optical density (OD) at 340 nm was monitored spectrophotometrically to determine the rate of change (OD$_{340}$ per min). The GK activity (OD$_{340}$/min) in control wells (10% DMSO minus GK activators) was compared with the activity in wells containing test GK activators, and the concentration of activator that produced a 50% increase in the activity of GK, i.e., the SC$_{1.5}$, was calculated. The table below provides the in vitro glucokinase activity for the compounds in the Examples:

| Example | SC1.5 (μM) |
|---|---|
| 1 | 3.771 |
| 2 | 1.672 |
| 3 | >30 (1.3 fold act. @ 30 μM) |
| 4 | 6.186 |
| 5 | 3.15 |
| 6 | 12.645 |
| 7 | 13.732 |
| 8 | 1.365 |
| 9 | 6.54 |
| 10 | 1.855 |
| 11 | 3.99 |
| 12 | 3.591 |
| 13 | 4.062 |
| 14 | 0.368 |
| 15 | 1.832 |
| 16 | 0.649 |
| 17 | 0.366 |
| 18 | 3.982 |
| 19 | 1.991 |
| 20 | 1.388 |
| 21 | 0.545 |
| 22 | 1.048 |
| 23 | 5.216 |
| 24 | 5.251 |
| 25 | 1.872 |
| 26 | 0.031 |
| 27 | 0.029 |
| 28 | 0.013 |
| 29 | 0.033 |
| 30 | 0.031 |
| 31 | 0.348 |
| 32 | 0.025 |
| 33 | 0.035 |
| 34 | 0.217 |
| 35 | 9.491 |
| 36 | 0.028 |
| 37 | 0.036 |
| 38 | 0.027 |
| 39 | 0.025 |
| 40 | 0.19 |
| 41 | 0.071 |
| 42 | 0.148 |
| 43 | 0.058 |
| 44 | 0.165 |
| 45 | 0.198 |
| 46 | 0.097 |
| 47 | 0.257 |
| 48 | 0.078 |
| 49 | 0.079 |
| 50 | 0.033 |
| 51 | 0.03 |
| 52 | 1.027 |
| 53 | 0.053 |
| 54 | 0.008 |
| 55 | 0.007 |
| 56 | 4.985 |
| 57 | 0.012 |
| 58 | 1.597 |
| 59 | 1.082 |
| 60 | 0.99 |
| 61 | 0.006 |
| 62 | 0.01 |
| 63 | 0.009 |
| 64 | 0.125 |
| 65 | 0.527 |
| 66 | 0.118 |
| 67 | 0.028 |
| 68 | 0.055 |
| 69 | 0.047 |
| 70 | 0.048 |
| 71 | 0.058 |
| 72 | 0.024 |
| 73 | 0.036 |
| 74 | 0.055 |
| 75 | 0.037 |
| 76 | 0.017 |
| 77 | 0.162 |

-continued

| Example | SC1.5 (μM) |
|---|---|
| 78 | 0.4 |
| 79 | 0.682 |
| 80 | 0.211 |
| 81 | 0.932 |
| 82 | 2.591 |
| 83 | 8.055 |
| 84 | 1.312 |
| 85 | 1.998 |
| 86 | 0.021 |
| 87 | 0.093 |
| 88 | 0.03 |
| 89 | 0.05 |
| 90 | 0.088 |
| 91 | 0.039 |
| 92 | 0.161 |
| 93 | 0.477 |
| 94 | 0.772 |
| 95 | 0.703 |
| 96 | 0.97 |
| 97 | 0.168 |
| 98 | 0.212 |
| 99 | 0.747 |
| 100 | 0.06 |
| 101 | 0.33 |
| 102 | 0.578 |
| 103 | 0.072 |
| 104 | 1.03 |
| 105 | >30 (1.4 fold act. @ 30 μM) |
| 106 | ~30 (1.5 fold act. @ 30 μM) |
| 107 | >30 (1.4 fold act. @ 30 μM) |
| 108 | >30 (1.4 fold act. @ 30 μM) |
| 109 | >30 (1.3 fold act. @ 30 μM) |
| 110 | 3.478 |
| 111 | 0.694 |
| 112 | 2.26 |
| 113 | 1.737 |
| 114 | 0.02 |
| 115 | 0.027 |
| 116 | 0.22 |
| 117 | 0.034 |
| 118 | 0.256 |
| 119 | 0.072 |
| 120 | 0.72 |
| 121 | 0.746 |
| 122 | 0.56 |
| 123 | 1.294 |
| 124 | 0.336 |
| 125 | 0.252 |
| 126 | 0.182 |
| 127 | 0.414 |
| 128 | 0.351 |
| 129 | 0.163 |
| 130 | 0.26 |
| 131 | 0.117 |
| 132 | 0.577 |
| 133 | 0.249 |
| 134 | 0.069 |
| 135 | 0.066 |
| 136 | 2.013 |
| 137 | 0.26 |
| 138 | 3.733 |
| 139 | 0.796 |
| 140 | 0.37 |
| 141 | 0.516 |
| 142 | 0.234 |
| 143 | 2.089 |
| 144 | 0.251 |
| 145 | 0.134 |
| 146 | 0.21 |
| 147 | 0.105 |
| 148 | 0.21 |
| 149 | 1.196 |
| 150 | 0.2 |
| 151 | 0.063 |
| 152 | 0.566 |
| 153 | 0.207 |
| 154 | 0.172 |

-continued

| Example | SC1.5 (μM) |
|---|---|
| 155 | 1.717 |
| 156 | 0.406 |
| 157 | 1.849 |
| 158 | 15.247 |
| 159 | 2.867 |
| 160 | 0.306 |
| 161 | 0.042 |
| 162 | 0.307 |
| 163 | 0.239 |
| 164 | 0.012 |
| 165 | 0.243 |
| 166 | 0.239 |
| 167 | 0.206 |
| 168 | 0.437 |
| 169 | 0.086 |
| 170 | 3.575 |
| 171 | 3.485 |
| 172 | 0.628 |
| 173 | 0.519 |
| 174 | 0.133 |
| 175 | 0.138 |
| 176 | 0.05 |
| 177 | 4.725 |
| 178 | 2.231 |
| 179 | 0.295 |
| 180 | 6.393 |
| 181 | 1.064 |
| 182 | 0.496 |
| 183 | 0.325 |
| 184 | 0.617 |
| 185 | 0.371 |
| 186 | 1.538 |
| 187 | 0.771 |
| 188 | 1.629 |
| 189 | 0.894 |
| 190 | 0.63 |
| 191 | 0.009 |
| 192 | 0.412 |
| 193 | 0.307 |
| 194 | 0.695 |
| 195 | 0.681 |
| 196 | 0.007 |
| 197 | 0.892 |
| 198 | 0.056 |
| 199 | 0.07 |
| 200 | 0.011 |
| 201 | 0.013 |
| 202 | 0.012 |
| 203 | 0.253 |
| 204 | 0.012 |
| 205 | 0.021 |
| 206 | 0.034 |
| 207 | 0.018 |
| 208 | 0.012 |
| 209 | 0.076 |
| 210 | 0.018 |
| 211 | 0.055 |
| 212 | 0.054 |
| 213 | 0.028 |
| 214 | 0.043 |
| 215 | 0.014 |
| 216 | 2.715 |
| 217 | 0.137 |
| 218 | 4.538 |
| 219 | 4.287 |
| 220 | 1.8 |
| 221 | 17.303 |
| 222 | 15.278 |
| 223 | 0.303 |
| 224 | >30 (1.4 fold act. @ 30 μM) |
| 225 | >30 (1.4 fold act. @ 30 μM) |
| 226 | 0.944 |
| 227 | 16.668 |
| 228 | 0.365 |
| 229 | 1.109 |
| 230 | 6.139 |
| 231 | 5.931 |

-continued

| Example | SC1.5 (µM) |
|---|---|
| 232 | 12.232 |
| 233 | 13.348 |
| 234 | 4.624 |
| 235 | 2.061 |
| 236 | 0.823 |
| 237 | 1.969 |
| 238 | 1.125 |
| 239 | 4.391 |
| 240 | 2.636 |
| 241 | 2.458 |
| 242 | 3.036 |
| 243 | 7.56 |
| 244 | 0.158 |
| 245 | 3.668 |
| 246 | 1.708 |
| 247 | 2.59 |
| 248 | 0.304 |
| 249 | 0.125 |
| 250 | 6.017 |
| 251 | 0.056 |
| 252 | 0.197 |
| 253 | 0.113 |
| 254 | 16.154 |
| 255 | 0.048 |
| 256 | 0.044 |
| 257 | 0.006 |
| 258 | 4.435 |
| 259 | 0.984 |
| 260 | 0.024 |
| 261 | 0.073 |
| 262 | 0.33 |
| 263 | 0.09 |

REFERENCES

Liang, Y., Kesavan, P., Wang, L., Niswender, K., Tanizawa, Y., Permut, M. A., Magnuson, M., and Matschinsky, F. M. Variable effects of maturity-onset-diabetes-of-youth (MODY)-associated glucokinase mutations on the substrate interactions and stability of the enzyme. Biochem. J. 309: 167-173, 1995.

Neet, K., Keenan, R. P., and Tippett, P. S. Observation of a kinetic slow transition in monomeric glucokinase. Biochemistry 29; 770-777, 1990.

Example 265

In Vivo Glucokinase Activity

Glucokinase Activator in vivo Screen Protocol in Lean and Diet Induced Obese Mice: Lean or Diet-Induced Obese (DIO) C57BL/6J mice were orally dosed via gavage with Glucokinase (GK) activator following a two hour fasting period. Blood glucose determinations were made at various (e.g. 0, 1, 2, 4 and 8 h post-oral gavage) times during the study.

C57Bl/6J mice were obtained from Jackson Laboratory (Bar Harbor, Me.) and were maintained in a light-dark cycle with lights on from 0600-1800 hr. For studies in lean mice, the mice were received at age ten weeks and given ad libitum access to control diet (LabDiet 5001 chow, PMI Nutrition, Brentwood, Mo.), and were at least age 11 weeks at the time of study. For studies in the DIO model, the mice were received at age five weeks and given ad libitum access to Bio-Serv F3282 High Fat Diet (Frenchtown, N.J.), and were at least age 16 weeks at the time of study. The experiments were conducted during the light phase of the light-dark cycle. Mice (n=6) are weighed and fasted for a two hour period prior to oral treatment. GK activators are formulated in Gelucire vehicle (Ethanol:Gelucire44/14:PEG400q.s. 4:66:30 v/w/v. For studies in lean mice, the mice were dosed orally with 5.0 µL per gram of body weight (i.e. 5 ml/kg×10.0 mg/ml formulation to equal a 50 mg/kg dose). For studies in DIO mice, the mice were dosed orally with 5.0 µL per gram of body weight (i.e. 5.0 ml/kg×5 mg/ml formulation to equal a 25 mg/kg dose). Immediately prior to dosing, a pre-dose (time zero) blood glucose reading was acquired by snipping off a small portion of the animal's tail and collecting 15 µL blood into a heparinized capillary tube for analysis. Following GK activator administration, additional blood glucose readings were taken at various time points post dose from the same tail wound. Results were interpreted by comparing the mean blood glucose values of vehicle treated mice with GK activator treated mice over the study period.

The Table below provides data for % glucose lowering of a representative number of compounds of the present invention vs control at 4 h post 25 or 30 mg/kg dose in C57B6 mice:

| Example | Dose (mg/K) | % gluc lowering @ 4 H |
|---|---|---|
| 16 | 25 | −35.95 |
| 17 | 25 | −35.8 |
| 18 | 25 | −10 |
| 19 | 25 | −29.5 |
| 21 | 25 | −26.5 |
| 26 | 25 | −36.9 |
| 27 | 30 | −52.2 |
| 28 | 25 | −45.4 |
| 31 | 25 | −31.6 |
| 32 | 25 | −37.5 |
| 43 | 30 | −38.1 |
| 47 | 30 | −33.2 |
| 48 | 30 | −57.4 |
| 49 | 30 | −38.3 |
| 51 | 30 | −53.9 |
| 64 | 30 | −58 |
| 66 | 30 | −55.4 |
| 77 | 30 | −39.2 |
| 86 | 30 | −57.4 |
| 88 | 30 | −49.3 |

It is to be understood that the invention is not limited to the particular embodiments of the invention described above, as variations of the particular embodiments may be made and still fall within the scope of the appended claims.

What is claimed is:
1. A compound of formula (I):

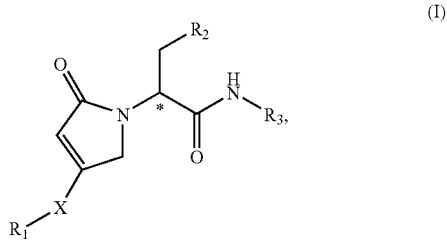

wherein:
X is O, NH or N(lower alkyl);
R₁ is -lower alkyl,
 -cycloalkyl,
 —CH₂-cycloalkyl,
 -heterocycloalkyl, -aryl, unsubstituted or mono-, bi- or tri-substituted independently with alkenyl, hydroxy, —NH$_2$, halogen, alkoxy, —CF$_3$, —OCF$_3$, —S(CH$_3$), —OCH$_3$, —S(O$_2$)CH$_3$, —CH$_2$-aryl, heteroaryl, cyano, alkoyl, —O-aryl, —O—CH$_2$-aryl, —N(CH$_3$)$_2$, cycloalkyl, heterocycloalkyl, —C(O)-heterocycloalkyl, unsubstituted lower alkyl, or lower alkyl mono- or bi-substituted with hydroxy,
—CH$_2$-aryl,
-heteroaryl, unsubstituted or substituted with lower alkyl or halogen,
-1-methyl-1H-indazol-4yl,
-benzooxazol-4-yl
-2-methyl-benzooxazol-4yl,
-2,3-dihydro-benzo[1,4]dioxin-5-yl,
-2,3-dihydro-benzo[1,4]dioxin-2-ylmethyl
-5,6,7,8-tetrahydro-naphthalen-1-yl,
-naphthalen-1-yl or
-isoquinolin;
R$_2$ is -lower alkyl,
-ether,
-alkoxy,
-cycloalkyl,
-heterocycloalkyl,
-aryl, unsubstituted or mono- or bi-substituted independently with halogen, or
-heteroaryl having at least one ring heteroatom being either O or S; and
R$_3$ is -lower alkyl-carbamoyl or
-an unsubstituted or substituted heteroaryl connected by a ring carbon atom to the amine group shown, with one heteroatom being nitrogen which is adjacent to the connecting ring carbon atom, said substituted heteroaryl being substituted at a position other than adjacent to said connecting carbon atom independently with halogen, ester, cyano, acid, cycloalkyl, aryl, 2-oxo-oxazolidin-5-ylmethyl, —N(lower alkyl)$_2$, —CH$_2$-dimethyl-[1,3]dioxolane, t-butyl-dimethyl-silanyloxy ethyl, unsubstituted —CH$_2$-aryl, —CH$_2$-aryl substituted with cyano or alkoxy, heterocycloalkyl, —CH$_2$-heterocycloalkyl, -6-(CH$_2$)-2,2-dimethyl-[1,3]dioxan-4-yl-acetic acid tert-butyl ester, unsubstituted lower alkyl, or lower alkyl mono-, bi- or tri-substituted independently with hydroxy, alkoxy, —N(lower alkyl)$_2$, —NH$_2$, ester, acid or carboxamide,
or a pharmaceutically acceptable salt thereof.

2. The compound according to claim 1, wherein:
R$_1$ is -aryl, unsubstituted or mono-, bi- or tri-substituted independently with alkenyl, hydroxy, —NH$_2$, halogen, alkoxy, —CF$_3$, —OCF$_3$, —S(CH$_3$), —OCH$_3$, —S(O$_2$)CH$_3$, —CH$_2$-aryl, heteroaryl, cyano, alkoyl, —O-aryl, —O—CH$_2$-aryl, —N(CH$_3$)$_2$, cycloalkyl, heterocycloalkyl, —C(O)-heterocycloalkyl, unsubstituted lower alkyl, or lower alkyl mono- or bi-substituted with hydroxy; and
R$_3$ is -an unsubstituted or substituted heteroaryl connected by a ring carbon atom to the amine group shown, with one heteroatom being nitrogen which is adjacent to the connecting ring carbon atom, said substituted heteroaryl being substituted at a position other than adjacent to said connecting carbon atom independently with halogen, ester, cyano, acid, cycloalkyl, aryl, 2-oxo-oxazolidin-5-ylmethyl, —N(lower alkyl)$_2$, —CH$_2$-dimethyl-[1,3]dioxolane, t-butyl-dimethyl-silanyloxy ethyl, unsubstituted —CH$_2$-aryl, —CH$_2$-aryl substituted with cyano or alkoxy, heterocycloalkyl, —CH$_2$-heterocycloalkyl, -6-(CH$_2$)-2,2-dimethyl-[1,3]dioxan-4-yl-acetic acid tert-butyl ester, unsubstituted lower alkyl, or lower alkyl mono-, bi- or tri-substituted independently with hydroxy, alkoxy, —N(lower alkyl)$_2$, —NH$_2$, ester, acid or carboxamide.

3. The compound according to claim 1, wherein X is NH or O.

4. The compound according to claim 1, wherein R$_1$ is phenyl, unsubstituted or mono-, bi- or tri-substituted independently with alkenyl, hydroxy, —NH$_2$, halogen, alkoxy, —CF$_3$, —S(CH$_3$), —OCH$_3$, —S(O$_2$)CH$_3$, —CH$_2$-aryl, heteroaryl, cyano, alkoyl, —O-aryl, —O—CH$_2$-aryl, —N(CH$_3$)$_2$, cycloalkyl, heterocycloalkyl, —C(O)-heterocycloalkyl, unsubstituted lower alkyl, or lower alkyl mono- or bi-substituted with hydroxy.

5. The compound according to claim 1, wherein R$_2$ is lower alkyl, cycloalkyl or heterocycloalkyl.

6. The compound according to claim 5, wherein said lower alkyl is substituted with S, N, OH, alkoxy or —SCH$_3$.

7. The compound according to claim 1, wherein said heteroaryl at R$_3$ is unsubstituted or substituted pyridine, pyrazole, pyrazine, thiadiazole, thiazole or benzothiazole.

8. The compound according to claim 1, wherein said heteroaryl at R$_3$ is substituted with halo, lower alkyl, lower alkyl hydroxy or lower alkyl dihydroxy.

9. The compound according to claim 1, wherein R$_1$ is 2,3-Dichloro-phenyl, 2,3-Difluoro-phenyl, 2,3-Dihydro-benzo[1,4]dioxin-5-yl, 2,3-Dihydro-benzo[1,4]dioxin-6-yl, 2,3-Dimethoxy-phenyl, 2,3-Dimethyl-phenyl, 2,4-Dichloro-phenyl, 2,4-Difluoro-phenyl, 2,5-Dichloro-phenyl, 2,5-Difluoro-phenyl, 2,6-Difluoro-phenyl, 5,6,7,8-Tetrahydro-naphthalen-1-yl, (S)-2-methoxy-1-methyl-ethoxy, 3-Chloro-2,6-difluoro-phenyl, 2,6-Difluoro-3-isopropoxy-phenyl, 2,6-Difluoro-3-methoxy-phenyl, 3-Ethoxy-2,6-difluoro-phenyl, 4-((S)-2,3-Dihydroxy-propyl)-phenyl, 4-(2-Hydroxy-2-methyl-propyl)-phenyl, 3-(1,2-Dihydroxy-ethyl)-2-fluoro-phenyl, 2-Fluoro-3-vinyl-phenyl, 2-Fluoro-3-(1-hydroxy-1-methyl-ethyl)-phenyl, 3-Cyclopropyl-2-fluoro-phenyl, 3-(2-Hydroxy-2-methyl-propyl)-phenyl, 3-Dimethylamino-2-fluoro-phenyl, 2-Fluoro-3-pyrrolidin-1-yl-phenyl, 2-Fluoro-3-hydroxy-phenyl, 2-Amino-3-hydroxy-phenyl, 3-Trifluoromethoxy-phenyl, 2-Chloro-3-ethoxy-phenyl, 3-Ethoxy-2-fluoro-phenyl, 2-Benzyloxy-phenyl, 2,3-Dihydro-benzo[1,4]dioxin-2-ylmethyl, 1-Methyl-1H-indazol-4-yl, 2-Bromo-phenyl, 2-Chloro-3-methoxy-phenyl, 2-Chloro-6-fluoro-phenyl, 2-Chloro-phenyl, 2-Ethoxy-phenyl, 2-Fluoro-3-methyl-phenyl, 2-Fluoro-5-methyl-phenyl, 2-Fluoro-phenyl, 2-Isopropoxy-phenyl, 2-Methoxy-phenyl, 2-Methyl-benzooxazol-4-yl, 2-Methylsulfanyl-phenyl, 2-Propyl-phenyl, 2-tert-Butyl-phenyl, 2-Trifluoromethyl-phenyl, 3-Bromo-2-fluoro-phenyl, 3-Bromo-phenyl, 3-Chloro-2-fluoro-phenyl, 3-Chloro-phenyl, 3-Cyano-phenyl, 3-Ethoxy-phenyl, 3-Fluoro-phenyl, 3-Methoxy-phenyl, 3-Trifluoromethyl-phenyl, 4-Methoxy-phenyl, Benzooxazol-4-yl, Benzyl, Cyclobutyl, Cyclohexyl, Cyclopentyl, Isopropyl, Methyl, Methyl-pyridin-3-yl, m-Tolyl, Naphthalen-1-yl, o-Tolyl, Phenyl, Propyl or Tetrahydro-pyran-4-yl.

10. The compound according to claim 1, wherein R$_2$ is 1,1-Difluoro-ethyl, 2,2,2-Trifluoro-1-methyl-ethyl, 2,2,2-Trifluoro-1-trifluoromethyl-ethyl, 2,2,2-Trifluoro-ethyl, 2,2-Dimethyl-propyl, 2,6-Dichloro-phenyl, 2,6-Difluoro-phenyl, (S)-sec-Butyl, (R)-1-Ethoxy-ethyl, 3-Methyl-cyclobutyl, 3-Methyl-cyclobutyl, (S)-Tetrahydro-pyran-2-yl, (R)-sec-Butyl, (S)-1-Ethoxy-ethyl, (1R,3S,4R)-3,4-Difluoro-cyclopentyl, 1-Fluoro-cyclopentyl, 1-Fluoro-1-methyl-ethyl, 2-Chloro-phenyl, 2-Fluoro-phenyl, 4-Fluoro-phenyl, Bicyclo[2.2.1]hept-2-yl, Bicyclo[2.2.1]hept-7-yl, Cyclobutyl, Cyclohexyl, Cyclopentyl, Difluoromethyl, Ethyl, Hydroxymethyl, Isopropyl, Methoxymethyl, Methyl, Methylsulfanylmethyl, Phenyl, tert-Butoxy, Tetrahydro-furan-2-yl, Tetrahydro-pyran-2-yl, Tetrahydro-pyran-4-yl or Trifluoromethyl.

11. The compound according to claim 1, wherein $R_3$ is 3-(2-Oxo-propyl)-[1,2,4]thiadiazol-5-yl, 3-Dimethylamino-[1,2,4]thiadiazol-5-yl, 3-Ethyl-[1,2,4]thiadiazol-5-yl, 3-Methyl-[1,2,4]thiadiazol-5-yl, 1-((R)-2-Amino-3-hydroxy-propyl)-1H-pyrazol-3-yl, 1-((2S,4R)-5-Carboxy-2,4-dihydroxy-pentyl)-1H-pyrazol-3-yl, 1-((2S,4R)-5-tert-Butoxycarbonyl-2,4-dihydroxy-pentyl)-1H-pyrazol-3-yl, 1-((S)-3-Diethylamino-2-hydroxy-propyl)-1H-pyrazol-3-yl, 1-((R)-2,3-Dihydroxy-propyl)-1H-pyrazol-3-yl, 1-((4S,6R)-6-tert-Butoxycarbonylmethyl-2,2-dimethyl-[1,3]dioxan-4-ylmethyl)-1H-pyrazol-3-yl, 1-((S)-2-Oxo-oxazolidin-5-ylmethyl)-1H-pyrazol-3-yl, 1-((R)-2,2-Dimethyl-[1,3]dioxolan-4-ylmethyl)-1H-pyrazol-3-yl, 1-((S)-2,3-Dihydroxy-propyl)-1H-pyrazol-3-yl, 1-((S)-2,2-Dimethyl-[1,3]dioxolan-4-ylmethyl)-1H-pyrazol-3-yl, 1-Carbamoylmethyl-1H-pyrazol-3-yl, 1-Carboxymethyl-1H-pyrazol-3-yl, 1-Ethoxycarbonylmethyl-1H-pyrazol-3-yl, 1-(2-Hydroxy-2-methyl-propyl)-1H-pyrazol-3-yl, 1-(2-Methoxy-2-methyl-propyl)-1H-pyrazol-3-yl, 1-(3-Cyano-benzyl)-1H-pyrazol-3-yl, 1-(2-tert-Butoxycarbonylamino-ethyl)-1H-pyrazol-3-yl, 1-(2-Hydroxy-ethyl)-1H-pyrazol-3-yl, 8-{1-[2-(tert-Butyl-dimethyl-silanyloxy)-ethyl]-1H-pyrazol-3-yl}-quinoline-4-carboxylic acid, 1-(2-Isopropoxy-ethyl)-1H-pyrazol-3-yl, 1-(2-Methoxy-ethyl)-1H-pyrazol-3-yl, 5-((S)-1,2-Dihydroxy-ethyl)-pyrazin-2-yl, 5-((S)-2,2-Dimethyl-[1,3]dioxolan-4-yl)-pyrazin-2-yl, 3-Allyloxycarbonylmethyl-[1,2,4]thiadiazol-5-yl, 3-(4-Methoxy-benzyl)-[1,2,4]thiadiazol-5-yl, 3-(3,3,3-Trifluoro-propyl)-[1,2,4]thiadiazol-5-yl, 3-(2-Methoxy-ethyl)-[1,2,4]thiadiazol-5-yl, 3-Methoxymethyl-[1,2,4]thiadiazol-5-yl, 3-Cyclopropyl-[1,2,4]thiadiazol-5-yl, 5-Fluoro-thiazol-2-yl, 1-Methyl-1H-pyrazol-3-yl, 5-Carboxy-pyridin-2-yl, 5-Chloro-thiazol-2-yl, 5-Methoxycarbonyl-pyridin-2-yl, Benzothiazol-2-yl, Methylcarbamoyl, Pyrazin-2-yl or Thiazol-2-yl.

12. The compound according to claim 1, having formula (Ia):

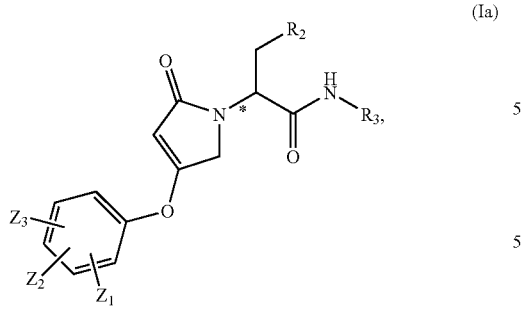

(Ia)

wherein:

$Z_1$, $Z_2$, $Z_3$ independently of each other, are hydrogen, alkenyl, hydroxy, —$NH_2$, halogen, alkoxy, —$CF_3$, —$OCF_3$, —$S(CH_3)$, —$OCH_3$, —$S(O_2)CH_3$, —$CH_2$-aryl, heteroaryl, cyano, alkoyl, —O-aryl, —O—$CH_2$-aryl, —$N(CH_3)_2$, cycloalkyl, heterocycloalkyl, —C(O)-heterocycloalkyl, unsubstituted lower alkyl, or lower alkyl mono- or bi-substituted with hydroxy;

$R_2$ is lower alkyl, alkoxy, ether, cycloalkyl, heterocycloalkyl, heteroaryl or aryl, said aryl being unsubstituted or mono- or bi-substituted independently with halogen; and $R_3$ is -lower alkyl-carbamoyl, or
-an unsubstituted or substituted heteroaryl connected by a ring carbon atom to the amine group shown, with one heteroatom being nitrogen which is adjacent to the connecting ring carbon atom, said substituted heteroaryl being substituted at a position other than adjacent to said connecting carbon atom independently with halogen, ester, cyano, acid, cycloalkyl, aryl, 2-oxo-oxazolidin-5-ylmethyl, —N(lower alkyl)$_2$, —$CH_2$-dimethyl-[1,3]dioxolane, t-butyl-dimethyl-silanyloxy ethyl, unsubstituted —$CH_2$-aryl, —$CH_2$-aryl substituted with cyano or alkoxy, heterocycloalkyl, —$CH_2$-heterocycloalkyl, -6-($CH_2$)-2,2-dimethyl-[1,3]dioxan-4-yl-acetic acid tert-butyl ester, unsubstituted lower alkyl, or lower alkyl mono-, bi- or tri-substituted independently with hydroxy, alkoxy, —N(lower alkyl)$_2$, —$NH_2$, ester, acid or carboxamide.

13. The compound according to claim 12, wherein:

$Z_1$, $Z_2$, $Z_3$ independently of each other, are halogen, alkyl, alkoxy, —$CF_3$, —$OCF_3$, —$S(O_2)CH_3$, —$CH_2$-aryl or heteroaryl;

$R_2$ is 2,6-difluoro-phenyl, cyclohexyl, cyclopentyl, isopropyl, 1-ethoxy-ethyl phenyl, tert-butoxy, tetrahydro-furan-2-yl, tetrahydro-pyran-2-yl, tetrahydro-pyran-4-yl or cyclobutyl; and $R_3$ is 3-Methyl-[1,2,4]thiadiazol-5-yl, 1-(2-Hydroxy-ethyl)-1H-pyrazol-3-yl, 1-(2-Methoxy-ethyl)-1H-pyrazol-3-yl, 1-(2-Hydroxy-2-methyl-propyl)-1H-pyrazol-3-yl, 1-(2-Methoxy-2-methyl-propyl)-1H-pyrazol-3-yl, 1-(2-Isopropoxy-ethyl)-1H-pyrazol-3-yl, 1-((S)-2,3-dihydroxy-propyl)-1H-pyrazol-3-yl, 1-((R)-2,3-dihydroxy-propyl)-1H-pyrazol-3-yl, 1-((R)-2,2-dimethyl-[1,3]dioxolan-4-ylmethyl)-1H-pyrazol-3-yl, 1-(3-Cyano-benzyl)-1H-pyrazol-3-yl, 1-(2-tert-Butoxycarbonylamino-ethyl)-1H-pyrazol-3 yl, 5-Fluoro-thiazol-2-yl, 1-Methyl-1H-pyrazol-3-yl, 5-Carboxy-pyridin-2-yl, 5-Chloro-thiazol-2-yl, 5-Methoxycarbonyl-pyridin-2-yl, Benzothiazol-2-yl, Methylcarbamoyl, Pyrazin-2-yl or Thiazol-2-yl.

14. The compound according to claim 1, having formula (Ib):

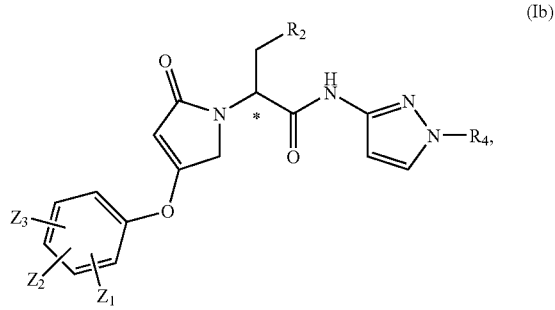

(Ib)

wherein:

$Z_1$, $Z_2$, $Z_3$ independently of each other, are hydrogen, alkenyl, hydroxy, —$NH_2$, halogen, alkoxy, —$CF_3$, —$OCF_3$, —$S(CH_3)$, —$OCH_3$, —$S(O_2)CH_3$, —$CH_2$-aryl, heteroaryl, cyano, alkoyl, —O-aryl, —O—$CH_2$- aryl, —N(CH₃)₂, cycloalkyl, heterocycloalkyl, —C(O)-heterocycloalkyl, unsubstituted lower alkyl, or lower alkyl mono- or bi-substituted with hydroxy;

R₂ is lower alkyl, alkoxy, ether, cycloalkyl, heterocycloalkyl, heteroaryl or aryl, said aryl being unsubstituted or mono- or bi-substituted independently with halogen; and R₄ is hydrogen, ester, cycloalkyl, aryl, 2-oxo-oxazolidin-5-ylmethyl, —CH₂-dimethyl-[1,3]dioxolane, t-butyl-dimethyl-silanyloxy ethyl, unsubstituted —CH₂-aryl, —CH₂-aryl substituted with cyano or alkoxy, heterocycloalkyl, —CH₂-heterocycloalkyl, unsubstituted lower alkyl, or lower alkyl mono-, bi- or tri-substituted independently with hydroxy, alkoxy, —N(lower alkyl)₂ or —NH₂.

15. The compound according to claim 14, wherein $Z_1$, $Z_2$ and $Z_3$, independently of each other, are hydrogen, trifluoromethyl, chloro, fluoro, bromo, alkoyl, pyrrolidine, piperidine, morpholine, cyclopentyl, ethoxy, methoxy or methyl.

16. The compound according to claim 14, wherein R₂ is lower alkyl, cyclopentyl, cyclobutyl, cyclohexyl, tetrahydropyranyl or tetrahydrofuranyl.

17. The compound according to claim 14, wherein R₄ is 1-(S)-2,3-dihydroxy-propyl, 1-(R)-2,3-dihydroxy-propyl, 2-hydroxy-2-methyl-propyl, 2-hydroxy-ethyl or 2-methoxy-ethyl.

18. The compound according to claim 1, wherein said compound is:
- (S)-3-Cyclopentyl-N-[1-(2-hydroxy-2-methyl-propyl)-1H-pyrazol-3-yl]-2-(4-methoxy-2-oxo-2,5-dihydro-pyrrol-1-yl)-propionamide,
- (S)-N-(5-Chloro-thiazol-2-yl)-3-cyclopentyl-2-(4-methoxy-2-oxo-2,5-dihydro-pyrrol-1-yl)-propionamide,
- (S)-N-Benzothiazol-2-yl-3-cyclopentyl-2-(4-methoxy-2-oxo-2,5-dihydro-pyrrol-1-yl)-propionamide,
- ((S)-3-Cyclopentyl-2-(4-methoxy-2-oxo-2,5-dihydro-pyrrol-1-yl)-N-(3-methyl-[1,2,4]thiadiazol-5-yl)-propionamide,
- (S)-3-Cyclopentyl-N-[1-(2-methoxy-2-methyl-propyl)-1H-pyrazol-3-yl]-2-(4-methoxy-2-oxo-2,5-dihydro-pyrrol-1-yl)-propionamide,
- (S)-3-Cyclopentyl-2-(4-methoxy-2-oxo-2,5-dihydro-pyrrol-1-yl)-N-(1-methyl-1H-pyrazol-3-yl)-propionamide,
- (2-{3-[(S)-3-Cyclopentyl-2-(4-methoxy-2-oxo-2,5-dihydro-pyrrol-1-yl)-propionylamino]-pyrazol-1-yl}-ethyl)-carbamic acid tert-butylester,
- (S)-3-Cyclopentyl-N-(5-fluoro-thiazol-2-yl)-2-(4-methoxy-2-oxo-2,5-dihydro-pyrrol-1-yl)-propionamide,
- (S)-3-Cyclopentyl-2-(4-methoxy-2-oxo-2,5-dihydro-pyrrol-1-yl)-N-pyrazin-2-yl-propionamide,
- 6-[(S)-3-Cyclopentyl-2-(4-methoxy-2-oxo-2,5-dihydro-pyrrol-1-yl)-propionylamino]-nicotinic acid methyl ester,
- 6-[(S)-3-Cyclopentyl-2-(4-methoxy-2-oxo-2,5-dihydro-pyrrol-1-yl)-propionylamino]-nicotinic acid,
- (S)-N-[1-(3-Cyano-benzyl)-1H-pyrazol-3-yl]-3-cyclopentyl-2-(4-methoxy-2-oxo-2,5-dihydro-pyrrol-1-yl)-propionamide,
- (S)-3-Cyclopentyl-N-[1-(2-hydroxy-2-methyl-propyl)-1H-pyrazol-3-yl]-2-[4-((S)-2-methoxy-1-methyl-ethoxy)-2-oxo-2,5-dihydro-pyrrol-1-yl]-propionamide,
- (S)-2-(4-Benzyloxy-2-oxo-2,5-dihydro-pyrrol-1-yl)-3-cyclopentyl-N-[1-(2-hydroxy-2-methyl-propyl)-1H-pyrazol-3-yl]-propionamide,
- (S)-3-Cyclopentyl-N-[1-(2-hydroxy-2-methyl-propyl)-1H-pyrazol-3-yl]-2-(4-isopropoxy-2-oxo-2,5-dihydro-pyrrol-1-yl)-propionamide,
- (S)-3-Cyclopentyl-N-[1-(2-hydroxy-2-methyl-propyl)-1H-pyrazol-3-yl]-2-(4-cyclopentyloxy-2-oxo-2,5-dihydro-pyrrol-1-yl)-propionamide,
- (S)-3-Cyclopentyl-N-[1-(2-hydroxy-2-methyl-propyl)-1H-pyrazol-3-yl]-2-(4-cyclohexyloxy-2-oxo-2,5-dihydro-pyrrol-1-yl)-propionamide,
- (S)-3-Cyclopentyl-N-[1-(2-hydroxy-2-methyl-propyl)-1H-pyrazol-3-yl]-2-[2-oxo-4-(tetrahydro-pyran-4-yloxy)-2,5-dihydro-pyrrol-1-yl]-propionamide,
- (S)-3-Cyclopentyl-N-[1-(2-hydroxy-2-methyl-propyl)-1H-pyrazol-3-yl]-2-(4-cyclobutoxy-2-oxo-2,5-dihydro-pyrrol-1-yl)-propionamide or
- (S)-3-Cyclopentyl-N-[1-(2-isopropoxy-ethyl)-1H-pyrazol-3-yl]-2-(4-cyclopentyloxy-2-oxo-2,5-dihydro-pyrrol-1-yl)-propionamide.

19. The compound according to claim 1, wherein said compound is:
- (S)-3-Cyclopentyl-N-[1-(2-methoxy-2-methyl-propyl)-1H-pyrazol-3-yl]-2-(4-cyclopentyloxy-2-oxo-2,5-dihydro-pyrrol-1-yl)-propionamide,
- (S)-3-Cyclopentyl-N-[1-(2-methoxy-2-methyl-propyl)-1H-pyrazol-3-yl]-2-(4-isopropoxy-2-oxo-2,5-dihydro-pyrrol-1-yl)-propionamide,
- (S)-3-Cyclopentyl-N-(pyrazin-2-yl)-2-(4-isopropoxy-2-oxo-2,5-dihydro-pyrrol-1-yl)-propionamide,
- (S)-3-Cyclohexyl-N-[1-(2-hydroxy-2-methyl-propyl)-1H-pyrazol-3-yl]-2-(2-oxo-4-propoxy-2,5-dihydro-pyrrol-1-yl)-propionamide,
- (S)-3-Cyclohexyl-N-[1-(2-hydroxy-2-methyl-propyl)-1H-pyrazol-3-yl]-2-(4-isopropoxy-2-oxo-2,5-dihydro-pyrrol-1-yl)-propionamide,
- (S)-3-Cyclopentyl-2-[4-(2-methoxy-phenoxy)-2-oxo-2,5-dihydro-pyrrol-1-yl]-N-thiazol-2-yl-propionamide,
- (S)-3-Cyclopentyl-N-[1-(2-hydroxy-2-methyl-propyl)-1H-pyrazol-3-yl]-2-[4-(2-methoxy-phenoxy)-2-oxo-2,5-dihydro-pyrrol-1-yl]-propionamide,
- (S)-3-Cyclohexyl-N-[1-(2-hydroxy-2-methyl-propyl)-1H-pyrazol-3-yl]-2-[4-(2-methoxy-phenoxy)-2-oxo-2,5-dihydro-pyrrol-1-yl]-propionamide,
- (S)-3-Cyclohexyl-N-(1-methyl-1H-pyrazol-3-yl)-2-[4-(2-methoxy-phenoxy)-2-oxo-2,5-dihydro-pyrrol-1-yl]-propionamide,
- (S)-3-Cyclohexyl-N-[1-((S)-2,3-dihydroxy-propyl)-1H-pyrazol-3-yl]-2-[4-(2-methoxy-phenoxy)-2-oxo-2,5-dihydro-pyrrol-1-yl]-propionamide,
- (S)-N-[1-(2-hydroxy-2-methyl-propyl)-1H-pyrazol-3-yl]-2-[4-(2-methoxy-phenoxy)-2-oxo-2,5-dihydro-pyrrol-1-yl]-3-(tetrahydro-furan-2-yl)-propionamide,
- (S)-3-Cyclohexyl-N-[1-(2-hydroxy-2-methyl-propyl)-1H-pyrazol-3-yl]-2-[2-oxo-4-(2-trifluoromethyl-phenoxy)-2,5-dihydro-pyrrol-1-yl]-propionamide,
- (S)-3-Cyclohexyl-2-[4-(2,3-dihydro-benzo[1,4]dioxin-5-yloxy)-2-oxo-2,5-dihydro-pyrrol-1-yl]-N-[1-(2-hydroxy-2-methyl-propyl)-1H-pyrazol-3-yl]-propionamide,
- N-[1-(2-hydroxy-2-methyl-propyl)-1H-pyrazol-3-yl]-2-[4-(2-methoxy-phenoxy)-2-oxo-2,5-dihydro-pyrrol-1-yl]-3-(tetrahydropyran-4-yl)-propionamide,
- 3-tert-Butoxy-N-[1-(2-hydroxy-2-methyl-propyl)-1H-pyrazol-3-yl]-2-[4-(2-methoxy-phenoxy)-2-oxo-2,5-dihydro-pyrrol-1-yl]-propionamide,
- (S)-3-Cyclohexyl-2-[4-(2,6-difluoro-phenoxy)-2-oxo-2,5-dihydro-pyrrol-1-yl]-N-[1-(2-hydroxy-2-methyl-propyl)-1H-pyrazol-3-yl]-propionamide,
- (S)-3-Cyclohexyl-2-[4-(2,6-difluoro-phenoxy)-2-oxo-2,5-dihydro-pyrrol-1-yl]-N-[1-((S)-2,3-dihydroxy-propyl)-1H-pyrazol-3-yl]-propionamide, (S)-3-Cyclohexyl-2-[4-(2,6-difluoro-phenoxy)-2-oxo-2, 5-dihydro-pyrrol-1-yl]-N-[1-((R)-2,3-dihydroxy-propyl)-1H-pyrazol-3-yl]-propionamide, 6-{(S)-3-Cyclohexyl-2-[4-(2,6-difluoro-phenoxy)-2-oxo-2,5-dihydro-pyrrol-1-yl]-propionylamino}-nicotinic acid methyl ester or 6-[2-[4-(2,6-difluoro-phenoxy)-2-oxo-2,5-dihydro-pyrrol-1-yl]-3-(tetrahydro-pyran-4-yl)-propionylamino]-nicotinic acid methyl ester.

20. The compound according to claim 1, wherein said compound is:

(S)-6-[2-[4-(2,6-difluoro-phenoxy)-2-oxo-2,5-dihydro-pyrrol-1-yl]-3-(tetrahydro-pyran-4-yl)-propionylamino]-nicotinic acid methyl ester, 2-[4-(2,6-Difluoro-phenoxy)-2-oxo-2,5-dihydro-pyrrol-1-yl]-N-[1-(2-hydroxy-2-methyl-propyl)-1H-pyrazol-3-yl]-3-(tetrahydro-pyran-4-yl)-propionamide, (S)-2-[4-(2,6-Difluoro-phenoxy)-2-oxo-2,5-dihydro-pyrrol-1-yl]-N-[1-(2-hydroxy-2-methyl-propyl)-1H-pyrazol-3-yl]-3-(tetrahydro-pyran-4-yl)-propionamide, 2-[4-(2,6-Difluoro-phenoxy)-2-oxo-2,5-dihydro-pyrrol-1-yl]-N-[1-((R)-2,3-dihydroxy-propyl)-1H-pyrazol-3-yl]-3-(tetrahydro-pyran-4-yl)-propionamide, (S)-2-[4-(2,6-difluoro-phenoxy)-2-oxo-2,5-dihydro-pyrrol-1-yl]-4-methyl-pentanoic acid [1-(2-hydroxy-2-methyl-propyl)-1H-pyrazol-3-yl]-amide, 6-{(S)-2-[4-(2,6-difluoro-phenoxy)-2-oxo-2,5-dihydro-pyrrol-1-yl]-4-methyl-pentanoylamino}-nicotinic acid methyl ester, (S)-2-[4-(2,6-difluoro-phenoxy)-2-oxo-2,5-dihydro-pyrrol-1-yl]-4-methyl-pentanoic acid [1-((R)-2,3-dihydroxy-propyl)-1H-pyrazol-3-yl]-amide, (S)-2-[4-(2-Chloro-3-methoxy-phenoxy)-2-oxo-2,5-dihydro-pyrrol-1-yl]-4-methyl-pentanoic acid [1-(2-hydroxy-2-methyl-propyl)-1H-pyrazol-3-yl]-amide, (S)-2-[4-(2-Chloro-3-methoxy-phenoxy)-2-oxo-2,5-dihydro-pyrrol-1-yl]-4-methyl-pentanoic acid [1-((R-2,3-dihydroxy-propyl)-1H-pyrazol-3-yl]-amide, 2-[4-(2-Chloro-3-methoxy-phenoxy)-2-oxo-2,5-dihydro-pyrrol-1-yl]-N-[1-(2-hydroxy-2-methyl-propyl)-1H-pyrazol-3-yl]-3-(tetrahydro-pyran-4-yl)-propionamide, (S)-2-[4-(2-Chloro-3-methoxy-phenoxy)-2-oxo-2,5-dihydro-pyrrol-1-yl]-N-[1-(2-hydroxy-2-methyl-propyl)-1H-pyrazol-3-yl]-3-(tetrahydro-pyran-4-yl)-propionamide, (R)-2-[4-(2-Chloro-3-methoxy-phenoxy)-2-oxo-2,5-dihydro-pyrrol-1-yl]-N-[1-(2-hydroxy-2-methyl-propyl)-1H-pyrazol-3-yl]-3-(tetrahydro-pyran-4-yl)-propionamide, 2-[4-(2-Chloro-3-methoxy-phenoxy)-2-oxo-2,5-dihydro-pyrrol-1-yl]-N-[1-((R)-2,3-dihydroxy-propyl)-1H-pyrazol-3-yl]-3-(tetrahydro-pyran-4-yl)-propionamide, (S)-2-[4-(2-Chloro-3-methoxy-phenoxy)-2-oxo-2,5-dihydro-pyrrol-1-yl]-3-cyclopentyl-N-[1-(2-hydroxy-2-methyl-propyl)-1H-pyrazol-3-yl]-propionamide, (S)-2-[4-(2-Chloro-3-methoxy-phenoxy)-2-oxo-2,5-dihydro-pyrrol-1-yl]-3-cyclopentyl-N-[1-((R)-2,3-dihydroxy-propyl)-1H-pyrazol-3-yl]-propionamide, (S)-3-Cyclohexyl-N-[1-(2-hydroxy-2-methyl-propyl)-1H-pyrazol-3-yl]-2-(4-methoxy-2-oxo-2,5-dihydro-pyrrol-1-yl)-propionamide, (S)-2-[4-(2-Chloro-3-methoxy-phenoxy)-2-oxo-2,5-dihydro-pyrrol-1-yl]-3-cyclohexyl-N-[1-(2-hydroxy-2-methyl-propyl)-1H-pyrazol-3-yl]-propionamide, 1-{2-[4-(2-Chloro-3-methoxy-phenoxy)-2-oxo-2,5-dihydro-pyrrol-1-yl]-3-cyclohexyl-propionyl}-3-methyl-urea, 2-[4-(2,6-Difluoro-phenoxy)-2-oxo-2,5-dihydro-pyrrol-1-yl]-3-(2,6-difluoro-phenyl)-N-[1-(2-hydroxy-2-methyl-propyl)-1-H-pyrazol-3-yl]-propionamide or (S)-3-Cyclohexyl-2-[4-(2,3-dihydro-benzo[1,4]dioxin-2-ylmethoxy)-2-oxo-2,5-dihydro-pyrrol-1-yl]-N-[1-(2-hydroxy-2-methyl-propyl)-1-H-pyrazol-3-yl]-propionamide.

21. The compound according to claim 1, wherein said compound is:

(S)-2-[4-(2-Chloro-phenoxy)-2-oxo-2,5-dihydro-pyrrol-1-yl]-3-cyclohexyl-N-[1-(2-hydroxy-2-methyl-propyl)-1-H-pyrazol-3-yl]-propionamide, ((S)-2-[4-(2-Chloro-phenoxy)-2-oxo-2,5-dihydro-pyrrol-1-yl]-3-cyclohexyl-N-[1-((R)-2,2-dimethyl-[1,3]dioxolan-4-yl-methyl)-1-H-pyrazol-3-yl]-propionamide, (S)-2-[4-(2-Chloro-phenoxy)-2-oxo-2,5-dihydro-pyrrol-1-yl]-3-cyclohexyl-N-[1-((R)-2,3-dihydroxy-propyl)-1-H-pyrazol-3-yl]-propionamide, (S)-2-[4-(2-Chloro-phenoxy)-2-oxo-2,5-dihydro-pyrrol-1-yl]-4-methyl-pentanoic acid [1-(2-hydroxy-2-methyl-propyl)-1H-pyrazol-3-yl]-amide, ((S)-2-[4-(2-Chloro-phenoxy)-2-oxo-2,5-dihydro-pyrrol-1-yl]-4-methyl-pentanoic acid [1-((R)-2,2-dimethyl-[1,3]dioxolan-4-yl-methyl)-1H-pyrazol-3-yl]-amide, (S)-2-[4-(2-Chloro-phenoxy)-2-oxo-2,5-dihydro-pyrrol-1-yl]-4-methyl-pentanoic acid [1-((R)-2,3-dihydroxy-propyl)-1H-pyrazol-3-yl]-amide, (S)-2-[4-(2-Chloro-6-fluoro-phenoxy)-2-oxo-2,5-dihydro-pyrrol-1-yl]-3-cyclohexyl-N-[1-(2-hydroxy-2-methyl-propyl)-1H-pyrazol-3-yl]-propionamide, (S)-2-[4-(2-Chloro-6-fluoro-phenoxy)-2-oxo-2,5-dihydro-pyrrol-1-yl]-3-cyclohexyl-N-(1-methyl-1H-pyrazol-3-yl)-propionamide, 6-{(S)-2-[4-(2-Chloro-6-fluoro-phenoxy)-2-oxo-2,5-dihydro-pyrrol-1-yl]-3-cyclohexyl-propionylamino}-nicotinic acid methyl ester, 6-{(S)-2-[4-(2-Chloro-6-fluoro-phenoxy)-2-oxo-2,5-dihydro-pyrrol-1-yl]-3-cyclohexyl-propionylamino}-nicotinic acid, (S)-2-[4-(2-Chloro-6-fluoro-phenoxy)-2-oxo-2,5-dihydro-pyrrol-1-yl]-3-cyclohexyl-N-pyrazin-2-yl-propionamide Hydrochloride, (S)-2-[4-(3-Chloro-2,6-difluoro-phenoxy)-2-oxo-2,5-dihydro-pyrrol-1-yl]-3-cyclohexyl-N-[1-(2-hydroxy-2-methyl-propyl)-1H-pyrazol-3-yl]-propionamide, 6-{(S)-2-[4-(3-Chloro-2,6-difluoro-phenoxy)-2-oxo-2,5-dihydro-pyrrol-1-yl]-3-cyclohexyl-propionylamino}-nicotinic acid methyl ester, 6-{(S)-2-[4-(3-Chloro-2,6-difluoro-phenoxy)-2-oxo-2,5-dihydro-pyrrol-1-yl]-3-cyclohexyl-propionylamino}-nicotinic acid, (S)-2-[4-(3-Chloro-2,6-difluoro-phenoxy)-2-oxo-2,5-dihydro-pyrrol-1-yl]-3-cyclohexyl-N-(1-methyl-1H-pyrazol-3-yl)-propionamide Hydrochloride, (S)-2-[4-(3-Chloro-2,6-difluoro-phenoxy)-2-oxo-2,5-dihydro-pyrrol-1-yl]-3-cyclohexyl-N-[1-((R)-2,3-dihydroxy-propyl)-1H-pyrazol-3-yl]-propionamide Hydrochloride, (S)-2-[4-(2,3-Dichloro-phenoxy)-2-oxo-2,5-dihydro-pyrrol-1-yl]-4-methyl-pentanoic acid [1-(2-hydroxy-2-methyl-propyl)-1H-pyrazol-3-yl]-amide Hydrochloride, (S)-2-[4-(2,3-Dichloro-phenoxy)-2-oxo-2,5-dihydro-pyrrol-1-yl]-4-methyl-pentanoic acid (1-methyl-1H-pyrazol-3-yl)-amide Hydrochloride, (S)-2-[4-(2,3-Dichloro-phenoxy)-2-oxo-2,5-dihydro-pyrrol-1-yl]-4-methyl-pentanoic acid [1-((R)-2,2-dimethyl-[1,3]dioxolan-4-yl-methyl)-1H-pyrazol-3-yl]-amide or (S)-2-[4-(2,3-Dichloro-phenoxy)-2-oxo-2,5-dihydro-pyrrol-1-yl]-4-methyl-pentanoic acid [1-((R)-2,3-dihydroxy-propyl)-1H-pyrazol-3-yl]-amide Hydrochloride.

22. The compound according to claim 1, wherein said compound is:

(S)-2-[4-(2-Ethoxy-phenoxy)-2-oxo-2,5-dihydro-pyrrol-1-yl]-4-methyl pentanoic acid [1-(2-hydroxy-2-methyl-propyl)-1H-pyrazol-3-yl]-amide Hydrochloride, (S)-2-[4-(2-Ethoxy-phenoxy)-2-oxo-2,5-dihydro-pyrrol-1-yl]-4-methyl-pentanoic acid (1-methyl-1H-pyrazol-3-yl)-amide Hydrochloride, (S)-2-[4-(2-Ethoxy-phenoxy)-2-oxo-2,5-dihydro-pyrrol-1-yl]-4-methyl-pentanoic acid [1-((R)-2,2-dimethyl-[1,3]dioxolan-4-yl-methyl)-1H-pyrazol-3-yl]-amide, (S)-2-[4-(2-Ethoxy-phenoxy)-2-oxo-2,5-dihydro-pyrrol-1-yl]-4-methyl-pentanoic acid [1-((R)-2,3-dihydroxy-propyl)-1H-pyrazol-3-yl]-amide Hydrochloride, (S)-2-[4-(2-Ethoxy-phenoxy)-2-oxo-2,5-dihydro-pyrrol-1-yl]-4-methyl-pentanoic acid [1-(2-hydroxy-ethyl)-1H-pyrazol-3-yl]-amide Hydrochloride, (S)-3-Cyclopentyl-2-[4-(2,6-difluoro-phenoxy)-2-oxo-2,5-dihydro-pyrrol-1-yl]-N-[1-(2-hydroxy-2-methyl-propyl)-1H-pyrazol-3-yl]-propionamide, (S)-3-Cyclopentyl-2-[4-(2,6-difluoro-phenoxy)-2-oxo-2,5-dihydro-pyrrol-1-yl]-N-[1-((R)-2,2-dimethyl-[1,3]dioxolan-4-yl-methyl)-1H-pyrazol-3-yl]-propionamide, (S)-3-Cyclopentyl-2-[4-(2,6-difluoro-phenoxy)-2-oxo-2,5-dihydro-pyrrol-1-yl]-N-[1-((R)-2,3-dihydroxy-propyl)-1H-pyrazol-3-yl]-propionamide, (S)-3-Cyclopentyl-2-[4-(2,6-difluoro-phenoxy)-2-oxo-2,5-dihydro-pyrrol-1-yl]-N-[1-(2-hydroxy-ethyl)-1H-pyrazol-3-yl]-propionamide, (S)-3-Cyclohexyl-N-(1-methyl-1H-pyrazol-3-yl)-2-[2-oxo-4-(2-trifluoromethyl-phenoxy)-2,5-dihydro-pyrrol-1-yl]-propionamide Hydrochloride, (S)-3-Cyclohexyl-N-[1-(2-methoxy-ethyl)-1H-pyrazol-3-yl]-2-[2-oxo-4-(2-trifluoromethyl-phenoxy)-2,5-dihydro-pyrrol-1-yl]-propionamide Hydrochloride, (S)-2-[4-(2,3-Dichloro-phenoxy)-2-oxo-2,5-dihydro-pyrrol-1-yl]-N-[1-(2-hydroxy-2-methyl-propyl)-1H-pyrazol-3-yl]-3-(tetrahydro-pyran-2-yl)-propionamide, (S)-2-[4-(2,6-Difluoro-phenoxy)-2-oxo-2,5-dihydro-pyrrol-1-yl]-N-[1-(2-hydroxy-2-methyl-propyl)-1H-pyrazol-3-yl]-3-(tetrahydro-pyran-2-yl)-propionamide, (2S,4R)-2-[4-(2,3-Dichloro-phenoxy)-2-oxo-2,5-dihydro-pyrrol-1-yl]-4-ethoxy-pentanoic acid [1-(2-hydroxy-2-methyl-propyl)-1H-pyrazol-3-yl]-amide, (2S,4S)-2-[4-(2,3-Dichloro-phenoxy)-2-oxo-2,5-dihydro-pyrrol-1-yl]-4-ethoxy-pentanoic acid [1-(2-hydroxy-2-methyl-propyl)-1H-pyrazol-3-yl]-amide, (S)-4-Methyl-2-[2-oxo-4-(3-trifluoromethyl-phenoxy)-2,5-dihydro-pyrrol-1-yl]-pentanoic acid [1-((R)-2,3-dihydroxy-propyl)-1H-pyrazol-3-yl]-amide, (S)-2-[4-(3-Chloro-2-fluoro-phenoxy)-2-oxo-2,5-dihydro-pyrrol-1-yl]-4-methyl-pentanoic acid [1-((R)-2,3-dihydroxy-propyl)-1H-pyrazol-3-yl]-amide, (S)-4-Methyl-2-[2-oxo-4-(5,6,7,8-tetrahydro-naphthalen-1-yloxy)-2,5-dihydro-pyrrol-1-yl]-pentanoic acid [1-((R)-2,3-dihydroxy-propyl)-1H-pyrazol-3-yl]-amide, (S)-2-[4-(4-Methoxy-phenoxy)-2-oxo-2,5-dihydro-pyrrol-1-yl]-4-methyl-pentanoic acid [1-((R)-2,3-dihydroxy-propyl)-1H-pyrazol-3-yl]-amide or (S)-4-Methyl-2-[4-(naphthalen-1-yloxy)-2-oxo-2,5-dihydro-pyrrol-1-yl]-pentanoic acid [1-((R)-2,3-dihydroxy-propyl)-1H-pyrazol-3-yl]-amide.

23. The compound according to claim 1, wherein said compound is:

(S)-2-[4-(2,5-Difluoro-phenoxy)-2-oxo-2,5-dihydro-pyrrol-1-yl]-4-methyl-pentanoic acid [1-((R)-2,3-dihydroxy-propyl)-1H-pyrazol-3-yl]-amide, (S)-2-[4-(2,4-Difluoro-phenoxy)-2-oxo-2,5-dihydro-pyrrol-1-yl]-4-methyl-pentanoic acid [1-((R)-2,3-dihydroxy-propyl)-1H-pyrazol-3-yl]-amide, (S)-2-[4-(2-Fluoro-5-methyl-phenoxy)-2-oxo-2,5-dihydro-pyrrol-1-yl]-4-methyl-pentanoic acid [1-((R)-2,3-dihydroxy-propyl)-1H-pyrazol-3-yl]-amide, (S)-2-[4-(2-Chloro-phenoxy)-2-oxo-2,5-dihydro-pyrrol-1-yl]-4-methyl-pentanoic acid [3-(2-methoxy-ethyl)-[1,2,4]thiadiazol-5-yl]-amide, (S)-2-[4-(2-Chloro-phenoxy)-2-oxo-2,5-dihydro-pyrrol-1-yl]-4-methyl-pentanoic acid (3-cyclopropyl-[1,2,4]thiadiazol-5-yl)-amide, (S)-2-[4-(2-Chloro-phenoxy)-2-oxo-2,5-dihydro-pyrrol-1-yl]-4-methyl-pentanoic acid [3-(3,3,3-trifluoro-propyl)-[1,2,4]thiadiazol-5-yl]-amide, (S)-2-[4-(2-Chloro-phenoxy)-2-oxo-2,5-dihydro-pyrrol-1-yl]-4-methyl-pentanoic acid (3-methyl-[1,2,4]thiadiazol-5-yl)-amide, (S)-2-[4-(2-Chloro-phenoxy)-2-oxo-2,5-dihydro-pyrrol-1-yl]-4-methyl-pentanoic acid (3-dimethylamino-[1,2,4]thiadiazol-5-yl)-amide, (S)-2-[4-(2-Chloro-phenoxy)-2-oxo-2,5-dihydro-pyrrol-1-yl]-4-methyl-pentanoic acid [3-(4-methoxy-benzyl)-[1,2,4]thiadiazol-5-yl]-amide, (S)-2-[4-(2-Chloro-phenoxy)-2-oxo-2,5-dihydro-pyrrol-1-yl]-4-methyl-pentanoic acid [3-(4-methoxy-benzyl)-[1,2,4]thiadiazol-5-yl]-amide, (5-{(S)-2-[4-(2-Chloro-phenoxy)-2-oxo-2,5-dihydro-pyrrol-1-yl]-4-methyl-pentanoylamino}-[1,2,4]thiadiazol-3-yl)-acetic acid allyl ester, (S)-2-[4-(2-Chloro-phenoxy)-2-oxo-2,5-dihydro-pyrrol-1-yl]-4-methyl-pentanoic acid (3-methoxymethyl-[1,2,4]thiadiazol-5-yl)-amide, (S)-2-[4-(2-Chloro-phenoxy)-2-oxo-2,5-dihydro-pyrrol-1-yl]-4-methyl-pentanoic acid [3-(2-oxo-propyl)-[1,2,4]thiadiazol-5-yl]-amide, (S)-2-[4-(3-Ethoxy-2-fluoro-phenoxy)-2-oxo-2,5-dihydro-pyrrol-1-yl]-4-methyl-pentanoic acid [1-(2-hydroxy-2-methyl-propyl)-1H-pyrazol-3-yl]-amide, (S)-2-[4-(3-Ethoxy-2-fluoro-phenoxy)-2-oxo-2,5-dihydro-pyrrol-1-yl]-4-methyl-pentanoic acid [1-((R)-2,3-dihydroxy-propyl)-1H-pyrazol-3-yl]-amide, (S)-2-[4-(3-Ethoxy-2,6-difluoro-phenoxy)-2-oxo-2,5-dihydro-pyrrol-1-yl]-4-methyl-pentanoic acid [1-((R)-2,2-dimethyl-[1,3]dioxolan-4-yl-methyl)-1H-pyrazol-3-yl]-amide, (S)-2-[4-(3-Ethoxy-2,6-difluoro-phenoxy)-2-oxo-2,5-dihydro-pyrrol-1-yl]-4-methyl-pentanoic acid [1-((R)-2,3-dihydroxy-propyl)-1H-pyrazol-3-yl]-amide, (S)-2-[4-(2,6-Difluoro-3-methoxy-phenoxy)-2-oxo-2,5-dihydro-pyrrol-1-yl]-4-methyl-pentanoic acid [1-((R)-2,2-dimethyl-[1,3]dioxolan-4-yl-methyl)-1H-pyrazol-3-yl]-amide, (S)-2-[4-(2,6-Difluoro-3-methoxy-phenoxy)-2-oxo-2,5-dihydro-pyrrol-1-yl]-4-methyl-pentanoic acid [1-((R)-2,3-dihydroxy-propyl)-1H-pyrazol-3-yl]-amide or (S)-4-Methyl-2-(2-oxo-4-o-tolyloxy-2,5-dihydro-pyrrol-1-yl)-pentanoic acid (1-methyl-1H-pyrazol-3-yl)-amide.

24. The compound according to claim 1, wherein said compound is:

- (S)-4-Methyl-2-(2-oxo-4-o-tolyloxy-2,5-dihydro-pyrrol-1-yl)-pentanoic acid {1-[2-(tert-butyl-dimethyl-silanyloxy)-ethyl]-1H-pyrazol-3-yl}-amide,
- (S)-4-Methyl-2-(2-oxo-4-o-tolyloxy-2,5-dihydro-pyrrol-1-yl)-pentanoic acid [1-(2-hydroxy-ethyl)-1H-pyrazol-3-yl]-amide,
- (S)-4-Methyl-2-(2-oxo-4-o-tolyloxy-2,5-dihydro-pyrrol-1-yl)-pentanoic acid [1-((R)-2,2-dimethyl-[1,3]dioxolan-4-yl-methyl)-1H-pyrazol-3-yl]-amide,
- (S)-4-Methyl-2-(2-oxo-4-o-tolyloxy-2,5-dihydro-pyrrol-1-yl)-pentanoic acid [1-((R)-2,3-dihydroxy-propyl)-1H-pyrazol-3-yl]-amide,
- (S)-4-Methyl-2-(2-oxo-4-o-tolyloxy-2,5-dihydro-pyrrol-1-yl)-pentanoic acid [1-(2-hydroxy-2-methyl-propyl)-1H-pyrazol-3-yl]-amide,
- (S)-2-[4-(2-Fluoro-3-hydroxy-phenoxy)-2-oxo-2,5-dihydro-pyrrol-1-yl]-4-methyl-pentanoic acid [1-(2-hydroxy-2-methyl-propyl)-1H-pyrazol-3-yl]-amide,
- (S)-2-[4-(2-Fluoro-3-hydroxy-phenoxy)-2-oxo-2,5-dihydro-pyrrol-1-yl]-4-methyl-pentanoic acid (1-methyl-1H-pyrazol-3-yl)-amide,
- (S)-2-[4-(3-Bromo-2-fluoro-phenoxy)-2-oxo-2,5-dihydro-pyrrol-1-yl]-4-methyl-pentanoic acid [1-((R)-2,2-dimethyl-[1,3]dioxolan-4-yl-methyl)-1H-pyrazol-3-yl]-amide,
- (S)-2-[4-(3-Bromo-2-fluoro-phenoxy)-2-oxo-2,5-dihydro-pyrrol-1-yl]-4-methyl-pentanoic acid [1-((R)-2,3-dihydroxy-propyl)-1H-pyrazol-3-yl]-amide,
- (S)-2-[4-(2-Fluoro-3-methyl-phenoxy)-2-oxo-2,5-dihydro-pyrrol-1-yl]-4-methyl-pentanoic acid [1-((R)-2,2-dimethyl-[1,3]dioxolan-4-yl-methyl)-1H-pyrazol-3-yl]-amide,
- (S)-2-[4-(2-Fluoro-3-methyl-phenoxy)-2-oxo-2,5-dihydro-pyrrol-1-yl]-4-methyl-pentanoic acid [1-((R)-2,3-dihydroxy-propyl)-1H-pyrazol-3-yl]-amide,
- (S)-2-[4-(2-Fluoro-3-methyl-phenoxy)-2-oxo-2,5-dihydro-pyrrol-1-yl]-4-methyl-pentanoic acid {1-[2-(tert-butyl-dimethyl-silanyloxy)-ethyl]-1H-pyrazol-3-yl}-amide,
- (S)-2-[4-(2-Fluoro-3-methyl-phenoxy)-2-oxo-2,5-dihydro-pyrrol-1-yl]-4-methyl-pentanoic acid [1-(2-hydroxy-ethyl)-1H-pyrazol-3-yl]-amide,
- (S)-2-[4-(2,6-Difluoro-3-isopropoxy-phenoxy)-2-oxo-2,5-dihydro-pyrrol-1-yl]-4-methyl-pentanoic acid [1-((R)-2,3-dihydroxy-propyl)-1H-pyrazol-3-yl]-amide,
- (S)-2-[4-(2,6-Difluoro-3-isopropoxy-phenoxy)-2-oxo-2,5-dihydro-pyrrol-1-yl]-4-methyl-pentanoic acid [1-(2-hydroxy-2-methyl-propyl)-1H-pyrazol-3-yl]-amide,
- (S)-2-[4-(2-Bromo-phenoxy)-2-oxo-2,5-dihydro-pyrrol-1-yl]-4-methyl-pentanoic acid [1-((R)-2,2-dimethyl-[1,3]dioxolan-4-yl-methyl)-1H-pyrazol-3-yl]-amide,
- (S)-2-[4-(2-Bromo-phenoxy)-2-oxo-2,5-dihydro-pyrrol-1-yl]-4-methyl-pentanoic acid [1-((R)-2,3-dihydroxy-propyl)-1H-pyrazol-3-yl]-amide,
- (S)-2-[4-(3-Cyano-phenoxy)-2-oxo-2,5-dihydro-pyrrol-1-yl]-4-methyl-pentanoic acid [1-(2-hydroxy-2-methyl-propyl)-1H-pyrazol-3-yl]-amide,
- (S)-2-[4-(3-Dimethylamino-2-fluoro-phenoxy)-2-oxo-2,5-dihydro-pyrrol-1-yl]-4-methyl-pentanoic acid [1-((R)-2,2-dimethyl-[1,3]dioxolan-4-yl-methyl)-1H-pyrazol-3-yl]-amide,
- (S)-2-[4-(3-Dimethylamino-2-fluoro-phenoxy)-2-oxo-2,5-dihydro-pyrrol-1-yl]-4-methyl-pentanoic acid [1-((R)-2,3-dihydroxy-propyl)-1H-pyrazol-3-yl]-amide hydrochloride or
- (S)-2-[4-(2-Fluoro-3-pyrrolidin-1-yl-phenoxy)-2-oxo-2,5-dihydro-pyrrol-1-yl]-4-methyl-pentanoic acid [1-((R)-2,2-dimethyl-[1,3]dioxolan-4-yl-methyl)-1H-pyrazol-3-yl]-amide.

25. The compound according to claim 1, wherein said compound is:

- (S)-2-[4-(2-Fluoro-3-pyrrolidin-1-yl-phenoxy)-2-oxo-2,5-dihydro-pyrrol-1-yl]-4-methyl-pentanoic acid [1-((R)-2,3-dihydroxy-propyl)-1H-pyrazol-3-yl]-amide,
- (S)-2-{4-[2-Fluoro-3-(1-hydroxy-1-methyl-ethyl)-phenoxy]-2-oxo-2,5-dihydro-pyrrol-1-yl}-4-methyl-pentanoic acid (1-methyl-1H-pyrazol-3-yl)-amide,
- (S)-2-[4-(2-Fluoro-3-vinyl-phenoxy)-2-oxo-2,5-dihydro-pyrrol-1-yl]-4-methyl-pentanoic acid [1-((R)-2,2-dimethyl-[1,3]dioxolan-4-yl-methyl)-1H-pyrazol-3-yl]-amide,
- (S)-2-[4-(2-Fluoro-3-vinyl-phenoxy)-2-oxo-2,5-dihydro-pyrrol-1-yl]-4-methyl-pentanoic acid [1-((R)-2,3-dihydroxy-propyl)-1H-pyrazol-3-yl]-amide,
- (S)-2-[4-(3-Cyclopropyl-2-fluoro-phenoxy)-2-oxo-2,5-dihydro-pyrrol-1-yl]-4-methyl-pentanoic acid [1-((R)-2,2-dimethyl-[1,3]dioxolan-4-yl-methyl)-1H-pyrazol-3-yl]-amide,
- (S)-2-[4-(3-Cyclopropyl-2-fluoro-phenoxy)-2-oxo-2,5-dihydro-pyrrol-1-yl]-4-methyl-pentanoic acid [1-((R)-2,3-dihydroxy-propyl)-1H-pyrazol-3-yl]-amide,
- (3-{(S)-2-[4-(3-Cyclopropyl-2-fluoro-phenoxy)-2-oxo-2,5-dihydro-pyrrol-1-yl]-4-methyl-pentanoylamino}-pyrazol-1-yl)-acetic acid ethyl ester,
- (3-{(S)-2-[4-(3-Cyclopropyl-2-fluoro-phenoxy)-2-oxo-2,5-dihydro-pyrrol-1-yl]-4-methyl-pentanoylamino}-pyrazol-1-yl)-acetic acid,
- (S)-2-[4-(3-Ethoxy-2-fluoro-phenoxy)-2-oxo-2,5-dihydro-pyrrol-1-yl]-4-methyl-pentanoic acid [5-((S)-2,2-dimethyl-[1,3]dioxolan-4-yl)-pyrazin-2-yl]-amide,
- (S)-2-[4-(3-Ethoxy-2-fluoro-phenoxy)-2-oxo-2,5-dihydro-pyrrol-1-yl]-4-methyl-pentanoic acid [5-((S)-1,2-dihydroxy-ethyl)-pyrazin-2-yl]-amide,
- (S)-2-[4-(3-Ethoxy-2,6-difluoro-phenoxy)-2-oxo-2,5-dihydro-pyrrol-1-yl]-4-methyl-pentanoic acid [5-((S)-2,2-dimethyl-[1,3]dioxolan-4-yl)-pyrazin-2-yl]-amide,
- (S)-2-[4-(3-Ethoxy-2,6-difluoro-phenoxy)-2-oxo-2,5-dihydro-pyrrol-1-yl]-4-methyl-pentanoic acid [5-((S)-1,2-dihydroxy-ethyl)-pyrazin-2-yl]-amide,
- (S)-2-[4-(2-Fluoro-3-vinyl-phenoxy)-2-oxo-2,5-dihydro-pyrrol-1-yl]-4-methyl-pentanoic acid pyrazin-2-ylamide,
- (S)-2-{4-[3-(1,2-Dihydroxy-ethyl)-2-fluoro-phenoxy]-2-oxo-2,5-dihydro-pyrrol-1-yl}-4-methyl-pentanoic acid pyrazin-2-ylamide,
- (S)-2-[4-(3-Cyclopropyl-2-fluoro-phenoxy)-2-oxo-2,5-dihydro-pyrrol-1-yl]-4-methyl-pentanoic acid (1-carbamoylmethyl-1H-pyrazol-3-yl)-amide,
- (S)-2-[4-(2,6-Difluoro-phenoxy)-2-oxo-2,5-dihydro-pyrrol-1-yl]-pentanoic acid [1-((R)-2,3-dihydroxy-propyl)-1H-pyrazol-3-yl]-amide,
- (S)-2-[4-(2,6-Difluoro-phenoxy)-2-oxo-2,5-dihydro-pyrrol-1-yl]-N-[1-((R)-2,2-dimethyl-[1,3]dioxolan-4-yl-methyl)-1H-pyrazol-3-yl]-butyramide,
- 2-[4-(2,6-Difluoro-phenoxy)-2-oxo-2,5-dihydro-pyrrol-1-yl]-N-[1-((R)-2,3-dihydroxy-propyl)-1H-pyrazol-3-yl]-3-(1-fluoro-cyclopentyl)-propionamide,
- (S)-2-[4-(3-Methoxy-phenoxy)-2-oxo-2,5-dihydro-pyrrol-1-yl]-4-methyl-pentanoic acid [1-((R)-2,3-dihydroxy-propyl)-1H-pyrazol-3-yl]-amide or (S)-2-[4-(2-chloro-3-ethoxy-phenoxy)-2-oxo-2,5-dihydro-pyrrol-1-yl]-4-methyl-pentanoic acid [1-((R)-2,3-dihydroxy-propyl)-1H-pyrazol-3-yl]-amide.

26. The compound according to claim 1, wherein said compound is:
(S)-2-[4-(3-Ethoxy-phenoxy)-2-oxo-2,5-dihydro-pyrrol-1-yl]-4-methyl-pentanoic acid [1-((R)-2,3-dihydroxy-propyl)-1H-pyrazol-3-yl]-amide,
(S)-2-[4-(3-Ethoxy-phenoxy)-2-oxo-2,5-dihydro-pyrrol-1-yl]-4-methyl-pentanoic acid [1-(2-hydroxy-2-methyl-propyl)-1H-pyrazol-3-yl]-amide,
(S)-3-Cyclohexyl-N-[1-((R)-2,3-dihydroxy-propyl)-1H-pyrazol-3-yl]-2-[4-(3-methoxy-phenoxy)-2-oxo-2,5-dihydro-pyrrol-1-yl]-propionamide,
(S)-2-[4-(3-Methoxy-phenoxy)-2-oxo-2,5-dihydro-pyrrol-1-yl]-4-methyl-pentanoic acid [1-(2-hydroxy-2-methyl-propyl)-1H-pyrazol-3-yl]-amide,
(S)-2-[4-(2-Fluoro-phenoxy)-2-oxo-2,5-dihydro-pyrrol-1-yl]-4-methyl-pentanoic acid [1-((R)-2,3-dihydroxy-propyl)-1H-pyrazol-3-yl]-amide,
(S)-2-[4-(2-Fluoro-phenoxy)-2-oxo-2,5-dihydro-pyrrol-1-yl]-4-methyl-pentanoic acid [1-(2-hydroxy-2-methyl-propyl)-1H-pyrazol-3-yl]-amide,
(S)-2-[4-(2-Fluoro-phenoxy)-2-oxo-2,5-dihydro-pyrrol-1-yl]-4-methyl-pentanoic acid [1-((R)-2,3-dihydroxy-propyl)-1H-pyrazol-3-yl]-amide,
2-[4-(2-chloro-phenoxy)-2-oxo-2,5-dihydro-pyrrol-1-yl]-3-cyclobutyl-N-[1-((R)-2,3-dihydroxy-propyl)-1H-pyrazol-3-yl]-propionamide,
2-[4-(2-Chloro-3-methoxyphenoxy)-2-oxo-2,5-dihydro-pyrrol-1-yl]-4-fluoro-4-methyl-pentanoic acid-[1-((R)-2,3-dihydroxy-propyl)-1H-pyrazol-3-yl]-amide,
2-[4-(2-Chloro-3-methoxy-phenoxy)-2-oxo-2,5-dihydro-pyrrol-1-yl]-4-fluoro-4-methyl-pentanoic acid [1-(2-hydroxy-2-methyl-propyl)-1H-pyrazol-3-yl]-amide,
(S)-2-[4-(2-chloro-phenoxy)-2-oxo-2,5-dihydro-pyrrol-1-yl]-4-methyl-pentanoic acid [1-((S)-2-oxo-oxazolidin-5-ylmethyl)-1H-pyrazol-3-yl]-amide,
(S)-2-[4-(2-chloro-phenoxy)-2-oxo-2,5-dihydro-pyrrol-1-yl]-4-methyl-pentanoic acid [1-((S)-3-diethylamino-2-hydroxy-propyl)-1H-pyrazol-3-yl]-amide,
(S)-2-[4-(2-Chloro-phenoxy)-2-oxo-2,5-dihydro-pyrrol-1-yl]-4-methyl-pentanoic acid [1-((S)-2,2-dimethyl-[1,3]dioxolan-4-yl-methyl)-1H-pyrazol-3-yl]-amide,
(S)-2-[4-(2-Chloro-phenoxy)-2-oxo-2,5-dihydro-pyrrol-1-yl]-4-methyl-pentanoic acid [1-((S)-2,3-dihydroxy-propyl)-1H-pyrazol-3-yl]-amide,
(R)-2-[4-(2-Chloro-phenoxy)-2-oxo-2,5-dihydro-pyrrol-1-yl]-4-methyl-pentanoic acid [1-((R)-2,3-dihydroxy-propyl)-1H-pyrazol-3-yl]-amide,
(S)-2-[4-(2-chloro-phenoxy)-2-oxo-2,5-dihydro-pyrrol-1-yl]-3-cyclobutyl-N-[1-((R)-2,3-dihydroxy-propyl)-1H-pyrazol-3-yl]-propionamide,
(R)-2-[4-(2-chloro-phenoxy)-2-oxo-2,5-dihydro-pyrrol-1-yl]-3-cyclobutyl-N-[1-((R)-2,3-dihydroxy-propyl)-1H-pyrazol-3-yl]-propionamide,
(R)-6-[2-[4-(2,6-difluoro-phenoxy)-2-oxo-2,5-dihydro-pyrrol-1-yl]-3-(tetrahydro-pyran-4-yl)-propionylamino]-nicotinic acid methyl ester,
(S)-N-[1-(2-hydroxy-2-methyl-propyl)-1H-pyrazol-3-yl]-2-[4-(2-methoxy-phenoxy)-2-oxo-2,5-dihydro-pyrrol-1-yl]-3-(tetrahydro-furan-2-yl)-propionamide or
(S)-N-[1-(2-hydroxy-2-methyl-propyl)-1H-pyrazol-3-yl]-2-[4-(2-methoxy-phenoxy)-2-oxo-2,5-dihydro-pyrrol-1-yl]-3-(tetrahydro-furan-2-yl)-propionamide.

27. The compound according to claim 1, wherein said compound is:
(S)-2-[4-(2-chloro-phenoxy)-2-oxo-2,5-dihydro-pyrrol-1-yl]-4-methyl-pentanoic acid [1-((R)-2-amino-3-hydroxy-propyl)-1H-pyrazol-3-yl]-amide,
(S)-2-[4-(2-chloro-phenoxy)-2-oxo-2,5-dihydro-pyrrol-1-yl]-N-[1-((R)-2,3-dihydroxy-propyl)-1H-pyrazol-3-yl]-3-phenyl-propionamide,
(S)-2-[4-(2-chloro-phenoxy)-2-oxo-2,5-dihydro-pyrrol-1-yl]-N-[1-((R)-2,2-dimethyl-[1,3]dioxolan-4-yl-methyl)-1H-pyrazol-3-yl]-3-(2-fluoro-phenyl)-propionamide,
(S)-2-[4-(2-chloro-phenoxy)-2-oxo-2,5-dihydro-pyrrol-1-yl]-N-[1-((R)-2,3-dihydroxy-propyl)-1H-pyrazol-3-yl]-3-(2-fluorophenyl)-propionamide,
(S)-2-[4-(2-chloro-phenoxy)-2-oxo-2,5-dihydro-pyrrol-1-yl]-N-[1-((R)-2,2-dimethyl-[1,3]dioxolan-4-yl-methyl)-1H-pyrazol-3-yl]-3-(2-fluoro-phenyl)-propionamide,
(S)-2-[4-(2-chloro-phenoxy)-2-oxo-2,5-dihydro-pyrrol-1-yl]-N-[1-((R)-2,3-dihydroxy-propyl)-1H-pyrazol-3-yl]-3-(2,6-difluorophenyl)-propionamide,
(S)-2-[4-(2-chloro-phenoxy)-2-oxo-2,5-dihydro-pyrrol-1-yl]-N-[1-((R)-2,2-dimethyl-[1,3]dioxolan-4-yl-methyl)-1H-pyrazol-3-yl]-3-(4-fluoro-phenyl)-propionamide,
(S)-2-[4-(2-chloro-phenoxy)-2-oxo-2,5-dihydro-pyrrol-1-yl]-N-[1-((R)-2,3-dihydroxy-propyl)-1H-pyrazol-3-yl]-3-(4-fluorophenyl)-propionamide,
(S)-2-[4-(2-chloro-phenoxy)-2-oxo-2,5-dihydro-pyrrol-1-yl]-N-[1-((R)-2,2-dimethyl-[1,3]dioxolan-4-yl-methyl)-1H-pyrazol-3-yl]-3-(2-chlorophenyl)-propionamide,
(S)-2-[4-(2-chloro-phenoxy)-2-oxo-2,5-dihydro-pyrrol-1-yl]-N-[1-((R)-2,3-dihydroxy-propyl)-1H-pyrazol-3-yl]-3-(2-chlorophenyl)-propionamide,
(S)-2-[4-(2-chloro-phenoxy)-2-oxo-2,5-dihydro-pyrrol-1-yl]-4-methyl-pentanoic acid (5-chloro-thiazol-2-yl)-amide,
(S)-2-[4-(2-chloro-phenoxy)-2-oxo-2,5-dihydro-pyrrol-1-yl]-4-methyl-pentanoic acid (5-chloro-thiazol-2-yl)-amide,
([6-(3-{(S)-2-[4-(2-chloro-phenoxy)-2-oxo-2,5-dihydro-pyrrol-1-yl]-[4R,6S]-4-methyl-pentanoylamino}-pyrazol-1-ylmethyl)-2,2-dimethyl-[1,3]dioxan-4-yl]-acetic acid tert-butyl ester,
(3R,5S)-6-(3-{(S)-2-[4-(2-chloro-phenoxy)-2-oxo-2,5-dihydro-pyrrol-1-yl]-4-methyl-pentanoylamino}-pyrazol-1-yl)-3,5-dihydroxy-hexanoic acid tert-butyl ester,
(3R,5S)-6-(3-{(S)-2-[4-(2-chloro-phenoxy)-2-oxo-2,5-dihydro-pyrrol-1-yl]-4-methylpentanoylamino}-pyrazol-1-yl)-3,5-dihydroxy-hexanoic acid,
(S)-3-cyclohexyl-N-[1-(2-hydroxy-2-methyl-propyl)-1H-pyrazol-3-yl]-2-[4-(2-isopropoxy-phenoxy)-2-oxo-2,5-dihydro-pyrrol-1-yl]-propionamide,
(S)-3-cyclohexyl-N-[1-(2-hydroxy-2-methyl-propyl)-1H-pyrazol-3-yl]-2-[4-(2-methylsulfanyl-phenoxy)-2-oxo-2,5-dihydro-pyrrol-1-yl]-propionamide,
(S)-2-[4-(2-tert-butyl-phenoxy)-2-oxo-2,5-dihydro-pyrrol-1-yl]-3-cyclohexyl-N-[1-(2-hydroxy-2-methyl-propyl)-1H-pyrazol-3-yl]-propionamide,
(S)-3-cyclohexyl-N-[1-(2-hydroxy-2-methyl-propyl)-1H-pyrazol-3-yl]-2-[2-oxo-4-(2-propyl-phenoxy)-2,5-dihydro-pyrrol-1-yl]-propionamide or
(S)-3-cyclohexyl-2-[4-(2,3-dimethoxy-phenoxy)-2-oxo-2,5-dihydro-pyrrol-1-yl]-N-[1-(2-hydroxy-2-methyl-propyl)-1H-pyrazol-3-yl]-propionamide.

28. The compound according to claim 1, wherein said compound is:

(S)-3-cyclohexyl-2-[4-(2,3-difluoro-phenoxy)-2-oxo-2,5-dihydro-pyrrol-1-yl]-N-[1-(2-hydroxy-2-methyl-propyl)-1H-pyrazol-3-yl]-propionamide, (S)-3-cyclohexyl-2-[4-(2,5-dichloro-phenoxy)-2-oxo-2,5-dihydro-pyrrol-1-yl]-N-[1-(2-hydroxy-2-methyl-propyl)-1H-pyrazol-3-yl]-propionamide, (S)-3-cyclohexyl-2-[4-(2,4-dichloro-phenoxy)-2-oxo-2,5-dihydro-pyrrol-1-yl]-N-[1-(2-hydroxy-2-methyl-propyl)-1H-pyrazol-3-yl]-propionamide, (S)-2-[4-(2-benzyloxy-phenoxy)-2-oxo-2,5-dihydro-pyrrol-1-yl]-3-cyclohexyl-N-[1-(2-hydroxy-2-methyl-propyl)-1H-pyrazol-3-yl]-propionamide, (S)-3-cyclohexyl-2-[4-(2,3-dimethyl-phenoxy)-2-oxo-2,5-dihydro-pyrrol-1-yl]-N-[1-(2-hydroxy-2-methyl-propyl)-1H-pyrazol-3-yl]-propionamide, (S)-2-[4-(3-bromo-phenoxy)-2-oxo-2,5-dihydro-pyrrol-1-yl]-3-cyclohexyl-N-[1-(2-hydroxy-2-methyl-propyl)-1H-pyrazol-3-yl]-propionamide, (S)-3-cyclohexyl-2-[4-(3-fluoro-phenoxy)-2-oxo-2,5-dihydro-pyrrol-1-yl]-N-[1-(2-hydroxy-2-methyl-propyl)-1H-pyrazol-3-yl]-propionamide, (S)-2-[4-(3-chloro-phenoxy)-2-oxo-2,5-dihydro-pyrrol-1-yl]-3-cyclohexyl-N-[1-(2-hydroxy-2-methyl-propyl)-1H-pyrazol-3-yl]-propionamide, (S)-3-cyclohexyl-N-[1-(2-hydroxy-2-methyl-propyl)-1H-pyrazol-3-yl]-2-[4-(3-methoxy-phenoxy)-2-oxo-2,5-dihydro-pyrrol-1-yl]-propionamide, (S)-3-cyclohexyl-N-[1-(2-hydroxy-2-methyl-propyl)-1H-pyrazol-3-yl]-2-[2-oxo-4-(3-trifluoromethyl-phenoxy)-2,5-dihydro-pyrrol-1-yl]-propionamide, (S)-3-cyclohexyl-N-[1-(2-hydroxy-2-methyl-propyl)-1H-pyrazol-3-yl]-2-(2-oxo-4-m-tolyloxy-2,5-dihydro-pyrrol-1-yl)-propionamide, (S)-3-cyclohexyl-N-[1-(2-hydroxy-2-methyl-propyl)-1H-pyrazol-3-yl]-2-[2-oxo-4-(3-trifluoromethoxy-phenoxy)-2,5-dihydro-pyrrol-1-yl]-propionamide, (S)-3-cyclohexyl-N-[1-(2-hydroxy-2-methyl-propyl)-1H-pyrazol-3-yl]-2-[4-(6-methyl-pyridin-3-yloxy)-2-oxo-2,5-dihydro-pyrrol-1-yl]-propionamide, (S)-3-cyclohexyl-N-[1-(2-hydroxy-2-methyl-propyl)-1H-pyrazol-3-yl]-2-(2-oxo-4-phenoxy-2,5-dihydro-pyrrol-1-yl)-propionamide, 2-[4-(2-Chloro-phenoxy)-2-oxo-2,5-dihydro-pyrrol-1-yl]-N-[1-(2-hydroxy-2-methyl-propyl)-1H-pyrazol-3-yl]-3-(trans-3-methyl-cyclobutyl)-propionamide, (S)-2-[4-(2-Chloro-phenoxy)-2-oxo-2,5-dihydro-pyrrol-1-yl]-N-[1-(2-hydroxy-2-methyl-propyl)-1H-pyrazol-3-yl]-3-(trans-3-methyl-cyclobutyl)-propionamide, (R)-2-[4-(2-Chloro-phenoxy)-2-oxo-2,5-dihydro-pyrrol-1-yl]-N-[1-(2-hydroxy-2-methyl-propyl)-1H-pyrazol-3-yl]-3-(trans-3-methyl-cyclobutyl)-propionamide, 2-[4-(2-Chloro-phenoxy)-2-oxo-2,5-dihydro-pyrrol-1-yl]-N-[1-(2-hydroxy-2-methyl-propyl)-1H-pyrazol-3-yl]-3-(cis-3-methyl-cyclobutyl)-propionamide, (S)-2-[4-(2-Chloro-phenoxy)-2-oxo-2,5-dihydro-pyrrol-1-yl]-4,4-difluoro-pentanoic acid [1-((R)-2,3-dihydroxy-propyl)-1H-pyrazol-3-yl]-amide or 2-[4-(2-Chloro-phenoxy)-2-oxo-2,5-dihydro-pyrrol-1-yl]-5,5,5-trifluoro-4-trifluoromethyl-pentanoic acid [1-((R)-2,3-dihydroxy-propyl)-1H-pyrazol-3-yl]-amide.

29. The compound according to claim 1, wherein said compound is:

2-[4-(2-Chloro-phenoxy)-2-oxo-2,5-dihydro-pyrrol-1-yl]-5,5,5-trifluoro-pentanoic acid [1-((R)-2,3-dihydroxy-propyl)-1H-pyrazol-3-yl]-amide, 2-[4-(2-Chloro-phenoxy)-2-oxo-2,5-dihydro-pyrrol-1-yl]-N-[1-((R)-2,3-dihydroxy-propyl)-1H-pyrazol-3-yl]-4,4-difluoro-butyramide, (S)-2-[4-(2-Chloro-phenoxy)-2-oxo-2,5-dihydro-pyrrol-1-yl]-N-[1-((R)-2,3-dihydroxy-propyl)-1H-pyrazol-3-yl]-4-hydroxy-butyramide, (S)-2-[4-(2-Chloro-phenoxy)-2-oxo-2,5-dihydro-pyrrol-1-yl]-N-[1-((R)-2,3-dihydroxy-propyl)-1H-pyrazol-3-yl]-4-methylsulfanyl-butyramide, 2-[4-(2-Chloro-phenoxy)-2-oxo-2,5-dihydro-pyrrol-1-yl]-N-[1-((R)-2,3-dihydroxy-propyl)-1H-pyrazol-3-yl]-4,4,4-trifluoro-butyramide, 3-(2,6-Dichloro-phenyl)-2-[4-(2,6-difluoro-phenoxy)-2-oxo-2,5-dihydro-pyrrol-1-yl]-N-[1-(2-hydroxy-2-methyl-propyl)-1H-pyrazol-3-yl]-propionamide, 2-[4-(2-Chloro-phenoxy)-2-oxo-2,5-dihydro-pyrrol-1-yl]-5,5,5-trifluoro-4-methyl-pentanoic acid [1-(2-hydroxy-2-methyl-propyl)-1H-pyrazol-3-yl]-amide, 2-[4-(2-Chloro-phenoxy)-2-oxo-2,5-dihydro-pyrrol-1-yl]-5,5-dimethyl-hexanoic acid [1-((R)-2,3-dihydroxy-propyl)-1H-pyrazol-3-yl]amide, 3-Bicyclo[2.2.1]hept-2-yl-2-[4-(2,6-difluoro-phenoxy)-2-oxo-2,5-dihydro-pyrrol-1-yl]-N-[1-(2-hydroxy-2-methyl-propyl)-1H-pyrazol-3-yl]-propionamide, 3-bicyclo[2.2.1]hept-7-yl-2-[4-(2-chloro-phenoxy)-2-oxo-2,5-dihydro-pyrrol-1-yl]-N-[1-(2-hydroxy-2-methyl-propyl)-1H-pyrazol-3-yl]-propionamide, (S)-2-[4-(2-Chloro-phenoxy)-2-oxo-2,5-dihydro-pyrrol-1-yl]-N-[1-((R)-2,3-dihydroxy-propyl)-1H-pyrazol-3-yl]-4-methoxy-butyramide, (S)-3-Cyclohexyl-2-[4-(3,4-dichloro-phenylamino)-2-oxo-2,5-dihydro-pyrrol-1-yl]-N-[1-(2-hydroxy-2-methyl-propyl)-1H-pyrazol-3-yl]-propionamide, (S)-3-cyclohexyl-N-[1-(2-hydroxy-2-methyl-propyl)-1H-pyrazol-3-yl]-2-(4-isopropylamino-2-oxo-2,5-dihydro-pyrrol-1-yl)-propionamide, (S)-3-cyclohexyl-2-[4-(ethyl-methyl-amino)-2-oxo-2,5-dihydro-pyrrol-1-yl]-N-[1-(2-hydroxy-2-methyl-propyl)-1H-pyrazol-3-yl]-propionamide, (S)-3-cyclopentyl-N-[1-(2-hydroxy-2-methyl-propyl)-1H-pyrazol-3-yl]-2-(4-isopropylamino-2-oxo-2,5-dihydro-pyrrol-1-yl)-propionamide (S)-2-{4-[3-(2-Hydroxy-2-methyl-propyl)-phenoxy]-2-oxo-2,5-dihydro-pyrrol-1-yl}-4-methyl-pentanoic acid (1-methyl-1H-pyrazol-3-yl)-amide, (S)-2-{4-[3-(2-Hydroxy-2-methyl-propyl)-phenoxy]-2-oxo-2,5-dihydro-pyrrol-1-yl}-4-methyl-pentanoic acid [1-(2-hydroxy-2-methyl-propyl)-1H-pyrazol-3-yl]-amide, (S)-2-{4-[3-(2-Hydroxy-2-methyl-propyl)-phenoxy]-2-oxo-2,5-dihydro-pyrrol-1-yl}-4-methyl-pentanoic acid [1-((R)-2,2-dimethyl-[1,3]dioxolan-4-ylmethyl)-1H-pyrazol-3-yl]-amide, (S)-2-{4-[3-(2-Hydroxy-2-methyl-propyl)-phenoxy]-2-oxo-2,5-dihydro-pyrrol-1-yl}-4-methyl-pentanoic acid [1-((R)-2,3-dihydroxy-propyl)-1H-pyrazol-3-yl]-amide or (S)-2-{4-[3-(2-Hydroxy-2-methyl-propyl)-phenoxy]-2-oxo-2,5-dihydro-pyrrol-1-yl}-4-methyl-pentanoic acid (1-methyl-1H-pyrazol-3-yl)-amide.

30. The compound according to claim 1, wherein said compound is:

(S)-4-Methyl-2-[4-(1-methyl-1H-indazol-4-yloxy)-2-oxo-2,5-dihydro-pyrrol-1-yl]-pentanoic acid [1-((R)-2,3-dihydroxy-propyl)-1H-pyrazol-3-yl]-amide, (S)-2-[4-(2-Amino-3-hydroxy-phenoxy)-2-oxo-2,5-dihydro-pyrrol-1-yl]-4-methyl-pentanoic acid [1-(2-hydroxy-2-methyl-propyl)-1H-pyrazol-3-yl]-amide, (S)-2-[4-(Benzooxazol-4-yloxy)-2-oxo-2,5-dihydro-pyrrol-1-yl]-4-methyl-pentanoic acid [1-(2-hydroxy-2-methyl-propyl)-1H-pyrazol-3-yl]-amide, (S)-4-Methyl-2-[4-(2-methyl-benzooxazol-4-yloxy)-2-oxo-2,5-dihydro-pyrrol-1-yl]-pentanoic acid [1-(2-hydroxy-2-methyl-propyl)-1H-pyrazol-3-yl]-amide, (S)-2-{4-[4-((S)-2,3-Dihydroxy-propyl)-phenoxy]-2-oxo-2,5-dihydro-pyrrol-1-yl}-4-methyl-pentanoic acid pyrazin-2-ylamide, (S)-2-{4-[4-(2-Hydroxy-2-methyl-propyl)-phenoxy]-2-oxo-2,5-dihydro-pyrrol-1-yl}-4-methyl-pentanoic acid pyrazin-2-ylamide, (S)-2-{4-[3-(2-Hydroxy-2-methyl-propyl)-phenoxy]-2-oxo-2,5-dihydro-pyrrol-1-yl}-4-methyl-pentanoic acid pyrazin-2-ylamide, (S)-2-{4-[2-Fluoro-3-(1-hydroxy-1-methyl-ethyl)-phenoxy]-2-oxo-2,5-dihydro-pyrrol-1-yl}-4-methyl-pentanoic acid pyrazin-2-ylamide, (S)-2-[4-(2-Chloro-phenoxy)-2-oxo-2,5-dihydro-pyrrol-1-yl]-4-methyl-hexanoic acid [1-((R)-2,2-dimethyl-[1,3]dioxolan-4-ylmethyl)-1H-pyrazol-3-yl]-amide, (S)-2-[4-(2-Chloro-phenoxy)-2-oxo-2,5-dihydro-pyrrol-1-yl]-4-methyl-hexanoic acid [1-((R)-2,3-dihydroxy-propyl)-1H-pyrazol-3-yl]-amide, (2R,4S)-2-[4-(2-Chloro-phenoxy)-2-oxo-2,5-dihydro-pyrrol-1-yl]-4-methyl-hexanoic acid [1-((R)-2,3-dihydroxy-propyl)-1H-pyrazol-3-yl]-amide, (2S,4S)-2-[4-(2-Chloro-phenoxy)-2-oxo-2,5-dihydro-pyrrol-1-yl]-4-methyl-hexanoic acid [1-((R)-2,3-dihydroxy-propyl)-1H-pyrazol-3-yl]-amide, (R)-2-[4-(2-Chloro-phenoxy)-2-oxo-2,5-dihydro-pyrrol-1-yl]-4-methyl-hexanoic acid [1-((R)-2,2-dimethyl-[1,3]dioxolan-4-ylmethyl)-1H-pyrazol-3-yl]-amide, (R)-2-[4-(2-Chloro-phenoxy)-2-oxo-2,5-dihydro-pyrrol-1-yl]-4-methyl-hexanoic acid [1-((R)-2,3-dihydroxy-propyl)-1H-pyrazol-3-yl]-amide, (2R,4R)-2-[4-(2-Chloro-phenoxy)-2-oxo-2,5-dihydro-pyrrol-1-yl]-4-methyl-hexanoic acid [1-((R)-2,3-dihydroxy-propyl)-1H-pyrazol-3-yl]-amide, (2S,4R)-2-[4-(2-Chloro-phenoxy)-2-oxo-2,5-dihydro-pyrrol-1-yl]-4-methyl-hexanoic acid [1-((R)-2,3-dihydroxy-propyl)-1H-pyrazol-3-yl]-amide, 2-[4-(3-Ethoxy-2,6-difluoro-phenoxy)-2-oxo-2,5-dihydro-pyrrol-1-yl]-N-[1-(2-hydroxy-2-methyl-propyl)-1H-pyrazol-3-yl]-3-(tetrahydro-pyran-4-yl)-propionamide, (S)-2-[4-(3-Ethoxy-2,6-difluoro-phenoxy)-2-oxo-2,5-dihydro-pyrrol-1-yl]-N-[1-(2-hydroxy-2-methyl-propyl)-1H-pyrazol-3-yl]-3-(tetrahydro-pyran-4-yl)-propionamide, (R)-2-[4-(3-Ethoxy-2,6-difluoro-phenoxy)-2-oxo-2,5-dihydro-pyrrol-1-yl]-N-[1-(2-hydroxy-2-methyl-propyl)-1H-pyrazol-3-yl]-3-(tetrahydro-pyran-4-yl)-propionamide or (2S,4S)-4-Ethoxy-2-[4-(3-ethoxy-2-fluoro-phenoxy)-2-oxo-2,5-dihydro-pyrrol-1-yl]-pentanoic acid [1-(2-hydroxy-2-methyl-propyl)-1H-pyrazol-3-yl]-amide, (S)-2-[4-(3-Ethoxy-2,6-difluoro-phenoxy)-2-oxo-2,5-dihydro-pyrrol-1-yl]-4-methyl-pentanoic acid [1-(2-hydroxy-2-methyl-propyl)-1H-pyrazol-3-yl]-amide, 2-[4-(2-Bromo-phenoxy)-2-oxo-2,5-dihydro-pyrrol-1-yl]-N-[1-(2-hydroxy-2-methyl-propyl)-1H-pyrazol-3-yl]-3-(tetrahydro-pyran-4-yl)-propionamide, (S)-2-[4-(2,6-Difluoro-phenoxy)-2-oxo-2,5-dihydro-pyrrol-1-yl]-N-[1-(2-hydroxy-2-methyl-propyl)-1H-pyrazol-3-yl]-3-(S)-tetrahydro-pyran-2-yl-propionamide or 2-[4-(2-Chloro-phenoxy)-2-oxo-2,5-dihydro-pyrrol-1-yl]-3-((1R,3S,4R)-3,4-difluoro-cyclopentyl)-N-[1-((R)-2,3-dihydroxy-propyl)-1H-pyrazol-3-yl]-propionamide.

31. A pharmaceutical composition, comprising a therapeutically effective amount of a compound according to claim 1 or a pharmaceutically acceptable salt thereof and a pharmaceutically acceptable carrier.

\* \* \* \* \*